US012041907B2

(12) United States Patent
Aharoni et al.

(10) Patent No.: US 12,041,907 B2
(45) Date of Patent: *Jul. 23, 2024

(54) CELLULOSE-SYNTHASE-LIKE ENZYMES AND USES THEREOF

(71) Applicant: YEDA RESEARCH AND DEVELOPMENT CO. LTD., Rehovot (IL)

(72) Inventors: Asaph Aharoni, Tel-Aviv (IL); Prashant Sonawane, Rehovot (IL); Maxim Itkin, Rehovot (IL); Adam Jozwiak, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 185 days.

This patent is subject to a terminal disclaimer.

(21) Appl. No.: 17/272,685

(22) PCT Filed: Sep. 5, 2019

(86) PCT No.: PCT/IL2019/051000
§ 371 (c)(1),
(2) Date: Mar. 2, 2021

(87) PCT Pub. No.: WO2020/049572
PCT Pub. Date: Mar. 12, 2020

(65) Prior Publication Data

US 2022/0217934 A1 Jul. 14, 2022

Related U.S. Application Data

(63) Continuation of application No. 16/123,248, filed on Sep. 6, 2018, now Pat. No. 10,806,119.

(30) Foreign Application Priority Data

Jul. 25, 2019 (IL) .......................................... 268269

(51) Int. Cl.
*A01H 6/82* (2018.01)
*C12N 9/10* (2006.01)
*C12N 15/82* (2006.01)

(52) U.S. Cl.
CPC ............. *A01H 6/82* (2018.05); *C12N 9/1059* (2013.01); *C12N 15/8218* (2013.01); *C12N 15/8243* (2013.01); *C12N 15/8247* (2013.01)

(58) Field of Classification Search
None
See application file for complete search history.

(56) References Cited

U.S. PATENT DOCUMENTS

| | | | |
|---|---|---|---|
| 4,987,071 A | 1/1991 | Cech et al. | |
| 5,959,180 A | 9/1999 | Moehs et al. | |
| 6,326,174 B1 | 12/2001 | Joyce et al. | |
| 7,375,259 B1 | 5/2008 | Mccue et al. | |
| 7,439,419 B1 | 10/2008 | Mccue et al. | |
| 9,718,850 B2 | 8/2017 | Gin et al. | |
| 9,994,883 B2 | 6/2018 | Goossens et al. | |
| 10,806,119 B2 * | 10/2020 | Aharoni | A01H 6/82 |
| 11,412,700 B2 * | 8/2022 | Aharoni | C12N 15/8243 |
| 2005/0108791 A1 | 5/2005 | Edgerton | |
| 2009/0070895 A1 | 3/2009 | Rae et al. | |
| 2009/0070897 A1 | 3/2009 | Goldman et al. | |
| 2011/0219476 A1 * | 9/2011 | Ono | C12N 15/825 435/243 |
| 2011/0265221 A1 | 10/2011 | Abad et al. | |
| 2012/0159676 A1 | 6/2012 | Umemoto et al. | |
| 2013/0167271 A1 | 6/2013 | Umemoto et al. | |
| 2016/0046912 A1 | 2/2016 | Muranaka et al. | |

FOREIGN PATENT DOCUMENTS

| | | |
|---|---|---|
| EP | 2982752 | 2/2016 |
| WO | WO 2000/066716 | 11/2000 |
| WO | WO 2011/061656 A1 | 4/2011 |
| WO | WO 2012/095843 A1 | 7/2012 |
| WO | WO 2014/195944 A1 | 12/2014 |

OTHER PUBLICATIONS

Arendt et al. "An endoplasmic reticulum-engineered yeast platform for overproduction of triterpenoids" Metabolic engineering. Mar. 1, 2017;40:165-75.

Arnqvist et al. "Reduction of cholesterol and glycoalkaloid levels in transgenic potato plants by overexpression of a type 1 sterol methyltransferase cDNA" Plant Physiology. Apr. 1, 2003;131(4):1792-9.

Augustin et al. "Molecular activities, biosynthesis and evolution of triterpenoid saponins" Phytochemistry. Apr. 1, 2011;72(6):435-57.

Belhaj "Plant genome editing made easy: targeted mutagenesis in model and crop plants using the CRISPR/Cas system. Plant methods" Oct. 11, 2013;9(1):1.

Biazzi et al. "CYP72A67 catalyzes a key oxidative step in Medicago truncatula hemolytic saponin biosynthesis" Molecular plant. Oct. 5, 2015;8(10):1493-506.

Camacho et al. "BLAST+: architecture and applications" BMC bioinformatics, Dec. 2009;10(1):421.

(Continued)

Primary Examiner — Brent T Page
(74) Attorney, Agent, or Firm — Mark S. Cohen; PEARL COHEN ZEDEK LATZER BARATZ LLP

(57) ABSTRACT

Provided herein are genetically modified cells and genetically modified plants having increased or decreased expression of a cellulose synthase like G (CSLG) enzyme. These cells and plants may have an increased or decreased content a steroidal alkaloid, a steroidal saponin, or a triterpenoid saponin, compared to a corresponding unmodified cell or plant. Also provided herein are methods of producing a steroidal alkaloid, a steroidal saponin, or a triterpenoid saponin in a genetically modified cell, as well as methods of reducing the content of a steroidal alkaloid, a steroidal saponin, or a triterpenoid saponin in a cell of a plant or a plant part, and methods of increasing the content of a steroidal alkaloid, a steroidal saponin, or a triterpenoid saponin in a cell of a plant or a plant part.

39 Claims, 107 Drawing Sheets

Specification includes a Sequence Listing.

(56) References Cited

OTHER PUBLICATIONS

Cárdenas et al. "GAME9 regulates the biosynthesis of steroidal alkaloids and upstream isoprenoids in the plant mevalonate pathway" Nature communications. Feb. 15, 2016;7:10654.
Cárdenas et al. "The bitter side of the nightshades: Genomics drives discovery in Solanaceae steroidal alkaloid metabolism" Phytochemistry. May 1, 2015;113:24-32.
Casamitjana-Martinez et al. "Root-specific CLE19 overexpression and the sol1/2 suppressors implicate a CLV-like pathway in the control of *Arabidopsis* root meristern maintenance" Current Biology. Aug. 19, 2003;13(16):1435-41.
Chen et al. "Short-chain dehydrogenase/reductase catalyzing the final step of noscapine biosynthesis is localized to laticifers in opium poppy" The Plant Journal. Jan. 2014;77(2):173-84.
Cheong et al. "Multicellular survival as a consequence of Parrondo's paradox" Proceedings of the National Academy of Sciences. Jun. 5, 2018;115(23):E5258-9.
Chitwood et al. "A quantitative genetic basis for leaf morphology in a set of precisely defined tomato introgression lines" The Plant Cell. Jul. 1, 2013;25(7):2465-81.
Christen et al. "Structural Insights on cholesterol endosynthesis: Binding of squalene and 2, 3-oxidosqualene to supernatant protein factor" Journal of structural biology. Jun. 1, 2015;190(3):261-70.
Database NCBI "Predicted: ethylene-responsive transcription factor 1-like [Solanum lycopersicum]" GeneBank accession No. XP_004229751. URL: http:www.ncbi.nlm.nih.gov/protein/460367786?report=genbank&log$=prottop&blast_rank=2&RID=ZUTPRBJX01R. originally accessed Nov. 23, 2016.
Database NCBI "Predicted: transcription factor BIM2-like [Solanum lycopersicum]" GeneBank accession No. XP_004234703.1. URL: http:www.ncbi.nlm.nih.gov/protein/460377857?report=genbank&log$=prottop&blast_rank=1&RID=TE9A3KF01R. originally accessed Mar. 12, 2013.
Database UniProt [Online], Oct. 1, 2000 (Oct. 1, 2000), "SubName: Full=Putative alcohol dehydrogenase {EC0:0000-313:EMBL:CAB91875.I, EC0:0000313:Ensemb1Plants:Solyc01g073640.2 1};", XP00' 2779764, retrieved from EBI accession No. UNIPROT:Q9LEG3 Database accession No. Q9LEG3.
Database Protein [Online], Dec. 23, 2015 (Dec. 23, 2015), "Predicted short-chain dehydrogenase reductase 3b-like (xanthoxin dehydrogenase)", XP002779765, retrieved from NCBI Database accession No. XP 015062676.
Database UniProt [Online] Apr. 3, 2013 (Apr. 3, 2013), "SubName: Full=Uncharacterized protein {EC0:0000313:Ensembl-Plants:PGSC0003DMT400079897};", XP002779766, retrieved from EBI accession No. UNIPROT:M1D2N5 Database accession No. M1D2N5.
Database NCBI [online], Apr. 15, 2005 (Apr. 15, 2005), Lycopersicon esculentum mRNA for putative alcohol dehydrogenase (yfe37 gene) GenBank:AJ277945.1, https://www.ncbi.nlm.nih.gov/nuccore/7981381.
Database NCBI [online], Nov. 22, 2016 (Nov. 22, 2016), Predicted: probable 2-oxoglutarate-dependent dioxygenase AOP1 isoform X1 [Solanum lycopersicum], NCBI Reference Sequence: XP_004233541.1, https://www.ncbi.nlm.nih.gov/protein/460375495?report=genbank.&log$=protalign&blast_rank=1&RID=UWXRDWSA016.
De Carolis et al. "2-Oxoglutarate-dependent dioxygenase and related enzymes: biochemical characterization" Phytochemistry. Aug. 10, 1994;36(5):1093-107.
De Carolis et al. "Isolation and characterization of a 2-oxoglutarate dependent dioxygenase involved in the second-to-last step in vindoline biosynthesis" Plant physiology. Nov. 1, 1990;94(3):1323-9.
Dinesh-Kumar et al. "Virus-induced gene silencing" In Plant Functional Genomics 2003 (pp. 287-293). Humana Press.
Eckert et al. "DNA polymerase fidelity and the polymerase chain reaction" Genome Research. Aug. 1, 1991:1(1):17-24.
Eich, Eckart. "Solanaceae and Convolvulaceae: Secondary metabolites: Biosynthesis, chemotaxonomy, biological and economic significance" (a handbook), pp. 414, 416, 420, 422, 434, 441-445. Springer Science & Business Media, 2008.
Eshed et al. "An Introgression line population of Lycopersicon pennellil in the cultivated tomato enables the identification and fine mapping of yield-associated QTL" Genetics. Nov. 1, 1996;141(3):1147-62.
Estornell et al. "A multisite gateway-based toolkit for targeted gene expression and hairpin RNA silencing in tomato fruits" Plant biotechnology journal. Apr. 2009;7(3):298-309.
Expósito-Rodríguez et al. "Selection of internal control genes for quantitative real-time RT-PCR studies during tomato development process" BMC plant biology. Dec. 2008;8(1):131.
Fernandez et al. "Flexible tools for gene expression and silencing in tomato" Plant Physiology. Dec. 1, 2009:151(4):1729-40.
Fernandez-Pozo et al. "The Sol Genomics Network (SGN)—from genotype to phenotype to breeding" Nucleic acids research. Nov. 26, 2014:43(D1):D1036-41.
Finsterbusch et al. "Δ5-3β-Hydroxysteroid dehydrogenase from Digitalis lanata Ehrh.—a multifunctional enzyme in steroid metabolism?" Planta. Oct. 1, 1999;209(4):478-86.
Fire et al. Potent and specific genetic interference by double-stranded RNA in Caenorhabditis elegans. nature. Feb. 1998;391(6669):806.
Friedman et al. "Potato glycoalkaloids: chemistry, analysis, safety, and plant physiology" Critical Reviews in Plant Sciences. Jan. 1, 1997:16(1):55-132.
Friedman M. "Tomato glycoalkaloids: role in the plant and in the diet. Journal of agricultural and food chemistry" Oct. 9, 2002:50(21):5751-80.
Friedman M. "Potato glycoalkaloids and metabolites: roles in the plant and in the diet" Journal of Agricultural and Food Chemistry. Nov. 15, 2006;54(23):8655-81.
Friedman et al. "Dehydrotomatine content in tomatoes" Journal of agricultural and food chemistry. Nov. 16, 1998;46(11):4571-6.
Friedman et al. "Anticarcinogenic effects of glycoalkaloids from potatoes against human cervical, liver, lymphoma, and stomach cancer cells" Journal of agricultural and food chemistry. Jul. 27, 2005;53(15):6162-9.
Gantasala et al. "Selection and validation of reference genes for quantitative gene expression studies by real-time PCR in eggplant (*Solanum melongena* L)" BMC research notes. Dec. 2013;6(1):312.
Garai S. "Triterpenold saponins" Nat. Prod. Chem. Res. Sep. 14, 2014;2.
Gatto et al. "Activity of extracts from wild edible herbs against postharvest fungal diseases of fruit and vegetables" Postharvest Biology and Technology, Jul. 1, 2011;61(1):72-82.
Gavidia et al. "Plant progesterone 5β-reductase is not homologous to the animal enzyme. Molecular evolutionary characterization of P5βR from Digitalis purpurea" Phytochemistry. Mar. 1, 2007;68(6):853-64.
Ginzberg et al. "Potato steroidal glycoalkaloids: biosynthesis and genetic manipulation" Potato Research. Feb. 1, 2009;52(1):1-5.
Guo et al. "par-1, a gene required for establishing polarity in C. elegans embryos, encodes a putative Ser/Thr kinase that is asymmetrically distributed" Cell. May 19, 1996;81(4):611-20.
Haralampidis et al. "Biosynthesis of triterpenoid saponins in plants" In History and Trends in Bioprocessing and Biotransformation 2002 (pp. 31-49). Springer, Berlin, Heidelberg.
Hasemann et al. "Structure and function of cytochromes P450: a comparative analysis of three crystal structures" Structure. Jan. 1, 1995;3(1):41-62.
Heim et al. "The basic helix-loop-helix transcription factor family in plants: a genome-wide study of protein structure and functional diversity" Molecular biology and evolution. May 1, 2003;20(5):735-47.
Heinig et al. "Analysis of steroidal alkaloids and saponins in Solanaceae plant extracts using UPLC-qTOF mass spectrometry" In Plant Isoprenoids 2014 (pp. 171-185). Humana Press, New York, NY.
Henry M. "Saponins and phylogeny: example of the "gypsogenin group" saponins" Phytochemistry Reviews. Jul. 1, 2005;4(2-3):89-94.

(56) References Cited

OTHER PUBLICATIONS

Herl et al. "Δ5-ΔB-Hydroxysteroid dehydrogenase (3BHSD) from Digitalis lanata. Heterologous expression and characterisation of the recombinant enzyme" Planta medica. Jun. 2007;73(07):704-10.
Herl et al. "Molecular cloning and heterologous expression of progesterone 5β-reductase from Digitalis lanata Ehrh" Phytochemistry. Feb. 1, 2006;67(3):225-31.
Hérold, M. C., & Henry, M. (2001). UDP-glucuronosyltransferase activity is correlated to saponin production in Gypsophila paniculata root in vitro cultures. Biotechnology letters, 23(5), 335-337.
Higuchi R. Recombinant PCR. PCR Protocols: A Guide to Methods and Applications. 1990:177-83 (Ch. 22).
Huhman et al. "Metabolic profiling of saponins in Medicago sativa and Medicago truncatula using HPLC coupled to an electrospray ion-trap mass spectrometer" Phytochemistry. Feb. 1, 2002;59(3):347-60.
Ingelbrecht et al. Different 3'end regions strongly influence the level of gene expression in plant cells. The Plant Cell. Jul. 1, 1989:1(7):871-80.
International search Report for PCT Application No. PCT/IL2018/050142 issued Jul. 10, 2018.
International Search Report for PCT Application No. PCT/IL2019/051000 issued Dec. 12, 2019.
Itkin et al. "Biosynthesis of antinutritional alkaloids in solanaceous crops is mediated by clustered genes. Science" Jul. 12, 2013;341(6142):175-9.
Itkin et al. "Glycoalkaloid Metabolism1 is required for steroidal alkaloid glycosylation and prevention of phytotoxicity in tomato" The Plant Cell. Dec. 1, 2011;23(12):4507-25.
Jarvis et al. "The genome of Chenopodium quinoa" Nature. Feb. 2017;542(7641):307.
Kai et al. Scopoletin is biosynthesized via ortho-hydroxylation of feruloyl CoA by a 2-oxoglutarate-dependent dioxygenase in *Arabidopsis thaliana*. The Plant Journal. Sep. 2008;55(6):988-99.
Kallberg et al. "Short-chain dehydrogenases/reductases (SDRs) Coenzyme-based functional assignments in completed genomes" European Journal of Biochemistry. Sep. 2002;269(18):4409-17.
Källberg et al. "Template-based protein structure modeling using the RaptorX web server" Nature protocols. Aug. 2012;7(8):1511.
Karimi M. et al. "Gateway™ vectors for Agrobacterium-mediated plant transformation" Trends Plant Sci. 2002, 7, 193-195.
Kavanagh et al. "Medium-and short-chain dehydrogenase/reductase gene and protein families" Cellular and Molecular Life Sciences. Dec. 1, 2008;65(24):3885.
Kawai et al. "Evolution and diversity of the 2-oxoglutarate-dependent dioxygenase superfamily in plants" The Plant Journal. Apr. 2014;78(2):328-43.
Kitaoka et al. "Investigating inducible short-chain alcohol dehydrogenases/reductases clarifies rice oryzalexin biosynthesis" The Plant Journal, Oct. 2016;88(2):271-9.
Kundu S. Distribution and prediction of catalytic domains in 2-oxoglutarate dependent dioxygenases. BMC research notes. Dec. 2012;5(1):410.
Kurosawa et al. "UDP-glucuronic acid: soyasapogenol glucuronosyltransferase involved in saponin biosynthesis in germinating soybean seeds" Planta. Aug. 1, 2002;215(4):620-9.
Laurila et al. "Formation of parental-type and novel glycoalkaloids in somatic hybrids between Solanum brevidens and S. tuberosum" Plant Science. Aug. 16, 1996;118(2):145-55.
Li et al. "ESI-QqTOF-MS/MS and APCI-IT-MS/MS analysis of steroid saponins from the rhizomes of Dioscorea panthaica". Journal of Mass Spectrometry. Jan. 1, 2006;41(1):1-22.
Lin et al. "Putative genes involved in saikosaponin biosynthesis in *Bupleurum* species" International journal of molecular sciences. Jun. 2013;14(6):12806-26.
Linscott et al. "Mapping a kingdom-specific functional domain of squalene synthase" Biochimica et Biophysica Acta (BBA)-Molecular and Cell Biology of Lipids. Sep. 1, 2016:1861(9):1049-57.
Liu et al. "Eight new triterpenoid saponins with antioxidant activity from the roots of Glycyrrhiza uralensis Fisch" Fitoterapia. Mar. 1, 2019;133:186-92.
Louveau et al. "Analysis of Two New Arabinosyltransferases Belonging to the Carbohydrate-Active Enzyme (CAZY) Glycosyl Transferase Family1 Provides Insights into Disease Resistance and Sugar Donor Specificity" The Plant Cell. Dec. 1, 2018;30(12):3038-57.
Marciani DJ. "Is fucose the answer to the immunomodulatory paradox of Quillaja saponins?" International immunopharmacology. Dec. 1, 2015:29(2):908-13.
McCue et al. "Metabolic compensation of steroidal glycoalkaloid biosynthesis in transgenic potato tubers: using reverse genetics to confirm the in vivo enzyme function of a steroidal alkaloid galactosyltransferase" Plant Science. Jan. 1, 2005;168(1):267-73.
McKibbin et al. "Production of high-starch, low-glucose potatoes through over-expression of the metabolic regulator SnRK1" Plant biotechnology journal. Jul. 2006;4(4):409-18.
Meitinger et al. "Purification of Δ5-3-ketosteroid isomerase from Digitalis lanata" Phytochemistry. Jan. 1, 2015:109:6-13.
Meitinger et al. "The catalytic mechanism of the 3-ketosteroid isomerase of Digitalis lanata involves an intramolecular proton transfer and the activity is not associated with the 3β-hydroxysteroid dehydrogenase activity" Tetrahedron Letters. Apr. 6, 2018:57(14):1567-71.
Meng et al. "Studies on triterpenoids and flavones in Glycyrrhiza uralensis Fisch. by HPLC-ESI-MSn and FT-ICR-MSn" Chinese Journal of Chemistry. Feb. 2009;27(2):299-305.
MikoŁajczyk-Bator et al. "Identification of saponins from sugar beet (Beta vulgaris) by low and high-resolution HPLC-MS/MS" Journal of Chromatography B. Sep. 1, 2016:1029:36-47.
Milner et al. "Bioactivities of glycoalkaloids and their aglycones from Solanum species" Journal of Agricultural and Food Chemistry. Mar. 14, 2011;59(8):3454-84.
Mintz-Oron et al. "Gene expression and metabolism in tomato fruit surface tissues" Plant Physiology, Jun. 1, 2008;147(2):823-51.
Moses et al. "Metabolic and functional diversity of saponins, biosynthetic Intermediates and semi-synthetic derivatives" Critical reviews in biochemistry and molecular biology, Nov. 1, 2014:49(6):439-62.
Mroczek et al. "Triterpene saponin content in the roots of red beet (*Beta vulgaris* L.) cultivars" Journal of agricultural and food chemistry. Dec. 11, 2012:60(50):12397-402.
Murakami et al. "Medicinal Foodstuffs. XXIII. 1) Structures of New Oleanane-Type Triterpene Oligoglycosides, Basellasaponins A, B, C, and D, from the Fresh Aerial Parts of *Basella rubra* L" Chemical and pharmaceutical bulletin. 2001;49(6):776-9.
Netala et al. "Triterpenold saponins: a review on biosynthesis, applications and mechanism of their action" Int J Pharm Pharm Sci. 2015;7(1):24-8.
Nomura et al. "Functional specialization of UDP-glycosyltransferase 73P12 in licorice to produce a sweet triterpenoid saponin, glycyrrhizin" The Plant Journal. Sep. 2019;99(6):1127-43.
Ochoa-Villarreal et al. "Plant cell culture strategies for the production of natural products" BMB reports. Mar. 31, 2016;49(3):149.
Ofner et al. "Solanum pennellii backcross inbred lines (BIL s) link small genomic bins with tomato traits" The Plant Journal. Jul. 2016;87(2):151-60.
Oka et al. "Reconstruction of de novo pathway for synthesis of UDP-glucuronic acid and UDP-xylose from intrinsic UDP-glucose in *Saccharomyces cerevisiae*" The FEBS journal. Jun. 2006;273(12):2645-57.
Okamoto et al. "A short-chain dehydrogenase involved in terpene metabolism from Zingiber zerumbet" The FEBS journal. Aug. 2011;278(16):2892-900.
Orzaez e al. "A visual reporter system for virus-induced gene silencing in tomato fruit based on anthocyanin accumulation". Plant physiology. Jul. 1, 2009;150(3):1122-34.
Pollier et al. "Metabolite profiling of triterpene saponins in Medicago truncatula hairy roots by liquid chromatography Fourier transform ion cyclotron resonance mass spectrometry" Journal of natural products. May 26, 2011;74(6):1462-76.
Richmond T. "Higher plant cellulose synthases. Genome biology" Aug. 2000;1(4):1-5.

(56) References Cited

OTHER PUBLICATIONS

Ringer et al. "Monoterpene metabolism. Cloning, expression, and characterization of (−)-isopiperitenol/(−)-carveol dehydrogenase of peppermint and spearmint" Plant physiology. Mar. 1, 2005:137(3):863-72.
Robinson et al. "Integrative genomics viewer" Nature biotechnology. Jan. 1, 2011:29(1):24-6.
Rocha-Sosa et al. "Both developmental and metabolic signals activate the promoter of a class I patatin gene". The EMBO journal. Jan. 1989;8(1):23.
Roddick JG. "The acetylcholinesterase-inhibitory activity of steroidal glycoalkaloids and their aglycones" Phytochemistry. Jan. 1, 1989;28(10):2631-4.
Roddick JG, "Steroidal glycoalkaloids: nature and consequences of bioactivity" In Saponins used in traditional and modern medicine 1996 (pp. 277-295). Springer, Boston, MA.
Sawai et al. "Triterpenoid biosynthesis and engineering in plants" Frontiers in plant science. Jun. 30, 2011;2:25.
Sayama et al. "The Sg-1 glycosyltransferase locus regulates structural diversity of triterpenoid saponins of soybean" The Plant Cell. May 1, 2012:24(5):2123-38.
Schilmiller et al. "Mass spectrometry screening reveals widespread diversity in trichome specialized metabolites of tomato chromosomal substitution lines" The Plant Journal. May 2010;62(3):391-403.
Schwahn et al. "Metabolomics-assisted refinement of the pathways of steroidal glycoalkaloid biosynthesis in the tomato clade" Journal of integrative plant biology. Sep. 2014:56(9):864-75.
Sethaphong et al. "Tertiary model of a plant cellulose synthase" Proceedings of the National Academy of Sciences. Apr. 30, 2013;110(18):7512-7.
Shakya et al. "LC-MS analysis of solanidane glycoalkaloid diversity among tubers of four wild potato species and three cultivars (Solanum tuberosum)" Journal of agricultural and food chemistry. Jul. 11, 2008;56(16):6949-58.
Shannon et al. "Cytoscape; a software environment for integrated models of biomolecular interaction networks" Genome research. Nov. 1, 2003;13(11):2498-504.
Sievers et al. "Fast, scalable generation of high-quality protein multiple sequence alignments using Clustal Omega. Molecular systems biology" Jan. 1, 2011;7(1), Article No. 539.
Sonawane et al. "Plant cholesterol biosynthetic pathway overlaps with phytosterol metabolism" Nature plants. Jan. 2017;3(1):16205.
Supplementary European Search Report for European Application No. 14808414.8 dated Oct. 10, 2016.
Tamura et al. "MEGA6: molecular evolutionary genetics analysis version 6.0" Molecular biology and evolution. Oct. 16, 2013;30(12):2725-9.
Thoma et al. "Insight into steroid scaffold formation from the structure of human oxidosqualene cyclase" Nature. Nov. 2004;432(7013):118.
Tiwari et al. "Plant secondary metabolism linked glycosyltransferases: an update on expanding knowledge and scopes" Biotechnology Advances. Sep. 1, 2016;34(5):714-39.
Tonfack et al. "The plant SDR superfam involvement in primary and secondary metabolism" Current Topics in Plant Biology. (2011) 12. 41-53.
Trapnell et al. "Differential gene and transcript expression analysis of RNA-seq experiments with TopHat and Cufflinks" Nature protocols. Mar. 2012;7(3):562.
Umemoto et al. "Two cytochrome P450 monooxygenases catalyze early hydroxylation steps in the potato steroid glycoalkaloid biosynthetic pathway" Plant physiology. Aug. 1, 2016;171(4):2458-67.
Unger et al. "Applications of the Restriction Free (RF) cloning procedure for molecular manipulations and protein expression" Journal of structural biology. Oct. 1, 2010;172(1):34-44.
Unger et al. "Recombinant protein expression in the baculovirus-infected insect cell system" In Chemical Genomics and Proteomics 2012 (pp. 187-199), Humana Press.
Vincken et al. "Saponins, classification and occurrence in the plant kingdom" Phytochemistry. Feb. 1, 2007;68(3):275-97.
Vuppaladadiyam et al. "Microalgae cultivation and metabolites production: a comprehensive review" Biofuels, Bioproducts and Biorefining. Mar. 2018;12(2):304-24.
Wang et al. "Identification of isoliquiritigenin as an activator that stimulates the enzymatic production of glycyrrhetinic acid monoglucuronide" Scientific reports. Oct. 2, 2017;7(1):12503.
Wu et al. A new liquid chromatography—mass spectrometry-based strategy to integrate chemistry, morphology, and evolution of eggplant (Solanum) species. Journal of Chromatography A. Nov. 1, 2013;1314:154-72.
Xu et al. "A novel glucuronosyltransferase has an unprecedented ability to catalyse continuous two-step glucuronosylation of glycyrrhetinic acid to yield glycyrrhizin" New Phytologist. Oct. 2016;212(1):123-35.
Yang et al. "Isolation and functional analysis of a strong specific promoter in photosynthetic tissues" Science in China Series C: Life Sciences. Dec. 1, 2003:46(6):651-60.
Friedman, M. (2013). Anticarcinogenic, cardioprotective, and other health benefits of tomato compounds lycopene, α-tomatine, and tomatidine in pure form and in fresh and processed tomatoes. *Journal of agricultural and food chemistry*, 61(40), 9534-9550.
Nakayasu, D. (2016). Elucidation of steroid saponin biosynthesis mechanism, KAKEN—Search for research topics, Kobe University, pp. 1-5.
Itkin, M., (2013). Biosynthesis of antinutritional alkaloids in solanaceous crops is mediated by clustered genes. Science, 341(6142), 175-179.
JP Application No. 2021-512835 Office Action dated Jan. 17, 2023.
"Solanum lycopersicum cellulose synthase-like protein G2 (LOC101255510), mRNA", NCBI Reference Sequence: XM_004243592.4, Aug. 8, 2018, 2 pages.

* cited by examiner 22-(R)-hydroxycholesterol
GAME8i
wild type
11
12
13
Time (min)

Steroidal saponins
m/z = 1331.6
GAME11i
control
18
19
20
21
22
Time (min)

steroidal saponin
m/z = 753.4
GAME12
control
18
19
20
21
22
Time (min)

m/z = 416.35
tomatidine
GAME1i
wild type
22
23
24
25
26
Time (min)

Cholesterol

Dehydrotomatidine (tomatidenol)

Tomatidine

Dehydrotomatine

α-tomatine

Dehydroesculeoside A or Dehydro-lycoperoside H/G

Esculeoside A or lycoperoside G/F

Cholesterol

Solasodine

α-solasonine

α-solamargine

*S. melongena* (cultivated eggplant)

tomatidine + UDP-glucuronic acid → tomatidine 3-O-glucuronide

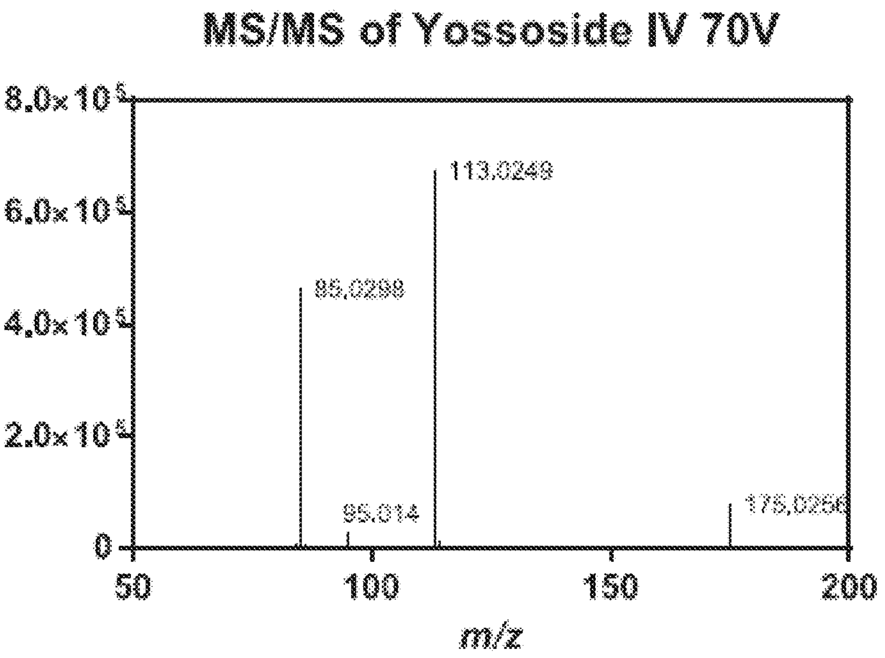
FIGURE 19B
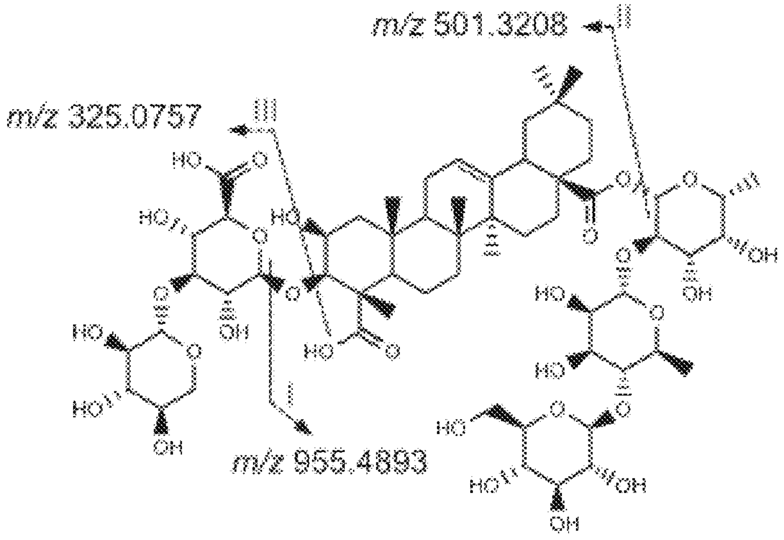
FIGURE 19C
| m/z (observed) | Predicted formula | Ion assignment | m/z (theoretical) | Δm/z (ppm) |
|---|---|---|---|---|
| 175.0256 | C6H7O6 | $[GlcA\text{-}H_2O]^-$ | 175.0246 | 7.4 |
| 113.0249 | C5H5O3 | $[GlcA\text{-}2H_2O\text{-}CO_2]^-$ | 113.0239 | 8.8 |
| 95.0140 | C5H3O2 | $[GlcA\text{-}3H_2O\text{-}CO_2]^-$ | 95.0133 | 7.4 |
| 85.0298 | C4H5O2 | $[GlcA\text{-}2H_2O\text{-}CO_2\text{-}CO]^-$ | 85.0290 | 9.4 |
FIGURE 19D

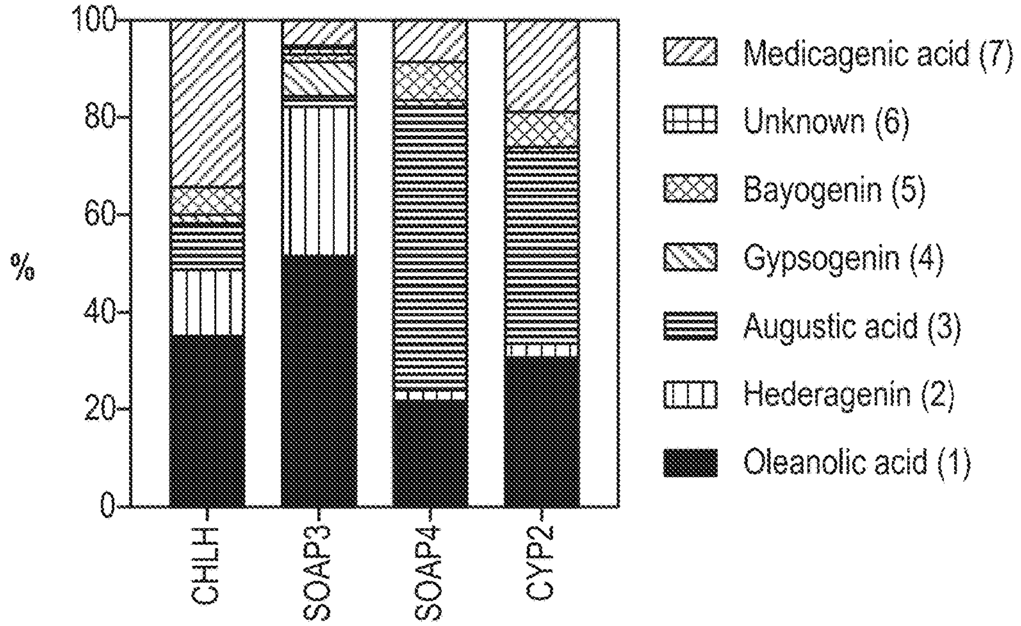
FIGURE 28A
(1)
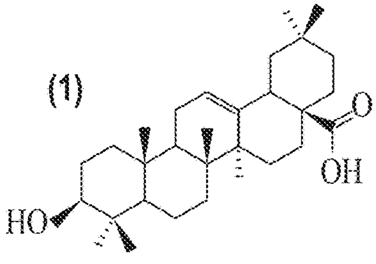
(2)
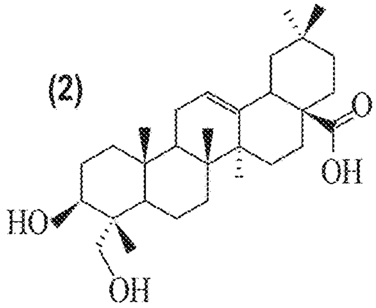
(3)
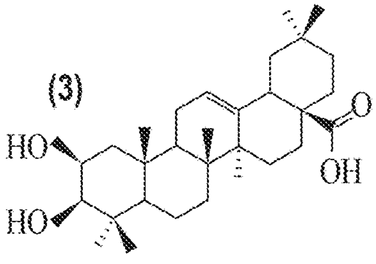
(4)
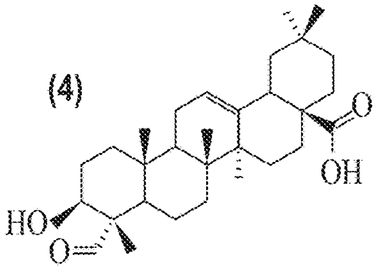
(5)
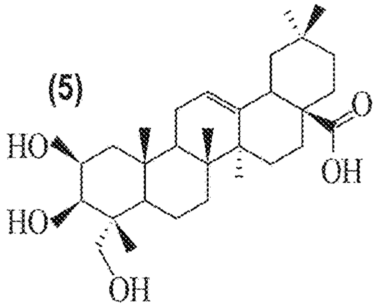
(7)
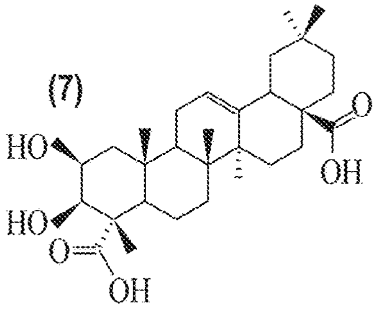
FIGURE 28B Medicagenic acid (MA)

Medicagenic acid 3-glucuronide

β-amyrin 11-oxo-β-amyrin glycyrrhetinic acid glycyrrhizin glycyrrhetinic acid 3-*O*-monoglucuronide

```
SEQ ID NO. 67 AtCESA1                  DRLAIRYDRDGEPSQLVPVDVFVSTVDPLKEPPLVTANTVLSILSVDYPVDKVACYVSDD 395
SEQ ID NO. 70 XP_021853954.1_SoCESA1   DRLAFRHDREGEPSQLAPIDVFVSTVDPLKEPPIITANTVLSILAVDYPVDKVSCYVSDD 400
SEQ ID NO. 68 AtCESA3                  DRLALRYDREGEPSQLAAVDIFVSTVDPLKEPPLVTANTVLSILAVDYPVDKVSCYVSDD 379
SEQ ID NO. 71 XP_021846548.1_SoCESA3   DRLALRYDREGEPSQLAAVDIFVSTVDPLKEPPLVTANTVLSILAVDYPVDKVSCYVSDD 378
SEQ ID NO. 69 AtCSLG1                  EKYA------AKPEDFPKLDVFICTADPYKEPPMMVVNTALSVMAYEYPSDKISVYVSDD 142
SEQ ID NO. 66 SOAP5                    GYES------IKPEQLPGLDVFIVTADPTKEPVLEVMNSVISSMALDYPVDRLAVYLSDD 133
                                          :         :*.:.:  :*:*: *.**  ***  :  .  *:.:*  :: :** *:::  *:***

SEQ ID NO. 67 AtCESA1                  GLDT-DGNELPRLIYVSREKRPGFQHHKKAGAMNALIRVSAVLTNGAYLLNVDCDHYFNN 568
SEQ ID NO. 70 XP_021853954.1_SoCESA1   GLDM-DGNELPRLVYVSREKRPGFQHHKKAGAMNALIRVSAVLTNGAYILNVDCDHYFNN 573
SEQ ID NO. 68 AtCESA3                  GLDA-EGNELPRLVYVSREKRPGFQHHKKAGAMNALVRVSAVLTNGPFILNLDCDHYINN 552
SEQ ID NO. 71 XP_021846548.1_SoCESA3   GLDT-DGNELPRLVYVSREKRPGFTHHKKAGAMNSLVRVSAVLTNGPFMLNLDCDHYINN 551
SEQ ID NO. 69 AtCSLG1                  DMDNTRKYIMPNLIYVSREKSKVSPHHFKAGALNTLLRVSGVMTNSPIILTLDCDMYSND 312
SEQ ID NO. 66 SOAP5                    -QNGESDVKMPLLVYVAREKRPGRPHRFKAGALNALLRVSSLMSNAPYLLVIDCDMYCHD 290
                                          :          :* *:**:***      *:  ****:*:*:***.:::*.   :* :*** *  ::

SEQ ID NO. 67 AtCESA1                  PATLLKEAIHVISCGYEDKTEWGKEIGWIYGSVTEDILTGFKMHARGWISIYCNPPRPAF 804
SEQ ID NO. 70 XP_021853954.1_SoCESA1   PATLLKEAIHVISCGYEDKSEWGKEIGWIYGSVTEDILTGFKMHARGWMSIYCMPPRPAF 809
SEQ ID NO. 68 AtCESA3                  PENLLKEAIHVISCGYEDKSDWGMEIGWIYGSVTEDILTGFKMHARGWRSIYCMPKLPAF 789
SEQ ID NO. 71 XP_021846548.1_SoCESA3   PDTLLKEAIHVISCGYEDKTDWGAEIGWIYGSVTEDILTGFKMHARGWRSIYCMPKLAAF 784
SEQ ID NO. 69 AtCSLG1                  AQDVLSLAHNVAGCIYEYNTNWGSKIGFRYGSLVEDYYTGFMLHCEGWRSVFCNPKKAAF 471
SEQ ID NO. 66 SOAP5                    EDELYQEARNLATCTYEANTLWGSEVGYSYECLLESTFTGYMLHCRGWKSVYLYPKRPCF 466
                                          : . * ::  * **  ::  **  ::*: *  .: *.   **: :*..** *::   *    .*

SEQ ID NO. 67 AtCESA1                  KGSAPINLSDRLNQVLRWALGSIEILLSRHCPIWYGYHGRLRLLERIAYINTIVYPITSI 864
SEQ ID NO. 70 XP_021853954.1_SoCESA1   KGSAPLNLSDRLNQVLRWALGSIEIMLSRHCPIWYGYKGRLRFLERLAYINTVVYPLTSI 869
SEQ ID NO. 68 AtCESA3                  KGSAPINLSDRLNQVLRWALGSVEILFSRHCPIWYGYNGRLKFLERFAYVNTTIYPITSI 849
SEQ ID NO. 71 XP_021846548.1_SoCESA3   KGSAPINLSDRLNQVLRWALGSVEILFSRHCPLWYGYGGRLKWLERFAYINTTIYPLTSI 844
SEQ ID NO. 69 AtCSLG1                  YGDSPKCLVDLVGQQIRWAVGLFEMSFSKYSPITYGIK-SLDLLMGLGYCNSPFKPFWSI 530
SEQ ID NO. 66 SOAP5                    LGCTTIDMKDATVQLIKWTSSLLGIALSKSSPLTLAMS-SMSILQSMCYAYITFTGLFAA 525
                                        * :      : *      * .:*:  .  .  .  : :*:   .*:     .     :   *  : *      .    :  :
```

FIGURE 48

CELLULOSE-SYNTHASE-LIKE ENZYMES AND USES THEREOF

CROSS REFERENCE TO RELATED APPLICATIONS

This application is a National Phase Application of PCT International Application No. PCT/IL2019/051000, International Filing Date Sep. 5, 2019, which claims the benefit of both U.S. patent application Ser. No. 16/123,248, filed Sep. 6, 2018 and Israel Patent Application Serial Number 268269, filed Jul. 25, 2019, which are incorporated in their entirety herein by reference.

SEQUENCE LISTING STATEMENT

The instant application contains a Sequence Listing which has been submitted electronically in ASCII format and is hereby incorporated by reference in its entirety. The ASCII copy, created on Sep. 5, 2019, is named P-603031-US-UPD-SQL-05SEP19_ST25.txt and is 387,336 bytes in size.

FIELD OF THE INVENTION

The disclosure relates in general to the field of altering the content of at least one steroidal alkaloid; at least one steroidal saponin; or at least one triterpenoid saponin in at least one cell of a plant or a plant part. In one embodiment, the present disclosure describes the cells or plants comprising altered content of at least one steroidal alkaloid; at least one steroidal saponin; or at least one triterpenoid saponin, and methods of producing same.

BACKGROUND

The plant kingdom produces hundreds of thousands of different small compounds, often genus or family specific. The massive structural diversity of more than 300,000 plant specialized metabolites (SMs) is generated through assorted modifications of their core structure. Plant SMs are most frequently glycosylated, and this glycosylation significantly impacts their compartmentalization, activity, solubility, stability, and toxicity. They are low molecular weight, nitrogen-containing, organic compounds, typically with a heterocyclic structure.

The broad group of saponin-alkaloid compounds is widespread in plants and derived from the cytosolic mevalonic acid isoprenoid biosynthetic pathway. Saponins and steroidal alkaloids (SAs) are two large classes of SMs produced by plants.

Saponins are a large group of SMs found in countless plant species and more than 100 families, representing a lipophilic triterpenoid or steroidal backbone (aglycone) decorated with one or more glycoside moieties.

As suggested by their name (Latin sāpō means soap), saponins display soap like properties in aqueous solutions due to their amphipathic structure. The unique physicochemical properties of these compounds provide a broad spectrum of functions in plants including antifungal, antibacterial and insecticidal. The activity of saponins depends on the structure of the aglycone but in many cases even more on the attached sugars. For example, oleanolic and medicagenic acid (MA) derived saponins display hemolytic activity due to the presence of a carboxyl at position C-28 while Avenacin A-1 requires L-arabinose attached at the C-3 position to be fungicidal. Moreover, cholesterol-derived steroidal saponins are widespread in the plant kingdom, are highly diverse in structures, and can be either saturated (e.g., sarasapogenin) or unsaturated (e.g., diosgenin) in the C-5,6 position.

Plentiful reports underline saponins' benefits to human health and medical applications starting from anti-inflammatory and immune-boosting (adjuvant) to anti-cancer properties. UDP-glycosyltransferases (UGTs) members of the carbohydrate-active enzyme (CAZY) glycosyltransferase 1 (GT1) superfamily carry out sugar transfer reactions on saponins and all other SMs classes. The most common saccharides decorating saponins include D-glucose, D-galactose, L-arabinose, D-glucuronic acid, D-xylose, L-rhamnose and D-fucose.

The presence of glucuronic acid attached at position C-3 of the sapogenin is particularly common for species of the Caryophyllales order, yet, the enzyme involved remains unknown.

Thus, there remains an unmet need for knowledge regarding the enzymes involved in the metabolic pathway to produce saponins, including triterpenoid saponins, including knowledge of Cellulose Synthase Like Gs that attach glucuronic acid to, for example, quillaic acid. Once known, key enzymes could be regulated in a plant in order to alter the content of naturally produced products. For example, an enzyme could be over-expressed or have increased stability, thereby producing a natural sweetener at increased quantities, or an enzyme could be down regulated at the gene level to reduce production of compounds adding a bitter taste to plant products, for example *quinoa*. Further, there remains an unmet need for methods to produce these saponins in heterologous systems in order to provide commercial quantities of high value saponins, for example but not limited to triterpenoid saponins. These high value saponins may be used for example as, but not limited to, sweeteners, foaming agents, emulsifiers, preservatives, anti-carcinogens, hypocholesterolemic agents, anti-inflammatory agents, anti-oxidants, biological adjuvants, anti-microbial agents, insecticidal agents, antifeedants, or anti-fungal agents, or any combination thereof.

In addition, some SMs, such as alkaloids, are often referred to as secondary metabolites, because they are not vital to cells that produce them, but contribute to the overall fitness of the organism. Alkaloids are low molecular weight nitrogen-containing organic compounds, typically with a heterocyclic structure, and their biosynthesis in plants is tightly controlled during development and in response to stress and pathogens.

For example, steroidal alkaloids (SAs), occasionally known as "*Solanum* alkaloids" due to their high prevalence in numerous members of the Solanales order, have been found to be common to numerous plants in a wide range of families. SAs have diverse structural composition and biological activity. They are low molecular weight, nitrogen-containing, cholesterol-derived organic compounds, typically with a heterocyclic structure consisting of a C-27 cholestane skeleton and a heterocyclic nitrogen component.

Estimated in the order of 1350 species, Solanum is one of the largest genera of flowering plants, representing about half of the species in the Solanaceae family (which is in the Solanales order). *Solanum* species include food plants, such as tomato (*Solanum lycopersicum*), potato (*Solanum tuberosum*), bittersweet (*Solanum dulcamara*), and eggplant (*Solanum* melogena), and the Solanaceae also includes the *Capsicum* genus (e.g., peppers), as well as many other genera. Steroidal alkaloids are also produced by a large number of species in the Liliaceae family. As a result, SAs have been the subject of extensive investigations (Eich E. 2008. Solanaceae and Convolvulaceae—secondary metabolites: biosynthesis, chemotaxonomy, biological and economic significance: a handbook. Berlin: Springer).

Consisting of a C-27 cholestane skeleton and a heterocyclic nitrogen component, SAs were suggested to be synthesized in the cytosol from cholesterol. Conversion of cholesterol to the alkamine SA should require several hydroxylation, oxidation, and transamination reactions (Eich 2008, supra), and in most cases, further glycosylation to form steroidal glycoalkaloids (SGAs) (Arnqvist L. et al. 2003. Plant Physiol. 131:1792-1799). Glycosylation of SAs produces steroidal glycoalkaloids (SGAs), in which the added oligosaccharide moiety components directly conjugate to the hydroxyl group at C-3-beta (C-3β) of the alkamine steroidal skeleton (aglycone). SGA biosynthesis depends on genes encoding UDP-glycosyltransferases (UGTs) that decorate the aglycone with various oligosaccharide moieties, including D-glucose, D-galactose, L-rhamnose, D-xylose, and L-arabinose, the first two monosaccharides being the predominant units.

SGAs are produced by numerous members of the Solanaceae family, as well as many other families of plants. Examples of these compounds include alpha-tomatine and dehydrotomatine in tomato (*Solanum lycopersicum*), alpha-chaconine and alpha-solanine in potato (*Solanum tuberosum*), and alpha-solamargine and alpha-solasonine in eggplant (*Solanum melongena*). SGAs are also found in various types of pepper in the genus *Capsicum*. More than 100 SGAs have been identified in tomatoes (Itkin et al., 2011, Plant Cell 23:4507-4525), and more than 50 have been identified in potatoes (Shakya and Navarre, 2008, J. Agric. Food Chem. 56:6949-6958). Eggplant also contains at least one variety of SGA (Friedmann, 2006, J. Agric. Food Chem. 54:8655-8681).

SAs and SGAs play a role in protecting plants against a broad range of pathogens and are known as phytoanticipins (antimicrobial compounds). SGAs contribute to plant resistance to a wide range of pathogens and predators, including bacteria, fungi, oomycetes, viruses, insects, and larger animals. Some SGAs in edible parts of plants are considered to be anti-nutritional compounds to humans and other mammals due to their toxic effects. For example, the SGAs alpha-chaconine and alpha-solanine are the principle toxic substances in potato, may cause gastrointestinal and neurological disorders and, at high concentrations, may be lethal to humans. Mechanisms of toxicity include disruption of membranes an dinhibition of acetylcholine esterase activity (Roddick J. G. 1989. Phytochemistry 28:2631-2634). For this reason, total SGA levels exceeding 200 mg/kg fresh weight of edible tuber are deemed unsafe for human consumption.

There is an ongoing attempt to elucidate the biosynthesis pathway of steroidal alkaloids and to control their production. U.S. Pat. No. 5,959,180 discloses DNA sequences from potato which encode the enzyme solanidine UDP-glucose glucosyltransferase (SGT). Further disclosed are means and methods for inhibiting the production of SGT and thereby reduce glycoalkaloid levels in Solanaceous plants, for example potato.

Similarly, U.S. Pat. Nos. 7,375,259 and 7,439,419 disclose nucleic acid sequences from potato that encode the enzymes UDP-glucose:solanidine glucosyltransferase (SGT2) and β-solanine/β-chaconine rhamnosyltransferase (SGT3), respectively. Recombinant DNA molecules containing the sequences, and use thereof, in particular, use of the sequences and antisense constructs to inhibit the production of SGT2/SGT3 and thereby reduce levels of the predominant steroidal glycoalkaloids α-chaconine and α-solanine in Solanaceous plants such as potato are also described.

Recently, three glycosyltransferases were identified that are putatively involved in the metabolism of tomato steroidal alkaloids (GLYCOALKALOID METABOLISM 1-3 (GAME1-3). More specifically, alterations in GAME1 expression modified the SA profile in tomato plants in both reproductive and vegetative parts. It is suggested that these genes are involved in the metabolism of tomatidine (the α-tomatine precursor) partially by generating the lycotetraose moiety (Itkin et al., 2011, supra).

International Patent Application Publication No. WO 00/66716 discloses a method for producing transgenic organisms or cells comprising DNA sequences which code for sterol glycosyltransferases. The transgenic organisms include bacteria, fungi, plants and animals, which exhibit an increased production of steroid glycoside, steroid alkaloid and/or sterol glycoside compared to that of wild-type organisms or cells. The synthesized compounds are useful in the pharmaceutical and foodstuff industries as well as for protecting plants.

U.S. Patent Application Publication No. 2012/0159676 discloses a gene encoding a glycoalkaloid biosynthesis enzyme derived from a plant belonging to the family Solanaceae for example potato (*Solanum tuberosum*). A method for producing/detecting a novel organism using a gene encoding the protein is also disclosed.

U.S. Patent Application Publication No. 2013/0167271 and International Application Publication No. WO 2012/095843 relate to a key gene in the biosynthesis of steroidal saponins and steroidal alkaloids and to means and methods for altering the gene expression and the production of steroidal saponins and steroidal alkaloids.

A paper of inventors of the present invention, published after the priority date of the present invention, describes an array of 10 genes that partake in SGA biosynthesis. 5-7 of the genes were found to exist as a cluster on chromosome 7 while additional two reside adjacent in a duplicated genomic region on chromosome twelve. Following systematic functional analysis, a novel SGA biosynthetic pathway starting from cholesterol up to the tetrasaccharide moiety linked to the tomato SGA aglycone has been proposed (Itkin M. et al., 2013 Science 341(6142):175-179).

It has also been found that the plant cholesterol biosynthetic pathway overlaps with phytosterol metabolism (Sonawane et al. 2016. Nat. Plants 3: 16205). For example, cholesterol ((3-beta)-cholest-5-en-3-ol) is a sterol (or modified steroid), a type of lipid molecule biosynthesized by all animal cells as an essential structural component of all animal cell membranes and essential to membrane structural integrity and fluidity, enabling animal cells to function without a cell wall. It is also a precursor for the biosynthesis of steroid hormones, bile acid, and vitamin D, as well as saponins, SAs, and SGAs. Cholestanol (5-beta-cholestan-3-beta-ol; coprostanol; 5-beta-coprostanol) is a cholesterol derivative found in feces and other biological matter. Cholestanol is a 27-carbon stanol formed from the biohydrogenation of cholesterol in the gut of most higher animals (birds and mammals) by the conversion of cholesterol.

Plants make cholesterol in very small amounts, but also manufacture phytosterols (which include plant sterols and stanols, similar to cholesterol and cholestanol), which can compete with cholesterol for reabsorption in the intestinal tract, thus potentially reducing cholesterol reabsorption. Cholesterol is often used in the manufacture of medicines, cosmetics, and other applications. There is an increased interest in producing higher levels of both plant phytosterols and plant-based cholesterol.

For example, in tomato (e.g., *Solanum lycopersicum, Solanum pennellii*), α-tomatine and dehydrotomatine represent the major SGAs accumulating predominantly in green tissues; young and mature leaves, flower buds, skin and seeds of immature and mature green fruit. Dehydrotomatidine (i.e. tomatidenol) is the first SA aglycone formed in SGA biosynthesis which could further be hydrogenated at the C-5 position to form tomatidine. Both aglycones are further glycosylated (tetrasaccharide moiety, i.e., lycotetrose) to produce dehydrotomatine and α-tomatine, respectively. Thus, the SGA pathway branches at dehydrotomatidine for either formation of tomatidine derived SGAs or glycosylated dehydrotomatine derivatives. Notably, dehydrotomatidine and tomatidine are only different in their structures by the presence or absence of the double bond at the C-5 position. The conversion of dehydrotomatidine to tomatidine was hypothesized in the past as a single reaction catalyzed by a hypothetical hydrogenase. In most tomato plant tissues, the relative portion of dehydrotomatine as compared to α-tomatine ranges from ~2.5-~10%. As tomato fruit matures and reaches to the red stage, the entire pool of α-tomatine and dehydrotomatine is largely being converted to esculeosides (major SGAs) and dehydroesculeosides (minor SGAs), respectively.

In cultivated potato (e.g., *Solanum tuberosum*), α-chaconine and α-solanine are the major SGAs sharing the same aglycone, solanidine (in which a C-5,6 double bond is present) and possess chacotriose and solatriose moieties, respectively. As there is no demissidine or demissine detected in cultivated potatoes, it was suggested that a hydrogenase enzyme able to convert solanidine to demissidine is lacking in these species. Several wild potato species (e.g. *S. demissum, S. chacoense, S. commersonii*) and their somatic hybrids (*S. brevidens* X *S. tuberosum*), predicted to contain an active hydrogenase, do produce demissidine or its glycosylated form, demissine being one of their major SGAs.

In eggplant (e.g., *Solanum melongena*), α-solamargine and α-solasonine are the most abundant SGAs derived from the solasodine aglycone (in which a C-5,6 double bond is present); while some wild *Solanum* species, e.g. *S. dulcamara* (bittersweet) produce soladulcidine or its glycosylated forms, soladulcine A and β-soladulcine (C-5,6 double bond is absent), as major SGAs from the solasodine aglycone.

In addition to SGAs, many *Solanum* species (e.g., eggplant) also produce cholesterol-derived unsaturated or saturated steroidal saponins. Unsaturated and saturated steroidal saponins are widespread in the plant kingdom, especially among monocots, e.g. the Agavaceae (e.g., *agave* and *yucca*), Asparagaceae (e.g., asparagus), Dioscoreaceae and Liliaceae families. Similar to SGAs, steroidal saponins are highly diverse in structures and could be either saturated (e.g. sarasapogenin) or unsaturated (e.g. diosgenin) in the C-5,6 position.

Cholesterol, the main sterol produced by all animals, serves as a key building block in the biosynthesis of SGAs. An array of tomato and potato GLYCOALKALOIDMETABOLISM (GAME) genes participating in core SGA biosynthesis starting from cholesterol were reported in recent years. The tomato SGAs biosynthetic pathway can be divided into two main parts. In the first, the SA aglycone is formed from cholesterol by the likely action of the GAME6, GAME8, GAME11, GAME4 and GAME12 enzymes. The second part results in the generation of SGA through the action of UDP-glycosyltransferases (UGTs). GAME1, GAME2, GAME17 and GAME18 in tomato, and STEROL ALKALOID GLYCOSYL TRANSFERASE1 (SGT1), SGT2 and SGT3 in potato.

Thus, there remains an unmet need for knowledge regarding the enzymes involved in the metabolic pathway to produce saponins, including triterpenoid saponins, including knowledge of Cellulose Synthase Like Gs that attach glucuronic acid to, for example, quillaic acid. Once known, key enzymes could be regulated in a plant in order to alter the content of naturally produced products. For example, an enzyme could be over-expressed or have increased stability, thereby producing a natural sweetener at increased quantities, or an enzyme could be down regulated at the gene level to reduce production of compounds adding a bitter taste to plant products, for example *quinoa*. Further, there remains an unmet need for methods to produce these saponins in heterologous systems in order to provide commercial quantities of high value saponins, for example but not limited to triterpenoid saponins. These high value saponins may be used for example as, but not limited to, sweeteners, foaming agents, emulsifiers, preservatives, anti-carcinogens, hypocholesterolemic agents, anti-inflammatory agents, anti-oxidants, biological adjuvants, anti-microbial agents, insecticidal agents, antifeedants, or anti-fungal agents, or any combination thereof.

In addition, the demand for higher food quantities and food with improved quality continues to increase. Improved nutritional qualities as well as removal of antinutritional traits are both of high demand. In the course of crop domestication, levels of anti-nutrients were reduced by breeding, However, many crop plants still contain significant amount of antinutritional substances, particularly steroidal glycoalkaloids.

Alternatively, the ability to manipulate the synthesis of these SGAs would provide the means to develop, through classical breeding or genetic engineering, crops with modified levels and composition of SGAs, conferring on the plant an endogenous chemical barrier against a broad range of insects and other pathogens.

In addition, there is a demand both for plant-based cholesterols and, conversely, for plants with increased levels of phytocholesterols or other phytosterols.

Thus, there is also a demand for, and it would be highly advantageous to have, means and methods for controlling the production of saponins, steroidal alkaloids, and steroidal glycoalkaloids with beneficial, particularly therapeutic, effects.

The disclosure provided herein below, meets these unmet needs by describing in some embodiments, at least the knowledge that plant SMs, more specifically saponins, are not merely glycosylated by UGT 1 family enzymes. It appears that proteins related to Cellulose Synthases (CESA), renowned for their role in primary cell wall biosynthesis, enable the attachment of glucuronic acid at the C-3 position of saponins. Metabolic evolution through neofunctionalization to a Cellulose Synthase Like (CSL) enzyme possessing a new form of triterpenoid glycosyl transferase activity was accompanied by altering its subcellular localization, directing it to the endoplasmic reticulum (ER). Modulation of this protein also resulted in strict control of the production of steroidal saponins and steroidal glycoalkaloids, while gene silencing resulted in accumulation of cholesterol pools.

The disclosure provided herein below, also meets these unmet needs by describing in some embodiments, at least the knowledge of key genes and enzymes in the biosynthesis pathway converting cholesterol to steroidal saponins, triterpenoid saponins, steroidal alkaloids, and steroidal glycoalkaloids.

SUMMARY

According to one aspect, provided herein is a genetically modified cell having increased expression of at least one heterologous gene compared to a corresponding unmodified cell, said at least one heterologous gene encoding a cellulose synthase like G (CSLG) enzyme, wherein said genetically modified cell comprises an increased content of at least one steroidal alkaloid, a derivative thereof, a metabolite thereof, or a biosynthetic intermediate thereof; of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, compared to a corresponding unmodified cell.

According to another aspect, provided herein is a genetically modified plant comprising at least one cell having altered expression of at least a cellulose synthase like G (CSLG) gene compared to the expression of CSLG in a corresponding unmodified plant, and wherein the genetically modified plant has an altered content of at least one steroidal alkaloid, a derivative thereof a metabolite thereof, of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof compared to the corresponding unmodified plant.

According to still another aspect, provided herein is a method of producing a steroidal alkaloid, a steroidal saponin, or a triterpenoid saponin in a genetically modified cell, the method comprising: (a) introducing an at least one heterologous gene into said cell, said at least one heterologous gene encoding a cellulose synthase like G (CSLG) enzyme, wherein said heterologous gene is optionally comprised in a vector; and (b) expressing said at least one heterologous gene in said cell; wherein said cell comprises an increased content of at least one steroidal alkaloid, at least one steroidal saponin, or at least one triterpenoid saponin compared to a corresponding unmodified cell.

According to yet another aspect, provided herein is a method of reducing the content of at least one steroidal alkaloid, a derivative thereof, a metabolite thereof, or a biosynthetic intermediate thereof; of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, in at least one cell of a plant or a plant part, the method comprising genetically modifying said at least one plant cell, said genetic modification comprising: (a) transforming said at least one plant cell with at least one silencing molecule targeted to a nucleic acid gene sequence encoding a Cellulose Synthase Like G (CSLG) enzyme; or (b) mutagenizing at least one nucleic acid sequence encoding a Cellulose Synthase Like G (CSLG) enzyme, wherein the mutagenesis comprises introducing (1) one or more point mutations into the nucleic acid sequence, (2) deletions within the nucleic acid sequence, or (3) insertions within the nucleic acid, or (4) any combination thereof, wherein said introducing comprising mutagenizing coding or non-coding sequence; wherein expression of the gene encoding the CSLG enzyme is reduced in the genetically modified plant cell compared to its expression in a corresponding unmodified plant cell, wherein the plant comprising said genetically modified cell comprises reduced content of at least one steroidal alkaloid, a derivative thereof, a metabolite thereof, or a biosynthetic intermediate thereof; of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, compared to the corresponding unmodified plant.

According to yet another aspect, provided herein is a method of increasing the content of at least one steroidal alkaloid, a derivative thereof, a metabolite thereof, or a biosynthetic intermediate thereof; of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, in at least one cell of a plant or plant part, the method comprising genetically modifying said at least one plant cell, said genetic modification comprising: (a) mutagenizing at least one nucleic acid sequence encoding a Cellulose Synthase Like G (CSLG) enzyme, wherein the mutagenesis comprises introducing (1) one or more point mutations into the nucleic acid sequence, (2) deletions within the nucleic acid sequence, or (3) insertions within the nucleic acid, or (4) any combination thereof, wherein said introducing comprising mutagenizing coding or non-coding sequence; and (b) expressing said nucleic acid encoding said CSLG; wherein the plant comprising said genetically modified cell comprises increased content of at least one steroidal alkaloid, a derivative thereof, a metabolite thereof, or a biosynthetic intermediate thereof; of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, compared to the corresponding unmodified plant.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The subject matter related to methods of production of steroidal glycoalkaloids, steroidal saponins, and triterpenoid saponins and uses thereof is particularly pointed out and distinctly claimed in the concluding portion of the specification. The methods of production of these steroidal glycoalkaloids, steroidal saponins, and triterpenoid saponins and uses thereof, however, both as to organization and method of operation, together with objects, features, and advantages thereof, may best be understood by reference to the following detailed description when read with the accompanying drawings in which:

FIG. 2 summarizes the coexpression analysis of steroidal alkaloid-associated genes in Solanaceous plants. Shared homologs of coexpressed genes for 'baits' from tomato (SlGAME1 and SlGAME4) and potato (StSGT1 and StGAME4). Continuous (r-value >0.8) and dashed (r-value >0.63) lines connect coexpressed genes. *, located in the tomato or potato chromosome 7 cluster. St, *Solanum tuberosum*; Sl, *S. lycopersicum*. Background of gene names corresponds to bait they were found to be coexpressed with (legend above). SP, serine proteinase; PI, proteinase inhibitor; UPL, ubiquitin protein ligase; ELP, extensin-like protein; PK, protein kinase; SR, sterol reductase; RL, receptor-like.

(FIG. 4A) GAME8-silenced transgenic (RNAi) leaves accumulated 22-(R)-hydroxycholesterol compared to wild type. (FIG. 4B) An array of cholestanol-type steroidal saponins (STSs) accumulates in GAME11 VIGS-silenced leaves. (FIG. 4C) An STS (m/z=753.4) accumulates in GAME12 VIGS-leaves. (FIG. 4D) Tomatidine, the steroidal alkaloid aglycone, accumulates in GAME1-silenced transgenic leaves. (FIGS. 4E to 4H) Enzyme activity assays of the 4 recombinant tomato GAME glycosyltransferases.

(FIG. 8A) α-tomatine levels in leaves (m/z=1034.5) (FIG. 8B) cholestanol-type steroidal saponins (STS) in leaves (m/z=1331.6, 1333.6, 1199.6, 1201.6 (major saponins)). (FIG. 8C) MS/MS spectrum of m/z=1331.6 (at 19.28 min.). (FIG. 8D) The fragmentation patterns of the saponin eluted at 19.28 min. and accumulating in GAME11-silenced leaves. Corresponding mass signals are marked with an asterisk on the MS/MS chromatogram in FIG. 8C.

(FIG. 10A) accumulation of a furastanol-type STS. (FIGS. 10B-10C) GAME/2-silenced leaves accumulate an STS (m/z=753.4), while it exists in only minor quantities in WT leaf. (FIG. 10D) MS/MS spectrum of m/z=753.4 at 19.71 min. with interpretation of the fragments.

(FIG. 11D) GAME8-silenced line accumulates both isomers in comparison to WT (Q).

FIG. 14D shows a proposed portion of an SGA biosynthetic pathway in Solanaceous plants, from tomatidine to the production of tomatidine 3-O-glucuronide, wherein a GAME15 cellulose synthase like G enzyme catalyzes the addition of a glucuronic acid at the position of the hydroxyl group of the tomatidine.

(FIG. 19A) Mass fragments originating from [M-H]11963.56=—m/z range for 300-1300; (FIG. 191) Mass fragments originating from the cleavage of glucuronic acid residue—m/z range for 50-1900; (FIG. 190) Mass fragments originating from the cleavage of glucuronic acid residue—m/z range for 50-1900; and (FIG. 19P) Structure of Yossoside X, arrows indicate fragmentation patterns. Structure and attachment of pentose is putative.

(FIG. 20A) The complete biosynthetic pathway leading to the production of Yossoside V; an acetylated triterpenoid saponin containing glucuronic acid attached at C-20 position (highlighted in red). Each product of SOAP enzymes activity is highlighted in green. SOAP enzymes are those enzymes involved in saponin production in spinach. (FIG. 20B) Gene co-expression network. Large solid circles at SOAP1, SOAP2 and SoCYP716A268v2, represent baits for these genes, the central circle comprising solid dots depicts genes co-expressed with all the baits. Enlarged and annotated dots represent genes silenced by Virus Induced Gene Silencing (VIGS) in spinach. (FIG. 20C) Extracted ion chromatograms (EIC) of oleanolic acid, augustic acid and medicagenic acid [m/z=455.205 (OA); m/z=471.205 (AA); m/z=501.202 (MA); in negative ion mode] from plants transiently expressing SOAP1-4, compared to plants expressing SOAP1-20, SOAP1-2 alone and to control (plants infiltrated with *Agrobacterium rhizogenes* harboring empty vector—EV).

TABLE 1

Figure 1:
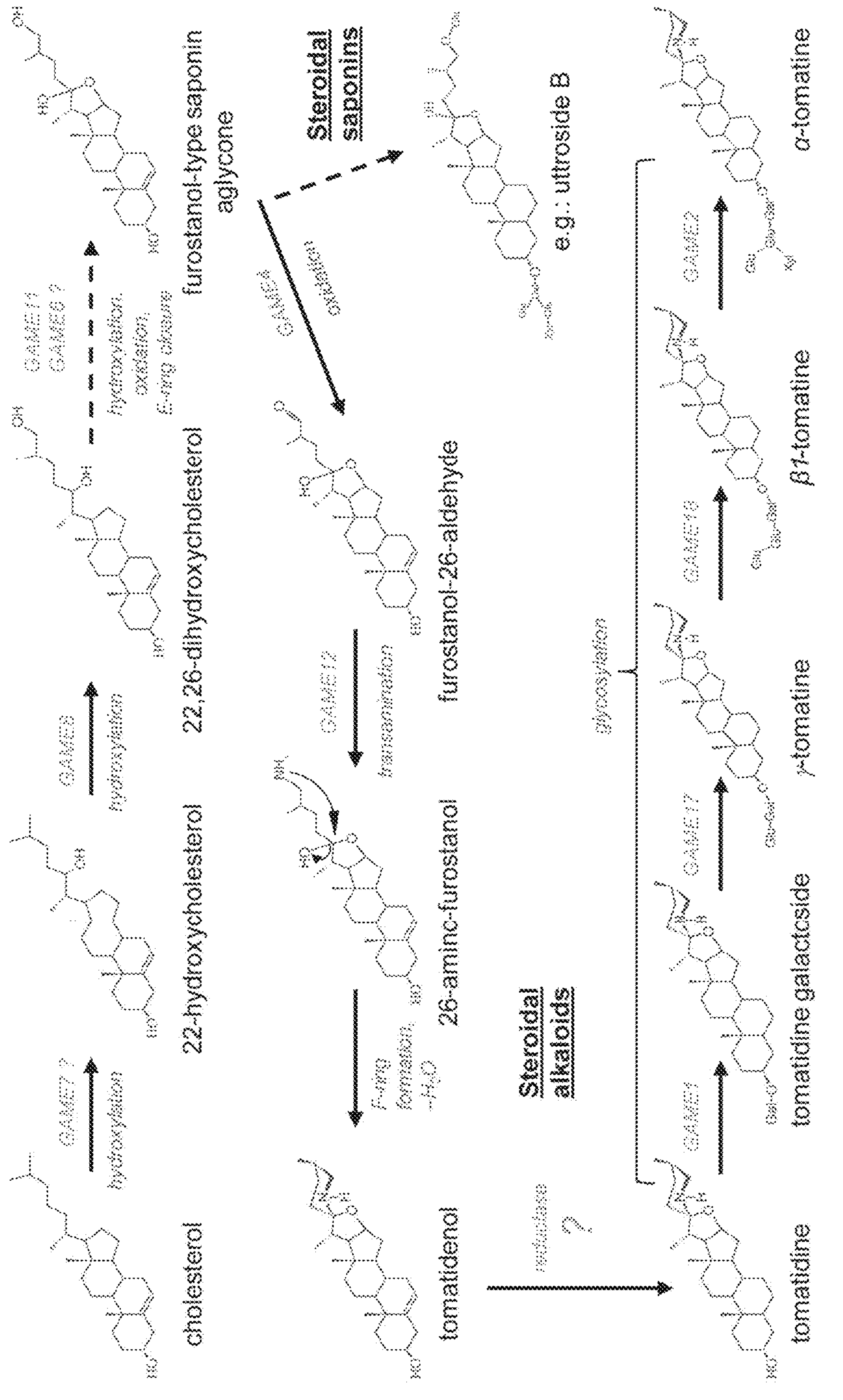
FIG. 1 shows the proposed biosynthetic pathway of steroidal glycoalkaloids in the triterpenoid biosynthetic pathway in Solanaceous plant from cholesterol toward α-tomatine. Dashed and solid arrows represent multiple or single enzymatic reactions in the pathway, respectively.

1H and 13C NMR spectral data for Yossoside V (3-O-[β-D-xylopyranosyl-(1->3)-β-D-glucuronopyranosyl]-28-O-[β-D-glucopyranosyl-(1->4)-α-L-rhamnopyranosyl-(1->2)-4-acetyl-β-D-fucopyranosyl]-medicagenic acid) and for Medicagenic acid-3-O-glucuronide.

Yossoside V

| aglycone part | | | sugars | | |
|---|---|---|---|---|---|
| Atoms No. | $^{13}C$ shift (ppm) | $^{1}H$ shift (ppm) | Atoms No. | $^{13}C$ shift (ppm) | $^{1}H$ shift (ppm) |
| 1 | 44.77 | 2.08 (eq) | | β-D-Fuc | |
| | | 1.24 (ax) | 1 | 94.94 | 5.38 (ax) |
| 2 | 70.68 | 4.30 | 2 | 74.58 | 3.74 (ax) |
| 3 | 86.47 | 4.05 (ax) | 3 | 74.57 | 3.88 (ax) |
| 4 | 53.01 | | 4 | 75.13 | 5.06 (eq) |
| 5 | 53.01 | 1.57 (ax) | 5 | 71.06 | 3.83 (ax) |
| 6 | 21.53 | 1.61 | 6 | 16.37 | 1.06 |
| | | 1.16 | acetyl | | |
| 7 | 33.65 | 1.35 (eq) | CO | 172.69 | |
| | | 1.49 (ax) | Methyl | 20.78 | 2.14 |
| 8 | 40.96 | | | | |
| 9 | 49.44 | 1.57 (ax) | | α-L-Rha | |
| 10 | 37.24 | | 1 | 101.48 | 5.33 (eq) |
| 11 | 24.68 | 1.93 (eq) | 2 | 71.66 | 3.90 (eq) |
| | | 1.99 (ax) | 3 | 72.04 | 3.83 (ax) |
| 12 | 123.51 | 5.26 | 4 | 84.52 | 3.53 (ax) |
| 13 | 144.57 | | 5 | 68.74 | 3.80 (ax) |
| 14 | 43.09 | | 6 | 18.28 | 1.32 |
| 15 | 28.96 | 1.18 (eq) | | | |
| | | 1.58 (ax) | | β-D-Glc | |
| 16 | 23.92 | 1.60 (eq) | 1 | 106.4 | 4.47 (ax) |
| | | 2.04 (ax) | 2 | 76.14 | 3.18 (ax) |
| 17 | 48 | | 3 | 78.28 | 3.34 (ax) |
| 18 | 42.8 | 2.81 | 4 | 71.46 | 3.27 (ax) |
| 19 | 47.22 | 1.13 | 5 | 78.09 | 3.25 (ax) |
| | | 1.71 | 6a | 62.85 | 3.66 |
| 20 | 31.4 | | 6b | 62.85 | 3.84 |
| 21 | 34.77 | 1.22 (eq) | | | |
| | | 1.38 (ax) | | β-D-GlcA | |
| 22 | 33.01 | 1.56 (eq) | 1 | 104.79 | 4.39 |
| | | 1.75 (ax) | 2 | 68.93 | 3.81 |
| 23 | 182.07 | | 3 | 70.94 | 3.81 |
| 24 | 13.57 | 1.37 (ax) | 4 | 74.31 | 3.43 |
| 25 | 17.08 | 1.24 (ax) | 5 | nd | nd |
| 26 | 17.66 | 0.78 (ax) | 6 | nd | |
| 27 | 26.24 | 1.14 (ax) | | | |
| 28 | 177.9 | | | β-D-Xyl | |
| 29 | 33.45 | 0.89 (eq) | 1 | 105.38 | 4.55 (ax) |
| 30 | 24.1 | 0.92 (ax) | 2 | 75.17 | 3.25 (ax) |
| | | | 3 | 77.31 | 3.31 |
| | | | 4 | 70.89 | 3.48 |
| | | | 5a | 66.85 | 3.87 |
| | | | 5b | 66.85 | 3.2 |

Medicagenic acid 3-O-glucuronide

| aglycone part | | | glucuronic acid | | |
|---|---|---|---|---|---|
| Atoms No. | $^{13}C$ shift (ppm) | $^{1}H$ shift (ppm) | Atoms No. | $^{13}C$ shift (ppm) | $^{1}H$ shift (ppm) |
| 1 | 43.72 | 1.24 (ax) | | β-D-GlcA | |
| | | 2.09 (eq) | 1 | 103.14 | 4.41 (ax) |
| 2 | 69 | 4.32 | 2 | 74.02 | 3.27 (ax) |
| 3 | 87.14 | 4.07 (ax) | 3 | 75.95 | 3.40 (ax) |
| 4 | 52.97 | | 4 | 74.52 | 3.60 (ax) |
| 5 | 51.73 | 1.62 (ax) | 5 | 72.09 | 3.39 (ax) |
| 6 | 20.49 | 1.29 | 6 | 175.6 | |
| | | 1.62 | | | |
| 7 | 32.44 | 1.24 (eq) | | | |
| | | 1.56 (ax) | | | |
| 8 | 39.44 | | | | |
| 9 | 48.18 | 1.60 (ax) | | | |
| 10 | 36.12 | | | | |
| 11 | 23.31 | 1.89 (eq) | | | |
| | | 2.02 (ax) | | | |
| 12 | 121.05 | 5.22 | | | |

TABLE 1-continued 1H and 13C NMR spectral data for Yossoside V (3-O-[β-D-xylopyranosyl-(1->3)-β-D-glucuronopyranosyl]-28-O-[β-D-glucopyranosyl-(1->4)-α-L-rhamnopyranosyl-(1->2)-4-acetyl-β-D-fucopyranosyl]-medicagenic acid) and for Medicagenic acid-3-O-glucuronide.

| | | | |
|---|---|---|---|
| 13 | 145.36 | | |
| 14 | 41.9 | | |
| 15 | 27.84 | 0.95 (eq) | |
| | | 1.87 (ax) | |
| 16 | 23.2 | 1.57 (eq) | |
| | | 1.88 (ax) | |
| 17 | nd | | |
| 18 | 42.07 | 2.90 | |
| 19 | 46.73 | 1.08 | |
| | | 1.65 (eq) | |
| 20 | 30.43 | | |
| 21 | 34.12 | 1.12 (eq) | |
| | | 1.34 (ax) | |
| 22 | 32.94 | 1.49 (eq) | |
| | | 1.72 (ax) | |
| 23 | 184.8 | | |
| 24 | 13.46 | 1.36 (ax) | |
| 25 | 15.8 | 1.26 (ax) | |
| 26 | 16.97 | 0.88 (ax) | |
| 27 | 25.15 | 1.14 (ax) | |
| 28 | nd | | |
| 29 | 32.56 | 0.87 (eq) | |
| 30 | 22.81 | 0.95 (ax) | |

Figure 22A:
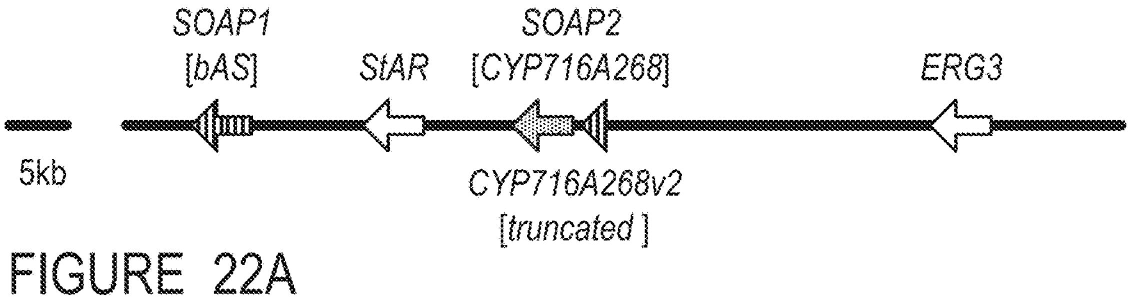
Figure 22B:
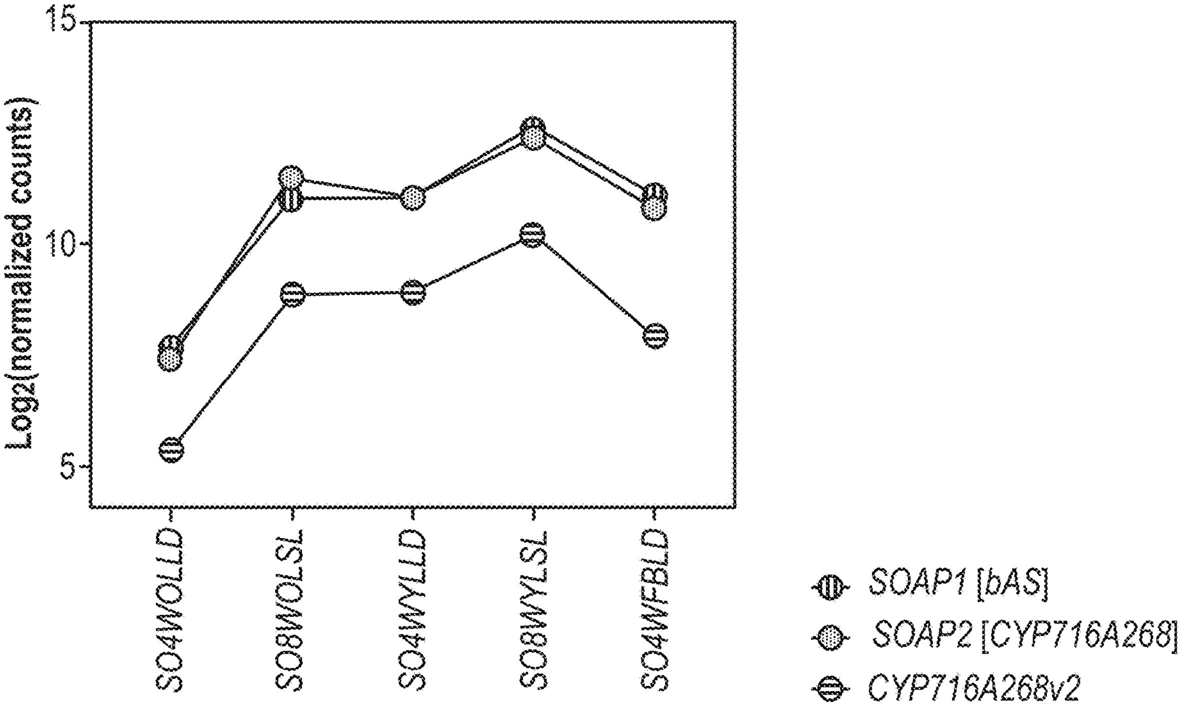
Figure 23A:
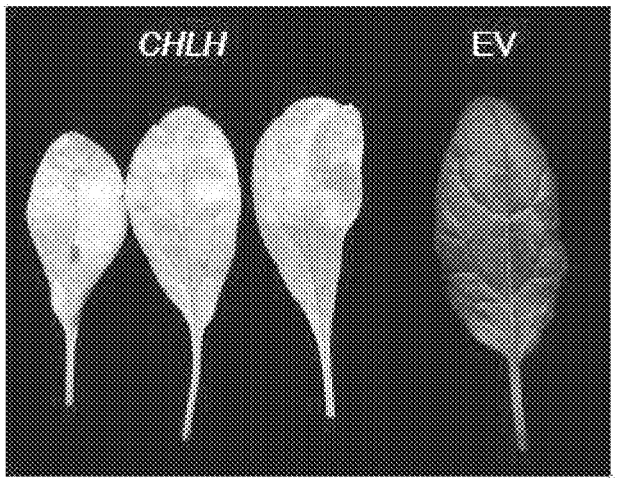
Figure 23B:
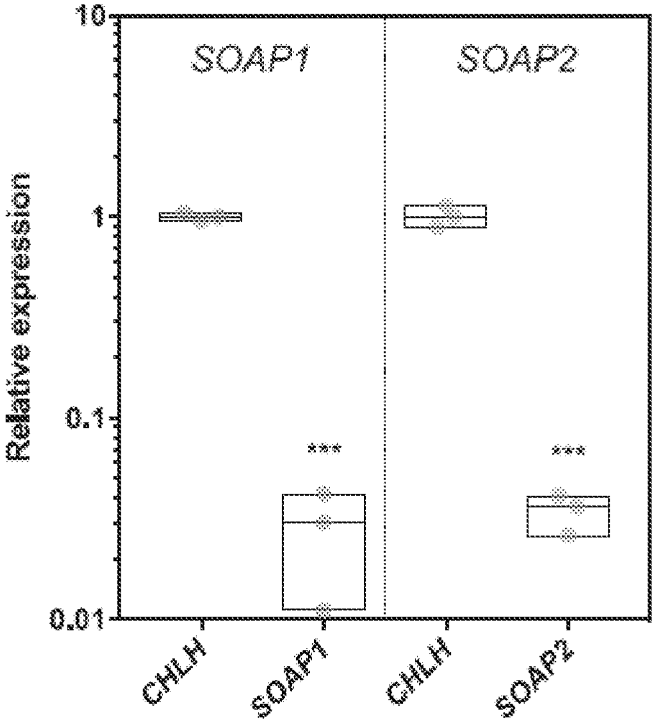
Figure 23C:
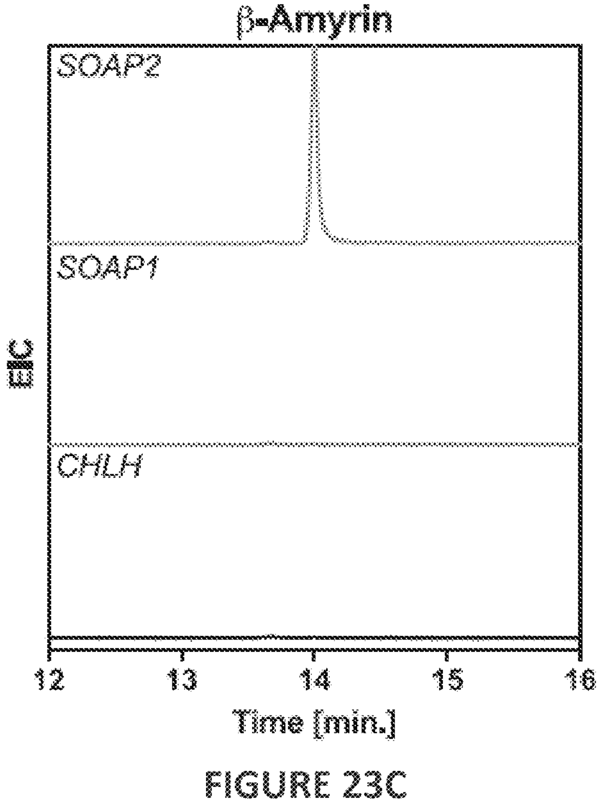
Figure 23D:
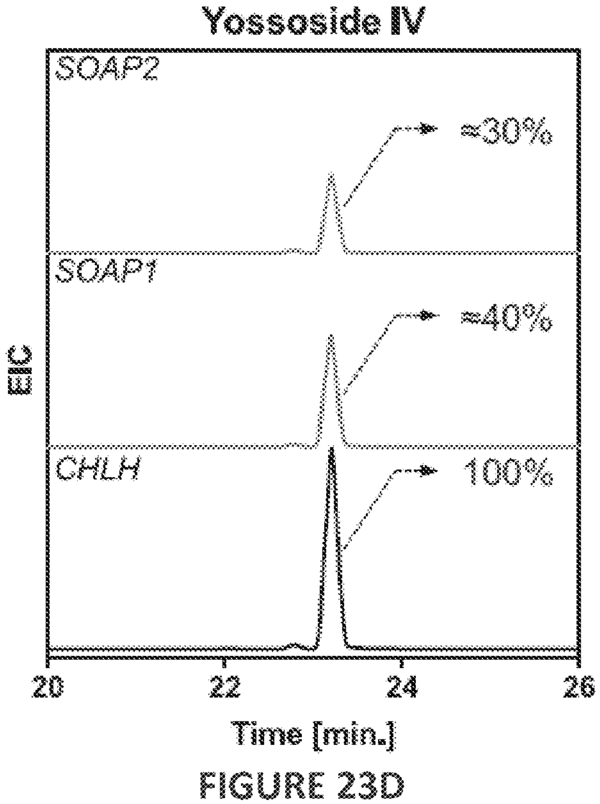

FIGS. 22A and 22B show that the genes involved in first steps of aglycone biosynthesis are located in close vicinity on the chromosome. (FIG. 22A) Schematic representation of the chromosomal region with genes involved in oleanolic acid biosynthesis. Semitransparent gray boxes contain SOAP1 (bAS)(SEQ ID NO: 422), CYP716A268 (SOAP2; SEQ ID NO: 46) and its truncated duplication CYP716A268v2 (SEQ ID NO: 47). Genes marked in dark grey are not directly involved in the biosynthesis of triterpenoid saponins. (FIG. 22B) Expression pattern of SOAP1, SOAP2 and CYP716A268v2 among five spinach transcriptomes; SO4WOLLD—mature leaf from four week old plant grown in long day; SO8WOLSL—mature leaf from eight week old plant grown in short day; SO4WYLLD—young leaf from four week old plant grown in long day; SO8WOLSL—young leaf from eight week old plant grown in short day; SO4WFBLD—flower bud from four week old plant grown in long day. For details see Materials and Methods.

FIGS. 23A-23D present data providing functional characterization of SOAP1 (bAS) and SOAP2 (CYP7123A2238) by silencing (VIGS) in spinach. (FIG. 23A) Chlorotic phenotype observed in plant with silenced magnesium-chelatase subunit H (CHLH). CHLH was used as a control and a marker of VIGS gene silencing. In general, this gene is not directly related to SOAP genes and saponin biosynthesis. EV stands for empty vector and represents a control leaf. (FIG. 23B) Real-time qPCR analysis of SOAP1 and SOAP2 expression in silenced plants. Values (±SD) represent mean of three independent biological experiments. Statistically significant differences compared with control plants (CHLH silenced) are indicated; *P<0.001. (FIG. 23C) Aligned gas chromatography-mass spectrometry (GC-MS) extracted ion chromatograms (EICs) of P-amyrin [m/z=218, main fragment] from the plants with silenced SOAP1 or SOAP2 compared to control (CHLH). P-Amyrin can be detected only in plants with silenced SOAP2 where its further conversion is blocked. (FIG. 23**D) Aligned liquid chromatography-mass spectrometry (LC-MS) EICs of Yossoside IV [m/z=12233.23, (−)-mode] from plants with silenced SOAP1 or SOAP2 compared to control (CHLH). Content of Yossoside IV was reduced to 40 and 30% in SOAP1 and SOAP2 silenced lines, respectively.

Figure 24A:
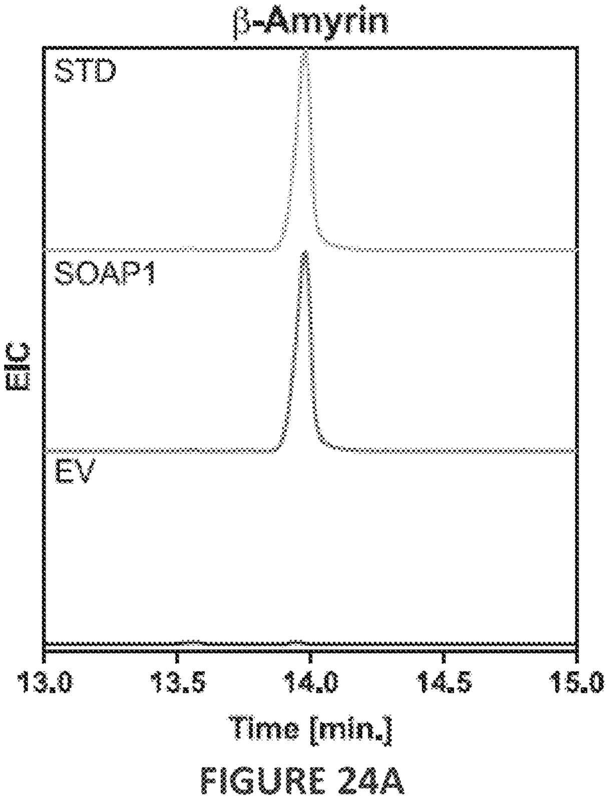
Figure 24B:
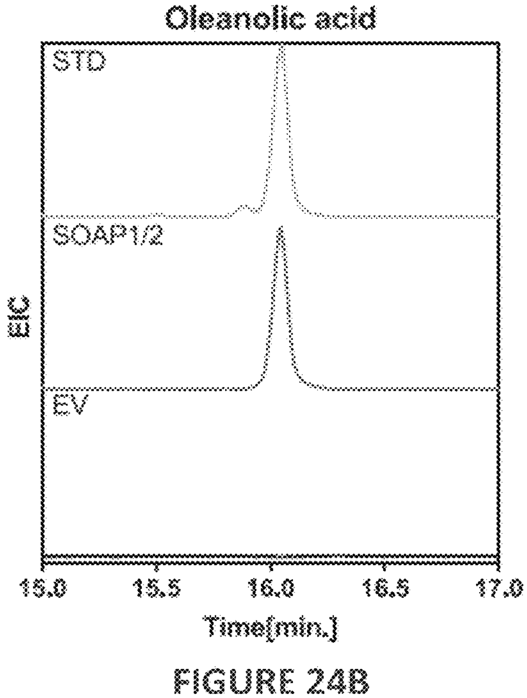

FIGS. 24A and 24B present data providing functional characterization of SOAP1 (bAS; SEQ ID NO: 45) and SOAP2 (CYP2416A268; SEQ ID NO: 46) by heterologous expression in *N. benthamiana*. (FIG. 24A) Aligned GC-MS extracted ion chromatograms (EICs) of β-amyrin [m/z=218, main fragment] from the transient expression of SOAP1 compared to empty vector (EV) alone and an authentic standard. Only chromatograms from in planta experiments are to scale. (FIG. 24B) Aligned GC-MS EICs of oleanolic acid [m/z=203, main fragment] from the transient expression of SOAP1 and SOAP2 compared to empty vector (EV) alone and an authentic standard. Only chromatograms from in planta experiments are to scale. For details of GC-MS analysis see Materials and Methods.

Figure 25:
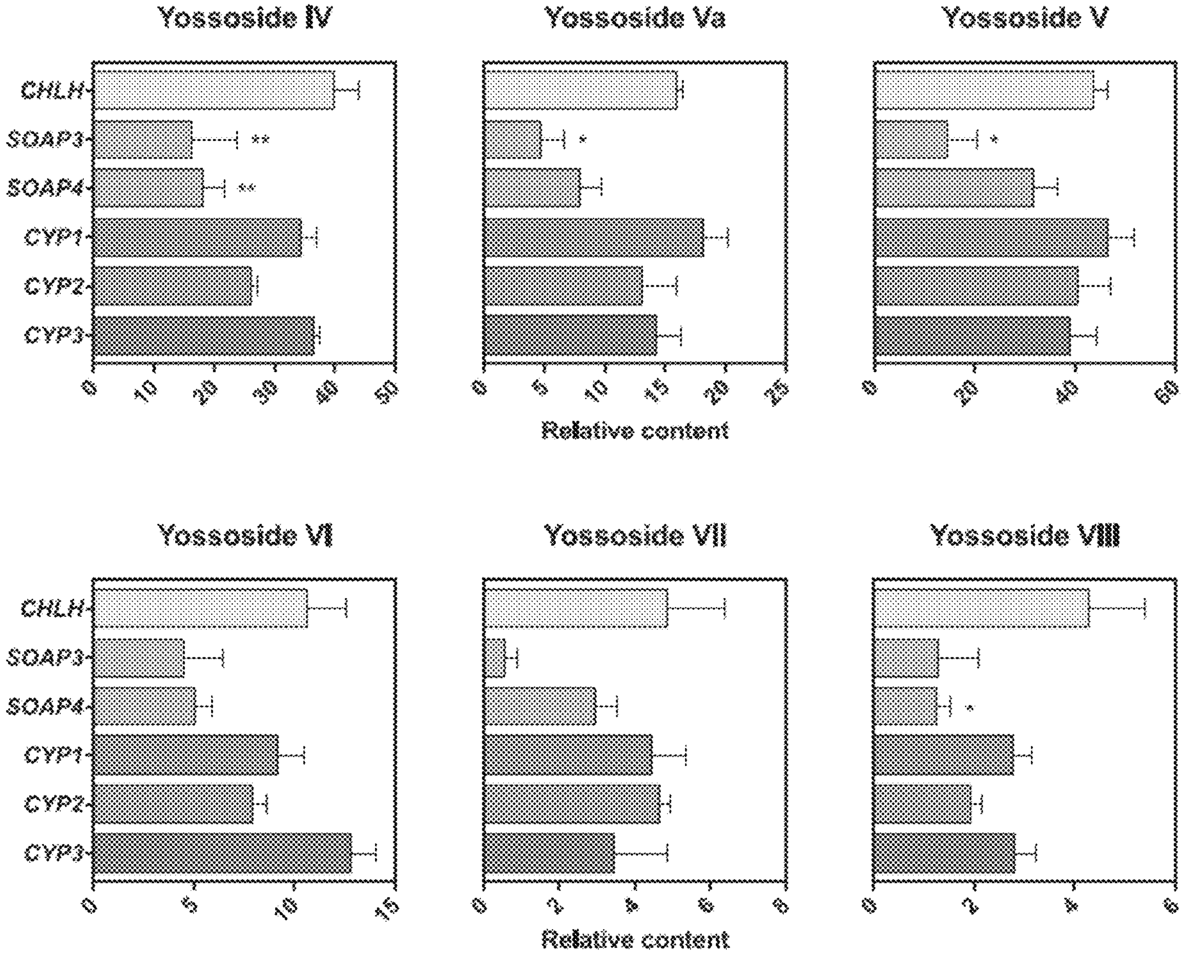
Figure 26A:
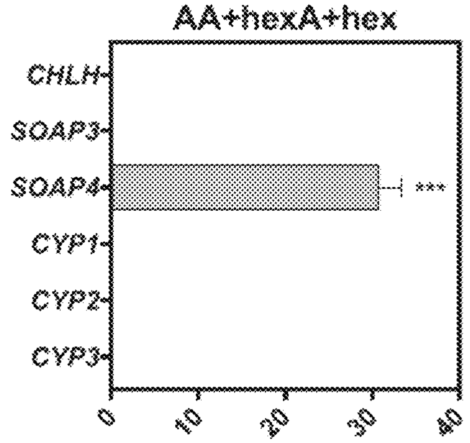
Figure 26B:
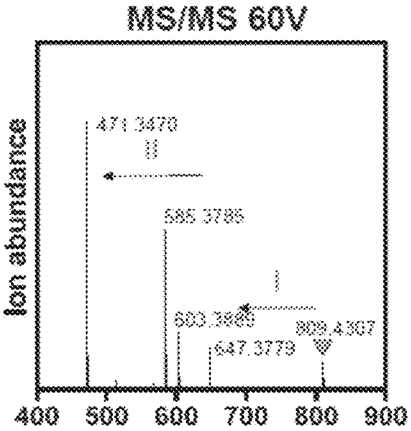
Figure 26C:
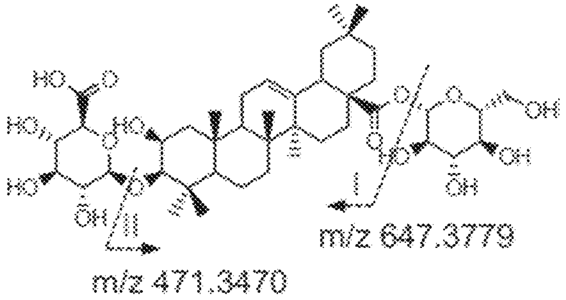
Figure 26D:
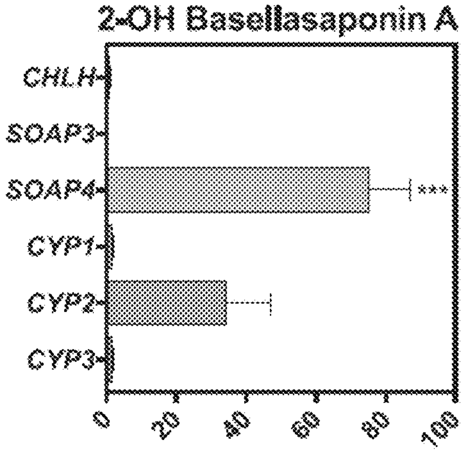
Figure 26E:
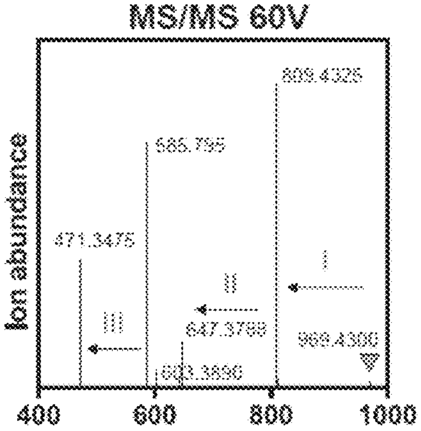
Figure 26F:
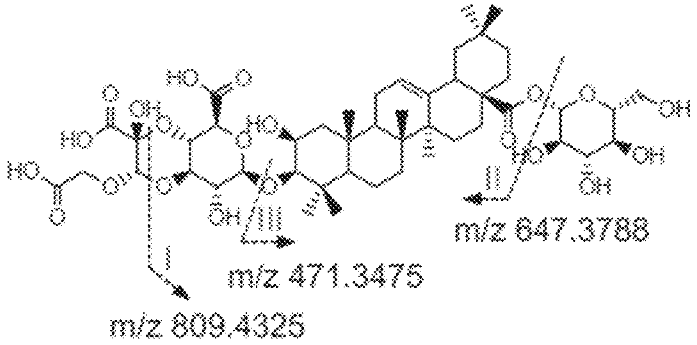
Figure 26G:
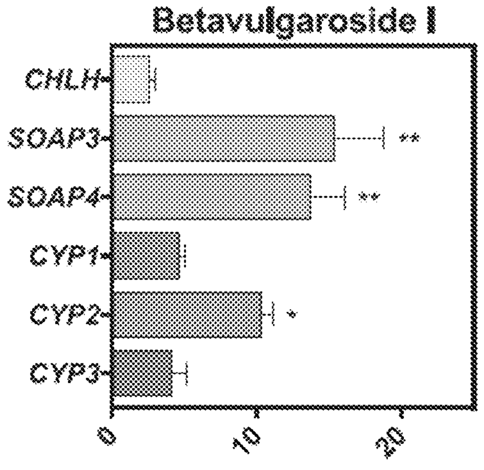
Figure 26H:
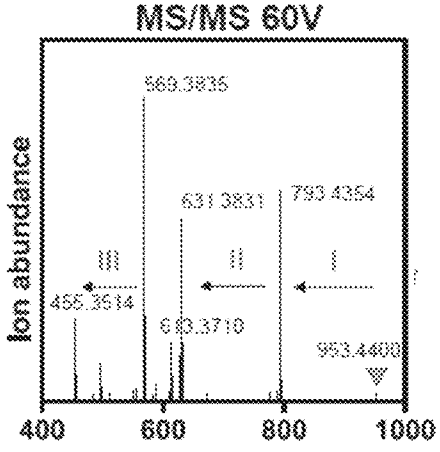
Figure 26I:
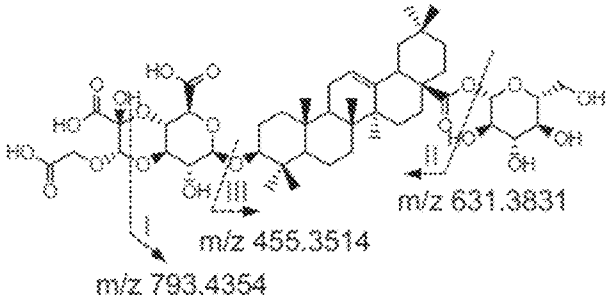
Figure 26J:
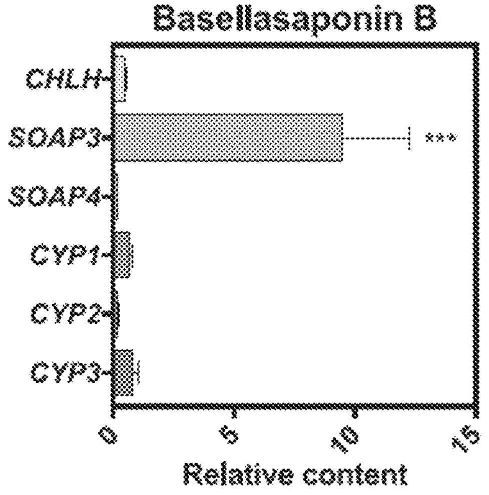
Figure 26K:
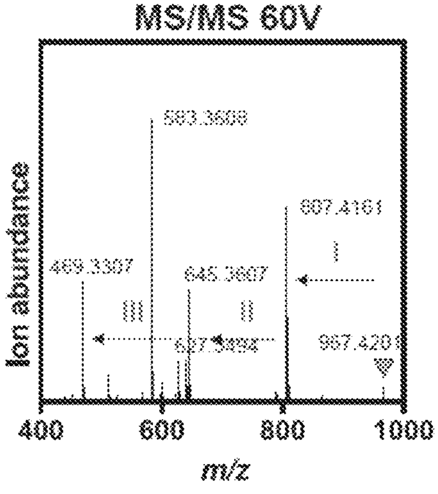
Figure 26L:
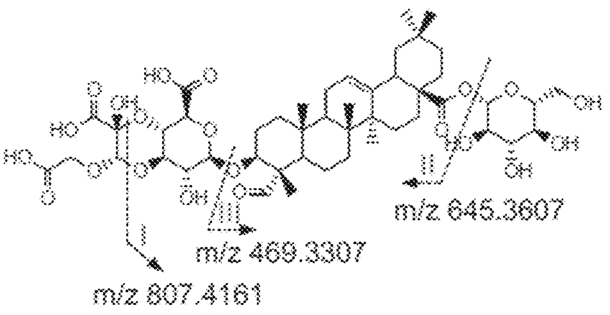

FIG. 25 presents data showing liquid chromatography-mass spectroscopy (LC-MS) analysis of selected saponins in spinach with (VIGS) silenced cytochrome P450 candidate genes. Relative content (normalized peak area) of selected saponin compounds in plants with silenced SOAP3 (CYP72A655; SEQ ID NO: 51), SOAP4 (CYP72A654; SEQ ID NO: 53), and additional three other CYPs (p450 cytochrome genes); for accession numbers see Table 11. Values (±SD) represent mean of three independent biological experiments. Statistically significant differences compared with control plants (CHLH silenced) are indicated; *P<0.05, **P<0.01.

FIGS. 26A-26L present characterization of saponins accumulating in spinach following silencing of cytochrome P450 genes (VIGS). (FIGS. 26A, 26D, 26G, and 26J) Relative content (normalized peak area) of selected triterpenoid saponin compounds in spinach leaves with silenced SOAP3 (CYP72A655; SEQ ID NO: 51), SOAP4 (CYP72A654; SEQ ID NO: 53) and additional three cytochrome p450 genes; for accession numbers see Table 11. Values (±SD) represent mean of three independent biological experiments. Statistically significant differences compared with control plants (CHLH silenced) are indicated; *P<0.05, P<0.01. AA-augustic acid (FIGS. 26B, 26E, 26H, and 26K) Tandem mass spectroscopy (MS/MS) spectra with marked main fragments. (FIGS. 26C, 26F, 26I, and 26**L) Putative structures of saponin compounds based on accurate mass measurement, fragmentation patterns, and literature. For more details see Table 16.

Figure 27:
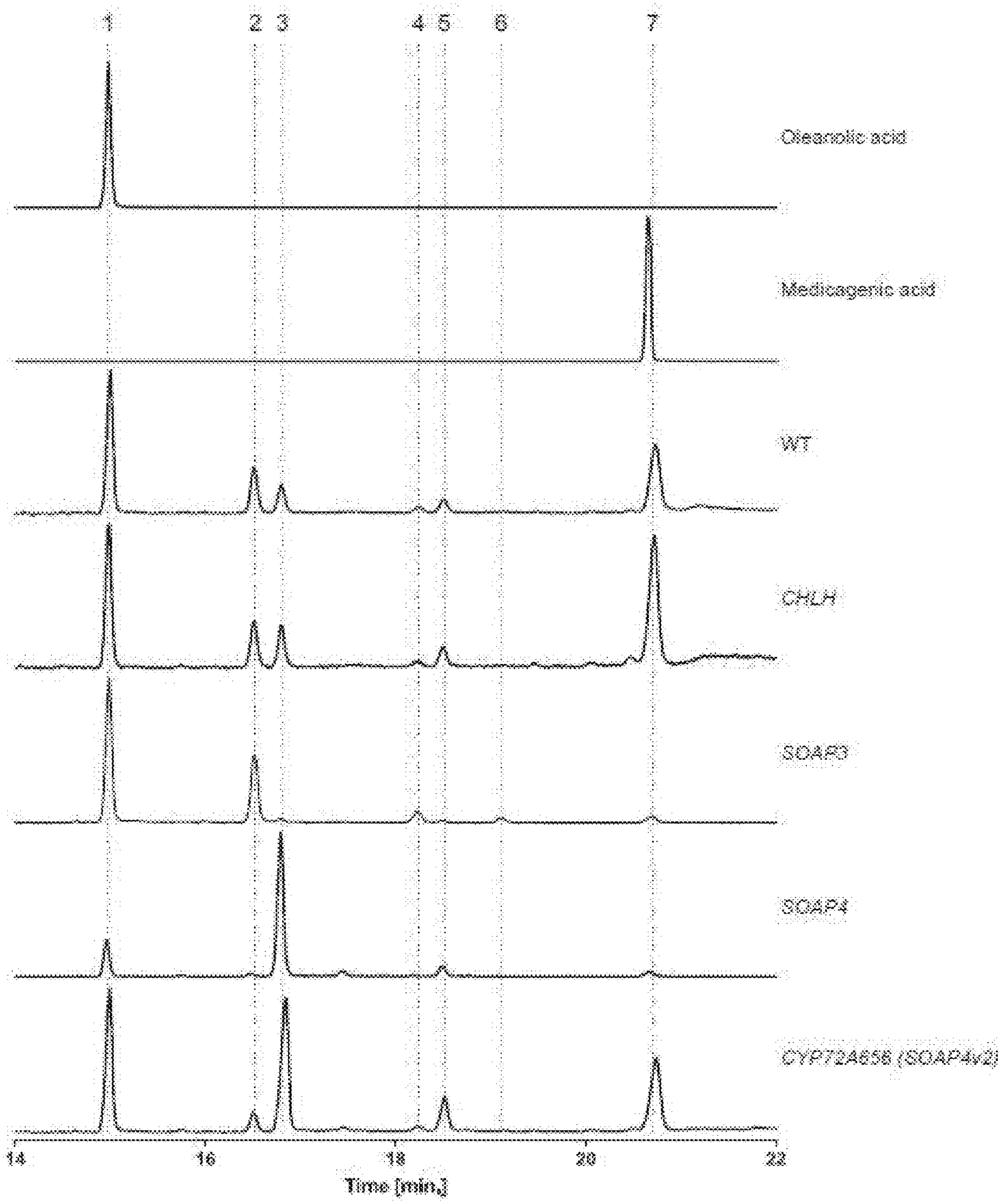

FIG. 27 presents GC-MS analysis of saponins' aglycones in spinach plants with silenced CYPs P450. EICs of triterpenoid aglycones [m/z=203 and 262; common fragments for all amyrin-type aglycones] released from the saponins accumulated in plants with silenced SOAP3 alone, SOAP4 alone, and CYP2 compared to control (CHLH silenced) and authentic standards of oleanolic and medicagenic acid. Scale of each EIC was normalized to the most abundant signal. Numbers from 1-7 represent names of detected compounds, 1—oleanolic acid; 2—hederagenin; 3—augustic acid; 4—gypsogenin, 5—bayogenin; 6—unknown; 7—medicagenic acid, respectively.

Figure 28C:
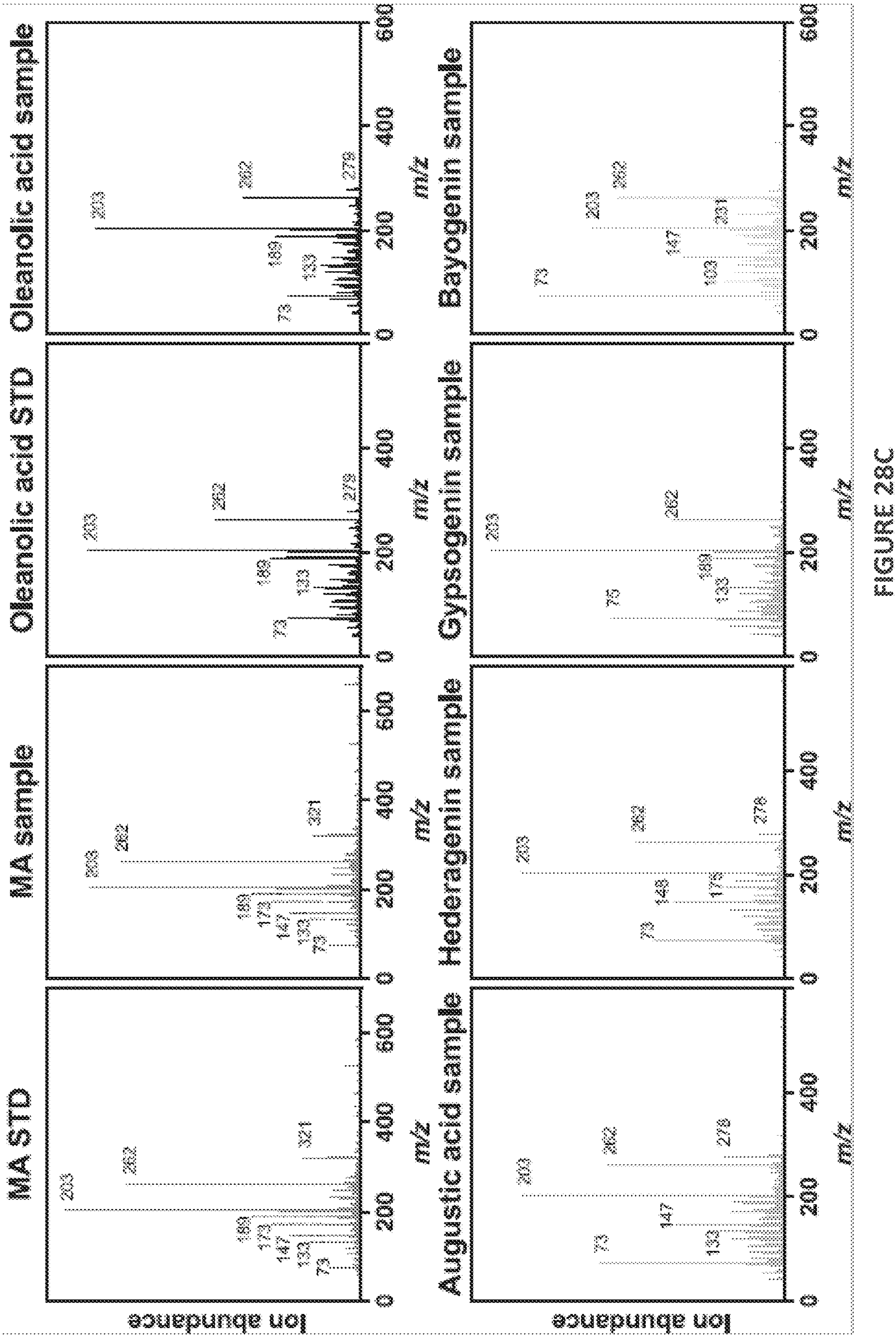

FIGS. 28A-28C presents the analysis and putative characterization of aglycones in spinach with silenced CYPs P450. (FIG. 28A) Relative content of detected sapogenins in plants with silenced SOAP3, SOAP4, CYP2 and CHLH as control. (FIG. 28B) Structures of characterized aglycones. Numbers from 1-7 represent names of detected compounds, 1—oleanolic acid; 2—hederagenin; 3—augustic acid; 4—gypsogenin; 5—bayogenin; 6—unknown; 7—medicagenic acid, respectively. (FIG. 28C) Fragmentation patterns of described compound and comparison with fragmentation patterns of authentic standards of oleanolic acid and medicagenic acid.

Figure 29:
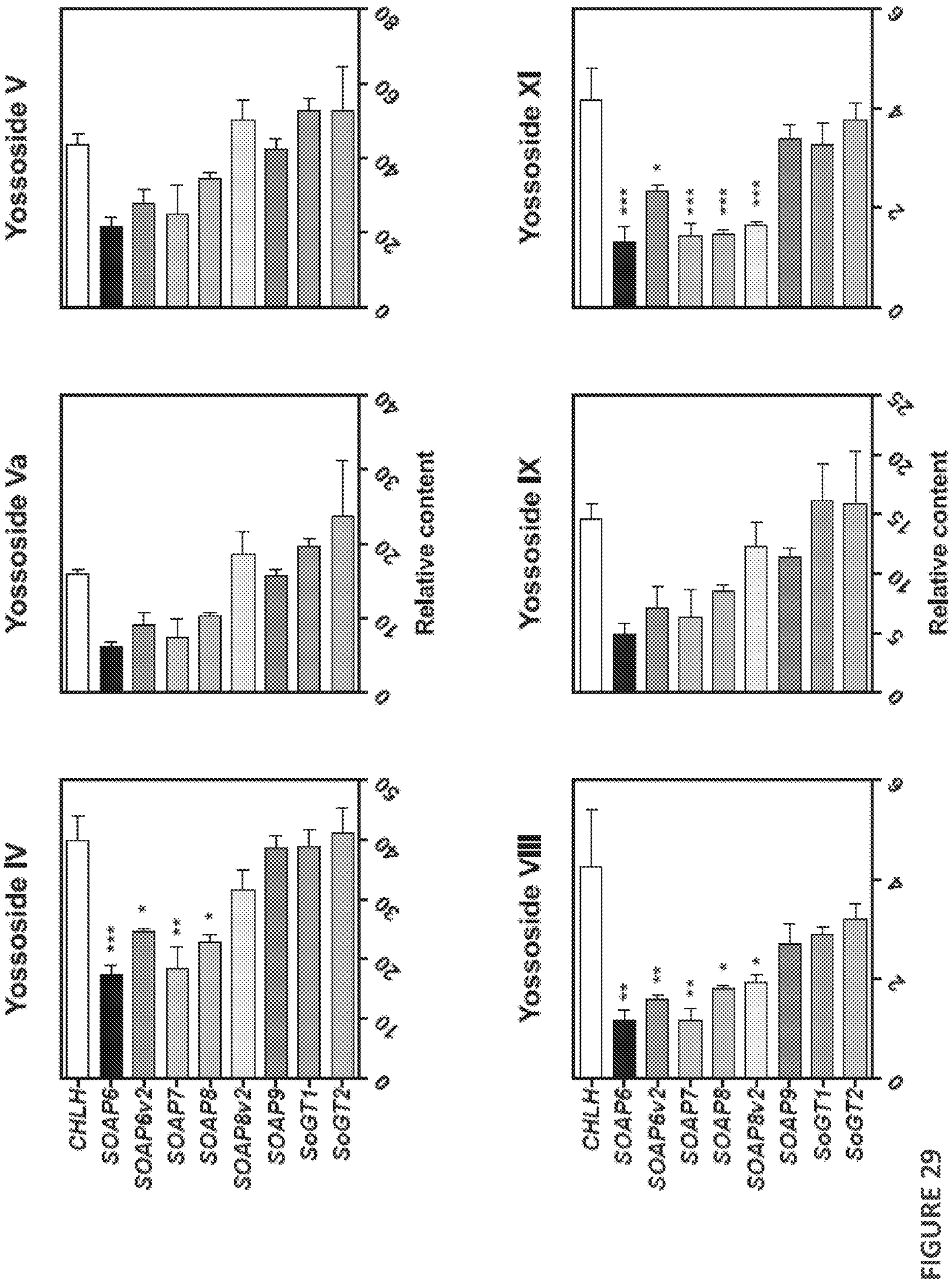

FIG. 29 presents LC-MS analysis of selected saponins in spinach with silenced (VIGS) for glycosyltransferase genes. Relative content (normalized peak area) of selected saponin compounds in plants with silenced SOAP6-9 (SEQ ID NOs: 55, 57, 59, and 61, respectively), SoGT1 (SEQ ID NO: 117 [gene] and SEQ ID NO: 118 [polypeptide]) and SoGT2 (SEQ ID NO: 119 [gene] and SEQ ID NO: 120 [polypeptide]); for accession numbers see Table 11. Sequences used for the glycosyl transferases are provided below.

Spinach GT1 nucleic acid gene sequence is set forth as follows:

(SEQ ID NO: 117)

```
atgtgtgacgacaaaaaatcatctgttttgagcat
agcattttatccgtggtttgctcttggtcacctta
cttcatttctccgattagccaacaaacttgcacaa
aatggtcacaatgtgtcctattttatcccaactaa
tacattacctagattacttcctcacaaccattacc
ctggccaccttactttcatccccgtcaccgtccca
cccgttgacggcctccctctcagagccgagaccac
caacgatgtcccctcctcggctatacaccttctta
tgactgccatggatttgacccgtgacactatcgag
gcccatttggttagtatcaaacccgatgttgtttt
ctacgactttgcttattggattcccgatctagccc
gaaaacacgggttcaagtcagtactctacattaca
tcctatatagcaagatgtgcttattttgcccccga
tttgaagtcgggtcatcagtccactggggccgaaa
ttattgcgccaccaccgggttttccgtctcagcat
ttccggatgcaagcacacgaggctgagactgtggc
agacgtaggtaaagagcaagatggattacaaggta
taactatttctgaaaggatgcgcattgcttttgga
aaatgcgacgcaattggagtaaagagttgtaagga
gatggaaaaggtgtatattgactactgtgagaaga
tatttggtaagtctgtactactagcaggtcctatg
gtccctaaaaccccatcttccaaacttgatgaata
ttttgatggttggcttacgggttttggtgctgcta
ctgtgatttattgtgcatttgggagtgaatgtgtt
ctcgaaattaaccaatttcaacaacttcttcttgg
actagagctcacaggaaggccattttttggtggcca
tgaagccgcctaagaagtatgaaacaatagagtcg
gccttaccagaagggtttgagaagagaacaaaagg
aaggggaatcgtacatgagggttgggtgcagcaac
aactgatattgcaacatccatcagtaggatgtttc
ataactcattgtggagttgggtctctttcggaagc
```

-continued

```
tatggtcagcaaatgtcaagtagtgttgatgcctc
aagctgtagaccaattcatcaatgcgaggatgatg
agtttagagttgaagattggggttgaggttgagaa
gagagaagatgatggtttgttcacaaaggaggctg
tgcataaggcggtctctttggtgatggaggaagaa
agtgaagtcgcaaaagagatgagggtaagtcatga
taaatggagagaattcttattacaggaaggtcttg
aggattcttatatcagtagcttcattcagagtcta
cgacagttaacgattggatga.
```

Spinach GT1 amino acid protein sequence is set forth as follows:

(SEQ ID NO: 118)

```
MAASNKEQSKLHIAMFPWFAYGHINPFIQLSNKLS
SHGIQISFFSIPGNIDRIKSSLNLSPPNQLIPLTI
PPTEGLSPNFDSSSEVTPQTAQLLTLALDQMQPQV
KALFPHPQPQVILFDFAYHWLPSVASELGIKAVHF
NTFPAVINSYLTVPSRMTDPNKPPTFEDLKNPPQG
YPKTSTASVKTFEAQDYLFLFKSFDGGPCHFEKIL
AFTNSCDAILYRTCNEIEGPFIDYFKTQINKPLLL
AGPSVPLPPSGELDEKWEMWLGKFPEKSVIYCSFG
SETYLNDAQIQELTLGLELTGLPFILVLNFGTSNS
TDAHNKLEASLPEGFRERIKDRGVLHTGWVQQQNI
LAHRSIGCFLTHAGFSSVIEGIVNDCQLAFLPLKA
DQFMIAKLFSGDLKAGVEVNRRDEDGSFAKEDIFE
AIKTIMVDTDKEPSRSIRENHSNWRKFLMNKEIEA
SY1ANLAHELKALVQKA.
```

Spinach GT2 nucleic acid gene sequence is set forth as follows:

(SEQ ID NO: 119)

```
gttcaagtcagtactctacattacatcctatatag
caagatgtgcttattttgcccccgatttgaagtcg
ggtcatcagtccactggggccgaaattattgcgcc
accaccgggttttccgtctcagcatttccggatgc
aagcacacgaggctgagactgtggcagacgtaggt
aaagagcaagatggattacaaggtataactatttc
tgaaaggatgcgcattgcttttggaaaatgcgacg
caattggagtaaagagttgtaaggagatggaaaag
gtgtatattgactactgtgagaagatatttggtaa
gtctgtactactagcaggtcctatggtccctaaaa
ccccatcttccaaacttgatgaatattttgatggt
```

-continued

```
tggcttacgggttttggtgctgctactgtgattta

ttgtgcatttgggagtgaatgtgttctcgaaatta

accaatttcaacaacttcttcttggactagagctc

acaggaaggccatttttggtggccatgaagccgcc

taagaagtatgaaacaatagagtcggccttaccag

aagggtttgagaagagaacaaaaggaaggggaatc

gtacatgagggttgggtgcagcaacaactgatatt

gcaacatccatcagtaggatgtttcataactcatt

gtggagttgggtctctttcggaagctatggtcagc

aaatgtcaagtagtgttgatgcctcaagctgtaga

ccaattcatcaatgcgaggatgatgagtttagagt

tgaagattggggttgaggttgagaagagagaagat

gatggtttgttcacaaaggaggctgtgcataaggc

ggtctctttggtgatggaggaagaaagtgaagtcg

caaaagagatgagggtaagtcatgataaatggaga

gaattcttattacaggaaggtcttgaggattctta

tatcagtagcttcattcagagtctacgacagttaa

cgattggatga.
```

Spinach GT2 amino acid gene polypeptide is set forth as follows:

```
                                    (SEQ ID NO: 120)
MCDDKKSSVLSIAFYPWFALGHLTSFLRLANKLAQ

NGHNVSYFIPTNTLPRLLPHNHYPGHLTFIPVTVP

PVDGLPLRAETTNDVPSSAIHLLMTAMDLTRDTIE

AHLVSIKPDWFYDFAYWIPDLARKHGFKSVLYITS

YIARCAYFAPDLKSGHQSTGAEIIAPPPGFPSQHF

RMQAHEAETVADVGKBQDGLQGITISERMRIAFGK

CDAIGVKSCKEMEKVYIDYCEKIFGKSVLLAGPMV

PKTPSSKLDEYFDGWLTGFGAATVIYCAFGSECVL

EINQFQQLLLGLELTGRPFLVAMKPPKKYETIESA

LPEGFEKRTKGRGIVHEGWVQQQLILQHPSVGCFI

THCGVGSLSEAMVSKCQWLMPQAVDQFINARMMSL

ELKIGVEVEKREDDGLFTKEAVHKAVSLVMEEESE

VAKEMRVSIIDKWREFLLQEGLEDSYISSFIQSLR

QLTIG.
```

Values (±SD) represent mean of three independent biological experiments. Statistically significant differences compared with control plants (CHLH silenced) are indicated; *P<0.05, P<0.01, *P<0001.

Figure 30A:
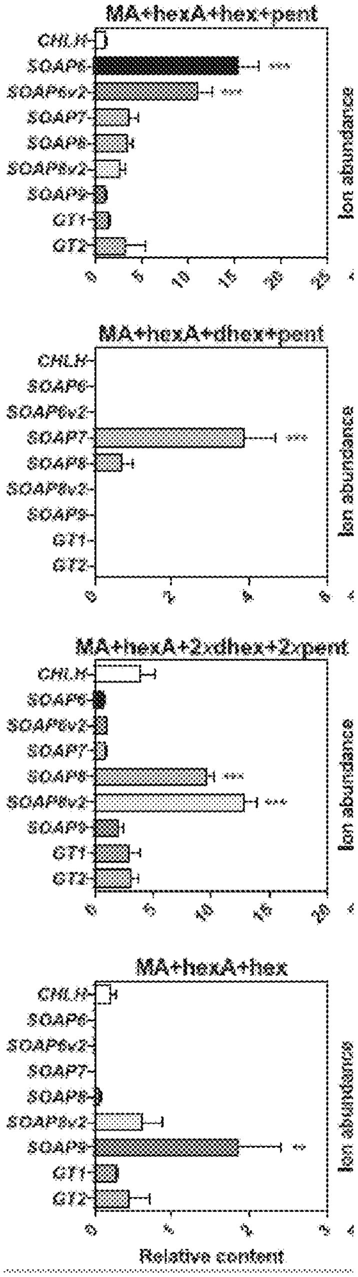
Figure 30B:
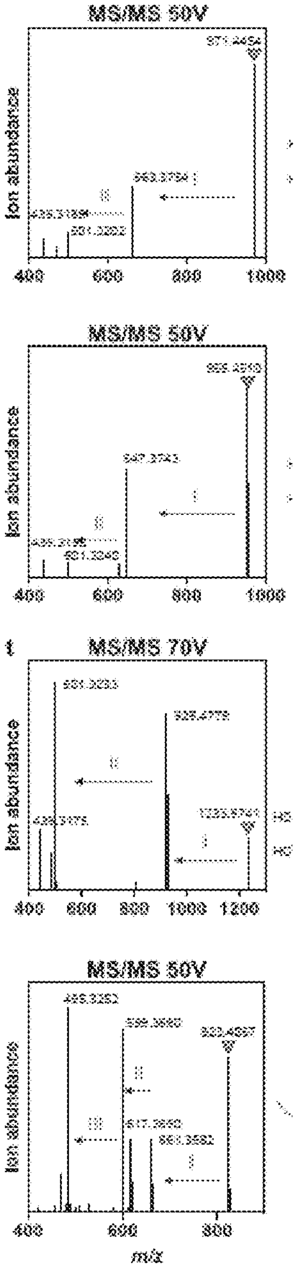
Figure 30C:
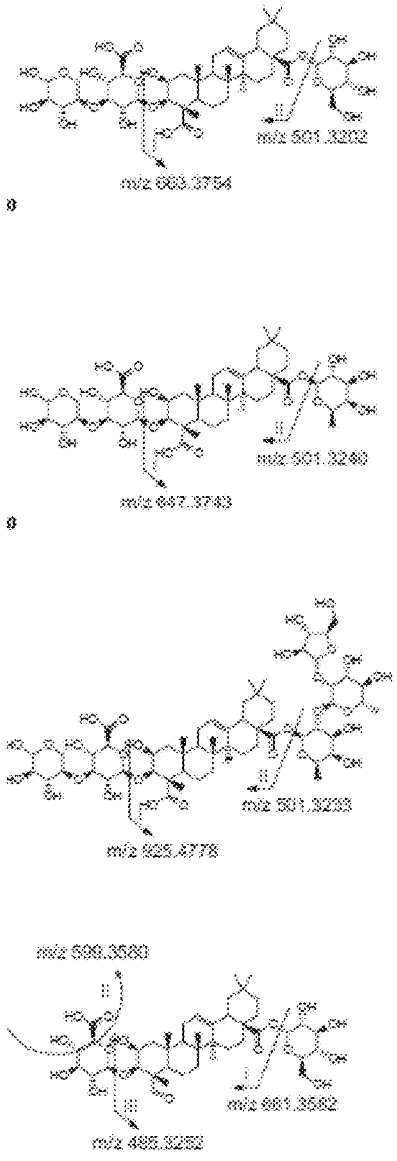

FIGS. 30A-30C present data showing putative characterization of saponins accumulated in spinach with silenced (VIGS) glycosyltransferases. (FIG. 30A) Relative content of selected compounds in plants with silenced SOAP6-SOAP9 (SEQ ID NO: 55, 57, 59, and 61, respectfully) and other two GTs. Values (±SD) represent mean of three independent biological experiments. Statistically significant differences compared with control plants (CHLH silenced) are indicated; P<0.01, *P<0.001. (FIG. 30B) MS/MS spectra with the main fragments marked. (FIG. 30C) Putative structures of accumulated saponins are based on accurate mass measurement and fragmentation patterns.

FIGS. 31A-31F present characterization of SOAP10 acetyltransferase in planta (spinach) and in vitro. (FIG. 31A) LC-MS analysis of samples from spinach plants with VIGS silenced SOAP10 (red trace) or CHLH (black trace) as control. Blue and yellow regions of the chromatogram contain desacetyl and acetylated saponins, respectively. Silencing of SOAP10 in spinach leaves resulted in decreased production of acetylated saponins and increased accumulation of desacetyl counterparts. (FIG. 31B) Relative content of selected desacetyl saponins (Yossoside IV and XII) and their acetylated counterparts (Yossoside V and VII) in spinach plants with VIGS silenced acyltransferases and CHLH as control. The ordinate axis is in log 10 scale. (FIG. 31C) Ratio of desacetyl to acetylated saponins in VIGS silenced spinach plants. Silencing of SOAP10 resulted in increased accumulation of desacetyl saponins. (FIGS. 31D, 31E, and 31F) SOAP10 recombinant protein activity in vitro. EICs of desacetyl saponins (FIG. 31D—m/z 1101.51; FIG. 31E—m/z 1263.57; FIG. 31F—m/z 1395.61) and acetylated counterparts (FIG. 31D—m/z 1313.52; FIG. 31E—m/z 1305.58; FIG. 31F—m/z 3137.62) in: substrate (bottom trace in each of FIGS. 31D, 31E, and 31F)—purified fraction of desacetyl saponins from spinach; in vitro enzymatic assay with recombinant SOAP10 incubated with substrate in presence of acetyl-CoA (middle trace in each of FIGS. 31D, 31E, and 31F); and in extract of spinach leaves (upper trace in each of FIGS. 31D, 31E, and 31F) for comparison. Dotted line separates regions on chromatogram with desacetyl and acetylated saponins on the left- and right-hand side, respectively. "Δm/z=42.01" depicts difference in molecular weight of the compounds resulting from acetylation. (SoAT1 (SEQ ID NO: 109 [gene] and SEQ ID NO: 113 [polypeptide]), SoAT2 (SEQ ID NO: 110 [gene] and SEQ ID NO: 131 [polypeptide]), SoAT3 (SEQ ID NO: 111 [gene] and SEQ ID NO: 115 [polypeptide]), and SoAT4 (SEQ ID NO: 112 [gene] and SEQ ID NO: 116 [polypeptide]), for functional activities of SoAT1-SoAT4 see Table 15.)

FIGS. 32A-32D present data from the expression of SOAPs 1-4 and 6-10 in *N. benthamiana*. (FIG. 32A) EIC of medicagenic acid and its (poly)glycosylated derivatives [m/z=501.32 (MA); m/z=663.38 (MA+hex); m/z=825.43 (MA+2hex); m/z=987.48 (MA+3hex); m/z=1149.53 (MA+4hex) in negative ion mode] from plants transiently expressing either SOAP1-4 alone or all nine SOAPs without SOAP5 (SEQ ID NOs: 65 or 93 [gene], SEQ ID NO: 66 [polypeptide]), compared to control. Inset shows region of the chromatogram magnified 20 times. (FIGS. 32B, 32C, and 32D) show MSE spectra of mono-, bis- and trishexosylmedicagenic acid, respectively. Arrows represent losses of hexosyl moieties.

FIGS. 33A-33F present technical analysis of Cellulose Synthase Like G gene (SOAP5; SEQ ID NOs: 65 or 93 [gene], SEQ ID NO: 66 [polypeptide]). The SOAP5 encoded enzyme attaches glucuronic acid to the triterpenoid aglycone and plays a key role in spinach saponin biosynthetic pathway. (FIG. 33A) Analysis of SOAP5 relative expression in spinach leaves after Virus Induced Gene Silencing (VIGs). Presented values were obtained from 4 independent biological replicates. Expression of SOAP5 was compared to the control (plants with silenced magnesium chelatase subunit H alone—CHLH). (FIG. 33B) Medicagenic acid accumulation in spinach leaves with silenced SOAP5 and other glycosyltransferases compared to control (CHLH). Significant differences are indicated, *P<0.001. (FIG. 33C) EIC of medicagenic acid 3-O-glucuronide [m/z=677.35 (MA-3-GlcA), in negative ion mode] from plants transiently expressing SOAP1-5, compared to plants expressing SOAP1-4 alone and to control (empty vector—EV). (FIG. 33D) EIC of MA-3-GlcA [m/z=677.35 in negative ion mode] from yeast expressing SOAP1-5+SoUGD1 compared to yeast expressing SOAP1-5, yeast controls (SOAP1-4+SoUGD1; SOAP5 alone and yeast cells transformed with EV). (FIG. 33E) Schematic representation of SOAP5 activity in spinach. SOAP5 attaches glucuronic acid (highlighted in red) to medicagenic acid at position C-3. (FIG. 33**F) Spinach saponin biosynthetic pathway reconstitution in *N. benthamiana*. EIC of Yossoside V [m/z=1305.57 in negative ion mode] in samples from *N. benthamiana* leaves transiently expressing all the ten SOAP genes compared to control plants (EV) and to spinach leaf extract.

Figure 34A:
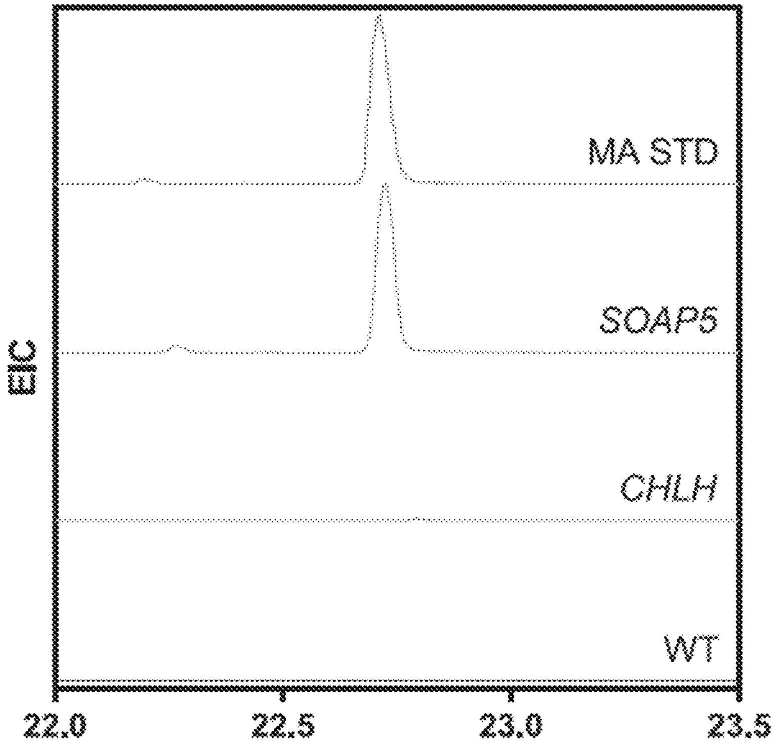
Figure 34B:
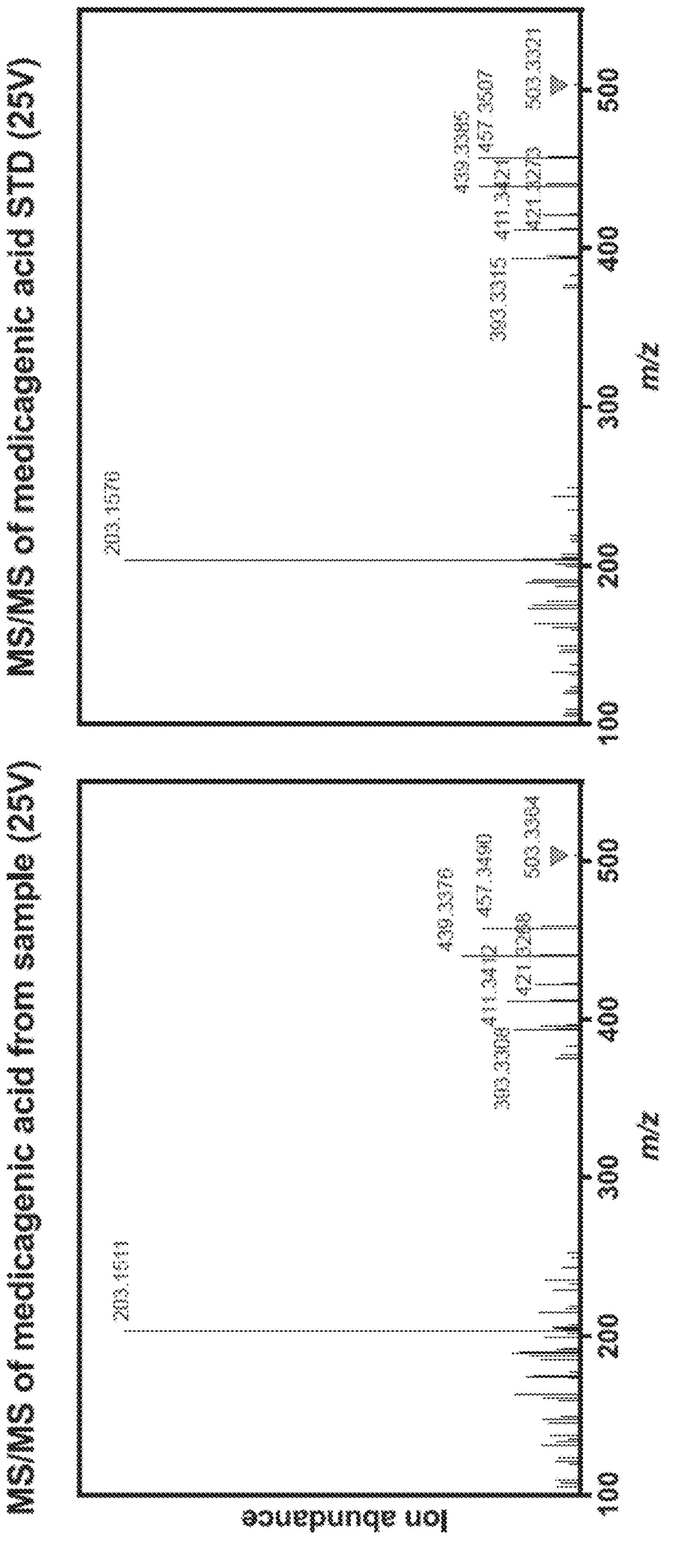

FIGS. 34A-34B present the data showing the results of silencing SOAP5 in spinach (VIGS). (FIG. 34A) EIC of medicagenic acid [m/z=501.3, in negative ion mode] from plants with silenced SOAP5 (SEQ ID NOs: 65 or 93), compared to control (CHLH silenced) and to wild type (WT). Only chromatograms from in planta experiments are to scale. (FIG. 34B) Tandem mass spectroscopy (MS/MS) of medicagenic acid [25V, positive ion mode] accumulated in the plant compared to the authentic standard. MA—medicagenic acid.

Figure 35A:
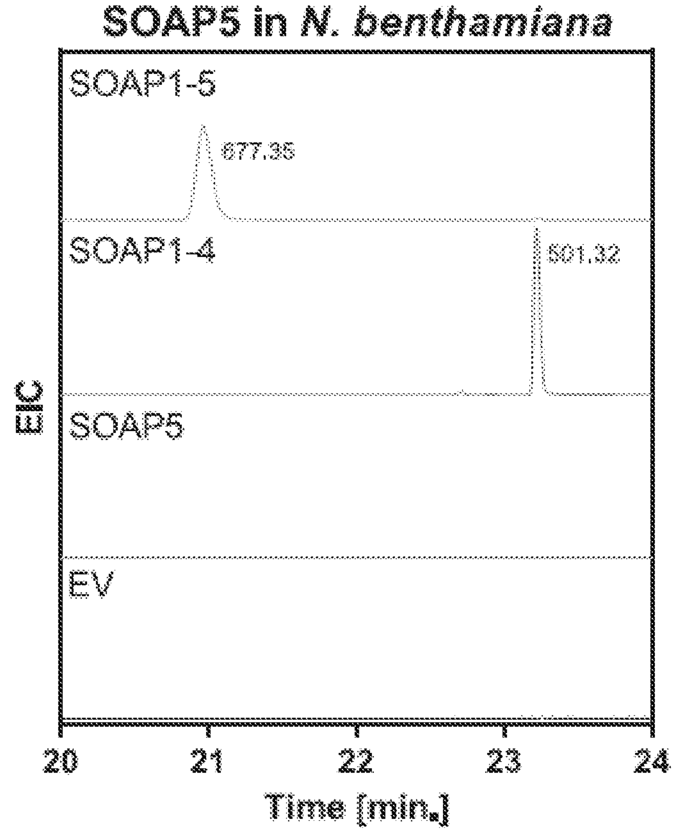
Figure 35B:
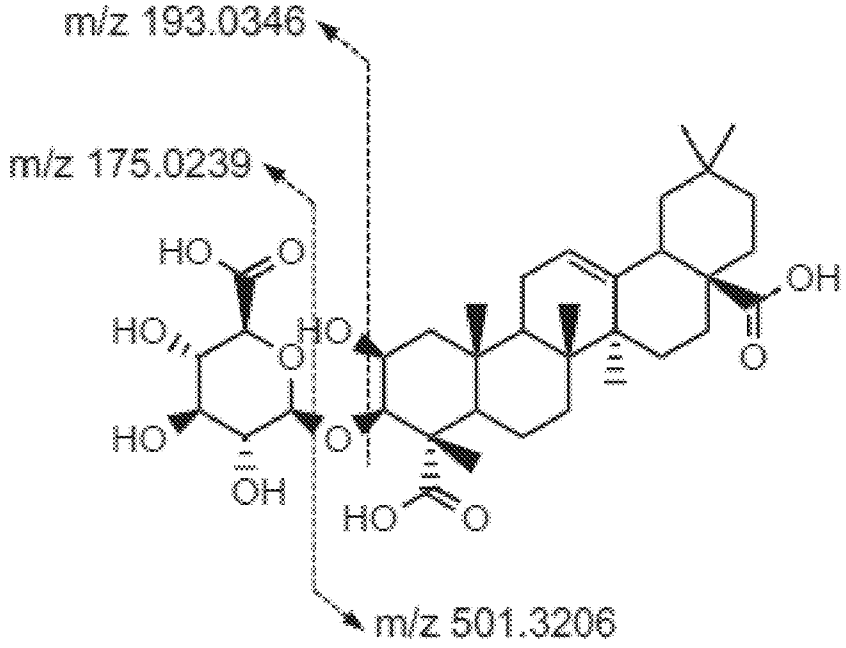
Figure 35C:
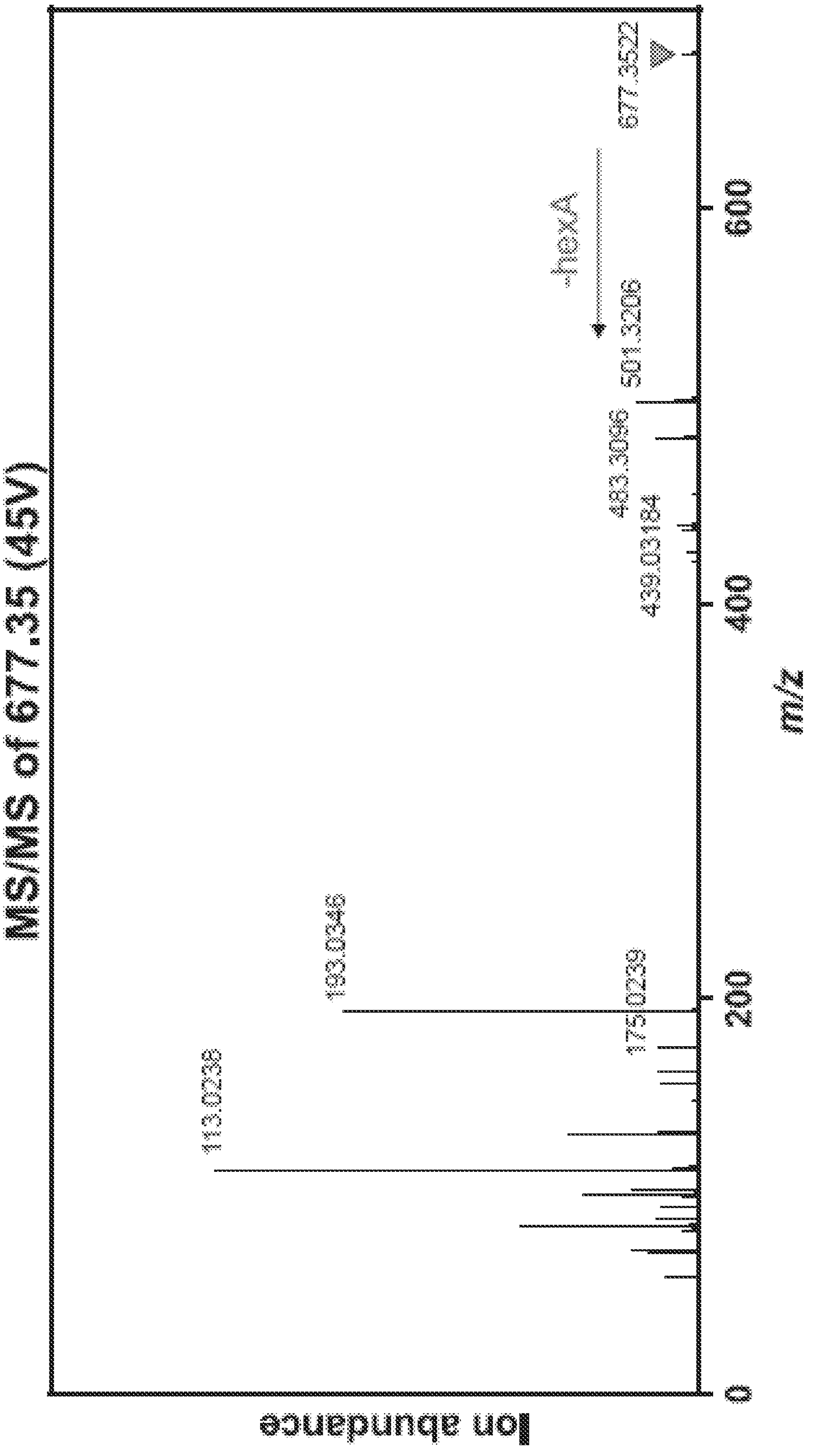

FIGS. 35A-35C present data showing transient expression of SOAP5 (SEQ ID NOS: 65 OR 93) in *N. benthamiana*. (FIG. 35A) EIC of medicagenic acid and medicagenic acid 3-glucuronide [m/z=501.32 (MA), m/z=677.35 (MA-3-GlcA), in negative ion mode] from plants transiently expressing SOAPs1-5 (SEQ ID NOs: 45, 46, 51, 53, and 65, respectively), compared to plants expressing SOAPs1-4 alone (SEQ ID NOs: 45, 46, 51, and 53, respectively), SOAP5 alone (SEQ ID NOS: 65 OR 93) and to control (empty vectror-EV). Chromatograms are to scale. (FIG. 35B) Structure of MA-3-GlcA with marked fragmentation routes (FIG. 35C) MS/MS of MA-3-GlcA [45V, negative ion mode], arrow indicates loss of glucuronic acid moiety. (FIG. 35D) shows important HMBC correlations of the hydrogens of medicagenic acid 3-O-glucuronide (MA-3-GlcA). Black arrows represent HMBC correlations of the six methyl groups of MA-3-GlcA. Red arrows represent HMBC correlations of other (selected)hydrogens of MA-3-GlcA. Numbers correspond to carbon atoms in medicagenic acid and glucuronic acid moiety. For more details see Table 1.

Figure 36A:
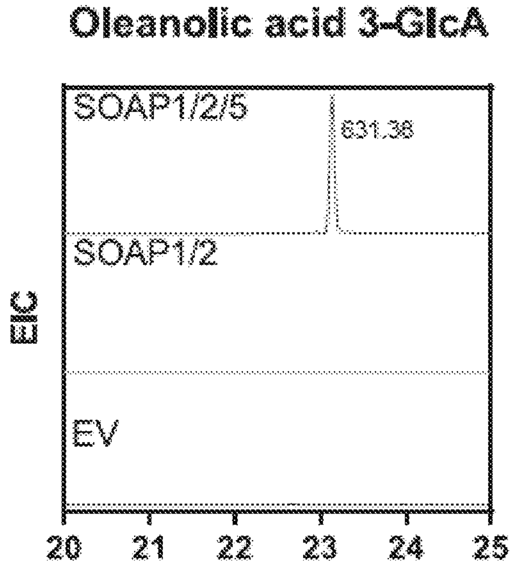
Figure 36B:
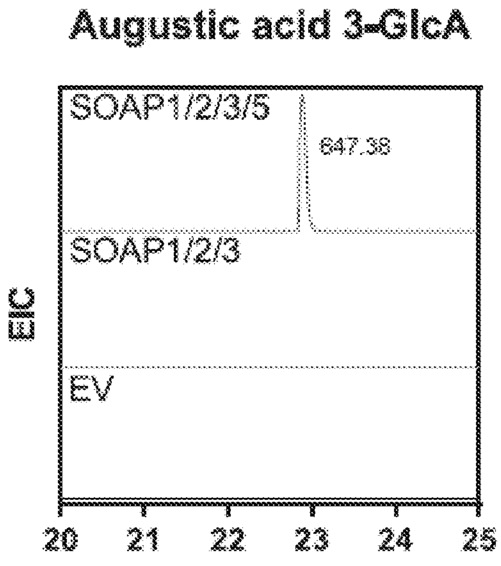
Figure 36C:
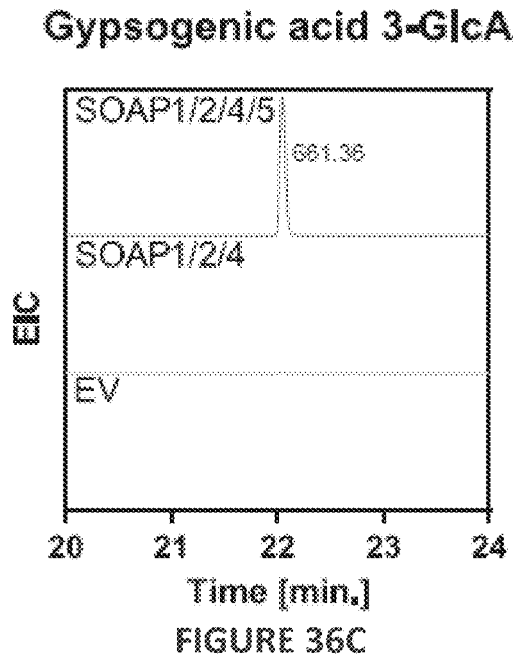
Figure 36D:
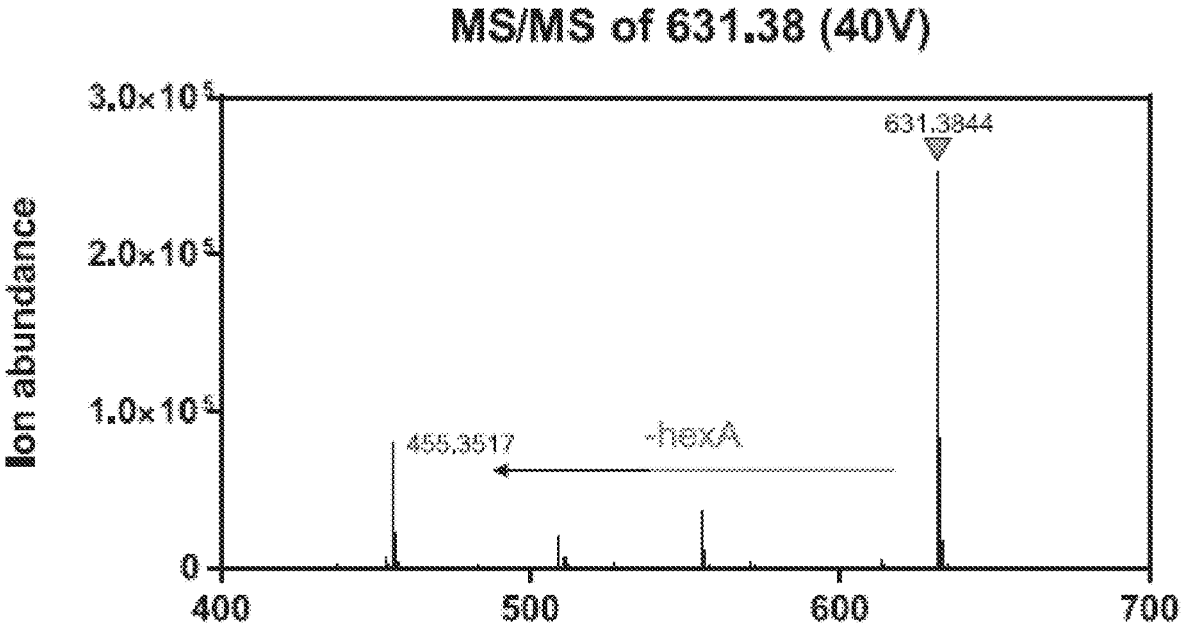
Figure 36E:
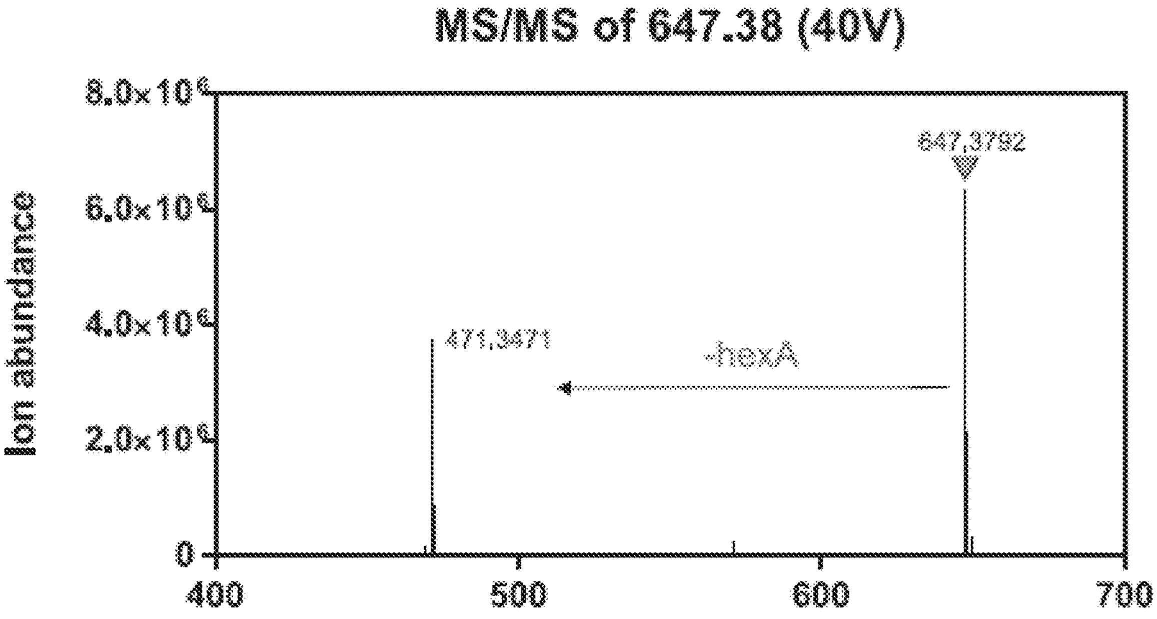
Figure 36F:
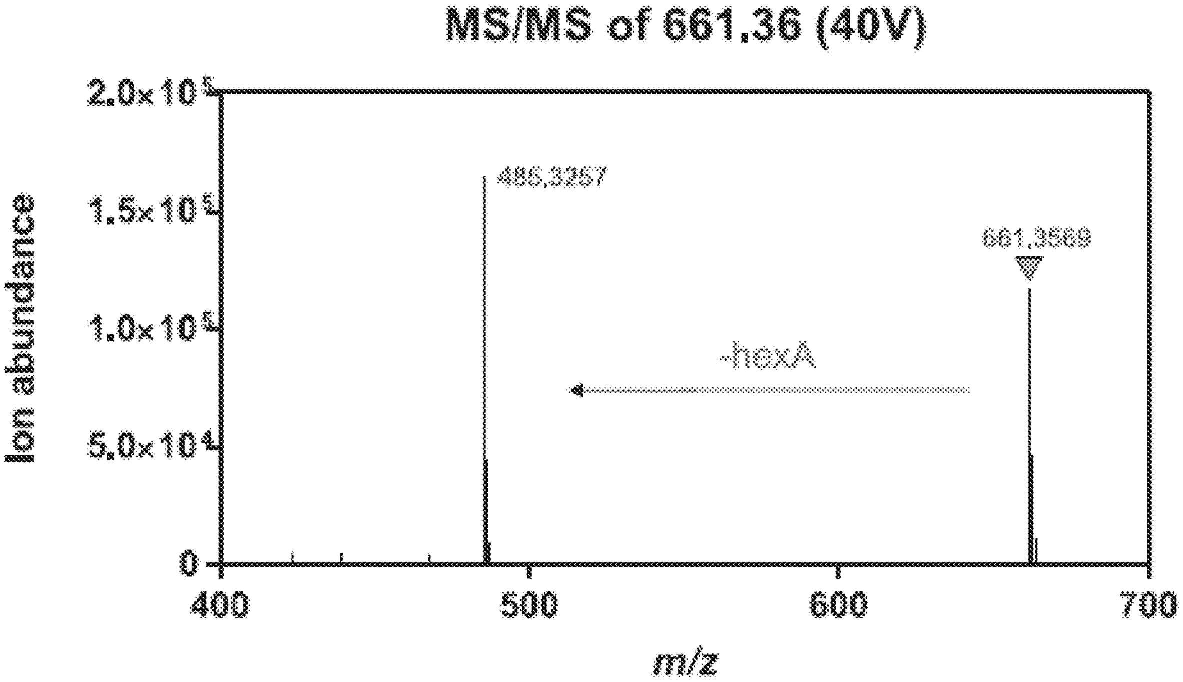
Figure 37A:
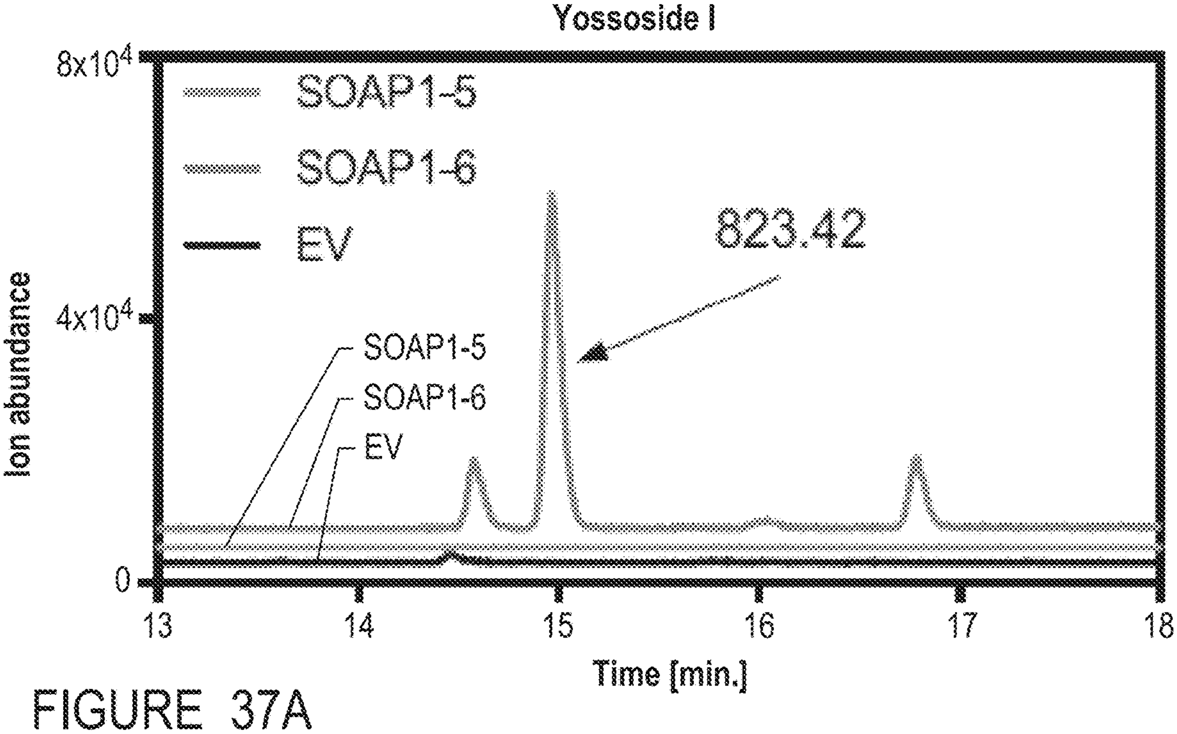
Figure 37B:
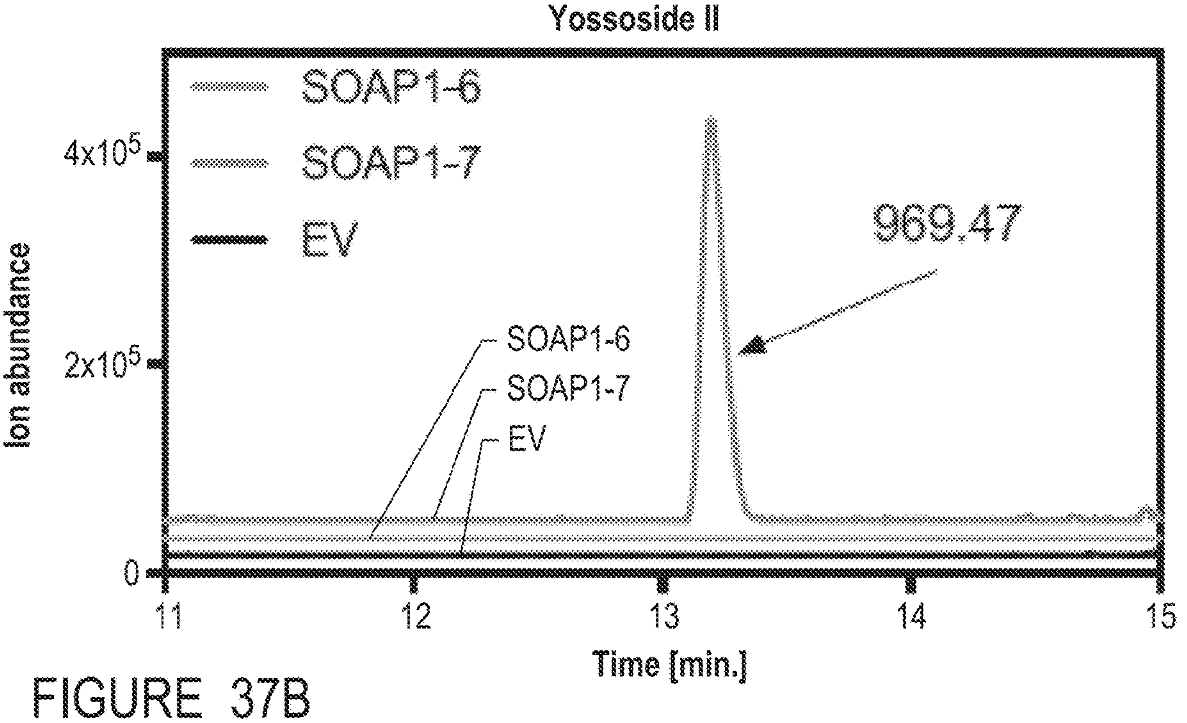
Figure 37C:
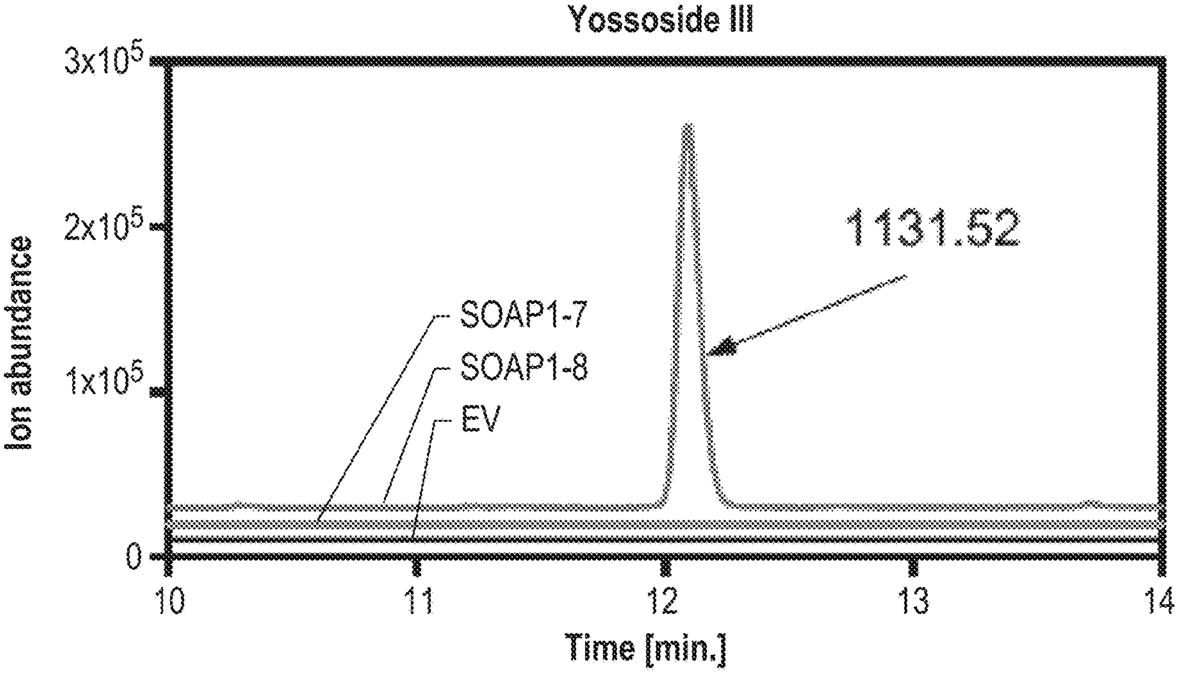
Figure 37D:
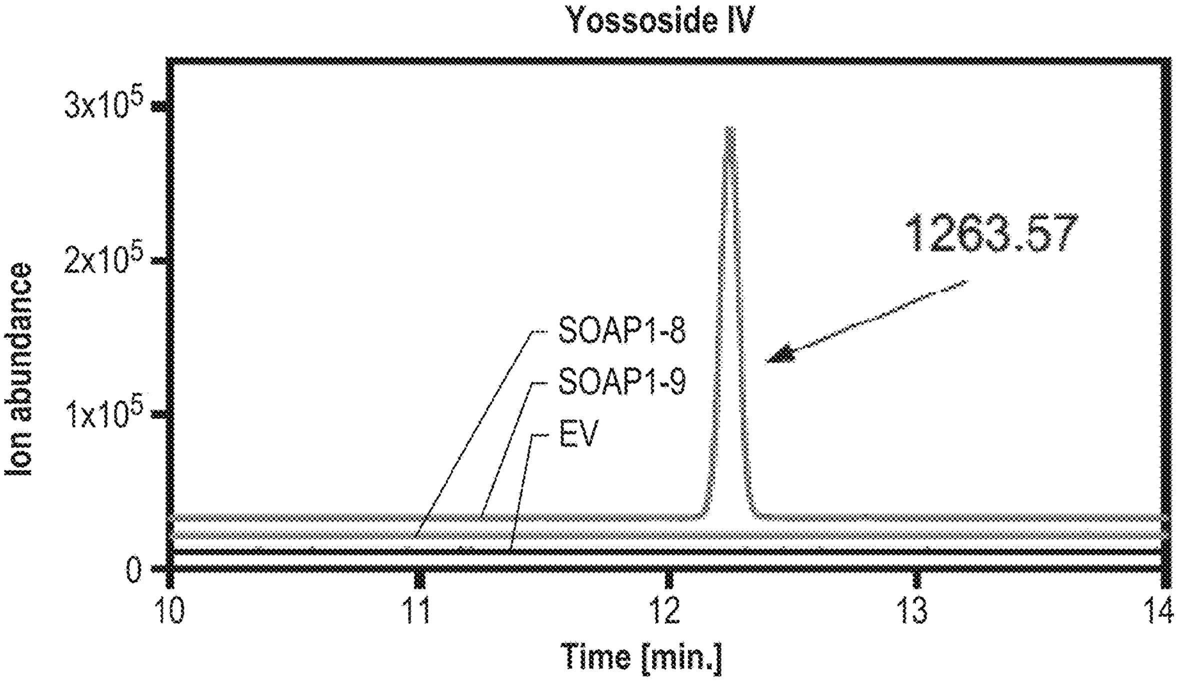
Figure 37E:
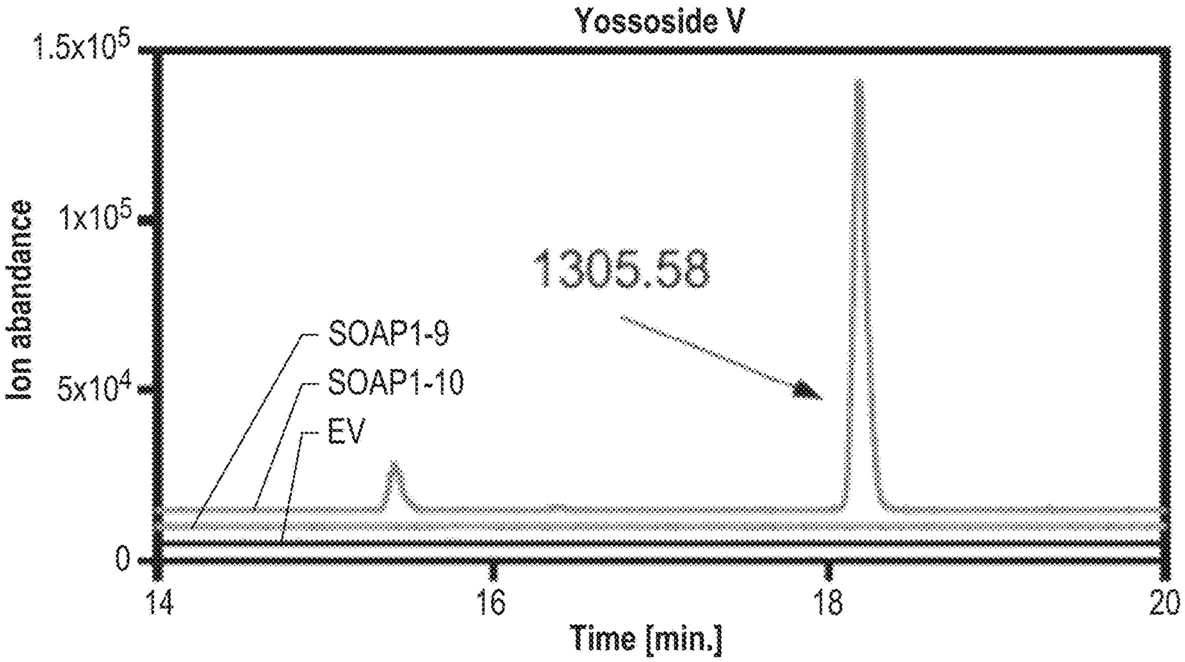
Figure 38A:
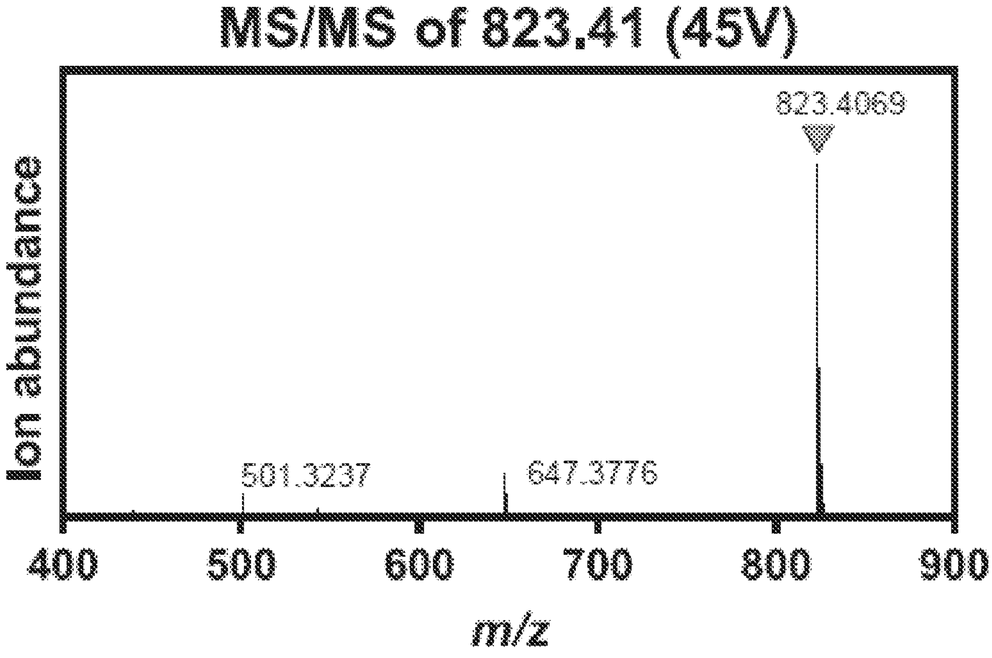
Figure 38B:
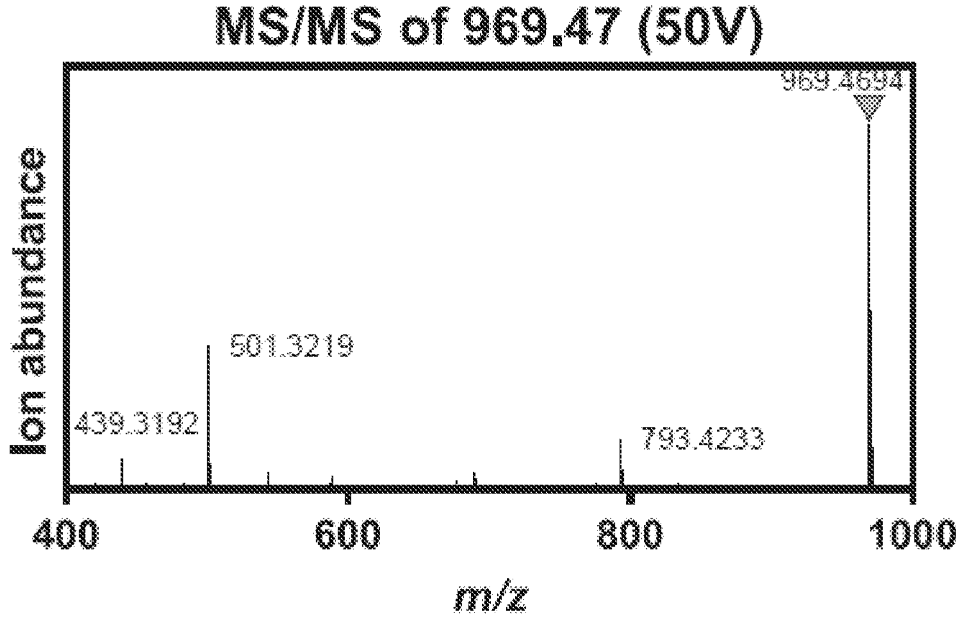
Figure 38C:
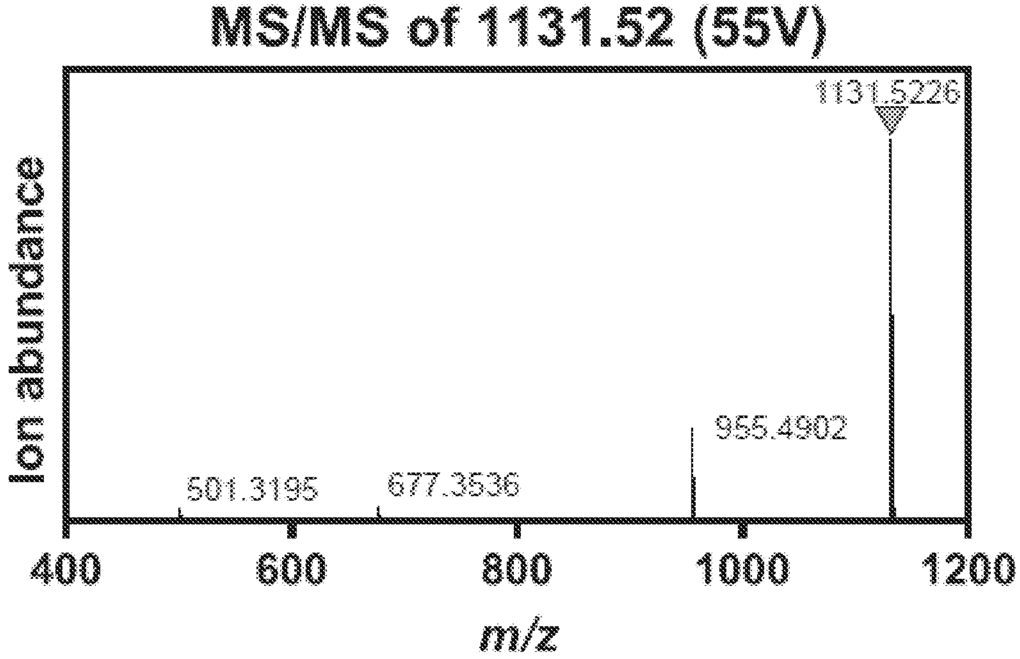
Figure 38D:
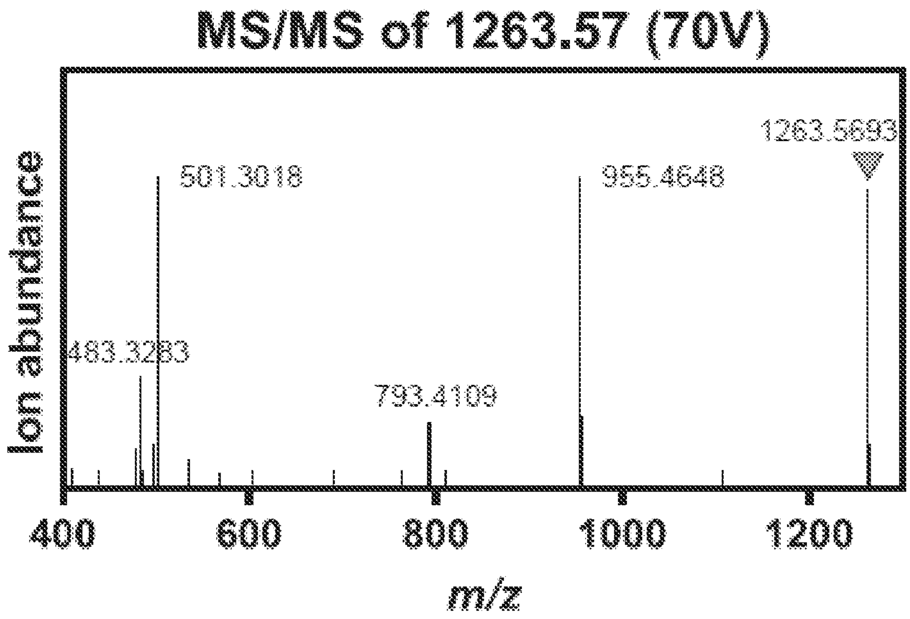
Figure 38E:
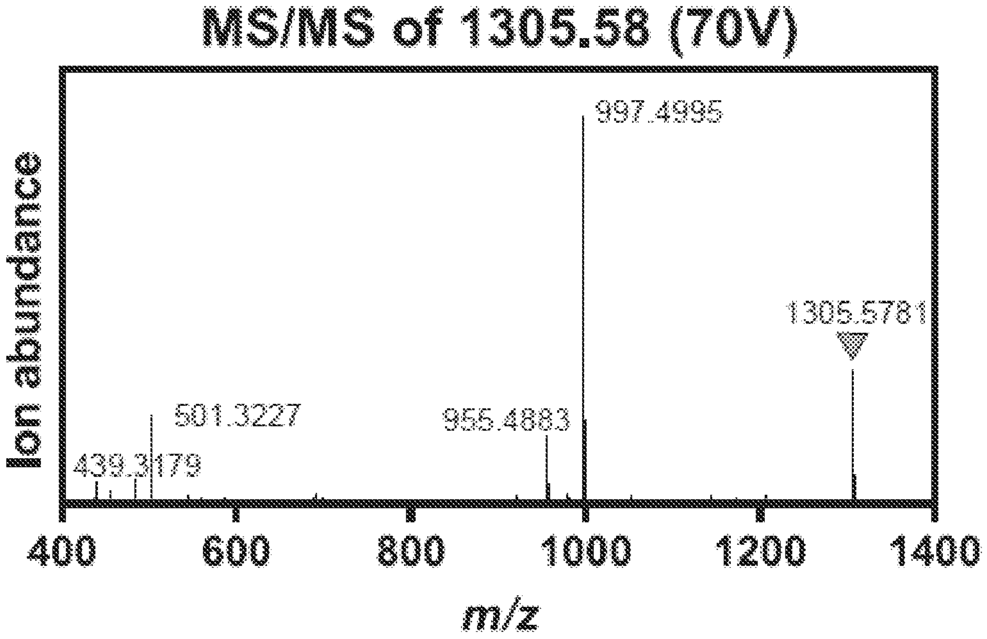

FIGS. 36A-36F present the substrate specificity of SOAP5 (SEQ ID NO: 66) (See Table 16). EIC of oleanolic acid 3-GlcA (FIG. 36A), augustic acid 3-GlcA (FIG. 36B), and gypsogenic acid 3-GlcA (FIG. 36C) [m/z=631.38 (OA-3-GlcA); m/z=647.38 (AA-3-GlcA); m/z=661.35 (GA-3-GlcA), in negative ion mode] from plants transiently expressing SOAP1/2/5 (FIG. 36A), SOAP1/2/3/5 (FIG. 36B), SOAP1/2/4/5 (FIG. 36C) compared to plants expressing same set of SOAPs without SOAP5 and to control (EV). Chromatograms are to scale. (FIGS. 36D, 36E, and 36F show tandem mass spectroscopy (MS/MS) of glucuronate derivatives from FIGS. 36A, 36B, and 36C, respectively, [40V, negative ion mode], arrows indicate loss of glucuronic acid (Am/z=176.03; GlcA-H2O).

FIGS. 37A-37E show the products of SOAPs activity in *N. benthamiana*. EICs of Yossoside I (m/z=823.42) (FIG. 37A), Yossoside II (m/z=969.27) (FIG. 37B), Yossoside III (m/z=1131.52) (FIG. 37C), Yossoside IV (m/z=1263.57) (FIG. 37D) and Yossoside V (m/z=1305.58) (FIG. 37E) from plants expressing transiently combinations of SOAP genes indicated on each chromatogram. For MS/MS spectra see FIG. 40B.

FIGS. 38A-38E shows mass spectroscopy (MS) based identification of the main products of SOAPs activity in *N. benthamiana*. (FIG. 38A) MS/MS of Yossoside I (Compound 7)—product of SOAP6 activity on MA-3-GlcA. (FIG. 38B) MS/MS of Yossoside II (Compound 8)—product of SOAP7 activity on Yossoside I. (FIG. 38C) MS/MS of Yossoside III (Compound 9)—product of SOAP8 activity on Yossoside II. (FIG. 38D) MS/MS of Yossoside IV (Compound 10)—product of SOAP9 activity on Yossoside III. (FIG. 38E) MS/MS of Yossoside V (Compound 11)—product of SOAP10 activity on Yossoside IV.

Figure 39A:
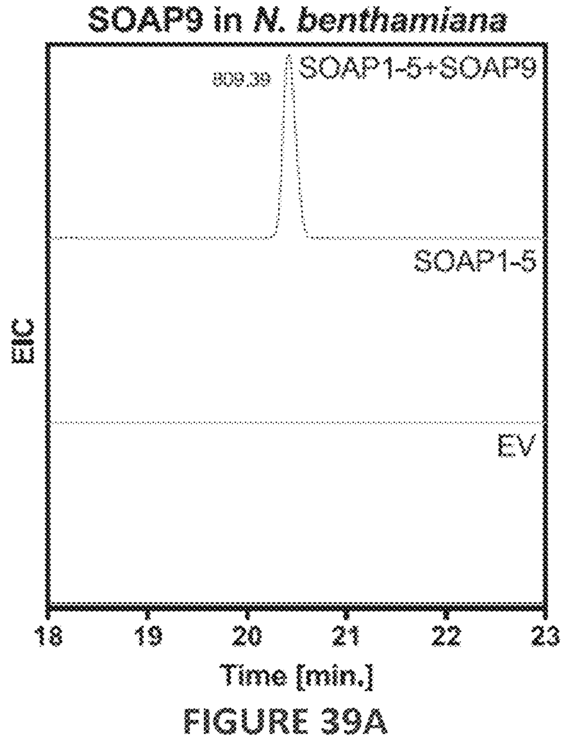
Figure 39B:
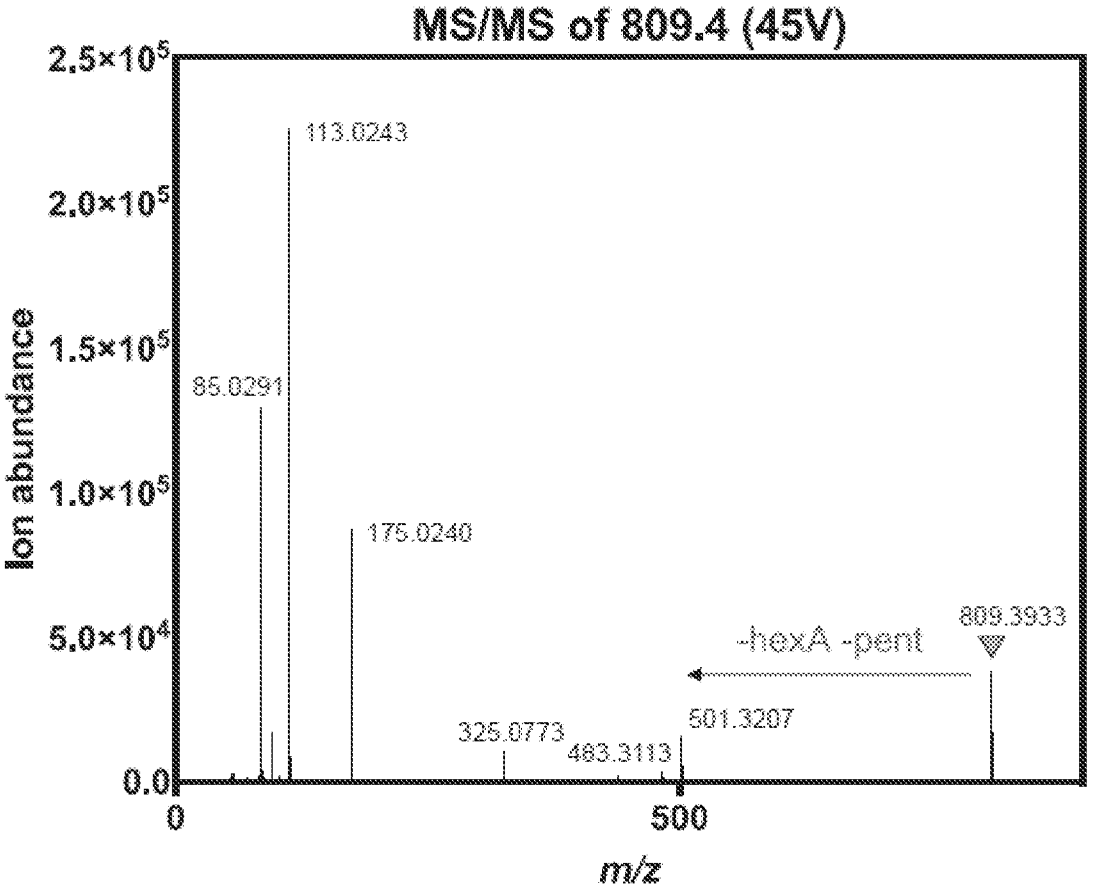
Figure 39C:
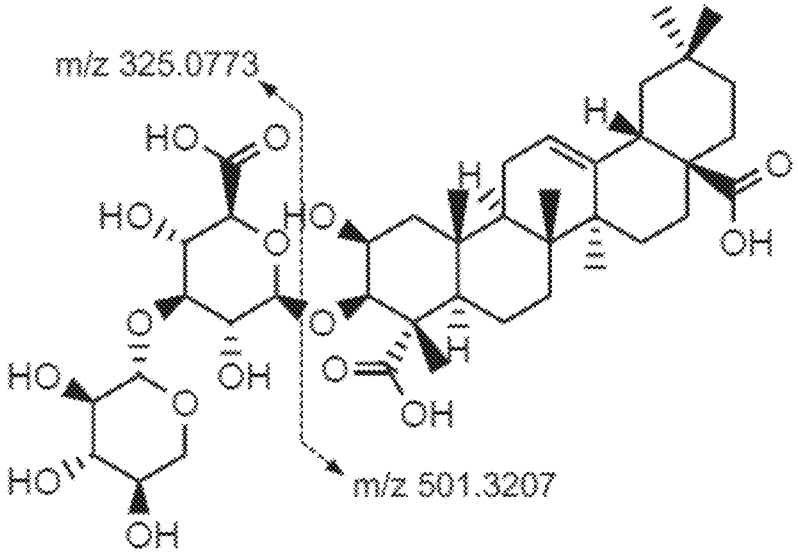

FIGS. 39A-39C present the results of SOAP9 activity in *N. benthamiana*. (FIG. 39A) EIC of medicagenic acid 3-GlcA-Xyl [m/z=809.40 in negative ion mode] from plants transiently expressing SOAP1-5+SOAP9 compared to plant expressing SOAP1-5 alone and to control (EV). (See Table 16) (FIG. 39B) MS/MS of 809.4 (45V), arrow indicates loss of glcA-xyl moiety (Am/z=308.07). (FIG. 39C) Structure of the SOAP9 product (Compound 10) with fragmentation patterns indicated by arrows.

Figure 40A:
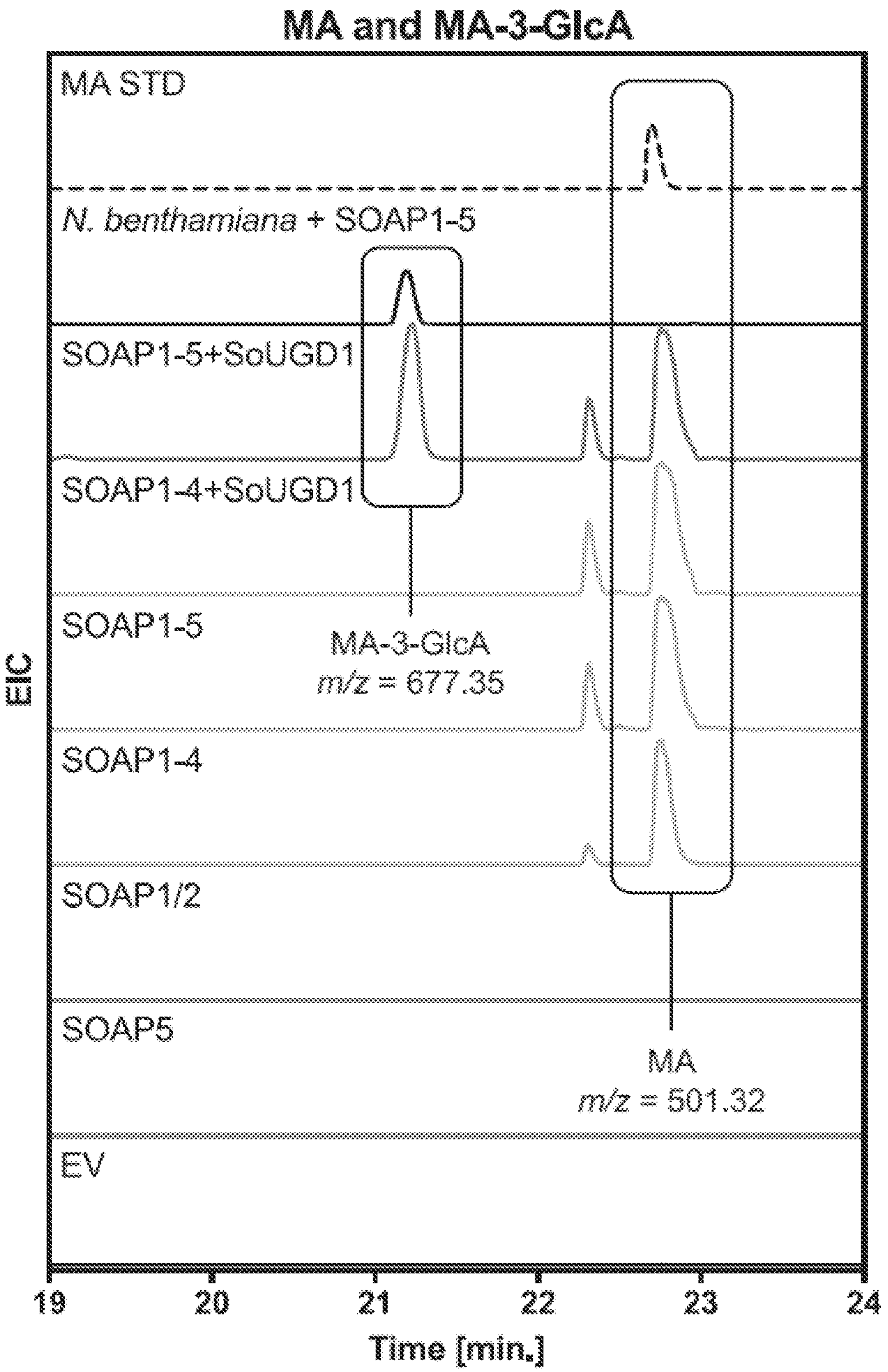
Figure 40B:
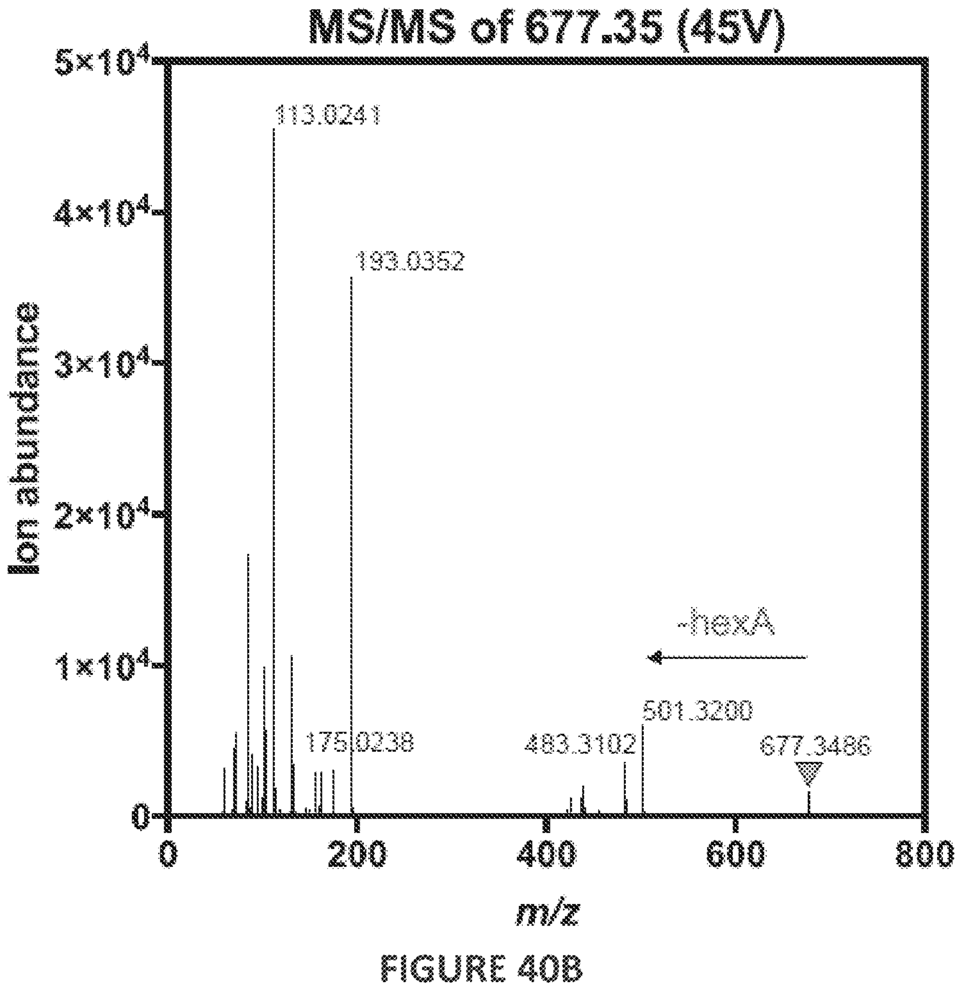
Figure 41A:
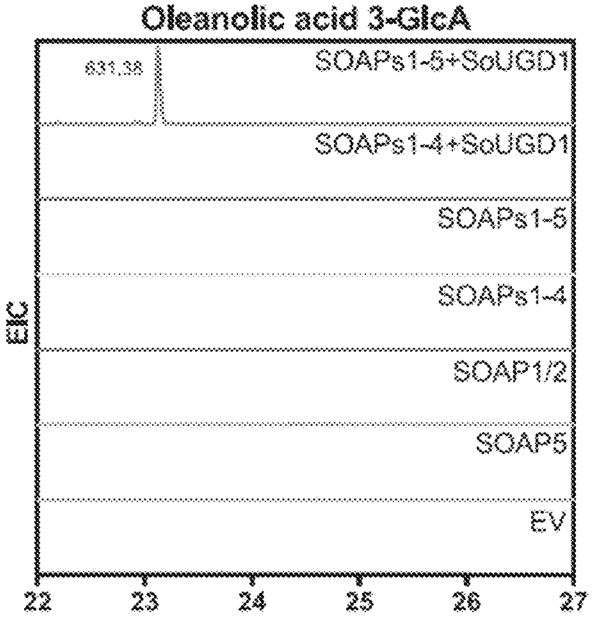
Figure 41B:
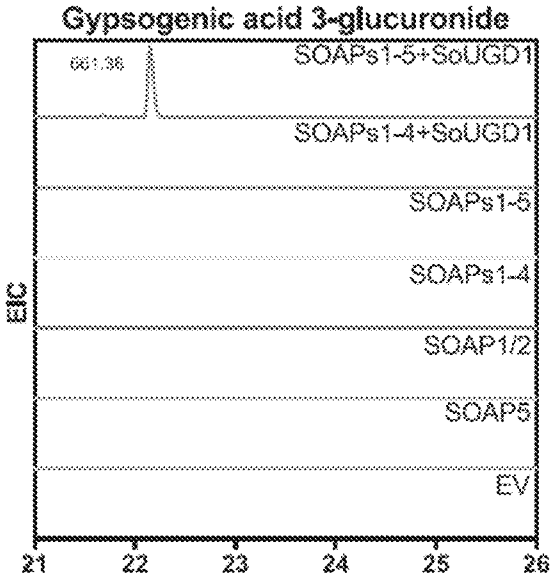
Figure 41C:
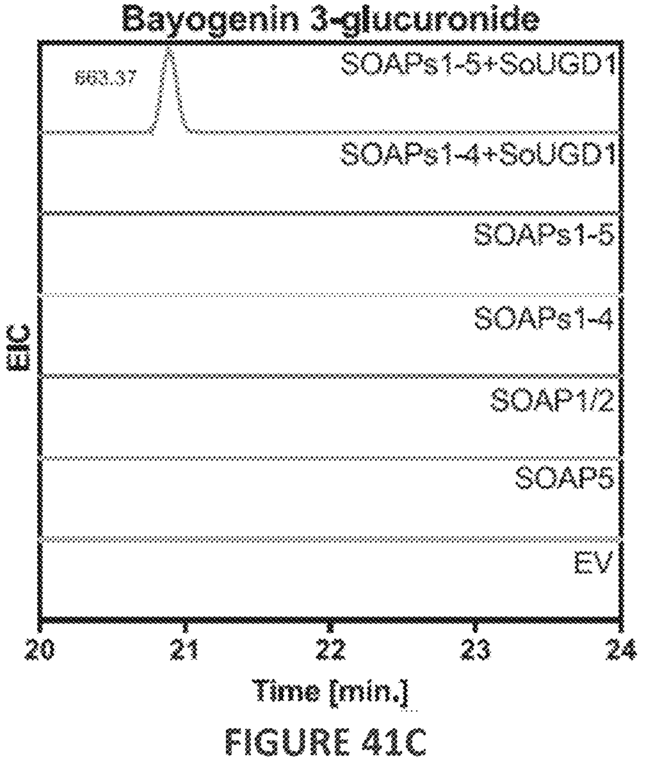
Figure 41D:
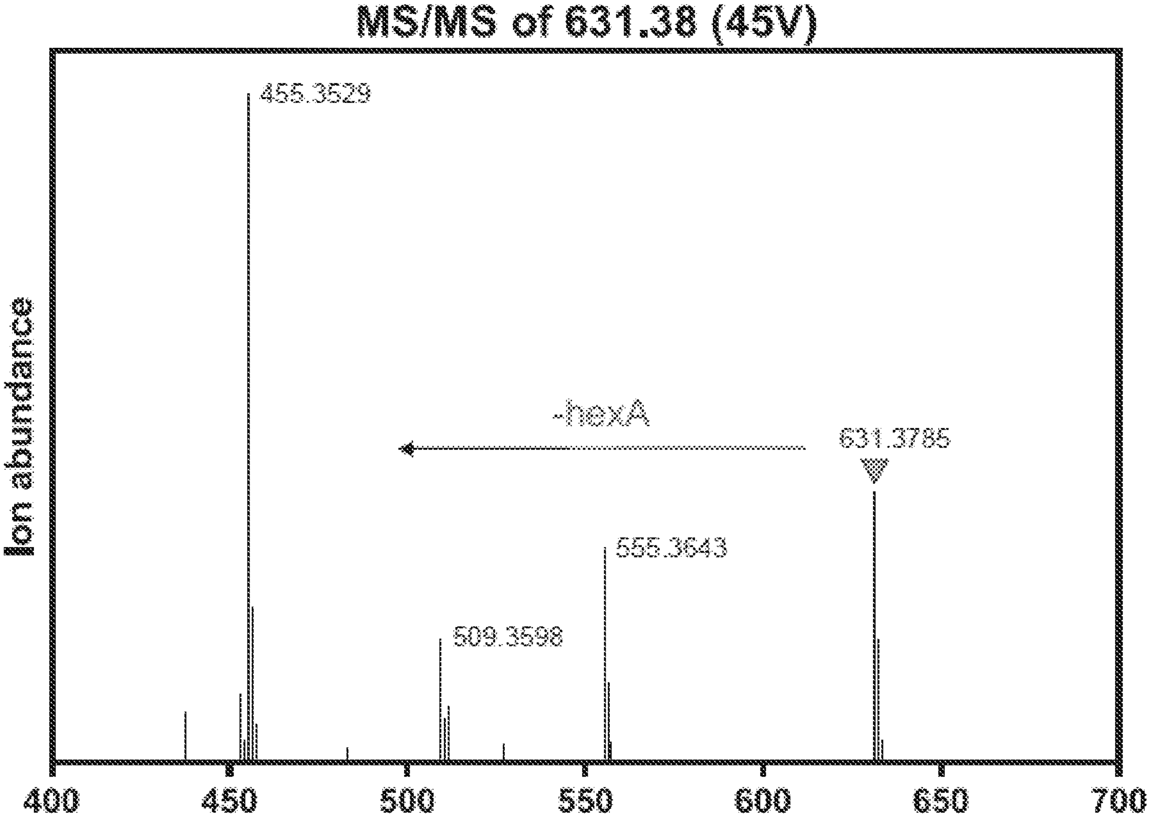
Figure 41E:
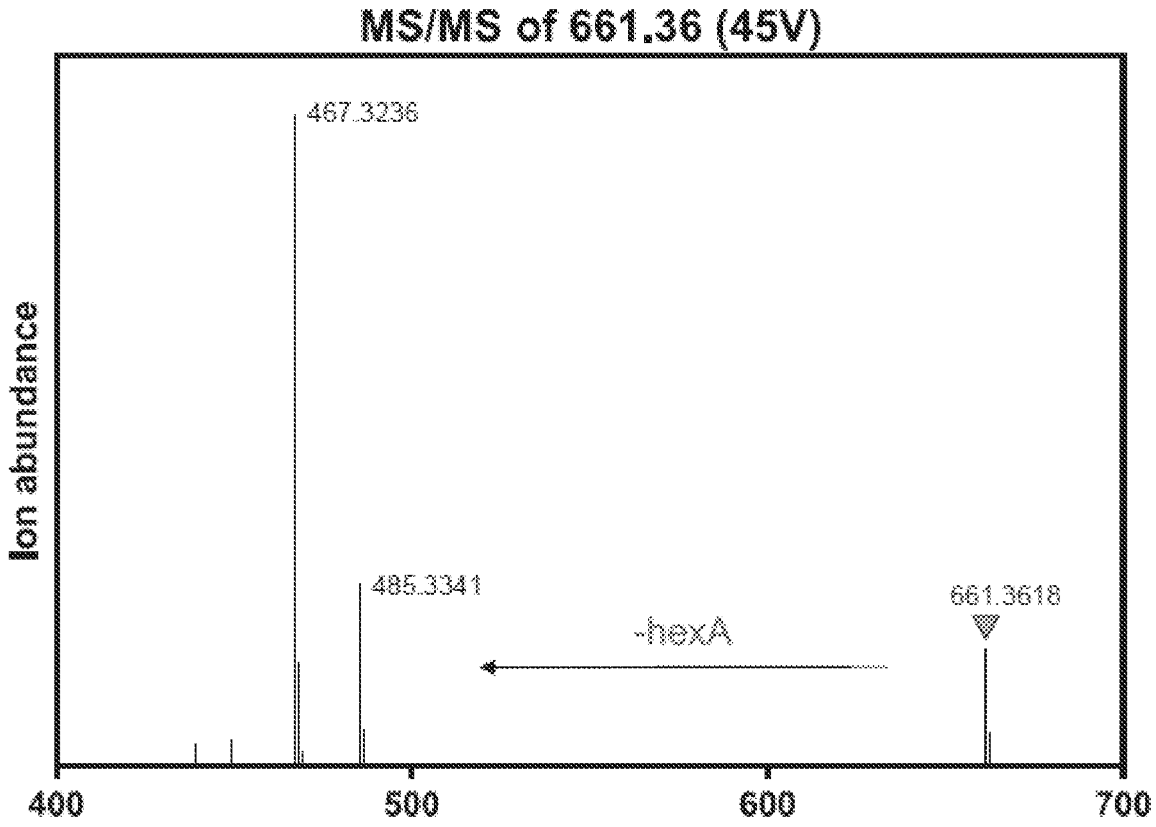
Figure 41F:
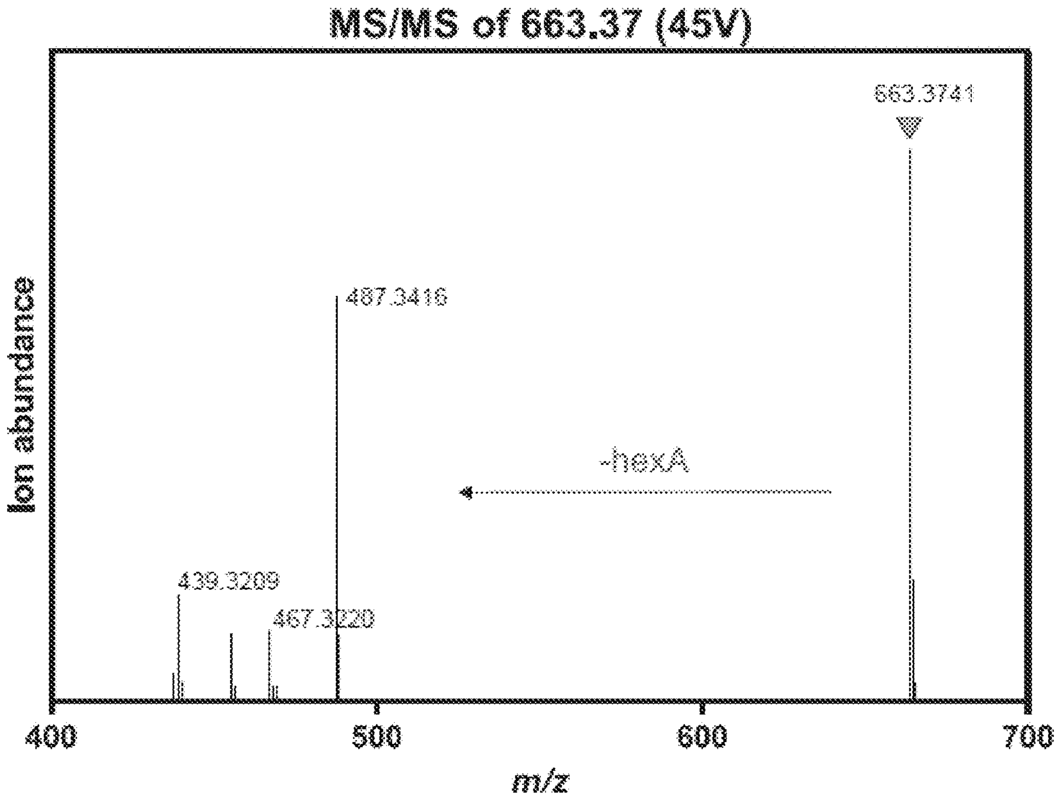

FIGS. 40A-40B show the results of expression of SOAP5 in yeast. (FIG. 40A) EIC of medicagenic acid and medicagenic acid 3-GlcA [m/z=501.32 (MA); m/z=677.35 (MA-3-GlcA), in negative ion mode] from yeast expressing SOAP1-5+UGD1 (SEQ ID NO: 74 [gene] and SEQ ID NO: 75 [protein]) compared to plants expressing SOAP1-5, yeast controls and to medicagenic acid authentic standard. Chromatograms are to scale. (FIG. 40B) MS/MS of medicagenic acid 3-GlcA from yeast cells [45 V, negative ion mode], arrows indicate loss of glucuronic acid.

FIGS. 41A-41F show SOAP5 substrate specificity in yeast cells. EIC of oleanolic acid 3-GlcA (FIG. 41A), gypsogenic acid 3-GlcA (FIG. 41B) and Bayogenin 3-GlcA (FIG. 41C) [m/z=631.38 (OA-3-GlcA); m/z=661.35 (GA-3-GlcA); m/z=663.37 (Bayogenin-3-GlcA), in negative ion mode] from yeast expressing SOAP1-5+UGD1 compared to cells expressing SOAP1-4+UGD alone, SOAP1-5 alone, SOAP1-4, SOAP1-2, SOAP5 alone, and to control (EV). Chromatograms are to scale. (FIGS. 41D, 41E, and 41F) MS/MS of glucuronate derivarives from A, B and C [45V, negative ion mode], arrows indicate loss of glucuronic acid (Am/z=176.03; GlcA-H2O).

FIGS. 42A-42F show Glucuronosyltransferase activity of Cellulose Synthase Like G (CSLG) enzymes is conserved among species belonging to phylogenetically distant orders. (FIG. 42A) The phylogenetic tree depicts close evolutionary relationship of SOAP5 from spinach with some CSLG proteins from *Caryophyllales, Malvales, Apiales, Fabales*, and *Solanales*. The tree consists of proteins belonging to Cellulose Synthase (CESA) and several families of Cellulose Synthase Like enzymes (CSLA, CSLB, CSLE and CSLG). Dotted line encircles clades with CSLG proteins, while blown up region corresponds to CSLG closely related to spinach SOAP5 including GAME15 and CSLG in the *Fabales* ordera. (FIG. 42B) Medicagenic acid is glucuronidated by CSLG from many species. EIC of MA-3-GlcA [m/z=677.35 in negative ion model of samples from *N. benthamiana* leaves transiently expressing SOAP1-4 combined with CSLG proteins from spinach (SOAP5; SEQ ID NO: 66), *Chenopodium quinoa* (CqCSL; SEQ ID NO: 96), *Beta vulgaris* (BvCSL; SEQ ID NO: 94), *Medicago sativa* (MsCSL; SEQ ID NO: 98), *Glycine max* (GmCSL; SEQ ID NO: 100), *Glycyrrhiza uralensis* (GuCSL; SEQ ID NO: 81 or SEQ ID NO: 102) and Lotus *japonicus* (LjCSL; SEQ ID NO: 104), compared to plants expressing SOAP1-4 alone and to control (EV). (FIG. 42C) Cellulose synthase like G proteins are key enzymes in the biosynthesis of triterpenoid saponins in multiple plant species. B-Amyrin (in the center) is oxidized by cytochromes P450 (doubled circle around β-Amyrin) giving rise to multiple aglycons (1—bayogenin; 2—serjanic acid; 3—oleanolic acid; 4—medicagenic acid; 5—glycyrrhetinic acid; 6—soyasapogenol A; 7—soyasapogenol B) that are decorated by CSLGs (double circle around aglycons 1-7) and other glycosyltransferases giving rise to triterpenoid saponins (8—bayogenin-hexA-hex-hex (*M. sativa*); 9—serjanic acid -hexA-hex (*Chenopodium quinoa* (*C. quinoa*)); 10 —betavulgaroside IV (*B. vulgaris*); 11—yossoside V (*S. oleracea*); 12—glycyrrhizin (*G. uralensis*); 13—soyasapogenol A—hexA-hex-pent (*L. japonicus*); 14—soyasaponin VI (*G. max*)). (FIG. 42D) Glycyrrhizin biosynthetic pathway in *G. uralensis*. Highlighted functional groups are the result of the activity of specified enzymes. (FIG. 42E) Extracted ion chromatogram (EIC) measurements of glycyrrhetinic acid 3-O-glucuronide and glycyrrhizin [m/z 645.36 and m/z 821.40 in negative ion mode] from *N. benthamiana* leaf samples transiently expressing five genes from glycyrrhizin biosynthetic pathway (bAS (SEQ ID NO: 45)+CYP88D6 (SEQ ID NO: 76)+CYP72A154 (SEQ ID NO: 78)+GuCSL (SEQ ID NO: 80 or SEQ ID NO: 103), and UGT73P12 (SEQ ID NO: 84)) compared to samples expressing four genes (-UGT73P12; (SEQ ID NO: 84)) and to control (bAS (SEQ ID NO: 45)+CYP88D6 (SEQ ID NO: 76)+CYP72A154 (SEQ ID NO: 78)). (FIG. 42F) Presents a phylogenetic tree of Cellulose Synthase Like (CSL) polypeptides with special emphasis on Cellulose Synthaes Like G (CSLG). The lower shaded background region consists of CSLG enzymes from many plant orders (i.e., *Carylophyllales, Fabales, Apiales, Malvales*, and *Solanales*). Within the CSLG enzymes (shaded background), related subclades include the subclade containing CSLG enzymes (in bold) with proven glucuronosyltransferase activity towards triterpenoid aglycones—CSLG from soybean, licorice, *Lotus japonicus*, alfalfa, red beet, *quinoa*, and spinach, and the subclade consisting of CSLGs from Solanales (*Solanum tuberosum*, potato; *Solanum lycopersicum*, tomato; *Solanum dulcamara*, bittersweet) and other orders; enzymes in bold are involved in steroidal alkaloid and steroidal saponin biosynthesis.

Figure 43A:
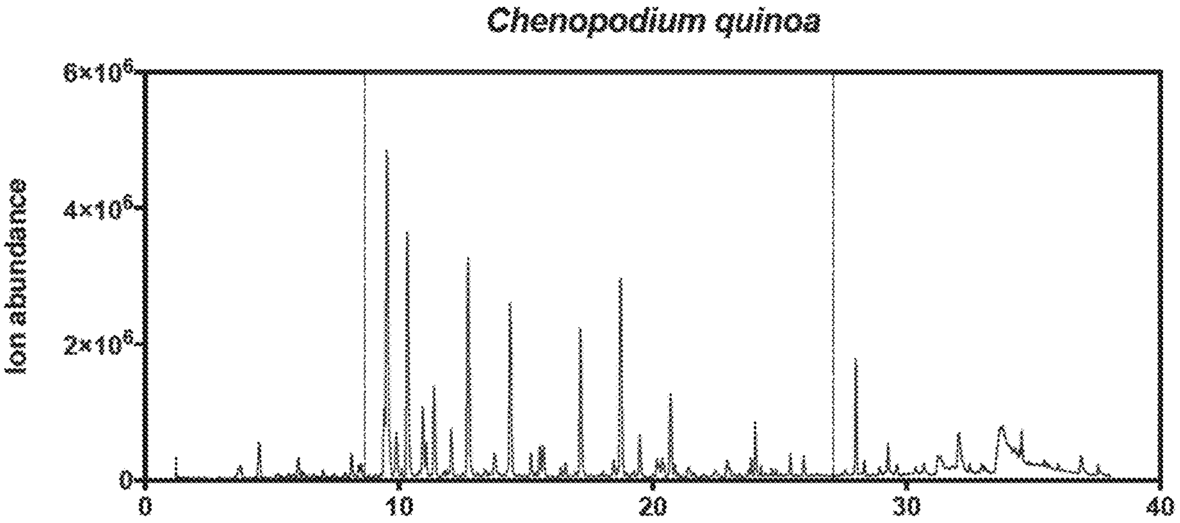
Figure 43B:
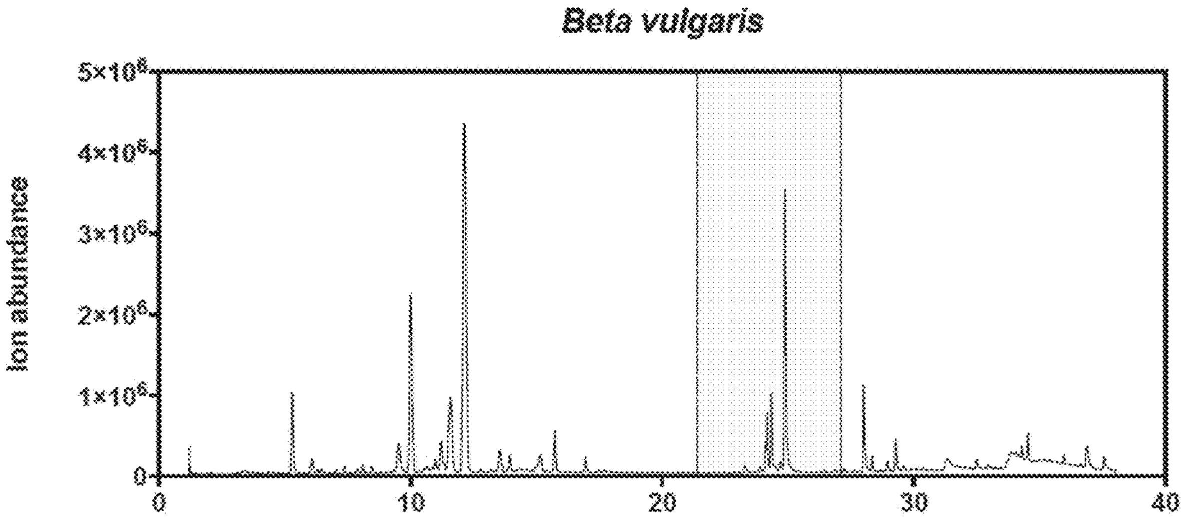
Figure 43C:
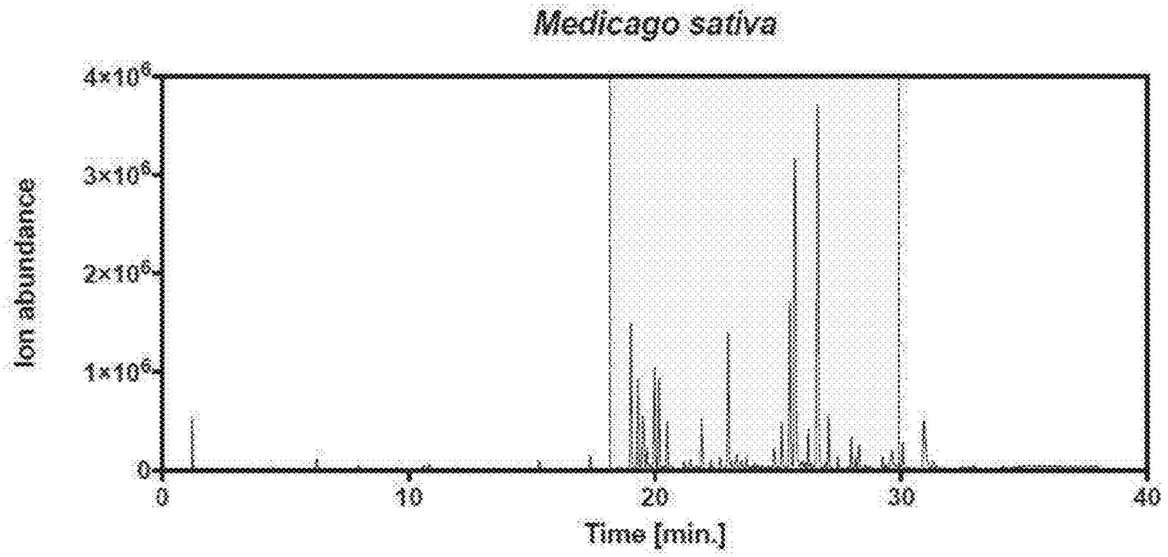

FIGS. 43A-43C shows LC-ESI-QTOF-MS analysis of saponins in *quinoa*, beetroot and alfalfa. Total Ion Chromatogram (TIC) of 80% methanolic extract of (FIG. 43A) one-month old *quinoa* plants (*Chenopodium quinoa* var. Read Head), (FIG. 43B) one-month old beetroot of (*Beta vulgaris* var. Bohan) and (FIG. 43C) 2-week-old seedlings of alfalfa (*Medicago sativa*). Semitransparent rectangles mark chromatogram region with saponins. For putative characterization see Table 12.

Figure 44A:
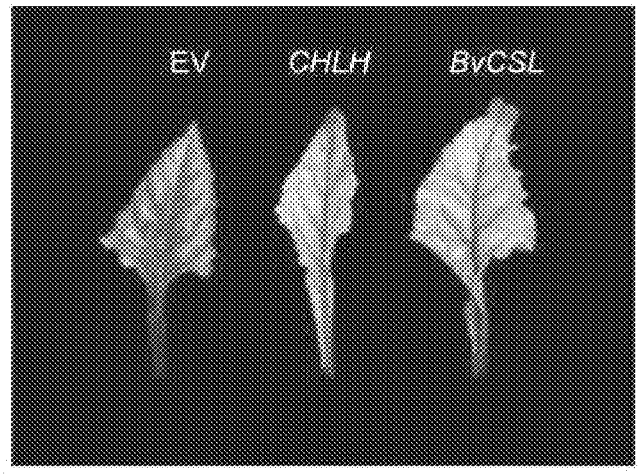
Figure 44B:
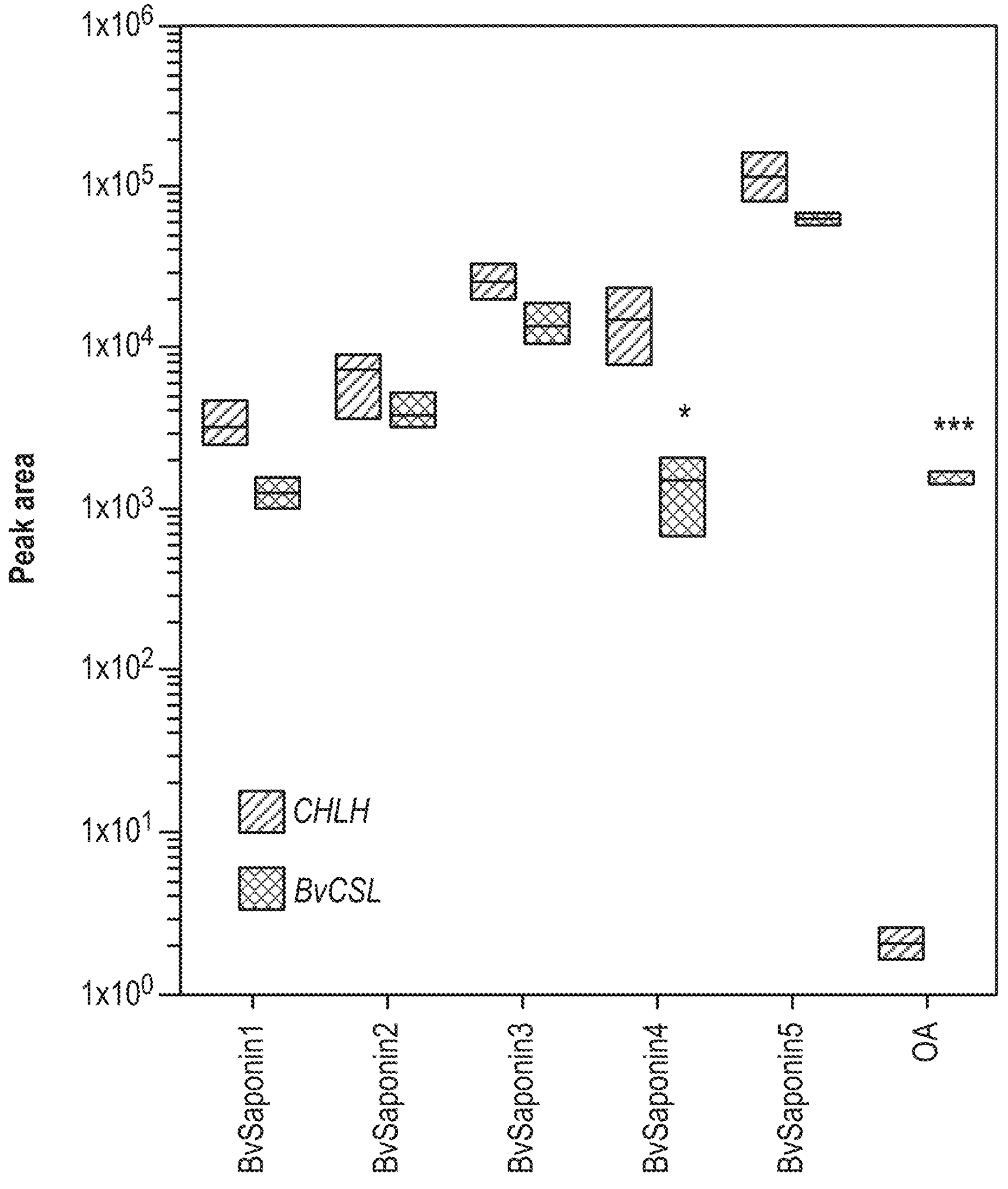
Figure 44C:
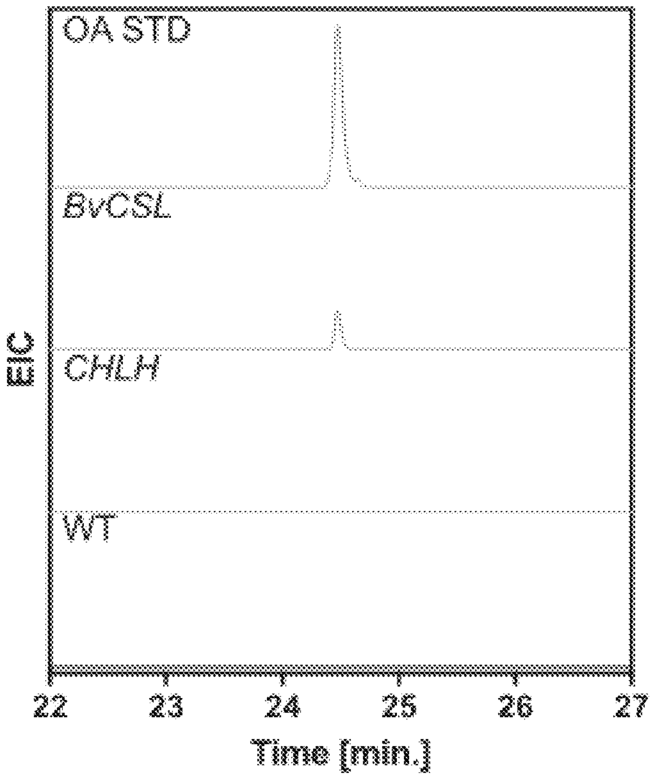

FIGS. 44A-44C show virus induced gene silencing (VIGS) of CSLG in red beet (FIG. 44A) Virus induced gene silencing in red beet; EV—empty vector, CHLH—magnesium chelatase subunit H, BvCSL—beetroot cellulose synthase like G (SEQ ID NO. 95 [gene]; VIGs silencing sequence SEQ ID NO: 107). (FIG. 44B) Analysis of relative content (peak area) of triterpenoid saponins and oleanolic acid in red beet plants with silenced BvCSL. The ordinate axis is in $\log_{10}$ scale. Values represent mean of three independent biological experiments. Statistically significant differences compared with control plants (CHLH silenced alone) are indicated; *P<0.05, *P<0.001. (FIG. 44**C) EIC of oleanolic acid [m/z=455.35, negative ion mode] from plants with silenced BvCSL compared to control (CHLH and WT) and authentic standard. (For metabolite identification see Table 12 *M. saliva*.)

Figure 45A:
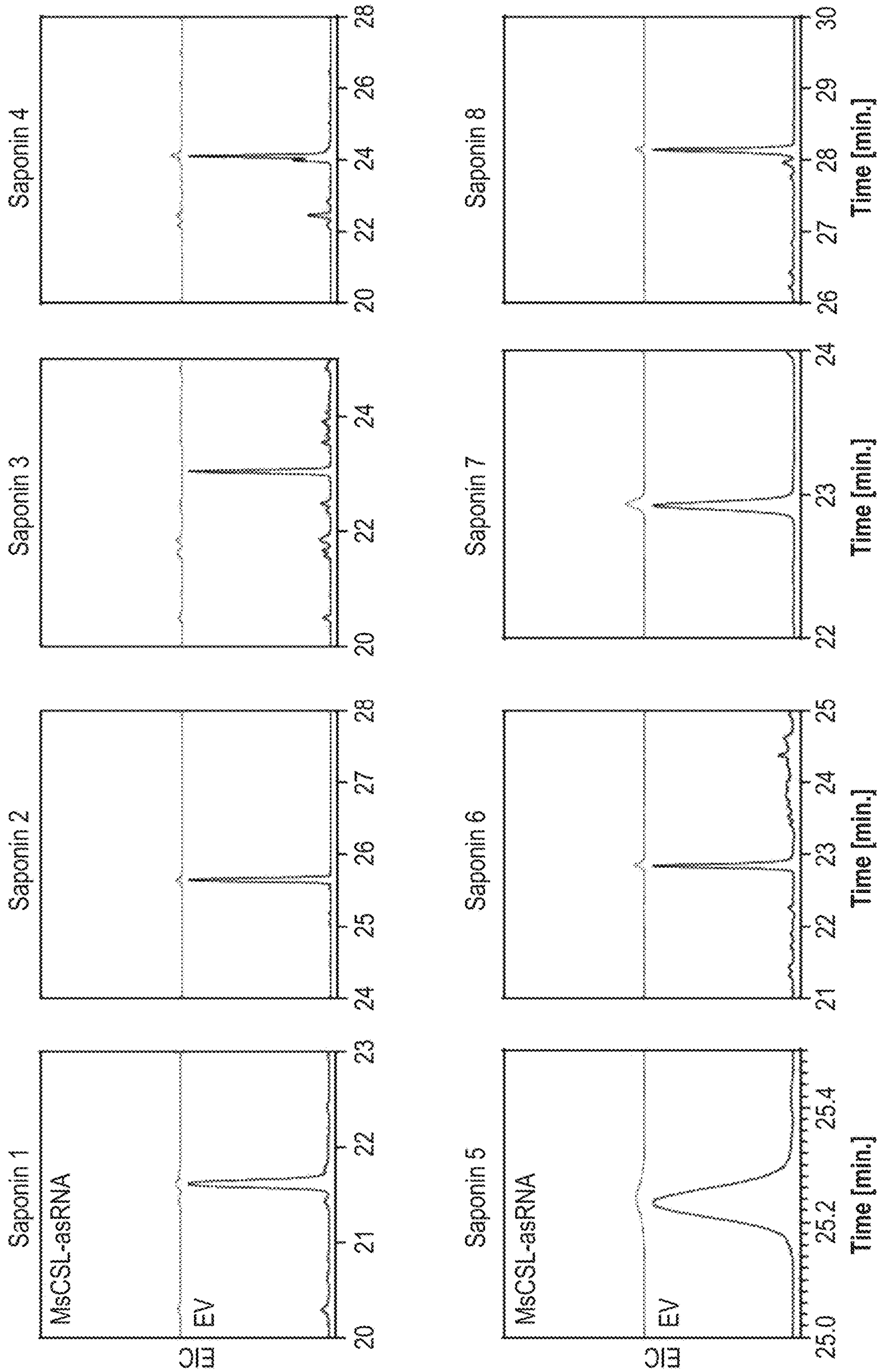
Figure 45B:
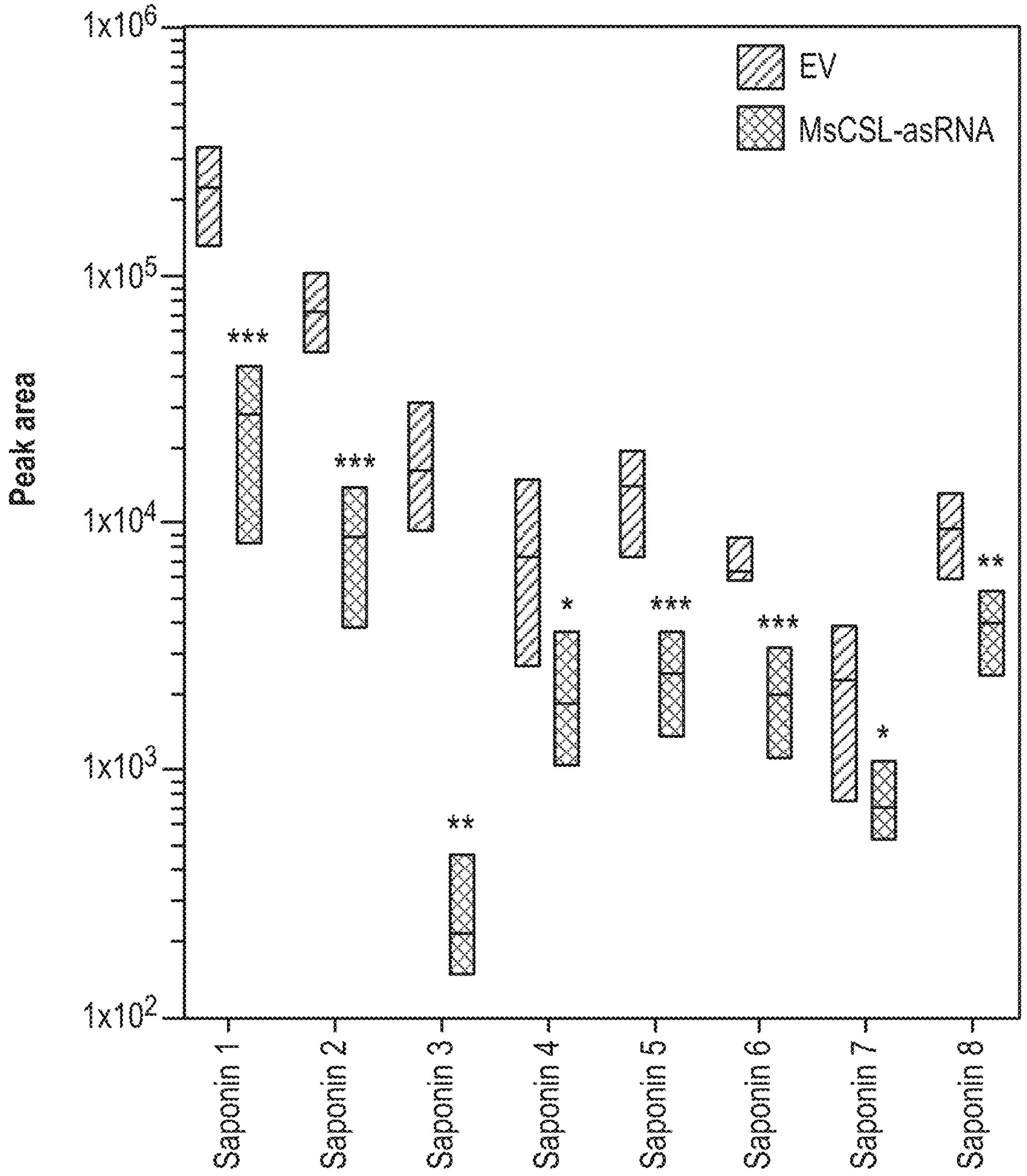
Figure 46A:
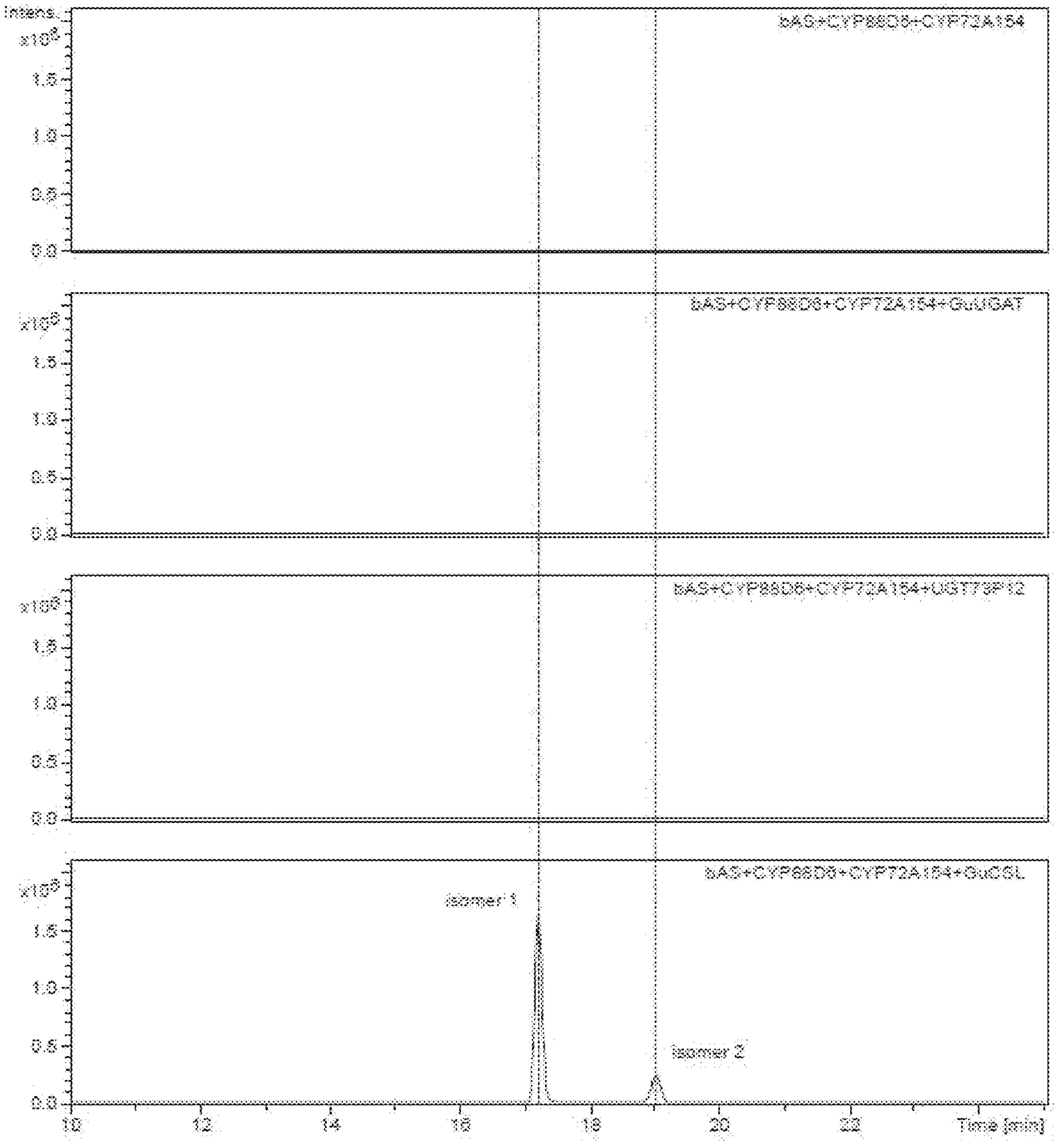
Figure 46B:
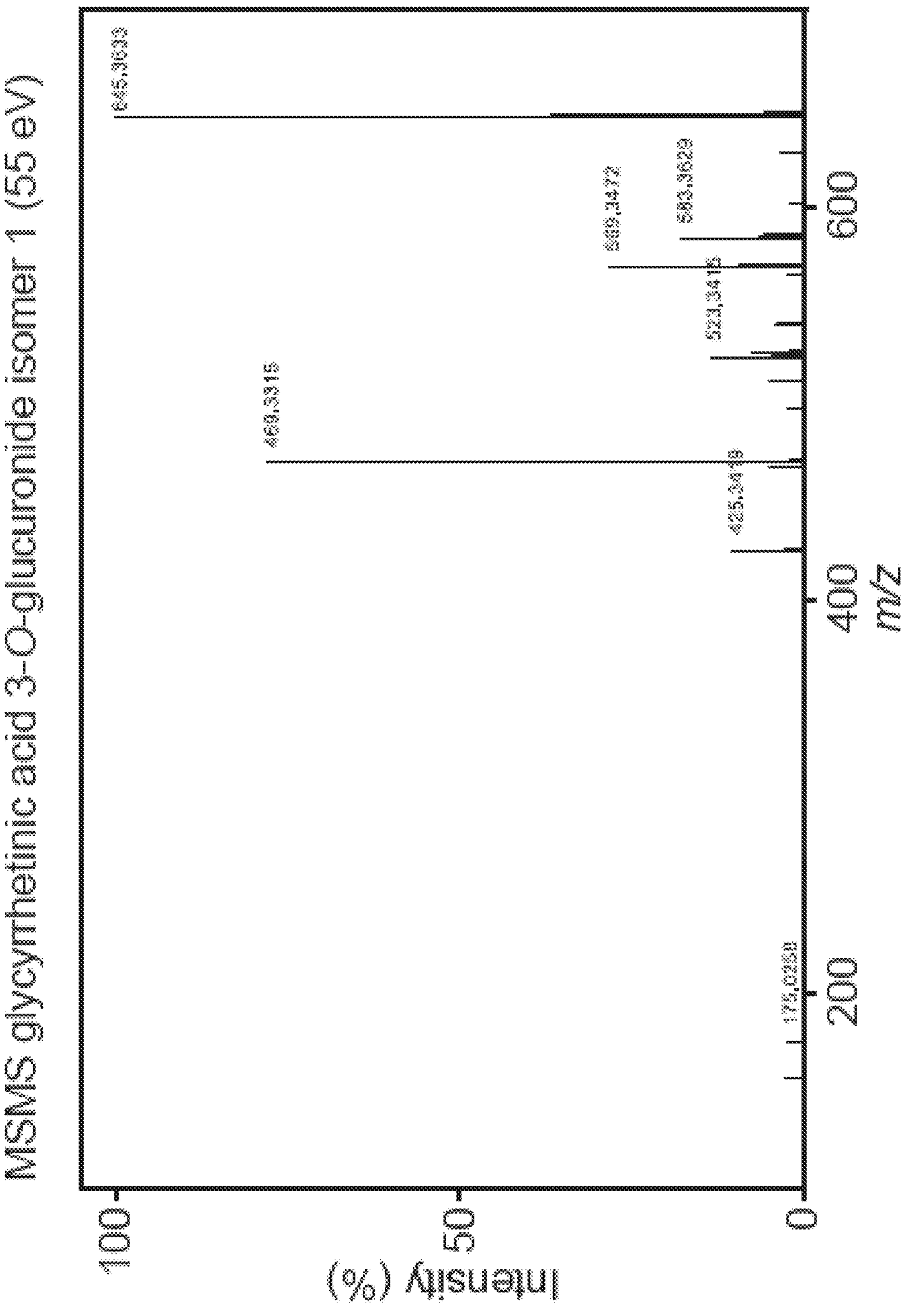
Figure 46C:
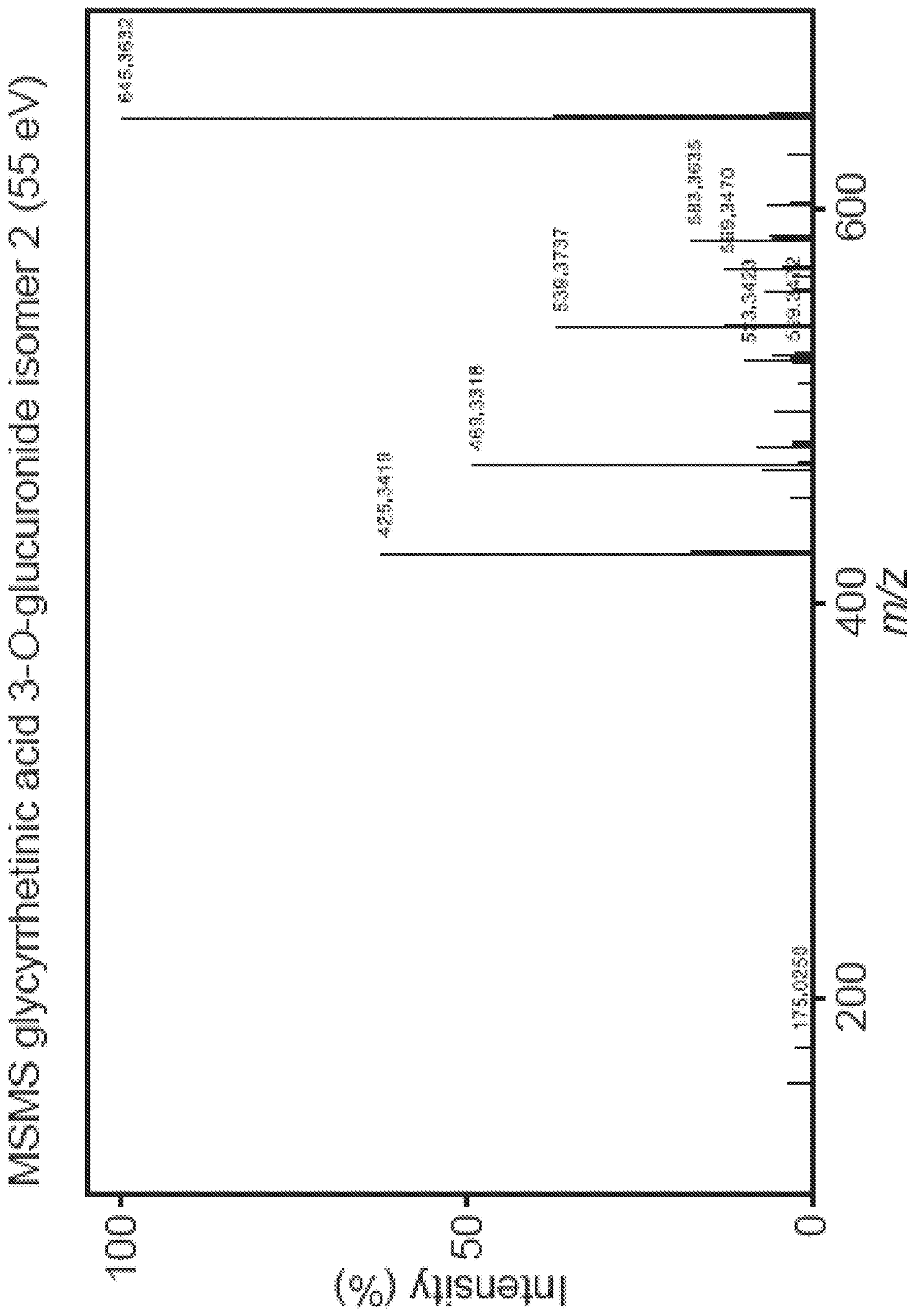
Figure 46D:
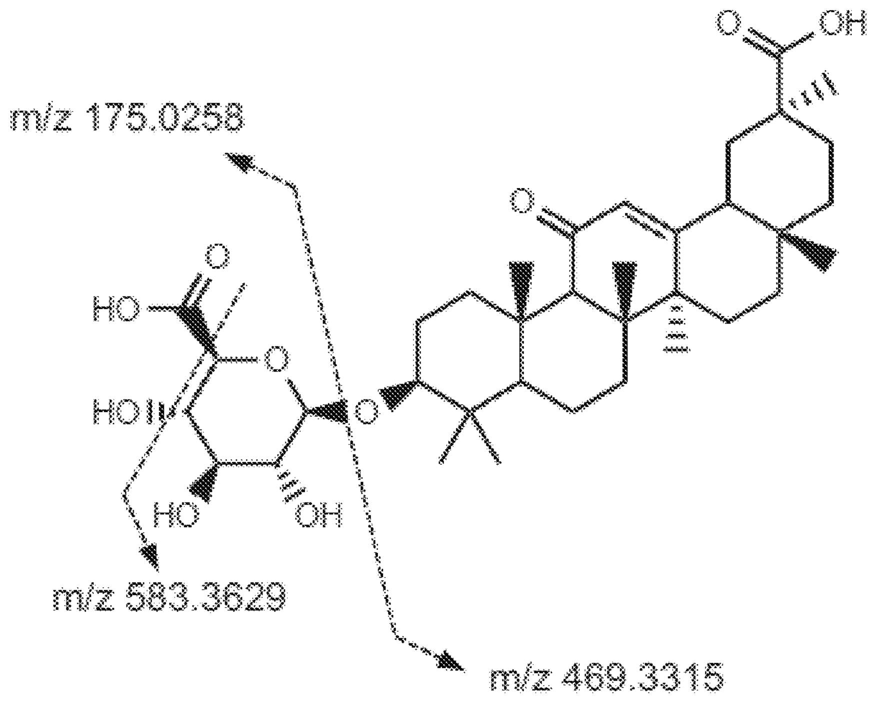
Figure 46E:
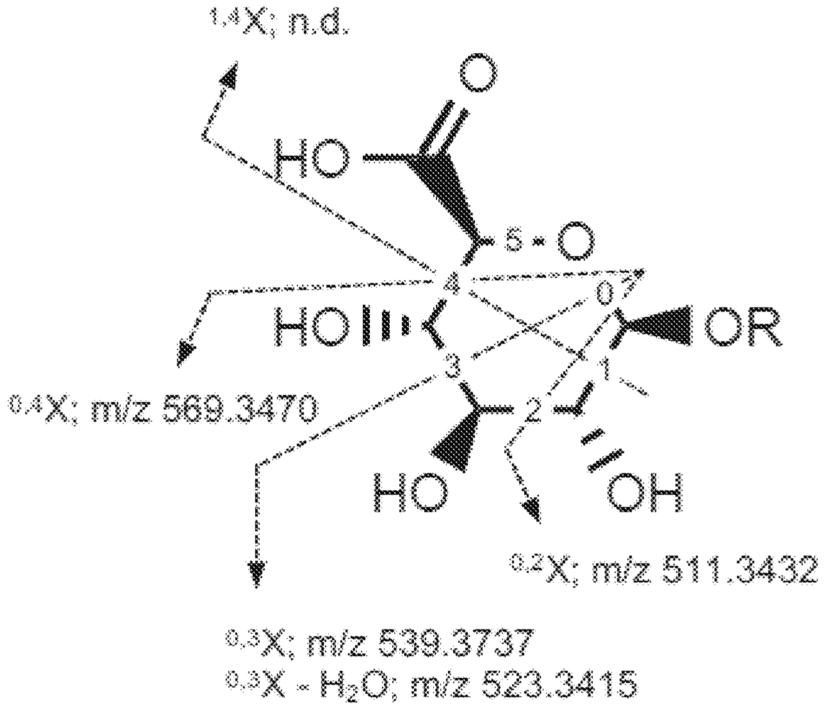
Figure 47A:
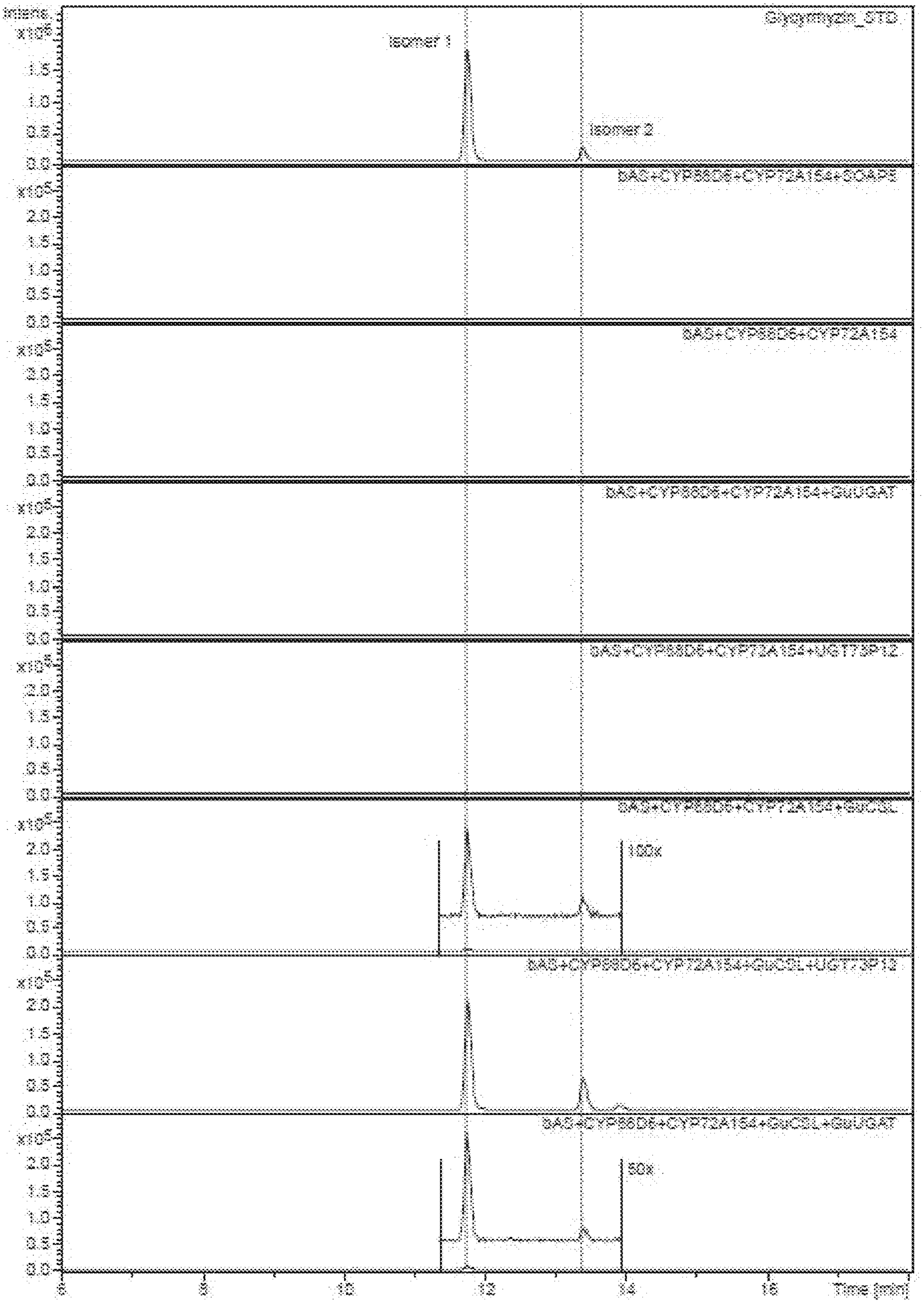
Figure 47B:
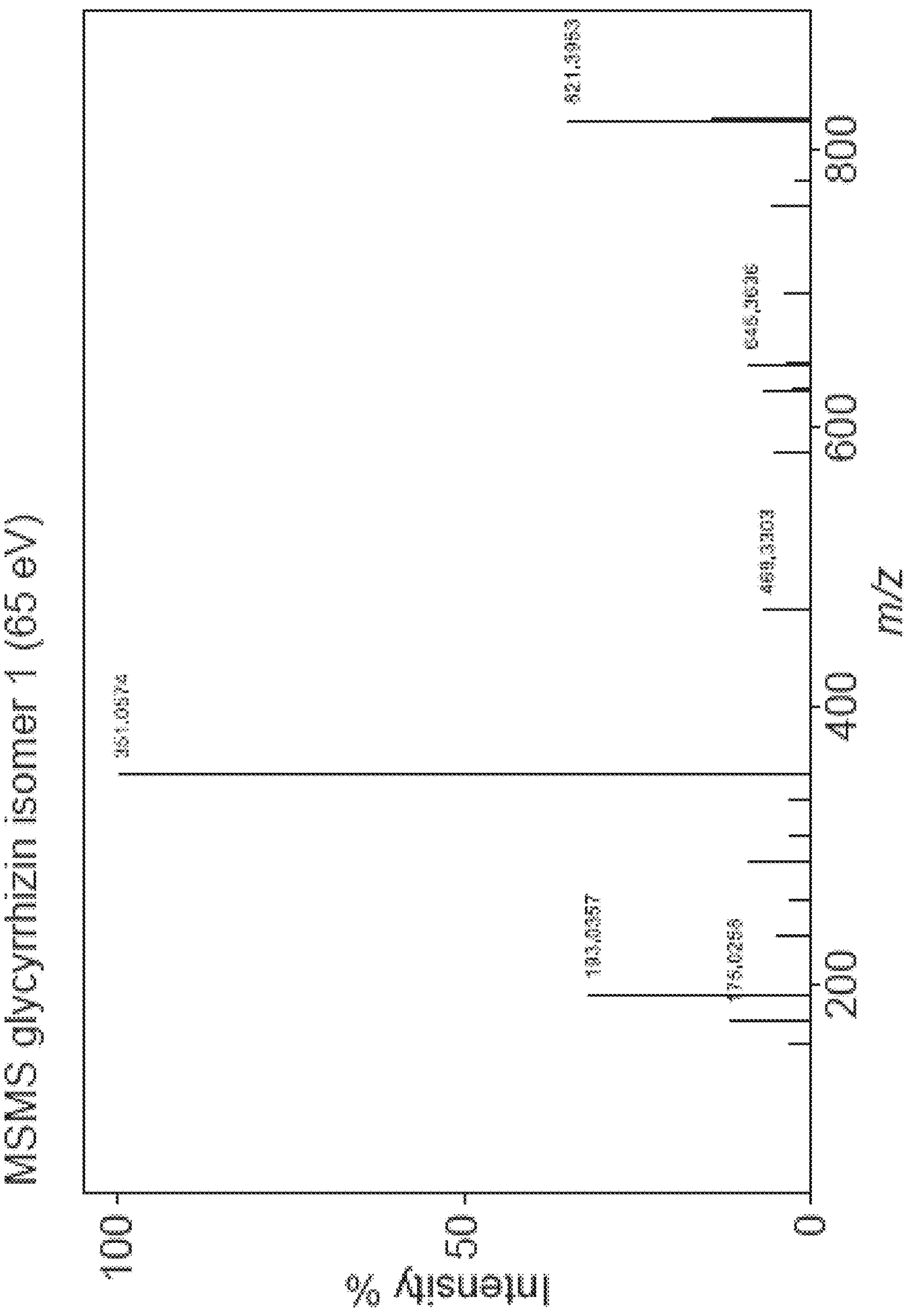
Figure 47C:
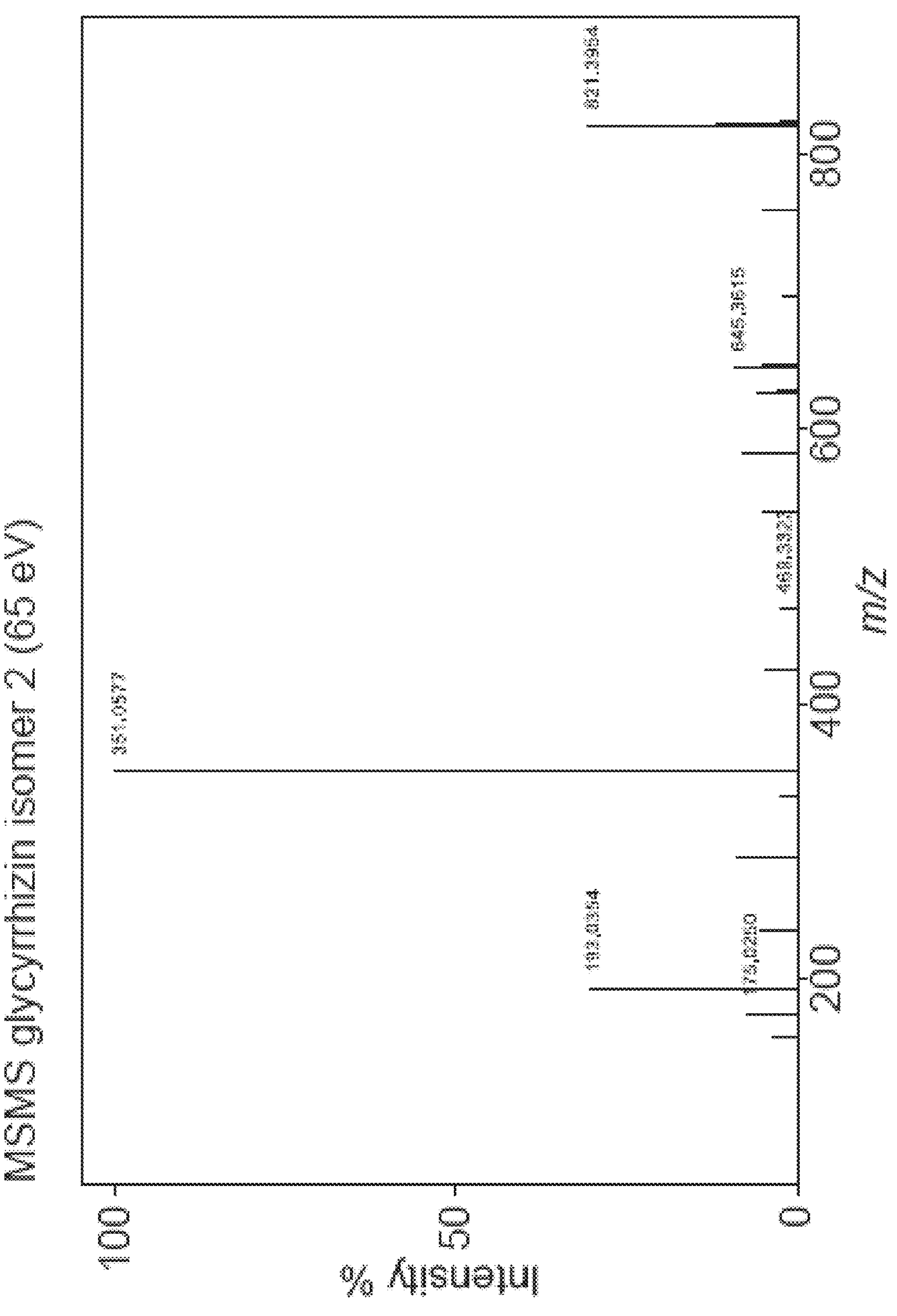
Figure 47D:
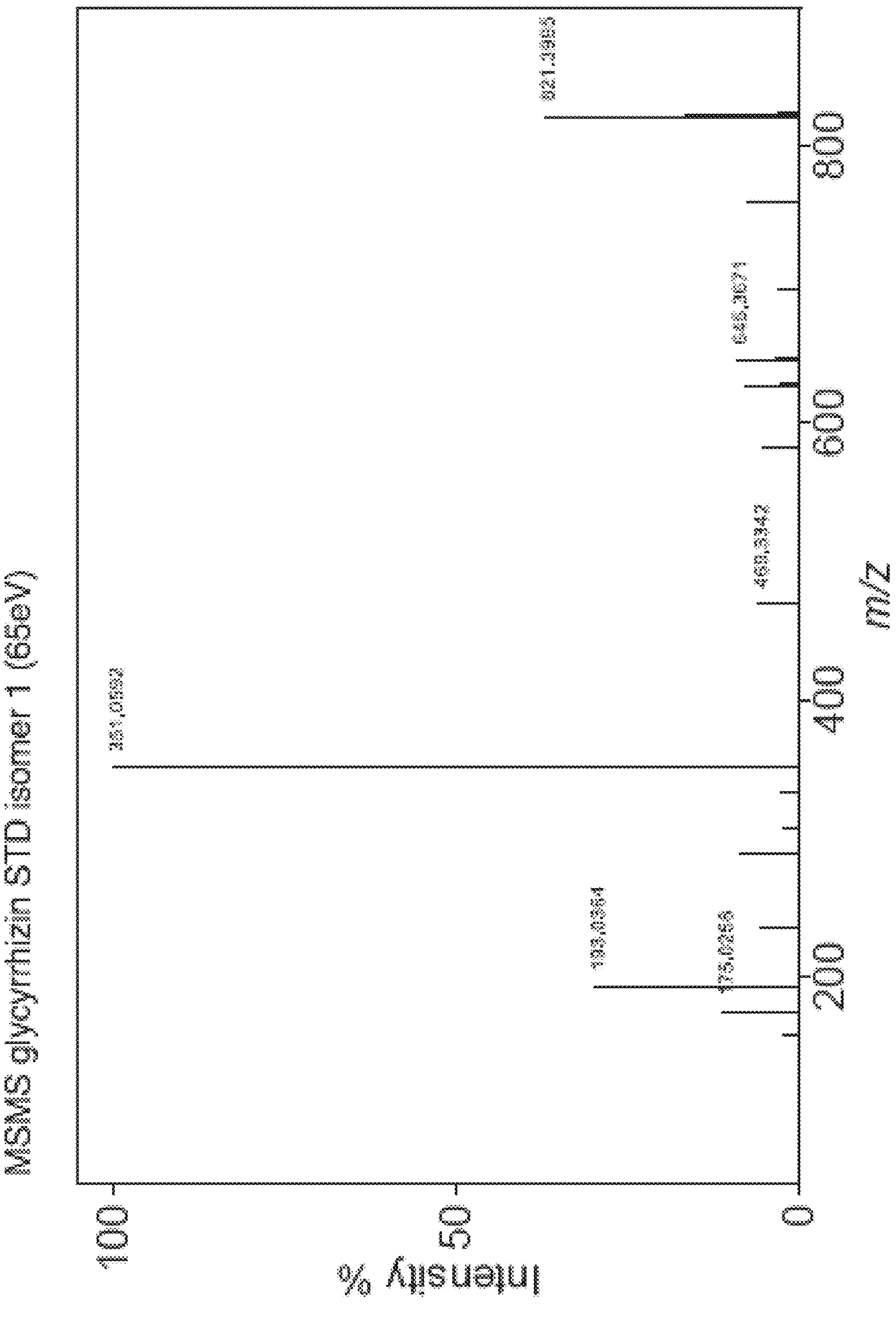
Figure 47E:
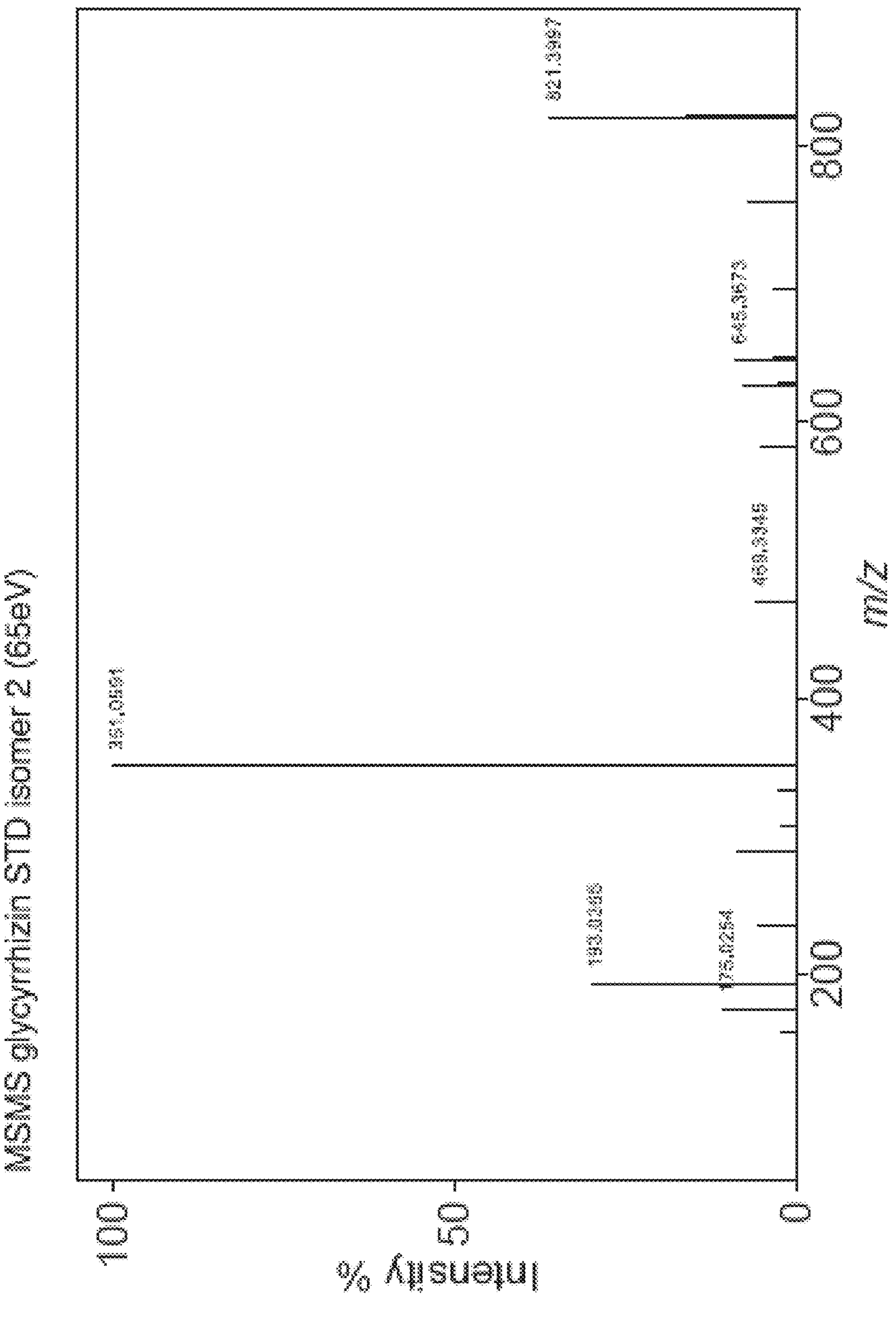
Figure 47F:
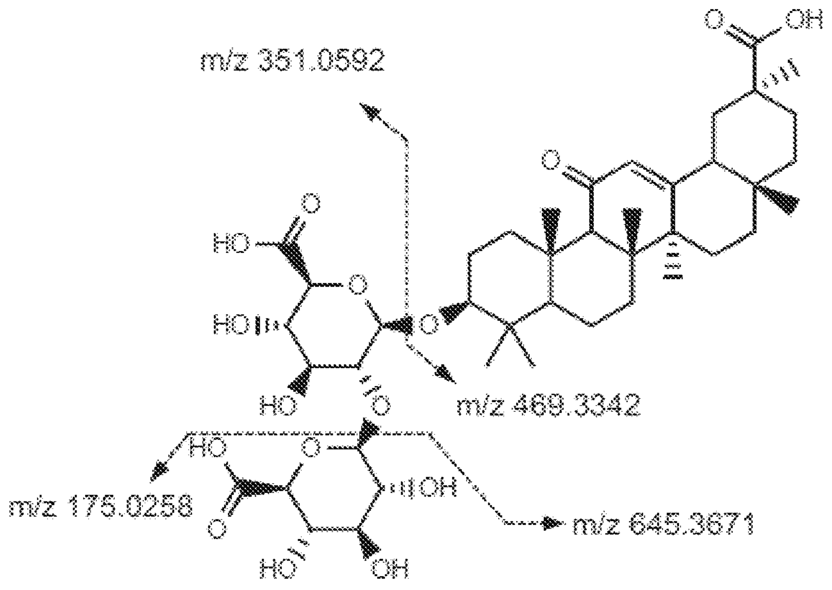

FIGS. 45A-45B show silencing of CSLG in alfalfa hairyroots. (FIG. 45A) EIC of representative saponins containing glucuronic acid attached to the aglycone from hairyroot cultures with silenced *Medicago saliva* Cellulose Synthase Like (MsCSL) compared to control (EV). (FIG. 45B) Analysis of triterpenoid saponins in alfalfa hairyroots with silenced MsCSL. The ordinate axis is in $\log_{10}$ scale. Values represent mean of five independent biological experiments. Statistically significant differences compared with control (roots transformed with EV alone) are indicated; *P<0.05, *P<0.01, *P<0.001. (asRNA—antisense RNA) The asRNA sequence used is set forth here:

(SEQ ID NO: 108)

CTACCCACTCTTCCGCTTCATAGATATAATCCCCTC
CACAATAGGATGACTTAGAGCAAGTATATAGATAA
TGAGGAAAAGTTGACCAAACATTTCATCAAAATCC
CTCACATTGAGTAGTCTCCATAAACCACCAAAGAA
GCAAACAATATTTATTGTGAGTAACACAATCACTG
GTGCCATGAGCAATGCTGCACCATCAAAATTAAAC
TTACCCTGCTCATATTTCTTTAGCTTATCTTTGTC
AATTGCTTTGTCCGATAAAGTGAATTTTGCCTTGT
TCAACCCAAACTTTTTTTTCGCTGTTTCTATAATT
GCGAAAACGCACCCAATTGATTTTACAATCCCACT
TCTTTGTTCATTCCACCAAATCATCGAGGAGCCAC
CAGTTGAAATTACCTCAATATAATGATGAATTTGA
CTGGATAGATACAATACTGTAAACACTATAAACCA
AGGATCTGTAACCTTTGGATATACAGGTATTCCCT
TTCAAGAAGCAAATCTGAGGAACGAATCCATATAA
GATGTAGGCTGTTGCAAATTGGGTTGTGCTTACCA
AGTAACAAAAAGTTAAACAATGAATAGTGGGCAAT
CTTGAAAGGCCATAAGTGAATGGGCTATATTTAGA
GATTGCAAGCAACAAAAGTTCAGATGACCACTTTA
TCGGTTGAATCAATCCCTCTTTCATGTCAGTTGGA
GCACATCCTAAGAAACATGGTCTTTTAGGGTAAAG
ATAAGTTGATCTCCATCCTCTACAATGGAGGAGAT
AGCCAGTAACGGTACTCTCAAGTTTTATAGCATAC
GAGAATCCCACCTCATTACCCCAATTTGTGTTTCT
CTCATAGGAACAAGAAGCCACTTCACATGCTTCTT
GTAAAATTACATCTCTTGAAATATTCTGCTTCTTA
GTTTGTTGACCACGTAACGCTTTTAGTGATTCTAC
ATACATGTTAGACTTGCCAAAGTTGTATAGAGCAT
CAAGTAGATAGTCCCCTTTTTGGTTTGGACTTCCA
AAGAGTAATGCACTTCTACTTATATAATTTCCACT

-continued

```
GCCAGTTAGACCTGGACCTCTTAATCCATGCATTC

CCTTCCACTTTGTCGTAAAAGCAGTCCTAGTCTGA

CTATCATATATGTCTTTCTTGCTAAGGTTGTGAAA

CATTTGAGGGAATTGAACAAAAGOAACATCTTTAG

AGGTTTCAGGATCAAGAAAAAAGCACATGGATTGT

TTGGCTGATGATGCATCATTACAATTCATATCACA

ATCTACGACAAGTACATAAGGTCCATrGCTGATTA

GCCCTGACACCCTAAGCAATGTATTGAGAGCTCCT

CCHTGAATCTGTGAGGAACAGATGGTCTTTTTTCA

CGAGATACATAAACAACTAGTGGCATTTCTTTTTG

GTCATTAATGATCTCGATCCGAGAAGGTCTATCGG

TCACCATACAAAGATTCTTTAGGTTGCTTCCGAAT

TTCTCAATATTTTTCTGCATTTTCTCGTATTTGGC

TTTGGTGGGCATATGTTCCTTGGAGTTTTCAACTT

GTGATGAGTTAGGATCCACTCTATTTAATCTCTTC

TTAATCTGGTCCCTCACTTCTTCAAATTCACGAGG

TCGATGAAGTCGTTCATTCTCACCCAAAGCAGTGA

AGAAAAACTTAGGACACCTTGACTTAACATCATAT

TTTTTACAAAAAGGAACCCAAACTTTAGCAAATTC

AAAAGCCTCTTTGATCCCAAAAAGAGTAATAGGAG

AACCTCCATCATCAGAAAGATAAATAGAAAGTTTA

TTAGAAGGGTAATCCATTGCAATAGCAGAAATAAC

AGTGTTCATAACATCAACCGTTGGTTCTTTTTCAG

GATCAATGGTACACACAAATATGTCGAGTCCCGGC

AACTTCTCCTCCGGCGGTAATTTCTCGGTCATAAC

TGAACGATTCACCAGCCTCCAACGGAATGCTTGGT

TGAAAAACCATAGAAATGATAGAATAATCTCAGCT

ATTGTCATTAGAAACCATGGATATGAAATAAACAA

ATTGCTGATACGGTAGTAAAAGAGAAACAAGACAC

ATGTGAAGTGGAAGATTATGTAAGCTCTTCTTAGA

GGTAACAATGGTTGAACTGTTTCTTTGTGAAATGT

GAAGGTTGCCAT
```

FIGS. 46A-46E show that the formation of glycyrrhetinic acid 3-O-monoglucuronide is catalyzed by GuCSLG. (FIG. 46A) EIC of glycyrrhetinic acid 3-O-monoglucuronide [m/z 645.36, in negative ion mode] of samples from *N. benthamiana* expressing proteins from *Glycyrrhiza uralensis*: bAS-β-amyrin synthase (SEQ ID NO: 48); CYP88D6-β-amyrin 11-oxidase (SEQ ID NO: 77); CYP72A154-11-oxo-b-amyrin 30-oxidase (SEQ ID NO: 79); GuUGAT (SEQ ID NO: 83)—glycosyltransferase previously reported to perform glucuronation of glycyrrhetinic acid; UGT73P12 (SEQ ID NO: 85)—glycosyltransferase transferring glcA onto glycyrrhetinic acid 3-O-monoglucuronide; GuCSL—cellulose synthase like G. (FIG. 46B) MS/MS of 654.36 (glycyrrhetinic acid 3-O-monoglucuronide isomer 1; 55 V). (FIG. 46C) MS/MS of 654.36 (isomer 2; 55 V). (FIG. 46D) Structure of the glycyrrhetinic acid 3-O-monoglucuronide with fragmentation patterns indicated by arrows. (FIG. 46E) Nomenclature of the cross-ring fragmentation of glucuronic acid with detected ions.

FIGS. 47A-47F show formation of glycyrrhizin (glycyrrhetinic acid 3-O-diglucuronide) in *N. benthamiana* requires GuCSLG. (FIG. 47A) EIC of glycyrrhizin [m/z=821.40, in negative ion mode] of samples from *N. benthamiana* expressing proteins from *G. uralensis*. bAS—b-amyrin synthase [0-amyrin synthase] (SEQ ID NO: 48); CYP88D6-b-amyrin 11-oxidase (SEQ ID NO: 76 [gene] and SEQ ID NO: 77 [polypeptide]); CYP72A154-11-oxo-b-amyrin 47-oxidase (SEQ ID NO: 78 [gene] and SEQ ID NO: 79 [polypeptide]); GuUGAT (SEQ ID NO: 82 [gene] and SEQ ID NO: 83 [polypeptide])—glycosyltransferase previously reported to perform glucuronation of glycyrrhetinic acid; UGT73P12-glycosyltransferase transferring glcA onto glycyrrhetinic acid 3-O-monoglucuronide (SEQ ID NO: 84 [gene] and SEQ ID NO: 85 [polypeptide]); GuCSL—cellulose synthase like G (SEQ ID NO: 80 or SEQ ID NO: 103 [gene], and SEQ ID NO: 81 or SEQ ID NO: 102 [polypeptide]). (FIG. 47B) MS/MS (65 V) of 821.40 (isomer 1)—product of bAS (SEQ ID NO: 45)+CYP88D6 (SEQ ID NO: 77)+CYP72A154 (SEQ ID NO: 79)+GuCSL (SEQ ID NO: 81 or SEQ ID NO: 102)+UGT73P12 (SEQ ID NO: 85). (FIG. 47C) MS/MS (65 V) of 821.40 (isomer 2)—product of bAS (SEQ ID NO: 45)+CYP88D6 (SEQ ID NO: 77)+CYP72A154 (SEQ ID NO: 79)+GuCSL (SEQ ID NO: 81 or SEQ ID NO: 102)+UGT73P12 (SEQ ID NO: 85). (FIG. 47D) and (FIG. 47E) MS/MS of glycyrrhizin authentic standard, isomer 1 and 2 respectively. (FIG. 47F) Structure of glycyrrhizin with fragmentation patterns indicated by arrows.

FIG. 48 presents the structure of SOAP5. (FIG. 48) Alignment of protein sequences of *Arabidopsis* AtCESA1 (SEQ ID NO: 67), AtCESA3 (SEQ ID NO: 68), and their orthologs in spinach (SoCESA1 (SEQ ID NO: 70) and SoCFSA3 (SEQ ID NO: 71)) together with SOAP5 (SEQ ID NO: 66) and its counterpart in *Arabidopsis*—AtCSLGl (SEQ ID NO: 69).

Figure 49A:
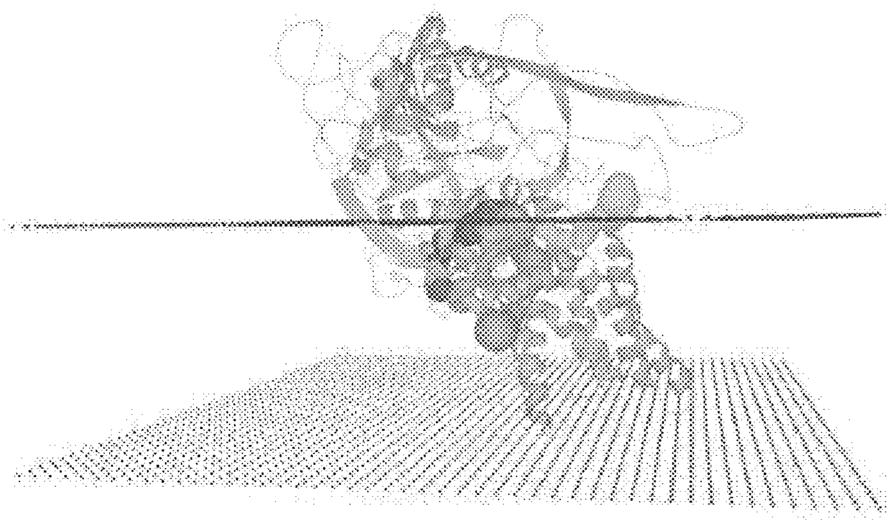
Figure 49B:
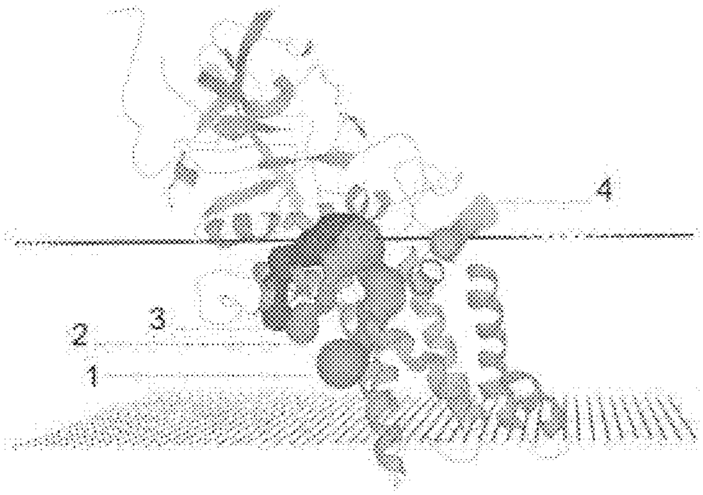
Figure 49C:
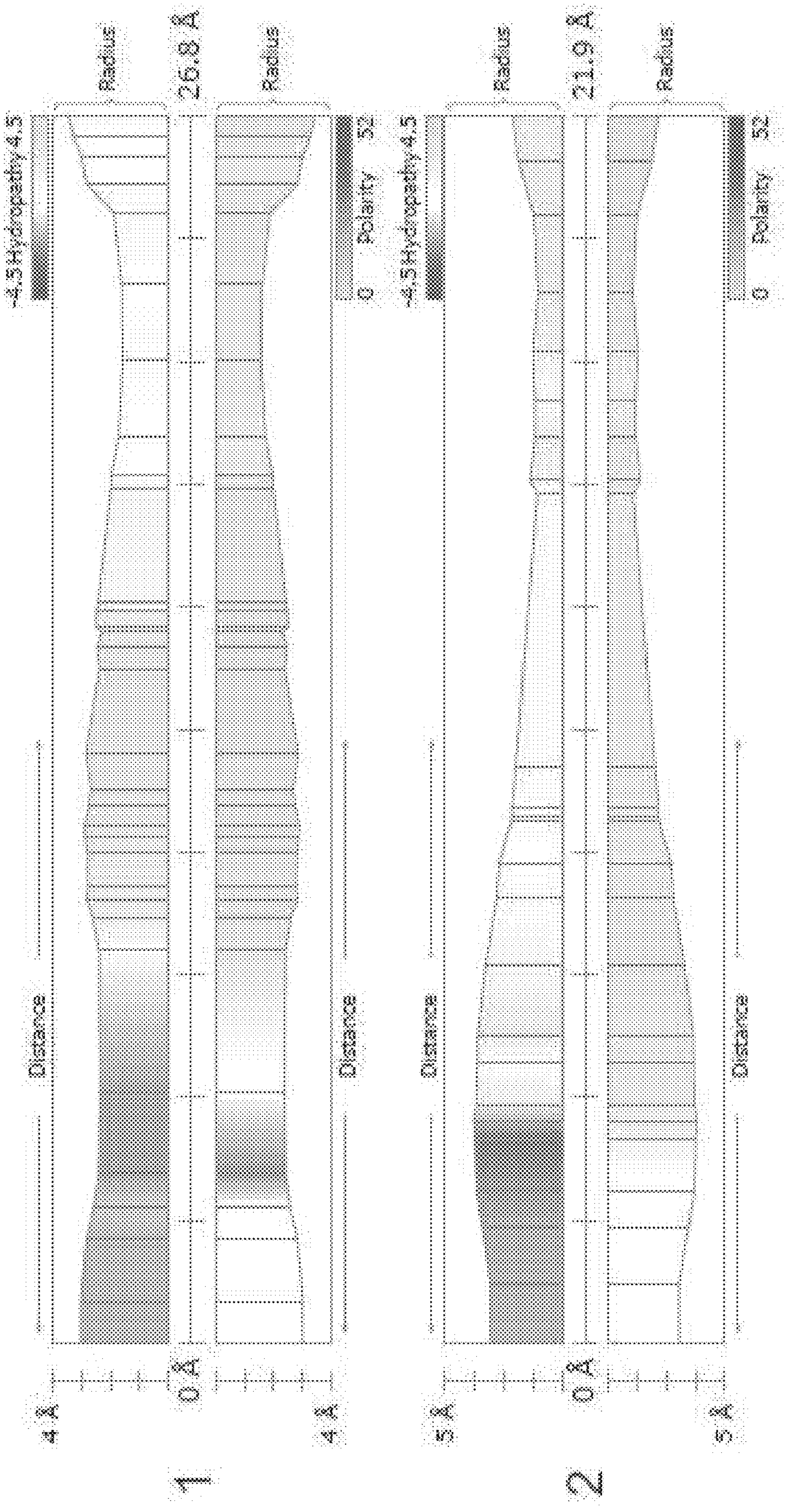
Figure 49C:
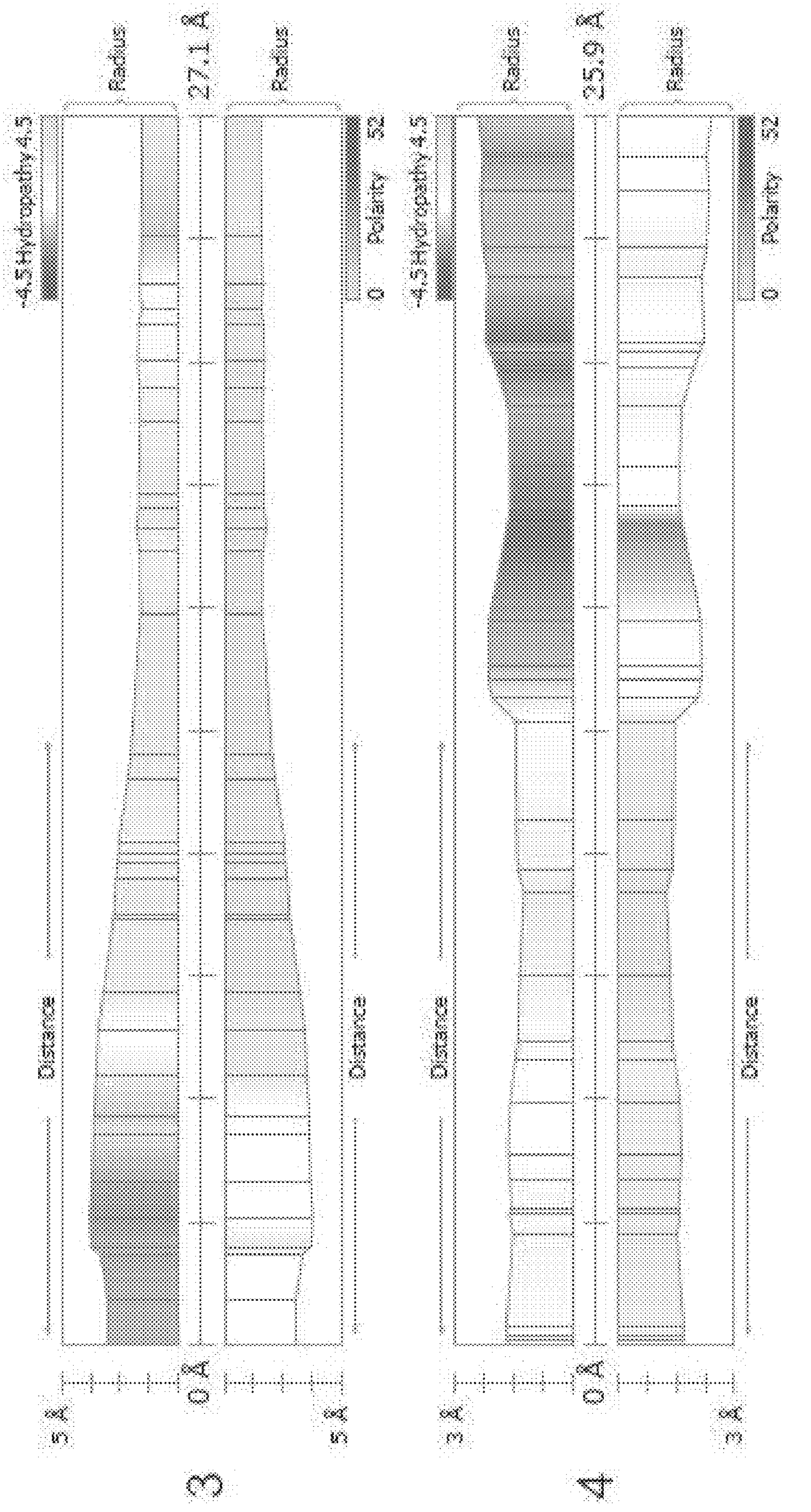

FIGS. 49A-49C present the predicted 3D structure of SOAP5. (FIGS. 49A and 49B) 3D model of SOAP5 with predicted tunnels, allowing medicagenic acid to reach the active site of the enzyme (blue—1,2,3) and to leave (yellow—4) the hydrophobic environment of the lipid bilayer. (FIG. 49C) Profiles and properties of the tunnels shown in (FIG. 49A).

Figure 50A:
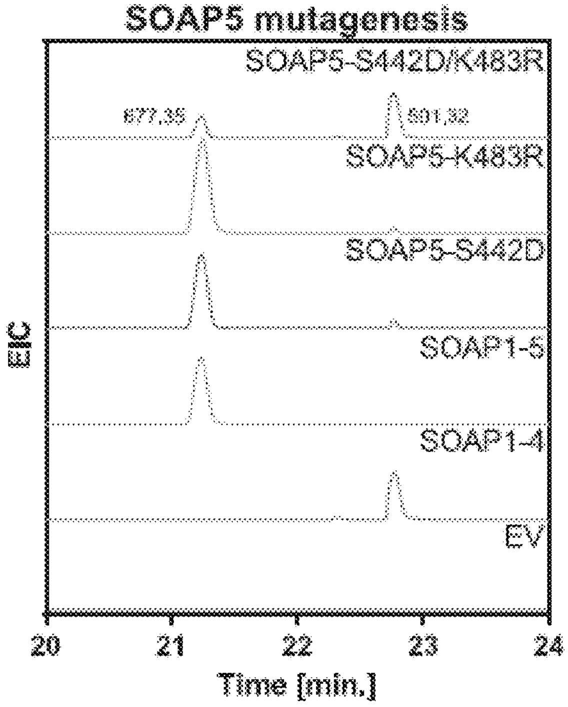
Figure 50B:
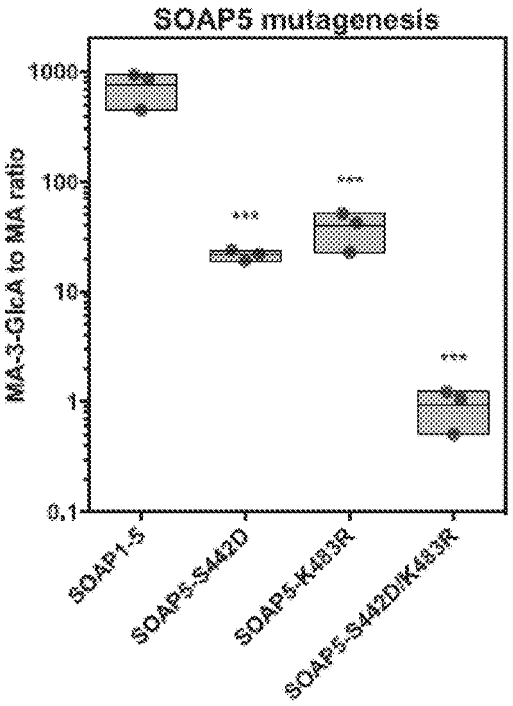

FIGS. 50A and 50B present site directed mutagenesis data of SOAP5 (FIG. 50A) EICs of medicagenic acid [m/z=501.32] and medicagenic acid 3-GlcA [m/z=677.35] from plants transiently expressing SOAP1-4 with mutated versions of SOAP5 compared to native SOAP5, SOAP1-4 alone and control (EV) (FIG. 50B) Accumulation of MA and MA-3-GlcA in plants expressing mutated variants of SOAP5 represented as a ratio of MA-3-GlcA to free MA. The ordinate axis is in $\log_{10}$ scale. Values represent mean of three independent biological experiments. Statistically significant differences compared with plants expressing native SOAP5 are indicated; ***P<0.001.

Figures 51A, 51B, 51C, 51D, 51E, 51F:
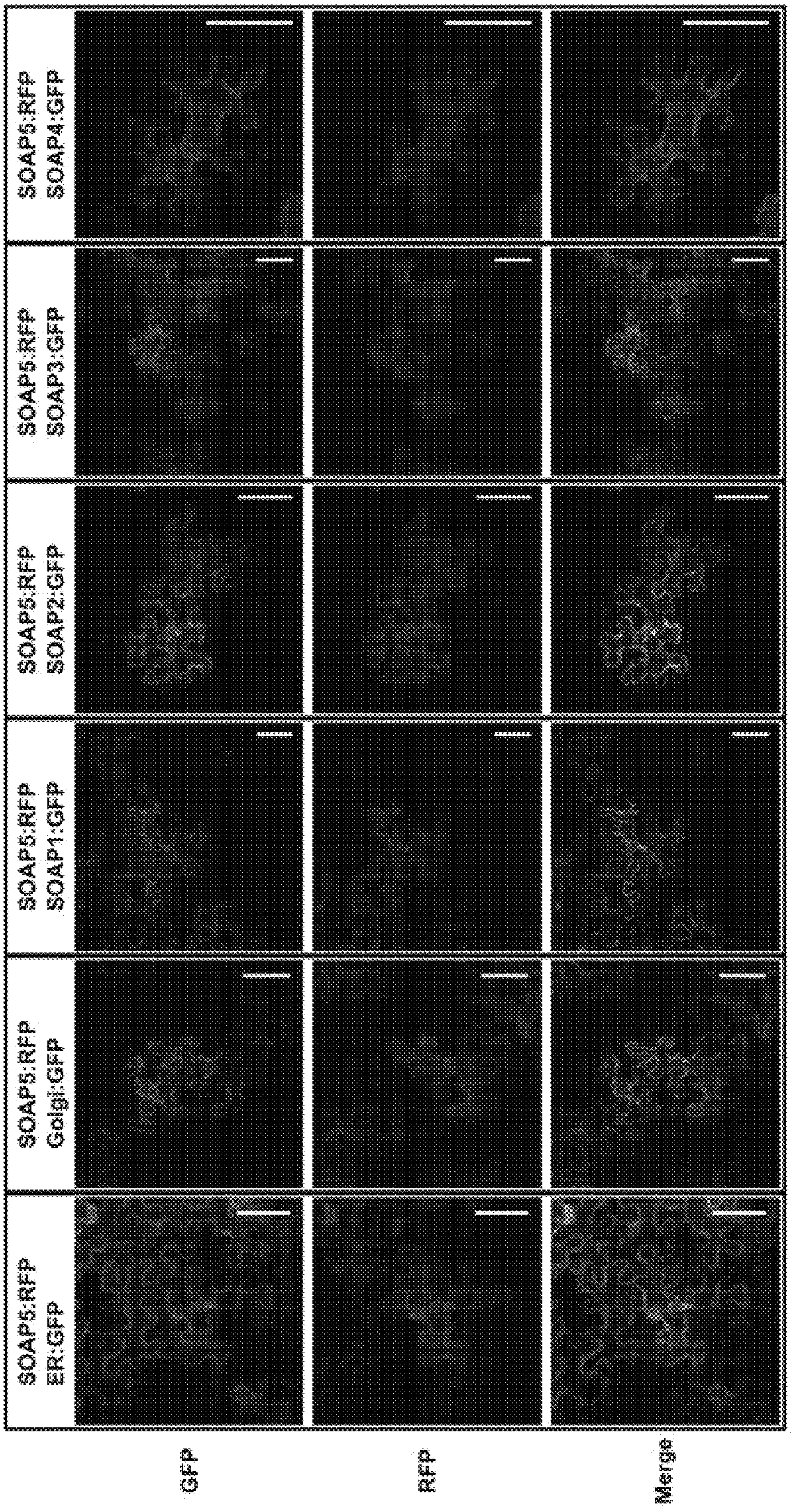
Figure 51G:
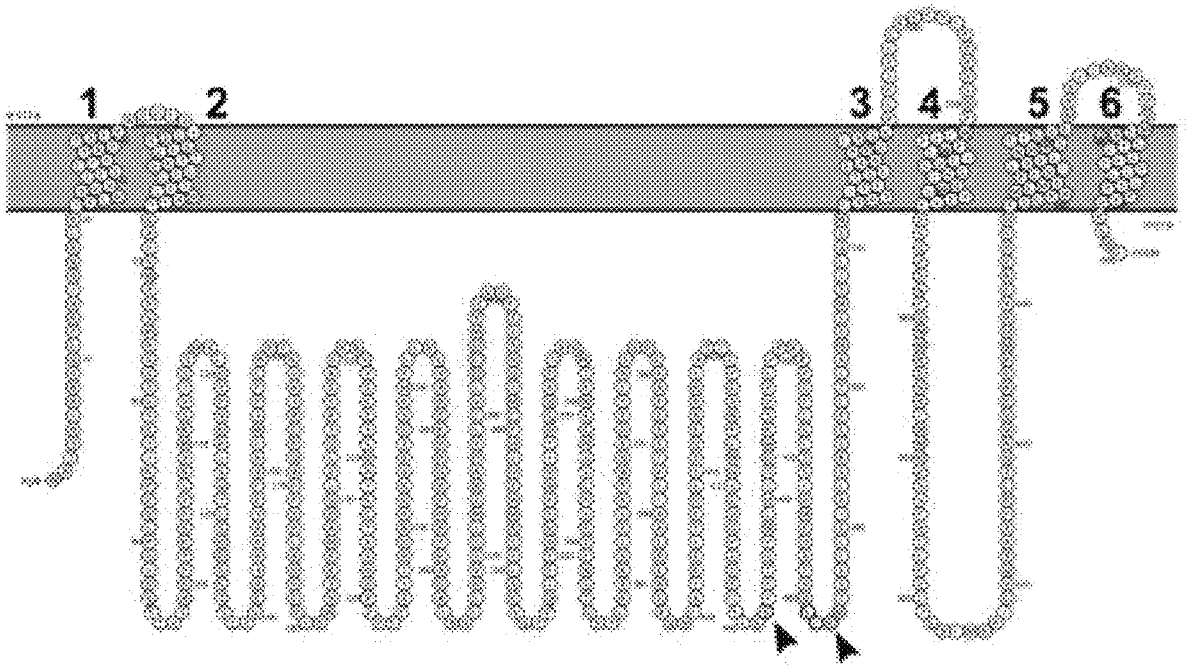
Figure 51H:
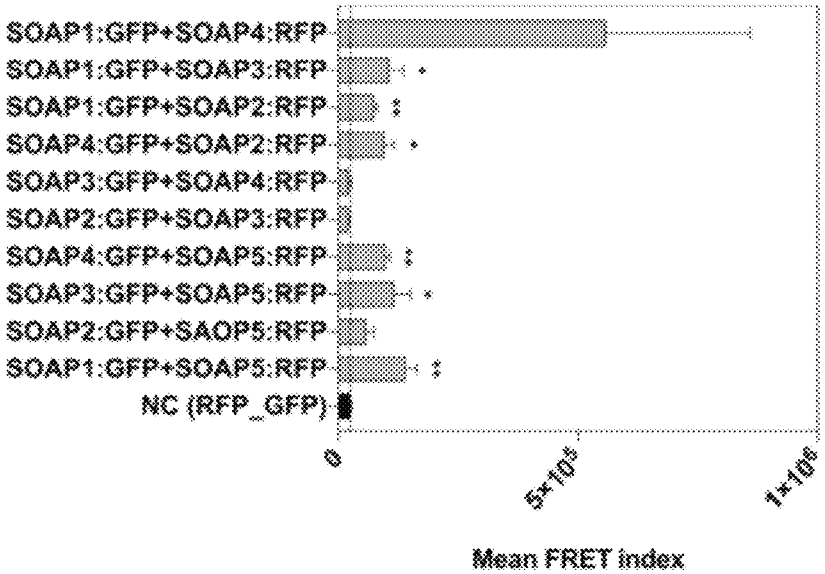
Figure 52A:
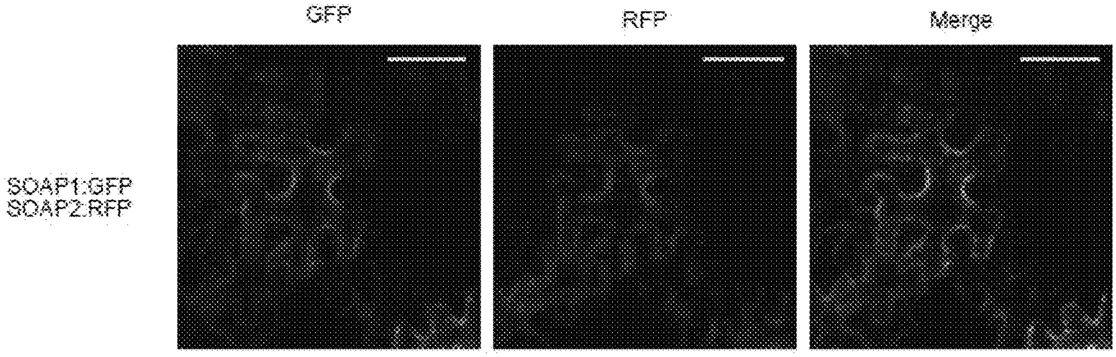
Figure 52B:
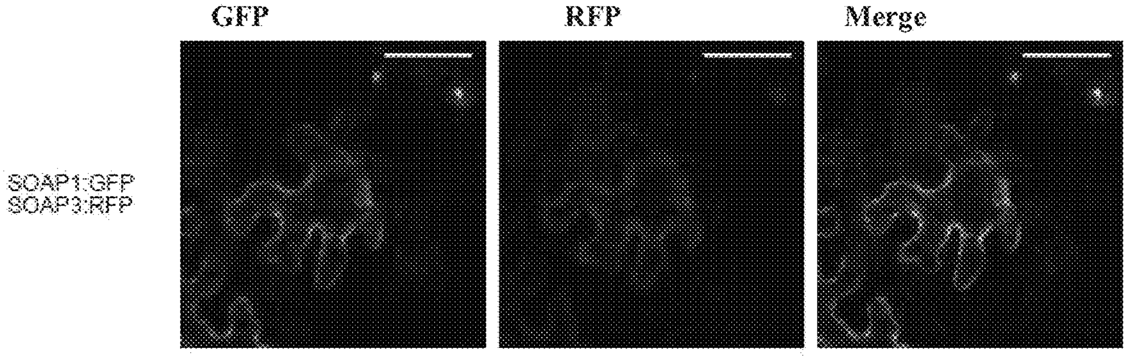
Figure 52C:
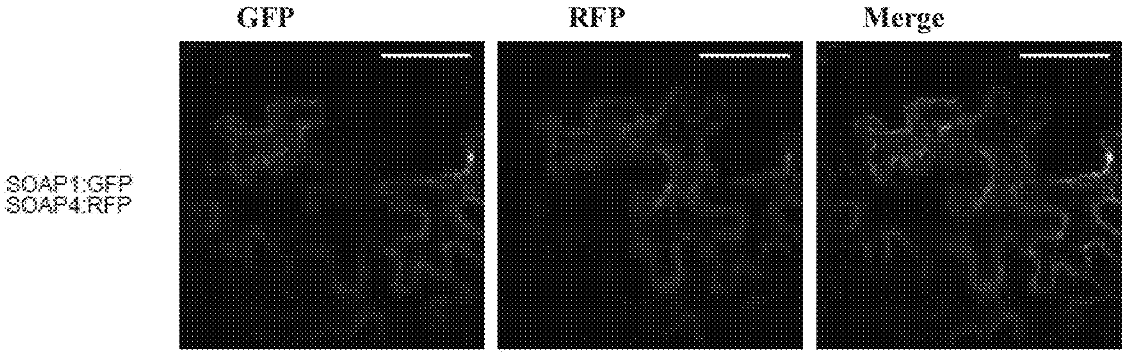
Figure 52D:
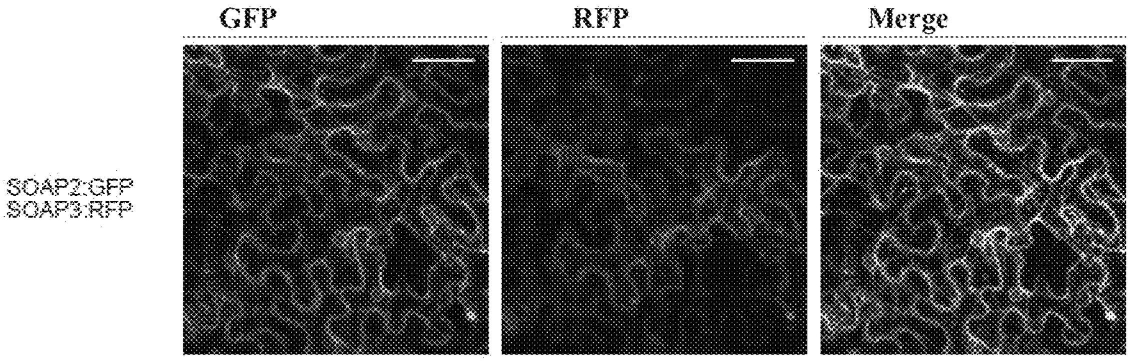
Figure 52E:
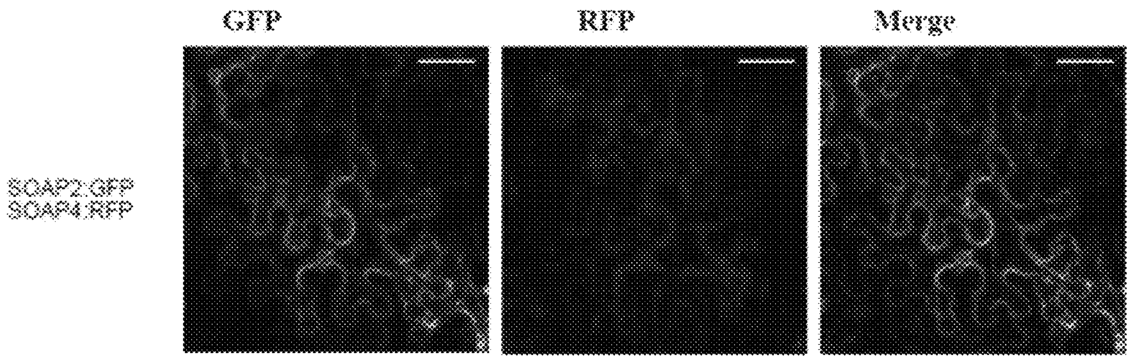
Figure 52F:
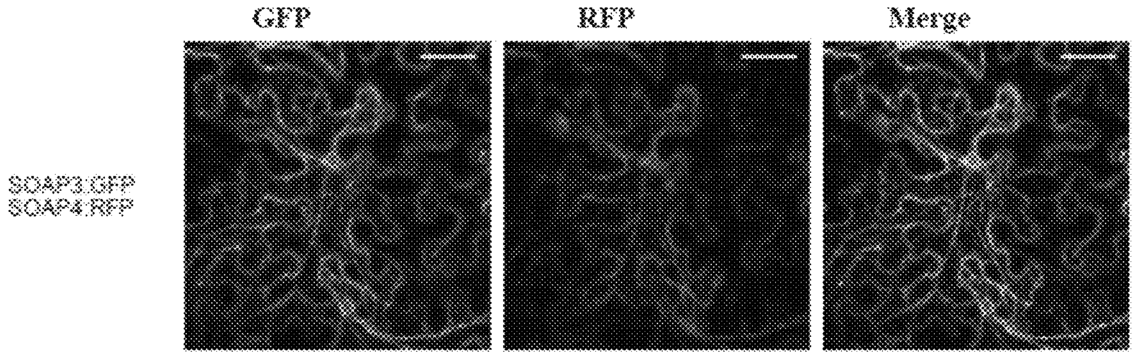

FIGS. 51A-51H present micrographs showing that SOAP proteins including SOAP5 are co-localized in the endoplasmic reticulum (ER) membrane. (FIGS. 51A-51F) Confocal images of SOAP5:RFP transiently co-expressed in *N. benthamiana* leaves with (FIG. 51A) ER:GFP marker; (FIG. 51B) Golgi:GFP marker; (FIG. 51C) SOAP1:GFP; (FIG. 51D) SOAP2:GFP; (FIG. 51E) SOAP3:GFP and SOAP4:GFP (FIG. 51F). Each panel contains images of GFP, RFP and both channels merged. Scale bar—50 μm. (FIG. 51G) Topology model of SOAP5 with conserved motifs (red), substituted amino acids (blue, pointed with arrows) and six transmembrane domains indicated. (FIG. 51H) FRET index of cells that expressed the indicated constructs. The values are means f SE. Significant differences comparing to negative control expressing free GFP and RFP (NC) are indicated; *P<0.05; **P<0.01.

FIGS. 52A-52F present micrographs showing SOAPs involved in triterpenoid aglycon formation are colocalized and reside in endoplasmic reticulum (ER). (FIGS. 52A-52F) Confocal images of SOAPs in fusion with fluorescent proteins (GFP and RFP) transiently co-expressed in *N. benthamiana* leaves. (FIG. 52A) SOAP1:GFP+SOAP2:RFP; (FIG. 52B) SOAP1:GFP+SOAP3:RFP; (FIG. 52C) SOAP1:GFP+SOAP4:RFP; (FIG. 52D) SOAP2:GFP+SOAP3:RFP; (FIG. 52E) SOAP2-GFP+SOAP4:RFP; (FIG. 35F) SOAP3:GFP+SOAP4:RFP (F). Each panel contains images of GFP, RFP and both channels merged together. Scale bar—50 picometers.

Figure 53:
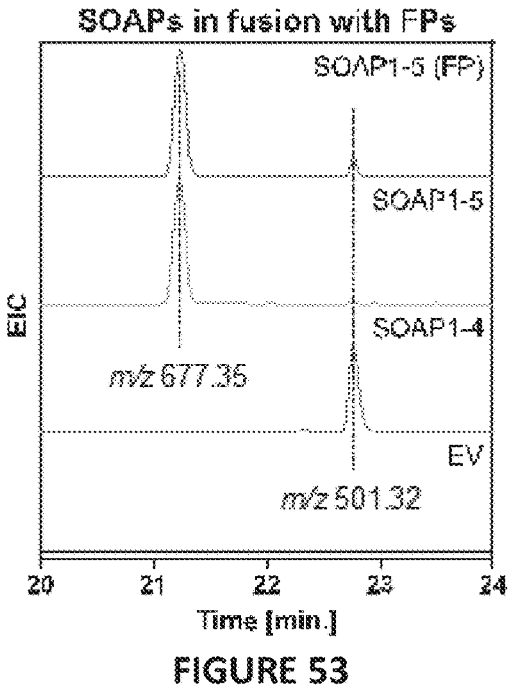

FIG. 53 present data showing that SOAPs in fusion with fluorescent proteins (FP) are still active. EICs of medicagenic acid [m/z=501.32] and medicagenic acid 3-GlcA [m/z=677.35] from *N. benthamiana* plants transiently expressing SOAP1:eGFP, SOAP2:eGFP, SOAP3:mRFP, SOAP4:eGFP and SOAP5:mRFP compared to native SOAP5, SOAP1-4 alone and control (EV). SOAP1:GFP, SOAP2:GFP, SOAP3:RFP, SOAP4:GFP and SOAP5:RFP compared to native SOAP1-S, SOAP1-4 alone and control (EV).

Figure 54A:
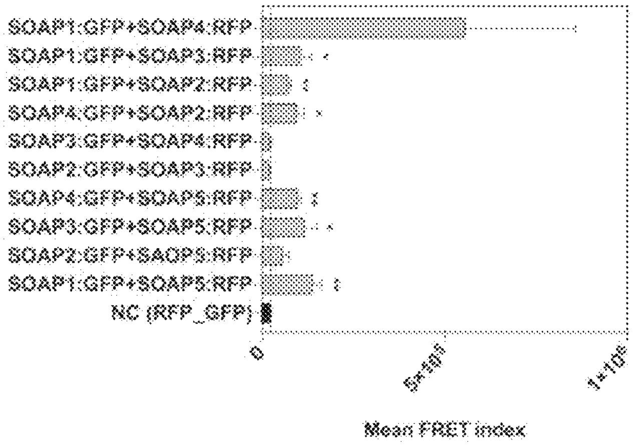
Figure 54B:
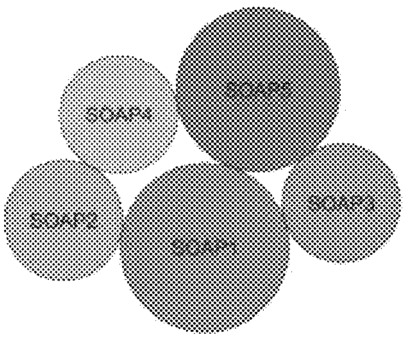

FIGS. 54A-54B present SOAPs in fusion with fluorescent proteins (FP) are still active. (FIG. 54A) Fluorescence resonance energy transfer (FRET) index of cells that expressed the indicated constructs. The values are means±SE. Significant differences comparing to negative control expressing free GFP and RFP (NC) are indicated with asterisks; *P<0.05; P<0.01. (FIG. 54**B) Schematic representation of possible protein localization within ER.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Specifically disclosed herein are genetically modified cells having increased expression of at least one heterologous gene compared to a corresponding unmodified cell, said at least one heterologous gene encoding a cellulose synthase like G (CSLG) enzyme, wherein said genetically modified cell comprises an increased content of at least one steroidal alkaloid, a derivative thereof, a metabolite thereof, or a biosynthetic intermediate thereof, of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, compared to the corresponding unmodified cell. In some embodiments, the genetically modified cell expressing a heterologous CSLG further expresses at least one additional heterologous gene encoding an enzyme, said enzyme selected from the group consisting of a saponin beta-amyrin synthase, a cytochrome P450, a glycosyltransferase, an acyltransferase, and an UDP-glucose 6-dehydrogenase 1, or any combination thereof.

The term "CSLG" encompasses Cellulose Synthase Like enzymes from the G family. There are various cellulose synthase Like (CSL) families, each with a different suffix, for example, A, B, E, and G. The suffix for each family is assigned according to enzyme's similarity to previously characterized proteins from *Arabidopsis thaliana*. CSL enzymes from different families have different technical characteristics. As used throughout, the terms "CSL" without a suffix of A, B, or E, in certain embodiments, may be used interchangeably with the term "CSLG", having all the same meaning and qualities.

"CSLG" proteins, in certain embodiments, may encompass "GAME15" proteins and "SOAP5" proteins.

Described herein are six tested CSLG genes, which in certain embodiments include the GAME15 genes and their encoded enzymes (6 enzymes from 6 species—tomato, wild tomato, potato, wild potato, eggplant, and pepper), which transfer Glucoronic Acid or other sugar moieties to generate steroidal alkaloids and which transfer Glucoronic Acid or other sugar moieties on furostanol-type saponin (aglycone) to generate steroidal saponins or precursors thereof or to generate steroidal alkaloids or precursors thereof (see, e.g., FIG. 1).

Described herein are seven tested CSLG genes (also known as SOAP5 genes) and their encoded enzymes (7 enzymes from 7 species—spinach, Chinese licorice, red beet, *quinoa*, alfalfa, soybean, and *Lotus japonicum*), which transfer glucuronic acid on triterpenoid aglycone. The term "triterpenoid aglycone" may in some embodiments, encompass the group of compounds derived from beta-amyrin. Thus, CSLG enzymes disclosed herein provide a unique activity.

A skilled artisan would appreciate that altering the content of at least one steroidal alkaloid, steroidal saponin, or triterpenoid saponin in a cell, for example a plant cell, a yeast cell, an algal cell, a bacterial cell, may comprise mutating an endogenous CSLG gene or regulating the CSLG gene expression, or may comprise adding a heterologous CSLG to a cell that does not express a CSLG enzyme or in order to supplement the activity of a CSLG enzyme expressed in the heterologous cell. In some embodiments, the plant cell may be comprised within a plant or plant part.

According to certain embodiments, expression of the at least one gene or any combination thereof is altered, the altering comprising mutagenizing the at least one gene, wherein the mutagenesis comprises introduction of one or more point mutations, or genome editing, or use or a bacterial CRISPR/CAS system, or a combination thereof. In certain embodiments, expression of the CSLG gene or polynucleotide is silenced, repressed, or reduced, e.g., by deletion, insertion or modification, or by introduction of at least one silencing molecule targeted to a CSLG gene.

It is to be understood that increasing the expression of the at least one gene or combination thereof may be achieved by various means, all of which are explicitly encompassed within the scope of present invention. According to certain embodiments, enhancing the expression of CSLG can be affected at the genomic and/or the transcript level using a variety of molecules that enhance transcription and/or translation including, but not limited to, transcription factors. Inserting a mutation to the at least one gene, including addition of promoters, enhancers, and the like can be also used, as long as the mutation results in up-regulation of the gene expression. According to other embodiments, expression is increased at the protein level using agonists and the like.

In some embodiments, these genetically modified cells produce steroidal alkaloids. In some embodiments, these genetically modified cells produce steroidal saponins. In some embodiments, these genetically modified cells produce triterpenoid saponins. In some embodiments, the genetically modified cells comprise an increased content of at least a steroidal alkaloid, a derivative thereof, a metabolite thereof, or a biosynthetic intermediate thereof, compared to a corresponding unmodified cell. In some embodiments, the genetically modified cells comprise an increased content of at least a steroidal saponin, a derivative thereof, a metabolite thereof, or a biosynthetic intermediate thereof, compared to a corresponding unmodified cell. In some embodiments, the genetically modified cells comprise an increased content of at least a triterpenoid saponin, a derivative thereof, a metabolite thereof, or a biosynthetic intermediate thereof, compared to a corresponding unmodified cell.

In some embodiments, derivatives of steroidal alkaloids, steroidal saponins, or triterpenoid saponins comprise glycosylated derivatives of, respectively, steroidal alkaloids, steroidal saponins, or triterpenoid saponins.

In some embodiments, the nucleic acid sequence encoding said at least one heterologous CSLG gene is set forth in any one of SEQ ID NOS: 30, 32, 34, 36, 38, 40, 65, 80, 93, 95, 97, 99, 101, 103, or 105; or a homolog thereof having at least 55% identity to and at least 55% coverage of, the nucleic acid sequence set forth in any one of SEQ ID NOS: 30, 32, 34, 36, 38, 40, 65, 80, 93, 95, 97, 99, 101, 103, or 105. In some embodiments, the nucleic acid sequence encoding said at least one heterologous CSLG gene is set forth in any one of SEQ ID NOS: 30, 32, 34, 36, 38, 40, 65, 80, 93, 95, 97, 99, 101, 103, or 105; or a homolog thereof having at least 55% identity to and at least 80% coverage of, the nucleic acid sequence set forth in any one of SEQ ID NOS: 30, 32, 34, 36, 38, 40, 65, 80, 93, 95, 97, 99, 101, 103, or 105.

In some embodiments, a CSLG enzyme homolog has at least 55%, 60%, 65%, 70%, 75%, 80%, 85%, 90%, 95% 98%, or 99% identity of the amino acid sequence. In some embodiments, a gene encoding a CSLG enzyme homolog has at least 55%, 60%, 65%, 70%, 75%, 80%, 85%, 90%, 95% 98%, or 99% identity of the nucleic acid sequence.

In some embodiments, a CSLG enzyme homolog has at least 55%, 60%, 65%, 70%, 75%, 80%, 85%, 90%, 95% 98%, 99%, or 100% coverage of the amino acid sequence. In some embodiments, a gene encoding a CSLG enzyme homolog has at least 55%, 60%, 65%, 70%, 75%, 80%, 85%, 90%, 95% 98%, 99%, or 100% coverage of the nucleic acid sequence.

In some embodiments, the nucleic acid sequence encoding said at least one heterologous CSLG gene is set forth in any one of SEQ ID NOS: 30, 32, 34, 36, 38, 40, 65, 80, 93, 95, 97, 99, 101, 103, or 105; or a homolog thereof having at least 80% identity to and at least 80% coverage of, the nucleic acid sequence set forth in any one of SEQ ID NOS: 30, 32, 34, 36, 38, 40, 65, 80, 93, 95, 97, 99, 101, 103, or 105.

In some embodiments, the amino acid sequence of said encoded CSLG enzyme is set forth in any one of SEQ ID NOS: 31, 33, 35, 37, 39, 41, 66, 81, 94, 96, 98, 100, 102, or 104; or a homolog thereof having at least 55% identity to and at least 55% coverage of, the amino acid sequence set forth in any one of SEQ ID NOS: 31, 33, 35, 37, 39, 41, 66, 81, 94, 96, 98, 100, 102, or 104. In some embodiments, the amino acid sequence of said encoded CSLG enzyme is set forth in any one of SEQ ID NOS: 31, 33, 35, 37, 39, 41, 66, 81, 94, 96, 98, 100, 102, or 104; or a homolog thereof having at least 55% identity to and at least 80% coverage of, the amino acid sequence set forth in any one of SEQ ID NOS: 31, 33, 35, 37, 39, 41, 66, 81, 94, 96, 98, 100, 102, or 104.

In some embodiments, the amino acid sequence of said encoded CSLG enzyme is set forth in any one of SEQ ID NOS: 31, 33, 35, 37, 39, 41, 66, 81, 94, 96, 98, 100, 102, or 104; or a homolog thereof having at least 80% identity to and at least 80% coverage of, the amino acid sequence set forth in any one of SEQ ID NOS: 31, 33, 35, 37, 39, 41, 66, 81, 94, 96, 98, 100, 102, or 104.

In some embodiments, the nucleic acid sequence encoding said at least one additional heterologous gene encodes: (a) a β-amyrin synthase, said nucleic acid sequence set forth in SEQ ID NO: 45; or a homolog thereof having at least 80% identity to and at least 80% coverage of, the nucleic acid sequence set forth in SEQ ID NO: 45; or (b) a cytochrome P450, said nucleic acid sequence set forth in any one of SEQ ID NO: 46, 51, or 53; or a homolog thereof having at least 80% identity to and at least 80% coverage of, the nucleic acid sequence set forth in any one of SEQ ID NO: 46, 51, or 53; or a (c) glycosyl transferase, said nucleic acid sequence set forth in any one of SEQ ID NO: 55, 57, 59, or 61; or a homolog thereof having at least 80% identity to and at least 80% coverage of, the nucleic acid sequence set forth in any one of SEQ ID NO: 55, 57, 59, or 61; or (d) an acetyltransferase, said nucleic acid sequence set forth in SEQ ID NO: 63; or a homolog thereof having at least 80% identity to and at least 80% coverage of, the nucleic acid sequence set forth in SEQ ID NO: 63; or (e) a UDP-glucose 6-dehydrogenase 1, said nucleic acid sequence set forth in SEQ ID NO: 74; or a homolog thereof having at least 80% identity to and at least 80% coverage of, the nucleic acid sequence set forth in SEQ ID NO: 74; or (f) any combination thereof of (a), (b), (c), (d), and (e).

In some embodiments, the amino acid sequence of said encoded at least one additional heterologous gene encodes: (a) a β-amyrin synthase, said amino acid sequence set forth in SEQ ID NO: 48; or a homolog thereof having at least 80% identity to and at least 80% coverage of, the amino acid sequence set forth in SEQ ID NO: 48; or (b) a cytochrome P450, said amino acid sequence set forth in any one of SEQ ID NO: 49, 52, or 54; or a homolog thereof having at least 80% identity to and at least 80% coverage of, the amino acid sequence set forth in any one of SEQ ID NO: 49, 52, or 54; or a (c) glycosyl transferase, said amino acid sequence set forth in any one of SEQ ID NO: 56, 58, 60, or 62; or a homolog thereof having at least 80% identity to and at least 80% coverage of, the amino acid sequence set forth in any one of SEQ ID NO: 56, 58, 60, or 62; or (d) an acetyltransferase, said amino acid sequence set forth in SEQ ID NO: 64; or a homolog thereof having at least 80% identity to and at least 80% coverage of, the amino acid sequence set forth in SEQ ID NO: 64; or (e) a UDP-glucose 6-dehydrogenase 1, said amino acid sequence set forth in SEQ ID NO: 75; or a homolog thereof having at least 80% identity to and at least 80% coverage of, the amino acid sequence set forth in SEQ ID NO: 75; or (f) any combination thereof of (a), (b), (c), (d), and (e).

Heterologous expression encompasses the expression of a gene or part of a gene in a host cell or host organism, for example but not limited to a plant cell, a yeast cell, an alga, or a plant, which does not naturally have this gene or gene fragment. Insertion of the gene in the heterologous host may be performed by any recombinant DNA technology known in the art, or for example in the case of yeast, may be performed by mating.

The triterpenoid saponin or said derivative, metabolite, or biosynthetic intermediate thereof, may have a broad range of commercial uses and may in some embodiments comprise a sweetener, foaming agent, emulsifier, preservative, anti-carcinogen, hypocholesterolemic agent, anti-inflammatory agent, anti-oxidant, biological adjuvant, anti-microbial agent, insecticidal agent, antifeedant, anti-fungal agent, or any combination thereof.

In some embodiments, (a) said steroidal glycoalkaloid comprises alpha-tomatine, tomatine, dehydrotomatine, hydroxytomatine, acetoxytomatine, dihydroxytomatine, alpha-chaconine, alpha-solanine, alpha-solasonine, alpha-solmargine, and their derivatives, related compounds or any combination thereof; (b) said steroidal saponin comprises uttroside B, tomatosides and their derivatives, related compounds, or any combination thereof; (c) said triterpenoid saponin comprises medicagenic acid 3-O-glucuronide (MA-3-GlcA) (Compound 6), Compound 7, Compound 8, Compound 9, Compound 10, Compound 11, glycyrrhizin (Compound 14), glycyrrhetinic acid 3-O-monoglucuronide (Compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof; (d) the biosynthetic intermediate of said triterpenoid saponin comprises Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof; or (e) any combination of these.

According to certain exemplary embodiments, the downstream steroidal glycoalkaloid is selected from the group consisting of esculeosides or dehydroesculeosides.

In some embodiments, the genetically modified cell further comprises an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, an "altered content" encompasses an increased content of a phytosterol/a phytocholesterol/phytocholestenol, derivative thereof, metabolike thereof, or biosynthetic intermediate thereof. In some embodiments, an "altered content" encompasses an increased content of a phytosterol, derivative thereof, metabolike thereof, or biosynthetic intermediate thereof.

In some embodiments, the genetically modified cell further comprises a reduced content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, the genetically modified cells are plant cells, yeast cells, or alga cells. In some embodiments, the genetically modified plant cells are comprised within a plant or a plant part. In some embodiments, the genetically modified cells are yeast cells. In some embodiments, the genetically modified cells are alga cells.

In some embodiments, said plant cell comprises a cell from a plant in the Poales order, the Caryophyllales order, the Solanales order, the Fabales order, the Ma/vales order, the *Apiales* order, the Brassicales order, the *Asparagales* order, the Dioscoreales order, or the Liliales order.

In some embodiments, (a) when said plant cell comprises a cell from a plant in the Poales order, said plant is selected from the group of genera consisting of the *Oryza* genus, the *Hordeum* genus, the *Avena* genus, and the *Triticum* genus; (b) when said plant cell comprises a cell from a plant in the Caryophyllales order, said plant is selected from the group of genera consisting of the *Spinacia* genus, the *Chenopodium* genus, the Beta genus, the Rheum genus, the *Vaccaria* genus, the *Saponaria* genus, and the *Gypsophila* genus; (c) when said plant cell comprises a cell from a plant in the Solanales order, said plant is selected from the group of genera consisting of the *Solanum* genus, the *Capsicum* genus, the *Nicotiana* genus, the *Hyoscyamus* genus, the *Datura* genus, and the *Atropa* genus; (d) when said plant cell comprises a cell from a plant in the Fabales order, said plant is selected from the group of genera consisting of the *Glycyrrhiza* genus, the *Medicago* genus, the *Glycine* genus, the *Lotus* genus, the *Cicer* genus, the *Phaseolus* genus, the *Pisum* genus, the *Arachis* genus, the *Lupinus* genus, and the *Acacia* genus; (e) when said plant cell comprises a cell from a plant in the Malvales order, said plant is selected from the *Theobroma* genus; (f) when said plant cell comprises a cell from a plant in the *Apiales* order, said plant is selected from the group of genera consisting of the *Daucus* genus, the *Apium* genus, the *Petroselinum* genus, the *Panax* genus, the *Bupleurum* genus, the *Hedera* genus, and the Centella genus; or (g) when said plant cell comprises a cell from a plant in the Brassicales order, said plant is selected from the group of genera consisting of the *Arabidopsis* genus, the *Brassica* genus, the *Capparis* genus, and the *Carica* genus.

In some embodiments, (a) when said plant cell comprises a cell from a plant in the Caryophyllales order, said plant is selected from the group consisting of spinach, beetroot, and *quinoa*; (b) when said plant cell comprises a cell from a plant in the Solanales order, said plant is selected from the group consisting of tomato, wild tomato, potato, wild potato, eggplant, pepper, bell pepper, cayenne pepper, chili pepper, pimiento, tabasco pepper, ground cherry, tobacco, and bittersweet; or (c) when said plant cell comprises a cell from a plant in the Fabales order, said plant is selected from the group consisting of alfalfa, soy, *Lotus japonicus*, and licorice.

In some embodiments, the plant cell is from a tomato plant having: (i) an increased content of alpha-tomatine or a derivative thereof, a metabolite thereof, or a biosynthetic intermediate thereof; or tomatidine or a derivative thereof, a metabolite thereof, or a biosynthetic intermediate thereof; or a steroidal saponin or a derivative thereof, a metabolite thereof, or a biosynthetic intermediate thereof; or (ii) an altered content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof; or a phytocholestenol or a derivative thereof, a metabolite thereof, or a biosynthetic intermediate thereof.

In some embodiments, the plant cell is from a tomato plant having: (i) an increased content of alpha-tomatine or a derivative thereof, a metabolite thereof, or a biosynthetic intermediate thereof; or tomatidine or a derivative thereof, a metabolite thereof, or a biosynthetic intermediate thereof, or a steroidal saponin or a derivative thereof, a metabolite thereof, or a biosynthetic intermediate thereof; or (ii) a reduced content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof, a cholestenol or a derivative thereof, a metabolite thereof, or a biosynthetic intermediate thereof; or a phytocholestenol or a derivative thereof, a metabolite thereof, or a biosynthetic intermediate thereof.

In some embodiments, the plant cell is from a potato plant having: (i) an increased content of alpha-chaconine or a derivative thereof, a metabolite thereof, or a biosynthetic intermediate thereof; or alpha-solanine or a derivative thereof, a metabolite thereof, or a biosynthetic intermediate thereof; or a steroidal saponin or a derivative thereof, a metabolite thereof, or a biosynthetic intermediate thereof; or (ii) an altered content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof; or a phytocholestenol or a derivative thereof, a metabolite thereof, or a biosynthetic intermediate thereof.

In some embodiments, the plant cell is from a potato plant having: (i) an increased content of alpha-chaconine or a derivative thereof, a metabolite thereof, or a biosynthetic intermediate thereof; or alpha-solanine or a derivative thereof, a metabolite thereof, or a biosynthetic intermediate thereof; or a steroidal saponin or a derivative thereof, a metabolite thereof, or a biosynthetic intermediate thereof; or (ii) a reduced content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof; or a phytocholestenol or a derivative thereof, a metabolite thereof, or a biosynthetic intermediate thereof.

In some embodiments, the plant cell is from an eggplant plant having: (i) an increased content of alpha-solasonine or a derivative thereof, a metabolite thereof, or a biosynthetic intermediate thereof; or alpha-solamargine or a derivative thereof, a metabolite thereof, or a biosynthetic intermediate thereof; or a steroidal saponin or a derivative thereof, a metabolite thereof, or a biosynthetic intermediate thereof; or (ii) an altered content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof; or a phytocholestenol or a derivative thereof, a metabolite thereof, or a biosynthetic intermediate thereof.

In some embodiments, the plant cell is from an eggplant plant having: (i) an increased content of alpha-solasonine or a derivative thereof, a metabolite thereof, or a biosynthetic intermediate thereof; or alpha-solamargine or a derivative thereof, a metabolite thereof, or a biosynthetic intermediate thereof; or a steroidal saponin or a derivative thereof, a metabolite thereof, or a biosynthetic intermediate thereof; or (ii) a reduced content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof; or a phytocholestenol or a derivative thereof, a metabolite thereof, or a biosynthetic intermediate thereof.

In some embodiments, said plant cell comprises a leaf cell, a petiole cell, a plant stem or stalk cell, a root cell, a bud cell, a tuber cell, a bean cell, a grain or kernel cell, a fruit cell, a nut cell, a legume cell, a seed or seed cell, a callus cell, a bract cell, or a flower cell. In some embodiments, said plant cell is comprised in a plant or a portion thereof, said portion thereof comprising a plant leaf, a plant petiole, a plant stem or stalk, a plant root, a plant bud, a plant tuber, a plant bean, a plant grain or kernel, a plant fruit, a plant nut, a plant legume, a plant seed, a plant bract, or a plant flower.

In some embodiments, said yeast is selected from a *Saccharomyces* genus, a *Schizosaccharomyces* genus, a *Pichia* genus, a *Yarrowia* genus, a *Kluyveromyces* genus, or a *Candida* genus.

In some embodiments, said alga is selected from a microalga, a multi-cellular alga, a cyanobacterium, a diatom, chlorophytes (green algae), rhodophytes (red algae), or phaeo-phytes (brown algae), a *Dunaliella*, a Chlamydamonas, or a Hematococus.

Specifically disclosed herein are genetically modified plants comprising at least one cell having altered expression of at least a cellulose synthase like G (CSLG) gene compared to the expression of CSLG in a corresponding unmodified plant, and wherein the genetically modified plant has an altered content of at least one steroidal alkaloid, a derivative thereof a metabolite thereof; of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof compared to the corresponding unmodified plant.

According to certain embodiments, expression of the at least one gene or any combination thereof is altered, the altering comprising mutagenizing the at least one gene, wherein the mutagenesis comprises introduction of one or more point mutations, or genome editing, or use of a bacterial CRISPR/CAS system, or a combination thereof.

According to certain embodiments, expression of the gene encoding at least one CSLG is elevated compared to its expression in the corresponding unmodified cell or plant, respectively. According to certain embodiments, the genetically modified cell or genetically modified plant comprises a polynucleotide encoding a CSLG, wherein expression of the polynucleotide is selectively increased. According to certain embodiments, the genetically modified plant comprises at least one cell comprising at least one transcribable polynucleotide encoding at least one protein selected from the group consisting of at least one CSLG.

According to certain embodiments, the genetically modified plant is a transgenic plant comprising at least one cell comprising at least one silencing molecule targeted to a polynucleotide encoding at least one CSLG. According to certain embodiments, the transgenic plant comprises a polynucleotide encoding a CSLG, wherein expression of the polynucleotide is selectively silenced, repressed, or reduced. According to certain embodiments, the transgenic plant comprises a polynucleotide encoding a CSLG, wherein the polynucleotide has been selectively edited by deletion, insertion, or modification to silence, repress, or reduce expression thereof, or wherein the genetically modified plant is a progeny of the gene edited plant. According to certain embodiments, the transgenic plant comprises at least one cell comprising at least one silencing molecule targeted to a CSLG gene. According to certain embodiments, the silencing molecule is selected from the group consisting RNA interference molecule and an antisense molecule, or wherein the silencing molecule is a component of a viral induced gene silencing system. According to certain embodiments, the silencing molecule comprises a polynucleotide having a nucleic acid sequence substantially complementary to a region of a CSLG gene.

According to some embodiments, the transgenic plant comprises a plurality of cells comprising the silencing molecule targeted to the at least one CSLG gene. According to additional embodiments, the majority of the plant cells comprise the silencing molecule.

It is to be understood that inhibiting the expression of the at least one gene or combination thereof may be achieved by various means, all of which are explicitly encompassed within the scope of present invention. According to certain embodiments, inhibiting the expression of CSLG can be effected at the genomic and/or the transcript level using a variety of molecules that interfere with transcription and/or translation including, but not limited to, antisense, siRNA, Ribozyme, or DNAzyme molecules. Inserting a mutation to the at least one gene, including deletions, insertions, site specific mutations, zinc-finger nucleases and the like can be also used, as long as the mutation results in down-regulation of the gene expression. According to other embodiments, expression is inhibited at the protein level using antagonists, enzymes that cleave the polypeptide and the like.

In some embodiments, said CSLG gene comprises the endogenous CSLG gene.

In some embodiments, said endogenous CSLG gene comprises a mutation, said mutation comprising at least one or more point mutations, or an insertion, or a deletion, or any combination thereof, and: (a) wherein said expressed CSLG enzyme has increased stability or increased activity or both and the altered content comprises an increased amount of the at least one steroidal alkaloid, a derivative thereof, a metabolite thereof, or a biosynthetic intermediate thereof, of the at least one steroidal saponin, a derivative thereof, a metabolite thereof, or a biosynthetic intermediate thereof; or of the at least one triterpenoid saponin, a derivative thereof, a metabolite thereof, or a biosynthetic intermediate thereof compared to the corresponding unmodified plant; or (b) wherein said expressed CSLG enzyme has decreased stability or decreased activity or both and the altered content comprises a decreased amount of the at least one steroidal alkaloid, a derivative thereof, a metabolite thereof, or a biosynthetic intermediate thereof; of the at least one steroidal saponin, a derivative thereof, a metabolite thereof, or a biosynthetic intermediate thereof; or of the at least one triterpenoid saponin, a derivative thereof, a metabolite thereof, or a biosynthetic intermediate thereof compared to the corresponding unmodified plant.

In some embodiments, (a) said endogenous CSLG gene is selectively silenced, repressed, or has reduced expression and said altered content comprises a reduced amount of the at least one steroidal alkaloid, a derivative thereof, a metabolite thereof, or a biosynthetic intermediate thereof; of the at least one steroidal saponin, a derivative thereof, a metabolite thereof, or a biosynthetic intermediate thereof; or of the at least one triterpenoid saponin, a derivative thereof, a metabolite thereof, or a biosynthetic intermediate thereof compared to the corresponding unmodified plant; or (b) said endogenous CSLG gene is overexpressed and said altered content comprises an increased amount of the at least one steroidal alkaloid, a derivative thereof, a metabolite thereof, or a biosynthetic intermediate thereof; of the at least one steroidal saponin, a derivative thereof, a metabolite thereof, or a biosynthetic intermediate thereof; or of the at least one triterpenoid saponin, a derivative thereof, a metabolite thereof, or a biosynthetic intermediate thereof compared to the corresponding unmodified plant.

In some embodiments, when said endogenous CSLG gene is selectively silenced, repressed, or has reduced expression, said cell further comprises at least one silencing molecule targeted to the polynucleotide encoding said CSLG gene, wherein the silencing molecule is selected from an RNA interference molecule or an antisense molecule, or wherein the silencing molecule is a component of a viral induced gene silencing system.

In some embodiments, said CSLG gene comprises a heterologous CSLG gene, and said altered expression comprises a de novo expression of said gene.

In some embodiments, said expression comprises increased expression compared to a corresponding unmodified cell, and said altered content comprising increased content of at least one steroidal alkaloid, a derivative thereof, a metabolite thereof, or a biosynthetic intermediate thereof; of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, compared to the corresponding unmodified plant.

In some embodiments, the nucleic acid sequence encoding said CSLG gene is set forth in any one of SEQ ID NOS: 30, 32, 34, 36, 38, 40, 65, 80, 93, 95, 97, 99, 101, 103, or 105; or a homolog thereof having at least 55% identity to and at least 55% coverage of, the nucleic acid sequence set forth in any one of SEQ ID NOS: 30, 32, 34, 36, 38, 40, 65, 80, 93, 95, 97, 99, 101, 103, or 105. In some embodiments, the nucleic acid sequence encoding said CSLG gene is set forth in any one of SEQ ID NOS: 30, 32, 34, 36, 38, 40, 65, 80, 93, 95, 97, 99, 101, 103, or 105; or a homolog thereof having at least 55% identity to and at least 80% coverage of, the nucleic acid sequence set forth in any one of SEQ ID NOS: 30, 32, 34, 36, 38, 40, 65, 80, 93, 95, 97, 99, 101, 103, or 105.

In some embodiments, the nucleic acid sequence encoding said CSLG gene is set forth in any one of SEQ ID NOS: 30, 32, 34, 36, 38, 40, 65, 80, 93, 95, 97, 99, 101, 103, or 105; or a homolog thereof having at least 80% identity to and at least 80% coverage of, the nucleic acid sequence set forth in any one of SEQ ID NOS: 30, 32, 34, 36, 38, 40, 65, 80, 93, 95, 97, 99, 101, 103, or 105.

In some embodiments, the amino acid sequence of said CSLG enzyme is set forth in any one of SEQ ID NOS: 31, 33, 35, 37, 39, 41, 66, 81, 94, 96, 98, 100, 102, or 104; or a homolog thereof having at least 55% identity to and at least 55% coverage of, the amino acid sequence set forth in any one of SEQ ID NOS: 31, 33, 35, 37, 39, 41, 66, 81, 94, 96, 98, 100, 102, or 104. In some embodiments, the amino acid sequence of said CSLG enzyme is set forth in any one of SEQ ID NOS: 31, 33, 35, 37, 39, 41, 66, 81, 94, 96, 98, 100, 102, or 104; or a homolog thereof having at least 55% identity to and at least 80% coverage of, the amino acid sequence set forth in any one of SEQ ID NOS: 31, 33, 35, 37, 39, 41, 66, 81, 94, 96, 98, 100, 102, or 104.

In some embodiments, the amino acid sequence of said CSLG enzyme is set forth in any one of SEQ ID NOS: 31, 33, 35, 37, 39, 41, 66, 81, 94, 96, 98, 100, 102, or 104; or a homolog thereof having at least 80% identity to and at least 80% coverage of, the amino acid sequence set forth in any one of SEQ ID NOS: 31, 33, 35, 37, 39, 41, 66, 81, 94, 96, 98, 100, 102, or 104.

In some embodiments, the altered expression of the at least one cellulose synthase like G (CSLG) gene is altered by introducing (1) one or more point mutations into the nucleic acid sequence, (2) deletions within the nucleic acid sequence, or (3) insertions within the nucleic acid, any combination thereof, or (4) any combination thereof, wherein said introducing comprising mutagenizing coding or non-coding sequence.

In some embodiments, the altered expression of the at least one CSLG gene is altered by introducing a silencing molecule targeted to the at least one CSLG gene and wherein: (a) when the nucleic acid of the CSLG is set forth in SEQ ID NO: 30, the silencing molecule is set forth in SEQ ID NO: 42 or a complementary sequence thereof, or a homolog thereof having at least 80% identity to and at least 80% coverage of, the nucleic acid sequence set forth in SEQ ID NO: 42 or a complementary sequence thereof; (b) when the nucleic acid of the CSLG is set forth in SEQ ID NO: 34, the silencing molecule is set forth in SEQ ID NO: 43 or a complementary sequence thereof, or a homolog thereof having at least 80% identity to and at least 80% coverage of, the nucleic acid sequence set forth in SEQ ID NO: 43 or a complementary sequence thereof; (c) when the nucleic acid of the CSLG is set forth in SEQ ID NO: 38, the silencing molecule is set forth in SEQ ID NO: 44 or a complementary sequence thereof, or a homolog thereof having at least 80% identity to and at least 80% coverage of, the nucleic acid sequence set forth in SEQ ID NO: 44 or a complementary sequence thereof; (d) when the nucleic acid of the CSLG is set forth in SEQ ID NO: 65 or SEQ ID NO: 93, the silencing molecule is set forth in SEQ ID NO: 106 or a complementary sequence thereof, or a homolog thereof having at least 80% identity to and at least 80% coverage of, the nucleic acid sequence set forth in SEQ ID NO: 65 or the nucleic acid sequence set forth in SEQ ID NO: 93; or (e) when the nucleic acid of the CSLG is set forth in SEQ ID NO: 95, the silencing molecule is set forth in SEQ ID NO: 107 or a complementary sequence thereof, or a homolog thereof having at least 80% identity to and at least 80% coverage of, the nucleic acid sequence set forth in SEQ ID NO: 95.

The triterpenoid saponin or said derivative, metabolite, or biosynthetic intermediate thereof, may have a broad range of commercial uses and may in some embodiments comprise a sweetener, foaming agent, emulsifier, preservative, anti-carcinogen, hypocholesterolemic agent, anti-inflammatory agent, anti-oxidant, biological adjuvant, anti-microbial agent, insecticidal agent, antifeedant, anti-fungal agent, or any combination thereof.

In some embodiments, (a) said steroidal glycoalkaloid comprises alpha-tomatine, tomatine, dehydrotomatine, hydroxytomatine, acetoxytomatine, di-hydroxytomatine, alpha-chaconine, alpha-solanine, alpha-solasonine, alpha-solmargine, or their derivatives and pathway intermediates or any combination thereof; (b) said steroidal saponin comprises uttroside B, tomatosides, and all related compounds, or their derivatives and pathway intermediates, or any combination thereof; (c) said triterpenoid saponin comprises medicagenic acid 3-O-glucuronide (MA-3-GlcA) (Compound 6), Compound 7, Compound 8, Compound 9, Compound 10, Compound 11, glycyrrhizin (Compound 14), glycyrrhetinic acid 3-O-monoglucuronide (Compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof; (d) the biosynthetic intermediate of said triterpenoid saponin comprises Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof; or (e) any combination of these.

In some embodiments, the genetically modified plant has an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, the genetically modified plant has an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof, wherein: (a) when the altered content of the at least one steroidal alkaloid, a derivative thereof, a metabolite thereof, or a biosynthetic intermediate thereof; of the at least one steroidal saponin, a derivative thereof, a metabolite thereof, or a biosynthetic intermediate thereof; or of the at least one triterpenoid saponin, a derivative thereof, a metabolite thereof, or a biosynthetic intermediate thereof comprises an increased amount compared to the corresponding unmodified plant, the altered content of the phytosterol, or a derivative thereof, a metabolite thereof, or a biosynthetic intermediate thereof; the cholesterol, or a derivative thereof, a metabolite thereof, or a biosynthetic intermediate thereof; the phytocholesterol, or a derivative thereof, a metabolite thereof, or a biosynthetic intermediate thereof; the cholestenol, or a derivative thereof, a metabolite thereof, or a biosynthetic intermediate thereof; or the phytocholestenol, or comprises a reduced amount compared to the corresponding unmodified plant a derivative thereof, a metabolite thereof, or a biosynthetic intermediate thereof; or (b) when the altered content of the at least one steroidal alkaloid, a derivative thereof, a metabolite thereof, or a biosynthetic intermediate thereof; of the at least one steroidal saponin, a derivative thereof, a metabolite thereof, or a biosynthetic intermediate thereof; or of the at least one triterpenoid saponin, a derivative thereof, a metabolite thereof, or a biosynthetic intermediate thereof comprises a reduced amount compared to the corresponding unmodified plant, the altered content of the phytosterol, or a derivative thereof, a metabolite thereof, or a biosynthetic intermediate thereof; the cholesterol, or a derivative thereof, a metabolite thereof, or a biosynthetic intermediate thereof; the phytocholesterol, or a derivative thereof, a metabolite thereof, or a biosynthetic intermediate thereof; the cholestenol, or a derivative thereof, a metabolite thereof, or a biosynthetic intermediate thereof, or the phytocholestenol, or a derivative thereof, a metabolite thereof, or a biosynthetic intermediate thereof comprises an increased amount compared to the corresponding unmodified plant.

In certain embodiments, an increase in each or sterodial saponins, steroidal alakoids, and or triterpenoid saponins may cause a change in the content level of the other(s). In some embodiments, the change comprises an increased content. In some embodiments, the change comprises a decrease content. In some embodiments, the change comprises an increased content of one and a decrease content of another.

In some embodiments, said plant comprises a plant in the Poales order, the Caryophyllales order, the Solanales order, the Fabales order, the Malvales order, the *Apiales* order, or the Brassicales order, the *Asparagales* order, the Dioscoreales order, or the Liliales order.

In some embodiments, (a) when said plant comprises a plant in the Poales order, said plant is selected from the group of genera consisting of the *Oryza* genus, the *Hordeum* genus, the *Avena* genus, and the *Triticum* genus; (b) when said plant comprises a plant in the Caryophvllales order, said plant is selected from the group of genera consisting of the *Spinacia* genus, the *Chenopodium* genus, the *Beta* genus, the *Rheum* genus, the *Vaccaria* genus, the *Saponaria* genus, and the *Gypsophila* genus; (c) when said plant comprises a plant in the Solanales order, said plant is selected from the group of genera consisting of the *Solanum* genus, the *Capsicum* genus, the *Nicotiana* genus, the *Hyoscyamus* genus, the *Datura* genus, and the *Atropa* genus; (d) when said plant comprises a plant in the Fabales order, said plant is selected from the group of genera consisting of the *Glycyrrhiza* genus, the *Medicago* genus, the *Glycine* genus, the *Lotus* genus, the *Cicer* genus, the *Phaseolus* genus, the *Pisum* genus, the *Arachis* genus, the *Lupinus* genus, and the *Acacia* genus; (e) when said plant comprises a plant in the *Malvales* order, said plant is selected from the *Theobroma* genus; (f) when said plant comprises a plant in the *Apiales* order, said plant is selected from the group of genera consisting of the *Daucus* genus, the *Apium* genus, the *Petroselinum* genus, the *Panax* genus, the *Bupleurum* genus, the *Hedera* genus, and the *Centella* genus; or (g) when said plant comprises a plant in the Brassicales order, said plant is selected from the group of genera consisting of the *Arabidopsis* genus, the *Brassica* genus, the *Capparis* genus, and the *Carica* genus.

In some embodiments, (a) when said plant comprises a plant in the Caryophyllales order, said plant is selected from the group consisting of spinach, beetroot, and *quinoa*; (b) when said plant comprises a plant in the Solanales order, said plant is selected from the group consisting of tomato, wild tomato, potato, wild potato, eggplant, pepper, bell pepper, cayenne pepper, chili pepper, pimiento, tabasco pepper, ground cherry, tobacco, and bittersweet; or (c) when said plant comprises a plant in the Fabales order, said plant is selected from the group consisting of alfalfa, soy, *Lotus japonicus*, and licorice.

In some embodiments, the plant is a tomato plant having: (i) an increased content of alpha-tomatine or a derivative thereof, a metabolite thereof, or a biosynthetic intermediate thereof, or tomatidine or a derivative thereof, a metabolite thereof, or a biosynthetic intermediate thereof; or a steroidal saponin or a derivative thereof, a metabolite thereof, or a biosynthetic intermediate thereof; or (ii) an altered content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof; or a phytocholestenol or a derivative thereof, a metabolite thereof, or a biosynthetic intermediate thereof.

In some embodiments, the plant is a tomato plant having: (i) an increased content of alpha-tomatine or a derivative thereof, a metabolite thereof, or a biosynthetic intermediate thereof; or tomatidine or a derivative thereof, a metabolite thereof, or a biosynthetic intermediate thereof; or a steroidal saponin or a derivative thereof, a metabolite thereof, or a biosynthetic intermediate thereof; or (ii) a reduced content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof; or a phytocholestenol or a derivative thereof, a metabolite thereof, or a biosynthetic intermediate thereof.

In some embodiments, the plant is a potato plant having: (i) an increased content of alpha-chaconine or a derivative thereof, a metabolite thereof, or a biosynthetic intermediate thereof; or alpha-solanine or a derivative thereof, a metabolite thereof, or a biosynthetic intermediate thereof; or a steroidal saponin or a derivative thereof, a metabolite thereof, or a biosynthetic intermediate thereof; or (ii) an altered content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof; or a phytocholestenol or a derivative thereof, a metabolite thereof, or a biosynthetic intermediate thereof.

In some embodiments, the plant is a potato plant having: (i) an increased content of alpha-chaconine or a derivative thereof, a metabolite thereof, or a biosynthetic intermediate thereof; or alpha-solanine or a derivative thereof, a metabolite thereof, or a biosynthetic intermediate thereof; or a steroidal saponin or a derivative thereof, a metabolite thereof, or a biosynthetic intermediate thereof; or (ii) a reduced content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof; or a phytocholestenol or a derivative thereof, a metabolite thereof, or a biosynthetic intermediate thereof.

In some embodiments, the plant is an eggplant plant having: (i) an increased content of alpha-solasonine or a derivative thereof, a metabolite thereof, or a biosynthetic intermediate thereof; or alpha-solamargine or a derivative thereof, a metabolite thereof, or a biosynthetic intermediate thereof; or a steroidal saponin or a derivative thereof, a metabolite thereof, or a biosynthetic intermediate thereof; or (ii) an altered content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof; or a phytocholestenol or a derivative thereof, a metabolite thereof, or a biosynthetic intermediate thereof.

In some embodiments, the plant is an eggplant plant having: (i) an increased content of alpha-solasonine or a derivative thereof, a metabolite thereof, or a biosynthetic intermediate thereof; or alpha-solamargine or a derivative thereof, a metabolite thereof, or a biosynthetic intermediate thereof; or a steroidal saponin or a derivative thereof, a metabolite thereof, or a biosynthetic intermediate thereof; or (ii) a reduced content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof; or a phytocholestenol or a derivative thereof, a metabolite thereof, or a biosynthetic intermediate thereof.

In some embodiments, said plant cell comprises a leaf cell, a petiole cell, a plant stem or stalk cell, a root cell, a bud cell, a tuber cell, a bean cell, a grain or kernel cell, a fruit cell, a nut cell, a legume cell, a seed or seed cell, a callus cells, a bract cell, a callus cell, and a flower cell.

Specifically disclosed herein are methods of producing steroidal alkaloids, steroidal saponins, or triterpenoid saponins in a genetically modified cell, the methods comprising: (a) introducing an at least one heterologous gene into said cell, said at least one heterologous gene encoding a cellulose synthase like G (CSLG) enzyme, wherein said heterologous gene is optionally comprised in a vector; and (b) expressing said at least one heterologous gene in said cell; wherein said cell comprises an increased content of at least one steroidal alkaloid, at least one steroidal saponin, or at least one triterpenoid saponin compared to a corresponding unmodified cell.

In some embodiments, said introducing further comprises introducing an at least one additional heterologous gene into said cell, said heterologous gene selected from the group consisting of the group encoding a saponin beta-amyrin synthase, a cytochrome P450, a glycosyltransferase, an acyltransferase, and a UDP-glucose 6-dehydrogenase I, or any combination thereof, wherein said at least one additional heterologous gene is optionally comprised in a vector; and further comprising expressing said at least one additional heterologous gene in said cell.

In some embodiments, (a) said at least one heterologous gene is operably linked to a promoter, a transcription termination sequence, or a combination thereof; or (b) said at least one additional heterologous gene is operably linked to a promoter, a transcription termination sequence, or a combination thereof; or (c) a combination thereof of (a) and (b).

In some embodiments, said introducing comprises transforming said at least one cell with (a) said at least one heterologous gene or a polynucleotide sequence encoding said at least one heterologous gene, or the vector comprising said at least one heterologous gene; or (b) said at least one additional heterologous gene or a polynucleotide sequences encoding said at least one additional heterologous gene, or the vector comprising said at least one additional heterologous gene; or (c)

a combination thereof of (a) and (b); wherein said expressing comprises transient expression or constitutive expression.

Specifically disclosed herein are methods of reducing the content of at least one steroidal alkaloid, a derivative thereof, a metabolite thereof, or a biosynthetic intermediate thereof; of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, in at least one cell of a plant or a plant part, the method comprising genetically modifying said at least one plant cell, said genetic modification comprising: (a) transforming said at least one plant cell with at least one silencing molecule targeted to a nucleic acid gene sequence encoding a Cellulose Synthase Like G (CSLG) enzyme; or (b) mutagenizing at least one nucleic acid sequence encoding a Cellulose Synthase Like G (CSLG) enzyme, wherein the mutagenesis comprises introducing (1) one or more point mutations into the nucleic acid sequence, (2) deletions within the nucleic acid sequence, or (3) insertions within the nucleic acid, or (4) any combination thereof, wherein said introducing comprising mutagenizing coding or non-coding sequence; wherein expression of the gene encoding the CSLG enzyme is reduced in the genetically modified plant cell compared to its expression in a corresponding unmodified plant cell, wherein the plant comprising said genetically modified cell comprises reduced content of at least one steroidal alkaloid, a derivative thereof, a metabolite thereof, or a biosynthetic intermediate thereof; of at least one steroidal saponin, a derivative thereof, a metabolite thereof, or a biosynthetic intermediate thereof, or of at least one triterpenoid saponin, a derivative thereof, a metabolite thereof, or a biosynthetic intermediate thereof, compared to the corresponding unmodified plant.

In some embodiments. (a) when the nucleic acid of the CSLG is set forth in SEQ ID NO: 30, the silencing molecule is set forth in SEQ ID NO: 42 or a complementary sequence thereof, or a homolog thereof having at least 80% identity to and at least 80% coverage of, the nucleic acid sequence set forth in SEQ ID NO: 42 or a complementary sequence thereof; (b) when the nucleic acid of the CSLG is set forth in SEQ ID NO: 34, the silencing molecule is set forth in SEQ ID NO: 43 or a complementary sequence thereof, or a homolog thereof having at least 80% identity to and at least 80% coverage of, the nucleic acid sequence set forth in SEQ ID NO: 43 or a complementary sequence thereof; (c) when the nucleic acid of the CSLG is set forth in SEQ ID NO: 38, the silencing molecule is set forth in SEQ ID NO: 44 or a complementary sequence thereof, or a homolog thereof having at least 80% identity to and at least 80% coverage of, the nucleic acid sequence set forth in SEQ ID NO: 44 or a complementary sequence thereof; (d) when the nucleic acid of the CSLG is set forth in SEQ ID NO: 65 or SEQ ID NO: 93, the silencing molecule is set forth in SEQ ID NO: 106 or a complementary sequence thereof, or a homolog thereof having at least 80% identity to and at least 80% coverage of, the nucleic acid sequence set forth in SEQ ID NO: 65 or the nucleic acid sequence set forth in SEQ ID NO: 93; or (e) when the nucleic acid of the CSLG is set forth in SEQ ID NO: 95, the silencing molecule is set forth in SEQ ID NO: 107 or a complementary sequence thereof, or a homolog thereof having at least 80% identity to and at least 80% coverage of, the nucleic acid sequence set forth in SEQ ID NO: 95.

In some embodiments: (a) said steroidal alkaloid, said steroidal saponin, or said triterpenoid saponin comprises a toxin or a bitter tasting compound or having hormone mimicking properties, or a combination thereof; or (b) said steroidal glycoalkaloid comprises alpha-tomatine, tomatine, alpha-chaconine, alpha-solanine, alpha-solasonine, alpha-solmargine, or any combination thereof; or (c) said steroidal saponin comprises utteroside B and tonatosides and related compounds (all steroidal saponins family), pathway intermediates and derivatives, or any combination thereof; or (d) said triterpenoid saponin comprises medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof; or (e) said intermediate comprises Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof; or (f) a combination thereof.

In certain embodiments, reduction of a triterpenoid saponin is desired, for example, but not limited to triterpenoid saponins having a bitter taste, as in *quinoa*, or being toxic. Other examples of triterpenoid saponins wherein reduction may be desired include triterpenoid saponins that have toxic properties or mimic hormones. Thus, in certain embodiments, increased production of triterpenoid saponins is beneficial and in other embodiments, decreased production of triterpenoid saponins is beneficial.

In some embodiments, the method further comprises altering the content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, the method further comprises increasing the content of a phytosterol, or a derivative thereof, a metabolite thereof, or a biosynthetic intermediate thereof, a cholesterol, or a derivative thereof, a metabolite thereof, or a biosynthetic intermediate thereof; a phytocholesterol, or a derivative thereof, a metabolite thereof, or a biosynthetic intermediate thereof, a cholestenol, or a derivative thereof, a metabolite thereof, or a biosynthetic intermediate thereof, or a phytocholestenol, or a derivative thereof, a metabolite thereof, or a biosynthetic intermediate thereof.

According to some embodiments, the method further comprises purifying the phytosterol, or derivative, metabolite, or biosynthetic intermediate thereof, the cholesterol, or derivative, metabolite, or biosynthetic intermediate thereof; the phytocholesterol, or derivative, metabolite, or biosynthetic intermediate thereof; the cholestenol, or derivative, metabolite, or biosynthetic intermediate; or the phytocholestenol, or derivative, metabolite, or biosynthetic intermediate thereof, extracted from the transformed plant. According to certain embodiments, the phytosterol comprises phytocholesterol. According to some embodiments, the phytosterol, or derivative, metabolite, or biosynthetic intermediate thereof, the cholesterol, or derivative, metabolite, or biosynthetic intermediate thereof; the phytocholesterol, or derivative, metabolite, or biosynthetic intermediate thereof; the cholestenol, or derivative, metabolite, or biosynthetic intermediate; or the phytocholestenol, or derivative, metabolite, or biosynthetic intermediate thereof, extracted from the transformed plant, comprises a nutrient or food additive, a high-value steroidal compound (e.g., pro-vitamin D and/or diosgenin), an anti-cholesterol agent (e.g., a plant phytosterol competing with dietary cholesterol in a mammalian or avian gut), or a cosmetic agent.

Specifically disclosed herein are methods of increasing the content of at least one steroidal alkaloid, a derivative thereof, a metabolite thereof, or a biosynthetic intermediate thereof; of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, in at least one cell of a plant or plant part, the method comprising genetically modifying said at least one plant cell, said genetic modification comprising: (a) mutagenizing at least one nucleic acid sequence encoding a Cellulose Synthase Like G (CSLG) enzyme, wherein the mutagenesis comprises introducing (1) one or more point mutations into the nucleic acid sequence, (2) deletions within the nucleic acid sequence, or (3) insertions within the nucleic acid, or (4) any combination thereof, wherein said introducing comprising mutagenizing coding or non-coding sequence; and (b) expressing said nucleic acid encoding said CSLG; wherein the plant comprising said genetically modified cell comprises increased content of at least one steroidal alkaloid, a derivative thereof, a metabolite thereof, or a biosynthetic intermediate thereof; of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, compared to the corresponding unmodified plant.

In some embodiments: (a) said steroidal alkaloid, said steroidal saponin, or said triterpenoid saponin comprises a toxin or a bitter tasting compound or having hormone mimicking properties, or a combination thereof; or (b) said steroidal glycoalkaloid comprises alpha-tomatine, tomatine, alpha-chaconine, alpha-solanine, alpha-solasonine, alpha-solmargine, or any combination thereof, or (c) said steroidal saponin comprises uttroside B, a tomatoside, or any combination thereof; or (d) said triterpenoid saponin comprises medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof; or (e) said intermediate comprises Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof, or (f) a combination thereof.

In some embodiments: (a) expression of the gene encoding the CSLG enzyme is increased in the genetically modified plant cell compared to its expression in a corresponding unmodified plant cell; or (b) said encoded CSLG enzyme has increased activity in the genetically modified plant cell compared to its activity in a corresponding unmodified plant cell; or (c) said encoded CSLG enzyme has increased stability in the genetically modified plant cell compared to its stability in a corresponding unmodified plant cell; or (d) any combination thereof of (a), (b), and (c).

In some embodiments, the method further comprises altering the content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, the method further comprises reducing the content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

Each possibility described herein represents a separate embodiment of the invention.

Genetically Modified Cells & Genetically Modified Plants

Disclosed herein are genetically modified cells and genetically modified plants, wherein expression of key genes in the steroidal glycoalkaloid/steroidal saponin/triterpenoid saponin metabolic pathway (biosynthesis pathway of steroidal alkaloids, steroidal saponins, and triterpenoid saponins) has been altered. Altering the expression of these genes results in concomitant alteration in the steroidal alkaloid profile, in the steroidal saponin profile, or in the triterpenoid profile. In an non-limiting example, changing the production level of steroidal alkaloid can result in improved plants comprising elevated content of steroidal alkaloids having increased resistance to pathogens, or plants having a reduced content of these secondary compounds in the plant edible parts and thus producing improved crops, wherein the improved crop has reduced or eliminated anti-nutritional content. Alternatively, or additionally, in another non-limiting example, controlling the expression of genes disclosed herein may be used for the production of desired steroidal alkaloids or plant-based cholesterol for further use, e.g., in the nutritional, cosmetic, or pharmaceutical industry. In another non-limiting example, disclosed herein are the means and methods for producing crop plants of the Solales order and other orders that are devoid of toxic amounts of deleterious steroidal alkaloids typically present in edible parts of these plants. Thus, the cells and plants disclosed herein are of significant nutritional and commercial value.

Disclosed herein are an array of co-expressed genes that participate in the biosynthesis pathway of steroidal alkaloids, steroidal saponins, or triterpenoid saponins. The present invention further discloses key genes in this pathway, altering the expression of which result in concomitant alteration in the steroidal alkaloid profile, in the steroidal saponin profile, or in the triterpenoid profile. In one non-limiting example, changing the production level of steroidal alkaloids can result in an improved plant comprising elevated content of steroidal alkaloids having increased resistance to pathogens, or plants having a reduced content of these secondary compounds in the plant edible parts and thus producing improved crops. Alternatively, or additionally, in one non-limiting example, controlling the expression of genes revealed in the present invention can be used, e.g., for the production of desired steroidal alkaloids or plant-based cholesterol or other phytosterols for further use, for example, in the nutrition, cosmetic, or pharmaceutical industries. Thus, the cells and plants of the present invention are thus of significant nutritional, cosmetic, pharmaceutical, and commercial value.

Disclosed herein are genetically modified cells (e.g., plant cells, yeast cells, algal cells, bacterial cells, insect cells) and plants comprising at least one genetically modified cell, wherein the genetically modified cells are expressing at least one heterologous gene encoding an enzyme within the steroidal alkaloid/steroidal saponin/triterpenoid saponin biosynthetic pathway. These enzymes include, in some embodiments, cellulose synthase like G (CSLG) enzymes, as well as saponin beta-amyrin synthases, cytochrome P450s, glycosyltransferases, and acyltransferases.

Figure 20A:
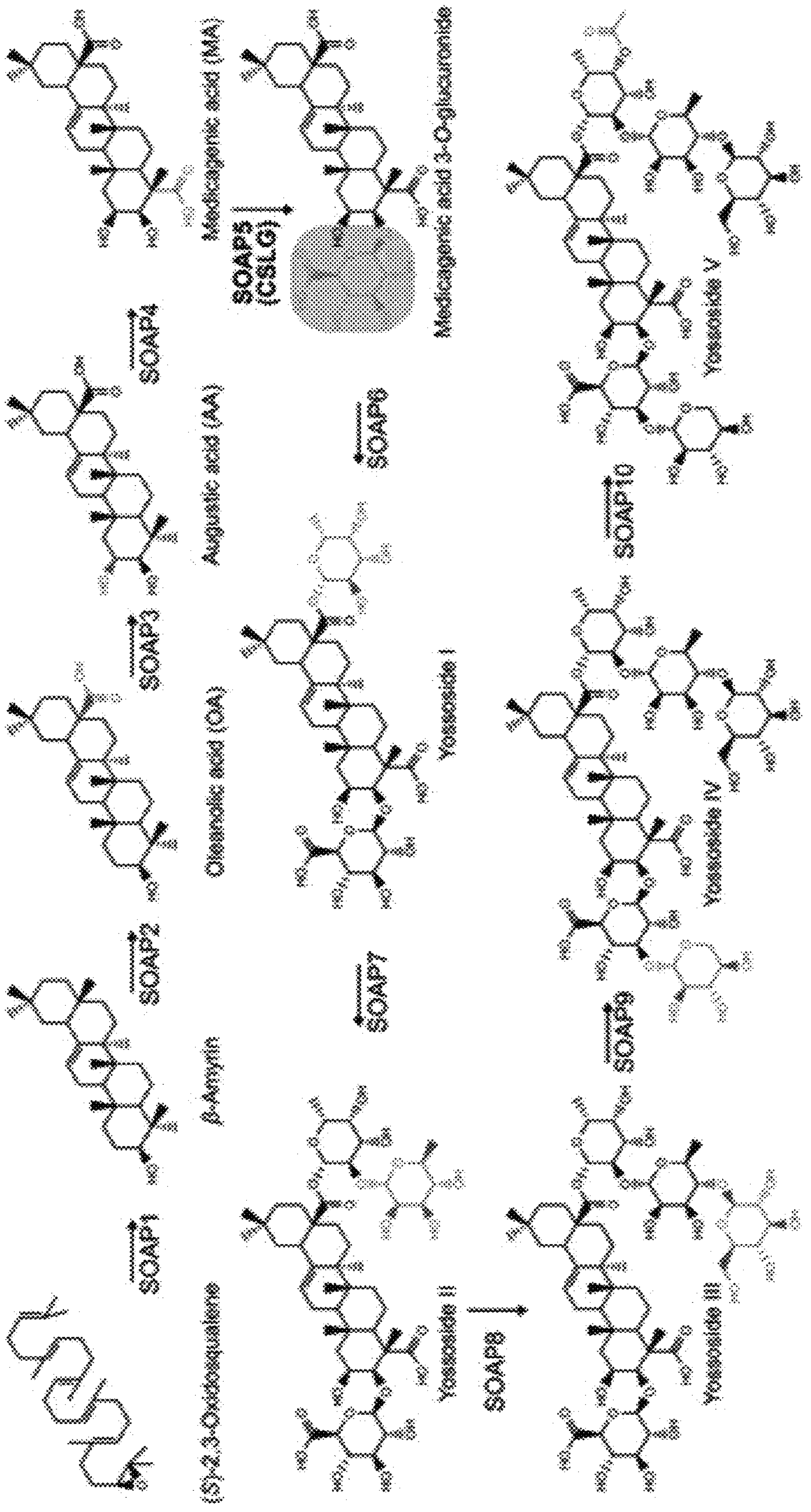
FIGS. 20A-20C show that the biosynthetic pathway of spinach saponins comprising co-expressed saponin β-amyrin synthase (SOAP) genes.
Figure 20B:
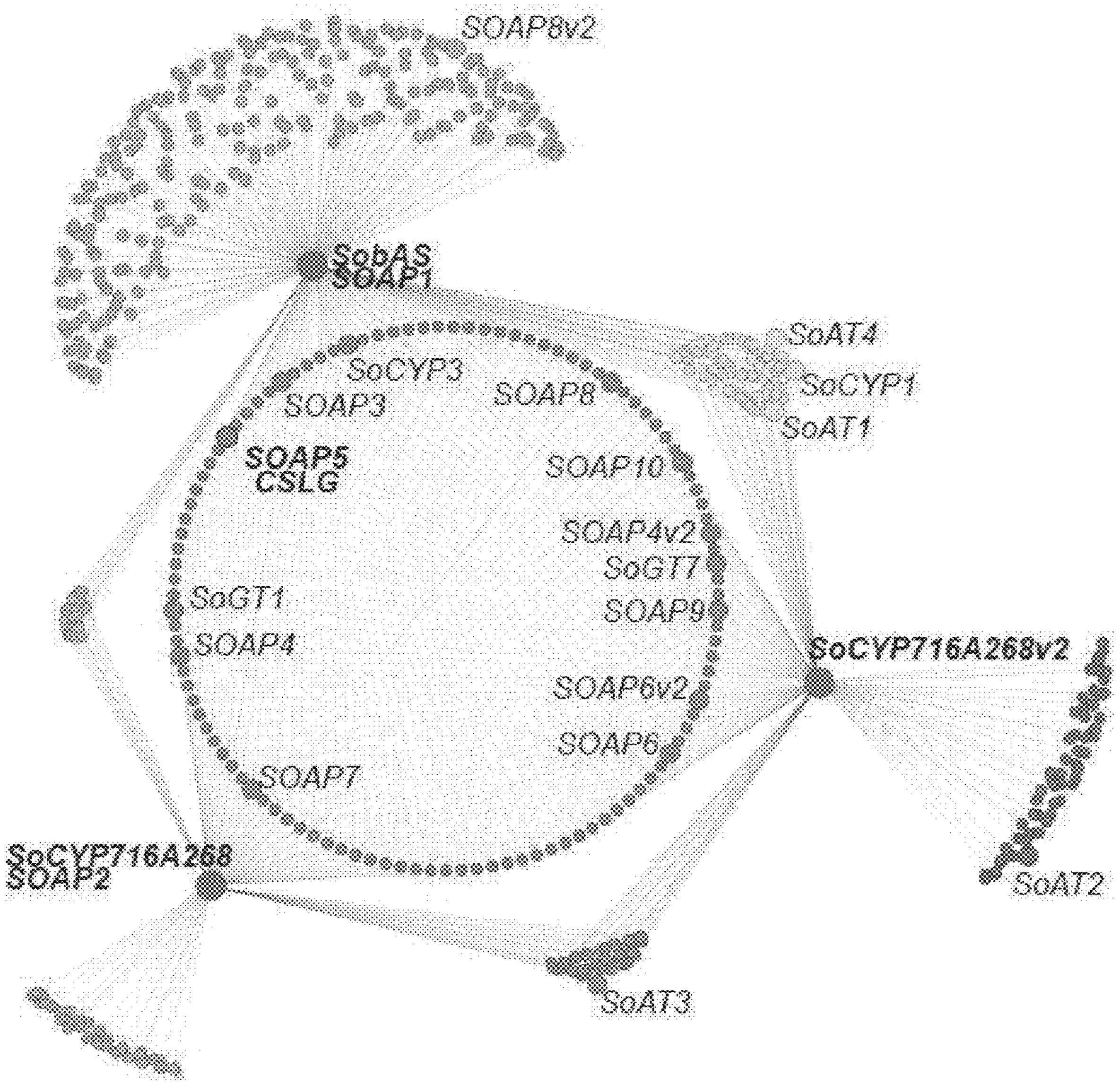
Figure 20C:
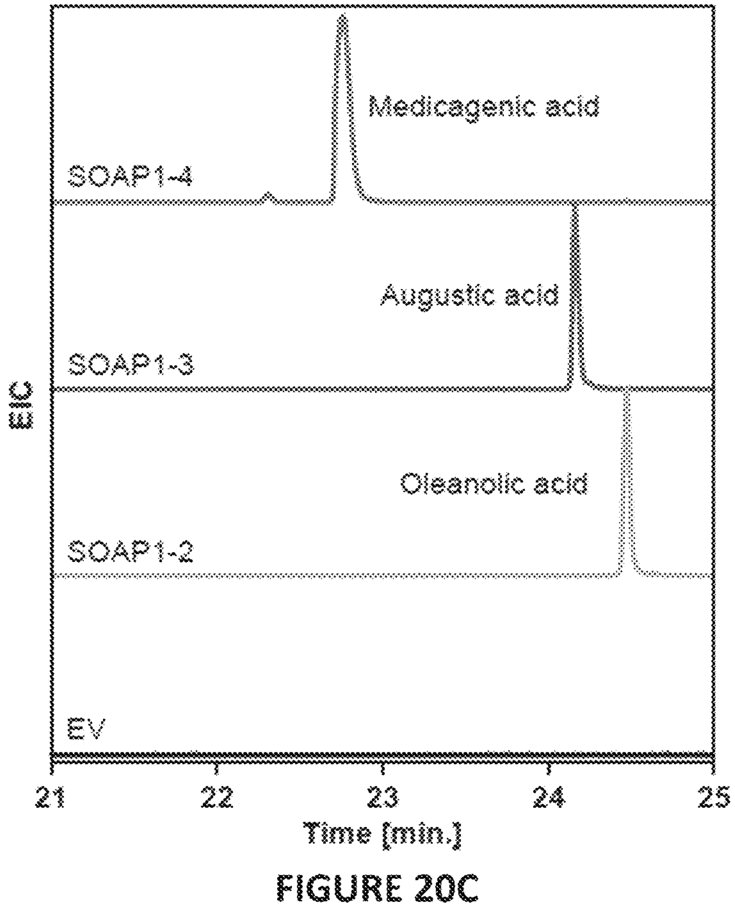

In some embodiments, a genetically modified cell disclosed herein, expresses at least one heterologous gene encoding an enzyme, said enzyme selected from the group consisting of a saponin beta-amyrin synthase, a cytochrome P450, a glycosyltransferase, an acyltransferase, a UDP-glucose 6-dehydrogenase 1, and a cellulose synthase like G (CSLG). FIG. 1 provides a non-limiting example of steroidal alkaloids and steroidal saponins in the triterpenoid biosynthetic pathway in Solanaceous plants (here, tomato) beginning with cholesterol, wherein a skilled artisan would recognize that the pathway may encompass production of saponin aglycones and glycosylated steroidal alkaloids biosynthetic intermediates and glycosylated saponins biosynthetic intermediates, and results in the production of a steroidal alkaloid (e.g., alpha-tomatine) or a steroidal saponin (e.g., uttroside B). FIG. 20A provides a non-limiting example of a triterpenoid saponin pathway in spinach, wherein a skilled artisan would recognize that the pathway may encompass production of saponin aglycones and glycosylated saponins biosynthetic intermediates, and results in the production of a triterpenoid saponin (Yossoside V; Compound 11).

Altering the expression of at least one of the genes in the steroidal alkaloid/steroidal saponin/triterpenoid saponin biosynthetic pathway, in some embodiments, results in concomitant alteration in the steroidal alkaloid profile or intermediates of that pathway, in the steroidal saponin profile or intermediates of that pathway, or in the triterpenoid saponin profile or intermediates of that pathway. In some embodiments, the altered expression in a genetically modified cells comprises increased expression compared with a corresponding unmodified cell. In some embodiments, increased expression comprises de novo expression from a gene encoding an enzyme not previously present in the cell. In some embodiments, increased expression comprises an increase of expression of a gene already present within the cells. In some embodiments, increased expression results in an increased amount of the encoded enzyme.

In some embodiments, the alteration in the steroidal alkaloid profile comprising an increase in at least one steroidal alkaloid or an intermediate thereof. In some embodiments, the alteration in the steroidal alkaloid profile comprising a decrease in at least one steroidal alkaloid or an intermediate thereof.

In some embodiments, the alteration in the steroidal saponin profile comprising an increase in at least one steroidal saponin or an intermediate thereof. In some embodiments, the alteration in the steroidal saponin profile comprising a decrease in at least one steroidal saponin or an intermediate thereof.

In some embodiments, the alteration in the triterpenoid saponin profile comprising an increase in at least one triterpenoid saponin or an intermediate thereof. In some embodiments, the alteration in the triterpenoid saponin profile comprising a decrease in at least one triterpenoid saponin or an intermediate thereof.

In some embodiments, introducing a nucleotide sequence encoding at least one of the enzymes of the steroidal alkaloid/steroidal saponin/triterpenoid saponin biosynthetic pathway into a heterologous cell, (for example but not limited to a plant cell, an algal cell, a yeast cell, an insect cell, or a bacterial cell) or an organism (for example but not limited to a plant), results in increased expression of the at least one enzyme and increased production of a steroidal alkaloid, a steroidal saponin, or a triterpenoid saponin. In some embodiments, introducing a nucleotide sequence encoding at least one of the enzymes of the steroidal alkaloid/steroidal saponin/triterpenoid saponin biosynthetic pathway into a heterologous cell or organism, results in production of a steroidal alkaloid, a steroidal saponin, or a triterpenoid saponin not naturally produced by the heterologous cell (for example but not limited to a plant cell, an algal cell, a yeast cell, an insect cell, or a bacterial cell) or organism (for example but not limited to a plant).

Throughout described herein are genetically modified cells and uses thereof. In some embodiments, a genetically modified cell is selected from any of an algal cell, a yeast cell, an insect cell, or a bacterial cell. One skilled in the art would know how to use the genes and nucleic acid sequences disclosed herein to genetically modified a eukaryotic cell, for example mammalian cells, or a prokaryotic cell, for example bacterium, to produce at least one steroidal alkaloid, steroidal saponin, or triterpenoid saponin. Further, one skilled in the art could use the genes and nucleic acid sequences disclosed herein to produce at least one steroidal alkaloid, steroidal saponin, or triterpenoid saponin in a cell-free in vitro system. In some embodiments, the genetically modified cell is a plant cell, and said plant cell is used to produce at least one steroidal alkaloid, steroidal saponin, or triterpenoid saponin. In some embodiments, the genetically modified cell is a plant cell or a yeast cell and said plant cell or yeast is used to produce at least one steroidal alkaloid, steroidal saponin, or triterpenoid saponin. In some embodiments, the genetically modified cell is a yeast cell, and said yeast cell is used to produce at least one steroidal alkaloid, steroidal saponin, or triterpenoid saponin. In some embodiments, the genetically modified cell is a algal cell, and said algal cell is used to produce at least one steroidal alkaloid, steroidal saponin, or triterpenoid saponin. In some embodiments, the genetically modified cell is an insect cell, and said insect cell is used to produce at least one steroidal alkaloid, steroidal saponin, or triterpenoid saponin. In some embodiments, the genetically modified cell is a bacterium, and said bacterium is used to produce at least one steroidal alkaloid, steroidal saponin, or triterpenoid saponin. In some embodiments, the genetically modified cell is a plant cell comprised in a plant or plant part and said plant cell is used to produce at least one steroidal alkaloid, steroidal saponin, or triterpenoid saponin in said plant or plant part. In some embodiments, the genetically modified cell is a plant cell comprised in a plant or plant part and said plant cell is used to reduce the production of at least one steroidal alkaloid, steroidal saponin, or triterpenoid saponin in said plant or plant part. In some embodiments, the genetically modified cell is a plant cell comprised in a plant or plant part and said plant cell is used to increase the production of at least one steroidal alkaloid, steroidal saponin, or triterpenoid saponin in said plant or plant part.

In some embodiments, heterologous expression comprises expressing an at least one heterologous plant gene from one plant species in a second plant species (see for example, Example 23 below). In some embodiments, heterologous expression comprises expressing an at least one heterologous plant gene from a plant species in a yeast cell (see for example, Example 21 below). In some embodiments, heterologous expression comprises expressing an at least one heterologous plant gene from a plant species in an algal cell. In some embodiments, heterologous expression comprises expressing an at least one heterologous plant gene from a plant species in bacterial cell. In some embodiments, heterologous expression comprises expressing an at least one heterologous plant gene from a plant species in an insect cell. In some embodiments, heterologous expression comprises expressing an at least one heterologous plant gene from a plant species in a cell of a plant, wherein the plant is of a different species.

In some embodiments, expressing at least one heterologous gene encoding an enzyme selected from a steroidal alkaloid, steroidal saponin, or triterpenoid saponin biosynthetic pathway alters the content of the steroidal alkaloid, steroidal saponin, or triterpenoid saponin produced by that pathway or alters the content of at least one biosynthetic intermediate thereof, or a combination thereof. In some embodiments, expressing more than one heterologous gene encoding at least two enzymes selected from a steroidal alkaloid, steroidal saponin, or triterpenoid saponin biosynthetic pathway alters the content of the steroidal alkaloid, steroidal saponin, or triterpenoid saponin produced by that pathway or alters the content of at least one biosynthetic intermediate thereof, or a combination thereof. In some embodiments, expressing more than one heterologous gene encoding at least three enzymes selected from a steroidal alkaloid, steroidal saponin, or triterpenoid saponin biosynthetic pathway alters the content of the steroidal alkaloid, steroidal saponin, or triterpenoid saponin produced by that pathway or alters the content of at least one biosynthetic intermediate thereof, or a combination thereof. In some embodiments, expressing more than one heterologous gene encoding at least four enzymes selected from a steroidal alkaloid, steroidal saponin, or triterpenoid saponin biosynthetic pathway alters the content of the steroidal alkaloid, steroidal saponin, or triterpenoid saponin produced by that pathway or alters the content of at least one biosynthetic intermediate thereof, or a combination thereof. In some embodiments, expressing more than one heterologous gene encoding at least five enzymes selected from a steroidal alkaloid, steroidal saponin, or triterpenoid saponin biosynthetic pathway alters the content of the steroidal alkaloid, steroidal saponin, or triterpenoid saponin produced by that pathway or alters the content of at least one biosynthetic intermediate thereof, or a combination thereof. In some embodiments, expressing more than one heterologous gene encoding at least six enzymes selected from a steroidal alkaloid, steroidal saponin, or triterpenoid saponin biosynthetic pathway alters the content of the steroidal alkaloid, steroidal saponin, or triterpenoid saponin produced by that pathway or alters the content of at least one biosynthetic intermediate thereof, or a combination thereof. In some embodiments, expressing more than one heterologous gene encoding at least seven enzymes selected from a steroidal alkaloid, steroidal saponin, or triterpenoid saponin biosynthetic pathway alters the content of the steroidal alkaloid, steroidal saponin, or triterpenoid saponin produced by that pathway or alters the content of at least one biosynthetic intermediate thereof, or a combination thereof. In some embodiments, expressing more than one heterologous gene encoding at least eight enzymes selected from a steroidal alkaloid, steroidal saponin, or triterpenoid saponin biosynthetic pathway alters the content of the steroidal alkaloid, steroidal saponin, or triterpenoid saponin produced by that pathway or alters the content of at least one biosynthetic intermediate thereof, or a combination thereof. In some embodiments, expressing more than one heterologous gene encoding at least nine enzymes selected from a steroidal alkaloid, steroidal saponin, or triterpenoid saponin biosynthetic pathway alters the content of the steroidal alkaloid, steroidal saponin, or triterpenoid saponin produced by that pathway or alters the content of at least one biosynthetic intermediate thereof, or a combination thereof. In some embodiments, expressing more than one heterologous gene encoding at least ten enzymes selected from a steroidal alkaloid, steroidal saponin, or triterpenoid saponin biosynthetic pathway alters the content of the steroidal alkaloid, steroidal saponin, or triterpenoid saponin produced by that pathway or alters the content of at least one biosynthetic intermediate thereof, or a combination thereof.

In some embodiments, disclosed herein is a genetically modified cell having increased expression of at least one heterologous gene compared to a corresponding unmodified cell, said at least one heterologous gene encoding a cellulose synthase like G (CSLG) enzyme, wherein said genetically modified cell comprises an increased content of at least one steroidal alkaloid, steroidal saponin, or triterpenoid saponin, a derivative thereof, a metabolite thereof, or a biosynthetic intermediate thereof, compared to a corresponding unmodified cell. In some embodiments, the genetically modified cell further expresses at least one additional heterologous gene encoding an enzyme, said enzyme selected from the group consisting of a saponin beta-amyrin synthase, a cytochrome P450, a glycosyltransferase, an acyltransferase, and an UDP-glucose 6-dehydrogenase 1, or any combination thereof.

In some embodiments, derivatives of steroidal alkaloids, steroidal saponins, or triterpenoid saponins comprise glycosylated derivatives of, respectively, steroidal alkaloids, steroidal saponins, or triterpenoid saponins.

In some embodiments, a genetically modified cell expresses a heterologous CSLG and a heterologous saponin beta-amyrin synthase. In some embodiments, a genetically modified cell expresses a heterologous CSLG and at least one heterologous cytochrome P450. In some embodiments, a genetically modified cell expresses a heterologous CSLG and 1, 2, or 3 heterologous cytochrome P450s. In some embodiments, a genetically modified cell expresses a heterologous CSLG, a heterologous saponin beta-amyrin synthase, and 1, 2, or 3 heterologous cytochrome P450s. In some embodiments, a genetically modified cell expresses a heterologous CSLG and at least one heterologous glycosyl transferase. In some embodiments, a genetically modified cell expresses a heterologous CSLG and at least 1, 2, 3, or 4 heterologous glycosyl transferases. In some embodiments, a genetically modified cell expresses a heterologous CSLG, a heterologous saponin beta-amyrin synthase, and at least 1, 2, 3, or 4 heterologous glycosyl transferases. In some embodiments, a genetically modified cell expresses a heterologous CSLG, a heterologous saponin beta-amyrin synthase, at least 1, 2, or 3 heterologous cytochrome P450s, and at least 1, 2, 3, or 4 heterologous glycosyl transferases.

In certain instances, it may be necessary to express additional genes not specifically part of the steroidal alkaloid, steroidal saponin, or triterpenoid saponin pathway, homologous or heterologous, in order that necessary substrates are available. In some embodiments, a genetically modified cell expresses a heterologous gene encoding an enzyme necessary for production of substrates of a steroidal alkaloid, steroidal saponin, or triterpenoid saponin biosynthetic pathway.

In some embodiments, a heterologous gene encoding an enzyme selected from a saponin beta-amyrin synthase, a cytochrome P450, a C-2hydroxylase, a C-23 oxidase, a glycosyltransferase, a UDP-glucose 6-dehydrogenase 1, an acyltransferase, or a cellulose like synthase G (CSLG) is expressed in a genetically modified cell. In some embodiments, a heterologous gene encoding an enzyme selected from a saponin beta-amyrin synthase, a cytochrome P450, C-2hydroxylase, a C-23 oxidase, a glycosyltransferase, an acyltransferase, or a cellulose like synthase G (CSLG) is expressed in a genetically modified cell. In some embodiments, a heterologous gene encoding an enzyme selected from a saponin beta-amyrin synthase, a cytochrome P450, a glycosyltransferase, a UDP-glycosyltransferase, a fucosyltransferase, a xylosyltransferase, an acyltransferase, a BAHD-acyltransferase, or a cellulose like synthase G (CSLG) in expressed in a genetically modified cell.

In some embodiments, a genetically modified cell expresses at least one heterologous gene encoding an enzyme comprising a CSLG activity. In some embodiments, a genetically modified cell expresses at least one heterologous gene encoding an enzyme comprising a saponin beta-amyrin synthase activity. In some embodiments, a genetically modified cell expresses at least one heterologous gene encoding an enzyme comprising a cytochrome P450 activity. In some embodiments, a genetically modified cell expresses at least two heterologous gene encoding two enzymes comprising cytochrome P450 activity. In some embodiments, a genetically modified cell expresses at least three heterologous gene encoding three enzymes comprising cytochrome P450 activity. In some embodiments, an enzyme comprising cytochrome p450 activity comprises a C-2 hydroxylase activity. In some embodiments, an enzyme comprising cytochrome p450 activity comprises a C-23 oxidase activity.

In some embodiments, a genetically modified cell expresses heterologous genes encoding enzymes comprising a saponin beta-amyrin synthase activity, cytochrome P450 activities, and CSLG activity, wherein the cytochrome P450 enzymes may comprise an enzyme providing a C-2 hydroxylase activity, an enzyme providing a C-23 oxidase activity, a combination of enzymes providing cytochrome P450 activity, C-2 hydroxylase activity, and C-23 oxidase activity.

In some embodiments, a genetically modified cell expresses at least one heterologous gene encoding a glycosyltransferase enzyme activity. In some embodiments, the glycosyltransferase enzyme comprises a UDP-glycosyltransferase, a fucosyltransferase, or a xylosyltransferase. In some embodiments, a genetically modified cell expresses multiple heterologous genes encoding glycosyltransferase enzymes. In some embodiments, a genetically modified cell expresses multiple heterologous genes encoding glycosyltransferases, selected from a UDP-glycosyltransferase, a fucosyltransferase, or a xylosyltransferase, or a combination thereof. In some embodiments, a genetically modified cell expresses multiple heterologous genes encoding glycosyltransferases, selected from a combination of known glycosyltransferases known in the art. In some embodiments, a genetically modified cell expresses a heterologous gene encoding a CSLG activity and a heterologous gene encoding at least one glycosyltransferase enzyme activity. In some embodiments, a genetically modified cell expresses a heterologous gene encoding a CSLG activity and a heterologous gene encoding at least one glycosyltransferase enzyme activity selected from a UDP-glycosyltransferase, a fucosyltransferase, or a xylosyltransferase, or a combination thereof. In some embodiments, a genetically modified cell expresses a heterologous gene encoding a CSLG activity and a heterologous gene encoding at least one glycosyltransferase enzyme activity selected from a UDP-glycosyltransferase, a fucosyltransferase, or a xylosyltransferase, or any glycosyltransferase known in the art, or a combination thereof.

In some embodiments, a genetically modified cell expresses a heterologous gene encoding an acyltransferase. In some embodiments, a genetically modified cell expresses a heterologous gene encoding a benzylalcohol acetyl-, anthocyanin-O-hydroxy-cinnamoyl-, anthranilate-N-hydroxy-cinnamoyl/benzoyl-, deacetylvindoline acetyltransferase (BAHD) acyltransferase. In some embodiments, a genetically modified cell expresses a heterologous gene encoding an enzyme providing a CSLG activity and a heterologous gene encoding an enzyme encoding an acetyltransferase activity. In some embodiments, a genetically modified cell expresses a heterologous gene encoding an enzyme providing a CSLG activity and a heterologous gene encoding an enzyme encoding a BAHD acetyltransferase activity.

In some embodiments, a genetically modified cell expresses a heterologous gene encoding the encodes an enzyme activity for a triterpenoid saponin substrate, wherein the enzyme comprises a glycosyltransferase. In some embodiments, a genetically modified cell expresses a heterologous gene encoding the encodes an enzyme activity for a triterpenoid saponin substrate, wherein the enzyme comprises a UDP-glucose 6-dehydrogenase 1. In some embodiments, for example when the cell is a bacterial cell, a heterologous gene encodes a Squalene epoxidase, or a Cytochrome P450 reductase, or a UDP-glucose 6-dehydrogenase 1, or any combination thereof.

In some embodiments, disclosed herein is a genetically modified plant comprising an at least one cell having altered expression of at least a CSLG gene compared to the expression of CSLG in a corresponding unmodified cell, wherein the at least one cell comprises a heterologous CSLG gene, and said altered expression comprises a de novo expression of said heterologous gene. In some embodiments, disclosed herein is a genetically modified plant comprising an at least one cell having altered expression of at least a CSLG gene compared to the expression of CSLG in a corresponding unmodified cell, wherein the at least one cell comprises a heterologous CSLG gene, and said altered expression comprises expression of a heterologous gene in the presence of an endogenous gene, which may be functional or non-functional.

In some embodiments, the expression of a heterologous CSLG gene is a genetically modified plant comprises increased expression compared to a corresponding unmodified cell, and wherein said cell in said plant comprises altered content of at least a triterpenoid saponin, metabolite thereof, derivative thereof, or biosynthetic intermediate thereof, compared to the corresponding unmodified plant.

In some embodiments, disclosed herein is an array of enzymes that participate in the biosynthetic pathway of triterpenoid saponins, wherein the biosynthesis pathway includes production of saponin aglycones and glycosylated saponins, and glycosylated triterpenoid saponins. In some embodiments, disclosed herein is an array of genes encoding that enzymes that participate in the biosynthetic pathway of triterpenoid saponins, wherein the biosynthesis pathway includes production of saponin aglycones and glycosylated saponins, and glycosylated triterpenoid saponins, including but not limited to 3-O—[β-D-xylopyranosyl-(1->3)-β-D-glucuronopyranosyl]-28-O—[β-D-glucopyranosyl-(1->4)-α-L-rhamnopyranosyl-(1->2)-4-acetyl-β-D-fucopyranosyl]-medicagenic acid (Yossoside V; Compound 11); 3-O—[β-D-xylopyranosyl-(1->3)-β-D-glucuronopyranosyl]-28-O—[β-D-glucopyranosyl-(1->4)-α-L-rhamnopyranosyl-(1->2)-β-D-fucopyranosyl]-medicagenic acid (Yossoside IV; Compound 10); 3-O—[β-D-glucuronopyranosyl]-28-O—[β-D-glucopyranosyl-(1->4)-α-L-rhamnopyranosyl-(1->2)-β-D-fucopyranosyl]-medicagenic acid (Yossoside III; Compound 9); 3-O—[β-D-glucuronopyranosyl]-28-O—[α-L-rhamnopyranosyl-(1->2)-β-D-fucopyranosyl]-medicagenic acid (Yossoside II; Compound 8), and 3-O-β-D-glucuronopyranosyl-28-O-β-D-fucopyranosyl-medicagenic acid (Yossoside I; Compound 7) (see FIG. 20A).

For example, but not limited to the enzymes active in the spinach triterpenoid biosynthetic pathway of Compound 11, which are described in detail in the Examples. Table 16 provided in Example 20, provides the amino acid and nucleic acid sequences of the enzymes in the spinach biosynthetic pathway, wherein CSLG enzyme adds a glucuronic acid to medicagenic acid to make the triterpenoid saponin medicagenic acid 3-glucuronide. Table 19 disclosed in Example 24 provides the amino acid sequence of a CSLG isolated from *Arabidopsis*. Table 17 disclosed in the Examples provides the nucleic acid and amino acid sequences of CSLG homologs from other plant species.

In some embodiments, a genetically modified cell disclosed herein expresses at least one heterologous gene encoding an enzyme comprised in a steroidal alkaloid, steroidal saponin, or triterpenoid biosynthetic pathway. In some embodiments, a genetically modified cell disclosed herein expresses an array of heterologous gene encoding enzymes comprised in a steroidal alkaloid, steroidal saponin, or triterpenoid biosynthetic pathway. In some embodiments, a genetically modified cell disclosed herein expresses at least two heterologous gene encoding two enzymes comprised in a steroidal alkaloid, steroidal saponin, or triterpenoid biosynthetic pathway. In some embodiments, a genetically modified cell disclosed herein expresses at least three heterologous gene encoding three enzymes comprised in a steroidal alkaloid, steroidal saponin, or triterpenoid biosynthetic pathway. In some embodiments, a genetically modified cell disclosed herein expresses at least four heterologous gene encoding four enzymes comprised in a steroidal alkaloid, steroidal saponin, or triterpenoid biosynthetic pathway. In some embodiments, a genetically modified cell disclosed herein expresses at least 5 heterologous gene encoding five enzymes comprised in a steroidal alkaloid, steroidal saponin, or triterpenoid biosynthetic pathway. In some embodiments, a genetically modified cell disclosed herein expresses at least six heterologous gene encoding six enzymes comprised in a steroidal alkaloid, steroidal saponin, or triterpenoid biosynthetic pathway. In some embodiments, a genetically modified cell disclosed herein expresses at least seven heterologous gene encoding seven enzymes comprised in a steroidal alkaloid, steroidal saponin, or triterpenoid biosynthetic pathway. In some embodiments, a genetically modified cell disclosed herein expresses at least eight heterologous gene encoding eight enzymes comprised in a steroidal alkaloid, steroidal saponin, or triterpenoid biosynthetic pathway. In some embodiments, a genetically modified cell disclosed herein expresses at least nine heterologous gene encoding nine enzymes comprised in a steroidal alkaloid, steroidal saponin, or triterpenoid biosynthetic pathway. In some embodiments, a genetically modified cell disclosed herein expresses at least ten heterologous gene encoding ten enzymes comprised in a steroidal alkaloid, steroidal saponin, or triterpenoid biosynthetic pathway.

In some embodiments, disclosed herein is a genetically modified plant comprising at least one cell having altered expression of at least a cellulose synthase like G (CSLG) gene compared to the expression of CSLG in a corresponding unmodified plant, and wherein the genetically modified plant has an altered content of at least one steroidal alkaloid, a derivative thereof, a metabolite thereof, or a biosynthetic intermediate thereof, of at least one steroidal saponin, a derivative thereof, a metabolite thereof, or a biosynthetic intermediate thereof, or of at least one triterpenoid saponin, a derivative thereof, a metabolite thereof, or a biosynthetic intermediate thereof, compared to the corresponding unmodified plant. In some embodiments, the CSLG gene comprises the endogenous CSLG gene. In some embodiments, the CSLG gene comprises a heterologous CSLG gene.

In some embodiments, derivatives of steroidal alkaloids, steroidal saponins, or triterpenoid saponins comprise glycosylated derivatives of, respectively, steroidal alkaloids, steroidal saponins, or triterpenoid saponins.

In some embodiments, a genetically modified plant or plant part disclosed herein expresses at least one heterologous gene encoding an enzyme comprised in a steroidal alkaloid, steroidal saponin, or triterpenoid biosynthetic pathway. In some embodiments, a genetically modified plant or plant part disclosed herein expresses an array of heterologous gene encoding enzymes comprised in a steroidal alkaloid, steroidal saponin, or triterpenoid biosynthetic pathway. In some embodiments, a genetically modified plant or plant part disclosed herein expresses at least two heterologous gene encoding two enzymes comprised in a steroidal alkaloid, steroidal saponin, or triterpenoid biosynthetic pathway. In some embodiments, a genetically modified plant or plant part disclosed herein expresses at least three heterologous gene encoding three enzymes comprised in a steroidal alkaloid, steroidal saponin, or triterpenoid biosynthetic pathway. In some embodiments, a genetically modified plant or plant part disclosed herein expresses at least four heterologous gene encoding four enzymes comprised in a steroidal alkaloid, steroidal saponin, or triterpenoid biosynthetic pathway. In some embodiments, a genetically modified plant or plant part disclosed herein expresses at least 5 heterologous gene encoding five enzymes comprised in a steroidal alkaloid, steroidal saponin, or triterpenoid biosynthetic pathway. In some embodiments, a genetically modified plant or plant part disclosed herein expresses at least six heterologous gene encoding six enzymes comprised in a steroidal alkaloid, steroidal saponin, or triterpenoid biosynthetic pathway. In some embodiments, a genetically modified plant or plant part disclosed herein expresses at least seven heterologous gene encoding seven enzymes comprised in a steroidal alkaloid, steroidal saponin, or triterpenoid biosynthetic pathway. In some embodiments, a genetically modified plant or plant part disclosed herein expresses at least eight heterologous gene encoding eight enzymes comprised in a steroidal alkaloid, steroidal saponin, or triterpenoid biosynthetic pathway. In some embodiments, a genetically modified plant or plant part disclosed herein expresses at least nine heterologous gene encoding nine enzymes comprised in a steroidal alkaloid, steroidal saponin, or triterpenoid biosynthetic pathway. In some embodiments, a genetically modified plant or plant part disclosed herein expresses at least ten heterologous gene encoding ten enzymes comprised in a steroidal alkaloid, steroidal saponin, or triterpenoid biosynthetic pathway.

In some embodiments, heterologous genes encoding enzymes of the steroidal alkaloid, steroidal saponin, or triterpenoid biosynthetic pathway comprising enzymes selected from a beta-amyrin synthase, a cytochrome P450, multiple cytochrome P450s, a glycosyltransferase, multiple glycosyltransferases, an acyltransferase, or a CSLG, or any combination thereof. In some embodiments, heterologous genes encoding enzymes of the steroidal alkaloid, steroidal saponin, or triterpenoid biosynthetic pathway comprising enzyme selected from a beta-amyrin synthase, a cytochrome P450, multiple cytochrome P450s, a glycosyltransferase, multiple glycosyltransferases, an acyltransferase, or a CSLG, or any combination thereof, and in addition express at least one heterologous gene necessary to provide a biosynthetic pathway substrate or substrates. In some embodiments, heterologous genes encode enzymes of the steroidal alkaloid, steroidal saponin, or triterpenoid biosynthetic pathway comprising a beta-amyrin synthase, a cytochrome P450, multiple cytochrome P450s, a glycosyltransferase, multiple glycosyltransferases, an acyltransferase, or a CSLG, or any combination thereof, and in addition express a heterologous gene necessary to provide biosynthetic pathway substrates, for example but not limited to a UDP-glucose 6-dehydrogenase 1 enzyme.

In some embodiments, a genetically modified cell expresses at least one heterologous gene encoding an enzyme of the steroidal alkaloid/steroidal saponin/triterpenoid saponin biosynthetic pathway, said at least one heterologous gene encoding a CSLG enzyme.

In some embodiments, the at least one heterologous gene encodes a cytochrome P450 wherein said cytochrome P450 comprises a C2-hydroxylase or a C-23 oxidase, or a glycosyltransferase wherein said glycosyltransferase comprises a fructosyltransferase, a xylosyltransferase, or a UDP-glycosyltransferase, or a acyltransferase wherein said acyltransferase comprises a benzylalcohol acetyl-, anthocyanin-O-hydroxy-cinnamoyl-, anthranilate-N-hydroxy-cinnamyol/benzoyl-, deacetylvindoline (BAHD) acetyletransferase, or any combination thereof.

In some embodiments, expression of a heterologous gene or genes comprises increased expression compared to a corresponding unmodified cell. In some embodiments, increased expression of a gene results in increased content of an enzyme encoded by the gene, compared to the content of the enzyme in a corresponding unmodified cell. One skilled in the art would appreciate that increased expression may, in some embodiments, comprise overexpression of the gene or genes, with resultant increased presence of an enzyme of enzymes encoded by the gene or genes, compared with a corresponding unmodified cell. In some embodiments, increased expression may comprise expression of a gene or genes, and the production of a resultant enzyme activity or activities, not naturally found in the cell or organism, for example but not limited to a plant cell, a plant, a yeast cell, an algal cell, an insect cell, or a bacterial cell.

A skilled artisan would appreciate that a corresponding unmodified cell may in certain embodiments provide a control cell, wherein the heterologous gene is not expressed or is not overexpressed.

In some embodiments, expression of a gene or genes in a heterologous cell comprises transient expression of the gene or genes. In some embodiments, expression of a gene or genes in a heterologous cell comprises constitutive expression of the gene or genes. In some embodiments, expression of a gene or genes in a heterologous cell comprises transient expression, or constitutive expression, or a combination thereof, of the gene or genes.

A skilled artisan would appreciate that transient expression encompasses the temporary expression of a gene or genes that are expressed for a short time after a nucleic acid has been introduced into eukaryotic cells, for example a plant cell or a yeast cell. Conversely, constitutive expression, also known as stable expression, encompasses continuous expression of a gene or genes.

One of ordinary skill in the art would appreciate that the term "gene" may encompass a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene. The fragments may range in size from a few nucleotides to the entire gene sequence minus one nucleotide. Thus, "a nucleic acid sequence comprising at least a part of a gene" may comprise fragments of the gene or the entire gene.

The skilled artisan would appreciate that the term "gene" optionally also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding regions and which are present on the mRNA are referred to as 5' non-translated sequences. The sequences which are located 3' or downstream of the coding region and which are present on the mRNA are referred to as 3' non-translated sequences.

In some embodiments, a gene comprises DNA sequence comprising the coding region. In some embodiments, a gene comprises DNA sequence comprising upstream and downstream regions, as well as the coding region, which comprises exons and any intervening introns of the gene. In some embodiments, upstream and downstream regions comprise non-coding regulatory regions. In some embodiments, upstream and downstream regions comprise regulatory sequences, for example but not limited to promoters, enhancers, and silencers. Non-limiting examples of regulatory sequences include, but are not limited to, AGGA box, TATA box, Inr, DPE, ZmUbi1, PvUbi1, PvUbi2, CaMV, 35S, OsAct1, zE19, E8, TA29, A9, pDJ3S, B33, PAT1, alcA, G-box, ABRE, DRE, and PCNA.

Regulatory regions, may in some embodiments, increase or decrease the expression of specific genes within a cell, for example but not limited to a yeast, an algal, an insect, a bacterium, or a plant cell or a plant described herein. Regulatory regions, may in some embodiments, increase or decrease the expression of specific genes within a plant cell. Regulatory regions, may in some embodiments, increase or decrease the expression of specific genes within an algal cell. Regulatory regions, may in some embodiments, increase or decrease the expression of specific genes within a yeast cell. Regulatory regions, may in some embodiments, increase or decrease the expression of specific genes within an insect cell. Regulatory regions, may in some embodiments, increase or decrease the expression of specific genes within a bacterium.

In some embodiments, a gene comprises the coding regions of the gene, which comprises exons and any intervening introns of the gene. In some embodiments, a gene comprises its regulatory sequences. In some embodiments, a gene comprises the gene promoter. In some embodiments, a gene comprises its enhancer regions. In some embodiments, a gene comprises 5' non-coding sequences. In some embodiments, a gene comprises 3' non-coding sequences.

In some embodiments, the skilled artisan would appreciate that DNA comprises a gene, which may include upstream and downstream sequences, as well as the coding region of the gene. In other embodiments, DNA comprises a cDNA (complementary DNA). One of ordinary skill in the art would appreciate that cDNA may encompass synthetic DNA reverse transcribed from RNA through the action of a reverse transcriptase. The cDNA may be single stranded or double stranded and can include strands that have either or both of a sequence that is substantially identical to a part of the RNA sequence or a complement to a part of the RNA sequence. Further, cDNA may include upstream and downstream regulatory sequences. In still other embodiments, DNA comprises a CDS (complete coding sequence). One of ordinary skill in the art would appreciate that CDS may encompass a DNA sequence, which encodes a full-length protein or polypeptide. A CDS typically begins with a start codon ("ATG") and ends at (or one before) the first in-frame stop codon ("TAA", "TAG", or "TGA"). The skilled artisan would recognize that a cDNA, in one embodiment, comprises a CDS.

The terms "polynucleotide", "polynucleotide sequence", "nucleic acid sequence", and "isolated polynucleotide" are used interchangeably herein. These terms encompass nucleotide sequences and the like. A polynucleotide may be a polymer of RNA or DNA or hybrid thereof, that is single- or double-stranded, linear or branched, and that optionally contains synthetic, non-natural or altered nucleotide bases. The terms also encompass RNA/DNA hybrids.

The terms "complementary" or "complement thereof" are used herein to refer to the sequences of polynucleotides which is capable of forming Watson & Crick base pairing with another specified polynucleotide throughout the entirety of the complementary region. This term is applied to pairs of polynucleotides based solely upon their sequences and not any particular set of conditions under which the two polynucleotides would actually bind.

The term "construct" as used herein refers to an artificially assembled or isolated nucleic acid molecule which includes the polynucleotide of interest. In general, a construct may include the polynucleotide or polynucleotides of interest, a marker gene, which in some cases can also be a gene of interest and appropriate regulatory sequences. It should be appreciated that the inclusion of regulatory sequences in a construct is optional, for example, such sequences may not be required in situations where the regulatory sequences of a host cell are to be used. Regulatory elements include, but are not limited to, a promoter, an enhance, an origin of replication, a transcription termination sequence, a polyadenylation signal, and the like. The term "construct" includes vectors but should not be seen as being limited thereto.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In some embodiments, the terms "operably linked" and "functionally linked" may be used interchangeably having all the same meanings and qualities.

The terms "promoter element," "promoter," or "promoter sequence" as used herein, refer to a DNA sequence that is generally located at the 5' end (i.e. precedes) the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

A polynucleotide sequence comprising a heterologous gene may be expressed in, for example, a plant cell, an algal cell, a yeast cell, an insect cell, or a bacterium under the control of a promoter that directs constitutive expression or regulated (transient) expression. In some embodiments, the plant cell is part of a whole plant or a portion thereof. Regulated expression comprises temporally or spatially regulated expression and any other form of inducible or repressible expression. Temporally means that the expression is induced at a certain time point, for instance, when a certain growth rate of the plant cell culture is obtained (e.g., the promoter is induced only in the stationary phase or at a certain stage of development). Spatially means that the promoter is only active in specific organs, tissues, or cells (e.g., for plants only in roots, leaves, epidermis, guard cells or the like). Other examples of regulated expression comprise promoters whose activity is induced or repressed by adding chemical or physical stimuli to the plant cell or yeast cell or an algal cell or an insect cell or a bacterium. In some embodiments, a promoter is an inducible promoter. In some embodiments, a promoter is a constitutive promoter. In some embodiments regulated expression of a heterologous gene of the triterpenoid biosynthetic pathway, for example but not limited to CSLG, comprises inducing or repressing gene expression by adding chemical or physical stimuli to a plant cell. In some embodiments regulated expression of a heterologous gene of the triterpenoid biosynthetic pathway, for example but not limited to CSLG, comprises inducing or repressing gene expression by adding chemical or physical stimuli to a yeast cell. In some embodiments regulated expression of a heterologous gene of the triterpenoid biosynthetic pathway, for example but not limited to CSLG, comprises inducing or repressing gene expression by adding chemical or physical stimuli to an algal cell. In some embodiments regulated expression of a heterologous gene of the triterpenoid biosynthetic pathway, for example but not limited to CSLG, comprises inducing or repressing gene expression by adding chemical or physical stimuli to an insect cell. In some embodiments regulated expression of a heterologous gene of the triterpenoid biosynthetic pathway, for example but not limited to CSLG, comprises inducing or repressing gene expression by adding chemical or physical stimuli to a bacterium.

In some embodiments, the expression is under control of environmental, hormonal, chemical, and/or developmental signals. Such promoters for plant cells include promoters that are regulated by (1) heat, (2) light, (3) hormones, such as abscisic acid, and methyl jasmonate (4) wounding or (5) chemicals such as salicylic acid, chitosans or metals. A constitutive promoter directs expression in a wide range of cells under a wide range of conditions. Examples of constitutive plant promoters useful for expressing heterologous polypeptides in plant cells include, but are not limited to, the cauliflower mosaic virus (CaMV) 35S promoter, which confers constitutive, high-level expression in most plant tissues including monocots, the nopaline synthase promoter and the octopine synthase promoter. In some embodiments, a promoter is an inducible promoter. In some embodiments provided herein, inducible plant promoters, include but are not limited to GAL1, GAL10, PHO5 and CUP1. In some embodiments, a yeast promoter is constitutive promoter. In some embodiments provided herein, constitutive yeast promoters, include but are not limited to PGK1, TDHS, ADH1, CYC1, ACT1, TEF1. In some embodiments, an algal promoter is an inducible promoter. In some embodiments, provided herein algal promoters may be regulated by changes of light, pH, salinity, temperature, or nutrients. In some embodiments, an inducible algal promoter responds to nitrogen levels, nitrogen stress, or nitrogen starvation. In some embodiments, an algal promoter is a constitutive promoter. In some embodiments, an inducible promoter for use in insect cells responds to environmental or nutritional signals.

An expression cassette is usually provided in a DNA or RNA construct comprising the at least one heterologous gene that is typically called an "expression vector," which is any genetic element, e.g., a plasmid, a chromosome, a virus, behaving either as an autonomous unit of polynucleotide replication within a cell (i.e., capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, bacteriophages, cosmids, plant viruses, and artificial chromosomes. The expression cassette may be provided in a DNA construct, which also has at least one replication system. In addition to the replication system, there will frequently be at least one marker present, which may be useful in one or more hosts, or different markers for individual hosts.

In another embodiment, selection genes provide selective markers that confer resistance to a selective agent, such as an antibiotic or herbicide. Potentially transformed cells are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

Useful selective marker genes include those conferring resistance to antibiotics such as kanamycin (nptII), hygromycin B (aph IV), nptII, hpt, aadA and gentamycin (aac3 and aacC4) or resistance to herbicides such as glufosinate (bar or pat) and glyphosate (EPSPS). In another embodiment, the selection gene is an antimetabolite. In one embodiment, the antimetabolite is dhf.

Screenable markers which provide an ability to visually identify transformants can also be employed, e.g., a gene expressing a colored or fluorescent protein such as a cat, lacZ, uidA, luciferase or green fluorescent protein (GFP) or a gene expressing a beta-glucuronidase or uidA gene (GUS) for which various chromogenic substrates are known. It is also contemplated that combinations of screenable and selectable markers will be useful for identification of transformed cells.

In one embodiment, the selection gene is a positive selectable marker gene that is conditional on non-toxic agents that may be substrates for growth or that induce growth and differentiation of the transformed tissues.

In one embodiment, plant cells that survive exposure to the selective agent, or cells that have been scored positive in a screening assay, may be cultured in regeneration media and allowed to mature into plants. Developing plantlets can be transferred to soil less plant growth mix, and hardened off, e.g., in an environmentally controlled chamber at about 85% relative humidity, 600 ppm CO2, and 25-250 microeinsteins m−2 s−1 of light, prior to transfer to a greenhouse or growth chamber for maturation. Plants are preferably matured either in a growth chamber or greenhouse. Plants are regenerated from about 6 weeks to 10 months after a transformant is identified, depending on the initial tissue. During regeneration, cells are grown to plants on solid media at about 19 to 28° C. After regenerating plants have reached the stage of shoot and root development, they may be transferred to a greenhouse for further growth and testing. Plants may be pollinated using conventional plant breeding methods known to those of skill in the art and seed produced.

Progeny may be recovered from transformed plants and tested for expression of the exogenous recombinant polynucleotide. Useful assays include, for example, "molecular biological" assays, such as Southern and Northern blotting and PCR; "biochemical" assays, such as detecting the presence of RNA, e.g. double stranded RNA, or a protein product, e.g., by immunological means (ELISAs and Western blots) or by enzymatic function; plant part assays, such as leaf or root assays; and also, by analyzing the phenotype of the whole regenerated plant.

One of skill in the art will be able to select an appropriate vector for introducing the encoding nucleic acid sequence in a relatively intact state. Thus, any vector which will produce a host cell, e.g., plant protoplast, carrying the introduced encoding nucleic acid should be sufficient. The selection of the vector, or whether to use a vector, is typically guided by the method of transformation selected.

For plant cells, markers may a) code for protection against a biocide, such as antibiotics, toxins, heavy metals, certain sugars or the like; b) provide complementation, by imparting prototrophy to an auxotrophic host; or c) provide a visible phenotype through the production of a novel compound in the plant. In some embodiments, genes that may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are β-glucuronidase, providing indigo production, luciferase, providing visible light production, Green Fluorescent Protein and variants thereof, NPTII, providing kanamycin resistance or G418 resistance, HPT, providing hygromycin resistance, and the mutated aroA gene, providing glyphosate resistance.

For yeast cells, markers may comprise marker providing complementation, by imparting prototrophy to an auxotrophic host, for example but not limited to HIS, LEU, TRP, and URA marker genes encoding the necessary complementary activity. In some embodiments, yeast markers provide resistance to a compound toxic to the yeast, for example but not limited to kanMX4—resistance to G418; natMX4-resistance to nourseothricin; hphMX4-resistance to hygromycin B; patMX3-resistance to glufosinate; and ZEO—resistance to zeocin.

Promoter activity encompasses the extent of transcription of a polynucleotide sequence, homologue, variant or fragment thereof that is operably linked to the promoter whose promoter activity is being measured. The promoter activity may be measured directly by measuring the amount of RNA transcript produced, for example, by Northern blot or indirectly by measuring the product coded for by the RNA transcript, such as when a reporter gene is linked to the promoter.

In some embodiments, an at least one heterologous gene encoding an enzyme, disclosed herein, is operably linked to a promoter. In some embodiments, operable linkage to the promoter results in transient expression. In some embodiments, operable linkage to the promoter results in constitutive expression. In some embodiments, one heterologous gene may be operably linked to a constitutive promoter while another heterologous gene is operably linked to a promoter providing transient expression. In some embodiments, a polynucleotide sequence comprises the at least one heterologous gene encoding an enzyme, wherein said polynucleotide is optionally comprised within a vector.

As used herein, the term an "enhancer" refers to a DNA sequence which can stimulate promoter activity and may be an innate element of the promoter or a heterologous element inserted to enhance the level or tissue-specificity of a promoter.

The term "expression", as used herein, refers to the production of a functional end-product e.g., an mRNA or a protein. In some embodiments, a genetically modified cell expresses at least one heterologous gene, wherein the functional end product comprises an mRNA, which in turn is transcribed to produce a functional end product comprising a steroidal alkaloid, a steroidal saponin, or a triterpenoid saponin.

The term "genetically modified cell" refers to a cell genetically modified by man. In some embodiments, the genetic modification includes transforming a plant cell or a yeast cell or an algal cell or an insect cell or a bactierium with heterologous polynucleotide comprising a gene encoding an enzyme. In some embodiments, the genetic modification includes transforming a plant cell or a yeast cell with heterologous polynucleotide comprising a gene encoding an enzyme active in a triterpenoid saponin biosynthetic pathway. A "genetically modified cell" and a "corresponding unmodified cell" as used herein refer to a genetically modified cell and to a cell of the same type lacking said modification, respectively.

In some embodiments, the "genetically modified cell" and the "corresponding unmodified cell" are, respectively, a genetically modified plant cell and a corresponding unmodified plant cell of the same type. In other embodiments, the "genetically modified cell" and the "corresponding unmodified cell" are, respectively, a genetically modified yeast cell and a corresponding unmodified yeast cell of the same type.

The term "genetically modified plant" refers to a plant comprising at least one cell genetically modified by man. The genetic modification includes modification of an endogenous gene(s), for example by introducing mutation(s) deletions, insertions, transposable element(s) and the like into an endogenous polynucleotide or gene of interest. Additionally, or alternatively, the genetic modification includes transforming the plant cell with heterologous polynucleotide. A "genetically modified plant" and a "corresponding unmodified plant" as used herein refer to a plant comprising at least one genetically modified cell and to a plant of the same type lacking said modification, respectively.

In some embodiments, suspensions of genetically modified cells and tissue cultures derived from the genetically modified cells are also encompassed. The cell suspension or tissue culture can be used for the production of desired steroidal alkaloids metabolites thereof, derivatives thereof, or biosynthetic intermediates thereof, or a combination thereof; steroidal saponins, metabolites thereof, derivatives thereof, or biosynthetic intermediates thereof, or a combination thereof; or triterpenoid saponins, metabolites thereof, derivatives thereof, or biosynthetic intermediates thereof, or a combination thereof. In some embodiments, the genetically modified cell or tissue culture is used for regenerating a genetically modified plant having at least one cell having altered expression of a CSLG enzyme.

One of ordinary skill in the art would appreciate that some embodiments further encompass seeds of the genetically modified plant, wherein plants grown from said seeds have altered expression of at least one CSLG in at least one cell compared to plants grown from corresponding unmodified seeds or seeds from a corresponding unmodified plant, thereby having at least one cell having altered content of at least one steroidal alkaloid, steroidal saponin, or triterpenoid saponin.

If transformation techniques require use of tissue culture, transformed cells may be regenerated into plants in accordance with techniques well known to those of skill in the art. The regenerated plants may then be grown and crossed with the same or different plant varieties using traditional breeding techniques to produce seeds, which are then selected under the appropriate conditions.

One of ordinary skill in the art would appreciate that a genetically modified plant may encompass a plant comprising at least one cell genetically modified by man. In some embodiment, the genetic modification includes transforming at least one plant cell or yeast cell or algal cell or insect cell or bacterium with a heterologous polynucleotide comprising a heterologous gene described herein. In some embodiment, the genetic modification includes transforming at least one plant cell or yeast cell or algal cell or insect cell or bacterium with a heterologous polynucleotide comprising more than one heterologous gene, each encoding an enzyme. In some embodiment, the genetic modification includes transforming at least one plant cell or yeast cell or algal cell or insect cell or bacterium with multiple heterologous polynucleotides encoding multiple heterologous genes encoding enzymes.

The skilled artisan would appreciate that a genetically modified plant comprising transforming at least one plant cell with a heterologous polynucleotide or multiple heterologous polynucleotides may in certain embodiments be termed a "transgenic plant".

A skilled artisan would appreciate that a comparison of a "genetically modified plant" to a "corresponding unmodified plant" as used herein encompasses comparing a plant comprising at least one genetically modified cell and to a plant of the same type lacking the modification.

The skilled artisan would appreciate that the term "transgenic" when used in reference to a plant as disclosed herein encompasses a plant that contains at least one heterologous transcribable polynucleotide in one or more of its cells. The skilled artisan would appreciate that the term "transgenic" when used in reference to a yeast as disclosed herein encompasses a yeast that contains at least one heterologous transcribable polynucleotide. The term "transgenic material" encompasses broadly a plant or a part thereof, including at least one cell, multiple cells or tissues that contain at least one heterologous polynucleotide in at least one of cell. Thus, comparison of a "transgenic plant" and a "corresponding non transgenic plant", or of a "genetically modified plant comprising at least one cell having altered expression, wherein said plant comprising at least one cell comprising a heterologous transcribable polynucleotide" and a "corresponding un modified plant" encompasses comparison of the "transgenic plant" or "genetically modified plant" to a plant of the same type lacking said heterologous transcribable polynucleotide. A skilled artisan would appreciate that, in some embodiments, a "transcribable polynucleotide" comprises a polynucleotide that can be transcribed into an RNA molecule by an RNA polymerase.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

Transformation of a cell may be stable or transient. The term "transient transformation" or "transiently transformed" refers to the introduction of one or more exogenous polynucleotides into a cell in the absence of integration of the exogenous polynucleotide into the host cell's genome. In contrast, the term "stable transformation" or "stably transformed" refers to the introduction and integration of one or more exogenous polynucleotides into the genome of a cell. The term "stable transformant" refers to a cell which has stably integrated one or more exogenous polynucleotides into the genomic or organellar DNA. It is to be understood that an organism or its cell transformed with the nucleic acids, constructs and/or vectors disclosed herein can be transiently as well as stably transformed.

The skilled artisan would appreciate that the term "construct" may encompass an artificially assembled or isolated nucleic acid molecule which includes the polynucleotide of interest. In general, a construct may include the polynucleotide or polynucleotides of interest, a marker gene which in some cases can also be a gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

Additionally, or alternatively, in some embodiments, the genetic modification includes transforming at least one plant cell with a heterologous polynucleotide or multiple heterologous polynucleotides. The skilled artisan would appreciate that a genetically modified plant comprising transforming at least one plant cell with a heterologous polynucleotide or multiple heterologous polynucleotides may in certain embodiments be termed a "transgenic plant".

Viral vectors are useful for transformation of more transformation-resistant plants (e.g., soybean or common bean). In some embodiments, viral vectors, such as bean pod mottle virus (BPMV; genus Comovirus) vectors, are used for foreign gene expression and virus-induced gene silencing (VIGS) (Zhang et al. (May 2010) Plant Physiol. 153: 52-65 ["Zhang 2010" ])). Cells are transformed, e.g., via biolistics or via direct DNA-rubbing inoculation (Zhang 2010).

In one embodiment, a gene gun or a biolistic particle delivery system (biolistics) is used for plant transformation to deliver exogenous DNA (transgenes) to cells (Rech et al. (2008) Nature Protocols 3(3): 410-418 ["Rech 2008" ]). In some embodiments, the plasmid is designed and apical meristems of plants (e.g., soybean, bean, cotton) are bombarded with microparticle-coated DNA, followed by in vitro culture and selection of transgenic plants (Rech 2008). In other embodiments, a callus of undifferentiated plant cells or a group of immature embryos growing on gel medium in vitro. In some embodiments, the cells are then treated with a series of plant hormones, such as auxins or gibberellins to obtain plants. Steroidal alkaloids metabolites thereof, derivatives thereof, or biosynthetic intermediates thereof, or a combination thereof; steroidal saponins, metabolites thereof, derivatives thereof, or biosynthetic intermediates thereof, or a combination thereof, or triterpenoid saponins, metabolites thereof, derivatives thereof, or biosynthetic intermediates thereof, or a combination thereof, can be produced through such transgenic plants or plant cells.

"Transient expression" of the proteins may be achieved by various means known in the art. In one embodiment, transient expression of the proteins is achieved by the use of genetically modified viruses. In some embodiments, agroinfiltration is used to induce transient expression of genes in a plant or an isolated leaf or another portion of a plant. A suspension of *Agrobacterium* (e.g., *Agrobacterium tumefaciens*) is introduced into the plant by, e.g., direct injection or vacuum filtration, or is brought into association with plant cells immobilized on a porous support (plant cell packs). The bacteria transfer the desired gene into the plant cells via transfer of Ti plasmid-derived T-DNA.

In some embodiments, the method of transformation of algae comprises any of the methods as described hereinabove. In one embodiment, transformation of algae is accomplished using glass bead-assisted transformation, particle gun-mediated (biolistic) transformation, treatment with cellulolytic enzymes to weaken their cell walls, or homologous recombination.

In another aspect, the nucleic acids disclosed herein can be transformed into algae. In one embodiment, the alga is a single cell alga. In another embodiment, the alga is a multi-cellular alga. In one embodiment, the alga is a cyanobacterium, diatom, *Chlamydomonas, Dunaliella*, or Hematococus. The genes can be over expressed in algae. Steroidal alkaloids metabolites thereof, derivatives thereof, or biosynthetic intermediates thereof, or a combination thereof, steroidal saponins, metabolites thereof, derivatives thereof, or biosynthetic intermediates thereof, or a combination thereof, or triterpenoid saponins, metabolites thereof, derivatives thereof, or biosynthetic intermediates thereof, or a combination thereof, can be produced through such transgenic algae. Method for algae transformation are well known in the art and fully described in U.S. Patent Application Publications US 20150011008; US 20150004704; US 20130130389; US 20120094385; US 20120034698; US 20110300633; and US 20040133937, which are incorporated by reference herein in their entirety. Further, cultivation of microalgae is well known in the art and has been described in Vuppaladadiyam et al., (2018) "Microalgae cultivation and metabolites production: a comprehensive review." Biofuls, Bioprod. Bioref. 12:304-324, which is incorporated by reference herein in its entirety.

In another aspect, the nucleic acids disclosed herein can be transformed into yeast. The genes can be over expressed in yeast. Methods for yeast transformation are described herein below and are well known in the art and fully described in U.S. Patent Application Publications US 20090264320; US 20010031724; US 20030049785; US 20050158861; US 20070264716; US 20090325247; and US 20100190223, which are incorporated by reference herein in their entirety. Steroidal alkaloids metabolites thereof, derivatives thereof, or biosynthetic intermediates thereof, or a combination thereof; steroidal saponins, metabolites thereof, derivatives thereof, or biosynthetic intermediates thereof, or a combination thereof; or triterpenoid saponins, metabolites thereof, derivatives thereof, or biosynthetic intermediates thereof, or a combination thereof, can be produced through such transgenic yeast.

In another embodiment, the nucleic acids disclosed herein can be transformed into a virus. In another embodiment, the nucleic acids may be over-expressed in a virus. Steroidal alkaloids metabolites thereof, derivatives thereof, or biosynthetic intermediates thereof, or a combination thereof, steroidal saponins, metabolites thereof, derivatives thereof, or biosynthetic intermediates thereof, or a combination thereof, or triterpenoid saponins, metabolites thereof, derivatives thereof, or biosynthetic intermediates thereof, or a combination thereof, can be produced through such viral over expression.

In some embodiments, in bacterial systems, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of *Escherichia coli* expression vectors (Studier et al., Methods in Enzymol. 185:60-89 1990).

In some embodiments, a polynucleotide sequence comprises the at least one heterologous gene. In some embodiments, the polynucleotide sequence encodes an enzyme. In some embodiments, the polynucleotide sequence encodes an enzyme of a steroidal alkaloid, steroidal saponin, or triterpenoid saponin biosynthetic pathway. In some embodiments, the polynucleotide sequence encodes an enzyme necessary for the production of a substrate or substrates of a steroidal alkaloid, steroidal saponin, or triterpenoid saponin biosynthetic pathway.

In some embodiments, a polynucleotide sequence comprises the at least 2, 3, 4, 5, 6, 7, 8, 9, or 10, or more heterologous genes. In some embodiments, the polynucleotide sequence encodes 2, 3, 4, 5, 6, 7, 8, 9, or 10, or more enzyme, wherein each gene encodes a single enzyme. In some embodiments, the polynucleotide sequence encodes 2, 3, 4, 5, 6, 7, 8, 9, or 10 enzymes of a steroidal alkaloid, steroidal saponin, or triterpenoid saponin biosynthetic pathway. In some embodiments, the polynucleotide sequence encodes 2, 3, 4, 5, 6, 7, 8, 9, or 10, or more enzymes of a steroidal alkaloid, steroidal saponin, or triterpenoid saponin pathway and an additional enzyme necessary for the production of a substrate of a steroidal alkaloid, steroidal saponin, or triterpenoid saponin biosynthetic pathway. In some embodiments, the polynucleotide sequence encodes 2, 3, 4, 5, 6, 7, 8, 9, or 10, or more enzymes of a steroidal alkaloid, steroidal saponin, or triterpenoid saponin pathway and additional enzymes necessary for the production of substrates of a steroidal alkaloid, steroidal saponin, or triterpenoid saponin biosynthetic pathway.

In some embodiments, the term "a nucleotide sequence" or "a polynucleotide sequence" encompasses a single contiguous polynucleotide sequence, and in other embodiments, the term encompasses multiple contiguous nucleotide sequences.

Based on the co-expressed gene array disclosed herein, a pathway from cholesterol to, e.g., α-tomatine is proposed (FIG. 1). It has been previously described that cholesterol is hydroxylated at C22 by GAME7 (US 2012/0159676) followed by GAME8 hydroxylation at the C26 position. The 22,26-dihydroxycholesterol is than hydroxylated at C16 and oxidized at C22 followed by closure of the E-ring by GAME11 and GAME6 to form the furostanol-type aglycone. This order of reactions is supported by the finding herein showing the accumulation of cholestanol-type saponins, lacking hydroxylation at C16 and the hemi-acetal E-ring when silencing GAME11 (FIGS. 8A-D). The furostanol-intermediate is oxidized by GAME4 to its 26-aldehyde which is the substrate for transamination catalyzed by GAME12. Nucleophilic attack of the amino-nitrogen at C22 leads to the formation of tomatidenol which is dehydrogenated to tomatidine. Tomatidine is subsequently converted by GAME1 to T-Gal (Itkin et al., 2011 supra). T-Gal in its turn is glucosylated by GAME17 into γ-tomatine, which is further glucosylated by GAME18 to $1-tomatine that is finally converted to α-tomatine by GAME2 (FIG. 1).

As described herein, by modifying expression of an enzyme and/or other protein involved in the biosynthetic pathway, the level of steroidal alkaloids, steroidal glycoalkaloids and steroidal saponin can be altered.

Figure 5A:
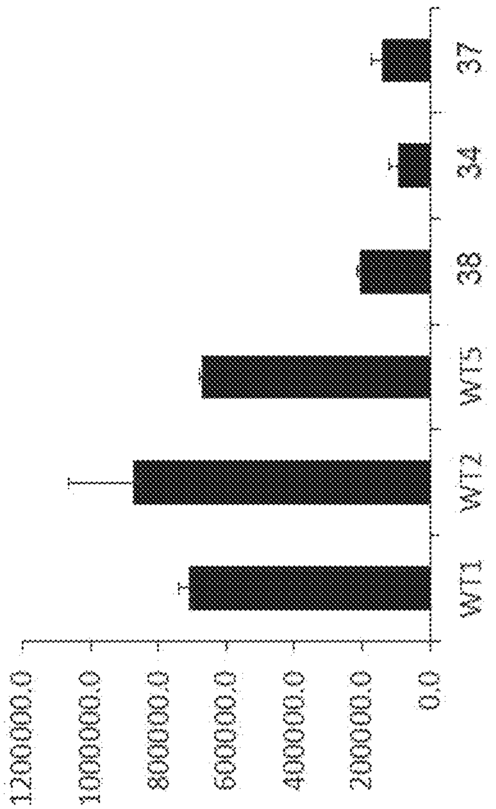
FIGS. 5A-5D show solanine/chaconine levels in peels of tuber of potato plant lines with altered expression of GAME9 compared to wild type plants. Solanine (FIG. 5A) and chaconine (FIG. 5B) level in tubers of GAME9 silenced plant; Solanine (FIG. 5C) and chaconine (FIG. 5D) levels in tubers of GAME9 overexpressing plants.
Figure 5B:
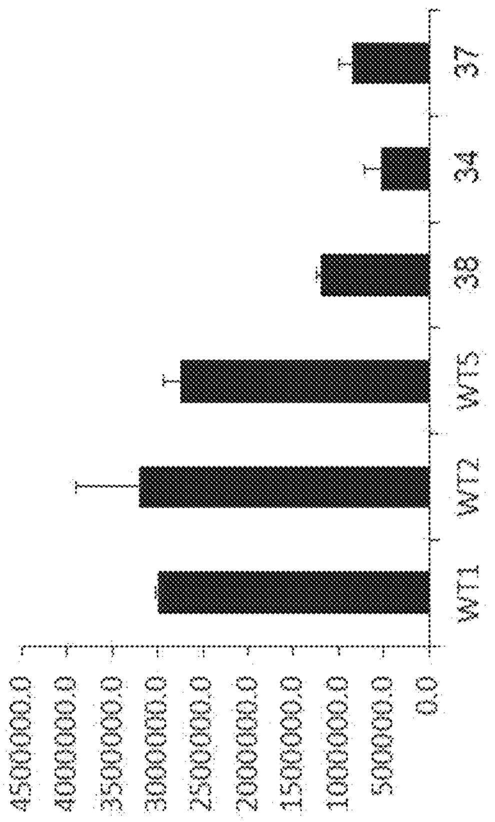
Figure 5C:
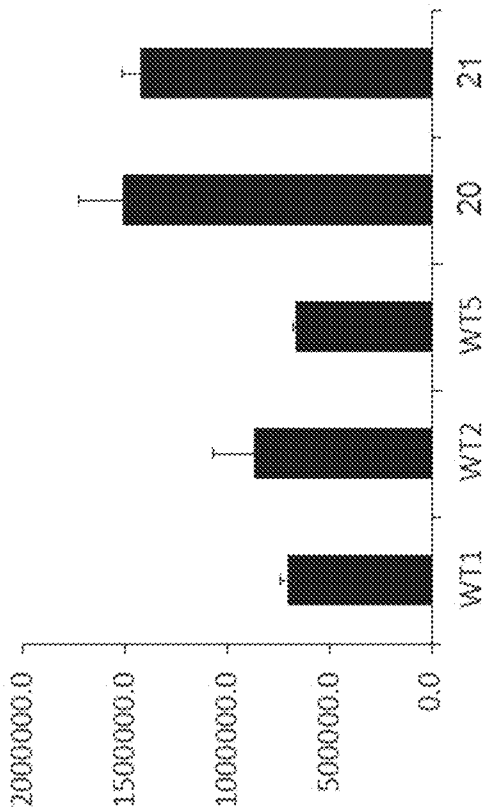
Figure 5D:
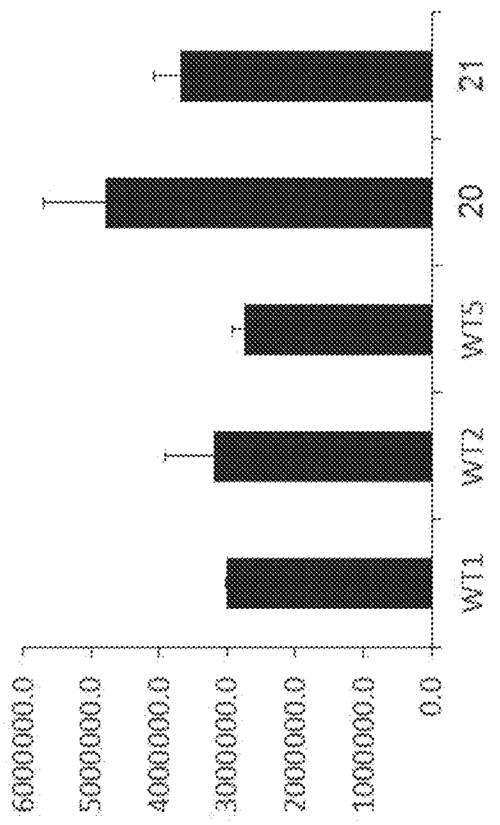
Figure 6:
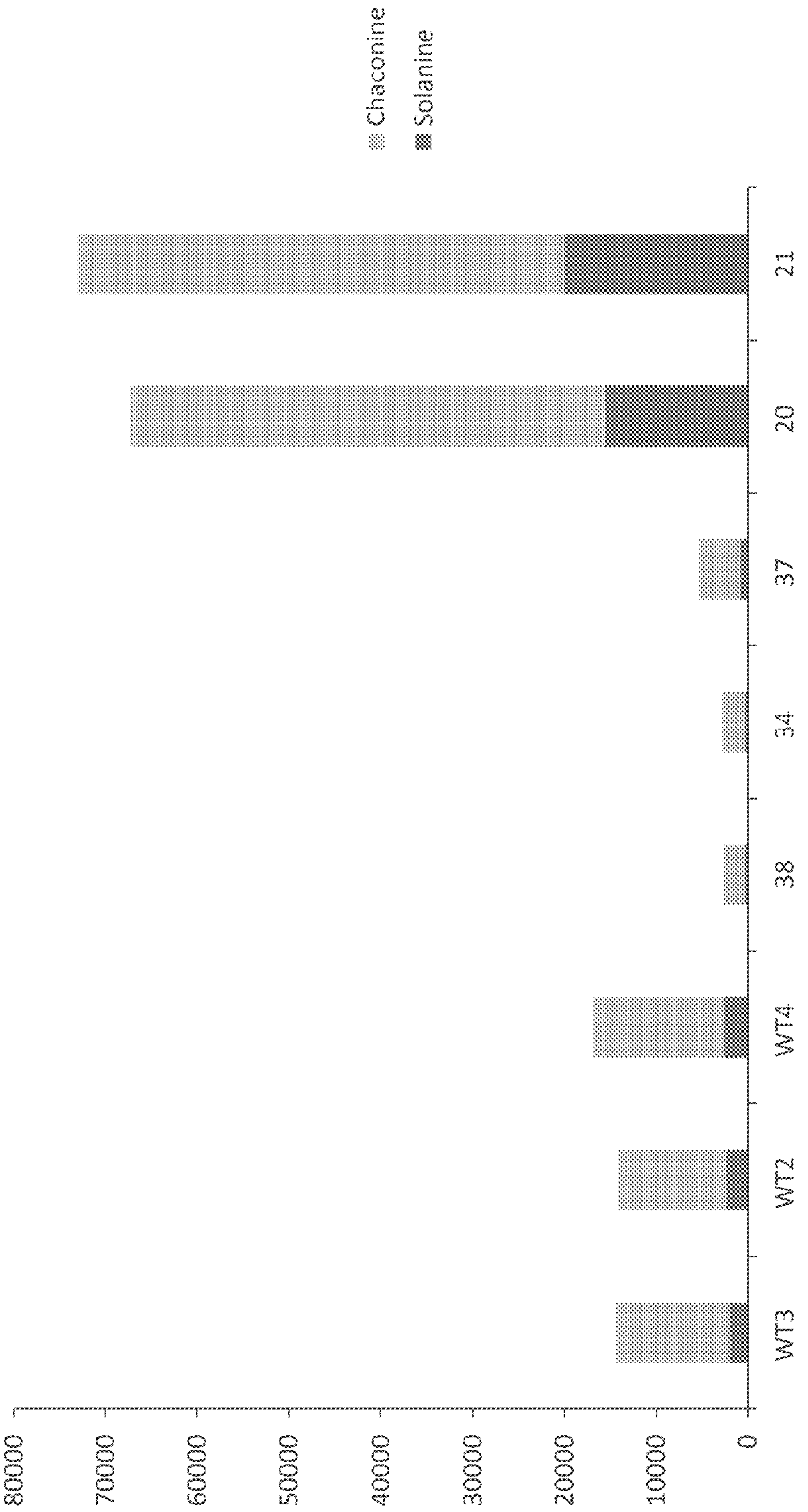
FIG. 6 shows solanine/chaconine levels in leaves of potato plant lines with either silenced (RNAi) or overexpressed (OX) GAME9 compared to wild type plants.
Figure 7:
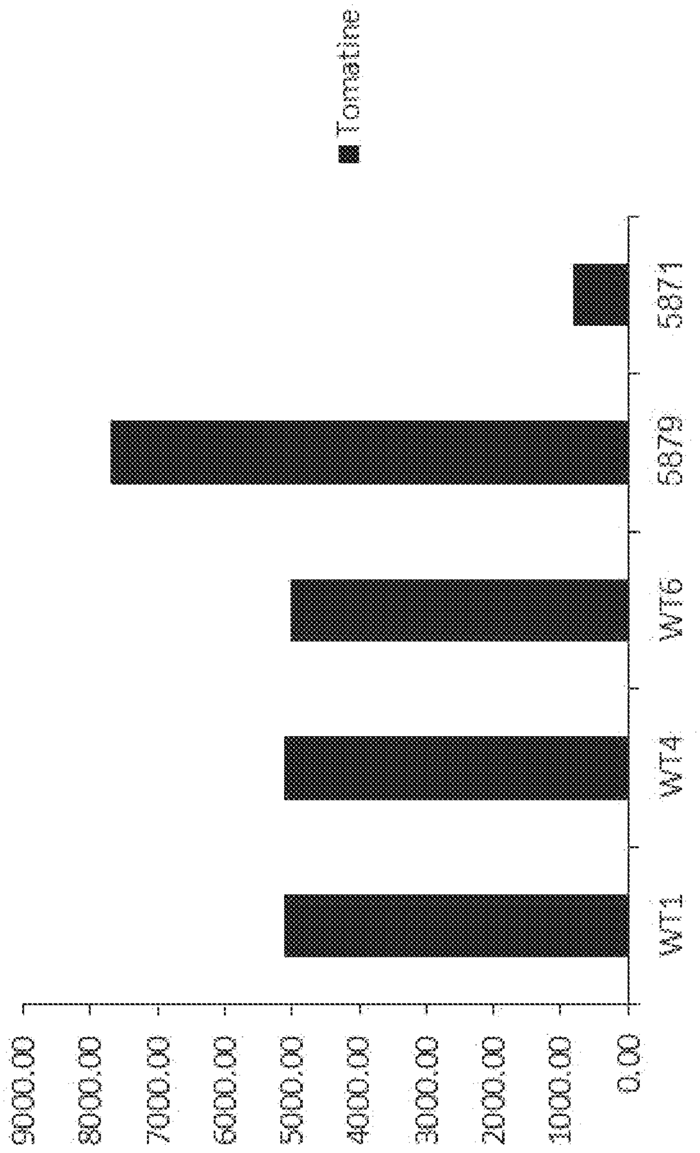
FIG. 7 shows tomatine levels in leaves of tomato plant lines with either silenced (RNAi, line 5871) or overexpressed (OX, line 5879) GAME9 compared to wild type plants.

Silencing of a single gene co-expressed with the clustered enzyme-encoding gene in potato plant, resulted in significant reduction in the amount of the steroidal glycoalkaloids α-chaconine and α-solanine, while overexpression of this gene resulted in significant increase in the content of these substances (FIGS. 5 and 6). This gene was found to include coding sequence comprising an AP2 domain, and therefore postulated to be a transcription factor, designated herein GAME9-transcription factor, encoded by GAME9.

A genetically modified plant comprising at least one cell having altered expression of at least one gene selected from the group consisting of a gene encoding GAME9-transcription factor, a gene encoding 2-oxoglutarate-dependent dioxygenase, a gene encoding basic helix-loop-helix (BHLH)-transcription factor or a combination thereof, wherein the genetically modified plant has an altered content of at least one steroidal alkaloid or a derivative, metabolite, or biosynthetic intermediate thereof compared to a corresponding unmodified plant, has been produced. As exemplified herein for 2-oxoglutarate-dependent dioxygenase (GAME11), manipulating the expression of the genes of the present invention can further lead to the manipulation of steroidal saponin synthesis.

Thus, according to additional aspect, provided herein is a genetically modified organism comprising at least one cell having altered expression of at least one gene selected from the group consisting of a gene encoding GAME9-transcription factor, a gene encoding 2-oxoglutarate-dependent dioxygenase, a gene encoding basic helix-loop-helix (BHLH)-transcription factor or a combination thereof compared to an unmodified or unedited organism, wherein the genetically modified organism has an altered content of at least one compound selected from steroidal saponins and/or steroidal alkaloids and their glycosylated and other derivatives thereof, metabolites thereof, or biosynthetic intermediates thereof, compared to a corresponding unmodified or unedited organism.

Unexpectedly, the present invention now shows that SGA levels can be severely reduced in potato tubers by modifying expression of an enzyme and/or transcription factors involved in the steroidal alkaloid biosynthetic pathway.

According to certain embodiments, the expression of the at least one gene selected from the group consisting of a gene encoding GAME9-transcription factor, a gene encoding 2-oxoglutarate-dependent dioxygenase, a gene encoding BHLH-transcription factor or the combination thereof in the genetically modified plant is inhibited compared to its expression in the corresponding unmodified or unedited plant, thereby the genetically modified plant comprises reduced content of at least one steroidal alkaloid or a derivative, metabolite, or biosynthetic intermediate thereof, compared to a corresponding unmodified plant.

The genes and encoded enzymes thereof, active in the spinach triterpenoid biosynthetic pathway of Compound 11, are described in detail in the Examples. Table 17, provided in Example 20, provides the amino acid and nucleic acid sequences of these enzyme and the genes encoding them. Table 19 provided in Example 24 provides the amino acid sequence of an additional CSLG enzyme, isolated from *Arabidopsis*.

In some embodiments, the polynucleotide sequence of said at least one heterologous gene is set forth in any one of SEQ ID NOS: 30, 32, 34, 36, 38, 40, 45, 46, 47, 51, 53, 55, 57, 59, 61, 63, 65, 80, 93, 95, 97, 99, 101, 103, or 105. In some embodiments, the polynucleotide sequence of said at least one heterologous gene comprises a nucleic acid sequence having at least 55% identity to the nucleic acid sequence set forth in any one of SEQ ID NOS: 30, 32, 34, 36, 38, 40, 45, 46, 47, 51, 53, 55, 57, 59, 61, 63, 65, 80, 93, 95, 97, 99, 101, 103, or 105.

In some embodiments, the polynucleotide sequence of said at least one heterologous gene is set forth in any one of SEQ ID NOS: 30, 32, 34, 36, 38, 40, 45, 46, 47, 51, 53, 55, 57, 59, 61, 63, 65, 80, 93, 95, 97, 99, 101, 103, or 105. In some embodiments, the polynucleotide sequence of said at least one heterologous gene comprises a nucleic acid sequence having at least 80% identity to the nucleic acid sequence set forth in any one of SEQ ID NOS: 30, 32, 34, 36, 38, 40, 45, 46, 47, 51, 53, 55, 57, 59, 61, 63, 65, 80, 93, 95, 97, 99, 101, 103, or 105.

In some embodiments, the nucleic acid sequence encoding said at least one heterologous CSLG enzyme is set forth in any one of SEQ ID NOS: 30, 32, 34, 36, 38, 40, 65, 80, 93, 95, 97, 99, 101, 103, or 105. In some embodiments, the nucleic acid sequence encoding said at least one heterologous CSLG enzyme is set forth in a homolog thereof having at least 55% identity to and at least 55% coverage of, the nucleic acid sequence set forth in any one of SEQ ID NOS: 30, 32, 34, 36, 38, 40, 65, 80, 93, 95, 97, 99, 101, 103, or 105. In some embodiments, the nucleic acid sequence encoding said at least one heterologous CSLG enzyme is set forth in any one of SEQ ID NOS: 30, 32, 34, 36, 38, 40, 65, 80, 93, 95, 97, 99, 101, 103, or 105. In some embodiments, the nucleic acid sequence encoding said at least one heterologous CSLG enzyme is set forth in a homolog thereof having at least 55% identity to and at least 80% coverage of, the nucleic acid sequence set forth in any one of SEQ ID NOS: 30, 32, 34, 36, 38, 40, 65, 80, 93, 95, 97, 99, 101, 103, or 105.

In some embodiments, the nucleic acid sequence encoding said at least one heterologous CSLG enzyme is set forth in any one of SEQ ID NOS: 30, 32, 34, 36, 38, 40, 65, 80, 93, 95, 97, 99, 101, 103, or 105. In some embodiments, the nucleic acid sequence encoding said at least one heterologous CSLG enzyme is set forth in a homolog thereof having at least 80% identity to and at least 80% coverage of, the nucleic acid sequence set forth in any one of SEQ ID NOS: 30, 32, 34, 36, 38, 40, 65, 80, 93, 95, 97, 99, 101, 103, or 105.

In some embodiments, the polynucleotide sequence of said at least one heterologous gene is set forth in SEQ ID NO: 30. In some embodiments, the polynucleotide sequence of said at least one heterologous gene is set forth in SEQ ID NO: 32. In some embodiments, the polynucleotide sequence of said at least one heterologous gene is set forth in SEQ ID NO: 34. In some embodiments, the polynucleotide sequence of said at least one heterologous gene is set forth in SEQ ID NO: 36. In some embodiments, the polynucleotide sequence of said at least one heterologous gene is set forth in SEQ ID NO: 38. In some embodiments, the polynucleotide sequence of said at least one heterologous gene is set forth in SEQ ID NO: 40. In some embodiments, the polynucleotide sequence of said at least one heterologous gene is set forth in SEQ ID NO: 45. In some embodiments, the polynucleotide sequence of said at least one heterologous gene is set forth in SEQ ID NO: 46. In some embodiments, the polynucleotide sequence of said at least one heterologous gene is set forth in SEQ ID NO: 47. In some embodiments, the polynucleotide sequence of said at least one heterologous gene is set forth in SEQ ID NO: 51. In some embodiments, the polynucleotide sequence of said at least one heterologous gene is set forth in SEQ ID NO: 53. In some embodiments, the polynucleotide sequence of said at least one heterologous gene is set forth in SEQ ID NO: 55. In some embodiments, the polynucleotide sequence of said at least one heterologous gene is set forth in SEQ ID NO: 57. In some embodiments, the polynucleotide sequence of said at least one heterologous gene is set forth in SEQ ID NO: 59. In some embodiments, the polynucleotide sequence of said at least one heterologous gene is set forth in SEQ ID NO: 61. In some embodiments, the polynucleotide sequence of said at least one heterologous gene is set forth in SEQ ID NO: 163 In some embodiments, the polynucleotide sequence of said at least one heterologous gene is set forth in SEQ ID NO: 65. In some embodiments, the polynucleotide sequence of said at least one heterologous gene is set forth in SEQ ID NO: 80. In some embodiments, the polynucleotide sequence of said at least one heterologous gene is set forth in SEQ ID NO: 93. In some embodiments, the polynucleotide sequence of said at least one heterologous gene is set forth in SEQ ID NO: 95. In some embodiments, the polynucleotide sequence of said at least one heterologous gene is set forth in SEQ ID NO: 97. In some embodiments, the polynucleotide sequence of said at least one heterologous gene is set forth in SEQ ID NO: 99. In some embodiments, the polynucleotide sequence of said at least one heterologous gene is set forth in SEQ ID NO: 101. In some embodiments, the polynucleotide sequence of said at least one heterologous gene is set forth in SEQ ID NO: 103. In some embodiments, the polynucleotide sequence of said at least one heterologous gene is set forth in SEQ ID NO: 105.

In some embodiments, the polynucleotide sequence of said at least one heterologous gene comprises a nucleic acid sequence having at least 55% identity to the nucleic acid sequence set forth in SEQ ID NO: 30. In some embodiments, the polynucleotide sequence of said at least one heterologous gene comprises a nucleic acid sequence having at least 55% identity to the nucleic acid sequence set forth in SEQ ID NO: 32. In some embodiments, the polynucleotide sequence of said at least one heterologous gene comprises a nucleic acid sequence having at least 55% identity to the nucleic acid sequence set forth in SEQ ID NO: 34. In some embodiments, the polynucleotide sequence of said at least one heterologous gene comprises a nucleic acid sequence having at least 55% identity to the nucleic acid sequence set forth in SEQ ID NO: 36. In some embodiments, the polynucleotide sequence of said at least one heterologous gene comprises a nucleic acid sequence having at least 55% identity to the nucleic acid sequence set forth in SEQ ID NO: 38. In some embodiments, the polynucleotide sequence of said at least one heterologous gene comprises a nucleic acid sequence having at least 55% identity to the nucleic acid sequence set forth in SEQ ID NO: 40. In some embodiments, the polynucleotide sequence of said at least one heterologous gene comprises a nucleic acid sequence having at least 55% identity to the nucleic acid sequence set forth in SEQ ID NO: 45. In some embodiments, the polynucleotide sequence of said at least one heterologous gene comprises a nucleic acid sequence having at least 55% identity to the nucleic acid sequence set forth in SEQ ID NO: 46. In some embodiments, the polynucleotide sequence of said at least one heterologous gene comprises a nucleic acid sequence having at least 55% identity to the nucleic acid sequence set forth in SEQ ID NO: 47. In some embodiments, the polynucleotide sequence of said at least one heterologous gene comprises a nucleic acid sequence having at least 55% identity to the nucleic acid sequence set forth in SEQ ID NO: 51. In some embodiments, the polynucleotide sequence of said at least one heterologous gene comprises a nucleic acid sequence having at least 55% identity to the nucleic acid sequence set forth in SEQ ID NO: 53. In some embodiments, the polynucleotide sequence of said at least one heterologous gene comprises a nucleic acid sequence having at least 55% identity to the nucleic acid sequence set forth in SEQ ID NO: 55. In some embodiments, the polynucleotide sequence of said at least one heterologous gene comprises a nucleic acid sequence having at least 55% identity to the nucleic acid sequence set forth in SEQ ID NO: 57. In some embodiments, the polynucleotide sequence of said at least one heterologous gene comprises a nucleic acid sequence having at least 55% identity to the nucleic acid sequence set forth in SEQ ID NO: 59. In some embodiments, the polynucleotide sequence of said at least one heterologous gene comprises a nucleic acid sequence having at least 55% identity to the nucleic acid sequence set forth in SEQ ID NO: 61. In some embodiments, the polynucleotide sequence of said at least one heterologous gene comprises a nucleic acid sequence having at least 55% identity to the nucleic acid sequence set forth in SEQ ID NO: 63. In some embodiments, the polynucleotide sequence of said at least one heterologous gene comprises a nucleic acid sequence having at least 55% identity to the nucleic acid sequence set forth in SEQ ID NO: 65. In some embodiments, the polynucleotide sequence of said at least one heterologous gene comprises a nucleic acid sequence having at least 55% identity to the nucleic acid sequence set forth in SEQ ID NO: 80. In some embodiments, the polynucleotide sequence of said at least one heterologous gene comprises a nucleic acid sequence having at least 55% identity to the nucleic acid sequence set forth in SEQ ID NO: 93. In some embodiments, the polynucleotide sequence of said at least one heterologous gene comprises a nucleic acid sequence having at least 55% identity to the nucleic acid sequence set forth in SEQ ID NO: 95. In some embodiments, the polynucleotide sequence of said at least one heterologous gene comprises a nucleic acid sequence having at least 55% identity to the nucleic acid sequence set forth in SEQ ID NO: 97. In some embodiments, the polynucleotide sequence of said at least one heterologous gene comprises a nucleic acid sequence having at least 55% identity to the nucleic acid sequence set forth in SEQ ID NO: 99. In some embodiments, the polynucleotide sequence of said at least one heterologous gene comprises a nucleic acid sequence having at least 55% identity to the nucleic acid sequence set forth in SEQ ID NO: 101. In some embodiments, the polynucleotide sequence of said at least one heterologous gene comprises a nucleic acid sequence having at least 55% identity to the nucleic acid sequence set forth in SEQ ID NO: 103. In some embodiments, the polynucleotide sequence of said at least one heterologous gene comprises a nucleic acid sequence having at least 55% identity to the nucleic acid sequence set forth in SEQ ID NO: 105.

In some embodiments, the polynucleotide sequence of said at least one heterologous gene comprises a nucleic acid sequence having at least 55%, 60%. 65%, 70%, 75%, 80%, 85%, 90%, 95%, 98%, or 99% identity to the nucleic acid sequence set forth in any of SEQ ID NO: 30, 32, 34, 36, 38, 40, 65, 80, 93, 95, 97, 99, 101, 103, or 105. In some embodiments, the polynucleotide sequence of said at least one heterologous gene comprises a nucleic acid sequence having at least 55%, 60%. 65%, 70%, 75%, 80%, 85%, 90%, 95%, 98%, 99%, or 100% coverage to the nucleic acid sequence set forth in any of SEQ ID NO: 30, 32, 34, 36, 38, 40, 65, 80, 93, 95, 97, 99, 101, 103, or 105.

In some embodiments, the polynucleotide sequence of said at least one heterologous gene comprises a nucleic acid sequence having at least 80% identity to the nucleic acid sequence set forth in SEQ ID NO: 30. In some embodiments, the polynucleotide sequence of said at least one heterologous gene comprises a nucleic acid sequence having at least 80% identity to the nucleic acid sequence set forth in SEQ ID NO: 32. In some embodiments, the polynucleotide sequence of said at least one heterologous gene comprises a nucleic acid sequence having at least 80% identity to the nucleic acid sequence set forth in SEQ ID NO: 34. In some embodiments, the polynucleotide sequence of said at least one heterologous gene comprises a nucleic acid sequence having at least 80% identity to the nucleic acid sequence set forth in SEQ ID NO: 36. In some embodiments, the polynucleotide sequence of said at least one heterologous gene comprises a nucleic acid sequence having at least 80% identity to the nucleic acid sequence set forth in SEQ ID NO: 38. In some embodiments, the polynucleotide sequence of said at least one heterologous gene comprises a nucleic acid sequence having at least 80% identity to the nucleic acid sequence set forth in SEQ ID NO: 40. In some embodiments, the polynucleotide sequence of said at least one heterologous gene comprises a nucleic acid sequence having at least 80% identity to the nucleic acid sequence set forth in SEQ ID NO: 45. In some embodiments, the polynucleotide sequence of said at least one heterologous gene comprises a nucleic acid sequence having at least 80% identity to the nucleic acid sequence set forth in SEQ ID NO: 46. In some embodiments, the polynucleotide sequence of said at least one heterologous gene comprises a nucleic acid sequence having at least 80% identity to the nucleic acid sequence set forth in SEQ ID NO: 47. In some embodiments, the polynucleotide sequence of said at least one heterologous gene comprises a nucleic acid sequence having at least 80% identity to the nucleic acid sequence set forth in SEQ ID NO: 51. In some embodiments, the polynucleotide sequence of said at least one heterologous gene comprises a nucleic acid sequence having at least 80% identity to the nucleic acid sequence set forth in SEQ ID NO: 53. In some embodiments, the polynucleotide sequence of said at least one heterologous gene comprises a nucleic acid sequence having at least 80% identity to the nucleic acid sequence set forth in SEQ ID NO. 55. In some embodiments, the polynucleotide sequence of said at least one heterologous gene comprises a nucleic acid sequence having at least 80% identity to the nucleic acid sequence set forth in SEQ ID NO: 57. In some embodiments, the polynucleotide sequence of said at least one heterologous gene comprises a nucleic acid sequence having at least 80% identity to the nucleic acid sequence set forth in SEQ ID NO: 59. In some embodiments, the polynucleotide sequence of said at least one heterologous gene comprises a nucleic acid sequence having at least 80% identity to the nucleic acid sequence set forth in SEQ ID NO: 61. In some embodiments, the polynucleotide sequence of said at least one heterologous gene comprises a nucleic acid sequence having at least 80% identity to the nucleic acid sequence set forth in SEQ ID NO: 63. In some embodiments, the polynucleotide sequence of said at least one heterologous gene comprises a nucleic acid sequence having at least 80% identity to the nucleic acid sequence set forth in SEQ ID NO: 65. In some embodiments, the polynucleotide sequence of said at least one heterologous gene comprises a nucleic acid sequence having at least 80% identity to the nucleic acid sequence set forth in SEQ ID NO: 80. In some embodiments, the polynucleotide sequence of said at least one heterologous gene comprises a nucleic acid sequence having at least 80% identity to the nucleic acid sequence set forth in SEQ ID NO: 93. In some embodiments, the polynucleotide sequence of said at least one heterologous gene comprises a nucleic acid sequence having at least 80% identity to the nucleic acid sequence set forth in SEQ ID NO: 95. In some embodiments, the polynucleotide sequence of said at least one heterologous gene comprises a nucleic acid sequence having at least 80% identity to the nucleic acid sequence set forth in SEQ ID NO: 97. In some embodiments, the polynucleotide sequence of said at least one heterologous gene comprises a nucleic acid sequence having at least 80% identity to the nucleic acid sequence set forth in SEQ ID NO: 99. In some embodiments, the polynucleotide sequence of said at least one heterologous gene comprises a nucleic acid sequence having at least 80% identity to the nucleic acid sequence set forth in SEQ ID NO: 101. In some embodiments, the polynucleotide sequence of said at least one heterologous gene comprises a nucleic acid sequence having at least 80% identity to the nucleic acid sequence set forth in SEQ ID NO: 103. In some embodiments, the polynucleotide sequence of said at least one heterologous gene comprises a nucleic acid sequence having at least 80% identity to the nucleic acid sequence set forth in SEQ ID NO: 105.

In some embodiments, the polynucleotide sequence of said at least one heterologous gene comprises a polynucleotide sequence encoding at least one steroidal alkaloid biosynthetic enzyme, steroidal saponin biosynthetic enzyme, or triterpenoid saponin biosynthetic enzyme. In some embodiments, the polynucleotide sequence of said at least one heterologous gene comprises a polynucleotide sequence encoding 2, 3, 4, 5, 6, 7, 8, 9, or 10, or more at least one steroidal alkaloid biosynthetic enzymes, steroidal saponin biosynthetic enzymes, or triterpenoid saponin biosynthetic enzymes, or combinations thereof.

A skilled artisan would appreciate that sequence homology encompasses similarity of sequence attributed to descent from a common ancestor. Homologous biological components (genes, proteins, structures) are called homologs. The extent to which nucleotide or protein sequences are related. The similarity between two sequences (DNA, RNA, or amino acid) can be expressed as percent sequence identity and/or percent positive substitutions.

A skilled artisan would appreciate that the term "homolog" encompasses a gene or a polypeptide (a protein) that is related to a second gene or polypeptide (protein), respectively, by descent from a common ancestral DNA or polypeptide (protein) sequence, respectively. Thus, a homolog of a gene, in some embodiments, comprises a similar nucleotide sequence to the gene. In some embodiments, a gene homolog encodes an identical polypeptide as is encoded by the gene. In some embodiments, a gene homolog encodes a polypeptide with the same functional properties as is encoded by the gene. In some embodiments, a gene homolog encodes a polypeptide that comprises a similar amino acid sequence as the polypeptide encoded by the gene. In one embodiment, the polypeptide homolog comprises a similar amino acid sequence as the polypeptide. In some embodiments, the polypeptide homolog comprises the same functional properties as the polypeptide. In some embodiments, the polypeptide homolog comprises similar functional properties as the polypeptide. In some embodiments, the polypeptide homolog comprises a same domain(s) as the polypeptide. In some embodiments, the polypeptide homolog comprises a similar domain(s) as the polypeptide.

A skilled artisan would appreciate that percent homology or percent identity may be determined, for example but no limited to, using BlastP software of the National Center of Biotechnology Information (NCBI) using default parameters. The homolog may also refer to an ortholog, a deletion, insertion, or substitution variant, including an amino acid substitution. In some embodiments, sequence identity or homology can be determined using any protein or nucleic acid sequence alignment algorithm such as Blast, ClustalW, MUSCLE, and HHpred.

Figure 42A:
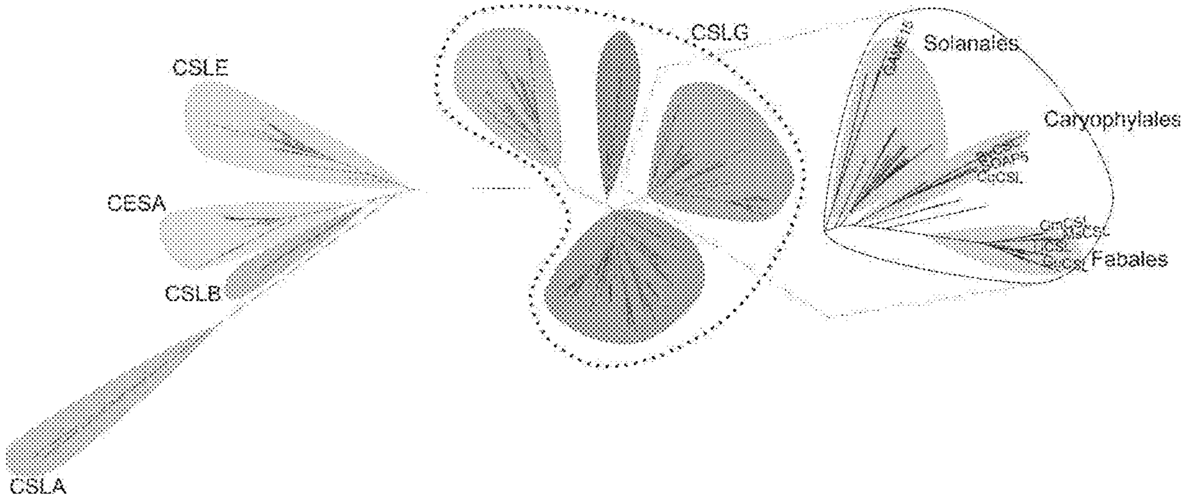
Figure 42B:
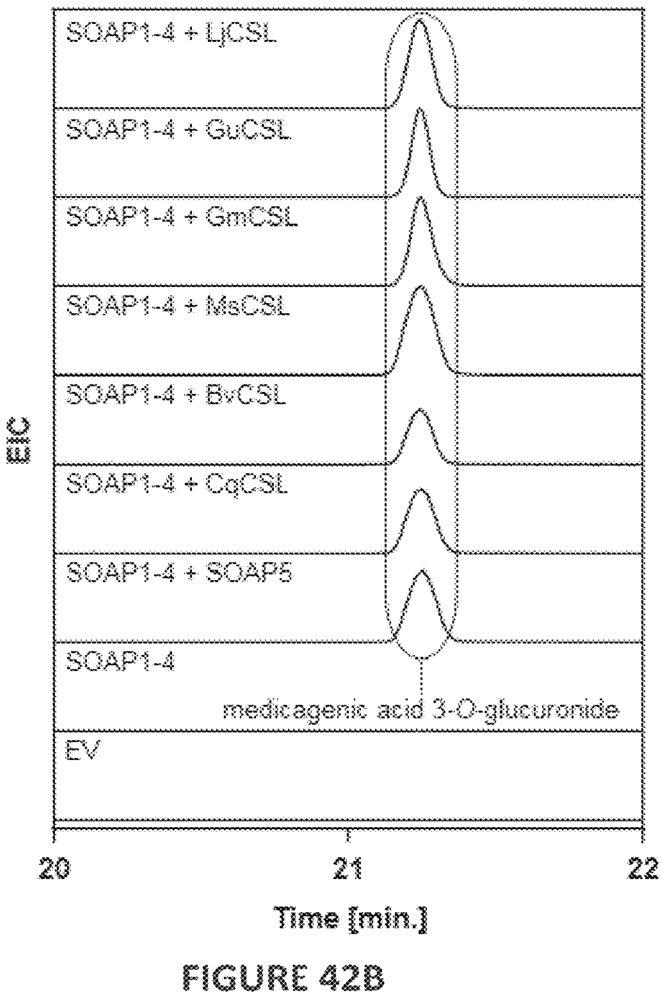
Figure 42C:
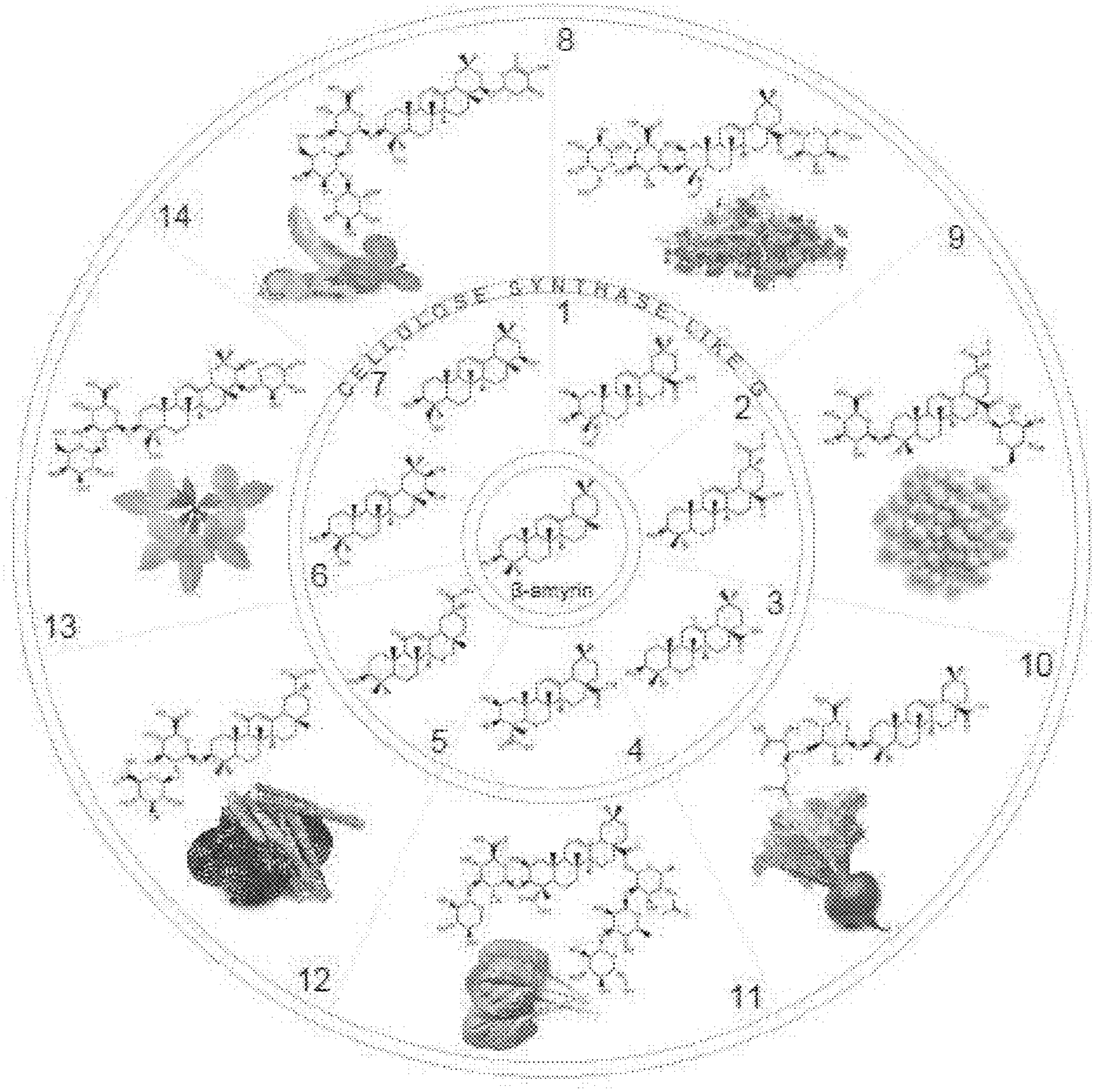
Figure 42D:
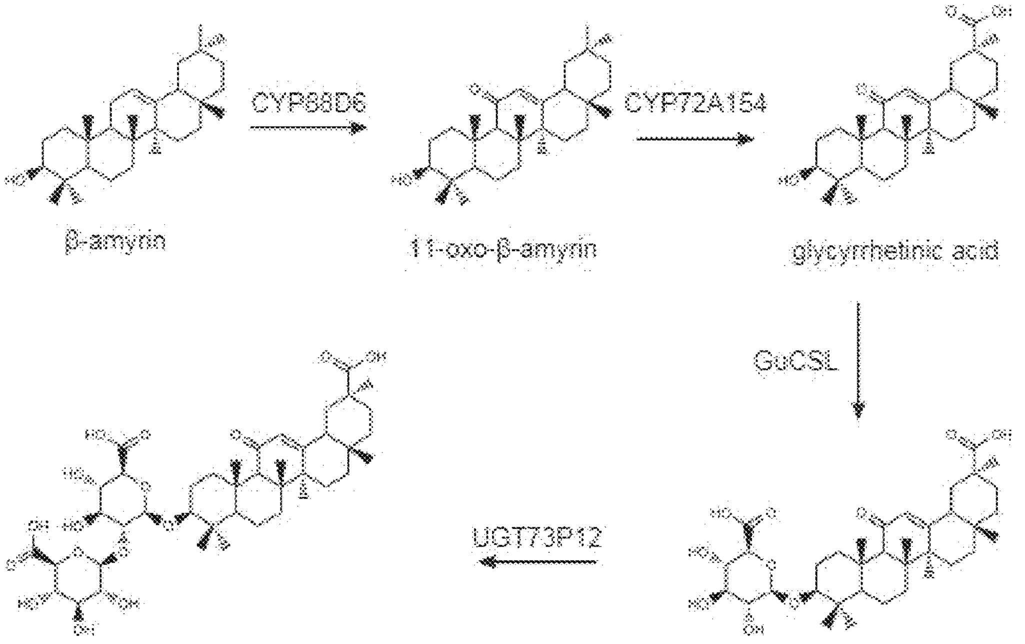
Figure 42E:
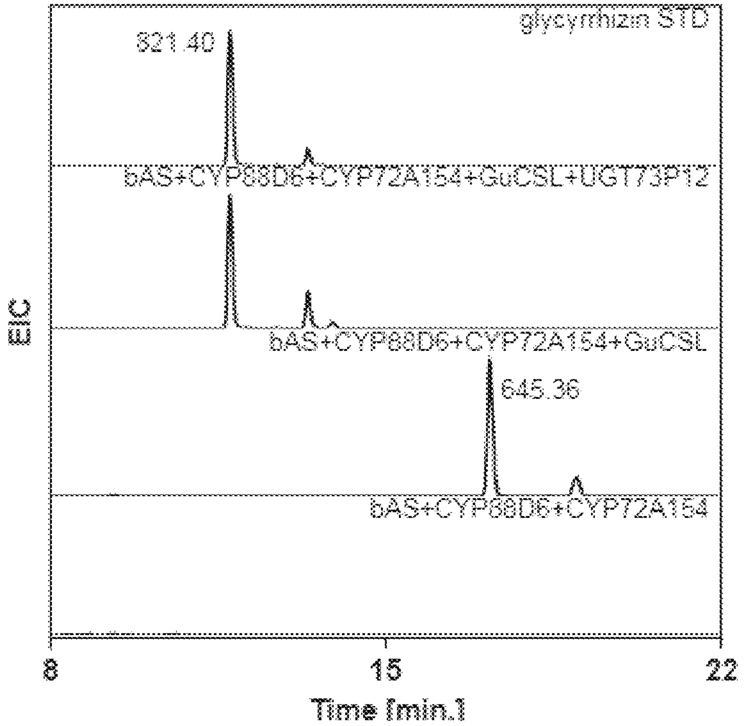
Figure 42F:
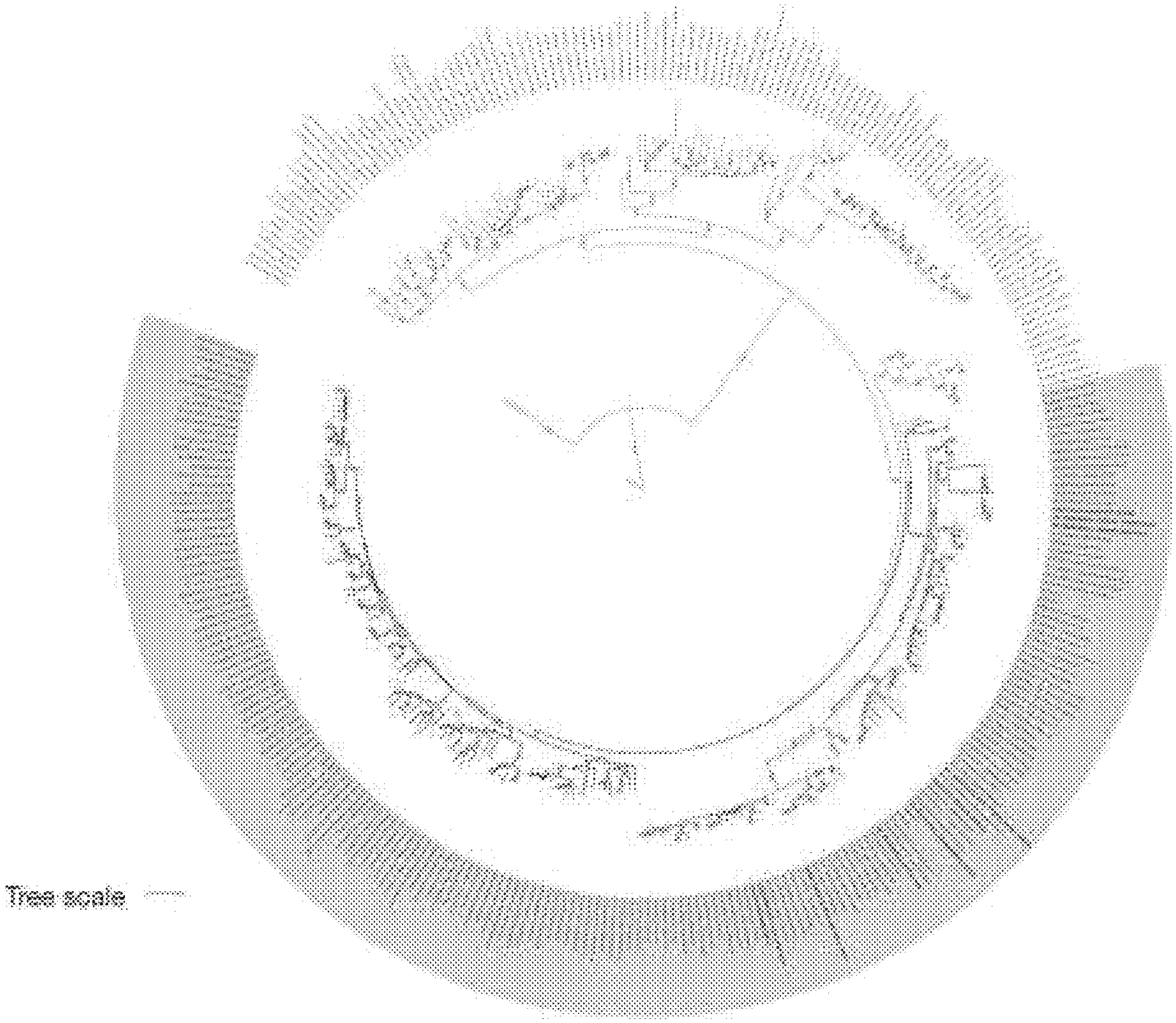

A skilled artisan would appreciate that homologs, may in some embodiments, have the same activity. In some embodiments, a SOAP gene homolog has the same activity as the corresponding SOAP gene. In some embodiments, a SOAP polypeptide homolog has the same enzyme activity as the corresponding SOAP polypeptide. In some embodiments, a SOAP5 homolog has the same enzyme activities as SOAP5. In some embodiments, a GAME gene homolog has the same activity as the corresponding GAME gene. In some embodiments, a GAME polypeptide homolog has the same enzyme activity as the corresponding GAME polypeptide. In some embodiments, a GAME15 homolog has the same enzyme activities as GAME15. In certain embodiments, a homolog of a CSLG gene encodes an enzyme having cellulose synthase like G activity. In certain embodiments, a homolog of a CSLG gene encodes an enzyme having glucuronic acid transferase activity. In certain embodiments, a homolog of a CSLG gene encodes an enzyme having cellulose synthase like G activity and glucuronic acid transferase activity. FIGS. 42A and 42F provide phylogenetic trees of cellulose synthase like enzymes, wherein the cellulose synthase like G subclade includes the SOAP5 and GAME15 enzymes described herein.

In some embodiments, a genetically modified cell disclosed herein comprises a nucleic acid sequence encoding said at least one heterologous CSLG gene, wherein the nucleic acid sequence of said CSLG is set forth in any one of SEQ ID NOS: 30, 32, 34, 36, 38, 40, 65, 80, 93, 95, 97, 99, 101, 103, or 105; or a homolog thereof having at least 55% identity to and at least 55% coverage of, the nucleic acid sequence set forth in any one of SEQ ID NOS: 30, 32, 34, 36, 38, 40, 65, 80, 93, 95, 97, 99, 101, 103, or 105. In some embodiments, a genetically modified cell disclosed herein comprises a nucleic acid sequence encoding said at least one heterologous CSLG gene, wherein the nucleic acid sequence of said CSLG is set forth in any one of SEQ ID NOS: 30, 32, 34, 36, 38, 40, 65, 80, 93, 95, 97, 99, 101, 103, or 105; or a homolog thereof having at least 55% identity to and at least 80% coverage of, the nucleic acid sequence set forth in any one of SEQ ID NOS: 30, 32, 34, 36, 38, 40, 65, 80, 93, 95, 97, 99, 101, 103, or 105.

In some embodiments, a genetically modified cell disclosed herein comprises a nucleic acid sequence encoding said at least one heterologous CSLG gene, wherein the nucleic acid sequence of said CSLG is set forth in any one of SEQ ID NOS: 30, 32, 34, 36, 38, 40, 65, 80, 93, 95, 97, 99, 101, 103, or 105; or a homolog thereof having at least 80% identity to and at least 80% coverage of, the nucleic acid sequence set forth in any one of SEQ ID NOS: 30, 32, 34, 36, 38, 40, 65, 80, 93, 95, 97, 99, 101, 103, or 105.

In some embodiments, a genetically modified cell disclosed herein comprises a nucleic acid sequence encoding an at least one additional heterologous gene in addition to a heterologous CSLG gene, wherein the additional gene encodes (a) a β-amyrin synthase, and said nucleic acid sequence set forth in SEQ ID NO: 45; or a homolog thereof having at least 80% identity to and at least 80% coverage of, the nucleic acid sequence set forth in SEQ ID NO: 45; or (b) a cytochrome P450, said nucleic acid sequence set forth in any one of SEQ ID NO: 46, 51, or 53; or a homolog thereof having at least 80% identity to and at least 80% coverage of, the nucleic acid sequence set forth in any one of SEQ ID NO: 46, 51, or 53; or (c) a glycosyl transferase, said nucleic acid sequence set forth in any one of SEQ ID NO: 55, 57, 59, or 61; or a homolog thereof having at least 80% identity to and at least 80% coverage of, the nucleic acid sequence set forth in any one of SEQ ID NO: 55, 57, 59, or 61; or (d) an acetyltransferase, said nucleic acid sequence set forth in SEQ ID NO: 63; or a homolog thereof having at least 80% identity to and at least 80% coverage of, the nucleic acid sequence set forth in SEQ ID NO: 63; or (e) a UDP-glucose 6-dehydrogenase 1, said nucleic acid sequence set forth in SEQ ID NO: 74; or a homolog thereof having at least 80% identity to and at least 80% coverage of, the nucleic acid sequence set forth in SEQ ID NO: 74; or (f) any combination thereof of (a), (b), (c), (d), and (e).

In some embodiments, a genetically modified plant disclosed herein comprises a nucleic acid sequence encoding said at least one heterologous CSLG gene, wherein the nucleic acid sequence of said CSLG is set forth in any one of SEQ ID NOS: 30, 32, 34, 36, 38, 40, 65, 80, 93, 95, 97, 99, 101, 103, or 105; or a homolog thereof having at least 55% identity to and at least 55% coverage of, the nucleic acid sequence set forth in any one of SEQ ID NOS: 30, 32, 36, 38, 40, 65, 80, 93, 95, 97, 99, 101, 103, or 105. In some embodiments, a genetically modified plant disclosed herein comprises a nucleic acid sequence encoding said at least one heterologous CSLG gene, wherein the nucleic acid sequence of said CSLG is set forth in any one of SEQ ID NOS: 30, 32, 34, 36, 38, 40, 65, 80, 93, 95, 97, 99, 101, 103, or 105; or a homolog thereof having at least 55% identity to and at least 80% coverage of, the nucleic acid sequence set forth in any one of SEQ ID NOS: 30, 32, 36, 38, 40, 65, 80, 93, 95, 97, 99, 101, 103, or 105.

In some embodiments, a genetically modified plant disclosed herein comprises a nucleic acid sequence encoding said at least one heterologous CSLG gene, wherein the nucleic acid sequence of said CSLG is set forth in any one of SEQ ID NOS: 30, 32, 34, 36, 38, 40, 65, 80, 93, 95, 97, 99, 101, 103, or 105; or a homolog thereof having at least 80% identity to and at least 80% coverage of, the nucleic acid sequence set forth in any one of SEQ ID NOS: 30, 32, 36, 38, 40, 65, 80, 93, 95, 97, 99, 101, 103, or 105.

In some embodiments, a genetically modified plant disclosed herein comprises a nucleic acid sequence encoding an at least one additional heterologous gene in addition to a heterologous CSLG gene, wherein the additional gene encodes (a) a β-amyrin synthase, and said nucleic acid sequence set forth in SEQ ID NO: 45; or a homolog thereof having at least 80% identity to and at least 80% coverage of, the nucleic acid sequence set forth in SEQ ID NO: 45; or (b) a cytochrome P450, said nucleic acid sequence set forth in any one of SEQ ID NO: 46, 51, or 53; or a homolog thereof having at least 80% identity to and at least 80% coverage of, the nucleic acid sequence set forth in any one of SEQ ID NO: 46, 51, or 53; or (c) a glycosyl transferase, said nucleic acid sequence set forth in any one of SEQ ID NO: 55, 57, 59, or 61; or a homolog thereof having at least 80% identity to and at least 80% coverage of, the nucleic acid sequence set forth in any one of SEQ ID NO: 55, 57, 59, or 61; or (d) an acetyltransferase, said nucleic acid sequence set forth in SEQ ID NO: 63; or a homolog thereof having at least 80% identity to and at least 80% coverage of, the nucleic acid sequence set forth in SEQ ID NO: 63; or (e) a UDP-glucose 6-dehydrogenase 1, said nucleic acid sequence set forth in SEQ ID NO: 74; or a homolog thereof having at least 80% identity to and at least 80% coverage of, the nucleic acid sequence set forth in SEQ ID NO: 74; or (f) any combination thereof of (a), (b), (c), (d), and (e).

In some embodiments, a polynucleotide sequence comprising an at least one heterologous gene encoding an enzyme disclosed here, comprises a nucleic acid sequence having at least 55%, at least 60%, at least 65%, at least 70%, at least 75%, at least 80%, at least 85%, at least 90%, or at least 95% homology to a sequence selected from 30, 32, 34, 36, 38, 40, 45, 46, 47, 51, 53, 55, 57, 59, 61, 63, 65, 80, 93, 95, 97, 99, 101, 103, or 105, or a combination thereof. In some embodiments, the nucleic acid sequence of a heterologous gene encoding an enzyme disclosed herein, comprises a nucleic acid sequence having at least 55%, at least 60%, at least 65%, at least 70%, at least 75%, at least 80%, at least 85%, at least 90%, or at least 95% identity to a sequence selected from 30, 32, 34, 36, 38, 40, 45, 46, 47, 51, 53, 55, 57, 59, 61, 63, 65, 80, 93, 95, 97, 99, 101, 103, or 105, or a combination thereof.

In some embodiments, the nucleic acid sequence of a heterologous gene encoding an enzyme disclosed herein, comprises a nucleic acid sequence selected from selected from 30, 32, 34, 36, 38, 40, 45, 46, 47, 51, 53, 55, 57, 59, 61, 63, 65, 80, 93, 95, 97, 99, 101, 103, or 105, or a combination thereof.

In some embodiments, a nucleic acid sequence having at least 55%, at least 60%, at least 65%, at least 70%, at least 75%, at least 80%, at least 85%, at least 90%, or at least 95% identity to a sequence selected from 30, 32, 34, 36, 38, 40, 45, 46, 47, 51, 53, 55, 57, 59, 61, 63, 65, 80, 93, 95, 97, 99, 101, 103, or 105, comprises a codon optimized gene sequence.

In some embodiments, optimizing a gene entails adapting the codon usage to the codon bias of host genes, which in one embodiment comprises a plant host. In some embodiments, optimizing a gene entails adapting the codon usage to the codon bias of host genes, which in one embodiment comprises a yeast host. In some embodiments, optimizing a gene entails adapting the codon usage to the codon bias of host genes, which in one embodiment comprises a algal host. Codon optimized gene sequences may in some embodiments, improve protein expression level in living organism by increasing translational efficiency of an at least one heterologous gene as described herein. In some embodiments, codon-optimization comprising codon optimization for expression in yeast. In some embodiments, codon-optimization comprising codon optimization for expression in algae. In some embodiments, codon-optimization comprising codon optimization for expression in a plant cell.

In some embodiments, the term "optimized" encompasses a desired change, which, in one embodiment, is a change in gene expression and, in another embodiment, in protein expression. In one embodiment, optimized gene expression is optimized regulation of gene expression. In another embodiment, optimized gene expression is an increase in gene expression. According to this aspect and in one embodiment, a 2-fold through 1000-fold increase in gene expression compared to wild-type is contemplated. In another embodiment, a 2-fold to 500-fold increase in gene expression, in another embodiment, a 2-fold to 100-fold increase in gene expression, in another embodiment, a 2-fold to 50-fold increase in gene expression, in another embodiment, a 2-fold to 20-fold increase in gene expression, in another embodiment, a 2-fold to 10-fold increase in gene expression, in another embodiment, a 3-fold to 5-fold increase in gene expression is contemplated.

In another embodiment, optimized gene expression may be an increase in gene expression under particular environmental conditions. In another embodiment, optimized gene expression may comprise a decrease in gene expression, which, in one embodiment, may be only under particular environmental conditions.

In another embodiment, optimized gene expression is an increased duration of gene expression. According to this aspect and in one embodiment, a 2-fold through 1000-fold increase in the duration of gene expression compared to wild-type is contemplated. In another embodiment, a 2-fold to 500-fold increase in the duration of gene expression, in another embodiment, a 2-fold to 100-fold increase in the duration of gene expression, in another embodiment, a 2-fold to 50-fold increase in the duration of gene expression, in another embodiment, a 2-fold to 20-fold increase in the duration of gene expression, in another embodiment, a 2-fold to 10-fold increase in the duration of gene expression, in another embodiment, a 3-fold to 5-fold increase in the duration of gene expression is contemplated. In another embodiment, the increased duration of gene expression is compared to gene expression in non-vector-expressing controls, or alternatively, compared to gene expression in wild-type-vector-expressing controls.

A skilled artisan would appreciate that in some embodiments, more than one heterologous gene encoding an enzyme is expressed in a genetically modified cell. In some embodiments, the cell comprises a polynucleotide sequence encoding more than one heterologous gene. In other embodiments, when more than one heterologous gene encoding an enzyme is expressed in a genetically modified cell, multiple polynucleotide sequences may be used to encode the multiple heterologous genes, wherein a polynucleotide sequence may comprise one or more genes. In some embodiments, when more than one heterologous gene encoding an enzyme is expressed in a genetically modified cell, multiple polynucleotide sequences may be used to encode the multiple heterologous genes, wherein each polynucleotide sequence comprises one a single gene. In some embodiments, when more than one heterologous gene encoding an enzyme is expressed in a genetically modified cell, multiple polynucleotide sequences may be used to encode the multiple heterologous genes, wherein each polynucleotide sequence comprises one or more genes.

As disclosed throughout, in some embodiments a genetically modified cell comprises a plant cell. In some embodiments, a genetically modified plant cell is comprised in a plant or plant part. In other embodiments, a genetically modified cell comprises a yeast cell. In other embodiments a genetically modified cell comprises an algal cell. In other embodiments, a genetically modified cell comprises an insect cell. In other embodiments, a genetically modified cell comprises a bacterium.

Additionally, a skilled artisan would appreciate that in some embodiments, more than one heterologous gene encoding an enzyme is expressed in a genetically modified plant. In some embodiments, the plant comprises a polynucleotide sequence encoding more than one heterologous gene. In other embodiments, when more than one heterologous gene encoding an enzyme is expressed in a genetically modified plant, multiple polynucleotide sequences may be used to encode the multiple heterologous genes, wherein a polynucleotide sequence may comprise one or more genes. In some embodiments, when more than one heterologous gene encoding an enzyme is expressed in a genetically modified plant, multiple polynucleotide sequences may be used to encode the multiple heterologous genes, wherein each polynucleotide sequence comprises one a single gene. In some embodiments, when more than one heterologous gene encoding an enzyme is expressed in a genetically modified plant, multiple polynucleotide sequences may be used to encode the multiple heterologous genes, wherein each polynucleotide sequence comprises one or more genes.

In some embodiments, the amino acid sequence of an enzyme encoded by an at least one heterologous gene comprises the amino acid sequence of a steroidal alkaloid biosynthetic enzyme, a steroidal saponin biosynthetic enzyme, and/or a triterpenoid biosynthetic enzyme.

In some embodiments, the amino acid sequence of an enzyme encoded by an at least one heterologous gene is set forth in any one of SEQ ID NOS: 31, 33, 35, 37, 39, 41, 48, 49, 50, 52, 54, 56, 58, 60, 62, 64, 64, 81, 94, 96, 98, 100, 102 or 104. In some embodiments, the amino acid sequence of an enzyme encoded by an at least one heterologous gene is set forth in SEQ ID NO: 31. In some embodiments, the amino acid sequence of an enzyme encoded by an at least one heterologous gene is set forth in SEQ ID NO: 33. In some embodiments, the amino acid sequence of an enzyme encoded by an at least one heterologous gene is set forth in SEQ ID NO: 35. In some embodiments, the amino acid sequence of an enzyme encoded by an at least one heterologous gene is set forth in SEQ ID NO: 37. In some embodiments, the amino acid sequence of an enzyme encoded by an at least one heterologous gene is set forth in SEQ ID NO: 39. In some embodiments, the amino acid sequence of an enzyme encoded by an at least one heterologous gene is set forth in SEQ ID NO: 41. In some embodiments, the amino acid sequence of an enzyme encoded by an at least one heterologous gene is set forth in SEQ ID NO: 48. In some embodiments, the amino acid sequence of an enzyme encoded by an at least one heterologous gene is set forth in SEQ ID NO: 49. In some embodiments, the amino acid sequence of an enzyme encoded by an at least one heterologous gene is set forth in SEQ ID NO: 50. In some embodiments, the amino acid sequence of an enzyme encoded by an at least one heterologous gene is set forth in SEQ ID NO: 52. In some embodiments, the amino acid sequence of an enzyme encoded by an at least one heterologous gene is set forth in SEQ ID NO: 54. In some embodiments, the amino acid sequence of an enzyme encoded by an at least one heterologous gene is set forth in SEQ ID NO: 56. In some embodiments, the amino acid sequence of an enzyme encoded by an at least one heterologous gene is set forth in SEQ ID NO: 58. In some embodiments, the amino acid sequence of an enzyme encoded by an at least one heterologous gene is set forth in SEQ ID NO: 60. In some embodiments, the amino acid sequence of an enzyme encoded by an at least one heterologous gene is set forth in SEQ ID NO: 62. In some embodiments, the amino acid sequence of an enzyme encoded by an at least one heterologous gene is set forth in SEQ ID NO: 64. In some embodiments, the amino acid sequence of an enzyme encoded by an at least one heterologous gene is set forth in SEQ ID NO: 66. In some embodiments, the amino acid sequence of an enzyme encoded by an at least one heterologous gene is set forth in SEQ ID NO: 69. In some embodiments, the amino acid sequence of an enzyme encoded by an at least one heterologous gene is set forth in SEQ ID NO: 81. In some embodiments, the amino acid sequence of an enzyme encoded by an at least one heterologous gene is set forth in SEQ ID NO: 94. In some embodiments, the amino acid sequence of an enzyme encoded by an at least one heterologous gene is set forth in SEQ ID NO: 96. In some embodiments, the amino acid sequence of an enzyme encoded by an at least one heterologous gene is set forth in SEQ ID NO: 98. In some embodiments, the amino acid sequence of an enzyme encoded by an at least one heterologous gene is set forth in SEQ ID NO: 100. In some embodiments, the amino acid sequence of an enzyme encoded by an at least one heterologous gene is set forth in SEQ ID NO: 102. In some embodiments, the amino acid sequence of an enzyme encoded by an at least one heterologous gene is set forth in SEQ ID NO: 104.

In some embodiments, the amino acid sequence of an enzyme encoded by an at least one heterologous gene is set forth in a sequence having at least 55% identity to the amino acid sequence set forth in any one of SEQ ID NOS: 31, 33, 35, 37, 39, 41, 48, 49, 50, 52, 54, 56, 58, 60, 62, 64, 64, 81, 94, 96, 98, 100, 102 or 104. In some embodiments, the amino acid sequence of an enzyme encoded by an at least one heterologous gene is set forth in a sequence having at least 55% identity to the amino acid sequence set forth in SEQ ID NO: 31. In some embodiments, the amino acid sequence of an enzyme encoded by an at least one heterologous gene is set forth in a sequence having at least 55% identity to the amino acid sequence set forth in SEQ ID NO: 33. In some embodiments, the amino acid sequence of an enzyme encoded by an at least one heterologous gene is set forth in a sequence having at least 55% identity to the amino acid sequence set forth in SEQ ID NO: 35. In some embodiments, the amino acid sequence of an enzyme encoded by an at least one heterologous gene is set forth in a sequence having at least 55% identity to the amino acid sequence set forth in SEQ ID NO: 37. In some embodiments, the amino acid sequence of an enzyme encoded by an at least one heterologous gene is set forth in a sequence having at least 55% identity to the amino acid sequence set forth in SEQ ID NO: 39. In some embodiments, the amino acid sequence of an enzyme encoded by an at least one heterologous gene is set forth in a sequence having at least 55% identity to the amino acid sequence set forth in SEQ ID NO: 41. In some embodiments, the amino acid sequence of an enzyme encoded by an at least one heterologous gene is set forth in a sequence having at least 55% identity to the amino acid sequence set forth in SEQ ID NO: 48. In some embodiments, the amino acid sequence of an enzyme encoded by an at least one heterologous gene is set forth in a sequence having at least 55% identity to the amino acid sequence set forth in SEQ ID NO: 49. In some embodiments, the amino acid sequence of an enzyme encoded by an at least one heterologous gene is set forth in a sequence having at least 55% identity to the amino acid sequence set forth in SEQ ID NO: 50. In some embodiments, the amino acid sequence of an enzyme encoded by an at least one heterologous gene is set forth in a sequence having at least 55% identity to the amino acid sequence set forth in SEQ ID NO: 52. In some embodiments, the amino acid sequence of an enzyme encoded by an at least one heterologous gene is set forth in a sequence having at least 55% identity to the amino acid sequence set forth in SEQ ID NO: 54. In some embodiments, the amino acid sequence of an enzyme encoded by an at least one heterologous gene is set forth in a sequence having at least 55% identity to the amino acid sequence set forth in SEQ ID NO: 56. In some embodiments, the amino acid sequence of an enzyme encoded by an at least one heterologous gene is set forth in a sequence having at least 55% identity to the amino acid sequence set forth in SEQ ID NO: 58. In some embodiments, the amino acid sequence of an enzyme encoded by an at least one heterologous gene is set forth in a sequence having at least 55% identity to the amino acid sequence set forth in SEQ ID NO: 60. In some embodiments, the amino acid sequence of an enzyme encoded by an at least one heterologous gene is set forth in a sequence having at least 55% identity to the amino acid sequence set forth in SEQ ID NO: 62. In some embodiments, the amino acid sequence of an enzyme encoded by an at least one heterologous gene is set forth in a sequence having at least 55% identity to the amino acid sequence set forth in SEQ ID NO: 64. In some embodiments, the amino acid sequence of an enzyme encoded by an at least one heterologous gene is set forth in a sequence having at least 55% identity to the amino acid sequence set forth in SEQ ID NO: 66. In some embodiments, the amino acid sequence of an enzyme encoded by an at least one heterologous gene is set forth in a sequence having at least 55% identity to the amino acid sequence set forth in SEQ ID NO: 69. In some embodiments, the amino acid sequence of an enzyme encoded by an at least one heterologous gene is set forth in a sequence having at least 55% identity to the amino acid sequence set forth in SEQ ID NO: 81. In some embodiments, the amino acid sequence of an enzyme encoded by an at least one heterologous gene is set forth in a sequence having at least 55% identity to the amino acid sequence set forth in SEQ ID NO: 94. In some embodiments, the amino acid sequence of an enzyme encoded by an at least one heterologous gene is set forth in a sequence having at least 55% identity to the amino acid sequence set forth in SEQ ID NO: 96. In some embodiments, the amino acid sequence of an enzyme encoded by an at least one heterologous gene is set forth in a sequence having at least 55% identity to the amino acid sequence set forth in SEQ ID NO: 98. In some embodiments, the amino acid sequence of an enzyme encoded by an at least one heterologous gene is set forth in a sequence having at least 55% identity to the amino acid sequence set forth in SEQ ID NO: 100. In some embodiments, the amino acid sequence of an enzyme encoded by an at least one heterologous gene is set forth in a sequence having at least 55% identity to the amino acid sequence set forth in SEQ ID NO: 102. In some embodiments, the amino acid sequence of an enzyme encoded by an at least one heterologous gene is set forth in a sequence having at least 55% identity to the amino acid sequence set forth in SEQ ID NO: 104.

In some embodiments, the amino acid sequence of an enzyme encoded by an at least one heterologous gene is set forth in a sequence having at least 55%, 60%, 65%, 70%, 75%, 80%, 85%, 90%, 95%, 98%, or 99% identity to the amino acid sequence set forth in any of SEQ ID NO: 31, 33, 35, 37, 39, 41, 48, 49, 50, 52, 54, 56, 58, 60, 62, 64, 64, 81, 94, 96, 98, 100, 102 or 104. In some embodiments, the amino acid sequence of an enzyme encoded by an at least one heterologous gene is set forth in a sequence having at least 55%, 60%, 65%, 70%, 75%, 80%, 85%, 90%, 95%, 98%, 99%, or 100% coverage to the amino acid sequence set forth in any of SEQ ID NO: 31, 33, 35, 37, 39, 41, 48, 49, 50, 52, 54, 56, 58, 60, 62, 64, 64, 81, 94, 96, 98, 100, 102 or 104.

In some embodiments, the amino acid sequence of an enzyme encoded by an at least one heterologous gene is set forth in a sequence having at least 80% identity to the amino acid sequence set forth in any one of SEQ ID NOS: 31, 33, 35, 37, 39, 41, 48, 49, 50, 52, 54, 56, 58, 60, 62, 64, 64, 81, 94, 96, 98, 100, 102 or 104. In some embodiments, the amino acid sequence of an enzyme encoded by an at least one heterologous gene is set forth in a sequence having at least 80% identity to the amino acid sequence set forth in SEQ ID NO: 31. In some embodiments, the amino acid sequence of an enzyme encoded by an at least one heterologous gene is set forth in a sequence having at least 80% identity to the amino acid sequence set forth in SEQ ID NO: 33. In some embodiments, the amino acid sequence of an enzyme encoded by an at least one heterologous gene is set forth in a sequence having at least 80% identity to the amino acid sequence set forth in SEQ ID NO: 35. In some embodiments, the amino acid sequence of an enzyme encoded by an at least one heterologous gene is set forth in a sequence having at least 80% identity to the amino acid sequence set forth in SEQ ID NO: 37. In some embodiments, the amino acid sequence of an enzyme encoded by an at least one heterologous gene is set forth in a sequence having at least 80% identity to the amino acid sequence set forth in SEQ ID NO: 39. In some embodiments, the amino acid sequence of an enzyme encoded by an at least one heterologous gene is set forth in a sequence having at least 80% identity to the amino acid sequence set forth in SEQ ID NO: 41. In some embodiments, the amino acid sequence of an enzyme encoded by an at least one heterologous gene is set forth in a sequence having at least 80% identity to the amino acid sequence set forth in SEQ ID NO: 48. In some embodiments, the amino acid sequence of an enzyme encoded by an at least one heterologous gene is set forth in a sequence having at least 80% identity to the amino acid sequence set forth in SEQ ID NO: 49. In some embodiments, the amino acid sequence of an enzyme encoded by an at least one heterologous gene is set forth in a sequence having at least 80% identity to the amino acid sequence set forth in SEQ ID NO: 50. In some embodiments, the amino acid sequence of an enzyme encoded by an at least one heterologous gene is set forth in a sequence having at least 80% identity to the amino acid sequence set forth in SEQ ID NO: 52. In some embodiments, the amino acid sequence of an enzyme encoded by an at least one heterologous gene is set forth in a sequence having at least 80% identity to the amino acid sequence set forth in SEQ ID NO: 54. In some embodiments, the amino acid sequence of an enzyme encoded by an at least one heterologous gene is set forth in a sequence having at least 80% identity to the amino acid sequence set forth in SEQ ID NO: 56. In some embodiments, the amino acid sequence of an enzyme encoded by an at least one heterologous gene is set forth in a sequence having at least 80% identity to the amino acid sequence set forth in SEQ ID NO: 58. In some embodiments, the amino acid sequence of an enzyme encoded by an at least one heterologous gene is set forth in a sequence having at least 80% identity to the amino acid sequence set forth in SEQ ID NO: 60. In some embodiments, the amino acid sequence of an enzyme encoded by an at least one heterologous gene is set forth in a sequence having at least 80% identity to the amino acid sequence set forth in SEQ ID NO: 62. In some embodiments, the amino acid sequence of an enzyme encoded by an at least one heterologous gene is set forth in a sequence having at least 80% identity to the amino acid sequence set forth in SEQ ID NO: 64. In some embodiments, the amino acid sequence of an enzyme encoded by an at least one heterologous gene is set forth in a sequence having at least 80% identity to the amino acid sequence set forth in SEQ ID NO: 66. In some embodiments, the amino acid sequence of an enzyme encoded by an at least one heterologous gene is set forth in a sequence having at least 80% identity to the amino acid sequence set forth in SEQ ID NO: 69. In some embodiments, the amino acid sequence of an enzyme encoded by an at least one heterologous gene is set forth in a sequence having at least 80% identity to the amino acid sequence set forth in SEQ ID NO: 81. In some embodiments, the amino acid sequence of an enzyme encoded by an at least one heterologous gene is set forth in a sequence having at least 80% identity to the amino acid sequence set forth in SEQ ID NO: 94. In some embodiments, the amino acid sequence of an enzyme encoded by an at least one heterologous gene is set forth in a sequence having at least 80% identity to the amino acid sequence set forth in SEQ ID NO: 96. In some embodiments, the amino acid sequence of an enzyme encoded by an at least one heterologous gene is set forth in a sequence having at least 80% identity to the amino acid sequence set forth in SEQ ID NO: 98. In some embodiments, the amino acid sequence of an enzyme encoded by an at least one heterologous gene is set forth in a sequence having at least 80% identity to the amino acid sequence set forth in SEQ ID NO: 100. In some embodiments, the amino acid sequence of an enzyme encoded by an at least one heterologous gene is set forth in a sequence having at least 80% identity to the amino acid sequence set forth in SEQ ID NO: 102. In some embodiments, the amino acid sequence of an enzyme encoded by an at least one heterologous gene is set forth in a sequence having at least 80% identity to the amino acid sequence set forth in SEQ ID NO: 104.

In some embodiments, the enzyme encoded by an at least one heterologous gene comprises an amino acid sequence having at least 55%, at least 60%, at least 65%, at least 70%, at least 75%, at least 80%, at least 85%, at least 90%, or at least 95% homology to a sequence selected from SEQ ID NOS: 31, 33, 35, 37, 39, 41, 48, 49, 50, 52, 54, 56, 58, 60, 62, 64, 66, 81, 94, 96, 98, 100, 102 or 104. In some embodiments, the enzyme encoded by the at least one heterologous gene comprises the amino acid sequence having at least 55%, at least 60%, at least 65%, at least 70%, at least 75%, at least 80%, at least 85%, at least 95% identity with a sequence selected from SEQ ID NOS: 31, 33, 35, 37, 39, 41, 48, 49, 50, 52, 54, 56, 58, 60, 62, 64, 66, 81, 94, 96, 98, 100, 102 or 104.

In some embodiments, the enzyme encoded by an at least one heterologous gene comprises an amino acid sequence having at least 80%, at least 85%, at least 90%, or at least 95% homology to a sequence selected from SEQ ID NOS: 31, 33, 35, 37, 39, 41, 48, 49, 50, 52, 54, 56, 58, 60, 62, 64, 66, 81, 94, 96, 98, 100, 102 or 104. In some embodiments, the enzyme encoded by the at least one heterologous gene comprises the amino acid sequence having at least 80%, at least 85%, at least 95% identity with a sequence selected from SEQ ID NOS: 31, 33, 35, 37, 39, 41, 48, 49, 50, 52, 54, 56, 58, 60, 62, 64, 66, 81, 94, 96, 98, 100, 102 or 104.

In some embodiments, the amino acid sequence of the encoded CSLG enzyme is set forth in any one of SEQ ID NOS: 31, 33, 35, 37, 39, 41, 66, 81, 94, 96, 98, 100, 102 or 104; or a homolog thereof having at least 55% identity to and at least 55% coverage of, the amino acid sequence set forth in any one of SEQ ID NOS: 31, 33, 35, 37, 39, 41, 66, 81, 94, 96, 98, 100, 102 or 104. In some embodiments, the amino acid sequence of the encoded CSLG enzyme is set forth in any one of SEQ ID NOS: 31, 33, 35, 37, 39, 41, 66, 81, 94, 96, 98, 100, 102 or 104; or a homolog thereof having at least 55% identity to and at least 80% coverage of, the amino acid sequence set forth in any one of SEQ ID NOS: 31, 33, 35, 37, 39, 41, 66, 81, 94, 96, 98, 100, 102 or 104.

In some embodiments, the amino acid sequence of the encoded CSLG enzyme is set forth in any one of SEQ ID NOS: 31, 33, 35, 37, 39, 41, 66, 81, 94, 96, 98, 100, 102 or 104; or a homolog thereof having at least 80% identity to and at least 80% coverage of, the amino acid sequence set forth in any one of SEQ ID NOS: 31, 33, 35, 37, 39, 41, 66, 81, 94, 96, 98, 100, 102 or 104.

In some embodiments, the amino acid sequence of said encoded at least one additional heterologous gene encodes a β-amyrin synthase, said amino acid sequence set forth in SEQ ID NO: 45; or a homolog thereof having at least 80% identity to and at least 80% coverage of, the amino acid sequence set forth in SEQ ID NO: 45. In some embodiments, the amino acid sequence of said encoded at least one additional heterologous gene encodes a cytochrome P450, said amino acid sequence set forth in any one of SEQ ID NO: 46, 51, or 53; or a homolog thereof having at least 80% identity to and at least 80% coverage of, the amino acid sequence set forth in any one of SEQ ID NO: 46, 51, or 53. In some embodiments, the amino acid sequence of said encoded at least one additional heterologous gene encodes a glycosyl transferase, said amino acid sequence set forth in any one of SEQ ID NO: 55, 57, 59, or 61; or a homolog thereof having at least 80% identity to and at least 80% coverage of, the amino acid sequence set forth in any one of SEQ ID NO: 55, 57, 59, or 61. In some embodiments, the amino acid sequence of said encoded at least one additional heterologous gene encodes an acetyltransferase, said amino acid sequence set forth in SEQ ID NO: 63; or a homolog thereof having at least 80% identity to and at least 80% coverage of, the amino acid sequence set forth in SEQ ID NO: 63. In some embodiments, the amino acid sequence of said encoded at least one additional heterologous gene encodes a UDP-glucose 6-dehydrogenase 1, said amino acid sequence set forth in SEQ ID NO: 74; or a homolog thereof having at least 80% identity to and at least 80% coverage of, the amino acid sequence set forth in SEQ ID NO: 74.

In some embodiments, a genetically modified plant cell has an altered expression of at least the endogenous CSLG gene compared to the expression of the endogenous CSLG in a corresponding unmodified cell. In some embodiments, a genetically modified plant cell has an altered expression of at least the endogenous CSLG gene compared to the expression of the endogenous CSLG in a corresponding unmodified cell, wherein the cell has an altered content of at least one triterpenoid saponin, derivative thereof, metabolite thereof, or biosynthetic intermediate thereof.

Altering the expression of the endogenous CSLG affects the steroidal alkaloid biosynthetic pathway, the steroidal saponin biosynthetic pathway, and/or the triterpenoid saponin biosynthetic pathway, and in some embodiments, results in concomitant alteration, respectively, in the steroidal alkaloid profile or intermediates of that pathway, in the steroidal saponin profile or intermediates of that pathway, or in the triterpenoid saponin profile or intermediates of that pathway.

In some embodiments, the altered expression in a genetically modified cells comprises increased CSLG expression compared with a corresponding unmodified cell. In some embodiments, increased expression results in an increased amount of the encoded enzyme. In some embodiments, increased expression of CSLG results in the alteration in the steroidal alkaloid profile comprising an increase in at least one steroidal alkaloid or an intermediate thereof. In some embodiments, increased expression of CSLG results in the alteration in the steroidal saponin profile comprising an increase in at least one steroidal saponin or an intermediate thereof. In some embodiments, increased expression of CSLG results in the alteration in the triterpenoid saponin profile comprising an increase in at least one triterpenoid saponin or an intermediate thereof.

In some embodiments, the altered expression in a genetically modified cells comprises decreased CSLG expression compared with a corresponding unmodified cell. In some embodiments, decreased expression results in a decreased amount of the encoded enzyme. In some embodiments, decreased expression of CSLG results in the alteration in the steroidal alkaloid profile comprising a decrease in at least one steroidal alkaloid or an intermediate thereof. In some embodiments, decreased expression of CSLG results in the alteration in the steroidal saponin profile comprising a decrease in at least one steroidal saponin or an intermediate thereof. In some embodiments, decreased expression of CSLG results in the alteration in the triterpenoid saponin profile comprising a decrease in at least one triterpenoid saponin or an intermediate thereof.

In some embodiments, the at least one cell having an altered endogenous CSLG gene expression comprises a plant cell. In some embodiments, the at least one cell having an altered endogenous CSLG gene expression comprises a plant cell comprised within a plant or plant part. In some embodiments, the at least one cell having an altered endogenous CSLG gene expression is a result of a mutation in said CSLG gene. In some embodiments, said mutation comprises at least one or more point mutations, or an insertion, or a deletion, or any combination thereof, wherein said expressed CSLG enzyme has increased stability or increased activity or both and the altered content comprises an increased amount of the at least one triterpenoid saponin, a derivative thereof, a metabolite thereof, or a biosynthetic intermediate thereof compared to the corresponding unmodified plant. In some embodiments, said mutation comprises at least one or more point mutations, or an insertion, or a deletion, or any combination thereof, wherein said expressed CSLG enzyme has decreased stability or decreased activity or both and the altered content comprises a decreased amount of the at least one triterpenoid saponin, a derivative thereof, a metabolite thereof, or a biosynthetic intermediate thereof compared to the corresponding unmodified plant.

According to certain embodiments, expression of the endogenous CSLG gene is altered, the altering comprising mutagenizing the CSLG gene, wherein the mutagenesis comprises introduction of one or more point mutations, insertions, deletions, or genome editing, or use of a bacterial CRISPR/CAS system, or a combination thereof. According to certain embodiments, expression of the gene encoding the CLSG enzyme is increased compared to its expression in the corresponding unmodified plant, thereby the genetically modified plant comprises increased content of at least one steroidal alkaloid, derivative thereof, metabolite thereof, or biosynthetic intermediate thereof; increased content of at least one steroidal saponin, derivative thereof, metabolite thereof, or biosynthetic intermediate thereof; or increased content of at least one triterpenoid saponin, derivative thereof, metabolite thereof, or biosynthetic intermediate thereof, compared to the corresponding unmodified plant. According to certain embodiments, expression of the gene encoding the CLSG enzyme is decreased compared to its expression in the corresponding unmodified plant, thereby the genetically modified plant comprises decreased content at least one steroidal alkaloid, derivative thereof, metabolite thereof, or biosynthetic intermediate thereof; decreased content at least one steroidal saponin, derivative thereof, metabolite thereof, or biosynthetic intermediate thereof; or decreased content at least one triterpenoid saponin, derivative thereof, metabolite thereof, or biosynthetic intermediate thereof, compared to the corresponding unmodified plant.

In some embodiments, derivatives of steroidal alkaloids, steroidal saponins, or triterpenoid saponins comprise glycosylated derivatives of, respectively, steroidal alkaloids, steroidal saponins, or triterpenoid saponins.

Inserting a mutation to the CSLG gene, including deletions, insertions, site specific mutations, zinc-finger nucleases and the like can be used for example for upregulation of gene expression, increased stability of the expressed CSLG enzyme, increased activity of the CSLG enzyme, down-regulation of the gene expression, decreased stability of the expressed CSLG enzyme, decreased activity of the CSLG enzyme, or elimination of activity of the CSLG enzyme.

According to certain embodiments, a mutated CSLG gene comprises a polynucleotide having at least one mutation in the nucleic acid sequence of a CSLG gene, wherein the nucleic acid sequence of said CSLG is set forth in any one SEQ ID NOS: 31, 33, 35, 37, 39, 41, 65, 80, 93, 95, 97, 99, 101, 103, or 105, or a complementary sequence thereof.

One of ordinary skill in the art would appreciate that a genetically modified plant may encompass a plant comprising at least one cell genetically modified by man. In some embodiments, the genetic modification includes modification of an endogenous gene(s), for example by introducing mutation(s) deletions, insertions, transposable element(s) and the like into an endogenous polynucleotide or gene of interest. Additionally, or alternatively, in some embodiments, the genetic modification includes transforming at least one plant cell with a heterologous polynucleotide or multiple heterologous polynucleotides. The skilled artisan would appreciate that a genetically modified plant comprising transforming at least one plant cell with a heterologous polynucleotide or multiple heterologous polynucleotides may in certain embodiments be termed a "transgenic plant" or a "genetically modified plant" having the same meanings and qualities.

Altering the expression of an endogenous CSLG gene may in certain embodiments be achieved by the introduction of one or more point mutations into a nucleic acid molecule encoding the corresponding protein. Mutations can be introduced using, for example, site-directed mutagenesis (see, e.g., Wu Ed., 1993 Meth. In Enzymol. Vol. 217, San Diego: Academic Press; Higuchi, "Recombinant PCR" in Innis et al. Eds., 1990 PCR Protocols, San Diego: Academic Press, Inc). Such mutagenesis can be used to introduce a specific, desired amino acid insertion, deletion or substitution. Several technologies for targeted mutagenesis are based on the targeted induction of double-strand breaks (DSBs) in the genome followed by error-prone DNA repair. Mostly commonly used for genome editing by these methods are custom designed nucleases, including zinc finger nucleases, endonucleases including meganucleases, and *Xanthomonas*-derived transcription activator-like effector nuclease (TALEN) enzymes.

In some embodiments, when the expression of the CSLG gene is altered, said altering comprises mutagenizing CSLG gene, said mutation present within a coding region of said CSLG gene, or a regulatory sequence of said CSLG gene, or a combination thereof.

Various types of mutagenesis can be used to modify CSLG and the encoded enzyme thereof in order to produce conservative or non-conservative variants. Any available mutagenesis procedure can be used. In some embodiments, the mutagenesis procedure comprises site-directed point mutagenesis. In some embodiments, the mutagenesis procedure comprises random point mutagenesis. In some embodiments, the mutagenesis procedure comprises in vitro or in vivo homologous recombination (DNA shuffling). In some embodiments, the mutagenesis procedure comprises mutagenesis using uracil-containing templates. In some embodiments, the mutagenesis procedure comprises oligonucleotide-directed mutagenesis. In some embodiments, the mutagenesis procedure comprises phosphorothioate-modified DNA mutagenesis. In some embodiments, the mutagenesis procedure comprises mutagenesis using gapped duplex DNA. In some embodiments, the mutagenesis procedure comprises point mismatch repair. In some embodiments, the mutagenesis procedure comprises mutagenesis using repair-deficient host strains. In some embodiments, the mutagenesis procedure comprises restriction-selection and restriction-purification. In some embodiments, the mutagenesis procedure comprises deletion mutagenesis. In some embodiments, the mutagenesis procedure comprises mutagenesis by total gene synthesis. In some embodiments, the mutagenesis procedure comprises double-strand break repair. In some embodiments, the mutagenesis procedure comprises mutagenesis by chimeric constructs. In some embodiments, the mutagenesis procedure comprises mutagenesis by CRISPR/Cas. In some embodiments, the mutagenesis procedure comprises mutagenesis by a meganuclease. In some embodiments, the mutagenesis procedure comprises mutagenesis by zinc-finger nucleases (ZFN). In some embodiments, the mutagenesis procedure comprises mutagenesis by transcription activator-like effector nucleases (TALEN). In some embodiments, the mutagenesis procedure comprises any other mutagenesis procedure known to a person skilled in the art.

In some embodiments, mutagenesis can be guided by known information about the naturally occurring molecule and/or the mutated molecule. By way of example, this known information may include sequence, sequence comparisons, physical properties, crystal structure and the like. In some embodiments, the mutagenesis is essentially random. In some embodiments the mutagenesis procedure is DNA shuffling.

A skilled artisan would appreciate that clustered regularly interspaced short palindromic repeats (CRISPR)/CRISPR associated protein (Cas) system comprises genome engineering tools based on the bacterial CRISPR/Cas prokaryotic adaptive immune system. This RNA-based technology is very specific and allows targeted cleavage of genomic DNA guided by a customizable small noncoding RNA, resulting in gene modifications by both non-homologous end joining (NHEJ) and homology-directed repair (HDR) mechanisms (Belhaj K. et al., 2013. Plant Methods 2013, 9:39). In some embodiments, a CRISPR/Cas system comprises a CRISPR/Cas9 system.

In some embodiments, a CRISPR/Cas system comprises a single-guide RNA (sgRNA) and/or a Cas protein known in the art. In some embodiments, a CRISPR/Cas system comprises a single-guide RNA (sgRNA) and/or a Cas protein newly created to cleave at a preselected site. The skilled artisan would appreciate that the terms "single-guide RNA", "sgRNA", and "gRNA" are interchangeable having all the same qualities and meanings, wherein an sgRNA may encompass a chimeric RNA molecule which is composed of a CRISPR RNA (crRNA) and trans-encoded CRISPR RNA (tracrRNA). In some embodiments, a crRNA is complementary to a preselected region of GAME15 DNA, wherein the crRNA "targets" the CRISPR associated polypeptide (Cas) nuclease protein to the preselected target site.

In some embodiments, the length of crRNA sequence complementary is 19-22 nucleotides long e.g., 19-22 consecutive nucleotides complementary to the target site. In another embodiment, the length of crRNA sequence complementary to the region of DNA is about 15-30 nucleotides long. In another embodiment, the length of crRNA sequence complementary to the region of DNA is about 15, 16, 17, 18, 19, 20, 21, 22, 23, 24, 25, 26, 27, 28, 29, or 30 nucleotides long. In another embodiment, the length of crRNA sequence complementary to the region of DNA is 20 nucleotides long. In some embodiments, the crRNA is located at the 5' end of the sgRNA molecule. In another embodiment, the crRNA comprises 100% complementation within the preselected target sequence. In another embodiment, the crRNA comprises at least 80% complementation within the preselected target sequence. In another embodiment, the crRNA comprises at least 85% complementation within the preselected target sequence. In another embodiment, the crRNA comprises at least 90% complementation within the preselected target sequence. In another embodiment, the crRNA comprises at least 95% complementation within the preselected target sequence. In another embodiment, the crRNA comprises at least 97% complementation within the preselected target sequence. In another embodiment, the crRNA comprises at least 99% complementation within the preselected target sequence. In another embodiment, a tracrRNA is 100-300 nucleotides long and provides a binding site for the Cas nuclease, e.g., a Cas9 protein forming the CRISPR/Cas9 complex.

In one embodiment, a mutagenesis system comprises a CRISPR/Cas system. In another embodiment, a CRISPR/Cas system comprises a Cas nuclease and a gRNA molecule, wherein said gRNA molecule binds within said preselected endogenous target site thereby guiding said Cas nuclease to cleave the DNA within said preselected endogenous target site.

In some embodiments, a CRISPR/Cas system comprise an enzyme system including a guide RNA sequence ("gRNA" or "sgRNA") that contains a nucleotide sequence complementary or substantially complementary to a region of a target polynucleotide, for example a preselected endogenous target site, and a protein with nuclease activity.

In another embodiment, a CRISPR/Cas system comprises a Type I CRISPR-Cas system, or a Type II CRISPR-Cas system, or a Type III CRISPR-Cas system, or derivatives thereof. In another embodiment, a CRISPR-Cas system comprises an engineered and/or programmed nuclease system derived from naturally accruing CRISPR-Cas systems. In another embodiment, a CRISPR-Cas system comprises engineered and/or mutated Cas proteins. In another embodiment, a CRISPR-Cas system comprises engineered and/or programmed guide RNA.

A skilled artisan would appreciate that a guide RNA may contain nucleotide sequences other than the region complementary or substantially complementary to a region of a target DNA sequence, for example a preselected endogenous target site. In another embodiment, a guide RNA comprises a crRNA or a derivative thereof. In another embodiment, a guide RNA comprises a crRNA: tracrRNA chimera.

In another embodiment, a gRNA molecule comprises a domain that is complementary to and binds to a preselected endogenous target site on at least one homologous chromosome. In another embodiment, a gRNA molecule comprises a domain that is complementary to and binds to a polymorphic allele on at least one homologous chromosome. In another embodiment, a gRNA molecule comprises a domain that is complementary to and binds to a preselected endogenous target site on both homologous chromosomes. In another embodiment, a gRNA molecule comprises a domain that is complementary to and binds to polymorphic alleles on both homologous chromosomes.

Cas enzymes comprise RNA-guided DNA endonuclease able to make double-stranded breaks (DSB) in DNA. The term "Cas enzyme" may be used interchangeably with the terms "CRISPR-associated endonucleases" or "CRISPR-associated polypeptides" having all the same qualities and meanings. In one embodiment, a Cas enzyme is selected from the group comprising Cas1, Cas1B, Cas2, Cas3, Cas4, Cas5, Cas6, Cas7, Cas8, Cas9, Cas10, C2cl, CasX, NgAgo, Cpf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4, or homologs thereof, or modified versions thereof. In another embodiment, a Cas enzyme comprises Cas9. In another embodiment, a Cas enzyme comprises Cas1. In another embodiment, a Cas enzyme comprises Cas1B. In another embodiment, a Cas enzyme comprises Cas2. In another embodiment, a Cas enzyme comprises Cas3. In another embodiment, a Cas enzyme comprises Cas4. In another embodiment, a Cas enzyme comprises Cas5. In another embodiment, a Cas enzyme comprises Cas6. In another embodiment, a Cas enzyme comprises Cas7. In another embodiment, a Cas enzyme comprises Cas8. In another embodiment, a Cas enzyme comprises Cas10. In another embodiment, a Cas enzyme comprises Cpf1. In another embodiment, a Cas enzyme comprises Csy1. In another embodiment, a Cas enzyme comprises Csy2. In another embodiment, a Cas enzyme comprises Csy3. In another embodiment, a Cas enzyme comprises Cse1. In another embodiment, a Cas enzyme comprises Cse2. In another embodiment, a Cas enzyme comprises Csc1. In another embodiment, a Cas enzyme comprises Csc2. In another embodiment, a Cas enzyme comprises Csa5. In another embodiment, a Cas enzyme comprises Csn2. In another embodiment, a Cas enzyme comprises Csm2. In another embodiment, a Cas enzyme comprises Csm3. In another embodiment, a Cas enzyme comprises Csm4. In another embodiment, a Cas enzyme comprises Csm5. In another embodiment, a Cas enzyme comprises Csm6. In another embodiment, a Cas enzyme comprises Cmr1. In another embodiment, a Cas enzyme comprises Cmr3. In another embodiment, a Cas enzyme comprises Cmr4. In another embodiment, a Cas enzyme comprises Cmr5. In another embodiment, a Cas enzyme comprises Cmr6. In another embodiment, a Cas enzyme comprises Csb1. In another embodiment, a Cas enzyme comprises Csb2. In another embodiment, a Cas enzyme comprises Csb3. In another embodiment, a Cas enzyme comprises Csx17. In another embodiment, a Cas enzyme comprises Csx14. In another embodiment, a Cas enzyme comprises Csx10. In another embodiment, a Cas enzyme comprises Csx16, CsaX. In another embodiment, a Cas enzyme comprises Csx3. In another embodiment, a Cas enzyme comprises Csx1, Csx15, Csf1. In another embodiment, a Cas enzyme comprises Csf2. In another embodiment, a Cas enzyme comprises Csf3. In another embodiment, a Cas enzyme comprises Csf4. In another embodiment, a Cas enzyme comprises Cpf1. In another embodiment, a Cas enzyme comprises C2cl. In another embodiment, a Cas enzyme comprises CasX. In another embodiment, a Cas enzyme comprises NgAgo. In another embodiment, a Cas enzyme is Cas homologue. In another embodiment, a Cas enzyme is a Cas orthologue. In another embodiment, a Cas enzyme is a modified Cas enzyme. In another embodiment, a Cas enzyme is any CRISPR-associated endonucleases known in the art.

A skilled artisan would appreciate that the terms "zinc finger nuclease" or "ZFN" are interchangeable having all the same meanings and qualities, wherein a ZFN encompasses a chimeric protein molecule comprising at least one zinc finger DNA binding domain operatively linked to at least one nuclease capable of double-strand cleaving of DNA. In some embodiments, a ZFN system comprises a ZFN known in the art. In some embodiments, a ZFN system comprises a ZFN newly created to cleave a preselected site.

In some embodiments, a ZFN creates a double-stranded break at a preselected endogenous target site. In some embodiments, a ZFN comprises a DNA-binding domain and a DNA-cleavage domain, wherein the DNA binding domain is comprised of at least one zinc finger and is operatively linked to a DNA-cleavage domain. In another embodiment, a zinc finger DNA-binding domain is at the N-terminus of the chimeric protein molecule and the DNA-cleavage domain is located at the C-terminus of the molecule. In another embodiment, a zinc finger DNA-binding domain is at the C-terminus of the chimeric protein molecule and the DNA-cleavage domain is located at the N-terminus of the molecule. In another embodiment, a zinc finger binding domain encompasses the region in a zinc finger nuclease that is capable of binding to a target locus, for example a preselected endogenous target site as disclosed herein. In another embodiment, a zinc finger DNA-binding domain comprises a protein domain that binds to a preselected endogenous target site on at least one homologous chromosome. In another embodiment, a zinc finger DNA-binding domain comprises a protein domain that binds to a polymorphic allele on at least one homologous chromosome. In another embodiment, a zinc finger DNA-binding domain comprises a protein domain that binds to a preselected endogenous target site on both homologous chromosomes. In another embodiment, a zinc finger DNA-binding domain comprises a protein domain that binds to polymorphic alleles on both homologous chromosomes.

The skilled artisan would appreciate that the term "chimeric protein" is used to describe a protein that has been expressed from a DNA molecule that has been created by operatively joining two or more DNA fragments. The DNA fragments may be from the same species, or they may be from a different species. The DNA fragments may be from the same or a different gene. The skilled artisan would appreciate that the term "DNA cleavage domain" of a ZFN encompasses the region in the zinc finger nuclease that is capable of breaking down the chemical bonds between nucleic acids in a nucleotide chain. Examples of proteins containing cleavage domains include restriction enzymes, topoisomerases, recombinases, integrases and DNAses.

A skilled artisan would appreciate that endonucleases include meganucleases, also known as homing endonucleases (HEases), which like restriction endonucleases, bind and cut at a specific DSB target site, however the DSB target sites for meganucleases are typically longer, about 18 bp or more. Meganuclease domains, structure and function are known, see for example, Guhan and Muniyappa (2003) Crit Rev Biochem Mol Biol 38:199-248; Lucas et al., (2001) Nucleic Acids Res 29:960-9; Jurica and Stoddard, (1999) Cell Mol Life Sci 55:1304-26; Stoddard, (2006) Q Rev Biophys 38:49-95; and Moure et al., (2002) Nat Struct Biol 9:764. In some examples a naturally occurring variant, and/or engineered derivative meganudease is used. Any meganudease can be used herein, including, but not limited to, l-Scel, l-Scell, l-Scelll, l-ScelV, l-SceV, l-SceVl, l-SceVII, l-Ceul, l-CeuAIIP, l-Crel, I-CrepsblP, l-CrepsbllP, l-CrepsblllP, l-CrepsblVP, l-Tlil, l-Ppol, Pl-Pspl, F-Scel, F-Scell, F-Suvl, F-Tevl, F-Tevll, l-Amal, l-Anil, l-Chul, l-Cmoel, l-Cpal, l-Cpall, I-Csml, l-Cvul, l-CvuAIP, l-Ddil, l-Ddill, l-Dirl, l-Dmol, l-Hmul, l-Hmull, l-HsNIP, l-Llal, l-Msol, l-Naal, l-Nanl, l-NcllP, l-NgrIP, l-Nitl, l-Njal, l-Nsp236IP, l-Pakl, l-PbolP, I-PculP, l-PcuAI, l-PcuVI, l-PgrIP, l-PoblP, l-Porl, l-PorllP, l-PbpIP, l-SpBetalP, I-Scal, l-SexlP, l-SnelP, l-Spoml, l-SpomCP, l-SpomlP, l-SpomllP, l-SqulP, I-Ssp68031, l-SthPhiJP, l-SthPhiST3P, l-SthPhiSTe3bP, l-TdelP, l-Tevl, l-Tevll, I-Tevlll, l-UarAP, l-UarHGPAIP, l-UarHGPA13P, l-VinIP, l-ZbilP, Pl-Mtul, PI-MtuHIP PI-MtuHIIP, Pl-Pful, Pl-Pfull, Pl-Pkol, Pl-Pkoll, PI-Rma438121P, PI-SpBetalP, Pl-Scel, Pl-Tful, Pl-Tfull, Pl-Thyl, PI-Tlil, PI-Tlill, or any active variants or fragments thereof. TAL effector nucleases can be used to make double-strand breaks at specific target sequences in the genome of a plant or other organism. TAL effector nucleases can be created by fusing a native or engineered transcription activatorlike (TAL) effector, or functional part thereof, to the catalytic domain of an endonuclease, such as, for example, Fokl. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) PNAS 10.1073/pnas.1013133107; Scholze & Boch (2010) Virulence 1:428-432; Christian et al. Genetics (2010) 186:757-761; Li et al. (2010) Nuc. Acids Res. (2010) doi:10.1093/nar/gkg704; and Miller et al. (2011) Nature Biotechnology 29:143-148; all of which are herein incorporated by reference.

In some embodiments, a TALEN system comprises a TAL effector DNA binding domain and a DNA cleavage domain, wherein said TAL effector DNA binding domain binds within said preselected endogenous target site, thereby targeting the DNA cleavage domain to cleave the DNA within said preselected endogenous target site.

A skilled artisan would appreciate that the terms "transcription activator-like effector nuclease", "TALEN", and "TAL effector nuclease" may be used interchangeably having all the same meanings and qualities, wherein a TALEN encompasses a nuclease capable of recognizing and cleaving its target site, for example a preselected endogenous target site as disclosed herein. In another embodiment, a TALEN comprises a fusion protein comprising a TALE domain and a nucleotide cleavage domain. In another embodiment, a TALE domain comprises a protein domain that binds to a nucleotide in a sequence-specific manner through one or more TALE-repeat modules. A skilled artisan would recognize that TALE-repeat modules comprise a variable number of about 34 amino acid repeats that recognize plant DNA sequences. Further, repeat modules can be rearranged according to a simple cipher to target new DNA sequences. In another embodiment, a TALE domain comprises a protein domain that binds to a preselected endogenous target site on at least one homologous chromosome. In another embodiment, a TALE domain comprises a protein domain that binds to a polymorphic allele on at least one homologous chromosome. In another embodiment, a TALE domain comprises a protein domain that binds to a preselected endogenous target site on both homologous chromosomes. In another embodiment, a TALE domain comprises a protein domain that binds to polymorphic alleles on both homologous chromosomes.

In one embodiment, a TALE domain comprises at least one of the TALE-repeat modules. In another embodiment, a TALE domain comprises from one to thirty TALE-repeat modules. In another embodiment, a TALE domain comprises more than thirty repeat modules. In another embodiment, a TALEN fusion protein comprises an N-terminal domain, one or more of TALE-repeat modules followed by a half-repeat module, a linker, and a nucleotide cleavage domain.

Chemical mutagenesis using an agent such as Ethyl Methyl Sulfonate (EMS) can be employed to obtain a population of point mutations and screen for mutants of the CSGL gene that may become silent or down-regulated. In plants, methods relaying on introgression of genes from natural populations can be used. Cultured and wild types species are crossed repetitively such that a plant comprising a given segment of the wild genome is isolated. Certain plant species, for example, maize (corn) and snapdragon, have natural transposons. These transposons are either autonomous, i.e. the transposase is located within the transposon sequence or non-autonomous, without a transposase. A skilled person can cause transposons to "jump" and create mutations. Alternatively, a nucleic acid sequence can be synthesized having random nucleotides at one or more predetermined positions to generate random amino acid substituting.

In some embodiments, the expression of an endogenous CSLG gene can be altered by the introduction of one or more point mutations into their regulatory sequences. In some embodiments, the expression of a heterologous CSLG gene can be altered by the introduction of one or more point mutations into their regulatory sequences.

A skilled artisan would appreciate that "regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. In some embodiments, regulatory sequences comprise promoters. In some embodiments, regulatory sequences comprise translation leader sequences. In some embodiments, regulatory sequences comprise introns. In some embodiments, regulatory sequences comprise polyadenylation recognition sequences. In some embodiments, regulatory sequences comprise RNA processing sites. In some embodiments, regulatory sequences comprise effector binding sites. In some embodiments, regulatory sequences comprise stem-loop structures.

A skilled artisan would appreciate that "promoter" refers to a DNA sequence capable of controlling the expression of a coding sequence or functional RNA. In some embodiments, a coding sequence is located 3' to a promoter sequence. It is understood by those skilled in the art that different promoters may direct the expression of a gene in different tissues or cell types, or at different stages of development, or in response to different environmental or physiological conditions. In some embodiments, the promoter comprises a constitutive promoter, i.e., a promoter that causes a gene to be expressed in most cell types at most times. In some embodiments, the promoter comprises a regulated promoter, i.e., a promoter that causes a gene to be expressed in response to sporadic specific stimuli. It is further recognized that in many cases the exact boundaries of regulatory sequences have not been completely defined yet.

A skilled artisan would appreciate that the term "3' non-coding sequences" or "transcription terminator" refers to DNA sequences located downstream of a coding sequence. In some embodiments, 3' non-coding sequences comprise polyadenylation recognition sequences. In some embodiments, 3' non-coding sequences comprise sequences encoding regulatory signals capable of affecting mRNA processing. In some embodiments, 3' non-coding sequences comprise sequences encoding regulatory signals capable of affecting gene expression. The polyadenylation signal is usually characterized by affecting the addition of polyadenylic acid tracts to the 3' end of the mRNA precursor. In some embodiments, mutations in the 3' non-coding sequences affect gene transcription. In some embodiments, mutations in the 3' non-coding sequences affect RNA processing. In some embodiments, mutations in the 3' non-coding sequences affect gene stability. In some embodiments, mutations in the 3' non-coding sequences affect translation of the associated coding sequence.

According to certain embodiments, expression of the gene encoding the CSLG enzyme is reduced compared to its expression in the corresponding unmodified plant, thereby the genetically modified plant comprises reduced content of at least one steroidal alkaloid, derivative thereof, metabolite thereof, or biosynthetic intermediate; reduced content of at least one steroidal saponin, derivative thereof, metabolite thereof, or biosynthetic intermediate; or reduced content of at least one triterpenoid saponin, derivative thereof, metabolite thereof, or biosynthetic intermediate, compared to the corresponding unmodified plant.

In some embodiments, derivatives of steroidal alkaloids, steroidal saponins, or triterpenoid saponins comprise glycosylated derivatives of, respectively, steroidal alkaloids, steroidal saponins, or triterpenoid saponins.

According to certain embodiments, the genetically modified plant is a transgenic plant comprising at least one cell comprising at least one silencing molecule targeted to a polynucleotide encoding a CLSG enzyme. According to certain embodiments, the transgenic plant comprises a polynucleotide encoding a CLSG enzyme, wherein expression of the polynucleotide expression is selectively silenced, repressed, or reduced. According to certain embodiments, the transgenic plant comprises a polynucleotide encoding a CSLG enzyme, wherein the polynucleotide has been selectively edited by deletion, insertion, or modification to silence, repress, or reduce expression thereof, or wherein the genetically modified plant is a progeny of the gene edited plant.

According to certain embodiments, the transgenic plant comprises at least one cell comprising at least one silencing molecule targeted to a CSLG gene.

In some embodiments, said endogenous CSLG gene is selectively silenced, repressed, or has reduced expression and said altered content comprises a reduced amount of the at least one steroidal alkaloid, a derivative thereof, a metabolite thereof, or a biosynthetic intermediate thereof; a reduced amount of the at least one steroidal saponin, a derivative thereof, a metabolite thereof, or a biosynthetic intermediate thereof: or a reduced amount of the at least one triterpenoid saponin, a derivative thereof, a metabolite thereof, or a biosynthetic intermediate thereof, compared to the corresponding unmodified plant. wherein when said endogenous CSLG gene is selectively silenced, repressed, or has reduced expression, said cell further comprises at least one silencing molecule targeted to the polynucleotide encoding said CSLG gene, wherein the silencing molecule is selected from an RNA interference molecule or an antisense molecule, or wherein the silencing molecule is a component of a viral induced gene silencing system.

According to certain embodiments, the transgenic plant comprises at least one cell comprising at least one silencing molecule targeted to the nucleic acid sequence set forth in any one of SEQ ID NOS: 30, 32, 34, 36, 38, 40, 65, 80, 93, 95, 97, 99, 101, 103, or 105.

According to certain embodiments, the transgenic plant comprises at least one cell comprising at least one silencing molecule targeted to the nucleic acid sequence set forth in SEQ ID NO: 30. According to certain embodiments, the transgenic plant comprises at least one cell comprising at least one silencing molecule targeted to the nucleic acid sequence set forth in SEQ ID NO: 32. According to certain embodiments, the transgenic plant comprises at least one cell comprising at least one silencing molecule targeted to the nucleic acid sequence set forth in SEQ ID NO: 34. According to certain embodiments, the transgenic plant comprises at least one cell comprising at least one silencing molecule targeted to the nucleic acid sequence set forth in SEQ ID NO: 36. According to certain embodiments, the transgenic plant comprises at least one cell comprising at least one silencing molecule targeted to the nucleic acid sequence set forth in SEQ ID NO: 38. According to certain embodiments, the transgenic plant comprises at least one cell comprising at least one silencing molecule targeted to the nucleic acid sequence set forth in SEQ ID NO: 40. According to certain embodiments, the transgenic plant comprises at least one cell comprising at least one silencing molecule targeted to the nucleic acid sequence set forth in SEQ ID NO: 65. According to certain embodiments, the transgenic plant comprises at least one cell comprising at least one silencing molecule targeted to the nucleic acid sequence set forth in SEQ ID NO: 80. According to certain embodiments, the transgenic plant comprises at least one cell comprising at least one silencing molecule targeted to the nucleic acid sequence set forth in SEQ ID NO: 93. According to certain embodiments, the transgenic plant comprises at least one cell comprising at least one silencing molecule targeted to the nucleic acid sequence set forth in SEQ ID NO: 95. According to certain embodiments, the transgenic plant comprises at least one cell comprising at least one silencing molecule targeted to the nucleic acid sequence set forth in SEQ ID NO: 97. According to certain embodiments, the transgenic plant comprises at least one cell comprising at least one silencing molecule targeted to the nucleic acid sequence set forth in SEQ ID NO: 99. According to certain embodiments, the transgenic plant comprises at least one cell comprising at least one silencing molecule targeted to the nucleic acid sequence set forth in SEQ ID NO: 101. According to certain embodiments, the transgenic plant comprises at least one cell comprising at least one silencing molecule targeted to the nucleic acid sequence set forth in SEQ ID NO: 103. According to certain embodiments, the transgenic plant comprises at least one cell comprising at least one silencing molecule targeted to the nucleic acid sequence set forth in SEQ ID NO: 105.

According to certain embodiments, the silencing molecule is selected from the group consisting of an RNA interference molecule and an antisense molecule, or wherein the silencing molecule is a component of a viral induced gene silencing system. According to certain embodiments, the silencing molecule comprises a polynucleotide having a nucleic acid sequence substantially complementary to a region of a CSLG gene having the nucleic acid sequence set forth in any one SEQ ID NOS: 30, 32, 34, 36, 38, 40, 65, 80, 93, 95, 97, 99, 101, 103, or 105, or a complementary sequence thereof. In some embodiments, an antisense molecule silencing, repressing, or reducing the expression of CSLG in a plant or plant cell comprises a polynucleotide having a nucleic acid sequence substantially complementary to a region of a CSLG gene having the nucleic acid sequence set forth in any one SEQ ID NOS: 30, 32, 34, 36, 38, 40, 65, 80, 93, 95, 97, 99, 101, 103, or 105, or a complementary sequence thereof. In some embodiments, an antisense molecule silencing, repressing, or reducing the expression of CSLG in a plant or plant cell has the nucleotide sequence set forth in SEQ ID NO: 108. In some embodiments, a VIGs molecule silencing, repressing, or reducing the expression of CSLG in a plant or plant cell has the nucleotide sequence set forth in SEQ ID NO: 42, SEQ ID NO: 43, SEQ ID NO: 44, SEQ ID NO: 106 or SEQ ID NO: 107. According to certain embodiments, the silencing molecule is targeted to a CSLG fragment having the nucleic acid sequence within the nucleic acid sequence set forth in any one SEQ ID NOS: 30, 32, 34, 36, 38, 40, 65, 80, 93, 95, 97, 99, 101, 103, or 105, or a complementary sequence thereof. In some embodiments, the genetically modified plant comprising said plant cell has a reduced content of a triterpenoid saponin, a metabolite thereof, a derivative thereof, or a biosynthetic intermediate thereof.

According to certain embodiments, the genetically modified or gene edited plant comprise at least one cell comprising at least one silencing molecule targeted to a CSLG gene. According to some embodiments, the at least one silencing molecule is selected from the group consisting of RNA interference molecule and antisense molecule. According to these embodiments, the genetically modified plant comprises reduced content of a steroidal alkaloid or a biosynthetic intermediate thereof, a steroidal saponin or a biosynthetic intermediate thereof, or a triterpenoid saponin or a biosynthetic intermediate thereof.

The silencing molecule target to a CSLG gene can be designed as is known to a person skilled in the art. According to certain embodiments, the silencing molecule comprises a polynucleotide having a nucleic acid sequence substantially complementary to a region of a CSLG gene, for example, but not limited to GAME15 or homologs thereof disclosed herein in tomato, wild tomato, potato, wild potato, and eggplant, or to a complementary sequence of the GAME15 gene. According to certain embodiments, the silencing molecule comprises a polynucleotide having a nucleic acid sequence substantially complementary to a region of a CSLG gene, for example, but not limited to SOAP5 or homologs thereof disclosed herein in Chinese licorice, *Arabidopsis*, red beet, *quinoa*, alfalfa, soybean, or *Lotus japonicus*, or to a complementary sequence of the SOAP5 gene.

According to certain embodiments, the silencing molecule is an antisense RNA.

According to certain exemplary embodiments, the silencing molecule is an RNA interference (RNAi) molecule. According to some embodiments, the silencing molecule is a double-stranded (ds)RNA molecule. According to certain embodiments, the first and the second polynucleotides are separated by a spacer. According to some embodiments, the spacer sequence is an intron. According to yet further embodiments, the expression of the first and the second polynucleotides is derived from one promoter. According to other embodiments, expression of the first and the second polynucleotides are derived from two promoters; the promoters can be identical or different.

In some embodiments, the term "RNA interference" or "RNAi" encompasses the silencing or decreasing of gene expression mediated by small double stranded RNAs. It is the process of sequence-specific, post-transcriptional gene silencing in animals and plants, initiated by inhibitory RNA (iRNA) that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

Typically, the term RNAi molecule refers to single- or double-stranded RNA molecules comprising both a sense and antisense sequence. For example, the RNA interference molecule can be a double-stranded polynucleotide molecule comprising self-complementary sense and antisense regions, wherein the antisense region comprises complementarity to a target nucleic acid molecule. Alternatively the RNAi molecule can be a single-stranded hairpin polynucleotide having self-complementary sense and antisense regions, wherein the antisense region comprises complementarity to a target nucleic acid molecule or it can be a circular single-stranded polynucleotide having two or more loop structures and a stem comprising self-complementary sense and antisense regions, wherein the antisense region comprises complementarity to a target nucleic acid molecule, and wherein the circular polynucleotide can be processed either in vivo or in vitro to generate an active molecule capable of mediating RNAi.

Antisense technology is the process in which an antisense RNA or DNA molecule interacts with a target sense DNA or RNA strand. A sense strand is a 5' to 3' mRNA molecule or DNA molecule. The complementary strand, or mirror strand, to the sense is called an antisense. When an antisense strand interacts with a sense mRNA strand, the double helix is recognized as foreign to the cell and will be degraded, resulting in reduced or absent protein production. Although DNA is already a double stranded molecule, antisense technology can be applied to it, building a triplex formation.

One skilled in the art would appreciate that the terms "complementary" or "complement thereof" are used herein to encompass the sequences of polynucleotides which is capable of forming Watson & Crick base pairing with another specified polynucleotide throughout the entirety of the complementary region. This term is applied to pairs of polynucleotides based solely upon their sequences and not any particular set of conditions under which the two polynucleotides would actually bind.

Antisense modulation of cell and/or tissue levels of CSLG may be effected by transforming the cell or tissue with at least one antisense compound, including antisense DNA, antisense RNA, a ribozyme, DNAzyme, a locked nucleic acid (LNA), and an aptamer. In some embodiments, the molecules are chemically modified. In other embodiments, the antisense molecule is antisense DNA or an antisense DNA analog.

RNA antisense strands can be either catalytic or non-catalytic. The catalytic antisense strands, also called ribozymes, cleave the RNA molecule at specific sequences. A non-catalytic RNA antisense strand blocks further RNA processing.

Antisense modulation of cells and/or tissue levels of the CSLG gene may be effected by transforming the organism cells or tissues with at least one antisense compound, including antisense DNA, antisense RNA, a ribozyme, DNAzyme, a locked nucleic acid (LNA), a VIGs, and an aptamer. In some embodiments the molecules are chemically modified. In other embodiments, the antisense molecule is antisense DNA or an antisense DNA analog.

RNAi refers to the introduction of homologous double stranded RNA (dsRNA) to target a specific gene product, resulting in post transcriptional silencing of that gene. This phenomenon was first reported in *Caenorhabditis elegans* by Guo and Kemphues (1995, Cell, 81(4):611-620) and subsequently Fire et al. (1998, Nature 391:806-811) discovered that it is the presence of dsRNA, formed from the annealing of sense and antisense strands present in the in vitro RNA preps, that is responsible for producing the interfering activity In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger. The short-nucleotide RNA sequences are homologous to the target gene that is being suppressed. Thus, the short-nucleotide sequences appear to serve as guide sequences to instruct a multicomponent nuclease, RISC, to destroy the specific mRNAs.

The dsRNA used to initiate RNAi, may be isolated from native source or produced by known means, e.g., transcribed from DNA. Plasmids and vectors for generating RNAi molecules against target sequence are now readily available from commercial sources.

The dsRNA can be transcribed from the vectors as two separate strands. In other embodiments, the two strands of DNA used to form the dsRNA may belong to the same or two different duplexes in which they each form with a DNA strand of at least partially complementary sequence. When the dsRNA is thus-produced, the DNA sequence to be transcribed is flanked by two promoters, one controlling the transcription of one of the strands, and the other that of the complementary strand. These two promoters may be identical or different. Alternatively, a single promoter can derive the transcription of single-stranded hairpin polynucleotide having self-complementary sense and antisense regions that anneal to produce the dsRNA.

Inhibition is sequence-specific in that nucleotide sequences corresponding to the duplex region of the RNA are targeted for genetic inhibition. RNA molecules containing a nucleotide sequence identical to a portion of the target gene are preferred for inhibition. RNA sequences with insertions, deletions, and single point mutations relative to the target sequence have also been found to be effective for inhibition. Thus, sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript. The length of the identical nucleotide sequences may be at least 25, 50, 100, 200, 300 or 400 bases. There is no upper limit on the length of the dsRNA that can be used. For example, the dsRNA can range from about 21 base pairs (bp) of the gene to the full length of the gene or more.

The term "RNA interference" or "RNAi" refers to the silencing or decreasing of gene expression mediated by small double stranded RNAs. It is the process of sequence-specific, post-transcriptional gene silencing in animals and plants, initiated by inhibitory RNA (iRNA) that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

One of ordinary skill in the art would appreciate that the term RNAi molecule refers to single- or double-stranded RNA molecules comprising both a sense and antisense sequence. For example, the RNA interference molecule can be a double-stranded polynucleotide molecule comprising self-complementary sense and antisense regions, wherein the antisense region comprises complementarity to a target nucleic acid molecule. Alternatively the RNAi molecule can be a single-stranded hairpin polynucleotide having self-complementary sense and antisense regions, wherein the antisense region comprises complementarity to a target nucleic acid molecule or it can be a circular single-stranded polynucleotide having two or more loop structures and a stem comprising self-complementary sense and antisense regions, wherein the antisense region comprises complementarity to a target nucleic acid molecule, and wherein the circular polynucleotide can be processed either in vivo or in vitro to generate an active molecule capable of mediating RNAi.

In some embodiments, the use of RNA interference (RNAi) to down regulate the expression of a CSLG gene is to attenuate the level in plants or a cell thereof or part thereof. In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger. The short-nucleotide RNA sequences are homologous to the target gene that is being suppressed. Thus, the short-nucleotide sequences appear to serve as guide sequences to instruct a multicomponent nuclease, RISC, to destroy the specific mRNAs.

The dsRNA used to initiate RNAi, may be isolated from native source or produced by known means, e.g., transcribed from DNA. Plasmids and vectors for generating RNAi molecules against target sequence are now readily available as exemplified herein below.

According to certain exemplary embodiments, the dsRNA is targeted to CSLG.

In some embodiments, the use of RNA interference (RNAi) to down regulate the expression of a CSLG gene is to attenuate the level of in plants or a cell thereof or part thereof. In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger. The short-nucleotide RNA sequences are homologous to the target gene that is being suppressed. Thus, the short-nucleotide sequences appear to serve as guide sequences to instruct a multicomponent nuclease, RISC, to destroy the specific mRNAs.

The dsRNA used to initiate RNAi, may be isolated from native source or produced by known means, e.g., transcribed from DNA. Plasmids and vectors for generating RNAi molecules against target sequence are now readily available as exemplified herein below.

The dsRNA can be transcribed from the vectors as two separate strands. In other embodiments, the two strands of DNA used to form the dsRNA may belong to the same or two different duplexes in which they each form with a DNA strand of at least partially complementary sequence. When the dsRNA is thus-produced, the DNA sequence to be transcribed is flanked by two promoters, one controlling the transcription of one of the strands, and the other that of the complementary strand. These two promoters may be identical or different. Alternatively, a single promoter can derive the transcription of single-stranded hairpin polynucleotide having self-complementary sense and antisense regions that anneal to produce the dsRNA.

Inhibition is sequence-specific in that nucleotide sequences corresponding to the duplex region of the RNA are targeted for genetic inhibition. RNA molecules containing a nucleotide sequence identical to a portion of the target gene are preferred for inhibition. RNA sequences with insertions, deletions, and single point mutations relative to the target sequence have also been found to be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript. The length of the identical nucleotide sequences may be at least 25, 50, 100, 200, 300 or 400 bases. There is no upper limit on the length of the dsRNA that can be used. For example, the dsRNA can range from about 21 base pairs (bp) of the gene to the full length of the gene or more.

Another agent capable of down-regulating the expression of CSLG is a Co-Suppression molecule. Co-suppression is a post-transcriptional mechanism where both the transgene and the endogenous gene are silenced.

Another agent capable of down-regulating the expression of CSLG is a DNAzyme molecule, which is capable of specifically cleaving an mRNA transcript or a DNA sequence of the CSLG. DNAzymes are single-stranded polynucleotides that are capable of cleaving both single- and double-stranded target sequences. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (for review of DNAzymes, see: Khachigian, L. M. (2002) Curr Opin Mol Ther 4, 119-121).

Examples of construction and amplification of synthetic, engineered DNAzymes recognizing single- and double-stranded target cleavage sites are disclosed in U.S. Pat. No. 6,326,174.

The terms "enzymatic nucleic acid molecule" or "enzymatic oligonucleotide" refers to a nucleic acid molecule which has complementarity in a substrate binding region to a specified gene target, and also has an enzymatic activity which is active to specifically cleave target RNA of CSLG, thereby silencing the gene. The complementary regions allow sufficient hybridization of the enzymatic nucleic acid molecule to the target RNA and subsequent cleavage. The term enzymatic nucleic acid is used interchangeably with for example, ribozymes, catalytic RNA, enzymatic RNA, catalytic DNA, aptazyme or aptamer-binding ribozyme, catalytic oligonucleotide, nucleozyme, DNAzyme, RNAenzyme. The specific enzymatic nucleic acid molecules described in the instant application are not limiting and an enzymatic nucleic acid molecule of disclosed herein requires a specific substrate binding site which is complementary to one or more of the target nucleic acid regions, and that it have nucleotide sequences within or surrounding that substrate binding site which impart a nucleic acid cleaving and/or ligation activity to the molecule. U.S. Pat. No. 4,987,071 discloses examples of such molecules.

According to certain embodiments, the CSLG gene or a silencing molecule targeted thereto form part of an expression vector comprising all necessary elements for expression of the gene or its silencing molecule. According to certain embodiments, the expression is controlled by a constitutive promoter. According to certain embodiments, the constitutive promoter is specific to a plant tissue. According to these embodiments, the tissue specific promoter is selected from the group consisting of root, tuber, leaves and fruit specific promoter. Root specific promoters are described, e.g. in Martinez, E. et al. 2003. Curr. Biol. 13:1435-1441. Fruit specific promoters are described among others in Estornell L. H et al. 2009. Plant Biotechnol. J. 7:298-309 and Fernandez A. I. Et al. 2009 Plant Physiol. 151:1729-1740. Tuber specific promoters are described, e.g. in Rocha-Sosa M, et al., 1989. EMBO J. 8:23-29; McKibbin R. S. et al., 2006. Plant Biotechnol J. 4(4):409-18. Leaf specific promoters are described, e.g. in Yutao Yang, Guodong Yang, Shijuan Liu, Xingqi Guo and Chengchao Zheng. Science in China Series C: Life Sciences. 46: 651-660.

According to certain embodiments, the expression vector further comprises regulatory elements at the 3' non-coding sequence. As used herein, the "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht I L et al. (1989. Plant Cell 1:671-680).

Those skilled in the art will appreciate that the various components of the nucleic acid sequences and the transformation vectors described herein, are operatively linked, so as to result in expression of said nucleic acid or nucleic acid fragment. Techniques for operatively linking the components of the constructs and vectors disclosed herein are well known to those skilled in the art. Such techniques include the use of linkers, such as synthetic linkers, for example including one or more restriction enzyme sites.

Detection of a mutated CSLG gene and/or the presence of silencing molecule targeted to the gene and/or over-expression of the genes is performed employing standard methods of molecular genetics, known to a person of ordinary skill in the art.

For measuring the gene(s) or silencing molecule(s) expression, cDNA or mRNA should be obtained from an organ in which the nucleic acid is expressed. The sample may be further processed before the detecting step. For example, the polynucleotides in the cell or tissue sample may be separated from other components of the sample, may be amplified, etc. All samples obtained from an organism, including those subjected to any sort of further processing are considered to be obtained from the organism.

Detection of the gene(s) or the silencing molecule(s) typically requires amplification of the polynucleotides taken from the candidate altered organism. Methods for DNA amplification are known to a person skilled in the art. Most commonly used method for DNA amplification is PCR (polymerase chain reaction; see, for example, PCR Basics: from background to Bench, Springer Verlag, 2000; Eckert et al., 1991. PCR Methods and Applications 1:17). Additional suitable amplification methods include the ligase chain reaction (LCR), transcription amplification and self-sustained sequence replication, and nucleic acid-based sequence amplification (NASBA).

According to certain embodiments, the nucleic acid sequence comprising the CSLG gene or its silencing molecule further comprises a nucleic acid sequence encoding a selectable marker. According to certain embodiments, the selectable marker confers resistance to antibiotic or to an herbicide; in these embodiments the transgenic plants are selected according to their resistance to the antibiotic or herbicide.

In some embodiments, said endogenous CSLG gene is selectively overexpressed and said altered content comprises an increased amount of the at least one triterpenoid saponin, a derivative thereof, a metabolite thereof, or a biosynthetic intermediate thereof compared to the corresponding unmodified plant.

Overexpression of the CSLG gene can be obtained by any method as is known to a person skilled in the art. According to certain embodiments, disclosed herein are genetically modified plants or parts thereof comprising at least one cell comprising at least one transcribable polynucleotide that is over expressed and encodes at least a CSLG enzyme, wherein the genetically modified plant or plant part comprises elevated content of at least one triterpenoid saponin, a derivative thereof, a metabolite thereof, or a biosynthetic intermediate thereof, compared to a corresponding non-genetically modified plant.

According to some embodiments, the polynucleotides disclosed herein are incorporated in a DNA construct enabling their expression in the plant cell. DNA constructs suitable for use in plants are known to a person skilled in the art. According to one embodiment, the DNA construct comprises at least one expression regulating element selected from the group consisting of a promoter, an enhancer, an origin of replication, a transcription termination sequence, a polyadenylation signal and the like.

The DNA constructs disclosed herein are designed according to the results to be achieved.

In crop plants, reduction of toxic steroidal alkaloids or steroidal glycoalkaloids or their derivatives, metabolites, or biosynthetic intermediates thereof is desired in the edible parts of the plant, including for example, but not limited to fruits, seeds, roots, leaves, and tubers. On the other hand, enriching the content of toxic steroidal glycoalkaloids or biosynthetic intermediates in non-edible parts of the plant, including for example, but not limited to non-edible roots and leaves contributes to the resistance of the plant against a broad range of pathogens. In exemplary embodiments, plants overexpressing the steroidal glycoalkaloids can be used for producing them in the pharmaceutical industry.

In crop plants, modulation of steroidal saponins is also desired. A skilled artisan would appreciate that modulation of steroidal saponins may in certain embodiments, produce high-value products from a certain compound, for example but not limited to for food, cosmetics and pharma industries. In some embodiments, modulation of steroidal saponins produces compounds in plants that will help in protection of plants against pathogens, for example but not limited to protection against bacetria, insect, virus, and insects. In some embodiments, modulation of steroidal saponins removes anti-nutritional compounds from plants.

In crop plants, reduction of toxic or bitter or hormone mimicking triterpenoid saponins or biosynthetic intermediates is desired in the edible parts of the plant, including, for example but not limited to, fruit and seeds. On the other hand, enriching the content of sweet tasting triterpenoid saponins or biosynthetic intermediates thereof is beneficial and could be used for producing natural sweeteners. Plants having increase content of triterpenoid saponins such as QS-21 can be used for producing adjuvants for the pharmaceutical industry.

According to yet additional embodiments, disclosed herein is a genetically modified or gene edited plant having enhanced expression of at least a CSLG gene, wherein the genetically modified or gene edited plant has an increased amount of at least one steroidal alkaloid, of at least one steroidal saponin, or of at least one triterpenoid saponin, compared to a corresponding unmodified or unedited plant. According to yet additional embodiments, disclosed herein is a genetically modified or gene edited plant having decreased expression of at least a CSLG gene, wherein the genetically modified or gene edited plant has a decreased amount of at least one steroidal alkaloid, a decreased amount of at least one steroidal saponin, a decreased amount of at least one triterpenoid saponin, compared to a corresponding unmodified or unedited plant.

The disclosure herein, and in the Examples below, show that by providing at least one heterologous gene encoding an enzyme or other protein involved in the biosynthetic pathway of a steroidal alkaloid, a steroidal saponin, and/or a triterpenoid saponin, for example but not limited to a heterologous CSLG, or by modifying an endogenous gene of the triterpenoid synthetic pathway, for example but not limited to a CSLG gene wherein said modification alters the expression thereof, or the activity or stability of the encoded enzyme, the level of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof can be altered.

In some embodiments, derivatives of steroidal alkaloids, steroidal saponins, or triterpenoid saponins comprise glycosylated derivatives of, respectively, steroidal alkaloids, steroidal saponins, or triterpenoid saponins.

In some embodiments the amount of the at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof is altered in a plant cell. In some embodiments the amount of the at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof is altered in an algal cell. In some embodiments the amount of the at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof is altered in a yeast. In some embodiments the amount of the at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof is altered in an insect cell. In some embodiments the amount of the at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof is altered in a bacterium. In some embodiments the amount of the at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof is altered in a plant. In some embodiments the amount of the at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof is altered in a plant part.

In some embodiments, derivatives of steroidal alkaloids, steroidal saponins, or triterpenoid saponins comprise glycosylated derivatives of, respectively, steroidal alkaloids, steroidal saponins, or triterpenoid saponins.

For example, in some embodiments, as exemplified below in the Examples, a genetically modified cell, for example a yeast cell or a plant cell or an algal cell or an insect cell or a bacterium, or a genetically modified plant or part thereof having increased expression of a saponin beta-amyrin synthase, a cytochrome P450, a glycosyltransferase, an acyltransferase, a glucuronosyltransferase, or a CSLG, or a combination thereof, has been shown to have an increased level of a triterpenoid saponin, a derivative thereof, a metabolite thereof, or a biosynthetic intermediate thereof. In other embodiments, as shown in the Examples, reducing or silencing expression of a saponin beta-amyrin synthase, cytochrome P450, glycosyltransferase, acyltransferase, glucuronosyltransferase, or CSLG gene has been shown to result in a reduced level of the corresponding triterpenoid saponin, derivative thereof, metabolite thereof, or biosynthetic intermediate thereof.

Steroidal Alkaloids, Derivatives Thereof, Metabolites Thereof, and Biosynthetic Intermediates Thereof In some embodiments, a genetically modified cell disclosed herein comprises an increased content of at least one steroidal alkaloid, a derivative thereof, a metabolite thereof, or a biosynthetic intermediate thereof, of any combination thereof. In some embodiments, a genetically modified plant comprising at least one genetically modified cell disclosed herein comprises an increased content of at least one steroidal alkaloid, a derivative thereof, a metabolite thereof, or a biosynthetic intermediate thereof, of any combination thereof. In some embodiments, an in vitro biosynthetic system produces at least one steroidal alkaloid, a derivative thereof, a metabolite thereof, or a biosynthetic intermediate thereof, of any combination thereof. In some embodiments, a genetically modified plant disclosed herein comprises an increased content of at least one steroidal alkaloid, a derivative thereof, a metabolite thereof, or a biosynthetic intermediate thereof, of any combination thereof. In some embodiments, a genetically modified plant comprising at least one genetically modified cell as disclosed herein, comprises a decreased content of at least one steroidal alkaloid, a derivative thereof, a metabolite thereof, or a biosynthetic intermediate thereof, of any combination thereof. In some embodiments, a genetically modified plant disclosed herein comprising at least one genetically modified cells comprises an increased content of at least one steroidal alkaloid, a derivative thereof, a metabolite thereof, or a biosynthetic intermediate thereof, of any combination thereof, and a decreased content of at least one steroidal alkaloid, a derivative thereof, a metabolite thereof, or a biosynthetic intermediate thereof, of any combination thereof.

In some embodiments, a method of producing a steroidal alkaloid in a genetically modified cell disclosed herein comprises producing an at least one steroidal alkaloid, a derivative thereof, a metabolite thereof, or a biosynthetic intermediate thereof, of any combination thereof. In some embodiments, a method of producing a steroidal alkaloid in a genetically modified plant or plant part comprises producing of at least one steroidal alkaloid, a derivative thereof, a metabolite thereof, or a biosynthetic intermediate thereof, of any combination thereof. In some embodiments, disclosed herein is a method of reducing the content of at least one steroidal alkaloid, a derivative thereof, a metabolite thereof, or a biosynthetic intermediate thereof, of any combination thereof in a plant or plant part comprising an at least one genetically modified cell as described herein. In some embodiments, disclosed herein is a method of increasing the content of at least one steroidal alkaloid, a derivative thereof, a metabolite thereof, or a biosynthetic intermediate thereof, of any combination thereof in a plant or plant part comprising an at least one genetically modified cell as described herein.

In the steroidal alkaloid biosynthetic pathway, steroidal alkaloids branch off from steroidal saponins after the formation of furostanol-type saponin aglycone (FIG. 1). Further steps involving, at least in part, oxidation, transamination, ring formation, etc., result in biosynthesis of steroidal alkaloids (FIG. 1).

Examples of steroidal glycoalkaloids include, but are not limited to, alpha-tomatine, tomatine, dehydrotomatine, alpha-chaonine, alpha-solanine, alpha-solasonine, alpha-solmargine, or any combination thereof.

In some embodiments, the genetically modified cell comprising said increased content comprises a plant cell, a yeast cell, an algal cell, an insect cell, or a bacterial. In some embodiments, the genetically modified cell comprising said increased content comprises a plant cell. In some embodiments, the genetically modified cell comprising said increased content comprises a yeast cell. In some embodiments, the genetically modified cell comprising said increased content comprises an algal cell. In some embodiments, the genetically modified cell comprising said increased content comprises an insect cell. In some embodiments, the genetically modified cell comprising said increased content comprises a bacterium.

According to certain exemplary embodiments, the downstream steroidal glycoalkaloid is selected from the group consisting of esculeosides or dehydroesculeosides.

In some embodiments, a genetically modified plant disclosed herein comprises an increased content of at least one steroidal alkaloid selected from any one of alpha-tomatine, tomatine, dehydrotomatine, alpha-chaconine, alpha-solanine, alpha-solasonine, alpha-solmargine, or any combination thereof. In some embodiments, a genetically modified plant disclosed herein comprises an increased content of alpha-tomatine. In some embodiments, a genetically modified plant disclosed herein comprises an increased content of tomatine. In some embodiments, a genetically modified plant disclosed herein comprises an increased content of dehydrotomatine. In some embodiments, a genetically modified plant disclosed herein comprises an increased content of alpha-chaconine. In some embodiments, a genetically modified plant disclosed herein comprises an increased content of alpha-solanine. In some embodiments, a genetically modified plant disclosed herein comprises an increased content of alpha-solasonine. In some embodiments, a genetically modified plant disclosed herein comprises an increased content of alpha-solmargine.

In some embodiments, a genetically modified plant disclosed herein comprises a decreased content of at least one steroidal alkaloid selected from any one of selected from any one of alpha-tomatine, tomatine, dehydrotomatine, alpha-chaconine, alpha-solanine, alpha-solasonine, alpha-solmargine, or any combination thereof. In some embodiments, a genetically modified plant disclosed herein comprises an increased content of alpha-tomatine. In some embodiments, a genetically modified plant disclosed herein comprises an increased content of tomatine. In some embodiments, a genetically modified plant disclosed herein comprises an increased content of dehydrotomatine. In some embodiments, a genetically modified plant disclosed herein comprises an increased content of alpha-chaconine. In some embodiments, a genetically modified plant disclosed herein comprises an increased content of alpha-solanine. In some embodiments, a genetically modified plant disclosed herein comprises an increased content of alpha-solasonine. In some embodiments, a genetically modified plant disclosed herein comprises an increased content of alpha-solmargine.

In some embodiments, a genetically modified plant disclosed herein comprises an increased content of at least one steroidal and a decreased content of at least one steroidal alkaloid selected from any one of alpha-tomatine, tomatine, dehydrotomatine, alpha-chaconine, alpha-solanine, alpha-solasonine, alpha-solmargine, or any combination thereof.

In some embodiments, a method of producing a steroidal alkaloid in a genetically modified cell comprises producing at least one steroidal alkaloid selected from any one of alpha-tomatine, tomatine, dehydrotomatine, alpha-chaconine, alpha-solanine, alpha-solasonine, alpha-solmargine, or any combination thereof. In some embodiments, a method of producing a steroidal alkaloid in a genetically modified cell comprises producing alpha-tomatine. In some embodiments, a method of producing a steroidal alkaloid in a genetically modified cell comprises producing tomatine. In some embodiments, a method of producing a steroidal alkaloid in a genetically modified cell comprises producing dehydrotomatine. In some embodiments, a method of producing a steroidal alkaloid in a genetically modified cell comprises producing alpha-chaconine. In some embodiments, a method of producing a steroidal alkaloid in a genetically modified cell comprises producing alpha-solanine. In some embodiments, a method of producing a steroidal alkaloid in a genetically modified cell comprises producing alpha-solasonine. In some embodiments, a method of producing a steroidal alkaloid in a genetically modified cell comprises producing alpha-solmargine.

In some embodiments, the method of producing at least one steroidal alkaloid in a genetically modified cell comprises producing at least one steroidal alkaloid in a plant cell, a yeast cell, an algal cell, an insect cell, or a bacterium. In some embodiments, the method of producing at least one steroidal alkaloid in a genetically modified cell comprises producing at least one steroidal alkaloid in a plant cell. In some embodiments, the method of producing at least one steroidal alkaloid in a genetically modified cell comprises producing at least one steroidal alkaloid in a yeast cell. In some embodiments, the method of producing at least one steroidal alkaloid in a genetically modified cell comprises producing at least one steroidal alkaloid in an algal cell. In some embodiments, the method of producing at least one steroidal alkaloid in a genetically modified cell comprises producing at least one steroidal alkaloid in an insect cell. In some embodiments, the method of producing at least one steroidal alkaloid in a genetically modified cell comprises producing at least one steroidal alkaloid in a bacterium. In some embodiments, the plant cell is comprised in a plant or plant part.

In some embodiments, a method of producing a steroidal alkaloid in a genetically modified plant comprises producing at least one steroidal alkaloid selected from any one of alpha-tomatine, tomatine, dehydrotomatine, alpha-chaconine, alpha-solanine, alpha-solasonine, alpha-solmargine, or any combination thereof. In some embodiments, a method of producing a steroidal alkaloid in a genetically modified plant comprises producing alpha-tomatine. In some embodiments, a method of producing a steroidal alkaloid in a genetically modified plant comprises producing tomatine. In some embodiments, a method of producing a steroidal alkaloid in a genetically modified plant comprises producing dehydrotomatine. In some embodiments, a method of producing a steroidal alkaloid in a genetically modified plant comprises producing alpha-chaconine. In some embodiments, a method of producing a steroidal alkaloid in a genetically modified plant comprises producing alpha-solanine. In some embodiments, a method of producing a steroidal alkaloid in a genetically modified plant comprises producing alpha-solasonine. In some embodiments, a method of producing a steroidal alkaloid in a genetically modified plant comprises producing alpha-solmargine. In some embodiments, a method of producing a steroidal alkaloid in a genetically modified plant comprises producing cholesterol. In some embodiments, a method of producing a steroidal alkaloid in a genetically modified plant comprises producing 22-hydroxycholesterol. In some embodiments, a method of producing a steroidal alkaloid in a genetically modified plant comprises producing 22, 26-dihydroxycholesterol. In some embodiments, a method of producing a steroidal alkaloid in a genetically modified plant comprises producing furostanol-type saponin aglycone. In some embodiments, a method of producing a steroidal alkaloid in a genetically modified plant comprises producing furostanol-26-aldehyde. In some embodiments, a method of producing a steroidal alkaloid in a genetically modified plant comprises producing 26-amino-furostanol. In some embodiments, a method of producing a steroidal alkaloid in a genetically modified plant comprises producing tomatidenol. In some embodiments, a method of producing a steroidal alkaloid in a genetically modified plant comprises producing tomatidine. In some embodiments, a method of producing a steroidal alkaloid in a genetically modified plant comprises producing tomatidine galactoside. In some embodiments, a method of producing a steroidal alkaloid in a genetically modified plant comprises producing gamma-tomatine. In some embodiments, a method of producing a steroidal alkaloid in a genetically modified plant comprises producing beta-1-tomatine.

In some embodiments, a method of producing a steroidal alkaloid in an in vitro translation system comprises producing at least one steroidal alkaloid selected from any one of alpha-tomatine, dehydrotomatine, tomatine, alpha-chaconine, alpha-solanine, alpha-solasonine, alpha-solmargine, or any combination thereof. In some embodiments, a method of producing a steroidal alkaloid in an in vitro translation system comprises producing alpha-tomatine. In some embodiments, a method of producing a steroidal alkaloid in an in vitro translation system comprises producing tomatine. In some embodiments, a method of producing a steroidal alkaloid in an in vitro translation system comprises producing alpha-chaconine. In some embodiments, a method of producing a steroidal alkaloid in an in vitro translation system comprises producing alpha-solanine. In some embodiments, a method of producing a steroidal alkaloid in an in vitro translation system comprises producing alpha-solasonine. In some embodiments, a method of producing a steroidal alkaloid in an in vitro translation system comprises producing alpha-solmargine.

In some embodiments, a method of reducing at least one steroidal alkaloid comprises reducing at least one steroidal alkaloid selected from any one of alpha-tomatine, dehydrotomatine, tomatine, alpha-chaconine, alpha-solanine, alpha-solasonine, alpha-solmargine, or any combination thereof. In some embodiments, a method of reducing the content of at least one steroidal alkaloid comprising alpha-tomatine. In some embodiments, a method of reducing at least one steroidal alkaloid comprises reducing tomatine. In some embodiments, a method of reducing at least one steroidal alkaloid comprises reducing dehydrotomatine. In some embodiments, a method of reducing at least one steroidal alkaloid comprises reducing alpha-chaconine. In some embodiments, a method of reducing at least one steroidal alkaloid comprises reducing alpha-solanine. In some embodiments, a method of reducing at least one steroidal alkaloid comprises reducing alpha-solasonine. In some embodiments, a method of reducing at least one steroidal alkaloid comprises reducing alpha-solmargine.

In some embodiments, a method of increasing at least one steroidal alkaloid comprises increasing at least one steroidal alkaloid selected from any one of alpha-tomatine, dehydrotomatine, tomatine, alpha-chaconine, alpha-solanine, alpha-solasonine, alpha-solmargine, or any combination thereof. In some embodiments, a method of increasing the content of at least one steroidal alkaloid comprising medicagenic acid alpha-tomatine. In some embodiments, a method of increasing at least one steroidal alkaloid comprises increasing tomatine. In some embodiments, a method of increasing at least one steroidal alkaloid comprises increasing alpha-chaconine. In some embodiments, a method of increasing at least one steroidal alkaloid comprises increasing alpha-solanine. In some embodiments, a method of increasing at least one steroidal alkaloid comprises increasing alpha-solasonine. In some embodiments, a method of increasing at least one steroidal alkaloid comprises increasing alpha-solmargine.

In some embodiments, the content of both at least one steroidal alkaloid and at least one steroidal alkaloid biosynthetic intermediate are altered. In some embodiments, an at least one steroidal alkaloid and an at least one steroidal alkaloid biosynthetic intermediate are increased. In some embodiments, an at least one steroidal alkaloids and an at least one steroidal alkaloid biosynthetic intermediate are decreased. In some embodiments, an at least one steroidal alkaloid is increased and an at least one steroidal alkaloid biosynthetic intermediate is decreased. In some embodiments, an at least one steroidal alkaloid is decreased and an at least one steroidal alkaloid biosynthetic intermediate is increased. In some embodiments, the content of a steroidal alkaloid is altered without measurably altering the content of a steroidal alkaloid intermediate. In some embodiments, the content of a steroidal alkaloid intermediate is altered without measurably altering the content of a steroidal alkaloid.

The term "intermediate" may be used interchangeably in some embodiments with the term "biosynthetic intermediate", having all the same qualities and meanings.

In some embodiments, a biosynthetic intermediate of a steroidal alkaloid comprises cholesterol, 22-hydroxycholesterol, 22,26-dihydroxycholesterol, furostanol-type saponin aglycone, furostanol-26-aldehyde, 26-amino-furostanol, tomatidenol, tomatidine, tomatidine galactoside, gamma-tomatine, beta-1-tomatine, or any combination thereof (FIG. 1).

In some embodiments, a genetically modified cell disclosed herein comprises an increased content of at least one biosynthetic intermediate of a steroidal alkaloid comprising cholesterol, 22-hydroxycholesterol, 22,26-dihydroxycholesterol, furostanol-type saponin aglycone, furostanol-26-aldehyde, 26-amino-furostanol, tomatidenol, tomatidine, tomatidine galactoside, gamma-tomatine, beta-1-tomatine, or any combination thereof. In some embodiments, a genetically modified cell comprises an increased content of at least one biosynthetic intermediate of a steroidal alkaloid comprising cholesterol. In some embodiments, a genetically modified cell comprises an increased content of at least one biosynthetic intermediate of a steroidal alkaloid comprising 22-hydroxycholesterol. In some embodiments, a genetically modified cell comprises an increased content of at least one biosynthetic intermediate of a steroidal alkaloid comprising 22,26-dihydroxycholesterol. In some embodiments, a genetically modified cell comprises an increased content of at least one biosynthetic intermediate of a steroidal alkaloid comprising furostanol-type saponin aglycone. In some embodiments, a genetically modified cell comprises an increased content of at least one biosynthetic intermediate of a steroidal alkaloid comprising furostonal-26-aldehyde. In some embodiments, a genetically modified cell comprises an increased content of at least one biosynthetic intermediate of a steroidal alkaloid comprising 26-amino-furostanol. In some embodiments, a genetically modified cell comprises an increased content of at least one biosynthetic intermediate of a steroidal alkaloid comprising tomatidenol. In some embodiments, a genetically modified cell comprises an increased content of at least one biosynthetic intermediate of a steroidal alkaloid comprising tomatidine. In some embodiments, a genetically modified cell comprises an increased content of at least one biosynthetic intermediate of a steroidal alkaloid comprising tomatidine galactoside. In some embodiments, a genetically modified cell comprises an increased content of at least one biosynthetic intermediate of a steroidal alkaloid comprising gamma-tomatine. In some embodiments, a genetically modified cell comprises an increased content of at least one biosynthetic intermediate of a steroidal alkaloid comprising beta-1-tomatine.

In some embodiments, a genetically modified plant disclosed herein comprises a decreased content of at least one biosynthetic intermediate of a steroidal alkaloid comprising cholesterol, 22-hydroxycholesterol, 22,26-dihydroxycholesterol, furostanol-type saponin aglycone, furostanol-26-aldehyde, 26-amino-furostanol, tomatidenol, tomatidine, tomatidine galactoside, gamma-tomatine, beta-1-tomatine, or any combination thereof. In some embodiments, a genetically modified plant comprises a decreased content of at least one biosynthetic intermediate of a steroidal alkaloid comprising cholesterol. In some embodiments, a genetically modified plant comprises a decreased content of at least one biosynthetic intermediate of a steroidal alkaloid comprising 22-hydroxysholesterol. In some embodiments, a genetically modified plant comprises a decreased content of at least one biosynthetic intermediate of a steroidal alkaloid comprising 22,26-dihydroxycholesterol. In some embodiments, a genetically modified plant comprises a decreased content of at least one biosynthetic intermediate of a steroidal alkaloid comprising furostanol-type saponin aglycone. In some embodiments, a genetically modified plant comprises a decreased content of at least one biosynthetic intermediate of a steroidal alkaloid comprising furostanol-26-aldehyde. In some embodiments, a genetically modified plant comprises a decreased content of at least one biosynthetic intermediate of a steroidal alkaloid comprising 26-amino-furstanol. In some embodiments, a genetically modified plant comprises a decreased content of at least one biosynthetic intermediate of a steroidal alkaloid comprising tomatidenol. In some embodiments, a genetically modified plant comprises a decreased content of at least one biosynthetic intermediate of a steroidal alkaloid comprising tomatidine. In some embodiments, a genetically modified plant comprises a decreased content of at least one biosynthetic intermediate of a steroidal alkaloid comprising tomatidine galactoside. In some embodiments, a genetically modified plant comprises a decreased content of at least one biosynthetic intermediate of a steroidal alkaloid comprising gamma-tomatine. In some embodiments, a genetically modified plant comprises a decreased content of at least one biosynthetic intermediate of a steroidal alkaloid comprising beta-1-tomatine.

In some embodiments, a genetically modified plant disclosed herein comprises an increased content of at least one steroidal alkaloid biosynthetic intermediate and a decreased content of at least one steroidal alkaloid biosynthetic intermediate, said intermediate selected from any one of cholesterol, 22-hydroxycholesterol, 22,26-dihydroxycholesterol, furostanol-type saponin aglycone, furostanol-26-aldehyde, 26-amino-furostanol, tomatidenol, tomatidine, tomatidine galactoside, gamma-tomatine, beta-1-tomatine, or any combination thereof.

In some embodiments, a method of reducing at least one steroidal alkaloid comprises reducing at least one steroidal alkaloid biosynthetic intermediate selected from any one of cholesterol, 22-hydroxycholesterol, 22,26-dihydroxycholesterol, furostanol-type saponin aglycone, furostanol-26-aldehyde, 26-amino-furostanol, tomatidenol, tomatidine, tomatidine galactoside, gamma-tomatine, beta-1-tomatine, or any combination thereof. In some embodiments, a method of reducing at least one steroidal alkaloid comprises reducing at least cholesterol. In some embodiments, a method of reducing at least one steroidal alkaloid comprises reducing at least 22-hydroxycholesterol. In some embodiments, a method of reducing at least one steroidal alkaloid comprises reducing at least 22,26-dihydroxycholesterol. In some embodiments, a method of reducing at least one steroidal alkaloid comprises reducing at least furostanol-type saponin aglycone. In some embodiments, a method of reducing at least one steroidal alkaloid comprises reducing at least furostonal-26-aldehyde. In some embodiments, a method of reducing at least one steroidal alkaloid comprises reducing at least 26-amino-furostanol. In some embodiments, a method of reducing at least one steroidal alkaloid comprises reducing at least tomatidenol. In some embodiments, a method of reducing at least one steroidal alkaloid comprises reducing at tomatidine. In some embodiments, a method of reducing at least one steroidal alkaloid comprises reducing at least tomatidine galactoside. In some embodiments, a method of reducing at least one steroidal alkaloid comprises reducing at least gamma-tomatine. In some embodiments, a method of reducing at least one steroidal alkaloid comprises reducing at least beta-1-tomaine.

In some embodiments, a method of increasing at least one steroidal alkaloid comprises increasing at least one steroidal alkaloid biosynthetic intermediate selected from any one of cholesterol, 22-hydroxycholesterol, 22,26-dihydroxycholesterol, furostanol-type saponin aglycone, furostanol-26-aldehyde, 26-amino-furostanol, tomatidenol, tomatidine, tomatidine galactoside, gamma-tomatine, beta-1-tomatine, or any combination thereof. In some embodiments, a method of increasing at least one steroidal alkaloid comprises increasing at least cholesterol. In some embodiments, a method of increasing at least one steroidal alkaloid comprises increasing at least 22-hydroxycholesterol. In some embodiments, a method of increasing at least one steroidal alkaloid comprises increasing at least 22,26-dihydroxycholesterol. In some embodiments, a method of increasing at least one steroidal alkaloid comprises increasing at least furostanol-type saponin aglycone. In some embodiments, a method of increasing at least one steroidal alkaloid comprises increasing at least furostanol-26-aldehyde. In some embodiments, a method of increasing at least one steroidal alkaloid comprises increasing at least 26-amino-furostanol. In some embodiments, a method of increasing at least one steroidal alkaloid comprises increasing at least tomatidenol. In some embodiments, a method of increasing at least one steroidal alkaloid comprises increasing at least tomatidine. In some embodiments, a method of increasing at least one steroidal alkaloid comprises increasing at least tomatidine galactoside. In some embodiments, a method of increasing at least one steroidal alkaloid comprises increasing at least gamma-tomatine. In some embodiments, a method of increasing at least one steroidal alkaloid comprises increasing at least beta-1-tomatine.

In some embodiments, steroidal alkaloids biosynthetic intermediate comprises any cholesterol, 22-hydroxycholesterol, 22,26-dihydroxycholesterol, furostanol-type saponin aglycone, furostanol-26-aldehyde, 26-amino-furostanol, tomatidenol, tomatidine, tomatidine galactoside, gamma-tomatine, beta-1-tomatine, or a combination thereof.

Unexpectedly, the present disclosure now shows that levels of steroidal alkaloids or their derivatives, metabolites, or biosynthetic intermediates can be increased in cells, for example plant cells or yeast cells or algal cells, or insect cells, or bacterium, or plants by genetically modifying the cell or plant to express at least one heterologous gene encoding an enzyme, for example an enzyme or enzymes of the steroidal alkaloid biosynthetic pathway. In other embodiments, described and exemplified herein are methods of genetically modifying an at least one endogenous gene in a plant cell, for example but not limited to a CSLG gene, to regulate expression, activity, or stability, or any combination thereof. The Examples below disclose enzyme activities and enzymes previously unknown to be pan of the steroidal alkaloid biosynthetic pathway. Without this knowledge, production of the steroidal alkaloid compounds was not possible.

In some embodiments, the steroidal alkaloid metabolic pathway can result in cells or plants comprising elevated content of steroidal alkaloids, a derivative thereof, a metabolite thereof, or a biosynthetic intermediate thereof, or in plants having an increased content of these compounds in the plant or plant parts. In some embodiments, plants including but not limited to crop plants are produced, wherein the crop has an increased content of a useful steroidal alkaloid or steroidal alkaloids. In some embodiments, disclosed herein are the means and methods for producing cells including but not limited to plant cells, yeast, or algal cells; plants including but not limited to crop plants, or a part of a plant; having increased levels of a steroidal alkaloid, or steroidal alkaloids, or derivatives thereof, or metabolites thereof, or a biosynthetic intermediate thereof. Alternatively, or additionally, controlling the expression of genes disclosed herein may be used for the production of desired steroidal alkaloids for further use, for example in the pharmaceutical industry or for the formulation of dietary or other supplements, for example but not limited to sweeteners. In some embodiments, these high value saponins may be purified and used, e.g., as sweeteners, foaming agents, emulsifiers, preservatives, anti-carcinogens, hypocholesterolemic agents, anti-inflammatory agents, anti-oxidants, biological adjuvants, anti-microbial agents, insecticidal agents, anti-feedants, or anti-fungal agents, or any combination thereof. The cells and plants disclosed herein comprise compounds of significant nutritional, pharmaceutical, and commercial value.

In some embodiments, derivatives of steroidal alkaloids comprise glycosylated derivatives of steroidal alkaloids.

In some embodiments, a genetically modified cell or genetically modified plant or plant part comprising at least one genetically modified plant cell, as described herein, comprises an altered content of at least a steroidal alkaloid, a derivative thereof, a metabolite thereof, or a biosynthetic intermediate thereof, compared to a corresponding unmodified cell or unmodified plant. In some embodiments, an altered content comprises an increased content. In some embodiments, for example, the genetically modified cell or genetically modified plant has an increased content of at least a steroidal alkaloid, a derivative thereof, a metabolite thereof, or a biosynthetic intermediate thereof, or any combination thereof.

In some embodiments, the genetically modified cell or genetically modified plant or plant part comprising at least one genetically modified plant cell, has an increased content of at least one steroidal alkaloid. In some embodiments, the genetically modified cell or genetically modified plant or plant part comprising at least one genetically modified plant cell, has an increased content of at least two steroidal alkaloids. In some embodiments, the genetically modified cell or genetically modified plant or plant part comprising at least one genetically modified plant cell, has an increased content of at least three steroidal alkaloids. In some embodiments, the genetically modified cell or genetically modified plant or plant part comprising at least one genetically modified plant cell, has an increased content of at least four steroidal alkaloids. In some embodiments, the genetically modified cell or genetically modified plant or plant part comprising at least one genetically modified plant cell, has an increased content of at least five steroidal alkaloids. In some embodiments, the genetically modified cell or genetically modified plant or plant part comprising at least one genetically modified plant cell, has an increased content of at least six steroidal alkaloids.

In some embodiments, the genetically modified cell or genetically modified plant or plant part comprising at least one genetically modified plant cell, has an increased content of at least a derivative of a steroidal alkaloid. In some embodiments, the genetically modified cell or genetically modified plant or plant part comprising at least one genetically modified plant cell, has an increased content of at least two derivatives of a steroidal alkaloid or of steroidal alkaloids. In some embodiments, the genetically modified cell or genetically modified plant or plant part comprising at least one genetically modified plant cell, has an increased content of at least three derivatives of a steroidal alkaloid or of steroidal alkaloids. In some embodiments, the genetically modified cell or genetically modified plant or plant part comprising at least one genetically modified plant cell, has an increased content of at least four derivatives of a steroidal alkaloid or of steroidal alkaloids. In some embodiments, the genetically modified cell or genetically modified plant or plant part comprising at least one genetically modified plant cell, has an increased content of at least five derivatives of a steroidal alkaloid or of steroidal alkaloids. In some embodiments, the genetically modified cell or genetically modified plant or plant part comprising at least one genetically modified plant cell, has an increased content of at least six derivatives of a steroidal alkaloid or of steroidal alkaloids.

In some embodiments, the genetically modified cell or genetically modified plant or plant part comprising at least one genetically modified plant cell, has an increased content of at least a metabolite of a steroidal alkaloid. In some embodiments, the genetically modified cell or genetically modified plant or plant part comprising at least one genetically modified plant cell, has an increased content of at least two metabolites of a steroidal alkaloid or of steroidal alkaloids. In some embodiments, the genetically modified cell or genetically modified plant or plant part comprising at least one genetically modified plant cell, has an increased content of at least three metabolites of a steroidal alkaloid or of steroidal alkaloids. In some embodiments, the genetically modified cell or genetically modified plant or plant part comprising at least one genetically modified plant cell, has an increased content of at least four metabolites of a steroidal alkaloid or of steroidal alkaloids. In some embodiments, the genetically modified cell or genetically modified plant or plant part comprising at least one genetically modified plant cell, has an increased content of at least five metabolites of a steroidal alkaloid or of steroidal alkaloids. In some embodiments, the genetically modified cell or genetically modified plant or plant part comprising at least one genetically modified plant cell, has an increased content of at least six metabolites of a steroidal alkaloid or of steroidal alkaloids.

In some embodiments, the genetically modified cell or genetically modified plant or plant part comprising at least one genetically modified plant cell, has an increased content of at least a biosynthetic intermediate of a steroidal alkaloid. In some embodiments, the genetically modified cell or genetically modified plant or plant part comprising at least one genetically modified plant cell, has an increased content of at least two biosynthetic intermediates of a steroidal alkaloid or of steroidal alkaloids. In some embodiments, the genetically modified cell or genetically modified plant or plant part comprising at least one genetically modified plant cell, has an increased content of at least three biosynthetic intermediates of a steroidal alkaloid or of steroidal alkaloids. In some embodiments, the genetically modified cell or genetically modified plant or plant part comprising at least one genetically modified plant cell, has an increased content of at least four biosynthetic intermediates of a steroidal alkaloid or of steroidal alkaloids. In some embodiments, the genetically modified cell or genetically modified plant or plant part comprising at least one genetically modified plant cell, has an increased content of at least five biosynthetic intermediates of a steroidal alkaloid or of steroidal alkaloids. In some embodiments, the genetically modified cell or genetically modified plant or plant part comprising at least one genetically modified plant cell, has an increased content of at least six biosynthetic intermediates of a steroidal alkaloid or of steroidal alkaloids.

As skilled artisan would recognize that the terms "content" and "level" in reference to a triterpenoid saponin, a derivative thereof, a metabolite thereof, or a biosynthetic intermediate thereof, encompasses the quantity of the compound, for example the quantity of a steroidal alkaloid, a derivative thereof, a metabolite thereof, or a biosynthetic intermediate thereof in a genetically modified cell or in a genetically modified plant, compared with a control cell or control plant. In this context, the terms "content" and "level" may be used interchangeably having all the same meanings and qualities.

In some embodiments, a steroidal alkaloid having increased content comprises a nutrition, cosmetic, or pharmaceutical agent, or any combination thereof. In some embodiments, a steroidal alkaloid having increased content comprises steroidal alkaloid selected from an alpha-tomatine, tomatine, dehydrotomatine, alpha-chaconine, alpha-solanine, alpha-solasonine, alpha-solmargine, or any combination thereof. In some embodiments, a steroidal alkaloid having increased content comprises at least 1, 2, 3, 4, 5, 6, or more steroidal alkaloid selected from alpha-tomatine, tomatine, dehydrotomatine, alpha-chaconine, alpha-solanine, alpha-solasonine, alpha-solmargine, or any combination thereof.

In some embodiments, a steroidal alkaloid having increased content comprises at least 1, 2, 3, 4, 5, 6, or more steroidal alkaloid selected from alpha-tomatine, tomatine, dehydrotomatine, alpha-chaconine, alpha-solanine, alpha-solasonine, alpha-solmargine, or any combination thereof.

In some embodiments, a steroidal alkaloid having increased content in a genetically modified cell, for example a plant cell or a yeast or an algal cell or an insect cell or a bacterium, or in a genetically modified plant or part thereof, comprises steroidal alkaloid selected from alpha-tomatine, tomatine, dehydrotomatine, alpha-chaconine, alpha-solanine, alpha-solasonine, alpha-solmargine, or any combination thereof.

In some embodiments, a genetically modified cell, for example a plant cell or a yeast or an algal cell or an insect cell or a bacterium, or in a genetically modified plant or part thereof, comprises an increased content of alpha-tomatine. In some embodiments, a genetically modified cell, for example a plant cell or a yeast or an algal cell or an insect cell or a bacterium, or in a genetically modified plant or part thereof, comprises an increased content of tomatine. In some embodiments, a genetically modified cell, for example a plant cell or a yeast or an algal cell or an insect cell or a bacterium, or in a genetically modified plant or part thereof, comprises an increased content of dehydrotomatine. In some embodiments, a genetically modified cell, for example a plant cell or a yeast or an algal cell or an insect cell or a bacterium, or in a genetically modified plant or part thereof, comprises an increased content of alpha-chaconine. In some embodiments, a genetically modified cell, for example a plant cell or a yeast or an algal cell or an insect cell or a bacterium, or in a genetically modified plant or part thereof, comprises an increased content of alpha-solanine. In some embodiments, a genetically modified cell, for example a plant cell or a yeast or an algal cell or an insect cell or a bacterium, or in a genetically modified plant or part thereof, comprises an increased content of alpha-solasonine. In some embodiments, a genetically modified cell, for example a plant cell or a yeast or an algal cell or an insect cell or a bacterium, or in a genetically modified plant or part thereof, comprises an increased content of alpha-solmargine. A skilled artisan would appreciate that in some embodiments, instances wherein the content of one steroidal alkaloid is increased additional steroidal alkaloids, or intermediates, or a combination thereof may also be increased in the same time cell.

In some embodiments, a genetically modified cell, for example a plant cell or a yeast or an algal cell, or a genetically modified plant or part thereof, comprises an increased content of a biosynthetic intermediate of a steroidal alkaloid, said intermediate comprising cholesterol, 22-hydroxycholesterol, 22,26-dihydroxycholesterol, furostanol-type-saponin aglycone, furostanol-26-aldehyde, 26-amino-furostanol, tomatidenol, tomatidine, tomatidine galactoside, gamma-tomatine, beta-1-tomatine, or any combination thereof. In some embodiments, a genetically modified cell, for example a plant cell or a yeast or an algal cell or an insect cell or a bactierum, or a genetically modified plant or part thereof, comprises an increased content of at least two biosynthetic intermediates of a steroidal alkaloid or of steroidal alkaloids, said intermediates comprising cholesterol, 22-hydroxycholesterol, 22,26-dihydroxycholesterol, furostanol-type-saponin aglycone, furostanol-26-aldehyde, 26-amino-furostanol, tomatidenol, tomatidine, tomatidine galactoside, gamma-tomatine, beta-1-tomatine, or any combination thereof.

In some embodiments, a genetically modified cell, for example a plant cell or a yeast or an algal cell or an insect cell or a bactierum, or a genetically modified plant or part thereof, comprises an increased content of a biosynthetic intermediate of a steroidal alkaloid, said intermediate comprising cholesterol. In some embodiments, a genetically modified cell, for example a plant cell or a yeast or an algal cell or an insect cell or a bacterium, or a genetically modified plant or part thereof, comprises an increased content of a biosynthetic intermediate of a steroidal alkaloid, said intermediate comprising 22-hydroxycholesterol. In some embodiments, a genetically modified cell, for example a plant cell or a yeast or an algal cell or an insect cell or a bacterium, or a genetically modified plant or part thereof, comprises an increased content of a biosynthetic intermediate of a steroidal alkaloid, said intermediate comprising 22,26-dihydroxysholesterol. In some embodiments, a genetically modified cell, for example a plant cell or a yeast or an algal cell or an insect cell or a bacterium, or a genetically modified plant or part thereof, comprises an increased content of a biosynthetic intermediate of a steroidal alkaloid, said intermediate comprising furostanol-type saponin aglycone. In some embodiments, a genetically modified cell, for example a plant cell or a yeast or an algal cell or an insect cell or a bacterium, or a genetically modified plant or part thereof, comprises an increased content of a biosynthetic intermediate of a steroidal alkaloid, said intermediate comprising furostanol-26-aldehyde. In some embodiments, a genetically modified cell, for example a plant cell or a yeast or an algal cell or an insect cell or a bacterium, or a genetically modified plant or part thereof, comprises an increased content of a biosynthetic intermediate of a steroidal alkaloid, said intermediate comprising 26-amino-furostanol, or any combination thereof. In some embodiments, a genetically modified cell, for example a plant cell or a yeast or an algal cell or an insect cell or a bacterium, or a genetically modified plant or part thereof, comprises an increased content of a biosynthetic intermediate of a steroidal alkaloid, said intermediate comprising tomatidenol. In some embodiments, a genetically modified cell, for example a plant cell or a yeast or an algal cell or an insect cell or a bacterium, or a genetically modified plant or part thereof, comprises an increased content of a biosynthetic intermediate of a steroidal alkyloid, said intermediate comprising tomatidine. In some embodiments, a genetically modified cell, for example a plant cell or a yeast or an algal cell or an insect cell or a bacterium, or a genetically modified plant or part thereof, comprises an increased content of a biosynthetic intermediate of a steroidal alkaloid, said intermediate comprising tomatidine galactoside, or any combination thereof. In some embodiments, a genetically modified cell, for example a plant cell or a yeast or an algal cell or an insect cell or a bacterium, or a genetically modified plant or part thereof, comprises an increased content of a biosynthetic intermediate of a steroidal alkaloid, said intermediate comprising gamma-tomatine, or any combination thereof. In some embodiments, a genetically modified cell, for example a plant cell or a yeast or an algal cell or an insect cell or a bacterium, or a genetically modified plant or part thereof, comprises an increased content of a biosynthetic intermediate of a steroidal alkaloid, said intermediate comprising beta-1-tomatine, or any combination thereof.

In some embodiments, a steroidal alkaloid having decreased content in a plant or plant part comprising at least one genetically modified cell, comprises a compound having a bitter taste or a toxin. In some embodiments, a steroidal alkaloid having decreased content comprises a steroidal alkaloid selected from alpha-tomatine, tomatine, dehydrotomatine, alpha-chaconine, alpha-solanine, alpha-solasonine, alpha-solmargine, or any combination thereof. In some embodiments, a steroidal alkaloid having decreased content comprises at least 1, 2, 3, 4, 5, 6, or more steroidal alkaloids selected from In some embodiments, a steroidal saponin having increased content in a genetically modified cell, for example a plant cell or a yeast or an algal cell or an insect cell or a bacterium, or in a genetically modified plant or part thereof, comprises a steroidal alkaloid selected from alpha-tomatine, tomatine, dehydrotomatine, alpha-chaconine, alpha-solanine, alpha-solasonine, alpha-solmargine, or any combination thereof.

In some embodiments, a steroidal alkaloid having decreased content comprises at least 1, 2, 3, 4, 5, 6, or more steroidal alkaloids selected from In some embodiments, a steroidal alkaloid having increased content in a genetically modified cell, for example a plant cell or a yeast or an algal cell or an insect cell or a bacterium, or in a genetically modified plant or part thereof, comprises a steroidal alkaloid selected from alpha-tomatine, tomatine, dehydrotomatine, alpha-chaconine, alpha-solanine, alpha-solasonine, alpha-solmargine, or any combination thereof.

In some embodiments, a steroidal alkaloid having decreased content in a genetically modified plant or part thereof comprising at least one genetically modified cell, comprises a steroidal alkaloid selected from alpha-tomatine, tomatine, dehydrotomatine, alpha-chaconine, alpha-solanine, alpha-solasonine, alpha-solmargine, or any combination thereof.

In some embodiments, a genetically modified plant or part thereof comprising at least one genetically modified plant cell, comprises a decreased content of alpha-tomatine. In some embodiments, a genetically modified plant or part thereof comprising at least one genetically modified plant cell, comprises a decreased content of tomatine. In some embodiments, a genetically modified plant or part thereof comprising at least one genetically modified plant cell, comprises a decreased content of dehydrotomatine. In some embodiments, a genetically modified plant or part thereof comprising at least one genetically modified plant cell, comprises a decreased content of alpha-chaconine. In some embodiments, a genetically modified plant or part thereof comprising at least one genetically modified plant cell, comprises a decreased content of alpha-solanine. In some embodiments, a genetically modified plant or part thereof comprising at least one genetically modified plant cell, comprises a decreased content of alpha-solasonine.

In some embodiments, a genetically modified plant or part thereof comprising at least one genetically modified plant cell, comprises a decreased content of a biosynthetic intermediate of a steroidal alkaloid, said intermediate comprising cholesterol, 22-hydroxycholesterol, 22,26-dihydroxycholesterol, furostanol-type-saponin aglycone, furostanol-26-aldehyde, 26-amino-furostanol, tomatidenol, tomatidine, tomatidine galactoside, gamma-tomatine, beta-1-tomatine, or any combination thereof.

In some embodiments, a genetically modified plant or part thereof comprising at least one genetically modified plant cell, comprises a decreased content of a biosynthetic intermediate of a steroidal alkaloid, said intermediate comprising cholesterol. In some embodiments, a genetically modified plant or part thereof comprising at least one genetically modified plant cell, comprises a decreased content of a biosynthetic intermediate of a steroidal alkaloid, said intermediate comprising 22-hydroxycholesterol. In some embodiments, a genetically modified plant or part thereof comprising at least one genetically modified plant cell, comprises a decreased content of a biosynthetic intermediate of a steroidal alkaloid, said intermediate comprising 22,26-dihydroxycholesterol. In some embodiments, a genetically modified plant or part thereof comprising at least one genetically modified plant cell, comprises a decreased content of a biosynthetic intermediate of a steroidal alkaloid, said intermediate comprising fursotanol-type saponin aglycone. In some embodiments, a genetically modified plant or part thereof comprising at least one genetically modified plant cell, comprises a decreased content of a biosynthetic intermediate of a steroidal alkaloid, said intermediate comprising furostanol-26-aldehyde. In some embodiments, a genetically modified plant or part thereof comprising at least one genetically modified plant cell, comprises a decreased content of a biosynthetic intermediate of a steroidal alkaloid, said intermediate comprising 26-amino-furostanol. In some embodiments, a genetically modified plant or part thereof comprising at least one genetically modified plant cell, comprises a decreased content of a biosynthetic intermediate of a steroidal alkaloid, said intermediate comprising tomatidenol. In some embodiments, a genetically modified plant or part thereof comprising at least one genetically modified plant cell, comprises a decreased content of a biosynthetic intermediate of a steroidal alkaloid, said intermediate comprising tomatidine. In some embodiments, a genetically modified plant or part thereof comprising at least one genetically modified plant cell, comprises a decreased content of a biosynthetic intermediate of a steroidal alkaloid, said intermediate comprising tomatidine galactoside. In some embodiments, a genetically modified plant or part thereof comprising at least one genetically modified plant cell, comprises a decreased content of a biosynthetic intermediate of a steroidal alkaloid, said intermediate comprising gamma-tomatine. In some embodiments, a genetically modified plant or part thereof comprising at least one genetically modified plant cell, comprises a decreased content of a biosynthetic intermediate of a steroidal alkaloid, said intermediate comprising beta-1-tomatine.

In some embodiments, a genetically modified cell disclosed herein comprises an increased content of at least one steroidal alkaloid, a derivative thereof, a metabolite thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof, a phytocholesterol, or a derivative thereof, a metabolite thereof, or a biosynthetic intermediate thereof; a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a genetically modified cell disclosed herein comprises an increased content of at least one steroidal alkaloid, a derivative thereof, a metabolite thereof, or a biosynthetic intermediate thereof, and a reduced content of a phytosterol, or a derivative thereof, a metabolite thereof, or a biosynthetic intermediate thereof; a cholesterol, or a derivative thereof, a metabolite thereof, or a biosynthetic intermediate thereof, a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified cell disclosed herein comprises a decreased content of at least one steroidal alkaloid, a derivative thereof, a metabolite thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof, a phytocholesterol, or a derivative thereof, a metabolite thereof, or a biosynthetic intermediate thereof; a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a genetically modified cell disclosed herein comprises a decreased content of at least one steroidal alkaloid, a derivative thereof, a metabolite thereof, or a biosynthetic intermediate thereof, and an increased content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified plant disclosed herein comprises an increased content of at least one steroidal alkaloid, a derivative thereof, a metabolite thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified plant disclosed herein comprises an increased content of at least one steroidal alkaloid, a derivative thereof, a metabolite thereof, or a biosynthetic intermediate thereof, and a decreased content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified plant disclosed herein comprises a decreased content of at least one steroidal alkaloid, a derivative thereof, a metabolite thereof, or a biosynthetic intermediate thereof and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified plant disclosed herein comprises a decreased content of at least one steroidal alkaloid, a derivative thereof, a metabolite thereof, or a biosynthetic intermediate thereof and an increased content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of producing at least one steroidal alkaloid, a derivative thereof, a metabolite thereof, or a biosynthetic intermediate thereof, in a genetically modified cell or a genetically modified plant comprises increasing the content of at least one steroidal alkaloid, a derivative thereof, a metabolite thereof, or a biosynthetic intermediate thereof, compared to an unmodified cell or an unmodified plant and altering the content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of producing at least one steroidal alkaloid, a derivative thereof, a metabolite thereof, or a biosynthetic intermediate thereof, in a genetically modified cell or a genetically modified plant comprises increasing the content of at least one steroidal alkaloid, a derivative thereof, a metabolite thereof, or a biosynthetic intermediate thereof, compared to an unmodified cell or an unmodified plant and decreasing the content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of reducing the content of at least one steroidal alkaloid, a derivative thereof, a metabolite thereof, or a biosynthetic intermediate thereof, comprises genetically modifying at least one plant cell or at least one cell of a plant or plant part, said genetically modified plant cell comprising a reduced content of at least one steroidal alkaloid, a derivative thereof, a metabolite thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a method of reducing the content of at least one steroidal alkaloid, a derivative thereof, a metabolite thereof, or a biosynthetic intermediate thereof, comprises genetically modifying at least one plant cell or at least one cell of a plant or plant part, said genetically modified plant cell comprising a reduced content of at least one steroidal alkaloid, a derivative thereof, a metabolite thereof, or a biosynthetic intermediate thereof, and an increased content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of increasing the content of at least one steroidal alkaloid, a derivative thereof, a metabolite thereof, or a biosynthetic intermediate thereof, comprises genetically modifying at least one plant cell or at least one cell of a plant or plant part, said genetically modified plant cell comprising an altered content of at least one steroidal alkaloid, a derivative thereof, a metabolite thereof, or a biosynthetic intermediate thereof, and a reduced content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a method of increasing the content of at least one steroidal alkaloid, a derivative thereof, a metabolite thereof, or a biosynthetic intermediate thereof, comprises genetically modifying at least one plant cell or at least one cell of a plant or plant part, said genetically modified plant cell comprising an increased content of at least one steroidal alkaloid, a derivative thereof, a metabolite thereof, or a biosynthetic intermediate thereof, and a reduced content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof, a cholestenol, or a derivative thereof, a metabolite thereof, or a biosynthetic intermediate thereof; or a phytocholestenol, or a derivative thereof, a metabolite thereof, or a biosynthetic intermediate thereof.

Steroidal Saponins, Derivatives Thereof; Metabolites Thereof; and Biosynthetic Intermediates Thereof In some embodiments, a genetically modified cell disclosed herein comprises an increased content of at least one steroidal saponin, a derivative thereof, a metabolite thereof, or a biosynthetic intermediate thereof, of any combination thereof. In some embodiments, a genetically modified plant comprising at least one genetically modified cell disclosed herein comprises an increased content of at least one steroidal saponin, a derivative thereof, a metabolite thereof, or a biosynthetic intermediate thereof, of any combination thereof. In some embodiments, an in vitro biosynthetic system produces at least one steroidal saponin, a derivative thereof, a metabolite thereof, or a biosynthetic intermediate thereof, of any combination thereof. In some embodiments, a genetically modified plant disclosed herein comprises an increased content of at least one steroidal saponin, a derivative thereof, a metabolite thereof, or a biosynthetic intermediate thereof, of any combination thereof. In some embodiments, a genetically modified plant comprising at least one genetically modified cell as disclosed herein, comprises a decreased content of at least one steroidal saponin, a derivative thereof, a metabolite thereof, or a biosynthetic intermediate thereof, of any combination thereof. In some embodiments, a genetically modified plant disclosed herein comprising at least one genetically modified cells comprises an increased content of at least one steroidal saponin, a derivative thereof, a metabolite thereof, or a biosynthetic intermediate thereof, of any combination thereof, and a decreased content of at least one steroidal saponin, a derivative thereof, a metabolite thereof, or a biosynthetic intermediate thereof, of any combination thereof.

In some embodiments, a method of producing a steroidal alkaloid in a genetically modified cell disclosed herein comprises producing an at least one steroidal saponin, a derivative thereof, a metabolite thereof, or a biosynthetic intermediate thereof, of any combination thereof. In some embodiments, a method of producing a steroidal saponin in a genetically modified plant or plant part comprises producing of at least one steroidal alkaloid, a derivative thereof, a metabolite thereof, or a biosynthetic intermediate thereof, of any combination thereof. In some embodiments, disclosed herein is a method of reducing the content of at least one steroidal saponin, a derivative thereof, a metabolite thereof, or a biosynthetic intermediate thereof, of any combination thereof in a plant or plant part comprising an at least one genetically modified cell as described herein. In some embodiments, disclosed herein is a method of increasing the content of at least one steroidal saponin, a derivative thereof, a metabolite thereof, or a biosynthetic intermediate thereof, of any combination thereof in a plant or plant part comprising an at least one genetically modified cell as described herein.

Steroidal saponins branch off from steroidal alkaloids after the formation of furostanol-type saponin aglycone (FIG. 1).

The commonly used nomenclature for saponins distinguishes between triterpenoid saponins (also called triterpene saponins) and steroidal saponins, which is based on the structure and biochemical background of their aglycones. Both sapogenin types are thought to derive from 2,3-oxidosqualene, a central metabolite in sterol biosynthesis. In phytosterol anabolism, 2,3-oxidosqualene is mainly cyclized into cycloartenol. “Steroidal sapogenins” are thought to derive from intermediates in the phytosterol pathway downstream of cycloartenol formation.

Steroidal saponins, include, but are not limited to, uttroside B, a tomatoside, or any combination thereof.

In some embodiments, the genetically modified cell comprising said increased content comprises a plant cell, a yeast cell, an algal cell, an insect cell, or a bacterial. In some embodiments, the genetically modified cell comprising said increased content comprises a plant cell. In some embodiments, the genetically modified cell comprising said increased content comprises a yeast cell. In some embodiments, the genetically modified cell comprising said increased content comprises an algal cell. In some embodiments, the genetically modified cell comprising said increased content comprises an insect cell. In some embodiments, the genetically modified cell comprising said increased content comprises a bacterium.

In some embodiments, a genetically modified plant disclosed herein comprises an increased content of at least one steroidal saponin selected from any one of uttroside B, a tomatoside, or any combination thereof. In some embodiments, a genetically modified plant disclosed herein comprises an increased content of uttroside B.

In some embodiments, derivatives of steroidal saponins comprise glycosylated derivatives of steroidal saponins.

In some embodiments, a genetically modified plant disclosed herein comprises a decreased content of at least one steroidal saponin selected from any one of uttroside B, a tomatoside, or any combination thereof. In some embodiments, a genetically modified plant disclosed herein comprises a decreased content of uttroside B.

In some embodiments, a genetically modified plant disclosed herein comprises an increased content of at least one steroidal saponin and a decreased content of at least one steroidal saponin selected from any one of uttroside B, a tomatoside, or any combination thereof.

In some embodiments, a method of producing a steroidal saponin in a genetically modified cell comprises producing at least one steroidal saponin selected from any one of uttroside B, a tomatoside, or any combination thereof. In some embodiments, a method of producing a steroidal saponin in a genetically modified cell comprises producing uttroside B.

In some embodiments, the method of producing at least one steroidal saponin in a genetically modified cell comprises producing at least one steroidal saponins in a plant cell, a yeast cell, an algal cell, an insect cell, or a bacterium. In some embodiments, the method of producing at least one steroidal saponin in a genetically modified cell comprises producing at least one steroidal saponins in a plant cell. In some embodiments, the method of producing at least one steroidal saponin in a genetically modified cell comprises producing at least one steroidal saponins in a yeast cell. In some embodiments, the method of producing at least one steroidal saponin in a genetically modified cell comprises producing at least one steroidal saponins in an algal cell. In some embodiments, the method of producing at least one steroidal saponin in a genetically modified cell comprises producing at least one steroidal saponins in an insect cell. In some embodiments, the method of producing at least one steroidal saponin in a genetically modified cell comprises producing at least one steroidal saponins in a bacterium. In some embodiments, the plant cell is comprised in a plant or plant part.

In some embodiments, a method of producing a steroidal saponin in a genetically modified plant comprises producing at least one steroidal saponin selected from any one of any one of uttroside B, a tomatoside, or any combination thereof. In some embodiments, a method of producing a steroidal saponin in a genetically modified plant comprises producing uttroside B.

In some embodiments, a method of producing a steroidal saponin in an in vitro translation system comprises producing at least one steroidal saponin selected from any one of any one of uttroside B, a tomatoside, or any combination thereof. In some embodiments, a method of producing a steroidal saponin in an in vitro translation system comprises producing uttroside B.

In some embodiments, a method of reducing at least one steroidal saponin comprises reducing at least one steroidal saponin selected from any one of any one of uttroside B, a tomatoside, or any combination thereof. In some embodiments, a method of reducing the content of at least one steroidal saponin comprising uttroside B.

In some embodiments, a method of increasing at least one steroidal saponin comprises increasing at least one steroidal saponin selected from any one of any one of uttroside B, a tomatoside, or any combination thereof. In some embodiments, the at least one steroidal saponin comprises uttroside B. In some embodiments, the at least one steroidal saponin comprises a tomatoside.

In some embodiments, the content of both at least one steroidal saponin and at least one steroidal saponin biosynthetic intermediate are altered. In some embodiments, an at least one steroidal saponin and an at least one steroidal saponin biosynthetic intermediate are increased. In some embodiments, an at least one steroidal saponins and an at least one steroidal saponin biosynthetic intermediate are decreased. In some embodiments, an at least one steroidal saponin is increased and an at least one steroidal saponin biosynthetic intermediate is decreased. In some embodiments, an at least one steroidal saponin is decreased and an at least one steroidal saponin biosynthetic intermediate is increased. In some embodiments, the content of a steroidal saponin is altered without measurably altering the content of a steroidal saponin intermediate. In some embodiments, the content of a steroidal saponin intermediate is altered without measurably altering the content of a steroidal saponin.

The term "intermediate" may be used interchangeably in some embodiments with the term "biosynthetic intermediate", having all the same qualities and meanings.

In some embodiments, a biosynthetic intermediate of a steroidal saponin comprises cholesterol, 22-hydroxycholesterol, 22,26-dihydroxycholesterol, furostanol-type saponin aglycone, or any combination thereof.

In some embodiments, a genetically modified cell disclosed herein comprises an increased content of at least one biosynthetic intermediate of a steroidal saponin comprising cholesterol, 22-hydroxycholesterol, 22,26-dihydroxycholesterol, furostanol-type saponin aglycone, or any combination thereof. In some embodiments, a genetically modified cell comprises an increased content of at least one biosynthetic intermediate of a steroidal saponin comprising cholesterol. In some embodiments, a genetically modified cell comprises an increased content of at least one biosynthetic intermediate of a steroidal saponin comprising 22-hydroxycholesterol. In some embodiments, a genetically modified cell comprises an increased content of at least one biosynthetic intermediate of a steroidal saponin comprising 22,26-dihydroxycholesterol. In some embodiments, a genetically modified cell comprises an increased content of at least one biosynthetic intermediate of a steroidal saponin comprising furostanol-type-saponin aglycone.

In some embodiments, a genetically modified plant disclosed herein comprises a decreased content of at least one biosynthetic intermediate of a steroidal saponin comprising cholesterol, 22-hydroxycholesterol, 22,26-dihydroxycholesterol, furostanol-type saponin aglycone, or any combination thereof. In some embodiments, a genetically modified plant comprises a decreased content of at least one biosynthetic intermediate of a steroidal saponin comprising cholesterol. In some embodiments, a genetically modified plant comprises a decreased content of at least one biosynthetic intermediate of a steroidal saponin comprising 22-hydroxycholesterol. In some embodiments, a genetically modified plant comprises a decreased content of at least one biosynthetic intermediate of a steroidal saponin comprising 22,26-dihydroxycholeseterol. In some embodiments, a genetically modified plant comprises a decreased content of at least one biosynthetic intermediate of a steroidal saponin comprising furostanol-type saponin aglycone.

In some embodiments, a genetically modified plant disclosed herein comprises an increased content of at least one steroidal saponin biosynthetic intermediate and a decreased content of at least one steroidal saponin biosynthetic intermediate, said intermediate selected from any one of cholesterol, 22-hydroxycholesterol, 22,26-dihydroxycholesterol, furostanol-type saponin aglycone, or any combination thereof.

In some embodiments, a method of reducing at least one steroidal saponin comprises reducing at least one steroidal saponin biosynthetic intermediate selected from any one of cholesterol, 22-hydroxycholesterol, 22,26-dihydroxycholesterol, furostanol-type saponin aglycone, or any combination thereof. In some embodiments, a method of reducing at least one steroidal saponin comprises reducing at least cholesterol. In some embodiments, a method of reducing at least one steroidal saponin comprises reducing at least 22-hydroxycholesterol. In some embodiments, a method of reducing at least one steroidal saponin comprises reducing at least 22,26-dihydroxycholesterol. In some embodiments, a method of reducing at least one steroidal saponin comprises reducing at least furostanol-type saponin aglycone.

In some embodiments, a method of increasing at least one steroidal saponin comprises increasing at least one steroidal saponin biosynthetic intermediate selected from any one of cholesterol, 22-hydroxycholesterol, 22,26-dihydroxycholesterol, furostanol-type saponin aglycone, or any combination thereof. In some embodiments, a method of increasing at least one steroidal saponin comprises increasing at least cholesterol. In some embodiments, a method of increasing at least one steroidal saponin comprises increasing at least 22-hydroxycholesterol. In some embodiments, a method of increasing at least one steroidal saponin comprises increasing at least 22,26-dihydroxycholesterol. In some embodiments, a method of increasing at least one steroidal saponin comprises increasing at least furostanol-type saponin aglycone.

In some embodiments, steroidal saponins biosynthetic intermediate comprises any cholesterol, 22-hydroxycholesterol, 22,26-dihydroxycholesterol, furostanol-type saponin aglycone, or a combination thereof.

Unexpectedly, the present disclosure now shows that levels of steroidal saponins or their derivatives, metabolites, or biosynthetic intermediates can be increased in cells, for example plant cells or yeast cells or algal cells, or insect cells, or bacterium, or plants by genetically modifying the cell or plant to express at least one heterologous gene encoding an enzyme, for example an enzyme or enzymes of the steroidal saponin biosynthetic pathway. In other embodiments, described and exemplified herein are methods of genetically modifying an at least one endogenous gene in a plant cell, for example but not limited to a CSLG gene, to regulate expression, activity, or stability, or any combination thereof. The Examples below disclose enzyme activities and enzymes previously unknown to be part of the steroidal saponin biosynthetic pathway. Without this knowledge, production of the steroidal saponin compounds was not possible.

In some embodiments, the steroidal saponin metabolic pathway can result in cells or plants comprising elevated content of steroidal saponins, a derivative thereof, a metabolite thereof, or a biosynthetic intermediate thereof, or in plants having an increased content of these compounds in the plant or plant parts. In some embodiments, plants including but not limited to crop plants are produced, wherein the crop has an increased content of a useful steroidal saponin or steroidal saponins. In some embodiments, disclosed herein are the means and methods for producing cells including but not limited to plant cells, yeast, or algal cells: plants including but not limited to crop plants, or a part of a plant; having increased levels of a steroidal saponin, or steroidal saponins, or derivatives thereof, or metabolites thereof, or a biosynthetic intermediate thereof. Alternatively, or additionally, controlling the expression of genes disclosed herein may be used for the production of desired steroidal saponins for further use, for example in the pharmaceutical industry or for the formulation of dietary or other supplements, for example but not limited to sweeteners. In some embodiments, these high value saponins may be purified and used, e.g., as sweeteners, foaming agents, emulsifiers, preservatives, anti-carcinogens, hypocholesterolemic agents, anti-inflammatory agents, anti-oxidants, biological adjuvants, anti-microbial agents, insecticidal agents, anti-feedants, or anti-fungal agents, or any combination thereof. The cells and plants disclosed herein comprise compounds of significant nutritional, pharmaceutical, and commercial value.

In some embodiments, a genetically modified cell or genetically modified plant or plant part comprising at least one genetically modified plant cell, as described herein, comprises an altered content of at least a steroidal saponin, a derivative thereof, a metabolite thereof, or a biosynthetic intermediate thereof, compared to a corresponding unmodified cell or unmodified plant. In some embodiments, an altered content comprises an increased content. In some embodiments, for example, the genetically modified cell or genetically modified plant has an increased content of at least a steroidal saponin, a derivative thereof, a metabolite thereof, or a biosynthetic intermediate thereof, or any combination thereof.

In some embodiments, the genetically modified cell or genetically modified plant or plant part comprising at least one genetically modified plant cell, has an increased content of at least one steroidal saponin. In some embodiments, the genetically modified cell or genetically modified plant or plant part comprising at least one genetically modified plant cell, has an increased content of at least two steroidal saponins. In some embodiments, the genetically modified cell or genetically modified plant or plant part comprising at least one genetically modified plant cell, has an increased content of at least three steroidal saponins. In some embodiments, the genetically modified cell or genetically modified plant or plant part comprising at least one genetically modified plant cell, has an increased content of at least four steroidal saponins. In some embodiments, the genetically modified cell or genetically modified plant or plant part comprising at least one genetically modified plant cell, has an increased content of at least five steroidal saponins. In some embodiments, the genetically modified cell or genetically modified plant or plant part comprising at least one genetically modified plant cell, has an increased content of at least six steroidal saponins.

In some embodiments, the genetically modified cell or genetically modified plant or plant part comprising at least one genetically modified plant cell, has an increased content of at least a derivative of a steroidal saponin. In some embodiments, the genetically modified cell or genetically modified plant or plant part comprising at least one genetically modified plant cell, has an increased content of at least two derivatives of a steroidal saponin or of steroidal saponins. In some embodiments, the genetically modified cell or genetically modified plant or plant part comprising at least one genetically modified plant cell, has an increased content of at least three derivatives of a steroidal saponin or of steroidal saponins. In some embodiments, the genetically modified cell or genetically modified plant or plant part comprising at least one genetically modified plant cell, has an increased content of at least four derivatives of a steroidal saponin or of steroidal saponins. In some embodiments, the genetically modified cell or genetically modified plant or plant part comprising at least one genetically modified plant cell, has an increased content of at least five derivatives of a steroidal saponin or of steroidal saponins. In some embodiments, the genetically modified cell or genetically modified plant or plant part comprising at least one genetically modified plant cell, has an increased content of at least six derivatives of a steroidal saponin or of steroidal saponins.

In some embodiments, the genetically modified cell or genetically modified plant or plant part comprising at least one genetically modified plant cell, has an increased content of at least a metabolite of a steroidal saponin. In some embodiments, the genetically modified cell or genetically modified plant or plant part comprising at least one genetically modified plant cell, has an increased content of at least two metabolites of a steroidal saponin or of steroidal saponins. In some embodiments, the genetically modified cell or genetically modified plant or plant part comprising at least one genetically modified plant cell, has an increased content of at least three metabolites of a steroidal saponin or of steroidal saponins. In some embodiments, the genetically modified cell or genetically modified plant or plant part comprising at least one genetically modified plant cell, has an increased content of at least four metabolites of a steroidal saponin or of steroidal saponins. In some embodiments, the genetically modified cell or genetically modified plant or plant part comprising at least one genetically modified plant cell, has an increased content of at least five metabolites of a steroidal saponin or of steroidal saponins. In some embodiments, the genetically modified cell or genetically modified plant or plant part comprising at least one genetically modified plant cell, has an increased content of at least six metabolites of a steroidal saponin or of steroidal saponins.

In some embodiments, the genetically modified cell or genetically modified plant or plant part comprising at least one genetically modified plant cell, has an increased content of at least a biosynthetic intermediate of a steroidal saponin. In some embodiments, the genetically modified cell or genetically modified plant or plant part comprising at least one genetically modified plant cell, has an increased content of at least two biosynthetic intermediates of a steroidal saponin or of steroidal saponins. In some embodiments, the genetically modified cell or genetically modified plant or plant part comprising at least one genetically modified plant cell, has an increased content of at least three biosynthetic intermediates of a steroidal saponin or of steroidal saponins. In some embodiments, the genetically modified cell or genetically modified plant or plant part comprising at least one genetically modified plant cell, has an increased content of at least four biosynthetic intermediates of a steroidal saponin or of steroidal saponins. In some embodiments, the genetically modified cell or genetically modified plant or plant part comprising at least one genetically modified plant cell, has an increased content of at least five biosynthetic intermediates of a steroidal saponin or of steroidal saponins. In some embodiments, the genetically modified cell or genetically modified plant or plant part comprising at least one genetically modified plant cell, has an increased content of at least six biosynthetic intermediates of a steroidal saponin or of steroidal saponins.

As skilled artisan would recognize that the terms “content” and “level” in reference to a triterpenoid saponin, a derivative thereof, a metabolite thereof, or a biosynthetic intermediate thereof, encompasses the quantity of the compound, for example the quantity of a steroidal alkaloid, a derivative thereof, a metabolite thereof, or a biosynthetic intermediate thereof in a genetically modified cell or in a genetically modified plant, compared with a control cell or control plant. In this context, the terms "content" and "level" may be used interchangeably having all the same meanings and qualities.

In some embodiments, a steroidal saponin having increased content comprises a nutrition, cosmetic, or pharmaceutical agent, or any combination thereof. In some embodiments, a steroidal saponin having increased content comprises steroidal saponin selected from an uttroside B, a tomatosideor any combination thereof. In some embodiments, a steroidal alkaloid having increased content comprises at least 1, 2, 3, 4, 5, 6, or more steroidal alkaloid selected from uttroside B, a tomatoside, or any combination thereof.

In some embodiments, a steroidal saponin having increased content comprises at least 1, 2, 3, 4, 5, 6, or more steroidal alkaloid selected from uttroside B, a tomatosideor any combination thereof.

In some embodiments, a steroidal saponin having increased content in a genetically modified cell, for example a plant cell or a yeast or an algal cell or an insect cell or a bacterium, or in a genetically modified plant or part thereof, comprises steroidal saponin selected from uttroside B, a tomatosideor any combination thereof.

In some embodiments, a genetically modified cell, for example a plant cell or a yeast or an algal cell or an insect cell or a bacterium, or in a genetically modified plant or part thereof, comprises an increased content of uttroside B. In some embodiments, a genetically modified cell, for example a plant cell or a yeast or an algal cell or an insect cell or a bacterium, or in a genetically modified plant or part thereof, comprises an increased content of a tomatoside.

In some embodiments, a genetically modified cell, for example a plant cell or a yeast or an algal cell, or a genetically modified plant or part thereof, comprises an increased content of a biosynthetic intermediate of a steroidal saponin, said intermediate comprising cholesterol, 22-hydroxycholesterol, 22,26-dihydroxycholesterol, furostanol-type-saponin aglycone, or any combination thereof. In some embodiments, a genetically modified cell, for example a plant cell or a yeast or an algal cell or an insect cell or a bactierum, or a genetically modified plant or part thereof, comprises an increased content of at least two biosynthetic intermediates of a steroidal saponin or of steroidal saponins, said intermediates comprising cholesterol, 22-hydroxycholesterol, 22,26-dihydroxycholesterol, furostanol-type-saponin aglycone, or any combination thereof.

In some embodiments, a genetically modified cell, for example a plant cell or a yeast or an algal cell or an insect cell or a bactierum, or a genetically modified plant or part thereof, comprises an increased content of a biosynthetic intermediate of a steroidal saponin, said intermediate comprising cholesterol. In some embodiments, a genetically modified cell, for example a plant cell or a yeast or an algal cell or an insect cell or a bacterium, or a genetically modified plant or part thereof, comprises an increased content of a biosynthetic intermediate of a steroidal saponin, said intermediate comprising 22-hydroxycholesterol. In some embodiments, a genetically modified cell, for example a plant cell or a yeast or an algal cell or an insect cell or a bacterium, or a genetically modified plant or part thereof, comprises an increased content of a biosynthetic intermediate of a steroidal saponin, said intermediate comprising 22,26-dihydroxysholesterol. In some embodiments, a genetically modified cell, for example a plant cell or a yeast or an algal cell or an insect cell or a bacterium, or a genetically modified plant or part thereof, comprises an increased content of a biosynthetic intermediate of a steroidal saponin, said intermediate comprising furostanol-type saponin aglycone.

In some embodiments, a steroidal saponin having decreased content in a plant or plant part comprising at least one genetically modified cell, comprises a compound having a bitter taste or a toxin. In some embodiments, a steroidal saponin having decreased content comprises a steroidal saponin selected from uttroside B, a tomatosideor any combination thereof. In some embodiments, a steroidal saponin having decreased content comprises at least 1, 2, 3, 4, 5, 6, or more steroidal saponins selected from In some embodiments, a steroidal saponin having increased content in a genetically modified cell, for example a plant cell or a yeast or an algal cell or an insect cell or a bacterium, or in a genetically modified plant or part thereof, comprises steroidal saponin selected from uttroside B, a tomatosideor any combination thereof.

In some embodiments, a steroidal saponin having decreased content comprises at least 1, 2, 3, 4, 5, 6, or more steroidal saponins selected from In some embodiments, a steroidal saponin having increased content in a genetically modified cell, for example a plant cell or a yeast or an algal cell or an insect cell or a bacterium, or in a genetically modified plant or part thereof, comprises a steroidal saponin selected from uttroside B, a tomatosideor any combination thereof.

In some embodiments, a steroidal saponin having decreased content in a genetically modified plant or part thereof comprising at least one genetically modified cell, comprises a steroidal saponin selected from uttroside B, a tomatosideor any combination thereof.

In some embodiments, a genetically modified plant or part thereof comprising at least one genetically modified plant cell, comprises a decreased content of uttroside B. In some embodiments, a genetically modified plant or part thereof comprising at least one genetically modified plant cell, comprises a decreased content of a tomatoside.

In some embodiments, a genetically modified plant or part thereof comprising at least one genetically modified plant cell, comprises a decreased content of a biosynthetic intermediate of a steroidal saponin, said intermediate comprising cholesterol, 22-hydroxycholesterol, 22,26-dihydroxycholesterol, furostanol-type-saponin aglycone, or any combination thereof.

In some embodiments, a genetically modified plant or part thereof comprising at least one genetically modified plant cell, comprises a decreased content of a biosynthetic intermediate of a steroidal saponin, said intermediate comprising cholesterol. In some embodiments, a genetically modified plant or part thereof comprising at least one genetically modified plant cell, comprises a decreased content of a biosynthetic intermediate of a steroidal saponin, said intermediate comprising 22-hydroxycholesterol. In some embodiments, a genetically modified plant or part thereof comprising at least one genetically modified plant cell, comprises a decreased content of a biosynthetic intermediate of a steroidal saponin, said intermediate comprising 22,26-dihydroxycholesterol. In some embodiments, a genetically modified plant or part thereof comprising at least one genetically modified plant cell, comprises a decreased content of a biosynthetic intermediate of a steroidal saponin, said intermediate comprising furostanol-type saponin aglycone.

In some embodiments, a genetically modified cell disclosed herein comprises an increased content of at least one steroidal saponin, a derivative thereof, a metabolite thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified cell disclosed herein comprises an increased content of at least one steroidal saponin, a derivative thereof, a metabolite thereof, or a biosynthetic intermediate thereof, and a reduced content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified cell disclosed herein comprises a decreased content of at least one steroidal saponin, a derivative thereof, a metabolite thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified cell disclosed herein comprises a decreased content of at least one steroidal saponin, a derivative thereof, a metabolite thereof, or a biosynthetic intermediate thereof, and an increased content of a phytosterol, or a derivative thereof, a metabolite thereof, or a biosynthetic intermediate thereof; a cholesterol, or a derivative thereof, a metabolite thereof, or a biosynthetic intermediate thereof, a phytocholesterol, or a derivative thereof, a metabolite thereof, or a biosynthetic intermediate thereof; a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a genetically modified plant disclosed herein comprises an increased content of at least one steroidal saponin, a derivative thereof, a metabolite thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof, a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified plant disclosed herein comprises an increased content of at least one steroidal saponin, a derivative thereof, a metabolite thereof, or a biosynthetic intermediate thereof, and a decreased content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified plant disclosed herein comprises a decreased content of at least one steroidal saponin, a derivative thereof, a metabolite thereof, or a biosynthetic intermediate thereof and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified plant disclosed herein comprises a decreased content of at least one steroidal saponin, a derivative thereof, a metabolite thereof, or a biosynthetic intermediate thereof and an increased content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of producing at least one steroidal saponin, a derivative thereof, a metabolite thereof, or a biosynthetic intermediate thereof, in a genetically modified cell or a genetically modified plant comprises increasing the content of at least one steroidal saponin, a derivative thereof, a metabolite thereof, or a biosynthetic intermediate thereof, compared to an unmodified cell or an unmodified plant and altering the content of a phytosterol, or a derivative thereof, a metabolite thereof, or a biosynthetic intermediate thereof; a cholesterol, or a derivative thereof, a metabolite thereof, or a biosynthetic intermediate thereof, a phytocholesterol, or a derivative thereof, a metabolite thereof, or a biosynthetic intermediate thereof, a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a method of producing at least one steroidal saponin, a derivative thereof, a metabolite thereof, or a biosynthetic intermediate thereof, in a genetically modified cell or a genetically modified plant comprises increasing the content of at least one steroidal saponin, a derivative thereof, a metabolite thereof, or a biosynthetic intermediate thereof, compared to an unmodified cell or an unmodified plant and decreasing the content of a phytosterol, or a derivative thereof, a metabolite thereof, or a biosynthetic intermediate thereof; a cholesterol, or a derivative thereof, a metabolite thereof, or a biosynthetic intermediate thereof, a phytocholesterol, or a derivative thereof, a metabolite thereof, or a biosynthetic intermediate thereof; a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a method of reducing the content of at least one steroidal saponin, a derivative thereof, a metabolite thereof, or a biosynthetic intermediate thereof, comprises genetically modifying at least one plant cell or at least one cell of a plant or plant part, said genetically modified plant cell comprising a reduced content of at least one steroidal saponin, a derivative thereof, a metabolite thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof, a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a method of reducing the content of at least one steroidal saponin, a derivative thereof, a metabolite thereof, or a biosynthetic intermediate thereof, comprises genetically modifying at least one plant cell or at least one cell of a plant or plant part, said genetically modified plant cell comprising a reduced content of at least one steroidal saponin, a derivative thereof, a metabolite thereof, or a biosynthetic intermediate thereof, and an increased content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof, a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of increasing the content of at least one steroidal saponin, a derivative thereof, a metabolite thereof, or a biosynthetic intermediate thereof, comprises genetically modifying at least one plant cell or at least one cell of a plant or plant part, said genetically modified plant cell comprising an altered content of at least one steroidal saponin, a derivative thereof, a metabolite thereof, or a biosynthetic intermediate thereof, and a reduced content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of increasing the content of at least one steroidal saponin, a derivative thereof, a metabolite thereof, or a biosynthetic intermediate thereof, comprises genetically modifying at least one plant cell or at least one cell of a plant or plant part, said genetically modified plant cell comprising an increased content of at least one steroidal saponin, a derivative thereof, a metabolite thereof, or a biosynthetic intermediate thereof, and a reduced content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

Triterpenoid Saponins, Derivatives Thereof; Metabolites Thereof; and Biosynthetic Intermediates Thereof In some embodiments, a genetically modified cell disclosed herein comprises an increased content of at least one triterpenoids saponin, a derivative thereof, a metabolite thereof, or a biosynthetic intermediate thereof, of any combination thereof. In some embodiments, a genetically modified plant comprising at least one genetically modified cell disclosed herein comprises an increased content of at least one triterpenoids saponin, a derivative thereof, a metabolite thereof, or a biosynthetic intermediate thereof, of any combination thereof. In some embodiments, an in vitro biosynthetic system produces at least one triterpenoids saponin, a derivative thereof, a metabolite thereof, or a biosynthetic intermediate thereof, of any combination thereof. In some embodiments, a genetically modified plant disclosed herein comprises an increased content of at least one triterpenoids saponin, a derivative thereof, a metabolite thereof, or a biosynthetic intermediate thereof, of any combination thereof. In some embodiments, a genetically modified plant comprising at least one genetically modified cell as disclosed herein, comprises a decreased content of at least one triterpenoids saponin, a derivative thereof, a metabolite thereof, or a biosynthetic intermediate thereof, of any combination thereof. In some embodiments, a genetically modified plant disclosed herein comprising at least one genetically modified cells comprises an increased content of at least one triterpenoids saponin, a derivative thereof, a metabolite thereof, or a biosynthetic intermediate thereof, of any combination thereof, and a decreased content of at least one triterpenoids saponin, a derivative thereof, a metabolite thereof, or a biosynthetic intermediate thereof, of any combination thereof.

In some embodiments, a method of producing a triterpenoid saponin in a genetically modified cell disclosed herein comprises producing an at least one triterpenoids saponin, a derivative thereof, a metabolite thereof, or a biosynthetic intermediate thereof, of any combination thereof. In some embodiments, a method of producing a triterpenoid saponin in a genetically modified plant or plant part comprises producing of at least one triterpenoids saponin, a derivative thereof, a metabolite thereof, or a biosynthetic intermediate thereof, of any combination thereof. In some embodiments, disclosed herein is a method of reducing the content of at least one triterpenoids saponin, a derivative thereof, a metabolite thereof, or a biosynthetic intermediate thereof, of any combination thereof in a plant or plant part comprising an at least one genetically modified cell as described herein. In some embodiments, disclosed herein is a method of increasing the content of at least one triterpenoids saponin, a derivative thereof, a metabolite thereof, or a biosynthetic intermediate thereof, of any combination thereof in a plant or plant part comprising an at least one genetically modified cell as described herein.

The commonly used nomenclature for saponins distinguishes between triterpenoid saponins (also called triterpene saponins) and steroidal saponins, which is based on the structure and biochemical background of their aglycones. Both sapogenin types are thought to derive from 2,3-oxidosqualene, a central metabolite in sterol biosynthesis. In phytosterol anabolism, 2,3-oxidosqualene is mainly cyclized into cycloartenol. "Triterpenoid sapogenins" branch off the phytosterol pathway by alternative cyclization of 2,3-oxidosqualene, while "steroidal sapogenins" are thought to derive from intermediates in the phytosterol pathway downstream of cycloartenol formation (see FIG. 3A).

Saponins may be selected from the group comprising dammarane-type saponins, tirucallane-type saponins, lupane-type saponins, oleanane-type saponins, taraxasterane-type saponins, ursane-type saponins, hopane-type saponins, cucurbitane-type saponins, cycloartane-type saponins, lanostane-type saponins, and steroid-type saponins. The aglycon backbones, the sapogenins, can be similarly classified and may be selected from the group comprising dammarane-type sapogenins, tirucallane-type sapogenins, lupane-type sapogenins, oleanane-type sapogenins, taraxasterane-type sapogenins, ursane-type sapogenins, hopane-type sapogenins, cucurbitane-type sapogenins, cycloartane-type sapogenins, lanostane-type sapogenins, and steroid-type sapogenins.

In some embodiments, the "triterpenoid sapogenins" disclosed herein may be selected from the group comprising dammarane-type sapogenins, tirucallane-type sapogenins, lupane-type sapogenins, oleanane-type sapogenins, ursane-type sapogenins, and hopane-type sapogenins. In some embodiment, the triterpenoid sapogenins as produced by the method of the disclosure are dammarane-type sapogenins, or tirucallane-type sapogenins, or lupane-type sapogenins, or oleanane-type sapogenins, or ursane-type sapogenins, or hopane-type sapogenins.

Triterpenoid sapogenins typically have a tetracyclic or pentacyclic skeleton. In some embodiments, the sapogenin building blocks themselves may have multiple modifications, for example but not limited to small functional groups, including hydroxyl, keto, aldehyde, and carboxyl moieties, of precursor sapogenin backbones such as βamyrin, lupeol, and dammarenediol.

The terms "triterpene" and "triterpenoid" may be used interchangeably having the same meaning and qualities. Triterpenoid saponins comprise multiple functions and may be used in different roles including but not limited to as a sweetener, a foaming agent, an emulsifier, a preservative, an anti-carcinogen, a hypocholesterolemic agent, an anti-inflammatory agent, an anti-oxidant, a biological adjuvant, an anti-microbial agent, an insecticidal agent, an antifeedant, an anti-fungal agent, or any combination thereof.

In some embodiments, a triterpenoid sapogenins, as disclosed herein, also encompass new-to-nature triterpenoid compounds, which are structurally related to the naturally occurring triterpenoid sapogenins. These new-to-nature triterpenoid sapogenins may be novel compounds that can be obtained after genetic engineering of the synthesizing eukaryotic host cell, for example a plant cell or a yeast cell.

Examples of triterpenoid saponins and biosynthetic intermediates thereof are presented in Table 2 below.

TABLE 2

Triterpenoid Saponins and Biosynthetic Intermediates Thereof

| COMPOUND | STRUCTURE | NAME |
|---|---|---|
| 1 | 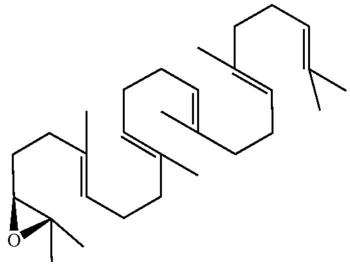 | (S)-2,3-Oxidosqualene |
| 2 | 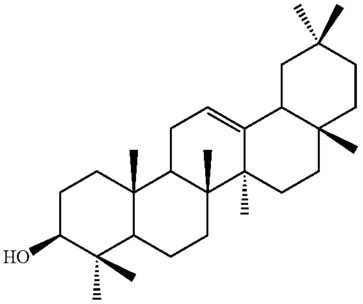 | β-Amyrin |

TABLE 2-continued
| Triterpenoid Saponins and Biosynthetic Intermediates Thereof | | |
|---|---|---|
| COMPOUND | STRUCTURE | NAME |
| 3 | 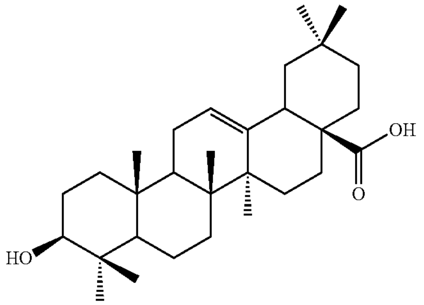 | Oleanolic acid (OA) |
| 4 | 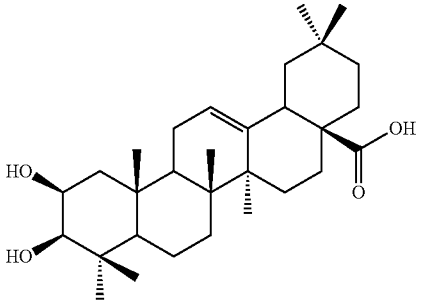 | Augustic acid (AA) |
| 5 | 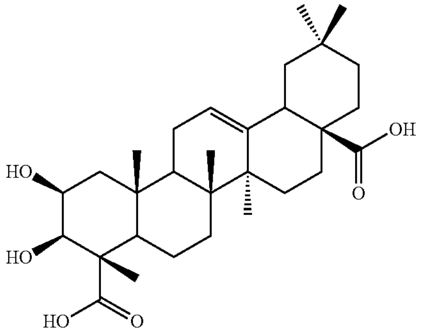 | Medicagenic acid (MA) |
| 6 | 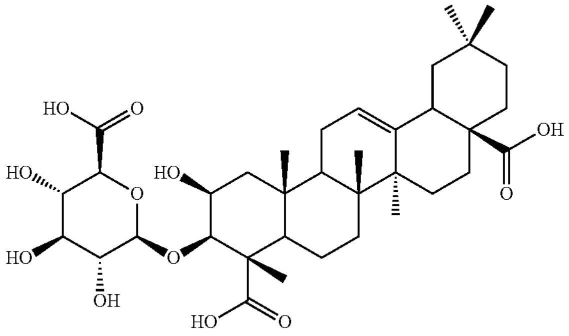 | Medicagenic acid 3-glucuronide |

TABLE 2-continued

Triterpenoid Saponins and Biosynthetic Intermediates Thereof

| COMPOUND | STRUCTURE | NAME |
|---|---|---|
| 7 | 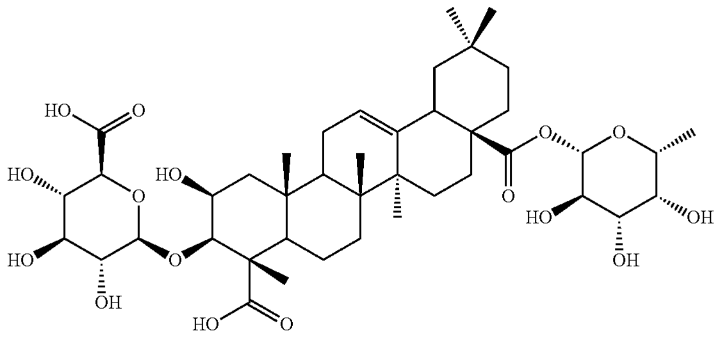 | Yossoside I (3-O-β-D-glucuronopyranosyl-28-O-β-D-fucopyranosyl-medicagenic acid) |
| 8 | 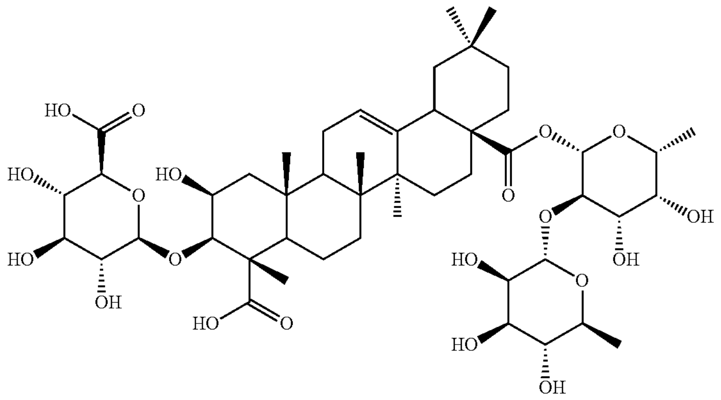 | Yossoside II (3-O-[β-D-glucuronopyranosyl]-28-O[α-L-rhamnopyranosyl-(1->2)-β-D-fucopyranosyl]-medicagenic acid) |
| 9 | 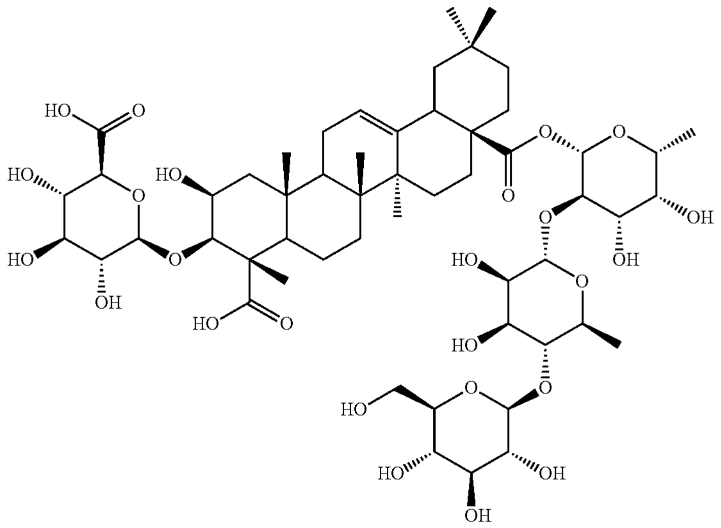 | Yossoside III (3-O-[β-D-glucuronopyranosyl]-28-O-[β-D-glucopyranosyl-(1->4)-α-L-rhamnopyranosyl-(1->2)-β-D-fucopyranosyl]-medicagenic acid) |

TABLE 2-continued

Triterpenoid Saponins and Biosynthetic Intermediates Thereof

| COMPOUND | STRUCTURE | NAME |
|---|---|---|
| 10 | 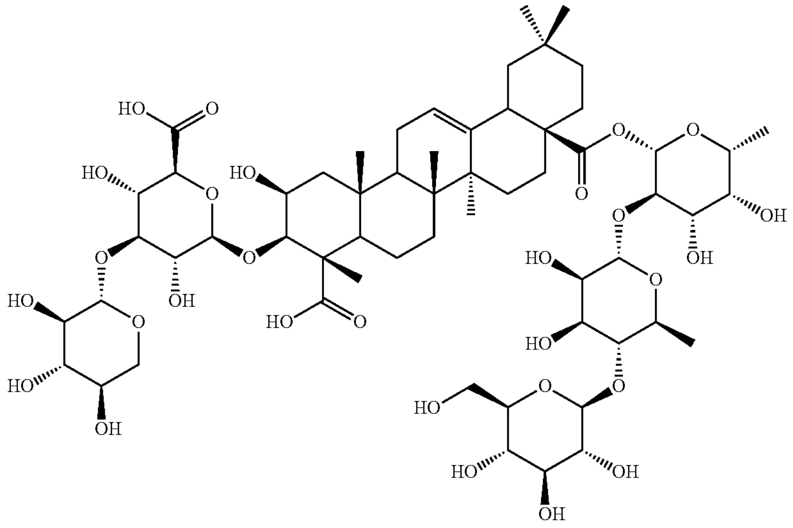 | Yossoside IV (3-O-[β-D-xylopyranosyl-(1->3)-β-D-glucuronopyranosyl]-28-O-[β-D-glucopyranosyl-(1->4)-α-L-rhamnopyranosyl-(1->2)-β-D-fucopyranosyl]-medicagenic acid) |
| 11 | 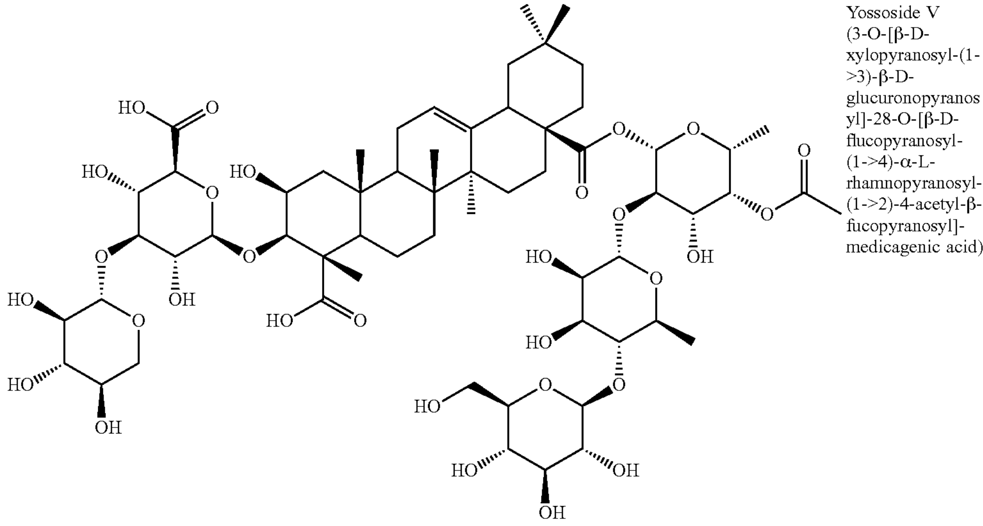 | Yossoside V (3-O-[β-D-xylopyranosyl-(1->3)-β-D-glucuronopyranosyl]-28-O-[β-D-flucopyranosyl-(1->4)-α-L-rhamnopyranosyl-(1->2)-4-acetyl-β-D-fucopyranosyl]-medicagenic acid) |
| 12 | 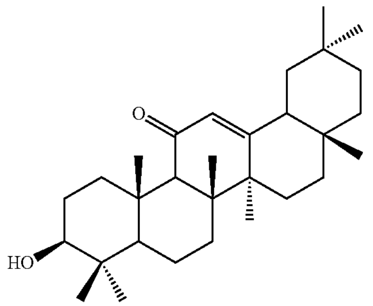 | 11-oxo-β-Amyrin |

TABLE 2-continued

| Triterpenoid Saponins and Biosynthetic Intermediates Thereof | | |
|---|---|---|
| COMPOUND | STRUCTURE | NAME |
| 13 | 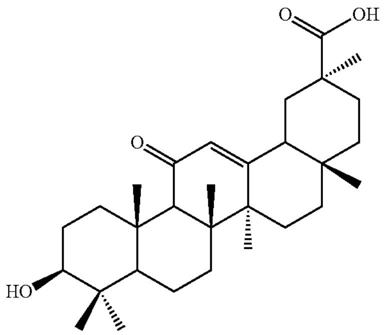 | glycyrrhetinic acid |
| 14 | 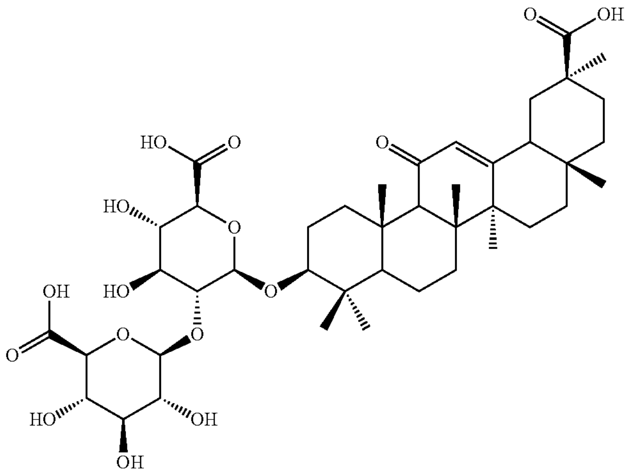 | glycyrrhizin |
| 15 | 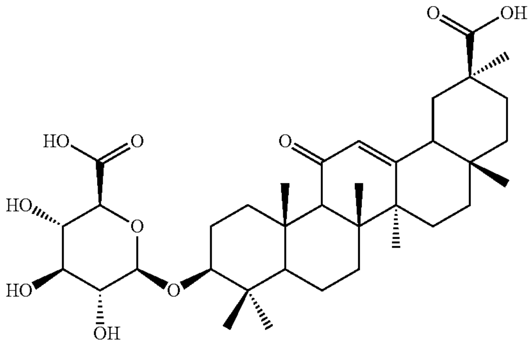 | glycyrrhetinic acid 3-O-monoglucuronide |
| 16 | not available | Yossoside Va |
| 17 | not available | Yossoside VI |
| 18 | not available | Yossoside VII |
| 19 | not available | Yossoside VIIa |
| 20 | not available | Yossoside VIII |
| 21 | not available | Yossoside IX |
| 22 | not available | Yossoside X |
| 23 | not available | Yossoside XI |
| 24 | not available | Yossoside XII |

TABLE 2-continued
| Triterpenoid Saponins and Biosynthetic Intermediates Thereof | | |
|---|---|---|
| COMPOUND | STRUCTURE | NAME |
| 25 | 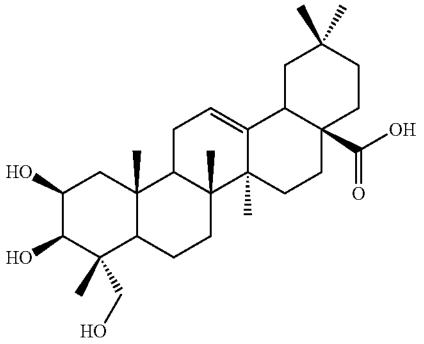 | Bayogenin |
| 26 | 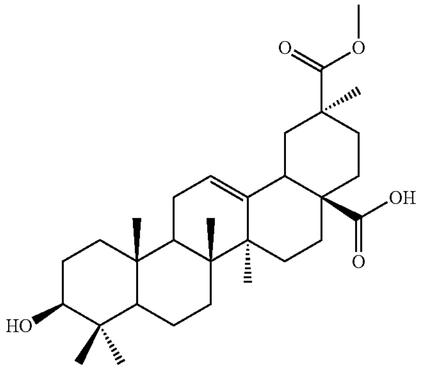 | Serjanic acid |
| 27 | 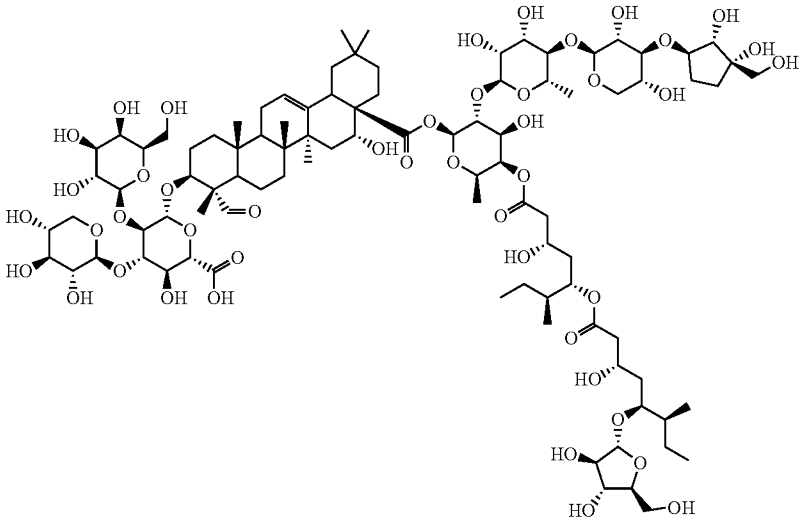 | QS-21 |
| 28 | 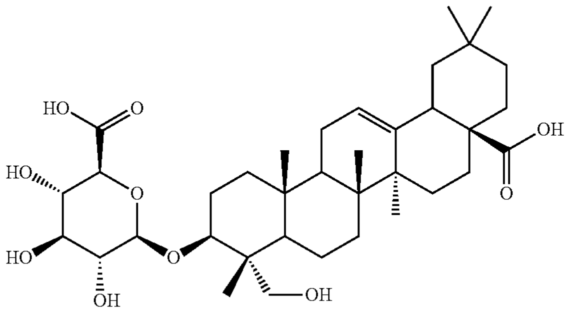 | Hederagenin-3GlcA |

TABLE 2-continued
Triterpenoid Saponins and Biosynthetic Intermediates Thereof
| COMPOUND | STRUCTURE | NAME |
|---|---|---|
| 29 | 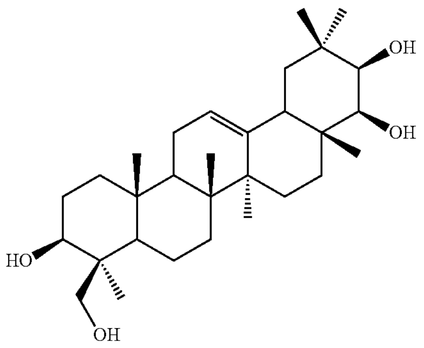 | Soyasapogenol A |
| 30 | 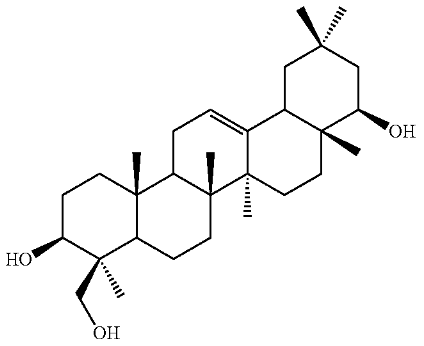 | Soyasapogenol B |
| 31 | 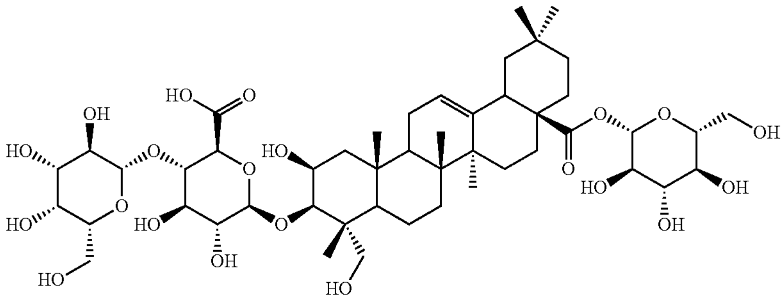 | Bayogenin-hexA-hex-hex |
| 32 | 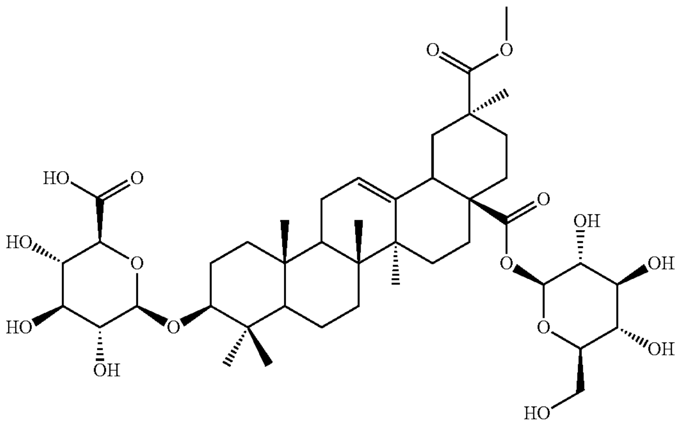 | Serjanic acid GlcA-glc |

TABLE 2-continued
| Triterpenoid Saponins and Biosynthetic Intermediates Thereof | | |
|---|---|---|
| COMPOUND | STRUCTURE | NAME |
| 33 | 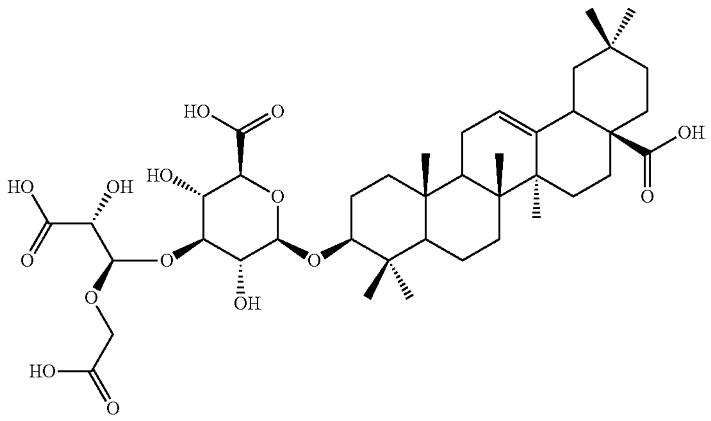 | betavulgaroside IV |
| 34 | 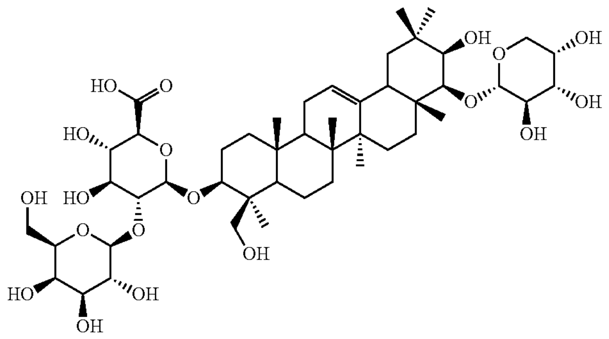 | Soyasapogenol A hexA-hex-pent |
| 35 | 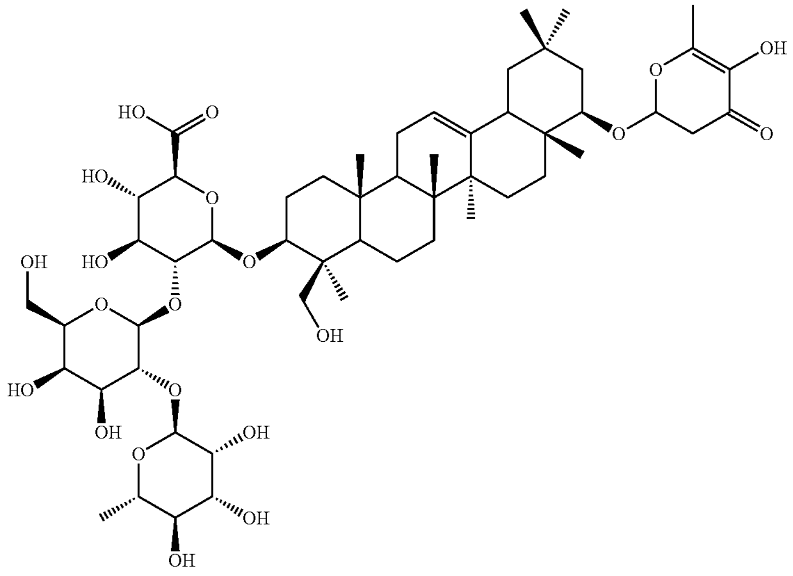 | soyasaponin VI |

In some embodiments, derivatives of triterpenoid saponins comprise glycosylated derivatives of triterpenoid saponins.

In some embodiments, a triterpenoid saponins disclosed herein comprise any one of medicagenic acid 3-O-glucuronide (MA-3-GlcA) (Compound 6), Compound 7, Compound 8, Compound 9, Compound 10, Compound 11, glycyrrhizin (Compound 14), glycyrrhetinic acid 3-O-monoglucuronide (Compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof.

In some embodiments, a triterpenoid saponin comprises medicagenic acid 3-O-glucuronide (MA-3-GlcA) (Compound 6). In some embodiments, a triterpenoid saponin comprises Compound 7. In some embodiments, a triterpenoid saponin comprises Compound 8. In some embodiments, a triterpenoid saponin comprises Compound 9. In some embodiments, a triterpenoid saponin comprises Compound 10. In some embodiments, a triterpenoid saponin comprises Compound 11. In some embodiments, a triterpenoid saponin comprises glycyrrhizin (Compound 14). In some embodiments, a triterpenoid saponin comprises glycyrrhetinic acid 3-O-monoglucuronide (Compound 15). In some embodiments, a triterpenoid saponin comprises bayogenin (Compound 25). In some embodiments, a triterpenoid saponin comprises bayogenin-hexA-hex-hex (Compound 31). In some embodiments, a triterpenoid saponin comprises serjanic acid (Compound 26). In some embodiments, a triterpenoid saponin comprises serjanic acid-hexA-hex (Compound 32). In some embodiments, a triterpenoid saponin comprises soyasapogenol A (Compound 29). In some embodiments, a triterpenoid saponin comprises soyasapogenol B (Compound 30). In some embodiments, a triterpenoid saponin comprises soyasapogenol A-hexA-hex-pent (Compound 34). In some embodiments, a triterpenoid saponin comprises soyasaponin VI (Compound 35). In some embodiments, a triterpenoid saponin comprises betavulgaroside IV (Compound 33). In some embodiments, a triterpenoid saponin comprises hederagenin-3GlcA. In some embodiments, a triterpenoid saponin comprises gypsogenin-3GlcA. In some embodiments, a triterpenoid saponin comprises gypsogenic acid-3GlcA. In some embodiments, a triterpenoid saponin comprises a QS-21 adjuvant.

Altering the content of a triterpenoid saponin may in some embodiments, be commercially beneficial, for example but not limited to the ability to produce the sweetener, glycyrrhizin (Compound 14). In some embodiments, it is commercially beneficial to produce a triterpenoid saponin comprising any of a sweetener, foaming agent, emulsifier, preservative, anti-carcinogen, hypocholesterolemic agent, anti-inflammatory agent, anti-oxidant, biological adjuvant, anti-microbial agent, insecticidal agent, antifeedant, antifungal agent, or any combination thereof. In other embodiments, altering the content of a triterpenoid saponin may be beneficial, for example but not limited to reducing or eliminating bitter tasting triterpenoid saponins, for example but not limited to in *quinoa*, which is produced from a *Chenopodium quinoa* plant in the Caryophyllales order of plants. In other embodiments, altering the content of a triterpenoid saponin may be beneficial, for example but not limited to reducing or eliminating triterpenoid saponins that have hormone mimicking properties.

In some embodiments, a genetically modified cell disclosed herein comprises an increased content of at least one triterpenoid saponin selected from any one of medicagenic acid 3-O-glucuronide (MA-3-GlcA)(Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof. In some embodiments, a genetically modified cell disclosed herein comprises an increased content of medicagenic acid 3-O-glucuronide (MA-3-GlcA) (Compound 6). In some embodiments, a genetically modified cell disclosed herein comprises an increased content of Compound 7. In some embodiments, a genetically modified cell disclosed herein comprises an increased content of Compound 8. In some embodiments, a genetically modified cell disclosed herein comprises an increased content of Compound 9. In some embodiments, a genetically modified cell disclosed herein comprises an increased content of Compound 10. In some embodiments, a genetically modified cell disclosed herein comprises an increased content of Compound 11. In some embodiments, a genetically modified cell disclosed herein comprises an increased content of glycyrrhizin (Compound 14). In some embodiments, a genetically modified cell disclosed herein comprises an increased content of Glycyrrhetinic acid 3-O-monoglucuronide (compound 15). In some embodiments, a genetically modified cell disclosed herein comprises an increased content of bayogenin (Compound 25). In some embodiments, a genetically modified cell disclosed herein comprises an increased content of bayogenin-hexA-hex-hex (Compound 31). In some embodiments, a genetically modified cell disclosed herein comprises an increased content of serjanic acid (Compound 26). In some embodiments, a genetically modified cell disclosed herein comprises an increased content of serjanic acid-hexA-hex (Compound 32). In some embodiments, a genetically modified cell disclosed herein comprises an increased content of soyasapogenol A (Compound 29). In some embodiments, a genetically modified cell disclosed herein comprises an increased content of soyasapogenol B (Compound 30). In some embodiments, a genetically modified cell disclosed herein comprises an increased content of soyasapogenol A-hexA-hex-pent (Compound 34). In some embodiments, a genetically modified cell disclosed herein comprises an increased content of soyasaponin VI (Compound 35). In some embodiments, a genetically modified cell disclosed herein comprises an increased content of betavulgaroside IV (Compound 33). In some embodiments, a genetically modified cell disclosed herein comprises an increased content of hederagenin-3GlcA. In some embodiments, a genetically modified cell disclosed herein comprises an increased content of gypsogenin-3GlcA. In some embodiments, a genetically modified cell disclosed herein comprises an increased content of gypsogenic acid-3GlcA. In some embodiments, a genetically modified cell disclosed herein comprises an increased content of a QS-21 adjuvant.

In some embodiments, the genetically modified cell comprising said increased content comprises a plant cell, a yeast cell, an algal cell, an insect cell, or a bacterial. In some embodiments, the genetically modified cell comprising said increased content comprises a plant cell. In some embodiments, the genetically modified cell comprising said increased content comprises a yeast cell. In some embodiments, the genetically modified cell comprising said increased content comprises an algal cell. In some embodiments, the genetically modified cell comprising said increased content comprises an insect cell. In some embodiments, the genetically modified cell comprising said increased content comprises a bacterium.

In some embodiments, a genetically modified plant disclosed herein comprises an increased content of at least one triterpenoid saponin selected from any one of medicagenic acid 3-O-glucuronide (MA-3-GlcA)(Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof. In some embodiments, a genetically modified plant disclosed herein comprises an increased content of medicagenic acid 3-O-glucuronide (MA-3-GlcA) (Compound 6). In some embodiments, a genetically modified plant disclosed herein comprises an increased content of Compound 7. In some embodiments, a genetically modified plant disclosed herein comprises an increased content of Compound 8. In some embodiments, a genetically modified plant disclosed herein comprises an increased content of Compound 9. In some embodiments, a genetically modified plant disclosed herein comprises an increased content of Compound 10. In some embodiments, a genetically modified plant disclosed herein comprises an increased content of Compound 11. In some embodiments, a genetically modified plant disclosed herein comprises an increased content of glycyrrhizin (Compound 14). In some embodiments, a genetically modified plant disclosed herein comprises an increased content of Glycyrrhetinic acid 3-O-monoglucuronide (compound 15). In some embodiments, a genetically modified plant disclosed herein comprises an increased content of bayogenin (Compound 25). In some embodiments, a genetically modified plant disclosed herein comprises an increased content of bayogenin-hexA-hex-hex (Compound 31). In some embodiments, a genetically modified plant disclosed herein comprises an increased content of serjanic acid (Compound 26). In some embodiments, a genetically modified plant disclosed herein comprises an increased content of serjanic acid-hexA-hex (Compound 32). In some embodiments, a genetically modified plant disclosed herein comprises an increased content of soyasapogenol A (Compound 29). In some embodiments, a genetically modified plant disclosed herein comprises an increased content of soyasapogenol B (Compound 30). In some embodiments, a genetically modified plant disclosed herein comprises an increased content of soyasapogenol A-hexA-hex-pent (Compound 34). In some embodiments, a genetically modified plant disclosed herein comprises an increased content of soyasaponin VI (Compound 35). In some embodiments, a genetically modified plant disclosed herein comprises an increased content of betavulgaroside IV (Compound 33). In some embodiments, a genetically modified plant disclosed herein comprises an increased content of hederagenin-3GlcA. In some embodiments, a genetically modified plant disclosed herein comprises an increased content of gypsogenin-3GlcA. In some embodiments, a genetically modified plant disclosed herein comprises an increased content of gypsogenic acid-3GlcA. In some embodiments, a genetically modified plant disclosed herein comprises an increased content of a QS-21 adjuvant.

In some embodiments, a genetically modified plant disclosed herein comprises a decreased content of at least one triterpenoid saponin selected from any one of medicagenic acid 3-O-glucuronide (MA-3-GlcA)(Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof. In some embodiments, a genetically modified plant disclosed herein comprises a decreased content of medicagenic acid 3-O-glucuronide (MA-3-GlcA) (Compound 6). In some embodiments, a genetically modified plant disclosed herein comprises a decreased content of Compound 7. In some embodiments, a genetically modified plant disclosed herein comprises a decreased content of Compound 8. In some embodiments, a genetically modified plant disclosed herein comprises a decreased content of Compound 9. In some embodiments, a genetically modified plant disclosed herein comprises a decreased content of Compound 10. In some embodiments, a genetically modified plant disclosed herein comprises a decreased content of Compound 11. In some embodiments, a genetically modified plant disclosed herein comprises a decreased content of glycyrrhizin (Compound 14). In some embodiments, a genetically modified plant disclosed herein comprises a decreased content of Glycyrrhetinic acid 3-O-monoglucuronide (compound 15). In some embodiments, a genetically modified plant disclosed herein comprises a decreased content of bayogenin (Compound 25). In some embodiments, a genetically modified plant disclosed herein comprises a decreased content of bayogenin-hexA-hex-hex (Compound 31). In some embodiments, a genetically modified plant disclosed herein comprises a decreased content of serjanic acid (Compound 26). In some embodiments, a genetically modified plant disclosed herein comprises a decreased content of serjanic acid-hexA-hex (Compound 32). In some embodiments, a genetically modified plant disclosed herein comprises a decreased content of soyasapogenol A (Compound 29). In some embodiments, a genetically modified plant disclosed herein comprises a decreased content of soyasapogenol B (Compound 30). In some embodiments, a genetically modified plant disclosed herein comprises a decreased content of soyasapogenol A-hexA-hex-pent (Compound 34). In some embodiments, a genetically modified plant disclosed herein comprises a decreased content of soyasaponin VI (Compound 35). In some embodiments, a genetically modified plant disclosed herein comprises a decreased content of betavulgaroside IV (Compound 33). In some embodiments, a genetically modified plant disclosed herein comprises a decreased content of hederagenin-3GlcA. In some embodiments, a genetically modified plant disclosed herein comprises a decreased content of gypsogenin-3GlcA. In some embodiments, a genetically modified plant disclosed herein comprises a decreased content of gypsogenic acid-3GlcA. In some embodiments, a genetically modified plant disclosed herein comprises a decreased content of a QS-21 adjuvant.

In some embodiments, a genetically modified plant disclosed herein comprises an increased content of at least one triterpenoid saponin and a decreased content of at least one triterpenoid saponin selected from any one of medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof.

In some embodiments, a method of producing a triterpenoid saponin in a genetically modified cell comprises producing at least one triterpenoid saponin selected from any one of medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof. In some embodiments, a method of producing a triterpenoid saponin in a genetically modified cell comprises producing medicagenic acid 3-O-glucuronide (MA-3-GlcA) (Compound 6). In some embodiments, a method of producing a triterpenoid saponin in a genetically modified cell comprises producing Compound 7. In some embodiments, a method of producing a triterpenoid saponin in a genetically modified cell comprises producing Compound 8. In some embodiments, a method of producing a triterpenoid saponin in a genetically modified cell comprises producing Compound 9. In some embodiments, a method of producing a triterpenoid saponin in a genetically modified cell comprises producing Compound 10. In some embodiments, a method of producing a triterpenoid saponin in a genetically modified cell comprises producing Compound 11. In some embodiments, a method of producing a triterpenoid saponin in a genetically modified cell comprises producing glycyrrhizin (Compound 14). In some embodiments, a method of producing a triterpenoid saponin in a genetically modified cell comprises producing Glycyrrhetinic acid 3-O-monoglucuronide (compound 15). In some embodiments, a method of producing a triterpenoid saponin in a genetically modified cell comprises producing bayogenin (Compound 25). In some embodiments, a method of producing a triterpenoid saponin in a genetically modified cell comprises producing bayogenin-hexA-hex-hex (Compound 31). In some embodiments, a method of producing a triterpenoid saponin in a genetically modified cell comprises producing serjanic acid (Compound 26). In some embodiments, a method of producing a triterpenoid saponin in a genetically modified cell comprises producing serjanic acid-hexA-hex (Compound 32). In some embodiments, a method of producing a triterpenoid saponin in a genetically modified cell comprises producing soyasapogenol A (Compound 29). In some embodiments, a method of producing a triterpenoid saponin in a genetically modified cell comprises producing soyasapogenol B (Compound 30). In some embodiments, a method of producing a triterpenoid saponin in a genetically modified cell comprises producing soyasapogenol A-hexA-hex-pent (Compound 34). In some embodiments, a method of producing a triterpenoid saponin in a genetically modified cell comprises producing soyasaponin VI (Compound 35). In some embodiments, a method of producing a triterpenoid saponin in a genetically modified cell comprises producing betavulgaroside IV (Compound 33). In some embodiments, a method of producing a triterpenoid saponin in a genetically modified cell comprises producing hederagenin-3GlcA. In some embodiments, a method of producing a triterpenoid saponin in a genetically modified cell comprises producing gypsogenin-3GlcA. In some embodiments, a method of producing a triterpenoid saponin in a genetically modified cell comprises producing gypsogenic acid-3GlcA. In some embodiments, a method of producing a triterpenoid saponin in a genetically modified cell comprises producing a QS-21 adjuvant.

In some embodiments, the method of producing at least one triterpenoid saponin in a genetically modified cell comprises producing at least one triterpenoid saponins in a plant cell, a yeast cell, an algal cell, an insect cell, or a bacterium. In some embodiments, the method of producing at least one triterpenoid saponin in a genetically modified cell comprises producing at least one triterpenoid saponins in a plant cell. In some embodiments, the method of producing at least one triterpenoid saponin in a genetically modified cell comprises producing at least one triterpenoid saponins in a yeast cell. In some embodiments, the method of producing at least one triterpenoid saponin in a genetically modified cell comprises producing at least one triterpenoid saponins in an algal cell. In some embodiments, the method of producing at least one triterpenoid saponin in a genetically modified cell comprises producing at least one triterpenoid saponins in an insect cell. In some embodiments, the method of producing at least one triterpenoid saponin in a genetically modified cell comprises producing at least one triterpenoid saponins in a bacterium. In some embodiments, the plant cell is comprised in a plant or plant part.

In some embodiments, a method of producing a triterpenoid saponin in a genetically modified plant comprises producing at least one triterpenoid saponin selected from any one of medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof. In some embodiments, a method of producing a triterpenoid saponin in a genetically modified plant comprises producing medicagenic acid 3-O-glucuronide (MA-3-GlcA) (Compound 6). In some embodiments, a method of producing a triterpenoid saponin in a genetically modified plant comprises producing Compound 7. In some embodiments, a method of producing a triterpenoid saponin in a genetically modified plant comprises producing Compound 8. In some embodiments, a method of producing a triterpenoid saponin in a genetically modified plant comprises producing Compound 9. In some embodiments, a method of producing a triterpenoid saponin in a genetically modified plant comprises producing Compound 10. In some embodiments, a method of producing a triterpenoid saponin in a genetically modified plant comprises producing Compound 11. In some embodiments, a method of producing a triterpenoid saponin in a genetically modified plant comprises producing glycyrrhizin (Compound 14). In some embodiments, a method of producing a triterpenoid saponin in a genetically modified plant comprises producing Glycyrrhetinic acid 3-O-monoglucuronide (compound 15). In some embodiments, a method of producing a triterpenoid saponin in a genetically modified plant comprises producing bayogenin (Compound 25). In some embodiments, a method of producing a triterpenoid saponin in a genetically modified plant comprises producing bayogenin-hexA-hex-hex (Compound 31). In some embodiments, a method of producing a triterpenoid saponin in a genetically modified plant comprises producing serjanic acid (Compound 26). In some embodiments, a method of producing a triterpenoid saponin in a genetically modified plant comprises producing serjanic acid-hexA-hex (Compound 32). In some embodiments, a method of producing a triterpenoid saponin in a genetically modified plant comprises producing soyasapogenol A (Compound 29). In some embodiments, a method of producing a triterpenoid saponin in a genetically modified plant comprises producing soyasapogenol B (Compound 30). In some embodiments, a method of producing a triterpenoid saponin in a genetically modified plant comprises producing soyasapogenol A-hexA-hex-pent (Compound 34). In some embodiments, a method of producing a triterpenoid saponin in a genetically modified plant comprises producing soyasaponin VI (Compound 35). In some embodiments, a method of producing a triterpenoid saponin in a genetically modified plant comprises producing betavulgaroside IV (Compound 33). In some embodiments, a method of producing a triterpenoid saponin in a genetically modified plant comprises producing hederagenin-3GlcA. In some embodiments, a method of producing a triterpenoid saponin in a genetically modified plant comprises producing gypsogenin-3GlcA. In some embodiments, a method of producing a triterpenoid saponin in a genetically modified plant comprises producing gypsogenic acid-3GlcA. In some embodiments, a method of producing a triterpenoid saponin in a genetically modified plant comprises producing a QS-21 adjuvant.

In some embodiments, a method of producing a triterpenoid saponin in an in vitro translation system comprises producing at least one triterpenoid saponin selected from any one of medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof. In some embodiments, a method of producing a triterpenoid saponin in an in vitro translation system comprises producing medicagenic acid 3-O-glucuronide (MA-3-GlcA) (Compound 6). In some embodiments, a method of producing a triterpenoid saponin in an in vitro translation system comprises producing Compound 7. In some embodiments, a method of producing a triterpenoid saponin in an in vitro translation system comprises producing Compound 8. In some embodiments, a method of producing a triterpenoid saponin in an in vitro translation system comprises producing Compound 9. In some embodiments, a method of producing a triterpenoid saponin in an in vitro translation system comprises producing Compound 10. In some embodiments, a method of producing a triterpenoid saponin in an in vitro translation system comprises producing Compound 11. In some embodiments, a method of producing a triterpenoid saponin in an in vitro translation system comprises producing glycyrrhizin (Compound 14). In some embodiments, a method of producing a triterpenoid saponin in an in vitro translation system comprises producing Glycyrrhetinic acid 3-O-monoglucuronide (compound 15). In some embodiments, a method of producing a triterpenoid saponin in an in vitro translation system comprises producing bayogenin (Compound 25). In some embodiments, a method of producing a triterpenoid saponin in an in vitro translation system comprises producing bayogenin-hexA-hex-hex (Compound 31). In some embodiments, a method of producing a triterpenoid saponin in an in vitro translation system comprises producing serjanic acid (Compound 26). In some embodiments, a method of producing a triterpenoid saponin in an in vitro translation system comprises producing serjanic acid-hexA-hex (Compound 32). In some embodiments, a method of producing a triterpenoid saponin in an in vitro translation system comprises producing soyasapogenol A (Compound 29). In some embodiments, a method of producing a triterpenoid saponin in an in vitro translation system comprises producing soyasapogenol B (Compound 30). In some embodiments, a method of producing a triterpenoid saponin in an in vitro translation system comprises producing soyasapogenol A-hexA-hex-pent (Compound 34). In some embodiments, a method of producing a triterpenoid saponin in an in vitro translation system comprises producing soyasaponin VI (Compound 35). In some embodiments, a method of producing a triterpenoid saponin in an in vitro translation system comprises producing betavulgaroside IV (Compound 33). In some embodiments, a method of producing a triterpenoid saponin in an in vitro translation system comprises producing hederagenin-3GlcA. In some embodiments, a method of producing a triterpenoid saponin in an in vitro translation system comprises producing gypsogenin-3GlcA. In some embodiments, a method of producing a triterpenoid saponin in an in vitro translation system comprises producing gypsogenic acid-3GlcA. In some embodiments, a method of producing a triterpenoid saponin in an in vitro translation system comprises producing a QS-21 adjuvant.

In some embodiments, a method of reducing at least one triterpenoid saponin comprises reducing at least one triterpenoid saponin selected from any one of medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof. In some embodiments, a method of reducing the content of at least one triterpenoid saponin comprising medicagenic acid 3-O-glucuronide (MA-3-GlcA) (Compound 6). In some embodiments, a method of reducing at least one triterpenoid saponin comprises reducing Compound 7. In some embodiments, a method of reducing at least one triterpenoid saponin comprises reducing Compound 8. In some embodiments, a method of reducing at least one triterpenoid saponin comprises reducing Compound 9. In some embodiments, a method of reducing at least one triterpenoid saponin comprises reducing Compound 10. In some embodiments, a method of reducing at least one triterpenoid saponin comprises reducing Compound 11. In some embodiments, a method of reducing at least one triterpenoid saponin comprises reducing glycyrrhizin (Compound 14). In some embodiments, a method of reducing at least one triterpenoid saponin comprises reducing Glycyrrhetinic acid 3-O-monoglucuronide (compound 15). In some embodiments, a method of reducing at least one triterpenoid saponin comprises reducing bayogenin (Compound 25). In some embodiments, a method of reducing at least one triterpenoid saponin comprises reducing bayogenin-hexA-hex-hex (Compound 31). In some embodiments, a method of reducing at least one triterpenoid saponin comprises reducing serjanic acid (Compound 26). In some embodiments, a method of reducing at least one triterpenoid saponin comprises reducing serjanic acid-hexA-hex (Compound 32). In some embodiments, a method of reducing at least one triterpenoid saponin comprises reducing soyasapogenol A (Compound 29). In some embodiments, a method of reducing at least one triterpenoid saponin comprises reducing soyasapogenol B (Compound 30). In some embodiments, a method of reducing at least one triterpenoid saponin comprises reducing soyasapogenol A-hexA-hex-pent (Compound 34). In some embodiments, a method of reducing at least one triterpenoid saponin comprises reducing soyasaponin VI (Compound 35). In some embodiments, a method of reducing at least one triterpenoid saponin comprises reducing betavulgaroside IV (Compound 33). In some embodiments, a method of reducing at least one triterpenoid saponin comprises reducing hederagenin-3GlcA. In some embodiments, a method of reducing at least one triterpenoid saponin comprises reducing gypsogenin-3GlcA. In some embodiments, a method of reducing at least one triterpenoid saponin comprises reducing gypsogenic acid-3GlcA. In some embodiments, a method of reducing at least one triterpenoid saponin comprises reducing a QS-21 adjuvant.

In some embodiments, a method of increasing at least one triterpenoid saponin comprises increasing at least one triterpenoid saponin selected from any one of medicagenic acid 3-O-glucuronide (MA-3-GlcA)(Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof. In some embodiments, a method of increasing the content of at least one triterpenoid saponin comprising medicagenic acid 3-O-glucuronide (MA-3-GlcA) (Compound 6). In some embodiments, a method of increasing at least one triterpenoid saponin comprises increasing Compound 7. In some embodiments, a method of increasing at least one triterpenoid saponin comprises increasing Compound 8. In some embodiments, a method of increasing at least one triterpenoid saponin comprises increasing Compound 9. In some embodiments, a method of increasing at least one triterpenoid saponin comprises increasing Compound 10. In some embodiments, a method of increasing at least one triterpenoid saponin comprises increasing Compound 11. In some embodiments, a method of increasing at least one triterpenoid saponin comprises increasing glycyrrhizin (Compound 14). In some embodiments, a method of increasing at least one triterpenoid saponin comprises increasing Glycyrrhetinic acid 3-O-monoglucuronide (compound 15). In some embodiments, a method of increasing at least one triterpenoid saponin comprises increasing bayogenin (Compound 25). In some embodiments, a method of increasing at least one triterpenoid saponin comprises increasing bayogenin-hexA-hex-hex (Compound 31). In some embodiments, a method of increasing at least one triterpenoid saponin comprises increasing serjanic acid (Compound 26). In some embodiments, a method of increasing at least one triterpenoid saponin comprises increasing serjanic acid-hexA-hex (Compound 32). In some embodiments, a method of increasing at least one triterpenoid saponin comprises increasing soyasapogenol A (Compound 29). In some embodiments, a method of increasing at least one triterpenoid saponin comprises increasing soyasapogenol B (Compound 30). In some embodiments, a method of increasing at least one triterpenoid saponin comprises increasing soyasapogenol A-hexA-hex-pent (Compound 34). In some embodiments, a method of increasing at least one triterpenoid saponin comprises increasing soyasaponin VI (Compound 35). In some embodiments, a method of increasing at least one triterpenoid saponin comprises increasing betavulgaroside IV (Compound 33). In some embodiments, a method of increasing at least one triterpenoid saponin comprises increasing hederagenin-3GlcA. In some embodiments, a method of increasing at least one triterpenoid saponin comprises increasing gypsogenin-3GlcA. In some embodiments, a method of increasing at least one triterpenoid saponin comprises increasing gypsogenic acid-3GlcA. In some embodiments, a method of increasing at least one triterpenoid saponin comprises increasing a QS-21 adjuvant.

In some embodiments, the content of both at least one triterpenoid saponin and at least one triterpenoid saponin biosynthetic intermediate are altered. In some embodiments, an at least one triterpenoid saponin and an at least one triterpenoid saponin biosynthetic intermediate are increased. In some embodiments, an at least one triterpenoid saponins and an at least one triterpenoid saponin biosynthetic intermediate are decreased. In some embodiments, an at least one triterpenoid saponin is increased and an at least one triterpenoid saponin biosynthetic intermediate is decreased. In some embodiments, an at least one triterpenoid saponin is decreased and an at least one triterpenoid saponin biosynthetic intermediate is increased. In some embodiments, the content of a triterpenoid saponin is altered without measurably altering the content of a triterpenoid saponin intermediate. In some embodiments, the content of a triterpenoid saponin intermediate is altered without measurably altering the content of a triterpenoid saponin.

The term "intermediate" may be used interchangeably in some embodiments with the term "biosynthetic intermediate", having all the same qualities and meanings.

In some embodiments, a biosynthetic intermediate of a triterpenoid saponin comprises Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof.

In some embodiments, a genetically modified cell disclosed herein comprises an increased content of at least one biosynthetic intermediate of a triterpenoid saponin comprising Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof. In some embodiments, a genetically modified cell comprises an increased content of at least one biosynthetic intermediate of a triterpenoid saponin comprising Compound 1. In some embodiments, a genetically modified cell comprises an increased content of at least one biosynthetic intermediate of a triterpenoid saponin comprising Compound 2. In some embodiments, a genetically modified cell comprises an increased content of at least one biosynthetic intermediate of a triterpenoid saponin comprising medicagenic acid (Compound 5). In some embodiments, a genetically modified cell comprises an increased content of at least one biosynthetic intermediate of a triterpenoid saponin comprising oleanolic acid (Compound 3). In some embodiments, a genetically modified cell comprises an increased content of at least one biosynthetic intermediate of a triterpenoid saponin comprising oleanolic acid-3GlcA. In some embodiments, a genetically modified cell comprises an increased content of at least one biosynthetic intermediate of a triterpenoid saponin comprising augustic acid (Compound 4). In some embodiments, a genetically modified cell comprises an increased content of at least one biosynthetic intermediate of a triterpenoid saponin comprising augustic acid-3GlcA. In some embodiments, a genetically modified cell comprises an increased content of at least one biosynthetic intermediate of a triterpenoid saponin comprising glycyrrhetinic acid (Compound 13).

In some embodiments, a genetically modified plant disclosed herein comprises a decreased content of at least one biosynthetic intermediate of a triterpenoid saponin comprising Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof. In some embodiments, a genetically modified plant comprises a decreased content of at least one biosynthetic intermediate of a triterpenoid saponin comprising Compound 1. In some embodiments, a genetically modified plant comprises a decreased content of at least one biosynthetic intermediate of a triterpenoid saponin comprising Compound 2. In some embodiments, a genetically modified plant comprises a decreased content of at least one biosynthetic intermediate of a triterpenoid saponin comprising medicagenic acid (Compound 5). In some embodiments, a genetically modified plant comprises a decreased content of at least one biosynthetic intermediate of a triterpenoid saponin comprising oleanolic acid (Compound 3). In some embodiments, a genetically modified plant comprises a decreased content of at least one biosynthetic intermediate of a triterpenoid saponin comprising oleanolic acid-3GlcA. In some embodiments, a genetically modified plant comprises a decreased content of at least one biosynthetic intermediate of a triterpenoid saponin comprising augustic acid (Compound 4). In some embodiments, a genetically modified plant comprises a decreased content of at least one biosynthetic intermediate of a triterpenoid saponin comprising augustic acid-3GlcA. In some embodiments, a genetically modified plant comprises a decreased content of at least one biosynthetic intermediate of a triterpenoid saponin comprising glycyrrhetinic acid (Compound 13).

In some embodiments, a genetically modified plant disclosed herein comprises an increased content of at least one triterpenoid saponin biosynthetic intermediate and a decreased content of at least one triterpenoid saponin biosynthetic intermediate, said intermediate selected from any one of Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof.

In some embodiments, a method of reducing at least one triterpenoid saponin comprises reducing at least one triterpenoid saponin biosynthetic intermediate selected from any one of Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof. In some embodiments, a method of reducing at least one triterpenoid saponin comprises reducing at least Compound 1. In some embodiments, a method of reducing at least one triterpenoid saponin comprises reducing at least Compound 2. In some embodiments, a method of reducing at least one triterpenoid saponin comprises reducing at least medicagenic acid (Compound 5) In some embodiments, a method of reducing at least one triterpenoid saponin comprises reducing at least oleanolic acid (Compound 3) In some embodiments, a method of reducing at least one triterpenoid saponin comprises reducing at least oleanolic acid-3GlcA In some embodiments, a method of reducing at least one triterpenoid saponin comprises reducing at least augustic acid (Compound 4) In some embodiments, a method of reducing at least one triterpenoid saponin comprises reducing at least augustic acid-3GlcA In some embodiments, a method of reducing at least one triterpenoid saponin comprises reducing at least glycyrrhetinic acid (Compound 13).

In some embodiments, a method of increasing at least one triterpenoid saponin comprises increasing at least one triterpenoid saponin biosynthetic intermediate selected from any one of Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof. In some embodiments, a method of increasing at least one triterpenoid saponin comprises increasing at least Compound 1. In some embodiments, a method of increasing at least one triterpenoid saponin comprises increasing at least Compound 2. In some embodiments, a method of increasing at least one triterpenoid saponin comprises increasing at least medicagenic acid (Compound 5) In some embodiments, a method of increasing at least one triterpenoid saponin comprises increasing at least oleanolic acid (Compound 3) In some embodiments, a method of increasing at least one triterpenoid saponin comprises increasing at least oleanolic acid-3GlcA In some embodiments, a method of increasing at least one triterpenoid saponin comprises increasing at least augustic acid (Compound 4) In some embodiments, a method of increasing at least one triterpenoid saponin comprises increasing at least augustic acid-3GlcA In some embodiments, a method of increasing at least one triterpenoid saponin comprises increasing at least glycyrrhetinic acid (Compound 13).

In some embodiments, triterpenoid saponins biosynthetic intermediate comprises any Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or a combination thereof.

Unexpectedly, the present disclosure now shows that levels of triterpenoid saponins or their derivatives, metabolites, or biosynthetic intermediates can be increased in cells, for example plant cells or yeast cells or algal cells, or insect cells, or bacterium, or plants by genetically modifying the cell or plant to express at least one heterologous gene encoding an enzyme, for example an enzyme or enzymes of the triterpenoid saponin biosynthetic pathway. In other embodiments, described and exemplified herein are methods of genetically modifying an at least one endogenous gene in a plant cell, for example but not limited to a CSLG gene, to regulate expression, activity, or stability, or any combination thereof. The Examples below disclose enzyme activities and enzymes previously unknown to be part of the triterpenoid saponin biosynthetic pathway. Without this knowledge, production of the triterpenoid saponin compounds was not possible.

In some embodiments, the triterpenoid saponin metabolic pathway can result in cells or plants comprising elevated content of triterpenoid saponins, a derivative thereof, a metabolite thereof, or a biosynthetic intermediate thereof, or in plants having an increased content of these compounds in the plant or plant parts. In some embodiments, plants including but not limited to crop plants are produced, wherein the crop has an increased content of a useful triterpenoid saponin or triterpenoid saponins. In some embodiments, disclosed herein are the means and methods for producing cells including but not limited to plant cells, yeast, or algal cells; plants including but not limited to crop plants, or a part of a plant, having increased levels of a triterpenoid saponin, or triterpenoid saponins, or derivatives thereof, or metabolites thereof, or a biosynthetic intermediate thereof. Alternatively, or additionally, controlling the expression of genes disclosed herein may be used for the production of desired triterpenoid saponins for further use, for example in the pharmaceutical industry or for the formulation of dietary or other supplements, for example but not limited to sweeteners. In some embodiments, these high value saponins may be purified and used, e.g., as sweeteners, foaming agents, emulsifiers, preservatives, anti-carcinogens, hypocholesterolemic agents, anti-inflammatory agents, antioxidants, biological adjuvants, anti-microbial agents, insecticidal agents, anti-feedants, or anti-fungal agents, or any combination thereof. The cells and plants disclosed herein comprise compounds of significant nutritional, pharmaceutical, and commercial value.

In some embodiments, a genetically modified cell or genetically modified plant or plant part comprising at least one genetically modified plant cell, as described herein, comprises an altered content of at least a triterpenoid saponin, a derivative thereof, a metabolite thereof, or a biosynthetic intermediate thereof, compared to a corresponding unmodified cell or unmodified plant. In some embodiments, an altered content comprises an increased content. In some embodiments, for example, the genetically modified cell or genetically modified plant has an increased content of at least a triterpenoid saponin, a derivative thereof, a metabolite thereof, or a biosynthetic intermediate thereof, or any combination thereof.

In some embodiments, the genetically modified cell or genetically modified plant or plant part comprising at least one genetically modified plant cell, has an increased content of at least one triterpenoid saponin. In some embodiments, the genetically modified cell or genetically modified plant or plant part comprising at least one genetically modified plant cell, has an increased content of at least two triterpenoid saponins. In some embodiments, the genetically modified cell or genetically modified plant or plant part comprising at least one genetically modified plant cell, has an increased content of at least three triterpenoid saponins. In some embodiments, the genetically modified cell or genetically modified plant or plant part comprising at least one genetically modified plant cell, has an increased content of at least four triterpenoid saponins. In some embodiments, the genetically modified cell or genetically modified plant or plant part comprising at least one genetically modified plant cell, has an increased content of at least five triterpenoid saponins. In some embodiments, the genetically modified cell or genetically modified plant or plant part comprising at least one genetically modified plant cell, has an increased content of at least six triterpenoid saponins.

In some embodiments, the genetically modified cell or genetically modified plant or plant part comprising at least one genetically modified plant cell, has an increased content of at least a derivative of a triterpenoid saponin. In some embodiments, the genetically modified cell or genetically modified plant or plant part comprising at least one genetically modified plant cell, has an increased content of at least two derivatives of a triterpenoid saponin or of triterpenoid saponins. In some embodiments, the genetically modified cell or genetically modified plant or plant part comprising at least one genetically modified plant cell, has an increased content of at least three derivatives of a triterpenoid saponin or of triterpenoid saponins. In some embodiments, the genetically modified cell or genetically modified plant or plant part comprising at least one genetically modified plant cell, has an increased content of at least four derivatives of a triterpenoid saponin or of triterpenoid saponins. In some embodiments, the genetically modified cell or genetically modified plant or plant part comprising at least one genetically modified plant cell, has an increased content of at least five derivatives of a triterpenoid saponin or of triterpenoid saponins. In some embodiments, the genetically modified cell or genetically modified plant or plant part comprising at least one genetically modified plant cell, has an increased content of at least six derivatives of a triterpenoid saponin or of triterpenoid saponins.

In some embodiments, the genetically modified cell or genetically modified plant or plant part comprising at least one genetically modified plant cell, has an increased content of at least a metabolite of a triterpenoid saponin. In some embodiments, the genetically modified cell or genetically modified plant or plant part comprising at least one genetically modified plant cell, has an increased content of at least two metabolites of a triterpenoid saponin or of triterpenoid saponins. In some embodiments, the genetically modified cell or genetically modified plant or plant part comprising at least one genetically modified plant cell, has an increased content of at least three metabolites of a triterpenoid saponin or of triterpenoid saponins. In some embodiments, the genetically modified cell or genetically modified plant or plant part comprising at least one genetically modified plant cell, has an increased content of at least four metabolites of a triterpenoid saponin or of triterpenoid saponins. In some embodiments, the genetically modified cell or genetically modified plant or plant part comprising at least one genetically modified plant cell, has an increased content of at least five metabolites of a triterpenoid saponin or of triterpenoid saponins. In some embodiments, the genetically modified cell or genetically modified plant or plant part comprising at least one genetically modified plant cell, has an increased content of at least six metabolites of a triterpenoid saponin or of triterpenoid saponins.

In some embodiments, the genetically modified cell or genetically modified plant or plant part comprising at least one genetically modified plant cell, has an increased content of at least a biosynthetic intermediate of a triterpenoid saponin. In some embodiments, the genetically modified cell or genetically modified plant or plant part comprising at least one genetically modified plant cell, has an increased content of at least two biosynthetic intermediates of a triterpenoid saponin or of triterpenoid saponins. In some embodiments, the genetically modified cell or genetically modified plant or plant part comprising at least one genetically modified plant cell, has an increased content of at least three biosynthetic intermediates of a triterpenoid saponin or of triterpenoid saponins. In some embodiments, the genetically modified cell or genetically modified plant or plant part comprising at least one genetically modified plant cell, has an increased content of at least four biosynthetic intermediates of a triterpenoid saponin or of triterpenoid saponins. In some embodiments, the genetically modified cell or genetically modified plant or plant part comprising at least one genetically modified plant cell, has an increased content of at least five biosynthetic intermediates of a triterpenoid saponin or of triterpenoid saponins. In some embodiments, the genetically modified cell or genetically modified plant or plant part comprising at least one genetically modified plant cell, has an increased content of at least six biosynthetic intermediates of a triterpenoid saponin or of triterpenoid saponins.

As skilled artisan would recognize that the terms "content" and "level" in reference to a triterpenoid saponin, a derivative thereof, a metabolite thereof, or a biosynthetic intermediate thereof, encompasses the quantity of the compound, for example the quantity of a triterpenoid saponin, a derivative thereof, a metabolite thereof, or a biosynthetic intermediate thereof in a genetically modified cell or in a genetically modified plant, compared with a control cell or control plant. In this context, the terms "content" and "level" may be used interchangeably having all the same meanings and qualities.

In some embodiments, a triterpenoid saponin having increased content comprises a sweetener, foaming agent, emulsifier, preservative, anti-carcinogen, hypocholesterolemic agent, anti-inflammatory agent, anti-oxidant, biological adjuvant, anti-microbial agent, insecticidal agent, anti-feedant, anti-fungal agent, or any combination thereof. In some embodiments, a triterpenoid saponin having increased content comprises triterpenoid saponin selected from a medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof. In some embodiments, a triterpenoid saponin having increased content comprises at least 1, 2, 3, 4, 5, 6, or more triterpenoid saponin selected from medicagenic acid 3-O-glucuronide (MA-3-GlcA)(Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof.

In some embodiments, a triterpenoid saponin having increased content comprises at least 1, 2, 3, 4, 5, 6, or more triterpenoid saponin selected from medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof.

In some embodiments, a triterpenoid saponin having increased content in a genetically modified cell, for example a plant cell or a yeast or an algal cell or an insect cell or a bacterium, or in a genetically modified plant or part thereof, comprises triterpenoid saponin selected from medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof.

In some embodiments, a genetically modified cell, for example a plant cell or a yeast or an algal cell or an insect cell or a bacterium, or in a genetically modified plant or part thereof, comprises an increased content of Compound 11. In some embodiments, a genetically modified cell, for example a plant cell or a yeast or an algal cell or an insect cell or a bacterium, or in a genetically modified plant or part thereof, comprises an increased content of medicagenic acid 3-O-glucuronide (MA-3-GlcA) (Compound 6). In some embodiments, a genetically modified cell, for example a plant cell or a yeast or an algal cell or an insect cell or a bacterium, or in a genetically modified plant or part thereof, comprises an increased content of Compound 7. In some embodiments, a genetically modified cell, for example a plant cell or a yeast or an algal cell or an insect cell or a bacterium, or in a genetically modified plant or part thereof, comprises an increased content of Compound 8. In some embodiments, a genetically modified cell, for example a plant cell or a yeast or an algal cell or an insect cell or a bacterium, or in a genetically modified plant or part thereof, comprises an increased content of Compound 9. In some embodiments, a genetically modified cell, for example a plant cell or a yeast or an algal cell or an insect cell or a bacterium, or in a genetically modified plant or part thereof, comprises an increased content of Compound 10. In some embodiments, a genetically modified cell, for example a plant cell or a yeast or an algal cell or an insect cell or a bacterium, or in a genetically modified plant or part thereof, comprises an increased content of glycyrrhizin (Compound 14). In some embodiments, a genetically modified cell, for example a plant cell or a yeast or an algal cell or an insect cell or a bacterium, or in a genetically modified plant or part thereof, comprises an increased content of Glycyrrhetinic acid 3-O-monoglucuronide (compound 15). In some embodiments, a genetically modified cell, for example a plant cell or a yeast or an algal cell or an insect cell or a bacterium, or in a genetically modified plant or part thereof, comprises an increased content of bayogenin (Compound 25). In some embodiments, a genetically modified cell, for example a plant cell or a yeast or an algal cell or an insect cell or a bacterium, or in a genetically modified plant or part thereof, comprises an increased content of bayogenin-hexA-hex-hex (Compound 31). In some embodiments, a genetically modified cell, for example a plant cell or a yeast or an algal cell or an insect cell or a bacterium, or in a genetically modified plant or part thereof, comprises an increased content of serjanic acid (Compound 26). In some embodiments, a genetically modified cell, for example a plant cell or a yeast or an algal cell or an insect cell or a bacterium, or in a genetically modified plant or part thereof, comprises an increased content of serjanic acid-hexA-hex (Compound 32). In some embodiments, a genetically modified cell, for example a plant cell or a yeast or an algal cell or an insect cell or a bacterium, or in a genetically modified plant or part thereof, comprises an increased content of soyasapogenol A (Compound 29). In some embodiments, a genetically modified cell, for example a plant cell or a yeast or an algal cell or an insect cell or a bacterium, or in a genetically modified plant or part thereof, comprises an increased content of soyasapogenol B (Compound 30). In some embodiments, a genetically modified cell, for example a plant cell or a yeast or an algal cell or an insect cell or a bacterium, or in a genetically modified plant or part thereof, comprises an increased content of soyasapogenol A-hexA-hex-pent (Compound 34). In some embodiments, a genetically modified cell, for example a plant cell or a yeast or an algal cell or an insect cell or a bacterium, or in a genetically modified plant or part thereof, comprises an increased content of soyasaponin VI (Compound 35). In some embodiments, a genetically modified cell, for example a plant cell or a yeast or an algal cell or an insect cell or a bacterium, or in a genetically modified plant or part thereof, comprises an increased content of betavulgaroside IV (Compound 33). In some embodiments, a genetically modified cell, for example a plant cell or a yeast or an algal cell or an insect cell or a bacterium, or in a genetically modified plant or part thereof, comprises an increased content of hederagenin-3GlcA. In some embodiments, a genetically modified cell, for example a plant cell or a yeast or an algal cell or an insect cell or a bacterium, or in a genetically modified plant or part thereof, comprises an increased content of gypsogenin-3GlcA. In some embodiments, a genetically modified cell, for example a plant cell or a yeast or an algal cell or an insect cell or a bacterium, or in a genetically modified plant or part thereof, comprises an increased content of gypsogenic acid-3GlcA. In some embodiments, a genetically modified cell, for example a plant cell or a yeast or an algal cell or an insect cell or a bacterium, or in a genetically modified plant or part thereof, comprises an increased content of QS-21 adjuvant. A skilled artisan would appreciate that in some embodiments, instances wherein the content of one triterpenoid saponin is increased additional triterpenoid saponins, or intermediates, or a combination thereof may also be increased in the same time cell.

In some embodiments, a genetically modified cell, for example a plant cell or a yeast or an algal cell, or a genetically modified plant or part thereof, comprises an increased content of a biosynthetic intermediate of a triterpenoid saponin, said intermediate comprising Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof. In some embodiments, a genetically modified cell, for example a plant cell or a yeast or an algal cell or an insect cell or a bactierum, or a genetically modified plant or part thereof, comprises an increased content of at least two biosynthetic intermediates of a triterpenoid saponin or of triterpenoid saponins, said intermediates comprising Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof; or any combination thereof.

In some embodiments, a genetically modified cell, for example a plant cell or a yeast or an algal cell or an insect cell or a bactierum, or a genetically modified plant or part thereof, comprises an increased content of a biosynthetic intermediate of a triterpenoid saponin, said intermediate comprising medicagenic acid (Compound 5). In some embodiments, a genetically modified cell, for example a plant cell or a yeast or an algal cell or an insect cell or a bacterium, or a genetically modified plant or part thereof, comprises an increased content of a biosynthetic intermediate of a triterpenoid saponin, said intermediate comprising Compound 1. In some embodiments, a genetically modified cell, for example a plant cell or a yeast or an algal cell or an insect cell or a bacterium, or a genetically modified plant or part thereof, comprises an increased content of a biosynthetic intermediate of a triterpenoid saponin, said intermediate comprising Compound 2. In some embodiments, a genetically modified cell, for example a plant cell or a yeast or an algal cell or an insect cell or a bacterium, or a genetically modified plant or part thereof, comprises an increased content of a biosynthetic intermediate of a triterpenoid saponin, said intermediate comprising oleanolic acid (Compound 3). In some embodiments, a genetically modified cell, for example a plant cell or a yeast or an algal cell or an insect cell or a bacterium, or a genetically modified plant or part thereof, comprises an increased content of a biosynthetic intermediate of a triterpenoid saponin, said intermediate comprising oleanolic acid-3GlcA. In some embodiments, a genetically modified cell, for example a plant cell or a yeast or an algal cell or an insect cell or a bacterium, or a genetically modified plant or part thereof, comprises an increased content of a biosynthetic intermediate of a triterpenoid saponin, said intermediate comprising augustic acid (Compound 4). In some embodiments, a genetically modified cell, for example a plant cell or a yeast or an algal cell or an insect cell or a bacterium, or a genetically modified plant or part thereof, comprises an increased content of a biosynthetic intermediate of a triterpenoid saponin, said intermediate comprising augustic acid-3GlcA. In some embodiments, a genetically modified cell, for example a plant cell or a yeast or an algal cell or an insect cell or a bacterium, or a genetically modified plant or part thereof, comprises an increased content of a biosynthetic intermediate of a triterpenoid saponin, said intermediate comprising glycyrrhetinic acid (Compound 13), or any combination thereof.

In some embodiments, a triterpenoid saponin having decreased content in a plant or plant part comprising at least one genetically modified cell, comprises a compound having a bitter taste or a toxin. In some embodiments, a triterpenoid saponin having decreased content comprises triterpenoid saponin selected from medicagenic acid 3-O-glucuronide (MA-3-GlcA)(Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof. In some embodiments, a triterpenoid saponin having decreased content comprises at least 1, 2, 3, 4, 5, 6, or more triterpenoid saponin selected from medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof.

In some embodiments, a triterpenoid saponin having decreased content comprises at least 1, 2, 3, 4, 5, 6, or more triterpenoid saponin selected from medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof.

In some embodiments, a triterpenoid saponin having decreased content in a genetically modified plant or part thereof comprising at least one genetically modified cell, comprises triterpenoid saponin selected from medicagenic acid 3-O-glucuronide (MA-3-GlcA)(Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof.

In some embodiments, a genetically modified plant or part thereof comprising at least one genetically modified plant cell comprises a decreased content of Compound 11. In some embodiments, a genetically modified plant or part thereof comprising at least one genetically modified plant cell, comprises a decreased content of medicagenic acid 3-O-glucuronide (MA-3-GlcA)(Compound 6). In some embodiments, a genetically modified plant or part thereof comprising at least one genetically modified plant cell, comprises a decreased content of Compound 7. In some embodiments, a genetically modified plant or part thereof comprising at least one genetically modified plant cell, comprises a decreased content of Compound 8. In some embodiments, a genetically modified plant or part thereof comprising at least one genetically modified plant cell, comprises a decreased content of Compound 9. In some embodiments, a genetically modified plant or part thereof comprising at least one genetically modified plant cell, comprises a decreased content of Compound 10. In some embodiments, a genetically modified plant or part thereof comprising at least one genetically modified plant cell, comprises a decreased content of glycyrrhizin (Compound 14). In some embodiments, a genetically modified plant or part thereof comprising at least one genetically modified plant cell, comprises a decreased content of Glycyrrhetinic acid 3-O-monoglucuronide (compound 15). In some embodiments, a genetically modified plant or part thereof comprising at least one genetically modified plant cell, comprises a decreased content of bayogenin (Compound 25). In some embodiments, a genetically modified plant or part thereof comprising at least one genetically modified plant cell, comprises a decreased content of bayogenin-hexA-hex-hex (Compound 31). In some embodiments, a genetically modified plant or part thereof comprising at least one genetically modified plant cell, comprises a decreased content of serjanic acid (Compound 26). In some embodiments, a genetically modified plant or part thereof comprising at least one genetically modified plant cell, comprises a decreased content of serjanic acid-hexA-hex (Compound 32). In some embodiments, a genetically modified plant or part thereof comprising at least one genetically modified plant cell, comprises a decreased content of soyasapogenol A (Compound 29). In some embodiments, a genetically modified plant or part thereof comprising at least one genetically modified plant cell, comprises a decreased content of soyasapogenol B (Compound 30). In some embodiments, a genetically modified plant or part thereof comprising at least one genetically modified plant cell, comprises a decreased content of soyasapogenol A-hexA-hex-pent (Compound 34). In some embodiments, a genetically modified plant or part thereof comprising at least one genetically modified plant cell, comprises a decreased content of soyasaponin VI (Compound 35). In some embodiments, a genetically modified plant or part thereof comprising at least one genetically modified plant cell, comprises a decreased content of betavulgaroside IV (Compound 33). In some embodiments, a genetically modified plant or part thereof comprising at least one genetically modified plant cell, comprises a decreased content of hederagenin-3GlcA. In some embodiments, a genetically modified plant or part thereof comprising at least one genetically modified plant cell, comprises a decreased content of gypsogenin-3GlcA. In some embodiments, a genetically modified plant or part thereof comprising at least one genetically modified plant cell, comprises a decreased content of gypsogenic acid-3GlcA. In some embodiments, a genetically modified plant or part thereof comprising at least one genetically modified plant cell, comprises a decreased content of QS-21 adjuvant. A skilled artisan would appreciate that in some embodiments, instances wherein the content of one triterpenoid saponin is decreased additional triterpenoid saponins, or intermediates, or a combination thereof may also be decreased in the same time cell.

In some embodiments, a genetically modified plant or part thereof comprising at least one genetically modified plant cell, comprises a decreased content of a biosynthetic intermediate of a triterpenoid saponin, said intermediate comprising Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof. In some embodiments, a genetically modified plant or part thereof comprising at least one genetically modified plant cell, comprises a decreased content of at least two biosynthetic intermediates of a triterpenoid saponin or of triterpenoid saponins, said intermediates comprising Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof, or any combination thereof.

In some embodiments, a genetically modified plant or part thereof comprising at least one genetically modified plant cell, comprises a decreased content of a biosynthetic intermediate of a triterpenoid saponin, said intermediate comprising medicagenic acid (Compound 5). In some embodiments, a genetically modified plant or part thereof comprising at least one genetically modified plant cell, comprises a decreased content of a biosynthetic intermediate of a triterpenoid saponin, said intermediate comprising Compound 1. In some embodiments, a genetically modified plant or part thereof comprising at least one genetically modified plant cell, comprises a decreased content of a biosynthetic intermediate of a triterpenoid saponin, said intermediate comprising Compound 2. In some embodiments, a genetically modified plant or part thereof comprising at least one genetically modified plant cell, comprises a decreased content of a biosynthetic intermediate of a triterpenoid saponin, said intermediate comprising oleanolic acid (Compound 3). In some embodiments, a genetically modified plant or part thereof comprising at least one genetically modified plant cell, comprises a decreased content of a biosynthetic intermediate of a triterpenoid saponin, said intermediate comprising oleanolic acid-3GlcA. In some embodiments, a genetically modified plant or part thereof comprising at least one genetically modified plant cell, comprises a decreased content of a biosynthetic intermediate of a triterpenoid saponin, said intermediate comprising augustic acid (Compound 4). In some embodiments, a genetically modified plant or part thereof comprising at least one genetically modified plant cell, comprises a decreased content of a biosynthetic intermediate of a triterpenoid saponin, said intermediate comprising augustic acid-3GlcA. In some embodiments, a genetically modified plant or part thereof comprising at least one genetically modified plant cell, comprises a decreased content of a biosynthetic intermediate of a triterpenoid saponin, said intermediate comprising glycyrrhetinic acid (Compound 13), or any combination thereof.

In some embodiments, a genetically modified cell disclosed herein comprises an increased content of at least one triterpenoid saponin, a derivative thereof, a metabolite thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified cell disclosed herein comprises an increased content of at least one triterpenoid saponin, a derivative thereof, a metabolite thereof, or a biosynthetic intermediate thereof, and a reduced content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof, a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified cell disclosed herein comprises a decreased content of at least one triterpenoid saponin, a derivative thereof, a metabolite thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified cell disclosed herein comprises a decreased content of at least one triterpenoid saponin, a derivative thereof, a metabolite thereof, or a biosynthetic intermediate thereof, and an increased content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified plant disclosed herein comprises an increased content of at least one triterpenoid saponin, a derivative thereof, a metabolite thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified plant disclosed herein comprises an increased content of at least one triterpenoid saponin, a derivative thereof, a metabolite thereof, or a biosynthetic intermediate thereof, and a decreased content of a phytosterol, or a derivative thereof, a metabolite thereof, or a biosynthetic intermediate thereof, a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified plant disclosed herein comprises a decreased content of at least one triterpenoid saponin, a derivative thereof, a metabolite thereof, or a biosynthetic intermediate thereof and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified plant disclosed herein comprises a decreased content of at least one triterpenoid saponin, a derivative thereof, a metabolite thereof, or a biosynthetic intermediate thereof and an increased content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of producing at least one triterpenoid saponin, a derivative thereof, a metabolite thereof, or a biosynthetic intermediate thereof, in a genetically modified cell or a genetically modified plant comprises altering the content of at least one triterpenoid saponin, a derivative thereof, a metabolite thereof, or a biosynthetic intermediate thereof, compared to an unmodified cell or an unmodified plant and decreasing the content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of producing at least one triterpenoid saponin, a derivative thereof, a metabolite thereof, or a biosynthetic intermediate thereof, in a genetically modified cell or a genetically modified plant comprises increasing the content of at least one triterpenoid saponin, a derivative thereof, a metabolite thereof, or a biosynthetic intermediate thereof, compared to an unmodified cell or an unmodified plant and decreasing the content of a phytosterol, or a derivative thereof, a metabolite thereof, or a biosynthetic intermediate thereof, a cholesterol, or a derivative thereof, a metabolite thereof, or a biosynthetic intermediate thereof; a phytocholesterol, or a derivative thereof, a metabolite thereof, or a biosynthetic intermediate thereof, a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a method of reducing the content of at least one triterpenoid saponin, a derivative thereof, a metabolite thereof, or a biosynthetic intermediate thereof, comprises genetically modifying at least one plant cell or at least one cell of a plant or plant part, said genetically modified plant cell comprising a reduced content of at least one triterpenoid saponin, a derivative thereof, a metabolite thereof, or a biosynthetic intermediate thereof, and an altered content of a phytosterol, or a derivative thereof, a metabolite thereof, or a biosynthetic intermediate thereof, a cholesterol, or a derivative thereof, a metabolite thereof, or a biosynthetic intermediate thereof, a phytocholesterol, or a derivative thereof, a metabolite thereof, or a biosynthetic intermediate thereof, a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a method of reducing the content of at least one triterpenoid saponin, a derivative thereof, a metabolite thereof, or a biosynthetic intermediate thereof, comprises genetically modifying at least one plant cell or at least one cell of a plant or plant part, said genetically modified plant cell comprising a reduced content of at least one triterpenoid saponin, a derivative thereof, a metabolite thereof, or a biosynthetic intermediate thereof, and an increased content of a phytosterol, or a derivative thereof, a metabolite thereof, or a biosynthetic intermediate thereof, a cholesterol, or a derivative thereof, a metabolite thereof, or a biosynthetic intermediate thereof, a phytocholesterol, or a derivative thereof, a metabolite thereof, or a biosynthetic intermediate thereof, a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a method of increasing the content of at least one triterpenoid saponin, a derivative thereof, a metabolite thereof, or a biosynthetic intermediate thereof, comprises genetically modifying at least one plant cell or at least one cell of a plant or plant part, said genetically modified plant cell comprising an increased content of at least one triterpenoid saponin, a derivative thereof, a metabolite thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof: a phytocholesterol, or a derivative thereof, a metabolite thereof, or a biosynthetic intermediate thereof, a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a method of increasing the content of at least one triterpenoid saponin, a derivative thereof, a metabolite thereof, or a biosynthetic intermediate thereof, comprises genetically modifying at least one plant cell or at least one cell of a plant or plant part, said genetically modified plant cell comprising an increased content of at least one triterpenoid saponin, a derivative thereof, a metabolite thereof, or a biosynthetic intermediate thereof, and a reduced content of a phytosterol, or a derivative thereof, a metabolite thereof, or a biosynthetic intermediate thereof, a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof, or a phytocholestenol, or a derivative thereof, a metabolite thereof, or a biosynthetic intermediate thereof.

Plants, Plant Parts, and Cells

According to some embodiments, the cell or organism described herein, comprising the at least one heterologous gene encoding an enzyme has an elevated content of at least one steroidal alkaloid, derivative thereof, metabolite thereof, or biosynthetic intermediate thereof; at least one steroidal saponin, derivative thereof, metabolite thereof, or biosynthetic intermediate thereof, or at least one triterpenoid saponin, derivative thereof, metabolite thereof, or biosynthetic intermediate thereof, compared to a corresponding non-genetically modified cell or non-transgenic plant, respectively. In other embodiments, the genetically modified plant or plant part comprising an at least one genetically modified cell described herein, comprising an at least one modified endogenous gene encoding an enzyme of the steroidal alkaloid pathway, the steroidal saponin pathway, or the triterpenoid synthetic pathway has an elevated content of at least one steroidal alkaloid, derivative thereof, metabolite thereof, or biosynthetic intermediate thereof; at least one steroidal saponin, derivative thereof, metabolite thereof, or biosynthetic intermediate thereof, at least one triterpenoid saponin, derivative thereof, metabolite thereof, or biosynthetic intermediate thereof, compared to a corresponding non-genetically modified plant. In other embodiments, the genetically modified plant or plant part comprising an at least one genetically modified cell described herein, comprising an at least one heterologous gene encoding an enzyme of the steroidal alkaloid synthetic pathway, the steroidal saponin synthetic pathway, or the triterpenoid synthetic pathway has an elevated content of at least one steroidal alkaloid, derivative thereof, metabolite thereof, or biosynthetic intermediate thereof; at least one steroidal saponin, derivative thereof, metabolite thereof, or biosynthetic intermediate thereof; at least one triterpenoid saponin, derivative thereof, metabolite thereof, or biosynthetic intermediate thereof, compared to a corresponding non-genetically modified plant. In other embodiments, the genetically modified plant or plant part comprising an at least one genetically modified cell described herein, comprising the at least one modified endogenous gene encoding an enzyme of the steroidal alkaloid synthetic pathway, the steroidal saponin synthetic pathway, or the triterpenoid synthetic pathway has a reduced content of at least one steroidal alkaloid, derivative thereof, metabolite thereof, or biosynthetic intermediate thereof; at least one steroidal saponin, derivative thereof, metabolite thereof, or biosynthetic intermediate thereof; at least one triterpenoid saponin, derivative thereof, metabolite thereof, or biosynthetic intermediate thereof, compared to a corresponding non-genetically modified plant. As described throughout, the skilled artisan would appreciate that modifications of endogenous genes include but are not limited to increasing expression, decreasing expressing, or mutating the gene, or a combination thereof as described in detail herein.

According to some embodiments, the cell or organism described herein, comprising the at least one heterologous CSLG gene encoding a CSLG enzyme has an elevated content of at least one steroidal alkaloid, derivative thereof, metabolite thereof, or biosynthetic intermediate thereof; at least one steroidal saponin, derivative thereof, metabolite thereof, or biosynthetic intermediate thereof; or at least one triterpenoid saponin, derivative thereof, metabolite thereof, or biosynthetic intermediate thereof, compared to a corresponding non-genetically modified cell or non-transgenic plant, respectively. In other embodiments, the genetically modified plant or plant part comprising an at least one genetically modified cell described herein, comprising an at least one modified endogenous CSLG gene encoding a CSLG enzyme of the steroidal alkaloid synthetic pathway, the steroidal saponin synthetic pathway, or the triterpenoid synthetic pathway has an elevated content of at least one steroidal alkaloid, derivative thereof, metabolite thereof, or biosynthetic intermediate thereof; at least one steroidal saponin, derivative thereof, metabolite thereof, or biosynthetic intermediate thereof; or at least one triterpenoid saponin, derivative thereof, metabolite thereof, or biosynthetic intermediate thereof compared to a corresponding non-genetically modified plant. In other embodiments, the genetically modified plant or plant part comprising an at least one genetically modified cell described herein, comprising an at least one heterologous CSLG gene encoding an enzyme of the steroidal alkaloid synthetic pathway, the steroidal saponin synthetic pathway, or the triterpenoid synthetic pathway has an elevated content of at least one steroidal alkaloid, derivative thereof, metabolite thereof, or biosynthetic intermediate thereof; at least one steroidal saponin, derivative thereof, metabolite thereof, or biosynthetic intermediate thereof; or at least one triterpenoid saponin, derivative thereof, metabolite thereof, or biosynthetic intermediate thereof compared to a corresponding non-genetically modified plant. In other embodiments, the genetically modified plant or plant part comprising an at least one genetically modified cell described herein, comprising the at least one modified endogenous CSLG gene encoding an enzyme of the steroidal alkaloid synthetic pathway, the steroidal saponin synthetic pathway, or the triterpenoid synthetic pathway has a reduced content of at least one steroidal alkaloid, derivative thereof, metabolite thereof, or biosynthetic intermediate thereof; at least one steroidal saponin, derivative thereof, metabolite thereof, or biosynthetic intermediate thereof, or at least one triterpenoid saponin, derivative thereof, metabolite thereof, or biosynthetic intermediate thereof compared to a corresponding non-genetically modified plant.

In some embodiments, derivatives of steroidal alkaloids, steroidal saponins, or triterpenoid saponins comprise glycosylated derivatives of, respectively, steroidal alkaloids, steroidal saponins, or triterpenoid saponins.

In some embodiments, a cell or plant species or plant part that does not normally express for example at least a saponin beta-amyrin synthase, a cytochrome P450, a glycosyltransferase, an acyltransferase, a glucuronosyltransferase, or a CSLG and/or does not normally produce a particular steroidal alkaloid, a derivative thereof, a metabolite thereof, or a biosynthetic intermediate thereof; a particular steroidal saponin, a derivative thereof, a metabolite thereof, or a biosynthetic intermediate thereof; or a particular triterpenoid saponin, a derivative thereof, a metabolite thereof, or a biosynthetic intermediate thereof, is genetically modified to express a saponin beta-amyrin synthase, a cytochrome P450, a glycosyltransferase, an acyltransferase, a glucuronosyltransferase, or a CSLG, or any combination thereof. In some embodiments, a cell or plant species or plant part that does not normally express a saponin beta-amyrin synthase, a cytochrome P450, a glycosyltransferase, an acyltransferase, a glucuronosyltransferase, or a CSLG and/or does not normally produce a particular steroidal alkaloid, a derivative thereof, a metabolite thereof, or a biosynthetic intermediate thereof; a particular steroidal saponin, a derivative thereof, a metabolite thereof, or a biosynthetic intermediate thereof; or a particular triterpenoid saponin, a derivative thereof, a metabolite thereof, or a biosynthetic intermediate thereof, is genetically modified to produce a steroidal alkaloid, a derivative thereof, a metabolite thereof, or a biosynthetic intermediate thereof, a steroidal saponin, a derivative thereof, a metabolite thereof, or a biosynthetic intermediate thereof, or a triterpenoid saponin, a derivative thereof, a metabolite thereof, or a biosynthetic intermediate thereof, or any combination thereof. In other embodiments, a cell or plant species or plant part that normally expresses a given amount of a saponin beta-amyrin synthase, a cytochrome P450, a glycosyltransferase, an acyltransferase, a glucuronosyltransferase, or a CSLG, or any combination thereof is genetically modified to overexpress a saponin beta-amyrin synthase, a cytochrome P450, a glycosyltransferase, an acyltransferase, a glucuronosyltransferase, or a CSLG, or any combination thereof. In other embodiments, a cell or plant species or plant part that normally expresses a given amount of a saponin beta-amyrin synthase, a cytochrome P450, a glycosyltransferase, an acyltransferase, a glucuronosyltransferase, or a CSLG, or any combination thereof is genetically modified to reduce or silence expression of a saponin beta-amyrin synthase, a cytochrome P450, a glycosyltransferase, an acyltransferase, a glucuronosyltransferase, or a CSLG, or any combination thereof.

In other embodiments, a cell or plant species or plant part that normally produces a given amount of a steroidal alkaloid, a derivative thereof, a metabolite thereof, or a biosynthetic intermediate thereof; a steroidal saponin, a derivative thereof, a metabolite thereof, or a biosynthetic intermediate thereof; or a triterpenoid saponin, a derivative thereof, a metabolite thereof, or a biosynthetic intermediate thereof, is genetically modified to overexpress a saponin beta-amyrin synthase, a cytochrome P450, a glycosyltransferase, an acyltransferase, a glucuronosyltransferase, or a CSLG, or any combination thereof leading to an increases production of a steroidal alkaloid, a derivative thereof, a metabolite thereof, or a biosynthetic intermediate thereof; a steroidal saponin, a derivative thereof, a metabolite thereof, or a biosynthetic intermediate thereof; or a triterpenoid saponin, a derivative thereof, a metabolite thereof, or a biosynthetic intermediate thereof, or any combination thereof.

In other embodiments, a cell or plant species or plant part that normally produces a given amount of a steroidal alkaloid, a derivative thereof, a metabolite thereof, or a biosynthetic intermediate thereof; a steroidal saponin, a derivative thereof, a metabolite thereof, or a biosynthetic intermediate thereof; or a triterpenoid saponin, a derivative thereof, a metabolite thereof, or a biosynthetic intermediate thereof, is genetically modified to reduce or silence expression of a saponin beta-amyrin synthase, a cytochrome P450, a glycosyltransferase, an acyltransferase, a glucuronosyltransferase, or a CSLG, or any combination thereof leading to a decreased production of a steroidal alkaloid, a derivative thereof, a metabolite thereof, or a biosynthetic intermediate thereof, a steroidal saponin, a derivative thereof, a metabolite thereof, or a biosynthetic intermediate thereof, a triterpenoid saponin, a derivative thereof, a metabolite thereof, or a biosynthetic intermediate thereof, or any combination thereof.

In some embodiments, disclosed herein are seeds of the genetically modified plant, wherein plants grown from said seeds and expressing at least one saponin beta-amyrin synthase, cytochrome P450, a glycosyltransferase, acyltransferase, a glucuronosyltransferase, or CSLG compared to plants grown from corresponding unmodified, thereby containing expression or overexpression of at least one saponin beta-amyrin synthase, cytochrome P450, a glycosyltransferase, acyltransferase, a glucuronosyltransferase, or CSLG and/or having increased content of a steroidal alkaloid, a derivative thereof, a metabolite thereof, or a biosynthetic intermediate thereof; a steroidal saponin, a derivative thereof, a metabolite thereof, or a biosynthetic intermediate thereof; or a triterpenoid saponin, a derivative thereof, a metabolite thereof, or a biosynthetic intermediate thereof.

The cells disclosed herein comprise numerous varieties, including, but not limited to, yeast, algal, insect, bacterium, and plant cells. In some embodiments, a genetically modified cell comprises a plant cell. In some embodiments, a genetically modified cell comprises a yeast cell. In some embodiments, a genetically modified cell comprises an algal cell. In some embodiments, a genetically modified cell comprises an insect cell. In some embodiments, a genetically modified cell comprises a bacterium.

Generally, most yeast, algae, insect cells, and bacterium do not naturally synthesize steroidal alkaloids, steroidal saponins, or triterpenoid saponins. In some embodiments, in order to produce a steroidal alkaloid, steroidal saponin, or triterpenoid saponin in a yeast or an algal cell or an insect cell or a bacterium, genetic modification of the yeast or algal cell or insect cell or bacterium comprises introduction of an enzyme or enzymes necessary to produce precursors or substrates, or a combination thereof, of the triterpenoid saponin biosynthetic pathway. For example, see Example 14 below wherein the *S. cerevisiae* were genetically modified to express a heterologous UDP-glucose 6-dehydrogenase I in order to produce the necessary precursors for substrates of the triterpenoid saponin biosynthetic pathway. In some embodiments, a genetically modified cell expresses at least one heterologous gene for the production of precursors, substrates, or a combination thereof, of the steroidal alkaloid biosynthetic pathway, a steroidal saponin biosynthetic pathway, or the triterpenoid biosynthetic pathway. In some embodiments, a genetically modified cell expresses at least one heterologous gene for the production of precursors, substrates, or a combination thereof, of the steroidal alkaloid biosynthetic pathway, the steroidal saponin biosynthetic pathway, or the triterpenoid biosynthetic pathway, and expresses at least one heterologous gene encoding an enzyme of the steroidal alkaloid biosynthetic pathway, the steroidal saponin biosynthetic pathway, or the triterpenoid biosynthetic pathway.

In some embodiments, cells comprise a micro-organism. In some embodiments, the genetically modified cell is a yeast cell. In some embodiments, the yeast is from the Saccharomycetes order. In some embodiments, the yeast is from the Saccharomycetes order and is selected from the group of genera consisting of the *Saccharomyces* genus (e.g., *Saccharomyces cerevisiae*), the *Schizosaccharomyces* genus, the *Pichia* genus (e.g., *Pichia pastoris*), the *Hansenula* genus (e.g., *Hansenula polymorpha*), the *Yarrowia* genus (e.g., *Yarrowia* lipollytica), the *Kluyveromyces* genus (e.g., *Kluyveromyces lactis*), and the *Candida* genus (e.g., *Candida albicans, Candida utilis*). In some embodiments, a yeast is selected from a *Saccharomyces* genus, a *Schizosaccharomyces* genus, a *Pichia* genus, a *Yarrowia* genus, a *Kluyveromyces* genus, or a *Candida* genus. In some embodiments, a yeast is selected from *Saccharomyces cerevisiae* or *Candida albicans*.

In some embodiments, a genetically modified yeast may be utilized in a method of producing a steroidal alkaloid, a steroidal saponin, or a triterpenoid saponin as described herein.

In some embodiments, the genetically modified cell is an algal cell. In some embodiments, the cell is any one of a variety of algae, including, but not limited to, chlorophytes (green algae), rhodophytes (red algae), or phaeo-phytes (brown algae). In some embodiments, the chlorophyte is from the Chlamydomonadales order or the Chlorellales order. In some embodiments, the chlorophyte is from the Chlamydomonadales order and is selected from the group of genera consisting of the *Chlamydomonas* genus (e.g., *Chlamydomonas reinhardtii*) and the *Dunaliella* genus. In some embodiments, the chlorophyte is from the Chlorellales order and is selected from the *Chlorella* genus.

In some embodiments, a genetically modified alga may be utilized in a method of producing a steroidal alkaloid, a steroidal saponin, or a triterpenoid saponin as described herein.

In some embodiments, the genetically modified cell disclosed herein is a bacterial cell. In one embodiment, the bacterial cell is an *Escherichia coli* cell. In another embodiment, the cell is an *Acremonium rutilum, Aspergillus oryzae, Yarrowia lipolytica, Bacillus* sp. JPJ, *Brevundimonas* sp. SGJ, *E. herbicola, Citrobacter freundii, Symbiobacterium*, or *Pseudomonas aeruginosa* cell. In another embodiment, the bacterial cell is from a bacterium involved in fermentation of dairy products. In one embodiment, the bacterium is *Streptococcus lactis*. In another embodiment, the bacterium is a *Lactobacillus*. In one embodiment, the *Lactobacillus* is *Lactobacillus bulgaricus*. In another embodiment, the bacterium is a *Lactococcus* or a *Leuconostoc*.

In some embodiments, a genetically modified bacterium may be utilized in a method of producing a steroidal alkaloid, a steroidal saponin, or a triterpenoid saponin as described herein.

In some embodiments, a genetically modified plant disclosed herein comprises an increased content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof, at least one triterpenoid saponin, a derivative thereof, a metabolite thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof, a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a genetically modified plant disclosed herein comprises an increased content of at least one steroidal alkaloid, a derivative thereof, a metabolite thereof, or a biosynthetic intermediate thereof, at least one steroidal saponin, a derivative thereof, a metabolite thereof, or a biosynthetic intermediate thereof, at least one triterpenoid saponin, a derivative thereof, a metabolite thereof, or a biosynthetic intermediate thereof, and a decreased content of a phytosterol, or a derivative thereof, a metabolite thereof, or a biosynthetic intermediate thereof, a cholesterol, or a derivative thereof, a metabolite thereof, or a biosynthetic intermediate thereof, a phytocholesterol, or a derivative thereof, a metabolite thereof, or a biosynthetic intermediate thereof, a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a genetically modified plant disclosed herein comprises a decreased content of at least one steroidal alkaloid, a derivative thereof, a metabolite thereof, or a biosynthetic intermediate thereof, at least one steroidal saponin, a derivative thereof, a metabolite thereof, or a biosynthetic intermediate thereof, at least one triterpenoid saponin, a derivative thereof, a metabolite thereof, or a biosynthetic intermediate thereof and an altered content of a phytosterol, or a derivative thereof, a metabolite thereof, or a biosynthetic intermediate thereof, a cholesterol, or a derivative thereof, a metabolite thereof, or a biosynthetic intermediate thereof, a phytocholesterol, or a derivative thereof, a metabolite thereof, or a biosynthetic intermediate thereof, a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a genetically modified plant disclosed herein comprises a decreased content of at least one steroidal alkaloid, a derivative thereof, a metabolite thereof, or a biosynthetic intermediate thereof, at least one steroidal saponin, a derivative thereof, a metabolite thereof, or a biosynthetic intermediate thereof, at least one triterpenoid saponin, a derivative thereof, a metabolite thereof, or a biosynthetic intermediate thereof and an increased content of a phytosterol, or a derivative thereof, a metabolite thereof, or a biosynthetic intermediate thereof, a cholesterol, or a derivative thereof, a metabolite thereof, or a biosynthetic intermediate thereof; a phytocholesterol, or a derivative thereof, a metabolite thereof, or a biosynthetic intermediate thereof, a cholestenol, or a derivative thereof, a metabolite thereof, or a biosynthetic intermediate thereof, or a phytocholestenol, or a derivative thereof, a metabolite thereof, or a biosynthetic intermediate thereof.

In some embodiments, a method of producing at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; or at least one triterpenoid saponin, a derivative thereof, a metabolite thereof, or a biosynthetic intermediate thereof, in a genetically modified cell or a genetically modified plant comprises increasing the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; or at least one triterpenoid saponin, a derivative thereof, a metabolite thereof, or a biosynthetic intermediate thereof, compared to an unmodified cell or an unmodified plant and altering the content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of producing at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; or at least one triterpenoid saponin, a derivative thereof, a metabolite thereof, or a biosynthetic intermediate thereof, in a genetically modified cell or a genetically modified plant comprises increasing the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof;

or at least one triterpenoid saponin, a derivative thereof, a metabolite thereof, or a biosynthetic intermediate thereof, compared to an unmodified cell or an unmodified plant and decreasing the content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of reducing the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; or at least one triterpenoid saponin, a derivative thereof, a metabolite thereof, or a biosynthetic intermediate thereof, comprises genetically modifying at least one plant cell or at least one cell of a plant or plant part, said genetically modified plant cell comprising a reduced content of at least one steroidal alkaloid, a derivative thereof, a metabolite thereof; at least one steroidal saponin, a derivative thereof, a metabolite thereof, or a biosynthetic intermediate thereof; or at least one triterpenoid saponin, a derivative thereof, a metabolite thereof, or a biosynthetic intermediate thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of reducing the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; or at least one triterpenoid saponin, a derivative thereof, a metabolite thereof, or a biosynthetic intermediate thereof, comprises genetically modifying at least one plant cell or at least one cell of a plant or plant part, said genetically modified plant cell comprising a reduced content of at least one steroidal alkaloid, a derivative thereof, a metabolite thereof; at least one steroidal saponin, a derivative thereof, a metabolite thereof, or a biosynthetic intermediate thereof; or at least one triterpenoid saponin, a derivative thereof, a metabolite thereof, or a biosynthetic intermediate thereof, or a biosynthetic intermediate thereof, and an increased content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of increasing the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; or at least one triterpenoid saponin, a derivative thereof, a metabolite thereof, or a biosynthetic intermediate thereof, comprises genetically modifying at least one plant cell or at least one cell of a plant or plant part, said genetically modified plant cell comprising an increased content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; or at least one triterpenoid saponin, a derivative thereof, a metabolite thereof, or a biosynthetic intermediate thereof, and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof, a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of increasing the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; or at least one triterpenoid saponin, a derivative thereof, a metabolite thereof, or a biosynthetic intermediate thereof, comprises genetically modifying at least one plant cell or at least one cell of a plant or plant part, said genetically modified plant cell comprising an increased content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; or at least one triterpenoid saponin, a derivative thereof, a metabolite thereof, or a biosynthetic intermediate thereof, and a reduced content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, the genetically modified cell is a plant cell. Plant cells can be obtained from a wide range of plants, as discussed below. The plant cell may be a leaf cell, a petiole cell, a plant stem or stalk cell, a root cell, a bud cell, a tuber cell, a bean cell, a grain or kernel cell, a fruit cell, a nut cell, a legume cell, a seed or seed cell, a bract cell, a callus cell, and a flower cell. In some embodiments, a genetically modified cell may then be comprised in a plant leaf, in a plant petiole, in a plant stem or stalk, in a plant root, in a plant bud, in a plant tuber, in a plant bean, in a plant grain or kernel, in a plant fruit, in a plant nut, in a plant legume, in a plant seed, in a plant bract, in a plant callus, or in a plant flower.

In some embodiments, the genetically modified plant cell is grown as such in culture, independent of a plant or plant part. Methods for culturing plants and plant parts are well known in the art, for example see Ochoa-Villarreal M, Howat S, Hong S, et al. Plant cell culture strategies for the production of natural products. BMB Rep. 2016; 49(3):149-158, which is incorporated herein in its entirety.

In some embodiments, the genetically modified plant cell is grown as such in culture, independent of a plant or plant part and is utilized in a method provided herein to produce steroidal alkaloids, steroidal saponins, or triterpenoid saponins. Suspensions of genetically modified cells and tissue cultures derived from the genetically modified cells are also encompassed within the scope described herein. The cell suspension and tissue cultures can be used for the production of a desired steroidal alkaloid, a derivative thereof, a metabolite thereof, or a biosynthetic intermediate thereof, a desired steroidal saponin, a derivative thereof, a metabolite thereof, or a biosynthetic intermediate thereof, a desired triterpenoid saponin, a derivative thereof, a metabolite thereof, or a biosynthetic intermediate thereof and, which are then extracted from the cells or the growth medium. Alternatively, the genetically modified plant cell and/or tissue culture are used for regenerating a transgenic plant having modified expression or overexpression of a saponin beta-amyrin synthase, a cytochrome P450, a glycosyltransferase, an acyltransferase, a glucuronosyltransferase, or a CSLG, therefore expressing or overexpressing a saponin beta-amyrin synthase, a cytochrome P450, a glycosyltransferase, an acyltransferase, a UDP-glucose 6-dehydrogenase 1, and a cellulose synthase like G (CSLG) in a cell or in a plant, as compared to a corresponding unmodified cell or plant, respectively. Therefore, having modified content of a steroidal alkaloid, a derivative thereof, a metabolite thereof, or a biosynthetic intermediate thereof; a steroidal saponin, a derivative thereof, a metabolite thereof, or a biosynthetic intermediate thereof, or a triterpenoid saponin, a derivative thereof, a metabolite thereof, or a biosynthetic intermediate thereof.

In some embodiments, the genetically modified plant cell is comprised in a plant. In some embodiments, the genetically modified plant cell is comprised in a plant, wherein the plant is utilized in a method provided herein to produce steroidal alkaloids, steroidal saponins, or triterpenoid saponins. In some embodiments, the genetically modified plant cell is comprised in a plant tissue. In some embodiments, the genetically modified plant cell is comprised in a plant tissue, wherein the plant tissue is utilized in a method provided herein to produce steroidal alkaloids, steroidal saponins, or triterpenoid saponins. In some embodiments, the genetically modified plant cell is comprised in a plant organ. In some embodiments, the genetically modified plant cell is comprised in a plant organ, wherein the plant organ is utilized in a method provided herein to produce steroidal alkaloids, steroidal saponins, or triterpenoid saponins. In some embodiments, the genetically modified plant cell is comprised in a plant part. In some embodiments, the genetically modified plant cell is comprised in a plant part, wherein the plant part is utilized in a method provided herein to produce steroidal alkaloids, steroidal saponins, or triterpenoid saponins.

In some embodiments, a genetically modified cell comprises a plant cell comprising a leaf cell, a petiole cell, a plant stem or stalk cell, a root cell, a bud cell, a tuber cell, a bean cell, a grain or kernel cell, a fruit cell, a nut cell, a legume cell, a seed or seed cell, a bract cell, a callus cell, or a flower cell. In some embodiments, a genetically modified cell comprises a plant cell comprised in a plant leaf, in a plant petiole, in a plant stem or stalk, in a plant root, in a plant bud, in a plant tuber, in a plant bean, in a plant grain or kernel, in a plant fruit, in a plant nut, in a plant legume, in a plant seed, in a plant bract, in a plant callus, or in a plant flower, or in a combination thereof. In some embodiments, a genetically modified plant cell is comprised within a plant part, wherein said plant part comprises a leaf, a petiole, a plant stem or stalk, a root, a bud, a tuber, a bean, a grain or kernel, a fruit, a nut, a legume, a seed or seed, a bract, a callus, or a flower.

In some embodiments, a genetically modified plant cell may be utilized in a method of producing a steroidal alkaloid, a steroidal saponin, or a triterpenoid saponin as described herein.

In some embodiments, a genetically modified cell comprises a genetically modified plant cell (e.g., cultured plant cells). In other embodiments, a genetically modified plant cell is comprised in plant or a plant organ(s), plant tissue(s), or plant part(s). In some embodiments, the term "plant" may be used interchangeably with the term "plant part" having all the same meanings and qualities.

In some embodiments, a genetically modified plant cell, plant, plant organ, plant tissue, or plant part may be utilized in a method of producing a steroidal alkaloid, a steroidal saponin, or a triterpenoid saponin as described herein.

The content of a steroidal alkaloid, a steroidal saponin, or a triterpenoid saponin, a derivative thereof, a metabolite thereof, or a biosynthetic intermediate thereof present in a genetically modified cell or plant or plant part is measured as exemplified hereinbelow and as is known to a person skilled in the art.

In some embodiments, an offspring plant comprises increased contents of a steroidal alkaloid, a derivative thereof, a metabolite thereof, or a biosynthetic intermediate thereof; a steroidal saponin, a derivative thereof, a metabolite thereof, or a biosynthetic intermediate thereof, a triterpenoid saponin, a derivative thereof, a metabolite thereof, or a biosynthetic intermediate thereof, compared to at least one of the progenitor plants.

In some embodiments, a plant or plant cell or plant tissue or plant part as disclosed herein is selected from the Caryophyllales order, the Solanales order, the Fabales order, the Malvales order, the *Apiales* order, the Brassicales order, the Poales order, the Lamiales order, the Cucurbitales order, the Asterales order, the Malpighiales order, the Rosales order, the Fagales order, the Sapindales order, the Arecales order, the Ericales order, the Gentianales order, the Ranunculales order, the Zingiberales order, the Saxifragales order, the Vitales order, the Pinales order, the Cornales order, the *Asparagales* order, the Dioscoreales order, and the Liliales order. In some embodiments, a plant or plant cell or plant tissue or plant part as disclosed herein comprises a cell from a plant selected from the Caryophyllales order, the Solanales order, the Fabales order, the Malvales order, the *Apiales* order, the Brassicales order, the Poales order, the Lamiales order, the Cucurbitales order, the Asterales order, the Malpighiales order, the Rosales order, the Fagales order, the Sapindales order, the Arecales order, the Ericales order, the Gentianales order, the Ranunculales order, the Zingiberales order, the Saxifragales order, the Vitales order, the Pinales order, the Cornales order, the *Asparagales* order, the Dioscoreales order, and the Liliales order.

In some embodiments, a plant or plant cell or plant tissue or plant part as disclosed herein comprises a cell from a plant in the Poales order, the Caryophyllales order, the Solanales order, the Fabales order, the Ma/vales order, the *Apiales* order, the Brassicales order, the *Asparagales* order, the Dioscoreales order, or the Liliales order.

In some embodiments, a plant or plant cell or plant tissue or plant part as disclosed herein is in the Caryophyllales order and is selected from the group of genera consisting of the *Spinacia* genus (e.g., *Spinacia oleracea*), the *Chenopodium* genus (e.g., *Chenopodium quinoa*), the *Beta* genus (e.g., *Beta vulgaris*) the *Rheum* genus (e.g., *Rheum hybri-*

*dum, Rheum* rhaponticum, *Rheum* rhabarbarum, *Rheum ribes*), the *Vaccaria* genus (e.g., *Vaccaria hispanica*), the *Saponaria* genus (e.g., *Saponaria vaccaria*), and the *Gypsophila* genus (e.g., *Gypsophila paniculata*). In some embodiments, a Caryophyllales plant is selected from the group consisting of spinach, beetroot, and *quinoa*.

In some embodiments, a plant or plant cell or plant tissue or plant part as disclosed herein is in the Solanales order and is selected from the group of genera consisting of the *Nicotiana* genus (e.g., *Nicotiana benthamiana*), the *Solanum* genus (e.g., *Solanum lycopersicum, Solanum tuberosum, Solanum melongena, Solanum pennellii, Solanum chacoense, Solanum dulcamara*), the *Capsicum* genus (e.g., *Capsicum annuum*), the *Hyoscyamus* genus, the *Datura* genus, and the *Atropa* genus. In some embodiments, a plant as disclosed herein comprises a Solanaceae crop plant. In some embodiments, a Solanaceae crop plant is selected from the group consisting of *Solanum lycopersicum, Solanum pennellii, Solanum tuberosum, Solanum chacoense, Capsicum annuum, Solanum dulcamara*, and *Solanum melongena*. In some embodiments, a Solanaceae or Solanales plant is selected from the group consisting of ground cherry, eggplant, potato, tomato, wild tomato, potato, wild potato, pepper, bell pepper, cayenne pepper, chili pepper, pimiento, tabasco pepper, tobacco, and bittersweet.

In some embodiments, the plant is in the *Fabales* order and is selected from the group of genera consisting of the *Glycyrrhiza* genus (e.g., *Glycyrrhiza uralensis, Glycyrrhiza glabra* [licorices]), the *Medicago* genus (e.g., *Medicago sativa, Medicago truncatula*), the *Quillaja* genus (e.g., *Quillaja saponaria*), the *Glycine* genus (e.g., *Glycine max* [soy/soybean]), the *Lotus* genus (e.g., *Lotus japonicus*), the *Cicer* genus (e.g., *Cicer arietinum* [chickpea, garbanzo bean]), the *Phaseolus* genus (e.g., *Phaseolus vulgaris* [string bean, common bean, French bean]), the *Pisum* genus (e.g., *Pisum sativum* [pea]), the *Arachis* genus (e.g., *Arachis hypogaea* [peanut]), the *Lupinus* genus (e.g., *Lupinus albus* [lupin/lupine]), and the *Acacia* genus. In some embodiments, a Fabales plant is selected from the group consisting of alfalfa, soy, *Lotus japonicus*, and licorice.

In some embodiments, the plant is from the Malvales order and is selected from the *Theobroma* genus (e.g., *Theobroma cacao*).

In some embodiments, the plant is from the *Apiales* order and is selected from the group of genera consisting of the *Daucus* genus (e.g., *Daucus carota*), the *Apium* genus (e.g., *Apium graveolens*), the *Petroselinum* genus (e.g., *Petroselinum crispum*), the *Panax* genus (e.g., *Panax ginseng*), the *Bupleurum* genus, the *Hedera* genus, and the *Centella* genus (e.g., *Centella asiatica*).

In some embodiments, the plant is from the Brassicales order and is selected from the group of genera consisting of the *Arabidopsis* genus (e.g., *Arabidopsis thaliana*), the *Brassica* genus (e.g., *Brassica oleracea* [cabbages], *Brassica juncea* [white mustard], *Brassica nigra* [black mustard], *Brassica napus*), the *Capparis* genus (e.g., *Capparis spinosa* [caper]), and the *Carica* genus (e.g., *Carica papaya* [*papaya*]).

In some embodiments, the plant is from the Poales order and is selected from the group of genera consisting of the *Oryza* genus (e.g., *Oryza sativa* and *Oryza glaberrima* [rice]), the *Hordeum* genus (e.g., *Hordeum vulgare* [barley]), the *Avena* genus (e.g., *Avena sativa* [oat], *Avena strigosa*), and the *Triticum* genus (e.g., *Triticum spelta* [spelt]).

In some embodiments, the plant is from the Lamiales order and is selected from the group of genera consisting of the *Salvia* genus (e.g., *Salvia hispanica* [chia]), the *Sesamum* genus (e.g., *Sesamum indicum* [sesame, benne]), and the *Olea* genus (e.g., *Olea europaea* [olive]).

In some embodiments, the plant is from the Cucurbitales order and is selected from the *Cucurbita* genus (e.g., squash/pumpkin, including, but not limited to, *Cucurbita pepo, Cucurbita maxima, Cucurbita argyrosperma*, or *Cucurbita moschata*).

In some embodiments, the plant is from the Asterales order and is selected from the group of genera consisting of the *Helianthus* genus (e.g., *Helianthus annuus* [sunflower], *Helianthus* verticallatus [whorled sunflower], *Helianthus tuberosus* [Jerusalem artichoke]), the *Artemesia* genus (e.g., *Artemesia annua*), the *Galatella* (Aster) genus (e.g., *Galatella sedifolia*), and the *Taraxacum* genus (e.g., *Taraxacum officinale* [dandelion]).

In some embodiments, the plant is from the Malpighiales order and is selected from the group of genera consisting of the *Linum* genus (e.g., *Linum usitatissimum* [flax, linseed]), the *Bruguiera* genus (e.g., *Bruguiera gymnorhiza*), the *Euphorbia* genus (e.g., *Euphorbia tirucalli*), the *Ricinus* genus (e.g., *Ricinus communis* [castor]), the *Kandelia* genus (e.g., *Kandelia candel*), and the *Rhizophora* genus (e.g., *Rhizophora stylosa*).

In some embodiments, the plant is from the Rosales order and is selected from the group of genera consisting of the *Prunus* genus (e.g., *Prunus dulcis* [almond], *Prunus amygdalus*) and the *Cannabis* genus (e.g., hemp, including *Cannabis sativa*).

In some embodiments, the plant is from the Fagales order and is selected from the group of genera consisting of the *Corylus* genus (e.g., hazel/hazelnut/cobnut/filbert nut, including, but not limited to, *Corylus avellana*), the *Betula* genus (e.g., *Betula pendula* [silver birch], *Betula pubescens* [white or downy birch], *Betula platyphylla*) and the *Juglans* genus (e.g., *Juglans regia* [Persian or English walnut], *Juglans nigra* [black walnut], *Juglans cinera* [butternut]).

In some embodiments, the plant is from the Sapindales order and is selected from the group of genera consisting of the *Anacardium* genus (e.g., *Anacardium occidentale* [cashew]), the *Pistacia* genus (e.g., *Pistacia vera* [pistachio]), the Citrus genus (numerous species and hybrids), the *Aesculus* genus (e.g., *Aesculus hippocastanum, Aesculus turbinata*), and the *Peganum* genus.

In some embodiments, the plant is from the Arecales order and is selected from the *Cocus* genus (e.g., *Cocus nucifera* [coconut]).

In some embodiments, the plant is from the Ericales order and is selected from the *Maesa* genus.

In some embodiments, the plant is from the Gentianales order and is selected from the group of genera consisting the *Nerium* genus (e.g., *Nerium oleander*), the *Gentianamacrophylla* genus (e.g., *Gentianamacrophylla straminea*), the Catharanthus genus (e.g., *Catharanthus roseus*), the *Rauwolfia* genus, and the *Cinchona* genus.

In some embodiments, the plant is from the Ranunculales order and is selected from the genera consisting of the *Nigella* genus (e.g., *Nigella sativa*), the *Papaver* genus, the *Eschscholtzia* genus (e.g., *Eschscholtzia californica*), the *Coptis* genus, the *Berberis* genus, and the *Thalictrum* genus.

In some embodiments, the plant is from the Zingiberales order and is selected from the *Cheilocostus* genus (e.g., *Cheilocostus speciosus*).

In some embodiments, the plant is from the Saxifragales order and is selected from the *Kalanchoe* genus (e.g., *Kalanchoe daigremontiana*).

In some embodiments, the plant is from the Vitales order and is selected from the *Vitis* genus (e.g., *Vitis vinifera* [grape]).

In some embodiments, the plant is from the Pinales order and is selected from the *Taxus* genus (e.g., *Taxus brevifolia, Taxus baccdata, Taxus cuspidata, Taxus canadensis, Taxus floridana*).

In some embodiments, the plant is from the Cornales order and is selected from the *Camptotheca* genus (e.g., *Camptotheca acuminata*). In some embodiments, the plant is from the *Asparagales* order and is selected from the *Agave* genus (e.g., *Agave* americana, *Agave attenuata, Agave tequilana*), the *Asparagus* genus (e.g., *Asparagus officinalis*), or the *Yucca* genus (e.g., *Yucca filamentosa*). In some embodiments, the plant is from the Dioscoreales order and is selected from the *Borderea* genus, the *Dioscorea* genus, the *Epipetrum* genus, the *Rajania* genus, the *Stenomeris* genus, or the *Taxus* genus. In some embodiments, the plant is from the Liliales order and is selected from the Liliaceae family (e.g., *Clintonia borealis, Nomocharis aperta, Calochortus catalinae, Streptopus* lariceolatus).

A skilled artisan would appreciate that plant breeding can be accomplished through many different techniques ranging from simply selecting plants with desirable characteristics for propagation, to methods that make use of knowledge of genetics and chromosomes, to more complex molecular techniques.

A skilled artisan would appreciate that the term "hybrid plant" may encompass a plant generated by crossing two plants of interest, propagating by seed or tissue and then growing the plants. When plants are crossed sexually, the step of pollination may include cross pollination or self-pollination or back crossing with an untransformed plant or another transformed plant. Hybrid plants include first generation and later generation plants.

Biological Activity

In some embodiments, the genetically modified cell or genetically modified plant comprises an endogenous enzyme comprising the same or similar activity with an enzyme encoded by the at least one heterologous gene. In other embodiments, the genetically modified cell or genetically modified plant does not comprise an endogenous enzyme comprising the same or similar activity with an enzyme encoded by the at least one heterologous gene. In some embodiments, the genetically modified plant cell or plant comprises an endogenous enzyme comprising altered activity of a steroidal alkaloid, a steroidal saponin, or a triterpenoid saponin biosynthesis enzyme.

In some embodiments, the biological activity of at least one saponin beta-amyrin synthase, cytochrome P450, a glycosyltransferase, acyltransferase, a glucuronosyltransferase, or CSLG, or combination thereof encoded by the heterologous gene is altered compared with an endogenous saponin beta-amyrin synthase, cytochrome P450, glycosyltransferase, acyltransferase, glucuronosyltransferase, or CSLG protein present in the genetically modified cell or genetically modified plant. In some embodiments, the biological activity of at least one endogenous saponin beta-amyrin synthase, cytochrome P450, a glycosyltransferase, acyltransferase, a glucuronosyltransferase, or CSLG, or combination thereof is altered compared with the endogenous saponin beta-amyrin synthase, cytochrome P450, glycosyltransferase, acyltransferase, glucuronosyltransferase, or CSLG protein present in the non-genetically modified cell or non-genetically modified plant.

A skilled artisan would recognize that the term "biological activity" refers to any activity associated with a protein that can be measured by an assay. In some embodiments, the biological activity of a saponin beta-amyrin synthase, a cytochrome P450, a glycosyltransferase, an acyltransferase, a glucuronosyltransferase, or a CSLG comprises an enzyme activity necessary for the biosynthesis of a steroidal alkaloid, a derivative thereof, a metabolite thereof, or a biosynthetic intermediate thereof: a steroidal saponin, a derivative thereof, a metabolite thereof, or a biosynthetic intermediate thereof; or a triterpenoid saponin, a derivative thereof, a metabolite thereof, or a biosynthetic intermediate thereof in a cell or a plant. In some embodiments, the biological activity of a saponin beta-amyrin synthase, a cytochrome P450, a glycosyltransferase, an acyltransferase, a glucuronosyltransferase, or a CSLG affects the content of a steroidal alkaloid, a derivative thereof, a metabolite thereof, or a biosynthetic intermediate thereof; a steroidal saponin, a derivative thereof, a metabolite thereof, or a biosynthetic intermediate thereof; or a triterpenoid saponin, a derivative thereof, a metabolite thereof, or a biosynthetic intermediate thereof, in at least a part of a plant. In some embodiments, an altered biological activity comprises increased enzyme activity. In some embodiments, an altered biological activity comprises decreased enzyme activity. In some embodiments, an altered biological activity comprises increased stability of the polypeptide. In some embodiments, an altered biological activity comprises decreased stability of the polypeptide. In some embodiments, an altered biological activity comprises increased expression so higher levels of the enzyme polypeptide. In some embodiments, an altered biological activity comprises decreased expression of the enzyme polypeptide.

In some embodiments, the biological activity of an enzyme is altered compared with a control enzyme.

In some embodiments, the altered biological activity comprises (a) increased enzyme activity of the saponin beta-amyrin synthase, cytochrome P450, glycosyltransferase, acyltransferase, glucuronosyltransferase, or CSLG; or increased stability of the saponin beta-amyrin synthase, cytochrome P450, glycosyltransferase, acyltransferase, glucuronosyltransferase, or CSLG; or decreased enzyme activity of the saponin beta-amyrin synthase, cytochrome P450, glycosyltransferase, acyltransferase, glucuronosyltransferase, or CSLG; or decreased stability of the saponin beta-amyrin synthase, cytochrome P450, glycosyltransferase, acyltransferase, glucuronosyltransferase, or CSLG.

In some embodiments, the biological activity of a saponin beta-amyrin synthase, cytochrome P450, glycosyltransferase, acyltransferase, glucuronosyltransferase, or CSLG is increased. In some embodiments, the biological activity of a saponin beta-amyrin synthase, cytochrome P450, glycosyltransferase, acyltransferase, glucuronosyltransferase, or CSLG is decreased. In some embodiments, a saponin beta-amyrin synthase, cytochrome P450, glycosyltransferase, acyltransferase, glucuronosyltransferase, or CSLG has increased stability. In some embodiments, a saponin beta-amyrin synthase, cytochrome P450, glycosyltransferase, acyltransferase, glucuronosyltransferase, or CSLG has decreased stability.

In some embodiments, the altered biological activity comprises increased enzyme activity of said at least one saponin beta-amyrin synthase, cytochrome P450, glycosyltransferase, acyltransferase, glucuronosyltransferase, or CSLG; or increased stability of said at least one saponin beta-amyrin synthase, cytochrome P450, glycosyltransferase, acyltransferase, glucuronosyltransferase, or CSLG; or decreased enzyme activity of said at least one saponin beta-amyrin synthase, cytochrome P450, glycosyltransferase, acyltransferase, glucuronosyltransferase, or CSLG; or decreased stability of said at least one saponin beta-amyrin synthase, cytochrome P450, glycosyltransferase, acyltransferase, glucuronosyltransferase, or CSLG; compared to the biological activity in the endogenous enzyme, if present, in said genetically modified cell or genetically modified plant.

Transgenic Plants, Transgenic Yeast, Transgenic Algae, Transgenic Insect Cells, Transgenic Bacterium Cloning of a polynucleotide encoding an enzyme encoded by the at least one heterologous gene, wherein the enzyme comprises at least one saponin beta-amyrin synthase, cytochrome P450, glycosyltransferase, acyltransferase, glucuronosyltransferase, or CSLG can be performed by any method as is known to a person skilled in the art. Cloning of a polynucleotide encoding an at least one saponin beta-amyrin synthase, cytochrome P450, glycosyltransferase, acyltransferase, glucuronosyltransferase, or CSLG as described herein, can be performed by any method as is known to a person skilled in the art. In certain embodiments, a polynucleotide encoding a CSLG enzyme is cloned. Various DNA constructs may be used to express the desired gene in a desired cell or organism. In some embodiments, various DNA constructs are used to expression a CSLG gene in a cell. In some embodiments, various DNA constructs are used to expression a CSLG gene in a plant cell, a yeast cell, an insect cell, an algal cell, or a bacterium. In some embodiments, various DNA constructs are used to expression a CSLG gene in a plant cell. In some embodiments, various DNA constructs are used to expression a CSLG gene in a yeast cell. In some embodiments, various DNA constructs are used to expression a CSLG gene in a plant cell or a yeast cell. In some embodiments, various DNA constructs are used to expression a CSLG gene in an algal cell. In some embodiments, various DNA constructs are used to expression a CSLG gene in an insect cell. In some embodiments, various DNA constructs are used to expression a CSLG gene in a bacterium. In some embodiments, various DNA constructs are used to expression a heterologous CSLG gene in the cell. In some embodiments, when the cell is a plant cell the CSLG gene is a heterologous gene. In some embodiments, when the cell is a plant cell the CSLG gene is a homologous gene, wherein said expression is altered, for example increased or decreased, or said CSLG gene is mutated to alter the activity of the CSLG enzyme. In some embodiments, when the cell is a plant cell, the plant cell is comprised within a plant or a plant part.

According to certain embodiments, the gene may comprise part of an expression vector comprising all necessary elements for expression of the gene and optional regulatory components.

According to certain embodiments, the expression is controlled by a constitutive promoter. According to other embodiments, the expression is controlled by a transient promoter. According to certain embodiments, the constitutive promoter is specific to a cell or to a plant or plant tissue. According to some embodiments, the tissue specific promoter is selected from the group consisting of root, tuber, leaves and fruit specific promoter. Root specific promoters are described, e.g. in Martinez, E. et al. 2003. Curr. Biol. 13:1435-1441. Fruit specific promoters are described among others in Estornell L. H et al. 2009. Plant Biotechnol. J. 7:298-309 and Fernandez A. I. Et al. 2009 Plant Physiol. 151:1729-1740. Tuber specific promoters are described, e.g. in Rocha-Sosa M, et al., 1989. EMBO J. 8:23-29; McKibbin R. S. et al., 2006. Plant Biotechnol J. 4(4):409-18. Leaf specific promoters are described, e.g. in Yutao Yang, Guodong Yang, Shijuan Liu, Xingqi Guo and Chengchao Zheng. Science in China Series C: Life Sciences. 46: 651-660. Accordingly, in some embodiments, a promoter comprises a yeast specific promoter. Accordingly, in some embodiments, a promoter comprises an algal specific promoter.

According to certain embodiments, the expression vector further comprises regulatory elements at the 3' non-coding sequence. As used herein, the "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. For plants, the use of different 3' non-coding sequences is exemplified by Ingelbrecht I L et al. (1989. Plant Cell 1:671-680).

Those skilled in the art will appreciate that the various components of the nucleic acid sequences and the transformation vectors described herein are operatively linked, so as to result in expression of said nucleic acid or nucleic acid fragment. Techniques for operatively linking the components of the constructs and vectors described herein are well known to those skilled in the art. Such techniques include the use of linkers, such as synthetic linkers, for example, including one or more restriction enzyme sites.

One skilled in the art would appreciate that the term "operably linked" may encompass the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation.

Methods for transforming a plant according to the teachings disclosed herein are known to those skilled in the art. As used herein the term "transformation" or "transforming" describes a process by which a foreign DNA, such as a DNA construct, including expression vector, enters and changes a recipient cell into a transformed, genetically altered or transgenic cell. Transformation may be stable, wherein the nucleic acid sequence is integrated into the organism genome and as such represents a stable and inherited trait, or transient, wherein the nucleic acid sequence is expressed by the cell transformed but is not integrated into the genome, and as such represents a transient trait. According to some embodiments the nucleic acid sequence disclosed herein is stably transformed into the cell.

The genetically altered cells or plants having altered content of the desired at least one saponin beta-amyrin synthase, cytochrome P450, glycosyltransferase, acyltransferase, glucuronosyltransferase, or CSLG; and altered content of at least one steroidal alkaloid, derivative thereof, metabolite thereof, or biosynthetic intermediate thereof; at least one steroidal saponin, derivative thereof, metabolite thereof, or biosynthetic intermediate thereof; or at least one triterpenoid saponin, derivative thereof, metabolite thereof, or biosynthetic intermediate thereof. In some embodiments, genetically modified cells or plants produced as described herein are typically first selected based on the expression of the gene or protein. Cells or plants having expressing the enzyme encoding from the at least one heterologous gene may be identified and, are then analyzed for the content of at least one saponin beta-amyrin synthase, cytochrome P450, glycosyltransferase, acyltransferase, glucuronosyltransferase, or CSLG and/or at least one steroidal alkaloid, derivative thereof, metabolite thereof, or biosynthetic intermediate thereof; at least one steroidal saponin, derivative thereof, metabolite thereof, or biosynthetic intermediate thereof; or a triterpenoid saponin, a derivative thereof, a metabolite thereof, or a biosynthetic intermediate thereof.

In some embodiments, the genetically altered plants having altered content of the desired at least one steroidal alkaloid, derivative thereof, metabolite thereof, or biosynthetic intermediate thereof; at least one steroidal saponin, derivative thereof, metabolite thereof, or biosynthetic intermediate thereof; or at least one triterpenoid saponin, derivative thereof, metabolite thereof, or biosynthetic intermediate thereof, according to the teachings herein are first selected based on the expression of the gene or protein. Plants having enhanced or aberrant expression of the gene or protein, are then analyzed for the content of at least one steroidal alkaloid, derivative thereof, metabolite thereof, or biosynthetic intermediate thereof; at least one steroidal saponin, derivative thereof, metabolite thereof, or biosynthetic intermediate thereof; or at least one triterpenoid saponin, derivative thereof, metabolite thereof, or biosynthetic intermediate thereof. In some embodiments, derivatives of steroidal alkaloids, steroidal saponins, or triterpenoid saponins comprise glycosylated derivatives of, respectively, steroidal alkaloids, steroidal saponins, or triterpenoid saponins.

Detection of at least one saponin beta-amyrin synthase, cytochrome P450, glycosyltransferase, acyltransferase, glucuronosyltransferase, or CSLG gene and/or at least one steroidal alkaloid, derivative thereof, metabolite thereof, or biosynthetic intermediate thereof; at least one steroidal saponin, derivative thereof, metabolite thereof, or biosynthetic intermediate thereof; or a triterpenoid saponin, a derivative thereof, a metabolite thereof, or a biosynthetic intermediate thereof is performed employing standard methods of molecular genetics, known to a person of ordinary skill in the art. Similarly, purification and/or detection of at least one steroidal alkaloid, derivative thereof, metabolite thereof, or biosynthetic intermediate thereof; at least one steroidal saponin, derivative thereof, metabolite thereof, or biosynthetic intermediate thereof; or a triterpenoid saponin, a derivative thereof, a metabolite thereof, or a biosynthetic intermediate thereof is performed employing standard methods of molecular genetics or protein chemistry known to a person of ordinary skill in the art.

For measuring the gene(s), cDNA or mRNA should be obtained from a cell or a plant in which the nucleic acid is expressed. The sample may be further processed before the detecting step. For example, the polynucleotides in the cell or tissue sample may be separated from other components of the sample, may be amplified, etc. All samples obtained from an organism, including those subjected to any sort of further processing are considered to be obtained from the organism.

For measuring the gene(s) or silencing molecule(s) expression, cDNA or mRNA should be obtained from an organ in which the nucleic acid is expressed. The sample may be further processed before the detecting step. For example, the polynucleotides in the cell or tissue sample may be separated from other components of the sample, may be amplified, etc. All samples obtained from an organism, including those subjected to any sort of further processing are considered to be obtained from the organism.

Detection of the gene(s) in some embodiments, requires amplification of the polynucleotides taken from the candidate genetically modified cell or genetically modified plant or part thereof. In some embodiments a plant part comprises a plant organ or a plant tissue.

Methods for DNA amplification are known to a person skilled in the art. Most commonly used method for DNA amplification is PCR (polymerase chain reaction; see, for example, PCR Basics: from background to Bench, Springer Verlag, 2000; Eckert et al., 1991. PCR Methods and Applications 1:17). Additional suitable amplification methods include the ligase chain reaction (LCR), transcription amplification and self-sustained sequence replication, and nucleic acid-based sequence amplification (NASBA).

According to certain embodiments, the nucleic acid sequence comprising the at least one saponin beta-amyrin synthase, cytochrome P450, glycosyltransferase, acyltransferase, glucuronosyltransferase, or CSLG, or any combination thereof may in some embodiments, further comprises a nucleic acid sequence encoding a selectable marker. According to certain embodiments, the selectable marker confers resistance to antibiotic or to an herbicide; in these embodiments the transgenic cells or plants are selected according to their resistance to the antibiotic or herbicide.

Breeding

In some embodiments, transformation techniques including breeding through transgene editing, use of transgenes, use of transient expression of a gene or genes, or use of molecular markers, or any combination thereof, may be used in the breeding of a plant having an altered expression. If transformation techniques require use of tissue culture, transformed cells may be regenerated into plants in accordance with techniques well known to those of skill in the art. The regenerated plants may then be grown and crossed with the same or different plant varieties using traditional breeding techniques to produce seed, which are then selected under the appropriate conditions.

The content of steroidal alkaloids and/or steroidal saponins is measured as exemplified hereinbelow and as is known to a person skilled in the art.

In some embodiments, an offspring plant comprises decreased anti-nutritional contents or decreased toxins compared to at least one of the progenitor plants. In some embodiments, an offspring plant comprises improved resistance to a plant pathogen, pest, or predator compared to at least one of the progenitor plants.

In some embodiments, a plant as disclosed herein comprises a crop plant from any of the orders listed in the previous section. In some embodiments, a plant as disclosed herein comprises a crop plant in the Poales order, the Caryophyllales order, the Solanales order, the Fabales order, the Malvales order, the *Apiales* order, the Brassicales order, the *Asparagales* order, the Dioscoreales order, or the Liliales order.

In some embodiments, when the plant comprises a crop plant in the Poales order, said plant is selected from the group of genera consisting of the *Oryza* genus, the *Hordeum* genus, the *Avena* genus, and the *Triticum* genus.

In some embodiments, when a plant is a crop plant in the Caryophvllales order, said plant is selected from the group of genera consisting of the *Spinacia* genus, the *Chenopodium* genus, the *Beta* genus, the *Rheum* genus, the *Vaccaria* genus, the *Saponaria* genus, and the Gypsophila genus. In some embodiments, the Caryophyllales plant is selected from the group consisting of spinach, beetroot, and *quinoa.*

In some embodiments, when a plant is a crop plant in the Solanales order, said plant from the group of genera consisting of the *Solanum* genus, the *Capsicum* genus, the *Nicotiana* genus, the *Hyoscyamus* genus, the *Datura* genus, and the *Atropa* genus. In some embodiments, when a plant is a crop plant in the Solanales order, said plant is selected from the group consisting of *Solanum lycopersicum, Solanum pennellii, Solanum tuberosum, Solanum chacoense, Capsicum annuum, Solanum melongena, Solanum dulcamara* and *Nicotiana benthamiana*. In some embodiments, the Solanales plant is selected from the group consisting of ground cherry, eggplant, potato, tomato, pepper, bell pepper, cayenne pepper, chili pepper, pimiento, tabasco pepper, tobacco, and bittersweet. In some embodiments, the Solanales plant comprises a Solanaceae plant.

In some embodiments, when a plant is a crop plant in the Fabales order, said plant is selected from the group of genera consisting of the *Glycyrrhiza* genus, the *Medicago* genus, the *Glycine* genus, the *Lotus* genus, the *Cicer* genus, the *Phaseolus* genus, the *Pisum* genus, the *Arachis* genus, the *Lupinus* genus, and the *Acacia* genus. In some embodiments, the Fabales plant is selected from the group consisting of alfalfa, soy, *Lotus japonicus*, and licorice.

In some embodiments, when a plant is a crop plant in the Malvales order, said plant is selected from the *Theobroma* genus.

In some embodiments, when a plant is a crop plant in the *Apiales* order, said plant is selected from the group of genera consisting of the *Daucus* genus, the *Apium* genus, the *Petroselinum* genus, the *Panax* genus, the *Bupleurum* genus, the *Hedera* genus, and the *Centella* genus.

In some embodiments, when a plant is a crop plant in the Brassicales order, said plant is selected from the group of genera consisting of the *Arabidopsis* genus, the *Brassica* genus, the *Capparis* genus, and the *Carica* genus.

In some embodiments, the plant is a crop plant of any order, family, genus, or species disclosed herein.

A skilled artisan would appreciate that plant breeding can be accomplished through many different techniques ranging from simply selecting plants with desirable characteristics for propagation, to methods that make use of knowledge of genetics and chromosomes, to more complex molecular techniques.

A skilled artisan would appreciate that the term "hybrid plant" may encompass a plant generated by crossing two plants of interest, propagating by seed or tissue and then growing the plants. When plants are crossed sexually, the step of pollination may include cross pollination or self-pollination or back crossing with an untransformed plant or another transformed plant. Hybrid plants include first generation and later generation plants. Disclosed herein is a method to manipulate and improve a plant trait, for a non-limiting example—increasing plant resistance, decreasing anti-nutritional properties in a plant, decreasing toxins or bitter tasting compounds in a plant, increasing pharmaceutical properties in a plant, or any combination thereof.

Biomarkers

A skilled artisan would appreciate that the term "biomarker" comprises any measurable substance in an organism whose presence is indicative of a biological state or a condition of interest. In some embodiments, the presence of a biomarker is indicative of the presence of a compound or a group of compounds of interest. In some embodiments, the concentration of a biomarker is indicative of the concentration of a compound or a group of compounds of interest. In some embodiments, the concentration of a biomarker is indicative of an organism phenotype.

CSLG enzymes are hereby disclosed to have an essential role in the biosynthesis of steroidal alkaloids, steroidal saponins, and triterpenoid saponins found in many plants. Thus, in some embodiments, the expression level of CSLG is indicative of the capacity of a plant to produce steroidal alkaloids, or derivatives, metabolites, or biosynthetic intermediates thereof; steroidal saponins, or derivatives, metabolites, or biosynthetic intermediates thereof, triterpenoid saponins, or derivatives, metabolites, or biosynthetic intermediates thereof; or combinations thereof.

Methods for Producing Steroidal Alkaloids, Steroidal Saponins, and Triterpenoid Saponins Provided herein are methods of producing a steroidal alkaloid, a steroidal saponin, or a triterpenoid saponin in a genetically modified cell or plant comprising a genetically modified plant cell or a plant part comprising a genetically modified plant part, the methods comprising: introducing a polynucleotide sequence into said cell, wherein said polynucleotide sequence is optionally comprised in a vector, wherein said polynucleotide sequence comprises at least one heterologous gene encoding an enzyme, said enzyme selected from the group consisting of a saponin beta-amyrin synthase, a cytochrome P450, a glycosyltransferase, an acyltransferase, a UDP-glucose 6-dehydrogenase I, and a cellulose synthase like G (CSLG); and expressing said at least one heterologous gene in said cell. In some embodiments, the polynucleotide sequence introduced comprises multiple polynucleotide sequences, wherein each polynucleotide sequence comprises at least one heterologous gene encoding an enzyme, said enzyme selected from the group consisting of a saponin beta-amyrin synthase, a cytochrome P450, a glycosyltransferase, an acyltransferase, a UDP-glucose 6-dehydrogenase I, and a cellulose synthase like G (CSLG). In some embodiments, the polynucleotide sequence introduced comprises 2, 3, 4, 5, 6, 7, 8, 9, 10, or more polynucleotide sequences each polynucleotide sequence comprising at least one heterologous gene encoding an enzyme, said enzyme selected from the group consisting of a saponin beta-amyrin synthase, a cytochrome P450, a glycosyltransferase, an acyltransferase, a UDP-glucose 6-dehydrogenase I, and a cellulose synthase like G (CSLG). In some embodiments, the polynucleotide sequence introduced comprises 2, 3, 4, 5, 6, 7, 8, 9, 10, or more polynucleotide sequences each comprises only one heterologous gene encoding an enzyme, said enzyme selected from the group consisting of a saponin beta-amyrin synthase, a cytochrome P450, a glycosyltransferase, an acyltransferase, a UDP-glucose 6-dehydrogenase I, and a cellulose synthase like G (CSLG). In some embodiments, the polynucleotide sequence introduced comprises 2, 3, 4, 5, 6, 7, 8, 9, 10, or more polynucleotide sequences each comprising any combination of 1, 2, 3, 4, 5, 6, 7, 8, 9, or 10, or more heterologous genes encoding an enzyme, said enzyme selected from the group consisting of a saponin beta-amyrin synthase, a cytochrome P450, a glycosyltransferase, an acyltransferase, a UDP-glucose 6-dehydrogenase I, and a cellulose synthase like G (CSLG). A skilled artisan would appreciate that the polynucleotide sequence or sequences are introduced into a cell where they are expressed, resulting in expression of the encoded enzyme or enzymes in the genetically modified cell.

In some embodiments, disclosed herein is a method of producing a steroidal alkaloid, a steroidal saponin, or a triterpenoid saponin in a genetically modified cell, the method comprising:

(a) introducing an at least one heterologous gene into said cell, said at least one heterologous gene encoding a cellulose synthase like G (CSLG) enzyme, wherein said heterologous gene is optionally comprised in a vector; and
(b) expressing said at least one heterologous gene in said cell;

wherein said cell comprises an increased content of at least one steroidal alkaloid, at least one steroidal saponin, or at least one triterpenoid saponin compared to a corresponding unmodified cell.

In some embodiments, said introducing further comprising introducing an at least one additional heterologous gene into said cell, said heterologous gene selected from the group consisting of the group encoding a saponin beta-amyrin synthase, a cytochrome P450, a glycosyltransferase, an acyltransferase, and a UDP-glucose 6-dehydrogenase I, or any combination thereof, wherein said at least one additional heterologous gene is optionally comprised in a vector; and further comprising expressing said at least one additional heterologous gene in said cell. In some embodiments, said at least one heterologous gene is operably linked to a promoter, a transcription termination sequence, or a combination thereof; or said at least one additional heterologous gene is operably linked to a promoter, a transcription termination sequence, or a combination thereof; or a combination thereof of (a) and (b).

In some embodiments, said introducing comprises transforming said at least one cell with said at least one heterologous gene or a polynucleotide sequence encoding said at least one heterologous gene, or the vector comprising said at least one heterologous gene; or said at least one additional heterologous gene or a polynucleotide sequences encoding said at least one additional heterologous gene, or the vector comprising said at least one additional heterologous gene; or a combination thereof of (a) and (b); wherein said expressing comprises transient expression or constitutive expression.

Cellulose synthase like G nucleic acid sequences encoding a CSLG enzyme are described in detail throughout and exemplified in the Examples. In some embodiments, the nucleic acid sequence encoding said at least one heterologous CSLG gene is set forth in any one of SEQ ID NOS: 30, 32, 34, 36, 38, 40, 65, 80, 93, 95, 97, 99, 101, 103, or 105; or a homolog thereof having at least 55% identity to and at least 55% coverage of, the nucleic acid sequence set forth in any one of SEQ ID NOS: 30, 32, 34, 36, 38, 40, 65, 80, 93, 95, 97, 99, 101, 103, or 105. Cellulose synthase like G nucleic acid sequences encoding a CSLG enzyme am described in detail throughout and exemplified in the Examples. In some embodiments, the nucleic acid sequence encoding said at least one heterologous CSLG gene is set forth in any one of SEQ ID NOS: 30, 32, 34, 36, 38, 40, 65, 80, 93, 95, 97, 99, 101, 103, or 105; or a homolog thereof having at least 55% identity to and at least 80% coverage of, the nucleic acid sequence set forth in any one of SEQ ID NOS: 30, 32, 34, 36, 38, 40, 65, 80, 93, 95, 97, 99, 101, 103, or 105.

Cellulose synthase like G nucleic acid sequences encoding a CSLG enzyme are described in detail throughout and exemplified in the Examples. In some embodiments, the nucleic acid sequence encoding said at least one heterologous CSLG gene is set forth in any one of SEQ ID NOS: 30, 32, 34, 36, 38, 40, 65, 80, 93, 95, 97, 99, 101, 103, or 105; or a homolog thereof having at least 80% identity to and at least 80% coverage of, the nucleic acid sequence set forth in any one of SEQ ID NOS: 30, 32, 34, 36, 38, 40, 65, 80, 93, 95, 97, 99, 101, 103, or 105.

In some embodiments, in a method of producing a triterpenoid saponin, the amino acid sequence of said encoded CSLG enzyme is set forth in any one of SEQ ID NOS: 31, 33, 35, 37, 39, 41, 66, 81, 94, 96, 98, 100, 102 or 104; or a homolog thereof having at least 55% identity to and at least 55% coverage of, the amino acid sequence set forth in any one of SEQ ID NOS: 31, 33, 35, 37, 39, 41, 66, 81, 94, 96, 98, 100, 102 or 104. In some embodiments, in a method of producing a triterpenoid saponin, the amino acid sequence of said encoded CSLG enzyme is set forth in any one of SEQ ID NOS: 31, 33, 35, 37, 39, 41, 66, 81, 94, 96, 98, 100, 102 or 104; or a homolog thereof having at least 55% identity to and at least 80/% coverage of, the amino acid sequence set forth in any one of SEQ ID NOS: 31, 33, 35, 37, 39, 41, 66, 81, 94, 96, 98, 100, 102 or 104.

In some embodiments, in a method of producing a triterpenoid saponin, the amino acid sequence of said encoded CSLG enzyme is set forth in any one of SEQ ID NOS: 31, 33, 35, 37, 39, 41, 66, 81, 94, 96, 98, 100, 102 or 104; or a homolog thereof having at least 80% identity to and at least 80% coverage of, the amino acid sequence set forth in any one of SEQ ID NOS: 31, 33, 35, 37, 39, 41, 66, 81, 94, 96, 98, 100, 102 or 104.

The GAME proteins, GAME1 and GAME4, were used as baits in potato or tomato, as described herein in the Examples. Genes that were co-expressed with GAME1 or GAME4 are shown in Tables 5-8, and the enzymes of the steroidal alkaloid pathway, along with a portion of the enzymes of steroidal saponin pathway, are presented in FIG. 1 and described in detail throughout and exemplified in the Examples. The SOAP nucleic acid sequences respectively encoding the SOAP enzymes of the triterpenoid saponin pathway presented in FIG. 20A, are described in detail throughout and exemplified in the Examples.

In some embodiments, in a method of producing a steroidal alkaloid, a steroidal saponin, or a triterpenoid saponin, the nucleic acid sequence encoding said at least one additional heterologous gene encodes a β-amyrin synthase, said nucleic acid sequence set forth in SEQ ID NO: 45; or a homolog thereof having at least 80% identity to and at least 80% coverage of, the nucleic acid sequence set forth in SEQ ID NO: 45; or a cytochrome P450, said nucleic acid sequence set forth in any one of SEQ ID NO: 46, 51, or 53; or a homolog thereof having at least 80% identity to and at least 80% coverage of, the nucleic acid sequence set forth in any one of SEQ ID NO: 46, 51, or 53; or a glycosyl transferase, said nucleic acid sequence set forth in any one of SEQ ID NO: 55, 57, 59, 61; or a homolog thereof having at least 80% identity to and at least 80% coverage of, the nucleic acid sequence set forth in any one of SEQ ID NO: 55, 57, 59, or 61; or an acyltransferase, said nucleic acid sequence set forth in SEQ ID NO: 63; or a homolog thereof having at least 80% identity to and at least 80% coverage of, the nucleic acid sequence set forth in SEQ ID NO: 63; or a UDP-glucose 6-dehydrogenase 1, said nucleic acid sequence set forth in SEQ ID NO: 74; or a homolog thereof having at least 80% identity to and at least 80% coverage of, the nucleic acid sequence set forth in SEQ ID NO: 74, or any combination thereof.

In some embodiments, in a method of producing a steroidal alkaloid, a steroidal saponin, or a triterpenoid saponin, the amino acid sequence of said encoded at least one additional heterologous gene encodes a β-amyrin synthase, said amino acid sequence set forth in SEQ ID NO: 48; or a homolog thereof having at least 80% identity to and at least 80% coverage of, the amino acid sequence set forth in SEQ ID NO: 48; or a cytochrome P450, said amino acid sequence set forth in any one of SEQ ID NO: 49, 52, or 54; or a homolog thereof having at least 80% identity to and at least 80% coverage of, the amino acid sequence set forth in any one of SEQ ID NO: 49, 52, or 54; or a glycosyl transferase, said amino acid sequence set forth in any one of SEQ ID NO: 56, 58, 60, or 62; or a homolog thereof having at least 80% identity to and at least 80% coverage of, the amino acid sequence set forth in any one of SEQ ID NO: 56, 58, 60, or 62; or an acyltransferase, said amino acid sequence set forth in SEQ ID NO: 64; or a homolog thereof having at least 80% identity to and at least 80% coverage of, the amino acid sequence set forth in SEQ ID NO: 64; or a UDP-glucose 6-dehydrogenase 1, said amino acid sequence set forth in SEQ ID NO: 75; or a homolog thereof having at least 80% identity to and at least 80% coverage of, the amino acid sequence set forth in SEQ ID NO: 75; or any combination thereof.

In some embodiments, in a method of producing a steroidal alkaloid or steroidal saponin, said steroidal alkaloid or steroidal saponin comprises an anti-nutritive agent, a cosmetic agent, or a pharmaceutical agent or any combination thereof. In some embodiments, in a method of producing a steroidal alkaloid or steroidal saponin, said steroidal alkaloid or steroidal saponin is selected from an anti-nutritive agent, a cosmetic agent, or a pharmaceutical agent, or any combination thereof.

In some embodiments, in a method of producing a triterpenoid saponin, said triterpenoid saponin comprises a sweetener, foaming agent, emulsifier, preservative, anti-carcinogen, hypocholesterolemic agent, anti-inflammatory agent, anti-oxidant, biological adjuvant, anti-microbial agent, insecticidal agent, antifeedant, or an anti-fungal agent, or any combination thereof. In some embodiments, in a method of producing a triterpenoid saponin, said triterpenoid saponin is selected from a sweetener, foaming agent, emulsifier, preservative, anti-carcinogen, hypocholesterolemic agent, anti-inflammatory agent, anti-oxidant, biological adjuvant, anti-microbial agent, insecticidal agent, antifeedant, or anti-fungal agent, or any combination thereof.

In some embodiments, in a method of producing a steroidal alkaloid, said steroidal alkaloid comprises alpha-tomatine, tomatine, alpha-chaconine, alpha-solanine, alpha-solasonine, alpha-solmargine, or any combination thereof. In some embodiments, iun a method of producing a steroidal alkaloid, said steroidal alkaloid is selected from the group consisting of alpha-tomatine, tomatine, alpha-chaconine, alpha-solanine, alpha-solasonine, alpha-solmargine, or any combination thereof.

In some embodiments, in a method of producing a steroidal saponin, said steroidal saponin comprises uttroside B, a tomatoside, or any combination thereof. In some embodiments, iun a method of producing a steroidal alkaloid, said steroidal alkaloid is selected from the group consisting of uttroside B, a tomatoside, or any combination thereof.

In some embodiments, in a method of producing a triterpenoid saponin, said triterpenoid saponin comprises medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof. In some embodiments, in a method of producing a triterpenoid saponin, said triterpenoid saponin is selected from medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof.

In some embodiments, derivatives of steroidal alkaloids, steroidal saponins, or triterpenoid saponins comprise glycosylated derivatives of, respectively, steroidal alkaloids, steroidal saponins, or triterpenoid saponins.

In some embodiments, in a method of producing a steroidal alkaloid, a steroidal saponin, or a triterpenoid saponin, said cell comprises a plant cell, a yeast cell, an alga cell, an insect cell, or a bacterium. In some embodiments, in a method of producing a steroidal alkaloid, a steroidal saponin, or a triterpenoid saponin, said cell comprises a plant cell, a yeast cell, or an alga cell. In some embodiments, in a method of producing a steroidal alkaloid, a steroidal saponin, or a triterpenoid saponin, said cell comprises a plant cell or a yeast cell. In some embodiments, in a method of producing a steroidal alkaloid, a steroidal saponin, or a triterpenoid saponin, said cell comprises a plant cell. In some embodiments, in a method of producing a steroidal alkaloid, a steroidal saponin, or a triterpenoid saponin, said cell comprises a yeast cell. In some embodiments, in a method of producing a steroidal alkaloid, a steroidal saponin, or a triterpenoid saponin, said cell comprises an alga cell. In some embodiments, in a method of producing a steroidal alkaloid, a steroidal saponin, or a triterpenoid saponin, said cell comprises an insect cell. In some embodiments, in a method of producing a steroidal alkaloid, a steroidal saponin, or a triterpenoid saponin, said cell comprises a bacterium.

In some embodiments, the at least one heterologous gene is operably linked to a promoter, a transcription termination sequence, or a combination thereof.

In some embodiments, the step of introducing comprises transforming said at least one cell with said polynucleotide sequence or a vector comprising the polynucleotide sequence, and wherein said expression comprises transient expression or constituitive expression. In some embodiments, the vector comprises an expression vector. In some embodiments, the vector comprises a plasmid vector. In some embodiments, the vector integrates into the host cell DNA. In some embodiments, part of the polynucleotide comprised in the vector integrates into the host cell DNA. In some embodiments, the vector does not integrate into the host cell DNA and replicates as a separate entity within the host cell.

In some embodiments, expression vectors used to produce genetically modified plant cells include both *Agrobacterium* and non-*Agrobacterium* vectors. *Agrobacterium*-mediated gene transfer exploits the natural ability of *Agrobacterium tumefaciens* to transfer DNA into plant chromosomes and is described in detail in G. Gheysen, G. Angenon, and M. Van Montagu, 1998, *Agrobacterium*-mediated plant transformation: a scientifically intriguing story with significant applications in K. Lindsey (Ed.), Transgenic Plant Research, Harwood Academic Publishers, Amsterdam, pp. 1-33; and in H. A. Stafford (2000), Botanical Review 66:99-118. A second group of transformation methods is the non-*Agrobacterium*-mediated transformation and these methods are known as direct gene transfer methods. An overview is brought by P. Barcelo and P. A. Lazzeri (1998), Direct gene transfer: chemical, electrical and physical methods in K. Lindsey (Ed.), Transgenic Plant Research, Harwood Academic Publishers, Amsterdam, pp. 35-55. Methods include particle gun delivery, microinjection, electroporation of intact cells, polyethyleneglycol-mediated protoplast transformation, electroporation of protoplasts, liposome-mediated transformation, silicon-whiskers-mediated transformation, etc. A suitable control plant would include a genetically unaltered or non-transgenic plant of the parental line used to generate a transgenic plant herein.

Genetically transformed hairy root cultures can be obtained by transformation with virulent strains of *Agrobacterium rhizogenes*. Protocols used for establishing of hairy root cultures vary, as well as the susceptibility of plant species to infection by *Agrobacterium* (Toivounen et al. 1993; Vanhala et al. 1995). It is known that the *Agrobacterium* strain used for transformation has a great influence on root morphology and the degree of secondary metabolite accumulation in hairy root cultures. It is possible by systematic clone selection, e.g., via protoplasts, to find high yielding, stable, and from single-cell-derived hairy root clones. This is possible because the hairy root cultures possess a great somaclonal variation. Another possibility of transformation is the use of viral vectors (Turpen 1999).

Any plant tissue or plant cells capable of subsequent clonal propagation, whether by organogenesis or embryogenesis, may be transformed with an expression vector of interest. The team "organogenesis" means a process by which shoots and roots are developed sequentially from meristematic centers; the term "embryogenesis" means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include protoplasts, leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyls meristem).

In some embodiments, disclosed herein is a vector comprising a polynucleotide sequence or at least a heterologous gene encoding an enzyme as described in detail above. In some embodiments, disclosed herein is a host cell, for example but not limited to a plant cell, a yeast, or an algal cell, comprising a polynucleotide sequence or at least a heterologous gene encoding an enzyme as described in detail above, or a vector comprising a polynucleotide or at least one heterologous gene encoding an enzyme as described throughout.

The term "vector" in certain embodiments, encompasses a nucleic acid molecule capable of transporting another nucleic acid molecule to which it has been operably or continuously linked. The vector may be of any suitable type including, but not limited to, a phage, virus, plasmid, phagemid, cosmid, bacmid or even an artificial chromosome. Certain vectors are capable of autonomous replication in a host cell into which they are introduced (e.g., vectors having an origin of replication that functions in the host cell). Other vectors can be integrated into the genome of a host cell upon introduction into the host cell, and are thereby replicated along with the host genome. Moreover, in some embodiments, vectors are capable of directing the expression of certain genes of interest. Such vectors are referred to herein as "recombinant expression vectors" (or simply, "expression vectors"). Suitable vectors have regulatory sequences, such as promoters, enhancers, terminator sequences, and the like as desired and according to a particular host organism (e.g., plant cell, yeast cell, or algal cell).

Typically, a recombinant vector according to the disclosure comprises at least one "heterologous gene encoding an enzyme" or "expression cassette comprising an at least one heterologous gene encoding an enzyme". Expression cassettes are generally DNA constructs, which in some embodiments include (5' to 3' in the direction of transcription): a promoter region, a polynucleotide sequence comprising at least one heterologous gene encoding an enzyme, homologue, variant, or fragment thereof of the disclosure as described above in detail, operably linked with the transcription initiation region, and a termination sequence including a stop signal for RNA polymerase and a polyadenylation signal. It is understood that all of these regions should be capable of operating in biological cells, such as plant cells or yeast cells or algal cells, to be transformed. The promoter region comprising the transcription initiation region, which preferably includes the RNA polymerase binding site, and the polyadenylation signal may be native to the biological cell to be transformed or may be derived from an alternative source, where the region is functional in the biological cell.

The term "recombinant host cell" ("expression host cell," "expression host system," "expression system" or simply "host cell"), as used herein, encompasses a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell that resides in a living tissue or organism. Host cells can be of fungal, plant or algal origin.

In some embodiments, disclosed herein is a transgenic plant or a cell derived thereof that is transformed with the above-described vector.

In some embodiments in methods of producing a steroidal alkaloid, a steroidal saponin, or a triterpenoid saponin, the encoded enzyme comprises a saponin beta-amyrin synthase, a cytochrome P450, a glycosyltransferase, an acyltransferase, a UDP-glucose 6-dehydrogenase I, or a cellulose synthase like G (CSLG). In some embodiments in methods of producing a steroidal alkaloid, a steroidal saponin, or a triterpenoid saponin, multiple enzymes are encoded by heterologous genes wherein the encoded enzymes comprises a combination of a saponin beta-amyrin synthase, a cytochrome P450, a glycosyltransferase, an acyltransferase, a UDP-glucose 6-dehydrogenase I, or a cellulose synthase like G (CSLG). In some embodiments in methods of producing a steroidal alkaloid, a steroidal saponin, or a triterpenoid saponin, 1, 2, 3, 4, 5, 6, 7, 8, 9, 10, or more enzymes are encoded by heterologous genes wherein the encoded enzymes comprises a combination of a saponin beta-amyrin synthase, a cytochrome P450, a glycosyltransferase, an acyltransferase, a UDP-glucose 6-dehydrogenase I, or a cellulose synthase like G (CSLG). In some embodiments in methods of producing a steroidal alkaloid, a steroidal saponin, or a triterpenoid saponin, the encoded enzyme comprises a CSLG.

In some embodiments, the cytochrome P450 comprises a C2-hydroxylase or is a C-23 oxidase. In some embodiments, the glycosyltransferase comprises a fructosyltransferase, a xylosyltransferase, or a UDP-glycosyltransferase, or a combination thereof. In some embodiments, the acyltransferase comprises a benzylalcohol acetyl-, anthocyanin-O-hydroxy-cinnamoyl-, anthranilate-N-hydroxy-cinnamyol/benzoyl-, deacetylvindoline (BAHD) acetyletransferase. In some embodiments, in a method of producing a triterpenoid saponin the encoded cytochrome P450 comprises a C2-hydroxylase or is a C-23 oxidase, or a combination thereof; said glycosyltransferase comprises a fructosyltransferase, a xylosyltransferase, or a UDP-glycosyltransferase, or a combination thereof; the said acyltransferase comprise a benzylalcohol acetyl-, anthocyanin-O-hydroxy-cinnamoyl-, anthranilate-N-hydroxy-cinnamyol/benzoyl-, deacetylvindoline (BAHD) acetyletransferase; or the encoded enzymes comprise a combination of any of these enzymes, wherein optionally additional enzymes are comprised within a polynucleotide sequence or sequences.

In some embodiments in a method of producing a steroidal alkaloid, a steroidal saponin, or a triterpenoid saponin, the polynucleotide sequence of said at least one heterologous gene is set forth in any one of SEQ ID NOS: 30, 32, 34, 36, 38, 40, 45, 46, 47, 51, 53, 55, 57, 59, 61, 63, 65, 80, 93, 95, 97, 99, 101, 103, or 105; or the polynucleotide sequence of said at least one heterologous gene comprises a nucleic acid sequence having at least 55% identity to the nucleic acid sequence set forth in any one of SEQ ID NOS: 30, 32, 34, 36, 38, 40, 45, 46, 47, 51, 53, 55, 57, 59, 61, 63, 65, 80, 93, 95, 97, 99, 101, 103, or 105. In some embodiments, wherein multiple heterologous genes are expressed, the skilled artisan would appreciate that a polynucleotide sequence or sequences may comprise a combination of any of SEQ ID NOS: 30, 32, 34, 36, 38, 40, 45, 46, 47, 51, 53, 55, 57, 59, 61, 63, 65, 80, 93, 95, 97, 99, 101, 103, or 105, as described in detail above. In some embodiments, wherein multiple heterologous genes are expressed, the skilled artisan would appreciate that a polynucleotide sequence or sequences may comprise a combination of comprises a nucleic acid sequence having at least 55% identity to the nucleic acid sequence set forth in any one of SEQ ID NOS: 30, 32, 34, 36, 38, 40, 45, 46, 47, 51, 53, 55, 57, 59, 61, 63, 65, 80, 93, 95, 97, 99, 101, 103, or 105.

In some embodiments in a method of producing a steroidal alkaloid, a steroidal saponin, or a triterpenoid saponin, the polynucleotide sequence of said at least one heterologous gene is set forth in any one of SEQ ID NOS: 30, 32, 34, 36, 38, 40, 45, 46, 47, 51, 53, 55, 57, 59, 61, 63, 65, 80, 93, 95, 97, 99, 101, 103, or 105; or the polynucleotide sequence of said at least one heterologous gene comprises a nucleic acid sequence having at least 80% identity to the nucleic acid sequence set forth in any one of SEQ ID NOS: 30, 32, 34, 36, 38, 40, 45, 46, 47, 51, 53, 55, 57, 59, 61, 63, 65, 80, 93, 95, 97, 99, 101, 103, or 105. In some embodiments, wherein multiple heterologous genes are expressed, the skilled artisan would appreciate that a polynucleotide sequence or sequences may comprise a combination of any of SEQ ID NOS: 30, 32, 34, 36, 38, 40, 45, 46, 47, 51, 53, 55, 57, 59, 61, 63, 65, 80, 93, 95, 97, 99, 101, 103, or 105, as described in detail above. In some embodiments, wherein multiple heterologous genes are expressed, the skilled artisan would appreciate that a polynucleotide sequence or sequences may comprise a combination of comprises a nucleic acid sequence having at least 80% identity to the nucleic acid sequence set forth in any one of SEQ ID NOS: 30, 32, 34, 36, 38, 40, 45, 46, 47, 51, 53, 55, 57, 59, 61, 63, 65, 80, 93, 95, 97, 99, 101, 103, or 105.

In some embodiments in a method of producing a steroidal alkaloid, a steroidal saponin, or a triterpenoid saponin, the polynucleotide sequence of said at least one heterologous gene encodes the amino acid sequence of said enzyme set forth in any one of SEQ ID NOS: 31, 33, 35, 37, 39, 41, 48, 49, 50, 52, 54, 56, 58, 60, 62, 64, 64, 81, 94, 96, 98, 100, 102 or 104; or the polynucleotide sequence of said at least one heterologous gene encodes the amino acid sequence of said enzyme set forth in the sequence having at least 55% identity to the amino acid sequence set forth in any one of SEQ ID NOS: 31, 33, 35, 37, 39, 41, 48, 49, 50, 52, 54, 56, 58, 60, 62, 64, 64, 81, 94, 96, 98, 100, 102 or 104.

In some embodiments in a method of producing a steroidal alkaloid, a steroidal saponin, or a triterpenoid saponin, the polynucleotide sequence of said at least one heterologous gene encodes the amino acid sequence of said enzyme set forth in any one of SEQ ID NOS: 31, 33, 35, 37, 39, 41, 48, 49, 50, 52, 54, 56, 58, 60, 62, 64, 64, 81, 94, 96, 98, 100, 102 or 104; or the polynucleotide sequence of said at least one heterologous gene encodes the amino acid sequence of said enzyme set forth in the sequence having at least 80% identity to the amino acid sequence set forth in any one of SEQ ID NOS: 31, 33, 35, 37, 39, 41, 48, 49, 50, 52, 54, 56, 58, 60, 62, 64, 64, 81, 94, 96, 98, 100, 102 or 104.

In some embodiments in a method of producing a steroidal alkaloid, a steroidal saponin, or a triterpenoid saponin, the genetically modified cell, for example but not limited to a plant cell, a yeast, or an algal cell comprises an increased content of at least a steroidal alkaloid, a steroidal saponin, or a triterpenoid saponin, compared to a corresponding unmodified cell. In some embodiments in a method of producing a steroidal alkaloid, a steroidal saponin, or a triterpenoid saponin, the genetically modified cell, for example but not limited to a plant cell, a yeast, an algal cell, an insect cell, or a bacterium, comprises an increased content of at least a steroidal alkaloid, a steroidal saponin, or a triterpenoid saponin, compared to a corresponding unmodified cell. In some embodiments in a method of producing a steroidal alkaloid, a steroidal saponin, or a triterpenoid saponin, the genetically modified cell comprises a plant cell comprising an increased content of at least a steroidal alkaloid, a steroidal saponin, or a triterpenoid saponin, compared to a corresponding unmodified cell. In some embodiments in a method of producing a steroidal alkaloid, a steroidal saponin, or a triterpenoid saponin, the genetically modified cell comprises a yeast cell comprising an increased content of at least a steroidal alkaloid, a steroidal saponin, or a triterpenoid saponin, compared to a corresponding unmodified cell. In some embodiments in a method of producing a steroidal alkaloid, a steroidal saponin, or a triterpenoid saponin, the genetically modified cell comprises a algal cell comprising an increased content of at least a steroidal alkaloid, a steroidal saponin, or a triterpenoid saponin, compared to a corresponding unmodified cell. In some embodiments in a method of producing a steroidal alkaloid, a steroidal saponin, or a triterpenoid saponin, the genetically modified cell comprises a plant cell comprising an increased content of at least a steroidal alkaloid, a steroidal saponin, or a triterpenoid saponin, compared to a corresponding unmodified cell, wherein said plant cell is comprised in a plant or plant part.

In some embodiments, in a method of producing a steroidal alkaloid, the steroidal alkaloid produced comprises an anti-nutritive agent, a cosmetic agent, or a pharmaceutical agent, or any combination thereof; or the steroidal alkaloid comprises an esculeoside or dehydroesculeoside; or the steroidal alkaloid comprises alpha-tomatine, tomatine, dehydrotomatine, alpha-chaconine, alpha-solanine, alpha-solasonine, alpha-solmargine, or any combination thereof. In some embodiments, in a method of producing a steroidal alkaloid, the steroidal alkaloid produced comprises alpha-tomatine, tomatine, dehydrotomatine, alpha-chaconine, alpha-solanine, alpha-solasonine, alpha-solmargine, or any combination thereof.

In some embodiments, in a method of producing a steroidal alkaloid, the steroidal alkaloid produced comprises alpha-tomatine. In some embodiments, in a method of producing a steroidal alkaloid, the steroidal alkaloid produced comprises tomatine. In some embodiments, in a method of producing a steroidal alkaloid, the steroidal alkaloid produced comprises dehydrotomatine. In some embodiments, in a method of producing a steroidal alkaloid, the steroidal alkaloid produced comprises alpha-chaconine. In some embodiments, in a method of producing a steroidal alkaloid, the steroidal alkaloid produced comprises alpha-solanine. In some embodiments, in a method of producing a steroidal alkaloid, the steroidal alkaloid produced comprises alpha-solasonine. In some embodiments, in a method of producing a steroidal alkaloid, the steroidal alkaloid produced comprises alpha-solmargine.

In some embodiments, in a method of producing a steroidal saponin, the steroidal saponin produced comprises an anti-nutritive agent, a cosmetic agent, or a pharmaceutical agent, or any combination thereof, or the steroidal alkaloid comprises uttroside B, a tomatoside, or any combination thereof. In some embodiments, in a method of producing a steroidal saponin, the steroidal saponin produced comprises uttroside B, a tomatoside, or any combination thereof.

In some embodiments, in a method of producing a steroidal saponin, the steroidal saponin produced comprises uttroside B. In some embodiments, in a method of producing a steroidal saponoin, the steroidal saponin produced comprises a tomatoside.

In some embodiments in a method of producing a triterpenoid saponin, the triterpenoid saponin produced comprises a sweetener, foaming agent, emulsifier, preservative, anti-carcinogen, hypocholesterolemic agent, anti-inflammatory agent, anti-oxidant, biological adjuvant, anti-microbial agent, insecticidal agent, antifeedant, anti-fungal agent, or any combination thereof; or the titerpenoid saponin comprises medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof; or a combination thereof. In some embodiments in a method of producing a triterpenoid saponin, the triterpenoid saponin produced comprises medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof.

In some embodiments in a method of producing a triterpenoid saponin, the triterpenoid saponin produced comprises medicagenic acid 3-O-glucuronide (MA-3-GlcA) (Compound 6). In some embodiments in a method of producing a triterpenoid saponin, the triterpenoid saponin produced comprises Compound 7. In some embodiments in a method of producing a triterpenoid saponin, the triterpenoid saponin produced comprises Compound 8. In some embodiments in a method of producing a triterpenoid saponin, the triterpenoid saponin produced comprises Compound 9. In some embodiments in a method of producing a triterpenoid saponin, the triterpenoid saponin produced comprises Compound 10. In some embodiments in a method of producing a triterpenoid saponin, the triterpenoid saponin produced comprises Compound 11 In some embodiments in a method of producing a triterpenoid saponin, the triterpenoid saponin produced comprises glycyrrhizin (Compound 14). In some embodiments in a method of producing a triterpenoid saponin, the triterpenoid saponin produced comprises Glycyrrhetinic acid 3-O-monoglucuronide (compound 15). In some embodiments in a method of producing a triterpenoid saponin, the triterpenoid saponin produced comprises bayogenin (Compound 25). In some embodiments in a method of producing a triterpenoid saponin, the triterpenoid saponin produced comprises bayogenin-hexA-hex-hex (Compound 31). In some embodiments in a method of producing a triterpenoid saponin, the triterpenoid saponin produced comprises serjanic acid (Compound 26). In some embodiments in a method of producing a triterpenoid saponin, the triterpenoid saponin produced comprises serjanic acid-hexA-hex (Compound 32). In some embodiments in a method of producing a triterpenoid saponin, the triterpenoid saponin produced comprises soyasapogenol A (Compound 29). In some embodiments in a method of producing a triterpenoid saponin, the triterpenoid saponin produced comprises soyasapogenol B (Compound 30). In some embodiments in a method of producing a triterpenoid saponin, the triterpenoid saponin produced comprises soyasapogenol A-hexA-hex-pent (Compound 34). In some embodiments in a method of producing a triterpenoid saponin, the triterpenoid saponin produced comprises soyasaponin VI (Compound 35). In some embodiments in a method of producing a triterpenoid saponin, the triterpenoid saponin produced comprises betavulgaroside IV (Compound 33). In some embodiments in a method of producing a triterpenoid saponin, the triterpenoid saponin produced comprises hederagenin-3GlcA, gypsogenin-3GlcA. In some embodiments in a method of producing a triterpenoid saponin, the triterpenoid saponin produced comprises gypsogenic acid-3GlcA. In some embodiments in a method of producing a triterpenoid saponin, the triterpenoid saponin produced comprises a QS-21 adjuvant, or any combination thereof.

In some embodiments, a method of producing a steroidal alkaloid, steroidal saponin, or triterpenoid saponin comprises increasing the content of the steroidal alkaloid, steroidal saponin, or triterpenoid saponin, respectively, compared to an unmodified cell or an unmodified plant and altering the content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof, a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of producing a steroidal alkaloid, steroidal saponin, or triterpenoid saponin comprises increasing the content of the steroidal alkaloid, steroidal saponin, or triterpenoid saponin, respectively, compared to an unmodified cell or an unmodified plant and decreasing the content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments in a method of producing a steroidal alkaloid, a steroidal saponin, or a triterpenoid saponin, the cell into which the polynucleotide sequence is introduced comprises a plant cell or a yeast cell. Alternatively, in some embodiments, it comprises an algal cell. Plant and yeast cells that may be genetically modified as described herein, have been disclosed above in detail. Those same plant and yeast cells may, in some embodiments, be used in a method of producing a steroidal alkaloid, a steroidal saponin, or a triterpenoid saponin. In some embodiments in a method of producing a steroidal alkaloid, a steroidal saponin, or a triterpenoid saponin, the cell into which the polynucleotide sequence is introduced comprises a plant cell or a yeast cell or an algal cell or an insect cell or a bacterium.

In some embodiments in a method of producing a steroidal alkaloid, a steroidal saponin, or a triterpenoid saponin, the cell comprises a plant cell that comprises a leaf cell, a petiole cell, a plant stem or stalk cell, a root cell, a bud cell, a tuber cell, a bean cell, a grain or kernel cell, a fruit cell, a nut cell, a legume cell, a seed or seed cell, a bract cell, a callus cell, and a flower cell.

In some embodiments in a method of producing a steroidal alkaloid, a steroidal saponin, or a triterpenoid saponin, the yeast cell, the algal cell, or the plant cell is from an order, genus, or species recited herein. For example, but not limited to a plant cell comprising a cell from a plant in the Poales order, the Caryophyllales order, the Solanales order, the Fabales order, the Malvales order, the *Apiales* order, the Brassicales order, the *Asparagales* order, the Dioscoreales order, or the Liliales order; or a yeast is selected from a *Saccharomyces* genus, a *Schizosaccharomyces* genus, a *Pichia* genus, a *Yarrowia* genus, a *Kluyveromyces* genus, or a *Candida* genus.

In some embodiments of producing a steroidal alkaloid, a steroidal saponin, or a triterpenoid saponin, the plant of the Caryophyllales order is selected from the group of genera consisting of the *Spinacia* genus, the *Chenopodium* genus, the *Beta* genus, and the *Rheum* genus; or the plant of the Solanales order is selected from the group of genera consisting of the *Nicotiana* genus, the *Solanum* genus, and the *Capsicum* genus; or the plant of the Fabales order is selected from the group of genera consisting of the *Glycyrrhiza* genus, the *Medicago* genus, the *Quillaja* genus, the *Glycine* genus, and the *Lotus* genus; or the plant of the *Apiales* order is selected from the group of genera consisting of the *Panax* genus, *Daucus* genus, the *Apium* genus, and the *Petroselinum* genus, or the plant from the Poales order is selected from the group of genera consisting of the *Oryza* genus (e.g., *Oryza* sativa and *Oryza glaberrima* [rice]), the *Hordeum* genus (e.g., *Hordeum vulgare* [barley]), the *Avena* genus (e.g., *Avena* saliva [oat], *Avena strigosa*), and the *Triticum* genus (e.g., *Triticum spelta* [spelt]), or the plant from the Brassicales order is selected from the group of genera consisting of the *Arabidopsis* genus (e.g., *Arabidopsis thaliana*), the *Brassica* genus (e.g., *Brassica oleracea* [cabbages], *Brassica juncea* [white mustard], *Brassica nigra* [black mustard], *Brassica napus*), the *Capparis* genus (e.g., *Capparis spinosa* [caper]), and the *Carica* genus (e.g., *Carica papaya* [papaya]).

In some embodiments in a method of producing a steroidal alkaloid, a steroidal saponin, or a triterpenoid saponin, the plant of the Solanales order is selected from the group of species consisting of *Nicotiana benthamiana, Solanum lycopersicum, Solanum tuberosum, Solanum melongena, Solanum pennellii, Solanum chacoense, Solanum dulcamara*, and *Capsicum annuum*; or the plant of the Fabales order is selected from the group of species consisting of *Glycyrrhiza uralensis, Medicago saliva. Medicago truncatula, Quillaja saponaria, Glycine max*, and *Lotus japonicus*; or the plant of the Malvales order is selected from the *Theobroma* genus: or the plant of the *Apiales* order is selected from the group of species consisting of *Panax ginseng, Daucus carota, Apium graveolens*, and *Petroselinum crispum*; or the plant is selected from the species *Theobroma cacao*, or the plant from the Poales order is selected from the group of genera consisting of the *Oryza* genus (e.g., *Oryza sativa* and *Oryza glaberrima* [rice]), the *Hordeum* genus (e.g., *Hordeum vulgare* [barley]), the *Avena* genus (e.g., *Avena sativa* [oat], *Avena strigosa*), and the *Triticum* genus (e.g., *Triticum spelta* [spelt]), or the plant from the Brassicales order is selected from the group of genera consisting of the *Arabidopsis* genus (e.g., *Arabidopsis thaliana*), the *Brassica* genus (e.g., *Brassica oleracea* [cabbages], *Brassica juncea* [white mustard], *Brassica nigra* [black mustard], *Brassica napus*), the *Capparis* genus (e.g., *Capparis spinosa* [caper]), and the *Carica* genus (e.g., *Carica papaya* [papaya]).

In some embodiments in a method of producing a steroidal alkaloid, a steroidal saponin, or a triterpenoid saponin, the yeast is selected from a *Saccharomyces* genus, a *Schizosaccharomyces* genus, a *Pichia* genus, a *Yarrowia* genus, a *Kluyveromyces* genus, or a *Candida* genus. In some embodiments, said yeast is a *Saccharomyces cerevisiae* or *Candida albicans*. In some embodiments in a method of producing a steroidal alkaloid, a steroidal saponin, or a triterpenoid saponin, the method further comprises a step of purifying said steroidal alkaloid, steroidal saponin, or triterpenoid saponin.

Methods of purifying steroidal alkaloids, steroidal saponins, or triterpenoids may include standard purifications techniques known in the art, for example but not limited to column liquid chromatography, preparative medium-pressure liquid chromatograph, and preparative HPLC. These techniques may be used in embodiments of purifying steroidal alkaloids, steroidal saponins, or triterpenoid saponins from plants, plant part, or plant cells. Alternatively, the plant cells or plant parts may be used as is without purifying the steroidal alkaloid, steroidal saponin, or triterpenoid saponin.

In some embodiments, when steroidal alkaloids, steroidal saponins, or triterpenoid saponins are produced in yeast cells, the steroidal alkaloids, steroidal saponins, or triterpenoid saponins are secreted from the cells. In some embodiments, a secreted steroidal alkaloid, steroidal saponin, or triterpenoid saponin is purified from a yeast cell medium.

In some embodiments, a steroidal alkaloid, steroidal saponin or triterpenoid saponin is extracted from a plant cell, a plant part, a plant, algae, a yeast, an insect cell, or bacterial culture using methods known in the art.

In some embodiments, provided herein is a method of producing at least one steroidal alkaloid, steroidal saponin, or triterpenoid saponin, the method further comprising the step of extracting said steroidal alkaloid, steroidal saponin, or triterpenoid saponin from the plant, plant part, colony, organ, tissue, or cells that produce said steroidal alkaloid, steroidal saponin, or triterpenoid saponin. In one embodiment, the plant part comprises a leaf, a petiole, a plant stem or stalk, a root, a bud, a tuber, a bean, a grain or kernel, a fruit, a nut, a legume, a seed or seed, a bract, or a flower.

Methods of Altering the Content of Steroidal Alkaloids, Steroidal Saponins, and Triterpenoid Saponins in a Plant or Plant Part or Plant Cell In some embodiments, disclosed herein is a method of altering the content of at least one steroidal alkaloid, steroidal saponin, or triterpenoid saponin in a genetically modified plant, a genetically modified plant part, or a genetically modified plant cell, the method comprising genetically modifying the CSLG gene in said plant, plant part, or said cell, wherein said modification comprises increasing expression of said CSLG gene, or increasing activity of the expressed CSLG enzyme, or increasing stability of the expressed CSLG enzyme, or any combination thereof; wherein said plant, plant part, or plant cell comprises an increased content of at least one steroidal alkaloid, steroidal saponin, or triterpenoid saponin compared to a corresponding unmodified plant, plant part, or plant cell. In other embodiments, disclosed herein is a method of altering the content of at least one steroidal alkaloid, steroidal saponin, or triterpenoid saponin in a genetically modified plant, a genetically modified plant part, or a genetically modified plant cell, the method comprising genetically modifying the CSLG gene in said plant, plant part, or said cell, wherein said modification comprises decreasing or eliminating expression of said CSLG gene, or decreasing activity of the expressed CSLG enzyme, or decreasing stability of the expressed CSLG enzyme, or any combination thereof; wherein said plant, plant part, or cell comprises a decreased content of at least one steroidal alkaloid, steroidal saponin, or triterpenoid saponin compared to a corresponding unmodified plant, plant part, or plant cell.

In some embodiments, a genetically modified plant described in detail herein, comprises an altered content of at least one steroidal alkaloid, steroidal saponin, or triterpenoid saponin disclosed herein.

In certain embodiments, disclosed herein is a method of reducing the content of at least one steroidal alkaloid, a derivative thereof, a metabolite thereof, or a biosynthetic intermediate thereof; one steroidal saponin, a derivative thereof, a metabolite thereof, or a biosynthetic intermediate thereof; or one triterpenoid saponin, a derivative thereof, a metabolite thereof, or a biosynthetic intermediate thereof, in at least one cell of a plant or a plant part, the method comprising genetically modifying said at least one plant cell, said genetic modification comprising:

(a) transforming said at least one plant cell with at least one silencing molecule targeted to a nucleic acid gene sequence encoding a Cellulose Synthase Like G (CSLG) enzyme; or (b) mutagenizing at least one nucleic acid sequence encoding a Cellulose Synthase Like G (CSLG) enzyme, wherein the mutagenesis comprises introducing (1) one or more point mutations into the nucleic acid sequence, (2) deletions within the nucleic acid sequence, or (3) insertions within the nucleic acid, or any combination thereof, wherein said introducing comprising mutagenizing coding or non-coding sequence;

wherein expression of the gene encoding the CSLG enzyme is reduced in the genetically modified plant cell compared to its expression in a corresponding unmodified plant cell, wherein the plant comprising said genetically modified cell comprises reduced content of one steroidal alkaloid, a derivative thereof, a metabolite thereof, or a biosynthetic intermediate thereof; one steroidal saponin, a derivative thereof, a metabolite thereof, or a biosynthetic intermediate thereof; or at least one triterpenoid saponin, a derivative thereof, a metabolite thereof, or a biosynthetic intermediate thereof, compared to the corresponding unmodified plant.

In certain embodiments, disclosed herein is a method of increasing the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof, or at least one triterpenoid saponin, a derivative thereof, a metabolite thereof, or a biosynthetic intermediate thereof, in at least one cell of a plant or plant part, the method comprising genetically modifying said at least one plant cell, said genetic modification comprising:

(a) mutagenizing at least one nucleic acid sequence encoding a Cellulose Synthase Like G (CSLG) enzyme, wherein the mutagenesis comprises introducing (1) one or more point mutations into the nucleic acid sequence, (2) deletions within the nucleic acid sequence, or (3) insertions within the nucleic acid, or any combination thereof, wherein said introducing comprising mutagenizing coding or non-coding sequence; and (b) expressing said nucleic acid encoding said CSLG; and wherein the plant comprising said genetically modified cell comprises increased content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; or at least one triterpenoid saponin, a derivative thereof, a metabolite thereof, or a biosynthetic intermediate thereof, compared to the corresponding unmodified plant.

Methods for mutagenizing at least one nucleic acid sequence encoding a steroidal alkaloid biosynthetic enzyme, a steroidal saponin biosynthetic enzyme, or a triterpenoid saponin biosynthetic enzyme, for example but not limited to a CSLG enzyme, have been described in detail above under the header Genetically Modified Cells & Genetically Modified Plants. Similarly, methods for transforming a plant cell with at least one silencing molecule targeted to a nucleic acid sequence encoding a steroidal alkaloid biosynthetic enzyme, a steroidal saponin biosynthetic enzyme, or a triterpenoid saponin biosynthetic enzyme, for example a nucleic acid sequence encoding a CSLG enzyme, have been described in detail above under the header Genetically Modified Cells & Genetically Modified Plants. These methods are incorporated herein in their entirety, wherein a skilled artisan would appreciate that the methods used to produce a genetically modified cell comprised within a genetically modified plant or plant part are in certain embodiments, the same methods used to reduce or increase the content of at least one steroidal alkaloid, steroidal saponin, or triterpenoid saponin in a plant or plant part, especially as the genetically modified plants or plant parts described have an altered content of at least one steroidal alkaloid, steroidal saponin, or triterpenoid saponin, derivative thereof, metabolite thereof, or biosynthetic intermediate thereof.

In some embodiments, when the at least one silencing molecule is targeted to a nucleic acid gene sequence encoding a CSLG enzyme, the nucleic acid sequence encoding said CSLG gene is set forth in any one of SEQ ID NOS: 30, 32, 34, 36 38, 40, 65, 80, 93, 95, 97, 99, 101, 103, or 105; or a homolog thereof having at least 80% identity to and at least 80% coverage of, the nucleic acid sequence set forth in any one of SEQ ID NOS: 30, 32, 34, 36 38, 40, 65, 80, 93, 95, 97, 99, 101, 103, or 105. In some embodiments, when a nucleic acid gene sequence encoding a CSLG enzyme is mutated, the nucleic acid sequence encoding said CSLG gene is set forth in any one of SEQ ID NOS: 30, 32, 34, 36 38, 40, 65, 80, 93, 95, 97, 99, 101, 103, or 105; or a homolog thereof having at least 80% identity to and at least 80% coverage of, the nucleic acid sequence set forth in any one of SEQ ID NOS: 30, 32, 34, 36 38, 40, 65, 80, 93, 95, 97, 99, 101, 103, or 105. In some embodiments, in a method of increasing or a method of decreasing an at least one steroidal alkaloid, steroidal saponin, or titerpenoid saponin, the amino acid sequence of said CSLG enzyme is set forth in any one of SEQ ID NOS: 31, 33, 35, 37, 39, 41, 66, 81, 94, 96, 98, 100, 102 or 104; or a homolog thereof having at least 80% identity to and at least 80% coverage of, the amino acid sequence set forth in any one of SEQ ID NOS: 31, 33, 35, 37, 39, 41, 66, 81, 94, 96, 98, 100, 102 or 104.

In some embodiments, derivatives of steroidal alkaloids, steroidal saponins, or triterpenoid saponins comprise glycosylated derivatives of, respectively, steroidal alkaloids, steroidal saponins, or triterpenoid saponins.

In some embodiments, the mutation comprises a mutation in a non-coding region. In some embodiments, the mutation comprises a mutation in a coding region. Not limiting examples of mutations in non-coding regions are those mutations that increase or decrease the expression of the CSLG gene. In some embodiments, the mutation comprises overexpression of the CSLG gene, wherein the genetically modified plant cell comprises an increase in at least one steroidal alkaloid, steroidal saponin, or triterpenoid saponin. Methods for overexpression are described in detail herein wherein the skilled artisan would appreciate that a constitutive or inducible promoter may be incorporated into the construct comprising the nucleic acid sequence encoding the CSLG gene. In some embodiments, the mutation comprises reduced expression of the CSLG gene, wherein the genetically modified plant cell comprises a decrease in at least one steroidal alkaloid, steroidal saponin, or triterpenoid saponin. Methods for specifically targeting a nucleic acid sequence in order to reduce expression are detailed throughout, wherein the skilled artisan would appreciate that reduction of expression would in certain embodiments, lead to reduction in content of at least one steroidal alkaloid, steroidal saponin, or triterpenoid saponin.

In some embodiments, in a method of increasing the content of a steroidal alkaloid, a derivative thereof, a metabolite thereof, or a biosynthetic intermediate thereof; a steroidal saponin, a derivative thereof, a metabolite thereof, or a biosynthetic intermediate thereof; or a triterpenoid saponin, a derivative thereof, a metabolite thereof, or a biosynthetic intermediate thereof of the gene encoding the CSLG enzyme is increased in the genetically modified plant cell compared to its expression in a corresponding unmodified plant cell; or said encoded CSLG enzyme has increased activity in the genetically modified plant cell compared to its activity in a corresponding unmodified plant cell; or said encoded CSLG enzyme has increased stability in the genetically modified plant cell compared to its stability in a corresponding unmodified plant cell, or any combination thereof. Methods for mutation of nucleic acids encoding genes of the steroidal alkaloid, steroidal saponin, or triterpenoid saponin biosynthetic pathway, for example but not limited to the CSLG gene, are described in detail above and include mutation the coding region for increased stability or activity or a combination thereof of the enzyme, and or mutation the nucleic acid sequence expressing the CSLG gene for over expression. One skilled in the art would appreciate that those methods of mutation could in certain embodiments be used herein as well.

In some embodiments, a method of reducing at least one steroidal alkaloid reduces a steroidal alkaloid comprising a toxin or a bitter tasting compound or a combination thereof, compared to the content of the steroidal alkaloid in a plant or plant part comprising a non-modified plant cell. In some embodiments, a method of reducing at least one steroidal alkaloid eliminates a steroidal alkaloid comprising a toxin or a bitter tasting compound or a combination thereof, compared to the content of the steroidal alkaloid in a plant or plant part comprising a non-modified plant cell. In some embodiments, a method of reducing at least one steroidal alkaloid reduces a steroidal alkaloid, derivative thereof, metabolite thereof, or biosynthetic intermediate thereof, comprising a toxin or a bitter tasting compound or a combination thereof, compared to the content of the steroidal alkaloid, derivative thereof, metabolite thereof, or biosynthetic intermediate thereof, in a plant or plant part comprising a non-modified plant cell. In some embodiments, a method of reducing at least one steroidal alkaloid, derivative thereof, metabolite thereof, or biosynthetic intermediate thereof, eliminates a steroidal alkaloid, derivative thereof, metabolite thereof, or biosynthetic intermediate thereof, comprising a toxin or a bitter tasting compound or a combination thereof, compared to the content of the steroidal alkaloid in a plant or plant part comprising a non-modified plant cell.

In some embodiments, the at least one steroidal alkaloid comprises an esculeoside or a dehydroesculeoside. In some embodiments, the at least one steroidal alkaloid comprises alpha-tomatine, tomatine, dehydrotomatine, alpha-chaconine, alpha-solanine, alpha-solasonine, alpha-solmargine, or any combination thereof. In some embodiments, the reduced at least one steroidal alkaloid comprises an esculeoside or a dehydroesculeoside. In some embodiments, the reduced at least one steroidal alkaloid comprises alpha-tomatine, tomatine, dehydrotomatine, alpha-chaconine, alpha-solanine, alpha-solasonine, alpha-solmargine, or any combination thereof. In some embodiments, the reduced at least one steroidal alkaloid biosynthetic intermediate comprises cholesterol, 22-hydroxycholesterol, 22,26-dihydroxycholesterol, furostanol-type saponin aglycone, furostanol-26-aldehyde, 26 amino-furostanol, tomatidenol, tomatidine, tomatidine galactoside, gamma-tomatine, or beta-1-tomatine, or any combination thereof.

In some embodiments, the reduced at least one steroidal alkaloid comprises eliminating or nearly eliminating an esculeoside or a dehydroesculeoside. In some embodiments, the reduced at least one steroidal alkaloid comprises eliminating or nearly eliminating alpha-tomatine, tomatine, dehydrotomatine, alpha-chaconine, alpha-solanine, alpha-solasonine, alpha-solmargine, or any combination thereof. In some embodiments, the reduced at least one steroidal alkaloid biosynthetic intermediate comprises eliminating or nearly eliminating cholesterol, 22-hydroxycholesterol, 22,26-dihydroxycholesterol, furostanol-type saponin aglycone, furostanol-26-aldehyde, 26 amino-furostanol, tomatidenol, tomatidine, tomatidine galactoside, gamma-tomatine, or beta-1-tomatine, or any combination thereof. In some embodiments, a method of reducing at least one steroidal alkaloid comprises eliminating a combination of at least one steroidal alkaloid and at least one steroidal alkaloid intermediate.

In some embodiments, a method of increasing at least one steroidal alkaloid increases a steroidal alkaloid comprising a toxin or a bitter tasting compound or a combination thereof, compared to the content of the steroidal alkaloid in a plant or plant part comprising a non-modified plant cell. In some embodiments, a method of increasing the content of a steroidal alkaloid, a derivative thereof, a metabolite thereof, or a biosynthetic intermediate thereof increases a steroidal alkaloid comprising an esculeoside or a dehydroesculeoside. In some embodiments, a method of increasing the content of a steroidal alkaloid, a derivative thereof, a metabolite thereof, or a biosynthetic intermediate thereof increases a steroidal alkaloid comprising alpha-tomatine, tomatine, dehydrotomatine, alpha-chaconine, alpha-solanine, alpha-solasonine, alpha-solmargine, or any combination thereof.

In some embodiments, a method of increasing the content of a steroidal alkaloid, a derivative thereof, a metabolite thereof, or a biosynthetic intermediate thereof increases at least one steroidal alkaloid biosynthetic intermediate comprises cholesterol, 22-hydroxycholesterol, 22,26-dihydroxycholesterol, furostanol-type saponin aglycone, furostanol-26-aldehyde, 26-amino-furostanol, tomatidenol, tomatidine, tomatidine galactoside, gamma-tomatine, or beta-1-tomatine, or any combination thereof. In some embodiments, a method of increasing the content of a steroidal alkaloid, a derivative thereof, a metabolite thereof, or a biosynthetic intermediate thereof increases a combination thereof.

In some embodiments, a method of reducing at least one steroidal saponin reduces a steroidal saponin comprising a toxin or a bitter tasting compound or a combination thereof, compared to the content of the steroidal saponin in a plant or plant part comprising a non-modified plant cell. In some embodiments, a method of reducing at least one steroidal saponin eliminates a steroidal saponin comprising a toxin or a bitter tasting compound or a combination thereof, compared to the content of the steroidal saponin in a plant or plant part comprising a non-modified plant cell. In some embodiments, a method of reducing at least one steroidal saponin reduces a steroidal saponin, derivative thereof, metabolite thereof, or biosynthetic intermediate thereof, comprising a toxin or a bitter tasting compound or a combination thereof, compared to the content of the steroidal saponin, derivative thereof, metabolite thereof, or biosynthetic intermediate thereof, in a plant or plant part comprising a non-modified plant cell. In some embodiments, a method of reducing at least one steroidal saponin, derivative thereof, metabolite thereof, or biosynthetic intermediate thereof, eliminates a steroidal saponin, derivative thereof, metabolite thereof, or biosynthetic intermediate thereof, comprising a toxin or a bitter tasting compound or a combination thereof, compared to the content of the steroidal saponin in a plant or plant part comprising a non-modified plant cell.

In some embodiments, the at least one steroidal saponin comprises uttroside B, a tomatoside, or any combination thereof. In some embodiments, the reduced at least one steroidal saponin comprises uttroside B, a tomatosideor any combination thereof. In some embodiments, the reduced at least one steroidal alkaloid biosynthetic intermediate comprises cholesterol, 22-hydroxycholesterol, 22,26-dihydroxycholesterol, furostanol-type saponin aglycone.

In some embodiments, the reduced at least one steroidal saponin comprises eliminating or nearly eliminating uttroside B, a tomatosideor any combination thereof. In some embodiments, the reduced at least one steroidal alkaloid biosynthetic intermediate comprises eliminating or nearly eliminating cholesterol, 22-hydroxycholesterol, 22,26-dihydroxycholesterol, furostanol-type saponin aglycone. In some embodiments, a method of reducing at least one steroidal saponin comprises eliminating a combination of at least one steroidal saponin and at least one steroidal saponin biosynthetic intermediate.

In some embodiments, a method of increasing at least one steroidal saponin increases a steroidal saponin comprising a toxin or a bitter tasting compound or a combination thereof, compared to the content of the steroidal saponin in a plant or plant part comprising a non-modified plant cell. In some embodiments, a method of increasing the content of a steroidal saponin, a derivative thereof, a metabolite thereof, or a biosynthetic intermediate thereof increases a steroidal saponin comprising uttroside B, a tomatoside, or any combination thereof.

In some embodiments, a method of increasing the content of a steroidal saponin, a derivative thereof, a metabolite thereof, or a biosynthetic intermediate thereof increases at least one steroidal saponin biosynthetic intermediate comprising cholesterol, 22-hydroxycholesterol, 22,26-dihydroxycholesterol, furostanol-type saponin aglycone or any combination thereof. In some embodiments, a method of increasing the content of a steroidal saponin, a derivative thereof, a metabolite thereof, or a biosynthetic intermediate thereof increases a combination thereof.

In some embodiments, a method of reducing at least one triterpenoid saponin reduces a triterpenoid saponin comprising a toxin or a bitter tasting compound or a combination thereof, compared to the content of the triterpenoid saponin in a plant or plant part comprising a non-modified plant cell. In some embodiments, a method of reducing at least one triterpenoid saponin eliminates a triterpenoid saponin comprising a toxin or a bitter tasting compound or a combination thereof, compared to the content of the triterpenoid saponin in a plant or plant part comprising a non-modified plant cell. In some embodiments, a method of reducing at least one triterpenoid saponin reduces a triterpenoid saponin, derivative thereof, metabolite thereof, or biosynthetic intermediate thereof, comprising a toxin or a bitter tasting compound or a combination thereof, compared to the content of the triterpenoid saponin, derivative thereof, metabolite thereof, or biosynthetic intermediate thereof, in a plant or plant part comprising a non-modified plant cell. In some embodiments, a method of reducing at least one triterpenoid saponin, derivative thereof, metabolite thereof, or biosynthetic intermediate thereof, eliminates a triterpenoid saponin, derivative thereof, metabolite thereof, or biosynthetic intermediate thereof, comprising a toxin or a bitter tasting compound or a combination thereof, compared to the content of the triterpenoid saponin in a plant or plant part comprising a non-modified plant cell.

In some embodiments, the reduced at least one triterpenoid saponin comprises medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof. In some embodiments, the reduced triterpenoid saponin intermediate comprises Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof. In some embodiments, a method of reducing at least one triterpenoid saponin comprises reducing a combination of at least one triterpenoid saponin and one triterpenoid saponin biosynthetic intermediate.

In some embodiments, the reduced at least one triterpenoid saponin comprises eliminating or nearly eliminating medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof. In some embodiments, the reduced triterpenoid saponin intermediate comprises eliminating or nearly eliminating Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof. In some embodiments, a method of reducing at least one triterpenoid saponin comprises eliminating a combination of at least one triterpenoid saponin and one triterpenoid saponin biosynthetic intermediate.

In some embodiments, a method of increasing the content of a triterpenoid saponin, a derivative thereof, a metabolite thereof, or a biosynthetic intermediate thereof increases a triterpenoid saponin comprising a sweetener, foaming agent, emulsifier, preservative, anti-carcinogen, hypocholesterolemic agent, anti-inflammatory agent, anti-oxidant, biological adjuvant, anti-microbial agent, insecticidal agent, anti-feedant, anti-fungal agent, or any combination thereof. In some embodiments, a method of increasing the content of a triterpenoid saponin, a derivative thereof, a metabolite thereof, or a biosynthetic intermediate thereof increases a triterpenoid saponin comprising medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof. In some embodiments, a method of increasing the content of a triterpenoid saponin, increases the triterpenoid saponin glycyrrhizin (Compound 14). In some embodiments, a method of increasing the content of a triterpenoid saponin, increases the triterpenoid saponin QS-21 adjuvant.

In some embodiments, a method of increasing the content of a triterpenoid saponin, a derivative thereof, a metabolite thereof, or a biosynthetic intermediate thereof increases a triterpenoid saponin biosynthetic intermediate comprising Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof. In some embodiments, a method of increasing the content of a triterpenoid saponin, a derivative thereof, a metabolite thereof, or a biosynthetic intermediate thereof increases a combination thereof.

In some embodiments, a method of increasing the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof, increases the content of the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof, at least one triterpenoid saponin, a derivative thereof, a metabolite thereof, or a biosynthetic intermediate thereof, and alters the content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, a method of increasing the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof, increases the content of the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof, and decreases the content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof, decreases the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof and an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments, the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof, decreases the content of at least one steroidal alkaloid, a derivative thereof, a metabolite thereof, or a biosynthetic intermediate thereof; at least one steroidal saponin, a derivative thereof, a metabolite thereof, or a biosynthetic intermediate thereof; at least one triterpenoid saponin, a derivative thereof, a metabolite thereof, or a biosynthetic intermediate thereof and an increased content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

In some embodiments in a method of altering (increasing or decreasing) the content of a steroidal alkaloid, a derivative thereof, a metabolite thereof, or a biosynthetic intermediate thereof; a steroidal saponin, a derivative thereof, a metabolite thereof, or a biosynthetic intermediate thereof; or a triterpenoid saponin, a derivative thereof, a metabolite thereof, or a biosynthetic intermediate thereof the method comprises genetically modifying at least one plant cell, wherein in some embodiments said plant cell comprises a leaf cell, a petiole cell, a plant stem or stalk cell, a root cell, a bud cell, a tuber cell, a bean cell, a grain or kernel cell, a fruit cell, a nut cell, a legume cell, a seed or seed cell, a bract cell, a callus cell, and a flower cell.

In some embodiments in a method of altering (increasing or decreasing) the content of a steroidal alkaloid, a derivative thereof, a metabolite thereof, or a biosynthetic intermediate thereof; a steroidal saponin, a derivative thereof, a metabolite thereof, or a biosynthetic intermediate thereof; or a triterpenoid saponin, a derivative thereof, a metabolite thereof, or a biosynthetic intermediate thereof, the method comprises genetically modifying at least one plant cell, wherein in some embodiments said plant cell comprises an order, genus, or species recited herein in detail. For example, but not limited to a plant cell comprising a cell from a plant in the Poales order, the Caryophyllales order, the Solanales order, the Fabales order, the Malvales order, the *Apiales* order, the Brassicales order, the *Asparagales* order, the Dioscoreales order, or the Liliales order.

In some embodiments of methods altering the content (increasing or decreasing) of a steroidal alkaloid, a steroidal saponin, or a triterpenoid saponin, the plant of the Caryophyllales order is selected from the group of genera consisting of the *Spinacia* genus, the *Chenopodium* genus, the *Beta* genus, and the *Rheum* genus; or the plant of the Solanales order is selected from the group of genera consisting of the *Nicotiana* genus, the *Solanum* genus, and the *Capsicum* genus; or the plant of the Fabales order is selected from the group of genera consisting of the *Glycyrrhiza* genus, the *Medicago* genus, the *Quillaja* genus, the *Glycine* genus, and the *Lotus* genus; or the plant of the *Apiales* order is selected from the group of genera consisting of the *Panax* genus, *Daucus* genus, the *Apium* genus, and the *Petroselinum* genus, or the plant from the Poales order is selected from the group of genera consisting of the *Oryza* genus (e.g., *Oryza sativa* and *Oryza glaberrima* [rice]), the *Hordeum* genus (e.g., *Hordeum vulgare* [barley]), the *Avena* genus (e.g., *Avena sativa* [oat], *Avena strigosa*), and the *Triticum* genus (e.g., *Triticum spelta* [spelt]), or the plant from the Brassicales order is selected from the group of genera consisting of the *Arabidopsis* genus (e.g., *Arabidopsis thaliana*), the *Brassica* genus (e.g., *Brassica oleracea* [cabbages], *Brassica juncea* [white mustard], *Brassica nigra* [black mustard], *Brassica napus*), the *Capparis* genus (e.g., *Capparis spinosa* [caper]), and the *Carica* genus (e.g., *Carica papaya* [papaya]).

In some embodiments of methods altering the content (increasing or decreasing) of a steroidal alkaloid, a steroidal saponin, or a triterpenoid saponin, the plant of the Solanales order is selected from the group of species consisting of *Nicotiana benthamiana, Solanum lycopersicum, Solanum tuberosum, Solanum melongena, Solanum pennellii, Solanum chacoense, Solanum dulcamara*, and *Capsicum annuum*; or the plant of the Fabales order is selected from the group of species consisting of *Glycyrrhiza uralensis, Medicago saliva, Medicago truncatula, Quillaja saponaria, Glycine max*, and *Lotus japonicus*; or the plant of the Malvales order is selected from the *Theobroma* genus; or the plant of the *Apiales* order is selected from the group of species consisting of *Panax ginseng, Daucus carota, Apium graveolens*, and *Petroselinum crispum*; or the plant is selected from the species *Theobroma* cacao.

Methods of Producing a Steroidal Alkaloid, Steroidal Saponin, or Triterpenoid Saponin in an In Vitro System In vitro systems are well known in the art. In some embodiments, an in vitro translation system used in the methods for producing a triterpenoid saponin disclosed herein comprises a rabbit reticulocyte lysate, a wheat germ extract, or an *E. coli* cell-free system. Detailed methods for using a cell free system and known and freely available in the art, for example but not limited to in formation found at: https://www.thermofisher.comil/en/home/references/ambion-tech-support/large-scale-transcription/general-articles/the-basics-in-vitro-translation.html.

In some embodiments, disclosed herein is a method of producing a steroidal alkaloid or a steroidal saponin in an in vitro system, the method comprising.

(a) combining a nucleic acid sequence or nucleic acid sequences encoding a cytochrome P450 (GAME7) gene, a cytochrome P450 (GAME8) gene, a 2-oxoglutarate-dependent dioxygenase (GAME11) gene, a cytochrome P450 (GAME6) gene, a cytochrome P450 (GAME4) gene, a transaminase (GAME 12) gene, a tomatidine UDP-galactosyltransferase (GAME/-SGT7) gene, a UDP-gycosyltransferase (GAME17) gene, a UDP-gycosyltransferase (GAME18) gene, a UDP-gycosyltransferase/xylosyltransferase (GAME2/SGT3) gene, and a cellulose synthase like G gene (CSLG or GAME15), wherein said nucleic acid sequence or nucleic acid sequences are optionally comprised in a vector or vectors; and (b) expressing said genes;

(c) incubating a combination of said expressed enzymes together;

wherein the product of said incubation comprises at least one steroidal alkaloid or steroidal saponin.

In some embodiments, the above nucleic acid sequence(s) further comprise an ethylene-responsive element binding factor 13 (GAME9) and/or a BHLH-transcription factor.

In some embodiments, disclosed herein is a method of producing a steroidal alkaloid or a steroidal saponin in an in vitro system, the method comprising:

(d) combining a nucleic acid sequence or nucleic acid sequences encoding a cytochrome P450 (GAME7) gene, a cytochrome P450 (GAME8) gene, a 2-oxoglutarate-dependent dioxygenase (GAME11) gene, a cytochrome P450 (GAME6) gene, and a cellulose synthase like G gene (CSLG or GAME15), wherein said nucleic acid sequence or nucleic acid sequences are optionally comprised in a vector or vectors; and (e) expressing said genes;

(f) incubating a combination of said expressed enzymes together;

wherein the product of said incubation comprises at least one steroidal alkaloid or a steroidal saponin, or a combination thereof. See for example but not limited to, the biosynthetic pathways and resultant intermediates and products presented therein in FIGS. 1, 8D, 13, and 14A-14D.

In some embodiments, the biosynthetic GAME genes and/or the CSLG gene are operably linked to a promoter, a transcription termination sequence, or a combination thereof as has been described in detail herein for making constructs. In some embodiments, in a method of producing a steroidal alkaloid or a steroidal saponin, the nucleic acid sequence encoding said CSLG gene is set forth in any one of SEQ ID NOS: 30, 32, 34, 36, 38, 40, 65, 80, 93, 95, 97, 99, 101, 103, or 105; or a homolog thereof having at least 55% identity to and at least 55% coverage of, the nucleic acid sequence set forth in any one of SEQ ID NOS: 30, 32, 34, 36, 38, 40, 65, 80, 93, 95, 97, 99, 101. In some embodiments, in a method of producing a steroidal alkaloid or a steroidal saponin, the nucleic acid sequence encoding said CSLG gene is set forth in any one of SEQ ID NOS: 30, 32, 34, 36, 38, 40, 65, 80, 93, 95, 97, 99, 101, 103, or 105; or a homolog thereof having at least 55% identity to and at least 80% coverage of, the nucleic acid sequence set forth in any one of SEQ ID NOS: 30, 32, 34, 36, 38, 40, 65, 80, 93, 95, 97, 99, 101.

In some embodiments, the biosynthetic GAME genes and/or the CSLG gene are operably linked to a promoter, a transcription termination sequence, or a combination thereof as has been described in detail herein for making constructs. In some embodiments, in a method of producing a steroidal alkaloid or a steroidal saponin, the nucleic acid sequence encoding said CSLG gene is set forth in any one of SEQ ID NOS: 30, 32, 34, 36, 38, 40, 65, 80, 93, 95, 97, 99, 101, 103, or 105; or a homolog thereof having at least 80% identity to and at least 80% coverage of, the nucleic acid sequence set forth in any one of SEQ ID NOS: 30, 32, 34, 36, 38, 40, 65, 80, 93, 95, 97, 99, 101.

In certain embodiments, an in vitro method of producing a steroidal alkaloid comprises producing a steroidal alkaloid selected from a esculeoside or a dehydroesculeoside. In certain embodiments, an in vitro method of producing a steroidal alkaloid comprises producing a steroidal alkaloid selected from alpha-tomatine, tomatine, alpha-chaconine, alpha-solanine, alpha-solasonine, alpha-solmargine, or any combination thereof.

In certain embodiments, an in vitro method of producing a steroidal saponin comprises producing a steroidal saponin selected from uttroside B, a tomatosideor any combination thereof.

In some embodiments, disclosed herein is a method of producing a triterpenoid saponin in an in vitro system, the method comprising:

(g) combining a nucleic acid sequence or nucleic acid sequences encoding a saponin beta-amyrin synthase gene (SOAP1), a cytochrome P450 gene (SOAP2), a cytochrome P450 gene expressing a C-2 hydroxylase (SOAP3), a cytochrome P450 gene expressing a C-23 oxidase (SOAP4), a glycosyl transferase gene expressing a UDP-glycosyltransferase or a fucocyl transferase (SOAP6), a glycosyl transferase gene expressing a UDP-glycosyltransferase (SOAP7), a glycosyl transferase gene expressing a UDP-glycosyltransferase (SOAP8); a glycosyl transferase gene expressing a UDP-glycosyltransferase or a xylosyl transferase (SOAP9), an acyltransferase gene (SOAP10), and a cellulose synthase like G gene (CSLG), wherein said nucleic acid sequence or nucleic acid sequences are optionally comprised in a vector or vectors; and (h) expressing said genes;

(i) incubating a combination of said expressed enzymes together; wherein the product of said incubation comprises at least one triterpenoid saponin.

In some embodiments, the biosynthetic SOAP genes and/or the CSLG gene are operably linked to a promoter, a transcription termination sequence, or a combination thereof as has been described in detail herein for making constructs. In some embodiments, in a method of producing a triterpenoid saponin the nucleic acid sequence encoding said CSLG gene is set forth in any one of SEQ ID NOS: 30, 32, 34, 36, 38, 40, 65, 80, 93, 95, 97, 99, 101, 103, or 105; or a homolog thereof having at least 55% identity to and at least 55% coverage of, the nucleic acid sequence set forth in any one of SEQ ID NOS: 30, 32, 34, 36, 38, 40, 65, 80, 93, 95, 97, 99, 101. In some embodiments, in a method of producing a triterpenoid saponin the nucleic acid sequence encoding said CSLG gene is set forth in any one of SEQ ID NOS: 30, 32, 34, 36, 38, 40, 65, 80, 93, 95, 97, 99, 101, 103, or 105; or a homolog thereof having at least 55% identity to and at least 80% coverage of, the nucleic acid sequence set forth in any one of SEQ ID NOS: 30, 32, 34, 36, 38, 40, 65, 80, 93, 95, 97, 99, 101.

In some embodiments, the biosynthetic SOAP genes and/or the CSLG gene are operably linked to a promoter, a transcription termination sequence, or a combination thereof as has been described in detail herein for making constructs. In some embodiments, in a method of producing a triterpenoid saponin the nucleic acid sequence encoding said CSLG gene is set forth in any one of SEQ ID NOS: 30, 32, 34, 36, 38, 40, 65, 80, 93, 95, 97, 99, 101, 103, or 105; or a homolog thereof having at least 80% identity to and at least 80% coverage of, the nucleic acid sequence set forth in any one of SEQ ID NOS: 30, 32, 34, 36, 38, 40, 65, 80, 93, 95, 97, 99, 101.

In some embodiments, the nucleic acid gene sequence or sequences encoding the other triterpenoid saponin biosynthetic enzymes are set forth as follows:

(a) the nucleic acid sequence encoding said β-amyrin synthase gene is set forth in SEQ ID NO: 45; or a homolog thereof having at least 80% identity to and at least 80% coverage of, the nucleic acid sequence set forth in SEQ ID NO: 45; and (b) the nucleic acid sequence or sequences encoding said cytochrome P450 genes, are set forth in any one of SEQ ID NO: 46, 51, or 53; or a homolog thereof having at least 80% identity to and at least 80% coverage of, the nucleic acid sequence set forth in any one of SEQ ID NO: 46, 51, or 53; and (c) the nucleic acid sequence or sequences encoding said glycosyl transferase genes, are set forth in any one of SEQ ID NO: 55, 57, 59, or 61; or a homolog thereof having at least 80% identity to and at least 80% coverage of, the nucleic acid sequence set forth in any one of SEQ ID NO: 55, 57, 59, or 61; and (d) the nucleic acid sequence encoding said acyltransferase is set forth in SEQ ID NO: 63; or a homolog thereof having at least 80% identity to and at least 80% coverage of, the nucleic acid sequence set forth in SEQ ID NO: 63.

In certain embodiments, an in vitro method of producing a triterpenoid saponin comprises producing a triterpenoid saponin selected from a sweetener, foaming agent, emulsifier, preservative, anti-carcinogen, hypocholesterolemic agent, anti-inflammatory agent, anti-oxidant, biological adjuvant, anti-microbial agent, insecticidal agent, antifeedant, anti-fungal agent, or any combination thereof.

In certain embodiments, an in vitro method of producing a triterpenoid saponin comprises producing a triterpenoid saponin selected from medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof.

As used in the specification and claims, the singular form "a", "an" and "the" include plural references unless the context clearly dictates otherwise. For example, the term "a molecule" also includes a plurality of molecules.

Throughout this application, various embodiments may be presented in a range format. It should be understood that the description in range format is merely for convenience and brevity and should not be construed as an inflexible limitation. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

Further, one skilled in the art would appreciate that the term "comprising" used throughout is intended to mean that the genetically modified or gene edited plants disclosed herein, and methods of altering expression of genes, and altering production of SA and/or SGA within these genetically modified or gene edited plants includes the recited elements, but not excluding others which may be optional. "Consisting of" shall thus mean excluding more than traces of other elements. The skilled artisan would appreciate that while, in some embodiments the term "comprising" is used, such a term may be replaced by the term "consisting of", wherein such a replacement would narrow the scope of inclusion of elements not specifically recited.

The following examples are presented in order to more fully illustrate some embodiments of the invention. They should, in no way be construed, however, as limiting the broad scope of the invention. They should, in no way be construed, however, as limiting the broad scope of the genetically modified cells and plants disclosed herein or the uses of said cells and plants to produce steroidal alkaloids, steroidal saponins, or triterpenoid saponins; or methods for increasing or decreasing the content of a steroidal alkaloid, steroidal saponin, or triterpenoid saponin in a plant or plant part. One skilled in the art can readily devise many variations and modifications of the principles disclosed herein without departing from the scope disclosed herein.

EXAMPLES

Example 1: Materials and Methods for Examples 2-13

Plant Material, Treatments, and Generation of Transgenic Plants

Tomato (*Solanum lycopersicum*; cv. Micro Tom) and potato (*Solanum tuberosum*; cultivar Desiree) plants were collected as described previously (Itkin et al., 2001, supra). In potato, when the green parts started to dry, mature tubers (Stage 3) were collected, washed of soil, dried and kept at 4° C., at complete darkness.

The GAME9-silenced (RNAi) and overexpression (OX) constructs were created by introducing the corresponding GAME9 DNA fragments to pK7GWIWG2(II) and pJCV52 binary vectors, respectively. Transgenic lines for silencing and overexpression of GAME9 in tomato and potato were generated and tissue extracts were prepared and analyzed according to Itkin et al. (2011, supra).

Table 3 below describes the oligonucleotides used for generation of the constructs described herein. The GAME4-silencing (RNAi; GAME4i), GAME4 overexpressing (GAME4oe) and GAME8-silencing constructs were generated as described previously (Itkin et al., 2001, supra; WO 2012/095843).

TABLE 3

Oligonucleotides used for construct production

| Name | Sequence 5' to 3'/ Description | SEQ ID NO. |
|---|---|---|
| S107g0434 20 EcoRI Fw | AAAAAgaattcCGGATCT TCTCTCGAACTGGTCAA To prepare GAME11 virus-induced gene silencing (VIGS) construct | 1 |

TABLE 3-continued

Oligonucleotides used for construct production

| Name | Sequence 5' to 3'/ Description | SEQ ID NO. |
|---|---|---|
| S107g0434 20 EcoRI Rv | AAAAAgaattcCACTTT CATTGCTTCATCCATTA GATCT To prepare GAME11 VIGS construct | 2 |
| S107g0435 00 EcoRI Fw | AAAAAgaattcCTTAGC TTATGGCCACATCACAC CTT To prepare GAME18 VIGS construct | 3 |
| S107g043500 EcoRI Rv | AAAAAgaattcACTCAA GATTTGGTGAAGCTGTG GTT To prepare GAME18 VIGS construct | 4 |
| G8-Fonvard (AscI) | AAAAAGGCGCGCCAATC ATAGAGAAGAAAGAAGA CG To construct RNAi of GAME8 | 5 |
| GS-Reverse (NotI) | AAAAAGCGGCCGCACTC CTGCAGGAATTGTCATT TCTC To construct RNAi at GAME8 | 6 |
| GAK1E9 RNAi NotI Fw | AaaaaCCGGCCGCATGAG TATTGTAATTGATCATGA TGAAATC To construct RNAi of GAME9 | 7 |
| GAME9 RNAi AscI Rv | AaaaGGCGCGCCCACAC GCCACAGATGGTTCTT To construct RNAi of GAME9 | 8 |
| GAME9-Tom GW Fw | GGGGACAAGTTTGTACA AAAAAGCAGGCTATGAG TATTGTAATTGATGATG ATGAAATC To pick up the gene from cdna for overexpression (good for tomato) | 9 |
| GAME9-Tom GW Rv | GGGGACCACTTTGTACA AGAAAGCTGGGTTCATA CTACCTTCTGTCCTAAG CCT To pick up the gene from cDNA for overexpression (good for tomato) | 10 |
| GAME9-Pot GW Fw | GGGGACAAGTTTGTACAA AAAAGCAGGCTATGAATA TTGCAATTGATGATGATG A To pick up the gene front cDNA for overexpression (good for potato) | 11 |
| GAME9-Pot GW Rv | GGGGACCACTTTGTACAAG AAAGCTGGGTTCATTTGTA TCAACATTTGTAAATTCAC AC | 12 |

TABLE 3-continued

Oligonucleotides used for construct production

| Name | Sequence 5' to 3'/ Description | SEQ ID NO. |
|---|---|---|
| | To pick up the gene from cDNA for overexpression (good for potato) | |

Co-Expression Analysis

The tomato GAME1 (Solyc07g043490) and its potato ortholog SGT11 (PGSC003DMG400011749) were used as 'baits' in the co-expression analysis, resulting in lists (sorted in descending order by r-value≥0.8) of co-expressed genes (for each 'bait' separately). Two homologous genes were subsequently identified (Solyc12g006460 and PGSC0003DMG400024274 in tomato and potato, respectively), which were highly correlated with the "bait" genes (r-value>0.9 in both species). Those genes were identified as GLYCOALKALOID METABOLISM 4(GAME4, WO 2012/095843). The GAME4 genes were further added as 'baits' to the previous (GAME1) co-expression analysis. The co-expression lists for GAME1 (SGT7) and GAME4 in both species were used to construct co-expression correlation network. The analysis was performed as follows: tomato RNAseq transcriptome data from different tissues and organs (flesh, peel, seeds, roots, leaves, buds, flowers, pollen) and developmental stages (25 experiments in total) (Itkin et al., 2011, ibid) and potato RNAseq transcriptome data from different tissues and organs (40 experiments in total) (US 2012/0159676), were used. First, an R script was used to perform co-expression analysis (for each species) and the list of co-expressed genes was constructed as a FASTA file, using a Perl script. Finally, BLASTall tools (Camacho C. et al., 2009. BMC Bioinform 10:421) were used to find shared homologs between the two species. The tblastx criteria for homolog similarity were set to p-value>0.05, minimum 25 nucleotides, and at least 60 percent similarity as an overall identity for each gene. The co-expression network was visualized with the Cytoscape program (Shannon P. et al., 2003. Genome Res. 13:2498-2504).

Phylogenetic Analysis

The protein sequences were aligned using the Muscle algorithm and the phylogenetic tree was analyzed and visualized by the SeaView v4.3.5 program using the maximum likelihood method by PhyML 3.0 (Expósito-Rodriguez M et al., 2008. BMC Plant Biol. 8:131) with the following settings: model—LG; The approximate likelihood ratio test (aLRT) Shimodaira-Hasegawa-like (SH-like) procedure was used as a statistical test to calculate branch support (branch support—aLRT (SH-like)); invariable sites—optimized; across site rate variation—optimized; tree searching operations—best for NNI & SPR; starting tree—BioNJ, optimize tree topology. The numbers on the branches indicate the fraction of bootstrap iterations supporting each node. The accession numbers of the proteins used for the preparation of this tree and the organism names are listed in Table 4 hereinbelow; the tree is presented in FIG. 12.

TABLE 4

Accession numbers of the sequences used for the construction of the phylogenetic tree

Figure 12:
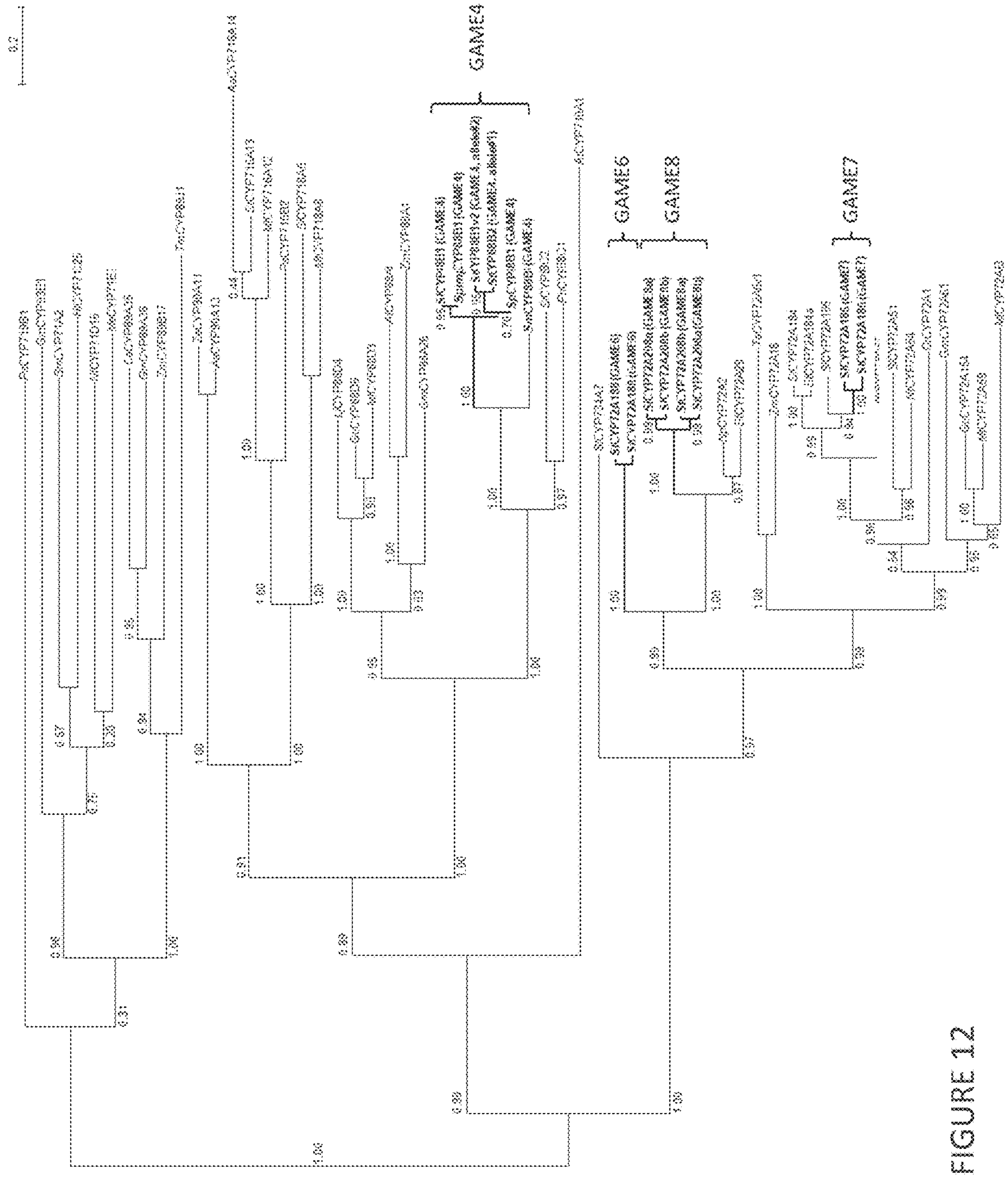
FIG. 12 shows the phylogenetic tree of GAME genes in the plant CYP450 protein family. The numbers on the branches indicate the fraction of bootstrap iterations supporting each node.

| Name as appears in FIG. 12 | Latin and common name | Accession number |
|---|---|---|
| GuCYP88D6 | *Glycyrrhiza uralensis* | BAG68929.1 |
| LjCYP88D4 | *Lotus japonicus* | BAG68927.1 |
| MtCYP88D3 | *Medicago truncatula* | BAG68926.1 |
| CmCYP88A2 | *Cucurbita maxima* | AF212991 |
| AtCYP88A3 | *Arabidopsis thaliana* | AAB71462.1 |
| PsCYP88A7 | *Pisum sativum* | AAO23064.1 |
| ZmCYP88A1 | *Zea Mays* | NP_001105586.1 |
| GmCYP88A26 | *Glycine max* | XP_003516638.1 |
| CaCYP89A35 | *Capsicum annuum* | DQ114394 |
| GmCYP89A36 | *Glycine max* | DQ340245 |
| ZmCYP89B17 | *Zea mays* | CO465851.1 |
| TmCYP89J1 | *Triticum monococcum* | AY914081 |
| SlCYP88B1 (GAME4) | *Solanum lycopersicum* | Solyc12g006460.1.1 |
| SpimpCYP88B1 (GAME4) | *Solanum pimpinellifolium* | contig 6356779 |
| SpCYP88B1 (GAME4) | *Solanum pinelii* | AW618484.1, BG135958.1 |
| StCYP88B2 (GAME4) | *Solanum tuberosum* group *Phureja* | PGSC0003DMP400041994 |
| StCYP88B1v2 (GAME4) | *Soanum tuberosum* group *Tuberosum* | PGSC0003DMP400041994 |
| SlCYP88C2 | *Solanum lycopersicum* | Solyc10g007860.2.1 |
| SmCYP88B3 (GAME4) | *Solanum melongena* | FS071104, FS071103 |
| OsCYP90A3 | *Oryza sativa* | AC123526.1 |
| SlCYP90A5 | *Solanum lycopersicum* | Solyc06g051750.2.1 |
| ScCYP90A8 | *Citrus sinensis* | DQ001728.1 |
| ZeCYP90A11 | *Zinnia elegans* | BAE16977.1 |
| PhCYP88C1 | *Petunia hybrida* | AAZ39647.1 |
| AaCYP90A13 | *Artemisia annua* | ABC94481.1 |
| AtCYP710A1 | *Arabidopsis thaliana* | AAC26690.1 |
| SmCYP71A2 | *Solanum melongena* | X71654.1 |
| GmCYP93E1 | *Glycine max* | AB231332 |
| HlCYP71C25 | *Hordeum lechleri* | AY462228 |
| NtCYP71D16 | *Nicotiana tabacum* | AF166332 |
| MeCYP71E7 | *Manihot esculenta* | AY217351 |
| TaCYP71F1 | *Triticum aestivum* | AB036772 |
| AoCYP71J1 | *Asparagus officinalis* | AB052131 |
| MaCYP71N1v2 | *Musa acuminata* | AY062167 |
| TaCYP72A6v1 | *Triticum aestivum* | AF123604 |
| ZmCYP72A16 | *Zea mays* | AF465265 |
| LeCYP72A51 | *Solanum lycopersicum* | Solyc10g051020.1.1 |
| GmCYP72A61 | *Glycine max* | DQ340241 |
| MtCYP716A12 | *Medicago truncatula* | ABC59076.1 |
| StCYP716A13 | *Solanum tuberosum* | PGSC0003DMP400013378 |
| AaCYP716A14 | *Artemisia annua* | DQ363134 |
| PsCYP716B2 | *Picea sitchensis* | AY779543 |
| SlCYP718A6 | *Solanum lycopersicum* | Solyc07g055970.1.1 |
| MtCYP718A8 | *Medicago truncatula* | XP_003617455.1 |
| PsCYP719B1 | *Papaver somniferum* | EE451150 |
| StCYP72A186 (GAME7) | *Solanum tuberosum* | PGSC0003DMG402012386 |
| SlCYP72A186 (GAME7) | *Solanum lycopersicum* | Solvc07g062520 |
| SlCYP72A188 (GAME6) | *Solanum lycopersicum* | Solyc07g043460 |
| StCYP72A188 (GAME6) | *Solanum tuberosum* | PGSC0003DMG400011750 |
| GuCYP72A154 | *Glycyrrhiza uralensis* | BAL45206.1 |
| MtCYP72A59 | *Medicago truncatula* | ABC59078.1 |
| NtCYP72A57 | *Nicotiana tabacum* | ABC69414.1 |
| NtCYP72A54 | *Nicotiana tabacum* | ABC69417.1 |
| CrCYP72A1 | *Catharanthus roseus* | gi461812 |
| MtCYP72A63 | *Medicago truncatula* | gi371940452 |
| NpCYP72A2 | *Nicotiana plumbaginifolia* | AAB05376.3 |
| SlCYP734A7 | *Solanum lycopersicum* | Solyc03g120060.1.1 |
| StCYP72A29 | *Solanum tuberosum* | BAB86912.1 |
| StSYP72a56 | *Solanum tuberosum* | PGSC0003DMG400017325 |
| StCYP72A208 (GAME8a) | *Solanum tuberosum* | PGSC0003DMG400026594 |
| StCYP72A208 (GAME8b) | *Solanum tuberosum* | PGSC0003DMG400026586 |
| SlCYP72A208 (GAME8a) | *Solanum lycopersicum* | TC243022 |
| SlCYP72A208 (GAME8b) | *Solanum lycopersicum* | SGN-U578058 |

Metabolite Analysis

Preparation of plant tissue extracts and profiling of semi-polar compounds (including steroidal alkaloids and steroidal saponins) by UPLC-qTOF-MS and phytosterol content of the tomato leaves were carried out as described previously (Itkin et al., 2011, supra).

Quantitative Real-Time PCR Assays

RNA was isolated and Quantitative Real-Time PCR was performed as described previously (Itkin et al., 2011, supra). In addition, the TIP41 gene (23) was used as an endogenous control for the potato samples. Oligonucleotides are listed in Table 3 hereinabove.

Production of Recombinant Enzyme

GAME2, GAME17 and GAME18 were amplified from cDNA and subcloned into pACYCDUET-1 using BamH I and Pst I (GAME2, GAME18) or BamHI and XhoI (GAME17) restriction sites, and the insert was verified by sequencing. The resulting plasmids, pAC-GAME2/17/18 were transformed to *E. coli* BL21 DE3. For expression of the GAME enzymes, fresh overnight cultures were diluted 1:100 in 25 ml 2xYT medium with 30 μg/ml chloramphenicol and incubated at 37° C. and 250 rpm until an $A_{600nm}$ of 0.4 was reached. Subsequently, IPTG was added to a concentration of 0.5 mM, and the incubation was continued overnight at 18° C. and 250 rpm. The next day, cells were harvested by centrifugation, and the pellet resuspended in 2 ml of 50 mM Tris HCl pH=7.0, 15% glycerol, 0.1 mM EDTA and 5 mM β-mercaptoethanol. After breaking the cells by sonication, insoluble material was removed by centrifugation, and the soluble fractions were used for characterization of the enzymes. Proteins were stored at −20° C. until further analysis.

Preparation of Substrates

For hydrolysis, 35 mg of α-tomatine was solved in 3 ml of 1N HCl, and was incubated for 15 min. at 100° C. Subsequently, the solution was put on ice, and $NH_3$ was added until the pH of the solution was 9.0. The solution was extracted with 4 ml water-saturated butanol. The butanol phase was evaporated to dryness under vacuum, the residual pellet solved in 1 ml methanol and stored at −20° C. until further use. The degradation products of α-tomatine were separated on a Luna 5 μm C18(2) 100 Å, LC Column 150×21.2 mm (Phenomenex, USA), using an isocratic elution with 25% acetonitrile in water and 0.1% formic acid. Compounds were detected using a 3100 Mass Detector (Waters), and collected. Fractions were freeze-dried, and purity of compounds was verified by LC-MS. For identification of products, liquid chromatography, coupled to quadrupole time-of-flight mass spectrometry (LC-QTOF-MS) was performed using a Waters Alliance 2795 HPLC connected to a Waters 2996 PDA detector and subsequently a QTOF Ultima V4.00.00 mass spectrometer (Waters, MS Technologies, UK) operated in positive ionization mode. The column used was an analytical Luna 3 μm C18 (2) 100 A; 150×2.0 mm (Phenomenex, USA) attached to a C18 pre-column (2.0×4 mm; AJO-4286: Phenomenex, USA). Degassed eluent A [ultra-pure water:formic acid (1000:1, v/v)] and eluent B [acetonitrile:formic acid (1000:1, v/v)] were used with flow rate of 0.19 ml/min. The gradient started at 5% B and increased linearly to 75% B in 45 min., after which the column was washed and equilibrated for 15 min. before the next injection. The injection volume was 5 μl. This procedure yielded several milligrams of pure γ-tomatine (tomatidine-galactoside-glucoside, T-Gal-Glu) and β1-tomatine (tomatidine-galactoside-diglucoside. T-Gal-Glu-Glu). Tomatidine galactoside (T-Gal) could not be purified in this way due to strong contamination with T-Gal-Glu. Therefore 5 mg tomatidine was incubated with GAME1 and UDP-galactose in 1 ml reaction mix, as described previously (Itkin et al., 2011, supra). T-Gal was purified from UDP-galactose by solid phase extraction. Waters OASIS HLB 3 cc columns (Waters Corp., Milford, MA) was conditioned with 6 mL 100% methanol followed by rinsing with 4 mL ultra-pure water. The reaction, supplemented with 10% methanol, was loaded and the cartridge was subsequently washed with 4 mL ultra-pure water. Compounds were eluted with 1 mL 75% methanol in ultra-pure water (v:v), and 0.4 mL 100% methanol. The solvent was removed from the combined eluate using a speed vacuum concentrator until a totally dry-pellet was obtained.

Enzyme Assays

The substrates T-Gal, β1—and γ-tomatine were dissolved to 1 mM in 50% DMSO. Enzyme assays were carried out in 50 mM Tris HCl pH=7.0 containing 5 mM β-mercaptoethanol using 5 μg/ml enzyme, 8 mM UDP-xylose and 0.02 mM substrate in a final reaction volume of 100 pl. After 2 h. of incubation under agitation at 37° C., reactions were stopped by addition of 300 μl methanol and 0.1% formic acid, and followed by brief vortexing and sonication for 15 min. Subsequently, the extracts were centrifuged for 5 min. at 13,000 rpm and filtered through 0.45 μm filters (Minisart SRP4, Biotech GmbH, Germany), and analyzed by LC-MS (see above). The amount of product was measured by the peak surface area in the LC-MS chromatogram, and compared to a control incubation in which an enzyme preparation of an *E. coli* harboring an empty pACYCDUET-1. Masses used for detection were α-tomatine (C50H83NO21; m/z=1034.55 ([M+H]+)), β1-tomatine T-Gal-Glu-Glu (C45H75NO17; m/z=902.51 ([M+H])), β2-tomatine (C44H73NO16; m/z=872.50 ([M+H]+)), γ-tomatine T-Gal-Glu(C39H65NO12; m/z=740.46 ([M+H])), and T-Gal (C33H55NO7; m/z=578.41 ([M+H])).

Virus Induced Gene Silencing (VIGS) Experiments

Vectors containing fragments of GAME genes were constructed and VIGS experiments were conducted as described previously (Orzaea D et al., 2009. Plant Physiol. 150:1122-1134; Li R et al., 2006 J. Mass Spec. 41:1-22). Plants infected with *Agrobacterium*, containing empty vector and helper vector pTRV1, were used as control. Oligonucleotides used to prepare the pTRV2_DR_GW vectors are listed in Table 3 hereinabove.

Genome Sequence Analysis of the Wild Tomato Species

Partial genomic data obtained by re-sequencing (Dr. Arnaud G. Bovy, unpublished data) of three tomato wild species genomes (i.e. *Solanum pennellii, S. pimpinellifolium* and *S. chmielewskii*) were analyzed for the presence or absence of sequences (contigs) that align to the SGAs biosynthesis gene clusters on tomato chromosomes 7 and 12. The TopHat toolkit (Trapnell C. 2012. Nat. Protoc. 7:562-578) was used for mapping reads of the wild species to the tomato genome (ITAG 2.4), as a reference genome. The mapped reads were visualized with the IGV genome browser (Robinson J T et al., 2011. Nat. Biotechnol. 29:24-26). In order to assemble and align the sequence of the contigs from the three wild species to the gene clusters on to the existing cultivated tomato sequences of chromosomes 7 and 12, a combination of the CLC workbench, CAP3 BWA and SAMtools software packages and an in-house Perl script were used.

Example 2: Genes Associated with SGA Biosynthesis

To discover genes associated with SGA biosynthesis, a co-expression analysis using transcriptome data from tomato and potato plants was performed. Coexpression with GAME1/SGT1 (chromosome 7) and GAME4 (chromosome 12) as "baits" in either potato or tomato are presented in a form of a heatmap in Tables 5-8 herein below. Genes that are highly co-expressed with either GAME1/SGT1 (chromosome 7) or GAME4 (chromosome 12) are depicted with a large font and bold.

TABLE 5

| Accession numbers, putative protein and co-expression r-values - tomato, chromosome 7 | | |
|---|---|---|
| Gene name | Putative protein | r-value of correlation with tomato GAME1 expression |
| Solyc07g043310 | Aminotransferase | −0.26 |
| Solyc07g043320 | Unknown Protein | 0.12 |
| Solyc07g043330 | GRAS family transcription factor | 0.72 |
| Solyc07g043340 | Unknown Protein | |
| Solyc07g043350 | Unknown Protein | |
| Solyc07g043360 | 60S ribosomal protein L27 | 0.10 |
| Solyc07g043370 | Transposase | |
| Solyc07g043380 | Unknown Protein | |
| Solyc07g043390 | Cellulose synthase family protein (GAME15) | 0.92 |
| Solyc07g043400 | Unknown Protein | |
| Solyc07g043410 | UDP-xylose xylosyltransferase (GAME2) | |
| Solyc07g043420 | 2-oxoglutarate-dependent dioxygenase | 0.79 |
| Solyc07g043430 | Gag-Pol polyprotein | |
| Solyc07g043440 | Glucosyltransferase-like protein | |
| Solyc07g043450 | Zeatin O-glucosyltransferase | |
| Solyc07g043460 | Cytochrome P450 (GAME 6) | 0.91 |
| Solyc07g043470 | Unknown Protein | |
| Solyc07g043480 | UDP-glucose glucosyltransferase | 0.88 |
| Solyc07g043490 | UDP-glucosyltransferase family 1 protein (GAME1) | 1.00 |
| Solyc07g043500 | UDP-glucosyltransferase | 0.95 |
| Solyc07g043510 | Cysteine-type peptidase | −0.24 |
| Solyc07g043520 | transposase | |
| Solyc07g043530 | Unknown Protein | |
| Solyc07g043540 | Unknown Protein | |
| Solyc07g043550 | UDP-arabinose 4-epimerase | 0.70 |
| Solyc07g043560 | Heat shock protein 4 | 0.24 |
| Solyc07g043570 | Aldo/keto reductase family protein | −0.09 |
| Solyc07g043580 | BHLH transcription factor | 0.43 |
| Solyc07g043590 | Amine oxidase family protein | 0.03 |
| Solyc07g043600 | Pentatricopeptide repeat-containing protein | 0.43 |
| Solyc07g043610 | Auxin response factor 6 | |
| Solyc07g043620 | Auxin response factor 6-1 | 0.65 |
| Solyc07g043630 | Acyl-CoA synthetase/AMP-acid ligase II | |
| Solyc07g043640 | Acyl-CoA synthetase/AMP-acid ligase II | |
| Solyc07g043650 | AMP-dependent synthetase and ligase | |
| Solyc07g043660 | Acyl-CoA synthetase/AMP-acid ligase II | −0.16 |
| Solyc07g043670 | Hydroxycinnamoyl CoA quinate transferase 2 | |
| Solyc07g043680 | Enoyl-CoA-hydratase | |
| Solyc07g043690 | Enoyl-CoA-hydratase | |
| Solyc07g043700 | Acyltransferase | |

TABLE 6

| Accession numbers, putative protein and co-expression r-values - potato, chromosome 7 | | |
|---|---|---|
| Gene name | Putative protein | r-value of correlation with potato SGT1 expression |
| PGSC0003DMG400011754 | Gamma aminobutyrate transaminase | −0.31 |
| PGSC0003DMG400011753 | Uro-adherence factor A | −0.40 |
| PGSC0003DMG400011742 | DELLA protein RGA | 0.15 |
| PGSC0003DMG400011741 | 60S ribosomal protein L27 | 0.43 |
| PGSC0003DMG400039612 | Conserved gene of unknown function | |
| PGSC0003DMG400011752 | Cellulose synthase (GAME15) | 0.90 |
| PGSC0003DMG400011740 | beta-solanine rhamnosyltransferase (SGT3) | 0.90 |
| PGSC0003DMG400011751 | 2-oxoglutarate-dependent dioxygenase | 0.87 |
| PGSC0003DMG400011750 | Cytochrome P-450 (GAME 6) | 0.92 |
| PGSC0003DMG400044993 | Unknown Protein | |
| PGSC0003DMG400011749 | solanidine galactosyltransferase (SGT1) | 1.00 |
| PGSC0003DMG402015928 | OTU-like cysteine protease family protein | −0.24 |
| PGSC0003DMG401015928 | Conserved protein of unknown function | −0.25 |
| PGSC0003DMG400015927 | UDP-arabinose 4-epimerase 1 | −0.21 |
| PGSC0003DMG400015920 | Heat shock 70 kDa protein | −0.17 |
| PGSC0003DMG402015926 | Aldo/keto reductase | −0.05 |
| PGSC0003DMG401015926 | Isoform 2 of Transcription factor PIF5 | −0.33 |
| PGSC0003DMG400015925 | Amine oxidase | 0.11 |
| PGSC0003DMG400015924 | Pentatricopeptide repeat-containing protein | 0.32 |
| PGSC0003DMG400015919 | ARF8 | 0.07 |
| PGSC0003DMG400036440 | AMP dependent ligase | |
| PGSC0003DMG400015923 | Acyl:coA ligase acetate-coA synthetase | |
| PGSC0003DMG400015922 | Acyl:coA ligase acetate-coA synthetase | |
| PGSC0003DMG400044288 | Acyltransferase | |
| PGSC0003DMG400015918 | Acyltransferase | 0.03 |

TABLE 7

| Accession numbers, putative protein and co-expression r-values - tomato, chromosome 12 | | |
|---|---|---|
| Gene name | Putative protein | r-value of correlation with tomato GAME4 expression |
| Solyc12g006530 | Cycloartenol synthase | 0.08 |
| Solyc12g006520 | Cycloartenol synthase | 0.05 |
| Solyc12g006510 | Cycloartenol Synthase | −0.12 |
| Solyc12g006500 | Phosphate translocator protein | 0.15 |
| Solyc12g006490 | Beta-1-3-galactosyl-o-glycosyl-glycoprotein | 0.03 |
| Solyc12g006480 | Nup205 protein | 0.35 |
| Solyc12g006470 | gamma-aminobutyrate Aminotransferase-like protein | 0.94 |
| Solyc12g006460 | Cytochrome P450 (GAME 4) | 1.00 |
| Solyc12g006450 | gamma-aminobutyrate Aminotransferase-like protein | −0.13 |
| Solyc12g006440 | Unknown Protein | 0.25 |
| Solyc12g006430 | UDP-glucuronosyltransferase 1-1 82A1 | |
| Solyc12g006420 | Topoisomerase II-associated protein PAT1 | 0.08 |
| Solyc12g006410 | UDP-arabinse 4-epimerase | |
| Solyc12g006400 | Unknown Protein | |
| Solyc12g006390 | 2-oxoglutarate-dependent dioxygenase | |
| Solyc12g006380 | 2-oxoglutarate-dependent dioxygenase | 0.15 |
| Solyc12g006370 | Amine oxidase family protein | −0.16 |
| Solyc12g006360 | Multidrug resistance protein mdtK | |

TABLE 7-continued

| Accession numbers, putative protein and co-expression r-values - tomato, chromosome 12 | | |
|---|---|---|
| Gene name | Putative protein | r-value of correlation with tomato GAME4 expression |
| Solyc12g006350 | Auxin response factor 6 | 0.35 |
| Solyc12g006340 | Auxin response factor 6 | 0.47 |
| Solyc12g006330 | Acyltransferase-like protein | |
| Solyc12g006320 | ATP-dependent RNA helicase | 0.14 |
| Solyc12g006310 | Endoplasmic reticulum-Golgi | 0.25 |
| Solyc12g006300 | WD-repeat protein-like | −0.03 |
| Solyc12g006290 | Reticulon family protein | 0.19 |
| Solyc12g006280 | Myb-like DNA-binding protein | |

TABLE 8

| Accession numbers, putative protein and co-expression r-values - potato, chromosome 12 | | |
|---|---|---|
| Gene name | Putative protein | r-value of correlation with potato GAME4 expression |
| PGSC0003DMG400020034 | Beta-amyrin synthase | −0.13 |
| PGSC0003DMG400024276 | Beta-Amyrin Synthase | −0.09 |
| PGSC0003DMG400024277 | Gene of unknown function | 0.10 |
| PGSC0003DMG400024278 | Phenylacetaldehyde synthase | 0.10 |
| PGSC0003DMG400024279 | Conserved gene of unknown function | −0.16 |
| PGSC0003DMG400024280 | Triose phosphate/phosphate translocator, non-green plastid, chloroplast | −0.06 |
| PGSC0003DMG400024271 | Acetylglucosaminyltransferase | −0.06 |
| PGSC0003DMG400024273 | Resistance protein PSH-RGH6 | 0.37 |
| PGSC0003DMG400024281 | Gamma aminobutyrate transaminase isoform2 | 0.94 |
| PGSC0003DMG400024274 | Cytochrome P450 monooxygenase GAME4 | 1.00 |
| PGSC0003DMG400024275 | Gamma aminobutyrate transaminase isoform3 | 0.37 |
| PGSC0003DMG400024282 | Fortune-1 | 0.36 |
| PGSC0003DMG400028806 | UDP-glycosyltransferase 82A1-like | −0.18 |
| PGSC0003DMG401028807 | Topoisomerase II-associated protein PAT1 | |
| PGSC0003DMG402028807 | UDP-arabinse 4-epimerase | |
| PGSC0003DMG400028824 | Gene of unknown function | |
| PGSC0003DMG400028808 | 2-oxoglutarate-dependent dioxygenase | −0.07 |
| PGSC0003DMG400028809 | 2-oxoglutarate-dependent dioxygenase | 0.61 |
| PGSC0003DMG400028810 | Amine oxidase | −0.04 |
| PGSC0003DMG400028825 | MATE transporter | |
| PGSC0003DMG400028826 | Auxin response factor 6 | |
| PGSC0003DMG400043090 | Integrase core domain containing protein | |
| PGSC0003DMG400037700 | WRKY transcription factor 27 | |
| PGSC0003DMG400028811 | Acyltransferase | |
| PGSC0003DMG400028812 | DEAD-box ATP-dependent RNA helicase 53 | 0.56 |
| PGSC0003DMG400028814 | WD-repeat protein | −0.10 |
| PGSC0003DMG401028829 | Polygalacturonase | |
| PGSC0003DMG400028815 | Reticulon family protein | 0.08 |
| PGSC0003DMG400028830 | Myb-like DNA-binding domain, SHAQKYF class family protein | |

Figure 2:
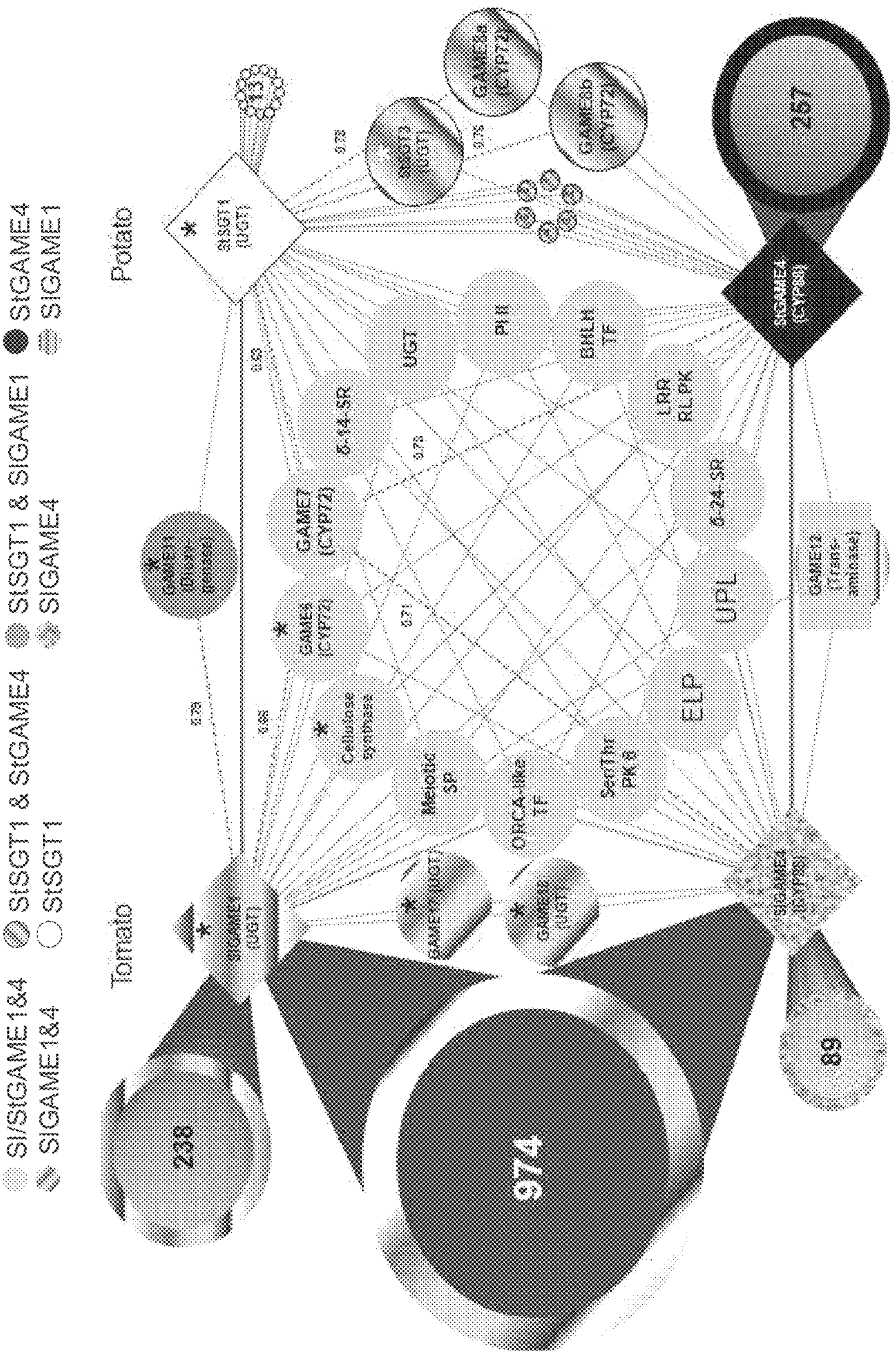
Figure 3:
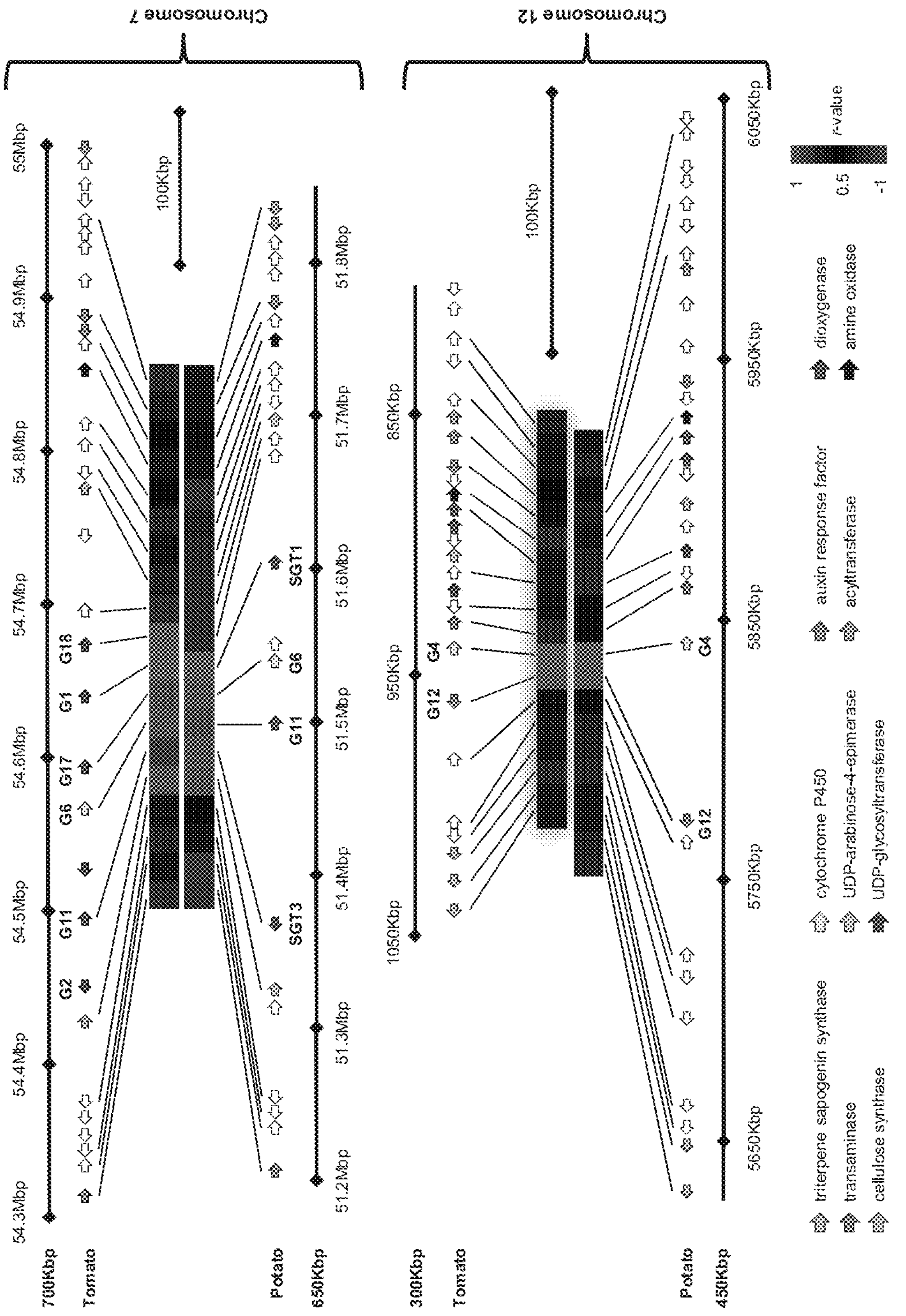
FIG. 3 presents schematic map of genes identified in the duplicated genomic regions in tomato and potato and their coexpression. Coexpression with GAME1/SGT1 (chromosome 7) and GAME4 (chromosome 12) as baits in either potato or tomato are presented in a form of a heatmap (Tables 5-8). Specific gene families are indicated by dark arrows while members of other gene families are in white arrows.

Sixteen genes from each species were co-expressed with GAME11SGT1 (Table 9, FIG. 2). One of these genes, previously designated GLYCOALKALOID METABOLISM 4 (GAME4), encodes a member of the 88D subfamily of cytochrome P450 proteins (FIG. 3). GAME4 and GAME1/SGT1 display a very similar expression profile in tomato and potato (WO 2010/095843). The GAME1/SGT1 and GAME4 genes in tomato and potato are positioned in chromosomes 7 and 12 such that they are physically next to several of their co-expressed genes (FIG. 2).

A cluster of GAME1/SGT1 co-expressed genes spans a ~200Kbp genomic region on chromosome seven. Together with GAME1, the tomato cluster is composed of 7 co-expressed genes. These include 3 UDP-glycosyltransferases [GAME2 (termed SGT3 in potato); GAME17 and GAME18], a cytochrome P450 of the 72A subfamily (GAME6), a 2-oxoglutarate-dependent dioxygenase (GAME11), and a cellulose synthase-like protein (GAME15). It appears that in potato this cluster contains 5 co-expressed genes as it lacks homologs of the tomato genes encoding GAME17 and GAME18 UDP-glycosyltransferases. Enzyme activity assays were performed with the four recombinant clustered tomato UDP-glycosyltransferases. GAME17 and GAME18 exhibited UDP-glucosyltransferase activity when incubated with tomatidine galactoside (T-Gal) and γ-tomatine (T-Gal-Glu) as a substrate, respectively, whereas GAME2 was shown to have an UDP-xylosyltransferase activity when incubated with β1-tomatine (T-Gal-Glu-Glu) as a substrate (FIGS. 4E, 4F, and 4G). GAME1 was previously shown to act as a tomatidine UDP-galactosyltransferase in tomato (Itkin et al., 2011, supra). When incubating the 4 recombinant UGT enzymes in a single test tube, with tomatidine, and all glycoside donors (UDP-galactose, -glucose and -xylose), the accumulation of the final SGA product α-tomatine was observed (FIG. 4H).

Two genes encoding putative transcription factors were identified among the genes co-expressed with GAME1/SGT1 and GAME4 (FIG. 4): one gene, designated GAME9, was identified by the tomato ID Solyc01g090340 and by the potato ID PGSC0003DMG400025989. It is described as ethylene-responsive element binding factor 13 and contains a putative AP2 domain. The other gene is the BHLH-transcription factor, identified by the tomato ID Solyc03g046570 and by the potato ID PGSC0003DMG400012262.

TABLE 9

Details of homologs co-expressed with known and putative steroidal alkaloid-associated genes in both potato and tomato presented in FIG. 2

| Name | Tomato ID Solyc | Potato reads | Tomato ID |
|---|---|---|---|
| Extensin-like protein | Solyc01g006400 | PGSC0003DMG400023230 | TCONS_00007692 |
| GAME 9 | Solyc01g090340 [amino acid SEQ ID NO: 13] [nucleic acid SEQ ID NO: 15] | PGSC0003DMG400025989 [amino acid SEQ ID NO: 14] [nucleic acid SEQ ID NO: 16] | TCONS_00011729 |
| Delta (24)-sterol reductase-like | Solyc02g069490 | PGSC0003DMG400021142 | TCONS_00044548 |
| BHLH transcription factor | Solyc03g046570 [amino acid SEQ ID NO: 17] [nucleic acid SEQ ID NO: 18] [nucleic acid SEQ ID NO: 19] | PGSC0003DMG400012262 [nucleic acid SEQ ID NO: 20] [nucleic acid SEQ ID NO: 21] | TCONS_00055879 |
| LRR receptor-like protein kinase | Solyc05g009100 | PGSC0003DMG400014576 | TCONS_0010281 |
| Glycosyltransferase | Solyc05g053120 | PGSC0003DMG402027210 | TCONS_00100675 |
| Cellulose synthase-like (GAME15) | Solyc07g043390 | PGSC0003DMG400011752 | TCONS_00135034 |
| GAME6 (CYP72) | Solyc07g043460 | PGSC0003DMG400011750 | TCONS_00137734 |
| GAME1 (Galactosyltransferase) | Solyc07g043490 | PGSC0003DMG400011749 | PCONS_00133014 |
| GAME7 (CYP72) | Solyc07g062520 (GAME1 r-value 0.66; GAME4 r-value 0.71) | PGSC0003DMG402012386 (SGT1 r-value 0.63; GAME4 r-value 0.73) | TCONS_00132326 |
| Srt/Thr protein kinase 6 | Solyc08g066050 | PGSC0003DMG400025461 | TCONS_00151251 |
| Meiotic serine proteinase | Solyc08g077860 | PGSC0003DMG401012339 | TCONS_00149157 |
| Sterol reductase | Solyc09g009040 | PGSC0003DMG400002720 | TCONS_00162820 |
| Ubiquitin protein ligase | Solyc10g008410 | PGSC0003DMG400021683 | TCONS_00183263 |
| Proteinase inhibitor II | Solyc11g020960 | PGSC0003DMG402003479 | TCONS_00194999 |
| GAME4 (CYP88) | Solyc12g006460 | PGSC0003DMG400024274 | TCONS_00210154 |
| Gamma-aminobutyrate Aminotransferase-like protein (transaminase) (GAME12) | Solyc12g006470 | PGSC0003DMG400024281 | |
| Beta-solanine rhamnosyltransferase (SGT3) | #N/A | PGSC0003DMG400011740 | |
| 2-oxoglutarate-dependent dioxygenase (GAME11) | Solyc07g043420 [amino acid SEQ ID NO: 22] [nucleic acid SEQ ID NO: 24] [nucleic acid SEQ ID NO: 25] | PGSC0003DMG400011751 [amino acid SEQ ID NO: 23] [nucleic acid SEQ ID NO: 26] [nucleic acid SEQ ID NO: 27] | |
| GAME18 (Glycosyltransferase) | Solyc07g043500 | #N/A | |
| GAME 17 (Glycosyltransferase) | Solyc07gP43480 | #N/A | |

Tomato and potato sequences were obtained from Sol Genomics Network (solgenomics.net). r-value for co-expression ≥ 0.8. TCON number, a contig reference name given by the inventors in the assembly of RNAsec data.
N/A, not available.

Example 3: Functional Analysis of GAME9-Transcription Factor

GAME9-silencing (RNAi) and overexpressing (OX) constructs were created by introducing the corresponding GAME9 DNA fragments to pK7GWIWG2(II) and pJCV52 binary vectors, respectively. Transgenic tomato and potato lines transformed with the respective GAME9 silencing and overexpressing constructs were generated as previously described (Itkin et al., 2011, supra). Tissue extracts were prepared and analyzed as described in Itkin et al. (2011, supra). SEQ II) NO: 18 presents the sequence of the GAME9 RNAi silencing molecule. The metabolic profiling of steroidal alkaloids using UPLC-TQ-MS was performed on extracts obtained from leaves and/or tubers of transgenic and wild type tomato and/or potato plants. In extract obtained from potato tuber peels of potato lines in which the gene encoding GAME9 was silenced (GAME9-RNAi lines) a reduction in α-solanine and α-chaconine was observed (FIGS. 5A and 51B, respectively). Leaves from potato GAME9-overexpression lines contained higher levels of α-solanine (FIG. 5C) and α-chaconine (FIG. 5D) compared to the wild type. A similar accumulation pattern was observed in potato leaves, having reduced amounts of α-chaconine and α-solanine in RNAi lines and increased amounts of these steroidal alkaloids in lines overexpressing the GAME9-transcription factor (FIG. 6).

In tomato, leaves extract of a line overexpressing the GAME9-transcription factor (designated 5879) contained higher levels of α-tomatine compared to its amount in leaf extract obtained from wild type plants. On the contrary, down regulation of the expression of GAME9-transcription factor (line 5871) resulted in significant reduction of α-tomatine content.

Example 4: Functional Characterization of the GAME Genes

GAME11 Silenced Plants

Virus induced gene silencing (VIGS) is a commonly used technique allowing systemic silencing of genes in various organs of the plant (Dinesh-Kumar S P et al., 2003. Methods Mol Biol 236:287-294). SEQ ID NO: 19 presents the sequence of the GAME11 RNAi silencing molecule.

Analysis of tomato leaves with VIGS-silenced GAME11, a putative dioxygenase in the cluster, revealed a significant reduction in α-tomatine levels and accumulation of several cholestanol-type steroidal saponins.

Figures 8A, 8B, 8C:
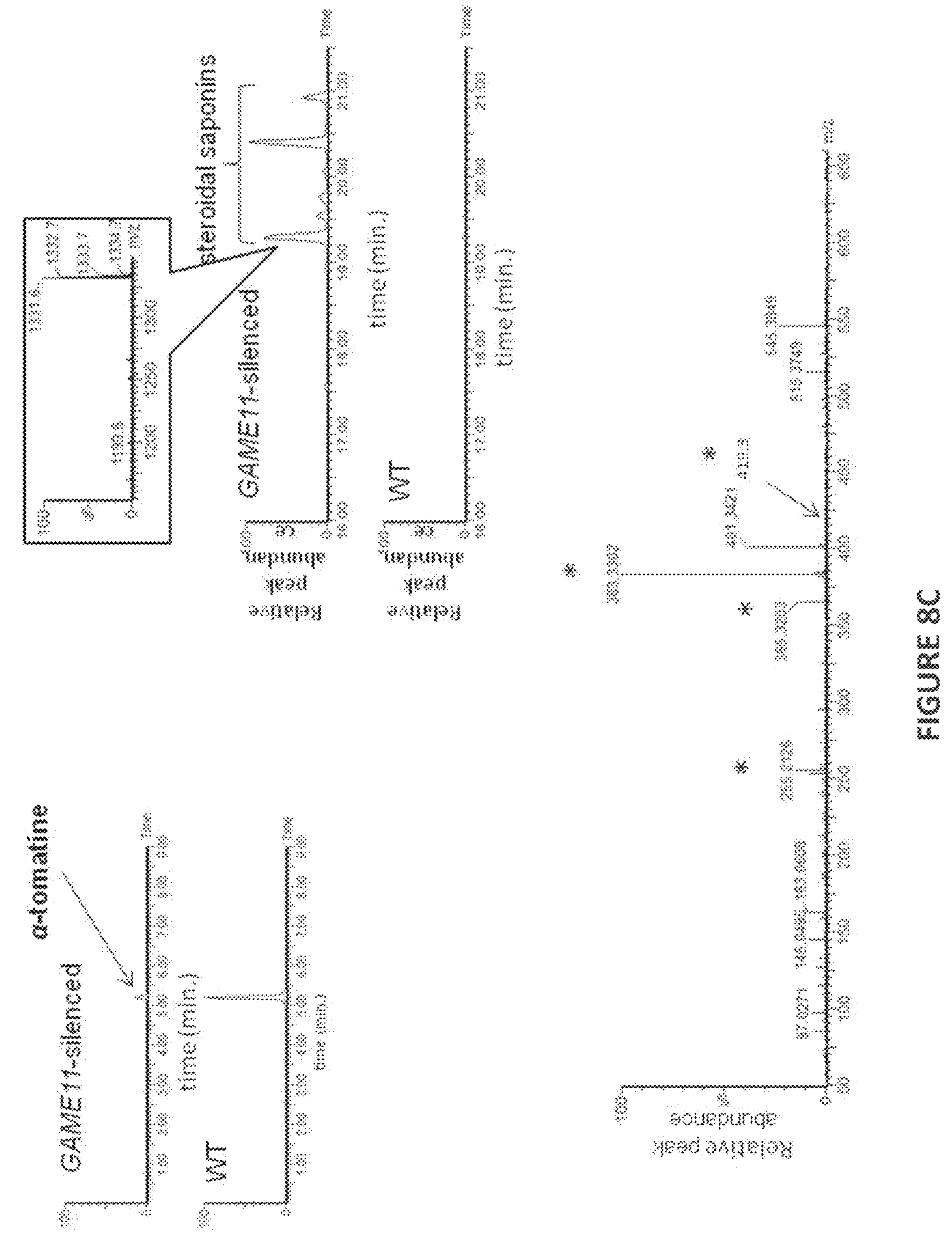
FIGS. 8A-8D show the effect of silencing of GAME11 dioxygenase in tomato.
Figure 8D:
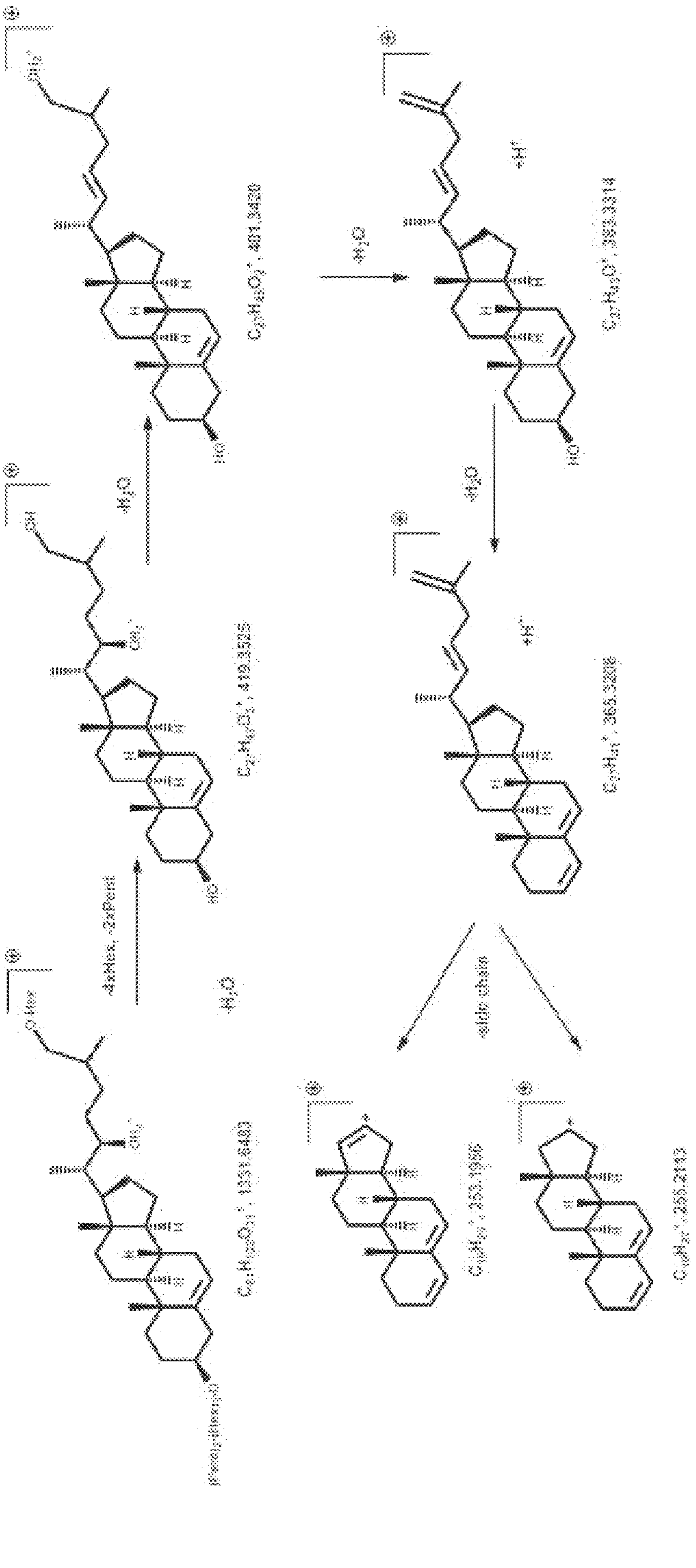

Silencing of GAME11 dioxygenase in tomato results in depletion of α-tomatine levels in leaves (m/z=1034.5) (FIG. 8A) while accumulating cholestanol-type steroidal saponins [i.e. STSs; m/z=1331.6, 1333.6, 1199.6, 1201.6 (major saponins)] (FIG. 8B). FIG. 8C shows MS/MS spectrum of m/z=1331.6 (at 19.28 min.). FIG. 8D shows the fragmentation patterns of the saponin eluted at 19.28 min. and accumulating in GAME11-silenced leaves. The corresponding mass signals are marked with an asterisk on the MS/MS chromatogram in FIG. 8C. The elemental composition and fragmentation patterns show that the compounds are cholestanol-type saponins, lacking one hydroxy-group and the E-ring (in comparison to furostanol-type saponins), which results in fragmentation, involving multiple losses of water molecules instead of tautomerisation and McLafferty rearrangement of the E-ring.

GAME18 Silenced Plants

The role of GAME18 in creating the tetrasaccharide moiety of α-tomatine was supported by Virus Induced Gene Silencing (VIGS) assays as GAME18-silenced fruit accumulated γ-tomatine which was not present in the control sample (FIG. 9).

Figure 9A:
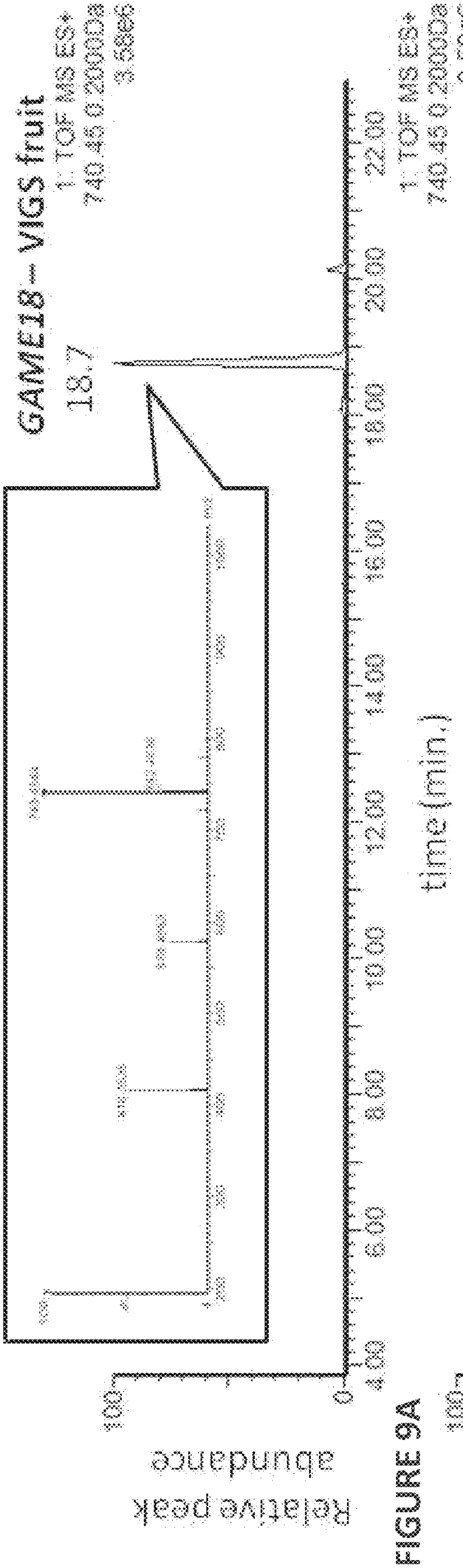
FIGS. 9A-9E show metabolites extracted from GAME18-silenced mature green tomato fruit. Peaks of newly accumulating compounds corresponding to the γ-tomatine standard (m/z=740.5) (FIGS. 9A-C), and γ-tomatine pentoside (m/z=872.5) (FIGS. 9D-E) are shown.
Figure 9B:
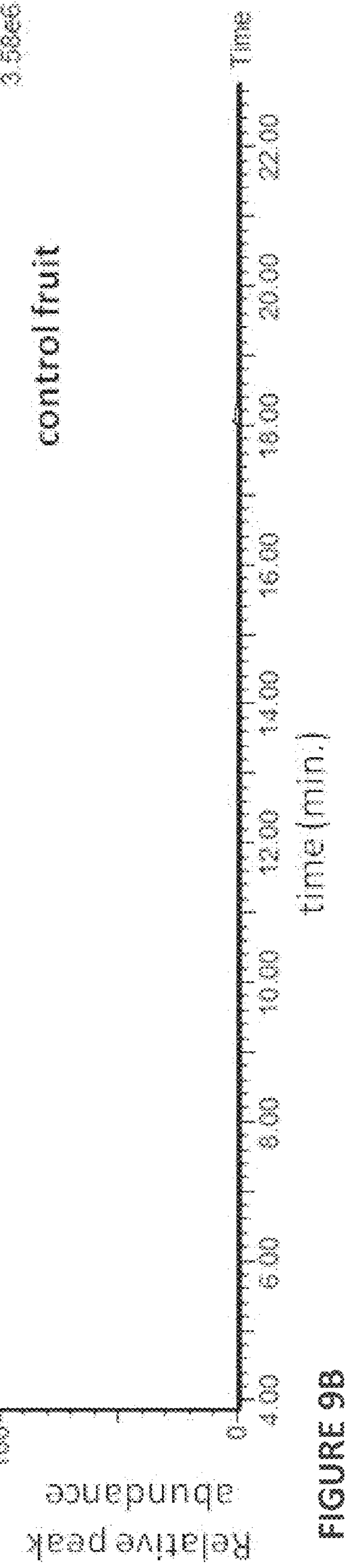
Figure 9C:
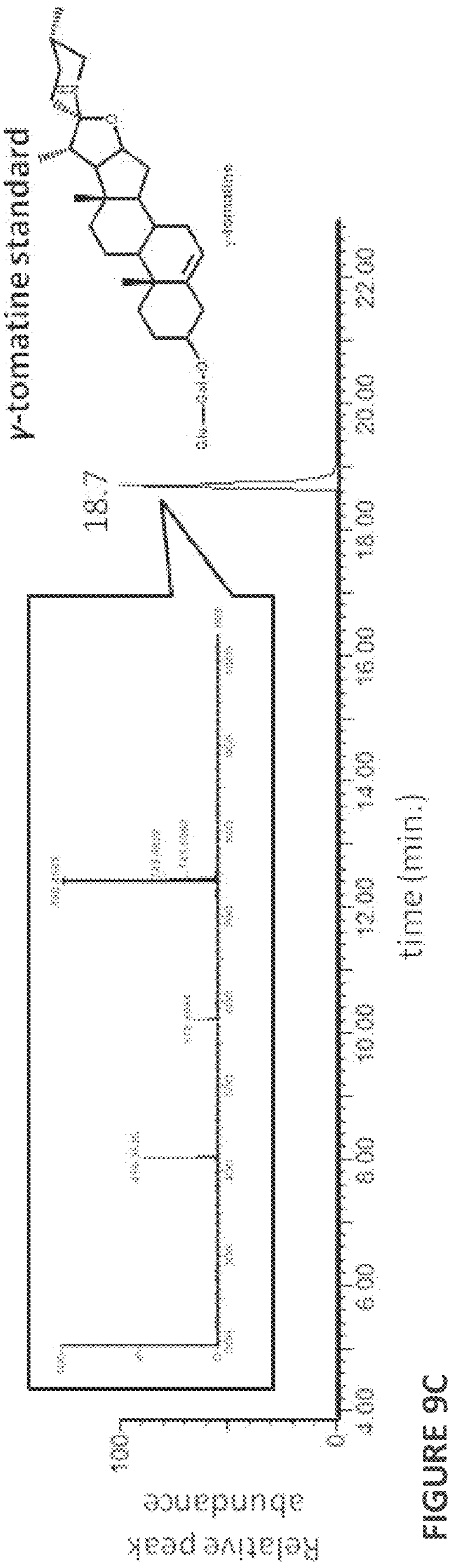
Figure 9D:
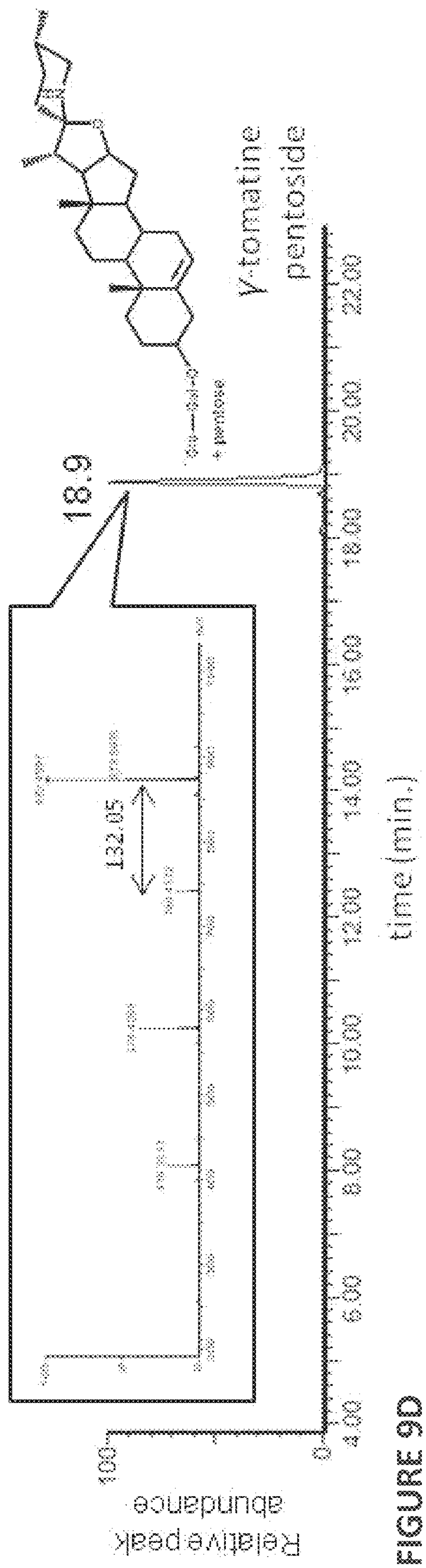
Figure 9E:
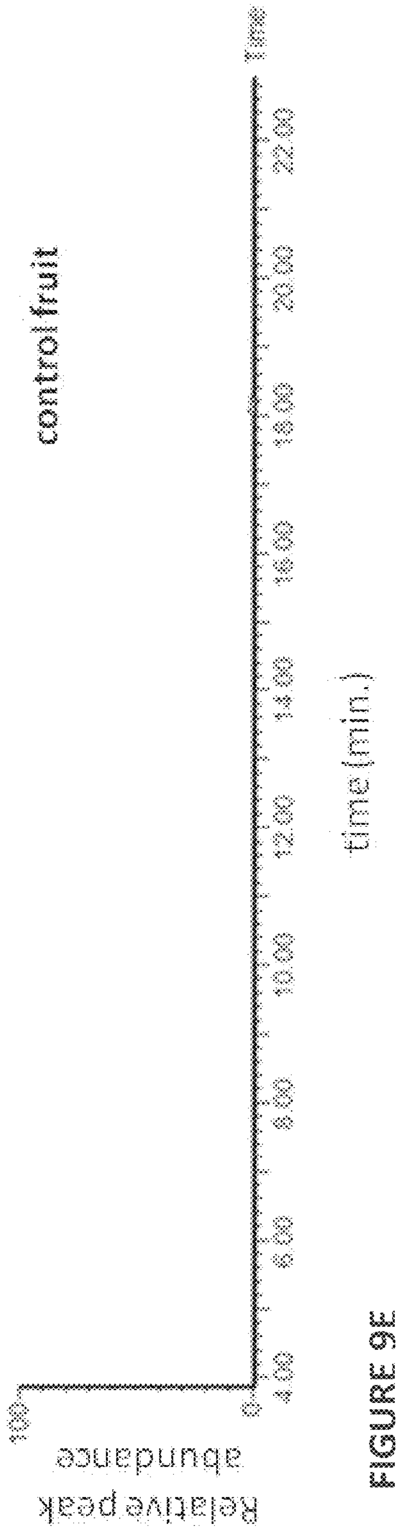

Among the metabolites extracted from GAME18-silenced mature green fruit, peaks of newly accumulating compounds were detected, corresponding to the γ-tomatine standard (m/z=740.5) (FIGS. 9A-C), and γ-tomatine pentoside (m/z=872.5) (FIGS. 9D-9E).

GAME12 Silenced Plants

Figures 4A, 4B, 4C, 4D:
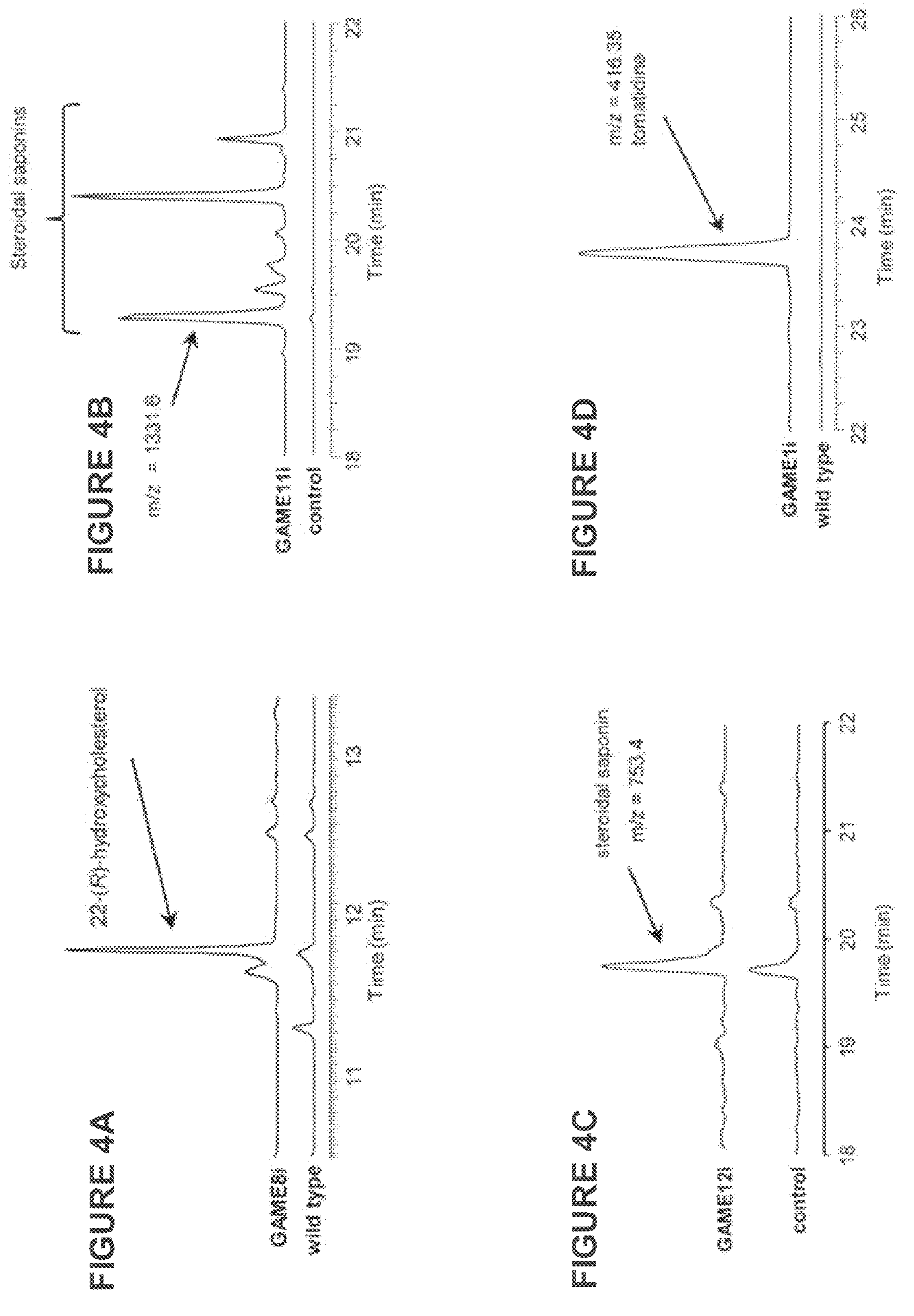
FIGS. 4A-4H shows functional analysis of tomato GAME genes.
Figure 4E:
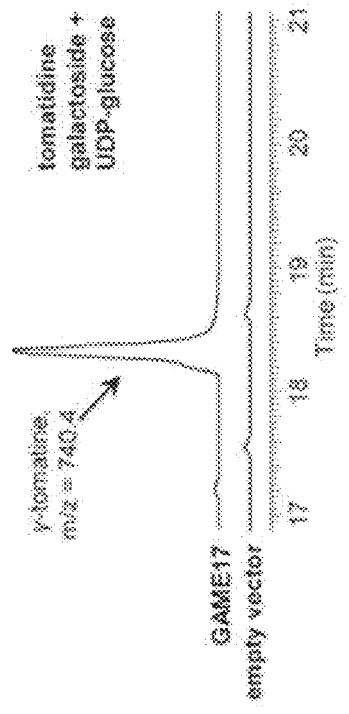
Figure 4F:
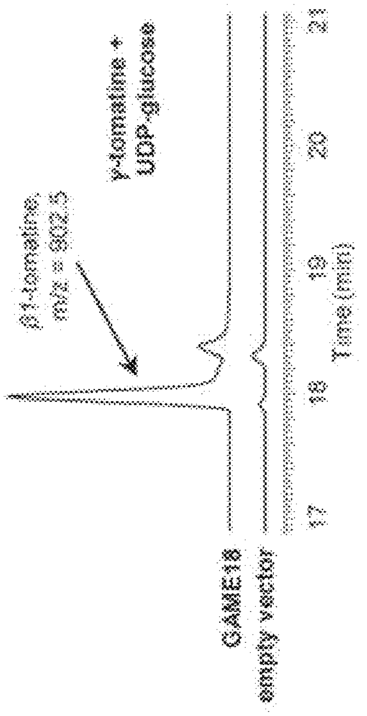
Figure 4G:
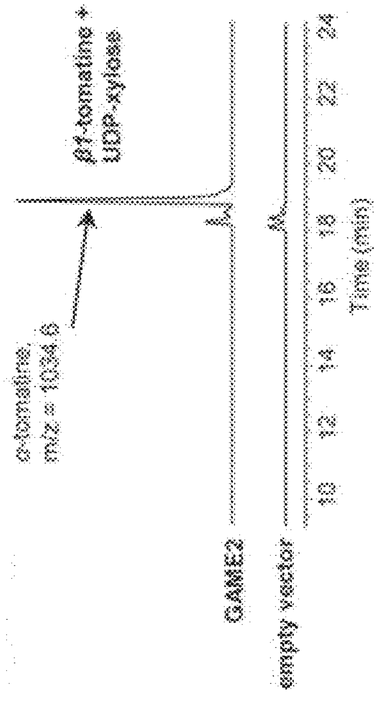
Figure 4H:
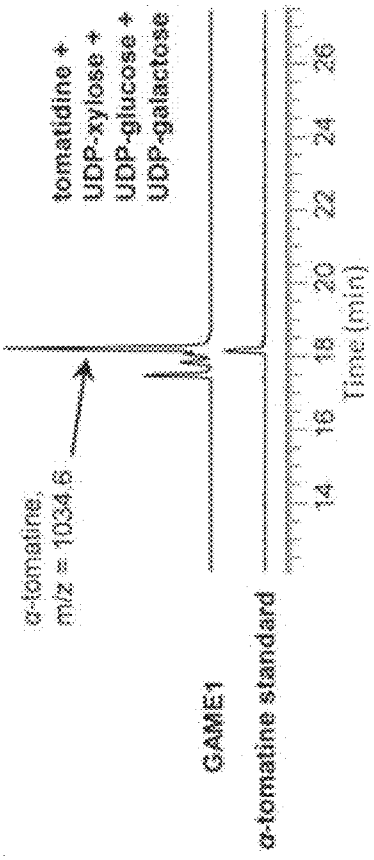
Figure 10A:
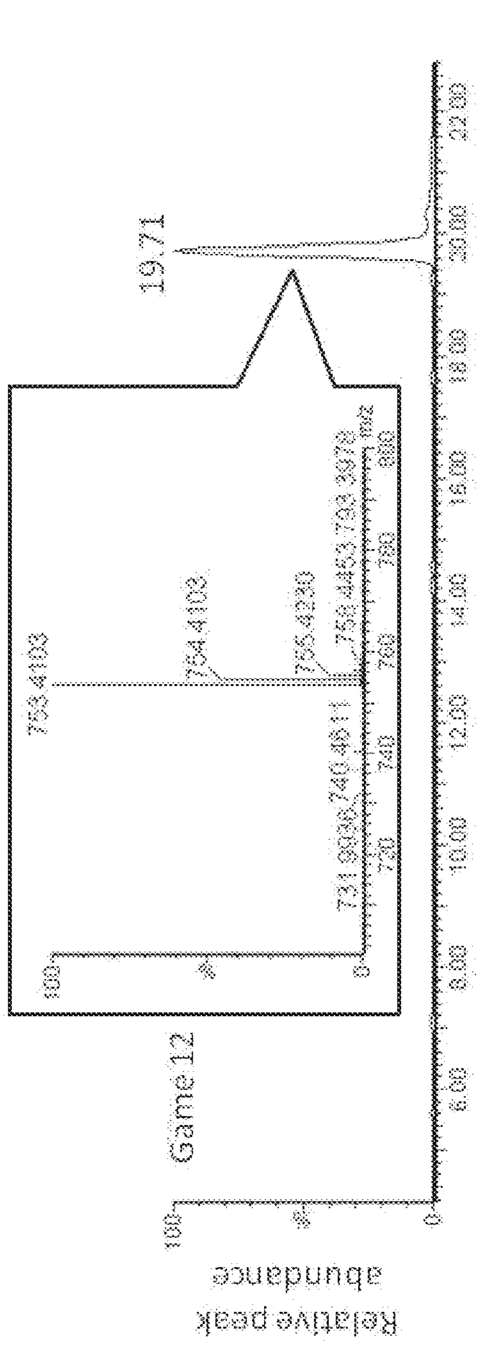
FIGS. 10A-10D show the effect of silencing of GAME12 transaminase in tomato.
Figure 10B:
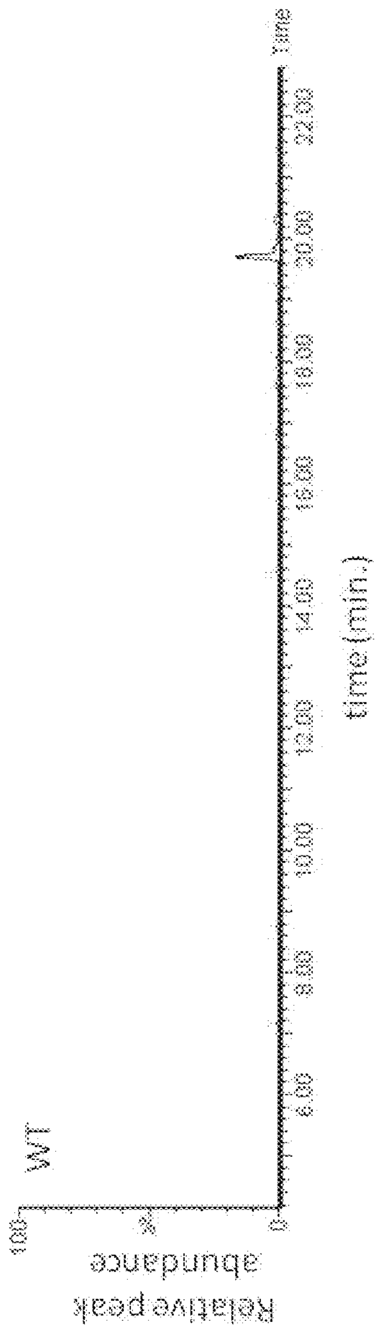
Figure 10C:
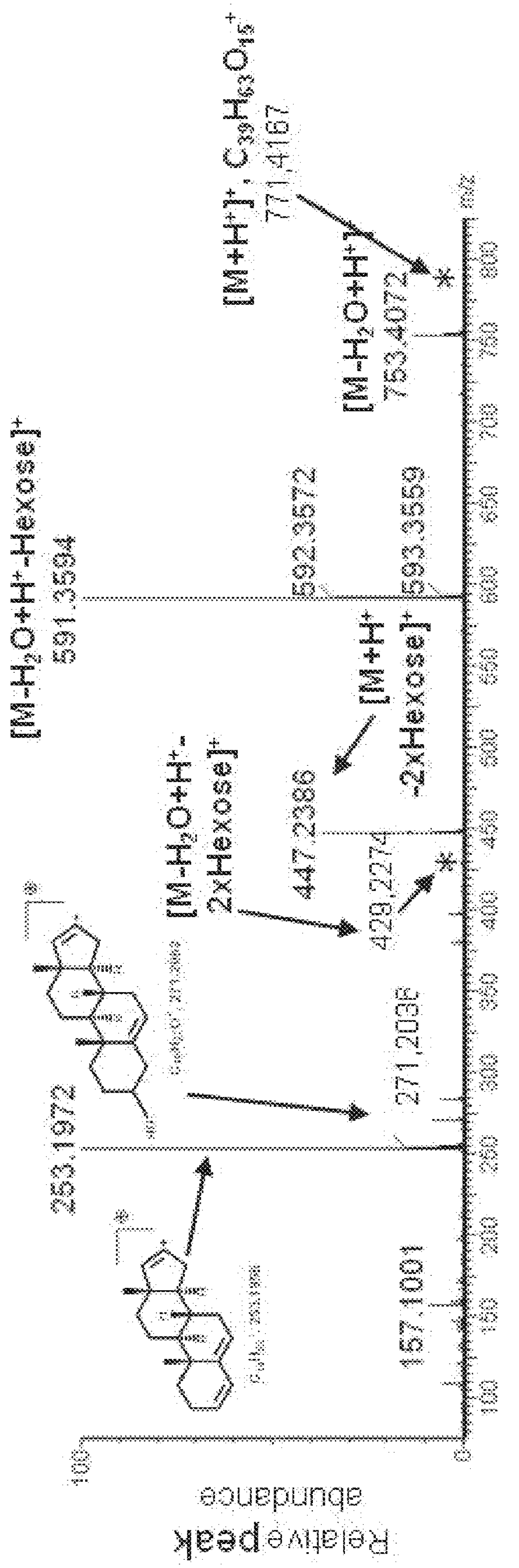
Figure 10D:
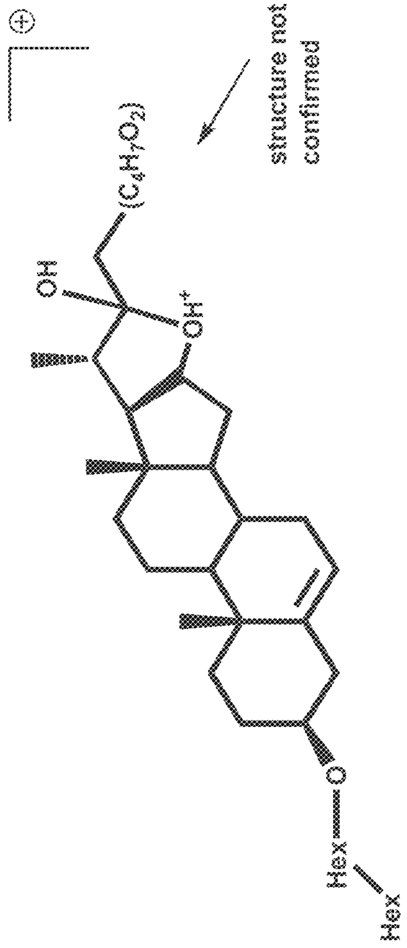

Silencing of GAME12 transaminase in tomato resulted in accumulation of a furastanol-type steroidal saponin (FIG. 4D). FIG. 10A shows that GAME12-silenced leaves accumulate an STS (m/z=753.4), while it exists in only minor quantities in wild type leaf FIG. 10B. FIG. 10C shows MS/MS spectrum of m/z=753.4 at 19.71 min. with interpretation of the fragments. Suggested structure of the STS at 19.71 min. is depicted in FIG. 10D, concluded from the characteristic mass fragments observed in the MS/MS experiment.

Function of GAME7 and GAME8

Figure 11A:
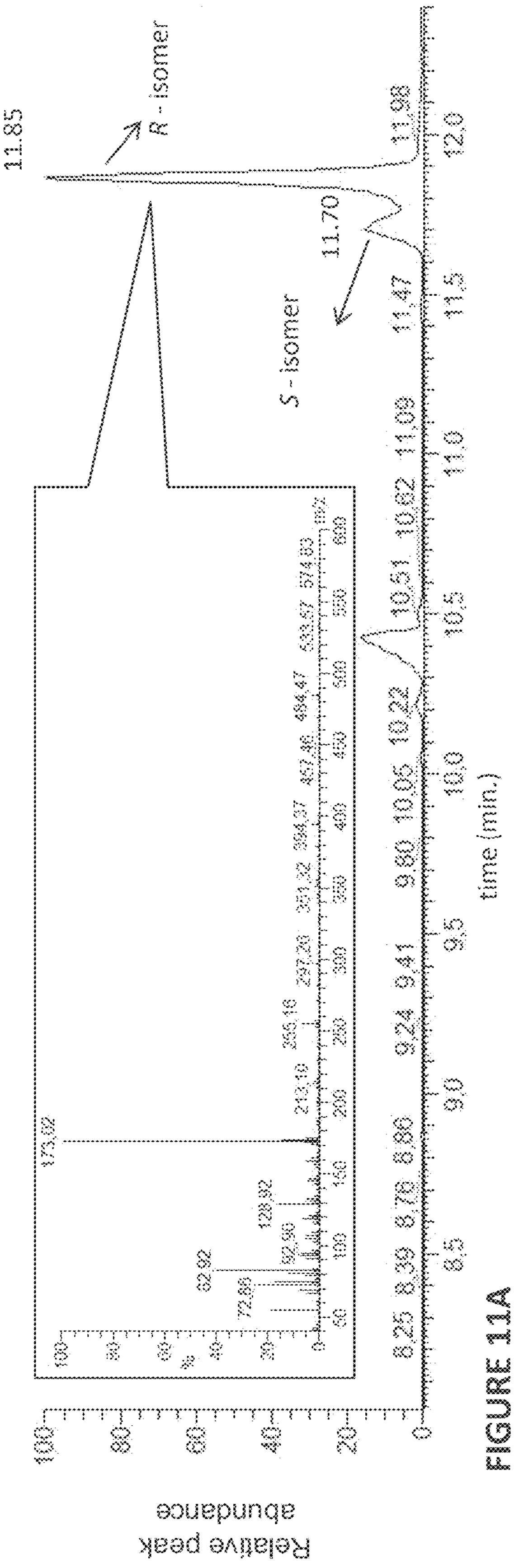
FIGS. 11A-11D show the effect silencing of GAME8 in tomato plants. GAME8-silenced leaves accumulated 22 -(S) and -(R)-cholesterol (FIG. 11A). Chromatograms (mass range 172.5-173.5) acquired via EI-GC/MS, MS spectra and structures (tri-methyl-silyl derivatives) of the compounds are shown. Commercial standards of 22-(R)- (FIG. 11B) and 22-(S)-cholesterol (FIG. 11C) were used to verify the putative identification.
Figure 11B:
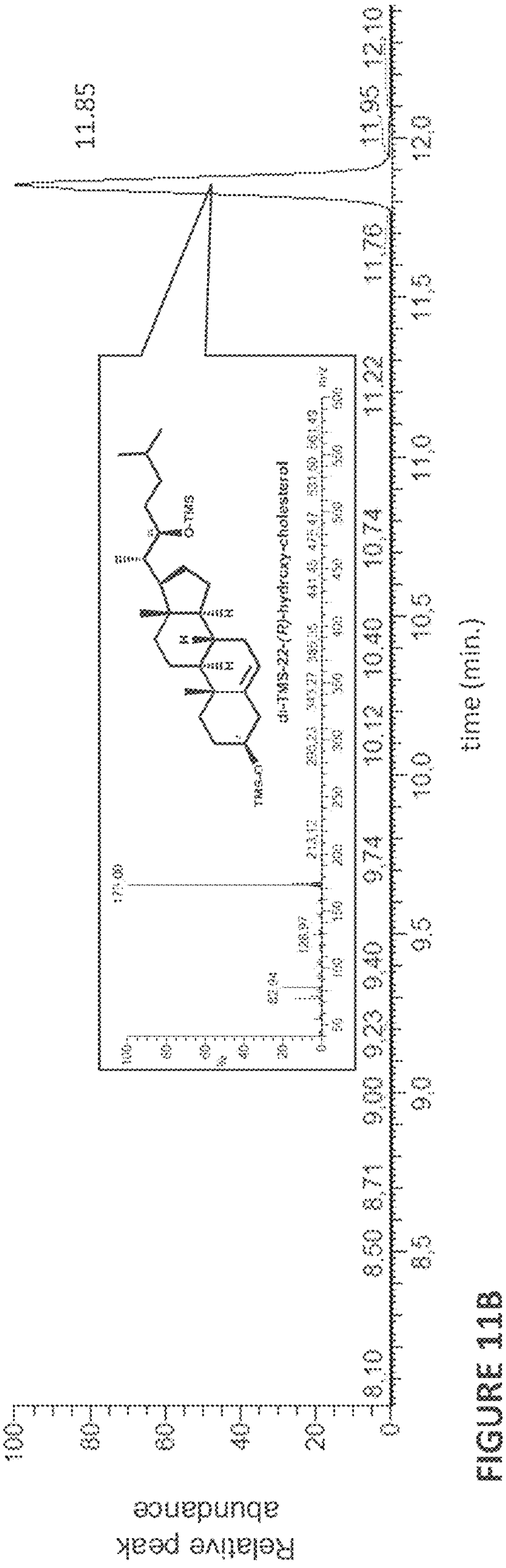
Figure 11C:
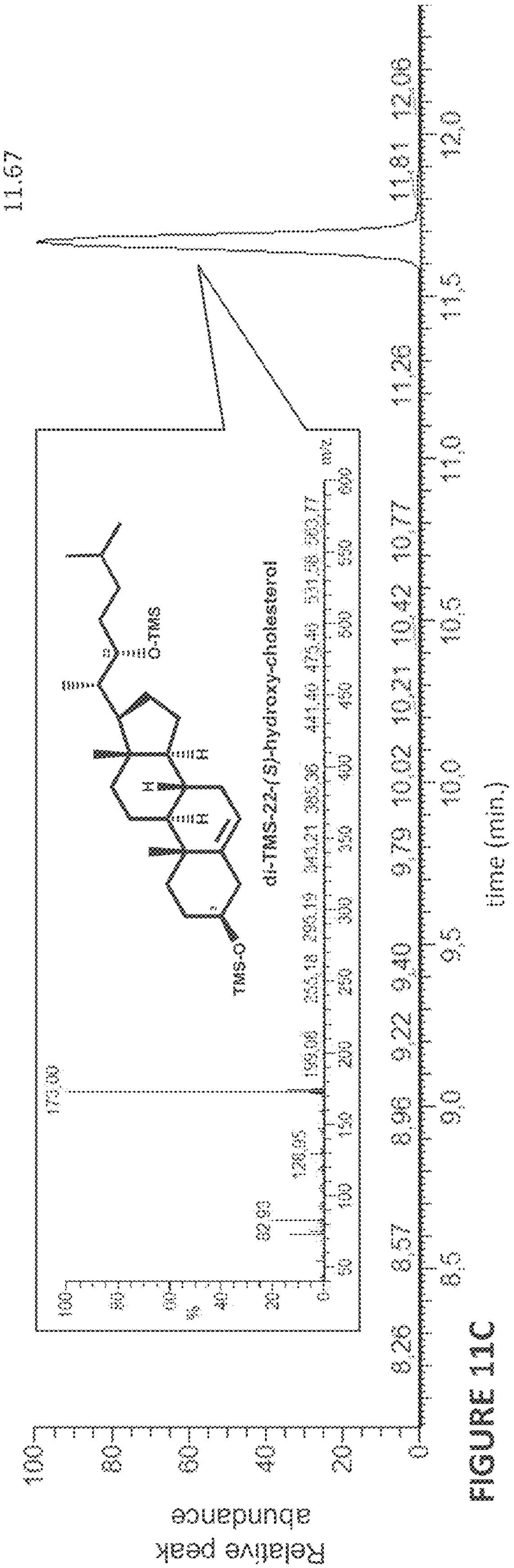
Figure 11D:
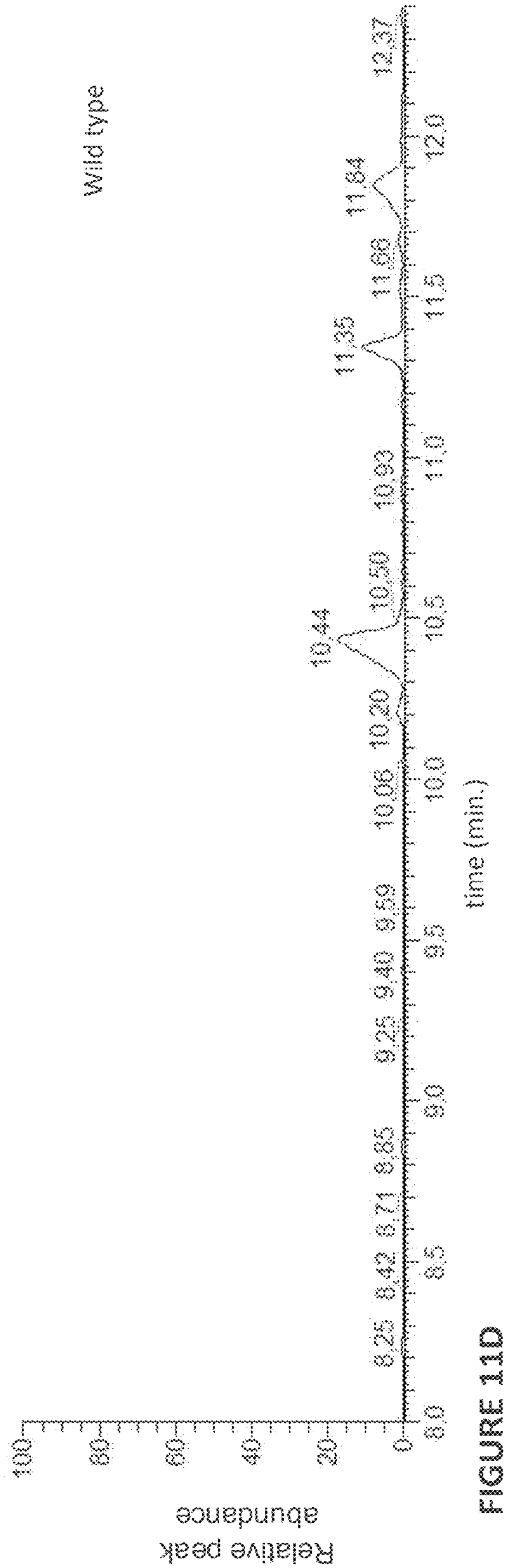

Genes that were tightly co-expressed and positioned elsewhere in the genome were also functionally examined. Two genes, designated GAME7 and GAME8 belong to the CYP72 subfamily of cytochrome P450s. GAME7 was co-expressed in both species (potato and tomato) while StGAME8a and StGAME8b were strongly co-expressed with StSGT1 and StGAME4 in potato. At present, we could not demonstrate SGA-related activity for GAME7 although as for GAME6 it was suggested to be involved in SGA metabolism (US 20120159676). Yet, GAME8-silenced tomato leaves accumulated 22-(R)-hydroxycholesterol (FIGS. 11A-11D), a proposed intermediate in the SGA biosynthetic pathway (FIG. 1). GAME8-silenced line accumulates both isomers in comparison to wild type (FIG. 11D). The (R)-isomer is more abundant and hence most likely to be the substrate of GAME8.

FIG. 12 shows the phylogenetic tree of GAME genes in the plant CYP450 protein family. The numbers on the branches indicate the fraction of bootstrap iterations supporting each node.

Example 5: Proposed Biosynthetic Pathway in Solanaceous Plants

Figure 13:
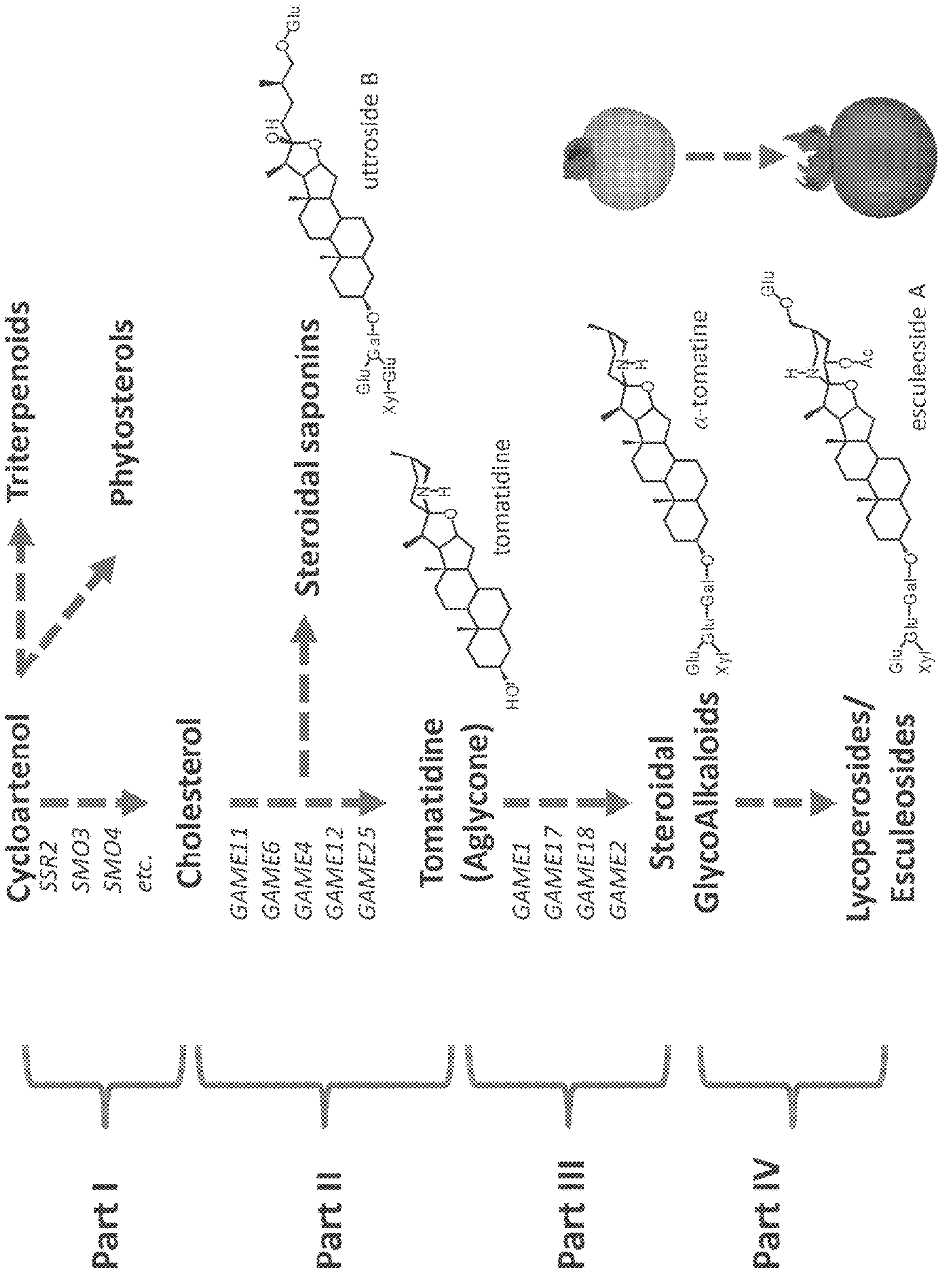
FIG. 13 shows a proposed expanded biosynthetic pathway in Solanaceous plants from Cycloartenol (Part I), through Cholesterol (Part II), through Tomatidine (Part III), through Steroidal Glycoalkaloids including α-tomatine to Lycoperosides/Esculeoside (Part IV). Dashed arrows represent multiple enzymatic reactions in the pathway.

An expanded biosynthetic pathway in Solanaceous plants has been proposed, as depicted in the schematic of FIG. 13 (dashed arrows represent multiple enzymatic reactions in the pathway) with respect to the tomato. This pathway can be broken down into four parts for convenience. In Part I, a series of reactions (catalyzed, e.g., by SSR2, SMO3, SMO4) converts cylcloartenol to cholesterol. Byproducts include triterpenoids and phytosterols. In Part II, a series of reactions (catalyzed, e.g., by GAME11, GAME6, GAME4, GAME12, GAME25) converts cholesterol to tomatidine (aglycone). Byproducts include steroidal saponins (e.g., uttroside B). In Part III, a series of reactions (catalyzed, e.g., by GAME1, GAME 17, GAME18, GAME2) converts tomatidine to steroidal glycoalkaloids (e.g., α-tomatine). In Part IV, a series of reactions converts steroidal glycoalkaloids (e.g., α-tomatine) of a green tomato to lycoperosides and/or esculeosides (e.g., esculeoside A) of a red tomato.

Figure 14A:
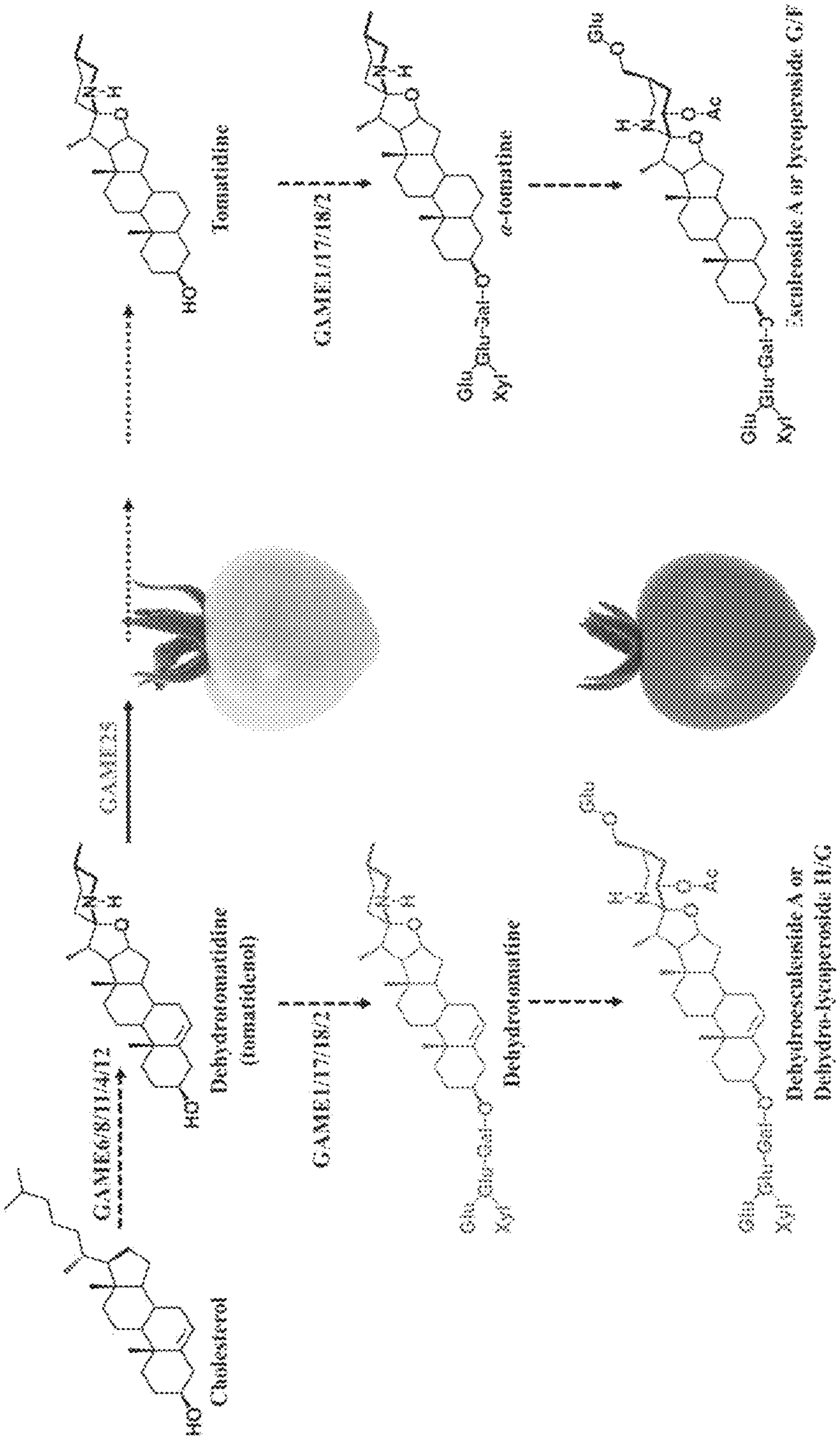
FIGS. 14A-14D show an overview of SGA biosynthesis in (A) tomato, (B) potato, and (C) eggplant.
Figure 14B:
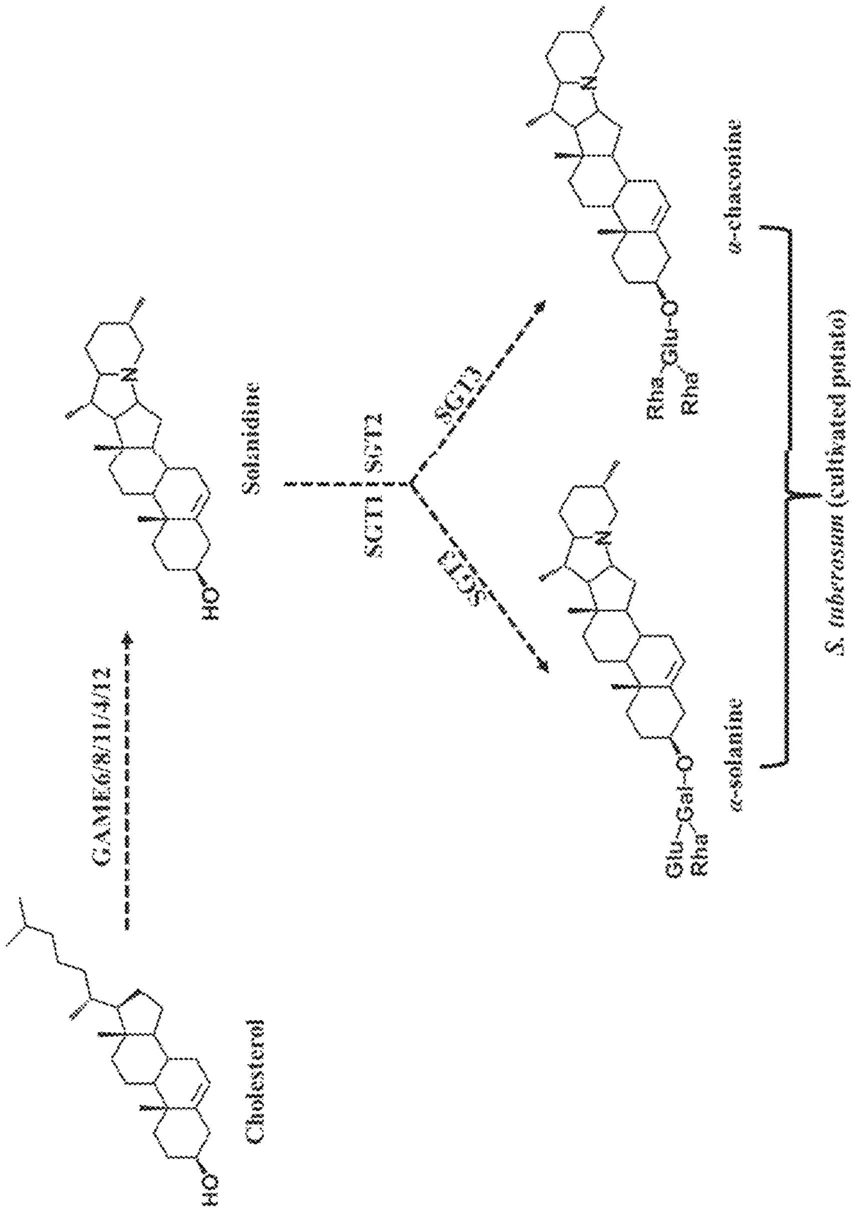
Figure 14C:
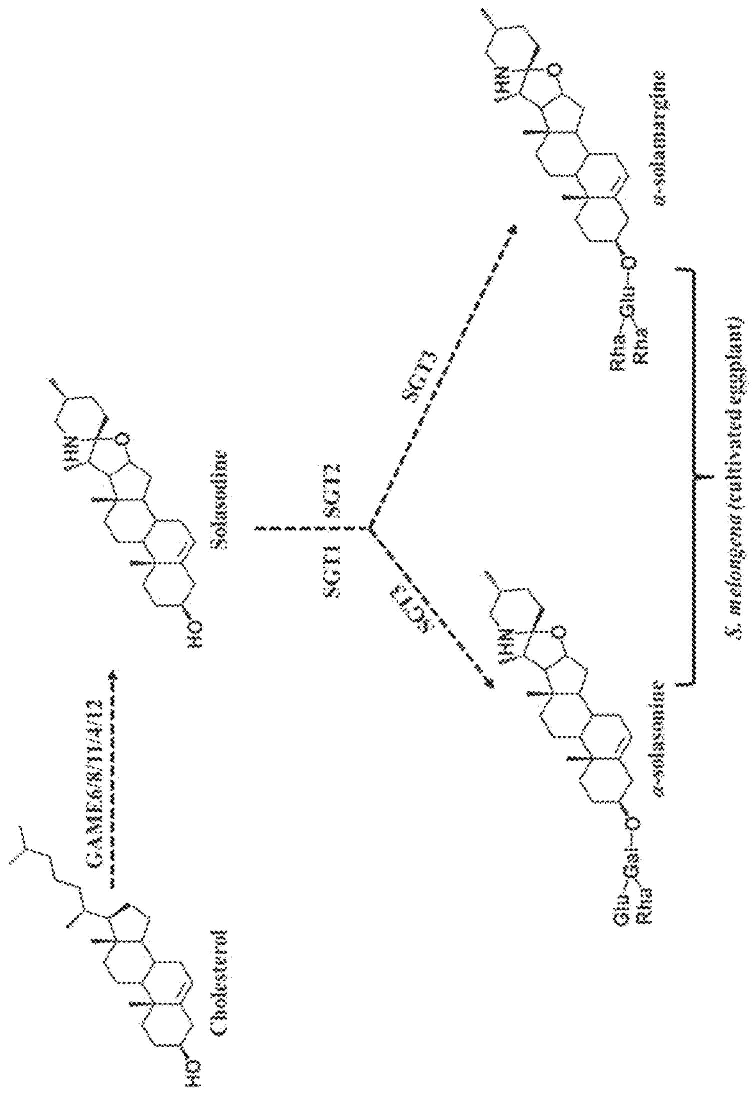
Figure 14D:
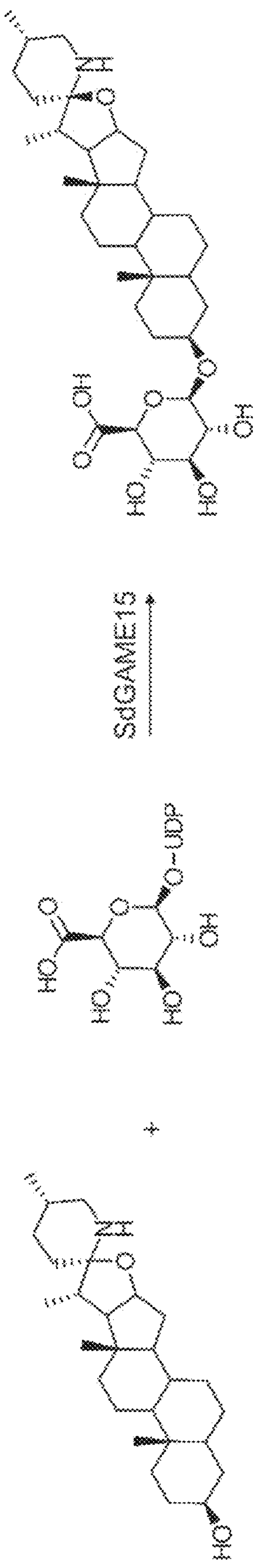

Example 6. Pathways Involving Steroidal Glycoalkaloid (SGA) Biosynthesis in Tomato, Potato, and Eggplant A cellulose synthase-like gene (GAME15) in tomato, potato, and eggplant has been identified as being associated with steroidal glycoalkaloid (SGA) biosynthesis (FIGS. 14A-14C). This gene has been shown to have been strongly co-expressed with other SGA biosynthesis genes (e.g., GAME4, GAME12) and also with regulators of SGA biosynthesis (e.g., GAME9). FIG. 14D provides a non-limiting example of a proposed pathway in Solanaceous plants, for example but not limited to, wherein a skilled artisan would recognize that the pathway encompasses production of tomatidine 3-O-glucoronide from tomatidine by a GAME15 glucuronic acid transferase activity. In certain embodiments, the GAME15 enzyme comprises a GAME15 present in a Solanaceous plant, for example but not limited to *Solanum tuberosum*, potato; *Solanum lycopersicum*, tomato; *Solanum dulcamara*, bitter-sweet; and *Solanum* melogena, eggplant.

Sequences were identified as follows:

Cellulose Synthase Like_Tomato

[SEQ ID NO: 30]

ATGAAAAAAACCATGGAGCTCAACAAAAGCACTGT

TCCACAACCTATCACCACCGTATACCGACTCCACA

TGTTCATCCACTCAATAATCATGCTTGCATTAATA

-continued

TACTACCGTGTATCTAATTTGTTTAAATTCGAAAA
CATTCTCAGTTTACAAGCACTTGCTTGGGCGCTCA
TCACTTTTGGTGAATTTAGTTTCATTCTCAAGTGG
TTCTTCGGACAAGGTACTCGTTGGCGCCCCGTTGA
ACGAGATGTTTTCCCTGAAAACATTACTTGCAAAG
ATTCCGATCTACCGCCAATTGACGTAATGGTATTC
ACTGCCAATCCTAAGAAAGAGCCAATTGTAGATGT
CATGAACACTGTGATATCCGCAATGGCTCTTGATT
ATCCCACCGATAAATTGGCTGTGTATCTCGCTGAT
GATGGAGGATGTCCATTGTCGTTGTACGCGATGGA
ACAAGCGTGTTTGTTTGCAAAGCTATGGTTACCTT
TCTGTAGAAACTATGGAATTAAAACGAGATGCCCA
AAAGCATTTTTTTCTCCGTTAGGAGATGATGACCG
TGTTCTTAAGAATGATGATTTTGCTGCTGAAATGA
AAGAAATTAAATTGAAATATGAAGAGTTCCAGCAG
AAGGTGGAACATGCTGGTGAATCTGGAAAAATCAA
TGGTAACGTAGTGCCTGATAGAGCTTCGCTTATTA
AGGTAATAAACGAGAGGGAGAACGAAAAGAGTGTG
GATGATATGACGAAAATGCCCTTGCTAGTTTATGT
ATCCCGTGAAAGAAGATTCAACCGTCTTCATCATT
TCAAGGGTGGATCTGCAAATGCTCTACTTCGAGTT
TCTGGAATAATGAGTAATGCCCCCTATGTACTGGT
GTTAGATTGTGATTTCTTCTGTCATGATCCAATAT
CAGCTAGGAAGGCAATGTGTTTTCATCTTGATCCA
AAGCTATCATCTGATTTAGGCTATGTTCAGTTCCC
TCAAGTCTTTTACAATGTCAGCAAGTCAGATATTT
ATGATGTCAAAATTAGACAGGCTTACAAGACAATA
TGGCATGGAATGGATGGTATCCAAGGCCCAGTGTT
ATCTGGGACTGGTTATTTTCTCAAGAGGAAAGCGT
TATACACAAGTGCAGGAGTAAAAGAGGCGTATCTT
AGTTCACCGGAAAAGCATTTTGGAAGGAGTAAAAG
GTTTCTTGCTTCATTAGAGGAGAAAAATGGTTATG
TTAAGGCAGATAAAGTCATATCAGAAGATATCATA
GAGGAAGCTAAGATGTTAGCTACTTGTGCATATGA
GGATGGCACACATTGGGGTCAAGAGATTGGTTATT
CATACGATTGTCATTTGGAGAGCACTTTTACTGGT
TATCTATTACACTGCAAAGGGTGGACATCTACTTA
TTTGTATCCAGACAGGCCATCTTTCTTGGGTTGTG
CCCCAGTTGATATGCAAGGTTTCTCATCACAGCTC
ATCAAATGGGTTGCTGCACTTACACAAGCTGGTTT

-continued

ATCACATCTCAATCCCATCACTTATGGTTTGAGTA
GTAGGATGAGGACTCTCCAATGCATGTGCTATGCC
TATTTGATGTATTTCACTCTTTATTCTTGGGGAAT
GGTTATGTATGCTAGTGTTCCTTCTATTGGCCTTT
TGTTTGACTTCCAAGTCTATCCTGAGGTACATGAT
CCGTGGTTTGCAGTGTATGTGATTGCTTTCATATC
GACAATTTTGGAGAATATGTCGGAGTCAATTCCAG
AAGGGGGATCAGTTAAAACGTGGTGGATGGAATAC
AGGGCATTGATGATGATGGGAGTTAGCGCAATATG
GTTAGGAGGATTGAAAGCTATATATGACAAGATAG
TCGGAACACAAGGAGAGAAATTGTATTTGTCGGAC
AAGGCAATTGACAAGGAAAAGCTCAAGAAATACGA
GAAGGGCAAATTTGATTTCCAAGGAATAGGGATAC
TTGCTCTGCCACTGATAGCATTTTCCGTGTTGAAC
CTCGTAGGCTTCATTGTTGGAGCTAATCATGTCTT
TATTACTATGAACTACGCAGGCGTGCTGGGCCAAC
TCCTCGTATCATCGTTCTTCGTCTTTGTTGTCGTC
ACTGTTGTCATTGATGTTGTATCTTTCTTAAAGGT
TTCTTAA

Cellulose Synthase Like (Tomato)

[SEQ ID NO: 31]

MKKTMELNKSTVPQPITTVYRLHMFIHSIIMLALIY
YRVSNLFKFENILSLQALAWALITFGEFSFILKWF
FGQGTRWRPVERDVFPENITCKDSDLPPIDVMVFT
ANPKKEPIVDVMNTVISAMALDYPTDKLAWLADDG
GCPLSLYAMEQACLFAKLWLPFCRNYGIKTRCPKA
FFSPLGDDDRVLKNDDFAAEMKEIKLKYEEFQQKV
EHAGESGKINGNVVPDRASLIKVTNERENEKSVDD
MTKMPLLVYVSRERRFNRLHHFKGGSANALLRVSG
IMSNAPYVLVLDCDFFCHDPISARKAMCFHLDPKL
SSDLAYVQFPQVFYNVSKSDIYDVKIRQAYKTTWH
GMDGIQGPVLSGTGYFLKRKALYTSPGVKEAYLSS
PEKHFGRSKRFLASLEEKNGYVKADKVISEDIIEE
AKMLATCAYEDGTHWGQEIGYSYDCHLESTFTGYL
LHCKGWTSTYLYPDRPSFLGCAPVDMQGFSSQLIK
WVAALTQAGLSHLNPITYGESSRMRTEQCMCYAYL
MYFTLYSWGMVMYASVPSIGLLFDFQVYPEVHDPW
FAVYVIAFISTILENMSESIPEGGSVKTWWMEYRA
LMMMGVSAIWLGGLKAIYDKIVGTQGEKLYLSDKA

-continued

IDKEKLKKYEKGKFDFQGIGILALPLIAFSVLNLV

GFIVGANHVFITMNYAGVLGQLEVSSFFVVVTVVI

DWSFLKVS

Cellulose Synthase Like (*Solanum pennellii*)

[SEQ ID NO: 32]

ATGAAAAAAACCATGGAGCTCAACAAAAGCACTGTT

CCACAACCTATCACCACCGTATACCGACTCCACAT

GTTCATCCACTCAATAATCATGCTTGCATTAATAT

ACTACCGTGTATCTAATTTGTTTAAATTCGAAAAC

ATTCTGAGTTTAGAAGCACTTGCTTGGCTACTCAT

CACTTTTGGTGAATTTAGTTTCATTCTCAAGTGGT

TCTTCGGACAAGGAACTCGTTGGCGCCCCGTTGAA

CGAGATGTTTTCCCTGAAAACATTACTTGCAAAGA

TTCCGATCTACCGCCAATTGACGTAATGGTGTTCA

CTGCCAATCCTAAGAAAGAGCCAATTGTAGATGTC

ATGAACACTGTGATATCCGCAATGGCTCTTGATTA

TCCCACCGATAAATTGGCTGTGTATCTGGCCGATG

ATGGAGGATGTCCATTGTCCTTGTACGCCATGGAA

CAAGCATGTTTGTTTGCAAAGCTATGGTTACCTTT

CTGTAGAAAGTATGGAATTAAAACGAGATGCCCAA

AAGCATTTTTTTCTCCGTTAGGAGATGATGACCGT

GTTCTTAAGAATGATGATTTTGCTGCTGAAATGAA

AGAAATTAAATTGAAATATGAAGAGTTCCAGCAGA

ACGTGGAACATGCTGGTGAATCTGGAAAAATCAAT

GGCAACGTAGTGCCTGACAGAGCTTCGCTTATTAA

GGTAATAAACGAGAGGGAGAACGAAAAGAGTGTCG

ATGATTTAACGAAAATGCCCTTGCTAGTTTATGTA

TCCCGTGAAAGAAGATTCAACCGTCTTCATCATTT

CAAGGGTGGATCTGCAAATGCTCTACTTCGAGTTT

CTGGAATAATGAGTAATGCCCCCTATGTACTGGTG

TTAGATTGTGATTTCTTCTGTCATGATCCGATATC

AGCTAGGAAAGCAATGTGTTTTCATCTTGATCCAA

AGCTATCATCTGATTTAGCCTATGTTCAGTTCCCT

CAAGTCTTTTACAATGTCAGCAAGTCCGATATTTA

TGATGTCAAAATTAGACAGGCTTACAAGACAATAT

GGCATGGAATGGATGGTATGCAAGGCCCAGTGTTA

TCTGGAACTGGTTATTTTCTCAAGAGGAAGGCGTT

ATACACAAGTCCAGGAGTAAAAGAGGCGTATCTTA

GTTCACCGGAAAAGCATTTTGGAAGGAGTAAAAAG

TTCCTTGGTTCATTAGAGGAGAAAAATGGTTATGT

-continued

TAAGGCAGATAAAGTCATATCAGAAGATATCATAG

AGGAAGCTAAGATCTTAGCTACTTGTGCATATGAG

GATGGCACACATTGGGGTCAAGAGATTGGTTATTC

ATACGATTGTCATTTGGAGAGCACTTTTTACTGGT

TATCTATTACACTGCAAAGGGTGGACATCTACTTA

TTTGTATCCAGACAGGCCATCTTTCTTGGGTTGTG

CCCCAGTTGATATGCAAGGTTTCTCATCACAGCTC

ATAAAATGGGTTGCTGCACTTACACAAGCTGGTCT

ATCACATCTCAATCCCATCACTTATGGTTTGAGTA

GTAGGATGAGAACTCTCCAATGCATGTGCTATGCC

TATTTGATGTATTTCACTCTTTATTCTTGGGGAAT

GGTTATGTATGCTAGTGTTCCTTCTATTGGCCTTT

TGTTTGGCTTCCAAGTCTACCCTGAGGTACATGAT

CCATGGTTTGCAGTGTATGTGATTGCTTTCATATC

GACAATTTTGGAGAATATGTCGGAGTCAATTCCAG

AAGGGGGATCAGTTAAAACGTGGTGGATGGAATAC

AGGGCATTGATGATGATGGGAGTTAGCGCAATATG

GTTAGGAGGATTGAAAGCTATATATGACAAGATAG

TCGGAACACAAGGAGAGAAATTGTATTTGTCGGAC

AAGGCAATTGACAAGGAAAAGCTCAAGAAATACGA

GAAGGGCAAATTTGATTTCCAAGGAATAGGGATAC

TTGCTCTGCCATTGATAGCATTTTCCGTGTTGAAC

CTCGTAGGCTTCATTGTTGGAGCTAATCATGTCTT

TATTACTATGAACTACGCAGGCGTGCTGGGCCAAC

TCCTCGTATCATCATTCTTCGTCTTTGTTGTCGTC

ACTGTTGTCATTGATGTTGTATCTTTCTTAAAGGT

TTCTTAA

Cellulose Synthase Like (*Solanum pennellii*)

[SEQ ID NO: 33]

MKKTMELNKSTVPQPTTTVYRLHMFIHSIIMLALIY

YRVSNLFKFENILSLQALAWLLITFGEFSFILKWF

FGQGTRWRPVERDVFPENITCKDSDLPPIDVMVFT

ANPKKEPIVDVMNTVISAMALDYPTDKLAVYLADD

GGCPLSLYAMEQACLFAKLWLPFCRKYGSKTRCPK

AFFSPLGDDDRVLKNDDFAAEMKEIKLKYEEFQQN

VEHAGESGKINGNVVPDRASLIKVINERENEKSVD

DLTKMPLLVYVSRERRFNRLHHFKGGSANALLRVS

GIMSNAPYVLVLDCDFFCHDPISARKAMCFHLDPK

LSSDLAYVQFPQVFYNVSKSDIYDVKIRQAYKTIW

HGMDGIQGPVLSGTGYFLKRKALYTSPGVKEAYLS

-continued

SPEKHFGRSKKFLASLEEKNGYVKADKVISEDIIE

EAKILATCAYEDGTHWGQEIGYSYDCHLESTFTGY

LLHCKGWTSTYLYPDRPSFLGCAPVDMQGFSSQLI

KWVAALTQAGLSHLNPITYGLSSRMRTLQCMCYAY

LMYFTLYSWGMVMYASVPSIGLLFGFQVYPEVHDP

WFAVYVIAFISTILENMSESIPEGGSVKTWWMEYR

ALMMMGVSAIWLGGLKAIYDKIVGTQGEKLYLSDK

AIDKEKLKKYEKGKFDFQGIGILALPLIAFSVLNL

VGFIVGANHVFITMNYAGVLGQLLVSSFFVFVVVT

VVIDVVSFLKVS

Cellulose Synthase Like (Potato)

[SEQ ID NO: 34]

ATGAAAAAAACCATGGAGCTCAACAAAAGCACTGT

TCCACAACCTATCACCACCATATACCGACTCCACA

TGTTTATCCACTCTATAATCATGGTTGCATTAATA

TACTACCGTGTATCTAATTTGTTTAAATTCGAAAA

CATTCTGAGTTTACAAGCACTTGCTTGGGTACTCA

TCACTTTTGGTGAATTTAGTTTCATTCTCAAGTGG

TTCTTCGGACAAGGAACTCGTTATCGCCCTGTTGA

AAGAGATGTTTTCCCTGAAAACATAACTTGCAAAG

ATTCCGATCTACCACCAATTGACGTAATGGTATTC

ACTGCCAATCCTAAGAAAGAGCCAATTGTGGATGT

CATGAACACTGTGATATCCGCAATGGCTCTTGATT

ATCCTACGGATAAATTGGCTGTGTATCTGGCTGAT

GATGGAGGATGTCCTTTGTCATTGTACGCCATGGA

AGAAGCATGTGTGTTTGCAAAGCTGTGGCTACCTT

TCTGTAGGAAGTATGGAATTAAAACTAGATGCCCT

AAAGCGTTTTTTTCTCCTTTAGGAGATGATGAACG

TGTTCTTAAGAATGATGATTTTGATGCTGAAATGA

AAGAAATTAAATTGAAATATGAAGAGTTCCAGCAG

AATGTGGAACGTGCTGGTGAATCTGGAAAAAATCAA

TGGTAACGTAGTGCCTGATAGAGCCTCGTTTATTA

AGGTAATAAACGACAGAAAAGCGGAGAGCGAAAAG

AGTGCCGATGATTTAACGAAAATGCCCTTGCTAGT

TTATGTATCCCGTGAAAGAAGATTCAACCGTCTTC

ATCACTTCAAGGGTGGATCTGCAAATGCTCTTCTT

CGAGTTTCTGGAATAATGAGTAATGCCCCCTATAT

ACTGGTGTTAGATTGTGATTTCTTCTGTCATGATC

CAATATCAGCTAGGAAGGCAATGTGTTTTCATCTT

GATCCAAAGCTATCATCTGATTTAGCTTATGTTCA

-continued

GTTCCCTCAAGTCTTTTACAATGTCAGCAAGTCCG

ATATTTATGATGTGAAAATTAGACAGGCTTACAAG

ACAATATGGCATGGAATGGATGGTATCCAAGGCCC

AGTGTTATCAGGAACTGGTTATTTTCTCAAGAGGA

ACGCGTTATACACGAGTCCAGGAGTAAAGGAGGAG

TATCTTAGTTCACCGGAAAAGCATTTTGGAAGGAG

TAAAAAGTTCCTTGCTTCACTAGAGGAGAAAAATG

GTTATGTTAAGGCAGAGAAAGTCATATCAGAAGAT

ATCGTAGAGGAAGCTAAGACCTTAGCTACTTGTGC

ATATGAGGATGGCACACATTGGGGTCAAGAGATTG

GTTATTCATACGATTGTCATTTGGAGAGCACTTTT

ACTGGTTATCTATTACACTGCAAAGGGTGGAGATC

GACTTATTTGTATCCAGACAGGCCATCTTTCTTGG

GTTGTGCCCCAGTTGATATGCAAGGTTTCTCCTCA

CAGCTCATAAAATGGGTTGCTGCACTTACACAAGC

TGGTTTATCACATCTCAATCCCATCACTTATGGCT

TTAGTAGCAGGATGAAAACTCTCCAATGCATGTGC

TATGCCTATTTGATATATTTCACTCTTTATTCTTG

GGGAATGGTTCTATATGCTAGTGTTCCTTCTATTG

GCCTTTTGTTTGGCTTCCAAGTCTATCCCGATGTA

CATGATCCATGGTTTGCAGTGTATGTGATTGCTTT

CATATCGGCAATTTTGGAGAATATGTCGGAGTCAA

TTCCTGATGGGGGATCATTTAAATCTTGGTGGATG

GAATACAGGGCACTGATGATGATGGGAGTTAGTGC

AATATGGTTAGGAGGATTGAAAGCTATATTAGACA

GGATAATCGGAACAGAAGGAGAGAAATTGTATTTA

TCGGACAAGGCAATTGACAAGGAAAAGCTCAAGAA

ATACGAGAAGGGGAAATTTGATTTCCAAGGAATAG

GGATACTTGCTGTACCATTGATAGCATTTTCCTTG

TTGAACCTCGTAGGCTTCATTGTTGGAGCTAATCA

TGTCTTTATTACTATGAACTACGCAGGTGTGCTTG

GCCAACTCCTCGTATCATCCTTCTTCGTCTTTGTC

GTGGTCACTGTTGTCATTGATGTCGTTTCTTTCTT

AAAGGTTTCTTAA

Cellulose Synthase Like (Potato)

[SEQ ID NO: 35]

MELNKSTVPQPITTIYRLHMFIHSIIMVALIYYRVS

NLFKFENILSLQALAWVLITFGEFSFILKWFFGQG

TRYRPVERDVFPENITCKDSDLPPIDVMWTANPKK

EPIVDVMNTVISAMALDYPTDKLAVYLADDGGCPL

-continued

SLYAMEEACVFAKLWLPFCRKYGIKTRCPKAFFSP

LGDDERVLKNDDFDAEMKEIKLKYEEFQQNVERAG

ESGKINGNVVPDRASFIKVINDRKAESEKSADDLT

KMPLLVTVSRERRFNRLHHFKGGSANALLRVSGIM

SNAPYILVLDCDFFCHDPISARKAMCFHLDPKLSS

DLAYVQFPQWYNVSKSDIYDVKIRQAYKTIWHGMD

GIQGPVLSGTGYFLKRKALYTSPGVKEEYLSSPEK

HFGRSKKFLASLEEKNGYVKAEKVISEDIVEEAKT

LATCAYEDGTHWGQEIGYSYDCHLESTFTGYLLHC

KGWRSTYLYPDRPSFLGCAPVDMQGFSSQLIKWVA

ALTQAGLSHLNPITYGFSSRMKTLQCMCYAYLIYF

TLYSWGMVLYASVPSIGLLFGFQYTPDVHDPWFAV

YVTAFISAILENMSESIPDGGSFKSWWMEYRALMM

MGVSAIWLGGLKAILDRIIGTEGEKLYLSDKAIDK

EKLKKYEKGKFDFQGIGILAVPLIAFSLLNLVGFI

VGANHVFITMNYAGVLGQLLVSSFFVFVVVTVVID

VVSFLKVS

Cellulose Synthase Like (*Solanum chacoense*)

[SEQ ID NO: 36]

ATGAAAAAAACCATGGAGCTCAACAAAAGCACTGT

TCCACAACCTATCACCACCATATACCGACTCCACA

TGTTCGTCCATTCTATAATCATGGCTGCATTAATA

TACTACCGTGTATCTAATTTGTTTAAATTCGAAAA

CATTCTGAGTTTACAAGCACTTGCTTGGGTACTCA

TCACTTTTGGTGAATTTAGTTTCATTCTCAAGTGG

TTCTTCGGACAAGGAACTCGTTGGCGCCCTGTTGA

AAGAGATGTTTTCCCTGAAAACATAACTTGCAAAG

ATTCCGATCTACCACCAATTGACGTAATGGTATTC

ACTGCCAATCCTAAGAAAGAGCCAATTGTGGATGT

CATGAACACTGTGATATCCGCAATGGCTCTAGATT

ATCCTACGGATAAATTGGCTCTGTATCTGGCTGAT

GATGGAGGATGTCCTTTGTCATTGTACGCCATGGA

AGAAGCATGTGTGTTTGCAAAGCTGTGGCTACCTT

TCTGTAGGAAGTATGGAATTAAAACCAGATGCCCT

AAAGCGTTTTTTTCTCCTTTAGGAGATGATGACCG

TGTTCTTAAGAATGATGATTTTGATGCTGAAATGA

AAGAAATTAAATTGAAATATGAAGAGTTCCAGCAG

AATGTGGAACGTGCTGGTGAATCTGGAAAAAATCAA

TGGTAACGTAGTGCCTGATAGAGCCTCGTTTATTA

AGGTAATAAACGACAGAAAAACGGAGAGCGAAAAG

-continued

AGTGCCGATGATTTAACGAAAATGCCCTTGCTAGT

TTATGTATCCCGTGAAAGAAGATTCAACCGTCTTC

ATCACTTCAAGGGTGGATCTGCAAATGCTCTTCTT

CGAGTTTCTGGAATAATGAGTAATGCCCCCTATAT

ACTGGTGTTAGATTGTGATTTCTTCTGTCATGATC

CAATATCAGCTAGGAAGGCAATGTGTTTTCATCTT

GATCCAAAGCTATCATCTGATTTAGCTTATGTTCA

GTTCCCTCAAGTCTTTTACAATGTCAGCAAGTCCG

ATATTTATGATGTCAAAATTAGACAGGCTTACAAG

ACAATATGGCATGGAATGGATGGTATCCAAGGCCC

AGTGTTATCAGGAACTGGTTATTTTCTGAAGAGGA

AGGCGTTATACACGAGTCCAGGAGTAAAGGAGGAG

TATCTTAGTTCACCGGAAAAGCATTTTGGAAGGAG

TAAAAAGTTCCTTGCTTCACTAGAGGAGAAAAATG

GTTATGTTAAGGCAGAGAAAGTCATATCAGAAGAT

ATCGTAGAGGAAGCTAAGACCTTAGCTACTTGTGC

ATATGAGGATGGTACACATTGGGGTCAAGAGATCG

GTTATTCATACGATTGTCATTTGGAGAGCACTTTT

ACTGGTTATCTATTACACTGCAAAGGGTGGACATC

GACTTATTTGTATCCAGACAGGCCATCTTTCTTGG

GTTGTGCTCCAGTTGATATGCAAGGTTTCTCCTCA

CAGCTCATAAAATGGGTTGCTGCACTTACACAAGC

TGGTTTATCACATCTCAATCCCATCACTTATGGCT

TGAGTAGCAGGATGAAAACTCTCCAATGCATGTGC

TATGCCTATTTGATATATTTCACTCTTTATTCTTG

GGGAATGGTTCTATATGCTAGTATTCCTTCTATTG

GTCTTTTGTTTGGCTTCCAAGTCTATCCGGAGGTA

CATGATCCATGGTTTGCAGTGTATGTGATTGCTTT

CATATCGACAATTTTGGAGAATATGTCGGAGTCAA

TTCCAGAAGGGGGATCATTTAAATCGTGGTGGATG

GAATACAGGGCACTGATGATGATGGGAGTTAGTGC

AATATGGTTAGGAGGATTGAAAGCTATATTAGACA

AGATAATCGGAACAGAAGGAGAGAAATTGTATTTG

TCAGACAAGGCAATTGACAAGGAAAAGCTCAAGAA

ATACGAGAAGGGGAAATTTGATTTGCAAGGAATAG

GGATACTTGCTGTACCATTGATAGCATTTTCCCTG

TTGAACCTGGTAGGCTTCATTGTTGGAGCTAATCA

TGTCTTTATTACTATGAACTACGCAGGTGTGCTTG

GCCAACTCCTCGTATCATCCTTCTTCGTCTTTGTC

GTGGTCACTGTTGTCATTGATGTCGTTTCTTTCTT

AAAGGTTTCTTAA

Cellulose Synthase Like (*Solanum chacoense*)

[SEQ ID NO: 37]
MKKTMELNKSTVPQPITTIYRLHMFVHSIIMAALIYYRVSNLFKFENILS LQALAWVLITFGEFSFILKWFFGQGTRWRPVERDWFPENITCKDSDLPPI DVMVFTANPKKEPIVDVMNTVISAMALDYPTDKLAVYLADDGGCPLSLYA MEEACVFAKLWLPFCRKYGIKTRCPKAFFSPLGDDDRVLKNDDFDAEMKE IKLKYEEFQQNVERAGESGKINGNVVPDRASFIKVINDRKTESEKSADDL TKMPLLVYVSRERRFNRLHHFKGGSANALLRVSGIMSNAPYILVLDCDFF CHDPISARKAMCFHLDPKLSSDLAYVQFPQVFYNVSKSDIYDVKIRQAYK TIWHGMDGIQGPVLSGTGYFLKRKALYTSPGVKEEYLSSPEKHFGRSKKF LASLEEKNGYVKAEKVISEDIVEEAKTLATCAYEDGTHWGQEIGYSYDCH LESTFTGYLLHCKGWTSTYLYPDRPSFLGCAPVDMQGFSSQLIKWVAALT QAGLSHLNPITYGLSSRMKTLQCMCYAYLIYFTLYSWGMVLYASIPSIGL LFGFQVYPEVHDPWFAVYVIAFISTILENMSESIPEGGSFKSWWMEYRAL MMMGVSAIWLGGLKAILDKIIGTEGEKLYLSDKAIDKEKLKKYEKGKFDF QGIGILAVPLIAFSLLNLVGFIVGANHVFITMNYAGVLGQLLVSSFFVFV VVTVVIDVVSFLKVS

Cellulose Synthase Like (Eggplant)

[SEQ ID NO: 38]
ATGAAAAAACAAATGGAGCTCAACAGAAGTGTTGTACCGCAACCTATCAC CACCATTTACCGTCTCCACATGTTTATCCATGCCCTAATCATGCTAGCAC TAATATACTACCGTGTCTCTAATTTGGCCAAATTCGAAAACATCCTCAGT TTACAAGCACTTGCTTGGGCTCTTATCACGTTAGGTGAACTTTGTTTCAT AGTCAAGTGGTTCTTCGGACAAGGGACTCGTTGGCGTCCTGTTGATAGGG ATGTCTTCCCTGAAAACATCACTTGTCCAGATTCCGAGCTACCCCCCATT GATGTCATGGTTTTCACTGCAAATCCTAAGAAAGAGCCAATTGTGGATGT CATGAACACTGTCATATCCGCAATGGCTCTTGATTACCCGACCGACAAAT TGGCCGTTTATTTGTCTGATGATGGAGGATGCCCCTTGACGTTGTACGCA ATGGAGGAAGCTTGTTCCTTTGCCAAGTTGTGGCTACCTTTTTGTAGGAA GTATGGAATCAAAACAAGGTGCCCTAAGGCGTTTTTTTCTCCATTAGGAG AAGATGACCGTGTATTGAAGAGTGATGACTTTGTTTCTGAAATGAAAGAA ATGAAGTCAAAATATGAAGAGTTCCAGCAGAACGTGGACCGTGCTGGTGA ATCCGGAAAAAATCAAAGGTGACGTAGTGCCTGATAGACCCGCGTTTCTTA AGGTACTAAATGACAGGAAGACGGAGAACGAGAAGAGTGCAGACGATTTA ACTAAAATGCCTTTGCTAGTATACGTATCCCGTGAAAGAAGAACTCACCG TCGCCATCACTTCAAGGGTGGATCTGCAAATGCTCTTCTTCGAGTTTCTG GGATAATCAGTAATGCCCCCTATATACTGGTTTTAGATTGTGATTTCTTC TGTCATGATCCAATATCAGCTCGGAAGGCAATGTGTTTCCATCTTGATCC AAAACTATCACCTGACTTAGCTTACGTGCAGTTCCCTCAAGTGTTTTACA ATGTTAGCAAGTCCGATATTTACGACGTCAAAATTAGACAGGCTTACAAG ACAATATGGCACGGGATGGATGGTATCCAAGGCCCAGTGTTATCGGGAAC

-continued

TGGTTATTTTTTAAAAAAGAAGGCGTTGTACACGAGTCCAGGTCTAAAAG ATGAGTATCTTAGTTCACCGGAAAAGCATTTCGGAACGAGTAGAAAGTTC ATTGCTTCACTAGAGGAGAATAATTATGTTAAGCAAGAGAAAGTCATATC AGAAGATATCATAGAGGAAGCTAAGAGACTGGCTACTTGTGCATACGAGG ATGGCACACATTGGGGTCAAGAGGCAAACAGGCCATCTTTCTTGGGTTGT GCCCCAGTTGATATGCAAGGTTTCTCCTCACAGCTCATAAAATGGGTTGC TGCACTCACACAAGCAGGTCTATCACATCTCAATCCCATCACTTACGGCT TCAAGAGCAGAATGAGAACTCTCCAAGTCTTGTGTTATGCCTATTTGATG TATTTCTCTCTTTATTCTTGGGGAATGGTTCTACATGCTAGTGTTCCTTC TATTGGCCTTCTCTCTGGCATTAAAATCTACCCGGAGGTGTATGATCCAT GGTTTGTTGTGTATGTGATTGCTTTCATATCAACAATTTTGGAGAATATG TCGGAATCAATTCCGGAAGGGGGATCGGTTAAAACGTGGTGGATGGAATA CAGGGCACTGATGATGATGGGAGTTAGTGCAATATGGCTAGGAGGAGTGA AAGCCATAGTAGACAAGATCATCGGAACGCAAGGAGAGAAATTGTATTTG TCGGACAAAGCAATTGACAAGGAAAAGCTCAAGAAATACGAGAAGGGGAA ATTTGATTTCCAAGGAATAGGAATACTTGCTGTACCATTGATAACATTTT CTGTGTTGAACCTGGTAGGCTTCTTGGTTGGAATTAATCAAGTGTTGATA ACGATGAAGTTCGCAGGCGTGCTGGGCCAACTCCTCGTATCATCCTTCTT CGTCTTTGTCGTCGTTACTGTTGTCATTGATGTCGTATCTTTCTTAAAGG ATTCTTAA

Cellulose Synthase Like (Eggplant)

[SEQ ID NO: 39]
MKKQMELNRSVVPQPITTIYRLHMFIHALIMLALIYYRVSNLAKFENILS LQALAWALITLGELCFIVKWFFGQGTRWRPVDRDVFPENITCPDSELPPI DVMVFTANPKKEPIVDVMNTVISAMALDYPTDKLAVYLSDDGGCPLTLYA MEEACSFAKLWLPFCRKYGIKTRCPKAFFSPLGEDDRVLKSDDFVSEMKE MKSKYEEFQQNVDRAGESGKIKGDVVPDRPAFLKVLNDRKTENEKSADDL TKMPLLVYVSRERRTHRRHHFKGGSANALLRVSGIISNAPYILVLDCDFF CHDPISARKAMCFHLDPKLSPDLAYVQFPQVFYNVSKSDIYDVKIRQAYK TIWHGMDGIQGPVLSGTGYFLKKKALYTSPGLKDEYLSSPEKHFGTSRKF IASLEENNYVKQEKVISEDIIEEAKRLATCAYEDGTHWGQEANRPSFLGC APVDMQGFSSQLIKWVAALTQAGLSHLNPITYGFKSRMRTLQVLCYAYLM YFSLYSWGMVLHASVPSIGLLSGIKIYPEVYDPWFVVYVIAFISTILENM SESIPEGGSVKTWWMEYRALMMMGVSAIWLGGVKAIVDKIIGTQGEKLYL SDKAIDKEKLKKYEKGKFDFQGIGILAVPLITFSVLNLVGFLVGINQVLI TMKFAGVLGQLLVSSFFVFVVVTVVIDVVSFLKDS

Cellulose Synthase Like (*Capsicum annuum*)

[SEQ ID NO: 40]
ATGGAGCTCAACAGATGTACGGTGCAGCAACCTACCACTGCCATATACCG ACTACACATGTTTCTCCACTCTCTAATCATGCTTGCATTAGTATACTATC

-continued

GTTTGTCTAATCTGTTTTACTTCGAAAACGTCCTCACTTTACAAGCATTT

GCATGGGGGCTTATCACCTTAGGTGAAATTTGTTTCATTGTCAAGTGGTT

CTTTGGTCAAGGGACTCGTTGGCGCCCCGTTGTCAGGGAAGTGTTCCTGG

ACAATATTACTTGCCAAGQTTCCTAGCTGCCCGCACTAGATGTGATGGTT

TTCACTGCCAATCCCAAGAAAGAGCCAATTGTGGATGTCATGAACACTGT

GATATCCGCAATGGCTCTTGATTACCCGACTGATAAATTGGCTGTGTATC

TGGCTGATGATGGAGGATGCCCCTTGACGTTGTACGCCATGGAGGAGGCC

TGTTCTTTTGCCAAGTTGTGGCTACCTTTCTGTAGGAAGTATGGAATCAA

AACAAGGTGCCCCAAAGCGTTTTTTTCTCCATTAGGAGAAGATGATCGTA

TCCTTAAGAACGATGACTTTGTAGCTGAAATGAAAGAAATTAAATTAAAA

TATGAGGAGTTCCAGCAGAATGTAAACCTTGCTGGTGAATCCGGAAAAAT

CAAAGGTGACGTAGTGCCTGATAGAGCCTCGTTTATTAAGGTAATAAATG

ACAGGAAAATGGAGAACAAGAAGAGTGCCGACGATATAACGAAAATGCCT

TTGCTAGTATACGTATCCCGTGAAAGAAGATTTAACAGTCGTCATCACTT

CAAGGGTGGATCTGCAAATGCTCTTCTTCGAGTTTCAGGGATAATGAGTA

ATGCCCCCTATTTACTGGTCTTAGATTGTGATTTCTTCTGTCATGATCCA

ACATCAGCTCGGAAGGCAATGTGTTTCCATCTTGATCCAAAACTATCACC

TTCCTTAGCTTATGTGCAGTTCCCTCAAGTGTTTTACAATGTCAGCAAGT

CCGATATATACGATGTCAAAATTAGACAGGCTTACAAGACAATATGGCAC

GGAATGGATGGTATCCAAGGCCCAGTGTTATCGGGAACTGGGTATTTTCT

GAAGAGGAAAGCGTTATACACGAGTCCAGGTCTAAAGGATGAGTATCTTA

TTTCACCGGAAAAGCATTTCGGATCAAGTAGAAAGTTCATTGCTTCTCTA

GAGGAGAACAATGGTTATGTTAAGCAAGAGAAACTCATAACAGAAGATAT

TATAGAGGAAGCGAAGACCTTGTCTACTTGTGCATACGAGGATGGTACAC

GATGGGGCGAAGAGATCGGTTATACCTACAATTGCCATTTGGAGAGCACT

TTTACCGGCTATCTTTTGCACTGCAAAGGGTGGACATCAACATATTTGTA

TCCAGAAAGGCCATCTTTCTTGGGTTGTGCCCCAGTTGATATGCAAGGAT

TCTCCTCACAACTCACAAAATGGGTTGCTGCACTCACACAAGCTGGTCTA

TCACATCTCAATCCCATCACTTACGGCATGAAGAGCAGGATTAAGACTAT

CCAATGCTTGTGCTATGCCTATTTGATGTATTTCTCTCTCTATTCTTGGG

GAATGGTTCTGCATGCTAGTGTTCCTTCTATTAGCCTTTTGCTTGGCATT

CAAGTCTACCCCGAGGTCTATGATCCATGGTTTGCAGTGTATGTGCTTGC

TTTCATATCGACAATTTTGGAGAACATGTCAGAGTCAATTCCAGAAGGCG

GTTCAGTTAAAACTTGGTGGATGGAATACAGGGCACTGATGATGATGGGA

GTTAGTGCAATATGGTTAGGAGGAGTGAAAGCTATAGTAGAAAAGATCAT

CGGAACTCAAGGAGAGAAATTATATTTGTCGGACAAAGCAATTGACAAGG

AAAAGCTCAAGAAATATGAGAAGGGGAAATTTGATTTCCAAGGGATAGGG

ATACTTGCTGTTCCATTGATAACATTCTCAGCGTTGAATTTGGTAGGCTT

CATGGTTGGAGCTAATCAAGTGATTCTTACTATGAAGTTCGAAGCTTTGC

-continued

TAGGCCAACTCCTTGTGTCATCCTTCTTCGTCTTTGTGGTGGTCACCGTT

GTCATAGATGTCCTATCTTTCTTAAAAGACTCTTAA

Cellulose Synthase Like (*Capsicum annuum*)

[SEQ ID NO: 41]

MELNRCTVQQPTTAIYRLHMFLHSLIMLALVYYRLSNLFYFENVLTLQAF

AWGLITLGEICFIVKWFFGQGTRWRPVVREVFLDNITCQDSELPALDVMV

FTANPKKEPIVDVMNTVISAMALDYPTDKLAVYLADDGGCPLTLYAMEEA

CSFAKLWLPFCRKYGIKTRCPKAFFSPLGEDDRILKNDDFVAEMKEIKLK

YEEFQQNVNLAGESGKIKGDVVPDRASFIKVINDRKMENKKSADDITKMP

LLVYVSRERRFNSRHHFKGGSANALLRVSGIMSNAPYLLVLDCDFFCHDP

TSARKAMCFHLDPKLSPSLAYVQFPQVFYNVSKSDIYDVKIRQAYKTIWH

GMDGIQGPVLSGTGYFLKRKALYTSPGLKDEYLISPEKHFGSSRKFIASL

EENNGYVKQEKLITEDIIEEAKTLSTCAYEDGTRWGEEIGYTYNCHLEST

FTGYLLHCKGWTSTYLYPERPSFLGCAPVDMQGFSSQLTKWVAALTQAGL

SHLNPITYGMKSRIKTIQCLCYAYLMYFSLYSWGMVLHASVPSISLLLGI

QVYPEVYDPWFAVYVLAFISTILENMSESIPEGGSVKTWWMEYRALMMMG

VSAIWLGGVKAIVEKIIGTQGEKLYLSDKAIDKEKLKKYEKGKFDFQGIG

ILAVPLITFSALNLVGFMVGANQVILTMKFEALLGQLLVSSFFVFVVVTV

VIDVLSFLKDS

The following sequences were generated for silencing GAME15 in their respective plants:

Region Used for GAME15 Silencing in Tomato

[SEQ ID NO: 42]

GGCTCTTGATTATCCCACCGATAAATTGGCTGTGTATCTCGCTGATGATG

GAGGATGTCCATTGTCGTTGTACGCCATGGAACAAGCGTGTTTGTTTGCA

AAGCTATGGTTACCTTTCTGTAGAAACTATGGAATTAAAACGAGATGCCC

AAAAGCATTTTTTTCTCCGTTAGGAGATGATGACCGTGTTCTTAAGAATG

ATGATTTTGCTGCTGAAATGAAAGAAATTAAATTGAAATATGAAGAGTTC

CAGCAGAAGGTGGAACATGC

Region Used for GAME15 Silencing in Potato

[SEQ ID NO: 43]

GGCTCTTGATTATCCTACGGATAAATTGGCTGTGTATCTGGCTGATGATG

GAGGATGTCCTTTGTCATTGTACGCCATGGAAGAAGCATGTGTGTTTGCA

AAGCTGTGGCTACCTTTCTGTAGGAAGTATGGAATTAAAACTAGATGCCC

TAAAGCGTTTTTTTCTCCTTTAGGAGATGATGAACGTGTTCTTAAGAATG

ATGATTTTGATGCTGAAATGAAAGAAATTAAATTGAAATATGAAGAGTTC

CAGCAGAATGTGGAACGTGCTGGTG

Region Used for GAME15 Silencing in Eggplant

[SEQ ID NO: 44]

```
GGCTCTTGATTACCCGACCGACAAATTGGCCGTTTATTTGTCTGATGATG

GAGGATGCCCCTTGACGTTGTACGCAATGGAGGAAGCTTGTTCCTTTGCC

AAGTTGTGGCTACCTTTTTGTAGGAAGTATGGAATCAAAACAAGGTGCCC

TAAGGCGTTTTTTTCTCCATTAGGAGAAGATGACCGTGTATTGAAGAGTG

ATGACTTTGTTTCTGAAATGAAAGAAATGAAGTCAAAATATGAAGAGTTC

CAGCAGAACGTGGACCGTGCTGGTGAATCCGGAAAAATCAAAGGTGACGT

AGTGCCTGATAGACCCGCGTTTCTTAAGGTACTAAATGACAGGAAGACGG

AGAACGAGAAGAGTGCAGACGATTTAACTAAAATGCCTTTGCTAGTATAC

GTATCCCGTGAAAGAAGAACTCACCGTCGCCATCACTTCAAGGGTGG
```

RNAi lines for the GAME15 gene in tomato and potato were generated. GAME15-RNAi transgenic tomato plants showed severe reduction in α-tomatine and downstream SGAs in leaves; α-tomatine was not detected in GAME15-silenced green fruit. Furthermore, no esculeosides or other SGAs were detected during tomato fruit developmental stages (e.g., breaker and red fruit). In addition, a 15-20 fold increase in cholesterol, which is a precursor for SGAs was observed in leaves and green fruit of GAME15-RNAi tomato plants. In potato, silencing of GAME15 resulted in a major reduction in α-chaconine and α-solanine, while the cholesterol pool in these lines increased.

Example 7: Generation of GAME15-RNAi Transgenic Tomato Potato and Eggplant Plants The GAME15-RNAi construct was generated by introducing a selected fragment (silencing sequences SEQ ID NO: 42 (tomato), SEQ ID NO: 43 (potato), and SEQ ID NO: 44 (eggplant)) to pENTR/D-TOPO (Invitrogen) (by NotI and AscI) and further subcloning of this fragment to the pK7GWIWG2 (II) binary vector using the Gateway LR Clonase II enzyme mix (Invitrogen). The vector was transformed into tomato, potato and eggplant as described previously (Itkin et al. 2011. The Plant Cell 23:4507-25; Sonawane et al. 2018. PNAS 115(23): E5418-E5428). Positive GAME25-downregulated lines were further used for LC-MS analysis.

Example 8: GAME15-Silenced Tomato Plants Showed Severely Reduced SGA Profile In order to determine the precise role of GAME15 in SGA metabolism, GAME15-RNAi (GAME15i) transgenic tomato lines (#21, #22 and #23) were generated using the tomato silencing sequence above (SEQ ID NO: 42).

Figure 15A:
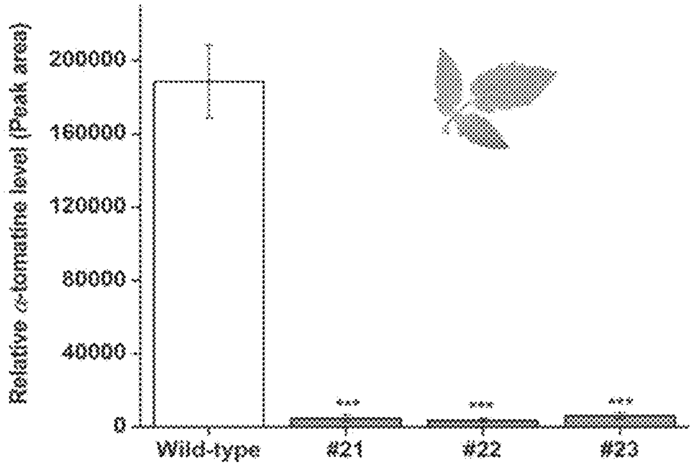
FIGS. 15A-15C show major SGA levels in (A) leaves and (B) green fruit and (C) red fruit of wild type (non-transformed) and GAME15-RNAi tomato lines determined by LC-MS. #21, #22 and #23 are three independent GAME15-RNAi transgenic tomato lines. Values indicate means of three biological replicates±standard error. Asterisks indicate significant changes from wild-type samples as calculated by a Student's t-test (*P-value<0.05; P-value<0.01; *P-value<0.001).

GAME15-RNAi leaves showed severe reduction in α-tomatine, compared with wild-type tomato leaves (FIG. 15A). Furthermore, the SGAs profile of GAME15i fruit was subsequently compared to wild-type ones at different stages of development and ripening. During the transition from green to red fruit in tomato, α-tomatine is converted to esculeosides and lycoperosides, while dehydrotomatine is converted to dehydroesculeosides and dehydrolycoperosides (FIG. 14A).

Figure 15B:
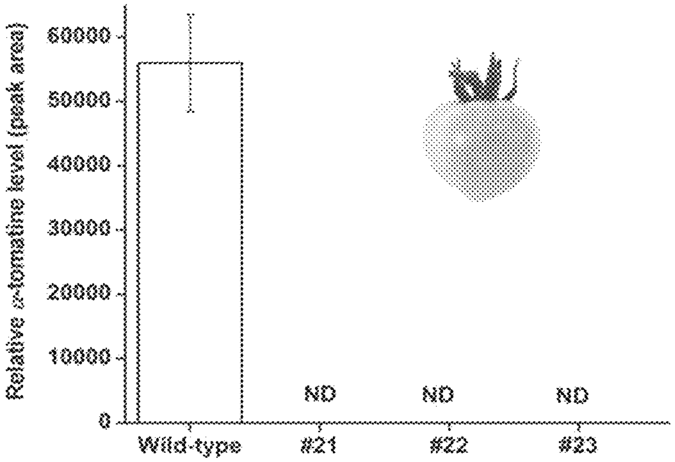
Figure 15C:
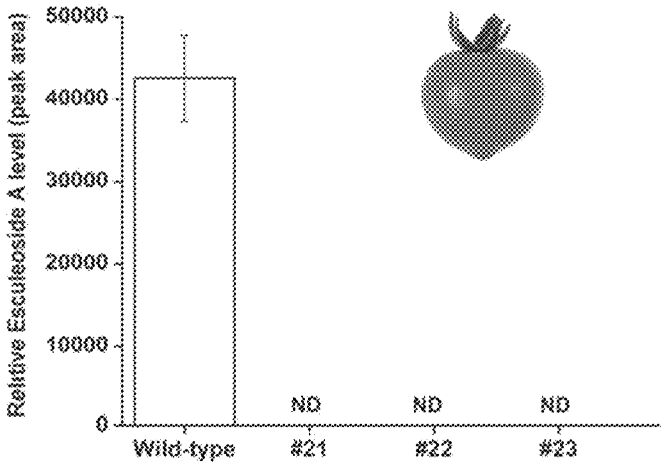

GAME15i green and red fruits did not show any trace of SGAs (e.g., α-tomatine or Esculeoside A) suggesting complete loss of SGAs in tomato fruits due to GAME15i silencing (FIGS. 15B and 15C).

Example 9: Altering GAME15 Expression has Major Impact on SGAs in Potato

Similar to tomato, GAME15i was also silenced in potato (#1, #2, and #3) to determine its effect on potato SGAs metabolism, using the potato silencing sequence above (SEQ ID NO: 43).

Figure 16:
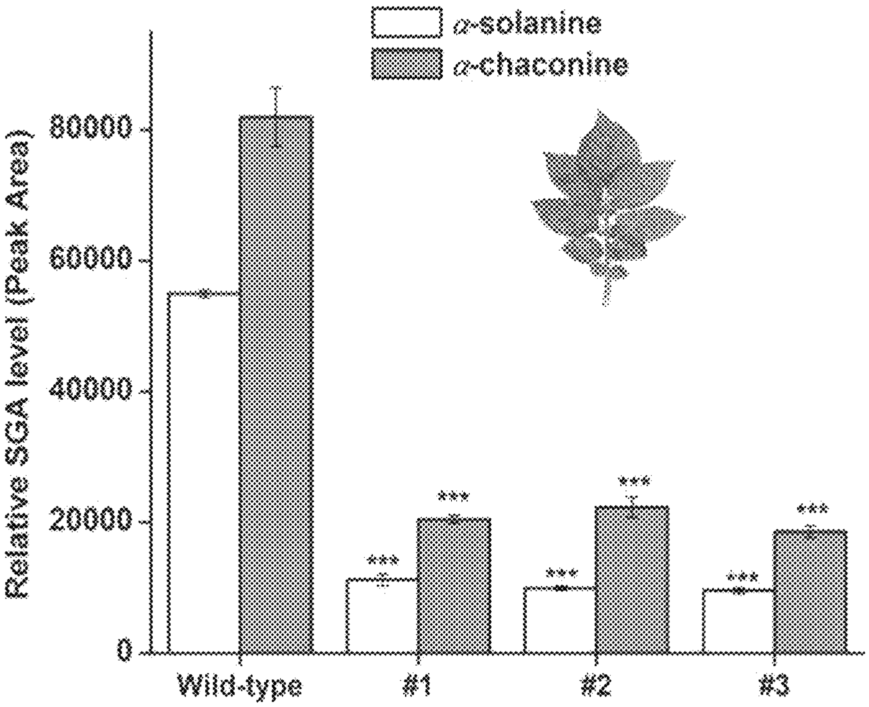
FIG. 16 shows levels of α-solanine and α-chaconine in leaves of GAME15-RNAi lines as determined by LC-MS. #1, #2 and #3 are three independent GAME15i transgenic potato lines. Values represent mean±standard error (n=3). Student's 1-test was used to assess whether the transgenic lines significantly differ from wild-type plants: (*P-value<0.05; P-value<0.01; *P-value<0.001).

Silencing of GAME15 in potato resulted in drastic reduction in α-chaconine (shaded bars) and α-solanine (open bars), major SGAs in potato leaf tissue (FIG. 16), in comparison with potato leaf tissue of the wild-type.

Example 10: High Cholesterol Accumulation in GAME15-Silenced Tomato Leaves

Figure 17:
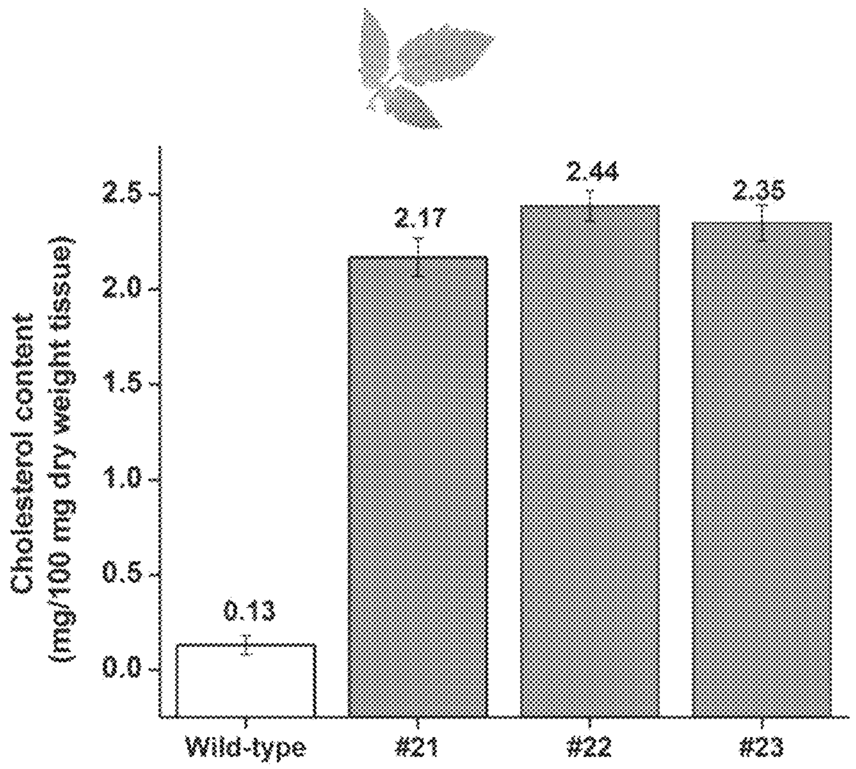
FIG. 17 shows the cholesterol content of tomato leaves derived from GAME/5 silenced plants. Values represent mean of three biological replicates±standard error. Asterisks indicate significant changes in leaves of the three independent transgenes (#21, #22 and #23) as compared to wild-type leaves (i.e. non-transformed) calculated by a Student's t-test (*P-value<0.05; P-value<0.01; *P-value<0.001). Epicholesterol was used as an internal standard in sample preparations and relative cholesterol level is expressed as ratios of cholesterol peak areas in sample compared to internal standard. The analysis was performed using GC-MS.

Cholesterol serves as a key precursor in the biosynthesis of SGAs (Sonawane et al., 2016, Nat. Plants 3: 16205). As severe reduction and subsequent complete loss of SGAs was observed in GAME15i-silenced tomato plants, the cholesterol levels in these plants were examined. An ~15-20-fold increase in cholesterol (SGA precursor) was observed in leaves of GAME15i-silenced tomato plants compared to the leaves of wild-type tomato plants (FIG. 17).

Example 11: Altering GAME15 Expression and Observing its Impact on SGAs in Eggplant Similar to potato, GAME15i is also silenced in eggplant to determine its effect on potato SGAs metabolism, using the eggplant silencing sequence above (SEQ ID NO: 44).

The effect of silencing of GAME15 in eggplant is observed with respect to reduced levels of α-solasonine and/or α-solamargine in comparison with wild-type eggplant (FIG. 14C).

Example 12: Overexpression of GAME15 in Tomato, Potato, and Eggplant

Alternatively, tomato, potato, and/or eggplant plants are genetically modified, or gene edited to overexpress GAME15.

To increase production of α-tomatine and esculeosides and/or lycoperosides in tomato plants (FIG. 14A), tomato plants are genetically modified, or gene edited to overexpress GAME15.

To increase production of α-solanine and/or α-chaconine in potato plants (FIG. 14B), potato plants are genetically modified, or gene edited to overexpress GAME15.

To increase production of α-solasonine and/or α-solamargine in eggplant (FIG. 14C), eggplant plants are genetically modified, or gene edited to overexpress GAME15.

Example 13: Plants and Crops with Modified Levels and Compositions of SGAs

Based on the foregoing, Solanaceous plants (e.g., tomato, potato, eggplant, and/or pepper plants) and/or crops are prepared, such as through classical breeding or genetic engineering (e.g., genetically modified or transgenic plants, gene edited plants, and the like), with modified levels and compositions of SGAs, conferring on the plant a chemical barrier against a broad range of insects and other pathogens and/or removing anti-nutritional compounds (e.g., chaconine and/or solanine from potato).

Furthermore, high cholesterol or high phytosterol tomato lines are used to engineer high value steroidal compounds (e.g., pro-vitamin D and/or diosgenin), such as through synthetic biology tools.

In addition, high phytosterol (e.g., phytocholesterol) lines are used to produce components used in cosmetic products.

In other instances, Solanaceous plants (e.g., tomato, potato, eggplant, and/or pepper plants) and/or crops are prepared with increased levels of SGAs and/or decreased levels of phytosterols.

Example 14—Materials and Methods for Examples 14-25

Liquid Chromatography-Mass Spectroscopy (LC-MS) and Tandem Mass Spectroscopy (MS/MS) Parameters for Saponin Analysis Four biological replicates (n=4) from sample were used for metabolic analysis. Briefly, 100 mg of frozen powdered plant tissue was extracted with 300 μL of 80% methanol mixed with internal standard (Ponasterone A, C=1.5 μg/mL), briefly vortexed and then sonicated for 20 min. at room temperature. Extracts were centrifuged for 10 min. at 14,000×g and filtered through 0.22 μm filters. Samples were analyzed using a high-resolution UPLC/qTOF system comprised of a UPLC (Waters Acquity) connected to a SYNAPT-G2 qTOF detector (tandem quadrupole/time-of-flight mass spectrometer, Waters). Separation of metabolites was performed on a 100×2.1 mm i.d., 1.7 μm UPLC BEH C18 column (Waters Acquity). The mobile phase consisted of 0.1% formic acid in acetonitrile:water (5:95, v/v; phase A) and 0.1% formic acid in acetonitrile (phase B). The flow rate was 0.3 mL/min, and the column temperature was kept at 35° C.

The following linear gradient was used for analysis of triterpenoid saponins in spinach, *Beta vulgaris*, triterpenoids produced in yeast cells and in vitro with use of SOAP10: from 100/6 to 85% phase A over 5 min., from 85% to 75% phase A over 2 min., then held at 75% phase A for 3 min.; gradient continued to 65% A over 10 min., from 65% to 40% A over 2 min.; from 40% phase A to 100% phase B over 1 min., then held at 100% phase B 3.5 minutes and then returned to the initial conditions (100% phase A) within 0.5 min. and conditioning at 100% phase A for 1 min.

To analyze triterpenoid saponins from *Chenopodium quinoa* and *Medicago sativa* 40 min. gradient was used: from 100% to 72% phase A over 22 min., from 72% to 0% phase A over 14 min., then held at 100% phase B for 2 min.; and then returned to the initial conditions (100% phase A) within 0.5 min. and conditioning at 100% phase A for 1.5 min.

The following settings were used: capillary 2 kV; cone 27 V; source temperature was set to 140° C., desolvation 450° C., desolvation gas flow 800 L/h. Argon was used as the collision gas. Electrospray ionization (ESI) was used in negative ionization mode at the m/z range of 50-1600 Da. The mass spectroscopy (MS) system was calibrated using sodium formate, and Leu-enkephalin was used as the lock mass. MassLynx software version 4.1 (Waters) was used to control the instrument and calculate accurate masses and elemental compositions. In addition, a mixture of 15 standard metabolites, injected after each of the 10 samples, was used as quality controls. Data acquisition was performed in the $MS^E$ mode with energy ramp that records an exact mass precursor and fragment ion information from every detectable component in a sample. $MS^E$ mode rapidly alternates between two functions; the first acquiring low-energy exact mass precursor ion spectra and the second acquiring elevated energy exact mass fragment ion spectra. The collision energy for low-energy function was set to 4 eV, and for the high-energy to 15-50 eV ramp.

For separation of the products of the *Glycyrrhiza uralensis* enzymes in *N. benthamiana* another gradient was used: starting at 75% phase A for 5 min., then from 75% to 50% phase A over 15 min., from 50% to 30% phase A over 2 min., from 30% phase A to 100% phase B, then held at 100% phase B for 3.5 min. and then returned to the initial conditions (75% phase A) within 0.5 min. and conditioning at 75% phase A for 1 min. The flow rate was 0.3 mL/min., and the column temperature was kept at 35° C. Samples were analyzed using a high-resolution UPLC/qTOF system comprised of a UPLC (1290 Infinity II, Agilent) connected to an Impact HD UHR-QqTOF (Bruker). Separation of metabolites was performed on a 100×2.1 mm i.d., 1.7 μm UPLC BEH C18 column (Waters Acquity). The mobile phase consisted of 0.1% formic acid in acetonitrile:water (5:95, v/v; phase A) and 0.1% formic acid in acetonitrile (phase B). ESI was used in negative ionization mode at the m/z range of 50-1700 Da with following parameters: drying gas: 200° C., 8 L/min; nebulizer: 2 Bar; capillary: 4.2 kV.

Metabolites were identified by comparing the retention times and mass fragments of standard compounds. When corresponding standards were not available, compounds were putatively identified by comparing their retention times, elemental composition and fragmentation pattern with those described in the literature (Table 14). Relative quantification of triterpenoid saponins in spinach was carried out using the TargetLynx (Waters) program. Peak area of saponins in each sample was normalized to peak area of internal standard in order to reduce variability originating from sample handling.

Gas Chromatograph-Mass Spectroscopy (GC-MS) Analysis of Spinach Triterpenoid Aglycones Powdered frozen tissue (200 mg) was extracted 3 times with 600 μL of 80% MeOH. Collected fractions were evaporated in speed-vac (25° C., 78 mbar, O/N). Dry residue was dissolved in 500 μL of 2M HCl in 50% MeOH and heated for 5 hours at 65° C. Hydrolyzed samples were evaporated to dryness in the speed-vac (50° C., 78 mbar, 1.5 h). Dry residue was dissolved in 200 μL of Toluene:MeOH (3:2; v/v) and 75 μL of trimethylsilyldiazomethane ($TMSCHN_2$) were added. Methylation mixture was incubated at room temperature for 40 minutes, evaporated to dryness and resuspended in 80 μL of MSTFA, incubated for 20 min. at room temperature and 10 minutes at 65° C. Sample was transferred to the glass insert and 1 μL was injected onto GC-MS as described before (31). The GC-MS system comprised a COMBI PAL autosampler (CTC Analytics), a trace GC ultra-gas chromatograph equipped with a programmable temperature vaporizing (PTV) injector, and a DSQ quadrupole mass spectrometer (Thermo Electron). GC was performed on a 30 m×0.25 mm×0.25 μm Zebron ZB-5 ms MS column (Phenomenex). The PTV split technique was performed as follows: Samples were analyzed in the constant temperature splitless mode. PTV inlet temperature was set at 280° C. Analytes were separated using the following chromatographic conditions: Helium was used as carrier gas at a flow rate of 1.2 mL/min. The thermal gradient started at 170° C., was held at this temperature for 1.5 min, ramped to 280° C. at 37° C./min. and then ramped to 300° C. at 1.5° C./min. and held at 300° C. for 5.0 min. Eluents were fragmented in the electron impact mode with an ionization voltage of 70 eV. The reconstructed ion chromatograms and mass spectra were evaluated using Xcalibur software (ThermoFinnigan). Compounds were identified by comparison of their retention index and mass spectrum to those generated for authentic standards analyzed on the same instrument and those reported in literature (E. Biazzi el al., CYP72A67 Catalyzes a Key Oxidative Step in *Medicago truncatula* Hemolytic Saponin Biosynthesis. *Molecular Plant.* 8, 1493-1506 (2015)).

Saponin Purification for NMR Analysis

The system consisted of an Agilent 1290 Infinity II UPLC system equipped with a quaternary pump, auto sampler, diode array detector, a Bruker/Spark Prospekt II LC-SPE system (Spark) and Impact HD UHR-QqTOF mass spectrometer (Bruker) connected via a Bruker NMR MS Interface (BNMI-HP) as described previously (B. Khakimov, L. H. Tseng, M. Godejohann, S. Bak, S. B. Engelsen, Screening for Triterpenoid Saponins in Plants Using Hyphenated Analytical Platforms. *Molecules.* 21, pii: E1614 (2016)). MS spectra, in negative mode, were acquired between m/z 50 and 1700. The calibration was done with a 10 mM sodium trifluoroacetate (NaTFA, Sigma-Aldrich) automatically which is introduced at the beginning and the end of each chromatographic run. Separation was done on a XBridge LC column (BEH C18, 5 μm particle size, and 250 mm×4.6 mm; Waters). The chromatographic conditions were as following; a flow rate of 0.9 mL/min. starting with a solvent composition of 74% A (5% ACN+0.1% FA) and 26% B (100% ACN+0.1% FA) with a linear gradient to 70% A at 60 min., followed by another linear gradient to 100% B at 62 min. 100% B hold for 3 min. followed linear gradient to 74% A at 65.5 and hold for 4.5 min. for equilibration. Saponins were collected on SPE cartridges in preset time windows and trapping was triggered by intensity threshold. Yossoside IV (m/z 1263.58, threshold 200,000, time window 18-23 min.); Yossoside XII (m/z 1233.57, threshold 58,000, time window 27-32 min.), Yossoside Va (m/z 1305.59, threshold 200,000, time window 32-40 min.); Yossoside X (m/z 1437.64, threshold 150,000, time window 40-48 min.) and Yossoside V (m/z 1305.59, threshold 200,000, time window 54-65 min.). For this trapping process, a makeup-flow of 2.5 mL/min. water was added to the eluent before it passed through the SPE cartridges in order to increase the retention of analytes on the cartridges. For the trapping 10 mm×2 mm SPE cartridges filled with GP resin were used. Each cartridge was loaded five times with the same compounds, 5-10 cartridges were used for trapping one saponin. Prior to NMR measurements, SPE cartridges were dried with a stream of nitrogen, the fraction from each cartridge was eluted with a total of 150 μL deuterated methanol. The sample was eluted into 96 well plate. Eluents containing same compound were pooled, dried under stream of nitrogen, freeze-dried, resuspended in 200 μL of $D_2O$ and freeze-dried again to remove traces of $H_2O$. Dry compounds were dissolved in 60 μL 90% MeOD-d4 10% $D_2O$ with 0.01% addition of 3-propionic-2,2,3,3-d4 acid sodium salt (TMSP, that was used as an internal chemical shift reference for $^1H$ and $^{13}C$ spectra) and transferred to a 1.7 mm NMR test tube.

NMR Methods

NMR spectra were recorded on a Bruker AVANCE NEO-600 NMR spectrometer equipped with a 1.7 mm TXI-z and a 5 mm TCI-xyz CryoProbes equipped with shielded gradient coils. All spectra were acquired at 293 K. NMR data of Yossoside V were recorded on both the 1.7 and 5 mm CryoProbes, and spectra of medicagenic acid 3-O-glucuronide (MA-3-GlcA) were acquired on the 5 mm CryoProbe (using a special NMR spinner turbine to hold the 1.7 mm test tube in a 5 mm probe).

$^1H$ and $^{13}C$ chemical shift assignment was based on different 1D and 2D NMR techniques, all using pulsed field gradient selection.

Figure 21:
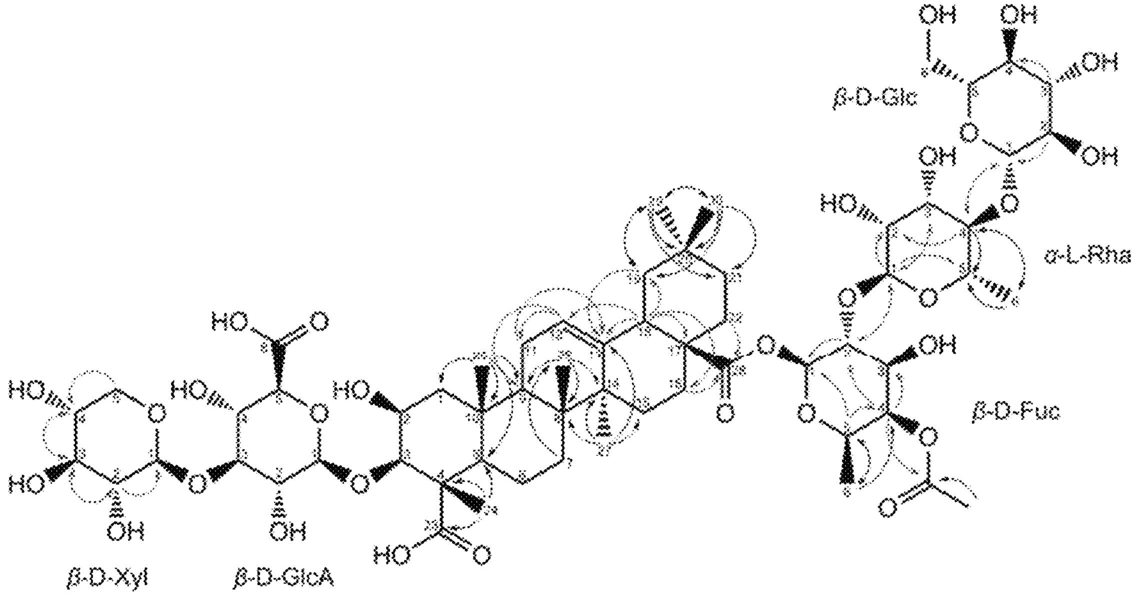
FIG. 21 presents important Heteronuclear Multiple Bond (HMBC) correlations of the hydrogens of Yossoside V. Black arrows represent HMBC correlations of the six methyl groups of Yossoside V. Red arrows represent HMBC correlations of other important hydrogens. Numbers correspond to carbon atoms in medicagenic acid and sugar moieties. For more details see Table 1. Table 1 presents spectral data summarized in tables that are split into two parts. The first part corresponds to atoms of medicagenic acid (aglycone part) while the second part corresponds to atoms of sugar moieties. The structures of Yossoside V and medicagenic acid 3-O-glucuronide with numbered atoms can be found in FIG. 21 and FIG. 35D, respectively. In Table 1: ax (axial) and eq (equatorial) depict protons in ring structures of aglycone and sugars.
Figure 35D:
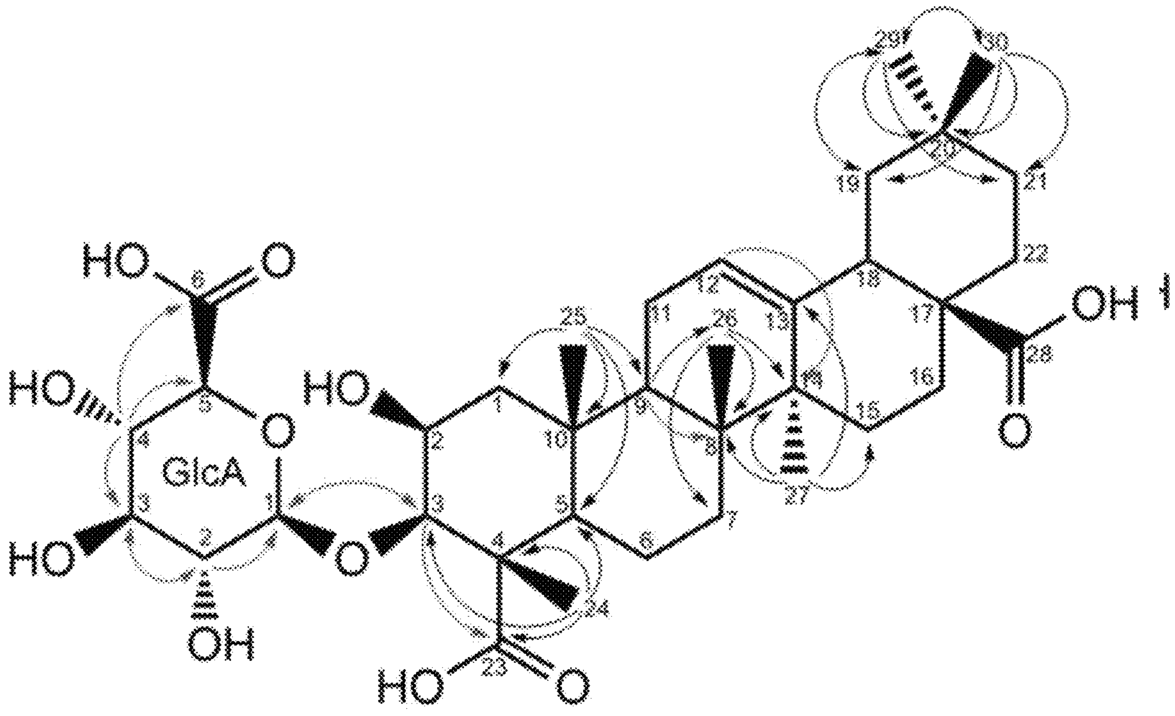

The structure and stereochemistry of the aglycone unit were determined by 1D'H and $^{13}C$, 2D homonuclear COSY and 2D heteronuclear HSQC and HMBC spectra. Identification of the monosaccharide units required recording also 2D homonuclear TOCSY spectra so as to complete the assignment and delineate connectivities between $^1H$ signals within the individual sugar units. Correlations observed in HMBC spectra between $^1H$ and $^{13}C$ that are 2-3 bonds apart, are shown in FIG. 21 and FIG. 35D for Yossoside V and MA-3-GlcA, respectively.

$^1H$ 1D NMR spectra were acquired using 16 k data points and a recycling delay of 2.5 s. $^{13}C$ spectral-editing DEPTQ NMR spectra were acquired using 65 k data points and a recycling delay of 3 s.

2D $^1H$-$^1H$ COSY, TOCSY and ROESY spectra were acquired using 16384-8192 $(t_2)$×400-512 $(t_1)$ data points. 2D TOCSY spectra were acquired using isotropic mixing times of 100-300 ms. A T-ROESY experiment was used in this study, TOCSY-less ROESY that effectively suppresses TOCSY transfer in ROESY experiments. 2D T-ROESY spectra were recorded using spin lock pulses of 100-400 ms.

2D $^1H$-$^{13}C$ HSQC and HMBC spectra were recorded using 4096 $(t_2)$×400-512 $(t_1)$ data points. Multiplicity editing HSQC enables differentiating between methyl and methine groups that give rise to positive correlation, vs methylene groups that appear as negative peaks. HMBC delay for evolution of long range couplings was set to observe long range couplings of $J_{H,C}$=8 Hz.

Chemical shift assignment was based on combined information derived from HMBC connectivities (FIG. 21 and FIG. 35D) and TOCSY correlations (data not shown).

$^1H$ and $^{13}C$ chemical shift values of Yossoside V and MA-3-GlcA are shown in Table 1. As expected, chemical shift values of the aglycone unit of the two compounds nicely fit and similar HMBC correlation pattern is observed (FIG. 21 and FIG. 35D). Assignment of the protons as axial or equatorial was based on the observed vicinal J couplings; large value (>10 Hz) indicates on axial protons, further supported by correlations observed in ROESY spectra.

Figure 18:
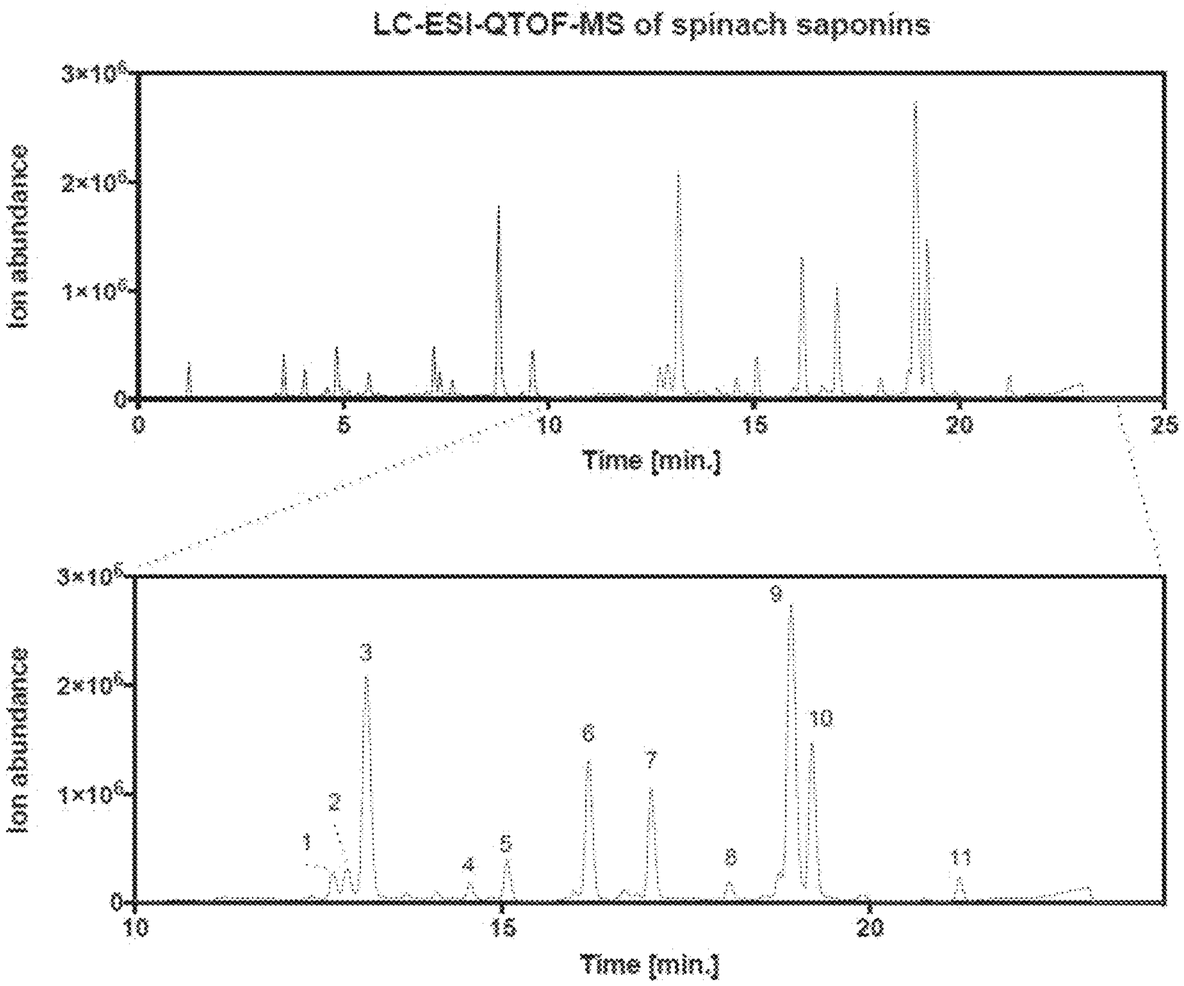
FIG. 18 are liquid chromatography-electrospray ionization-quadrupole-time of flight-mass spectrometry (LC-ESI-QTOF-MS) scans of spinach saponins. The upper scan shows the total ion chromatogram (TIC) of spinach leaf extract acquired in negative ion mode. Chromatogram fragment displayed and expanded below, shows saponins present in the sample. The lower scan presents an expanded region of the chromatogram with main saponins being numbered. The numbers represent different Yossosides as listed in Table 13 presented in Example 15.

HMBC correlations in aglycone region are in accordance with those observed in other triterpenoid saponins (H. Schröder et al., A triterpene saponin from Herniaria glabra. *Phytochemistry.* 34,1609-13 (1993), E. P. Mazzola et al., Utility of coupled-HSQC experiments in the intact structural elucidation of three complex saponins from Blighia sapida. *Carbohydr Res.* 346, 759-68 (2011)). The linkage site between medicagenic acid and glucuronic acid in MA-3-GlcA was supported by strong HMBC connectivity between the anomeric hydrogen of GlcA and C3 of the aglycone, as well as a complementary correlation observed between MA-H3/anomeric C1 of GlcA (red arrow in FIG. 18D). Similarly, linkage sites between the saccharide units were determined based on complementary 3-bond HMBC connectivities observed between the anomeric hydrogen/carbon of one sugar and the proton/carbon of the directly attached glycan as indicated by the interglycan arrows between Fuc-Rha-Glc (FIG. 21). The addition of xylose in Yossoside V (Xyl connected to GlcA) seems to restrict the conformational space of GlcA as is indicated by a lack of previously observed correlation between GlcA and the aglycone and lack of J couplings within GlcA. However, chemical shift prediction further supports the assignment of GlcA in Yossoside V.

RNA-Seq Library Preparation and Data Analysis

RNA-Seq libraries were prepared as described previously (S. Zhong et al., High-throughput illumina strand-specific RNA sequencing library preparation. *Cold Spring Harb Proto*. 8, 940-9 (2011)) with minor modifications. Briefly, 5 μg of total RNA was used for poly(A) RNA capture using Dynabeads Oligo $(dT)_{25}$ (Invitrogen), fragmented at 94° C. for 5 minutes and eluted. The first-strand cDNA was synthesized using reverse transcriptase SuperScript III (Invitrogen) with random primers and dNTP, whereas the second-strand cDNA was generated using DNA polymerase I (Enzymatics) using dUTP. After end-repair (Enzymatics), dA-tailing with Klenow 3'-5' (Enzymatics) and adapter ligation (Quick T4 DNA Ligase, NEB), the dUTP-containing second-strand was digested by uracil DNA glycosylase (Enzymatics). The resulting first-strand adaptor-ligated cDNA was used for PCR enrichment (NEBNext High-Fidelity PCR Master Mix, NEB) for 14 cycles. Indexed libraries were pooled and sequenced (paired-end, 125 bp) on a single lane of HiSeq2500 (Illumina) at the Crown Institute for Genomics, The Nancy and Stephen Grand Israel National Center for Personalized Medicine, Weizmann Institute of Science. The quality of the raw data was assessed using FastQC (S. W. Wingett, S. Andrews, FastQ Screen: A tool for multi-genome mapping and quality control. Version 2. F1000Res. 7, 1338 (2018)). Raw reads were aligned against version 1.0.1 of the spinach reference genome (The *Beta vulgaris* resource (http://bvseq.boku.ac.at/Genome/Download/index.shtml)) using Tophat v2.0.13 (C. Trapnell, L. Pachter, S. L. Salzberg, TopHat: discovering splice junctions with RNA-Seq. Bioinformatics. 25, 1105-11 (2009)). Quantification was performed using HTSeq (S. Anders S, P. T. Pyl, W. Huber, HTSeq-a Python framework to work with high-throughput sequencing data. *Bioinformatics*. 31, 166-9 (2015)) followed by normalization and differential gene expression analysis using DESeq2 (M. I. Love, W. Huber, S. Anders, Moderated estimation of fold change and dispersion for RNA-seq data with DESeq2. *Genome Biol.* 15, 550 (2014)).

Co-Expression Analysis

Co-expression analysis was done using CoExpNetViz software (O. Tzfadia, T. Diels, S. De Meyer, K. Vandepoele, A. Aharoni, Y. Van de Peer, CoExpNetViz: Comparative Co-Expression Networks Construction and Visualization Tool. Front Plant Sci. 6, 1194 (2016)). Briefly, spinach bAS (SOAP1), CYP716A268 (SOAP2) and CYP716A268v2 (SOAP2-like) were used as 'baits' in co-expression analysis with correlation threshold set at 5 and 95 for lower ad higher percentile rank, respectively. Lists of co-expressed genes was additionally filtered according to correlation coefficient (r>0.9; PCC) for each bait (Table 14). The analysis was performed using spinach RNA-Seq transcriptome data from different tissues and developmental stages (SO4WOLLD—mature leaf from four week old plant grown in long day; SO8WOLSL—mature leaf from eight week old plant grown in short day; SO4WYLLD—young leaf from four week old plant grown in long day; SO8WOLSL—young leaf from eight week old plant grown in short day; SO4WFBLD—flower bud from four week old plant grown in long day). The co-expression network was visualized with the Cytoscape software (P. Shannon P et al., Cytoscape: a software environment for integrated models of biomolecular interaction networks. Genome Res. 13, 2498-504 (2003)).

Cloning

Phusion High-Fidelity DNA Polymerase (New England Biolabs) was used for all PCR amplification steps according to the manufacturer's instructions. Restriction enzymes and T4 Ligase used for cloning were purchased from New England Biolabs. Oligonucleotide primers were purchased from Sigma-Aldrich. DNA excised from agarose gels was purified using the Gel/PCR extraction kit (Hy-Labs). *E. coli* TOP10 cells (Invitrogen) were used for plasmid isolation prior to transformation into other heterologous hosts. Plasmid DNA was isolated from *E. coli* cultures using the AccuPrep® Plasmid Mini Extraction Kit (Bioneer). For a list of primers used for cloning, see Table 11.

Constrict Preparation for VIGS

For the silencing of candidate genes in spinach, all gene sequences (200-400 bp) were amplified from spinach leaf cDNA template. Purified amplicons were inserted into modified pTRV2 vector (~200 bp of magnesium chelatase subunit H inserted with EcoRI) digested with SacI.

GoldenBraid System and Expression in *N. benthamiana*

For *N. benthamiana* transient expression of multiple genes from the same *Agrobacterium* strain, multigene constructs were created using GoldenBraid 3.0 (GB) system (M. Vazquez-Vilar et al., GB3.0: a platform for plant bio-design that connects functional DNA elements with associated biological data. Nucleic Acids Res. 45, 2196-2209 (2017)). In the first step, all the CDS and tomato Ubiquitin promoter and terminator were domesticated by removing BsaI and BsmBI restriction sites and inserting them into pUPD2 GoldenBraid entry vector. In the next step, genes were subcloned together with terminator and promoter into pDGB3α1 or pDGB3α2 GB vector. First level a vectors allow transient expression of a single gene in *N. benthamiana*. Subsequently, pDGB3α1:SOAP1 was combined with pDGB3α2:SOAP2 into pDGB3Ω1:SOAP1+SOAP2 and pDGB3α1:SOAP3 with pDGB3α2:SOAP4 into pDGB3Ω2:SOAP3+SOAP4. Combination of the omega vectors allows expression of four genes providing production of medicagenic acid in *N. benthamiana*. Other genes, cellulose synthase like G (SOAP5), glycosyltransferases (SOAP6-9) and acyltransferase (SOAP10) were used in alpha vectors. Genes from *C. quinoa, B. vulgaris, L. japonicus, Glycine max* (*G. max*) *M. sativa* and *G. uralensis* were cloned using same approach. For cDNA template preparation RNA extracted from 2-week-old seedlings (*L. japonicus, G. max, M. sativa* and *G. uralensis*), mature leaves (*B. vulgaris*) or from leaves surrounding flower buds (*C. quinoa*) was used.

Cloning into Yeast System (pESC)

For the expression of SOAP1 (bAS), CYPs (SOAP2-4) and CSLG (SOAP5) in *S. cerevisiae*, the sequences were amplified from cloned pDGB3α vectors carrying the sequence of interest and the purified amplicons were inserted into series of pESC ($Amp^R$) plasmids allowing simultaneous expression of two genes from one plasmid. SOAP1 and SOAP2 were inserted into pESC-HIS plasmid using NotI/SacI and BamHI/SalI restriction enzymes, respectively. SOAP3 and SOAP4 were inserted into pESC-LEU plasmid using NotI/SacI and BamHI/XhoI restriction enzymes, respectively. SOAP5 and SoUGD1 were inserted into pESC-LEU plasmid using NotI/SacI and SalI/XhoI restriction enzymes, respectively.

Cloning into pET-28b and Expression in *E. coli*

SOAP10 was cloned into the pET-28b ($Kan^R$) vector using NdeI/NotI restriction sites and expressed in *E. coli* BL21 (DE3) cells.

In Vitro Enzymatic Assay with SOAP10

Bacterial cells transformed with pET-28b:SOAP10 were grown in LB medium at 37° C. When cultures reached A600=0.6, protein expression was induced with 200 μM of isopropyl-1-thio-β-D-galactopyranoside (IPTG) at 15° C., for 24 h. Bacterial cells were lysed by sonication in 50 mM Tris-HCl pH 8.0, 10% glycerol, 0.1% Triton X-100, 1 mM PMSF and 100 mg/mL lysozyme.

The fraction of spinach desacetyl saponins was used as a substrate in SOAP10 enzyme assay. In a 200 μL tube 6 μL of cell lysate was mixed with 2 μL of 6.18 mM acetyl coenzyme A (Acetyl-CoA) and 2 mL of saponin substrate (10 μg). Reaction was carried out for 2.5 h at 28° C. Cell lysate without SOAP10 was used as a control. The reactions were stopped by addition of 20 μL methanol, followed by brief vortex. Finally, the extracts were centrifuged for 10 min. at 14,000×g and analyzed by LC-MS, as described above.

VIGS Procedure

Virus Induced Gene Silencing was performed as described previously (M. Senthil-Kumar, K. S. Mysore, Tobacco rattle virus-based virus-induced gene silencing in *Nicotiana benthamiana*. Nat Protoc. 9, 1549-62 (2014)). Briefly, pTRV1 and pTRV2 constructs harboring sequence for silencing were transformed into *Agrobacterium tumefaciens* (GV3101) electrocompetent cells. Transformants were grown on LB plates containing 50 μg/mL kanamycin and 50 μg/mL gentamicin at 28° C. 10 mL of LB medium supplemented with antibiotics was inoculated with a single colony and grew O/N at 28° C. Cells were centrifuged at 3,000×g for 10 min. and supernatant removed. Pellet was resuspended in 5 mL of infiltration medium (100 mM MES buffer, 2 mM $Na_3PO_4.12H_2O$, 100 μM acetosyringone) and centrifuged again. Pellet was resuspended again in 10 mL of infiltration medium and incubated at room temperature for 2 h. *Agrobacterium* suspensions (OD600=0.3 for each strain) were infiltrated into the underside of 1-week old spinach cotyledons (one per plant) with a needleless 1 mL syringe. Plants were grown in 16 h photoperiod at 23° C. After 2 weeks first signs of silencing of Magnesium Chelatase subunit H (CHCL) were visible. Plants were grown for another 2 weeks prior tissue collection. Leaves were harvested, frozen in liquid nitrogen and stored at −80° C. for later processing. Biological replicates consisted of 4 leaves all from different plants. Table 10 below provides the spinach and red beet nucleic acid sequences used to silence CSLGs in red beet and spinach

TABLE 10

VIGs Sequences

| Name | SEQ ID NO: | Nucleic Acid Sequence |
|---|---|---|
| SoCSLG (SOAP5) VIGS spinach | 106 | TTCCGTAGCCATCTTCTCGCTCTTCTACTACCG TTTCACTTCCTTCTTCAACTCCGACATCTCCAT ACTTGCTTACTCCTTACTCACCACCGCCGAACT CTTCTTAACCTTTCTATGGGCTTTTACTCAGGC TTCCCGGTGGCGTCCCGTAATGAGGGAAGTCTC CGGGTACGAATCCATCAAACCCGAACAACTACC GGGTTTGGATGTCTTCATTGTCACTGCTGACCC GACAAAGGAGCCAGTTCTGGAGGTGATGAACTC CGTGATATCATCCATGGCGTTGGATTATCCGGT TGATAGACTGGCGGTTTACTTGTCGGATGACGG TGGTTCTCCGTTGTCGAAGG |
| BvCSLG VIGS_ red beet | 107 | CCTTCGGCTCCTCCACAAAATTCATTGCGTCAG TTAGTTCAAACTCCAAGCAAAATATGGCCTTGA AGGAAATGACAAGAGACGACTTGTTAGAAGAGG CTAAAAATTTGGCTACTTGTGCATATGAATCAA ACACTGAATGGGGTAACAAGATTGGATATTCGT ATGAGTGTTTGTTGGAGAGTACATTTACCGGAT ATCTCTTACATTGCAAAGGATGGATTTCCGTGT ATCTTTACCCAAAAAGACCCTGCTTCTTAGGAT GCACGACGATTGACATGAAAGATGCCATGGTTC AACTAATGAAATGGACCTCTGGATTACTAGGAG TTGGCATATCAAAGTTTAGCCCTCTAACTTATG CCTTTTCGAGGATGTCTATATTACAAAGCATGT GCTACGGTTACTTCACATTTTCAGCCCTTTTCG GAGTTTCGT |

Site-Directed Mutagenesis of SOAP5

Site-directed mutagenesis of SOAP5 was performed using QuikChange Site-Directed Mutagenesis Kit (Agilent) according to the manufacturer's instructions.

Gene Expression Analysis—qPCR

Gene expression analysis was performed with three/four biological replicates (n=3/4) for each VIGS silenced line. RNA isolation was performed by the Trizol method (Sigma-Aldrich). DNase I (Sigma-Aldrich)-treated RNA was reverse transcribed using a high-capacity cDNA reverse transcription kit (Applied Biosystems). Gene-specific oligonucleotides were designed with Primer Blast software (NCBI). The Translation Elongation Factor Alpha 1 (EF1-α) gene was used as an endogenous control. Oligonucleotides used are listed in Table 11.

TABLE 11

List of primers used

| | A | B | C | D | E | F | G |
|---|---|---|---|---|---|---|---|
| 1 | gene name | annotation | species | locus | purpose | primer name | sequence |
| 2 | OXIDOSQUALENE CYCLASE | | | | | | |
| 3 | SOAP1 | β-amyrin synthase, bAS | *Spinacia oleracea* | Sp_107620_ kqnh | VIGS | Sp107620_ vF | CTAGAGCTCATGTTCAA GAAGTTATACCC |
| 4 | | | | | | Sp107620_ vR | TTCGAGCTCCCTCCTTT TGTGTAGTAA |
| 5 | | | | | expression in *N. benthamiana* | Sp107620_ GB_1F | GCGCCGTCTCGCTCGAA TGTGGAGGTTGAAGGTT GG |
| 6 | | | | | | Sp107620_ GB_1R | GCGCCGTCTCGCTGTCT CATATGTGATCTCCT |
| 7 | | | | | | Sp107620_ GB_2F | GCGCCGTCTCGACAGCC TCGACGACATTAAAG |

TABLE 11-continued

List of primers used

| 1 | A gene name | B annotation | C species | D locus | E purpose | F primer name | G sequence |
|---|---|---|---|---|---|---|---|
| 8 | | | | | | Sp107620_ GB_2R | GCGCCGTCTCGCTCAAA GCTCAAGTAGAGTTGAT AGAAGGTAA |
| 9 | | | | | expression in yeast | Sp107620_ NotI_F | AAAAGCGGCCGCATGTG GAGGTTGAAGGTTGGA |
| 10 | | | | | | Sp107620_ SacI_R | AAAAGAGCTCTCAAGTA GAGTTGATAGAAGGTAA TG |
| 11 | | | | | colocali- zation | Sp107620_ GB_1F | GCGCCGTCTCGCTCGAA TGTGGAGGTTGAAGGTT GG |
| 12 | | | | | | Sp107620_ GB_CT_R | GCGCCGTCTCGCTCACG AACCAGTAGAGTTGATA GAAGGTAATGA |
| 13 | CYTOCHROMES P450 | | | | | | |
| 14 | SoCYP1 | CYP715A56 | *Spinacia oleracea* | Sp_046690_ sjiw | VIGS | Sp046690_ vF | CTAGAGCTCCTTCGTCG TTGTTGTCGTCG |
| 15 | | | | | | Sp046690_ vR | TTCGAGCTCCCTATGAC GAGCCCAAGCAT |
| 16 | SoCYP2 | CYP72A656 | *Spinacia oleracea* | Sp_148230_ dgra | VIGS | Sp148230_ vF | CTAGAGCTCAGCTCTAC TTTGCGTGCTCA |
| 17 | | | | | | Sp148230_ vR | TTCGAGCTCTCTGGCCC TCATAGTTCGGA |
| 18 | SoCYP3 | CYP72A685 | *Spinacia oleracea* | Sp_085350_ pxjs | VIGS | Sp085350_ vF | CTAGAGCTCTTGTTGGG TTGCTTGTCCCT |
| 19 | | | | | | Sp085350_ vR | TTCGAGCTCGGTCTTTG TTGGCACGAACC |
| 20 | SOAP2 | CYP716A268 | *Spinacia oleracea* | Sp_107660_ kiqg | VIGS | Sp107660_ vF | CTAGAGCTCTGGTGGGC GAGTCATTTGAA |
| 21 | | | | | | Sp107660_ vR | TTCGAGCTCCAAGCCAG CCAGAAGGTGTA |
| 22 | | | | | expression in *N. benthamiana* | Sp107660_ GB_1F | GCGCCGTCTCGCTCGAA TGGAACTCTTCTTTATG TGTGG |
| 23 | | | | | | Sp107660_ GB_1R | GCGCCGTCTCGCTCAAA GCTTAAGCAGCTACAGT TCGAGG |
| 24 | | | | | expression in yeast | Sp107660_ BamHI_F | AAAAGGATCCATGGAAC TCTTCTTTATGTGTGGG |
| 25 | | | | | | Sp107660_ SalI_R | AAAAGTCGACTTAAGCA GCTACAGTTCGAGGATG |
| 26 | | | | | colocali- zation | Sp107660_ GB_1F | GCGCCGTCTCGCTCGAA TGGAACTCTTCTTTATG TGTGG |
| 27 | | | | | | Sp107660_ GB_CT_R | GCGCCGTCTCGCTCACG AACCAGCAGCTACAGTT CGAGGAT |
| 28 | SOAP3 | CYP72A655 | *Spinacia oleracea* | Sp_085340_ meek | VIGS | Sp085340_ vF | CTAGAGCTCGTTGCATT GCTTGTCCCTGG |
| 29 | | | | | | Sp085340_ vR | TTCGAGCTCTGATTGCA GAAGGCGTAGGG |

TABLE 11-continued

List of primers used

| A<br>1 gene name | B<br>annotation | C<br>species | D<br>locus | E<br>purpose | F<br>primer name | G<br>sequence |
|---|---|---|---|---|---|---|
| 30 | | | | expression in *N. benthamiana* | Sp085340_GB_1F | GCGCCGTCTCGCTCGAATGATAGAAATCGGGTATATTGTAAA |
| 31 | | | | | Sp085340_GB_1R | GCGCCGTCTCGCTCAAAGCTTAGTCCCTGAGCTTATGTATAAT |
| 32 | | | | expression in yeast | Sp085340_NotI_F | AAAAGCGGCCGCATGATAGAAATCGGGTATATTGTAAAATG |
| 33 | | | | | Sp085340_SacI_R | AAAAGAGCTCTTAGTCCCTGAGCTTATGTATAATGAG |
| 34 | | | | colocalization | Sp085340_GB_1F | GCGCCGTCTCGCTCGAATGATAGAAATCGGGTATATTGTAAA |
| 35 | | | | | Sp085340_GB_CT_R | GCGCCGTCTCGCTCACGAACCGTCCCTGAGCTTATGTATAATG |
| 36 SOAP4 | CYP72A654 | *Spinacia oleracea* | Sp_040350_wdny | VIGS | Sp040350_vF | CTAGAGCTCTTTCAAAGAGCGCGAGTGGT |
| 37 | | | | | Sp040350_vR | TTCGAGCTCGCCTGCACCAGAATTGTTGA |
| 38 | | | | expression in *N. benthamiana* | Sp040350_GB_1F | GCGCCGTCTCGCTCGAATGATTTCAAAGAGCGCGAGT |
| 39 | | | | | Sp040350_GB_1R | GCGCCGTCTCGTTGTCTCTTGACCAGCCAAG |
| 40 | | | | | Sp040350_GB_2F | GCGCCGTCTCGACAACCTCAGTGGCCCTAAC |
| 41 | | | | | Sp040350_GB_2R | GCGCCGTCTCGCTCAAAGCTTAAAATCGATGTAAAATAATGTGGG |
| 42 | | | | expression in yeast | Sp040350_BamHI_F | AAAAGGATCCATGATTTCAAAGAGCGCGAGT |
| 43 | | | | | Sp040350_XhoI_R | AAAACTCGAGTTAAAATCGATGTAAAATAATGTGGG |
| 44 | | | | colocalization | Sp040350_GB_1F | GCGCCGTCTCGCTCGAATGATTTCAAAGAGCGCGAGT |
| 45 | | | | | Sp040350_GB_CT_R | GCGCCGTCTCGCTCACGAACCAAATCGATGTAAAATAATGTGGGC |
| 46 GuCYP88D6 | CYP88D6 | *Glycyrrhiza-uralensis* | Glyur000561s00023451.1 | expression in *N. benthamiana* | GuCYP88D6_GB_1F | GCGCCGTCTCGCTCGAATGGAAGTACATTGGGTTTGC |
| 47 | | | | | GuCYP88D6_GB_1R | GCGCCGTCTCGCTCAAAGCCTAAGCACATGATACCTTTATCAC |
| 48 GuCYP72A154 | CYP72A154 | *Glycyrrhiza-uralensis* | Glyur000890s00019071.1 | expression in *N. benthamiana* | GuCYP72A154_GB_1F | GCGCCGTCTCGCTCGAATGGATGCATCTTCCACACC |
| 49 | | | | | GuCYP72A154_GB_1R | GCGCCGTCTCGAAAGACCAATGGATTTTGATTGTG |

TABLE 11-continued

| A<br>1 gene name | B<br>annotation | C<br>species | D<br>locus | E<br>purpose | F<br>primer name | G<br>sequence |
|---|---|---|---|---|---|---|
| List of primers used | | | | | | |
| 50 | | | | | GuCYP72A154_<br>GB_2F | GCGCCGTCTCGCTTTCC<br>AAAGATGATGCTGCA |
| 51 | | | | | GuCYP72A154_<br>GB_2R | GCGCCGTCTCGTTGTCT<br>CTTGCCCTGCCAGG |
| 52 | | | | | GuCYP72A154_<br>GB_3F | GCGCCGTCTCGACAACC<br>GCAGCTTTGCTGGC |
| 53 | | | | | GuCYP72A154_<br>GB_3R | GCGCCGTCTCGCTCAAA<br>GCTTACAGTTTATGCAG<br>AATGATGGG |
| 54 | | | GLYCOSYLTRANSFERASES | | | |
| 55 SOAP5 | Cellulose<br>Synthase<br>Like<br>G2, CSLG2 | *Spinacia*<br>*oleracea* | Sp_076690_<br>ejcm/<br>Spo12715 | VIGS | Sp076690_<br>vF | CTAGAGCTCTTCCGTAG<br>CCATCTTCTCGC |
| 56 | | | | | Sp076690_<br>vR | TTCGAGCTCCCTTCGAC<br>AACGGAGAACCA |
| 57 | | | | expression<br>in *N.*<br>*benthamiana* | Sp076690_<br>GB_1F | GCGCCGTCTCGCTCGAA<br>TGGCAACTTCTCACATT<br>CGC |
| 58 | | | | | Sp076690_<br>GB_1R | GCGCCGTCTCGGAAGAC<br>GGTTAACAATGGCTC |
| 59 | | | | | Sp076690_<br>GB_2F | GCGCCGTCTCGCTTCAC<br>ATCTTCCTCCATTCC |
| 60 | | | | | Sp076690_<br>GB_2R | GCGCCGTCTCGGCCTCT<br>TTTCCCTGGCTACA |
| 61 | | | | | Sp076690_<br>GB_3F | GCGCCGTCTCGAGGCCT<br>GGTCGTCCTCATCG |
| 62 | | | | | Sp076690_<br>GB_3R | GCGCCGTCTCGCTCAAA<br>GCTTATAACCATCCCTT<br>AACAACAGG |
| 63 | | | | expression<br>in yeast | Spo12715F_<br>NotI_F | AAAAGCGGCCGCATGGC<br>AACTTCTCACATTCGCA<br>A |
| 64 | | | | | Spo12715R_<br>SacI_R | AAAAGAGCTCTTATAAC<br>CATCCCTTAACAACAGG<br>GTAG |
| 65 | | | | colocali-<br>zation | Sp076690_<br>GB_1F | GCGCCGTCTCGCTCGAA<br>TGGCAACTTCTCACATT<br>CGC |
| 66 | | | | | Sp076690_<br>GB_CT_R | GCGCCGTCTCGCTCACG<br>AACCTAACCATCCCTTA<br>ACAACAGG |
| 67 | | | | mutagenesis | Spo12715_<br>M1_F | CGTATGAGTGCTTGTTG<br>GAGGATACATTCACTGG<br>ATATATG |
| 68 | | | | | Spo12715_<br>M1_R | CATATATCCAGTGAATG<br>TATCCTCCAACAAGCAC<br>TCATACG |
| 69 | | | | | Spo12715_<br>M2_F | CTACGGTTCAACTAATA<br>AGATGGACCTCCTCATT<br>ACTTGG |
| 70 | | | | | Spo12715_<br>M2_R | CCAAGTAATGAGGAGGT<br>CCATCTTATTAGTTGAA<br>CCGTAG |

TABLE 11-continued

List of primers used

| 1 | A gene name | B annotation | C species | D locus | E purpose | F primer name | G sequence |
|---|---|---|---|---|---|---|---|
| 71 | SoGT1 | UGT79M1 | *Spinacia oleracea* | Sp_049940_ mmut | VIGS | Sp049940_ vF | CTAGAGCTCAGCTTTCC TCCCATGGCATC |
| 72 | | | | | | Sp049940_ vR | TTCGAGCTCACTTGTGG CTGGAGTTGAGG |
| 73 | SoGT2 | UGT79N1 | *Spinacia oleracea* | Sp_148240_ fnwi | VIGS | Sp148240_ vF | CTAGAGCTCCCCTCCTC GGCTATACACCT |
| 74 | | | | | | Sp148240_ vR | TTCGAGCTCCCTACGTC TGCCACAGTCTC |
| 75 | SOAP6 | UGT74BB2 | *Spinacia oleracea* | Sp_170930_ hjgq | VIGS | Sp170930vF | CTAGAGCTCCCGAAGCC TCACTCCAACTT |
| 76 | | | | | | Sp170930vR | TTCGAGCTCTCAGAACT CGGGGATTGTGC |
| 77 | | | | | expression in *N. benthamiana* | Sp170930_ GB_1F | GCGCCGTCTCGCTCGAA TGACGGGAAAAGGAAGA ACG |
| 78 | | | | | | Sp170930_ GB_1R | GCGCCGTCTCGCTCAAA GCTTAGGAGGACGCAAG CCAGT |
| 79 | SOAP6v2 | UGT74BB1 | *Spinacia oleracea* | Sp_170920_ oudh | VIGS | Sp170920_ vF | CTAGAGCTCTCGTGGCT CGTATGGGAAAG |
| 80 | | | | | | Sp170920_ vR | TTCGAGCTCAGGAACAG ATTCAGCCGCAA |
| 81 | SOAP7 | UGT79K1 | *Spinacia oleracea* | Sp_020820_ yeau | VIGS | Sp020820_ vF | CTAGAGCTCTAGCCACA AAGCTGGGGATG |
| 82 | | | | | | Sp020820_ vR | TTCGAGCTCGGGAGGAA TTCAACCTCGGG |
| 83 | | | | | expression in *N. benthamiana* | Sp020820_ GB_1F | GCGCCGTCTCGCTCGAA TGGGTAAAACAGTAGCA GCT |
| 84 | | | | | | Sp020820_ GB_1R | GCGCCGTCTCGCTCAAA GCTTAATTTGCAGTAAG AAAGCGTTTC |
| 85 | SOAP8 | UGT79L2 | *Spinacia oleracea* | Sp_113700_ suxh | VIGS | Sp113700_ vF | CTAGAGCTCGTGATGTT CCCATGGCTTGC |
| 86 | | | | | | Sp113700_ vR | TTCGAGCTCAAGGTCGG GCTTATGGGTTG |
| 87 | | | | | expression in *N. benthamiana* | Sp113700_ GB_1F | GCGCCGTCTCGCTCGAA TGGGTGGAGAGAAAGAG TTG |
| 88 | | | | | | Sp113700_ GB_1R | GCGCCGTCTCGCTCAAA GCCTAAGGAACAAGGGC TTGTAA |
| 89 | SOAP8v2 | UGT79L1 | *Spinacia oleracea* | Sp_072870_ funr | VIGS | Sp072870_ vF | CTAGAGCTCGGCTTGCC TTTGGACACTTG |
| 90 | | | | | | Sp072870_ vR | TTCGAGCTCAAGACAAG GTCGGGCTTCTG |
| 91 | SOAP9 | UGT73BS1 | *Spinacia oleracea* | Sp_170320_ dmqi | VIGS | Sp170320_ vF | CTAGAGCTCGTGTGCTG CTGAGGTTGTTG |
| 92 | | | | | | Sp170320_ vR | TTCGAGCTCGTCGCAGT GTACCGGATAGG |
| 93 | | | | | expression in *N. benthamiana* | Sp170320_ GB_1F | GCGCCGTCTCGCTCGAA TGGAGCTTTCAAACCCT AGC |

TABLE 11-continued

List of primers used

| A<br>1 gene name | B<br>annotation | C<br>species | D<br>locus | E<br>purpose | F<br>primer name | G<br>sequence |
|---|---|---|---|---|---|---|
| 94 | | | | | Sp170320_GB_1R | GCGCCGTCTCGGCGACGAACCACCTTCTTCA |
| 95 | | | | | Sp170320_GB_2F | GCGCCGTCTCGTCGCGTAACAATTTAAGTGATTTG |
| 96 | | | | | Sp170320_GB_2R | GCGCCGTCTCGCTCAAAGCTTATTCTGAGTTTGTGGACACTG |
| 97 BvCSLG | CSLG2 | *Beta vulgaris* | XM_010673823.2 | VIGS | BvCSL_vF | AAAAGAGCTCCCTTCGGCTCCTCCACAAAA |
| 98 | | | | | BvCSL_vR | AAAAGAGCTCACGAAACTCCGAAAAGGGCT |
| 99 | | | | expression in*N. benthamiana* | BvCSL_GB_1F | GCGCCGTCTCGCTCGAATGTCTTCTCTCCACATTTGC |
| 100 | | | | | BvCSL_GB_1R | GCGCCGTCTCGGCCTCTTTTCCCTGGATACG |
| 101 | | | | | BvCSL_GB_2F | GCGCCGTCTCGAGGCCAAATCGTCCTCATCG |
| 102 | | | | | BvCSL_GB_2R | GCGCCGTCTCGCATCTCTTGTCATTTCCTTCAAG |
| 103 | | | | | BvCSL_GB_3F | GCGCCGTCTCGGATGACTTGTTAGAAGAGGCT |
| 104 | | | | | BvCSL_GB_3R | GCGCCGTCTCGCTCAAAGCTCAATCACGTCCTTTTCTTACTTT |
| 105 CqCSLG | CSLG2 | *Chenopodium quinoa* | XM_021866098.1 | expression in *N. benthamiana* | CgCSL_GB_1F | GCGCCGTCTCGCTCGAATGGCGGCAACACACATTTG |
| 106 | | | | | CgCSL_GB_1R | GCGCCGTCTCGGCCTCTTTTCCCTGGCTACA |
| 107 | | | | | CgCSL_GB_2F | GCGCCGTCTCGAGGCCAGGTCATCCTCATCG |
| 108 | | | | | CgCSL_GB_2R | GCGCCGTCTCGCTCAAAGCTTATTCTTTCTTTCTAAGTTTGTCTG |
| 109 MsCSLG | CSLG2 | *Medicago sativa* | MSAD_299835 | expression in *N. benthamiana* | MsCSL_GB_1F | GCGCCGTCTCGCTCGAATGGCAACCTTCACATTTCAC |
| 110 | | | | | MsCSL_GB_1R | GCGCCGTCTCGCATCTCTTGAAATATTCTGCTTCT |
| 111 | | | | | MsCSL_GB_2F | GCGCCGTCTCGGATGTAATTTTACAAGAAGCATGTG |
| 112 | | | | | MsCSL_GB_2R | GCGCCGTCTCGCTCAAAGCCTACCCACTCTTCCGCTTCA |
| 113 | | | | silencing in *M. sativa* hairyroots | MsCSL_asGB_1F | GCGCCGTCTCGCTCGAATGCTACCCACTCTTCCGCTTCA |

TABLE 11-continued

List of primers used

| A 1 | gene name | B annotation | C species | D locus | E purpose | F primer name | G sequence |
|---|---|---|---|---|---|---|---|
| 114 | | | | | | MsCSL_asGB_1R | GCGCCGTCTCGCTCAAAGCATGGCAACCTTCACATTTCAC |
| 115 | GmCSL | CSLG2 | *Glycine max* | NM_001365113.1 | expression in *N. benthamiana* | GmCSL_GB_1F | GCGCCGTCTCGCTCGAATGGCGACCTTCCACACAGA |
| 116 | | | | | | GmCSL_GB_1R | GCGCCGTCTCGGGATCTCTTCCAAATTCGTCA |
| 117 | | | | | | GmCSL_GB_2F | GCGCCGTCTCGATCCTAAAAATCGTTCCATTGTGT |
| 118 | | | | | | GmCSL_GB_2R | GCGCCGTCTCGCTCAAAGCCTATTGCACCTTGCTTTTCATG |
| 119 | GuCSL | CSLG2 | *Glycyr-rhiza-uralensis* | Glyur003152s00037491.1 | expression in *N. benthamiana* | GuCSL_GB_1F | GCGCCGTCTCGCTCGAATGGCAAGCTTCACCCTTCA |
| 120 | | | | | | GuCSL_GB_1R | GCGCCGTCTCGATACCAGAGTGTTCATCACCT |
| 121 | | | | | | GuCSL_GB_2F | GCGCCGTCTCGGTATCTGCCCTTGCCATGGA |
| 122 | | | | | | GuCSL_GB_2R | GCGCCGTCTCGAGATCTCGCTCTGACCTGAA |
| 123 | | | | | | GuCSL_GB_3F | GCGCCGTCTCGATCTCATCAAGGCTAAATACGAG |
| 124 | | | | | | GuCSL_GB_3R | GCGCCGTCTCGCTCAAAGCCTATCCACTCTTGCTTTTCATG |
| 125 | GuUGAT | UGAT | *Glycyr-rhiza-uralensis* | KT759000.1 | expression in *N. benthamiana* | GuUGAT_GB_1F | GCGCCGTCTCGCTCGAATGACCATGGGTAACGAGAAT |
| 126 | | | | | | GuUGAT_1GB_R | GCGCCGTCTCGGCGACGATCCTCCTTCCTCC |
| 127 | | | | | | GuUGAT_GB_2F | GCGCCGTCTCGTCGCACAACGATTTTAACTCTTTA |
| 128 | | | | | | GuUGAT_GB_2R | GCGCCGTCTCGCTCAAAGCTTAATGGGCACGCGACCTCA |
| 129 | GuUGT73P12 | UGT73P12 | *Glycyr-rhiza-uralensis* | Scaffold00629 (LC314779) | expression in *N. benthamiana* | GuUGT73P12_GB_1F | GCGCCGTCTCGCTCGAATGGACTCCTTTGGGGTTGA |
| 130 | | | | | | GuUGT73P12_GB_1R | GCGCCGTCTCGGCCTCATTTCACGGAACAGT |
| 131 | | | | | | GuUGT73P12_GB_2F | GCGCCGTCTCGAGGCCAGATTTCATAGTCACT |
| 132 | | | | | | GuUGT73P12_GB_2R | GCGCCGTCTCGCTCAAAGCTTAAGCCACTGCCTCCATTAA |

TABLE 11-continued

List of primers used

| 1 | A gene name | B annotation | C species | D locus | E purpose | F primer name | G sequence |
|---|---|---|---|---|---|---|---|
| 133 | ACYLTRANSFERASES | | | | | | |
| 134 | SoAT1 | un-character-ized acetyl-transferase At3g50280-like | *Spinacia oleracea* | Sp_074630_ygho | VIGS | Spo04549_vF | CTAGAGCTCAGGCGTTGCTATCGATCCAG |
| 135 | | | | | | Spo04549_vR | TTCGAGCTCCATGGCCTTGAGTCTCAGCA |
| 136 | SoAT2 | O-acyltrans-ferase WSD1-like | *Spinacia oleracea* | Sp_123780_pgiy | VIGS | Spo21561_vF | CTAGAGCTCCCGGAAATGAAGGTCTGGGT |
| 137 | | | | | | Spo21561_vR | TTCGAGCTCAGGGGGTTCGAGCATTTGTC |
| 138 | SoAT3 | acyl-CoA--sterolO-acyltrans-ferase 1 | *Spinacia oleracea* | Sp_149180_nwmy | VIGS | Spo15788_vF | CTAGAGCTCTGATAAGGGCCCACTTTGCG |
| 139 | | | | | | Spo15788_vR | TTCGAGCTCCTCCAGTTCGAGCCCTAACAA |
| 140 | SoAT4 | malonyl-CoA: anthocya-nidin 5-O-glucoside-6"-O-malonyl-transfer-ase-like | *Spinacia oleracea* | Sp_198340_focw | VIGS | Spo13090_vF | CTAGAGCTCAAGCCAAAGCAAAAGGCACC |
| 141 | | | | | | Spo13090_vR | TTCGAGCTCTCGGTTTCCCCCACCAAAAA |
| 142 | SOAP10 | salutari-dinol 7-O-acetyl-transferase | *Spinacia oleracea* | Sp_125800_kzws | VIGS | Spo02253_vF | CTAGAGCTCCAACAACTTCCAAAGGCGGC |
| 143 | | | | | | Spo02253_vR | TTCGAGCTCTCTTGAAGCCCATTGCTGCT |
| 144 | | | | | expression in *E. coli* | Spo02253_NdeI_F | GAAACATATGGGGGAAGTCAACCATGAAGAAG |
| 145 | | | | | | Spo02253_NotI_R | CTTTGCGGCCGCCTAATTAGGAGTAGCAAAAGCAAGG |
| 146 | | | | | expression in *N. benthamiana* | Spo02253_GB_1F | GCGCCGTCTCGCTCGAATGGGGGAAGTCAACCATGA |
| 147 | | | | | | Spo02253_GB_1R | GCGCCGTCTCGCTGTCTCAAATTTGGTGGGTT |
| 148 | | | | | | Spo02253_GB_2F | GCGCCGTCTCGACAGTGACAGGGTTTATTTGG |
| 149 | | | | | | Spo02253_GB_2R | GCGCCGTCTCGGCCTCCCATCGTTGGGAATT |
| 150 | | | | | | Spo02253_GB_3F | GCGCCGTCTCGAGGCCCCCTAAGGTCAGGAA |

TABLE 11-continued

List of primers used

| | A | B | C | D | E | F | G |
|---|---|---|---|---|---|---|---|
| 1 | gene name | annotation | species | locus | purpose | primer name | sequence |
| 151 | | | | | | Spo02253_ GB_3R | GCGCCGTCTCGCTCAAA GCCTAATTAGGAGTAGC AAAAGCAAG |
| 152 | | | | OTHERS | | | |
| 153 | SoCHLH | Magnesium chelatase subunit H | *Spinacia oleracea* | Sp_082000_ pjxp | VIGS | SoCHLH_vF | ACTAGAATTCCAAGTGG GGATGAGTGATGCTTG |
| 154 | | | | | | SoCHLH_vR | GTTCGAATTCCTAGCAG TGCTGATGATGGAACTC |
| 155 | BvCHLH | Magnesium chelatase subunit H | *Beta vulgaris* | XM_ 010674548.2 | VIGS | BvCHLH_vF | AAAAGAATTCGGAGGCA AGAGGGGCTAAAG |
| 156 | | | | | | BvCHLH_vR | AAAAGAATTCTTTCCTC TTCAAGTCCGCCC |
| 157 | SoUGD1 | UDP-glu-cose 6-dehydro-genase 1 | *Spinacia oleracea* | Sp_189830_ psca | expression in yeast | SoUGD1_ SalI_F | AAAAGTCGACATGGTGA AGAAACTGAAGATTTGC TG |
| 158 | | | | | | SoUGD1_ XhoI_R | AAAACTCGAGTTAAGCT ACGGCAGGCATGTC |

Transient Expression and Candidate Gene Screening in *N. benthamiana* pDBG3α and pDBG3Ω constructs were transformed into *Agrobacterium* tumafaciens (GV3101) electrocompetent cells. Transformants were grown on LB plates containing 50 μg/mL kanamycin (pDBG3α) or 200 μg/mL spectinomycin (pDBG3®) and 50 μg/mL gentamicin at 28° C. 10 mL of LB medium supplemented with antibiotics was inoculated with a single colony and grew O/N at 28° C. Cells were centrifuged at 3,000×g for 10 min. and supernatant removed. Pellet was resuspended in 5 ml of infiltration medium (100 mM MES buffer, 2 mM $Na_3PO_4.12H_2O$, 100 μM acetosyringone) and centrifuged again. Pellet was resuspended again in 10 mL of infiltration medium and incubated at room temperature for 2 h. *Agrobacterium* suspensions (OD600=0.3 for each strain) were infiltrated into the underside of *N. benthamiana* leaves with a needleless 1 mL syringe. Plants were grown 4-5 weeks under a 16 h light cycle prior to infiltration. Leaves were harvested 4 days post-infiltration, frozen in liquid nitrogen and stored at −80° C. for later processing. Biological replicates consisted of several leaves all from different tobacco plants.

Expression of SOAP Genes in *S. cerevisiae* WA T11 and Metabolite Extraction pESC constructs were transformed into *Saccharomyces cerevisiae* WAT11 using Yeastmaker™ yeast transformation system (Clontech). Yeast cells were transformed with various combinations of pESC vectors allowing expression of one (SOAP5), two (SOAP1-2), four (SOAP1-4), five (SOAP1-S or SOAP1-4+SoUGD1) and 6 genes (SOAP1-5+SoUGD1). Transformed yeast were grown on SD minimal media supplemented with appropriate amino acids and 2% glucose. Colonies were screened and presence of transgene confirmed by colony PCR. For induction of gene expression transformed cells were transferred to minimal medium with 2% galactose and grown for 24 h at 30° C. Cultures were centrifuged for 10 min. at 700×g, pellet was resuspended in 1 mL of $H_2O$, transferred to 2 mL Eppendorf tube and centrifuged again at 8,000×g for a minute. Cell pellet was weighed, equal amount of water and double amount of glass beads (diameter 500 μm) was added and vortexed 5 times for one minute, each time keeping the cells on ice for one minute between vortexings. Lysed cells were mixed with 500 μL of methanol and centrifuged at 14'000 rpm for 5 minutes, clear supernatant was collected and dried in the SpeedVac O/N. Dry residues were dissolved in 150 μL of 80% methanol, filtered through 0.22 μm filter and analyzed on LC-MS.

Subcellular Localization and Confocal Microscopy Analysis

Plasmids allowing expression of studied proteins in fusion with fluorescent protein (FP) were prepared using GoldenBraid system (M. Vazquez-Vilar et al., (2017) ibid). SOAP1:GFP, SOAPs 2-4 in fusion with -GFP or —RFP and SOAP5.RFP were used. As cell compartment markers plasmids obtained from ABRC (ER-gk CD3-955 and G-gk CD3-963) were used (B. K. Nelson, X. Cai, A. Nebenführ, A multicolored set of in vivo organelle markers for co-localization studies in *Arabidopsis* and other plants. Plant J. 51, 1126-36 (2007)).

For subcellular localization studies of spinach cellulose synthase like G, SOAP5:RFP was transiently expressed together with ER or Golgi marker in *N. benthamiana* epidermal cells. A bacterial absorbance A600 nm of 0.15 was used for infiltrating each *Agrobacterium* strain. After 72 h post infiltration, leaf discs (~0.4 cm diameter) were collected and analyzed for fluorescence with confocal microscopy using the following parameters: Fluorescence was observed by a Nikon eclipse A1 microscope with laser at 488 nm for excitation and images were acquired for GFP (ER or Golgi marker) and 561 nm for red fluorescent protein (RFP) signals. To increase signal-to-noise ratio, each scan pixel was sampled four times and averaged. The same parameters were used for checking colocalization of SOAP genes.

Fluorescence Resonance Energy Transfer (FRET) Analysis

Mean FRET index (i.e., the mean of acceptor, mRFP-fused protein, intensity due to FRET in each pixel after threshold application to remove background noise) were calculated using the FRET Analyzer plugin (M. Hachet-Haas et al., FRET and colocalization analyzer a method to validate measurements of sensitized emission FRET acquired by confocal microscopy and available as an ImageJ Plug-in. Microsc Res Tech. 69, 941-56 (2006)) FIJI/ImageJ. The mean FRET index was calculated for three independent images for each protein combination being tested for proximity/interaction. Cells expressing GFP and RFP only were used to calculate donor and acceptor bleed through.

Phylogenetic Analysis

Homology searches were performed with various query sequences at the non-redundant protein database of NCBI (http://blast.ncbi.nlm.nih.gov/Blast.cgi) using the Blastp option. Protein sequences were aligned using the Muscle algorithm and phylogenetic tree was inferred with RAxML rapid bootstrapping and subsequent ML search (A. Stamatakis, RAxML version 8: a tool for phylogenetic analysis and post-analysis of large phylogenies. Bioinformatics. 30, 1312-3 (2014)). Likelihood of final tree was evaluated and optimized under GAMMA model of rate heterogeneity across sites. GAMMA model parameters were estimated up to an accuracy of 0.1000000000 Log Likelihood units. One thousand bootstrap replicates using the fast bootstrap option of RAxML were performed. Used substitution matrix was DAYHOFF. Phylogenetic tree was visualized with iTOL (I. Letunic, P. Bork, Interactive tree of life (iTOL) v3: an online tool for the display and annotation of phylogenetic and other trees. Nucleic Acids Res. 44, W242-5 (2016)).

Silencing of MsCSL M *M. sativa* Hairy Roots

Vector pDBG3α2 with antisense RNA targeting MsCSL under 35S promoter and with 35S:KanR cassette was generated using GoldenBraid system. Transformation of *M. sativa* and generation of transgenic hairy roots was performed as described previously (A. Boisson-Dernier, M. Chabaud, F. Garcia, G. Bécard, C. Rosenberg, D. G. Barker, *Agrobacterium rhizogenes*-transformed roots of *Medicago truncatula* for the study of nitrogen-fixing and endomycorrhizal symbiotic associations. Mol Plant Microbe Interact. 14,695-700 (2001)). Instead of Arqua1, ATCC15834 strain of *A. rhizogenes* was used. Transgenic roots were collected, ground and metabolites extracted as described above.

Template-Based Protein Structure Modeling

A homology model of SOAP5 was generated with RaptorX (M. Källberg et al., Template-based protein structure modeling using the RaptorX web server. Nature Protocols. 7, 1511-1522 (2012)) using the crystal structure of *Rhodobacter sphaeroides* cellulose synthase in complex with cyclic-di-GMP and UDP as a template (PDB entry: 4P00)(J. L. Morgan, J. T. McNamara, J. Zimmer, Mechanism of activation of bacterial cellulose synthase by cyclic di-GMP. Nat Struct Mol Biol. 21, 489-96 (2014)). Best model was used as a template for MOLE 2.5, a universal toolkit for automated location and characterization of channels, tunnels and pores (L. Pravda et al., MOLEonline: a web-based tool for analyzing channels, tunnels and pores (2018 update). Nucleic Acids Res. 46, W368-W373 (2018)). Scheme representing transmembrane topology of SOAP5 was generated with Protter (U. Omasits, C. H. Ahrens, S. Müller, B. Wollscheid, Protter: interactive protein feature visualization and integration with experimental proteomic data. Bioinformatics. 30, 884-6 (2014)).

Example 15: Triterpenoid Saponins Biosynthesis Pathway in Spinach

Objective: To discover the triterpenoid saponins biosynthesis pathway in spinach (*Spinacia oleracea*), member of the Caryophyllales, particularly enzymes involved in the glycosylation of triterpenoid saponins.

Methods: Liquid chromatography-Mass spectroscopy methods were used in the analysis of saponins in spinach leaves. See Materials and Methods above.

Figure 19A:
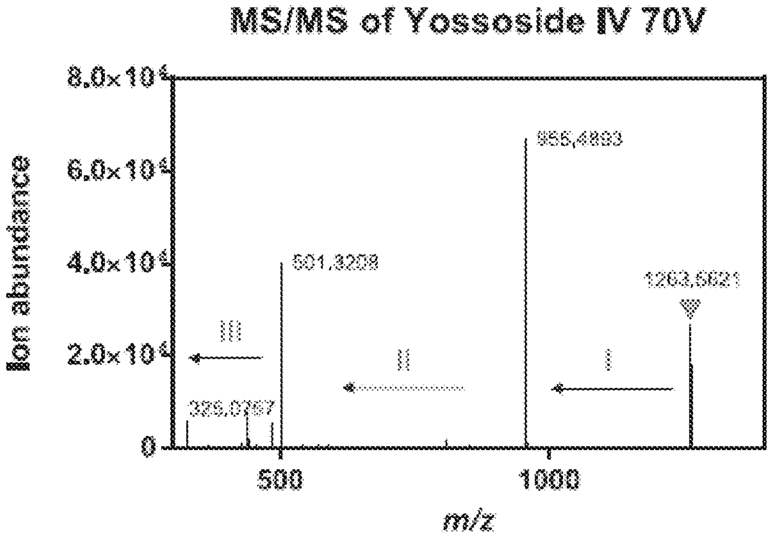
FIGS. 19A-19P provide Tandem mass spectrometry (MS/MS) results and structures of Yossoside IV (FIGS. 19A-19D); of Yossoside Va (FIGS. 19E-19G); of Yossoside V (FIGS. 19H-19J); of Yossoside IX (FIGS. 19K-19M); and of Yossoside X (FIGS. 19N-19P). Details of the MS/MS figures showing results and structures are as follows.
Figure 19E:
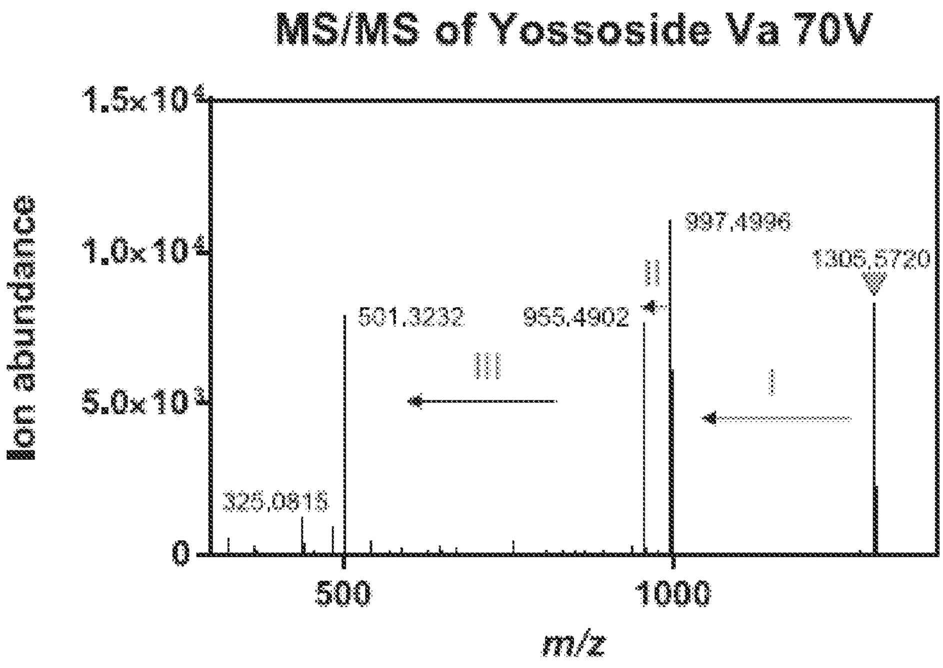
(FIG. 19E) Mass fragments originating from [M-H]1305.57190=—m/z range for 300-1400.
Figure 19F:
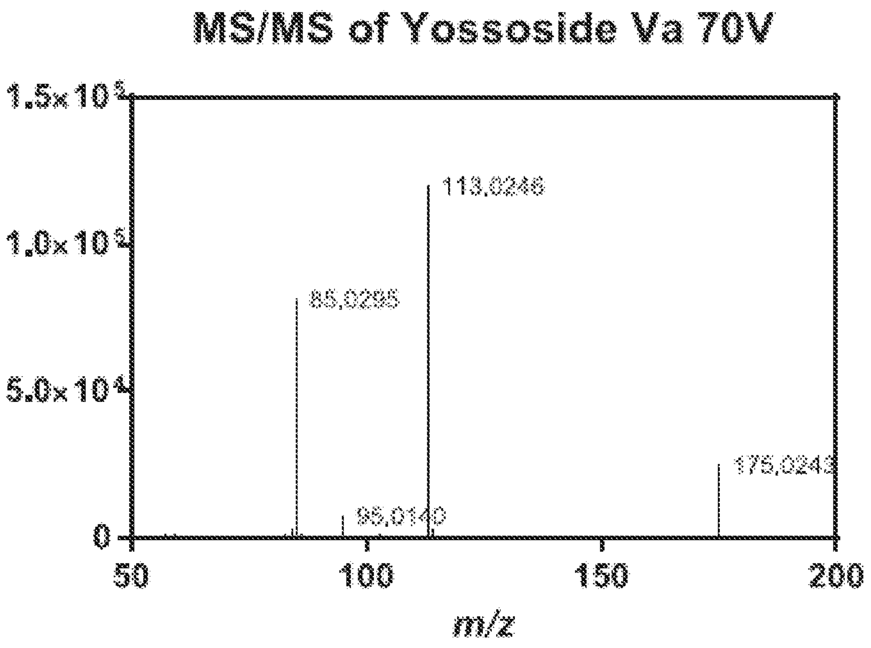
(FIG. 19F) Mass fragments originating from the cleavage of glucuronic acid residue—m/z range for 50-1900.
Figure 19G:
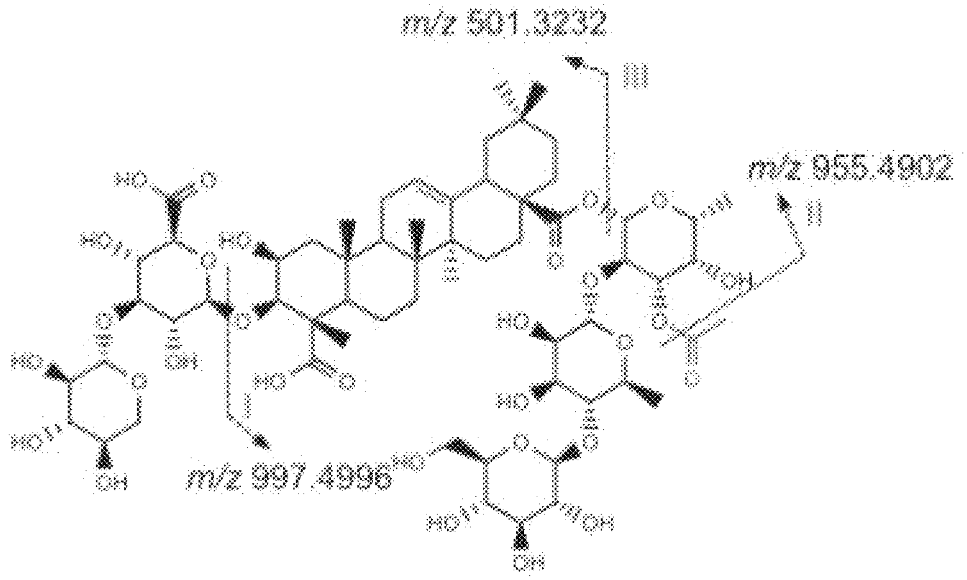
(FIG. 19G) Structure of Yossoside Va, arrows indicate fragmentation patterns. Position of acetyl group is putative.
Figure 19H:
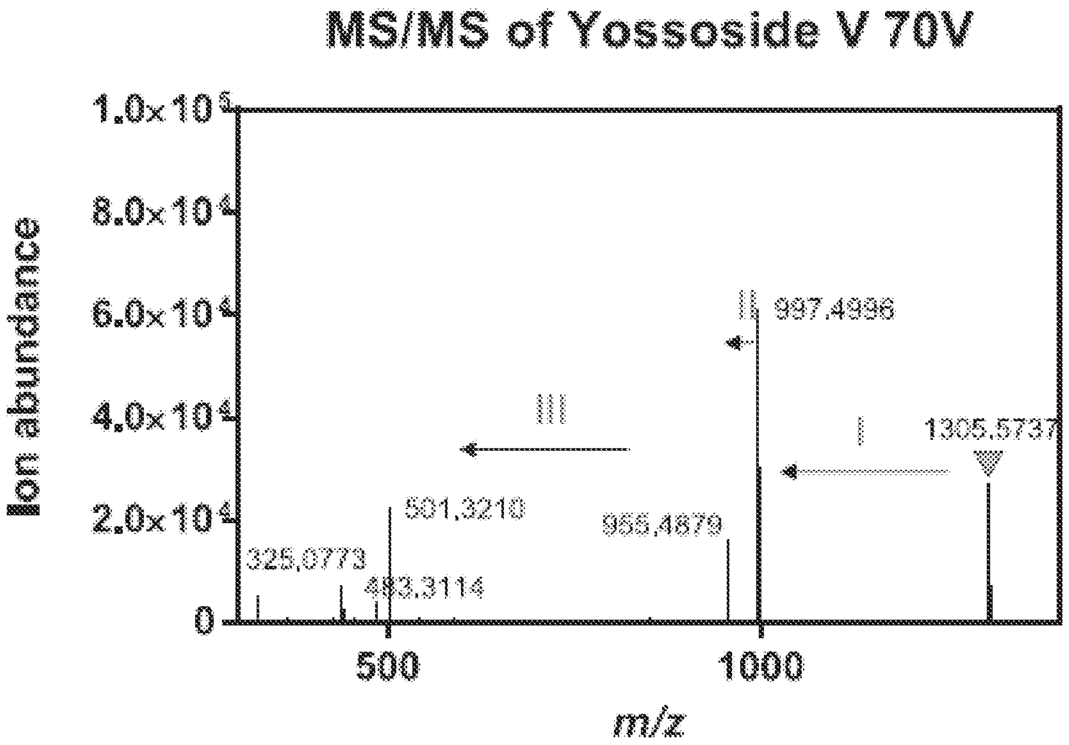
(FIG. 19H) Mass fragments originating from [M-H]1305.5737=—m/z range for 300-1400.
Figure 19I:
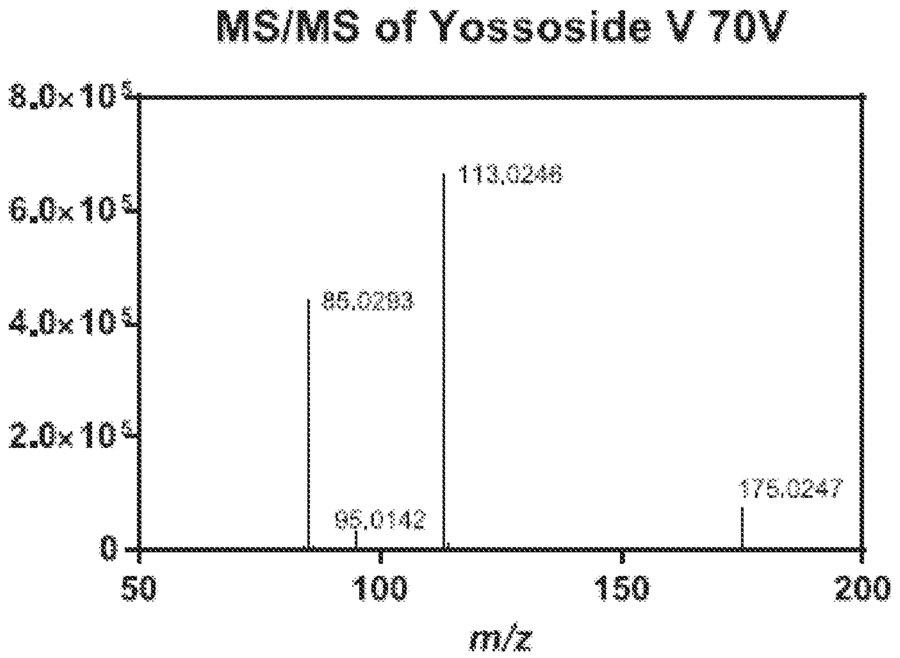
(FIG. 19B) Mass fragments originating from the cleavage of glucuronic acid residue—m/z range for 50-1900.
(FIG. 19C) Structure of Yossoside IV, arrows indicate fragmentation patterns.
(FIG. 19D) Table with assignments of MS/MS peaks originating from the fragmentation of glucuronic acid bound to MA.
(FIG. 19J) Structure of Yossoside V, arrows indicate fragmentation patterns.
(FIG. 19K) Mass fragments originating from [M-H] 1407.6060=—m/z range for 300-1500.
(FIG. 19L) Mass fragments originating from the cleavage of glucuronic acid residue—m/z range for 50-1900.
(FIG. 19M) Structure of Yossoside IX, arrows indicate fragmentation patterns. Structures and places of attachment of pentoses are putative.
(FIG. 19N) Mass fragments originating from [M-H] 1437.6150=—m/z range for 300-1500.
Figure 19J:
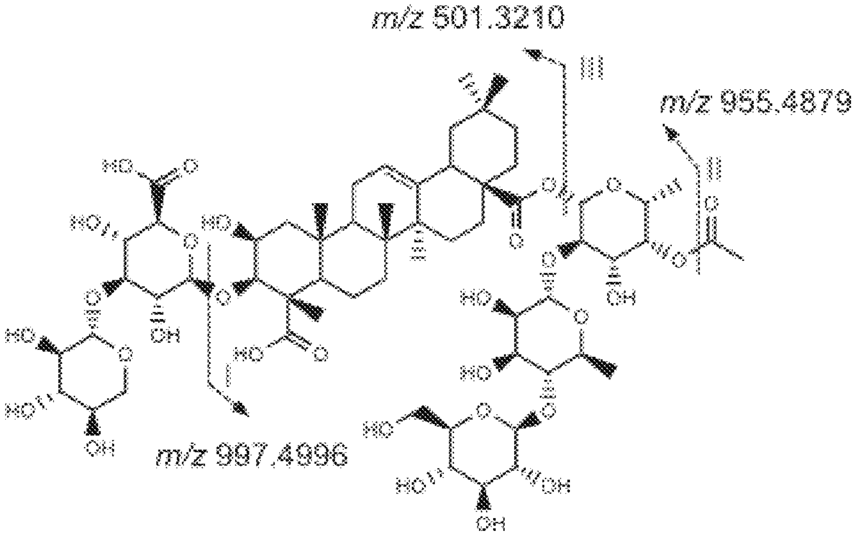
Figure 19K:
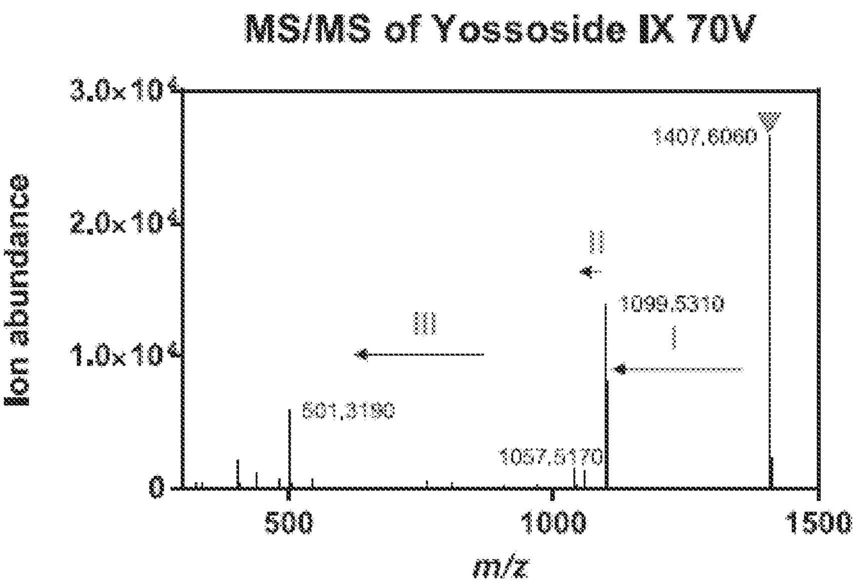
Figure 19L:
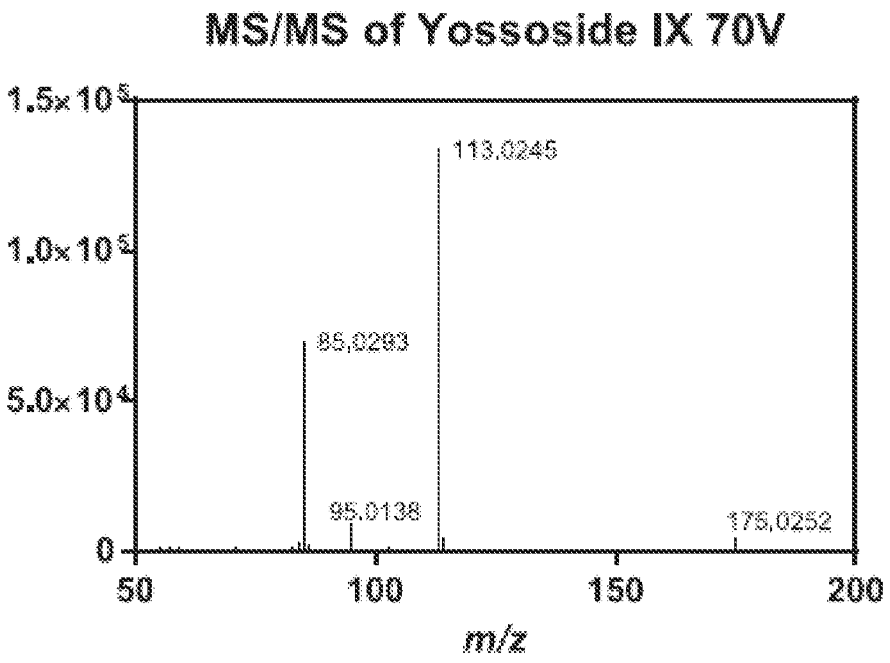
Figure 19M:
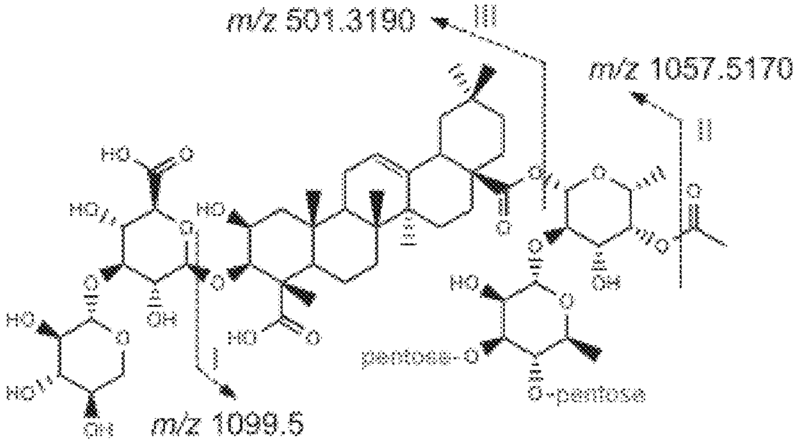
Figure 19N:
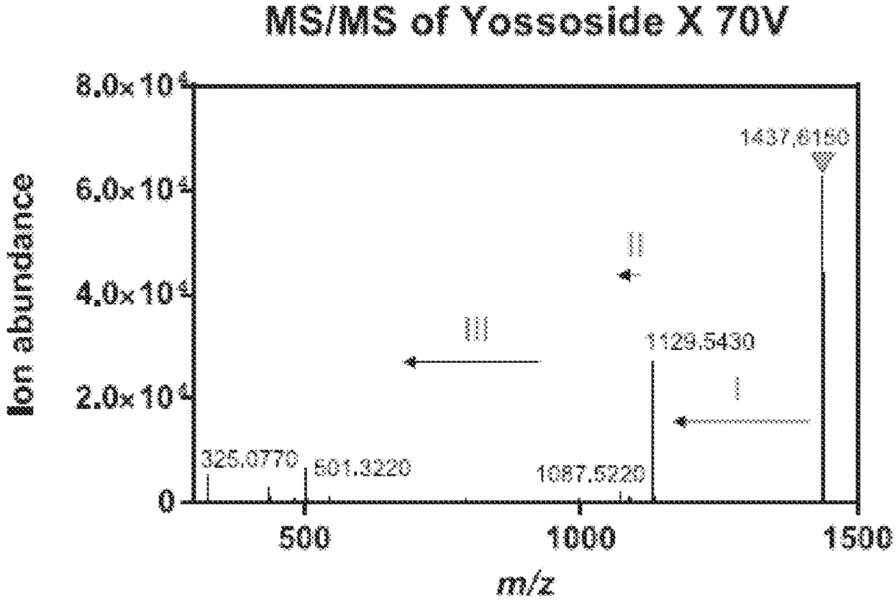
Figure 19O:
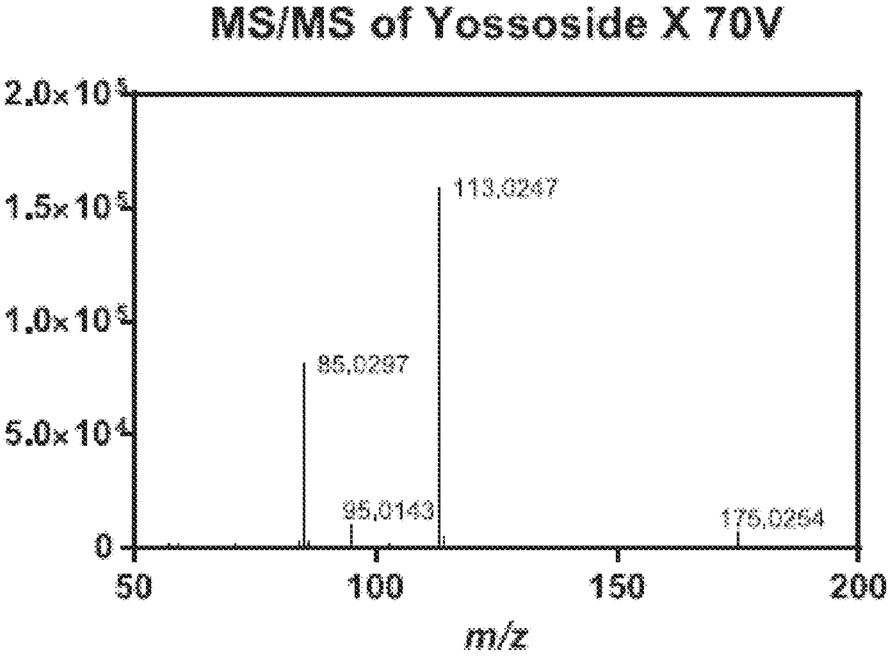
Figure 19P:
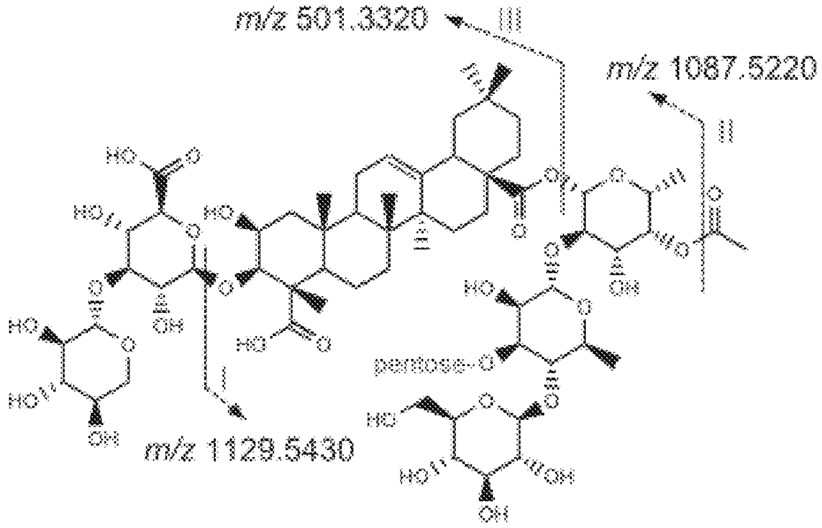

Results:

Analysis of spinach leaves (using LC-MS) revealed a complex triterpenoid saponin mixture (FIG. 18, FIGS. 19A-19P, Table 12) comprising more than 20 molecules with medicagenic acid as an aglycone and approximately half of them were acetylated. Table 13 below provides the details for each compound identified by number in the lower scan of FIG. 18. Table 12 below uses the following terms: Sample—type of experiment/genotype that sample was derived from; Ret. Time—Retention time, in minutes; Putative Name—putative metabolite identification; Mol. Formula—molecular formula of the metabolite or its FA adduct; Theor. m/z—theoretical monoisotopic mass calculated for the ion [M−H]−, [M+H]+; Found m/z—mass found; m/z error (ppm)—difference between theoretical and found m/z values in ppm; MS/MS fragments—fragments, obtained from the ion [M−H]−, [M+H]+; MS/MS CE (eV)—collision energy used for fragmentation; UV/Vis—UV/Vis absorbance maxima. The UV/Vis spectra (200-600 nm) were acquired on a UPLC (Waters, Acquity) instrument equipped with an Acquity 2996 PDA detector under LC conditions as described in the Materials and Methods. (S)—identification confirmed by the standard compound; (NMR)—identification confirmed by NMR; MA—medicagenic acid; AA—augustic acid (2-hydroxy oleanolic acid); B—bayogenin; PG—polygalagenin; OA—oleanolic acid; G—gypsogenin; GA—gypsogenic acid; H—hederagenin; GhA—glycyrrhetinic acid; hexA—hexuronic acid; hex—hexose; dhex—deoxyhexose; pent—pentose; GlcA—glucuronic acid; Ac—acetyl.

TABLE 12

Mass Spectroscopy based identification of triterpenoid saponins in studied plants.
Section A

| | A | B | C | D | E | F | G | H | I | J | K | L | M | N | O |
|---|---|---|---|---|---|---|---|---|---|---|---|---|---|---|---|
| 1 | | Sample | combination of genes expressed in *N. benthamiana* | Ret. Time | Putative Name | Aglycone + sugars | Mol formula | ES(+) Theor m/z [M + H]$^+$ | ES(+) Found m/z [M + H]$^+$ | m/z error (ppm) | ES(-) Theor m/z [M - H]$^-$ | ES(-) Found m/z [M - H]$^-$ | m/z error (ppm) | MS/MS ES(+) frag-ments | MS/MS ES(+) CE (eV) |
| 2 | Spinach | WT | — | 13.7 | | MA + dhex + dhex + pent + hexA | C53 H82 O24 | — | — | — | 1101.5118 | 1101.5116 | −0.2 | — | — |
| 3 | Spinach | | — | 12.5 | Yossoside VI | MA + dhex + dhex + hex + hexA | C54 H84 O25 | — | — | — | 1131.5223 | 1131.5261 | −1.9 | — | — |
| 4 | Spinach | | — | 19.4 | | MA + dhex + dhex + Ac + pent + hexA | C55 H84 O25 | — | — | — | 1143.5223 | 1143.5265 | 3.7 | — | — |
| 5 | Spinach | | — | 14.7 | Yossoside XII | MA + dhex + dhex + pent + pent + hexA | C58 H90 O28 | — | — | — | 1233.5599 | 1233.5554 | 1.1 | — | — |
| 6 | Spinach | | — | 12.8 | Yossoside IV | MA + dhex + dhex + hex + pent + hexA | C59 H92 O29 | — | — | — | 1263.5646 | 1263.5713 | 0.6 | — | — |
| 7 | Spinach | | — | 20.84 | Yossoside VII | MA + dhex + dhex + Ac + pent + pent + hexA | C60 H92 O29 | — | — | — | 1275.5646 | 1275.5640 | −0.5 | — | — |
| 8 | Spinach | | — | 15.8 | Yossoside Va | MA + dhex + dhex + Ac + hex + pent + hexA | C61 H94 O30 | — | — | — | 1305.5752 | 1305.5773 | 1.6 | — | — |
| 9 | Spinach | | — | 18.6 | Yossoside V (NMR) | MA + dhex + dhex + Ac + hex + pent + hexA | C61 H94 O30 | — | — | — | 1305.5752 | 1305.5781 | 2.2 | — | — |
| 10 | Spinach | | — | 14.2 | Yossoside VIII | MA + dhex + dhex + pent + pent + pent + hexA | C63 H98 O32 | — | — | — | 1365.5963 | 1365.5981 | 1.3 | — | — |
| 11 | Spinach | | — | 12.4 | Yossoside XI | MA + dhex + dhex + hex + pent + pent + hexA | C64 H100 O33 | — | — | — | 1395.6069 | 1395.6068 | −0.1 | — | — |
| 12 | Spinach | | — | 18.9 | Yossoside IX | MA + dhex + dhex + Ac + pent + pent + pent + hexA | C65 H100 O33 | — | — | — | 1407.6069 | 1407.6107 | 2.7 | — | — |
| 13 | Spinach | | — | 16.7 | Yossoside X | MA + dhex + dhex + Ac + hex + pent + pent + hexA | C66 H102 O34 | — | — | — | 1437.6174 | 1437.6160 | 0.6 | — | — |
| 14 | | | | | | | | | | | | | | | |
| 15 | Spinach | VIGS - CYPs | — | 16.6 | | AA + hex + hexA | C42 H66 O15 | — | — | — | 809.4323 | 809.4337 | 1.7 | — | — |
| 16 | Spinach | | — | 10.3 | | B + hex + hexA | C42 H66 O16 | — | — | — | 825.4273 | 825.4278 | 0.6 | — | — |
| 17 | Spinach | | — | 15.4 | | AA + hex + pent + hexA | C47 H74 O19 | — | — | — | 941.4746 | 941.4737 | −1.0 | — | — |
| 18 | Spinach | | — | 15.4 | | AA + hex + hexA + 3-oxopyruvic acid and glycolic acid isomer 1 | C47 H70 O21 | — | — | — | 969.4331 | 969.4326 | −0.5 | — | — |
| 19 | Spinach | | — | 16.2 | | AA + hex + hexA + 3-oxopyruvic acid and glycolic acid isomer 2 | C47 H70 O21 | — | — | — | 969.4331 | 969.4327 | −0.4 | — | — |

TABLE 12-continued

| | | | | | | | | | | | | | | | |
|---|---|---|---|---|---|---|---|---|---|---|---|---|---|---|---|
| 20 | Spinach | | — | 13.1 | | AA + hex + hex + hexA | C48 H76 O20 | — | — | — | 971.4852 | 971.4866 | 1.4 | — | — |
| 21 | Spinach | | — | 14.4 | | AA + hex + pent + pent + hexA | C52 H82 O23 | — | — | — | 1073.5169 | 1073.5216 | 4.4 | — | — |
| 22 | Spinach | | — | 11.6 | | PG + hex + pent + pent + hexA | C52 H80 O24 | — | — | — | 1087.4961 | 1087.4990 | 2.7 | — | — |
| 23 | Spinach | | — | 18.7 | Yossoside VIIa | MA + dhex + dhex + Ac + pent + pent + hexA | C60 H92 O29 | — | — | — | 1275.5646 | 1275.5675 | 2.3 | — | — |
| 24 | Spinach | | — | 17.2 | | OA + hex + hexA + 3-oxopyruvic acid and glycolic acid (Betavulgaroside I) isomer 1 | C47 H70 O20 | — | — | — | 953.4382 | 953.4366 | −1.7 | — | — |
| 25 | Spinach | | — | 18.4 | | OA + hex + hexA + 3-oxopyruvic acid and glycolic acid (Betavulgaroside I) isomer 2 | C47 H70 O20 | — | — | — | 953.4382 | 953.4369 | −1.4 | — | — |
| 26 | Spinach | | — | 14.6 | | G + hex + hexA + 3-oxopyruvic acid and glycolic acid (Basellasaponin B) | C47 H68 O21 | — | — | — | 967.4175 | 967.4183 | 0.8 | — | — |
| 27 | Spinach | | — | 16.1 | | GA + hex + pent + dhex + dhex + hexA | C59 H92 O28 | — | — | — | 1247.5697 | 1247.5695 | −0.2 | — | — |
| 28 | Spinach | | — | 21.2 | | GA + hex + pent + dhex + dhex + Ac + hexA | C61 H94 O29 | — | — | — | 1289.5803 | 1289.5781 | −1.7 | — | — |
| 29 | | | | | | | | | | | | | | | |
| 30 | Spinach | VIGS - GTs + CSL | — | 10.74 | | MA + hex + hexA + 3-oxopyruvic acid and glycolic acid isomer 1 | C47 H68 O23 | — | — | — | 999.4073 | 999.4097 | 2.4 | — | — |
| 31 | Spinach | | — | 11.90 | | MA + hex + hexA + 3-oxopyruvic acid and glycolic acid isomer 2 | C47 H68 O23 | — | — | — | 999.4081 | 999.4097 | 1.6 | — | — |
| 32 | Spinach | | — | 15.30 | | MA + dhex + hexA + 3-oxopyruvic acid and glycolic acid | C47 H68 O22 | — | — | — | 983.4124 | 983.4155 | 3.2 | — | — |
| 33 | Spinach | | — | 15.31 | | MA + hexA + dhex + pent (Betavulgaroside III) | C47 H72 O20 | — | — | — | 955.4539 | 955.4543 | 0.4 | — | — |
| 34 | Spinach | | — | 11.00 | | MA + pent + hex + hexA | C47 H72 O21 | — | — | — | 971.4488 | 971.4506 | 1.9 | — | — |
| 35 | Spinach | | — | 13.40 | | MA + dhex + dhex + hexA | C48 H74 O20 | — | — | — | 969.4695 | 969.4661 | −3.5 | — | — |
| 36 | Spinach | | — | 17.10 | | OA + hexA + hex + pent | C47 H74 O18 | — | — | — | 925.4797 | 925.4789 | −0.9 | — | — |
| 37 | Spinach | | — | 12.50 | | AA/H + hexA + hex | C42 H66 O15 | — | — | — | 809.4323 | 809.4335 | 1.5 | — | — |
| 38 | Spinach | | — | 14.62 | | G + hexA + hex | C42 H64 O15 | — | — | — | 807.4167 | 807.4156 | −1.4 | — | — |
| 39 | Spinach | | — | 12.90 | | GA/PG + hex + hexA | C42 H64 O16 | — | — | — | 823.4116 | 823.4129 | 1.6 | — | — |

TABLE 12-continued

| | | | | | | | | | | | | | | | |
|---|---|---|---|---|---|---|---|---|---|---|---|---|---|---|---|
| 40 | Spinach | | — | 10.00 | | MA + dhex + pent + pent + hex + hexA | C58 H90 O29 | — | — | — | 1249.5490 | 1249.5537 | 3.8 | — | — |
| 41 | Spinach | | — | 8.50 | | MA + dhex + hex + hex + hexA | C54 H84 O26 | — | — | — | 1147.5173 | 1147.5226 | 4.6 | — | — |
| 42 | Spinach | | — | 9.80 | | MA + dhex + pent + hex + hexA | C53 H82 O25 | — | — | — | 1117.5067 | 1117.5078 | 1.0 | — | — |
| 43 | Spinach | | — | 11.00 | | MA + hex + hexA | C42 H64 O17 | — | — | — | 839.4065 | 839.4077 | 1.4 | — | — |
| 44 | Spinach | | — | 21.10 | | MA + pent + hexA | C41 H62 O16 | — | — | — | 809.3960 | 809.3938 | −2.7 | — | — |
| 45 | Spinach | | — | 15.25 | | PG/GA + hex + hexA | C42 H64 O16 | — | — | — | 823.4116 | 823.4132 | 1.9 | — | — |
| 46 | Spinach | | — | 13.20 | | MA + dhex + dhex + pent + pent + hexA | C58 H90 O28 | — | — | — | 1233.5540 | 1233.5499 | −3.3 | — | — |
| 47 | Spinach | | — | 17.60 | | MA + dhex + dhex + Ac + pent + pent + hexA | C60 H92 O29 | — | — | — | 1275.5646 | 1275.5627 | −1.5 | — | — |
| 48 | Spinach | | — | 11.15 | | MA + hex + hex | C42 H66 O16 | — | — | — | 825.4273 | 825.4283 | 1.2 | — | — |
| 49 | Spinach | | — | 22.73 | | MA | C30 H46 O6 | 503. 3373 | 503. 3365 | −1.6 | 501.3216 | 501.3217 | 0.2 | see FIG. S19 | 25 |
| 50 | | | | | | | | | | | | | | | |
| 51 | *Medicago sativa* | Differ- ential | — | 21.61 | Saponin 1 | B + hex + hex + hexA | C48 H76 O21 | — | — | — | 987.4801 | 987.4788 | −1.3 | — | — |
| 52 | *Medicago sativa* | signals form | — | 25.63 | Saponin 2 | B + hex + hexA | C42 H66 O16 | — | — | — | 825.4273 | 825.4273 | 0.0 | — | — |
| 53 | *Medicago sativa* | *M. sativa* hairy | — | 23.04 | Saponin 3 | Soyasapogenol A + dhex + hex + hexA | C48 H78 O19 | — | — | — | 957.5059 | 957.5059 | −0.2 | — | — |
| 54 | *Medicago sativa* | roots with | — | 24.11 | Saponin 4 | GA/PG + hex + hexA + malonyl | C45 H66 O19 | — | — | — | 909.4120 | 909.4120 | 0.0 | — | — |
| 55 | *Medicago sativa* | silenced MsCSL | — | 25.23 | Saponin 5 | B + dhex + hex + hexA | C48 H76 O20 | — | — | — | 971.4852 | 971.4849 | −0.3 | — | — |
| 56 | *Medicago sativa* | | — | 22.84 | Saponin 6 | H + hex + hex + dhex + hexA | C54 H86 O24 | — | — | — | 1117.5431 | 1117.5420 | −1.0 | — | — |
| 57 | *Medicago sativa* | | — | 22.92 | Saponin 7 | GA/PG + hex + hexA | C42 H64 O16 | — | — | — | 823.4116 | 823.4078 | −4.6 | — | — |
| 58 | *Medicago sativa* | | — | 28.14 | Saponin 8 | Soyasapogenol B + dhex + hex + hex + hexA | C54 H88 O23 | — | — | — | 1103.5638 | 1103.5635 | −0.3 | — | — |
| 59 | | | | | | | | | | | | | | | |
| 60 | *Beta vulgaris* | Differ- ential | | 14.95 | BvSaponin 1 (betavulgaroside V) | OA + hexA + hex + hex + Act | C53 H82 O25 | — | — | — | 1117.5067 | 1117.5060 | −0.6 | — | — |
| 61 | *Beta vulgaris* | signals from | | 15.24 | BvSaponin 2 | OA + hexA + hex + hex + pent | C53 H84 O23 | — | — | — | 1087.5325 | 1087.5316 | −0.8 | — | — |
| 62 | *Beta vulgaris* | *B. vulgaris* | | 15.67 | BvSaponin 3 (belavulgaroside IX) | OA + hexA + hex + pent + Act | C52 H80 O24 | — | — | — | 1087.4961 | 1087.4978 | 1.6 | — | — |
| 63 | *Beta vulgaris* | with silenced | | 16.95 | BvSaponin 4 | OA + hex + pent + hexA | C47 H74 O18 | — | — | — | 925.4773 | 925.4782 | −1.6 | — | — |
| 64 | *Beta vulgaris* | BvCSL | | 17.54 | BvSaponin 5 (betavulgaroside III) | OA + hexA + hex + Act | C47 H72 O20 | — | — | — | 955.4539 | 955.4536 | −0.3 | — | — |
| 65 | | | | | | | | | | | | | | | |
| 66 | Expression in *N. benthamiana* | genes from | SOAP1-4 + SOAP5 | 20.98 | medicagenic acid 3-O-glucuronide (NMR) | MA + GIcA | C36 H54 O12 | — | — | — | 677.3543 | 677.3522 | −2.2 | — | — |

TABLE 12-continued

| | | | | | | | | | | | | | | | |
|---|---|---|---|---|---|---|---|---|---|---|---|---|---|---|---|
| 67 | Expression in *N. benthamiana* | spinach | SOAP1-5 + SOAP6 | 14.96 | Yossoside I | MA + GlcA + Fuc | C42 H64 O16 | — | — | — | 823.4116 | 823.4104 | −1.5 | — | — |
| 68 | Expression in *N. benthamiana* | | SOAP1-6 + SOAP7 | 13.21 | Yossoside II | MA + GlcA + Fuc + Rha | C48 H74 O20 | — | — | — | 969.4695 | 969.4693 | −0.2 | — | — |
| 69 | Expression in *N. benthamiana* | | SOAP1-7 + SOAP8 | 12.08 | Yossoside III | MA + GlcA + Fuc + Rha + Glc | C54 H84 O25 | — | — | — | 1131.5200 | 1131.5199 | −0.1 | — | — |
| 70 | Expression in *N. benthamiana* | | SOAP1-8 + SOAP9 | 12.37 | Yossoside IV | MA + GlcA + Fuc + Rha + Glc + Xyl | C59 H92 O29 | — | — | — | 1263.5646 | 1263.5649 | 0.2 | — | — |
| 71 | Expression in *N. benthamiana* | | SOAP1-9 + SOAP10 | 18.18 | Yossoside V | MA + GlcA + Fuc + Ac + Rha + Glc + Xyl | C61 H94 O30 | — | — | — | 1305.5752 | 1305.5736 | −1.2 | — | — |
| 72 | | | | | | | | | | | | | | | |
| 73 | Expression in *N. benthamiana* | genes from | bAS + CYP72A154 + CYP88D6 + GuCSL | 17.2 | glycyrrhetinic acid 3-O-glucuronide | GhA + GlcA | C36 H54 O10 | — | — | — | 645.3644 | 645.3644 | 0.1 | — | — |
| 74 | Expression in *N. benthamiana* | *G. uralensis* | bAS + CYP72A154 + CYP88D6 + GuCSL | 19.0 | glycyrrhetinic acid 3-O-glucuronide | GhA + GlcA | C36 H54 O10 | — | — | — | 645.3644 | 645.3636 | 1.2 | — | — |
| 75 | | | | | | | | | | | | | | | |
| 76 | Expression in *N. benthamiana* | | bAS + CYP72A154 + CYP88D6 + SOAP5 | 17.2 | glycyrrhelinic acid 3-O-glucuronide | GhA + GlcA | C36 H54 O10 | — | — | — | 645.3644 | 645.3648 | −0.6 | — | — |
| 77 | Expression in *N. benthamiana* | | bAS + CYP72A154 + CYP88D6 + SOAP5 | 19.0 | glycyrrhelinic acid 3-O-glucuronide | GhA + GlcA | C36 H54 O10 | — | — | — | 645.3644 | 645.3659 | −2.3 | — | — |
| 78 | | | | | | | | | | | | | | | |
| 79 | Expression in *N. benthamiana* | | bAS + CYP72A154 + CYP88D6 + GuCSL + UGT73P12 | 11.8 | glycyrrhizin isomer 1 (S) | GhA + GlcA + GlcA | C42 H62 O16 | — | — | — | 821.3965 | 821.3963 | 0.3 | — | — |
| 80 | Expression in *N. benthamiana* | | bAS + CYP72A154 + CYP88D6 + GuCSL + UG173P12 | 13.4 | glycyrrhizin isomer 2 (S) | GhA + GlcA + GlcA | C42 H62 O16 | — | — | — | 821.3965 | 821.3960 | 0.6 | — | — |
| 81 | | | | | | | | | | | | | | | |
| 82 | Expression in *N. benthamiana* | | SOAP1-4 + GuCSL | 14.2 | medicagenic acid 3-O-glucuronide (S) | MA + GlcA | C36 H54 O12 | — | — | — | 677.3543 | 677.3535 | 1.0 | — | — |

Section B

| | A | B | P | Q | R | S | T |
|---|---|---|---|---|---|---|---|
| 1 | | Sample | MS/MS ES(−) fragments | MS/MS ES(−) CE (eV) | UV/Vis | Detected in other species | Ref-erences |
| 2 | Spinach | WT | 969.4370 [M pent H]-; 955.4099 [M dhex H]-; 793.4330 [M hexA pent H]-; 501.3204 [M-hexA-pent-dhex-dhex-H]- | ramp 15-50 eV | — | — | — |
| 3 | Spinach | | 955.4599 [M-hexA-H]-; 823.4120 [M-hex-dhex-H]-; 677.3536 [M-hex-dhex-dhex-H]-; 501.3264 [M-hex-dhex-dhex-hexA-H]- | ramp 15-50 eV | — | — | — |

TABLE 12-continued

| | | | | | | |
|---|---|---|---|---|---|---|
| 4 | Spinach | 1011.4806 [M-pent-H]-; 835.4438 [M-pent-hexA-H]-; | ramp 15-50 eV | — | — | — |
| 5 | Spinach | 925.4760 [M-hexA-pent-H]-; 501.3236 [M-hexA-pent-pent-dhex-dhex-H]- | 70 | — | — | — |
| 6 | Spinach | 955.4893 [M-hexA-pent-H]-; 809.3924 [M-hexA-pent-dhex-H]-; 501.3208 [M-hexA-pent-hex-dhex-dhex-H]- | 70 | — | — | — |
| 7 | Spinach | 1143.5160 [M-pent-]-; 1011.4427 [M-pent-pent-H]-; 967.4788 [M-pent-hexA-H]-; 823.4001 [M-pent-pent-dhex-Ac-H]-; 677.3595 [M-pent-pent-dhex-Ac-dhex-H]-; 501.3212 [M-pent-pent-dhex-Ac-dhex-hexA-H]- | ramp 15-50 eV | — | — | — |
| 8 | Spinach | 997.4996 [M-hexA-pent-H]-; 955.4902 [M-hexA-pent-Ac-H]-; 501.3232 [M-hexA-pent-dhex-dhex-Ac-hex-H] | 70 | — | — | — |
| 9 | Spinach | 997.4996 [M-hexA-pent-H]-; 955.4879 [M-hexA-pent-Ac-H]-; 501.3210 [M-hexA-pent-dhex-dhex-Ac-hex-H] | 70 | — | — | — |
| 10 | Spinach | 1057.5228 [M-hexA-pent-H]-; 925.4678 [M-hexA-pent-pent-H]-; 647.3792 [M-hexA-pent-pent-pent-dhex-H]-; 501.3193 [M-hexA-pent-pent-pent-dhex-dhex-H]- | 70 | — | — | — |
| 11 | Spinach | 1263.5773 [M-pent-H]-; 1087.5323 [M-hexA-pent-H]-; 955.4877 [M-hexA-pent-pent-H]-; 809.3958 [M-hexA-pent-pent-dhex-H]-; 501.3225 [M-hexA-pent-pent-dhex-dhex-hex-H]- | 70 | — | — | — |
| 12 | Spinach | 1099.5310 [M-hexA-pent-H]-; 1057.5170 [M-hexA-pent-Ac-H]-; 501.3190 [M-hexA-pent-pent-pent-dhex-Ac-dhex-H]- | 70 | — | — | — |
| 13 | Spinach | 1129.5430 [M-pent-hexA-H]-; 1087.5220 [M-pent-hexA-Ac-H]-; 501.3220 [M-hexA-pent-pent-hex-dhex-Ac-dhex-H]- | 70 | — | — | — |

TABLE 12-continued

| | | | | | | | | |
|---|---|---|---|---|---|---|---|---|
| 14 | | | | | | | | |
| 15 | Spinach | VIGS - CYPs | 647.3809 [M-hex-H]-; 603.3903 [M-hex-CO2-H]-; 585.3805 [M-hex-CO2-H2O-H]-; 471.3473 [M-hex-hexA-H]- | 60 | — | — | — | |
| 16 | Spinach | | 663.3741 EM-hex-H]-; 619.3843 [M-hex-CO2 + 301]-; 601.3750 [M-hex-CO2-H2O-H]-; 487.3431 [M-hex-hexA-H]- | ramp 15-50 eV | — | — | — | |
| 17 | Spinach | | 809.4302 [M-pent-H]-; 647.3781 [M-pent-hex-H]-; 603.3877 [M-pent-hex-CO2H]-; 585.3781 [M-pent-hex-CO2-H2O-N-; 471.3474 [M-pent-hex-hexA-H]- | ramp 15-50 eV | — | — | — | |
| 18 | Spinach | | 809.4344 [M-oxopyruvic and glycolic acid-H]-; 647.3788 [M-hex-oxopyruvic and glycolic acid-H]-; 585.3795 [M-hex-oxopyruvic and glycolic acid-CO2-H2O-H]-; 471.3475 [M-hex-oxopyruvic and glycolic acid-hexA-H]- | 60 | — | — | — | |
| 19 | Spinach | | 809.4325 [M-oxopyruvic and glycolic acid-H]-; 647.3788 [M-hex-oxopyruvic and glycolic acid-H]-; 585.3802 [M-hex-oxopyruvic and glycolic acid-CO2- | ramp 15-50 eV | — | — | — | |
| 20 | Spinach | | 809.4267 [M-hex-H]-; 417.3479 [M-hex-hex-hexA-H]- | ramp 15-50 eV | — | — | — | |
| 21 | Spinach | | 911.4585 [M-hex-H]-; 647.3829 [M-hex-pent-pent-H]-; 471.3446 [M-hex-pent-pent-hexA-H]- | ramp 15-50 eV | — | — | — | |
| 22 | Spinach | | 955.4252 [M-pent H]-; 925.4381 [M-hex-H]-; 617.3693 [M-hex-pent-hexA-H]-; 485.3267 [M-hex-pent-pent-hexA-H]- | ramp 15-50 eV | — | — | — | |
| 23 | Spinach | | 1143.5077 [M-pent- ]-; 1011.4468 [M-pent-pent-H]-; 677.3535 [M-pent-pent-dhex-Ac-dhex-H]-; 501.3269 [M-pent-pent-dhex-Ac-dhex-hexA-H]- | ramp 15-50 eV | — | — | — | |
| 24 | Spinach | | 793.4354 [M-oxopyruvic and glycolic acid-H]-; 631.3831 [M-oxopyruvic and glycolic acid-hex-H]-; 569.3835 [M-oxopyruvic and glycolic acid-hex-CO2-H2O-H]-; 455.3514 [M- | 60 | — | *Beta vulgaris*/ *Basella rubra* | (54) | |

TABLE 12-continued

| | | | | | | | |
|---|---|---|---|---|---|---|---|
| | | | oxopyruvic and glycolic acid-hex-hexA-H]- | | | | |
| 25 | Spinach | | 793.4374 [M-oxopyruvic and glycolic acid-H]-; 631.3844 [M-oxopyruvic and glycolic ac-hex-H]-; 569.3845 [M-oxopyruvic and glycolic acid-hex-CO2-H2O-H]-; 455.3517 [M-oxopyruvic and glycolic acid-hex-hexA-H]- | ramp 15-50 eV | — | *Beta vulgaris*/ *Basella rubra* | (54) |
| 26 | Spinach | | 807.4161 [M-oxopyruvic and glycolic acid-H]-; 645.3607 [M-oxopyruvic and glycolic ac-hex-H]-; 583.3608 [M-oxopyruvic and glycolic acid-hex-CO2-H2O-H]-; 469.3307 [M-oxopyruvic and glycolic acid-hex-hexA-H]- | 60 | — | *Basella rubra* | (55) |
| 27 | Spinach | | 1115.5173 [M-pent-H]-; 969.4326 [M dhex-pent-H]; 939.4197 [M-hex-dhex-H]-; 823.4352 [M-dhex-pent-dhex-H]-; 485.3267 [M-pent-hex-dhex-dhex-hexA-H]- | ramp 15-50 eV | — | — | — |
| 28 | Spinach | | 969.4322 [M-dhex-pent-Ac-H]-; 939.4189 [M-hex-dhex-Ac-H]-; 823.4349 [M-dhex-pent-dhex-Ac-H]-; 485.3265 [M-pent-hex-dhex-dhex-hexA-Ac-H]- | ramp 15-50 eV | — | — | — |
| 29 | | | | | | | |
| 30 | Spinach | VIGS - GTs + CSL | 955.4204 [M-CO2-H]-; 897.4148 [M-CO2-C2H2O2-H]-; 839.4088 [M-CO2-C2H2O2-C2H2O2-H]-; 677.3586 [M-oxopyruvic and glycolic acid-hex-H]-; 663.3751 [M-oxopyruvic and glycolic acid-hexA-H]-; 501.3274 [M-oxopyruvic and glycolic acid-hex-hexA-H]- | ramp 15-50 eV | — | — | — |
| 31 | Spinach | | 955.4201 [M-CO2-H]-; 897.4130 [M-CO2-C2H2O2-H]-; 839.4070 [M-CO2-C2H2O2-C2H2O2-H]-; 677.3503 [M-oxopyruvic and glycolic acid-hex-H]-; 663.3727 [M-oxopyruvic and glycolic acid-hexA-H]-; 501.3252 [M-oxopyruvic and glycolic acid-hex-hexA-H]- | ramp 15-50 eV | — | — | — |

TABLE 12-continued

| | | | | | | |
|---|---|---|---|---|---|---|
| 32 | Spinach | 939.4240 [M CO2-H]-; 881.4178 [M-CO2-C2H2O2-H]-; 823.4127 [M-CO2-C2H2O2-C2H2O2-H]-; 677.3565 [M-oxopyruvic and glycolic acid-dhex-H]-; 647.3713 [M-oxopyruvic and glycolic acid-hexA-H]-; 501.3176 [M-oxopyruvic and glycolic acid-hex-hexA-H]- | ramp 15-50 eV | — | — | — |
| 33 | Spinach | 647.3743 [M-hexA-pent-H]-; 501.3240 [M-hexA-pent-dhex-H]- | 50 | — | *Beta vulgaris* | (56) |
| 34 | Spinach | 663.3754 [M-hexA-pent-H]-; 501.3202 [M-hexA-pent-hex] | 50 | — | — | — |
| 35 | Spinach | 823.4380 [M-dhex-H]-; 677.3533 [M-dhex-dhex-H]-; 501.3225 [M-dhex-dhex-hexA-H]- | ramp 15-50 eV | — | — | — |
| 36 | Spinach | 793.4344 [M-pent-H]-; 631.3828 [M-pent-hex-H]-; 569.3834 [M-pent-hex-CO2-H2O-H]-; 455.3518 [M-pent-hex-hexA-H]- | ramp 15-50 eV | — | — | — |
| 37 | Spinach | 647.3774 [M-hex-H]-; 471.3475 [M-hex-hexA-H]- | ramp 15-50 eV | — | — | — |
| 38 | Spinach | 645.3638 [M-hex-H]-; 469.3323 [M-hex-hexA-H]- | ramp 15-50 eV | — | — | — |
| 39 | Spinach | 661.3593 [M-hex-H]-; 647.3801 [M-hexA-H]-; 617.3719 [M-hex-CO2-H-; 599.3574 [M-hex-CO2-H2O-H]-; 485.3271 [M-hex-hexA-H]- | ramp 15-50 eV | — | — | — |
| 40 | Spinach | 1117.5071 [M-pent-H]-, 985.4347 [M-pent-pent-H]-; 809.4266 [M-pent-hex-dhex-H]-; 501.3194 [M-hexA-hex-pent-pent-dhex-H]- | ramp 15-50 eV | — | — | — |
| 41 | Spinach | 985.4608 [M-hex-H]-; 823.3881 [M-hex-hex-H]-; 677.3605 [M-hex-hex-dhex-H]-; 501.3212 [M-hex-hex-dhex-hexA-H]- | ramp 15-50 eV | — | — | — |
| 42 | Spinach | 985.4552 [M-pent H]-; 955.4471 [M-hex-H]-; 677.3557 [M-pent-hex-dhex-H]; 501.3250 [M-pent-hex-dhex-hexA-H]- | ramp 15-50 eV | — | — | — |

TABLE 12-continued

| | | | | | | | |
|---|---|---|---|---|---|---|---|
| 43 | Spinach | | 677.3486 [M-hex H]-, 501.3224 [M-hex-hexA-N]- | ramp 15-50 eV | — | — | — |
| 44 | Spinach | | 501.3207 [M-hexA-pent-H]-; 325.0773 [hexA + pent-H2O-H]- | ramp 15-50 eV | — | — | — |
| 45 | Spinach | | 661.3582 [M-hex-H]-; 647.3805 [M-hexA-H]-; 617.3690 [M-hex-CO2-H-; 599.3580 [M-hex-CO2-H2O-H]-; 485.3252 [M-hex-hexA-H]- | 50 | — | — | — |
| 46 | Spinach | | 925.4778 [M-hexA-pent-H]-; 501.3233 [M-hexA-pent-dhex-dhex-pent-H]- | 70 | — | — | — |
| 47 | Spinach | | 1143.5116 [M-pent-H]-; 1101.5002 [M-pent-Ac-H]-; 955.4487 [M-pent-Ac-dhex-H]-; 967.4825 [M-pent-hexA-H]-; 793.4345 [M-pent-hexA-pent-Ac-H]-; 501.3212 [M-dhex-dhex-Ac-pent-pent-hexA-H]- | ramp 15-50 eV | — | — | — |
| 48 | Spinach | | 663.3739 [M-hex-H]-; 501.3222 [M-hex-hex-H]- | ramp 15-50 eV | — | — | — |
| 49 | Spinach | | | | — | — | — |
| 50 | | | | | | | |
| 51 | *Medicago sativa* | Differ-ential signals form *M. sativa* | 825.4302 [M-hex-H]-; 663.3773 [M-hex-hex-H]-; 487.3424 [M0hex-hex-hexA-H]- | 45 | — | *Medicago truncatula* | (Main text reference 14) |
| 52 | *Medicago sativa* | | 663.3765 [M-hex-H]-; 487.3432 [M-hex-hexA-H]- | 45 | — | *Medicago truncatula* | (Main text reference 14) |
| 53 | *Medicago sativa* | hairy roots with silenced MsCSL | 939.4989 [M H20 H]-; 895.5098 [M-CO2-H2O-H]-; 811.4492 [M-dhex-H]-; 767.4695 [M-dhex-CO2-H]-; 749.4526 [M-dhex-CO2-H2O-H]-; 631.3887 [M-dhex-hex-H2O-H]-; 613.3731 [M-dhex-hex-H2O-H2O-H]-; 473.3685 [M-hex-dhex-hexA-H]- | 45 | — | *Medicago truncatula* | (Main text reference 14) |
| 54 | *Medicago sativa* | | 865.4245 [M-CO2-H]-; 823.4179 [M-malonyl-H]-; 805.3989 [M-malonyl-H2O-H]-; 703.3777 [M-hex-CO2-H]-; 643.3525 [M-malonyl-hex-H2O-H]-; 599.3606 [M-malonyl-hex-CO2-H2O-H]-; 485.3273 [M-malonyl-hex-hexA-H]- | 45 | — | *Medicago truncatula* | (Main text reference 14) |

TABLE 12-continued

| | | | | | | | |
|---|---|---|---|---|---|---|---|
| 55 | *Medicago sativa* | | 953.4714 [M-H2O-H]-; 909.4915 [M-CO2-H2O-H]-; 825.4289 [M-dhex-H]-; 763.4302 [M-dhex-CO2-H2O-H]-; 645.3669 [M-dhex-hex-H2O-H]-; 601.3768 [M-dhex-hex-H2O-H2O-CO2-H]-; 555.3728 [M-dhex-hex-108-H]-; 487.3447 [M-dhex-hex-hexA-H]- | 60 | — | *Medicago truncatula* | (Main text reference 14) |
| 56 | *Medicago sativa* | | 1099.5315 [M-H2O-H]-; 955.4952 [M-hex-H]-; 893.5005 [M-hex-CO2-H2O-H]-; 791.4280 [M-hex-dhex-H2O-H]-; 7747.4368 [M-hex-dhex-CO2-H2O-H]-; 29.4260 [M-hex-dhex-H2O-H2O-CO2-H]-; 629.3726 [M-hex-dhex-hex-H]-; 585.3829 [M-hex-dhex-hex-CO2-H]-; 539.3792 [M-hex-dhex-hex-108-H]-; 471.3504 [M-hex-dhex-hex-hexA-H]- | 60 | — | *Medicago truncatula* | (Main text reference 14) |
| 57 | *Medicago sativa* | | 661.3595 [M-hex-H]-; 617.3698 [M-hex-CO2-H]-; 599.3587 [M-hex-CO2-H2O-H]-; 485.3268 [M-hex-hexA-H]- | 45 | — | *Medicago truncatula* | (Main text reference 14) |
| 58 | *Medicago sativa* | | 1085.5536 [M-H2O-H]-; 1041.5638 [M-H2O-CO2-H]-; 957.5061 [M-dhex-H]-; 895.5071 [M-dhex-H2O-CO2-H]-; 795.4548 [M-dhex-hex-H]-; 777.4427 [M-dhex-hex-H2O-H]-; 759.4297 [M-dhex-hex-H2O-H2O-H]-; 457.3681 [M-hex-hex-dhex-hexA-H]- | 45 | — | *Medicago truncatula* | (Main text reference 14) |
| 59 | | | | | | | |
| 60 | *Beta vulgaris* | Differ-ential signals from *B. vulgaris* with silenced BvCSL | 997.5342 [M-C3H4O5-H]-; 955.5225 [M-Act-H]-; 835.4744 [M-C3H4O5-hex-H]-; 793.4632 [M-Act-hex-H]-; 731.4594 [M-Act-hex-CO2-H2O-H]-; 631.4028 [M-Act-hex-hex-H]-; 613.3919 [M-Act-hex-hex-H2O-H]-; 455.3650 [M-Act-hex-hex-hexA-H]- | 60 | — | *Beta vulgaris* | (57) |
| 61 | *Beta vulgaris* | | 955.5191 [M-pent-H]-; 925.5099 [M-hex-H]-; 793.4655 [M-hex-pent-H]-; 731.4594 [M-hex-CO2-pent- | 60 | — | *Beta vulgaris* | (57) |

TABLE 12-continued

| | | | | | | | |
|---|---|---|---|---|---|---|---|
| | | | H2O-H]-; 613.3902 [M-hex-pent-hex-H2O-H]-; 569.4006 [M-hex-pent-hex-H2O-CO2-H]-; 551.3894 [M-hex-pent-hex-H2O-CO2-H2O-H]-; 455.3650 [M-hex-pent-hex-hexA-H]- | | | | |
| 62 | *Beta vulgaris* | | 967.5213 [M-C3H4O5-H]-; 925.5092 [M-Act-H]-; 805.4618 [M-C3H4O5-hex-H]-; 763.4507 [M-hex-Act-H]-; 743.4590 [M-C3H4O5-hex-H2O-CO2-H]-; 593.3999 [M-C3H4O5-hex-H2O-CO2-pent-H2O-H]-; 455.3639 [M-Act-hex-pent-hexA-H]- | 60 | — | *Beta vulgaris* | (57) |
| 63 | *Beta vulgaris* | | 763.4516 [M-hex-H]-; 701.4487 [M-hex-CO2-H2O-H]-; 631.4028 [M-hex-pent-H]-; 569.4016 [M-hex-CO2-H2O-pent-H]-; 551.3904 [M-hex-CO2-H2O-pent-H2O-H]-; 455.3654 [M-hex-pent-hexA-H]- | 60 | — | *Beta vulgaris* | (57) |
| 64 | *Beta vulgaris* | | 835.4753 [M-C3H4O5-H]-; 793.4630 [M-Act-H]-; 673.4167 [M-C3H4O5-hex-H]-; 631.4045 [M-Act-hex-H]-; 569.4015 [M-Act-hex-CO2-H2O-H]-; 455.3655 [M-hex-hexA-Act-H]- | 60 | — | *Beta vulgaris* | (57) |
| 65 | | | | | | | |
| 66 | Expression in *N. benthamiana* | genes from spinach | 501.3206 [M-GlcA-H]-; 483.3096 [M-GlcA-H2O-H]-; 439.3184 [M-GlcA-H2O-CO2-H]-; 193.0346 [GlcA-H]-; 175.0238 [GlcA-H2O-H]- | 45 | — | — | — |
| 67 | Expression in *N. benthamiana* | | 647.3776 [M-hexA-H]-; 501.3237 [M-hexA-dhex-H]- | 45 | — | — | — |
| 68 | Expression in *N. benthamiana* | | 793.4233 [M-hexA-H]-; 501.3219 [M-hexA-dhex-dhex-H]-; 439.3192 [M-hexA-dhex-dhex-CO2-H2O-H]- | 50 | — | — | — |
| 69 | Expression in *N. benthamiana* | | 955.4902 [M-hexA-H]-; 677.3536 [M-hex-dhex-dhex-H]-; 501.3195 [M-hexA-hex-dhex-dhex-H]- | 55 | — | — | — |
| 70 | Expression in *N. benthamiana* | | 955.4648 [M-hexA-pent-H]-; 793.4109 [M-hexA- | 70 | — | — | — |

TABLE 12-continued

| | | | | | | | |
|---|---|---|---|---|---|---|---|
| | | | pent-hex-H]-; 501.3018 [M-hexA-pent-hex-dhex-dhex-H]-; 483.3283 [M-hexA-pent-hex-dhex-dhex-H2O-H]- | | | | |
| 71 | Expression in *N. benthamiana* | | 997.4995 [M-hexA-pent-H]-; 955.4883 [M-hexA-pent-Ac-H]-; 501.3227 [M-hexA-pent-hex-dhex-dhex-Ac-H]-; 439.3179 [M-hexA-pent-hex-dhex-dhex-Ac-CO2-H2O-H]- | 70 | — | — | — |
| 72 | | | | | | | |
| 73 | Expression in *N. benthamiana* | genes from *G. uralensis* | 583.3629 [M-CO2-H2O-H]-; 569.3469 [M-C2O3H4-H; $^{04}$X]-; 523.3415 [M-C3O4H6-H2O-H; $^{03}$X-H2O ]-; 469.3315 [M-GIcA-H]-; 425.3419 [M-GIcA-CO2-H]- | 55 | — | *Glycyrrhiza uralensis* | (58) |
| 74 | Expression in *N. benthamiana* | | 583.3635 [M-CO2-H2O-H]-; 569.3470 [M-C2O3H4-H; $^{04}$X]-; 523.3423 [M-C3O4H6-H2O-H; $^{03}$X-H2O ]-; 469.3318 [M-GIcA-H]-; 425.3419 [M-GIcA-CO2-H]- | 55 | — | *Glycyrrhiza uralensis* | (58) |
| 75 | | | | | | | |
| 76 | Expression in *N. benthamiana* | | 583.3631 [M-CO2-H2O-H]-; 569.3468 [M-C2O3H4-H; $^{04}$X]-; 523.3418 [M-C3O4H6-H2O-H; $^{03}$X-H2O ]-; 469.3317 [M-GIcA-H]-; 425.3422 [M-GIcA-CO2-H]- | 55 | — | *Glycyrrhiza uralensis* | (58) |

TABLE 12-continued

| | | | | | | |
|---|---|---|---|---|---|---|
| 77 | Expression in *N. benthamiana* | 583.3633 [M-CO2-H2O-H]-; 569.3470 [M-C2O3H4-H; $^{04}$X]-; 523.3421 [M-C3O4H6-H2O-H; $^{03}$X-H20 ]-; 469.3320 [M-GlcA-H]-; 425.3415 [M-GlcA-CO2-H]- | 55 | — | *Glycyrrhiza* uralensis | (58) |
| 78 | | | | | | |
| 79 | Expression in *N. benthamiana* | 645.3636 [M-GlcA-H]-; 469.3303 [M-GlcA-GlcA-H]-; 351.0574 [GlcA + GlcA-H]-; 193.0357 [GlcA-H]-; 175.0258 [GlcA-H2O-H]- | 65 | — | *Glycyrrhiza uralensis* | (58) |
| 80 | Expression in *N. benthamiana* | 645.3615 [M-GlcA-H]-; 469.3323 [M-GlcA-GlcA-H]-; 351.0577 [GlcA-FGlcA-H]-; 193.0354 [GlcA-H]-; 175.0250 [GlcA-H2O-H]- | 65 | — | *Glycyrrhiza* uralensis | (58) |
| 81 | | | | | | |
| 82 | Expression in *N. benthamiana* | 501.3212 [M-GlcA-H]-; 483.3084 [M-GlcA-H2O-H]-; 439.3176 [M-GlcA-H2O-CO2-H]-; 193.0334 [GlcA-H]-; 175.0342 [GlcA-H2O-H]- | 45 | — | — | — |

TABLE 13

Summary of Saponin Composition in Spinach

| No. | Name | Molecular Formula | m/z measured [M − H] | m/z calculated [M − H] | Δm/z ppm |
|---|---|---|---|---|---|
| 1 | Yossoside XI | C64H100O33 | 1395.6068 | 1395.6069 | −0.1 |
| 2 | Yossoside VI | C47H88O30 | 1131.5261 | 1131.5282 | −1.9 |
| 3 | Yossoside IV | C52H96O34 | 1263.5713 | 1263.5705 | 0.6 |
| 4 | Yossoside VIII | C63H98O32 | 1365.5981 | 1365.5963 | 1.3 |
| 5 | Yossoside XII | C58H90O28 | 1233.5554 | 1233.5540 | 1.1 |
| 6 | Yossoside Va | C61H94O30 | 1305.5773 | 1305.5752 | 1.6 |
| 7 | Yossoside X | C66H102O34 | 1437.6160 | 1437.6151 | 0.6 |
| 8 | Yossoside VII | C60H92O29 | 1275.5675 | 1275.5646 | 2.3 |
| 9 | Yossoside V | C61H94O30 | 1305.5781 | 1305.5752 | 2.2 |
| 10 | Yossoside IX | C65H100O33 | 1407.6107 | 1407.6069 | 2.7 |
| 11 | Yossoside VIIa | C60H92O29 | 1275.5640 | 1275.5646 | −0.5 |

Mass spectrometry fragmentation analysis and a series of 1D and 2D-NMR experiments established the structure of the most abundant spinach saponin (termed here Yossoside V). It comprises medicagenic acid (the aglycone) with glucuronic acid and xylose attached to the hydroxyl at the C-3 position and acetyl-fucose, rhamnose and glucose linked to the carboxyl at C-28 (FIGS. 20A-20C, FIG. 21).

Summary: Eleven triterpenoid saponins were identified in spinach, wherein Yossiside V was the most abundant.

Example 16: Identification of Saponin Biosynthesis Genes Using Spinach Transcriptome Data Objective: To identify triterpenoid aglycone biosynthesis genes in the triterpenoid saponin biosynthetic pathway.

Methods: See Materials and Methods above.

Results: Transcriptome data was generated from five spinach tissues exhibiting varying content of saponins, and gene candidates selected based on their differential expression between samples with high and low saponin content, as well as their homology to known triterpenoid aglycone biosynthesis genes (E. Biazzi et al., CYP72A67 Catalyzes a Key Oxidative Step in *Medicago truncatula* Hemolytic Saponin Biosynthesis. *Molecular Plant.* 8, 1493-1506 (2015)).

Inspecting the genomic location of three of the candidates, including: saponin β-amyrin synthase (SobAS; termed SOAP1; Sp_107620_kpnh; SEQ ID NO: 45 [gene sequence] SEQ ID NO: 48 [polypeptide sequence]), cytochrome P450 CYP716A268 (SOAP2; Sp_107660_kiqg; SEQ ID NO: 46 [gene sequence], SEQ ID NO: 49 [polypeptide sequence]), and CYP716A268v2 (SOAP2-like; Sp_107670_ptqx; SEQ ID NO: 47 [gene sequence] SEQ ID NO: 6 [polypeptide sequence]) revealed their close physical genomic location in the form of a metabolic gene cluster (FIGS. 22A and 22B).

Virus Induced Gene Silencing (VIGS) assays of SOAP1 and SOAP2 in spinach resulted in reduced saponin content (FIGS. 23A-23D), while their over-expression in *N. benthamiana* resulted the production of β-amyrin and oleanolic acid (FIGS. 24A and 24B).

Summary: These results provided strong evidence for the involvement of these genes in spinach saponin biosynthesis.

Example 17: Co-Expression Analysis for Identification of Additional Saponin Biosynthesis Genes & Characterization of Enzymes Encoded Objective: To identify additional triterpenoid aglycone biosynthesis genes in the triterpenoid saponin biosynthetic pathway.

Methods: See Materials and Methods above.

Results: SOAP1, SOAP2 and SOAP2-like nucleotides (nucleotide sequences SEQ ID NOs: 45-47 were expressed were subsequently used as baits in co-expression analysis (r>0.9; Pearson correlation coefficient—PCC) and an additional five genes encoding p450 cytochromes, eight genes encoding glycosyltransferases, and five genes encoding acyltransferases were identified for functional characterization using VIGS (FIGS. 20A and 20B: Table 14). [SOAP1, Soap2, and SOAP2-like nucleotide encode polypeptide sequences: SEQ ID NO: 48, SEQ ID NO: 49, and SEQ ID NO: 50, respectively) These experiments revealed that CYP72A655 (SOAP3; Sp_085340_meek; SEQ ID NO: 51 [nucleotide], SEQ ID NO: 52 [polypeptide]) and CYP72A654 (SOAP4; Sp_040350_wdny; SEQ ID NO: 53 [nucleotide], SEQ ID NO: 54 [polypeptide]) participate in the biosynthesis of the Yossoside aglycone (FIG. 25). In Table 14 below, terms used include: coexpressed gene—gene with coexpression correlation coefficient greater than 0.9; annotation—gene functional annotation based on blast analysis against *Arabidopsis* proteome (TAIR10); and aa seq-amino acid sequence of coexpressed gene Lengthy table referenced here

US12041907-20240723-T00001

Please refer to the end of the specification for access instructions.

Down regulation of SOAP3 and SOAP4 expression led to reduced accumulation of medicagenic acid derived saponins and caused accumulation of glycosylated intermediates (augustic acid, bayogenin and hederagenin; (FIG. 25, FIGS. 26A-26L, FIG. 27, FIGS. 28A-28C).

The structure of accrued pathway intermediates demonstrated that SOAP3 (SEQ ID NO: 52) is a C-2 hydroxylase and SOAP4 (SEQ ID NO: 54) is a C-23 oxidase (FIG. 20A). CYP2 (CYP72A656; Sp_148230_dgra)(SEQ ID NO: 72 [gene] and SEQ ID NO: 73 [polypeptide]), which was also identified, displays high homology to SOAP4 (almost 92% at the amino acid level), likely exhibits the same activity in the saponin biosynthesis pathway. Additionally, reduced saponin content was observed in plants with silenced: SOAP6 (UGT74BB2; Sp_170930_hjgq; SEQ ID NO: 55 [gene] and SEQ ID NO: 56 [polypeptide]), SOAP7 (UGT79K1; Sp_020820_yeau; SEQ ID NO: 57 [gene] and SEQ ID NO: 58 [polypeptide]), SOAP8 (UGT79L2; Sp_113700_suxh SEQ ID NO: 59 [gene] and SEQ ID NO: 60 [polypeptide]) and SOAP9 (UGT73BS1; Sp_170320_dmqi SEQ ID NO: 61 [gene] and SEQ ID NO: 62 [polypeptide]) glycosyltransferases (FIG. 29).

Figure 31A:
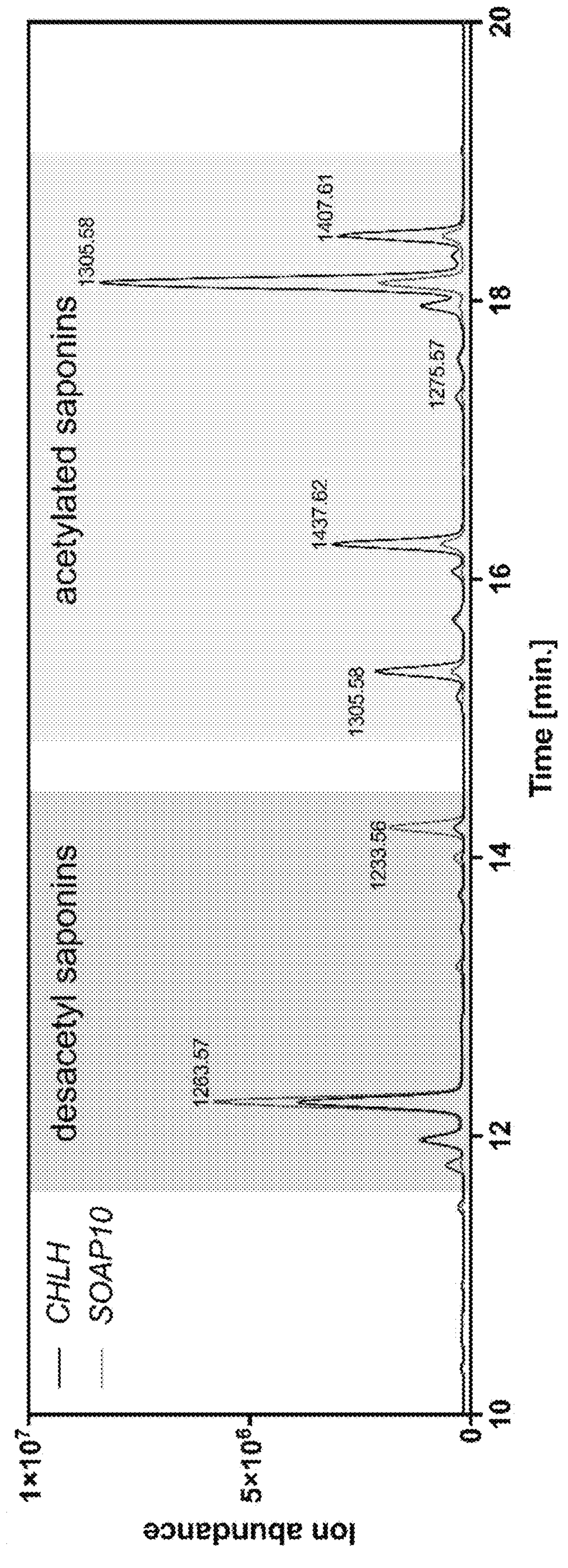
Figure 31B:
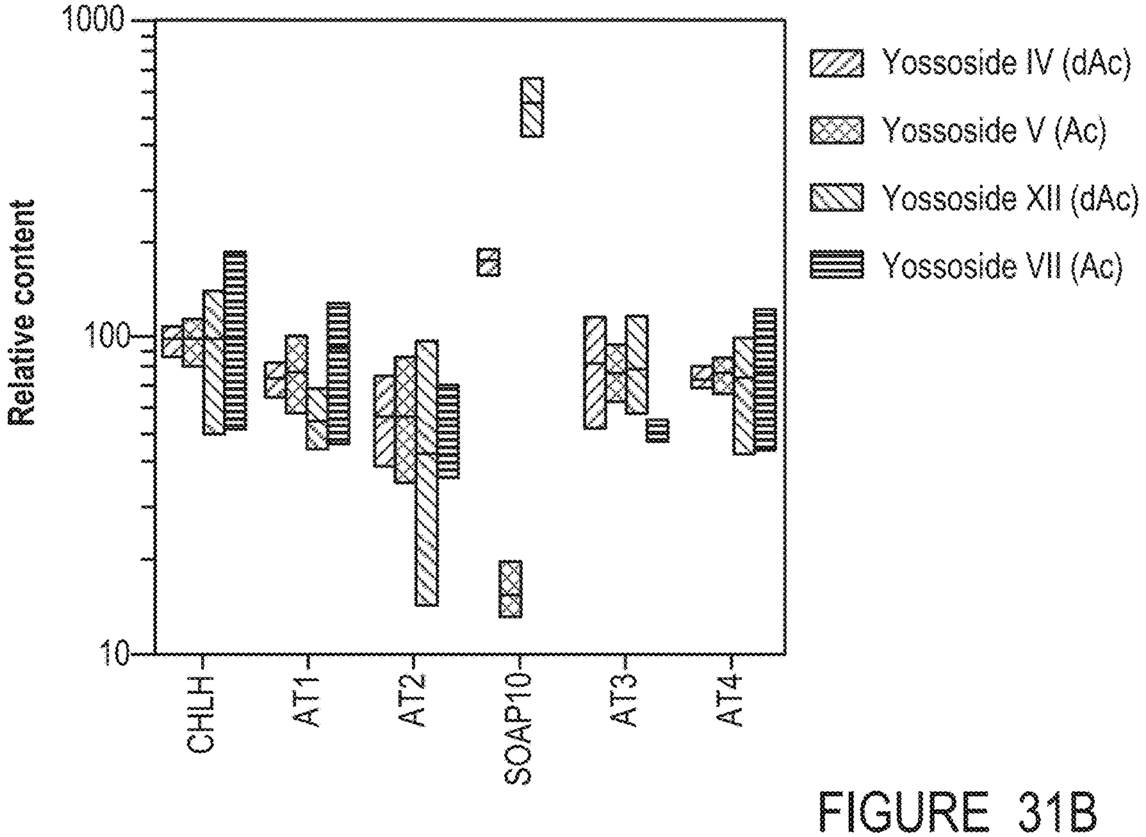
Figure 31C:
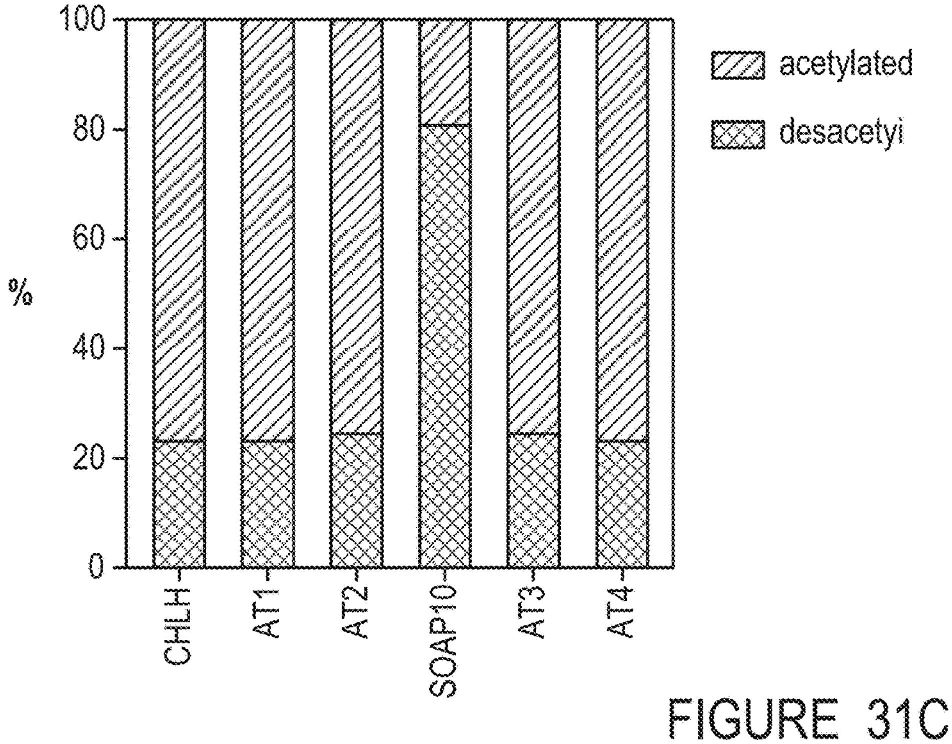
Figure 31D:
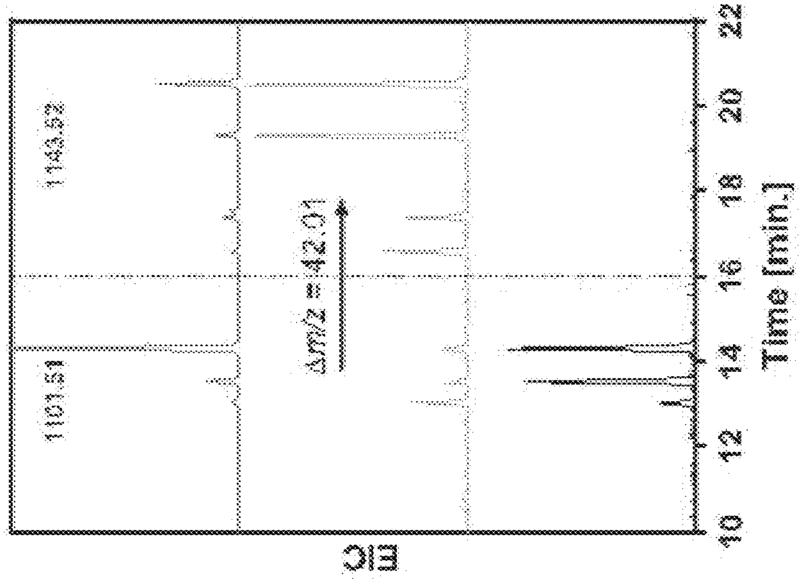
Figure 31E:
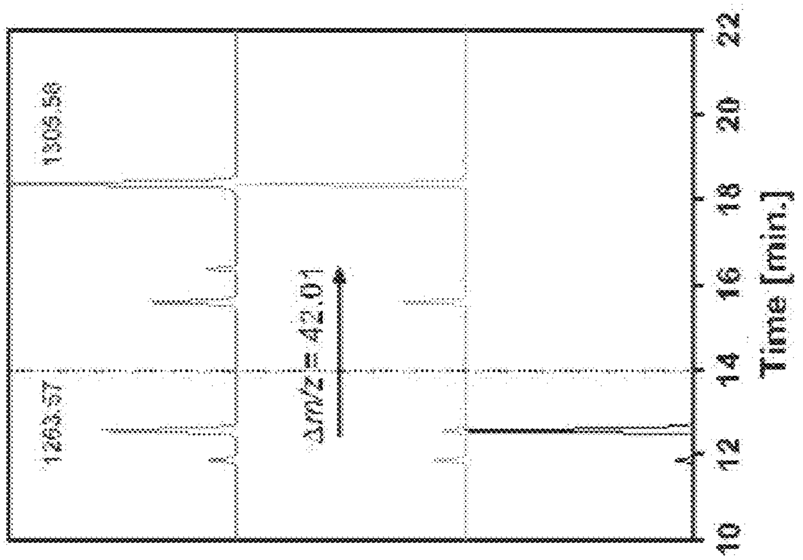
Figure 31F:
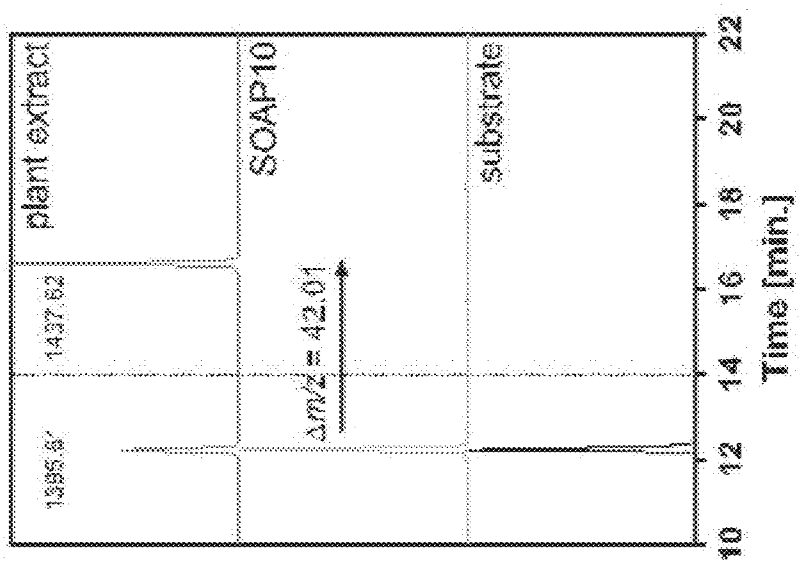
Figure 32A:
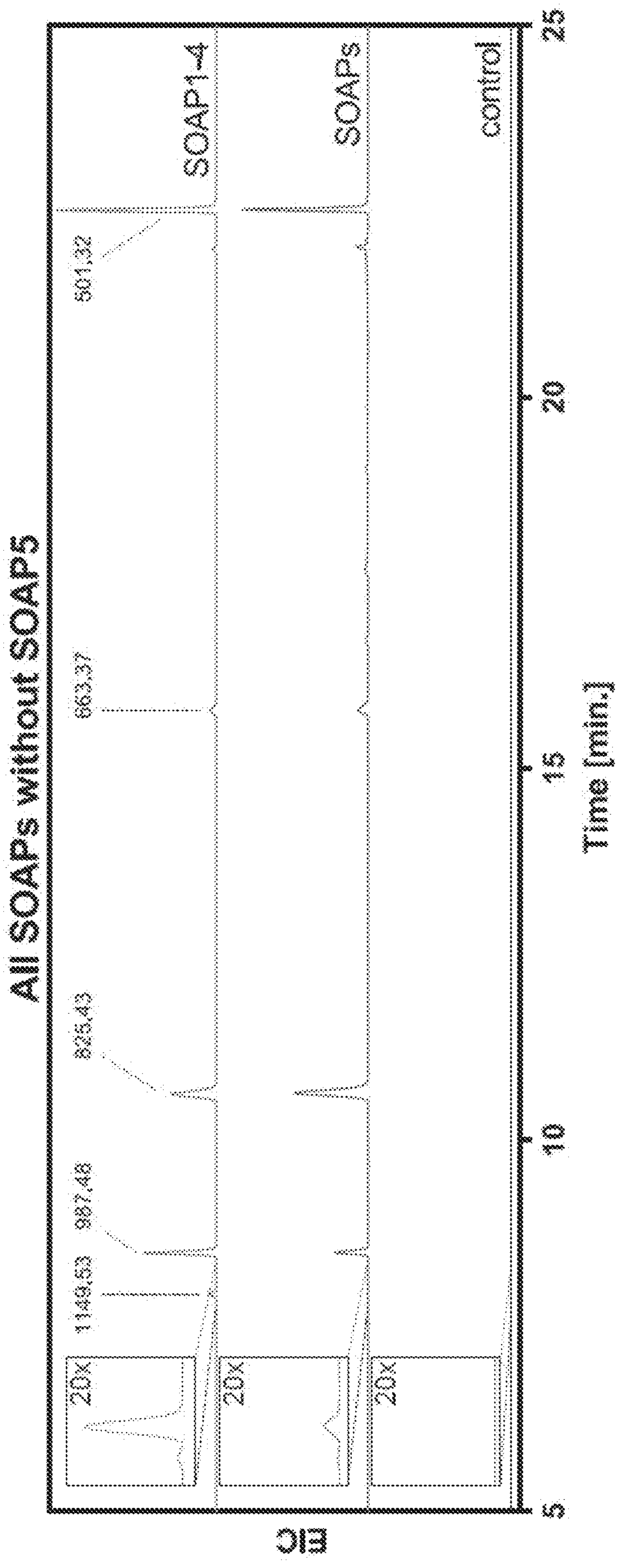
Figure 32B:
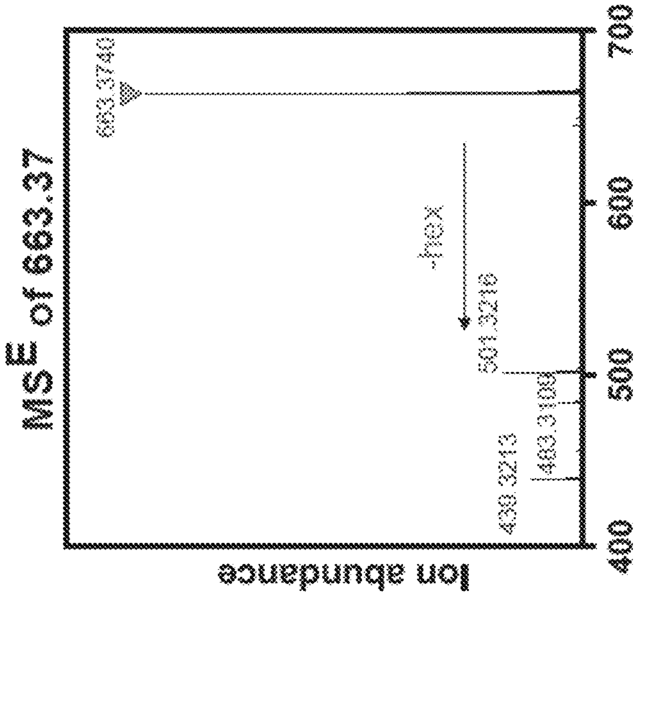
Figure 32C:
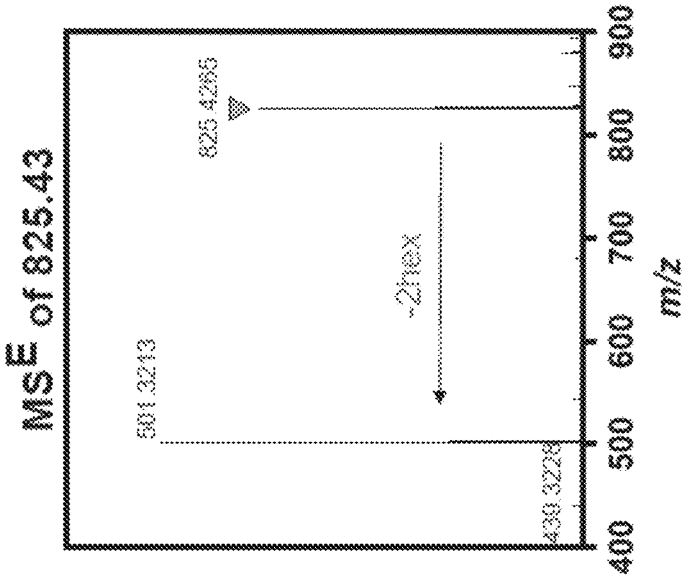
Figure 32D:
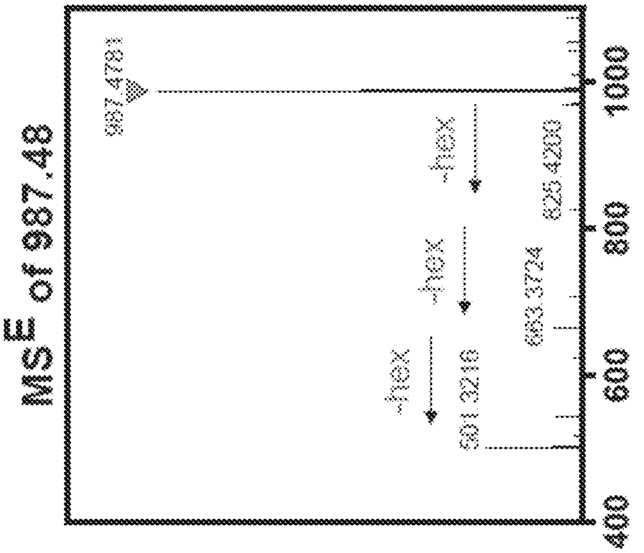

The same plants accumulated pathway intermediates lacking certain sugars: deoxyhexoses (SOAP6 (SEQ ID NO: 56) and SOAP7 (SEQ ID NO: 58)), hexose (SOAP8 (SEQ ID NO: 60)) and pentose (SOAP9 (SEQ ID NO: 62)) (FIGS. 30A-30C). Moreover, VIGS of one of the five co-expressed acyltransferases (AT) (i.e., SOAP10; Sp_125800_kzws; SEQ ID NO: 63 [gene], SEQ ID NO: 64 [polypeptide]) resulted in an increased ratio of desacetyl to acetylated saponins (from 20 to 80%) (FIGS. 31A-31C). The acetyltransferase activity of recombinant SOAP10 expressed in *E. coli* was subsequently confirmed in vitro, as it acetylated Yossoside IV and other Yossosides (e.g., Yossoside VI and Yossoside XII) with two deoxyhexoses attached at the C-28 position (FIGS. 14A-14C).

Example 18: Validation of SOAP Genes

Objective: To validate the function of all nine genes [i.e., β-amyrin synthase (bAS; SOAP1; SEQ ID NO: 45); cytochrome P450 (CYP450s; SOAP2, 3, 4; SEQ ID NO: 46, 51, 53, respectively); UDP-glycosyltransferases (UGTs; SOAP 6, 7, 8, 9; SEQ ID NO: 55, 57, 59, 61 respectively) and acyltransferase (AT; SOAP10; SEQ ID NO: 63)]

Methods: See Materials and Methods above.

Results: The nine genes of interest (SOAP 1-4 and 6-10) were transiently expressed in *N. benthamiana* leaves. Expression of the first four biosynthetic genes (SOAP1 to SOAP4) resulted in the formation of medicagenic acid (FIG. 20A). Curiously, co-expression of all nine genes did not lead to production of any saponin that had previously been detected in spinach leaves. Nevertheless, the accumulation of medicagenic acid and glycosylated derivatives [MA+hex; MA+2× hex, MA+3× hex) that are normally not present in spinach leaves were detected (FIGS. 32A-32D).

Summary: While reconstitution of medicagenic acid was achieved, expression of the nine genes SOAP1-4 and 6-10 did not result in the production of any saponins.

Example 19: Analysis of Cellulose Synthase Like G Spinach Homolog as a Component of the Saponin Biosynthetic Pathway Objective: To identify the missing gene or genes necessary for reconstitution of the biosynthetic pathway of saponins.

Methods: See Materials and Methods above.

Results: At this point, it was realized that at least one enzyme was absent in order to reconstitute the saponin biosynthetic pathway. In an effort to identify the missing enzyme or enzymes the list of genes obtained by co-expression analysis was revisted. The only gene co-expressed with all baits in the co-expression set that appeared related to sugar metabolism was a Cellulose Synthase Like G spinach homolog (SoCSLG) (T. Richmond, Higher plant cellulose synthases, Genome Biology. 1, 3001.1-3001.6 (2000)). Although its contribution to saponin biosynthesis seemed unlikely based on this functional annotation, its function within this pathway was studied.

Notably, SoCSLG silencing resulted in high accumulation of medicagenic acid in spinach leaves (FIGS. 33A-33F; FIGS. 34A and 34B) suggesting its role in triterpenoid saponin biosynthesis. Next, SoCSLG (SEQ ID NOS: 65 OR 93) was transiently expressed together with SOAP1-4 (SEQ ID NO: 45, SEQ ID NO: 46, SEQ ID NO: 51, SEQ ID NO: 53, respectively), in *N. benthamiana* leaves. The combined activity of all five enzymes resulted in the formation of medicagenic acid 3-O-glucuronide (MA-3-GlcA); the first glycosylated intermediate in the spinach triterpenoid saponin biosynthetic pathway (FIGS. 20A-20C and FIGS. 32A-32F; FIGS. 35A-35C).

Furthermore, combinatorial expression of CSLG (SOAP5, Sp_076690_ejcm (SEQ ID NOS: 65 or 93 [gene], SEQ ID NO: 66 [polypeptide]) with bAS (SOAP1; SEQ ID NO: 45) and CYP450s (SOAP2 [SEQ ID NO: 46], SOAP3 [SEQ ID NO: 51] and SOAP4 [SEQ ID NO: 53]) demonstrated that apart from medicagenic acid, SOAP5 [SEQ ID NO: 66] could glucuronidate other triterpenoid aglycones including oleanolic acid, augustic acid, hederagenin, gypsogenin and gypsogenic acid, though they were never detected in significant amounts in spinach (FIGS. 36A-36F). SOAP5 (SoCSLG) was identified as the spinach saponin glucuronic acid transferase. Conversely, inhibition of expression of SOAP5 (SEQ ID NOS. 65 or 93) could in some embodiments, results in a decrease or inhibition of glucuronidating triterpenoid aglycones including but not limited to medicagenic acid, oleanolic acid, augustic acid, hederagenin, gypsogenin, and gypsogenic acid.

To examine if SOAP5 was indeed a missing component in the spinach saponin pathway a combination of all ten SOAP genes (See Table 16) were transiently expressed in *N. benthamiana* leaves. Metabolite analysis showed the presence of the most abundant spinach saponin Yossoside V signifying the identification of all required steps and enzymes in the native pathway (FIGS. 33A-33F).

Summary: Enzymes for all required steps in the native pathway of spinach saponin Yossoside V (Compound 11) have been identified and demonstrated to be functionally active in a heterologous plant system.

Example 20: Characteristics of the Triterpenoid Biosynthetic Pathway

Objective: To elucidate further details of the spinach saponin metabolic pathway.

Methods: See Materials and Methods above.

Results: The identification of SOAP5 (SEQ ID NO: 66) as the spinach saponin glucuronic acid transferase enabled deciphering the pathway further. It was discovered that SOAP6 (SEQ ID NO: 56) works directly on MA-3-GlcA linking a fucose to the carboxyl group at position C-28 of the aglycone, giving rise to Yossoside I (Compound 7). In fact, this makes SOAP6 the first characterized fucosyltransferase involved in triterpenoid metabolism (T. Louveau et al., Analysis of two new arabinosyltransferases belonging to the carbohydrate-active enzyme (CAZY) glycosyl transferase family 1 provides insights into disease resistance and sugar donor specificity. The Pant Cell. 30, 3038-3057 (2018)) (FIGS. 37A-37E, FIGS. 38A-38E).

Expression of SOAP7 (SEQ ID NO: 57) generated the Yossoside II product only when expressed together with the other six SOAP1-6 genes (See Table 16). Based on the LC-MS/MS analysis, SOAP7 (SEQ ID NO: 58) is a glycosyltransferase transferring rhamnose onto the fucose of Yossoside I (FIGS. 37A-37E, FIGS. 38A-38E). Yossoside II is further converted into Yossoside M by SOAP8 (SEQ ID NO: 60), a glucosyltransferase that accepts as a substrate only an aglycone having a fucose and rhamnose attached to the C-28 position (FIG. 20A; FIGS. 37A-37E, FIGS. 38A-38E). Expression of SOAP9 (SEQ ID NO: 61 [gene], SEQ ID NO: 62 [polypeptide]) showed that it is a xylosyltransferase attaching a pentose to glucuronic acid linked to the MA at C-3. In case of SOAP9, the sugar moieties decorating the triterpenoid backbone at C-28 are not crucial for its activity (FIGS. 39A-39C). The in planta and in vitro studies showed that SOAP10 takes part in last step of saponin biosynthesis in spinach transferring acetyl group to the fucose moiety (FIGS. 31A-31F). The nucleotide and amino acid sequences of the acetyl transferases used for comparison are presented below in Table 15.

TABLE 15

Nucleotide and Amino Acid Sequences of Acetyl Transferase Enzymes

| NAME | SEQ ID NO: | AA SEQ/NT SEQ |
|---|---|---|
| sp_074630_ygho_Spo04549_AT1 gene | 109 | ATGGCCAAATCTGAGCAAGAAACAATGGCCAAATCTGAGCAAGAAACATCCAT<br>CAAACTTGTTTCAGAATGCTTTGTAAAACCAAAATATGAGATTAAATCCGCTAA<br>GCAACCTTACCACTTAGGTCCCATGGATCTAGTTATGTTAACTATCGATCCTAT<br>ACAAAAAGGTCTTGTCTTTACAATAAAGAATTCCCCACTCTTTTTGTCATCCGA<br>ATCCCATGATAATATTGAAATTATTCGAACCAAAGTTGTGTCACGTTTATTAGA<br>AAAGCTTAAACACTCACTTTCTATAGCTCTAGTCCACTTCTACCCGTTAGCAGG<br>TCGTTTCACTACACAAAAACAACCCGAGCATAACACGAGCTTGGTCTTTATTGA<br>TTGCAACAAAGGTCCCGGAGCGCGGTTCATCCACGCTACTTCCCTTGACTTTAC<br>TATCTCCGATATACTTTCACCGGTTGATGTTTCCATCGTTCATTCTTTCTTTGATC<br>TCGGTGAAAAGCATGTAAACTACGATTGTCATACTAAGGCGTTGCTATCGATCC<br>AGGTAACAGAACTTTTAGATGGGGTGTTTATTGGGTTTAGCATGAGTCATAGTG<br>TGGTTGATGGTACCTCTTTTATTCATTTTGTCAATACCTTGTCTGAAATTTTTAA<br>ATCTGATGATTTTACCACTATTTCACGTGCCCCAATACTTAATTATAGGCCTTGT<br>GATATTCCGATCCTTAAATTTCCGTTTCTTGATGTGGAGGGGTTTATATGTCGTG<br>CGTATAACCCTGGGCCGTTAAGGGAAAGAATCTTCCACTTTTCACTAAATTCGA<br>TGCTGAGACTCAAGGCCATGGCTAACCAAGAATGTGGTACCCAAAATGTTTTA<br>TCATCTTTCCAAGCTTTGACTGCGGTTGTATGGAGGTCCATCACCCGAGTTCGG<br>AACTTACCAAAGGATGAGCAAACCACGTGTTTTATGGCTATGGGTTCTCGAACT<br>AGGCTCAACCCGCCTCTTTCGGATGACTATTTTGGGAATTTTATGATTAGTACC<br>AAATTTGCTTGCAAGGCAGAGGAATTATTGGGTAACAGTTTAGGTTGGGTAGC<br>AATGAATTTACGTAAAATCATTATGTCCACTGACGAGAAATCGATACTTGCTAC<br>GTACAAAGCATTGGCTGATTCCCCAATAGTGATTCCGCGTGAAACGATCCCCG<br>GTCCTCATGGGATGACCAGAGTAATAATTGGAGGATCTTCAAGGTTCGATATG<br>TATGGGCCTGAATTTGGATTGGGTCGAGCTTTGGCCGCTCGCATGGGTTATGGG<br>AATAAGGATGATGGGAAAATAACAGCAAATCCTGGGTGTGAAGGAGGTGGAA<br>GTGTTGATTTGGAAATTTGCCTTAGGCCTCATATTATGGCCTCTCTTGAAGTTGA<br>TCAAGAGTTTATGGGTTTTGTGTCCTAG |
| sp_123780_pgiy_Spo21561_AT2 gene | 110 | ATGACTCCAAATCTGCAAATAGTAACCAACGGAGGCAAACCGGAAAATGATG<br>AAGCAGAACCCGTATCACCTACCGGACAATACTTCAACAGCAAAGTGTTGTCT<br>GTTTGTGTCCTTGCCATTCTAGAAATTGATGTTCCTATAGATGACTCGTGTGTAA<br>TTCCACAACTCCGTGATGTCTTCCTACCCATGAACCCCAGATTTTCATCTATCAT<br>GATATCTGACAATAAAGATGTAAAACAATGGAAAAGAGTGGAAGTGAACCTTC<br>AAGATCATGTTGTCGTCCCTAGCGTCCCAGATGGCTTATCGGTTGAATCATACG<br>ACAAGTACTTTGATGAATATCTGACAAAAATAACAGTGGATCCATTACCACAG<br>GATAGGCCTTTATGGGAACTTCATGTTATAAAATACCCAACAAGCAAAGCAGC<br>GGGTCATTTCATCTGGAAGCTTCACCATGCACTTGGTGACGGCTACACTCTAAT<br>GGGAGTACTTCTGTCCGGCGTGAACAGAGCAGATGATCCTTCCCTTCCGTTAAC<br>TTTCCCTTCAACACGATCAAGCTCACTAGTTACAAACAACAAGATGAATATTAT<br>CAGCTGGGTGCCAAGAACTTTTTCAGCAATCTACAACGGTGTTTATAATTTTGG<br>ATGGAGTTTTCTAAAAAGCACTTGCAAGGCAGATGATAAGACACCTATCAGAT<br>CCGGAAATGAAGGTCTGGGTTTCCACCCAATGAAGATCTCGACAATAGAACTA<br>TCCCTAGACCAAATCAAATTTATCAAAACAAAACTCGGCGCAACGGTAAATGA<br>CATTCTTGCAGGCATAATTTTCCTCGGGGTTCGAAAATACATGCAAGGAACTGA<br>TACAGAATCTGGAAACTCAGAATCAACGGCATTGGTGCTGTTTAACACTAGGA<br>ACATTGGAGGTTATATGACCGCTGAGCAAATGAAGAAAGCACAAATGAAAAT<br>ATGGGGGAACCAATTTGCATTTTTGCATATAGCAATACCTCAATTAATCAATGA<br>CAAATGCTCGAACCCCCTTGACTATGTCTATGAAGCACGAAAACAGATCTCTA<br>GGTTCAAAAGCTCACCATCAGTCTATCTAACAGCTCAGTGCCTAGAGCTGCTAG<br>GAAATGCAAAGGACCTGAGGCAGCAGCTGAATTTATCCAGAGTACAACGAATA<br>AAGGAAGCATATTAA |
| sp_149180_nwmy_Spo15788_AT3 gene | 111 | ATGTTAGAGCTAGCAGAAGACGAGGTGAAGAACTTCTTCAAGGTATGGGCAAT<br>AGTTTTTGCATCTTTAAGCTATTGTTATTACATAGGCAAGCTAATTAATCCAAA<br>AGGTTATACAAGATTAGTAGCAATAATCCCAATTATTACTCTCTTTTTAGCACT<br>TCCTTTAAATCTCACATCTTTTCATCTTGGTGGTATGACTTGTTTCTTTATTGCTT<br>GGCTTGCTAATTTCAAACTCTTGCTTTTTGCTTTTGATAAGGGCCCACTTTGCGC<br>TAATTCTTCAATCTCATTCGCCAAATTTCTTGCACTTTCTTGCTTACCCATCAAA<br>ATCCAACACCCACCTCATAAAAAGTCATTAAAATCACACCCATCTATTTATAAT<br>TACATCATTAAAGGGATACTTTTATGTCTAATAATTAAAATCTATGATTATGGT<br>GATTACATTCATCCAAAAATCATATGGCTAATCTTTTTCTTCCACTCCTATTTTA<br>CCATAGAGTTAGTCTTTGCATTCCTAGCAACATCGACTAATATTTTGTTAGGGC<br>TCGAACTGGAGCCACAGTTCAATGAACCCTTAATATCAACCTCATTGCAAGACT<br>TTTGGGGTAAGAGATGGAATATCATGGTGACAAGGATACTTAGGCCTACGGTG<br>TACCTTCCCACACTAGAGTACTCCACTAAGGTCGTTGGACGCACGTGGGCCAC<br>ACTTCCGGCGGTGATGTCCACGTTCTTTGTGTCAGCCATTATGCACGAGCTCAT<br>CTTCTACTACTTGGGGCGCAACTGGCCCACATTCGAGGTGACGTGGTTCTTTCT<br>CCTGCATGGATTATGTCTTTGTGTTGAGATTGTCGCTAAGAAGTTAGTTGGTGG<br>GAAATGGAGGATCCCACGGTGGATTTCCGGCCCTGCCACGGTGTTGTTTGTGGT<br>GGGTACTGGGTTTTGGCTGTTCTTGCCGCCGTTGTTGAAGGCTGGGTTGGATAC<br>TAGACCGTTTCAAGAGTTTGCGGCCGTTGCCAAGTTTGTAAGGAGTTTGAAGGC<br>AGCTCTCACATTTTG |

TABLE 15-continued

Nucleotide and Amino Acid Sequences of Acetyl Transferase Enzymes

| NAME | SEQ ID NO: | AA SEQ/NT SEQ |
|---|---|---|
| sp_198<br>340_fo<br>cw_Spo<br>13090_<br>AT4<br>gene | 112 | ATGGCTCCTCCTTCTTCTTCTTCAACTACGGGTTCTGGTAATGGTTCTAGTTTTG<br>CAGTCAATATAATGGCGTCGTTCTACATTTCCCCACAACAACCTTCCACCACAA<br>ATTCACATTCTATCCCTCTCACTTTCTTTGACATTCCTTGGCTTCAATATCCTCC<br>GCTCCAACCTCTCTTCTTCTTTCAACTTCCATCTACACCCCAATCTTCTTCTTCTT<br>CTTCTTCTTCTTCTTCTTCTTCTTTCGACCACAACTTGTACTTGGAGTTTAGCTCC<br>ACCATCCTCCCTAGGCTCAAACACTCCCTCGCTTCTGCCTTGCAATATTACTTTC<br>CCTTTTCTGGAAAACTCACCACTACTACCCATACTATCCCGAATAACCTAGTTT<br>TCTCGACAGACTCATCAGATTCTGTTGAGTTGACTGTTTCTCTGTGTGATGCTGA<br>TTTTAATGGTCTATGCAGCTTTCTACCCAGGTCTACTCATCTCTTCCAACAATTG<br>GTTCCCTCCTTGCCAAATATTGAATCCTCCAACCTCACTACATTCCCTGCACCTT<br>TATTAGCTATTCAGATCACATTCTTTCCCACCTCTTCTCCTGGTTTCTCTATTGG<br>CTTTGCTTCTCATCCTGTGCTTTCTGATCAGAGGACCTTCAGTAACTTCCTTTAC<br>TCTTGGGCCTCTTTCTCCAAGTTTGATAATCTAAACATTTCACTTGCCCCTTCCT<br>TCCCTGTCTCTGACAGGTCTGTCATTCTCGACCCTGATAGACTTGAGCCCCTTCT<br>GTTGGAGCAGTGGTTGGGATTGGAGTCCAAACCAACCATGTCAACAAAGATGA<br>AGCTACGTCCTCCTCCTGCTTATGTCCGTGGCTCGCTCCGGTCCACATTCGTCAT<br>GGGCCCATCTGATATTGCTAATGCTACACAATGGTTACAAACCCAGTGTGAGA<br>AGCTCAACAGATCATATCCTGTTCTCTTGTCACCCTACGTCGTCACTTGTGCCTT<br>TATATGGACCTGTTTTCTGAGAGCCCGAGTCCAGAACAGTGCTGTTACTAAAGC<br>CAAAGCAAAAGGCACCATGTACTTTGGATTTATTGCTGGTGGTATTACCCGTTT<br>ACCCTATCGGGTACCTGCTAAGTATCTTGGCAACTGTGTCGGGTTTGGACGGGC<br>AGCAGCGCAGAGGGAGGAGCTACTGAAGGAAGGTGAGGGGATGTTGGCAGCT<br>GCTGATGCAATTGGGCTAACCATTAAAAAGTTGGATAAAGATGTTTTAGGAGG<br>AGCTGAGAAATGGATATATGAATGGCAGACATTAATGGAATCCGAAGATCATA<br>TTCATGTGGTTGGGTCGCCCAAGGTGAACCTTTATGAGACGGATTTTTGGTGGG<br>GGAAACCGAAGAAGATAGAGGAAATTTCAACTGATGTTACCAGAGCCATCTCT<br>CTTACACAGAGCAGGGACATGAAAAGGGGAATTGAAATTGGCCTCACTTTACC<br>AAACTCCATTATGGATGACTTCTCCTCTATCTTCACTCAAGGCCTCCTTGTTTTT<br>CAAAATTAG |
| sp_074<br>630_yg<br>ho_Spo<br>04549_<br>AT1<br>poly-<br>peptide | 113 | MAKSEQETMAKSEQETSIKLVSECFVKPKYEIKSAKQPYHLGPMDLVMLTIDPIQK<br>GLVFTIKNSPLFLSSESHDNIEIIRTKVVSRLLEKLKHSLSIALVHFYPLAGRFTTQKQ<br>PEHNTSLVFIDCNKGPGARFIHATSLDFTISDILSPVDVSIVHSFFDLGEKHVNYDCH<br>TKALLSIQVTELLDGVFIGFSMSHSVVDGTSFIHFVNTLSEIFKSDDFTTISRAPILNY<br>RPCDIPILKFPFLDVEGFICRAYNPGPLRERIFHFSLNSMLRLKAMANQECGTQNVL<br>SSFQALTAVVWRSITRVRNLPKDEQTTCFMAMGSRTRLNPPLSDDYFGNFMISTKF<br>ACKAEELLGNSLGWVAMNLRKIIMSTDEKSILATYKALADSPIVIPRETIPGPHGMT<br>RVIIGGSSRFDMYGPEFGLGRALAARMGYGNKDDGKITANPGCEGGGSVDLEICLR<br>PHIMASLEVDQEFMGFVS |
| sp_123<br>780_pg<br>iy_Spo<br>21561_<br>AT2<br>poly-<br>peptide | 114 | MTPNLQIVTNGGKPENDEAEPVSPTGQYFNSKVLSVCVLAILEIDVPIDDSCVIPQLR<br>DVFLPMNPRFSSIMISDNKDVKQWKRVEVNLQDHVVVPSVPDGLSVESYDKYFDE<br>YLTKITVDPLPQDRPLWELHVIKYPTSKAAGHFIWKLHHALGDGYTLMGVLLSGV<br>NRADDPSLPLTFPSTRSSSLVTNNKMNIISWVPRTFSAIYNGVYNFGWSFLKSTCKA<br>DDKTPIRSGNEGLGFHPMKISTIELSLDQIKFIKTKLGATVNDILAGIIFLGVRKYMQ<br>ATDTESGNSESTALVLFNTRNIGGYMTAEQMKKAQMKIWGNQFAFLHIAIPQLIND<br>KCSNPLDYVYEARKQISRFKSSPSVYLTAQCLELLGNAKDLRQQLNLSRVQRIKQA<br>Y |
| sp_149<br>180_nw<br>my_Sp<br>o15788<br>_AT3<br>poly-<br>peptide | 115 | MLELAEDEVKNFFKVWAIVFASLSYCYYIGKLINPKGYTRLVAIIPIITLFLALPLNL<br>TSFHLGGMTCFFIAWLANFKLLLFAFDKGPLCANSSISFAKFLALSCLPIKIQHPPHK<br>KSLKSHPSIYNYIIKGILLCLIIKIYDYGDYIHPKIIWLIFFFHSYFTIELVFAFLATSTNI<br>LLGLELEPQFNEPLISTSLQDFWGKRWNIMVTRILRPTVYLPTLEYSTKVVGRTWA<br>TLPAVMSTFFVSAIMHELIFYYLGRNWPTFEVTWFFLLHGLCLCVEIVAKKLVGGK<br>WRIPRWISGPATVLFVVGTGFWLFLPPLLKAGLDTRPFQEFAAVAKFVRSLKAALT<br>F |
| sp_198<br>340_fo<br>cw_ Spo<br>13090_<br>AT4<br>poly-<br>peptide | 116 | MAPPSSSSTTGSGNGSSFAVNIMASFYISPQQPSTTNSHSIPLTFFDIPWLQYPPLQPL<br>FFFQLPSTPQSSSSSSSSSSSSFDHNLYLEFSSTILPRLKHSLASALQYYFPFSGKLTTT<br>THTIPNNLVFSTDSSDSVELTVSLCDADFNGLCSFLPRSTHLFQQLVPSLPNIESSNLT<br>TFPAPLLAIQITFFPTSSPGFSIGFASHPVLSQRTFSNFLYSWASFSKFDNLNISLAPS<br>FPVSDRSVILDPDRLEPLLLEQWLGLESKPTMSTKMKLRPPPAYVRGSLRSTFVMG<br>PSDIANATQWLQTQCEKLNRSYPVLLSPYVVTCAFIWTCFLRARVQNSAVTKAKA<br>KGTMYFGFIAGGITRLPYRVPAKYLGNCVGFGRAAAQREELLKEGEGMLAAADAI<br>GLTIKKLDKDVLGGAEKWIYEWQTLMESEDHIHVVGSPKVNLYETDFWWGKPKK<br>IEEISTDVTRAISLTQSRDMKRGIEIGLTLPNSIMDDFSSIFTQGLLVFQN |

To our knowledge, SOAP10 (SEQ ID NO: 64) is the first member of the benzylalcohol acetyl-, anthocyanin-O-hydroxy-cinnamoyl-, anthranilate-N-hydroxy-cinnamoyl/benzoyl-, deacetylvindoline acetyltransferase (BAHD) superfamily of acyltransferases reported to be involved in triterpenoid saponin biosynthesis.

Table 16 below presents the amino acid and nucleotide sequences of the 10 enzymes, and genes encoding these enzymes, that comprise the biosynthetic triterpenoid saponin biosynthetic pathway producing Compound 11 (Yossoside V) in spinach.

TABLE 16

Nucleotide and Amino Acid Sequences for Triterpenoid Biosynthetic Pathway Enzyme in Spinach

| NAME | ENZYME ACTIVITY | SEQ ID NO: | AA SEQ/NT SEQ |
|---|---|---|---|
| SOAP1 | saponin β-amyrin synthase | 45 | atgtggaggttgaaggttggagaaggggctaatgacccatacttatatagcactaataactttgttg<br>ggcgtcaaacttgggagtttgatcctaactatggcacccctgaggatattcaagaggtcgaagat<br>gctcgccgcgatttttacaataatcggtttaaagtgaagccttgtaacgatctcttatggcgttttcag<br>ttcttaagagagaaaaacttcaagcaaaccatacctcaagtgaaggtgggtgacggggaggag<br>atcacatatgagaccgcctcgacgacattaaagagagcggtgaatattttcacagccttgcagtct<br>gaacatggccattggccggctgaaattgctggccctcagttcttccttcctcctttggtattttgctta<br>tacattacaggagatcttaactctgttttcggaccagaacatcgtagagaaattcttcgcagcatcta<br>ctatcaccagaacgaagatggaggttggggattacatattgaaggacatagcaccatgttctgta<br>ccgcactgaattacatatgtttacgaatgcttggaataggacctgatgaaggtgatgacaacgcgt<br>gccctagagcgcgtaaatggattctcgaccatggtagcgttacacatatcccttcttggggtaaaa<br>cttggttatctatactgggcctgttcgattggctgaagtaaccccaatgccacctgagttctggatc<br>cttcctacttttctccctatgcatccagcaaaaatgtggtgctactgtcgaatggtgtatatgccaatg<br>tcatacttgtatgggaagagattcgtaggtccaatcacacctctcattaaacaacttagggaagaa<br>ctctacaacgaaccctttgaacaaattagttggaagaaaatgcgacatttgtgtgcaccggaggat<br>ctctactatcctcatccattgattcaagacttgatgtgggacgctctttacctttacggaacctctcc<br>tgacccgttggcctttcaacaagttgatacgaaagaaagcattagaggttacaatggaacacata<br>cattatgaagatgagaacagtcgttacataacaattggatgtgtcgagaaggttttatgtatgttaac<br>ctgttgggtggaagacctaaaggggatcattacaagaaacatcttgcaagagtacaagattaca<br>tttggattgctgaagatggattgaaaatgcagagttttggaagtcaacaatgggattgtgggttttca<br>gtacaggcattattagcttctaatcttagtctcgacgaaattggacctgctcttaagaaaggccattt<br>cttcattaaggagtcacaggtgaaggacaatccatccggcgacttcaaagctatgcatcgccata<br>tctcaaagggatcgtggactttctccgaccaagatcatggttggcaagtctccgattgcactgccg<br>aaggccttaagtgttgtctaatcttatcaacaatgcccccggaaattgttggagaaaagatggacc<br>ctgaacgcctttatgattctgtcaatgtcttgctttctctacagagtaataaaggagggctagctgcc<br>tgggaaccagcaggggctcaagaatggttggaggtcctaaacccaacagaattctttgaagaca<br>ttgtgattgaacatgagtatgtagagtgtacggcttcagcaattcaagctttaataatgttcaagaag<br>ttatacccaggacacaggaaaaaagagattgaaaattttgtagtaaacgcagtcaagtaccttgaa<br>aacacccaatatcctagtggaggatggtatggaaattggggggatttgtttcatatatggaacatggt<br>ttgcactaggagggctagcagcaggtgggaagacatactataattgtgctgctgttaggaagggt<br>gttgatttttttgcttactacacaaaggaggatggtggttggggtgaaagttatatttcttgtcccaat<br>aagaatttgtgccaatagagggaaaatccaatttggttcagactggttgggctttgatgggtcta<br>cttcatgctggacaggcggagagggatccaactcctctgcatcgtgcagcaaagcttttgattaat<br>tcacaactcgaaaatggcgatttccctcaacaggaaataacaggagtcttcatgaagaattgcatg<br>ttacattatccgatgtacagaagcatttatccactgtgggcaattgcagaatacagaaagcgtgttt<br>cattaccttctatcaactctacttga |
| SOAP2 | cyto-chrome P450 | 46 | atggaactcttctttatgtgtgggctagtccttttcctctccctatctctagcctccttcttccttttctata<br>accaccatagaacccgggggtacaagctacccccgggcaagatggggtggccggtggtggg<br>cgagtcatttgaatttttttcaaaccgggtggaaaggttacccggaaaagttcatatttgatagactg<br>aacaagtacaccccaagccaagtgttcaagacttccatcgtaggagaaaaggttgcggttttatgt<br>ggcgcggcgggtaacaagttcttgtactcaaacgagaacaaattagtacaagcttggtggccta<br>gctctgttgataagatctttccttcttacccaaacttcctccaaagaagaggctaagaagatgcg<br>gaaactcctccctaacttcctcaagcccgaggctttacataggtacatacccatcatggatagcatt<br>gccatccggcacatggagtccgggtgggagggaaaggacaaggtagaagtcttccctttggct<br>aagaattacaccttctggctggcttgccgactcttcttaagcgtcgaggacccggctcatgtagcc<br>aagttctccgaaccattcaacgacatagccgcagggatcatctcgatgccaatcgacctccccg<br>gaacacccttcaaccgagggatcaagtcgtctaacgtcgtaagaaagagttgagggccatcat<br>aaagcagaggaaacttgacttagcagatggcaaggcttcacctacacaagatattctgtctcatat<br>gttgttgacttgtactgaagatggcaagtttatgagtgaaatggatattgctgataagattctgggac<br>ttcttattggtggacatgatactgctagtgcttcttgtacttttgttaagtttcttgctgagcttcctc<br>acatatatgaaggtgtctacaaagagcaaatggagatagcaaattcaaaaaaagcaggagaact<br>tctaaattgggaggacatacaaaaaatgaaatactcatggaatgtagcttgtgaagttatgcgtttg<br>gctcctccacttcaagtgggtttcaggaagccctttctgatttcatgtataacggattccaaatccc<br>caagggctggaagttatattggagtgcaaattcaacacatatgaacccggaatgcttcccggagc<br>ccaagacgttcgacccatcgaggttccgacggtacgggaccagcaccatacacatacgtcccctt<br>cggaggaggaccgagaatgtgcccgggcaaggagtatgcaaggctagagatattagtgttcat<br>gcacaacgttgtcaagaggtttaaatgggaaaaaatgcttcctgatgagaaggttattgtcaatcc<br>catgcctatcccagaacatggccttcctgtccgccttttccctcatcctcgaactgtagctgcttaa |
| SOAP2-Like | | 47 | atggagttcttctttctgtgtggtctagtcttttacttctccatatctctagcctccttcaccttttctataa<br>ccaccatacaacccgggtttacccgctacccgcgggcgagatggggtggccggtggtgggcg<br>actcgtttgaatttttttcaaaccgggtggaacggttacccggaaaatttcatctttgatagactcaac<br>aaatacaccccaagccaagtgttcaagactttcatcctaagagaaaaggttgtgttttatttgaaa<br>ggttgtag |

TABLE 16-continued

Nucleotide and Amino Acid Sequences for Triterpenoid Biosynthetic Pathway Enzyme in Spinach

| NAME | ENZYME ACTIVITY | SEQ ID NO: | AA SEQ/NT SEQ |
|---|---|---|---|
| SOAP1 | saponin β-amyrin synthase | 48 | MELFFMCGLVLFISLSLASFFLFYNHHRTRGYKLPPGKMGW<br>PVVGESFEFFQTGWKGYPEKFIFDRLNKYTPSQVFKTSIVGEK<br>VAVLCGAAGNKFLYSNENKLVQAWWPSSVDKIFPSSTQTSS<br>KEEAKKMRKLLPNFLKPEALHRYIPIMDSIAIRHMESGWEGK<br>DKVEVFPLAKNYTFWLACRLFLSVEDPAHVAKFSEPFNDIAA<br>GIISMPIDLPGTPFNRGIKSSNVVRKELRAIIKQRKLDLADGKA<br>SPTQDILSHMLLTCTEDGKFMSEMDIADKILGLLIGGHDTAS<br>ASCTFVVKFLAELPHIYEGVYKEQMEIANSKKAGELLNWEDI<br>QKMKYSWNVACEVMRLAPPLQGGFREALSDFMYNGFQIPK<br>GWKLYWSANSTHMNPECFPEPKTFDPSRFDGTGPAPYTYVP<br>FGGGPRMCPCKEYARLEILVFMHNVVKRFKWEKMLPDEKVI<br>VNPMPIPEHGLPVRLFPHPRTVAA |
| SOAP2 | cyto-chrome P450 | 49 | MWRLKVGEGANDPYLYSTNNFVGRQTWEFDPNYGTPEDIQ<br>EVEDARRDFYNNRFKVKPCNDLLWRFQFLREKNFKQTIPQV<br>KVGDGEEITYETASTTLKRAVNIFTALQSEHGHWPAEIAGPQ<br>FFLPPLVFCLYITGDLNSVFGPEHRREILRSIYYHQNEDGGWG<br>LHIEGHSTMFCTALNYICLRMLGIGPDEGDDNACPRARKWIL<br>DHGSVTHIPSWGKTWLSILGLFDWSGSNPMPPEFWILPTFLP<br>MHPAKMWCYCRMVYMPMSYLYGKRFVGPITPLIKQLREEL<br>YNEPFEQISWKKMRHLCAPEDLYYPHPLIQDLMWDALYLFT<br>EPLLTRWPFNKLIRKKALEVTMEHIHYEDENSRYITIGCVEKV<br>LCMLACWVEDPKGDHYKKHLARVQDYIWIAEDGLKMQSFG<br>SQQWDCGFSVQALLASNLSLDEIGPALKKGHFFIKESQVKDN<br>PSGDFKAMHRHISKGSWTFSDQDHGWQVSDCTAEGIKCCLI<br>LSTMPPEIVGEKMDPERLYDSVNVLLSLQSNKGGLAAWEPA<br>GAQEWLEYLNPTEFFEDIVIEHEYVECTASAIQALIMFKKLYP<br>GHRKKEIENFVVNAVKYLENTQYPSGGWYGNWGICFIYGT<br>WFALGGLAAGGKTYYNCAAVRKGVDFLLTTQKEDGGWGE<br>SYISCPNKEFVPIEGKSNLVQTGWALMGLLHAGQAERDPTPL<br>HRAAKLLINSQLENGDFPQQEITGVFMKNCMLHYPMYRSIYP<br>LWAIAEYRKRVSLPSINST |
| SOAP2-Like | | 50 | MEFFFLCGLVFYFSISLASFFLFYNHHTTRVYPLPAGEMGWP<br>VVGDSFEFFQTGWNGYPENFIFDRLNKYTPSQVFKIFILREK<br>VVFYLRRL |
| SOAP3 | cyto-chrome P450 (C-2 hydrox-ylase) | 51 | atgatagaaatcgggtatattgtaaaatgggtaatttgtttagtgattgttagatgggtatggaagatt<br>gtgaattgggtttggtttacaccaaaaaggcttgagaagtttctaagaaaacaaggtttagatgga<br>aattcatacaattttgttgggtgatctcaaaaatattctaaaatgcgtaaaaaagctagacaaa<br>aacctattccttttactcatgacttctttcatcgtatcttgcctttccacaatcaccatttcaataaatacg<br>gggaaagcttctttcatggatggggcctataccagttgtgaatgttgcagaacaagagcaagtaa<br>agggtgtgttcactaggataaaagagtttcagaaggccaaattaaacccacttgttgcattgcttgt<br>ccctggacttgtgagcgctgaaggtgataaatgggtcaagcacaggaagctcatcaacccggct<br>tttcatatggaaaagcttaagcttatgcatccagcatttggcgccagtgttttggatatggtgaacaa<br>gtgggagaagatagtatctaaaacaggttcctctgaagtggatgtgtggccgtttgtttccagcct<br>gactgcagatgctatctctcgtgctgcttttggcagtagctatgatgaaggaagaaagatatttgag<br>ttggttcttgaacaaactgaaatcaccctacgccttctgcaatcagtttatatccctggatggatgtat<br>gtgccaacaaagaccaacaggaggatgaaaacagtaaactctgaaatacaaaatttattaaaccg<br>ggataatcgttaagagaaagaaggcaatggaggccggcgaagctgccaaggatgatttgttgg<br>ggatattgttggaatccaactacaaagatactaaaatgttctcagtaataagaaaaaactaagca<br>tgactttccaggaattgattgatgagtgcaaactgttctacttagcagggcaagagtcgacctcgg<br>tgttgctagcatggacaatgattctgttgggaaagcacacagagtggcaagcacgagcacgaga<br>agaagtagttgcaacgtttggtaaaaacgaacctgattttgaaggcttaaaccatttgaagatagtg<br>acaatgatactgaatgaggtgttgaggttgtaccctccagtgtgtacaatcacccgtaagaatttca<br>accacgacgtacagcttggaaatctgacagtccctcgtggtgctatggttacgatgtcagcatatc<br>gtattcaaagagatcctaaaatatggggtgatgatgaaaagagtttaacccacagagattttcag<br>aaggggttgcaaaggctacaaaggggaatattgcattctttccgtttggtttaggccgcttaattt<br>gcatcggacagaactttgcacttattgaagctaaaatggcagtgtccatggttttacaacgcttttct<br>tttgagctatcaccgtcttatactcatgctcctaccactatcctcactcttcaaccccaacaaggtgct<br>catctcattatacataagctcagggactaa |
| SOAP3 | cyto-chrome P450 (C-2 hydrox-ylase) | 52 | MIEIGYIVKWVICLVIVRWVWKIVNWVWFTPKRLEKFLRKQ<br>GLDGNSYRFLLGDLKDMSKMRKEARQKPIPFTHDFFHRILPF<br>HNHHFNKYGESFFSWMGPIPVVNVAEQEQVKGVFTRIKEFQ<br>KAKLNPLVALLVPGLVSAEGDKWVKHRKLINPAFHMEKLK<br>LMHPAFGASVLDMVNKWEKIVSKTGSSEVDVWPFVSSLTAD<br>AISRAAFGSSYDEGRKIFELVLEQTEITLRLLQSVYIPGWMYV<br>PTKTNRRMKTYNSEIQNLLTGIIVKRKKAMEAGEAAKDDLL<br>GILLESNYKDTENVLSNKKKLSMTFQELIDECKLFYLAGQES<br>TSVLLAWTMILLGKHTEWQARAREEVVATFGKNEPDFEGLN |

TABLE 16-continued

Nucleotide and Amino Acid Sequences for Triterpenoid Biosynthetic Pathway Enzyme in Spinach

| NAME | ENZYME ACTIVITY | SEQ ID NO: | AA SEQ/NT SEQ |
|---|---|---|---|
| | | | HLKIVTMILNEVLRLYPPVCTITRKNFNHDVQLGNLTVPRGA<br>MVTMSAYRIQRDPKIWGDDAKEFNPQRFSEGVAKATKGNIA<br>FFPFGWGPRICIGQNFALIEAKMAVSMVLQRFSFELSPSYTHA<br>PTTILTLQPQQGAHLIIHLKLRD |
| SOAP4 | cyto-<br>chrome<br>P450<br>(C-23<br>oxidase) | 53 | atgatttcaaagagcgcgagtggtgttgcaattgcttcattgggttgcattatcatactgtattggatg<br>tgaaattactaaaagggctatggttaacaccaaaaaagctagagaaatgtctaaaacaacaag<br>gtcttgttggtaattcctacaaattttttgattggagatatgaaagaaagctcaaaattgcgtaacgaa<br>gctttacaaaaacccattcctttcactcatgattattacaaccgtattcagcctttcatccatcagattc<br>tcaacaattctggtgcaggcaaaaatatctacacatggttgggaccagtgccaacaatactaatta<br>cacaacctgagttaataaaggatgctttcaataggatgaacaattttcagaaaccaagattaaatcc<br>atatactcaaatgctttcaactggacttccgaactatgagggtcagaaatgggctaaacacagga<br>agcttctcaaccctgcttttcaacttgataagctcaagcttatgatccatacttttgaaacctgtgttac<br>ggatacactgaataagtgggagaagctagtttgtaaaacaggttcttcagaggttgatatatggcc<br>atatttgacaactttaacgggagatggtattgctagagctgcatttggaagtagctttgaagatgga<br>agaagaatattcgagcttctcacactgcagaaggatattgttattagtcttctcaaatattcttatattc<br>caggatttaaatatatgccaataaagggtaaccggaagatgaaagaagcggacaatgaaataaa<br>acctctgttgacgaatataattaatagaaggaggaaacgatggaggccggagaagctcccaa<br>agacgacttgttagggatgctacttgaatccaatcaaacgaagctcgacaagttaataaaatg<br>aaagtggtagtagcaagcgaaaatctgatctaacgatgagcttccctgagatgatcgatgcttgc<br>aagcagttcttcttggctgctcaagagaccacctcagtggccctaacatggacaatgcttttgttag<br>ccaagcaccaagattggcaaacacgagctcgacaagaagtacttgctacatttggaatgaatac<br>cccagactttgatggcatacataatcgtcttaagattgtgacaatgatactctacgaggtgttaaggt<br>tgtatccgccagtccctgcaacatcgcaaagggttcatgatcgtgaaacaaactaggaaatttgg<br>gtaataccacaaagggtaggagtttcattttccatacttcatgcacacttgaaccctgaaatttggg<br>gtgatgatgccaaagaattcaagcctgatagatttgcagaagggattgcaaaagcaacaaaagg<br>gaataactcttacttcccctttggttggggacctaggatttgcattggccaaaacttcgcactagttg<br>aggcgaaaatggcattgtgtatgattttgcagcgtttctctttcgatctctcgccttcatacatccatg<br>ctccgactagtctcatatcccttcaacctcagcatggtgcccacattattttacatcgattttaa |
| SOAP4 | cyto-<br>chrome<br>P450<br>(C-23<br>oxidase) | 54 | MISKSASGVAIASLGCIIILYWMWKLLKGLWLTPKKLEKCLK<br>QQGLVGNSYKFLIGDMKESSKLRNEALQKPIPFTHDYYNRIQ<br>PFIHQILNNSGAGKNIYTWLGPVPTILITQPELIKDAFNRMNNF<br>QKPRLNPYTQMLSTGLPNYEGQKWAKHRKLLNPAFQLDKL<br>KLMIHTFETCVTDTLNKWEKLVCKTGSSEVDIWPYLTTLTG<br>DGIARAAFGSSFEDGRRIFELLTLQKDIVISLLKYSYIPGFKYM<br>PIKGNRKMKEADNEIKPLLTNIINRRRKAMEAGEAPKDDLLG<br>MLLESNANEARQVNENESGSSKRKSDLTMSFPEMIDACKQF<br>FLAGQETTSVALTWTMLLLAKHQDWQTRARQEVLATFGMN<br>TPDFDGIHNRLKIVIMILYEVLRLYPPVPATSRRVHDRETKLG<br>DLVIPQGVGVSFSILHAHLNPEIWGDDAKEFKPDRFAEGIAK<br>ATKGNNSYFPFGWGPRICIGQNFALVEAKMALCMILQRFSFD<br>LSPSYTHAPTSLISLQPQHGAHIILHRF |
| SOAP6 | Glycosyl<br>trans-<br>ferases<br>(UDP-<br>glyco-<br>syla-<br>trans-<br>ferase;<br>Fucosyl-<br>trans-<br>ferase) | 55 | atgacgggaaaaggaagaacgatggaggtgatcatgatgccatttcaccaccaaggtcacttaa<br>ccccgatgctccaattcgcgaagcgcttcgcttggaaaggtgctggctcgatccggatcaccctc<br>gccaccaccctctccaccgcccaaaatatgaccaattccaaaaacaacaacaacaataaccgatt<br>acgatttcctgacggtcgaaagcatctacgacgataccgatgattctcagctcaaattcatgggtc<br>gtatgggaaagttcaaattccgaagcctcactccaacttaccatctaatcactactaaagcatc<br>gacaataataaatgtatgctcgtttatgatgcgtatctgccttgggcactggatgtgggcaaggac<br>cataacatacaggctgcggctttcttcgtccaggcttgtgcgtatatggcatccttttaccctatgttt<br>tagaggaatttgggtcggatgatcaacatcctgttgttgcggctgctaaggctgaatctcgttcctag<br>tttgtcggttgagctgccgtcgcgggaggaaatggaacgatttcgcctcctttatgtgcatttcc<br>ccgagttctgatgataaacccaatactgttaagaaatcgcttcaccctgtctaccggatggtggttt<br>catcaattacaacccttcatcttactaatttcgtctcatcaactcctttgatcaccttgaacatcagct<br>ggatgtcttagcacatgaagcagtagggtgtttcataacccattgcggttggaactcgataattga<br>ggcgaccaactttggggttccgatgttggggatgccacagttcatggaccagtttttggatgctca<br>ttttatggagaaggtttggggtgtttggaattagggctaaggctgatgagaaaaactttgttacttgtg<br>acgaaatcaagtgcggtgtcaatgaaattatgtacggagataaggcaaatatgatcaaggagaat<br>gcagcaaagtggaaagacttggctaaggaggcagttggtgaaggaggcagttcagttcagaat<br>atcgacgagatcattaactggcttgcgtcacctaa |
| SOAP6 | Glycosyl<br>trans-<br>ferases<br>(UDP-<br>glyco-<br>syla-<br>trans-<br>ferase;<br>Fucosyl-<br>trans-<br>ferase | 56 | MTGKGRTMEVIMMPFHHQGHLTPMLQFAKRFAWKGAGSIR<br>ITLATTLSTAQNMTNSKNNNNNNDYDFLTVESIYDDTDDSQL<br>KFMGRMGKFKSEASLQLGRLITTKSIDNNKCMLVYDAYLPW<br>ALDVGKDHNIQAAAFFVQACAYMASFYPMFLEEFGSDDQHP<br>VVAAAKAESVPSLSVELPSREEMERYAPKCAQSPSSDDKPNT<br>VKKSLHPVYRMVVSSITTLHLADFVLINSPDHLEHQLDVLAH<br>EAVGCFITHCGWNSIIEATNFGVPMLGMPQFMDQFLDAHFM<br>EKVWGVGIRAKADEKNFVTCDEIKCGVNEIMYGDKANMIK<br>ENAAKWKDLAKEAVGEGGSSDKNIDEIINWLASS |

TABLE 16-continued

Nucleotide and Amino Acid Sequences for Triterpenoid Biosynthetic Pathway Enzyme in Spinach

| NAME | ENZYME ACTIVITY | SEQ ID NO: | AA SEQ/NT SEQ |
|---|---|---|---|
| SOAP7 | Glycosyl transferases (UDP-glycosyl-transferase) | 57 | atgggtaaaacagtagcagcttcagagcagttacacatagtaatgatcccatggtttgcttatgga<br>cacattcttccctattttgagctttcaaacaaacttgctgaaaggccataaaatcaccttggtagtt<br>ccaaacaaagtcaaacttgatttagaaccaaagatccgtcatccttcatttatcagcttacatgcatt<br>cactgtcccacacattgaacccttacctccggggactgagacatgttcagacgtccccattgaact<br>tcagcaccaccttgctgttgccatggacagggcccggcctgaggtggagtccatcatatcagcc<br>attgacgatccgaagccggatctgttgttctacgataacgcttactgggtgcctgagatagccaca<br>aagctggggatgaagtctgtgtttaccagattgcatgtgctttaagtatcacccgcattaagcaaa<br>ccccgagtgcgagtgcgagtgcgagtgcgagtgccaagctcttcactttacccaagtgggtgct<br>gacgcctaaggtgttaggcgacgcaagagccaattatggagaagggatcacctattaccagag<br>agtgaagaagactaagttcctgtgatgctatcgccttacgcacatgccgggagattgaagggg<br>aatcctctgatatcctggctgcacaatataacaagccagtcttcttaacaggtccggtcctacccga<br>ggttgaattcctcccccctttggacaattcctgggctgagtggctaccaagtttgggcctaagtc<br>cgtggttttatgttgcttcggaagccagtacgtccctgacaaggctcaactacagagatggccct<br>tgcccttgaggatactggtcttcccttcttgatgtccgttaagccacccacagagtgcgccaccata<br>gaggaggcgttgccagaagggttctcagagagagtcaaggaacgcggggtggttcatggtgg<br>atgggtgcaacagctacaaatactagctcacccatcagtgggttgcttatttgtcattgtgggtac<br>gggtcaatgtgggaggggttgttgagtgataaccagctagtcttattaccacagcttcctgaccag<br>ttaatgatggctcaaatgttggcagaaaagctcaaggtggtgtgatagtggacagagaagaag<br>atgatgggtgggtttccaggaagaacttgtgccaagcagtcaagtagtcatggatcctcattccg<br>agtttgcagctttactcaagaacaaccatgctaacttcagagacaagttgctaaccaacggttttat<br>ggctaattaccttgaagttttgaccattgatttgatttcgctttcttactgcaattaa |
| SOAP7 | Glycosyl transferases glycosyl- (UDP-transferase) | 58 | MGKTVAASEQLHIVMIPWFAYGHILPYFELSNKLAEKGHKIT<br>LVVPNKVKLDLEPKIRHPSLISLHAFTVPHIEPLPPGTETCSDV<br>PIELQHHLAVAMDRARPEVESIISAIDDPKPDLLFYDNAYWV<br>PEIATKLGMKSVFYQIACALSITRIKQTPSASASASASAKLFTL<br>PKWVLTPKVLGDARANYGEGITYYQRVKKALSSCDAIALRT<br>CREIEGESSDILAAQYNKPVFLTGPVLPEVEFLPPLDNSWAE<br>WLAKFGPKSVVLCCFGSQYVPDKAQLQEMALALEDTGLPFL<br>MSVKPPTECATIEEALPEGESERVKERGVVHGGWVQQLQILA<br>HPSVGCFICHCGYGSMWEGLLSDNQLVLLPQLPDQLMMAQ<br>MLAEKLKVGVMVDREEDDGWVSRKNLCQAVKSVMDPHSE<br>FAALLKNNHANFRDKLLTNGFMANYLEVFDQDLKRFLTAN |
| SOAP8 | Glycosyl transferases (UDP-glycosyl-transferase) | 59 | atgggtggagagaaagagttgcggatagtgatgttcccatggcttgcctttggacattttatcccat<br>accttcacctttcaaacaaacttgctgaaaaaggccacaaaatcaccttgttgcttcccaacaaag<br>ctagcttcagttggatcacttaaccttcatccttctctcataactttccattcaattactgtcccacc<br>cctcgaaactctcccttatggcactgaaacaactcggatatctccctcgaccaacatggtaact<br>ctcgatttccatggaccgcactcggcccgaggtggagtctttcctatcaacccataagcccgacc<br>tcgtcctctacgacatggcccattgggtacccgagattgctgctaaggtcgggattaagtcagttt<br>catacaacgttgtatgtgctattgctgtatctcatgttagacctagcctccctcttccaaaaggaacg<br>gcagcacatgtaccccctgccattgtcgtctgtccctaagtggagtcttaatcagcacggttcatcaa<br>caccatatttggggaagggataacgttacttgaacagtctgtaatctccctctcgtctcggatgc<br>aatagccatccgcacgtgcagggagattgaaggggtatattgtgaccgtgttgctgccacattca<br>acaagcctgtccttgtcaccagccacgccttgcctgatcttgaactcgaactctctccgttggaga<br>ctcgagggccgagtggctagctaggttcgagccagggtcagtgatcttttgctgccttggtagtc<br>agcatgtcttagacgcaccccaactgcaagagttggccaggggttggaaatgacaggactacc<br>cttcttgatggctgtaaaacccccctgtggggtgtacctccttggaggaggtgcttccagaagggtt<br>taatgatcggttagcgggcgaggggtggttcacgtgggtgggtgcagcagcagcagataat<br>ggcgcacccatcgttagggtgctttgtgaccctttgtgggtcttcgtcgatgtgggaggggttagt<br>gagtgaaagtcagttggtattactcccacaactggcagaccaaactctgtatgccaagttaatggc<br>agatgagctcaaggtgggtgtgaaggtggagagagaagagaacgggtggatgacgaagcga<br>agtctatgtgaagctatcaagagtgtgatggatgaagatagtgatataagtcatgtagttaggaaa<br>aatcatgctaaatatagaagtatgttgattagccctggctttattagtggctacattgacaacttcatc<br>aaggatttacaagcccttgttccttag |
| SOAP8 | Glycosyl transferases (UDP-glycosyl-transferase) | 60 | MGGEKELRIVMFPWLAFGHFIPYLHLSNKLAEKGHKITLLLP<br>NKARLQLESLNLHPSLITFHSITVPPLETLPVGTETTADISLDQ<br>HGELSISMDRTRPEVESFLSTHKPDLVLYDMAHWVPEIAAKV<br>GIKSVSYNVVCAIAVSHVRPSLPLPKGTAAHVPLPLSSVPKW<br>SLNQHGSSTPYFGEGITLLERSVISLSSADAIAIRTCREIEGVYC<br>DRVAATFNKPVLVTSHALPDLELELSPLETRWAEWLARFEP<br>GSVIFCCLGSQHVLDAPQLQELALGLEMTGLPFLMAVKPPV<br>GCTSLEEVLPEGFNDRVSGRGVVHGGWVQQQQIMAHPSLG<br>CFVTLCGSSSMWEGLVSESQLVLLPQLADQTLYAKLMADEL<br>KVGVKVEREENGWMTKRSLCEAIKSVMDEDSDISHVVRKN<br>HAKYRSMLISPGFISGYIDNFIKDLQALVP |
| SOAP9 | Glycosyl-transferases | 61 | atggagctttcaaaccctaccacaacccctaccttaaacgcaacccaacccttacgaagctatttc<br>attccattaatcacagttccaagccacatttccaatcttgttgacattgctaaactcttctcatcacgg<br>ggagtacatgtgactatcctcaccacccaccacacctccctccgcttcaaacaatccatacatgat<br>tggggcttcaaaatcgacctccacatcgtcgacttcccgttcagggaagtcggcttaccggaagg |

TABLE 16-continued

Nucleotide and Amino Acid Sequences for Triterpenoid Biosynthetic Pathway Enzyme in Spinach

| NAME | ENZYME ACTIVITY | SEQ ID NO: | AA SEQ/NT SEQ |
|---|---|---|---|
| | (UDP-<br>glyco-<br>sytl-<br>trans-<br>ferase;<br>Xylosyl<br>trans-<br>ferase) | | agtggaaaattacagtgatgccacccctgatcaagcaagccagcttttccaggcctttatgatgct<br>tcagaagcctatggaggatgccattcgggctgctaagcccgacttcatcgtttccgataggtattat<br>cattggtctactaatatgcacgtgacttgctattccacggctcatctttcatatcagatgttattttg<br>cattgtgtgctgctgaggttgttgccaagtttgcccctcatgagaaggttgaatctgacactgacct<br>ctttttccttcctgacctccctgataccatccacatgacccgtttgcagcttcccgaatggattcaga<br>cccgaaacatgttcactgttctcaatgagagaatggacgaggccgatagggagtgctacggtgtt<br>attgtaaacagctgctacgagttggagagagcttatgctgacttctaccgcagcaacttgggtcga<br>cgtgcttggtgtatcggtccctatccggtacactgcgacaaggttggtaaaaagaaaggagatga<br>cagcaaaaaacattcatgttttgaatggcttaataaaatgggagaaggagaagttatatacgtgag<br>ttttggcactctgtcgtgtttcagccctgctcaaatctcagagctggctactgcactcgaaatgtctg<br>gtcacccgtttatctgggtagtaaggaatggtgagaaattgttacctgatggatttgaagaaagaat<br>tacagagcaggacaaaggggtgttaataaaaagactgggcgccacaagtgaaaatacttgagca<br>cccagctgtaggcggatttctgactcattgtggatggaactcaactgtagaaagtttagcagcagg<br>tgtgccaatggtcacatggccgcttggtgccgagcaattcttcaatgaaaagttgattagtggagtt<br>ttgaaggtgggggtcgaggtcgggtctgagaagtggagtaggggtatagtaccgaatactgata<br>tgattgagaaggataaaatagaaagggcgattaaagagctgatgagtaaagaacccgaggccg<br>aggaaaggaggcagaaggttaaggagttgagtaaggctccaagaaatgcggttgaagaaggt<br>ggttcgtctcgtaacaatttaagtgatttgattgaaaaattacaacgtttaaaggcgaatgaaatatc<br>agtgtccacaaactcagaataa |
| SOAP9 | Glycosyl<br>trans-<br>ferasce<br>(UDP-<br>glyco-<br>syl-<br>trans-<br>ferase;<br>Xylosyl<br>trans-<br>ferase) | 62 | MELSNPTTTPTLNATQPLRGYFIPLITVPSHISNLVDIAKLFSSR<br>GVHVTILTTHHTSLRFKQSIHDWGFKIDLHIVDFPFREVGLPE<br>GVENYSDATPEQASQLFQAFMMLQKPMEDAIRAAKPDFIVS<br>DRYYHWSTDLARELAIPRLIFHVRCYFALCAAEVVAKFAPHE<br>KVESDTDLFFLPDLPDTIHMTRLQLPEWIQTRNMFTVLNERM<br>DEADRECYGVIVNSCYELERAYADFYRSNLGRRAWCIGPYP<br>VHCDKVGKKKGDDSKKHSCFEWLDKMGEGEVIYVSFGTLS<br>CFSPAQISELATALEMSGHPFIWVVRNGEKLLPDGFEERITEQ<br>DKGVLIKDWAPQVKILEHPAVGGFLTHCGWNSTVESLAAGV<br>PMVTWPLGAEQFFNEKLISGVLKVGVEVGSEKWSRGIVPNT<br>DMIEKDKIERAIKELMSKEPEAEERRQKVKELSKAPRNAVEE<br>GGSSRNNLSDLIEKLQRLKANEISVSTNSE |
| SOAP 10 | Acyl<br>trans-<br>ferase<br>(BAHD<br>acyl<br>trans-<br>ferase) | 63 | atgggggaagtcaaccatgaagaagtagaaattgaaataatatcaatagaaaccataaaaccatc<br>atcactacttccaccaaaaactcctccaaaaaccatcacactttctcacctcgatcaagctgcccct<br>ttgtactactatcctttacttttatactacactaacactactactactaccccaacatcacaaattcgag<br>ttgacataacaagtaccctaaaaacttcacttagcaaaacacttgacaaattccaccctattgcagg<br>tcgatgtgtggacgactctacaatttgttgcaaccaccaaggaataccattcattgaaaccaaagtt<br>gactccaatatcttggatgtcatgaactcgcctgagaaaatgaagttgcttatcaagtttctccctca<br>tgcagagtttcaagatgtgactcgaccagtctcggatttaaaccatttggcgtttcaagtcaatgtttt<br>ccggtgtggtggggtgatcattggctcctatgtgctccacaagctccttgatggaatctctcttgga<br>actttctttaaaaattggtcaaccattgctaatgatgagcgagttaaggacgacgacctagtacaac<br>ctgactttgaagccactattaaggcgttccctccgcgtacagcaactccaatgcttcctcgtaatca<br>acaacttccaaaggcggctgaaaaaccaaataataatccagtcaaagttcttgtgacaaagagct<br>tcgtatttgacattgtttctttaaagaagatgatgttcatggctaagagtgaattggttcctaaaccca<br>ccaaatttgagaccgtgacagggtttatttgggaacaaaccttatcaacattgcgtaattctggagtt<br>gaagttgaacatacatcgcttataatacctgtaaacatccgcccaaggatgagtccgccactccc<br>aagaggatccatgggtaacttgctcaagaatgcaaaggcacaggccaacaccagcagcagca<br>atgggcttcaagaccttgttaaagaaatccattcatctttgtctcaaacaacccagaaaattaatact<br>cctcctcctcctcctcctcctcctcctactactactgctacaacaatccattcatctttgtctcaaacaa<br>cccagaaaattaatactcctcctcctactactacaacaatccattcatctttgtctcaaacaacccag<br>aaaattaatactactactactacagcagaggttattttgactaaacggaaagttgacaatccagtta<br>cacagaatcgagaaggaaactacctcttcaccagttggtgcaagattgggttggatgaggctga<br>cttcgggttcggaaagcccgtttgggtaattcccaacgatgggagacccccctaaggtcaggaat<br>atgattttccttactgattataggcatcccgaaacaggcgttgaaggaattgcagcatgattacgt<br>tggaagagaaacaaatgcaatgtttaaagtcaaacccagaattccttgcttttgctactcctaattag |
| SOAP 10 | Acyl<br>trans-<br>ferase<br>(BAHD<br>acyl<br>trans-<br>ferase) | 64 | MGEVNHEEVEIEIISIETIKPSSLLPPKTPPKTITLSHLDQAAPL<br>YYYPLLLYYTNTTTTTPTSQIRVDITSTLKTSLSKTLDKFHPIA<br>GRCVDDSTICCNHQGIPFIETKVDSNILDVMNSPEKMKLLIKF<br>LPHAEFQDVTRPVSDLNHLAFQVNVFRCGGVIIGSYVLHKLL<br>DGISLGTFFKNWSTIANDERVKDDDLVQPDFEATIKAPPPRT<br>ATPMLPRNQQLPKAAEKPNNNPVKVLVTKSFVFDIVSLKKM<br>MFMAKSELVPKPTKFETVTGFIWEQTLSTLRNSGVEVEHTSL<br>IIPVNIRPRMSPPLPRGSMGNLLKNAKAQANTSSSNGLQDLV<br>KEIHSSLSQTTQKINTPPPPPPPPPTTTATTIHSSLSQTTQKINTP<br>PPTTTTIHSSLSQTTQKINTTTTTAEVILTKRKVDNPVTQNRE<br>GNYLFTSWCKIGLDEADFGFGKPVWVIPNDGRPPKVRNMIFL<br>TDYRHPETGVEGIAAWITLEEKQMQCLKSNPEFLAFATPN |
| SOAP5 | Cel-<br>lulose<br>synthase | 65 | atggcaacttctcacattcgcaatgtccaattaaccagagccattgttaaccgtctccacatcttcct<br>ccattccgtagccatcttctcgctcttctactaccgtttcacttccttcttcaactccgacatctccata<br>cttgcttactccttactcaccaccgccgaactcttcttaacctttctatgggcttttactcaggctttcc |

TABLE 16-continued

Nucleotide and Amino Acid Sequences for Triterpenoid Biosynthetic Pathway Enzyme in Spinach

| NAME | ENZYME ACTIVITY | SEQ ID NO: | AA SEQ/NT SEQ |
|---|---|---|---|
| | Like G (glucu-ronic acid trans-ferase) | | ggtggcgtcccgtaatgagggaagtctccgggtacgaatccatcaaacccgaacaactaccgg<br>gtttggatgtcttcattgtcactgctgacccgacaaaggagccagttctggaggtgatgaactccg<br>tgatatcatccatggctttggattatccggttgatagactggcggtttacttgtcggatgacggtggt<br>tctccgttgtcgaaggaggcgattaagaaggcttatgagtttgctaagctttggattcctttttgtaat<br>aagtataatgttaagacaaggtgtcctcaggctttcttctcgcctcttgctgatggggaaaggcttg<br>attggaattctgagtttatggctgatcaattggaactccagaccaaatatgaagcttttagaaactat<br>gtggagaaagaaagtggagataacaccaaatgtactgcagttcatgatcgacctccttgcgttga<br>gattatacatgacaacaaacagaacggagaaagtgatgtgaagatgccccttctggtttatgtagc<br>cagggaaaagagacctggtcgtcctcatcgtttcaaagctggagcccttaatgctcttcttcgagt<br>atccagtttaatgagcaatgcaccttacttattggtgttggattgtgatatgtactgccatgatccaac<br>ttctgctcgtcaatctatgtgcttccatcttgacacaaacatggcttcctctcttgcatatgtgcaatac<br>cctcaaatttctataatgttagcaaaaatgacatctatgatggccaagccagatcagctcatatga<br>cgaaatggaaaggcatggatggactcagaggcccggtcttgaatggaactgggtattatttgaa<br>gcgaaaagcattatttggaaagcctaataacgaagatgaatacctcaacagtcaaccagaaaag<br>gcctttggctcctccacaaaattaattgctgcactaagagagaactccaagcaaaatcttgccata<br>aaggaattgacagaagatgagttgtaccaagaggctagaaatttggctacttgcacatatgaagc<br>aaacacactatggggcagtgaggtaggatattcgtatgagtgcttgttggagagtacattcactgg<br>atatatgttacattgcagaggatggaaatctgtgtatctttacccaaaaagaccatgcttcttgggat<br>gcacaacgattgatatgaaggatgctacggttcaactaataaaatggacctcctcattacttggaat<br>tgccctgtcgaagtctagccctctaactttggccatgtccagtatgtcaatcctgcaaagcatgtgtt<br>acgcgtacatcacatttacaggccttttttgcagctccattggttatatatggtgttgtccttccaataa<br>gcctattgaagggctttcctattttccctaaggtatcggatccatggattttgccatttgtgttgatattt<br>gtatcctcccatcttcaacatctatatgaggtcctggaaagtgacaaatcagcaacacaatggtgg<br>aatgaggtgagaatttggatgatgaaatcagtgacagcctgtttgtttgggttgacggaagcgata<br>atgaagaagattggagtacaaactgcaacattcagattaacaaataaggtagttgagaaggaaaa<br>gatggataaatacgagaaggagaggtttgatttctcaggagcagctatgctttggttcctcttaat<br>attttggtggtactaaatatggtgtcattcattggtggactcatgagggtcataatcaacaacagttat<br>gatcaaatgtttgcacaacttttcctctcctttttttgtcctacttcttagctaccctgttgttaagggatg<br>gttataa |
| SOAP5 | Cel-lulose synthase Like G (glucu-ronic acid trans-ferase) | 66 | MATSHIRNVQLTRAIVNRLHIFLHSVAIFSLFYYRFTSFFNSDI<br>SILAYSLLTTAELFLTFLWAFTQAFRWRPVMREVSGYESIKPE<br>QLPGLDVFIVTADPTKEPVLEVMNSVISSMALDYPVDRLAVY<br>LSDDGGSPLSKEAIKKAYEFAKLWIPFCNKYNVKTRCPQAFF<br>SPLADGERLDWNSEFMADQLELQTKYEAFRNYVEKESGDNT<br>KCTAVHDRPPCVEIIHDNKQNGESDVKMPLLVYVAREKRPG<br>RPHRFKAGALNALLRVSSLMSNAPYLLVLDCDMYCHDPTSA<br>RQSMCFHLDTNMASSLAYVQYPQIFYNVSKND1YDGQARSA<br>HMTKWKGMDGLRGPVLNGTGYYLKRKALFGKPNNEDEYL<br>NSQPEKAFGSSTKLIAALRENSKQNLAIKELTEDELYQEARN<br>LATCTYEANTLWGSEVGYSYECLLESTFTGYMLHCRGWKS<br>VLYPKRPCFLGCTTIDMKDATVQLIKWTSSLLGIALSKSSPL<br>TLAMSSMSILQSMCYAYITFTGLFAAPLVIYGVVLPISLLKGF<br>PIFPKVSDPWILPFVLIFVSSHLQHLYEVLESDKSATQWWNEV<br>RIWMMKSVTACLFGLTEAIMKKIGVQTATFRLTNKVVEKEK<br>MDKYEKERFDFSGAAMLMVPLNILVVLNMVSFIGGLMRVII<br>NNSYDQMFAQLFLSFFVLLLSYPVVKGWL |
| SOAP5 | Cel-lulose synthase Like G (glucu-ronic acid trans-ferase) | 93 | ATGGCAACTTCTCACATTCGCAATGTCCAATTAACCAGAG<br>CCATTGTTAACCGTCTCCACATCTTCCTCCATTCCGTAGCC<br>ATCTTCTCGCTCTTCTACTACCGTTTCACTTCCTTCTTCAAC<br>TCCGACATCTCCATACTTGCTTACTCCTTACTCACCACCGC<br>CGAACTCTTCTTAACCTTCTATGGGCTTTACTCAGGCTT<br>TCCGGTGGCGTCCCGTAATGAGGGAAGTCTCCGGGTACGA<br>ATCCATCAAACCCGAACAACTACCGGGTTTGGATGTCTTC<br>ATTGTCACTGCTGACCCGACAAAGGAGCCAGTTCTGGAGG<br>TGATGAACTCCGTGATATCATCCATGGCGTTGGATTATCC<br>GGTTGATAGACTGGCGGTTTACTTGTCGGATGACGGTGGT<br>TCTCCGTTGTCGAAGGAGGCGATTAAGAAGGCTTATGAGT<br>TTGCTAAGGTTTGGATTCCTTTTTGTAATAAGTATAATGTT<br>AAGACAAGGTGTCCTCAGGCTTTCTTCTCGCCTCTTGCTGA<br>TGGGGAAAGGCTTGATTGGAATTCTGAGTTTATGGCTGAT<br>CAATTGGAACTCCAGACCAAATATGAAGCTTTTAGAAACT<br>ATGTGGAGAAAGAAAGTGGAGATAACACCAAATGTACTG<br>CAGTTCATGATCGACCTCCTTGCGTTGAGATTATACAGA<br>CAACAAACAGAACGGAGAAAGTGATGTGAAGATGCCCCT<br>TCTGGTTTATGTAGCCAGGGAAAAGAGACCTGGTCGTCCT<br>CATCGTTTCAAAGCTGGAGCCCTTAATGCTCTTCTTCGAGT<br>ATCCAGTTTAATGAGCAATGCACCTTACTTATTGGTGTTGG<br>ATTGTGATATGTACTGCCATGATCCAACTTCTGCTCGTCAA<br>TCTATGTGCTTCCATCTTGACACAAACATGGCTTCCTCTCT<br>TGCATATGTGCAATACCCTCAAATTTTCTATAATGTTAGCA<br>AAAATGACATCTATGATGGCCAAGCCAGATCAGCTCATAT |

TABLE 16-continued

| Nucleotide and Amino Acid Sequences for Triterpenoid Biosynthetic Pathway Enzyme in Spinach | | | |
|---|---|---|---|
| NAME | ENZYME ACTIVITY | SEQ ID NO: | AA SEQ/NT SEQ |
| | | | GACGAAATGGAAAGGCATGGATGGACTCAGAGGCCCGGT<br>CTTGAATGGAACTGGGTATTATTTGAAGCGAAAAGCATTA<br>TTTGGAAAGCCTAATAACGAAGATGAATACCTCAACAGTC<br>AACCAGAAAAGGCcTTTGGCTCCTCCACAAAATTAATTGC<br>TGCACTAAGAGAGAACTCCAAGCAAAATCTTGCCATAAA<br>GGAATTGACAGAAGATGAGTTGTACCAAGAGGCTAGAAA<br>TTTGGCTACTTGCACATATGAAGCAAACACACTATGGGGC<br>AGTGAGGTAGGATATTCGTATGAGTGCTTGTTGGAGAGTA<br>CATTCACTGGATATATGTTACATTGCAGAGGATGGAAATC<br>TGTGTATCTTTACCCAAAAAGACCATGCTTCTTGGGATGC<br>ACAACGATTGATATGAAGGATGCTACGGTTCAACTAATAA<br>AATGGACCTCCTCATTACTTGGAATTGCCCTGTCGAAGTCT<br>AGCCCTCTAACTTTGGCCATGTCCAGTATGTCAATCCTGCA<br>AAGCATGTGTTACGCGTACATCACATTTACAGGCCTTTTTG<br>CAGCTCCATTGGTTATATATGGTGTTGTCCTTCCAATAAGC<br>CTATTGAAGGGCTTTCCTATTTTCCCTAAGGTATCGGATCC<br>ATGGATTTTGCCATTTGTGTTGATATTTGTATCCTCCCATC<br>TTCAACATCTATATGAGGTCCTGGAAAGTGACAAATCAGC<br>AACACAATGGTGGAATGAGGTGAGAATTTGGATGATGAA<br>ATCAGTGACAGCCTGTTTGTTTGGGTTGACGGAAGCGATA<br>ATGAAGAAGATTGGAGTACAAACTGCAACATTCAGATTA<br>ACAAATAAGGTAGTTGAGAAGGAAAAGATGGATAAATAC<br>GAGAAGGAGAGGTTTGATTTCTCAGGAGCAGCTATGCTTA<br>TGGTTCCTCTTAATATTTTGGTGGTACTAAATATGGTGTCA<br>TTCATTGGTGGACTCATGAGGGTCATAATCAACAACAGTT<br>ATGATCAAATGTTTGCACAACTTTTCCTCTCCTTTTTTGTC<br>CTACTTCTTAGCTACCCTGTTGTTAAGGGATGGTTA |

Summary. This study uncovered numerous surprising details. For example, SOAP6 may serve as a template in the homology-based search for fucosyltransferase decorating quillaic acid in the biosynthetic pathway of QS-21, a potent vaccine adjuvant form *Quillaja saponaria* (D. J. Marciani, Is fucose the answer to the immunomodulatory paradox of *Quillaja* saponins? Int Immunopharmacol. 29, 908-913 (2015)). Also, SOAP10, a member of the BAHD superfamily of acyltransferases is involved in triterpenoid saponin biosynthesis.

Example 21: Production of Triterpenoid Intermediates in Yeast

Objective: To produce of triterpenoid intermediates in a further heterologous system, in the case the yeast *Saccharomyces cerevisiae.*

Methods: See Materials and Methods above.

Figure 33B:
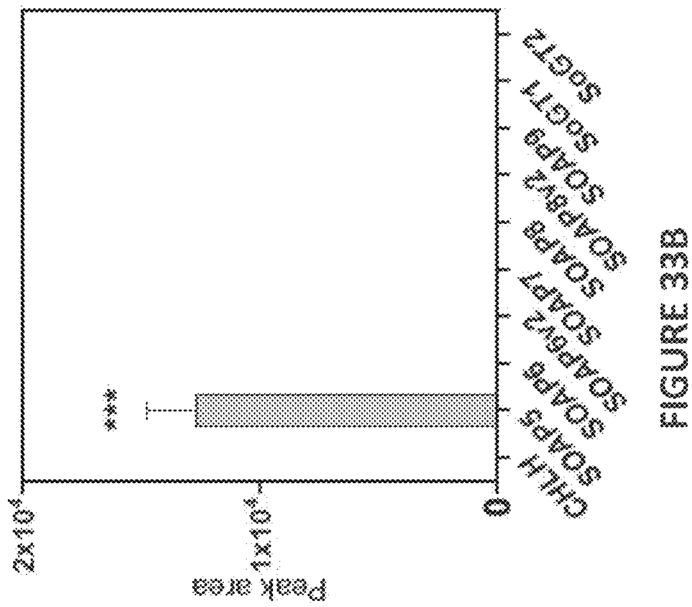
Figure 33A:
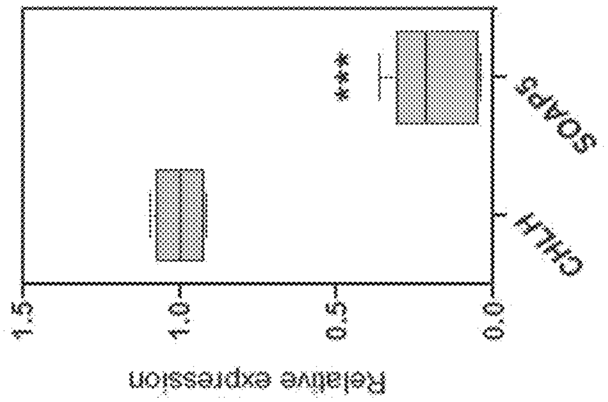
Figure 33C:
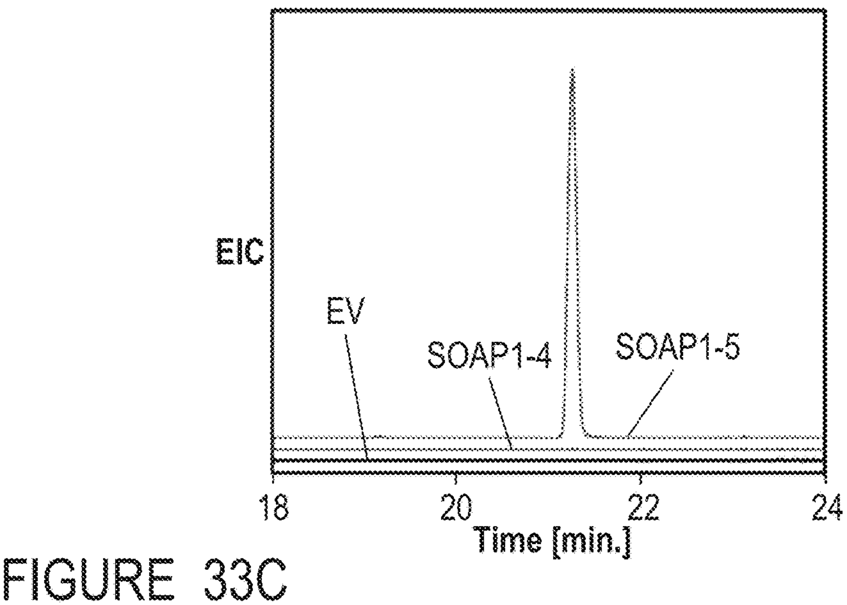
Figure 33D:
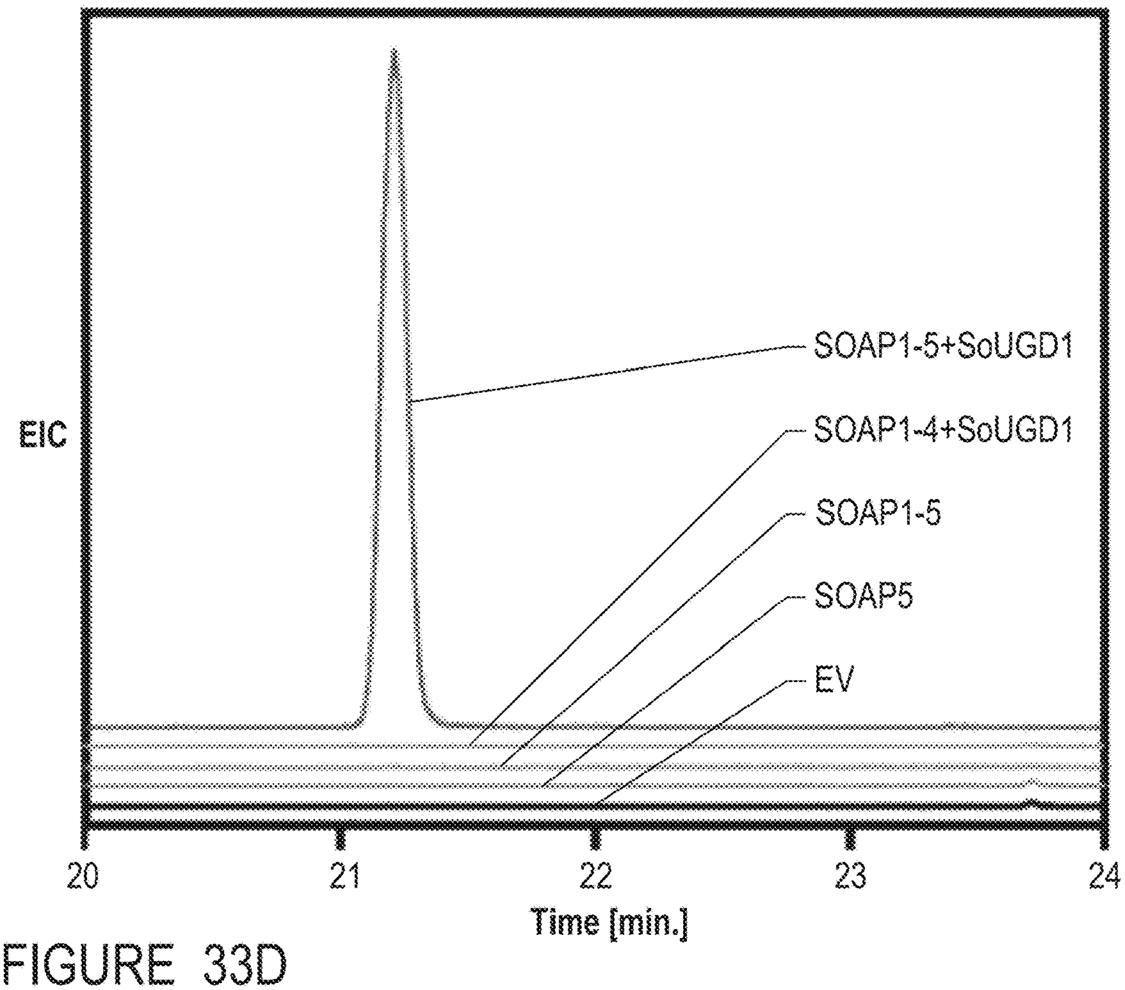
Figure 33E:
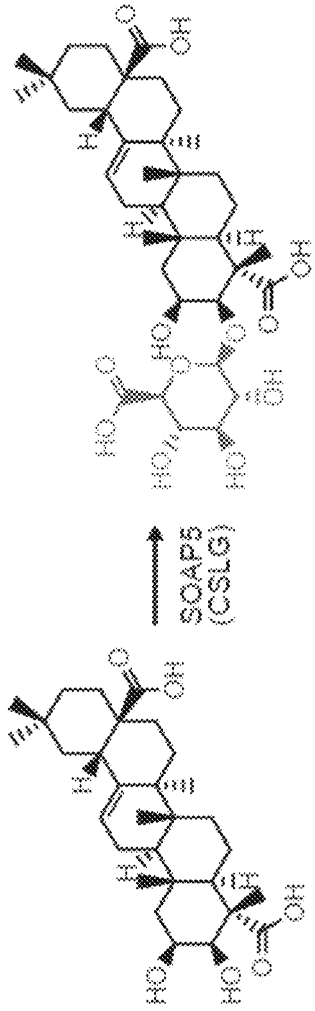
Figure 33F:
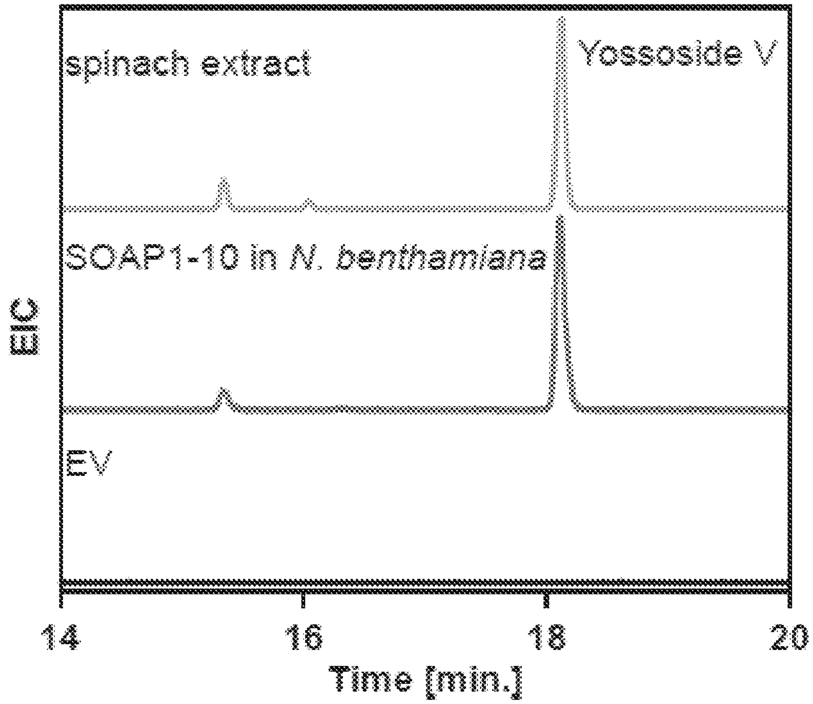

Results: To rule out the involvement of additional plant enzymes in the formation of MA-3-GlcA we expressed SOAP5 in *Saccharomyces cerevisiae* (FIG. 33D). Since yeast do not produce amyrin-type triterpenoids nor UDP-glucuronate, expression of enzymes that generate these precursors was required in order to provide the substrates essential for SOAP5 activity (P. Arendt et al., An endoplasmic reticulum-engineered yeast platform for overproduction of triterpenoids. Metabolic Engineering. 40, 165-175 (2017); T. Oka, Y. Jigami, Reconstruction of de novopathway for synthesis of UDP-glucuronic acid and UDP-xylose from intrinsic UDP-glucose in *Saccharomyces cerevisiae*. FEBS Journal. 273, 2645-2657 (2006)).

Expression of SOAPs1, 2, 3, and 4 in yeast resulted in formation of medicagenic acid (FIGS. 40A-40B). However, adding SOAP5 was not enough to produce medicagenic acid 3-O-glucuronide (FIGS. 33A-33F). To provide activated sugar for SOAP5 the UDP-glucose 6-dehydrogenase 1 from spinach (SoUGD1, Sp_189830_psca) catalyzing the conversion of UDP-glucose to UDP-glucuronate, was expressed (SEQ ID NO: 74 [gene] and SEQ ID NO: 75 [polypeptide]).

(SEQ ID NO: 74)

ATGGTGAAGATTTGCTGCATTGGGGCTGGTTATGTAGGAGGCCCTACTAT
GGCTGTTATAGCACTCAAGTGCCCAAAGATTGAAGTTGTAGTGGTTGATA
TATCTGTGTCTCGGATCACTGCATGGAACAGCGAGCAGCTTCCAATCTAT
GAGCCGGGTCTAGATGATGTGGTTAAGGAATGCCGTGGAAGGAACCTTTT
CTTCAGCACTGATGTAGAAAAGCATGTTGCTGAGGCTGATATTGTTTTTG
TCTCTGTGAATACCCCTACCAAAACCACAGGTCTTGGAGCAGGCAAAGCT
GCTGATTTGACCTACTGGGAGAGTGCTGCCCGTATGATTGCTGATGTTTC
AAAGTCTGACAAAATCGTTGTTGAGAAATCAACTGTGCCAGTGAAAACTG
CTGAGGCAATCGAAAAGATTCTGACGCACAACAGCAAGGGAATCAACTAC
CAGATCCTTTCAAATCCGGAGTTCCTTGCTGAAGGTACTGCTATTCAGGA
CCTTTTTCACCCTGACAGGGTTCTCATCGGTGGCCGGGAAACCCCAGCAG
GCCTCAAGGCAGTCCAAGCATTGAAGGATGTGTATGCTCAATGGGTTCCT
GATGAACGGATCTTAACCACCAATCTTTGGTCTGCTGAGCTCTCAAAGCT
TGCTGCCAACGCCTTCTTAGCACAGAGGATTTCATCTGTCAATGCAATGT
CAGCTCTTTGTGAGGCTACTGGAGCAGATGTTACCCAAGTCGCATATGCT
GTTGGTAAGGACAGTAGGATTGGGCAAAAGTTTTTGAACGCTAGTGTTGG
TTTTGGAGGGTCTTGCTTCCAGAAAGACATTCTGAACTTGGTTTACATTT

-continued

GTGAGTGCAACGGTCTCCCTGAGGTGGCCGAGTATTGGAAACAGGTAATC

AAGGTGAATGATTATCAGAAGAATCGTTTTGTGAATAGGGTTGTGGCCTC

CATGTTCAACACTGTATCGAACAAGAAGATTGCTGTTCTTGGATTTGCAT

TCAAAAAGGATACAGGGGATACTAGGGAGACACCCGCCATAGATGTGTGC

AAGGGTTTGTTGGGAGACAAGGCAAGGTTGAGCATCTACGATCCACAAGT

CACTGAGGATCAGATTCAGCGAGATCTCACCATGAACAAGTTTGACTGGG

ACCACCCAATTCACCTCCAGCCCACAAGTCCCACAACTGTTAAGCAAGTG

AGTGTTGTTTGGGACGCTTATGAGGCCACCAAAGATGCTCATGCTGTGTG

TATTCTGACTGAGTGGGATGAATTTAAGAAACTTGATTACAAAAGGATTT

TTGACAACATGCAGAAGCCAGCTTTTGTGTTTGATGGAAGGAACATTGTG

AATGCAGATGAGCTGAGGCAGATTGGGTTCATTGTGTACTCAATTGGTAA

ACCTTTGGATTCATGGCTCAAGGACATGCCTGCTGTGGCTTAA (SEQ ID NO: 75)

MVKICCIGAGYVGGPTMATIALKCPKIEVVVAIDISVSRITAWNSEQLPI

YEPGLDDVVIKECRGRINLEFSTDVEKRVAEADIVFVSVNTPTKITGLGA

GKAADLTYWESAARMIADVSKSDKIVVEKSTVPVKTAEAIEKILTHNSKG

INYQILSNPEFLAEGTAIQDLFHPDRVLIGGRETPAGLKAVQALKDVYAQ

SWVPDERILTTNLWSAELSKLAANAFLAQRISSVNAMSALCEATGADVTQ

VAYAVGKDSRIGQKFLNASVGFGGSCFQKDILNLVYICECNGLPEVAEYW

KQVIKVNDYQKNRFVNRVVASMFNTVSNKKIAVLGFAFKKDTGDTRETPA

IDVCKGLLGDKARLSIYDPQVTEDQIQRDLTMNKFDWDHPIHLQPTSPTT

VKQVSVVWDAYEATKDAHAVCILTEWDEFKKLDYKRIFDNMQKPAFVFDG

RNIVNADELRQIGFIVYSIGKPLDSWLKDMPAVA

Consequently, only yeast cells expressing SOAP5 together with all other five genes were able to produce MA-3-GlcA (FIGS. 33A-33F; FIGS. 40A-40B). Similar to *N. benthamiana* assays, SOAP5 was capable of glucuronidation of triterpenoid intermediates (oleanolic acid, gypsogenic acid and bayogenin) in yeast cells (FIGS. 41A-41F).

Summary: Demonstrated that it was possible to produce and glucuronidate triterpenoid intermediates in a system heterologous to the source enzymes.

Example 22: Examination of Cellulose Synthase Like Enzymes in Additional Plant Species Objective: To identify and analyze functional Cellulose Synthase Like G (CSLG) enzymes in non-spinach plant species.

Methods: See Materials and Methods above.

Results: Glucuronic acid attached to a saponin aglycone via the hydroxyl at position C-3 is a common feature for many saponins found in plants, especially in the Caryophyllidae, primitive Rosidae and Asteridae (M. Henry, Saponins and Phylogeny: Example of the "Gypsogenin group" Saponins. Phytochem Rev. 4, 89-94 (2005)). To examine if conjugation of glucuronic acid to the triterpenoid backbone by a CSLG enzyme is not limited to spinach and its family, phylogenetic analysis of CSLG proteins was performed in more than 70 plant species including mosses, gymnosperms, and flowering plants. It appeared that spinach SOAP5 is related to CSLG proteins from the Caryophyllales, Malvales, *Apiales*, and Fabales orders (FIGS. 42A-42E).

Saponin profiling of selected species, as well as published data, demonstrated the presence of glucuronide-oleanane-type saponins in soy (*Glycine* mar), alfalfa (*Medicago sativa*), *Lotus japonicus* and licorice (*Glycyrrhiza uralensis*) as well as in the Caryophyllales species like beetroot (*Beta vulgaris*) and *quinoa* (*Chenopodium quinoa*) (FIGS. 43A-43C).

The closest homologues of the spinach SOAP5 were then cloned from all of the aforementioned species and expressed transiently in *N. benthamiana* together with SOAP1-4. MA-3-GlcA formation was observed for all tested CSLG enzymes (FIGS. 42A-42E). Table 17 below provides the nucleic acid and amino acid sequences of these SOAP5 homologs.

TABLE 17

SOAPS Cellulose synthase Like G homologs (having glucuronic acid transferase activity)

| Name | SEQ ID NO: | Nucleic Acid/Amino Acid Sequence |
| --- | --- | --- |
| BvCSLG polypeptide from red beet_ (XM_010673823.2_) | 94 | MSSLHICKVQTTRAILSRFHILFHSLAILALFYYRFTSFSTTKSGILPWTLL TTAEVVLGFWALTQAFRWRPVLRDVAGWDSIKEEQLPGVDVFICTADPIKEP VLEVMNTVLSAMALDYPAEKLGVYLSDDGGSPLTREAIKEASKFAKVWLPFC SKYGIKTRCTQAFFSSFCDGERLDWNQDFKADELVLKSKYEAFKNYVEKASE DESKCTMAHDRSPCVEIIHDNKQNGEGEVKMPLLVYVSREKRPNRPHRFKAG ALNALLRVSGVLSNGPYLLVLDCDMYCNDPTSARQSMCFHLDPKLAPSLAFV QYPQIFYNTSKNDIYDGQARSAYKTKWQGMDGIRGPVTTGTGYYLKRKALYG QPKNEDEFLINQPEKAFGSSTKFIASVSSNSKQNMALKEMTRDDLLEEAKNL ATCAYESNTEWGNKIGYSYECLLESTFTGYLLHCKGWISVYLYPKRPCFLGC TTIDMKDAMVQLMKWTSGLLGVGISKFSPLTYAFSRMSILQSMCYGYFTFSA LFGVSFLIYGIVLPVCLLKGVPVFPKVSDPWIGVFVVVFASSLLQHLYEVLS SDDSIKTWWNEIRIWIIKSVTASLFGTMDAIMKKIGIQKASFRLTNKVVDKE KLEKYEKGKFDFQGAAVFMVPLIILVVLNMVSFVGGLRRAIINKNCDEMFGQ LFLSFFLLVLSYPVLEGIVTKVRKGRD |
| BvCSLG_ gene from red beet (XM_010673823.2) | 95 | CATCACAGCCACATGGGAAACAAAAAGTCTTAACCTCGGCCATCTCGTGTGC CTCGTGCACATTCAACATTGATTTTAATTGTGTGCTTTCTCCAAAATGTACC ATACTATATCATCTTGTCAGAATTCCAAACTCCAACTATAACCACCATTGAA GTCATCTACACACAAACACACACACTCTTTCTCCCTAAAAATGTCTTCTCTC CACATTTGCAAAGTCCAAACAACAAGAGCAATACTTAGCCGTTTCCACATAC TCTTCCACTCCTTAGCCATCCTTGCTTTATTCTACTACCGTTTTACATCGTT CTCTACCACCAAATCAGGCATACTTCCATGGACCTTACTAACCACAGCAGAG |

TABLE 17-continued

SOAPS Cellulose synthase Like G homologs (having glucuronic acid transferase activity)

| Name | SEQ ID NO: | Nucleic Acid/Amino Acid Sequence |
|---|---|---|
| | | GTGGTTCTAGGCTTTGTATGGGCGTTAACACAGGCCTTTCGATGGCGGCCTG TGTTGCGAGATGTAGCTGGATGGGATTCCATCAAGGAGGAACAACTGCCAGG GGTGGACGTGTTCATATGCACAGCTGATCCAATAAAGGAGCCGGTGTTAGAG GTGATGAACACGGTGCTTTCGGCGATGGCATTGGATTACCCGGCAGAGAAGT TGGGTGTTTATCTTTCGGATGATGGAGGTTCTCCCTTGACTAGGGAGGCTAT TAAGGAGGCTTCTAAGTTTGCTAAGGTTTGGCTTCCTTTTTGTAGTAAGTAT GGTATCAAGACTAGGTGTCCTCAGGCTTTCTTCTCTTCTTTTTGTGATGGGG AAAGACTTGATTGGAATCAGGACTTTAAGGCTGATGAATTGGTGCTCAAGTC AAAATATGAAGCTTTTAAGAATTATGTGGAGAAAGCAAGTGAAGATGAAAGC AAATGCACCATGGCACATGATCGTTCCCCTTGCGTTGAGATFATACATGACA ACAAGCAAAATGGAGAAGGCGAAGTGAAAATGCCCCTTTTGGTCTACGTATC CAGGGAAAAGAGACCAAATCGTCCTCATCGTTTCAAAGCCGGAGCTCTTAAT GCTCTTCTCAGAGTATCAGGTGTATTTGAGCAACGGGCCTTACTTATTGGTG TTGGACTGTGATATGTACTGCAATGATCCAACTTCTGCTCGTCAATCTATGT GCTTTCATCTTGACCCAAAATTGGCTCCTTCACTTGCATTTGTGCAATACCC ACAAATTTTCTACAACACCAGTAAAAATGATATCTATGATGGCCAAGCTAGA TCCGCGTACAAGACAAAATGGCAAGGAATGGATGGTATTAGAGGACCAGTCT TGACAGGAACAGGGTATTACTTGAAGAGGAAAGCATTGTATGGACAACCTCA TAACGAAGATGAATTTCTCATTAATCAACCAGAGAAGGCCTTCGGCTCCTCC ACAAAATTCATTGCGTCAGTTAGTTCAAACTCCAAGCAAAATATGGCCTTGA AGGAAATGACAAGAGACGACTTGTTAGAAGAGGCTAAAAATTTGGCTACTTG TGCATATGAATCAAACACTGAATGGGGTAACAAGATTGGATATTCGTATGAG TGTTTGTTGGAGAGTACATTTACCGGATATCTCTTACATTGCAAAGGATGGA TTTCCGTGTATCTTTACCCAAAAAGACCCTGCTTCTTAGGATGCACGACGAT TGACATGAAAGATGCCATGGTTCAACTAATGAAATGGACCTCTGGATTACTA GGAGTTGGCATATCAAAGTTTAGCCCTCTAACTTATGCCTTTTCGAGGATGT CTATATTACAAAGCATGTGCTACGGTTACTTCACATTTTCAGCCCTTTTCGG AGTTTCGTTCTTAATATATGGCATCGTCCTTCCAGTATGCCTATTGAAGGGT GTTCCTGTTTTTCCTAAGGTATCGGATCCATGGATTGGAGTTTTCGTGGTAG TATTTGCATCCTCCCTCCTTCAACATTTATACGAGGTTCTCTCAAGTGACGA TTCCATTAAAACATGGTGGAACGAGATCAGAATTTGGATCATCAAATCGGTA ACAGCTTCCTTATTTGGAACAATGGATGCAATAATGAAAAAGATCGGCATAC AAAAGGCTAGTTTCCGATTAACTAACAAGGTTGTGGACAAGGAAAAGCTCGA AAAATATGAGAAGGGCAAGTTTGATTTCCAAGGAGCAGCTGTGTTCATGGTT CCTCTTATCATTTTAGTGGTACTAAATATGGTGTCATTTGTTGGCGGATTAA GAAGGGCAATAATCAACAAGAATTGTGATGAAATGTTTGGGCAACTTTTCCT CTCATTCTTTCTCTTAGTTCTTAGCTACCCCGTTTTAGAAGGGATAGTAACA AAAGTAAGAAAAAGGACGTGATTGAGATGAATTTGCATTGTTTGGTAAAAGAT CCAAACTTAGAGAAAGAGATTGCGTAGGAGATCAAAGGAAACAATGTGAGAG ATTTACAGGCTTCATGAGGCTTAAGACCTCATTAATTTTTGTGACAATTTAC AAATTCTGTCTCTATATTTTGGTCAAGACGTATCATTTGAAAATTTCCATGG TTAGGTAGTTAGATTTCAATGTTCCACGTTTGTAAATAAGAAGATAAAATAA GGAAATTTGTGATTTTAGCTTTACATTTCTATGAGATAGTCCTTTGTTGTGA TGAAAGTTCTGTTCTTAGTGAAAATAATAAAACGTGACATCAAAATTTTGAG TATAT |
| CqCSLG Protein from quinoa_ (XM_021866098.1)_ | 96 | MAATHICKVQTRRVIINRIHILFHSLAILALFYYRFSSFSNPHISLFPWVLL TIADLVFTFIWAMTQAFRWRPVLHDVSGYESINPRDLPKIDIFICTADPTKE PVLEVMNSVISSMALDYPPEKMAVYLSDDGGSPLTREAIKKAVEFAKVWIPF CNMYGIKTRCPDAFFSALGNDERLHRDQDFNAHESLLKSKYEAFKKYVEKES GDINKCTVVHDREPCIEIIHDSKQDGEAEVKMPLVVYVAREKRPGHPHRFKA GALNALLRVSGLLSNAPYLLVLDCDMYCHDPTSARQSMCFHLDPNMSPSLAF VQYPQIFYNTSRNDIYDGQARSAHTTKWQGMDGLRGPVLNGTGYYLKKKAIY GRPHNEDEYLINEPEKAFGSSTKFIASLKENSNQDLVLKEFTNDLLQEARNL ATCTYEANSLWGVEVGFSYDCLLESSYTGYLLHCKGWRSVYLYPKRPCFLGC TTIDMKDAIVQLIKWTSGLLGVAMSKFSPLTYAMSRMSILQSMCYAYITCSG LLAVPLFIYGVVLPFCLLRGVPVFPKVSDPWMLGFVFVFVSSHVQHLFEVLA SDHSVQQWWNEVRIWIMKAITACLFGSTEAIMKKIGIQKTTFRLTNKVVEKE KLDKYEKGKFDFSGAAMLMVPLIILTTLNLVSFVGGLVRVINHNNYDDMFGQ LFLSFYLLLLSYPTFEGIVTKVTDKLRKKE |
| CqCSLG Gene from quinoa_ (XM_021866098.1)_ | 97 | AAAAGTGAAACTGGTGACTTAGTCTTGTGTCACCCGGGTTCCTCGAGCACAT ATTCTTCAAGATTTTGGTTTTTTGTACGGAGTATTTATATACACAAAAATTA GGAACCAAATAGGAAGACTCATATCATTTCAAAATGGCGGCAACACACATTT GCAAAGTCCAAACCAAAAGAGTCATTATCAACCGTATTCATATCCTCTTTCA CTCTTTAGCCATTCTTGCTCTCTTCTACTACCGTTTCTCGTCTTTCTCCAAC CCTCATATCTCCCTTTTTCCATGGGTATTATTGACTATCGCCGACCTCGTTT TCACCTTCATTTGGGCCATGACTCAGGCCTTCCGTTGGCGCCCCGTCTTGCA CGATGTGTCTGGCTATGAGTCCATCAATCCCACGCGATCTTCCAAAGATCGAT ATTTTTATATGCACCGCTGATCCCACXAAGGAGCCTGTGTTCTGAAGTGATG AACTCGGTGATATCATCCATGGCGCTCGATTATCCGCCTGAAAAAATGGCGG TGTATTTGTCGGATGATGGTGGTTCTCCTTTGACTAGAGAGGCTATTAAGAA GGCTGTTGAATTTGCTAAGGTTTGGATTCCTTTTTGTAATATGTATGGTATT |

TABLE 17-continued

SOAPS Cellulose synthase Like G homologs (having glucuronic acid transferase activity)

| Name | SEQ ID NO: | Nucleic Acid/Amino Acid Sequence |
|---|---|---|
| | | AAGACTAGGTGTCCTGATGCTTTCTTCTCCGCTTTGGGTAATGATGAAAGAC |
| | | TTCATCGTGATCAAGACTTTAACGCTCATGAATCACTCCTCAAGTCGAAATA |
| | | CGAAGCTTTTAAGAAATATGTGGAGAAAGAAAGCGGTGATATTAATAAATGC |
| | | ACCGTTGTGCATGATCGTGAACCTTGCATTGAGATTATACATGACAGTAAAC |
| | | AGGATGGAGAAGCTGAAGTGAAAATGCCCCTTGTAGTTTATGTAGCCAGGGA |
| | | AAAGAGACCAGGTCATCCTCATCGTTTCAAAGCTGGAGCCCTTAACGCTCTT |
| | | CTCCGAGTATCAGGACTATTGAGCAATGCGCCTTACTTATTGGTGTTAGACT |
| | | GTGATATGTACTGTCATGATCCAACCTCTGCTCGTCAATCTATGTGCTTCCA |
| | | TCTTGACCCGAACATGTCTCCCTCTCTTGCCTTTGTTCAATACCCTCAAATT |
| | | TTCTACAACACTAGTAAAAATGATATCTATGATGGTCAAGCCAGATCAGCTC |
| | | ATACGACGAAATGGCAAGGCATGGATGGACTCAGAGGACCGGTCTTGAATGG |
| | | AACTGGGTATTATCTGAAGAAGAAGGCGATATATGGAAGGCCCCATAATGAA |
| | | GATGAATACCTCATCAATGAACCAGAAAAGGCTTTTGGTTCTTCCACAAAAT |
| | | TCATTGCTTCACTTAAAGAAAACTCGAACCAGGATCTTGTCTTGAAGGAATT |
| | | CACAAACGATTTGTTACAAGAGGCTAGAAATTTGGCTACTTGCACTTATGAA |
| | | GCAAACTCGCTATGGGGTGTTGAGGTAGGGTTTTCGTATGATTGCCTGTTGG |
| | | AGAGTTCATACACTGGATATCTCTTACATTGTAAAGGATGGAGATCTGTGTA |
| | | TCTTTATCCCAAAAGACCGTGCTTCTTGGGATGCACGACAATTGACATGAAG |
| | | GATGCTATTGTTCAATTAATAAAATGGACTTCCGGATTACTTGGAGTTGCCA |
| | | TGTCAAAGTTTAGCCCTCTTACTTATGCCATGTCCAGAATGTCTATATTGCA |
| | | AAGCATGTGTTACGCGTACATCACGTGTTCAGGTCTTCTAGCAGTTCCACTC |
| | | TTTATATATGGTGTTGTTCTACCATTCTGCCTACTTAAGGGCGTTCCTGTTT |
| | | TTCCTAAGGTATCGGATCCATGGATGTTGGGTTTCGTGTTTGTATTTGTATC |
| | | CTCCCATGTTCAACATCTATTCGAAGTGCTAGCAAGTGATCATTCAGTGCAA |
| | | CAGTGGTGGAATGAGGTGAGAATCTGGATCATGAAAGCGATAACAGCCTGCT |
| | | TGTTTGGATCAACTGAAGCAATAATGAAGAAGATTGGGATACAGAAAACAAC |
| | | ATTCAGATTAACAAATAAGGTTGTGGAGAAAGAGAAGTTGGATAAATACGAG |
| | | AAGGGAAAGTTCGATTTCTCAGGAGCAGCAATGCTAATGGTTCCTCTCATCA |
| | | TTTTGACTATACTAAATTTGGTGTCGTTCGTTGGGGCACTTGTAAGGGTGAT |
| | | CAACCACAACAACTATGATGATATGTTCGGGCAACTTTTCCTGTCATTTTAT |
| | | CTCCTACTTCTTAGCTACCCTACTTTCGAAGGGATTGTTACAAAAGTTACAG |
| | | ACAAACTTAGAAAGAAAGAATAAGGAGTGATTGAGTAACTGCCTAGTACAGT |
| | | TTTCACTTCACTTCTCTAGATTAGTCCTTGTTTTTGTTTATGTTTATTAAGA |
| | | TCAGCAACACTTGTAGACGGTTGCAATAATGAGTTCAATACCGTTTGTTCTG |
| | | TCCCTCTTGCAAGAACAAGTATATAAATACTTTTCATTAGCCGGTTGCATTG |
| | | TTGGATTCATATAGATGAATATTTCAAATATTTCATCITTTTGAACTTACAC |
| | | ACTAATGATTTATATCTGGAATTTTGAAA |
| MsCSLG | 98 | MATFTFHKETVQPLLPLRRAYIIFHFTCVLFLFYYRISNLFISYPWFLMTIA |
| Protein | | EIILSFLWFFNQAFRWRLVNRSVMTEKLPPEEKLPGLDIFVCTIDPEKEPTV |
| from | | DVMNTVISAIAMDYPSNKLSIYLSDDGGSPITLFGIKEAFEFAKVWVPFCKK |
| Alfalfa_ | | YDVKSRCPKFFFTALGENERLHRPREFEEVRDQIKKRLNRVDPNSSQVENSR |
| (MSAD_299835) | | EHMPTKAKYEKMQKNIEKFGSNLKNLCMVTDRPSRIEIINDQKEMPLVVYVS |
| | | REKRPSVPHRFKGGALNTLLRVSGLTSNGPYVLVVDCDMNCNDASSAKQSMC |
| | | FFLDPETSKDVAFVQFPQMFHNLSKKDIYDSQTRTAFTTKWKGMDGLRGPGL |
| | | TGSGNYISRSALLFGSPNQKGDYLLDALYNFGKSNMYVESLKALRGQQTKKQ |
| | | NISRDVILQEACEVASCSYERNTNWGNEVGFSYAIKLESTVTGYLLHCRGWR |
| | | STYLYPKRPCFLGCAPTDMKEGLIQPIKWSSELLLLAISKYSPFTYGLSRLP |
| | | TIHCLTFCYLVSTTQFATAYILYGFVPQICFLKGIPVYPKVTDPWFIVFTVL |
| | | YLSSQIHHYIEVISTGGSSMIWWNEQRSGIVKSIGCVFAIIETAKKKFGLNK |
| | | AKFTLSDKAIDKDKLKKYEQGKFNFDGAALLMAPVIVLLTINIVCFFGGLWR |
| | | LLNVRDFDEMFGQLFLIIYILALSHPIVEGIISMKRKSG |
| MsCSLG | 99 | ATGGCAACCTTCACATTTCACAAAGAAACAGTTCAACCATTGTTACCTCTAA |
| Gene from | | GAAGAGCTTACATAATCTTCCACTTCACATGTGTCTTGTTTCTCTTTTACTA |
| Alfalfa_ | | CCGTATCAGCAATTTGTTTATTTCATATCCATGGTTTCTAATGACAATAGCT |
| (MSAD_299835) | | GAGATTATTCTATCATTTCTATGGTTTTTCAACCAAGCATTCCGTTGGAGGC |
| | | TGGTGAATCGTTCAGTTATGACCGAGAAATTACCGCCGGAGGAGAAGTTGCC |
| | | GGGACTCGACATATTTGTGTGTACCATTGATCCTGAAAAAGAACCAACGGTT |
| | | GATGTTATGAACACTGTTATTTCTGCTATTGCAATGGATTACCCTTCTAATA |
| | | AACTTTCTATTTATCTTTCTGATGATGGAGGTTCTCCTATTACTCTTTTTGG |
| | | GATCAAAGAGGCTTTTGAATTTGCTAAAGTTTGGGTTCCTTTTTGTAAAAAA |
| | | TATGATGTTAAGTCAAGGTGTCCTAAGTTTTTCTTCACTGCTTTGGGTGAGA |
| | | ATGAACGACTTCATCGACCTCGTGAATTTGAAGAAGTGAGGGACCAGATTAA |
| | | GAAGAGATTAAATAGAGTGGATCCTAACTCATCACAAGTTGAAAACTCGAAG |
| | | GAACATATGCCCACCAAAGCCAAATACGAGAAAATGCAGAAAAATATTGAGA |
| | | AATTCGGAAGCAACCTAAAGAATCTTTGTATGGTGACCGATAGACCTTCTCG |
| | | GATCGAGATCATTAATGACCAAAAAGAAATGCCACTAGTTGTTTATGTATCT |
| | | CGTGAAAAAAGACCATCTGTTCCTCACAGATTCAAAGGAGGAGCTCTCAATA |
| | | CATTGCTTAGGGTGTCAGGGCTAATCAGCAATGGACCTTATGTACTTGTCGT |
| | | AGATTGTGATATGAATTGTAATGATGCATCATCAGCCAAACAATCCATGTGC |
| | | TTTTTTCTTGATCCTGAAACCTCTAAAGATGTTGCTTTTGTTCAATTCCCTC |
| | | AAATGTTTCACAACCTTAGCAAGAAAGACATATATGATAGTCAGACTAGGAC |

TABLE 17-continued

SOAPS Cellulose synthase Like G homologs (having glucuronic acid transferase activity)

| Name | SEQ ID NO: | Nucleic Acid/Amino Acid Sequence |
|---|---|---|
| | | TGCTTTTACGACAAAGTGGAAGGGAATGGATGGATTAAGAGGTCCAGGTCTAACTGGCAGTGGAAATTATATAAGTAGAAGTGCATTACTCTTTGGAAGTCCAAACCAAAAAGGGGACTATCTACTTGATGCTCTATACAACTTTGGCAAGTCTAACATGTATGTAGAATCACTAAAAGCGTTACGTGGTCAACAAACTAAGAAGCAGAATATTTCAAGAGATGTAATTTTACAAGAAGCATGTGAAGTGGCTTCTTGTTCCTATGAGAGAAACACAAATTGGGGTAATGAGGTGGGATTCTCGTATGCTATAAAACTTGAGAGTACCGTTACTGGCTATCTCCTCCATTGTAGAGGATGGAGATCAACTTATCTTTACCCTAAAAGACCATGTTTCTTAGGATGTGCTCCAACTGACATGAAAGAGGGATTGATTCAACCGATAAAGTGGTCATCTGAACTTTTGTTGCTTGCAATCTCTAAATATAGCCCATTCACTTATGGCCTTTCAAGATTGCCCACTATTCATTGTTTAACTTTTGTTACTTGGTAAGCACAACCCAATTTGCAACAGCCTACATCTTATATGGATTCGTTCCTCAGATTTGCTTCTTGAAGGGAATACCTGTATATCCAAAGGTTACAGATCCTTGGTTTATAGTGTTTACAGTATTGTATCTATCCAGTCAAATTCATCATTATATTGAGGTAATTTCAACTGGTGGCTCCTCGATGATTTGGTGGAATGAACAAAGAAGTGGGATTGTAAAATCAATTGGGTGCGTTTTCGCAATTATAGAAACAGCGAAAAAAAAGTTTGGGTTGAACAAGGCAAAATTCACTTTATCGGACAAAGCAATTGACAAAGATAAGCTAAAGAAATATGAGCAGGGTAAGTTTAATTTTGATGGTGCAGCATTGCTCATGGCACCAGTGATTGTGTTACTCACAATAAATATTGTTTGCTTCTTTGGTGGTTTATGGAGACTACTCAATGTGAGGGATTTTGATGAAATGTTTGGTCAACTTTTCCTCATTATCTATATACTTGCTCTAAGTCATCCTATTGTGGAGGGGATTATATCTATGAAGCGGAAGAGTGGGTAG |
| GmCSLG Protein from Soybean_ (NM_001365133.1_ soja) | 100 | MATFHTETVQSGLALSRLHILFHSVALLFLYYYRISHILLEPSFVWIFMTIAELIFGELWLFKQAFRWRPVSRAVMPEKLPSDGKLFALDIFVCTVDPEKEPTVQVMDTVISAIAMDYPSNKLAVYLSDDGGCPVTLYGIREASRFAKEWVPFCRKYGINSRCPKAFFSPMGEDERELLLLRNHEFLAEQEQLKAKYNIMQKNIDEFGRDPKNRSIVFDRPARIEIINEQSEIPLWYVSRERRPNVPHTYKGGALNTLLRVSGLFSNGPYVLVVDCDMYCNDPSSAKQAMCFFLDPETSKDIAFVQFPQMFHNLSMKDIYDSQHRHAFTTMWQGMDGLRGPGLSGSGNYLSRSALIFPSPYEKDGYEHNAQNKFGNSTMYIESLKAIQGQQTYKTSISRNVILQEAQAVASCSYEIDTNWGNEVGFSYVILLESTVTGYLLHCRGWRSTYLYPKRPCFLGCAPTDFMEGMLQLVKWSSELFLLGISKYSPFTYGISRIPILHNFTFCYFTSTCQYIVALIVYGIIPQVCFLKGTPVFPKVTEPWFVVFAILYVSSQSQHLIEVLYGGGSLGTWWDEQRIWIVKSIVGGIFGSILAIKKRFGLNKAKFILSNKVVAKEKFEKYEQGKFEFEDAALFMSPLVGLLIVNILCFFGGLWRLFNVKDFEKMSGQLFLLGYLAALSYPIFEGIITMKSKVQ |
| GmCSLG gene from Soybean_ (NM_001365133.1_ soja) | 101 | TATATGCATGTTGACCGGTAAACATGGCGACCTTCCACACAGAAACCGTGCAATCAGGGTTGGCCTTGAGCAGACTCCACATCCTATTCCACTCGGTGGCACTCTTGTTTCTCTATTACTACCGCATAAGCCACATCTTACTGGAACCAAGCTTTGTATGGATTTTCATGACCATAGCGGAGCTTATCTTCGGCGAGCTCTGGCTCTTCAAACAGGCGTTCCGGTGGCGGCCCGTGTCGAGGGCCGTCATGCCGGAGAAGCTGCCGAGCGACGGCAAGCTTCCGGCGCTCGACATCTTCGTCTGGACGGTTGACCCCGAAAAGGAGCCGACGGTGCAGGTGATGGACACCGTCATCTCCGCCATTGCCATGGACTACCCCTCCAACAAGCTCGCCGTGTACCTTTCCGACGATGGCGGGTGTCCGGTGACTCTGTATGGGATCAGAGAGGCTTCTCGGTTCGCAAAGGAGTGGGTTCCGTTCTGCAGAAAGTATGGGATCAATTCACGGTGCCCCAAGGCCTTCTTCTCTCCCATGGGGGAGGATGAACGTGAACTGCTTCTTCTTCGCAACCAATGAATTCTTGGCAGAGCAAGAACAACTCAAGGCTAAATACAATATAATGCAAAAAAATATTGACGAATTTGGAAGAGACCCTAAAAATCGTTCCATTGTGTTTGATAGACCAGCTCGCATTGAGATTATAAATGAGCAATCCGAAATACCACTGGTTGTTTATGTGTCTCGTGAAAGAAGGCCAAATGTTCCTCATACATACAAAGGGGGAGCCCTCAACACATTGCTCAGAGTCTCAGGGCTATTCAGTAACGGGCCCTATGTACTTGTAGTTGATTGTGATATCTATTGCAATGATCCATCATCAGCTAAACAAGTCCAATTCCCTCAAATGTTTCACAACCTTAGCATGAAAGACATCTACGATAGTCAACATAGGCATGCTTTTACAACAATGTGGCAAGGAATGGATGGACTAAGAGGTCCAGGTCTTTCTGGTAGTGGCAATTACTTAAGTAGAAGTQCATTAATCTTTCCAAGCCCATATGAAAAAGACGGCTATGAACATAATGCCCAAAACAAATTTGGCAACTCTACCATGTACATTGAATCATTAAAGGCCATTCAAGGACAACAAACTTATAAAACGAGCATTTCAAGAAATGTGATTTTACAGGAAGCACAAGCAGTGGCCTCTTGTTCCTATGAAATAGACACAAATTGGGGTAATGAGGTAGGATTCTCATATGTTATATTACTGGAGAGTACAGTTACTGGCTATCTTCTTCACTGTAGAGGATGGAGATCAACTTACCTTTACCCCAAAAGACCTTGTTTCTTGGGATGTGCCCCCACTGACTTCATGGAAGGCATGCTTCAGTTGGTGAAATGGAGTTCTGAACTTTTCTTGCTAGGAATATCCAAATACAGCCCTTTCACTTATGGGATTTCAAGAATTCCTATTGTGCACAACTTTACCTTTTGCTACTTCACATCTAGATGTCAATATATTGTTGCCTTAATAGTATATGGCATCATTCCTCAAGTATGCTTCTTGAAAGGAACTCCTGTGTTTCCTAAGGTTACAGAACCATGGTTTCTAGTTTTTCCAATATTATATGTATCCTCTCAAAGTCAACATTTGATTGAAGTCCTTTATGGTGGTGGCTCTTTGGGAACATGGTGGGATGAACAAAGAATATGGATTGTAAAGTCAATTGTTGGAGGCATATTTGGATCTATACTAGCAATCAAGAAACGTTTTGGGTTAAACAAAGCAAAATTCATTTTATCAAATAAAGTTGT |

TABLE 17-continued

SOAPS Cellulose synthase Like G homologs (having glucuronic acid transferase activity)

| Name | SEQ ID NO: | Nucleic Acid/Amino Acid Sequence |
|---|---|---|
| | | TGCCAAAGAGAAGTTTGAGAAATATGAACAAGGTAAGTTCGAGTTCGAAGAT GCAGCTTTGTTCATGTCTCCATTGGTTCGATTACTCATAGTGAATATTCTTT GCTTCTTTGGTGGTTTATGGAGACTATTTAATGTGAAAGATTTTGAAAAGAT GTCTGGCCAACTTTTTCTACTTGGCTATCTGGCGGCGCTCAGTTATCCCATT TTTGAGGGGATAATAACCATGAAAAGCAAGGTGCAATAGTAGTTTGTCAATG ATTAGGCTAATTTAGGTATTTGAACTTTGTTCACAAATAATTTGCTTCATAT GAAAATCTAAAGTGCATGCTAAATGTTTGTATCTTAATATGTAATTAGCGTG CTTTTATTTCATGCATGAGAATATGGCTATCGATTTTAATTAGGAGCAAAAT GTATGTTCTTACTCCATTTTTAATGCAATTTCTTTATTTTCTTGCCAATTAA A |
| LjCSLG Protein from Lotus japonicus_ (Lj3g3v1981230.1)_ | 104 | MANFTLHTETVQAWLPLSRLHILIHSVFVILLLYYRTTRLIHAPTAPWILMT VAEALLAVLWLFNQAFRWRPVSRSVKTEKLPRDENLPGLDIFVCTIDPEKEP TAGVMDTVVSAVAMDYPPDKLSVYLSDDGGCAVTEYGIREACEFAKVWVPFC RKYGIKSRCPKVFFSPMGFDEETILRTDEFRAEQEKIKAQYETMQKNIEKFG SDPKNCRIVTDRPSKIEVINEQSEIPRVVYVSRERRPSLPHKFKGGALNTLV RVSGLISNGPYVLAVDCDMYCNDPSSAKQAMCFFLDPETSKYIAFVQFPQMF HNLSKKDIYDNQSRTAFKAMWQGMDGLSGPGLSGSGNYLSRSALLFGSPNQK GDYLLDAQNYFGESPLYIESLKAIRGQQTTKKNISRDESLLEAKVVASASYE TNTEWGSEVGFSYGILLESTITGYLLHCRGWKSAYLYPKTPCFLGCAPTDIK EGMLQLVKWLSELCLFAVSKYSPFTYGFSRLPIMPTFTYCFLAASSLYAIVF ILYGIVPQVCFLKGIPVFPKATDPWFAVFAVLYVATQIQHLIEVLSGNGSVS MWWDEQRIWILKSVTSVFAMIEGIKKWLGLNKKKFNLSNKAVDKEKVKKYEQ GRFDFQGAALYMSPMVVLLLVNIVCFFGGLWRLFKEKDFADMFGQLFLLSYV MALSYPILEGIVTMKMKSG |
| LjCSLG Gene from Lotus japonicus_ (Lj3g3v1981230.1)_ | 105 | ATGGCCAATTTCACTCTCCACACAGAAACCGTTCAAGCATGGCTCCCTCTAA GCAGACTCCACATTCTTATACACTCAGTGTTCCTCATCCTTCTCCTCTACTA CCGCACAACGCGTCTCATCCACGCGCCGACCGCGCCGTGGATCCTGATGACC GTTGCGGAGGCTCTCCTCGCCGTCCTTTGGCTCTTCAACCAGGCCTTCCGGT GGCGACCGGTGAGCCGCTCCGTGAAGACAGAGAAGCTGCCGCGCGACGAGAA TCTCCCCGGGCTGGACATATTTGTGTGCACGATTGATCCTCAGAAGGAGCCA ACGGCAGGGGTGATGGACACGGTTGTTTCCGCCGTGGCGATGGATTACCCGC CGGATAAGCTATCCGTGTATCTTTCTGATGATGGTGGTTGCGCCGTGACGGA GTATGGGATTAGAGAGGCTTGTGAGTTTGCCAAGGTGTGGGTTCCTTTTTGT AGAAAGTATGGGATCAAGTCGAGGTGTCCAAAAGTTTTCTTCTCTCCGATGG GGGAAGATGAAGAGATTCTAAGGACAGATGAGTTCAGAGCAGAGCAAGAGAA GATCAAGGCCCAATACGAGACTATGCAGAAAAACATCGAGAAATTTGGTTCA GACCCCAAAAATTGTCGTATTGTCACTGACAGACCCTCTAAGATCGAGGTTA TAAATGAGCAATCAGAAATCCCACGTGTTGTGTACGTCTCTCGTGAAAGAAG GCCATCACTTCCTCACAAGTTCAAAGGAGGAGCTCTCAACACATTGGTCAGA GTGTCAGGTCTAATCAGCAATGGACCTTATGTGCTTGCAGTGGATTGTGATA TGTATTGCAATGATCCATCCTCTGCCAAGCAAGCAATGTGCTTCTTCCTTGA TCCAGAAACATCTAAATACAATTGCATTTGTCCAATTCCCTCAAATGTTTCA CAACCTTAGTAAGAAAGACATCTATGATAATCAATCTAGGACTGCTTTTAAG GCAATGTGGCAAGGCATGGATGGACTCAGTGGTCCAGGTCTTTCTGGCAGTG GTAACTACTTGAGTAGAAGTGCATTGCTATTTGGAAGTCCAAACCAAAAAGG TGACTATCTGCTTGATGCTCAAAACTACTTTGGCGAGTCTCCCTTCTACATT GAATCATTGAAGGCCATCCGTGGACAACAAACTACCAAAAAGAATATCTCAA GAGACGAAAGTTTACTAGAAGCTAAAGTGGTGGCCTCTGCTTCCTACGAGAC AAACACAGAATGGGGCTCAGAGGTTGGATTCTCATATGGCATCTTACTGGAG AGTACTATTACTGGTTACCTTTTGCACTGCAGAGGATGGAAATCAGCTTATC TTTACCCAAAAACACCATGTTTCTTAGGGTGTGCCCCCACTGACATTAAAGA AGGCATGCTTCAGTTGGTGAAGTGGTTGTCTGAGCTTTGCTTGTTTGCTGTC TCTAAGTACAGCCCTTTTACATATGGGTTTTCAAGATTGCCCATTATGCCTA CCTTCACTTATTGTTTCCTGGCAGCTTCATCCCTATATGCTATTGTCTTCAT CCTTTATGGCATTGTACCTCAAGTGTGCTTCTTGAAAGGAATCCCTGTGTTT CCAAAGGCCACAGACCCTTGGTTTGCAGTGTTTGCAGTATTGTATGTAGCCA CCCAGATTCAACATTTGATTGAAGTCCTTTCTGGCAATGGCTCGGTCTCGAT GTGGTGGGATGAACAAAGAATTTGGATTCTGAAGTCAGTTACTAGCGTATTT GCAATGATAGAGGGAATCAAGAAATGGTTAGGATTGAACAAGAAAAAATTCA ACCTGTCAAACAAAGCGGTTGACAAGGAGAAGGTCAAGAAATATGAGCAAGG TAGGTTTGATTTCCAAGGAGCAGCTCTGTACATGTCTCCAATGGTTGTGTTG CTCCTAGTGAACATTGTTTGCTTCTTTGGCGGTTTATGGAGACTGTTTAAGG AGAAAGATTTTGCAGATATGTTTGGTCAACTTTTCCTACTCAGCTATGTGAT GGCTCTCAGTTATCCCATTCTTGAGGGGATAGTAACTATGAAAATGAAGAGT GGGTAG |

Silencing the beetroot CSLG (BvSOAP5), as in the case of spinach SOAP5, resulted in decreased levels of saponins and elevated accumulation of oleanolic acid (FIGS. 44A-44C). Similarly, suppressed expression of CLSG in alfalfa hairyroot resulted in decreased accumulation of saponins with attached glucuronic acid (FIGS. 45A and 45B).

Summary: These results demonstrate heterologous functionality of enzymes within the saponin biosynthetic pathway.

Example 23: Heterologous Production of Glycyrrhizin Using Cellulose Synthase Like G from Licorice Objective: The discovery of CSLG glucuronosyltransferase activity fills a large knowledge gap in the biosynthetic pathways of numerous glucuronide-type triterpenoid saponins. One such pathway only partly deciphered to date generates glycyrrhizin; a triterpenoid saponin produced in licorice consisting of glycyrrhetinic acid decorated with two glucuronic acid moieties at the C-3 position. Glycyrrhizin (i.e. GL) and glycyrrhetinic acid monoglucuronide (i.e. GAMG), the single glucuronidated derivative, are important natural products long used in traditional Chinese and Japanese medicine and nowadays in the food, cosmetics and pharmaceutical industry. These molecules are low-calorie sweeteners with no glycemic index; GAMG is 941-fold sweeter than sucrose and 5-fold more than that of GL (K. Mizutani, T. Kuramoto, Y. Tamura, N. Ohtake, S. Doi, M. Nakaura, O. Tanaka, Sweetness of glycyrrhetic acid 3-O-beta-D-monoglucuronide and the related glycosides. *Biosci Biotechnol Biochem.* 58, 554-5 (1994)). Commercial production of GL and GAMG depends on the currently limited availability of wild *G. uralensis* and inefficient industrial processing. Despite its importance, sustainable production of GL and GAMG in heterologous systems is currently impossible since the enzyme catalyzing attachment of the first glucuronic acid to the aglycone was not identified (Y. Nomura et al., Functional specialization of UDP-glycosyltransferase 73P12 in licorice to produce a sweet triterpenoid saponin, glycyrrhizin. *Plant. J.* doi: 10.1111/tpj.14409 (2019)). The goal here was to produce glycyrrhizin in a heterologous system Methods: See Materials and Methods above.

Results: Some of the saponins, especially those produced by plants from Fabales, are of high importance due to their unique properties. Glycyrrhizin, triterpenoid saponin consisting of glycyrrhetinic acid decorated with two glucuronic acid moieties at position C-3 is produced by *G. uralensis* and widely used as calorie-free sweetener and a drug in many Asian countries. Four out of five enzymes involved in glycyrrhizin production were already characterized (bAS, CYP88D6 and CYP72A154, UGT73P12) but the enzyme responsible for attaching the first glucuronic acid to the aglycone was missing (Y. Nomura et al., Functional specialization of UDP-glycosyltransferase 73P12 in licorice to produce a sweet triterpenoid saponin, glycyrrhizin. Plant J. doi: 10.1111/tpj.14409 (2019)). The question asked here was if cellulose synthase like G from licorice (GuCSL) was able to perform this reaction.

The cellulose synthase like G gene from G. uraliensis was identified and used for expression in a heterologous system. The nucleotide and amino acid sequences of the expressed genes and the encoded polypeptides is provided below in Table 18.

TABLE 18

Components of the triterpenoid Glyeyrrhizin Biosynthetic Pathway in *G. uraliensis*

| Name | Enzyme Activity | SEQ ID NO: | Nucleotide Sequence/Amino Acid Sequence |
|---|---|---|---|
| GuCYP88D6_ GLYUR000561S-00023451.1 | β-amyrin11-oxidase | 76 | ATGGAAGTACATTGGGTTTGCATGTCCGCTGCCACTTTGTT GGTATGCTACATTTTTGGAAGCAAGTTTGTGAGGAATTTGA ATGGGTGGTATTATGATGTAAAACTAAGAAGGAAAGAACAC CCACTACCCCCAGGTGACATGGGATGGCCTCTTATCGGCGA TCTATTGTCCTTCATCAAAGATTTCTCATCGGGTCACCCTG ATTCATTCATCAACAACCTTGTTCTCAAATATGGACGAAGT GGTATCTACAAGACTCACTTGTTTGGGAATCCAAGCATCAT TGTTTGTGAGCCTCAGATGTGTAGGCGAGTTCTCACTGATG ATGTGAACTTTAAGCTTGGTTATCCAAAATCTATCAAAGAG TTGGCACGATGTAGACCCATGATTGATGTCTCTAATGCGGA ACATAGGCTTTTTCGACGCCTCATTACTTCCCCAATCGTGG GTCACAAGGCGCTAGCAATGTACCTAGAGCGTATGAGGAAA TTGTGATCAATTCGTTGGAAGAATTGTCCAGCATGAAGCAC CCCGTTGAGCTCTTGAAAGAGATGAAGAAGGTTTCCTTTAA AGCCATTGTCCACGTTTTCATGGGCTTCTTCCAATCAGGAC ATCATTAAAAAAATTGGAAGTTCGTTTACTGATTTGTACAA TGGCATGTTCTCTATCCCCATTAACGTACCTGGTTTTACAT TCCACAAAGCACTCGAGGCACGTAAGAAGCTAGCCAAAATA GTTCAACCCGTTGTGGATGAAAGGCGGTTGATGATAGAAAA TGGTCCACAAGAAGGGAGCCAAAGAAAAGATCTTATTGATA TTCTTTTGGAAGTCAAAGATGAGAATGGACGAAAATTGGAG GACGAGGATATTAGCGATTTATTAATAGGGCTTTTGTTTGC TGGCCATGAAAGTACAGCAACCAGTTTAATGTGGTCAATTA CATATCTTACACAGCATCCCCATATCTTGAAAAAGGCTAAG GAAGAGCAGGAAGAAATAACGAGGACAAGATTTTCCTCGCA GAAACAATTAAGTCTTAAGGAAATTAAGCAAATGGTTTATC TTTCTCAGGTAATTGATGAAACTTTACGATGTGCCAATATT GCCTTTGCAACTTTTCGAGAGGCAACTGCTGATGTGAACAT CAATGGTTATATCATACCAAAGGGATGGAGAGTGCTAATTT GGGCAAGAGCCATTCATATGGATTCTGAATATTACCCAAAT CCAGAAGAATTTAATCCATCGAGATGGGATGATTACAATGC |

TABLE 18-continued

Components of the triterpenoid Glyeyrrhizin Biosynthetic Pathway in *G. uraliensis*

| Name | Enzyme Activity | SEQ ID NO: | Nucleotide Sequence/Amino Acid Sequence |
|---|---|---|---|
| | | | CAAAGCAGGAACCTTCCTTCCTTTTGGAGCAGGAAGTAGAC TTTGTCCTGGAGCCGACTTGGCGAAACTTGAAATTTCCATA TTTCTTCATTATTTCCTCCTTAATTACAGGTTGGAGAGAAT AAATCCAGAATGTCACGTTACCAGCTTACCAGTATCTAATC CCACAGACAATTGTCTCGCTAAGGTGATAAAGGTCTCATGT GCTTAG |
| GuCYP88D6_ GLYUR000561S-00023451.1 | β-amyrin11-oxidase | 77 | MEVHWVCMSAATLLVCYIFGSKFVRNLNGWYYDVKLRRKEH PLPPGDMGWPLIGDLLSFIKDFSSGHPDSFINNLVLKYGRS GIYKTHLFGNPSIIVXEPQMCRRVLTDDVNFKLGYPKSIKE LARCRPMIDVSNAEHRLFRRLITSPIVGHKALAMYLERLEE IVINSLEELSSMKHPVELLKEMKKVSFKAIVHVFMGSSNQD IIKKIGSSFTDLYNGMFSIPINWGFTFHKALEARKKLAKIV QPWDERRLMIENGPQEGSQRKDLIDILLEVKDENGRKLEDE DISDLLIGLLFAGHESTATSLMWSITYLTQHPHILKKAKEE QEEITRTRFSSQKQLSLKEIKQMVYLSQVIDETLRCANIAF ATFREATADVNINGYIIPKGWRVLIWARAIHMDSEYYPNPE EFNPSRWDDYNAKAGTFLPFGAGSRLCPGADLAKLEISIFL HYFLLNYRLERINPECHVTSLPVSXPTDNCLAKVIKVSCA |
| GuCYP72A154_ GLYUR000890S-00019071.1 | 11-oxo-β-amyrin30-oxidase | 78 | ATGGATGCATCTTCCACACCAGGGGCTATCTGGGTTGTTCT GACAGTGATACTAGCTGCGATTCCCATATGGGCATGCCATA TGGTGAACACGCTGTGGCTGAGGCCAAAGAGGTTGGAAAGG CATCTCAGAGCTCAAGGTCTTCATGGTGACCCTTACAAGCT CTCACTTGACAACTCCAAGCAAACCTATATGCTCAAGTTGC AACAAGAAGCACAATCAAAATCCATTGGTCTCTCCAAAGAT GATGCTGCACCACGAATCTTCTCCCTTGCCCATCAAACTGT ACACAAATATGGAAAGAACTCCTTTGCATGGGAAGGGACAG CACCAAAGGTGATCATCACAGACCCAGAGCAAATTAAGGAA GTCTTTAACAAGATTCAGGACTTCCCCAAACCAAAATTAAA TCCCATCGCCAAGTATATTAGCATCGGTCTAATACAGTATG AGGGTGACAAATGGGCCAAACATCGAAAGATTATCAATCCG GCATTCCACTTAGAAAAATTGAAAGGTATGCTGCCAGCATT TTCTCATAGCTGCCATGAAATGATTAGCAAATGGAAGGGGT TATTGTCATCAGATGGAACATGTGAGGTTGATGTTTGGCCC TTCCTTCAAAATCTCACTTGTGATGTAATTTCTAGGACGGC ATTCGGAAGCAGCTATGCAGAAGGAGCAAAAATATTTGAAC TTTTGAAAAGGCAGGGATATGCTTTGATGACAGCACGATAC GCACGCATTCCATTATGCTTGGCTTCTACCATCAACTACCA AAAGGAGGATGAAGGAAATTGAAAGAGGCATACGTGATTCA CTTGAAGGTATCATTAGAAAACGAGAAAAAGCATTGAAGAG TGGCAAAAGCACCGATGACGACTTATTAGGCATACTTTTGC AATCAAATCACATTGAAAATAAACKTAGATGAAAACAGTAA GAGTGCTGGAATGACCACCCAAGAAGTAATGGAGGAATGCA AACTTTTTTACCTGGCAGGGCAAGAGNTTGAAAATAAAGGA GATGAAAACAGTAAGAGTGCTGGAATGACCACCCAAGAAGT AATGGAGGAATGCAAACTTTTTTACCTGGCAGGGCAAGAGA CCACCGCAGCTTTGCTGGCCTGGACAATGGTGTTATTAGGC AAGCATCCTGAATGGCAAGCACGCGCAAGGCAGGAAGTTTT GCAAGTAACCATGATTTTATATGAGGTACTCAGGCTGTACC CACCTGGGATTTACCTCACCCGAGCTCTTCGAAAGGATTTG AAACTTGGAAACCTTTTGCTACCTGCTGGAGTACAGGTTTC CGTACCAATACTTTTGATTCACCATGATGAAGGTATATGGG GCAATGATGCAAAGGAGTTCAATCCTGAAAGGTTTGCTGAA GGAATTGCAAAGGCAACAAAAGGCCAAGTTTGCTATTTCCC TTTTGGATGGGGTCCTAGAATATGTGTTGGGCAAAACTTTG CCTTATTAGAAGCCAAGATTCTTATTGTCATTGCTGCTGCA GAATTTCTCATTTGAGCTATCTCCGACTTATGCACATGTTC CTACCACGGTGCTTACTTTGCAGCCAAAACATGGGGCACCC ATCATTCTGCATAAACTGTAA |
| GuCYP72A154_ GLYUR000890S-00019071.1 | 11-oxo-β-amyrin30-oxidase | 79 | MDASSTPGAIWVVLTVILAAIPIWACHMVNTLWLRPKRLER HLRAQGLHGDPYKLSLDNSKQTYMLKLQQEAQSKSIGLSKD DAAPRIFSLAHQTVHKYGKNSFAWEGTAPKVIITDPEQIKE VFNKIQDFPKPKLNPIAKYISIGLIQYEGDKWAKHRKIINP AFHLEKLKGMLPAFSHSCHEMISKWKGLLSSDGTCHVDVWP FLQNLTCDVISRTAFGSSYAEGAKIFELLKRQGYALMTARY ARIPLWWLLPSTTKRRMKEIERGIRDSLEGIIRKREKALKS GKSTDDDLLGILLQSNHIENKGDENSKSAGMTTQEVMEECK LFYLAGQEXENKGDENSKSAGMTTQEVMEECKLFYTAGQET TAALLAWTMVLLGKHPEWQARARQEVLQVTMILYEVLRLYP PGIYLTRALRKDLKLGNLLLPAGVQVSVPILLIHHDEGIWG NDAKEFNPERFAEGIAKATKGQVCYFPFGWGPRICVGQNFA |

TABLE 18-continued

Components of the triterpenoid Glyeyrrhizin Biosynthetic Pathway in *G. uraliensis*

| Name | Enzyme Activity | SEQ ID NO: | Nucleotide Sequence/Amino Acid Sequence |
|---|---|---|---|
| | | | LLEAKTVLSLLLQNFSFELSPTYAHVPTTVLTLQPKHGAPI ILHKL |
| GuCSL_ GLYUR003152S- 00037491.1 (SOAPS homolog: Cellulose Synthase Like G) | Cellulose Synthase Like G (Glucuronic acid transferase) | 80 | ATGGCAAGCTTCACCCTTCACACAGAAACCGTTCAGTCATG GCTACTCCTCAGCAGACTTCACATACTGCTGCACCTCGCAG TTGTACTGCTCCTCTTATACTACCGCATCACACGTTTCCCC TTCCATGCTCCSACTCTACCGTGGACTCTGATGACCGTAGG TGAGGCTATTATGGCACTGCTGTGGTTCTTCAACCAGGCCT TCCGGTGGCGGCCGGTGAGCCGCTCGGTGATGACGGAGAAG CTGCCCAGCGACGCGAAGCTGCCGGGGCTTGACATATTCGT GTGCACGCTTGACCCCGAGAAGGAGCCCACCGTGGAGGTGA TGAACACTCTGGTCTCTGCCCTTGCCATGGACTACCCCCCT GACAAGCTCTCCGTTTACCTCTCCGACGATGGCGCCGCCCC GGTCACTCTTTACGGCGTGAGAGAGGCTTCTGAGTTCGCGA GGGTGTGGGTCCCTTTCTGCAAAAACTATGGGATCAACTCA AGGTGTCCCAAGGTTTTCTTCTCTCCCAGTGCTGAGGATGA ACACCTTCTTCGCACCGACGAGTTCAGGTCAGAGCGAGACC TCATCAAGGCTAAATACGAGAAAATGCAGAAAAATATTGAG AAATTTGGTTCGGATGCCAAAAATTGTCGTATGGTGACTGA CAGACCTCCTCGGATCGAGATATTGATTGACCAACCAGACA TGCCACGTGTTGTTTACGTGTCTCGGGAAAGAAGGCCATCA CTCCCTCACAAGTTCAAAGGAGGAGCCCTCAATACATTGCT CAGAGTCTCAGGTCTAATCAGCAATGGGCCTTATGTACTTG TAGTGGACTGTGATATGTATTGCAATGACCCATCCTCAGCC AAACAAGCCATGTGTTTCTTTCTTGATCCTGAAACCTCTAA ATYTATTGCATTTGTCCAATTCCCTCAAATGTTTCACAACC TTGGCAAAAAAGACATCTATGACAATCAATCTAGGACTGCT TTTAAGACAATGTGGCAAGGGATGGATGGACTAAGAGGTCC TGGTCTTTCTGGCAGCGGTAATTACTTGAATAGAAGTGCAT TACTATTTGGAAGTCCAAATCAAAAAGATGACTATCTGGAT GATGCCCAAAACTACTTTGGCAAGTCTACCATGTACATAGA ATCACTAAAGGCCATTCGTGGACAAAAAACTATGAAAAAGA ATATTTCAAGAGATGAAATTTTACGAGAAGCTCAAGTATTA GCCTCTTGTTCCTATGAGACAAACACAGAATGGGGAGCAGA GGTAGGATTCTCATATGGCATCTTACTGGAGAGTTCAATCA CTGGCTATCTTTTYCACTGCAGAGGATGGAAATCAGCATAT CTTTACCCAAAGACACCATGTTTCTTAGGGTGTGCCCCAAC TGACATCAAGGAAGGAATGCTCCAATTGGTGAAGTGGTTGT CTGAATACTGCTTGCTRGGATTCTCTAAATACAGCCCTTTC ACTTATGGCTTTTCAAGAATGCCCATTATGCCTACCTTAGT CTATTGCTTCTTGACAACWACAACCCCTTTATTCCATTGTCT TCATCCTTTATGGCATTGTCCCCCAAGTTTGCTTCTTAAAA GGAATACCCGTGTTTCCAAAGGTCACAGACCCTTGGTTTGC AGTGTTTGCAACACTGTATATATCCACCCAGATTCAACATT TGATAGAGGTCCTTTCTGGTGATGGCTCTGTGGCAATGTGG TGGGATGAACAGKGAATCTGGATTCTGAAGTCAGTCACTAG CGTGTTCGCAATCATAGAGGCAGCTAAGAAAGGGTTAGGAT TGAACAAGAAGAAATTCATGTTGTCAAACAAAGCAATTGAC AAGGAGAAGCTCAAGAAGTATGAGCAAGGTAGGTTTGATTT CCAAGGTGCAGCTCTGTTCATGTCCCCAATGGTTGTGTTGC TCATAGTGAACGTTGTTTCCTTCATTGGTGCTCATATGGAG ACTATTCAATGCAAAGGATATTGAAGATATGTTTGGTCAGC TTTTCCTAGTTAGTTATGTAATGGCCCTTAGTTATCCCATT TTTGAAGGGATAATAACCATGAAAAGCAAGAGTGGATAG |
| GuCSLG_ GLYUR003152S- 00037491.1 (SOAP5 homolog: Cellulose Synthase Like G) | Cellulose Synthase Like G (Glucuronic acid transferase) | 81 | MASFTLHTETVQSWLLLSRLHIILLHLAVVLLLLYYRITRF PFHAPTLPWTLMTVGEAIMAVLWFFNQAFRWRPVSRSVMTE KLPSDAKLPGLDIFVCTLDPEKEPTVEVMNTLVSALAMDYP PDKLSVYLSDDGAAPVTLYGVREASEFARVWVPFCKKYGIK SRCPKVFFSPSAEDEHLLRTDEFRSERDLIKAKYEKMQKNI EKFGSDAKMCRMVTDRPPRIEILIDQPDMPRVVYVSRERRP SLPHKFKGGALNTLLRVSGLISNGPYVLVVDCDMYCNDPSS AKQAMCFFLDPETSKXIAFVQFPQMFHNLGKKDIYDNQSRT AFKTMWQGMDGLRGPGLSGSGNYLNRSALLFGSPNQKDDYL DDAQNYXGKSTMYIESLKAIRGQKTMKKNISRDEILREAQV LASCSYETNTEWGAEVGFSYGILLESSITGYLXHCRGWKSA YLYPKTPCFLGCAPTDIKEGMLQLVKWLSEYCLLGFSKYSP FTYGFSRMPIMPTLVYCFLTTTTLYSIVFILYGIVPQVCFL KGIPVFPKVTDPWFAVFATLYISTQIQHLIEVLSGDGSVAM WWDEQXIWILKSVTSVFAIIEAAKKGLGLNKRKFMLSNKAI DKEKLKKYEQGRFDFQGAALFMSPMWLLIVNVVSFIGGIWR LFNAKDIEDMFGQLFLVSYVMALSYPIFEGIITMKSKSG |

TABLE 18-continued

Components of the triterpenoid Glyeyrrhizin Biosynthetic Pathway in *G. uraliensis*

| Name | Enzyme Activity | SEQ ID NO: | Nucleotide Sequence/Amino Acid Sequence |
|---|---|---|---|
| GuUGAT_ KT759000.1 | Glycyrrhetinic acid glucuronosyl-transferase | 82 | ATGACCATGGGTAACGAGAATCGGGAGCTGCACATAATCTT CTTCCCCTTTCTGGCGAACGGCCACATCATCCCCTGCGTGG ACTTGGCCAGAGTCTTCGCCGCAAGAGGAATCAGAGCCACC ATAGTCACCACCCACCTCAACGTTCCCTACATTTCCAGAAC CATCGGAAAAGCCAACATCAACATCAGAACCATCAAGTTCC CTTCCACCGAAGACTCTGGCCTTCCCGAAGGCTGCGAGAAT ACCGAGTCAGCACTCGCCCCTGACAAGTTCATCAAGTTCAT GAAGGCCACCCTGCTCCTGAGGGACCCACTTGAACACGTGT TACAGGAAGAGCAACCACACTCTTGGTCGCCGACATGTTCT TCCCTTGGGCCACCGACTCCGCCGCAAAATTCGGCATCCCT AGGATCGTGTTCCACGGCCTCGGTTACTTCCCACTCTGCGT TCTTGCATGCACGAGACAGTACAAGCCTCAGGACAAGGTTT CATCTTACACGGAACCCTTCGTGGTTCCGAATCTCCCGGGT GAAATAACACTGACGAAGATGCAGCTGCCGCAGTTGCCTCA GCACGACAAGGTCTTCACCCAGTTGTTGGAAGAGTCAAACG AATCGGAGTTGAAGAGCTTCGGTGTGATTGTAAACAGCTTC TACGAACTTGAACCGGTTTACGCGGATCATTACAGGAACGA GCTTGGGAGAAGAGCTTGGCATTTGGGTCCGGTTTCATTAT GCAGTAGGGACACGGAGGAAAAATCGCGGAGGGGAAGGGAA GCTGCAATTGATGAGAACGAGTGCTTGAAGTGGCTTCAATC AAAGGAACCCAATTCGGTTGTTTATGTTTGTTTCGGTAGCA TGATGGTTTTCAGTGACGCTCAGCTAAAAGAGATTGCGATG GGTCTTGAGGCTTCAGGGAAGCCATTCATATGGGTGGTGAA GAAAGGAGGGGGTAAAAGTGAAGGTGAGAAATTGGAGTGGC TTCCAGAAGGGTTTGAGGAGAGAATGGGGGAAAGTAATAAG GGACTAATCATAAGGGGTTGGGCACCACAGGTGATGATTTT GGACCATGGAGCGGTTGGAGGGTTTGTGACACATTGTGGGT GGAATTCAACGCTGGAAGGAGTGTGTGCAGGGGTGCCAATG GTGACTTGGCCCATGTATGGGGAACAATTTTACAACGCCAA GTTTCTGACGGACATAGTGAAAATTGGGGTGGGTGTTGGGG TTCAAACGTGGATTGGGATGGGAGGAGGAGAGCCTGTGAAG AAGGAAGTGATAGAGCAGGCAGTGAGAAGGATAATGGTGGG GCAGGAAGCAGAGGAAATGAGAAACAGAGCCAAGGAACTGA GCCAGATGGCAAAGCGTGCTGTGGAGGAAGGAGGATCGTCT CACAACGATTTTAACTCTTTAATTGAGGATTTGAGGTCGCG TGCCCATTAA |
| GuUGAT_ KT759000.1 | Glycyrrhetinic acid glucuronosyl-transferase | 83 | MTMGNENRELHIIFFPFLANGHIIPCVDLARVFAARGIRAT IVTTHLNVPYISRTIGKANINIRTIKFPSTEDSGLPEGCEN TESALAPDKFIKFMKATLLLRDPLEHVLQEEQPHCLVADMF FPWATDSAAKFGIPRIVFHGLGYFPLCVLACTRQYKPQDKV SSYTEPFVVPNLPGEITLTKMQLPQLPQHDKVFTQLLEESN ESELKSFGVIVNSFYELEPVYADHYRNELGRRAWHLGPVSL CSRDTEEKSRRGREAAIDENECLKWLQSKEPNSVVYVCFGS MMVFSDAQLKEIAMGLEASGKPFIWVVKKGGAKSEGEKLEW LPEGFEERMGESNKGLIIRGWAPQVMILDHGAVGGFVTHCG WNSTLEGVCAGVPMVTWPMYGEQFYNAKFLTDIVKIGVGVG VQTWIGMGGGEPVKKEVIEQAVRRIMVGQEAEEMRNRAKEL SQMAKRAVEEGGSSHNDFNSLIEDLRSRAH |
| GuUGT73P12_ SCAFFOLD00629 (LC314779) | Glycyrrhetinic acid 3-O-mono-glucuronide glucuronosyl-transferase | 84 | ATGGACTCCTTTGGGGTTGAAGGTGATCACCAAGCCGACAC CACAGTGCTGAAGGCGGTTTTTCTTCCCTTCATCTCAAAAA GTCATCTCATCCGTGAGGTGGACAAAGCAAGGATCTTCGCC ATGCACGGCGTGGATGTCACCATCATCACCACCCCGGCCAA CGCTGCCACTTTCCAAACCTCCATTGACCGCGACTCCAGCC GCGGCCGCTCCATCAGAACGCACATCGTTCCGTTCCCCCAA GTCCCCGGTCTACCACAGGGACTCGAGAGACTCGACGCCGA CACTCCTCAACACTTGCTCTCCAAGATCTACCATGGACTAT CCATTCTGCAAGAGCAGTTCCAACAACTGTTCCGTGAAATG AGGCCAGATTTCATAGTCACTGACATGTACTACCCTTGGAG CGTCGATGCCGCCGCCGAGTTGGGGATTCCGAGGTTGGTTT GTAACGGTGGAAGCTACTTCGCTCAGTCAGCTGTTAACTCC GTTGAGCTATTTTCACCACAAGCCAAGGTTGATTCAAATAC CGAGACTTTTCTGCTTCCTGGGTTACCCCATGAGGTTGAGA TGACACGTTTGCAACTACCGGATTGGCTTAGAGGAGCACCG AATGAGTACACCTATTTGATGAAGATGATCAAGGATTCAGA GAGGAAGAGTTATGGGTCATTGTTCAATAGCTTTTATGAGC TTGAAGGGACTTATGAGGAACATTACAAGAAAGCCATGGGA ACCAAGAGTTGGAGTGTGGGGCCAGTTTCTTTGTGGGTGAA CCAAGATGCTTCTGATAAGGCTTGTAGGGGGGATGTTAAAG AAGGAAAAGGAGATGGGGTGGTGCTTACTTGGCTGGATTCT AAAACAGAGGACTCTGTTTTGTATGTGAGTTTTGGGAGCAT GAACAAGTTCCCTAAAACTCAGCTTGTTGAGATAGCTCATG |

TABLE 18-continued

| Name | Enzyme Activity | SEQ ID NO: | Nucleotide Sequence/Amino Acid Sequence |
|---|---|---|---|
| Components of the triterpenoid Glyeyrrhizin Biosynthetic Pathway in *G. uraliensis* | | | |
| | | | CCCTCGAAGATTCTGGCCATGATTTCATTTGGGTCGTTGGC AAAATTGAAGAAGGTGAAGGTGGTGCTGATTTTTTGAGGGA ATTTGAGAAGAAAGTGAAAGAAAAAAACAGAGGTTATCTGA TATGGGGTTGGGCACCACAGCTTCTGATTCTGGAGCATCCT GCGGTTGGAGCAGTGGTGACTCATTGTGGGTGGAACACCGT TATGGAAAGTGTGAATGCAAGTTTGCCATTGGCAACTTGGC CATTGTTTGCGGAGCAGTTCTTCAATGAGAAGCTAGTGGTT GATGTGGTGAAGATTGGTGTGCCAGTTGGGGTTAAGGAATG GAGAAATTGGAATGAGTTTGGGGATGAGGTTGTGAAGAGGG AGGACATAGGAAAGGCCATTGCTTTTTTGATGGGTGGTGGG GATGAATCCTTGGAAATGAGGAAGAGGGTCAAGGTGCTCAG TGGTGCTACAAAGAAAGCTATTCAGGTTGGTGGGTCTTCTC ACACCAAGTTGAAAGAACTCATAGAAGAGCTCAAGTCAATC AAGCTACAAAAGGTCAACAACAAATTAATGGAGGCAGTGGC TTAA |
| GuUGT73P12_ SCAFFOLD00629 (LC314779) | Glycyrrhetinic acid 3-O-mono-glucuronide glucuronosyl-transferase | 85 | MDSFGVEGDHQADTTVLKAVFLPFISKSHLIREVDKARIFA MIGVDVTIITTPANAATFQTSIDRDSSRGRSIRTHIVPFPQ VPGLPQGLERLDADTPQHLLSKIYHGLSILQEQFQQLFREM RPDFIVTDMYYPWSVDAAAELGIPRLVCNGGSYFAQSAVNS VELFSPQAKVDSNTETFLLPGLPHEVEMTRLQLPDWLRGAP NEYTYLMKMIKDSERKSYGSLFNSFYELEGTYEEHYKKAMG TKSWSVGPVSLWVNQDASDKACRGDVKEGKGDGVVLTWLDS KTEDSVLWSFGSMNKFPKTQLVEIAHALEDSGHDFIWVVGK IEEGEGGADFLREFEKKVKEKNRGYLIWGWAPQLLILEHPA VGAVVTHCGWNTVMESVNASLPLATWPLFAEQFFNEKLWDV VKIGVPVGVKEWRNWNEFGDEVVKREDIGKAIAFLMGGGDE SLEMRKRVKVLSGATKKAIQVGGSSHTKLKELIEELKSIKL QKVNNKLMEAVA |
| GuCSLG Protein from Chinese liquorice_ (Glyur003152s-00037491.1_ Glycyrrhizaural-ensis) (SOAP5 hornolog; Cellulose Synthase Like G) | Cellulose Synthase Like G (Glucuronic acid transferase) | 102 | MASFTLHTETVQSWLLLSRLHILLHLAVVLLLLYYRITRFP FHAPTLPWTLMTVGEAIMAVLWFFNQAFRWRPVSRSVMTEK LPSDAKLPGLDIFVCTLDPEKEPTVEYMNTLVSALAMDYPP DKLSVYLSDDGAAPVTLYGVREASEFARVWVPFCKKYGIKS RCPKVFFSPSAEDEHLLRTDEFRSERDLIKAKYEKMQKNIE KFGSDAKNCRMVTDRPPRIEILIDQPDMPRVVYVSRERRPS LPHKFKGGALNTLLRVSGLISNGPYVLWDCDMYCNDPSSAK QAMCFFLDPETSKSIAFVQFPQMFFTNLGKKDIYDNQSRTA FKTMWQGMDGLRGPGLSGSGNYLNRSALLFGSPNQKDDYLD DAQNYLGKSTMYIESLKAIRGQKFMKKNISRDEILREAQVL ASCSYETNTEWGAEYGFSYGILLESSITGYLFHCRGWKSAY LYPKTPCFLGCAPTDIKEGMLQLVKWLSEYCLLGFSKYSPF TYGFSRMPIMPTLVYCFLTTTTLYSIVFILYGIVPQVCFLK GIPVFPKVTDPWFAVFATLYISTQIQHLIEVLSGDGSVAMW WDEQGIWILKSVTSVFAIIEAAKKGLGLNKKKFMLSNKAID KEKLKKYEQGRFDFQGAALFMSPMVVLLIVNVVSFIGGIWR LFNAKDIEDMFGQLFLVSYVMALSYPIFEGIITMKSKSG |
| GuCSLG Gene from Chinese liquorice_ (Glyur003152s-00037491.1 Glycyrrhizaural-ensis) (SOAP5 homolog; Cellulose Svynthase Like G) | Cellulose Synthase Like G (Glucuronic acid transferase) | 103 | ATGGCAAGCTTCACCCTTCACACAGAAACCGTTCAGTCATG GCTACTCCTCAGCAGACTTCACATACTGCTGCACCTCGCAG TTGTACTGCTCCTCTTATACTACCGCATCACACGTTTCCCC TTCCATGCTCCGACTCTACCGTGGACTCTGATGACCGTAGG TGAGGCTATTATGGCAGTGCTGTGGTTCTTCAACCAGGCCT TCCGGTGGCGGCCGGTGAGCCGCTCGGTGATGACGGAGAAG CTGCCCAGCGACGCGAAGCTGCCGGGGCTTGACATATTCGT GTGCACGCTTGACCCCGAGAAGGAGCCCACCGTGGAGGTGA TGAACACTCTGGTCTCTGCCCTTGCCATGGACTACCCCCCT GACAAGCTCTCCGTTTACCTCTCCGACGATGGCGCCGCCCC GGTCACTCTTTACGGCGTGAGAGAGGCTTCTGAGTTCGCGA GGGTGTGGGTCCCTTTCTGCAAAAAGTATGGGATCAAGTCA AGGTGTCCCAAGGTTTTCTTCTCTCCCAGTGCTGAGGATGA ACACCTTCTTCGCACCGACGAGTTCAGGTCAGAGCGAGACC TCATCAAGGCTAAATACGAGAAAATGCAGAAAAATALTGAG AAATTTGGTTCGGATGCCAAAAATTGTCGTATGGTGACTGA CAGACCTCCTCGGATCGAGATATTGATTGACCAACCAGACA TGCCACGTGTTGTTTACGTGTCTCGGGAAAGAAGGCCATCA CTCCCTCACAAGTTCAAAGGAGGAGCCCTCAATACATTGCT CAGAGTCTCAGGTCTAATCAGCAATGGGCCTTATGTACTTG TAGTGGACTGTGATATGTATTGCAATGACCCATCCTCAGCC AAACAAGCCATGTGTTTCTTTCTTGATCCTGAAACCTCTAA ATCTATTGCATTTGTCCAATTCCCTCAAATGTTTCACAACC TTGGCAAAAAAGACATCTATGACAATCAATCTAGGACTGCT TTTAAGACAATGTGGCAAGGGATGGATGGACTAAGAGGTCC |

TABLE 18-continued

| Components of the triterpenoid Glyeyrrhizin Biosynthetic Pathway in *G. uraliensis* | | | |
|---|---|---|---|
| Name | Enzyme Activity | SEQ ID NO: | Nucleotide Sequence/Amino Acid Sequence |
| | | | TGGTCTTTCTGGCAGCGGTAATTACTTGAATAGAAGTCTCA<br>TTACTATTTGGAAGTCCAAATCAAAAAGATGACTATCTGGA<br>TGATGCCCAAAACTACTTAGGCAAGTCTACCATGTACATAG<br>AATCACTAAAGGCCATTCGTGGACAAAAAACTATGAAAAAG<br>AATATTTCAAGAGATGAAATTTTACGAGAAGCTCAAGTATT<br>AGCCTCTTGTTCCTATGAGACAAACACAGAATGGGGAGCAG<br>AGGTAGGATTCTCATATGGCATCTTACTGGAGAGTTCAATC<br>ACTGGCTATCTTTTCCACTGCAGAGGATGGAAATCAGCATA<br>TCTTTACCCAAAGACACCATGTTTCTTAGGGTGTGCCCCAA<br>CTGACATCAAGGAAGGAATGCTCCAATTGGTGAAGTGGTTG<br>TTCTGAATACTGCTTGCTAGGATTCTCTAAATACAGCCCTT<br>TCACTTATGGCTTTTCAAGAATGCCCATTATGCCTACCTTA<br>GTCTATTGCTTCTTGACAACAACAACCCTTTATTCCATTGT<br>CTTCATCCTTTATGGCATTGTCCCCCAAGTTTGCTTCTTAA<br>AAGGAATACCCGTGTTTCCAAAGGTCACAGACCCTTGGTTT<br>GCAGTGNTGCAACACTGTATATATCCACCCAGATTCAACAT<br>TTGATAGAGGTCCTTTCTGGTGATGGCTCTGTGGCAATGTG<br>GTGGGATGAACAGGGAATCTGGATTCTGAAGTCAGTCACTA<br>GCGTGTTCGCAATCATAGAGGCAGCTAAGAAAGGGTTAGGA<br>TTGAACAAGAAGAAATTCATGTTGTCAAACAAAGCAATTGA<br>CAAGGAGAAGCTCAAGAAGTATGAGCAAGGTAGGTTTGATT<br>TCCAAGGTGCAGCTCTGTTCATGTCCCCAATGGTTGTGTTG<br>CTCATAGTGAACGTTGTTTCCTTCATTGGRGGCATATGGAG<br>ACTATTCAATGCAAAGGATATTGAAGATATGTTTGGTCAGC<br>TTTTCCTAGTTAGTTATGTAATGGCCCTTAGTTATCCCATT<br>TTTGAAGGGATAATAACCATGAAAAGCAAGAGTGGATAG |

Expression of spinach bAS (SoSOAP1; SEQ ID NO: 45), GuCYP88D6(SEQ ID NO: 76) GuCYP72A154 (SEQ ID NO. 78), and GuCSL (SEQ ID NO: 80) in *N. benthamiana* resulted in formation of glycyrrhetinic acid 3-O-monoglucuronide (GA-3-GlcA) (FIGS. 46A-46E). On the other hand, previously reported GuUGAT (SEQ ID NO: 82) believed to catalyze the continuous two-step glucuronidation of glycyrrhetinic acid to yield glycyrrhizin failed to attach GlcA to the aglycone in the assays performed here (G. Xu, W. Cai, W. Gao, C Liu, A novel glucuronosyltransferase has an unprecedented ability to catalyse continuous two-step glucuronosylation of glycyrrhetinic acid to yield glycyrrhizin. New Phytol. 212, 123-35 (2016)).

Transient expression of GuUGT73P12 (SEQ ID NO: 84), which was previously shown to attach the second GlcA, together with GuCSL and other enzymes gave glycyrrhizin as a final product in *N. benthamiana* (FIGS. 47A-47F). The assays also showed that GuCSL (SEQ ID NO: 81) can perform addition of the second glucuronic acid moiety to GA-3-GlcA, but with very low efficiency.

Furthermore, it will be shown in a heterologous system (*N. benthamiana*) that the first glycosylation step in the biosynthesis of QS-21 from *Q. saponaria* may be performed by a CSLG which attaches glucuronic acid to the quillaic acid at position C-3.

Summary: The discovery of a new type of biosynthetic reaction performed by cellulose synthase like G enzymes provides a valuable strategy for engineering pathways of important specialized metabolites and their sustainable production in heterologous systems (plant or fungal).

Example 24: Structural Analysis of Cellulose Synthase Like G

Objective: To analyze the structure of Cellulose Synthase Like G (CSLG) and compare it with the classical Cellulose Synthase A (CESA).

Methods: See Materials and Methods above.

Results: Phylogenetic analysis showed that CSLGs are evolutionarily distinct from the classical Cellulose Synthase A (CESA) enzymes that mediate cellulose biosynthesis (approximately 30% amino acid sequence similarity). However, these two protein groups share several structural features. A predicted 3D model obtained by template-based tertiary structure modelling of the spinach SOAP5 CSLG protein showed that it consists of two domains traversing a lipid bilayer (TMD) at the amino-termini and an additional four TMDs at the carboxy terminal end (M. Kullberg et al., Template-based protein structure modeling using the RaptorX web server. Nature Protocols. 7, 1511-1522(2012)). A 445 amino acid long loop protruding from the lipid bilayer is located between the transmembrane domains (FIG. 48; FIG. 49A). The amino acid sequences of the spinach SOAP5 enzyme, the cellulose synthase like G enzyme from *Arabidopsis*, and the cellulose synthase A enzyme subunits from *Arabidopsis* and their orthologs in spinach are presented below in Table 19. In addition, other cellulose synthase like genes are presented from the A, B, and E families. The current understanding is that cellulose synthase like genes from A, B, and E families each have completely different activities. Until the work presented here, only few CSLs were known, and none from CSLG family, were characterized. Those that were analyzed are involved in sugar metabolism, biosynthesis of beta-glucans and hemicelluloses. It was never shown that any CSL (despite family it belongs) can work on triterpenoids. Thus, the results presented throughout the examples provided surprising and unexpected activities for a cellulose like synthase.

TABLE 12

Amino Acid and Nucleotide Sequences of *Arabidopsis* CSLG and CESA enzymes

| NAME | ENZYME ACTIVITY | SEQ ID NO: | AA SEQ |
|---|---|---|---|
| *Arabidopsis* CESA1 | Cellulose Synthase A (subunit 1) | 67 | MEASAGLVAGSYRRNELVRIRHESDGGTKPLKNMNG<br>QICQICGDDVGLAETGDVFVACNECAFPVCRPCYEY<br>ERKDGTQCCPQCKTRFRRHRGSPRVEGDEDEDDVDD<br>IENEFNYAQGANKARHQRHGEEFSSSSRHESQPIPL<br>LTHGHTVSGEIRTPDTQSVRTTSGPLGPSDRNAISS<br>PYIDPRQPVPVRIVDPSKDLNSYGLGNVDWKERVEG<br>WKLKQEKNMLQMTGKYHEGKGGEIEGTGSNGEELQM<br>ADDTRLPMSRVVPIPSSRLTPYRVVIILRLIILCFF<br>LQYRTTHPVKNAYPLWLTSVTCEIWFAFSWLLDQFP<br>KWYPINRETYLDRLAIRYDRDGEPSQLVPVDVFVST<br>YDPLKEPPLVTANTVLSILSVDYPVDKVACYVSDDG<br>SAMLTFESLSETAEFAKKWVPFCKKFNIEPRAPEFY<br>FAQKIDYLKDKIQPSFVKERRAMKREYEEFKVRINA<br>LVAKAQKIPEEGWTMQDGTPWPGNNTRDHPGMIQVF<br>LGHSGGLDTDGNELPRLIYVSREKRPGFQHHKKAGA<br>MNALIRVSAVLTNGAYLLNVDCDHYFNNSKAIKEAM<br>CFMMDPAIGKKCCYVQFPQRFDGIDLHDRYANRNIV<br>FFDINMKGLDGIQGPVYVGTGCCFNRQALYGYDPVL<br>TEEDLEPNIIVKSCCGSRKKGKSSKKYNYEKRRGIN<br>RSDSNAPLFNMEDIDEGFEGYDDERSILMSQRSVEK<br>RFGQSPVFIAATFMEQGGIPPTTNPATLLKEAIHVI<br>SCGYEDKTEWGKEIGWTYGSVTEDILTGFKMHARGW<br>ISIYCNPPRPAFKGSAPINLSDRLNQVLRWALGSIE<br>ILLSRHCPIWYGYHGRLRLLERIAYINTIVYPITSI<br>PLIAYCILPAFCLITDRFIIPEISNYASIWFILLFI<br>SIAVTGILELRWSGVSIEDWWRNEQFWVIGGTSAHL<br>FAVFQGLLKVLAGIDTNFTVTSKATDEDGDFAELYI<br>FKWTALLIPPTTVLLVNLIGIVAGVSYAVNSGYQSW<br>GPLFGKLFFALWVIAHLYPFLKGLLGRQNRTPTIVI<br>VWSVLLASIFSLLWVRINPFVDANPNANNFNGKGGV<br>F |
| *Arabidopsis* CESA3 | Cellulose Synthase A (subunit 3) | 68 | MESEGETAGKPMKNIVPQTCQICSDNVGKTVDGDRF<br>VACDICSFPVCRPCYEYERKDGNQSCPQCKTRYKRL<br>KGSPAIPGDKDEDGLADEGTVEFNYPQKEKISERML<br>GWHLTRGKGEEMGEPQYDKEVSHNHLPRLTSRQDTS<br>GEFSAASPERLSVSSTIAGGKRLPYSSDVNQSPNRR<br>IVDPVGLGNVAWKERVDGWKMKQEKNTGPVSTQAAS<br>ERGGVDIDASTDILADEALLNDEARQPLSRKVSIPS<br>SRINPYRMVIMLRLVILCLFLHYRITNPVPNAFALW<br>LVSVICEIWFALSWILDQFPKWFPVNRETYLDRLAL<br>RYDREGEPSQLAAVDIFVSTVDPLKEPPLVTANTVL<br>SILAVDYPVDKVSCYVFDDGAAMLSFESLAETSEFA<br>RKWVPFCKKYSIEPRAPEWYFAAKIDYLKDKVQTSF<br>VKDRRAMKREYEEFKIRINALVSKALKCPEEGWVMQ<br>DGTPWPGNNTGDHPGMIQVFLGQNGGLDAEGNELPR<br>LVYVSREKRPGFQHHKKAGAMNALVRVSAVLTNGPF<br>DLKLDCDHYINNSKALREAMCFLMDPNLGKQVCYVQ<br>FPQRFDGIDKNDRYANRNTVFFDINLRGLDGIQGPV<br>YVGTGCVFNRTALYGYEPPIKVKHKKPSLLSKLCGG<br>SRKKNSKAKKESDKKKSGRHTDSTVPVFNLDDIEEG<br>VEGAGFPPEKALLMSQMSLEKRFGQSAVFVASTLME<br>NGGVPPSATPENLLKEAIHVISCGYEDKSDWGMEIG<br>WIYGSVTEDILTGFKMHARGWRSIYCMPKLPAFKGS<br>APINLSDRLNQVLRWALGSVEILFSRHCPIWYGYNG<br>RLKFLERFAYWTTIYPITSIPLLMYCTLLAVCLFTN<br>QFIIPQISNIASIWFLSLFLSIFATGILEMRWSGVG<br>IDEWWRNEQFWVIGGVSAHLFAVFQGILKVLAGIDT<br>NFTVTSKASDEDGDFAELYLFKWTTLLIPPTLLIVN<br>LVGVVAGYSYAINSGYQSWGPLFGKLFFAFWVIVHL<br>YPFLKGLMGRQNRTPTIVVVWSVLLASIFSLLWVRI<br>DPFTSRVTGPDILECGINC |
| *Arabidopsis* CSLG1 | Cellulose Synthase Like G | 69 | METHRKNSVVGNILHTCHPCRRTIPYRIYAIFHTCG<br>IIALMYHHVHSLVTANNTLITCLLLLSDIVLAFMWA<br>TTTSLRLNPVHRTECPEKYAAKPEDFPKLDVFICTA<br>DPYKEPPMMVVNTALSVMAYEYPSDKISVYVSDDGG<br>SSLTFFALIEAAKFSKQWLPFCKKNNVQDRSPEVYF<br>SSESHSRSDEAENLKMMYEDMKSRVEHVVESGKVET<br>AFITCDQFRGVFDLWTDKFSRHDHPTIIQVLQNSET<br>DMDNTRKYIMPNLFYVSREKSKVSPHHFKAGALNTL<br>LRVSGVMTNSPIILTLDCDMYSNDPATLVRALCYLT<br>DPEIKSGLGYVQFPQKFLGISKNDTYACENKRLFII |

TABLE 12-continued

Amino Acid and Nucleotide Sequences of *Arabidopsis* CSLG and CESA enzymes

| NAME | ENZYME ACTIVITY | SEQ ID NO: | AA SEQ |
|---|---|---|---|
| | | | NMVGFDGLMGPTHVGTGCFFNRRAFYGPPYMLILPE INELKPYRIADKSIKAQDVLSLAHNVAGCIYEYNTN WGSKIGFRYGSLVEDYYTGFMLHCEGWRSVFCNPKK AAFYGDSPKCLVDLVGQQIRWAVGLFEMSFSKYSPI TYGIKSLDLLMGLGYCNSPFKPFWSIPLTVYGLLPQ LALISGVSVFPKASDPWFWLYITLFFGAYAQDLSDF LLEGGTYRKWWNDQRMLMIKGLSSFFFGFIEFILKT LNLSTPKFNVTSKANDDDEQRKRYEQEIFDFGTSSS MFLPLTTVAIVNLLAFVWGLYGILFCGGELYLELML VSFAWNCLPIYGAMVLRKDDGKLSKRTCFLAGNLHV GSYCVKLLRPQVTSPLRLIHNNNTSGWFKRKKHNMN ESV |
| Spinach CESA1 | cellulose synthase A catalytic subunit 1 [UDP-forming] | 70 | MEATGGMVAGSYKRNELVRIRHDSTDSGSKSLKNLD GQICQICGDTVGVTSNGGVFVACNECAFPVCRPCYE YERKDGNQCCPQCKTRYKRQKGSLRVEGDDEEEDVD DLDNEFNYERGTSKARHQWQGEDVDLSSSSRHGSQP IPLLTNGQVVSGEIPSATPDNQSVRSTSGPIGPEKR GNHSLPYIDPCLPVPVRIVDPSKDLNSYGLGSVDWK ERVESWKLKQEKNMTHTGNRYSEGKGGDVEGSGSNG EELQLADDVRQPMSRIVPIPSSFILTPYRAVIIFRL IILVFFLQFRITHPVEDAYPLWLTSVICEIWFAMSW ILDQFPKWYPINRETYLDRLAFRHDREGEPSQLAPI DVFVSTVDPLKEPPIITANTVLSILAVDYPVDKVSC YVSDDGSAMLTFEGLSETAEFARKWVPFCKKFSIEP RAPEFYFQQKIDYLKDKIQPSFVKERRAMKREYEEF KVRINALVAKAQKVPEEGWTMQDGTAWPGNNPRDHP GMIQVFLGHSGGLDMDGNELPRLVYVSREKRPGFQH HKKAGAMNALIRVSAVLTNGAYILNVDCDHYFNNSK CLKEAMCFMMDPALGKKVCYVQFPQRFDGIDLHDRY ANRNIVFFDINMKGQDGIQGPVYVGTGCCFNRQALY GYDPVLTEEDFEPNFIIKNCFGSRKKGKSGNKKYMD KKRGPKRSESSIPIFNMEDIEEGVEGYEDEKSLLMS QKRLEKRFGQSPVFIAATFMEMGGIPPTTNPATLLK EAIHVISCGYEDKSEWGKEIGWIYGSVIEDILTGFK MHARGWMSIYCMPPRPAFKGSAPLNLSDRLNQVLRW ALGSIEIMLSRHCPIWYGYKGRLRFLERLAYINTVV YPLTSIPLIAYCILPAICLLTNKFIIPTLSNFASIL FIMLFMSLAATGILELRWSGVSIEDWWRNEQFWVIG GTSAHLFAVFQGLLKVLAGIDTNFTVTSKAADEDGD FAELYIFKWTALLIPPTTVLIVNLVGVVAGVSYAIN SGYQSWGPLFGKLFFSFWVIAHLYPFLKGLLGRQNR TPTIVIVWSVLLASIFSLLWVRINPFTTDAEKAAAG NQCGINC |
| Spinach CESA3 | cellulose synthase A catalytic subunit 3 [UDP-forming] | 71 | MMEDSQSGVKPTKQANEQVCQICSDNIGTTVDGEPF VACDVCSFPVCRACYEYERKDGTQSCPQCKTRYKRQ KGSPAIHGEKVEDSDVEDWSDVNEPLGSSILKEKPQ ERMLGWHMNHGQSGELGPPTYDKEAPISHIPRLATG RTVSGDLSAASPGRFSMPSPGASTGANIRVSREFAS PGFGNVAWKERIDGWKMKQEKSTGPPSVSHAPSEGR FANDIDASTETAMDDPLLNDETRQPLSRKVPIPSSR INPYRMYIVLRLAVLGIFLHYRVTNPVPNAYALWLI SVICEIWFAFSWILDQFPKWLPINRETYLDRLALRY DREGEPSQLAAVDIFVSTVDPLKEPPLVTANTVLSI LAVDYPVDKVSCYVSDDGAAMLTFEALSETSEFARK WYPFTKKYNIEPRAPEWYFSQKIDYLKDKVQTTFVK DRRAMKREYEEFKIRINGLVAKATKVPEEGWVMQDG TPWPGNNTRDHPGMIQVFLGQSGGLDTDGNELPRLV YVSREKRPGFTHHKKAGAMNSLVRVSAVLTNGPFML NLDCDHYINNSKALREAMCFMMDPNLGKYCCYVQFP QRFDGIDRNDRYANRNTVFFDINLRGLDGIQGPVYY GTGCVFNRTALYGYEPPIKPKPKKKGILSSCFGGSR KKSSKKDSKKKSKTIADPTVPIFNLEDIEEGVEGTG FDDEKSLLMSQISLEKRFGKSEVFVASTLMENGGVP QSATPDTLLKEAIHVISCGYEDKTDWGAEIGWIYGS VTEDILTGFKMHARGWRSIYCMPKLAAFKGSAPINL SDRLNQVLRWALGSVEILFSRHCPLWYGYGGRLKWL ERFAYINTTIYPLTSIPLLAYCTLPAVCLLTGKFII PQISNLASVWFLSLFLSIFATGILEMRWSGVGIDEW WRNEQFWVIGGISAHLFAVFQGLLKVLAGIDTNFTV TSKASDEDGDFTELYLFKWTTLLIPPTTILIVNLVA |

TABLE 12-continued

Amino Acid and Nucleotide Sequences of *Arabidopsis* CSLG and CESA enzymes

| NAME | ENZYME ACTIVITY | SEQ ID NO: | AA SEQ |
|---|---|---|---|
| | | | VVAGISYAINSGYQSWGPLFGKLFFAFWVIVHLYPF<br>LKGLMGRQNRTPTIVVVWSILLASIFSLLWVRVDPF<br>TTRVTGPDVHICGINC |
| ATCSLA1_<br>At4g16590 | | 86 | ATGTCTCTATTTCTGAAGCCCTTCCTCTTCCTATAC<br>GACACCACTCTTAGTCTTCTCTTACTTCTGTTCAAT<br>GGATGGAGTCTTGAGGATACAGCAGCAGCCCAAAAG<br>AGGCGTGAAGCAGACAAAAATGCTGCAGAAACTGAA<br>TGGATCCAACTCCAATACTTGTGGACCAAAACAAGG<br>AGTGTTGTACTACTTCCCGTTTTCAAGGGTTTGGTG<br>GTTATGTGTTTGGTTCTATCCATTATAGTGTTCTTC<br>GAGAGTTTTTACATGAACTTTGTGATACTCTTCGTC<br>AAGTTATTTAAACTGTAAACCCCATAAAGTGTACAA<br>ATGGGAGGCCATGCAAGAAGATGTTGAGGTTGGACC<br>CGATAACTACCCAATGGTTCTTATCCAAATACCAAT<br>GTACAATGAAAAAGAGGAAGGTGTGGACGTAGAGAT<br>TGCAAAATGGCAAAGCCAAGGCATAAACATAAGGTG<br>TGAAAGGAGAGATAACAGGAACGGCTACAAAGCCGG<br>AGCTATGAAAGAAGCTCTTACGCAGAGCTACGTCAA<br>GCAATGCGACTTCGTAGCAGTCTTCGATGCTGATTT<br>CCAACCCGAGCCCGATTATCTCATCCGCGCTGTCCC<br>TTTCCTTGTCCACAACCCTGACGTTGCTCTAGTTCA<br>AGCCCGATGGATATTTGTTAACGCGAACAAATGCTT<br>GATGACGAGGATGCAAGAGATGTCTCTCAACTATCA<br>TTTCAAAGTGGAACAAGAATCAGGGTCGACTAGACA<br>TGCTTTCTTCGGGTTTAATGGAACCGCGGGTGTATG<br>GAGAATATCGGCAATGGAAGCAGCAGGAGGATGGAA<br>ATCAAGGACCACAGTAGAGGACATGGACTTGGCTGT<br>TCGTGTTGGTCTTCATGGCTGGAAATTTGTCTACCT<br>TAACGACCTCACGGTGAGAAACGAGCTTCCAAGCAA<br>ATTTAAGGCCTACAGATTCCAGCAACATAGGTGGTC<br>CTGTGGACCGGCGAATCTATTTAGAAAAATGACGAT<br>GGAGATCATTTTCAATAAGAGAGTATCAATTTGGAA<br>GAAAGTGGCGGTACACTTCTTGACATTCTTCTTCTA<br>CTGTATAATTGTGCCAACAAGTGTCTTCTTCCCTGA<br>AATCCACATCCCATCTTGGTCTACCATTTACGTTCC<br>CTCTTTGATCAGTATCTTCCACACCCTGGCAACTCC<br>AAGATCCTTCTACCTCGTGATATTTTGGGTCTTGTT<br>CGAGAATGTAATGGCTATGCATCGAACCAAAGGTAC<br>GTGCATTGGCCTACTTGAAGGAGGAAGAGTAAACGA<br>ATGGGTTGTGACCGAAAAACTAGGAGATGCTTTGAA<br>GAGTAAGCTACTCTCTCGGGTAGTCCAAAGAAAATC<br>TTGTTATCAAAGAGTGAATTCCAAGGAAGTGATGGT<br>GGGGGTATACATATTAGGATGTGCACTCTATGGCCT<br>GATCTATGGGCACACATGGTTACATTTCTATCTTTT<br>TCTTCAGGCCACAGCCTTTTTCGTCTCCGGTTTTGG<br>TTTTGTCGGAACCTAA |
| ATCSLA1_<br>At4g16590 | | 87 | MSLFLKPFLFLYDTTLSLLLLLFNGWSLEDTAAAQK<br>RREADKNAAETEWIQLQYLWTKTRSVVLLPVFKGLV<br>VMCLVLSIIVFFESFYMNFVILFVKLFKRKPHKVYK<br>WEAMQEDVEVGPDNYPMVLIQIPMYNEKEEGVDVEI<br>AKWQSQGINIRCERRDNRNGYKAGAMKEALTQSYVK<br>QCDFVAVFDADFQPEPDYLIRAVPFLVHNPDVALVQ<br>ARWIFVNANKCLMTRMQEMSLNYHFKVEQESGSTRH<br>AFFGFNGTAGVWRISAMEAAGGWKSRITVEDMDLAV<br>RVGLHGWKFVYLNDLTVRNELPSKFKAYRFQQHRWS<br>CGPANLFRKMTMEIIFNKRVSIWKKFYVIYSFFFVR<br>KVAVHFLTFFFYCIIVPTSVFFPEIHIFSWSTIYVP<br>SLISIFHTLATPRSFYLVIFWVLFENVMAMHRTKGT<br>CIGLLEGGRVNEWVVTEKLGDALKSKLLSRVVQRKS<br>CYQRVNSKEVMVGVYILGCALYGLIYGHTWLHFYLF<br>LQATAFFVSGFGFVGT |
| ATCSLB1_<br>AT2G32610 | | 88 | ATGGCGGATTCAAGCTTTTCTCTTCCTCCTCTTTGT<br>GAAAGGATCTCATACACGAACTATTTTCTAAGAGCT<br>GTATATCTCACGGTTCTAGGCCTTTTCTTTTCTCTT<br>CTCTTGCACGGAATCCGACATACGAQCGAATACGAC<br>AACGTTTGGCTCGTGGCTTTCTTTTGTGAATCTTGT<br>TTCTTCTTGGTATGTCTGCTTATTACTTGCCTAAAA<br>TGGAGTCCTGCTGATACTAAACCCTTTCCTGATAGA<br>CTTGATGAAAGGGTTCATGACCTTCCTTCGGTGGAT<br>ATGTTCGTGCCCACAGCAGATCCGGTTCGAGAGCCA |

TABLE 12-continued

Amino Acid and Nucleotide Sequences of *Arabidopsis* CSLG and CESA enzymes

| NAME | ENZYME ACTIVITY | SEQ ID NO: | AA SEQ |
|---|---|---|---|
| | | | CCGATTATGGTTGTGGACACCGTGCTTTCGCTGTTA<br>GCTGTAAATTATCCGGCAAATAAACTAGCTTGTTAT<br>GTGTCGGACGATGGATGCTCACCTCTCACTTATTTC<br>TCTCTCAAGGAAGCTTCTAAGTTCGCCAAGATTTGG<br>GTACCGTTCTGCAAAAAGTACAACACTAGAGTTAGA<br>GCTCCTTCTAGATATTTTCTGAAACCTATAAGCGTC<br>GCAACAGAGGATTATGAATTCAATAGAGACTGGGAA<br>AAGACGAAGAGGGAGTACGAGAAGTTGAGGCGGAAA<br>GTGGAAGATGCCACCGGAGATTCTCATATGTTGGAT<br>GTAGAAGATGATTTTGAAGCATTCTCAAAGAGAAAA<br>CCAAATGATCATTCAACTCTAGTTAAGGTGGTATGG<br>GAGAACAAGGGAGGTGTAGGAGACGAGAAAGAGATC<br>CCTCATATCATATACATATCAAGAGAGAAAAGACCA<br>AATTATGTTCATAATCAAAAATGTGGAGCCATGAAC<br>TTTCTGGCAAGAGTGTCAGGGTTGATGACAAACGCA<br>CCATACATCTTGAACGTGGATTGCGACATGTATGCC<br>AATGATGCAGATGTAGTCCGACAAGCAATGTGTATA<br>CTTCTGCAAGAATCATTAAATATGAAACATTGTGCT<br>TTTGTTCAATTCCGTCAAGAATTCTATGATTCAAGC<br>ACCGAGCTAATAGTCGTCCTACAATCACATTTGGGA<br>CGAGGAATCGCGGGAATCCAAGGACCGATATATATA<br>GGATCAGGATGCGTCCACACGAGAAGAGTTATGTAT<br>GGTTTATCTCCAGACGATTTCGAAGTTGATGGAAGT<br>CTTTCTTCAGTTGCTACAAGGGAGTTTTTGGTTAAG<br>GATAGTTTAGGGAGAAGATTTGGTAATTCTAAAGAG<br>ATGATGAAATCAGTGGTTGATGCAATACAAAGAAAT<br>CCAAATCCACAAAATATACTTACAAACTCCATAGAA<br>GCGGCTCGAGAAGTGGGACATTGTCAGTACGAGTAC<br>CAAACCAGCTGGGGAAACACCATCGGCTGGTTATAT<br>GATTCAGTGGCGGAAGATTTAAACACGAGTATCGGA<br>ATACATTCGAGAGGTTGGACTAGCTCATACATTTCT<br>CCGGATACACCTGCATTTCTTGGATCTATGCCGGCA<br>GGAGTAGCCGAGGCGTTACTCCAGCAGCGTCGATGG<br>GCGACAGGATGGATCGAAATCCTTTTCAACAAGCAA<br>AGTCCGTTGCGAGGATTGTTTAGCAAGAAAATAAGA<br>TTCCGACAACGATTAGCTTATCTTTGCATTATCACC<br>TGTCTAAGGTCAATCCCTGAGCTTATTTATTGTCTC<br>CTTCCTGCTTATTGCCTACTCCACAACTCTACCTTA<br>TTCCCCAAGGGACTTTATTTAGGCATAACTGTCACA<br>CTTGTTGGGATACATTGTCTCTATACTCTATGGGAA<br>TTTATGAGCCTTGGTTATTCCGTACAATCGTGGCTA<br>GTCTCCCAATCAGTTTGGAGAATAGTAGCCACTAGT<br>AGTTGGTTATTTAGCATCTTTGATATCACACTCAAG<br>CTTCTTGGCATCTCGGAAACGGTGTTCATAATCACT<br>AAAAAGACTGTGGCTGGGACCAAGTCAGCATTAGGG<br>TCTGGACCCTCTCAAGGAGAAGACGTTGGTCCAAAC<br>TCAGACTTGTTTAAATTTGAATTTGATGGCTCACTT<br>TGTTTCTTGCCTGGCACATTTATTGTGTTGGTGAAT<br>ATAGCCGCTCTAGCTGTTTTTTCTGTGGGTCTACAA<br>CGGTCGAGTTACAGCCATGAAGGACTCTTGGTTCGG<br>GTCTGGCAGAGGCTTGCGGATGTGTTTTGGTAATGA<br>TGTTGTTCCTTCCATTTCTAATGGGTTTGTTTAAGA<br>AAGGAAAATATGGAACCCCATTGTCTACTCTCTCTA<br>TAGCTGGCTTTTTAGCAGTTTTATTTGTTGTTTTCT<br>CTGTTTGA |
| ATCSLB1_<br>AT2G32610 | | 89 | MADSSFSLPPLCERISYTNYFLRAVYLTVLGLFFSL<br>LLHRIRHTSEYDNVWLVAFFCESCFFLVCLLITCLK<br>WSPADTKPFPDRLDERVHDLPSVDMFVPTADPVREP<br>PIMVVDTVLSLLAYNYPANKLACYVSDDGCSPLTYF<br>SLKEASKFAKIWVPFCKKYNTRVRAPSRYFLKPISV<br>ATEDYEFNRDWEKTKREYEKLRRKVEDATGDSHMLD<br>VEDDFEAFSNTKPNDHSTLVKVVWENKGGVGDEKEI<br>PHIIYISREKRPNYVHNQKCGAMNFLARYSGLMTNA<br>PYILNVDCDMYANDADVVRQAMCILLQESLNMKHCA<br>FVQFRQEFYDSSTELIVVLQSHLGRGIAGIQGPIYI<br>GSGCVHTRRVMYGLSPDDFEVDGSLSSVATREFLVK<br>DSLARRFGNSKEMMKSVVDAIQRNPNPQNILTNSIE<br>AAREVGHCQYEYQTSWGNTIGWLYDSVAEDLNTSIG<br>IHSRGWTSSYISPDTPAFLGSMPAGVPEALLQQRRW<br>ATGWIEILFNKQSPLRGLFSKKIRFRQRLAYLCIIT<br>CLRSIPELIYCLLPAYCLLHNSTLFPKGLYLGITVT<br>LVGIHCLYTLWEFMSLGYSVQSWLVSQSVWRIVATS |

TABLE 12-continued

Amino Acid and Nucleotide Sequences of *Arabidopsis* CSLG and CESA enzymes

| NAME | ENZYME ACTIVITY | SEQ ID NO: | AA SEQ |
|---|---|---|---|
| | | | SWLFSIFDITLKLLGISETYFIITKKTVAGTKSALGSGPSQGEDVGPNSDLFKFEFDGSLCFLPGTFIVLVNIAALAVFSVGLQRSSYSHEGGGSGLAEACGCVLVMMLFLPFLMGLFKKGKYGTPLSTLSIAGFLAVLFVVFSV |
| ATCSLE1_ AT1G55850 | | 90 | ATGGTAAACAAAGACGACCGGATTAGACCGGTTCATGAAGCCGACGGTGAACCGCTTTTTGAGACTAGGAGAAGAACCGGTAGAGTGATTGCGTACCGGTTTTTCTCAGCCTCGGTTTTCGTGTGTATCTGTTTGATTTGGTTCTACAGAATTGGTGAGATTGGTGATAACCGTACCGTTTTAGATCGATTAATCTGGTTTGTTATGTTTATTGTGGAGATTTGGTTCGGTTTATATTGGGTAGTCACACAATCTTCCGGGTGGAATCCGGTTTGGCGATTTCCCTTCTCCGATAGACTCTCTCGGAGATACGGAAGCGACCTTCCGAGGCTCGACGTCTTCGTTTGCACGGCGGATCCGGTGATTGAGCCGCCGTTGTTGGTGGTAAACACAGTCTTATCTGTGACGGCTCTTGACTACCCACCGGAGAAACTCGCCGTTTATCTCTCAGATGACGGTGGTTCTGAGCTGACGTTCTATGCTCTCACGGAGGCAGCTGAGTTTGCTAAAACTTGGGTTCCCTTCTGCAAGAAGTTCAACGTTGAGCCAACATCTCCCGCTGCTTACTTGTCTTCCAAGGCAAACTGTCTTGATTCTGCGGCTGAGGAGGTGGCTAAGCTGTATAGAGAAATGGCGGCGAGGATTGAAACGGCGGCGAGACTGGGACGAATACCGGAGGAGGCGCGGGTGAAGTACGGTGACGGGTTTTCAGAGTGGGATGCTGACGCTACTCGAAGAAACCATGGAACCATTCTTCAAGTTTTGGTAGATGGAAGAGAAGGGAATACAATAGCAATACCAACGTTGGTGTATTTATCAAGAGAAAAGAGACCTCAACATCATCATAACTTCAAGGCTGGAGCAATGAACGCATTGCTGAGGGTTTCTTCGAAAATTACTTGTGGGAAAATCATACTAAACTTGGACTGTGATATGTACGCAAACAACTCAAAGTCAACACGCGACGCGCTCTGCATCCTCCTCGATGAGAAAGAGGGAAAAGAGATTGCTTTCGTGCAGTTTCCGCAGTGTTTTGACAATGTTACAAGAAATGATTTGTATGGAAGCATGATGCGAGTAGGAATTGATCTGGAATTTCTTGGATTGGATGGAAATGGTGGTCCGTTATACATTGGAACTGGATGCTTTCACAGAAGAGATGTGATCTGTGGAAGAAAGTATGGAGAGGAAGAAGAAGAAGAAGAATCTGAGAGAATTCACGAAAATTTAGAGCCTGAGATGATTAAGGCTCTCGCGAGCTGCACTTATGAGGAAAACACTCAATGGGGAAAGGAGATGGGTGTGAAATATGGTTGCCCGGTAGAGGATGTAATAACTGGTTTGACGATTCAGTGTCGCGGATGGAAATCAGCCTACCTGAACCCGGAAAAGCAAGCATTTCTCGGGGTAGCGCCGACCAATTTGCATCAAATGCTAGTGCAGCAGAGGAGATGGTCAGAGGGAGACTTTCAGATTATGCTTTCGAAGTATAGTCCGGTTTGGTATGGAAAAGGAAAGATCAGTTTAGGACTGATACTTGGTTACTGTTGCTATTGTCTTTGGGCTCCATCTTCACTACCTGTGCTCATTTACTCTGTTTTGACTTCTCTCTGTCTCTTCAAAGGCATTCCTCTGTTTCCAAAGGTCTCGAGCTCGTGGTTTATTCCGTTTGGATACGTCACTGTTGCAGCTACCGCATATAGCCTAGCCGAGTTCTTGTGGTGCGGAGGGACGTTCCGTGGATGGTGGAACGAGCAAAGGATGTGGCTTTATAGAAGAACAAGCTCGTTTCTTTTCGGATTTATGGACACGATTAAGAAGCTACTTGGAGTTTCTGAGTCTGCGTTTGTGATCACAGCAAAAGTAGCAGAAGAAGAAGCAGCAGAGAGATACAAGGAAGAGGTAATGGAGTTTGGAGTGGAGTCTCCCATGTTTCTCGTCCTCGGAACACTCGGTATGCTCAATCTCTTCTGCTTCGCCGCAGCGGTTGCGAGACTTGTTTCCGGAGACGGTGGAGATTTGAAAACAATGGGGATGCAATTTGTGATAACAGGAGTACTAGTTGTCATAAACTGGCCTCTGTATAAAGGTATGTTGTTGAGGCAAGACAAAGGAAAGATGCGAATGAGCGTTACAGTTAAATCAGTTGTTTTAGCTTTATCTGCCTGTACCTGTTTAGCGTTTTTGTAA |
| ATCSLE1_ AT1G55850 | | 91 | MVNKDDRIRPVHEADGEPLFETRRRTCRVIAYRFFSASVFVCICLIWFYRIGEIGDNRTVLDRLIWFVMFIVEIWFGLYWVVTQSSRWNPVWRFPFSDRLSRRYGSDLPRLDVFVCTADPVIEPPLLVVNTVLSVTALDYPPEKLAVYLSDDGGSELTFYALTEAAEFAKIWVPFCKKFN |

TABLE 12-continued

Amino Acid and Nucleotide Sequences of
Arabidopsis CSLG and CESA enzymes

| NAME | ENZYME ACTIVITY | SEQ ID NO: | AA SEQ |
|---|---|---|---|
| | | | VEPTSPAAYLSSKANCLDSAAEEVAKLYREMAARIE<br>TAARLGRIPEEARVKYGDGFSQWDADATRRNHGTIL<br>QVLVDGREGNTIAIPTLVYLSREKRPQFIHHNFKAG<br>AMNALLRVSSKITCGKIILNLDCDMYANNSKSTRDA<br>LCILLDEKEGKEIAFVQFPQCFDNVTRNDLYGSMMR<br>VGIDVEFLGLDGNGGPLYIGTGCFHRRDVICGRKYG<br>EEEEEEESERIHENLEPEMIKALASCTYEENTQWGK<br>EMGVKYGCPVEDVITGLHQGRGWKSAYLNPEKQAFL<br>GVAPTNLHQMLVQQRRWSEGDFQIMLSKYSPVWYGK<br>GKISLGLILGYCCYCLWAPSSLPVLIYSVLTSLCLF<br>KGIPLFPKVSSSWFIPFGYVTVAATAYSLAEFLWCG<br>GTFRGWWNEQRMWLYRRTSSFLFGFMDTTKKLLGVS<br>ESAFVITAKVAEEEAAERYKEEVMEFGVESPMFLVL<br>GTLGMLNLFCFAAAVARLVSGDGGDLKTMGMQFVIT<br>GVLVVINWPLYKGMLLRQDKGKMPMSVTVKSVVLAL<br>SACTCLAFL |
| ATCSLG1_<br>AT4G24010 | | 92 | ATGGAGACTCATAGAAAGAACTCGGTCGTCGGCAAC<br>ATCCTCCACACGTGTCATCCTTGCCGGCGCACCATT<br>CCATATAGAATCTACGCCATATTTCACACGTGTGGC<br>ATCATAGCTCTCATGTATCACCATGTACACTCACTT<br>GTCACAGCAAACAACACTCTTATAACATGTCTTCTT<br>CTCCTCTCCGATATTGTTCTCGCCTTCATGTGGGCA<br>ACCACAACTTCCCTCCGCTTAAACCCGGTTCATCGG<br>ACCGAGTGCCCGGAGAAATATGCAGCTAAACCGGAG<br>GACTTTCCAAAGCTGGACGTGTTTATATGCACGGCT<br>GATCCGTACAAGGAGCCTCCAATGATGGTTGTTAAC<br>ACCGCTTTATCGGTGATGGCTTACGAGTATCCGTCA<br>GATAAGATCTCGGTGTATGTATCGGACGATGGAGGA<br>TCGTCGTTGACTTTCTTTGCTCTTATTGAAGCTGGT<br>AAGTTCTCTAAGCAGTGGTTGCCCTTTTGCAAGAAG<br>AATAATGTTCAAGATCGGTCTCCTGAAGTTTATTTC<br>TCTTCAGAGTCACATTCTCGAAGTGATGAAGCTGAA<br>AACCTTAAGATGATGTACGAAGACATGAAGAGTAGA<br>GTAGAACATGTGGTGGAGAGTGGAAAAGTTGAAACT<br>GCGTTTATCACATGCGACCAATTTCGTGGGGTATTC<br>GATTTGTGGACCGACAAATTCAGTCGTCATGACGAT<br>CCCACAATTATTCAGGTGTTGCAAAATAGCGAGACA<br>GATATGGACAATACCAGAAAATATATAATGCCAAAC<br>CTAATCTATGTTTCAAGAGAGAAGAGTAAAGTTTCA<br>CCACATCATTTCAAAGCTGGTGCTCTTAATACTTTG<br>CTTACGAGTATCAGGGGTGATGACAAATTCACCGAT<br>CATTCTAACACTAGACTGTGATATGTATTCGAACGA<br>CCCGGCAACACTGGTTCGTGCTTTGTGCTATTTAAC<br>AGATGCTGAAATCAAATCCGGTTTAGGATATGTGCA<br>GTTTCCTCAGAAATTTCTAGGAATAAGCAAAAATGA<br>TATATATGCTTGTGAAAACAAACGCCTCTTCATTAT<br>TAATATGGTTGGGTTTGATGGTCTAATGGGTCCAAC<br>TCATGTGGGAACTGGTTGTTTCTTTAATCGACGAGC<br>TTTCTATGGACCTCCATATATGTTGATTTTACCGGA<br>GATAAATGAACTAAAGCCTTATCGGATTGCGGATAA<br>GTCTATCAAAGCCCAAGATGTTTTGTCATTAGCACA<br>CAATGTAGCAGGATGTATCTATGAGTACAATACTCA<br>ATTGGGGATCCAAGATTGGATTCAGATATGGGTCAT<br>TAGTAGAAGACTACTACACAGGGTTTATGCTCCATT<br>GTGAAGGATGGAGATCAGTATTTTGCAACCCAAAAA<br>AAGCTGCATTTTATGGAGATTCCCCAAAGTGCCTAG<br>TTGATCTTGTGGGTCAACAAATCCGTTGGGCAGTTG<br>GGCTTTTCGAAATGTCCTTTTCAAAGTATAGCCCAA<br>TTACCTATGGAATCAAGTCACTGGACCTTTTAATGG<br>GTTTTAGGTTATTGCAACTCTCCGTTTAAGCCATTT<br>TGGTCAATTCCTCTGACCGTCTATGGACTTTTACCA<br>CAGCTTGCACTCATTTCTGGAGTTAGTGTCTTCCCC<br>AAGGCATCTGATCCGTGGTTTTGGCTTTACATCATT<br>TTATTCTTTTGGGGCTTATGCCCAAGATCTATCAGA<br>CTTTTTATTGGAAGGAGGAACTTATGGGAAATGGTG<br>GAACGATCAAAGAATGTTGATGATAAAAGGACTCTC<br>TTCATTCTTCTTTGGTTTTATAGAGTTCATTCTCAA<br>AACCCTAAACCTCTCCACACCTAAGTTCAACGTCAC<br>CAGTAAAGCCAATGATGATGACGAACGAGGAAGCG<br>GTACGAGCAAGAAATCTTTGATTTCGGAACCTCTTC<br>GTCCATGTTCTTGCCCTTGACCACGGTTGCCATAGT<br>GAATCTGCTTGCTTTTGTCTGGGGGCTTTATCTGTA |

TABLE 12-continued

| Amino Acid and Nucleotide Sequences of *Arabidopsis* CSLG and CESA enzymes | | | |
|---|---|---|---|
| NAME | ENZYME ACTIVITY | SEQ ID NO: | AA SEQ |
| | | | TTCTCTTCTGCGGAGGAGAACTCTACCTTGAGCTGA<br>TGCTGGTGAGCTTCGCCTGTGGTGAATTGCTTACCG<br>ATCTACGGGGCTATGGTGTTGAGGAAAGATGATGGA<br>AAATTATCAAAAAGAACTTGTTTCTTAGCTGGGAAC<br>CTCCACGTTGGTTCTTATTGTGTCAAGTTACTTCGT<br>CCTCAAGTAACTTCACCCCTTAGGTTAATTCACAAC<br>AATAATACGTCTGGCTGGTTCAAGCGGAAGAAACAC<br>AATATGAATGAATCTGTGTAA |

Three channels were also detected that could possibly form the passage of the triterpenoid aglycone into the enzyme active site and a channel that could be the exit path for the glucuronidated product (FIGS. 49A-49C). In cellulose synthase A (CESA) proteins, transmembrane domains (TMDs) form a pore that allows passing of polysaccharide chains through the membrane to the extracellular space. The out-of-membrane domain in CESAs holds the enzyme active site, as well as four motifs that are conserved among all such proteins and predicted to be involved in substrate and/or acceptor binding, i.e., DD, DCD, ED and QVLRW (L. Sethaphong et al., Tertiary model of a plant cellulose synthase, Proc. Natl. Acad. Sci. U.S.A. 18, 7512-7 (2013)) (FIG. 48—red boxes). Alignment of amino acid sequences of CESA and SOAP5 from spinach showed that ED (in SOAP5: ES) and QVLRW (in SOAP5: QLIKW) motifs are not conserved in SOAP5 (FIG. 48).

To check if the presence of CESA type amino acid motifs can affect SOAP5 activity, three mutated version of SOAP5 were created, as follows: (i) serine 442 substituted by aspartic acid (S442D), (ii) lysine 483 swapped with arginine (K483R) and (iii) both substitutions (S442D/K483R). Expression of mutated proteins together with SOAP1-4 in *N. benthamiana* demonstrated that modification of these motifs in SOAP5 alters enzyme performance. Wild type SOAP5 converts the entire medicagenic acid pool to MA-3-GlcA (MA-3-GlcA:MA: ratio 0:1), SOAP5-S442D or SOAP5-K483R could still effectively glucuronidate MA (MA-3-GlcA:MA ratio 0.03:1 and 0.09:1, respectively), while SOAP5-S442D/K483R was only able to partially process MA (MA-3-GlcA:MA ratio 0.90:1) (FIGS. 50A and 50B). Our observations indicate that change of the neutral amino acid to a negatively charged one causes steric hindrance in the enzyme active site in addition to affecting binding of the anionic substrate (UDP-GlcA), thus simultaneously reducing the enzymes efficiency. Changes of the amino acids (S442D and K483R) in the active site during the enzymes evolution could have been crucial for accepting UDP-GlcA instead of UDP-Glc and resulted in neofunctionalization of CESA proteins.

Summary: It appears that differences in key amino acid residues of CESA result in neofunctionalization of the enzyme to a CSLG enzyme activity. Another feature of CSLG that is crucial for its new triterpenoid related function was localization to endoplasmic reticulum (ER).

Example 25: Subcellular Localization of the Triterpenoid Saponin Biosynthetic Pathway Objective: To investigate the subcellular localization of the triterpenoid saponin biosynthetic pathway.

Methods: See Materials and Methods above.

Results: The subcellular localization of the triterpenoid saponin biosynthetic pathway was studies. The ER membrane system is a pertinent environment for the production of specialized metabolites such as steroids and triterpenoids. Many enzymes involved in triterpenoid biosynthesis, including squalene synthase, squalene epoxidase, oxidosqualene cyclases and most of the known CYP450s are membrane bound and operate within the ER compartment (C. A. Hasemann et al., Structure and function of cytochromes P450: a comparative analysis of three crystal structures. Structure. 1, 41-62(1995); K. B. Linscott, T. D. Niehaus, X. Zhuang, S. A. Bell, J. Chappell, Mapping a kingdom-specific functional domain of squalene synthase. BBA—Molecular and Cell Biology of Lipids. 1861, 1049-1057 (2016); M. Christen et al., Structural insights on cholesterol endosynthesis: Binding of squalene and 2,3-oxidosqualene to supernatant protein factor. Journal of Structural Biology. 190, 261-270 (2015); R. Thoma et al., Insight into steroid scaffold formation from the structure of human oxidosqualene cyclase, Nature. 7013, 118-22 (2004)).

Transient expression of SOAP5 fused to a fluorescent reporter (SOAP5:mRFP) together with a cellular compartment marker (ER marker in fusion with GFP) demonstrated its localization to the ER network (FIGS. 51A-51F). Previously it was shown that the microsomal fraction from germinating soybean seeds contains a protein able to glucuronidate soyasapogenol B, supporting transmembrane localization of SOAP5 (Y. Kurosawa, H. Takahara, M Shiraiwa, UDP-glucuronic acid:soyasapogenol glucuronosyltransferase involved in saponin biosynthesis in germinating soybean seeds. Planta. 215, 620-9 (2002)). Next, fluorescently tagged versions of SOAP1, 2, 3, 4 and 5 were expressed in various combinations and ER co-localization of all proteins examined was observed (FIGS. 35A-35F, FIG. 52A-52F). Detection of high quantities of MA-3-GlcA in leaves simultaneously expressing all fusion proteins demonstrated that the fluorescent signals observed originated from functional, and hence properly folded and subcellularly localized proteins (FIG. 53). Also observed using fluorescence resonance energy transfer (FRET) was that SOAP1-5 proteins are located in proximity to each other and therefore possibly interact (FIGS. 54A-54B). Accurate colocalization of studied proteins could explain the high efficiency of performed reactions by decreasing the diffusion of the intermediates.

Summary: These studies showed that at least enzymes SOAP1-5 are localized in the ER in close proximity to each other.

GENERAL CONCLUSIONS FROM THE EXAMPLES

These studies on steroidal alkaloid, steroidal saponin, and triterpenoid saponin biosynthesis in tomato, potato, eggplant, and spinach resulted in discovery and characterization of genes that complete the biosynthetic pathway of complex triterpenoid saponins and elucidate the biosynthetic pathways of complex steroidal alkaloids and steroidal saponins. Discovery of the unprecedented function of cellulose synthase like G proteins as glucuronosyltransferases of triterpenoid aglycones in seven plant species belonging to two distinct orders, proves that glycosylation of specialized metabolites is not exclusively performed by GTs belonging to 1 family Carbohydrate-Active enZYmes Database (CAZY). This finding will most likely trigger the discovery of additional functions of CSL enzymes related to other specialized metabolites (SMs). Additionally, the discovery of unique SOAP6 fucosyltransferase activity was demonstrated, as well as characterization of first BAHD acyltransferase (SOAP10) capable of acetylating sugar moieties of triterpenoid saponins. Similarly, GAME15 may in certain embodiments glycosylate steroidal alkaloids and steroidal saponins. In some embodiments, GAME15 glycoylation comprises transfer of a glucuronic acid (glucuronosyltransferase activity). Moreover, decreased expression of steroidal alkaloids and steroidal saponins provides a new approach to the increase in content of plant cholesterols, phytocholesterols, cholestenols, phytocholestenols, and phytosterols, which are useful as nutritional, cosmetic, and pharmaceutical agents, The unexpected finding of CSLG proteins activity as triterpenoid glucuronosyltransferases shows that glycosylation of SMs is not exclusively executed by family 1 type UGTs. Hence, this report is likely to trigger the discovery of CSL enzymes functioning in modification of other classes of terpenoids and SMs, as well as in other classes of steroidal alkaloids and/or steroidal saponins. It moreover provides a fundamental example of how enzyme activity in one of the few principal plant processes, i.e., the cellulose synthesis machinery constructing cell walls, is ‘hijacked’ in order to produce a set of unrelated, defense specialized metabolites. Co-localization of SOAP5 at the spinach ER membrane with most other pathway proteins rather than the cytosol (in which UGTs localize) was part of evolving its new function. It suggests the importance of physical proximity between these enzymes for efficient triterpenoids production. This physical proximity was also reflected at the gene level as well, with respect to the GAME genes as a gene cluster in tomato. Apart from glucuronic acid, a yet undisclosed fucosyltransferase was identified acting on metabolites (i.e. SOAP6), as all plant fucosyltransferases to date were associated with fucosylation of cell wall polysaccharides and glycoproteins. While BAHD type acyltransferases are frequently associated with modification of SMs they were on no occasion reported to acylate triterpenoids as is demonstrated here for SOAP10 acetylating the C-28 fucose moiety of spinach triterpenoid saponins. With similarity to glucuronidation, the acylated fucose domain in triterpenoid saponins is important for their efficacy as therapeutic agents, e.g., adjuvanticity of the renowned QS-21, a potent saponin vaccine adjuvant from *Quillaja saponaria.*

This work delivers unparalleled strategy for heterologous engineering plants or yeast or other eukaryotic cell systems for sustainable production of high-value metabolites (e.g. glycyrrhizin, soyasaponins, QS-21 adjuvant) for food and pharmaceutical industries by filling a gap in biosynthetic pathways of many glucuronide-type triterpenoid saponins. In addition, it supports engineering endogenous genes within a plant triterpenoid saponin biosynthetic pathway to either increase beneficial triterpenoid saponins, for example but not limited to glycyrrhizin in Chinese licorice, or decrease bitter or unwanted triterpenoid saponins, for example but not limited to their reduction in quinoa. Likewise, toxins and bitter tasting compounds are decreased by the reduction of unwanted steroidal alkaloids and/or steroidal saponins.

While certain features of genetically modified cells and uses thereof for producing steroidal alkaloids, steroidal saponins, and triterpenoid saponins have been illustrated and described herein, many modifications, substitutions, changes, and equivalents will now occur to those of ordinary skill in the art. The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. It is, therefore, to be understood that the appended claims are intended to cover all such modifications and changes as fall within the true spirit of the disclosure herein.

LENGTHY TABLES

The patent contains a lengthy table section. A copy of the table is available in electronic form from the USPTO web site (https://seqdata.uspto.gov/?pageRequest=docDetail&DocID=US12041907B2). An electronic copy of the table will also be available from the USPTO upon request and payment of the fee set forth in 37 CFR 1.19(b)(3).

What is claimed is:

1. A method of reducing the content of at least one steroidal alkaloid, a derivative thereof, a metabolite thereof, or a biosynthetic intermediate thereof; of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, in at least one cell of a plant or a plant part, the method comprising genetically modifying said at least one plant cell, said genetic modification comprising:

(a) transforming said at least one plant cell with at least one silencing molecule targeted to a nucleic acid gene sequence encoding a Cellulose Synthase Like G (CSLG) enzyme, wherein the nucleic acid sequence encoding said CSLG gene is set forth in any one of SEQ ID NOS: 30, 32, 34, 36, 38, 40, 65, 80, 93, 95, 97, 99, 101, 103, or 105; or a homolog thereof having at least 90% identity to and at least 90% coverage of, the nucleic acid sequence set forth in any one of SEQ ID NOS: 30, 32, 34, 36, 38, 40, 65, 80, 93, 95, 97, 99, 101, 103, or 105; or (b) mutagenizing at least one nucleic acid sequence encoding a Cellulose Synthase Like G (CSLG) enzyme, wherein the mutagenesis comprises introducing (1) one or more point mutations into the nucleic acid sequence, (2) deletions within the nucleic acid sequence, or (3) insertions within the nucleic acid, or (4) any combination thereof, wherein said introducing comprising mutagenizing coding or non-coding sequence;

wherein expression of the gene encoding the CSLG enzyme is reduced in the genetically modified plant cell compared to its expression in a corresponding unmodified plant cell, wherein the plant comprising said genetically modified cell comprises reduced content of at least one steroidal alkaloid, a derivative thereof, a metabolite thereof, or a biosynthetic intermediate thereof; of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, compared to the corresponding unmodified plant.

2. The method of claim 1, wherein:

(a) when the nucleic acid of the CSLG is set forth in SEQ ID NO: 30, the silencing molecule is set forth in SEQ ID NO: 42 or a complementary sequence thereof, or a homolog thereof having at least 90% identity to the nucleic acid sequence set forth in SEQ ID NO: 42 or a complementary sequence thereof;

(b) when the nucleic acid of the CSLG is set forth in SEQ ID NO: 34, the silencing molecule is set forth in SEQ ID NO: 43 or a complementary sequence thereof, or a homolog thereof having at least 90% identity to, the nucleic acid sequence set forth in SEQ ID NO: 43 or a complementary sequence thereof;

(c) when the nucleic acid of the CSLG is set forth in SEQ ID NO: 38, the silencing molecule is set forth in SEQ ID NO: 44 or a complementary sequence thereof, or a homolog thereof having at least 90% identity to, the nucleic acid sequence set forth in SEQ ID NO: 44 or a complementary sequence thereof;

(d) when the nucleic acid of the CSLG is set forth in SEQ ID NO: 65 or SEQ ID NO: 93, the silencing molecule is set forth in SEQ ID NO: 106 or a complementary sequence thereof, or a homolog thereof having at least 90% identity to the nucleic acid sequence set forth in SEQ ID NO: 65 or the nucleic acid sequence set forth in SEQ ID NO: 93; or (e) when the nucleic acid of the CSLG is set forth in SEQ ID NO: 95, the silencing molecule is set forth in SEQ ID NO: 107 or a complementary sequence thereof, or a homolog thereof having at least 90% identity to the nucleic acid sequence set forth in SEQ ID NO: 95.

3. The method of claim 1, wherein (a) said steroidal alkaloid, said steroidal saponin, or said triterpenoid saponin comprises a toxin or a bitter tasting compound or having hormone mimicking properties, or a combination thereof; or (b) said steroidal glycoalkaloid comprises an esculeoside, a dehydroesculeoside, alpha-tomatine, tomatine, alpha-chaconine, alpha-solanine, alpha-solasonine, alpha-solmargine, or any combination thereof; or (c) said steroidal saponin comprises uttroside B, a tomatoside, or any combination thereof; or (d) said triterpenoid saponin comprises medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), betavulgaroside IV (Compound 33), hederagenin-3GlcA, gypsogenin-3GlcA, gypsogenic acid-3GlcA, or a QS-21 adjuvant, or any combination thereof; or (e) said intermediate comprises Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof, or (f) a combination thereof.

4. The method according to claim 1, further comprising altering the content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof, or a phytocholestenol, or a derivative thereof, a metabolite thereof, or a biosynthetic intermediate thereof.

5. A genetically modified cell having increased expression of at least one heterologous gene compared to a corresponding unmodified cell, said at least one heterologous gene encoding a cellulose synthase like G (CSLG) enzyme, wherein said genetically modified cell comprises an increased content of at least one steroidal alkaloid, a derivative thereof, a metabolite thereof, or a biosynthetic intermediate thereof; of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, compared to a corresponding unmodified cell, wherein the amino acid sequence of said encoded CSLG enzyme is set forth in any one of SEQ ID NOS: 31, 33, 35, 37, 39, 41, 66, 81, 94, 96, 98, 100, 102, or 104; or a homolog thereof having at least 90% identity to and at least 90% coverage of, the amino acid sequence set forth in any one of SEQ ID NOS: 31, 33, 35, 37, 39, 41, 66, 81, 94, 96, 98, 100, 102, or 104.

6. The genetically modified cell according to claim 5, wherein said genetically modified cell comprising an increased content of at least one steroidal alkaloid, a derivative thereof, a metabolite thereof, or a biosynthetic intermediate thereof, of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, further expresses at least one additional heterologous gene encoding an enzyme, said enzyme selected from the group consisting of a saponin beta-amyrin synthase, a cytochrome P450, a glycosyltransferase, an acyltransferase, and an UDP-glucose 6-dehydrogenase 1, or any combination thereof.

7. The genetically modified cell according to claim 5, wherein the nucleic acid sequence encoding said at least one heterologous CSLG gene is set forth in any one of SEQ ID NOS: 30, 32, 34, 36, 38, 40, 65, 80, 93, 95, 97, 99, 101, 103, or 105; or a homolog thereof having at least 90% identity to and at least 90% coverage of, the nucleic acid sequence set forth in any one of SEQ ID NOS: 30, 32, 34, 36, 38, 40, 65, 80, 93, 95, 97, 99, 101, 103, or 105.

8. The genetically modified cell according to claim 5, wherein the nucleic acid sequence encoding said at least one additional heterologous gene encodes (a) a β-amyrin synthase, said nucleic acid sequence set forth in SEQ ID NO: 45;

or a homolog thereof having at least 90% identity to the nucleic acid sequence set forth in SEQ ID NO: 45; or (b) a cytochrome P450, said nucleic acid sequence set forth in any one of SEQ ID NO: 46, 51, or 53; or a homolog thereof having at least 90% identity to and the nucleic acid sequence set forth in any one of SEQ ID NO: 46, 51, or 53; or (c) a glycosyl transferase, said nucleic acid sequence set forth in any one of SEQ ID NO: 55, 57, 59, or 61; or a homolog thereof having at least 90% identity to the nucleic acid sequence set forth in any one of SEQ ID NO: 55, 57, 59, or 61; or (d) an acetyltransferase, said nucleic acid sequence set forth in SEQ ID NO: 63; or a homolog thereof having at least 90% identity to the nucleic acid sequence set forth in SEQ ID NO: 63; or (e) a UDP-glucose 6-dehydrogenase 1, said nucleic acid sequence set forth in SEQ ID NO: 74; or a homolog thereof having at least 90% identity to the nucleic acid sequence set forth in SEQ ID NO: 74; or (f) any combination thereof of (a), (b), (c), (d), and (e).

9. The genetically modified cell according to claim 6, wherein the amino acid sequence of said encoded at least one additional heterologous gene encodes (a) a β-amyrin synthase, said amino acid sequence set forth in SEQ ID NO: 48; or a homolog thereof having at least 90% identity to the amino acid sequence set forth in SEQ ID NO: 48; or (b) a cytochrome P450, said amino acid sequence set forth in any one of SEQ ID NO: 49, 52, or 54; or a homolog thereof having at least 90% identity to the amino acid sequence set forth in any one of SEQ ID NO: 49, 52, or 54; or (c) a glycosyl transferase, said amino acid sequence set forth in any one of SEQ ID NO: 56, 58, 60, or 62; or a homolog thereof having at least 90% identity to the amino acid sequence set forth in any one of SEQ ID NO: 56, 58, 60, or 62; or (d) an acetyltransferase, said amino acid sequence set forth in SEQ ID NO: 64; or a homolog thereof having at least 90%identity to the amino acid sequence set forth in SEQ ID NO: 64; or (e) a UDP-glucose 6-dehydrogenase 1, said amino acid sequence set forth in SEQ ID NO: 75; or a homolog thereof having at least 90% identity to the amino acid sequence set forth in SEQ ID NO: 75; or (f) any combination thereof of (a), (b), (c), (d), and (e).

10. The genetically modified cell according claim 5, wherein said triterpenoid saponin or said derivative, metabolite, or biosynthetic intermediate thereof, comprises a sweetener, foaming agent, emulsifier, preservative, anti-carcinogen, hypocholesterolemic agent, anti-inflammatory agent, anti-oxidant, biological adjuvant, anti-microbial agent, insecticidal agent, antifeedant, anti-fungal agent, or any combination thereof.

11. The genetically modified cell according to claim 5, (a) wherein said steroidal glycoalkaloid comprises an esculeoside, a dehydroesculeoside, alpha-tomatine, tomatine, dehydrotomatine, alpha-chaconine, alpha-solanine, alpha-solasonine, alpha-solmargine, or any combination thereof; or (b) wherein said steroidal saponin comprises uttroside B, a tomatoside, or any combination thereof; or (c) wherein said triterpenoid saponin comprises medicagenic acid 3-O-glucuronide (MA-3-GlcA) (Compound 6), Compound 7, Compound 8, Compound 9, Compound 10, Compound 11, glycyrrhizin (Compound 14), glycyrrhetinic acid 3-O-monoglucuronide (Compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), beta-vulgaroside IV (Compound 33), hederagenin-3GlcA, gypsogenin-3GlcA, gypsogenic acid-3GlcA, or a QS-21 adjuvant, or any combination thereof; or (d) wherein the biosynthetic intermediate of said triterpenoid saponin comprises Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof, or (e) a combination thereof.

12. The genetically modified cell according to claim 5, having an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof, or a phytocholestenol, or a derivative thereof, a metabolite thereof, or a biosynthetic intermediate thereof.

13. The genetically modified cell according to claim 5, wherein said cell comprises a plant cell, a yeast cell, or an alga cell.

14. The genetically modified cell according to claim 13, wherein said plant cell comprises a cell from a plant in the *Poales* order, the *Caryophyllales* order, the *Solanales* order, the *Fabales* order, the *Malvales* order, the *Apiales* order, the *Brassicales* order, the *Asparagales* order, the *Dioscoreales* order, or the *Liliales* order.

15. The genetically modified cell according to claim 14, wherein:

(a) when said plant cell comprises a cell from a plant in the Poales order, said plant is selected from the group of genera consisting of the *Oryza* genus, the *Hordeum* genus, the *Avena* genus, and the *Triticum* genus;

(b) when said plant cell comprises a cell from a plant in the Caryophyllales order, said plant is selected from the group of genera consisting of the *Spinacia* genus, the *Chenopodium* genus, the Beta genus, the Rheum genus, the *Vaccaria* genus, the *Saponaria* genus, and the *Gypsophila* genus;

(c) when said plant cell comprises a cell from a plant in the Solanales order, said plant is selected from the group of genera consisting of the *Solanum* genus, the *Capsicum* genus, the *Nicotiana* genus, the *Hyoscyamus* genus, the *Datura* genus, and the *Atropa* genus;

(d) when said plant cell comprises a cell from a plant in the Fabales order, said plant is selected from the group of genera consisting of the *Glycyrrhiza* genus, the *Medicago* genus, the Glycine genus, the Lotus genus, the *Cicer* genus, the *Phaseolus* genus, the *Pisum* genus, the *Arachis* genus, the *Lupinus* genus, and the *Acacia* genus;

(e) when said plant cell comprises a cell from a plant in the Malvales order, said plant is selected from the *Theobroma* genus;

(f) when said plant cell comprises a cell from a plant in the *Apiales* order, said plant is selected from the group of genera consisting of the *Daucus* genus, the *Apium* genus, the Petroselinum genus, the *Panax* genus, the *Bupleurum* genus, the *Hedera* genus, and the *Centella* genus; or (g) when said plant cell comprises a cell from a plant in the *Brassicales* order, said plant is selected from the group of genera consisting of the *Arabidopsis* genus, the *Brassica* genus, the *Capparis* genus, and the *Carica* genus.

16. The genetically modified cell according to claim 15, wherein:

(a) when said plant cell comprises a cell from a plant in the *Caryophyllales* order, said plant is selected from the group consisting of spinach, beetroot, and *quinoa;*

(b) when said plant cell comprises a cell from a plant in the *Solanales* order, said plant is selected from the group consisting of tomato, wild tomato, potato, wild potato, eggplant, pepper, bell pepper, cayenne pepper, chili pepper, pimiento, tabasco pepper, ground cherry, tobacco, and bittersweet; or (c) when said plant cell comprises a cell from a plant in the *Fabales* order, said plant is selected from the group consisting of alfalfa, soy, *Lotus japonicus*, and licorice.

17. The genetically modified cell according to claim 16, wherein:

(a) the plant cell is from a tomato plant having:

(i) an increased content of alpha-tomatine or a derivative thereof, a metabolite thereof, or a biosynthetic intermediate thereof, or tomatidine or a derivative thereof, a metabolite thereof, or a biosynthetic intermediate thereof; or dehydrotomatine or a derivative thereof, a metabolite thereof, or a biosynthetic intermediate thereof; or a steroidal saponin or a derivative thereof, a metabolite thereof, or a biosynthetic intermediate thereof; or (ii) an altered content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof, or a phytocholestenol or a derivative thereof, a metabolite thereof, or a biosynthetic intermediate thereof, or (b) the plant cell is from a potato plant having:

(i) an increased content of alpha-chaconine or a derivative thereof, a metabolite thereof, or a biosynthetic intermediate thereof; or alpha-solanine or a derivative thereof, a metabolite thereof, or a biosynthetic intermediate thereof; or a steroidal saponin or a derivative thereof, a metabolite thereof, or a biosynthetic intermediate thereof, or (ii) an altered content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof, or a phytocholestenol or a derivative thereof, a metabolite thereof, or a biosynthetic intermediate thereof, or (c) the plant cell is from an eggplant plant having:

(i) an increased content of alpha-solasonine or a derivative thereof, a metabolite thereof, or a biosynthetic intermediate thereof; or alpha-solamargine or a derivative thereof, a metabolite thereof, or a biosynthetic intermediate thereof; or a steroidal saponin or a derivative thereof, a metabolite thereof, or a biosynthetic intermediate thereof;

(ii) an altered content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof; or a phytocholestenol or a derivative thereof, a metabolite thereof, or a biosynthetic intermediate thereof.

18. The genetically modified cell according to claim 13, wherein said plant cell comprises a leaf cell, a petiole cell, a plant stem or stalk cell, a root cell, a bud cell, a tuber cell, a bean cell, a grain or kernel cell, a fruit cell, a nut cell, a legume cell, a seed or seed cell, a callus cell, a bract cell, or a flower cell.

19. The genetically modified cell according claim 13, wherein said plant cell is comprised in a plant or a portion thereof, said portion thereof comprising a plant leaf, a plant petiole, a plant stem or stalk, a plant root, a plant bud, a plant tuber, a plant bean, a plant grain or kernel, a plant fruit, a plant nut, a plant legume, a plant seed, a plant bract, or a plant flower.

20. The genetically modified cell according to claim 13, wherein said yeast is selected from a *Saccharomyces* genus, a *Schizosaccharomyces* genus, a *Pichia* genus, a *Yarrowia* genus, a *Kluyveromyces* genus, or a *Candida* genus.

21. The genetically modified cell according to claim 13, wherein said alga is selected from a microalga, a multicellular alga, a cyanobacterium, a diatom, chlorophytes (green algae), rhodophytes (red algae), or phaeo-phytes (brown algae), a *Dunaliella*, a *Chlamydamonas*, or a *hematococus.*

22. A genetically modified plant comprising at least one cell having altered expression of at least a cellulose synthase like G (CSLG) gene compared to the expression of CSLG in a corresponding unmodified plant, and wherein the genetically modified plant has an altered content of at least one steroidal alkaloid, a derivative thereof a metabolite thereof; of at least one steroidal saponin, a derivative thereof, a metabolite thereof, or a biosynthetic intermediate thereof, or of at least one triterpenoid saponin, a derivative thereof, a metabolite thereof, or a biosynthetic intermediate thereof compared to the corresponding unmodified plant, wherein the amino acid sequence of said CSLG enzyme is set forth in any one of SEQ ID NOS: 31, 33, 35, 37, 39, 41, 66, 81, 94, 96, 98, 100, 102, or 104; or a homolog thereof having at least 90% identity to and at least 90% coverage of, the amino acid sequence set forth in any one of SEQ ID NOS: 31, 33, 35, 37, 39, 41, 66, 81, 94, 96, 98, 100, 102, or 104.

23. The genetically modified plant of claim 22, wherein said CSLG gene comprises the endogenous CSLG gene.

24. The genetically modified plant of claim 23, wherein said endogenous CSLG gene comprises a mutation, said mutation comprising at least one or more point mutations, or an insertion, or a deletion, or any combination thereof, and (a) wherein said expressed CSLG enzyme has increased stability or increased activity or both and the altered content comprises an increased amount of the at least one steroidal alkaloid, a derivative thereof, a metabolite thereof, or a biosynthetic intermediate thereof; of the at least one steroidal saponin, a derivative thereof, a metabolite thereof, or a biosynthetic intermediate thereof; or of the at least one triterpenoid saponin, a derivative thereof, a metabolite thereof, or a biosynthetic intermediate thereof compared to the corresponding unmodified plant; or (b) wherein said expressed CSLG enzyme has decreased stability or decreased activity or both and the altered content comprises a decreased amount of the at least one steroidal alkaloid, a derivative thereof, a metabolite thereof, or a biosynthetic intermediate thereof; of the at least one steroidal saponin, a derivative thereof, a metabolite thereof, or a biosynthetic intermediate thereof, or of the at least one triterpenoid saponin, a derivative thereof, a metabolite thereof, or a biosynthetic intermediate thereof compared to the corresponding unmodified plant.

25. The genetically modified plant of claim 23, wherein:

(a) said endogenous CSLG gene is selectively silenced, repressed, or has reduced expression and said altered content comprises a reduced amount of the at least one steroidal alkaloid, a derivative thereof, a metabolite thereof, or a biosynthetic intermediate thereof; of the at least one steroidal saponin, a derivative thereof, a metabolite thereof, or a biosynthetic intermediate thereof, or of the at least one triterpenoid saponin, a derivative thereof, a metabolite thereof, or a biosynthetic intermediate thereof compared to the corresponding unmodified plant; or (b) said endogenous CSLG gene is overexpressed and said altered content comprises an increased amount of the at least one steroidal alkaloid, a derivative thereof, a metabolite thereof, or a biosynthetic intermediate thereof; of the at least one steroidal saponin, a derivative thereof, a metabolite thereof, or a biosynthetic intermediate thereof; or of the at least one triterpenoid saponin, a derivative thereof, a metabolite thereof, or a biosynthetic intermediate thereof compared to the corresponding unmodified plant.

26. The genetically modified plant of claim 25, wherein when said endogenous CSLG gene is selectively silenced, repressed, or has reduced expression, said cell further comprises at least one silencing molecule targeted to the polynucleotide encoding said CSLG gene, wherein the silencing molecule is selected from an RNA interference molecule or an antisense molecule, or wherein the silencing molecule is a component of a viral induced gene silencing system.

27. The genetically modified plant of claim 22, wherein said CSLG gene comprises a heterologous CSLG gene, and said altered expression comprises a de novo expression of said gene.

28. The genetically modified plant according to claim 27, wherein said expression comprises increased expression compared to a corresponding unmodified cell, and said altered content comprising increased content of at least one steroidal alkaloid, a derivative thereof, a metabolite thereof, or a biosynthetic intermediate thereof; of at least one steroidal saponin, a derivative thereof, a metabolite thereof, or a biosynthetic intermediate thereof; or of at least one triterpenoid saponin, a derivative thereof, a metabolite thereof, or a biosynthetic intermediate thereof, compared to the corresponding unmodified plant.

29. The genetically modified plant according to claim 22, wherein the nucleic acid sequence encoding said CSLG gene is set forth in any one of SEQ ID NOS: 30, 32, 34, 36, 38, 40, 65, 80, 93, 95, 97, 99, 101, 103, or 105; or a homolog thereof having at least 90% identity to and at least 90% coverage of, the nucleic acid sequence set forth in any one of SEQ ID NOS: 30, 32, 34, 36, 38, 40, 65, 80, 93, 95, 97, 99, 101, 103, or 105.

30. The genetically modified plant according to claim 22, wherein the altered expression of the at least one cellulose synthase like G (CSLG) gene is altered by introducing (1) one or more point mutations into the nucleic acid sequence, (2) deletions within the nucleic acid sequence, or (3) insertions within the nucleic acid, any combination thereof, or (4) any combination thereof, wherein said introducing comprising mutagenizing coding or non-coding sequence.

31. The genetically modified plant according to claim 30, wherein the altered expression of the at least one CSLG gene is altered by introducing a silencing molecule targeted to the at least one CSLG gene and wherein:

(a) when the nucleic acid of the CSLG is set forth in SEQ ID NO: 30, the silencing molecule is set forth in SEQ ID NO: 42 or a complementary sequence thereof, or a homolog thereof having at least 90% identity to the nucleic acid sequence set forth in SEQ ID NO: 42 or a complementary sequence thereof;

(b) when the nucleic acid of the CSLG is set forth in SEQ ID NO: 34, the silencing molecule is set forth in SEQ ID NO: 43 or a complementary sequence thereof, or a homolog thereof having at least 90% identity to the nucleic acid sequence set forth in SEQ ID NO: 43 or a complementary sequence thereof;

(c) when the nucleic acid of the CSLG is set forth in SEQ ID NO: 38, the silencing molecule is set forth in SEQ ID NO: 44 or a complementary sequence thereof, or a homolog thereof having at least 90% identity to the nucleic acid sequence set forth in SEQ ID NO: 44 or a complementary sequence thereof;

(d) when the nucleic acid of the CSLG is set forth in SEQ ID NO: 65 or SEQ ID NO: 93, the silencing molecule is set forth in SEQ ID NO: 106 or a complementary sequence thereof, or a homolog thereof having at least 90% identity to the nucleic acid sequence set forth in SEQ ID NO: 65 or the nucleic acid sequence set forth in SEQ ID NO: 93; or (e) when the nucleic acid of the CSLG is set forth in SEQ ID NO: 95, the silencing molecule is set forth in SEQ ID NO: 107 or a complementary sequence thereof, or a homolog thereof having at least 90% identity to the nucleic acid sequence set forth in SEQ ID NO: 95.

32. The genetically modified plant according to claim 22, wherein said triterpenoid saponin, derivative thereof, metabolite thereof, or the biosynthetic intermediate thereof comprises a sweetener, foaming agent, emulsifier, preservative, anti-carcinogen, hypocholesterolemic agent, anti-inflammatory agent, anti-oxidant, biological adjuvant, antimicrobial agent, insecticidal agent, antifeedant, anti-fungal agent, or any combination thereof.

33. The genetically modified plant according to claim 22, (a) wherein said steroidal glycoalkaloid comprises an esculeoside, a dehydroesculeoside, alpha-tomatine, tomatine, alpha-chaconine, alpha-solanine, alpha-solasonine, alpha-solmargine, or any combination thereof, or (b) wherein said steroidal saponin comprises uttroside B, a tomatoside, or any combination thereof; or (c) wherein said triterpenoid sapoinin comprises medicagenic acid 3-O-glucuronide (MA-3-GlcA) (Compound 6), Compound 7, Compound 8, Compound 9, Compound 10, Compound 11, glycyrrhizin (Compound 14), Glycyrrhetinic acid 3-O-monoglucuronide (compound 15), bayogenin (Compound 25), bayogenin-hexA-hex-hex (Compound 31), serjanic acid (Compound 26), serjanic acid-hexA-hex (Compound 32), soyasapogenol A (Compound 29), soyasapogenol B (Compound 30), soyasapogenol A-hexA-hex-pent (Compound 34), soyasaponin VI (Compound 35), beta-vulgaroside IV (Compound 33), hederagenin-3GlcA, gypsogenin-3GlcA, gypsogenic acid-3GlcA, or a QS-21 adjuvant, or any combination thereof; or (d) wherein the biosynthetic intermediate of a triterpenoid saponin comprises Compound 1, Compound 2, medicagenic acid (Compound 5), oleanolic acid (Compound 3), oleanolic acid-3GlcA, augustic acid (Compound 4), augustic acid-3GlcA, or glycyrrhetinic acid (Compound 13), or any combination thereof; or (e) a combination thereof.

34. The genetically modified plant according to claim 22, having an altered content of a phytosterol, or a derivative thereof, a metabolite thereof, or a biosynthetic intermediate thereof; a cholesterol, or a derivative thereof, a metabolite thereof, or a biosynthetic intermediate thereof; a phytocholesterol, or a derivative thereof, a metabolite thereof, or a biosynthetic intermediate thereof; a cholestenol, or a derivative thereof, a metabolite thereof, or a biosynthetic intermediate thereof; or a phytocholestenol, or a derivative thereof, a metabolite thereof, or a biosynthetic intermediate thereof.

35. The genetically modified plant according to claim 22, wherein said plant is selected from the *Poales* order, the *Caryophyllales* order, the *Solanales* order, the *Fabales* order, the *Malvales* order, the *Apiales* order, the *Brassicales* order, the *Asparagales* order, the *Dioscoreales* order, or the *Liliales* order.

36. The genetically modified plant according to claim 35, wherein:

(a) when said plant comprises a plant in the Poales order, said plant is selected from the group of genera consisting of the *Oryza* genus, the *Hordeum* genus, the *Avena* genus, and the *Triticum* genus;

(b) when said plant comprises a plant in the *Caryophyllales* order, said plant is selected from the group of genera consisting of the *Spinacia* genus, the *Chenopodium* genus, the *Beta* genus, the *Rheum* genus, the *Vaccaria* genus, the *Saponaria* genus, and the *Gypsophila* genus;

(c) when said plant comprises a plant in the *Solanales* order, said plant is selected from the group of genera consisting of the *Solanum* genus, the *Capsicum* genus, the *Nicotiana* genus, the *Hyoscyamus* genus, the *Datura* genus, and the *Atropa* genus;

(d) when said plant comprises a plant in the *Fabales* order, said plant is selected from the group of genera consisting of the *Glycyrrhiza* genus, the *Medicago* genus, the *Glycine* genus, the Lotus genus, the *Cicer* genus, the *Phaseolus* genus, the *Pisum* genus, the *Arachis* genus, the *Lupinus* genus, and the *Acacia* genus;

(e) when said plant comprises a plant in the *Malvales* order, said plant is selected from the *Theobroma* genus;

(f) when said plant comprises a plant in the *Apiales* order, said plant is selected from the group of genera consisting of the *Daucus* genus, the *Apium* genus, the *Petroselinum* genus, the *Panax* genus, the *Bupleurum* genus, the *Hedera* genus, and the *Centella* genus; or (g) when said plant comprises a plant in the *Brassicales* order, said plant is selected from the group of genera consisting of the *Arabidopsis* genus, the *Brassica* genus, the *Capparis* genus, and the *Carica* genus.

37. The genetically modified plant according to claim 36, wherein:

(a) when said plant comprises a plant in the *Caryophyllales* order, said plant is selected from the group consisting of spinach, beetroot, and *quinoa;*

(b) when said plant comprises a plant in the *Solanales* order, said plant is selected from the group consisting of tomato, wild tomato, potato, wild potato, eggplant, pepper, bell pepper, cayenne pepper, chili pepper, pimiento, tabasco pepper, ground cherry, tobacco, and bittersweet; or (c) when said plant comprises a plant in the *Fabales* order, said plant is selected from the group consisting of alfalfa, soy, *Lotus japonicus*, and licorice.

38. The genetically modified plant according to claim 37, wherein:

(a) the plant is a tomato plant having:

(i) an increased content of alpha-tomatine or a derivative thereof, a metabolite thereof, or a biosynthetic intermediate thereof; or tomatidine or a derivative thereof, a metabolite thereof, or a biosynthetic intermediate thereof; or dehydrotomatine or a derivative thereof, a metabolite thereof, or a biosynthetic intermediate thereof; or a steroidal saponin or a derivative thereof, a metabolite thereof, or a biosynthetic intermediate thereof; or (ii) an altered content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof, or a phytocholestenol or a derivative thereof, a metabolite thereof, or a biosynthetic intermediate thereof; or (b) the plant is a potato plant having:

(i) an increased content of alpha-chaconine or a derivative thereof, a metabolite thereof, or a biosynthetic intermediate thereof; or alpha-solanine or a derivative thereof, a metabolite thereof, or a biosynthetic intermediate thereof; or a steroidal saponin or a derivative thereof, a metabolite thereof, or a biosynthetic intermediate thereof; or (ii) an altered content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof, or a phytocholestenol or a derivative thereof, a metabolite thereof, or a biosynthetic intermediate thereof; or (c) the plant is an eggplant plant having:

(i) an increased content of alpha-solasonine or a derivative thereof, a metabolite thereof, or a biosynthetic intermediate thereof; or alpha-solamargine or a derivative thereof, a metabolite thereof, or a biosynthetic intermediate thereof, or a steroidal saponin or a derivative thereof, a metabolite thereof, or a biosynthetic intermediate thereof;

(ii) an altered content of a phytosterol or a derivative thereof, a metabolite thereof, or a biosynthetic intermediate thereof; a cholesterol or a derivative thereof, a metabolite thereof, or a biosynthetic intermediate thereof; a phytocholesterol or a derivative thereof, a metabolite thereof, or a biosynthetic intermediate thereof; a cholestenol or a derivative thereof, a metabolite thereof, or a biosynthetic intermediate thereof, or a phytocholestenol or a derivative thereof, a metabolite thereof, or a biosynthetic intermediate thereof.

39. The genetically modified plant according to claim 22, wherein said plant cell comprises a leaf cell, a petiole cell, a plant stem or stalk cell, a root cell, a bud cell, a tuber cell, a bean cell, a grain or kernel cell, a fruit cell, a nut cell, a legume cell, a seed or seed cell, a callus cells, a bract cell, a callus cell, and a flower cell.

* * * * *

SEQUENCE LISTING

```
<160> NUMBER OF SEQ ID NOS: 124

<210> SEQ ID NO 1
<211> LENGTH: 35
<212> TYPE: DNA
```

<213> ORGANISM: Artificial Sequence
<220> FEATURE:
<223> OTHER INFORMATION: Syn. Polynucl.

<400> SEQUENCE: 1
aaaaagaatt ccggatcttc tctcgaactg gtcaa 35

<210> SEQ ID NO 2
<211> LENGTH: 39
<212> TYPE: DNA
<213> ORGANISM: Artificial Sequence
<220> FEATURE:
<223> OTHER INFORMATION: Syn. Polynucl.

<400> SEQUENCE: 2
aaaaagaatt ccactttcat tgcttcatcc attagatct 39

<210> SEQ ID NO 3
<211> LENGTH: 37
<212> TYPE: DNA
<213> ORGANISM: Artificial Sequence
<220> FEATURE:
<223> OTHER INFORMATION: Syn. Polynucl.

<400> SEQUENCE: 3
aaaaagaatt ccttagctta tggccacatc acacctt 37

<210> SEQ ID NO 4
<211> LENGTH: 37
<212> TYPE: DNA
<213> ORGANISM: Artificial Sequence
<220> FEATURE:
<223> OTHER INFORMATION: Syn. Polynucl.

<400> SEQUENCE: 4
aaaaagaatt cactcaagat ttggtgaagc tgtggtt 37

<210> SEQ ID NO 5
<211> LENGTH: 36
<212> TYPE: DNA
<213> ORGANISM: Artificial Sequence
<220> FEATURE:
<223> OTHER INFORMATION: Syn. Polynucl.

<400> SEQUENCE: 5
aaaaaggcgc gccaatcata gagaagaaag aagacg 36

<210> SEQ ID NO 6
<211> LENGTH: 38
<212> TYPE: DNA
<213> ORGANISM: Artificial Sequence
<220> FEATURE:
<223> OTHER INFORMATION: Syn. Polynucl.

<400> SEQUENCE: 6
aaaaagcggc cgcactcctg caggaattgt catttctc 38

<210> SEQ ID NO 7
<211> LENGTH: 43
<212> TYPE: DNA
<213> ORGANISM: Artificial Sequence
<220> FEATURE:
<223> OTHER INFORMATION: Syn. Polynucl.

<400> SEQUENCE: 7
aaaaagcggc cgcatgagta ttgtaattga tgatgatgaa atc 43

<210> SEQ ID NO 8
<211> LENGTH: 33
<212> TYPE: DNA
<213> ORGANISM: Artificial Sequence
<220> FEATURE:
<223> OTHER INFORMATION: Syn. Polynucl.

<400> SEQUENCE: 8
aaaaggcgcg cccacacgcc acagatggtt ctt 33

<210> SEQ ID NO 9
<211> LENGTH: 59
<212> TYPE: DNA
<213> ORGANISM: Artificial Sequence
<220> FEATURE:
<223> OTHER INFORMATION: Syn. Polynucl.

<400> SEQUENCE: 9
ggggacaagt ttgtacaaaa aagcaggcta tgagtattgt aattgatgat gatgaaatc 59

<210> SEQ ID NO 10
<211> LENGTH: 54
<212> TYPE: DNA
<213> ORGANISM: Artificial Sequence
<220> FEATURE:
<223> OTHER INFORMATION: Syn. Polynucl.

<400> SEQUENCE: 10
ggggaccact ttgtacaaga aagctgggtt catactacct tctgtcctaa gcct 54

<210> SEQ ID NO 11
<211> LENGTH: 55
<212> TYPE: DNA
<213> ORGANISM: Artificial Sequence
<220> FEATURE:
<223> OTHER INFORMATION: Syn. Polynucl.

<400> SEQUENCE: 11
ggggacaagt ttgtacaaaa aagcaggcta tgaatattgc aattgatgat gatga 55

<210> SEQ ID NO 12
<211> LENGTH: 59
<212> TYPE: DNA
<213> ORGANISM: Artificial Sequence
<220> FEATURE:
<223> OTHER INFORMATION: Syn. Polynucl.

<400> SEQUENCE: 12
ggggaccact ttgtacaaga aagctgggtt catttgtatc aacatttgta aattcacac 59

<210> SEQ ID NO 13
<211> LENGTH: 219
<212> TYPE: PRT
<213> ORGANISM: Solanum Lycopersicum

<400> SEQUENCE: 13

Met Ser Ile Val Ile Asp Asp Asp Glu Ile Phe Ser Leu Pro Ser Leu
1 5 10 15

Asp Glu Leu Glu Ser Ile Thr His Leu Leu Tyr Asp Asp Asp Ser Asp
20 25 30

Phe Phe Glu Thr Leu Ser Pro Met Ser Leu Asp Val Thr Thr Leu Leu
35 40 45

Pro Asn Ile Pro Thr Ser Asn Ser Ile Glu Ser Pro Val Thr Pro Glu

```
    50                  55                  60

Glu Thr Lys Glu Pro Ser Val Ala Cys Glu Asp Ala Pro Gln Asp Trp
65                  70                  75                  80

Arg Arg Phe Ile Gly Val Arg Arg Arg Gln Trp Gly Thr Phe Ser Ala
                85                  90                  95

Glu Ile Arg Asp Pro Asn Arg Arg Gly Ala Arg Leu Trp Leu Gly Thr
            100                 105                 110

Tyr Glu Ser Pro Arg Asp Ala Ala Leu Ala Tyr Asp Gln Ala Ala Tyr
        115                 120                 125

Lys Ile Arg Gly Thr Lys Val Arg Leu Asn Phe Pro Asp Leu Ile Gly
    130                 135                 140

Ser Asp Val Pro Met Pro Pro Arg Val Thr Ala Arg Arg Arg Thr Arg
145                 150                 155                 160

Ser Arg Ser Arg Ser Pro Glu Pro Leu Thr Thr Ser Ser Ser Ser Ser
                165                 170                 175

Ser Ser Ser Ser Ser Ser Ser Ser Ser Ser Ser Glu Asn Gly Thr Lys
            180                 185                 190

Lys Arg Lys Ile Asp Leu Ile Asn Ser Ile Ala Lys Ser Lys Leu Leu
        195                 200                 205

Cys Gly Met Asp Leu Gln Met Leu Ile Gln Met
    210                 215


<210> SEQ ID NO 14
<211> LENGTH: 222
<212> TYPE: PRT
<213> ORGANISM: Solanum tuberosum

<400> SEQUENCE: 14

Met Asn Ile Ala Ile Asp Asp Asp Glu Ile Phe Ser Leu Pro Ser Leu
1               5                   10                  15

Asp Glu Leu Glu Ser Ile Thr His Leu Leu Tyr Asp Asp Asp Ser Asp
            20                  25                  30

Phe Phe Glu Thr Leu Ser Pro Met Ser Leu Asp Ser Thr Thr Leu Leu
        35                  40                  45

Pro Asn Asn Pro Thr Pro Asn Ser Leu Glu Ser Pro Val Arg Pro Glu
    50                  55                  60

Gly Thr Lys Glu Thr Phe Val Ala Arg Glu His Glu Glu Ser Ala Pro
65                  70                  75                  80

Gln Asp Trp Arg Arg Phe Ile Gly Val Arg Arg Arg Gln Trp Gly Thr
                85                  90                  95

Phe Ser Ala Glu Ile Arg Asp Pro Asn Arg Arg Gly Ala Arg Leu Trp
            100                 105                 110

Leu Gly Thr Tyr Glu Ser Pro Gln Asp Ala Ala Leu Ala Tyr Asp Gln
        115                 120                 125

Ala Ala Tyr Lys Ile Arg Gly Thr Lys Ala Arg Leu Asn Phe Pro Asp
    130                 135                 140

Leu Ile Gly Ser Asp Val Pro Met Pro Pro Arg Val Thr Ala Arg Arg
145                 150                 155                 160

Arg Thr Arg Ser Arg Ser Arg Ser Pro Glu Pro Ser Thr Thr Ser Ser
                165                 170                 175

Ser Ser Ser Ser Ser Ser Ser Ser Ser Ser Ser Ser Ser Met Glu Asn
            180                 185                 190

Gly Thr Lys Lys Arg Lys Ile Asp Leu Ile Asn Ser Ile Ala Lys Ala
        195                 200                 205
```

```
Lys Leu Leu Cys Gly Val Asn Leu Gln Met Leu Ile Gln Met
    210                 215                 220


<210> SEQ ID NO 15
<211> LENGTH: 988
<212> TYPE: DNA
<213> ORGANISM: Solanum Lycopersicum

<400> SEQUENCE: 15

taatattaca ttacattcat cacatattat tcatccaaaa caagaatgag tattgtaatt     60

gatgatgatg aaatcttctc tttacctagc cttgatgaac ttgaatccat cacacatctt    120

ctttatgacg acgattccga tttttcgaa actctttccc caatgagttt agatgttaca    180

acattattgc ctaatattcc tacctccaat tcaattgaat cccccgtaac accggaggaa    240

acaaaagaac catctgtggc gtgtgaggac gcgccacaag attggaggcg gttcataggg    300

gtgaggcgga ggcagtgggg cacgttttca gccgaaataa gagatccaaa taggagagga    360

gcgaggctgt ggctcggaac ttatgagtcc ccgagggatg cagcattagc ttatgaccaa    420

gccgcttaca agattcgggg aaccaaagtt cggcttaatt ttcctgacct gattggctcg    480

gacgtaccta tgccacctag agtaacggct aggcgtcgta cacgctcacg ctcacgctca    540

cccgagccat taacaacttc gtcctcgtca tcctcatcat cctcgtcctc gtcctcgtcc    600

tcgtcggaaa atggaacgaa gaaaaggaaa atagatttga taaactcaat agcaaaatcc    660

aaattacttt gtgggatgga tttacaaatg ttaatacaaa tgtgagaaaa gagcaaaggt    720

ttatttttct tcgtttgaca attaagtact acgtcgtata attaatagac tcatcaaggt    780

cattgtgtaa atgcacttct ttcacgacct tctcctttat gagattgtta tgaattttac    840

attatttcct ttatcaacta tatatttatc gttttcatac gcggtggagt tcatctgaat    900

ttctctttct aaggttatat atagagaagg atgttgaatt tttcgtcttc ttttttttat    960

taaataaaaa atctatcttc tacatcag                                       988


<210> SEQ ID NO 16
<211> LENGTH: 754
<212> TYPE: DNA
<213> ORGANISM: Solanum tuberosum

<400> SEQUENCE: 16

gaaaatttca ttcatccaaa agaagaatga atattgcaat tgatgatgat gaaatcttct     60

ctttacctag cctcgatgaa cttgaatcta tcacacatct tctttatgat gatgattccg    120

attttttga aactctttca ccaatgagtt tagatagcac aacattattg cctaataatc    180

ctactccaaa ttcacttgaa tcccccgtaa gaccggaggg aacaaaggaa acatttgtgg    240

cgcgcgaaca cgaagaaagc gcgccacaag attggaggcg gttcatagga gtgaggcgaa    300

ggcagtgggg cacgttttca gccgaaataa gagatccaaa taggagaggc gcgaggctgt    360

ggctaggaac ttatgagtcc ccgcaggatg cagcattggc ttatgaccaa gctgcttaca    420

agattcgggg taccaaagct cggctcaatt ttccggactt aattggctcg gacgtgccta    480

tgccaccaag agtaacggct aggcgtcgta ctcgctcacg ctcgcgctca cccgagccat    540

caacaacttc ttcgtcctca tcctcgtcct cgtcctcatc ctcgtcctcg tccatggaaa    600

atgggacgaa aaaaaggaaa atagatttga taaactcaat agccaaagcc aaattactct    660

gtggtgtgaa tttacaaatg ttgatacaaa tgtgagaaaa gagcaaaggt ttattttttt    720

cttcgtttaa caattaagta ttacgtataa ttaa                                754
```

<210> SEQ ID NO 17
<211> LENGTH: 224
<212> TYPE: PRT
<213> ORGANISM: Solanum Lycopersicum

<400> SEQUENCE: 17

Met Pro Ser Leu Gly Val Phe Ser Ile Leu Ile Ser Arg Met Ala Cys
1 5 10 15

Tyr Ile Ile Val Asn Leu Ser Ser Leu Ile Ala Ile Ser Arg Ser Thr
20 25 30

Pro Gly Pro Val Glu Gly Ser Val Glu His Ser Gln Ile Ile Arg Asn
35 40 45

Gly Ser Thr His Glu Asp Asp Ile Val Ile Asn Pro Thr Leu Leu Ala
50 55 60

Ser Val Gln Ser Phe Val Glu Pro Asn Leu Thr Ala Ala Ala Leu Tyr
65 70 75 80

Arg Ala Thr His Asp Ser His Met Ala Ala Asp Glu Ala Ile Ala Phe
85 90 95

Asn Met Pro Leu Gln Pro Asn Leu Phe Glu Asn Ala Ser Val Glu Pro
100 105 110

Ser Pro Asp Ala Glu His Pro Ser Gln Thr Gln Ser Leu Cys Trp Pro
115 120 125

Asp Lys Arg Asp Thr Ile Glu Ser Glu Val Leu Ser Tyr Gly Arg Asn
130 135 140

Asp Gln Glu Glu Val Lys Phe Asp Gly Glu Ala Val Gly Arg Ser His
145 150 155 160

Ala Tyr Ser Gln Arg Leu Leu Asn Ile Ile Asn Gln Thr Leu Ala Ser
165 170 175

Val Gly Val Asp Pro Ser Leu Ala Asp Val Arg Val Gln Leu Asp Ile
180 185 190

Ser Lys Lys Thr Ser Ser Gly Ala Thr Thr Thr Arg Leu Ser Ser Gly
195 200 205

Glu Asn Tyr Gly Gly Ala Pro Lys Arg Leu Arg Thr Glu Gly Ser Met
210 215 220

<210> SEQ ID NO 18
<211> LENGTH: 2497
<212> TYPE: DNA
<213> ORGANISM: Solanum Lycopersicum

<400> SEQUENCE: 18
atgccaagtt taggggtgtt ttcaatactc atctctagaa tggcttgcta tatcattgtt 60
aatttaagtt ctcttattgc tatttctgct gttgagtaaa aagcatagta gttccttgca 120
tcatttgcac tttcatctgt ttgatgttat gctgtggatt cttttcctaa gtgttgactt 180
tttctctacc tccctattta ggaaaaagag gcaatagtat tttaagtcca tctcttaagg 240
aatggctaat gttgaaatat aacaaagaac ttccttcttt ggcaacacat ggttggcttc 300
ttgtccttta gctatgtgat tttctgtact tcgattttat tccctcctcc acttcttatt 360
tggcagttta gttgtagcat taaaatagat tcattctaac cagatggctt acttatggaa 420
tcttcaactc tttaataata gtaatggaaa attatgaagt cagtgcacca tgagaaagaa 480
gacattgttt gacccaagag aagtaaactg agctatataa aattggattg agcgctttaa 540
ttactgcaga tattaccctc tgaaaagtac tggatcaaag aaaaaaatgt tctctgatgt 600
tacctatacc tgtatgcccc agttgctgta cagtaaaggt ataattcagt agtcatttcg 660
tatgcttgcc aaatacagaa aaatgcagac gttagctgta tttctagggg aaactcctcg 720
cctacagttc aaacaaaggt tttacatttg cttataattt cctccctcca aagcaaagtg 780
accggatttt gggctctttt aggaggagag ttgggcacaa ctttaggatg gaagcagtaa 840
tgcttttctg gaagtaaaac taatgctctt ctcttattat tgacagagaa gtactcctgg 900
gcccgtggaa ggctctgttg aacattctca aataatcaga aacggctcta ctcatgagga 960
tgatattgtc attaacccaa cattgcttgc aagtgtccag agctttgtag aaccgaactt 1020
gactgctgct gctttatata gagcaacaca cgattctcat atggcagcgg atgaggcaat 1080
tgcctttaac atgccactgc aacctaattt atttgaaaat gcatctgttg aaccatctcc 1140
tgatgctgag cacccttctc agacacaatc attatgttgg ccagataaac gagatacaat 1200
tgagtcggag gttctgagct atggcagaaa tgatcaagaa gaagtgaaat tcgatggtga 1260
agcagttgga agatcacatg catatagtca aaggtaagat gatttatcag gagttcaata 1320
gctatgactt gatgtccttg taaggtggaa attcaaattt atttcttcta tgaccccatg 1380
acttgctaat ttctgtaatg atgccaaact tgtattacac ctacgaagta ggcatgtgat 1440
acagtatcac tttaagtccc ttggacccag tgggcctagt ggcagtcacg gtcttagaag 1500
aattatccta tggttgtcaa gtgcatgaaa tagatttaga ctagttaatg tttctcgtgg 1560
ttattagctg gttggctaga atgcaaagtg tagccttttt aagccccttc cagcatgagt 1620
ttttttgtaa aacctgctgt aacttgtggg tttgcatttt ttttgtgaat aaaattgcca 1680
gttcaacaaa gatttcagtg gcttgaagga agtcatttta tatgacccgg catggtttac 1740
ctgttgaagg ttaataacaa gcggaaccct ggatttcgag atttgagtct cactttagga 1800
tttttcagac ttcccattaa cacaaagtca tgtataacac acatgttcgt atcattctta 1860
cttgtgcagt tgtcctctgt acctttaggc acattttaat ctgaactcgg ttgatctgaa 1920
attatattat gatgccagta aactactgat tttggattct atttatgtga catattgggt 1980
cttggtattg agcaggttgc ttaatatcat aaaccagact ctagcatctg tgggagtgga 2040
tccgtcactg gccgatgtta gagtacagct tgatatcagc aaaaaaacaa gcagtggagc 2100
cacaactaca agattaagca gtggagagaa ctatggtggt gctcctaaaa ggcttaggac 2160
agaaggtagt atgtgattat taatctagca tggctccact cctaattttt ctgcatcttg 2220
tcatcgtttt gatggggaga tagttgaagt ggttggtctc cgtggatgag gtggtgcaca 2280
aacagcttat ggttgtccag ttaggtttcc atttaaatat gagaagctgc attgtcattc 2340
ttaagggtat ttagttttga attgagataa gtcgactttg atagttctgt cagtgtgata 2400
tggttatgcc tatcgatttg ccatggatct gttttcgtag ttgatattta aacagggaaa 2460
tttgaagttg tttcaaatgt tagcatgaag aatttta 2497

<210> SEQ ID NO 19
<211> LENGTH: 996
<212> TYPE: DNA
<213> ORGANISM: Solanum Lycopersicum

<400> SEQUENCE: 19
atgccaagtt taggggtgtt ttcaatactc atctctagaa tggcttgcta tatcattgtt 60
aatttaagtt ctcttattgc tatttctaga agtactcctg ggcccgtgga aggctctgtt 120
gaacattctc aaataatcag aaacggctct actcatgagg atgatattgt cattaaccca 180
acattgcttg caagtgtcca gagctttgta gaaccgaact tgactgctgc tgctttatat 240

-continued

```
agagcaacac acgattctca tatggcagcg gatgaggcaa ttgcctttaa catgccactg    300

caacctaatt tatttgaaaa tgcatctgtt gaaccatctc ctgatgctga gcacccttct    360

cagacacaat cattatgttg gccagataaa cgagatacaa ttgagtcgga ggttctgagc    420

tatggcagaa atgatcaaga agaagtgaaa ttcgatggtg aagcagttgg aagatcacat    480

gcatatagtc aaaggttgct taatatcata aaccagactc tagcatctgt gggagtggat    540

ccgtcactgg ccgatgttag agtacagctt gatatcagca aaaaaacaag cagtggagcc    600

acaactacaa gattaagcag tggagagaac tatggtggtg ctcctaaaag gcttaggaca    660

gaaggtagta tgtgattatt aatctagcat ggctccactc ctaatttttc tgcatcttgt    720

catcgttttg atggggagat agttgaagtg gttggtctcc gtggatgagg tggtgcacaa    780

acagcttatg gttgtccagt taggtttcca tttaaatatg agaagctgca ttgtcattct    840

taagggtatt tagttttgaa ttgagataag tcgactttga tagttctgtc agtgtgatat    900

ggttatgcct atcgatttgc catggatctg ttttcgtagt tgatatttaa acagggaaat    960

ttgaagttgt ttcaaatgtt agcatgaaga atttta                               996
```

<210> SEQ ID NO 20
<211> LENGTH: 3899
<212> TYPE: DNA
<213> ORGANISM: Solanum tuberosum

<400> SEQUENCE: 20

```
ttttttaca aaaaactttt tatccaacac caccgagtag cttgactcgc ccccttaaaa      60

aattatttta aaaataaaat attttttttt tcttatccca ctcctctccc ctaaaaaaaa    120

aataagttca aaagaattct ttttggggggt gagtgggtag tgaggtggga ggctaggggg    180

ggtactgggt agaggatggg gtgggtgata agaaaaaata aatcttcaaa aagaaaaaaa    240

agttctttta tcttcttaaa ttgctaaatt cttaacattt aattatttaa atgttcttta    300

aaaaaatttc tattacatat atttatgtgt acacaccatt accattttca aaaaaaataa    360

atatttatgt atacacaacg tcaacagaaa attctacata tatgcccatg tggcataaga    420

agggtgtttt taaattcact taatcaagta aagggggtgtt tttaaggctg ttaatagttg    480

gaggattaaa gtaataattc atgccaagtt taggggtgtt ttcaatactt atctctagaa    540

tggtctccct attccttgct atattgttgt taatttaagt tctcttattg ctattctgct    600

atgttgagta aaaagcacag tagttccttg catcatttgc acttctcatc tgtttgatgg    660

tatgctgtgg attctttttt caagtggtgt tggacttgtt tgcttggatg ataatctttc    720

atgtttactc cttattgttg aactttttttt ctacctccct attaaggaaa aaaaggcaat    780

agtattttca gtccatctct taaggaatgg ctaatgttga agatataatg aagaacttcc    840

ttctttggca acacatggtt ggcttcttgt cctctagcta tgtgatattt tatacttcga    900

tttttattcc ctccttcact tcttgtttgg cagtttagtt atagcattaa aatagattca    960

ttataaccag atggcttact gaaggaatct tctactcttt aataatagtg ttaaattagg   1020

tcttaggcct aactcacacc ccaaaagcta gctcaaaggg aggaggattg ttcaagcctt   1080

gtaaggagtc cacccatctc aaagggagga ggcttgttca agccttataa ggagtccacc   1140

catctcatta accaccgatg tgggactttt gtcattcttt aacaaatagt attagaaaat   1200

tatgaagtca gtgcaccatg agaaagaaga cattgtttga cccaagagaa gtaaactgag   1260

ctatataaaa tcggattgag actttaattt actgcagata ttaccctctg aaaagtactg   1320

gattaaagaa aaaaatgttc tctgatgtta ccctatacct gtgtgcccca gttactgtac   1380
```

```
agtaaagtca taattcagta gttattttgg atgctttcca aatacagaaa aatgcagacg   1440
ttagctgttt ttgtagggga aactcctcgc ctatggttca aacaaaggct ttacatttgt   1500
ttttaatttt ctccctccaa agcaaagtta ccggatttca ggctgtttta ggaggagagt   1560
tgggcacaac tttaggatgg aagcagtagt gtttttctga aagtaaaact aatgctcttc   1620
tcttattatt gacagagaag cactcctggg cccgtggaag gctctgttga acattctcaa   1680
ataatcagaa acggctctac tcatgaggat gatattgtca ttaacgcaac attgctttcg   1740
agtgcccaga gctttgtaga accgaacttg actgctgctg ctttatatag agcaacacac   1800
gattctcata tggcagcgga tgaagcaatt gcctttaaca tgccactgca acctaattta   1860
tttgaaaatg catctgttga accatctcct gatgctgagc acccttccca gccacaatca   1920
ttatgttggc caggtaaacg agatacaatt gagtcggagg ttctgagcta tggcagaaat   1980
gatcaggaag aagtgaaatg cgatggtgaa gcagttgcaa gatcacatgc gtatactcaa   2040
aggtaagatg atttatcacg agttcaatag ctatgacttg atgtcctggt aaggtggaaa   2100
ttcaaattta tttcttctac gcccccatga cttgctaatt tctgtaatga tgccaaactt   2160
gtattacacc tacgaaatag gcatgtgata cagaatcact ttaagtacct tggacccagt   2220
gggcctagtg gcagtcaagg tcttagaaga attacctgta gtgttccaat ttcttattgt   2280
cctgtgattg ccaagtgcat gaaatagatt cagactaggt aatgtttctc gtggttatta   2340
gctggttggt tgaaatgcag attgtagcct ttctgagccc cttccagtat agttttttttt   2400
gtaaaacctg ctgcaacttg tgggtttgca ttttttttgtg aataaaattg ccaattcaaa   2460
aaagatttca gtggcttgaa ggaagtcatt tatatgaccc ggcattgttt acccgagcaa   2520
tcaaatatca atcaggtttc cctgcatggc ttcccccaac ttttctacct gacccatcaa   2580
atggaaatct aagttgaagg ttaataacaa gcggatctct ggatttcgag gtttgagtct   2640
cacttaagga ttttccagac ttcccattaa aacgaagaaa tgtataacaa acatgtacat   2700
atcattctga cttgagcagt tgtcctctga acctttaggc acattctgat ctgatttcag   2760
ttgatctgaa attatattat gatgctagta tactactgat tttggattct atttatgtga   2820
catattgagt cttggtattg agcaggttgc ttaatatcat aaaccagaca ctagcatctg   2880
tgggagtgga tccttcactg gccgatgtta gagtacagct tgatatcagc aaaaaaaccaa   2940
gcagtggagc cacaactaca acattaagca gtgaagagaa ctatgatggt gctcctaaaa   3000
ggcttaggac agaaggtagt atgtgattgt caatctagca tggttccact cctaattttt   3060
ctgcatcttg tcattgtttc gatggggaga tacttgaagt ggttggtctc tgtggatgag   3120
gtggtgcaca aacagcttat ggttgtccag ttaggtttcc atttaaatat gagaagctgc   3180
attgtcattc ttaagggtat ttagatagtc gactttggaa attctgtcag tgtgatgtgg   3240
ttatgcctat cgatttgaga tgcctccatg gatctggttt catagttgat atttaaacag   3300
ggaaatttga agttgtttca aatgtcagca tgaagaattt tatgtacatt accaaatctt   3360
ttcctttttca gtattttgtg attagttcac ttaaacagga tgctggcttt tcaattgtgt   3420
tttcagaaat aaaagtcagc acttgtatca ttgtgaaaaa ctgaaaattt tggtctttaa   3480
gtcgaatcaa caacataatg caagtattta ctgataacgg cgtttggtca gatgaatacg   3540
gcagtttcac aatgattgca tatgaatatg ctcatgttag tccatggtat atattgtaat   3600
tttatcctaa agatatcgta atgagaagtt agatgagttt gatgcgatga actgatgaag   3660
cattggtaat gggttattgg tttagcagtt ttgctaattc tcatttatat ttgggatatc   3720
```

```
cgttgtcaaa tgtttgaggt tcttttctta acacattaat cgaattaata aattaaactc   3780

tcggctattc tactaggtgc caatatttgc ttttgagcaa gatgcaatat gtcgttcatt   3840

tggtttgtca ccttgtttct aagtgagttt taatctataa cagaatgttt gttggtaaa    3899


<210> SEQ ID NO 21
<211> LENGTH: 990
<212> TYPE: DNA
<213> ORGANISM: Solanum tuberosum

<400> SEQUENCE: 21

atgccaagtt taggggtgtt ttcaatactt atctctagaa tggcttgcta tattgttgtt     60

aatttaagtt ctcttattgc tattagaagc actcctgggc ccgtggaagg ctctgttgaa    120

cattctcaaa taatcagaaa cggctctact catgaggatg atattgtcat taacgcaaca    180

ttgctttcga gtgcccagag ctttgtagaa ccgaacttga ctgctgctgc tttatataga    240

gcaacacacg attctcatat ggcagcggat gaagcaattg cctttaacat gccactgcaa    300

cctaatttat ttgaaaatgc atctgttgaa ccatctcctg atgctgagca cccttcccag    360

ccacaatcat tatgttggcc aggtaaacga gatacaattg agtcggaggt tctgagctat    420

ggcagaaatg atcaggaaga agtgaaatgc gatggtgaag cagttgcaag atcacatgcg    480

tatactcaaa ggtaggttgc ttaatatcat aaaccagaca ctagcatctg tgggagtgga    540

tccttcactg gccgatgtta gagtacagct tgatatcagc aaaaaaccaa gcagtggagc    600

cacaactaca acattaagca gtgaagagaa ctatgatggt gctcctaaaa ggcttaggac    660

agaaggtagt atgtgattgt caatctagca tggttccact cctaattttt ctgcatcttg    720

tcattgtttc gatggggaga tacttgaagt ggttggtctc tgtggatgag gtggtgcaca    780

aacagcttat ggttgtccag ttaggtttcc atttaaatat gagaagctgc attgtcattc    840

ttaagggtat ttagagtcga ctttggaaat tctgtcagtg tgatgtggtt atgcctatcg    900

atttgagatg cctccatgga tctggtttca tagttgatat ttaaacaggg aaatttgaag    960

ttgtttcaaa tgtcagcatg aagaatttta                                     990


<210> SEQ ID NO 22
<211> LENGTH: 342
<212> TYPE: PRT
<213> ORGANISM: Solanum Lycopersicum

<400> SEQUENCE: 22

Met Ala Asp Leu Leu Ser Asn Trp Ser Ser Thr Leu Glu Ala Val Pro
1               5                   10                  15

Lys Ser His Cys Ile Pro Glu His Glu Arg Pro Ser Asp Pro Val Glu
            20                  25                  30

Ile Gly Asp Ser Ile Pro Val Ile Asp Leu Gly Lys Ala Asn Gly Glu
        35                  40                  45

Glu Arg Ser Val Val Val Lys Asp Leu Leu Lys Ala Phe Glu Glu Tyr
    50                  55                  60

Gly Phe Phe Gln Ile Ile Asn His Gly Val Pro Val Asp Leu Met Asp
65                  70                  75                  80

Glu Ala Met Lys Val Tyr Lys Glu Phe Phe Ser Leu Pro Ala Glu Glu
                85                  90                  95

Lys Glu Asn Tyr Ala Lys Asp Ala Ala Asn Asn Thr Asn Arg Gly Ala
            100                 105                 110

Ala Thr Leu Tyr Ser Ser Ser Ala Lys His Tyr Asp Ser Glu Glu His
        115                 120                 125
```

```
Arg Tyr Trp Arg Asp Val Leu Glu His Ser Cys Asn Leu Asp Gly Glu
    130                 135                 140

Asp Lys Lys Thr Trp Pro Asp Asn Pro Pro Arg Tyr Arg Glu Val Ile
145                 150                 155                 160

Gly Ala Tyr Gly Asp Glu Leu Arg Arg Val Ser Lys Val Ile Leu Gly
                165                 170                 175

Met Leu Ser Glu Gly Leu Gly Leu Glu Ala Gly Phe Phe Asp Lys Glu
            180                 185                 190

Leu Gly Gln Arg Met Leu Val Asn His Tyr Pro Ala Cys Pro Asn Pro
        195                 200                 205

Ser Leu Thr Leu Gly Val Gly Gly His Cys Asp Pro Asn Leu Ile Thr
    210                 215                 220

Ile Ile Gln Gln Glu Val Tyr Gly Leu Gln Ile Leu Lys Asp Asp Lys
225                 230                 235                 240

Trp Ile Gly Val Gln Pro Ile Arg Asn Ala Phe Val Val Asn Ser Gly
                245                 250                 255

Leu Pro Ile Thr Val Tyr Ser Asn Gly Lys Leu Thr Ser Val Ala His
            260                 265                 270

Arg Val Val Thr Asn Thr Thr Glu Ser Arg Thr Ser Ile Gly Thr Phe
        275                 280                 285

Ile Cys Pro His Glu Ile Val Glu Pro Ala Lys Ala Leu Val Gly Pro
    290                 295                 300

Glu Asn Pro Pro Gln Phe Lys Pro Phe His Trp Gly Ile Asp Phe Met
305                 310                 315                 320

Pro His Tyr Leu Ser Lys Lys Ser Val Tyr His Ala Ser Leu Glu Pro
                325                 330                 335

Phe Lys Thr Glu Ala Asn
            340
```

<210> SEQ ID NO 23
<211> LENGTH: 341
<212> TYPE: PRT
<213> ORGANISM: Solanum tuberosum

<400> SEQUENCE: 23

```
Met Ala Asp Leu Leu Ser Asn Trp Ser Ser Thr Leu Glu Ala Val Pro
1               5                   10                  15

Pro Ser His Cys Ile Pro Val His Glu Arg Pro Ser Asp Pro Val Glu
            20                  25                  30

Ile Val Asp Asn Ile Pro Val Ile Asp Leu Gly Lys Ala Asn Gly Glu
        35                  40                  45

Glu Arg Ser Val Val Val Lys Glu Leu Leu Lys Ala Phe Glu Glu Tyr
    50                  55                  60

Gly Phe Phe Gln Ile Ile Asn His Gly Val Pro Val Asp Leu Met Asp
65                  70                  75                  80

Glu Ala Met Lys Val Tyr Lys Glu Phe Phe Ser Leu Pro Ala Ala Glu
                85                  90                  95

Lys Ala Glu Tyr Ala Lys Asp Ala Ala Asn Asp Thr Asn Arg Gly Ala
            100                 105                 110

Ala Thr Leu Tyr Ser Ser Ser Ala Lys His Tyr Asp Ser Glu Glu His
        115                 120                 125

Arg Tyr Trp Arg Asp Val Leu Glu His Ser Cys Asn Leu Asp Gly Lys
    130                 135                 140

Asp Lys Lys Thr Trp Pro Ser Asn Pro Pro Arg Tyr Arg Glu Val Ile
```

```
145                 150                 155                 160

Gly Ala Tyr Gly Asp Glu Leu Arg Arg Val Ser Lys Val Ile Leu Gly
                165                 170                 175

Leu Leu Ala Glu Gly Leu Gly Leu Glu Ala Gly Phe Phe Asp Thr Glu
            180                 185                 190

Leu Gly Gln Arg Met Leu Val Asn His Tyr Pro Ala Cys Pro Asp Pro
        195                 200                 205

Ser Leu Thr Leu Gly Val Gly Gly His Cys Asp Pro Asn Leu Ile Thr
    210                 215                 220

Ile Ile Gln Gln Glu Val Tyr Gly Leu Gln Ile Leu Lys Asp Asp Lys
225                 230                 235                 240

Trp Ile Gly Val Gln Pro Ile Arg Asn Ala Phe Val Val Asn Ser Gly
                245                 250                 255

Leu Pro Ile Thr Val Val Ser Asn Gly Lys Leu Thr Ser Val Ala His
            260                 265                 270

Arg Val Val Thr Asn Thr Thr His Ser Arg Thr Ser Ile Gly Thr Phe
        275                 280                 285

Ile Cys Pro His Asp Ile Val Glu Pro Ala Lys Ala Leu Val Gly Pro
    290                 295                 300

Glu Asn Pro Pro Gln Phe Lys Ser Phe Asn Trp Gly Ile Asp Phe Met
305                 310                 315                 320

Pro His Tyr Leu Ser Lys Lys Ser Val Tyr His Ala Ser Leu Glu Pro
                325                 330                 335

Phe Lys Ile Asp Ala
            340


<210> SEQ ID NO 24
<211> LENGTH: 1726
<212> TYPE: DNA
<213> ORGANISM: Solanum Lycopersicum

<400> SEQUENCE: 24

aaaaaatatt tgtttttaaa atgtgtaatt tttagtggca tgctctaaaa aaaaataaaa     60

ttatctgagc atcagttttg gttatgcaat ttccttccct ataaatggcc ctccatatct    120

caaatgagat atcaaacaat ttgcagaagt agtagtatta acatttagaa gataactttg    180

tttcccaggt aaataaatca ataaatcctc cttttctttg tttgtttgtt tatttgttga    240

gatatttatg atttttggtt ttggtttaga ttgattgtca atggcggatc ttctctcgaa    300

ctggtcaagc acattagaag cagttcctaa aagtcattgc atcccagagc atgaaagacc    360

atcagatcca gttgaaattg gcgacagtat tccagtcatt gatttgggaa aagctaatgg    420

tgaagaacga agtgttgttg ttaaagatct gttgaaagct tttgaagaat atgggttttt    480

tcaggtacgc aactctgttt cttttttttt tgttcccgtt aatgtgaaat tgaaatgatg    540

atatatgaac aaacagataa tcaatcatgg agtacctgta gatctaatgg atgaagcaat    600

gaaagtgtac aaagaatttt tcagtcttcc agctgaagaa aaagaaaatt atgcaaaaga    660

tgcagctaat aataccaata ggggtgcagc tacactgtac agtagcagtg ctaagcatta    720

tgattcagag gagcatcgtt actggagaga tgtgttggaa catagctgca atcttgatgg    780

agaagacaaa aaaacttggc ccgataaccc tccaagatat aggtacctac ctatctaaac    840

tatgtatggt ttagcaatta atttccctct tttcttacac atgtattttg gttgtacttc    900

agggaggtta ttggtgccta tggtgatgaa ttgagaaggg tgagcaaagt tatcttgggt    960

atgttaagtg aagggctagg tttggaggca gggttctttg acaaagaact tgggcagaga   1020
```

-continued

```
atgcttgtga atcactatcc agcatgtcca aatccaagtt taactttggg agttggtgga   1080

cattgtgatc ctaatctcat aaccattatc caacaagaag tctatggtct tcaaatattg   1140

aaggatgaca aatggattgg tgtgcagcct attcgcaatg catttgtggt taattctggt   1200

ttaccaatta cggtatgtat gtgtgtaggt cttctctaac accccctttt tttcttctct   1260

tataatgttt gctatgcata caggtatata gcaatggaaa gctaactagt gttgcacatc   1320

gtgtggtgac aaacacaact gagtcacgaa cctccattgg tacttttatt tgcccacatg   1380

agattgttga acctgcaaaa gcacttgttg gtcctgagaa tcctccacag ttcaaaccct   1440

tccattgggg aatcgatttt atgccacatt acctcagcaa gaaatcagtg taccacgctt   1500

cattggagcc cttcaaaaca gaagctaatt aagcattaag gatatatcaa atctatgctg   1560

ctgctgctac tacttctttt aatttccact gaaataagag ctttaattca aaatgtcttt   1620

ctagtttgta ttctacttac ttcatgaata agaaacttcc aatcctattc tctactggtt   1680

tcgatctaca tgaatatttt attatttcca ttgcattttc aatcag                  1726
```

<210> SEQ ID NO 25
<211> LENGTH: 1422
<212> TYPE: DNA
<213> ORGANISM: Solanum Lycopersicum

<400> SEQUENCE: 25

```
aaaaaatatt tgtttttaaa atgtgtaatt tttagtggca tgctctaaaa aaaaataaaa     60

ttatctgagc atcagttttg gttatgcaat ttccttccct ataaatggcc ctccatatct    120

caaatgagat atcaaacaat ttgcagaagt agtagtatta acatttagaa gataactttg    180

tttcccagat tgattgtcaa tggcggatct tctctcgaac tggtcaagca cattagaagc    240

agttcctaaa agtcattgca tcccagagca tgaaagacca tcagatccag ttgaaattgg    300

cgacagtatt ccagtcattg atttgggaaa agctaatggt gaagaacgaa gtgttgttgt    360

taaagatctg ttgaaagctt ttgaagaata tgggtttttt cagataatca atcatggagt    420

acctgtagat ctaatggatg aagcaatgaa agtgtacaaa gaatttttca gtcttccagc    480

tgaagaaaaa gaaaattatg caaaagatgc agctaataat accaataggg gtgcagctac    540

actgtacagt agcagtgcta agcattatga ttcagaggag catcgttact ggagagatgt    600

gttggaacat agctgcaatc ttgatggaga agacaaaaaa acttggcccg ataaccctcc    660

aagatatagg gaggttattg gtgcctatgg tgatgaattg agaagggtga gcaaagttat    720

cttgggtatg ttaagtgaag ggctaggttt ggaggcaggg ttctttgaca aagaacttgg    780

gcagagaatg cttgtgaatc actatccagc atgtccaaat ccaagtttaa ctttgggagt    840

tggtggacat tgtgatccta atctcataac cattatccaa caagaagtct atggtcttca    900

aatattgaag gatgacaaat ggattggtgt gcagcctatt cgcaatgcat ttgtggttaa    960

ttctggttta ccaattacgg tatatagcaa tggaaagcta actagtgttg cacatcgtgt   1020

ggtgacaaac acaactgagt cacgaacctc cattggtact tttatttgcc cacatgagat   1080

tgttgaacct gcaaaagcac ttgttggtcc tgagaatcct ccacagttca aacccttcca   1140

ttggggaatc gattttatgc cacattacct cagcaagaaa tcagtgtacc acgcttcatt   1200

ggagcccttc aaaacagaag ctaattaagc attaaggata tatcaaatct atgctgctgc   1260

tgctactact tcttttaatt tccactgaaa taagagcttt aattcaaaat gtctttctag   1320

tttgtattct acttacttca tgaataagaa acttccaatc ctattctcta ctggtttcga   1380
```

-continued

```
tctacatgaa tattttatta tttccattgc attttcaatc ag                    1422


<210> SEQ ID NO 26
<211> LENGTH: 1619
<212> TYPE: DNA
<213> ORGANISM: Solanum tuberosum

<400> SEQUENCE: 26

ctttgttatg caattttctt ccctataaat ggccctccat agctcaaatg agatatcaga     60

caatttaaag aagtactatt aacatttaga agatttcttt ctttcccagg taaataaatc    120

attttccctc tttccttctt gctctttctt tgtttatttg ttcagatttt taccctttttt    180

gttttggtta gattcattga caatggcgga ccttctttca aactggtcaa gcacattaga    240

agcagttcct ccaagtcatt gcatcccagt gcatgaaaga ccatcggatc cagttgaaat    300

tgtggacaat attccagtca ttgatttggg aaaagctaat ggtgaagaac gaagtgttgt    360

tgttaaagaa cttttgaaag cttttgaaga atatgggttt tttcaggttt attatttata    420

caatagtaca actctgttct tttttctttt tttttcttat tgtatttaaa aatgatctga    480

aattgaaatg atgaaataga taatcaatca tggagtaccc gtagatctaa tggatgaagc    540

aatgaaagtg tacaaagaat ttttcagtct gccagcagca gagaaagcag aatatgcaaa    600

ggatgcagct aatgatacaa ataggggtgc agctacactg tacagtagca gcgctaagca    660

ttatgattca gaggagcatc gttactggag agatgtcttg gaacatagct gcaatcttga    720

tgggaaagac aaaaaaactt ggcctagtaa ccctccaaga tataggtacc tacctaaact    780

atgcttagca aaattccctc ttgttatttt tcttacctag tatttgcttg tccttcaggg    840

aggttattgg tgcatatgga gatgaattga gaagggtgag caaagttatc ttgggtctgt    900

tagctgaagg gctaggtttg gaggcagggt tctttgacac agaacttggg cagagaatgc    960

ttgtgaatca ctatccagca tgcccagatc caagtttaac cttgggagtt ggtggacatt   1020

gtgatcctaa tctcataacc attatccaac aagaagtgta tggtcttcaa atattgaagg   1080

atgacaaatg gattggtgtg cagcctatcc gcaatgcatt tgtggtcaat tctggtttac   1140

caattacggt aggtgtaaca ctttctctta attttcatgg tctacaagcg attctcttat   1200

tgctctgttt tttttgtata aatacaggta gttagcaatg gaaagctaac tagtgttgca   1260

catcgtgtgg tgacaaacac aactcattca cgaacctcca ttggtacttt tatttgccca   1320

cacgatattg ttgagcctgc aaaagcactt gttggtccgg agaatcctcc acagttcaaa   1380

tcctttaatt ggggaattga ttttatgcca cattacctca gcaagaaatc agtttaccac   1440

gcatcattgg agcccttcaa aatcgatgct taagcatttg tgtgccagaa ggatcaagtc   1500

tatgctgcta cttttaattt ccactaaaat aagagcttta atttacaatg tctttctagt   1560

ttgtatccta cctttgttac ctatttcatg aataagaatc tttctttcct attctcttc    1619


<210> SEQ ID NO 27
<211> LENGTH: 1292
<212> TYPE: DNA
<213> ORGANISM: Solanum tuberosum

<400> SEQUENCE: 27

ctttgttatg caattttctt ccctataaat ggccctccat agctcaaatg agatatcaga     60

caatttaaag aagtactatt aacatttaga agatttcttt ctttcccaga ttcattgaca    120

atggcggacc ttctttcaaa ctggtcaagc acattagaag cagttcctcc aagtcattgc    180

atcccagtgc atgaaagacc atcggatcca gttgaaattg tggacaatat tccagtcatt    240
```

gatttgggaa aagctaatgg tgaagaacga agtgttgttg ttaaagaact tttgaaagct 300
tttgaagaat atgggttttt tcagataatc aatcatggag tacccgtaga tctaatggat 360
gaagcaatga aagtgtacaa agaatttttc agtctgccag cagcagagaa agcagaatat 420
gcaaaggatg cagctaatga tacaaatagg ggtgcagcta cactgtacag tagcagcgct 480
aagcattatg attcagagga gcatcgttac tggagagatg tcttggaaca tagctgcaat 540
cttgatggga aagacaaaaa aacttggcct agtaaccctc caagatatag ggaggttatt 600
ggtgcatatg gagatgaatt gagaagggtg agcaaagtta tcttgggtct gttagctgaa 660
gggctaggtt tggaggcagg gttctttgac acagaacttg ggcagagaat gcttgtgaat 720
cactatccag catgcccaga tccaagttta accttgggag ttggtggaca ttgtgatcct 780
aatctcataa ccattatcca acaagaagtg tatggtcttc aaatattgaa ggatgacaaa 840
tggattggtg tgcagcctat ccgcaatgca tttgtggtca attctggttt accaattacg 900
gtagttagca atggaaagct aactagtgtt gcacatcgtg tggtgacaaa cacaactcat 960
tcacgaacct ccattggtac ttttatttgc ccacacgata ttgttgagcc tgcaaaagca 1020
cttgttggtc cggagaatcc tccacagttc aaatccttta attggggaat tgattttatg 1080
ccacattacc tcagcaagaa atcagtttac cacgcatcat tggagccctt caaaatcgat 1140
gcttaagcat ttgtgtgcca gaaggatcaa gtctatgctg ctacttttaa tttccactaa 1200
aataagagct ttaatttaca atgtctttct agtttgtatc ctacctttgt tacctatttc 1260
atgaataaga atctttcttt cctattctct tc 1292

<210> SEQ ID NO 28
<211> LENGTH: 220
<212> TYPE: DNA
<213> ORGANISM: Artificial Sequence
<220> FEATURE:
<223> OTHER INFORMATION: Syn. Polynucl.

<400> SEQUENCE: 28
atgagtattg taattgatga tgatgaaatc ttctctttac ctagccttga tgaacttgaa 60
tccatcacac atcttcttta tgacgacgat tccgattttt tcgaaactct ttccccaatg 120
agtttagatg ttacaacatt attgcctaat attcctacct ccaattcaat tgaatccccc 180
gtaacaccgg aggaaacaaa agaaccatct gtggcgtgtg 220

<210> SEQ ID NO 29
<211> LENGTH: 251
<212> TYPE: DNA
<213> ORGANISM: Artificial Sequence
<220> FEATURE:
<223> OTHER INFORMATION: Syn. Polynucl.

<400> SEQUENCE: 29
cggatcttct ctcgaactgg tcaagcacat tagaagcagt tcctaaaagt cattgcatcc 60
cagagcatga aagaccatca gatccagttg aaattggcga cagtattcca gtcattgatt 120
tgggaaaagc taatggtgaa gaacgaagtg ttgttgttaa agatctgttg aaagcttttg 180
aagaatatgg gttttttcag ataatcaatc atggagtacc tgtagatcta atggatgaag 240
caatgaaagt g 251

<210> SEQ ID NO 30
<211> LENGTH: 2142
<212> TYPE: DNA

<213> ORGANISM: Solanum Lycopersicum

<400> SEQUENCE: 30

```
atgaaaaaaa ccatggagct caacaaaagc actgttccac aacctatcac caccgtatac     60
cgactccaca tgttcatcca ctcaataatc atgcttgcat taatatacta ccgtgtatct    120
aatttgttta aattcgaaaa cattctcagt ttacaagcac ttgcttgggc gctcatcact    180
tttggtgaat ttagtttcat tctcaagtgg ttcttcggac aaggtactcg ttggcgcccc    240
gttgaacgag atgttttccc tgaaaacatt acttgcaaag attccgatct accgccaatt    300
gacgtaatgg tattcactgc caatcctaag aaagagccaa ttgtagatgt catgaacact    360
gtgatatccg caatggctct tgattatccc accgataaat tggctgtgta tctcgctgat    420
gatggaggat gtccattgtc gttgtacgcc atggaacaag cgtgtttgtt tgcaaagcta    480
tggttacctt tctgtagaaa ctatggaatt aaaacgagat gcccaaaagc atttttttct    540
ccgttaggag atgatgaccg tgttcttaag aatgatgatt ttgctgctga aatgaaagaa    600
attaaattga aatatgaaga gttccagcag aaggtggaac atgctggtga atctggaaaa    660
atcaatggta acgtagtgcc tgatagagct tcgcttatta aggtaataaa cgagagggag    720
aacgaaaaga gtgtggatga tatgacgaaa atgcccttgc tagtttatgt atcccgtgaa    780
agaagattca accgtcttca tcatttcaag ggtggatctg caaatgctct acttcgagtt    840
tctggaataa tgagtaatgc cccctatgta ctggtgttag attgtgattt cttctgtcat    900
gatccaatat cagctaggaa ggcaatgtgt tttcatcttg atccaaagct atcatctgat    960
ttagcctatg ttcagttccc tcaagtcttt tacaatgtca gcaagtcaga tatttatgat   1020
gtcaaaatta gacaggctta caagacaata tggcatggaa tggatggtat ccaaggccca   1080
gtgttatctg ggactggtta ttttctcaag aggaaagcgt tatacacaag tccaggagta   1140
aaagaggcgt atcttagttc accggaaaag cattttggaa ggagtaaaag gtttcttgct   1200
tcattagagg agaaaaatgg ttatgttaag gcagataaag tcatatcaga agatatcata   1260
gaggaagcta agatgttagc tacttgtgca tatgaggatg gcacacattg gggtcaagag   1320
attggttatt catacgattg tcatttggag agcactttta ctggttatct attacactgc   1380
aaagggtgga catctactta tttgtatcca gacaggccat ctttcttggg ttgtgcccca   1440
gttgatatgc aaggtttctc atcacagctc atcaaatggg ttgctgcact tacacaagct   1500
ggtttatcac atctcaatcc catcacttat ggtttgagta gtaggatgag gactctccaa   1560
tgcatgtgct atgcctattt gatgtatttc actctttatt cttggggaat ggttatgtat   1620
gctagtgttc cttctattgg ccttttgttt gacttccaag tctatcctga ggtacatgat   1680
ccgtggtttg cagtgtatgt gattgctttc atatcgacaa ttttggagaa tatgtcggag   1740
tcaattccag aagggggatc agttaaaacg tggtggatgg aatacagggc attgatgatg   1800
atgggagtta gcgcaatatg gttaggagga ttgaaagcta tatatgacaa gatagtcgga   1860
acacaaggag agaaattgta tttgtcggac aaggcaattg acaaggaaaa gctcaagaaa   1920
tacgagaagg gcaaatttga tttccaagga atagggatac ttgctctgcc actgatagca   1980
ttttccgtgt tgaacctcgt aggcttcatt gttggagcta atcatgtctt tattactatg   2040
aactacgcag gcgtgctggg ccaactcctc gtatcatcgt tcttcgtctt tgttgtcgtc   2100
actgttgtca ttgatgttgt atctttctta aaggtttctt aa                      2142
```

<210> SEQ ID NO 31
<211> LENGTH: 713

<212> TYPE: PRT
<213> ORGANISM: Solanum Lycopersicum

<400> SEQUENCE: 31

Met Lys Lys Thr Met Glu Leu Asn Lys Ser Thr Val Pro Gln Pro Ile
1 5 10 15

Thr Thr Val Tyr Arg Leu His Met Phe Ile His Ser Ile Ile Met Leu
20 25 30

Ala Leu Ile Tyr Tyr Arg Val Ser Asn Leu Phe Lys Phe Glu Asn Ile
35 40 45

Leu Ser Leu Gln Ala Leu Ala Trp Ala Leu Ile Thr Phe Gly Glu Phe
50 55 60

Ser Phe Ile Leu Lys Trp Phe Phe Gly Gln Gly Thr Arg Trp Arg Pro
65 70 75 80

Val Glu Arg Asp Val Phe Pro Glu Asn Ile Thr Cys Lys Asp Ser Asp
85 90 95

Leu Pro Pro Ile Asp Val Met Val Phe Thr Ala Asn Pro Lys Lys Glu
100 105 110

Pro Ile Val Asp Val Met Asn Thr Val Ile Ser Ala Met Ala Leu Asp
115 120 125

Tyr Pro Thr Asp Lys Leu Ala Val Tyr Leu Ala Asp Asp Gly Gly Cys
130 135 140

Pro Leu Ser Leu Tyr Ala Met Glu Gln Ala Cys Leu Phe Ala Lys Leu
145 150 155 160

Trp Leu Pro Phe Cys Arg Asn Tyr Gly Ile Lys Thr Arg Cys Pro Lys
165 170 175

Ala Phe Phe Ser Pro Leu Gly Asp Asp Asp Arg Val Leu Lys Asn Asp
180 185 190

Asp Phe Ala Ala Glu Met Lys Glu Ile Lys Leu Lys Tyr Glu Glu Phe
195 200 205

Gln Gln Lys Val Glu His Ala Gly Glu Ser Gly Lys Ile Asn Gly Asn
210 215 220

Val Val Pro Asp Arg Ala Ser Leu Ile Lys Val Ile Asn Glu Arg Glu
225 230 235 240

Asn Glu Lys Ser Val Asp Asp Met Thr Lys Met Pro Leu Leu Val Tyr
245 250 255

Val Ser Arg Glu Arg Arg Phe Asn Arg Leu His His Phe Lys Gly Gly
260 265 270

Ser Ala Asn Ala Leu Leu Arg Val Ser Gly Ile Met Ser Asn Ala Pro
275 280 285

Tyr Val Leu Val Leu Asp Cys Asp Phe Phe Cys His Asp Pro Ile Ser
290 295 300

Ala Arg Lys Ala Met Cys Phe His Leu Asp Pro Lys Leu Ser Ser Asp
305 310 315 320

Leu Ala Tyr Val Gln Phe Pro Gln Val Phe Tyr Asn Val Ser Lys Ser
325 330 335

Asp Ile Tyr Asp Val Lys Ile Arg Gln Ala Tyr Lys Thr Ile Trp His
340 345 350

Gly Met Asp Gly Ile Gln Gly Pro Val Leu Ser Gly Thr Gly Tyr Phe
355 360 365

Leu Lys Arg Lys Ala Leu Tyr Thr Ser Pro Gly Val Lys Glu Ala Tyr
370 375 380

Leu Ser Ser Pro Glu Lys His Phe Gly Arg Ser Lys Arg Phe Leu Ala
385 390 395 400

```
Ser Leu Glu Glu Lys Asn Gly Tyr Val Lys Ala Asp Lys Val Ile Ser
                405                 410                 415

Glu Asp Ile Ile Glu Glu Ala Lys Met Leu Ala Thr Cys Ala Tyr Glu
            420                 425                 430

Asp Gly Thr His Trp Gly Gln Glu Ile Gly Tyr Ser Tyr Asp Cys His
        435                 440                 445

Leu Glu Ser Thr Phe Thr Gly Tyr Leu Leu His Cys Lys Gly Trp Thr
    450                 455                 460

Ser Thr Tyr Leu Tyr Pro Asp Arg Pro Ser Phe Leu Gly Cys Ala Pro
465                 470                 475                 480

Val Asp Met Gln Gly Phe Ser Ser Gln Leu Ile Lys Trp Val Ala Ala
                485                 490                 495

Leu Thr Gln Ala Gly Leu Ser His Leu Asn Pro Ile Thr Tyr Gly Leu
            500                 505                 510

Ser Ser Arg Met Arg Thr Leu Gln Cys Met Cys Tyr Ala Tyr Leu Met
        515                 520                 525

Tyr Phe Thr Leu Tyr Ser Trp Gly Met Val Met Tyr Ala Ser Val Pro
    530                 535                 540

Ser Ile Gly Leu Leu Phe Asp Phe Gln Val Tyr Pro Glu Val His Asp
545                 550                 555                 560

Pro Trp Phe Ala Val Tyr Val Ile Ala Phe Ile Ser Thr Ile Leu Glu
                565                 570                 575

Asn Met Ser Glu Ser Ile Pro Glu Gly Gly Ser Val Lys Thr Trp Trp
            580                 585                 590

Met Glu Tyr Arg Ala Leu Met Met Met Gly Val Ser Ala Ile Trp Leu
        595                 600                 605

Gly Gly Leu Lys Ala Ile Tyr Asp Lys Ile Val Gly Thr Gln Gly Glu
    610                 615                 620

Lys Leu Tyr Leu Ser Asp Lys Ala Ile Asp Lys Glu Lys Leu Lys Lys
625                 630                 635                 640

Tyr Glu Lys Gly Lys Phe Asp Phe Gln Gly Ile Gly Ile Leu Ala Leu
                645                 650                 655

Pro Leu Ile Ala Phe Ser Val Leu Asn Leu Val Gly Phe Ile Val Gly
            660                 665                 670

Ala Asn His Val Phe Ile Thr Met Asn Tyr Ala Gly Val Leu Gly Gln
        675                 680                 685

Leu Leu Val Ser Ser Phe Phe Val Phe Val Val Val Thr Val Val Ile
    690                 695                 700

Asp Val Val Ser Phe Leu Lys Val Ser
705                 710
```

<210> SEQ ID NO 32
<211> LENGTH: 2142
<212> TYPE: DNA
<213> ORGANISM: Solanum pennellii

<400> SEQUENCE: 32

```
atgaaaaaaa ccatggagct caacaaaagc actgttccac aacctatcac caccgtatac      60

cgactccaca tgttcatcca ctcaataatc atgcttgcat taatatacta ccgtgtatct     120

aatttgttta aattcgaaaa cattctcagt ttacaagcac ttgcttggct actcatcact     180

tttggtgaat ttagtttcat tctcaagtgg ttcttcggac aaggaactcg ttggcgcccc     240

gttgaacgag atgttttccc tgaaaacatt acttgcaaag attccgatct accgccaatt     300
```

```
gacgtaatgg tgttcactgc caatcctaag aaagagccaa ttgtagatgt catgaacact    360
gtgatatccg caatggctct tgattatccc accgataaat tggctgtgta tctggccgat    420
gatggaggat gtccattgtc cttgtacgcc atggaacaag catgtttgtt tgcaaagcta    480
tggttacctt tctgtagaaa gtatggaatt aaaacgagat gcccaaaagc atttttttct    540
ccgttaggag atgatgaccg tgttcttaag aatgatgatt ttgctgctga aatgaaagaa    600
attaaattga aatatgaaga gttccagcag aacgtggaac atgctggtga atctggaaaa    660
atcaatggca acgtagtgcc tgacagagct tcgcttatta aggtaataaa cgagagggag    720
aacgaaaaga gtgtcgatga tttaacgaaa atgcccttgc tagtttatgt atcccgtgaa    780
agaagattca accgtcttca tcatttcaag ggtggatctg caaatgctct acttcgagtt    840
tctggaataa tgagtaatgc cccctatgta ctggtgttag attgtgattt cttctgtcat    900
gatccgatat cagctaggaa agcaatgtgt tttcatcttg atccaaagct atcatctgat    960
ttagcctatg ttcagttccc tcaagtcttt tacaatgtca gcaagtccga tatttatgat   1020
gtcaaaatta gacaggctta caagacaata tggcatggaa tggatggtat ccaaggccca   1080
gtgttatctg gaactggtta ttttctcaag aggaaggcgt tatacacaag tccaggagta   1140
aaagaggcgt atcttagttc accggaaaag cattttggaa ggagtaaaaa gttccttgct   1200
tcattagagg agaaaaatgg ttatgttaag gcagataaag tcatatcaga agatatcata   1260
gaggaagcta agatcttagc tacttgtgca tatgaggatg gcacacattg gggtcaagag   1320
attggttatt catacgattg tcatttggag agcactttta ctggttatct attacactgc   1380
aaagggtgga catctactta tttgtatcca gacaggccat ctttcttggg ttgtgcccca   1440
gttgatatgc aaggtttctc atcacagctc ataaaatggg ttgctgcact tacacaagct   1500
ggtctatcac atctcaatcc catcacttat ggtttgagta gtaggatgag aactctccaa   1560
tgcatgtgct atgcctattt gatgtatttc actctttatt cttggggaat ggttatgtat   1620
gctagtgttc cttctattgg ccttttgttt ggcttccaag tctaccctga ggtacatgat   1680
ccatggtttg cagtgtatgt gattgctttc atatcgacaa ttttggagaa tatgtcggag   1740
tcaattccag aagggggatc agttaaaacg tggtggatgg aatacagggc attgatgatg   1800
atgggagtta gcgcaatatg gttaggagga ttgaaagcta tatatgacaa gatagtcgga   1860
acacaaggag agaaattgta tttgtcggac aaggcaattg acaaggaaaa gctcaagaaa   1920
tacgagaagg gcaaatttga tttccaagga atagggatac ttgctctgcc attgatagca   1980
ttttccgtgt tgaacctcgt aggcttcatt gttggagcta atcatgtctt tattactatg   2040
aactacgcag gcgtgctggg ccaactcctc gtatcatcat tcttcgtctt tgttgtcgtc   2100
actgttgtca ttgatgttgt atctttctta aaggtttctt aa                      2142
```

<210> SEQ ID NO 33
<211> LENGTH: 713
<212> TYPE: PRT
<213> ORGANISM: Solanum pennellii

<400> SEQUENCE: 33

```
Met Lys Lys Thr Met Glu Leu Asn Lys Ser Thr Val Pro Gln Pro Ile
1               5                   10                  15

Thr Thr Val Tyr Arg Leu His Met Phe Ile His Ser Ile Ile Met Leu
            20                  25                  30

Ala Leu Ile Tyr Tyr Arg Val Ser Asn Leu Phe Lys Phe Glu Asn Ile
        35                  40                  45
```

-continued

```
Leu Ser Leu Gln Ala Leu Ala Trp Leu Leu Ile Thr Phe Gly Glu Phe
    50                  55                  60

Ser Phe Ile Leu Lys Trp Phe Phe Gly Gln Gly Thr Arg Trp Arg Pro
65                  70                  75                  80

Val Glu Arg Asp Val Phe Pro Glu Asn Ile Thr Cys Lys Asp Ser Asp
                85                  90                  95

Leu Pro Pro Ile Asp Val Met Val Phe Thr Ala Asn Pro Lys Lys Glu
            100                 105                 110

Pro Ile Val Asp Val Met Asn Thr Val Ile Ser Ala Met Ala Leu Asp
        115                 120                 125

Tyr Pro Thr Asp Lys Leu Ala Val Tyr Leu Ala Asp Asp Gly Gly Cys
    130                 135                 140

Pro Leu Ser Leu Tyr Ala Met Glu Gln Ala Cys Leu Phe Ala Lys Leu
145                 150                 155                 160

Trp Leu Pro Phe Cys Arg Lys Tyr Gly Ile Lys Thr Arg Cys Pro Lys
                165                 170                 175

Ala Phe Phe Ser Pro Leu Gly Asp Asp Asp Arg Val Leu Lys Asn Asp
            180                 185                 190

Asp Phe Ala Ala Glu Met Lys Glu Ile Lys Leu Lys Tyr Glu Glu Phe
        195                 200                 205

Gln Gln Asn Val Glu His Ala Gly Glu Ser Gly Lys Ile Asn Gly Asn
    210                 215                 220

Val Val Pro Asp Arg Ala Ser Leu Ile Lys Val Ile Asn Glu Arg Glu
225                 230                 235                 240

Asn Glu Lys Ser Val Asp Asp Leu Thr Lys Met Pro Leu Leu Val Tyr
                245                 250                 255

Val Ser Arg Glu Arg Arg Phe Asn Arg Leu His His Phe Lys Gly Gly
            260                 265                 270

Ser Ala Asn Ala Leu Leu Arg Val Ser Gly Ile Met Ser Asn Ala Pro
        275                 280                 285

Tyr Val Leu Val Leu Asp Cys Asp Phe Phe Cys His Asp Pro Ile Ser
    290                 295                 300

Ala Arg Lys Ala Met Cys Phe His Leu Asp Pro Lys Leu Ser Ser Asp
305                 310                 315                 320

Leu Ala Tyr Val Gln Phe Pro Gln Val Phe Tyr Asn Val Ser Lys Ser
                325                 330                 335

Asp Ile Tyr Asp Val Lys Ile Arg Gln Ala Tyr Lys Thr Ile Trp His
            340                 345                 350

Gly Met Asp Gly Ile Gln Gly Pro Val Leu Ser Gly Thr Gly Tyr Phe
        355                 360                 365

Leu Lys Arg Lys Ala Leu Tyr Thr Ser Pro Gly Val Lys Glu Ala Tyr
    370                 375                 380

Leu Ser Ser Pro Glu Lys His Phe Gly Arg Ser Lys Lys Phe Leu Ala
385                 390                 395                 400

Ser Leu Glu Glu Lys Asn Gly Tyr Val Lys Ala Asp Lys Val Ile Ser
                405                 410                 415

Glu Asp Ile Ile Glu Glu Ala Lys Ile Leu Ala Thr Cys Ala Tyr Glu
            420                 425                 430

Asp Gly Thr His Trp Gly Gln Glu Ile Gly Tyr Ser Tyr Asp Cys His
        435                 440                 445

Leu Glu Ser Thr Phe Thr Gly Tyr Leu Leu His Cys Lys Gly Trp Thr
    450                 455                 460

Ser Thr Tyr Leu Tyr Pro Asp Arg Pro Ser Phe Leu Gly Cys Ala Pro
```

```
465                 470                 475                 480

Val Asp Met Gln Gly Phe Ser Ser Gln Leu Ile Lys Trp Val Ala Ala
                485                 490                 495

Leu Thr Gln Ala Gly Leu Ser His Leu Asn Pro Ile Thr Tyr Gly Leu
            500                 505                 510

Ser Ser Arg Met Arg Thr Leu Gln Cys Met Cys Tyr Ala Tyr Leu Met
        515                 520                 525

Tyr Phe Thr Leu Tyr Ser Trp Gly Met Val Met Tyr Ala Ser Val Pro
    530                 535                 540

Ser Ile Gly Leu Leu Phe Gly Phe Gln Val Tyr Pro Glu Val His Asp
545                 550                 555                 560

Pro Trp Phe Ala Val Tyr Val Ile Ala Phe Ile Ser Thr Ile Leu Glu
                565                 570                 575

Asn Met Ser Glu Ser Ile Pro Glu Gly Gly Ser Val Lys Thr Trp Trp
            580                 585                 590

Met Glu Tyr Arg Ala Leu Met Met Met Gly Val Ser Ala Ile Trp Leu
        595                 600                 605

Gly Gly Leu Lys Ala Ile Tyr Asp Lys Ile Val Gly Thr Gln Gly Glu
    610                 615                 620

Lys Leu Tyr Leu Ser Asp Lys Ala Ile Asp Lys Glu Lys Leu Lys Lys
625                 630                 635                 640

Tyr Glu Lys Gly Lys Phe Asp Phe Gln Gly Ile Gly Ile Leu Ala Leu
                645                 650                 655

Pro Leu Ile Ala Phe Ser Val Leu Asn Leu Val Gly Phe Ile Val Gly
            660                 665                 670

Ala Asn His Val Phe Ile Thr Met Asn Tyr Ala Gly Val Leu Gly Gln
        675                 680                 685

Leu Leu Val Ser Ser Phe Phe Val Phe Val Val Val Thr Val Val Ile
    690                 695                 700

Asp Val Val Ser Phe Leu Lys Val Ser
705                 710
```

<210> SEQ ID NO 34
<211> LENGTH: 2148
<212> TYPE: DNA
<213> ORGANISM: Solanum tuberosum

<400> SEQUENCE: 34

```
atgaaaaaaa ccatggagct caacaaaagc actgttccac aacctatcac caccatatac     60

cgactccaca tgtttatcca ctctataatc atggttgcat taatatacta ccgtgtatct    120

aatttgttta aattcgaaaa cattctgagt ttacaagcac ttgcttgggt actcatcact    180

tttggtgaat ttagtttcat tctcaagtgg ttcttcggac aaggaactcg ttatcgccct    240

gttgaaagag atgttttccc tgaaaacata acttgcaaag attccgatct accaccaatt    300

gacgtaatgg tattcactgc caatcctaag aaagagccaa ttgtggatgt catgaacact    360

gtgatatccg caatggctct tgattatcct acggataaat tggctgtgta tctggctgat    420

gatggaggat gtcctttgtc attgtacgcc atggaagaag catgtgtgtt tgcaaagctg    480

tggctacctt tctgtaggaa gtatggaatt aaaactagat gccctaaagc gttttttttct    540

cctttaggag atgatgaacg tgttcttaag aatgatgatt ttgatgctga aatgaaagaa    600

attaaattga aatatgaaga gttccagcag aatgtggaac gtgctggtga atctggaaaa    660

atcaatggta acgtagtgcc tgatagagcc tcgtttatta aggtaataaa cgacagaaaa    720
```

gcggagagcg aaaagagtgc cgatgattta acgaaaatgc ccttgctagt ttatgtatcc 780
cgtgaaagaa gattcaaccg tcttcatcac ttcaagggtg gatctgcaaa tgctcttctt 840
cgagtttctg gaataatgag taatgccccc tatatactgg tgttagattg tgatttcttc 900
tgtcatgatc caatatcagc taggaaggca atgtgttttc atcttgatcc aaagctatca 960
tctgatttag cttatgttca gttccctcaa gtcttttaca atgtcagcaa gtccgatatt 1020
tatgatgtca aaattagaca ggcttacaag acaatatggc atggaatgga tggtatccaa 1080
ggcccagtgt tatcaggaac tggttatttt ctgaagagga aggcgttata cacgagtcca 1140
ggagtaaagg aggagtatct tagttcaccg gaaaagcatt ttggaaggag taaaaagttc 1200
cttgcttcac tagaggagaa aaatggttat gttaaggcag agaaagtcat atcagaagat 1260
atcgtagagg aagctaagac cttagctact tgtgcatatg aggatggcac acattggggt 1320
caagagattg gttattcata cgattgtcat ttggagagca cttttactgg ttatctatta 1380
cactgcaaag ggtggagatc gacttatttg tatccagaca ggccatcttt cttgggttgt 1440
gccccagttg atatgcaagg tttctcctca cagctcataa aatgggttgc tgcacttaca 1500
caagctggtt tatcacatct caatcccatc acttatggct ttagtagcag gatgaaaact 1560
ctccaatgca tgtgctatgc ctatttgata tatttcactc tttattcttg gggaatggtt 1620
ctatatgcta gtgttccttc tattggcctt ttgtttggct tccaagtcta tcccgatgta 1680
catgatccat ggtttgcagt gtatgtgatt gctttcatat cggcaatttt ggagaatatg 1740
tcggagtcaa ttcctgatgg gggatcattt aaatcttggt ggatggaata cagggcactg 1800
atgatgatgg gagttagtgc aatatggtta ggaggattga aagctatatt agacaggata 1860
atcggaacag aaggagagaa attgtattta tcggacaagg caattgacaa ggaaaagctc 1920
aagaaatacg agaaggggaa atttgatttc caaggaatag ggatacttgc tgtaccattg 1980
atagcatttt ccttgttgaa cctcgtaggc ttcattgttg gagctaatca tgtctttatt 2040
actatgaact acgcaggtgt gcttggccaa ctcctcgtat catccttctt cgtctttgtc 2100
gtggtcactg ttgtcattga tgtcgtttct ttcttaaagg tttcttaa 2148

<210> SEQ ID NO 35
<211> LENGTH: 711
<212> TYPE: PRT
<213> ORGANISM: Solanum tuberosum

<400> SEQUENCE: 35

Met Glu Leu Asn Lys Ser Thr Val Pro Gln Pro Ile Thr Thr Ile Tyr
1 5 10 15

Arg Leu His Met Phe Ile His Ser Ile Ile Met Val Ala Leu Ile Tyr
20 25 30

Tyr Arg Val Ser Asn Leu Phe Lys Phe Glu Asn Ile Leu Ser Leu Gln
35 40 45

Ala Leu Ala Trp Val Leu Ile Thr Phe Gly Glu Phe Ser Phe Ile Leu
50 55 60

Lys Trp Phe Phe Gly Gln Gly Thr Arg Tyr Arg Pro Val Glu Arg Asp
65 70 75 80

Val Phe Pro Glu Asn Ile Thr Cys Lys Asp Ser Asp Leu Pro Pro Ile
85 90 95

Asp Val Met Val Phe Thr Ala Asn Pro Lys Lys Glu Pro Ile Val Asp
100 105 110

Val Met Asn Thr Val Ile Ser Ala Met Ala Leu Asp Tyr Pro Thr Asp
115 120 125

-continued

```
Lys Leu Ala Val Tyr Leu Ala Asp Asp Gly Gly Cys Pro Leu Ser Leu
    130                 135                 140

Tyr Ala Met Glu Glu Ala Cys Val Phe Ala Lys Leu Trp Leu Pro Phe
145                 150                 155                 160

Cys Arg Lys Tyr Gly Ile Lys Thr Arg Cys Pro Lys Ala Phe Phe Ser
                165                 170                 175

Pro Leu Gly Asp Asp Glu Arg Val Leu Lys Asn Asp Asp Phe Asp Ala
            180                 185                 190

Glu Met Lys Glu Ile Lys Leu Lys Tyr Glu Glu Phe Gln Gln Asn Val
        195                 200                 205

Glu Arg Ala Gly Glu Ser Gly Lys Ile Asn Gly Asn Val Val Pro Asp
    210                 215                 220

Arg Ala Ser Phe Ile Lys Val Ile Asn Asp Arg Lys Ala Glu Ser Glu
225                 230                 235                 240

Lys Ser Ala Asp Asp Leu Thr Lys Met Pro Leu Leu Val Tyr Val Ser
                245                 250                 255

Arg Glu Arg Arg Phe Asn Arg Leu His His Phe Lys Gly Gly Ser Ala
            260                 265                 270

Asn Ala Leu Leu Arg Val Ser Gly Ile Met Ser Asn Ala Pro Tyr Ile
        275                 280                 285

Leu Val Leu Asp Cys Asp Phe Phe Cys His Asp Pro Ile Ser Ala Arg
    290                 295                 300

Lys Ala Met Cys Phe His Leu Asp Pro Lys Leu Ser Ser Asp Leu Ala
305                 310                 315                 320

Tyr Val Gln Phe Pro Gln Val Phe Tyr Asn Val Ser Lys Ser Asp Ile
                325                 330                 335

Tyr Asp Val Lys Ile Arg Gln Ala Tyr Lys Thr Ile Trp His Gly Met
            340                 345                 350

Asp Gly Ile Gln Gly Pro Val Leu Ser Gly Thr Gly Tyr Phe Leu Lys
        355                 360                 365

Arg Lys Ala Leu Tyr Thr Ser Pro Gly Val Lys Glu Glu Tyr Leu Ser
    370                 375                 380

Ser Pro Glu Lys His Phe Gly Arg Ser Lys Lys Phe Leu Ala Ser Leu
385                 390                 395                 400

Glu Glu Lys Asn Gly Tyr Val Lys Ala Glu Lys Val Ile Ser Glu Asp
                405                 410                 415

Ile Val Glu Glu Ala Lys Thr Leu Ala Thr Cys Ala Tyr Glu Asp Gly
            420                 425                 430

Thr His Trp Gly Gln Glu Ile Gly Tyr Ser Tyr Asp Cys His Leu Glu
        435                 440                 445

Ser Thr Phe Thr Gly Tyr Leu Leu His Cys Lys Gly Trp Arg Ser Thr
    450                 455                 460

Tyr Leu Tyr Pro Asp Arg Pro Ser Phe Leu Gly Cys Ala Pro Val Asp
465                 470                 475                 480

Met Gln Gly Phe Ser Ser Gln Leu Ile Lys Trp Val Ala Ala Leu Thr
                485                 490                 495

Gln Ala Gly Leu Ser His Leu Asn Pro Ile Thr Tyr Gly Phe Ser Ser
            500                 505                 510

Arg Met Lys Thr Leu Gln Cys Met Cys Tyr Ala Tyr Leu Ile Tyr Phe
        515                 520                 525

Thr Leu Tyr Ser Trp Gly Met Val Leu Tyr Ala Ser Val Pro Ser Ile
    530                 535                 540
```

```
Gly Leu Leu Phe Gly Phe Gln Val Tyr Pro Asp Val His Asp Pro Trp
545                 550                 555                 560

Phe Ala Val Tyr Val Ile Ala Phe Ile Ser Ala Ile Leu Glu Asn Met
                565                 570                 575

Ser Glu Ser Ile Pro Asp Gly Gly Ser Phe Lys Ser Trp Trp Met Glu
            580                 585                 590

Tyr Arg Ala Leu Met Met Met Gly Val Ser Ala Ile Trp Leu Gly Gly
        595                 600                 605

Leu Lys Ala Ile Leu Asp Arg Ile Ile Gly Thr Glu Gly Glu Lys Leu
    610                 615                 620

Tyr Leu Ser Asp Lys Ala Ile Asp Lys Glu Lys Leu Lys Lys Tyr Glu
625                 630                 635                 640

Lys Gly Lys Phe Asp Phe Gln Gly Ile Gly Ile Leu Ala Val Pro Leu
                645                 650                 655

Ile Ala Phe Ser Leu Leu Asn Leu Val Gly Phe Ile Val Gly Ala Asn
            660                 665                 670

His Val Phe Ile Thr Met Asn Tyr Ala Gly Val Leu Gly Gln Leu Leu
        675                 680                 685

Val Ser Ser Phe Phe Val Phe Val Val Val Thr Val Val Ile Asp Val
    690                 695                 700

Val Ser Phe Leu Lys Val Ser
705                 710


<210> SEQ ID NO 36
<211> LENGTH: 2148
<212> TYPE: DNA
<213> ORGANISM: Solanum chacoense

<400> SEQUENCE: 36

atgaaaaaaa ccatggagct caacaaaagc actgttccac aacctatcac caccatatac      60

cgactccaca tgttcgtcca ttctataatc atggctgcat taatatacta ccgtgtatct     120

aatttgttta aattcgaaaa cattctgagt ttacaagcac ttgcttgggt actcatcact     180

tttggtgaat ttagtttcat tctcaagtgg ttcttcggac aaggaactcg ttggcgccct     240

gttgaaagag atgttttccc tgaaaacata acttgcaaag attccgatct accaccaatt     300

gacgtaatgg tattcactgc caatcctaag aaagagccaa ttgtggatgt catgaacact     360

gtgatatccg caatggctct agattatcct acggataaat tggctgtgta tctggctgat     420

gatggaggat gtcctttgtc attgtacgcc atggaagaag catgtgtgtt tgcaaagctg     480

tggctacctt tctgtaggaa gtatggaatt aaaaccagat gccctaaagc gttttttct      540

cctttaggag atgatgaccg tgttcttaag aatgatgatt ttgatgctga aatgaaagaa     600

attaaattga aatatgaaga gttccagcag aatgtggaac gtgctggtga atctggaaaa     660

atcaatggta acgtagtgcc tgatagagcc tcgtttatta aggtaataaa cgacagaaaa     720

acggagagcg aaaagagtgc cgatgattta acgaaaatgc ccttgctagt ttatgtatcc     780

cgtgaaagaa gattcaaccg tcttcatcac ttcaagggtg gatctgcaaa tgctcttctt     840

cgagtttctg gaataatgag taatgccccc tatatactgg tgttagattg tgatttcttc     900

tgtcatgatc caatatcagc taggaaggca atgtgttttc atcttgatcc aaagctatca     960

tctgatttag cttatgttca gttccctcaa gtcttttaca atgtcagcaa gtccgatatt    1020

tatgatgtca aaattagaca ggcttacaag acaatatggc atggaatgga tggtatccaa    1080

ggcccagtgt tatcaggaac tggttatttt ctgaagagga aggcgttata cacgagtcca    1140
```

```
ggagtaaagg aggagtatct tagttcaccg gaaaagcatt ttggaaggag taaaaagttc   1200

cttgcttcac tagaggagaa aaatggttat gttaaggcag agaaagtcat atcagaagat   1260

atcgtagagg aagctaagac cttagctact tgtgcatatg aggatggtac acattggggt   1320

caagagatcg gttattcata cgattgtcat ttggagagca cttttactgg ttatctatta   1380

cactgcaaag ggtggacatc gacttatttg tatccagaca ggccatcttt cttgggttgt   1440

gctccagttg atatgcaagg tttctcctca cagctcataa aatgggttgc tgcacttaca   1500

caagctggtt tatcacatct caatcccatc acttatggct tgagtagcag gatgaaaact   1560

ctccaatgca tgtgctatgc ctatttgata tatttcactc tttattcttg ggaatggtt    1620

ctatatgcta gtattccttc tattggtctt ttgtttggct tccaagtcta tccggaggta   1680

catgatccat ggtttgcagt gtatgtgatt gctttcatat cgacaatttt ggagaatatg   1740

tcggagtcaa ttccagaagg gggatcattt aaatcgtggt ggatggaata cagggcactg   1800

atgatgatgg gagttagtgc aatatggtta ggaggattga aagctatatt agacaagata   1860

atcggaacag aaggagagaa attgtatttg tcagacaagg caattgacaa ggaaaagctc   1920

aagaaatacg agaaggggaa atttgatttc caaggaatag ggatacttgc tgtaccattg   1980

atagcatttt ccctgttgaa cctggtaggc ttcattgttg gagctaatca tgtctttatt   2040

actatgaact acgcaggtgt gcttggccaa ctcctcgtat catccttctt cgtctttgtc   2100

gtggtcactg ttgtcattga tgtcgtttct ttcttaaagg tttcttaa               2148
```

<210> SEQ ID NO 37
<211> LENGTH: 715
<212> TYPE: PRT
<213> ORGANISM: Solanum chacoense

<400> SEQUENCE: 37

```
Met Lys Lys Thr Met Glu Leu Asn Lys Ser Thr Val Pro Gln Pro Ile
1               5                   10                  15

Thr Thr Ile Tyr Arg Leu His Met Phe Val His Ser Ile Ile Met Ala
            20                  25                  30

Ala Leu Ile Tyr Tyr Arg Val Ser Asn Leu Phe Lys Phe Glu Asn Ile
        35                  40                  45

Leu Ser Leu Gln Ala Leu Ala Trp Val Leu Ile Thr Phe Gly Glu Phe
    50                  55                  60

Ser Phe Ile Leu Lys Trp Phe Phe Gly Gln Gly Thr Arg Trp Arg Pro
65                  70                  75                  80

Val Glu Arg Asp Val Phe Pro Glu Asn Ile Thr Cys Lys Asp Ser Asp
                85                  90                  95

Leu Pro Pro Ile Asp Val Met Val Phe Thr Ala Asn Pro Lys Lys Glu
            100                 105                 110

Pro Ile Val Asp Val Met Asn Thr Val Ile Ser Ala Met Ala Leu Asp
        115                 120                 125

Tyr Pro Thr Asp Lys Leu Ala Val Tyr Leu Ala Asp Asp Gly Gly Cys
    130                 135                 140

Pro Leu Ser Leu Tyr Ala Met Glu Glu Ala Cys Val Phe Ala Lys Leu
145                 150                 155                 160

Trp Leu Pro Phe Cys Arg Lys Tyr Gly Ile Lys Thr Arg Cys Pro Lys
                165                 170                 175

Ala Phe Phe Ser Pro Leu Gly Asp Asp Asp Arg Val Leu Lys Asn Asp
            180                 185                 190

Asp Phe Asp Ala Glu Met Lys Glu Ile Lys Leu Lys Tyr Glu Glu Phe
```

-continued

```
        195                 200                 205

Gln Gln Asn Val Glu Arg Ala Gly Glu Ser Gly Lys Ile Asn Gly Asn
    210                 215                 220

Val Val Pro Asp Arg Ala Ser Phe Ile Lys Val Ile Asn Asp Arg Lys
225                 230                 235                 240

Thr Glu Ser Glu Lys Ser Ala Asp Asp Leu Thr Lys Met Pro Leu Leu
                245                 250                 255

Val Tyr Val Ser Arg Glu Arg Arg Phe Asn Arg Leu His His Phe Lys
            260                 265                 270

Gly Gly Ser Ala Asn Ala Leu Leu Arg Val Ser Gly Ile Met Ser Asn
        275                 280                 285

Ala Pro Tyr Ile Leu Val Leu Asp Cys Asp Phe Phe Cys His Asp Pro
    290                 295                 300

Ile Ser Ala Arg Lys Ala Met Cys Phe His Leu Asp Pro Lys Leu Ser
305                 310                 315                 320

Ser Asp Leu Ala Tyr Val Gln Phe Pro Gln Val Phe Tyr Asn Val Ser
                325                 330                 335

Lys Ser Asp Ile Tyr Asp Val Lys Ile Arg Gln Ala Tyr Lys Thr Ile
            340                 345                 350

Trp His Gly Met Asp Gly Ile Gln Gly Pro Val Leu Ser Gly Thr Gly
        355                 360                 365

Tyr Phe Leu Lys Arg Lys Ala Leu Tyr Thr Ser Pro Gly Val Lys Glu
    370                 375                 380

Glu Tyr Leu Ser Ser Pro Glu Lys His Phe Gly Arg Ser Lys Lys Phe
385                 390                 395                 400

Leu Ala Ser Leu Glu Glu Lys Asn Gly Tyr Val Lys Ala Glu Lys Val
                405                 410                 415

Ile Ser Glu Asp Ile Val Glu Glu Ala Lys Thr Leu Ala Thr Cys Ala
            420                 425                 430

Tyr Glu Asp Gly Thr His Trp Gly Gln Glu Ile Gly Tyr Ser Tyr Asp
        435                 440                 445

Cys His Leu Glu Ser Thr Phe Thr Gly Tyr Leu Leu His Cys Lys Gly
    450                 455                 460

Trp Thr Ser Thr Tyr Leu Tyr Pro Asp Arg Pro Ser Phe Leu Gly Cys
465                 470                 475                 480

Ala Pro Val Asp Met Gln Gly Phe Ser Ser Gln Leu Ile Lys Trp Val
                485                 490                 495

Ala Ala Leu Thr Gln Ala Gly Leu Ser His Leu Asn Pro Ile Thr Tyr
            500                 505                 510

Gly Leu Ser Ser Arg Met Lys Thr Leu Gln Cys Met Cys Tyr Ala Tyr
        515                 520                 525

Leu Ile Tyr Phe Thr Leu Tyr Ser Trp Gly Met Val Leu Tyr Ala Ser
    530                 535                 540

Ile Pro Ser Ile Gly Leu Leu Phe Gly Phe Gln Val Tyr Pro Glu Val
545                 550                 555                 560

His Asp Pro Trp Phe Ala Val Tyr Val Ile Ala Phe Ile Ser Thr Ile
                565                 570                 575

Leu Glu Asn Met Ser Glu Ser Ile Pro Glu Gly Gly Ser Phe Lys Ser
            580                 585                 590

Trp Trp Met Glu Tyr Arg Ala Leu Met Met Met Gly Val Ser Ala Ile
        595                 600                 605

Trp Leu Gly Gly Leu Lys Ala Ile Leu Asp Lys Ile Ile Gly Thr Glu
    610                 615                 620
```

Gly Glu Lys Leu Tyr Leu Ser Asp Lys Ala Ile Asp Lys Glu Lys Leu
625 630 635 640

Lys Lys Tyr Glu Lys Gly Lys Phe Asp Phe Gln Gly Ile Gly Ile Leu
645 650 655

Ala Val Pro Leu Ile Ala Phe Ser Leu Leu Asn Leu Val Gly Phe Ile
660 665 670

Val Gly Ala Asn His Val Phe Ile Thr Met Asn Tyr Ala Gly Val Leu
675 680 685

Gly Gln Leu Leu Val Ser Ser Phe Phe Val Phe Val Val Val Thr Val
690 695 700

Val Ile Asp Val Val Ser Phe Leu Lys Val Ser
705 710 715

<210> SEQ ID NO 38
<211> LENGTH: 2058
<212> TYPE: DNA
<213> ORGANISM: Solanum melongena

<400> SEQUENCE: 38
atgaaaaaac aaatggagct caacagaagt gttgtaccgc aacctatcac caccatttac 60
cgtctccaca tgtttatcca tgccctaatc atgctagcac taatatacta ccgtgtctct 120
aatttggcca aattcgaaaa catcctcagt ttacaagcac ttgcttgggc tcttatcacg 180
ttaggtgaac tttgtttcat agtcaagtgg ttcttcggac aagggactcg ttggcgtcct 240
gttgataggg atgtcttccc tgaaaacatc acttgtccag attccgagct accccccatt 300
gatgtcatgg ttttcactgc aaatcctaag aaagagccaa ttgtggatgt catgaacact 360
gtcatatccg caatggctct tgattacccg accgacaaat tggccgttta tttgtctgat 420
gatggaggat gccccttgac gttgtacgca atggaggaag cttgttcctt tgccaagttg 480
tggctacctt tttgtaggaa gtatggaatc aaaacaaggt gccctaaggc gttttttttct 540 ccattaggag aagatgaccg tgtattgaag agtgatgact ttgtttctga aatgaaagaa 600
atgaagtcaa aatatgaaga gttccagcag aacgtggacc gtgctggtga atccggaaaa 660
atcaaaggtg acgtagtgcc tgatagaccc gcgtttctta aggtactaaa tgacaggaag 720
acggagaacg agaagagtgc agacgattta actaaaatgc ctttgctagt atacgtatcc 780
cgtgaaagaa gaactcaccg tcgccatcac ttcaagggtg gatctgcaaa tgctcttctt 840
cgagtttctg ggataatcag taatgccccc tatatactgg ttttagattg tgatttcttc 900
tgtcatgatc caatatcagc tcggaaggca atgtgtttcc atcttgatcc aaaactatca 960
cctgacttag cttacgtgca gttccctcaa gtgttttaca atgttagcaa gtccgatatt 1020
tacgacgtca aaattagaca ggcttacaag acaatatggc acgggatgga tggtatccaa 1080
ggcccagtgt tatcgggaac tggttatttt ttaaaaaaga aggcgttgta cacgagtcca 1140
ggtctaaaag atgagtatct tagttcaccg gaaaagcatt tcggaacgag tagaaagttc 1200
attgcttcac tagaggagaa taattatgtt aagcaagaga aagtcatatc agaagatatc 1260
atagaggaag ctaagagact ggctacttgt gcatacgagg atggcacaca ttggggtcaa 1320
gaggcaaaca ggccatcttt cttgggttgt gccccagttg atatgcaagg tttctcctca 1380
cagctcataa aatgggttgc tgcactcaca caagcaggtc tatcacatct caatcccatc 1440
acttacggct tcaagagcag aatgagaact ctccaagtct tgtgttatgc ctatttgatg 1500
tatttctctc tttattcttg gggaatggtt ctacatgcta gtgttccttc tattggcctt 1560

```
ctctctggca ttaaaatcta cccggaggtg tatgatccat ggtttgttgt gtatgtgatt   1620

gctttcatat caacaatttt ggagaatatg tcggaatcaa ttccggaagg gggatcggtt   1680

aaaacgtggt ggatggaata cagggcactg atgatgatgg gagttagtgc aatatggcta   1740

ggaggagtga aagccatagt agacaagatc atcggaacgc aaggagagaa attgtatttg   1800

tcggacaaag caattgacaa ggaaaagctc aagaaatacg agaaggggaa atttgatttc   1860

caaggaatag gaatacttgc tgtaccattg ataacatttt ctgtgttgaa cctggtaggc   1920

ttcttggttg gaattaatca agtgttgata acgatgaagt tcgcaggcgt gctgggccaa   1980

ctcctcgtat catccttctt cgtctttgtc gtcgttactg ttgtcattga tgtcgtatct   2040

ttcttaaagg attcttaa                                                 2058
```

<210> SEQ ID NO 39
<211> LENGTH: 685
<212> TYPE: PRT
<213> ORGANISM: Solanum melongena

<400> SEQUENCE: 39

```
Met Lys Lys Gln Met Glu Leu Asn Arg Ser Val Val Pro Gln Pro Ile
1               5                   10                  15

Thr Thr Ile Tyr Arg Leu His Met Phe Ile His Ala Leu Ile Met Leu
            20                  25                  30

Ala Leu Ile Tyr Tyr Arg Val Ser Asn Leu Ala Lys Phe Glu Asn Ile
        35                  40                  45

Leu Ser Leu Gln Ala Leu Ala Trp Ala Leu Ile Thr Leu Gly Glu Leu
    50                  55                  60

Cys Phe Ile Val Lys Trp Phe Phe Gly Gln Gly Thr Arg Trp Arg Pro
65                  70                  75                  80

Val Asp Arg Asp Val Phe Pro Glu Asn Ile Thr Cys Pro Asp Ser Glu
                85                  90                  95

Leu Pro Pro Ile Asp Val Met Val Phe Thr Ala Asn Pro Lys Lys Glu
            100                 105                 110

Pro Ile Val Asp Val Met Asn Thr Val Ile Ser Ala Met Ala Leu Asp
        115                 120                 125

Tyr Pro Thr Asp Lys Leu Ala Val Tyr Leu Ser Asp Asp Gly Gly Cys
    130                 135                 140

Pro Leu Thr Leu Tyr Ala Met Glu Glu Ala Cys Ser Phe Ala Lys Leu
145                 150                 155                 160

Trp Leu Pro Phe Cys Arg Lys Tyr Gly Ile Lys Thr Arg Cys Pro Lys
                165                 170                 175

Ala Phe Phe Ser Pro Leu Gly Glu Asp Asp Arg Val Leu Lys Ser Asp
            180                 185                 190

Asp Phe Val Ser Glu Met Lys Glu Met Lys Ser Lys Tyr Glu Glu Phe
        195                 200                 205

Gln Gln Asn Val Asp Arg Ala Gly Glu Ser Gly Lys Ile Lys Gly Asp
    210                 215                 220

Val Val Pro Asp Arg Pro Ala Phe Leu Lys Val Leu Asn Asp Arg Lys
225                 230                 235                 240

Thr Glu Asn Glu Lys Ser Ala Asp Asp Leu Thr Lys Met Pro Leu Leu
                245                 250                 255

Val Tyr Val Ser Arg Glu Arg Arg Thr His Arg Arg His His Phe Lys
            260                 265                 270

Gly Gly Ser Ala Asn Ala Leu Leu Arg Val Ser Gly Ile Ile Ser Asn
        275                 280                 285
```

```
Ala Pro Tyr Ile Leu Val Leu Asp Cys Asp Phe Phe Cys His Asp Pro
    290                 295                 300

Ile Ser Ala Arg Lys Ala Met Cys Phe His Leu Asp Pro Lys Leu Ser
305                 310                 315                 320

Pro Asp Leu Ala Tyr Val Gln Phe Pro Gln Val Phe Tyr Asn Val Ser
                325                 330                 335

Lys Ser Asp Ile Tyr Asp Val Lys Ile Arg Gln Ala Tyr Lys Thr Ile
            340                 345                 350

Trp His Gly Met Asp Gly Ile Gln Gly Pro Val Leu Ser Gly Thr Gly
        355                 360                 365

Tyr Phe Leu Lys Lys Lys Ala Leu Tyr Thr Ser Pro Gly Leu Lys Asp
    370                 375                 380

Glu Tyr Leu Ser Ser Pro Glu Lys His Phe Gly Thr Ser Arg Lys Phe
385                 390                 395                 400

Ile Ala Ser Leu Glu Glu Asn Asn Tyr Val Lys Gln Glu Lys Val Ile
                405                 410                 415

Ser Glu Asp Ile Ile Glu Glu Ala Lys Arg Leu Ala Thr Cys Ala Tyr
            420                 425                 430

Glu Asp Gly Thr His Trp Gly Gln Glu Ala Asn Arg Pro Ser Phe Leu
        435                 440                 445

Gly Cys Ala Pro Val Asp Met Gln Gly Phe Ser Ser Gln Leu Ile Lys
    450                 455                 460

Trp Val Ala Ala Leu Thr Gln Ala Gly Leu Ser His Leu Asn Pro Ile
465                 470                 475                 480

Thr Tyr Gly Phe Lys Ser Arg Met Arg Thr Leu Gln Val Leu Cys Tyr
                485                 490                 495

Ala Tyr Leu Met Tyr Phe Ser Leu Tyr Ser Trp Gly Met Val Leu His
            500                 505                 510

Ala Ser Val Pro Ser Ile Gly Leu Leu Ser Gly Ile Lys Ile Tyr Pro
        515                 520                 525

Glu Val Tyr Asp Pro Trp Phe Val Val Tyr Val Ile Ala Phe Ile Ser
    530                 535                 540

Thr Ile Leu Glu Asn Met Ser Glu Ser Ile Pro Glu Gly Gly Ser Val
545                 550                 555                 560

Lys Thr Trp Trp Met Glu Tyr Arg Ala Leu Met Met Met Gly Val Ser
                565                 570                 575

Ala Ile Trp Leu Gly Gly Val Lys Ala Ile Val Asp Lys Ile Ile Gly
            580                 585                 590

Thr Gln Gly Glu Lys Leu Tyr Leu Ser Asp Lys Ala Ile Asp Lys Glu
        595                 600                 605

Lys Leu Lys Lys Tyr Glu Lys Gly Lys Phe Asp Phe Gln Gly Ile Gly
    610                 615                 620

Ile Leu Ala Val Pro Leu Ile Thr Phe Ser Val Leu Asn Leu Val Gly
625                 630                 635                 640

Phe Leu Val Gly Ile Asn Gln Val Leu Ile Thr Met Lys Phe Ala Gly
                645                 650                 655

Val Leu Gly Gln Leu Leu Val Ser Ser Phe Phe Val Phe Val Val Val
            660                 665                 670

Thr Val Val Ile Asp Val Val Ser Phe Leu Lys Asp Ser
        675                 680                 685
```

<210> SEQ ID NO 40
<211> LENGTH: 2136

<212> TYPE: DNA
<213> ORGANISM: Capsicum annuum

<400> SEQUENCE: 40

```
atggagctca acagatgtac ggtgcagcaa cctaccactg ccatataccg actacacatg     60
tttctccact ctctaatcat gcttgcatta gtatactatc gtttgtctaa tctgttttac    120
ttcgaaaacg tcctcacttt acaagcattt gcatgggggc ttatcacctt aggtgaaatt    180
tgtttcattg tcaagtggtt ctttggtcaa gggactcgtt ggcgccccgt tgtcagggaa    240
gtgttcctgg acaatattac ttgccaagat tccgagctgc ccgcactaga tgtgatggtt    300
ttcactgcca atcccaagaa agagccaatt gtggatgtca tgaacactgt gatatccgca    360
atggctcttg attacccgac ggataaattg gctgtgtatc tggctgatga tggaggatgc    420
cccttgacgt tgtacgccat ggaggaggcc tgttcttttg ccaagttgtg gctacctttc    480
tgtaggaagt atggaatcaa aacaaggtgc cccaaagcgt ttttttctcc attaggagaa    540
gatgatcgta tccttaagaa cgatgacttt gtagctgaaa tgaaagaaat taaattaaaa    600
tatgaggagt tccagcagaa tgtaaacctt gctggtgaat ccggaaaaat caaaggtgac    660
gtagtgcctg atagagcctc gtttattaag gtaataaatg acaggaaaat ggagaacaag    720
aagagtgccg acgatataac gaaaatgcct ttgctagtat acgtatcccg tgaaagaaga    780
tttaacagtc gtcatcactt caagggtgga tctgcaaatg ctcttcttcg agtttcaggg    840
ataatgagta atgcccccta tttactggtc ttagattgtg atttcttctg tcatgatcca    900
acatcagctc ggaaggcaat gtgtttccat cttgatccaa aactatcacc ttccttagct    960
tatgtgcagt tccctcaagt gttttacaat gtcagcaagt ccgatatata cgatgtcaaa   1020
attagacagg cttacaagac aatatggcac ggaatggatg gtatccaagg cccagtgtta   1080
tcgggaactg ggtattttct gaagaggaaa gcgttataca cgagtccagg tctaaaggat   1140
gagtatctta tttcaccgga aaagcatttc ggatcaagta gaaagttcat tgcttctcta   1200
gaggagaaca atggttatgt taagcaagag aaactcataa cagaagatat tatagaggaa   1260
gcgaagacct tgtctacttg tgcatacgag gatggtacac gatggggcga agagatcggt   1320
tatacctaca attgccattt ggagagcact tttaccggct atcttttgca ctgcaaaggg   1380
tggacatcaa catatttgta tccagaaagg ccatctttct tgggttgtgc cccagttgat   1440
atgcaaggat tctcctcaca actcacaaaa tgggttgctg cactcacaca agctggtcta   1500
tcacatctca atcccatcac ttacggcatg aagagcagga ttaagactat ccaatgcttg   1560
tgctatgcct atttgatgta tttctctctc tattcttggg gaatggttct gcatgctagt   1620
gttccttcta ttagcctttt gcttggcatt caagtctacc ccgaggtcta tgatccatgg   1680
tttgcagtgt atgtgcttgc tttcatatcg acaattttgg agaacatgtc agagtcaatt   1740
ccagaaggcg gttcagttaa aacttggtgg atggaataca gggcactgat gatgatggga   1800
gttagtgcaa tatggttagg aggagtgaaa gctatagtag aaaagatcat cggaactcaa   1860
ggagagaaat tatatttgtc ggacaaagca attgacaagg aaaagctcaa gaaatatgag   1920
aaggggaaat ttgatttcca agggataggg atacttgctg ttccattgat aacattctca   1980
gcgttgaatt tggtaggctt catggttgga gctaatcaag tgattcttac tatgaagttc   2040
gaagctttgc taggccaact ccttgtgtca tccttcttcg tctttgtggt ggtcaccgtt   2100
gtcatagatg tcctatcttt cttaaaagac tcttaa                              2136
```

<210> SEQ ID NO 41

<211> LENGTH: 711
<212> TYPE: PRT
<213> ORGANISM: Capsicum annuum

<400> SEQUENCE: 41

```
Met Glu Leu Asn Arg Cys Thr Val Gln Gln Pro Thr Thr Ala Ile Tyr
1               5                   10                  15

Arg Leu His Met Phe Leu His Ser Leu Ile Met Leu Ala Leu Val Tyr
            20                  25                  30

Tyr Arg Leu Ser Asn Leu Phe Tyr Phe Glu Asn Val Leu Thr Leu Gln
        35                  40                  45

Ala Phe Ala Trp Gly Leu Ile Thr Leu Gly Glu Ile Cys Phe Ile Val
    50                  55                  60

Lys Trp Phe Phe Gly Gln Gly Thr Arg Trp Arg Pro Val Val Arg Glu
65                  70                  75                  80

Val Phe Leu Asp Asn Ile Thr Cys Gln Asp Ser Glu Leu Pro Ala Leu
                85                  90                  95

Asp Val Met Val Phe Thr Ala Asn Pro Lys Lys Glu Pro Ile Val Asp
            100                 105                 110

Val Met Asn Thr Val Ile Ser Ala Met Ala Leu Asp Tyr Pro Thr Asp
        115                 120                 125

Lys Leu Ala Val Tyr Leu Ala Asp Asp Gly Gly Cys Pro Leu Thr Leu
    130                 135                 140

Tyr Ala Met Glu Glu Ala Cys Ser Phe Ala Lys Leu Trp Leu Pro Phe
145                 150                 155                 160

Cys Arg Lys Tyr Gly Ile Lys Thr Arg Cys Pro Lys Ala Phe Phe Ser
                165                 170                 175

Pro Leu Gly Glu Asp Asp Arg Ile Leu Lys Asn Asp Asp Phe Val Ala
            180                 185                 190

Glu Met Lys Glu Ile Lys Leu Lys Tyr Glu Glu Phe Gln Gln Asn Val
        195                 200                 205

Asn Leu Ala Gly Glu Ser Gly Lys Ile Lys Gly Asp Val Val Pro Asp
    210                 215                 220

Arg Ala Ser Phe Ile Lys Val Ile Asn Asp Arg Lys Met Glu Asn Lys
225                 230                 235                 240

Lys Ser Ala Asp Asp Ile Thr Lys Met Pro Leu Leu Val Tyr Val Ser
                245                 250                 255

Arg Glu Arg Arg Phe Asn Ser Arg His His Phe Lys Gly Gly Ser Ala
            260                 265                 270

Asn Ala Leu Leu Arg Val Ser Gly Ile Met Ser Asn Ala Pro Tyr Leu
        275                 280                 285

Leu Val Leu Asp Cys Asp Phe Phe Cys His Asp Pro Thr Ser Ala Arg
    290                 295                 300

Lys Ala Met Cys Phe His Leu Asp Pro Lys Leu Ser Pro Ser Leu Ala
305                 310                 315                 320

Tyr Val Gln Phe Pro Gln Val Phe Tyr Asn Val Ser Lys Ser Asp Ile
                325                 330                 335

Tyr Asp Val Lys Ile Arg Gln Ala Tyr Lys Thr Ile Trp His Gly Met
            340                 345                 350

Asp Gly Ile Gln Gly Pro Val Leu Ser Gly Thr Gly Tyr Phe Leu Lys
        355                 360                 365

Arg Lys Ala Leu Tyr Thr Ser Pro Gly Leu Lys Asp Glu Tyr Leu Ile
    370                 375                 380

Ser Pro Glu Lys His Phe Gly Ser Ser Arg Lys Phe Ile Ala Ser Leu
```

```
385                 390                 395                 400

Glu Glu Asn Asn Gly Tyr Val Lys Gln Glu Lys Leu Ile Thr Glu Asp
                405                 410                 415

Ile Ile Glu Glu Ala Lys Thr Leu Ser Thr Cys Ala Tyr Glu Asp Gly
            420                 425                 430

Thr Arg Trp Gly Glu Glu Ile Gly Tyr Thr Tyr Asn Cys His Leu Glu
        435                 440                 445

Ser Thr Phe Thr Gly Tyr Leu Leu His Cys Lys Gly Trp Thr Ser Thr
    450                 455                 460

Tyr Leu Tyr Pro Glu Arg Pro Ser Phe Leu Gly Cys Ala Pro Val Asp
465                 470                 475                 480

Met Gln Gly Phe Ser Ser Gln Leu Thr Lys Trp Val Ala Ala Leu Thr
                485                 490                 495

Gln Ala Gly Leu Ser His Leu Asn Pro Ile Thr Tyr Gly Met Lys Ser
            500                 505                 510

Arg Ile Lys Thr Ile Gln Cys Leu Cys Tyr Ala Tyr Leu Met Tyr Phe
        515                 520                 525

Ser Leu Tyr Ser Trp Gly Met Val Leu His Ala Ser Val Pro Ser Ile
    530                 535                 540

Ser Leu Leu Leu Gly Ile Gln Val Tyr Pro Glu Val Tyr Asp Pro Trp
545                 550                 555                 560

Phe Ala Val Tyr Val Leu Ala Phe Ile Ser Thr Ile Leu Glu Asn Met
                565                 570                 575

Ser Glu Ser Ile Pro Glu Gly Gly Ser Val Lys Thr Trp Trp Met Glu
            580                 585                 590

Tyr Arg Ala Leu Met Met Met Gly Val Ser Ala Ile Trp Leu Gly Gly
        595                 600                 605

Val Lys Ala Ile Val Glu Lys Ile Ile Gly Thr Gln Gly Glu Lys Leu
    610                 615                 620

Tyr Leu Ser Asp Lys Ala Ile Asp Lys Glu Lys Leu Lys Lys Tyr Glu
625                 630                 635                 640

Lys Gly Lys Phe Asp Phe Gln Gly Ile Gly Ile Leu Ala Val Pro Leu
                645                 650                 655

Ile Thr Phe Ser Ala Leu Asn Leu Val Gly Phe Met Val Gly Ala Asn
            660                 665                 670

Gln Val Ile Leu Thr Met Lys Phe Glu Ala Leu Leu Gly Gln Leu Leu
        675                 680                 685

Val Ser Ser Phe Phe Val Phe Val Val Val Thr Val Val Ile Asp Val
    690                 695                 700

Leu Ser Phe Leu Lys Asp Ser
705                 710
```

<210> SEQ ID NO 42
<211> LENGTH: 270
<212> TYPE: DNA
<213> ORGANISM: Artificial Sequence
<220> FEATURE:
<223> OTHER INFORMATION: Syn. Polynucl.

<400> SEQUENCE: 42

```
ggctcttgat tatcccaccg ataaattggc tgtgtatctc gctgatgatg gaggatgtcc      60

attgtcgttg tacgccatgg aacaagcgtg tttgtttgca aagctatggt tacctttctg     120

tagaaactat ggaattaaaa cgagatgccc aaaagcattt ttttctccgt taggagatga     180

tgaccgtgtt cttaagaatg atgattttgc tgctgaaatg aaagaaatta aattgaaata     240
```

tgaagagttc cagcagaagg tggaacatgc 270

<210> SEQ ID NO 43
<211> LENGTH: 275
<212> TYPE: DNA
<213> ORGANISM: Artificial Sequence
<220> FEATURE:
<223> OTHER INFORMATION: Syn. Polynucl.

<400> SEQUENCE: 43
ggctcttgat tatcctacgg ataaattggc tgtgtatctg gctgatgatg gaggatgtcc 60
tttgtcattg tacgccatgg aagaagcatg tgtgtttgca aagctgtggc tacctttctg 120
taggaagtat ggaattaaaa ctagatgccc taaagcgttt ttttctcctt taggagatga 180
tgaacgtgtt cttaagaatg atgattttga tgctgaaatg aaagaaatta aattgaaata 240
tgaagagttc cagcagaatg tggaacgtgc tggtg 275

<210> SEQ ID NO 44
<211> LENGTH: 447
<212> TYPE: DNA
<213> ORGANISM: Artificial Sequence
<220> FEATURE:
<223> OTHER INFORMATION: Syn. Polynucl.

<400> SEQUENCE: 44
ggctcttgat tacccgaccg acaaattggc cgtttatttg tctgatgatg gaggatgccc 60
cttgacgttg tacgcaatgg aggaagcttg ttcctttgcc aagttgtggc taccttttttg 120 taggaagtat ggaatcaaaa caaggtgccc taaggcgttt ttttctccat taggagaaga 180
tgaccgtgta ttgaagagtg atgactttgt ttctgaaatg aaagaaatga agtcaaaata 240
tgaagagttc cagcagaacg tggaccgtgc tggtgaatcc ggaaaaatca aaggtgacgt 300
agtgcctgat agacccgcgt ttcttaaggt actaaatgac aggaagacgg agaacgagaa 360
gagtgcagac gatttaacta aaatgccttt gctagtatac gtatcccgtg aaagaagaac 420
tcaccgtcgc catcacttca agggtgg 447

<210> SEQ ID NO 45
<211> LENGTH: 2292
<212> TYPE: DNA
<213> ORGANISM: Spinacia oleracea

<400> SEQUENCE: 45
atgtggaggt tgaaggttgg agaaggggct aatgacccat acttatatag cactaataac 60
tttgttgggc gtcaaacttg ggagtttgat cctaactatg gcacccctga ggatattcaa 120
gaggtcgaag atgctcgccg cgatttttac aataatcggt ttaaagtgaa gccttgtaac 180
gatctcttat ggcgttttca gttcttaaga gagaaaaact tcaagcaaac catacctcaa 240
gtgaaggtgg gtgacgggga ggagatcaca tatgagaccg cctcgacgac attaaagaga 300
gcggtgaata ttttcacagc cttgcagtct gaacatggcc attggccggc tgaaattgct 360
ggccctcagt tcttccttcc tcctttggta ttttgcttat acattacagg agatcttaac 420
tctgttttcg gaccagaaca tcgtagagaa attcttcgca gcatctacta tcaccagaac 480
gaagatggag gttggggatt acatattgaa ggacatagca ccatgttctg taccgcactg 540
aattacatat gtttacgaat gcttggaata ggacctgatg aaggtgatga caacgcgtgc 600
cctagagcgc gtaaatggat tctcgaccat ggtagcgtta cacatatccc ttcttggggt 660

```
aaaacttggt tatctatact gggcctgttc gattggtctg gaagtaaccc aatgccacct    720
gagttctgga tccttcctac ttttctccct atgcatccag caaaaatgtg gtgctactgt    780
cgaatggtgt atatgccaat gtcatacttg tatgggaaga gattcgtagg tccaatcaca    840
cctctcatta aacaacttag ggaagaactc tacaacgaac cctttgaaca aattagttgg    900
aagaaaatgc gacatttgtg tgcaccggag gatctctact atcctcatcc attgattcaa    960
gacttgatgt gggacgctct ttaccttttt acggaacctc tcctgacccg ttggcctttc   1020
aacaagttga tacgaaagaa agcattagag gttacaatgg aacacataca ttatgaagat   1080
gagaacagtc gttacataac aattggatgt gtcgagaagg ttttatgtat gttagcctgt   1140
tgggtggaag accctaaagg ggatcattac aagaaacatc ttgcaagagt acaagattac   1200
atttggattg ctgaagatgg attgaaaatg cagagttttg gaagtcaaca atgggattgt   1260
gggttttcag tacaggcatt attagcttct aatcttagtc tcgacgaaat tggacctgct   1320
cttaagaaag gccatttctt cattaaggag tcacaggtga aggacaatcc atccggcgac   1380
ttcaaagcta tgcatcgcca tatctcaaag ggatcgtgga ctttctccga ccaagatcat   1440
ggttggcaag tctccgattg cactgccgaa ggccttaagt gttgtctaat cttatcaaca   1500
atgcccccgg aaattgttgg agaaaagatg gaccctgaac gcctttatga ttctgtcaat   1560
gtcttgcttt ctctacagag taataaagga gggctagctg cctgggaacc agcaggggct   1620
caagaatggt tggaggtcct aaacccaaca gaattctttg aagacattgt gattgaacat   1680
gagtatgtag agtgtacggc ttcagcaatt caagctttaa taatgttcaa gaagttatac   1740
ccaggacaca ggaaaaaaga gattgaaaat tttgtagtaa acgcagtcaa gtaccttgaa   1800
aacacccaat atcctagtgg aggatggtat ggaaattggg ggatttgttt catatatgga   1860
acatggtttg cactaggagg gctagcagca ggtgggaaga catactataa ttgtgctgct   1920
gttaggaagg gtgttgattt tttgcttact acacaaaagg aggatggtgg ttggggtgaa   1980
agttatattt cttgtcccaa taaggaattt gtgccaatag agggaaagtc caatttggtt   2040
cagactggtt gggctttgat gggtctactt catgctggac aggcggagag ggatccaact   2100
cctctgcatc gtgcagcaaa gcttttgatt aattcacaac tcgaaaatgg cgatttccct   2160
caacaggaaa taacaggagt cttcatgaag aattgcatgt tacattatcc gatgtacaga   2220
agcatttatc cactgtgggc aattgcagaa tacagaaagc gtgtttcatt accttctatc   2280
aactctactt ga                                                       2292
```

<210> SEQ ID NO 46
<211> LENGTH: 1452
<212> TYPE: DNA
<213> ORGANISM: Spinacia oleracea

<400> SEQUENCE: 46

```
atggaactct tctttatgtg tgggctagtc cttttcctct ccctatctct agcctccttc     60
ttccttttct ataaccacca tagaacccgg gggtacaagc tacccccggg caagatgggg    120
tggccggtgg tgggcgagtc atttgaattt tttcaaaccg ggtggaaagg ttacccggaa    180
aagttcatat ttgatagact gaacaagtac accccaagcc aagtgttcaa gacttccatc    240
gtaggagaaa aggttgcggt tttatgtggc gcggcgggta acaagttctt gtactcaaac    300
gagaacaagt tagtacaagc ttggtggcct agctctgttg ataagatctt tccttcttct    360
acccaaactt cctccaaaga agaggctaag aagatgcgga aactcctccc taacttcctc    420
aagcccgagg ctttacatag gtacataccc atcatggata gcattgccat ccggcacatg    480
```

```
gagtccgggt gggagggaaa ggacaaggta gaagtcttcc ctttggctaa gaattacacc    540

ttctggctgg cttgccgact cttcttaagc gtcgaggacc cggctcatgt agccaagttc    600

tccgaaccat tcaacgacat agccgcaggg atcatctcga tgccaatcga cctccccgga    660

acacccttca accgagggat caagtcgtct aacgtcgtaa ggaaagagtt gagggccatc    720

ataaagcaga ggaaacttga cttagcagat ggcaaggctt cacctacaca agatattctg    780

tctcatatgt tgttgacttg tactgaagat ggcaagttta tgagtgaaat ggatattgct    840

gataagattc tgggacttct tattggtgga catgatactg ctagtgcttc ttgtactttt    900

gttgttaagt ttcttgctga gcttcctcac atatatgaag gtgtctacaa agagcaaatg    960

gagatagcaa attcaaaaaa agcaggagaa cttctaaatt gggaggacat acaaaaaatg   1020

aaatactcat ggaatgtagc ttgtgaagtt atgcgtttgg ctcctccact tcaaggtggt   1080

ttcagggaag ccctttctga tttcatgtat aacggattcc aaatccccaa gggctggaag   1140

ttatattgga gtgcaaattc aacacatatg aacccggaat gcttcccgga gcccaagacg   1200

ttcgacccat cgaggttcga cggtacggga ccagcaccat acacatacgt cccctttcgga   1260

ggaggaccga gaatgtgccc gggcaaggag tatgcaaggc tagagatatt agtgttcatg   1320

cacaacgttg tcaagaggtt taaatgggaa aaaatgcttc ctgatgagaa ggttattgtc   1380

aatcccatgc ctatcccaga acatggcctt cctgtccgcc ttttccctca tcctcgaact   1440

gtagctgctt aa                                                        1452
```

<210> SEQ ID NO 47
<211> LENGTH: 279
<212> TYPE: DNA
<213> ORGANISM: Spinacia oleracea

<400> SEQUENCE: 47

```
atggagttct tctttctgtg tggtctagtc ttttacttct ccatatctct agcctccttc     60

ttcctttttct ataaccacca tacaacccgg gtttacccgc tacccgcggg cgagatgggg    120

tggccggtgg tgggcgactc gtttgaattt tttcaaaccg ggtggaacgg ttacccggaa    180

aatttcatct ttgatagact caacaaatac accccaagcc aagtgttcaa gactttcatc    240

ctaagagaaa aggttgtgtt ttatttgaga aggttgtag                            279
```

<210> SEQ ID NO 48
<211> LENGTH: 483
<212> TYPE: PRT
<213> ORGANISM: Spinacia oleracea

<400> SEQUENCE: 48

```
Met Glu Leu Phe Phe Met Cys Gly Leu Val Leu Phe Leu Ser Leu Ser
1               5                   10                  15

Leu Ala Ser Phe Phe Leu Phe Tyr Asn His His Arg Thr Arg Gly Tyr
            20                  25                  30

Lys Leu Pro Pro Gly Lys Met Gly Trp Pro Val Val Gly Glu Ser Phe
        35                  40                  45

Glu Phe Phe Gln Thr Gly Trp Lys Gly Tyr Pro Glu Lys Phe Ile Phe
    50                  55                  60

Asp Arg Leu Asn Lys Tyr Thr Pro Ser Gln Val Phe Lys Thr Ser Ile
65                  70                  75                  80

Val Gly Glu Lys Val Ala Val Leu Cys Gly Ala Ala Gly Asn Lys Phe
                85                  90                  95
```

-continued

```
Leu Tyr Ser Asn Glu Asn Lys Leu Val Gln Ala Trp Trp Pro Ser Ser
            100                 105                 110

Val Asp Lys Ile Phe Pro Ser Ser Thr Gln Thr Ser Ser Lys Glu Glu
        115                 120                 125

Ala Lys Lys Met Arg Lys Leu Leu Pro Asn Phe Leu Lys Pro Glu Ala
    130                 135                 140

Leu His Arg Tyr Ile Pro Ile Met Asp Ser Ile Ala Ile Arg His Met
145                 150                 155                 160

Glu Ser Gly Trp Glu Gly Lys Asp Lys Val Glu Val Phe Pro Leu Ala
                165                 170                 175

Lys Asn Tyr Thr Phe Trp Leu Ala Cys Arg Leu Phe Leu Ser Val Glu
            180                 185                 190

Asp Pro Ala His Val Ala Lys Phe Ser Glu Pro Phe Asn Asp Ile Ala
        195                 200                 205

Ala Gly Ile Ile Ser Met Pro Ile Asp Leu Pro Gly Thr Pro Phe Asn
    210                 215                 220

Arg Gly Ile Lys Ser Ser Asn Val Val Arg Lys Glu Leu Arg Ala Ile
225                 230                 235                 240

Ile Lys Gln Arg Lys Leu Asp Leu Ala Asp Gly Lys Ala Ser Pro Thr
                245                 250                 255

Gln Asp Ile Leu Ser His Met Leu Leu Thr Cys Thr Glu Asp Gly Lys
            260                 265                 270

Phe Met Ser Glu Met Asp Ile Ala Asp Lys Ile Leu Gly Leu Leu Ile
        275                 280                 285

Gly Gly His Asp Thr Ala Ser Ala Ser Cys Thr Phe Val Val Lys Phe
    290                 295                 300

Leu Ala Glu Leu Pro His Ile Tyr Glu Gly Val Tyr Lys Glu Gln Met
305                 310                 315                 320

Glu Ile Ala Asn Ser Lys Lys Ala Gly Glu Leu Leu Asn Trp Glu Asp
                325                 330                 335

Ile Gln Lys Met Lys Tyr Ser Trp Asn Val Ala Cys Glu Val Met Arg
            340                 345                 350

Leu Ala Pro Pro Leu Gln Gly Gly Phe Arg Glu Ala Leu Ser Asp Phe
        355                 360                 365

Met Tyr Asn Gly Phe Gln Ile Pro Lys Gly Trp Lys Leu Tyr Trp Ser
    370                 375                 380

Ala Asn Ser Thr His Met Asn Pro Glu Cys Phe Pro Glu Pro Lys Thr
385                 390                 395                 400

Phe Asp Pro Ser Arg Phe Asp Gly Thr Gly Pro Ala Pro Tyr Thr Tyr
                405                 410                 415

Val Pro Phe Gly Gly Gly Pro Arg Met Cys Pro Gly Lys Glu Tyr Ala
            420                 425                 430

Arg Leu Glu Ile Leu Val Phe Met His Asn Val Val Lys Arg Phe Lys
        435                 440                 445

Trp Glu Lys Met Leu Pro Asp Glu Lys Val Ile Val Asn Pro Met Pro
    450                 455                 460

Ile Pro Glu His Gly Leu Pro Val Arg Leu Phe Pro His Pro Arg Thr
465                 470                 475                 480

Val Ala Ala
```

<210> SEQ ID NO 49
<211> LENGTH: 763
<212> TYPE: PRT
<213> ORGANISM: Spinacia oleracea

<400> SEQUENCE: 49

Met Trp Arg Leu Lys Val Gly Glu Gly Ala Asn Asp Pro Tyr Leu Tyr
1               5                   10                  15

Ser Thr Asn Asn Phe Val Gly Arg Gln Thr Trp Glu Phe Asp Pro Asn
            20                  25                  30

Tyr Gly Thr Pro Glu Asp Ile Gln Glu Val Glu Asp Ala Arg Arg Asp
        35                  40                  45

Phe Tyr Asn Asn Arg Phe Lys Val Lys Pro Cys Asn Asp Leu Leu Trp
    50                  55                  60

Arg Phe Gln Phe Leu Arg Glu Lys Asn Phe Lys Gln Thr Ile Pro Gln
65                  70                  75                  80

Val Lys Val Gly Asp Gly Glu Glu Ile Thr Tyr Glu Thr Ala Ser Thr
                85                  90                  95

Thr Leu Lys Arg Ala Val Asn Ile Phe Thr Ala Leu Gln Ser Glu His
            100                 105                 110

Gly His Trp Pro Ala Glu Ile Ala Gly Pro Gln Phe Phe Leu Pro Pro
        115                 120                 125

Leu Val Phe Cys Leu Tyr Ile Thr Gly Asp Leu Asn Ser Val Phe Gly
    130                 135                 140

Pro Glu His Arg Arg Glu Ile Leu Arg Ser Ile Tyr Tyr His Gln Asn
145                 150                 155                 160

Glu Asp Gly Gly Trp Gly Leu His Ile Glu Gly His Ser Thr Met Phe
                165                 170                 175

Cys Thr Ala Leu Asn Tyr Ile Cys Leu Arg Met Leu Gly Ile Gly Pro
            180                 185                 190

Asp Glu Gly Asp Asp Asn Ala Cys Pro Arg Ala Arg Lys Trp Ile Leu
        195                 200                 205

Asp His Gly Ser Val Thr His Ile Pro Ser Trp Gly Lys Thr Trp Leu
    210                 215                 220

Ser Ile Leu Gly Leu Phe Asp Trp Ser Gly Ser Asn Pro Met Pro Pro
225                 230                 235                 240

Glu Phe Trp Ile Leu Pro Thr Phe Leu Pro Met His Pro Ala Lys Met
                245                 250                 255

Trp Cys Tyr Cys Arg Met Val Tyr Met Pro Met Ser Tyr Leu Tyr Gly
            260                 265                 270

Lys Arg Phe Val Gly Pro Ile Thr Pro Leu Ile Lys Gln Leu Arg Glu
        275                 280                 285

Glu Leu Tyr Asn Glu Pro Phe Glu Gln Ile Ser Trp Lys Lys Met Arg
    290                 295                 300

His Leu Cys Ala Pro Glu Asp Leu Tyr Tyr Pro His Pro Leu Ile Gln
305                 310                 315                 320

Asp Leu Met Trp Asp Ala Leu Tyr Leu Phe Thr Glu Pro Leu Leu Thr
                325                 330                 335

Arg Trp Pro Phe Asn Lys Leu Ile Arg Lys Lys Ala Leu Glu Val Thr
            340                 345                 350

Met Glu His Ile His Tyr Glu Asp Glu Asn Ser Arg Tyr Ile Thr Ile
        355                 360                 365

Gly Cys Val Glu Lys Val Leu Cys Met Leu Ala Cys Trp Val Glu Asp
    370                 375                 380

Pro Lys Gly Asp His Tyr Lys Lys His Leu Ala Arg Val Gln Asp Tyr
385                 390                 395                 400

Ile Trp Ile Ala Glu Asp Gly Leu Lys Met Gln Ser Phe Gly Ser Gln

```
                405                 410                 415

Gln Trp Asp Cys Gly Phe Ser Val Gln Ala Leu Leu Ala Ser Asn Leu
            420                 425                 430

Ser Leu Asp Glu Ile Gly Pro Ala Leu Lys Lys Gly His Phe Phe Ile
        435                 440                 445

Lys Glu Ser Gln Val Lys Asp Asn Pro Ser Gly Asp Phe Lys Ala Met
    450                 455                 460

His Arg His Ile Ser Lys Gly Ser Trp Thr Phe Ser Asp Gln Asp His
465                 470                 475                 480

Gly Trp Gln Val Ser Asp Cys Thr Ala Glu Gly Leu Lys Cys Cys Leu
                485                 490                 495

Ile Leu Ser Thr Met Pro Pro Glu Ile Val Gly Glu Lys Met Asp Pro
            500                 505                 510

Glu Arg Leu Tyr Asp Ser Val Asn Val Leu Leu Ser Leu Gln Ser Asn
        515                 520                 525

Lys Gly Gly Leu Ala Ala Trp Glu Pro Ala Gly Ala Gln Glu Trp Leu
    530                 535                 540

Glu Val Leu Asn Pro Thr Glu Phe Phe Glu Asp Ile Val Ile Glu His
545                 550                 555                 560

Glu Tyr Val Glu Cys Thr Ala Ser Ala Ile Gln Ala Leu Ile Met Phe
                565                 570                 575

Lys Lys Leu Tyr Pro Gly His Arg Lys Lys Glu Ile Glu Asn Phe Val
            580                 585                 590

Val Asn Ala Val Lys Tyr Leu Glu Asn Thr Gln Tyr Pro Ser Gly Gly
        595                 600                 605

Trp Tyr Gly Asn Trp Gly Ile Cys Phe Ile Tyr Gly Thr Trp Phe Ala
    610                 615                 620

Leu Gly Gly Leu Ala Ala Gly Gly Lys Thr Tyr Tyr Asn Cys Ala Ala
625                 630                 635                 640

Val Arg Lys Gly Val Asp Phe Leu Leu Thr Thr Gln Lys Glu Asp Gly
                645                 650                 655

Gly Trp Gly Glu Ser Tyr Ile Ser Cys Pro Asn Lys Glu Phe Val Pro
            660                 665                 670

Ile Glu Gly Lys Ser Asn Leu Val Gln Thr Gly Trp Ala Leu Met Gly
        675                 680                 685

Leu Leu His Ala Gly Gln Ala Glu Arg Asp Pro Thr Pro Leu His Arg
    690                 695                 700

Ala Ala Lys Leu Leu Ile Asn Ser Gln Leu Glu Asn Gly Asp Phe Pro
705                 710                 715                 720

Gln Gln Glu Ile Thr Gly Val Phe Met Lys Asn Cys Met Leu His Tyr
                725                 730                 735

Pro Met Tyr Arg Ser Ile Tyr Pro Leu Trp Ala Ile Ala Glu Tyr Arg
            740                 745                 750

Lys Arg Val Ser Leu Pro Ser Ile Asn Ser Thr
        755                 760
```

<210> SEQ ID NO 50
<211> LENGTH: 92
<212> TYPE: PRT
<213> ORGANISM: Spinacia oleracea

<400> SEQUENCE: 50

```
Met Glu Phe Phe Phe Leu Cys Gly Leu Val Phe Tyr Phe Ser Ile Ser
1               5                   10                  15
```

```
Leu Ala Ser Phe Phe Leu Phe Tyr Asn His His Thr Thr Arg Val Tyr
            20                  25                  30

Pro Leu Pro Ala Gly Glu Met Gly Trp Pro Val Val Gly Asp Ser Phe
        35                  40                  45

Glu Phe Phe Gln Thr Gly Trp Asn Gly Tyr Pro Glu Asn Phe Ile Phe
    50                  55                  60

Asp Arg Leu Asn Lys Tyr Thr Pro Ser Gln Val Phe Lys Thr Phe Ile
65                  70                  75                  80

Leu Arg Glu Lys Val Val Phe Tyr Leu Arg Arg Leu
                85                  90


<210> SEQ ID NO 51
<211> LENGTH: 1563
<212> TYPE: DNA
<213> ORGANISM: Spinacia oleracea

<400> SEQUENCE: 51

atgatagaaa tcgggtatat tgtaaaatgg gtaatttgtt tagtgattgt tagatgggta     60

tggaagattg tgaattgggt ttggtttaca ccaaaaaggc ttgagaagtt tctaagaaaa    120

caaggtttag atggaaattc atacagattt ttgttgggtg atctcaaaga tatgtctaaa    180

atgcgtaaag aagctagaca aaaacctatt cctttttactc atgacttctt tcatcgtatc    240

ttgcctttcc acaatcacca tttcaataaa tacggggaaa gcttcttttc atggatgggg    300

cctataccag ttgtgaatgt tgcagaacaa gagcaagtaa agggtgtgtt cactaggata    360

aaagagtttc agaaggccaa attaaaccca cttgttgcat tgcttgtccc tggacttgtg    420

agcgctgaag gtgataaatg ggtcaagcac aggaagctca tcaacccggc ttttcatatg    480

gaaaagctta agcttatgca tccagcattt ggcgccagtg ttttggatat ggtgaacaag    540

tgggagaaga tagtatctaa aacaggttcc tctgaagtgg atgtgtggcc gtttgtttcc    600

agcctgactg cagatgctat ctctcgtgct gcttttggca gtagctatga tgaaggaaga    660

aagatatttg agttggttct tgaacaaact gaaatcaccc tacgccttct gcaatcagtt    720

tatatccctg gatggatgta tgtgccaaca aagaccaaca ggaggatgaa aacagtaaac    780

tctgaaatac aaaatttatt aaccgggata atcgttaaga gaaagaaggc aatggaggcc    840

ggcgaagctg ccaaggatga tttgttgggg atattgttgg agtccaacta caaagatact    900

gaaaatgttc tcagtaataa gaaaaaacta agcatgactt tccaggaatt gattgatgag    960

tgcaaactgt tctacttagc agggcaagag tcgacctcgg tgttgctagc atggacaatg   1020

attctgttgg gaaagcacac agagtggcaa gcacgagcac gagaagaagt agttgcaacg   1080

tttggtaaaa acgaacctga ttttgaaggc ttaaaccatt tgaagatagt gacaatgata   1140

ctgaatgagg tgttgaggtt gtaccctcca gtgtgtacaa tcacccgtaa gaatttcaac   1200

cacgacgtac agcttggaaa tctgacagtc cctcgtggtg ctatggttac gatgtcagca   1260

tatcgtattc aaagagatcc taaaatatgg ggtgatgatg caaaagagtt taacccacag   1320

agattttcag aaggggttgc aaaggctaca aaggggaata ttgcattctt tccgtttggt   1380

tgggggccgc gaatttgcat cggacagaac tttgcactta ttgaagctaa aatggcagtg   1440

tccatggttt tacaacgctt ttcttttgag ctatcaccgt cttatactca tgctcctacc   1500

actatcctca ctcttcaacc ccaacaaggt gctcatctca ttatacataa gctcagggac   1560

taa                                                                 1563


<210> SEQ ID NO 52
```

<211> LENGTH: 520
<212> TYPE: PRT
<213> ORGANISM: Spinacia oleracea

<400> SEQUENCE: 52

```
Met Ile Glu Ile Gly Tyr Ile Val Lys Trp Val Ile Cys Leu Val Ile
1               5                   10                  15

Val Arg Trp Val Trp Lys Ile Val Asn Trp Val Trp Phe Thr Pro Lys
            20                  25                  30

Arg Leu Glu Lys Phe Leu Arg Lys Gln Gly Leu Asp Gly Asn Ser Tyr
        35                  40                  45

Arg Phe Leu Leu Gly Asp Leu Lys Asp Met Ser Lys Met Arg Lys Glu
    50                  55                  60

Ala Arg Gln Lys Pro Ile Pro Phe Thr His Asp Phe Phe His Arg Ile
65                  70                  75                  80

Leu Pro Phe His Asn His His Phe Asn Lys Tyr Gly Glu Ser Phe Phe
                85                  90                  95

Ser Trp Met Gly Pro Ile Pro Val Val Asn Val Ala Glu Gln Glu Gln
            100                 105                 110

Val Lys Gly Val Phe Thr Arg Ile Lys Glu Phe Gln Lys Ala Lys Leu
        115                 120                 125

Asn Pro Leu Val Ala Leu Leu Val Pro Gly Leu Val Ser Ala Glu Gly
    130                 135                 140

Asp Lys Trp Val Lys His Arg Lys Leu Ile Asn Pro Ala Phe His Met
145                 150                 155                 160

Glu Lys Leu Lys Leu Met His Pro Ala Phe Gly Ala Ser Val Leu Asp
                165                 170                 175

Met Val Asn Lys Trp Glu Lys Ile Val Ser Lys Thr Gly Ser Ser Glu
            180                 185                 190

Val Asp Val Trp Pro Phe Val Ser Ser Leu Thr Ala Asp Ala Ile Ser
        195                 200                 205

Arg Ala Ala Phe Gly Ser Ser Tyr Asp Glu Gly Arg Lys Ile Phe Glu
    210                 215                 220

Leu Val Leu Glu Gln Thr Glu Ile Thr Leu Arg Leu Leu Gln Ser Val
225                 230                 235                 240

Tyr Ile Pro Gly Trp Met Tyr Val Pro Thr Lys Thr Asn Arg Arg Met
                245                 250                 255

Lys Thr Val Asn Ser Glu Ile Gln Asn Leu Leu Thr Gly Ile Ile Val
            260                 265                 270

Lys Arg Lys Lys Ala Met Glu Ala Gly Glu Ala Ala Lys Asp Asp Leu
        275                 280                 285

Leu Gly Ile Leu Leu Glu Ser Asn Tyr Lys Asp Thr Glu Asn Val Leu
    290                 295                 300

Ser Asn Lys Lys Lys Leu Ser Met Thr Phe Gln Glu Leu Ile Asp Glu
305                 310                 315                 320

Cys Lys Leu Phe Tyr Leu Ala Gly Gln Glu Ser Thr Ser Val Leu Leu
                325                 330                 335

Ala Trp Thr Met Ile Leu Leu Gly Lys His Thr Glu Trp Gln Ala Arg
            340                 345                 350

Ala Arg Glu Glu Val Val Ala Thr Phe Gly Lys Asn Glu Pro Asp Phe
        355                 360                 365

Glu Gly Leu Asn His Leu Lys Ile Val Thr Met Ile Leu Asn Glu Val
    370                 375                 380

Leu Arg Leu Tyr Pro Pro Val Cys Thr Ile Thr Arg Lys Asn Phe Asn
```

-continued

```
385                 390                 395                 400

His Asp Val Gln Leu Gly Asn Leu Thr Val Pro Arg Gly Ala Met Val
                405                 410                 415

Thr Met Ser Ala Tyr Arg Ile Gln Arg Asp Pro Lys Ile Trp Gly Asp
            420                 425                 430

Asp Ala Lys Glu Phe Asn Pro Gln Arg Phe Ser Glu Gly Val Ala Lys
        435                 440                 445

Ala Thr Lys Gly Asn Ile Ala Phe Phe Pro Phe Gly Trp Gly Pro Arg
    450                 455                 460

Ile Cys Ile Gly Gln Asn Phe Ala Leu Ile Glu Ala Lys Met Ala Val
465                 470                 475                 480

Ser Met Val Leu Gln Arg Phe Ser Phe Glu Leu Ser Pro Ser Tyr Thr
                485                 490                 495

His Ala Pro Thr Thr Ile Leu Thr Leu Gln Pro Gln Gln Gly Ala His
            500                 505                 510

Leu Ile Ile His Lys Leu Arg Asp
        515                 520


<210> SEQ ID NO 53
<211> LENGTH: 1596
<212> TYPE: DNA
<213> ORGANISM: Spinacia oleracea

<400> SEQUENCE: 53

atgatttcaa agagcgcgag tggtgttgca attgcttcat tgggttgcat tatcatactg     60

tattggatgt ggaaattact aaaagggcta tggttaacac caaaaaagct agagaaatgt    120

ctaaaacaac aaggtcttgt tggtaattcc tacaaatttt tgattggaga tatgaaagaa    180

agctcaaaat tgcgtaacga agctttacaa aaacccattc ctttcactca tgattattac    240

aaccgtattc agcctttcat ccatcagatt ctcaacaatt ctggtgcagg caaaaatatc    300

tacacatggt tgggaccagt gccaacaata ctaattacac aacctgagtt aataaaggat    360

gctttcaata ggatgaacaa ttttcagaaa ccaagattaa atccatatac tcaaatgctt    420

tcaactggac ttccgaacta tgagggtcag aaatgggcta aacacaggaa gcttctcaac    480

cctgcttttc aacttgataa gctcaagctt atgatccata cttttgaaac ctgtgttacg    540

gatacactga ataagtggga gaagctagtt tgtaaaacag gttcttcaga ggttgatata    600

tggccatatt tgacaacttt aacgggagat ggtattgcta gagctgcatt tggaagtagc    660

tttgaagatg gaagaagaat attcgagctt ctcacactgc agaaggatat tgttattagt    720

cttctcaaat attcttatat tccaggattt aaatatatgc caataaaggg taaccggaag    780

atgaaagaag cggacaatga aataaaacct ctgttgacga atataattaa tagaaggagg    840

aaagcgatgg aggccggaga agctcccaaa gacgacttgt tagggatgct acttgaatcc    900

aatgcaaacg aggctcgaca agttaatgaa aatgaaagtg gtagtagcaa gcgaaaatct    960

gatctaacga tgagcttccc tgagatgatc gatgcttgca agcagttctt cttggctggt   1020

caagagacca cctcagtggc cctaacatgg acaatgcttt tgttagccaa gcaccaagat   1080

tggcaaacac gagctcgaca agaagtactt gctacatttg gaatgaatac cccagacttt   1140

gatggcatac ataatcgtct taagattgtg acaatgatac tctacgaggt gttaaggttg   1200

tatccgccag tccctgcaac atcgcgaagg gttcatgatc gtgaaacaaa gctaggagat   1260

ttggtaatac cacaaggggt aggagtttca ttttccatac ttcatgcaca cttgaaccct   1320

gaaatttggg gtgatgatgc caaagaattc aagcctgata gatttgcaga agggattgca   1380
```

aaagcaacaa aagggaataa ctcttacttc ccctttggtt ggggacctag gatttgcatt 1440
ggccaaaact tcgcactagt tgaggcgaaa atggcattgt gtatgatttt gcagcgtttc 1500
tctttcgatc tctcgccttc atacatccat gctccgacta gtctcatatc ccttcaacct 1560
cagcatggtg cccacattat tttacatcga ttttaa 1596

<210> SEQ ID NO 54
<211> LENGTH: 531
<212> TYPE: PRT
<213> ORGANISM: Spinacia oleracea

<400> SEQUENCE: 54

```
Met Ile Ser Lys Ser Ala Ser Gly Val Ala Ile Ala Ser Leu Gly Cys
1               5                   10                  15

Ile Ile Ile Leu Tyr Trp Met Trp Lys Leu Leu Lys Gly Leu Trp Leu
            20                  25                  30

Thr Pro Lys Lys Leu Glu Lys Cys Leu Lys Gln Gln Gly Leu Val Gly
        35                  40                  45

Asn Ser Tyr Lys Phe Leu Ile Gly Asp Met Lys Glu Ser Ser Lys Leu
    50                  55                  60

Arg Asn Glu Ala Leu Gln Lys Pro Ile Pro Phe Thr His Asp Tyr Tyr
65                  70                  75                  80

Asn Arg Ile Gln Pro Phe Ile His Gln Ile Leu Asn Asn Ser Gly Ala
                85                  90                  95

Gly Lys Asn Ile Tyr Thr Trp Leu Gly Pro Val Pro Thr Ile Leu Ile
            100                 105                 110

Thr Gln Pro Glu Leu Ile Lys Asp Ala Phe Asn Arg Met Asn Asn Phe
        115                 120                 125

Gln Lys Pro Arg Leu Asn Pro Tyr Thr Gln Met Leu Ser Thr Gly Leu
    130                 135                 140

Pro Asn Tyr Glu Gly Gln Lys Trp Ala Lys His Arg Lys Leu Leu Asn
145                 150                 155                 160

Pro Ala Phe Gln Leu Asp Lys Leu Lys Leu Met Ile His Thr Phe Glu
                165                 170                 175

Thr Cys Val Thr Asp Thr Leu Asn Lys Trp Glu Lys Leu Val Cys Lys
            180                 185                 190

Thr Gly Ser Ser Glu Val Asp Ile Trp Pro Tyr Leu Thr Thr Leu Thr
        195                 200                 205

Gly Asp Gly Ile Ala Arg Ala Ala Phe Gly Ser Ser Phe Glu Asp Gly
    210                 215                 220

Arg Arg Ile Phe Glu Leu Leu Thr Leu Gln Lys Asp Ile Val Ile Ser
225                 230                 235                 240

Leu Leu Lys Tyr Ser Tyr Ile Pro Gly Phe Lys Tyr Met Pro Ile Lys
                245                 250                 255

Gly Asn Arg Lys Met Lys Glu Ala Asp Asn Glu Ile Lys Pro Leu Leu
            260                 265                 270

Thr Asn Ile Ile Asn Arg Arg Arg Lys Ala Met Glu Ala Gly Glu Ala
        275                 280                 285

Pro Lys Asp Asp Leu Leu Gly Met Leu Leu Glu Ser Asn Ala Asn Glu
    290                 295                 300

Ala Arg Gln Val Asn Glu Asn Glu Ser Gly Ser Ser Lys Arg Lys Ser
305                 310                 315                 320

Asp Leu Thr Met Ser Phe Pro Glu Met Ile Asp Ala Cys Lys Gln Phe
                325                 330                 335
```

```
Phe Leu Ala Gly Gln Glu Thr Thr Ser Val Ala Leu Thr Trp Thr Met
            340                 345                 350

Leu Leu Leu Ala Lys His Gln Asp Trp Gln Thr Arg Ala Arg Gln Glu
        355                 360                 365

Val Leu Ala Thr Phe Gly Met Asn Thr Pro Asp Phe Asp Gly Ile His
    370                 375                 380

Asn Arg Leu Lys Ile Val Thr Met Ile Leu Tyr Glu Val Leu Arg Leu
385                 390                 395                 400

Tyr Pro Pro Val Pro Ala Thr Ser Arg Arg Val His Asp Arg Glu Thr
                405                 410                 415

Lys Leu Gly Asp Leu Val Ile Pro Gln Gly Val Gly Val Ser Phe Ser
            420                 425                 430

Ile Leu His Ala His Leu Asn Pro Glu Ile Trp Gly Asp Asp Ala Lys
        435                 440                 445

Glu Phe Lys Pro Asp Arg Phe Ala Glu Gly Ile Ala Lys Ala Thr Lys
    450                 455                 460

Gly Asn Asn Ser Tyr Phe Pro Phe Gly Trp Gly Pro Arg Ile Cys Ile
465                 470                 475                 480

Gly Gln Asn Phe Ala Leu Val Glu Ala Lys Met Ala Leu Cys Met Ile
                485                 490                 495

Leu Gln Arg Phe Ser Phe Asp Leu Ser Pro Ser Tyr Ile His Ala Pro
            500                 505                 510

Thr Ser Leu Ile Ser Leu Gln Pro Gln His Gly Ala His Ile Ile Leu
        515                 520                 525

His Arg Phe
    530
```

<210> SEQ ID NO 55
<211> LENGTH: 1092
<212> TYPE: DNA
<213> ORGANISM: Spinacia oleracea

<400> SEQUENCE: 55

```
atgacgggaa aaggaagaac gatggaggtg atcatgatgc catttcacca ccaaggtcac      60

ttaaccccga tgctccaatt cgcgaagcgc ttcgcttgga aaggtgctgg ctcgatccgg     120

atcaccctcg ccaccaccct ctccaccgcc caaaatatga ccaattccaa aaacaacaac     180

aacaataacg attacgattt cctgacggtc gaaagcatct acgacgatac cgatgattct     240

cagctcaaat tcatgggtcg tatgggaaag ttcaagtccg aagcctcact ccaacttggc     300

cgtctaatca ctactaagag catcgacaat aataaatgta tgctcgttta tgatgcgtat     360

ctgccttggg cactggatgt gggcaaggac cataacatac aggctgcggc tttcttcgtc     420

caggcttgtg cgtatatggc atccttttac cctatgtttt tagaggaatt tgggtcggat     480

gatcaacatc ctgttgttgc ggctgctaag gctgaatctg ttcctagttt gtcggttgag     540

ctgccgtcgc gggaggaaat ggaacgatac gcgccgaaat gtgcacaatc cccgagttct     600

gatgataaac ccaatactgt taagaaatcg cttcaccctg tctaccggat ggtggtttca     660

tcaattacaa cccttcatct tgctgatttc gtgctcatca actcctttga tcaccttgaa     720

catcagctgg atgtcttagc acatgaagca gtagggtgtt tcataaccca ttgcggttgg     780

aactcgataa ttgaggcgac caactttggg gttccgatgt tggggatgcc acagttcatg     840

gaccagtttt tggatgctca ttttatggag aaggtttggg gtgttggaat tagggctaag     900

gctgatgaga aaaactttgt tacttgtgac gaaatcaagt gcggtgtcaa tgaaattatg     960
```

```
tacggagata aggcaaatat gatcaaggag aatgcagcaa agtggaaaga cttggctaag   1020

gaggcagttg gtgaaggagg cagttcagat aagaatatcg acgagatcat taactggctt   1080

gcgtcctcct aa                                                        1092


<210> SEQ ID NO 56
<211> LENGTH: 363
<212> TYPE: PRT
<213> ORGANISM: Spinacia oleracea

<400> SEQUENCE: 56

Met Thr Gly Lys Gly Arg Thr Met Glu Val Ile Met Met Pro Phe His
1               5                   10                  15

His Gln Gly His Leu Thr Pro Met Leu Gln Phe Ala Lys Arg Phe Ala
            20                  25                  30

Trp Lys Gly Ala Gly Ser Ile Arg Ile Thr Leu Ala Thr Thr Leu Ser
        35                  40                  45

Thr Ala Gln Asn Met Thr Asn Ser Lys Asn Asn Asn Asn Asn Asn Asp
    50                  55                  60

Tyr Asp Phe Leu Thr Val Glu Ser Ile Tyr Asp Asp Thr Asp Asp Ser
65                  70                  75                  80

Gln Leu Lys Phe Met Gly Arg Met Gly Lys Phe Lys Ser Glu Ala Ser
                85                  90                  95

Leu Gln Leu Gly Arg Leu Ile Thr Thr Lys Ser Ile Asp Asn Asn Lys
            100                 105                 110

Cys Met Leu Val Tyr Asp Ala Tyr Leu Pro Trp Ala Leu Asp Val Gly
        115                 120                 125

Lys Asp His Asn Ile Gln Ala Ala Ala Phe Phe Val Gln Ala Cys Ala
    130                 135                 140

Tyr Met Ala Ser Phe Tyr Pro Met Phe Leu Glu Glu Phe Gly Ser Asp
145                 150                 155                 160

Asp Gln His Pro Val Val Ala Ala Ala Lys Ala Glu Ser Val Pro Ser
                165                 170                 175

Leu Ser Val Glu Leu Pro Ser Arg Glu Glu Met Glu Arg Tyr Ala Pro
            180                 185                 190

Lys Cys Ala Gln Ser Pro Ser Ser Asp Asp Lys Pro Asn Thr Val Lys
        195                 200                 205

Lys Ser Leu His Pro Val Tyr Arg Met Val Val Ser Ser Ile Thr Thr
    210                 215                 220

Leu His Leu Ala Asp Phe Val Leu Ile Asn Ser Phe Asp His Leu Glu
225                 230                 235                 240

His Gln Leu Asp Val Leu Ala His Glu Ala Val Gly Cys Phe Ile Thr
                245                 250                 255

His Cys Gly Trp Asn Ser Ile Ile Glu Ala Thr Asn Phe Gly Val Pro
            260                 265                 270

Met Leu Gly Met Pro Gln Phe Met Asp Gln Phe Leu Asp Ala His Phe
        275                 280                 285

Met Glu Lys Val Trp Gly Val Gly Ile Arg Ala Lys Ala Asp Glu Lys
    290                 295                 300

Asn Phe Val Thr Cys Asp Glu Ile Lys Cys Gly Val Asn Glu Ile Met
305                 310                 315                 320

Tyr Gly Asp Lys Ala Asn Met Ile Lys Glu Asn Ala Ala Lys Trp Lys
                325                 330                 335

Asp Leu Ala Lys Glu Ala Val Gly Glu Gly Gly Ser Ser Asp Lys Asn
```

```
            340                 345                 350

Ile Asp Glu Ile Ile Asn Trp Leu Ala Ser Ser
        355                 360


<210> SEQ ID NO 57
<211> LENGTH: 1374
<212> TYPE: DNA
<213> ORGANISM: Spinacia oleracea

<400> SEQUENCE: 57

atgggtaaaa cagtagcagc ttcagagcag ttacacatag taatgatccc atggtttgct      60

tatggacaca ttcttcccta ttttgagctt tcaaacaaac ttgctgaaaa aggccataaa     120

atcaccttgg tagttccaaa caaagtcaaa cttgatttag aaccaaagat ccgtcatcct     180

tccttaatca gcttacatgc attcactgtc ccacacattg aacccttacc tccggggact     240

gagacatgtt cagacgtccc cattgaactt cagcaccacc ttgctgttgc catggacagg     300

gcccggcctg aggtggagtc catcatatca gccattgacg atccgaagcc ggatctgttg     360

ttctacgata acgcttactg ggtgcctgag atagccacaa agctggggat gaagtctgtg     420

ttttaccaga ttgcatgtgc tttaagtatc acccgcatta agcaaacccc gagtgcgagt     480

gcgagtgcga gtgcgagtgc caagctcttc actttaccca agtgggtgct gacgcctaag     540

gtgttaggcg acgcaagagc caattatgga gaagggatca cctattacca gagagtgaag     600

aaggctctaa gttcctgtga tgctatcgcc ttacgcacat gccgggagat tgaaggggaa     660

tcctctgata tcctggctgc acaatataac aagccagtct tcttaacagg tccggtccta     720

cccgaggttg aattcctccc ccctttggac aattcctggg ctgagtggct agccaagttt     780

gggcctaagt ccgtggtttt atgttgcttc ggaagccagt acgtccctga caaggctcaa     840

ctacaggaga tggcccttgc ccttgaggat actggtcttc ccttcttgat gtccgttaag     900

ccacccacag agtgcgccac catagaggag gcgttgccag aagggttctc agagagagtc     960

aaggaacgcg gggtggttca tggtggatgg gtgcaacagc tacaaatact agctcaccca    1020

tcagtgggtt gctttatttg tcattgtggg tacgggtcaa tgtgggaggg gttgttgagt    1080

gataaccagc tagtcttatt accacagctt cctgaccagt taatgatggc tcaaatgttg    1140

gcagaaaagc tcaaggtggg tgtgatggtg gacagagaag aagatgatgg gtgggtttcc    1200

aggaagaact tgtgccaagc agtcaagtct gtcatggatc ctcattccga gtttgcagct    1260

ttactcaaga acaaccatgc taacttcaga gacaagttgc taaccaacgg ttttatggct    1320

aattaccttg aagtttttga ccaggatttg aaacgctttc ttactgcaaa ttaa          1374


<210> SEQ ID NO 58
<211> LENGTH: 457
<212> TYPE: PRT
<213> ORGANISM: Spinacia oleracea

<400> SEQUENCE: 58

Met Gly Lys Thr Val Ala Ala Ser Glu Gln Leu His Ile Val Met Ile
1               5                   10                  15

Pro Trp Phe Ala Tyr Gly His Ile Leu Pro Tyr Phe Glu Leu Ser Asn
            20                  25                  30

Lys Leu Ala Glu Lys Gly His Lys Ile Thr Leu Val Val Pro Asn Lys
        35                  40                  45

Val Lys Leu Asp Leu Glu Pro Lys Ile Arg His Pro Ser Leu Ile Ser
    50                  55                  60
```

```
Leu His Ala Phe Thr Val Pro His Ile Glu Pro Leu Pro Pro Gly Thr
65                  70                  75                  80

Glu Thr Cys Ser Asp Val Pro Ile Glu Leu Gln His His Leu Ala Val
                85                  90                  95

Ala Met Asp Arg Ala Arg Pro Glu Val Glu Ser Ile Ile Ser Ala Ile
            100                 105                 110

Asp Asp Pro Lys Pro Asp Leu Leu Phe Tyr Asp Asn Ala Tyr Trp Val
        115                 120                 125

Pro Glu Ile Ala Thr Lys Leu Gly Met Lys Ser Val Phe Tyr Gln Ile
    130                 135                 140

Ala Cys Ala Leu Ser Ile Thr Arg Ile Lys Gln Thr Pro Ser Ala Ser
145                 150                 155                 160

Ala Ser Ala Ser Ala Ser Ala Lys Leu Phe Thr Leu Pro Lys Trp Val
                165                 170                 175

Leu Thr Pro Lys Val Leu Gly Asp Ala Arg Ala Asn Tyr Gly Glu Gly
            180                 185                 190

Ile Thr Tyr Tyr Gln Arg Val Lys Lys Ala Leu Ser Ser Cys Asp Ala
        195                 200                 205

Ile Ala Leu Arg Thr Cys Arg Glu Ile Glu Gly Glu Ser Ser Asp Ile
    210                 215                 220

Leu Ala Ala Gln Tyr Asn Lys Pro Val Phe Leu Thr Gly Pro Val Leu
225                 230                 235                 240

Pro Glu Val Glu Phe Leu Pro Pro Leu Asp Asn Ser Trp Ala Glu Trp
                245                 250                 255

Leu Ala Lys Phe Gly Pro Lys Ser Val Val Leu Cys Cys Phe Gly Ser
            260                 265                 270

Gln Tyr Val Pro Asp Lys Ala Gln Leu Gln Glu Met Ala Leu Ala Leu
        275                 280                 285

Glu Asp Thr Gly Leu Pro Phe Leu Met Ser Val Lys Pro Pro Thr Glu
    290                 295                 300

Cys Ala Thr Ile Glu Glu Ala Leu Pro Glu Gly Phe Ser Glu Arg Val
305                 310                 315                 320

Lys Glu Arg Gly Val Val His Gly Gly Trp Val Gln Gln Leu Gln Ile
                325                 330                 335

Leu Ala His Pro Ser Val Gly Cys Phe Ile Cys His Cys Gly Tyr Gly
            340                 345                 350

Ser Met Trp Glu Gly Leu Leu Ser Asp Asn Gln Leu Val Leu Leu Pro
        355                 360                 365

Gln Leu Pro Asp Gln Leu Met Met Ala Gln Met Leu Ala Glu Lys Leu
    370                 375                 380

Lys Val Gly Val Met Val Asp Arg Glu Glu Asp Asp Gly Trp Val Ser
385                 390                 395                 400

Arg Lys Asn Leu Cys Gln Ala Val Lys Ser Val Met Asp Pro His Ser
                405                 410                 415

Glu Phe Ala Ala Leu Leu Lys Asn Asn His Ala Asn Phe Arg Asp Lys
            420                 425                 430

Leu Leu Thr Asn Gly Phe Met Ala Asn Tyr Leu Glu Val Phe Asp Gln
        435                 440                 445

Asp Leu Lys Arg Phe Leu Thr Ala Asn
    450                 455
```

<210> SEQ ID NO 59
<211> LENGTH: 1347
<212> TYPE: DNA

<213> ORGANISM: Spinacia oleracea

<400> SEQUENCE: 59
atgggtggag agaaagagtt gcggatagtg atgttcccat ggcttgcctt tggacatttt 60
atcccatacc ttcacctttc aaacaaactt gctgaaaaag gccacaaaat caccttgttg 120
cttcccaaca aagctaggct tcagttggag tcacttaacc ttcatccttc tctcataact 180
ttccattcaa ttactgtccc acccctcgaa actctccctt atggcactga aacaactgcg 240
gatatctccc tcgaccaaca tggtgaactc tcgatttcca tggaccgcac tcggcccgag 300
gtggagtctt tcctatcaac ccataagccc gacctcgtcc tctacgacat ggcccattgg 360
gtacccgaga ttgctgctaa ggtcgggatt aagtcagttt catacaacgt tgtatgtgct 420
attgctgtat ctcatgttag acctagcctc cctcttccaa aaggaacggc agcacatgta 480
cccctgccat tgtcgtctgt ccctaagtgg agtcttaatc agcacggttc atcaacacca 540
tattttgggg aagggataac gttacttgaa cggtctgtaa tctccctctc gtctgcggat 600
gcaatagcca tccgcacgtg cagggagatt gaaggggtat attgtgaccg tgttgctgcc 660
acattcaaca agcctgtcct tgtcaccagc cacgccttgc ctgatcttga actcgaactc 720
tctccgttgg agactcgctg ggccgagtgg ctagctaggt tcgagccagg gtcagtgatc 780
ttttgctgcc ttggtagtca gcatgtctta gacgcacccc aactgcaaga gttggccctg 840
gggttggaaa tgacaggact acccttcttg atggctgtaa aaccccctgt ggggtgtacc 900
tccttggagg aggtgcttcc agaagggttt aatgatcggg ttagcgggcg aggggtggtt 960
cacggtgggt gggtgcagca gcagcagata atggcgcacc catcgttagg gtgctttgtg 1020
accctttgtg ggtcttcgtc gatgtgggag gggttagtga gtgaaagtca gttggtatta 1080
ctcccacaac tggcagacca aactctgtat gccaagttaa tggcagatga gctcaaggtg 1140
ggtgtgaagg tggagagaga agagaacggg tggatgacga agcgaagtct atgtgaagct 1200
atcaagagtg tgatggatga agatagtgat ataagtcatg tagttaggaa aaatcatgct 1260
aaatatagaa gtatgttgat tagccctggc tttattagtg gctacattga caacttcatc 1320
aaggatttac aagcccttgt tccttag 1347

<210> SEQ ID NO 60
<211> LENGTH: 448
<212> TYPE: PRT
<213> ORGANISM: Spinacia oleracea

<400> SEQUENCE: 60

Met Gly Gly Glu Lys Glu Leu Arg Ile Val Met Phe Pro Trp Leu Ala
1               5                   10                  15

Phe Gly His Phe Ile Pro Tyr Leu His Leu Ser Asn Lys Leu Ala Glu
            20                  25                  30

Lys Gly His Lys Ile Thr Leu Leu Leu Pro Asn Lys Ala Arg Leu Gln
        35                  40                  45

Leu Glu Ser Leu Asn Leu His Pro Ser Leu Ile Thr Phe His Ser Ile
    50                  55                  60

Thr Val Pro Pro Leu Glu Thr Leu Pro Tyr Gly Thr Glu Thr Thr Ala
65                  70                  75                  80

Asp Ile Ser Leu Asp Gln His Gly Glu Leu Ser Ile Ser Met Asp Arg
                85                  90                  95

Thr Arg Pro Glu Val Glu Ser Phe Leu Ser Thr His Lys Pro Asp Leu
            100                 105                 110

```
Val Leu Tyr Asp Met Ala His Trp Val Pro Glu Ile Ala Ala Lys Val
        115                 120                 125

Gly Ile Lys Ser Val Ser Tyr Asn Val Val Cys Ala Ile Ala Val Ser
    130                 135                 140

His Val Arg Pro Ser Leu Pro Leu Pro Lys Gly Thr Ala Ala His Val
145                 150                 155                 160

Pro Leu Pro Leu Ser Ser Val Pro Lys Trp Ser Leu Asn Gln His Gly
                165                 170                 175

Ser Ser Thr Pro Tyr Phe Gly Glu Gly Ile Thr Leu Leu Glu Arg Ser
            180                 185                 190

Val Ile Ser Leu Ser Ser Ala Asp Ala Ile Ala Ile Arg Thr Cys Arg
        195                 200                 205

Glu Ile Glu Gly Val Tyr Cys Asp Arg Val Ala Ala Thr Phe Asn Lys
    210                 215                 220

Pro Val Leu Val Thr Ser His Ala Leu Pro Asp Leu Glu Leu Glu Leu
225                 230                 235                 240

Ser Pro Leu Glu Thr Arg Trp Ala Glu Trp Leu Ala Arg Phe Glu Pro
                245                 250                 255

Gly Ser Val Ile Phe Cys Cys Leu Gly Ser Gln His Val Leu Asp Ala
            260                 265                 270

Pro Gln Leu Gln Glu Leu Ala Leu Gly Leu Glu Met Thr Gly Leu Pro
        275                 280                 285

Phe Leu Met Ala Val Lys Pro Pro Val Gly Cys Thr Ser Leu Glu Glu
    290                 295                 300

Val Leu Pro Glu Gly Phe Asn Asp Arg Val Ser Gly Arg Gly Val Val
305                 310                 315                 320

His Gly Gly Trp Val Gln Gln Gln Gln Ile Met Ala His Pro Ser Leu
                325                 330                 335

Gly Cys Phe Val Thr Leu Cys Gly Ser Ser Ser Met Trp Glu Gly Leu
            340                 345                 350

Val Ser Glu Ser Gln Leu Val Leu Leu Pro Gln Leu Ala Asp Gln Thr
        355                 360                 365

Leu Tyr Ala Lys Leu Met Ala Asp Glu Leu Lys Val Gly Val Lys Val
    370                 375                 380

Glu Arg Glu Glu Asn Gly Trp Met Thr Lys Arg Ser Leu Cys Glu Ala
385                 390                 395                 400

Ile Lys Ser Val Met Asp Glu Asp Ser Asp Ile Ser His Val Val Arg
                405                 410                 415

Lys Asn His Ala Lys Tyr Arg Ser Met Leu Ile Ser Pro Gly Phe Ile
            420                 425                 430

Ser Gly Tyr Ile Asp Asn Phe Ile Lys Asp Leu Gln Ala Leu Val Pro
        435                 440                 445
```

<210> SEQ ID NO 61
<211> LENGTH: 1476
<212> TYPE: DNA
<213> ORGANISM: Spinacia oleracea

<400> SEQUENCE: 61

```
atggagcttt caaaccctac cacaacccct accttaaacg caacccaacc cttacgaggc      60

tatttcattc cattaatcac agttccaagc cacatttcca atcttgttga cattgctaaa     120

ctcttctcat cacggggagt acatgtgact atcctcacca cccaccacac ctccctccgc     180

ttcaaacaat ccatacatga ttggggcttc aaaatcgacc tccacatcgt cgacttcccg     240
```

```
ttcagggaag tcggcttacc ggaaggagtg gaaaattaca gtgatgccac ccctgagcaa    300

gcaagccagc ttttccaggc ctttatgatg cttcagaagc ctatggagga tgccattcgg    360

gctgctaagc ccgacttcat cgtttccgat aggtattatc attggtctac tgatcttgca    420

cgtgagcttg ctattccacg gctcatcttt catgtcagat gttattttgc attgtgtgct    480

gctgaggttg ttgccaagtt tgcccctcat gagaaggttg aatctgacac tgacctcttt    540

ttccttcctg acctccctga taccatccac atgacccgtt tgcagcttcc cgaatggatt    600

cagacccgaa acatgttcac tgttctcaat gagagaatgg acgaggccga tagggagtgc    660

tacggtgtta ttgtaaacag ctgctacgag ttggagagag cttatgctga cttctaccgc    720

agcaacttgg gtcgacgtgc ttggtgtatc ggtccctatc cggtacactg cgacaaggtt    780

ggtaaaaaga aaggagatga cagcaaaaaa cattcatgtt ttgaatggct tgataaaatg    840

ggagaaggag aagttatata cgtgagtttt ggcactctgt cgtgtttcag ccctgctcaa    900

atctcagagc tggctactgc actcgaaatg tctggtcacc cgtttatctg ggtagtaagg    960

aatggtgaga aattgttacc tgatggattt gaagaaagaa ttacagagca ggacaaaggg   1020

gtgttaataa aagactgggc gccacaagtg aaaatacttg agcacccagc tgtaggcgga   1080

tttctgactc attgtggatg gaactcaact gtagaaagtt tagcagcagg tgtgccaatg   1140

gtcacatggc cgcttggtgc cgagcaattc ttcaatgaaa agttgattag tggagttttg   1200

aaggtggggg tcgaggtcgg gtctgagaag tggagtaggg gtatagtacc gaatactgat   1260

atgattgaga aggataaaat agaaagggcg attaaagagc tgatgagtaa agaacccgag   1320

gccgaggaaa ggaggcagaa ggttaaggag ttgagtaagg ctccaagaaa tgcggttgaa   1380

gaaggtggtt cgtctcgtaa caatttaagt gatttgattg aaaaattaca acgtttaaag   1440

gcgaatgaaa tatcagtgtc cacaaactca gaataa                             1476
```

<210> SEQ ID NO 62
<211> LENGTH: 491
<212> TYPE: PRT
<213> ORGANISM: Spinacia oleracea

<400> SEQUENCE: 62

```
Met Glu Leu Ser Asn Pro Thr Thr Thr Pro Thr Leu Asn Ala Thr Gln
1               5                   10                  15

Pro Leu Arg Gly Tyr Phe Ile Pro Leu Ile Thr Val Pro Ser His Ile
            20                  25                  30

Ser Asn Leu Val Asp Ile Ala Lys Leu Phe Ser Ser Arg Gly Val His
        35                  40                  45

Val Thr Ile Leu Thr Thr His His Thr Ser Leu Arg Phe Lys Gln Ser
    50                  55                  60

Ile His Asp Trp Gly Phe Lys Ile Asp Leu His Ile Val Asp Phe Pro
65                  70                  75                  80

Phe Arg Glu Val Gly Leu Pro Glu Gly Val Glu Asn Tyr Ser Asp Ala
                85                  90                  95

Thr Pro Glu Gln Ala Ser Gln Leu Phe Gln Ala Phe Met Met Leu Gln
            100                 105                 110

Lys Pro Met Glu Asp Ala Ile Arg Ala Ala Lys Pro Asp Phe Ile Val
        115                 120                 125

Ser Asp Arg Tyr Tyr His Trp Ser Thr Asp Leu Ala Arg Glu Leu Ala
    130                 135                 140

Ile Pro Arg Leu Ile Phe His Val Arg Cys Tyr Phe Ala Leu Cys Ala
145                 150                 155                 160
```

```
Ala Glu Val Val Ala Lys Phe Ala Pro His Glu Lys Val Glu Ser Asp
                165                 170                 175

Thr Asp Leu Phe Phe Leu Pro Asp Leu Pro Asp Thr Ile His Met Thr
            180                 185                 190

Arg Leu Gln Leu Pro Glu Trp Ile Gln Thr Arg Asn Met Phe Thr Val
        195                 200                 205

Leu Asn Glu Arg Met Asp Glu Ala Asp Arg Glu Cys Tyr Gly Val Ile
    210                 215                 220

Val Asn Ser Cys Tyr Glu Leu Glu Arg Ala Tyr Ala Asp Phe Tyr Arg
225                 230                 235                 240

Ser Asn Leu Gly Arg Arg Ala Trp Cys Ile Gly Pro Tyr Pro Val His
                245                 250                 255

Cys Asp Lys Val Gly Lys Lys Lys Gly Asp Asp Ser Lys Lys His Ser
            260                 265                 270

Cys Phe Glu Trp Leu Asp Lys Met Gly Glu Gly Glu Val Ile Tyr Val
        275                 280                 285

Ser Phe Gly Thr Leu Ser Cys Phe Ser Pro Ala Gln Ile Ser Glu Leu
    290                 295                 300

Ala Thr Ala Leu Glu Met Ser Gly His Pro Phe Ile Trp Val Val Arg
305                 310                 315                 320

Asn Gly Glu Lys Leu Leu Pro Asp Gly Phe Glu Glu Arg Ile Thr Glu
                325                 330                 335

Gln Asp Lys Gly Val Leu Ile Lys Asp Trp Ala Pro Gln Val Lys Ile
            340                 345                 350

Leu Glu His Pro Ala Val Gly Gly Phe Leu Thr His Cys Gly Trp Asn
        355                 360                 365

Ser Thr Val Glu Ser Leu Ala Ala Gly Val Pro Met Val Thr Trp Pro
    370                 375                 380

Leu Gly Ala Glu Gln Phe Phe Asn Glu Lys Leu Ile Ser Gly Val Leu
385                 390                 395                 400

Lys Val Gly Val Glu Val Gly Ser Glu Lys Trp Ser Arg Gly Ile Val
                405                 410                 415

Pro Asn Thr Asp Met Ile Glu Lys Asp Lys Ile Glu Arg Ala Ile Lys
            420                 425                 430

Glu Leu Met Ser Lys Glu Pro Glu Ala Glu Glu Arg Arg Gln Lys Val
        435                 440                 445

Lys Glu Leu Ser Lys Ala Pro Arg Asn Ala Val Glu Glu Gly Gly Ser
    450                 455                 460

Ser Arg Asn Asn Leu Ser Asp Leu Ile Glu Lys Leu Gln Arg Leu Lys
465                 470                 475                 480

Ala Asn Glu Ile Ser Val Ser Thr Asn Ser Glu
                485                 490


<210> SEQ ID NO 63
<211> LENGTH: 1539
<212> TYPE: DNA
<213> ORGANISM: Spinacia oleracea

<400> SEQUENCE: 63

atgggggaag tcaaccatga agaagtagaa attgaaataa tatcaataga aaccataaaa     60

ccatcatcac tacttccacc aaaaactcct ccaaaaacca tcacactttc tcacctcgat    120

caagctgccc ctttgtacta ctatccttta cttttatact acactaacac tactactact    180

accccaacat cacaaattcg agttgacata acaagtaccc taaaaacttc acttagcaaa    240
```

```
acacttgaca aattccaccc tattgcaggt cgatgtgtgg acgactctac aatttgttgc    300

aaccaccaag gaataccatt cattgaaacc aaagttgact ccaatatctt ggatgtcatg    360

aactcgcctg agaaaatgaa gttgcttatc aagtttctcc ctcatgcaga gtttcaagat    420

gtgactcgac cagtctcgga tttaaaccat ttggcgtttc aagtcaatgt tttccggtgt    480

ggtggggtga tcattggctc ctatgtgctc cacaagctcc ttgatggaat ctctcttgga    540

actttcttta aaaattggtc aaccattgct aatgatgagc gagttaagga cgacgaccta    600

gtacaacctg actttgaagc cactattaag gcgttccctc cgcgtacagc aactccaatg    660

cttcctcgta atcaacaact tccaaaggcg gctgaaaaac caaataataa tccagtcaaa    720

gttcttgtga caaagagctt cgtatttgac attgtttctt taaagaagat gatgttcatg    780

gctaagagtg aattggttcc taaacccacc aaatttgaga ccgtgacagg gtttatttgg    840

gaacaaacct tatcaacatt gcgtaattct ggagttgaag ttgaacatac atcgcttata    900

atacctgtaa acatccgccc aaggatgagt ccgccactcc caagaggatc catgggtaac    960

ttgctcaaga atgcaaaggc acaggccaac accagcagca gcaatgggct tcaagacctt   1020

gttaaagaaa tccattcatc tttgtctcaa acaacccaga aaattaatac tcctcctcct   1080

cctcctcctc ctcctcctac tactactgct acaacaatcc attcatcttt gtctcaaaca   1140

acccagaaaa ttaatactcc tcctcctact actacaacaa tccattcatc tttgtctcaa   1200

acaacccaga aaattaatac tactactact acagcagagg ttattttgac taaacggaaa   1260

gttgacaatc cagttacaca gaatcgagaa ggaaactacc tcttcaccag ttggtgcaag   1320

attgggttgg atgaggctga cttcgggttc ggaaagcccg tttgggtaat tcccaacgat   1380

gggagacccc ctaaggtcag gaatatgatt ttccttactg attataggca tcccgaaaca   1440

ggcgttgaag gaattgcagc atggattacg ttggaagaga aacaaatgca atgtttaaag   1500

tcaaacccag aattccttgc ttttgctact cctaattag                          1539
```

<210> SEQ ID NO 64
<211> LENGTH: 512
<212> TYPE: PRT
<213> ORGANISM: Spinacia oleracea

<400> SEQUENCE: 64

```
Met Gly Glu Val Asn His Glu Glu Val Glu Ile Glu Ile Ile Ser Ile
1               5                   10                  15

Glu Thr Ile Lys Pro Ser Ser Leu Leu Pro Pro Lys Thr Pro Pro Lys
            20                  25                  30

Thr Ile Thr Leu Ser His Leu Asp Gln Ala Ala Pro Leu Tyr Tyr Tyr
        35                  40                  45

Pro Leu Leu Leu Tyr Tyr Thr Asn Thr Thr Thr Thr Thr Pro Thr Ser
    50                  55                  60

Gln Ile Arg Val Asp Ile Thr Ser Thr Leu Lys Thr Ser Leu Ser Lys
65                  70                  75                  80

Thr Leu Asp Lys Phe His Pro Ile Ala Gly Arg Cys Val Asp Asp Ser
                85                  90                  95

Thr Ile Cys Cys Asn His Gln Gly Ile Pro Phe Ile Glu Thr Lys Val
            100                 105                 110

Asp Ser Asn Ile Leu Asp Val Met Asn Ser Pro Glu Lys Met Lys Leu
        115                 120                 125

Leu Ile Lys Phe Leu Pro His Ala Glu Phe Gln Asp Val Thr Arg Pro
    130                 135                 140
```

```
Val Ser Asp Leu Asn His Leu Ala Phe Gln Val Asn Val Phe Arg Cys
145                 150                 155                 160

Gly Gly Val Ile Ile Gly Ser Tyr Val Leu His Lys Leu Leu Asp Gly
                165                 170                 175

Ile Ser Leu Gly Thr Phe Phe Lys Asn Trp Ser Thr Ile Ala Asn Asp
            180                 185                 190

Glu Arg Val Lys Asp Asp Asp Leu Val Gln Pro Asp Phe Glu Ala Thr
        195                 200                 205

Ile Lys Ala Phe Pro Pro Arg Thr Ala Thr Pro Met Leu Pro Arg Asn
    210                 215                 220

Gln Gln Leu Pro Lys Ala Ala Glu Lys Pro Asn Asn Asn Pro Val Lys
225                 230                 235                 240

Val Leu Val Thr Lys Ser Phe Val Phe Asp Ile Val Ser Leu Lys Lys
                245                 250                 255

Met Met Phe Met Ala Lys Ser Glu Leu Val Pro Lys Pro Thr Lys Phe
            260                 265                 270

Glu Thr Val Thr Gly Phe Ile Trp Glu Gln Thr Leu Ser Thr Leu Arg
        275                 280                 285

Asn Ser Gly Val Glu Val Glu His Thr Ser Leu Ile Ile Pro Val Asn
    290                 295                 300

Ile Arg Pro Arg Met Ser Pro Pro Leu Pro Arg Gly Ser Met Gly Asn
305                 310                 315                 320

Leu Leu Lys Asn Ala Lys Ala Gln Ala Asn Thr Ser Ser Ser Asn Gly
                325                 330                 335

Leu Gln Asp Leu Val Lys Glu Ile His Ser Ser Leu Ser Gln Thr Thr
            340                 345                 350

Gln Lys Ile Asn Thr Pro Pro Pro Pro Pro Pro Pro Pro Pro Thr Thr
        355                 360                 365

Thr Ala Thr Thr Ile His Ser Ser Leu Ser Gln Thr Thr Gln Lys Ile
    370                 375                 380

Asn Thr Pro Pro Pro Thr Thr Thr Thr Ile His Ser Ser Leu Ser Gln
385                 390                 395                 400

Thr Thr Gln Lys Ile Asn Thr Thr Thr Thr Thr Ala Glu Val Ile Leu
                405                 410                 415

Thr Lys Arg Lys Val Asp Asn Pro Val Thr Gln Asn Arg Glu Gly Asn
            420                 425                 430

Tyr Leu Phe Thr Ser Trp Cys Lys Ile Gly Leu Asp Glu Ala Asp Phe
        435                 440                 445

Gly Phe Gly Lys Pro Val Trp Val Ile Pro Asn Asp Gly Arg Pro Pro
    450                 455                 460

Lys Val Arg Asn Met Ile Phe Leu Thr Asp Tyr Arg His Pro Glu Thr
465                 470                 475                 480

Gly Val Glu Gly Ile Ala Ala Trp Ile Thr Leu Glu Glu Lys Gln Met
                485                 490                 495

Gln Cys Leu Lys Ser Asn Pro Glu Phe Leu Ala Phe Ala Thr Pro Asn
            500                 505                 510
```

<210> SEQ ID NO 65
<211> LENGTH: 2091
<212> TYPE: DNA
<213> ORGANISM: Spinacia oleracea

<400> SEQUENCE: 65
atggcaactt ctcacattcg caatgtccaa ttaaccagag ccattgttaa ccgtctccac 60

-continued

```
atcttcctcc attccgtagc catcttctcg ctcttctact accgtttcac ttccttcttc    120
aactccgaca tctccatact tgcttactcc ttactcacca ccgccgaact cttcttaacc    180
tttctatggg cttttactca ggctttccgg tggcgtcccg taatgaggga agtctccggg    240
tacgaatcca tcaaacccga acaactaccg ggtttggatg tcttcattgt cactgctgac    300
ccgacaaagg agccagttct ggaggtgatg aactccgtga tatcatccat ggctttggat    360
tatccggttg atagactggc ggtttacttg tcggatgacg gtggttctcc gttgtcgaag    420
gaggcgatta agaaggctta tgagtttgct aagctttgga ttcctttttg taataagtat    480
aatgttaaga caaggtgtcc tcaggctttc ttctcgcctc ttgctgatgg ggaaaggctt    540
gattggaatt ctgagtttat ggctgatcaa ttggaactcc agaccaaata tgaagctttt    600
agaaactatg tggagaaaga aagtggagat aacaccaaat gtactgcagt tcatgatcga    660
cctccttgcg ttgagattat acatgacaac aaacagaacg gagaaagtga tgtgaagatg    720
ccccttctgg tttatgtagc cagggaaaag agacctggtc gtcctcatcg tttcaaagct    780
ggagccctta atgctcttct tcgagtatcc agtttaatga gcaatgcacc ttacttattg    840
gtgttggatt gtgatatgta ctgccatgat ccaacttctg ctcgtcaatc tatgtgcttc    900
catcttgaca caaacatggc ttcctctctt gcatatgtgc aataccctca aatttctat     960
aatgttagca aaaatgacat ctatgatggc caagccagat cagctcatat gacgaaatgg   1020
aaaggcatgg atggactcag aggcccggtc ttgaatggaa ctgggtatta tttgaagcga   1080
aaagcattat ttggaaagcc taataacgaa gatgaatacc tcaacagtca accagaaaag   1140
gcctttggct cctccacaaa attaattgct gcactaagag agaactccaa gcaaaatctt   1200
gccataaagg aattgacaga agatgagttg taccaagagg ctagaaattt ggctacttgc   1260
acatatgaag caaacacact atggggcagt gaggtaggat attcgtatga gtgcttgttg   1320
gagagtacat tcactggata tatgttacat tgcagaggat ggaaatctgt gtatctttac   1380
ccaaaaagac catgcttctt gggatgcaca acgattgata tgaaggatgc tacggttcaa   1440
ctaataaaat ggacctcctc attacttgga attgccctgt cgaagtctag ccctctaact   1500
ttggccatgt ccagtatgtc aatcctgcaa agcatgtgtt acgcgtacat cacatttaca   1560
ggccttttg cagctccatt ggttatatat ggtgttgtcc ttccaataag cctattgaag    1620
ggctttccta ttttccctaa ggtatcggat ccatggattt tgccatttgt gttgatattt   1680
gtatcctccc atcttcaaca tctatatgag gtcctggaaa gtgacaaatc agcaacacaa   1740
tggtggaatg aggtgagaat ttggatgatg aaatcagtga cagcctgttt gtttgggttg   1800
acggaagcga taatgaagaa gattggagta caaactgcaa cattcagatt aacaaataag   1860
gtagttgaga aggaaaagat ggataaatac gagaaggaga ggtttgattt ctcaggagca   1920
gctatgctta tggttcctct taatattttg gtggtactaa atatggtgtc attcattggt   1980
ggactcatga gggtcataat caacaacagt tatgatcaaa tgtttgcaca acttttcctc   2040
tcctttttttg tcctacttct tagctaccct gttgttaagg gatggttata a           2091
```

<210> SEQ ID NO 66
<211> LENGTH: 696
<212> TYPE: PRT
<213> ORGANISM: Spinacia oleracea

<400> SEQUENCE: 66

```
Met Ala Thr Ser His Ile Arg Asn Val Gln Leu Thr Arg Ala Ile Val
1               5                   10                  15
```

-continued

```
Asn Arg Leu His Ile Phe Leu His Ser Val Ala Ile Phe Ser Leu Phe
            20                  25                  30

Tyr Tyr Arg Phe Thr Ser Phe Phe Asn Ser Asp Ile Ser Ile Leu Ala
        35                  40                  45

Tyr Ser Leu Leu Thr Thr Ala Glu Leu Phe Leu Thr Phe Leu Trp Ala
    50                  55                  60

Phe Thr Gln Ala Phe Arg Trp Arg Pro Val Met Arg Glu Val Ser Gly
65                  70                  75                  80

Tyr Glu Ser Ile Lys Pro Glu Gln Leu Pro Gly Leu Asp Val Phe Ile
                85                  90                  95

Val Thr Ala Asp Pro Thr Lys Glu Pro Val Leu Glu Val Met Asn Ser
            100                 105                 110

Val Ile Ser Ser Met Ala Leu Asp Tyr Pro Val Asp Arg Leu Ala Val
        115                 120                 125

Tyr Leu Ser Asp Asp Gly Gly Ser Pro Leu Ser Lys Glu Ala Ile Lys
    130                 135                 140

Lys Ala Tyr Glu Phe Ala Lys Leu Trp Ile Pro Phe Cys Asn Lys Tyr
145                 150                 155                 160

Asn Val Lys Thr Arg Cys Pro Gln Ala Phe Phe Ser Pro Leu Ala Asp
                165                 170                 175

Gly Glu Arg Leu Asp Trp Asn Ser Glu Phe Met Ala Asp Gln Leu Glu
            180                 185                 190

Leu Gln Thr Lys Tyr Glu Ala Phe Arg Asn Tyr Val Glu Lys Glu Ser
        195                 200                 205

Gly Asp Asn Thr Lys Cys Thr Ala Val His Asp Arg Pro Pro Cys Val
    210                 215                 220

Glu Ile Ile His Asp Asn Lys Gln Asn Gly Glu Ser Asp Val Lys Met
225                 230                 235                 240

Pro Leu Leu Val Tyr Val Ala Arg Glu Lys Arg Pro Gly Arg Pro His
                245                 250                 255

Arg Phe Lys Ala Gly Ala Leu Asn Ala Leu Leu Arg Val Ser Ser Leu
            260                 265                 270

Met Ser Asn Ala Pro Tyr Leu Leu Val Leu Asp Cys Asp Met Tyr Cys
        275                 280                 285

His Asp Pro Thr Ser Ala Arg Gln Ser Met Cys Phe His Leu Asp Thr
    290                 295                 300

Asn Met Ala Ser Ser Leu Ala Tyr Val Gln Tyr Pro Gln Ile Phe Tyr
305                 310                 315                 320

Asn Val Ser Lys Asn Asp Ile Tyr Asp Gly Gln Ala Arg Ser Ala His
                325                 330                 335

Met Thr Lys Trp Lys Gly Met Asp Gly Leu Arg Gly Pro Val Leu Asn
            340                 345                 350

Gly Thr Gly Tyr Tyr Leu Lys Arg Lys Ala Leu Phe Gly Lys Pro Asn
        355                 360                 365

Asn Glu Asp Glu Tyr Leu Asn Ser Gln Pro Glu Lys Ala Phe Gly Ser
    370                 375                 380

Ser Thr Lys Leu Ile Ala Ala Leu Arg Glu Asn Ser Lys Gln Asn Leu
385                 390                 395                 400

Ala Ile Lys Glu Leu Thr Glu Asp Glu Leu Tyr Gln Glu Ala Arg Asn
                405                 410                 415

Leu Ala Thr Cys Thr Tyr Glu Ala Asn Thr Leu Trp Gly Ser Glu Val
            420                 425                 430
```

```
Gly Tyr Ser Tyr Glu Cys Leu Leu Glu Ser Thr Phe Thr Gly Tyr Met
        435                 440                 445

Leu His Cys Arg Gly Trp Lys Ser Val Tyr Leu Tyr Pro Lys Arg Pro
    450                 455                 460

Cys Phe Leu Gly Cys Thr Thr Ile Asp Met Lys Asp Ala Thr Val Gln
465                 470                 475                 480

Leu Ile Lys Trp Thr Ser Ser Leu Leu Gly Ile Ala Leu Ser Lys Ser
                485                 490                 495

Ser Pro Leu Thr Leu Ala Met Ser Ser Met Ser Ile Leu Gln Ser Met
            500                 505                 510

Cys Tyr Ala Tyr Ile Thr Phe Thr Gly Leu Phe Ala Ala Pro Leu Val
        515                 520                 525

Ile Tyr Gly Val Val Leu Pro Ile Ser Leu Leu Lys Gly Phe Pro Ile
    530                 535                 540

Phe Pro Lys Val Ser Asp Pro Trp Ile Leu Pro Phe Val Leu Ile Phe
545                 550                 555                 560

Val Ser Ser His Leu Gln His Leu Tyr Glu Val Leu Glu Ser Asp Lys
                565                 570                 575

Ser Ala Thr Gln Trp Trp Asn Glu Val Arg Ile Trp Met Met Lys Ser
            580                 585                 590

Val Thr Ala Cys Leu Phe Gly Leu Thr Glu Ala Ile Met Lys Lys Ile
        595                 600                 605

Gly Val Gln Thr Ala Thr Phe Arg Leu Thr Asn Lys Val Val Glu Lys
    610                 615                 620

Glu Lys Met Asp Lys Tyr Glu Lys Glu Arg Phe Asp Phe Ser Gly Ala
625                 630                 635                 640

Ala Met Leu Met Val Pro Leu Asn Ile Leu Val Val Leu Asn Met Val
                645                 650                 655

Ser Phe Ile Gly Gly Leu Met Arg Val Ile Ile Asn Asn Ser Tyr Asp
            660                 665                 670

Gln Met Phe Ala Gln Leu Phe Leu Ser Phe Phe Val Leu Leu Leu Ser
        675                 680                 685

Tyr Pro Val Val Lys Gly Trp Leu
    690                 695


<210> SEQ ID NO 67
<211> LENGTH: 1081
<212> TYPE: PRT
<213> ORGANISM: Arabodopsis thaliana

<400> SEQUENCE: 67

Met Glu Ala Ser Ala Gly Leu Val Ala Gly Ser Tyr Arg Arg Asn Glu
1               5                   10                  15

Leu Val Arg Ile Arg His Glu Ser Asp Gly Gly Thr Lys Pro Leu Lys
            20                  25                  30

Asn Met Asn Gly Gln Ile Cys Gln Ile Cys Gly Asp Asp Val Gly Leu
        35                  40                  45

Ala Glu Thr Gly Asp Val Phe Val Ala Cys Asn Glu Cys Ala Phe Pro
    50                  55                  60

Val Cys Arg Pro Cys Tyr Glu Tyr Glu Arg Lys Asp Gly Thr Gln Cys
65                  70                  75                  80

Cys Pro Gln Cys Lys Thr Arg Phe Arg Arg His Arg Gly Ser Pro Arg
                85                  90                  95

Val Glu Gly Asp Glu Asp Glu Asp Asp Val Asp Asp Ile Glu Asn Glu
            100                 105                 110
```

```
Phe Asn Tyr Ala Gln Gly Ala Asn Lys Ala Arg His Gln Arg His Gly
        115                 120                 125

Glu Glu Phe Ser Ser Ser Ser Arg His Glu Ser Gln Pro Ile Pro Leu
    130                 135                 140

Leu Thr His Gly His Thr Val Ser Gly Glu Ile Arg Thr Pro Asp Thr
145                 150                 155                 160

Gln Ser Val Arg Thr Thr Ser Gly Pro Leu Gly Pro Ser Asp Arg Asn
                165                 170                 175

Ala Ile Ser Ser Pro Tyr Ile Asp Pro Arg Gln Pro Val Pro Val Arg
            180                 185                 190

Ile Val Asp Pro Ser Lys Asp Leu Asn Ser Tyr Gly Leu Gly Asn Val
        195                 200                 205

Asp Trp Lys Glu Arg Val Glu Gly Trp Lys Leu Lys Gln Glu Lys Asn
    210                 215                 220

Met Leu Gln Met Thr Gly Lys Tyr His Glu Gly Lys Gly Gly Glu Ile
225                 230                 235                 240

Glu Gly Thr Gly Ser Asn Gly Glu Glu Leu Gln Met Ala Asp Asp Thr
                245                 250                 255

Arg Leu Pro Met Ser Arg Val Val Pro Ile Pro Ser Ser Arg Leu Thr
            260                 265                 270

Pro Tyr Arg Val Val Ile Ile Leu Arg Leu Ile Ile Leu Cys Phe Phe
        275                 280                 285

Leu Gln Tyr Arg Thr Thr His Pro Val Lys Asn Ala Tyr Pro Leu Trp
    290                 295                 300

Leu Thr Ser Val Ile Cys Glu Ile Trp Phe Ala Phe Ser Trp Leu Leu
305                 310                 315                 320

Asp Gln Phe Pro Lys Trp Tyr Pro Ile Asn Arg Glu Thr Tyr Leu Asp
                325                 330                 335

Arg Leu Ala Ile Arg Tyr Asp Arg Asp Gly Glu Pro Ser Gln Leu Val
            340                 345                 350

Pro Val Asp Val Phe Val Ser Thr Val Asp Pro Leu Lys Glu Pro Pro
        355                 360                 365

Leu Val Thr Ala Asn Thr Val Leu Ser Ile Leu Ser Val Asp Tyr Pro
    370                 375                 380

Val Asp Lys Val Ala Cys Tyr Val Ser Asp Asp Gly Ser Ala Met Leu
385                 390                 395                 400

Thr Phe Glu Ser Leu Ser Glu Thr Ala Glu Phe Ala Lys Lys Trp Val
                405                 410                 415

Pro Phe Cys Lys Lys Phe Asn Ile Glu Pro Arg Ala Pro Glu Phe Tyr
            420                 425                 430

Phe Ala Gln Lys Ile Asp Tyr Leu Lys Asp Lys Ile Gln Pro Ser Phe
        435                 440                 445

Val Lys Glu Arg Arg Ala Met Lys Arg Glu Tyr Glu Glu Phe Lys Val
    450                 455                 460

Arg Ile Asn Ala Leu Val Ala Lys Ala Gln Lys Ile Pro Glu Glu Gly
465                 470                 475                 480

Trp Thr Met Gln Asp Gly Thr Pro Trp Pro Gly Asn Asn Thr Arg Asp
                485                 490                 495

His Pro Gly Met Ile Gln Val Phe Leu Gly His Ser Gly Gly Leu Asp
            500                 505                 510

Thr Asp Gly Asn Glu Leu Pro Arg Leu Ile Tyr Val Ser Arg Glu Lys
        515                 520                 525
```

-continued

```
Arg Pro Gly Phe Gln His His Lys Lys Ala Gly Ala Met Asn Ala Leu
    530                 535                 540

Ile Arg Val Ser Ala Val Leu Thr Asn Gly Ala Tyr Leu Leu Asn Val
545                 550                 555                 560

Asp Cys Asp His Tyr Phe Asn Asn Ser Lys Ala Ile Lys Glu Ala Met
                565                 570                 575

Cys Phe Met Met Asp Pro Ala Ile Gly Lys Lys Cys Cys Tyr Val Gln
            580                 585                 590

Phe Pro Gln Arg Phe Asp Gly Ile Asp Leu His Asp Arg Tyr Ala Asn
        595                 600                 605

Arg Asn Ile Val Phe Phe Asp Ile Asn Met Lys Gly Leu Asp Gly Ile
    610                 615                 620

Gln Gly Pro Val Tyr Val Gly Thr Gly Cys Cys Phe Asn Arg Gln Ala
625                 630                 635                 640

Leu Tyr Gly Tyr Asp Pro Val Leu Thr Glu Glu Asp Leu Glu Pro Asn
                645                 650                 655

Ile Ile Val Lys Ser Cys Cys Gly Ser Arg Lys Lys Gly Lys Ser Ser
            660                 665                 670

Lys Lys Tyr Asn Tyr Glu Lys Arg Arg Gly Ile Asn Arg Ser Asp Ser
        675                 680                 685

Asn Ala Pro Leu Phe Asn Met Glu Asp Ile Asp Glu Gly Phe Glu Gly
    690                 695                 700

Tyr Asp Asp Glu Arg Ser Ile Leu Met Ser Gln Arg Ser Val Glu Lys
705                 710                 715                 720

Arg Phe Gly Gln Ser Pro Val Phe Ile Ala Ala Thr Phe Met Glu Gln
                725                 730                 735

Gly Gly Ile Pro Pro Thr Thr Asn Pro Ala Thr Leu Leu Lys Glu Ala
            740                 745                 750

Ile His Val Ile Ser Cys Gly Tyr Glu Asp Lys Thr Glu Trp Gly Lys
        755                 760                 765

Glu Ile Gly Trp Ile Tyr Gly Ser Val Thr Glu Asp Ile Leu Thr Gly
    770                 775                 780

Phe Lys Met His Ala Arg Gly Trp Ile Ser Ile Tyr Cys Asn Pro Pro
785                 790                 795                 800

Arg Pro Ala Phe Lys Gly Ser Ala Pro Ile Asn Leu Ser Asp Arg Leu
                805                 810                 815

Asn Gln Val Leu Arg Trp Ala Leu Gly Ser Ile Glu Ile Leu Leu Ser
            820                 825                 830

Arg His Cys Pro Ile Trp Tyr Gly Tyr His Gly Arg Leu Arg Leu Leu
        835                 840                 845

Glu Arg Ile Ala Tyr Ile Asn Thr Ile Val Tyr Pro Ile Thr Ser Ile
    850                 855                 860

Pro Leu Ile Ala Tyr Cys Ile Leu Pro Ala Phe Cys Leu Ile Thr Asp
865                 870                 875                 880

Arg Phe Ile Ile Pro Glu Ile Ser Asn Tyr Ala Ser Ile Trp Phe Ile
                885                 890                 895

Leu Leu Phe Ile Ser Ile Ala Val Thr Gly Ile Leu Glu Leu Arg Trp
            900                 905                 910

Ser Gly Val Ser Ile Glu Asp Trp Trp Arg Asn Glu Gln Phe Trp Val
        915                 920                 925

Ile Gly Gly Thr Ser Ala His Leu Phe Ala Val Phe Gln Gly Leu Leu
    930                 935                 940

Lys Val Leu Ala Gly Ile Asp Thr Asn Phe Thr Val Thr Ser Lys Ala
```

945 950 955 960

Thr Asp Glu Asp Gly Asp Phe Ala Glu Leu Tyr Ile Phe Lys Trp Thr
965 970 975

Ala Leu Leu Ile Pro Pro Thr Thr Val Leu Leu Val Asn Leu Ile Gly
980 985 990

Ile Val Ala Gly Val Ser Tyr Ala Val Asn Ser Gly Tyr Gln Ser Trp
995 1000 1005

Gly Pro Leu Phe Gly Lys Leu Phe Phe Ala Leu Trp Val Ile Ala
1010 1015 1020

His Leu Tyr Pro Phe Leu Lys Gly Leu Leu Gly Arg Gln Asn Arg
1025 1030 1035

Thr Pro Thr Ile Val Ile Val Trp Ser Val Leu Leu Ala Ser Ile
1040 1045 1050

Phe Ser Leu Leu Trp Val Arg Ile Asn Pro Phe Val Asp Ala Asn
1055 1060 1065

Pro Asn Ala Asn Asn Phe Asn Gly Lys Gly Gly Val Phe
1070 1075 1080

<210> SEQ ID NO 68
<211> LENGTH: 1065
<212> TYPE: PRT
<213> ORGANISM: Arabodopsis thaliana

<400> SEQUENCE: 68

Met Glu Ser Glu Gly Glu Thr Ala Gly Lys Pro Met Lys Asn Ile Val
1 5 10 15

Pro Gln Thr Cys Gln Ile Cys Ser Asp Asn Val Gly Lys Thr Val Asp
20 25 30

Gly Asp Arg Phe Val Ala Cys Asp Ile Cys Ser Phe Pro Val Cys Arg
35 40 45

Pro Cys Tyr Glu Tyr Glu Arg Lys Asp Gly Asn Gln Ser Cys Pro Gln
50 55 60

Cys Lys Thr Arg Tyr Lys Arg Leu Lys Gly Ser Pro Ala Ile Pro Gly
65 70 75 80

Asp Lys Asp Glu Asp Gly Leu Ala Asp Glu Gly Thr Val Glu Phe Asn
85 90 95

Tyr Pro Gln Lys Glu Lys Ile Ser Glu Arg Met Leu Gly Trp His Leu
100 105 110

Thr Arg Gly Lys Gly Glu Glu Met Gly Glu Pro Gln Tyr Asp Lys Glu
115 120 125

Val Ser His Asn His Leu Pro Arg Leu Thr Ser Arg Gln Asp Thr Ser
130 135 140

Gly Glu Phe Ser Ala Ala Ser Pro Glu Arg Leu Ser Val Ser Ser Thr
145 150 155 160

Ile Ala Gly Gly Lys Arg Leu Pro Tyr Ser Ser Asp Val Asn Gln Ser
165 170 175

Pro Asn Arg Arg Ile Val Asp Pro Val Gly Leu Gly Asn Val Ala Trp
180 185 190

Lys Glu Arg Val Asp Gly Trp Lys Met Lys Gln Glu Lys Asn Thr Gly
195 200 205

Pro Val Ser Thr Gln Ala Ala Ser Glu Arg Gly Gly Val Asp Ile Asp
210 215 220

Ala Ser Thr Asp Ile Leu Ala Asp Glu Ala Leu Leu Asn Asp Glu Ala
225 230 235 240

```
Arg Gln Pro Leu Ser Arg Lys Val Ser Ile Pro Ser Ser Arg Ile Asn
                245                 250                 255

Pro Tyr Arg Met Val Ile Met Leu Arg Leu Val Ile Leu Cys Leu Phe
            260                 265                 270

Leu His Tyr Arg Ile Thr Asn Pro Val Pro Asn Ala Phe Ala Leu Trp
        275                 280                 285

Leu Val Ser Val Ile Cys Glu Ile Trp Phe Ala Leu Ser Trp Ile Leu
    290                 295                 300

Asp Gln Phe Pro Lys Trp Phe Pro Val Asn Arg Glu Thr Tyr Leu Asp
305                 310                 315                 320

Arg Leu Ala Leu Arg Tyr Asp Arg Glu Gly Glu Pro Ser Gln Leu Ala
                325                 330                 335

Ala Val Asp Ile Phe Val Ser Thr Val Asp Pro Leu Lys Glu Pro Pro
            340                 345                 350

Leu Val Thr Ala Asn Thr Val Leu Ser Ile Leu Ala Val Asp Tyr Pro
        355                 360                 365

Val Asp Lys Val Ser Cys Tyr Val Phe Asp Asp Gly Ala Ala Met Leu
    370                 375                 380

Ser Phe Glu Ser Leu Ala Glu Thr Ser Glu Phe Ala Arg Lys Trp Val
385                 390                 395                 400

Pro Phe Cys Lys Lys Tyr Ser Ile Glu Pro Arg Ala Pro Glu Trp Tyr
                405                 410                 415

Phe Ala Ala Lys Ile Asp Tyr Leu Lys Asp Lys Val Gln Thr Ser Phe
            420                 425                 430

Val Lys Asp Arg Arg Ala Met Lys Arg Glu Tyr Glu Glu Phe Lys Ile
        435                 440                 445

Arg Ile Asn Ala Leu Val Ser Lys Ala Leu Lys Cys Pro Glu Glu Gly
    450                 455                 460

Trp Val Met Gln Asp Gly Thr Pro Trp Pro Gly Asn Asn Thr Gly Asp
465                 470                 475                 480

His Pro Gly Met Ile Gln Val Phe Leu Gly Gln Asn Gly Gly Leu Asp
                485                 490                 495

Ala Glu Gly Asn Glu Leu Pro Arg Leu Val Tyr Val Ser Arg Glu Lys
            500                 505                 510

Arg Pro Gly Phe Gln His His Lys Lys Ala Gly Ala Met Asn Ala Leu
        515                 520                 525

Val Arg Val Ser Ala Val Leu Thr Asn Gly Pro Phe Ile Leu Asn Leu
    530                 535                 540

Asp Cys Asp His Tyr Ile Asn Asn Ser Lys Ala Leu Arg Glu Ala Met
545                 550                 555                 560

Cys Phe Leu Met Asp Pro Asn Leu Gly Lys Gln Val Cys Tyr Val Gln
                565                 570                 575

Phe Pro Gln Arg Phe Asp Gly Ile Asp Lys Asn Asp Arg Tyr Ala Asn
            580                 585                 590

Arg Asn Thr Val Phe Phe Asp Ile Asn Leu Arg Gly Leu Asp Gly Ile
        595                 600                 605

Gln Gly Pro Val Tyr Val Gly Thr Gly Cys Val Phe Asn Arg Thr Ala
    610                 615                 620

Leu Tyr Gly Tyr Glu Pro Pro Ile Lys Val Lys His Lys Lys Pro Ser
625                 630                 635                 640

Leu Leu Ser Lys Leu Cys Gly Gly Ser Arg Lys Lys Asn Ser Lys Ala
                645                 650                 655

Lys Lys Glu Ser Asp Lys Lys Lys Ser Gly Arg His Thr Asp Ser Thr
```

-continued

```
            660                 665                 670

Val Pro Val Phe Asn Leu Asp Asp Ile Glu Glu Gly Val Glu Gly Ala
        675                 680                 685

Gly Phe Asp Asp Glu Lys Ala Leu Leu Met Ser Gln Met Ser Leu Glu
    690                 695                 700

Lys Arg Phe Gly Gln Ser Ala Val Phe Val Ala Ser Thr Leu Met Glu
705                 710                 715                 720

Asn Gly Gly Val Pro Pro Ser Ala Thr Pro Glu Asn Leu Leu Lys Glu
                725                 730                 735

Ala Ile His Val Ile Ser Cys Gly Tyr Glu Asp Lys Ser Asp Trp Gly
            740                 745                 750

Met Glu Ile Gly Trp Ile Tyr Gly Ser Val Thr Glu Asp Ile Leu Thr
        755                 760                 765

Gly Phe Lys Met His Ala Arg Gly Trp Arg Ser Ile Tyr Cys Met Pro
    770                 775                 780

Lys Leu Pro Ala Phe Lys Gly Ser Ala Pro Ile Asn Leu Ser Asp Arg
785                 790                 795                 800

Leu Asn Gln Val Leu Arg Trp Ala Leu Gly Ser Val Glu Ile Leu Phe
                805                 810                 815

Ser Arg His Cys Pro Ile Trp Tyr Gly Tyr Asn Gly Arg Leu Lys Phe
            820                 825                 830

Leu Glu Arg Phe Ala Tyr Val Asn Thr Thr Ile Tyr Pro Ile Thr Ser
        835                 840                 845

Ile Pro Leu Leu Met Tyr Cys Thr Leu Leu Ala Val Cys Leu Phe Thr
    850                 855                 860

Asn Gln Phe Ile Ile Pro Gln Ile Ser Asn Ile Ala Ser Ile Trp Phe
865                 870                 875                 880

Leu Ser Leu Phe Leu Ser Ile Phe Ala Thr Gly Ile Leu Glu Met Arg
                885                 890                 895

Trp Ser Gly Val Gly Ile Asp Glu Trp Trp Arg Asn Glu Gln Phe Trp
            900                 905                 910

Val Ile Gly Gly Val Ser Ala His Leu Phe Ala Val Phe Gln Gly Ile
        915                 920                 925

Leu Lys Val Leu Ala Gly Ile Asp Thr Asn Phe Thr Val Thr Ser Lys
    930                 935                 940

Ala Ser Asp Glu Asp Gly Asp Phe Ala Glu Leu Tyr Leu Phe Lys Trp
945                 950                 955                 960

Thr Thr Leu Leu Ile Pro Pro Thr Thr Leu Leu Ile Val Asn Leu Val
                965                 970                 975

Gly Val Val Ala Gly Val Ser Tyr Ala Ile Asn Ser Gly Tyr Gln Ser
            980                 985                 990

Trp Gly Pro Leu Phe Gly Lys Leu  Phe Phe Ala Phe Trp  Val Ile Val
        995                 1000                1005

His Leu  Tyr Pro Phe Leu Lys  Gly Leu Met Gly Arg  Gln Asn Arg
    1010                1015                1020

Thr Pro  Thr Ile Val Val Val  Trp Ser Val Leu Leu  Ala Ser Ile
    1025                1030                1035

Phe Ser  Leu Leu Trp Val Arg  Ile Asp Pro Phe Thr  Ser Arg Val
    1040                1045                1050

Thr Gly  Pro Asp Ile Leu Glu  Cys Gly Ile Asn Cys
    1055                1060                1065
```

<210> SEQ ID NO 69

<211> LENGTH: 760
<212> TYPE: PRT
<213> ORGANISM: Arabodopsis thaliana

<400> SEQUENCE: 69

Met Glu Thr His Arg Lys Asn Ser Val Val Gly Asn Ile Leu His Thr
1 5 10 15

Cys His Pro Cys Arg Arg Thr Ile Pro Tyr Arg Ile Tyr Ala Ile Phe
20 25 30

His Thr Cys Gly Ile Ile Ala Leu Met Tyr His His Val His Ser Leu
35 40 45

Val Thr Ala Asn Asn Thr Leu Ile Thr Cys Leu Leu Leu Leu Ser Asp
50 55 60

Ile Val Leu Ala Phe Met Trp Ala Thr Thr Thr Ser Leu Arg Leu Asn
65 70 75 80

Pro Val His Arg Thr Glu Cys Pro Glu Lys Tyr Ala Ala Lys Pro Glu
85 90 95

Asp Phe Pro Lys Leu Asp Val Phe Ile Cys Thr Ala Asp Pro Tyr Lys
100 105 110

Glu Pro Pro Met Met Val Val Asn Thr Ala Leu Ser Val Met Ala Tyr
115 120 125

Glu Tyr Pro Ser Asp Lys Ile Ser Val Tyr Val Ser Asp Asp Gly Gly
130 135 140

Ser Ser Leu Thr Phe Phe Ala Leu Ile Glu Ala Ala Lys Phe Ser Lys
145 150 155 160

Gln Trp Leu Pro Phe Cys Lys Lys Asn Asn Val Gln Asp Arg Ser Pro
165 170 175

Glu Val Tyr Phe Ser Ser Glu Ser His Ser Arg Ser Asp Glu Ala Glu
180 185 190

Asn Leu Lys Met Met Tyr Glu Asp Met Lys Ser Arg Val Glu His Val
195 200 205

Val Glu Ser Gly Lys Val Glu Thr Ala Phe Ile Thr Cys Asp Gln Phe
210 215 220

Arg Gly Val Phe Asp Leu Trp Thr Asp Lys Phe Ser Arg His Asp His
225 230 235 240

Pro Thr Ile Ile Gln Val Leu Gln Asn Ser Glu Thr Asp Met Asp Asn
245 250 255

Thr Arg Lys Tyr Ile Met Pro Asn Leu Ile Tyr Val Ser Arg Glu Lys
260 265 270

Ser Lys Val Ser Pro His His Phe Lys Ala Gly Ala Leu Asn Thr Leu
275 280 285

Leu Arg Val Ser Gly Val Met Thr Asn Ser Pro Ile Ile Leu Thr Leu
290 295 300

Asp Cys Asp Met Tyr Ser Asn Asp Pro Ala Thr Leu Val Arg Ala Leu
305 310 315 320

Cys Tyr Leu Thr Asp Pro Glu Ile Lys Ser Gly Leu Gly Tyr Val Gln
325 330 335

Phe Pro Gln Lys Phe Leu Gly Ile Ser Lys Asn Asp Ile Tyr Ala Cys
340 345 350

Glu Asn Lys Arg Leu Phe Ile Ile Asn Met Val Gly Phe Asp Gly Leu
355 360 365

Met Gly Pro Thr His Val Gly Thr Gly Cys Phe Phe Asn Arg Arg Ala
370 375 380

Phe Tyr Gly Pro Pro Tyr Met Leu Ile Leu Pro Glu Ile Asn Glu Leu 385 390 395 400

Lys Pro Tyr Arg Ile Ala Asp Lys Ser Ile Lys Ala Gln Asp Val Leu
405 410 415

Ser Leu Ala His Asn Val Ala Gly Cys Ile Tyr Glu Tyr Asn Thr Asn
420 425 430

Trp Gly Ser Lys Ile Gly Phe Arg Tyr Gly Ser Leu Val Glu Asp Tyr
435 440 445

Tyr Thr Gly Phe Met Leu His Cys Glu Gly Trp Arg Ser Val Phe Cys
450 455 460

Asn Pro Lys Lys Ala Ala Phe Tyr Gly Asp Ser Pro Lys Cys Leu Val
465 470 475 480

Asp Leu Val Gly Gln Gln Ile Arg Trp Ala Val Gly Leu Phe Glu Met
485 490 495

Ser Phe Ser Lys Tyr Ser Pro Ile Thr Tyr Gly Ile Lys Ser Leu Asp
500 505 510

Leu Leu Met Gly Leu Gly Tyr Cys Asn Ser Pro Phe Lys Pro Phe Trp
515 520 525

Ser Ile Pro Leu Thr Val Tyr Gly Leu Leu Pro Gln Leu Ala Leu Ile
530 535 540

Ser Gly Val Ser Val Phe Pro Lys Ala Ser Asp Pro Trp Phe Trp Leu
545 550 555 560

Tyr Ile Ile Leu Phe Phe Gly Ala Tyr Ala Gln Asp Leu Ser Asp Phe
565 570 575

Leu Leu Glu Gly Gly Thr Tyr Arg Lys Trp Trp Asn Asp Gln Arg Met
580 585 590

Leu Met Ile Lys Gly Leu Ser Ser Phe Phe Phe Gly Phe Ile Glu Phe
595 600 605

Ile Leu Lys Thr Leu Asn Leu Ser Thr Pro Lys Phe Asn Val Thr Ser
610 615 620

Lys Ala Asn Asp Asp Asp Glu Gln Arg Lys Arg Tyr Glu Gln Glu Ile
625 630 635 640

Phe Asp Phe Gly Thr Ser Ser Ser Met Phe Leu Pro Leu Thr Thr Val
645 650 655

Ala Ile Val Asn Leu Leu Ala Phe Val Trp Gly Leu Tyr Gly Ile Leu
660 665 670

Phe Cys Gly Gly Glu Leu Tyr Leu Glu Leu Met Leu Val Ser Phe Ala
675 680 685

Val Val Asn Cys Leu Pro Ile Tyr Gly Ala Met Val Leu Arg Lys Asp
690 695 700

Asp Gly Lys Leu Ser Lys Arg Thr Cys Phe Leu Ala Gly Asn Leu His
705 710 715 720

Val Gly Ser Tyr Cys Val Lys Leu Leu Arg Pro Gln Val Thr Ser Pro
725 730 735

Leu Arg Leu Ile His Asn Asn Asn Thr Ser Gly Trp Phe Lys Arg Lys
740 745 750

Lys His Asn Met Asn Glu Ser Val
755 760

<210> SEQ ID NO 70
<211> LENGTH: 1086
<212> TYPE: PRT
<213> ORGANISM: Spinacia oleracea

<400> SEQUENCE: 70

-continued

Met Glu Ala Thr Gly Gly Met Val Ala Gly Ser Tyr Lys Arg Asn Glu
1 5 10 15

Leu Val Arg Ile Arg His Asp Ser Thr Asp Ser Gly Ser Lys Ser Leu
20 25 30

Lys Asn Leu Asp Gly Gln Ile Cys Gln Ile Cys Gly Asp Thr Val Gly
35 40 45

Val Thr Ser Asn Gly Gly Val Phe Val Ala Cys Asn Glu Cys Ala Phe
50 55 60

Pro Val Cys Arg Pro Cys Tyr Glu Tyr Glu Arg Lys Asp Gly Asn Gln
65 70 75 80

Cys Cys Pro Gln Cys Lys Thr Arg Tyr Lys Arg Gln Lys Gly Ser Leu
85 90 95

Arg Val Glu Gly Asp Asp Glu Glu Glu Asp Val Asp Asp Leu Asp Asn
100 105 110

Glu Phe Asn Tyr Glu Arg Gly Thr Ser Lys Ala Arg His Gln Trp Gln
115 120 125

Gly Glu Asp Val Asp Leu Ser Ser Ser Ser Arg His Gly Ser Gln Pro
130 135 140

Ile Pro Leu Leu Thr Asn Gly Gln Val Val Ser Gly Glu Ile Pro Ser
145 150 155 160

Ala Thr Pro Asp Asn Gln Ser Val Arg Ser Thr Ser Gly Pro Ile Gly
165 170 175

Pro Glu Lys Arg Gly Asn His Ser Leu Pro Tyr Ile Asp Pro Cys Leu
180 185 190

Pro Val Pro Val Arg Ile Val Asp Pro Ser Lys Asp Leu Asn Ser Tyr
195 200 205

Gly Leu Gly Ser Val Asp Trp Lys Glu Arg Val Glu Ser Trp Lys Leu
210 215 220

Lys Gln Glu Lys Asn Met Thr His Thr Gly Asn Arg Tyr Ser Glu Gly
225 230 235 240

Lys Gly Gly Asp Val Glu Gly Ser Gly Ser Asn Gly Glu Glu Leu Gln
245 250 255

Leu Ala Asp Asp Val Arg Gln Pro Met Ser Arg Ile Val Pro Ile Pro
260 265 270

Ser Ser His Leu Thr Pro Tyr Arg Ala Val Ile Ile Phe Arg Leu Ile
275 280 285

Ile Leu Val Phe Phe Leu Gln Phe Arg Ile Thr His Pro Val Glu Asp
290 295 300

Ala Tyr Pro Leu Trp Leu Thr Ser Val Ile Cys Glu Ile Trp Phe Ala
305 310 315 320

Met Ser Trp Ile Leu Asp Gln Phe Pro Lys Trp Tyr Pro Ile Asn Arg
325 330 335

Glu Thr Tyr Leu Asp Arg Leu Ala Phe Arg His Asp Arg Glu Gly Glu
340 345 350

Pro Ser Gln Leu Ala Pro Ile Asp Val Phe Val Ser Thr Val Asp Pro
355 360 365

Leu Lys Glu Pro Pro Ile Ile Thr Ala Asn Thr Val Leu Ser Ile Leu
370 375 380

Ala Val Asp Tyr Pro Val Asp Lys Val Ser Cys Tyr Val Ser Asp Asp
385 390 395 400

Gly Ser Ala Met Leu Thr Phe Glu Gly Leu Ser Glu Thr Ala Glu Phe
405 410 415

Ala Arg Lys Trp Val Pro Phe Cys Lys Lys Phe Ser Ile Glu Pro Arg

-continued

```
            420                 425                 430

Ala Pro Glu Phe Tyr Phe Gln Gln Lys Ile Asp Tyr Leu Lys Asp Lys
        435                 440                 445

Ile Gln Pro Ser Phe Val Lys Glu Arg Arg Ala Met Lys Arg Glu Tyr
    450                 455                 460

Glu Glu Phe Lys Val Arg Ile Asn Ala Leu Val Ala Lys Ala Gln Lys
465                 470                 475                 480

Val Pro Glu Glu Gly Trp Thr Met Gln Asp Gly Thr Ala Trp Pro Gly
                485                 490                 495

Asn Asn Pro Arg Asp His Pro Gly Met Ile Gln Val Phe Leu Gly His
            500                 505                 510

Ser Gly Gly Leu Asp Met Asp Gly Asn Glu Leu Pro Arg Leu Val Tyr
        515                 520                 525

Val Ser Arg Glu Lys Arg Pro Gly Phe Gln His His Lys Lys Ala Gly
    530                 535                 540

Ala Met Asn Ala Leu Ile Arg Val Ser Ala Val Leu Thr Asn Gly Ala
545                 550                 555                 560

Tyr Ile Leu Asn Val Asp Cys Asp His Tyr Phe Asn Asn Ser Lys Cys
                565                 570                 575

Leu Lys Glu Ala Met Cys Phe Met Met Asp Pro Ala Leu Gly Lys Lys
            580                 585                 590

Val Cys Tyr Val Gln Phe Pro Gln Arg Phe Asp Gly Ile Asp Leu His
        595                 600                 605

Asp Arg Tyr Ala Asn Arg Asn Ile Val Phe Phe Asp Ile Asn Met Lys
    610                 615                 620

Gly Gln Asp Gly Ile Gln Gly Pro Val Tyr Val Gly Thr Gly Cys Cys
625                 630                 635                 640

Phe Asn Arg Gln Ala Leu Tyr Gly Tyr Asp Pro Val Leu Thr Glu Glu
                645                 650                 655

Asp Phe Glu Pro Asn Phe Ile Ile Lys Asn Cys Phe Gly Ser Arg Lys
            660                 665                 670

Lys Gly Lys Ser Gly Asn Lys Lys Tyr Met Asp Lys Lys Arg Gly Pro
        675                 680                 685

Lys Arg Ser Glu Ser Ser Ile Pro Ile Phe Asn Met Glu Asp Ile Glu
    690                 695                 700

Glu Gly Val Glu Gly Tyr Glu Asp Glu Lys Ser Leu Leu Met Ser Gln
705                 710                 715                 720

Lys Arg Leu Glu Lys Arg Phe Gly Gln Ser Pro Val Phe Ile Ala Ala
                725                 730                 735

Thr Phe Met Glu Met Gly Gly Ile Pro Pro Thr Thr Asn Pro Ala Thr
            740                 745                 750

Leu Leu Lys Glu Ala Ile His Val Ile Ser Cys Gly Tyr Glu Asp Lys
        755                 760                 765

Ser Glu Trp Gly Lys Glu Ile Gly Trp Ile Tyr Gly Ser Val Thr Glu
    770                 775                 780

Asp Ile Leu Thr Gly Phe Lys Met His Ala Arg Gly Trp Met Ser Ile
785                 790                 795                 800

Tyr Cys Met Pro Pro Arg Pro Ala Phe Lys Gly Ser Ala Pro Leu Asn
                805                 810                 815

Leu Ser Asp Arg Leu Asn Gln Val Leu Arg Trp Ala Leu Gly Ser Ile
            820                 825                 830

Glu Ile Met Leu Ser Arg His Cys Pro Ile Trp Tyr Gly Tyr Lys Gly
        835                 840                 845
```

Arg Leu Arg Phe Leu Glu Arg Leu Ala Tyr Ile Asn Thr Val Val Tyr
    850                 855                 860

Pro Leu Thr Ser Ile Pro Leu Ile Ala Tyr Cys Ile Leu Pro Ala Ile
865                 870                 875                 880

Cys Leu Leu Thr Asn Lys Phe Ile Ile Pro Thr Leu Ser Asn Phe Ala
                885                 890                 895

Ser Ile Leu Phe Ile Met Leu Phe Met Ser Ile Ala Ala Thr Gly Ile
            900                 905                 910

Leu Glu Leu Arg Trp Ser Gly Val Ser Ile Glu Asp Trp Trp Arg Asn
        915                 920                 925

Glu Gln Phe Trp Val Ile Gly Gly Thr Ser Ala His Leu Phe Ala Val
    930                 935                 940

Phe Gln Gly Leu Leu Lys Val Leu Ala Gly Ile Asp Thr Asn Phe Thr
945                 950                 955                 960

Val Thr Ser Lys Ala Ala Asp Glu Asp Gly Asp Phe Ala Glu Leu Tyr
                965                 970                 975

Ile Phe Lys Trp Thr Ala Leu Leu Ile Pro Pro Thr Thr Val Leu Ile
            980                 985                 990

Val Asn Leu Val Gly Val Val Ala  Gly Val Ser Tyr Ala  Ile Asn Ser
        995                 1000                1005

Gly Tyr  Gln Ser Trp Gly Pro  Leu Phe Gly Lys Leu  Phe Phe Ser
    1010                1015                1020

Phe Trp  Val Ile Ala His Leu  Tyr Pro Phe Leu Lys  Gly Leu Leu
    1025                1030                1035

Gly Arg  Gln Asn Arg Thr Pro  Thr Ile Val Ile Val  Trp Ser Val
    1040                1045                1050

Leu Leu  Ala Ser Ile Phe Ser  Leu Leu Trp Val Arg  Ile Asn Pro
    1055                1060                1065

Phe Thr  Thr Asp Ala Glu Lys  Ala Ala Ala Gly Asn  Gln Cys Gly
    1070                1075                1080

Ile Asn  Cys
    1085

<210> SEQ ID NO 71
<211> LENGTH: 1060
<212> TYPE: PRT
<213> ORGANISM: Spinacia oleracea

<400> SEQUENCE: 71

Met Met Glu Asp Ser Gln Ser Gly Val Lys Pro Thr Lys Gln Ala Asn
1               5                   10                  15

Glu Gln Val Cys Gln Ile Cys Ser Asp Asn Ile Gly Thr Thr Val Asp
            20                  25                  30

Gly Glu Pro Phe Val Ala Cys Asp Val Cys Ser Phe Pro Val Cys Arg
        35                  40                  45

Ala Cys Tyr Glu Tyr Glu Arg Lys Asp Gly Thr Gln Ser Cys Pro Gln
    50                  55                  60

Cys Lys Thr Arg Tyr Lys Arg Gln Lys Gly Ser Pro Ala Ile His Gly
65                  70                  75                  80

Glu Lys Val Glu Asp Ser Asp Val Glu Asp Val Val Ser Asp Val Asn
                85                  90                  95

Glu Pro Leu Gly Ser Ser Ile Leu Lys Glu Lys Pro Gln Glu Arg Met
            100                 105                 110

Leu Gly Trp His Met Asn His Gly Gln Ser Gly Glu Leu Gly Pro Pro

-continued

```
        115                 120                 125

Thr Tyr Asp Lys Glu Ala Pro Ile Ser His Ile Pro Arg Leu Ala Thr
    130                 135                 140

Gly Arg Thr Val Ser Gly Asp Leu Ser Ala Ala Ser Pro Gly Arg Phe
145                 150                 155                 160

Ser Met Pro Ser Pro Gly Ala Ser Thr Gly Ala Asn Ile Arg Val Ser
                165                 170                 175

Arg Glu Phe Ala Ser Pro Gly Phe Gly Asn Val Ala Trp Lys Glu Arg
            180                 185                 190

Ile Asp Gly Trp Lys Met Lys Gln Glu Lys Ser Thr Gly Pro Pro Ser
        195                 200                 205

Val Ser His Ala Pro Ser Glu Gly Arg Phe Ala Asn Asp Ile Asp Ala
    210                 215                 220

Ser Thr Glu Ile Ala Met Asp Asp Pro Leu Leu Asn Asp Glu Thr Arg
225                 230                 235                 240

Gln Pro Leu Ser Arg Lys Val Pro Ile Pro Ser Ser Arg Ile Asn Pro
                245                 250                 255

Tyr Arg Met Val Ile Val Leu Arg Leu Ala Val Leu Gly Ile Phe Leu
            260                 265                 270

His Tyr Arg Val Thr Asn Pro Val Pro Asn Ala Tyr Ala Leu Trp Leu
        275                 280                 285

Ile Ser Val Ile Cys Glu Ile Trp Phe Ala Phe Ser Trp Ile Leu Asp
    290                 295                 300

Gln Phe Pro Lys Trp Leu Pro Ile Asn Arg Glu Thr Tyr Leu Asp Arg
305                 310                 315                 320

Leu Ala Leu Arg Tyr Asp Arg Glu Gly Glu Pro Ser Gln Leu Ala Ala
                325                 330                 335

Val Asp Ile Phe Val Ser Thr Val Asp Pro Leu Lys Glu Pro Pro Leu
            340                 345                 350

Val Thr Ala Asn Thr Val Leu Ser Ile Leu Ala Val Asp Tyr Pro Val
        355                 360                 365

Asp Lys Val Ser Cys Tyr Val Ser Asp Asp Gly Ala Ala Met Leu Thr
    370                 375                 380

Phe Glu Ala Leu Ser Glu Thr Ser Glu Phe Ala Arg Lys Trp Val Pro
385                 390                 395                 400

Phe Thr Lys Lys Tyr Asn Ile Glu Pro Arg Ala Pro Glu Trp Tyr Phe
                405                 410                 415

Ser Gln Lys Ile Asp Tyr Leu Lys Asp Lys Val Gln Thr Thr Phe Val
            420                 425                 430

Lys Asp Arg Arg Ala Met Lys Arg Glu Tyr Glu Glu Phe Lys Ile Arg
        435                 440                 445

Ile Asn Gly Leu Val Ala Lys Ala Thr Lys Val Pro Glu Glu Gly Trp
    450                 455                 460

Val Met Gln Asp Gly Thr Pro Trp Pro Gly Asn Asn Thr Arg Asp His
465                 470                 475                 480

Pro Gly Met Ile Gln Val Phe Leu Gly Gln Ser Gly Gly Leu Asp Thr
                485                 490                 495

Asp Gly Asn Glu Leu Pro Arg Leu Val Tyr Val Ser Arg Glu Lys Arg
            500                 505                 510

Pro Gly Phe Thr His His Lys Lys Ala Gly Ala Met Asn Ser Leu Val
        515                 520                 525

Arg Val Ser Ala Val Leu Thr Asn Gly Pro Phe Met Leu Asn Leu Asp
    530                 535                 540
```

-continued

```
Cys Asp His Tyr Ile Asn Asn Ser Lys Ala Leu Arg Glu Ala Met Cys
545                 550                 555                 560

Phe Met Met Asp Pro Asn Leu Gly Lys Tyr Cys Cys Tyr Val Gln Phe
                565                 570                 575

Pro Gln Arg Phe Asp Gly Ile Asp Arg Asn Asp Arg Tyr Ala Asn Arg
            580                 585                 590

Asn Thr Val Phe Phe Asp Ile Asn Leu Arg Gly Leu Asp Gly Ile Gln
        595                 600                 605

Gly Pro Val Tyr Val Gly Thr Gly Cys Val Phe Asn Arg Thr Ala Leu
    610                 615                 620

Tyr Gly Tyr Glu Pro Pro Ile Lys Pro Lys Pro Lys Lys Lys Gly Ile
625                 630                 635                 640

Leu Ser Ser Cys Phe Gly Gly Ser Arg Lys Lys Ser Ser Lys Lys Asp
                645                 650                 655

Ser Lys Lys Lys Ser Lys His Ala Asp Pro Thr Val Pro Ile Phe Asn
            660                 665                 670

Leu Glu Asp Ile Glu Glu Gly Val Glu Gly Thr Gly Phe Asp Asp Glu
        675                 680                 685

Lys Ser Leu Leu Met Ser Gln Ile Ser Leu Glu Lys Arg Phe Gly Lys
    690                 695                 700

Ser Glu Val Phe Val Ala Ser Thr Leu Met Glu Asn Gly Gly Val Pro
705                 710                 715                 720

Gln Ser Ala Thr Pro Asp Thr Leu Leu Lys Glu Ala Ile His Val Ile
                725                 730                 735

Ser Cys Gly Tyr Glu Asp Lys Thr Asp Trp Gly Ala Glu Ile Gly Trp
            740                 745                 750

Ile Tyr Gly Ser Val Thr Glu Asp Ile Leu Thr Gly Phe Lys Met His
        755                 760                 765

Ala Arg Gly Trp Arg Ser Ile Tyr Cys Met Pro Lys Leu Ala Ala Phe
    770                 775                 780

Lys Gly Ser Ala Pro Ile Asn Leu Ser Asp Arg Leu Asn Gln Val Leu
785                 790                 795                 800

Arg Trp Ala Leu Gly Ser Val Glu Ile Leu Phe Ser Arg His Cys Pro
                805                 810                 815

Leu Trp Tyr Gly Tyr Gly Gly Arg Leu Lys Trp Leu Glu Arg Phe Ala
            820                 825                 830

Tyr Ile Asn Thr Thr Ile Tyr Pro Leu Thr Ser Ile Pro Leu Leu Ala
        835                 840                 845

Tyr Cys Thr Leu Pro Ala Val Cys Leu Leu Thr Gly Lys Phe Ile Ile
    850                 855                 860

Pro Gln Ile Ser Asn Leu Ala Ser Val Trp Phe Leu Ser Leu Phe Leu
865                 870                 875                 880

Ser Ile Phe Ala Thr Gly Ile Leu Glu Met Arg Trp Ser Gly Val Gly
                885                 890                 895

Ile Asp Glu Trp Trp Arg Asn Glu Gln Phe Trp Val Ile Gly Gly Ile
            900                 905                 910

Ser Ala His Leu Phe Ala Val Phe Gln Gly Leu Leu Lys Val Leu Ala
        915                 920                 925

Gly Ile Asp Thr Asn Phe Thr Val Thr Ser Lys Ala Ser Asp Glu Asp
    930                 935                 940

Gly Asp Phe Thr Glu Leu Tyr Leu Phe Lys Trp Thr Thr Leu Leu Ile
945                 950                 955                 960
```

-continued

```
Pro Pro Thr Thr Ile Leu Ile Val Asn Leu Val Ala Val Val Ala Gly
                965                 970                 975

Ile Ser Tyr Ala Ile Asn Ser Gly Tyr Gln Ser Trp Gly Pro Leu Phe
            980                 985                 990

Gly Lys Leu Phe Phe Ala Phe Trp  Val Ile Val His Leu  Tyr Pro Phe
        995                 1000                1005

Leu Lys  Gly Leu Met Gly Arg  Gln Asn Arg Thr Pro  Thr Ile Val
    1010                 1015                 1020

Val Val  Trp Ser Ile Leu Leu  Ala Ser Ile Phe Ser  Leu Leu Trp
    1025                 1030                 1035

Val Arg  Val Asp Pro Phe Thr  Thr Arg Val Thr Gly  Pro Asp Val
    1040                 1045                 1050

His Ile  Cys Gly Ile Asn Cys
    1055                 1060
```

```
<210> SEQ ID NO 72
<211> LENGTH: 1431
<212> TYPE: DNA
<213> ORGANISM: Spinacia oleracea

<400> SEQUENCE: 72

atgaaagaaa gctctacttt gcgtgctcaa gctttgaaca aacccattcc ttttactcat     60

gattactacc aacgtattca gcctttcacc catcagattc tcaacaattc ttgtgcaggt    120

gcaggtaaaa atatctacac atggttggga ccagtgccaa caatactaat tacacagcct    180

gagttaataa aggatgcttt caataggatg aacaatttcc aaaaaccaag attgaatcca    240

tatactcaaa tactttcaac tggacttccg aactatgagg gccagaaatg ggctaaacac    300

aggaagcttc tcaaccctgc ttttcaactt gataagctca agcttatgat ccctgctttt    360

gaaacctgcg ttactgatac actaaataag tgggagaagc tagtttctaa aacaggttct    420

tcagaggttg atgtgtggcc acatttcaca actctaacgg gagatggtat tgctagagct    480

gcatttggaa gtagctttga ggatggaaga aggatattcg accttcttaa agagcaaaag    540

gatcttgtta ttagtcttct caaatattct tatattccag gattcaaata tttgcccaca    600

aaaggtaaca agatgatgaa agaaacggaa aacgaaatca aacctttatt gacgaatttg    660

attcacaaaa ggaagaaggc aatggaggct ggagaagctc ccaaagacga cttgttggga    720

atgctacttg aatccaatgc aaacgaggct cgacaagtta acgaaaatga aagtggaagt    780

aggaagcgac aatccgatat aacaatgagc ttccatgaga tgattgacgc gtgcaagttg    840

ttcttcttgg ctggccaaga gactacttct gtggcgctaa catgggcaat gatttttgttg   900

gcgaagcacc aagattacca aacacgagca cgagaagaag tacttgctac atttggaacg    960

aaaactcctg actttgatgg tgtacataat cgccttaaga ttgtgacaac tatagtccac   1020

gaggtgctaa gattgtatcc gccaatccct gcaacatcac gaagggcaca tgaacgcgaa   1080

acaaaactag gagatttggt aataccacaa ggggtaggag tttcattttc catactacat   1140

gctcacttga accctgaaat ttggggtgat gatgccaaag aattcaagcc tgaaagattt   1200

tcagaaggga ttgcaaaggc aaccaaagga aataactctt acttcccctt tggttgggga   1260

cctaggattt gcattggtca agccttcgca ctaatccagg ttaaaatggc attgtctatg   1320

attttacaac gtttctcttt cgagctttca ccgtcctaca tccatgctcc aactagtcta   1380

ttagcccttc aaccccagca tggtgctcat gttatcttac atcgacttta a            1431
```

```
<210> SEQ ID NO 73
```

<211> LENGTH: 476
<212> TYPE: PRT
<213> ORGANISM: Spinacia oleracea

<400> SEQUENCE: 73

```
Met Lys Glu Ser Ser Thr Leu Arg Ala Gln Ala Leu Asn Lys Pro Ile
1               5                   10                  15

Pro Phe Thr His Asp Tyr Tyr Gln Arg Ile Gln Pro Phe Thr His Gln
            20                  25                  30

Ile Leu Asn Asn Ser Cys Ala Gly Ala Gly Lys Asn Ile Tyr Thr Trp
        35                  40                  45

Leu Gly Pro Val Pro Thr Ile Leu Ile Thr Gln Pro Glu Leu Ile Lys
    50                  55                  60

Asp Ala Phe Asn Arg Met Asn Asn Phe Gln Lys Pro Arg Leu Asn Pro
65                  70                  75                  80

Tyr Thr Gln Ile Leu Ser Thr Gly Leu Pro Asn Tyr Glu Gly Gln Lys
                85                  90                  95

Trp Ala Lys His Arg Lys Leu Leu Asn Pro Ala Phe Gln Leu Asp Lys
            100                 105                 110

Leu Lys Leu Met Ile Pro Ala Phe Glu Thr Cys Val Thr Asp Thr Leu
        115                 120                 125

Asn Lys Trp Glu Lys Leu Val Ser Lys Thr Gly Ser Ser Glu Val Asp
    130                 135                 140

Val Trp Pro His Phe Thr Thr Leu Thr Gly Asp Gly Ile Ala Arg Ala
145                 150                 155                 160

Ala Phe Gly Ser Ser Phe Glu Asp Gly Arg Arg Ile Phe Asp Leu Leu
                165                 170                 175

Lys Glu Gln Lys Asp Leu Val Ile Ser Leu Leu Lys Tyr Ser Tyr Ile
            180                 185                 190

Pro Gly Phe Lys Tyr Leu Pro Thr Lys Gly Asn Lys Met Met Lys Glu
        195                 200                 205

Thr Glu Asn Glu Ile Lys Pro Leu Leu Thr Asn Leu Ile His Lys Arg
    210                 215                 220

Lys Lys Ala Met Glu Ala Gly Glu Ala Pro Lys Asp Asp Leu Leu Gly
225                 230                 235                 240

Met Leu Leu Glu Ser Asn Ala Asn Glu Ala Arg Gln Val Asn Glu Asn
                245                 250                 255

Glu Ser Gly Ser Arg Lys Arg Gln Ser Asp Ile Thr Met Ser Phe His
            260                 265                 270

Glu Met Ile Asp Ala Cys Lys Leu Phe Phe Leu Ala Gly Gln Glu Thr
        275                 280                 285

Thr Ser Val Ala Leu Thr Trp Ala Met Ile Leu Leu Ala Lys His Gln
    290                 295                 300

Asp Tyr Gln Thr Arg Ala Arg Glu Glu Val Leu Ala Thr Phe Gly Thr
305                 310                 315                 320

Lys Thr Pro Asp Phe Asp Gly Val His Asn Arg Leu Lys Ile Val Thr
                325                 330                 335

Thr Ile Val His Glu Val Leu Arg Leu Tyr Pro Pro Ile Pro Ala Thr
            340                 345                 350

Ser Arg Arg Ala His Glu Arg Glu Thr Lys Leu Gly Asp Leu Val Ile
        355                 360                 365

Pro Gln Gly Val Gly Val Ser Phe Ser Ile Leu His Ala His Leu Asn
    370                 375                 380

Pro Glu Ile Trp Gly Asp Asp Ala Lys Glu Phe Lys Pro Glu Arg Phe
```

385 390 395 400

Ser Glu Gly Ile Ala Lys Ala Thr Lys Gly Asn Asn Ser Tyr Phe Pro
405 410 415

Phe Gly Trp Gly Pro Arg Ile Cys Ile Gly Gln Ala Phe Ala Leu Ile
420 425 430

Gln Val Lys Met Ala Leu Ser Met Ile Leu Gln Arg Phe Ser Phe Glu
435 440 445

Leu Ser Pro Ser Tyr Ile His Ala Pro Thr Ser Leu Leu Ala Leu Gln
450 455 460

Pro Gln His Gly Ala His Val Ile Leu His Arg Leu
465 470 475

<210> SEQ ID NO 74
<211> LENGTH: 1443
<212> TYPE: DNA
<213> ORGANISM: Spinacia oleracea

<400> SEQUENCE: 74
atggtgaaga tttgctgcat tggggctggt tatgtaggag gccctactat ggctgttata 60
gcactcaagt gcccaaagat tgaagttgta gtggttgata tatctgtgtc tcggatcact 120
gcatggaaca gcgagcagct tccaatctat gagccgggtc tagatgatgt ggttaaggaa 180
tgccgtggaa ggaacctttt cttcagcact gatgtagaaa agcatgttgc tgaggctgat 240
attgtttttg tctctgtgaa tacccctacc aaaaccacag gtcttggagc aggcaaagct 300
gctgatttga cctactggga gagtgctgcc cgtatgattg ctgatgtttc aaagtctgac 360
aaaatcgttg ttgagaaatc aactgtgcca gtgaaaactg ctgaggcaat cgaaaagatt 420
ctgacgcaca acagcaaggg aatcaactac cagatccttt caaatccgga gttccttgct 480
gaaggtactg ctattcagga ccttttcac cctgacaggg ttctcatcgg tggccgggaa 540
accccagcag gcctcaaggc agtccaagca ttgaaggatg tgtatgctca atgggttcct 600
gatgaacgga tcttaaccac caatctttgg tctgctgagc tctcaaagct tgctgccaac 660
gccttcttag cacagaggat ttcatctgtc aatgcaatgt cagctctttg tgaggctact 720
ggagcagatg ttacccaagt cgcatatgct gttggtaagg acagtaggat tgggcaaaag 780
tttttgaacg ctagtgttgg ttttggaggg tcttgcttcc agaaagacat tctgaacttg 840
gtttacattt gtgagtgcaa cggtctccct gaggtggccg agtattggaa acaggtaatc 900
aaggtgaatg attatcagaa gaatcgtttt gtgaataggg ttgtggcctc catgttcaac 960
actgtatcga acaagaagat tgctgttctt ggatttgcat tcaaaaagga tacaggggat 1020
actagggaga cacccgccat agatgtgtgc aagggtttgt tgggagacaa ggcaaggttg 1080
agcatctacg atccacaagt cactgaggat cagattcagc gagatctcac catgaacaag 1140
tttgactggg accacccaat tcacctccag cccacaagtc ccacaactgt taagcaagtg 1200
agtgttgttt gggacgctta tgaggccacc aaagatgctc atgctgtgtg tattctgact 1260
gagtgggatg aatttaagaa acttgattac aaaaggattt ttgacaacat gcagaagcca 1320
gcttttgtgt ttgatggaag gaacattgtg aatgcagatg agctgaggca gattgggttc 1380
attgtgtact caattggtaa acctttggat tcatggctca aggacatgcc tgctgtggct 1440
taa 1443

<210> SEQ ID NO 75
<211> LENGTH: 480
<212> TYPE: PRT

<213> ORGANISM: Spinacia oleracea

<400> SEQUENCE: 75

Met Val Lys Ile Cys Cys Ile Gly Ala Gly Tyr Val Gly Gly Pro Thr
1 5 10 15

Met Ala Val Ile Ala Leu Lys Cys Pro Lys Ile Glu Val Val Val Val
20 25 30

Asp Ile Ser Val Ser Arg Ile Thr Ala Trp Asn Ser Glu Gln Leu Pro
35 40 45

Ile Tyr Glu Pro Gly Leu Asp Asp Val Val Lys Glu Cys Arg Gly Arg
50 55 60

Asn Leu Phe Phe Ser Thr Asp Val Glu Lys His Val Ala Glu Ala Asp
65 70 75 80

Ile Val Phe Val Ser Val Asn Thr Pro Thr Lys Thr Thr Gly Leu Gly
85 90 95

Ala Gly Lys Ala Ala Asp Leu Thr Tyr Trp Glu Ser Ala Ala Arg Met
100 105 110

Ile Ala Asp Val Ser Lys Ser Asp Lys Ile Val Val Glu Lys Ser Thr
115 120 125

Val Pro Val Lys Thr Ala Glu Ala Ile Glu Lys Ile Leu Thr His Asn
130 135 140

Ser Lys Gly Ile Asn Tyr Gln Ile Leu Ser Asn Pro Glu Phe Leu Ala
145 150 155 160

Glu Gly Thr Ala Ile Gln Asp Leu Phe His Pro Asp Arg Val Leu Ile
165 170 175

Gly Gly Arg Glu Thr Pro Ala Gly Leu Lys Ala Val Gln Ala Leu Lys
180 185 190

Asp Val Tyr Ala Gln Trp Val Pro Asp Glu Arg Ile Leu Thr Thr Asn
195 200 205

Leu Trp Ser Ala Glu Leu Ser Lys Leu Ala Ala Asn Ala Phe Leu Ala
210 215 220

Gln Arg Ile Ser Ser Val Asn Ala Met Ser Ala Leu Cys Glu Ala Thr
225 230 235 240

Gly Ala Asp Val Thr Gln Val Ala Tyr Ala Val Gly Lys Asp Ser Arg
245 250 255

Ile Gly Gln Lys Phe Leu Asn Ala Ser Val Gly Phe Gly Gly Ser Cys
260 265 270

Phe Gln Lys Asp Ile Leu Asn Leu Val Tyr Ile Cys Glu Cys Asn Gly
275 280 285

Leu Pro Glu Val Ala Glu Tyr Trp Lys Gln Val Ile Lys Val Asn Asp
290 295 300

Tyr Gln Lys Asn Arg Phe Val Asn Arg Val Val Ala Ser Met Phe Asn
305 310 315 320

Thr Val Ser Asn Lys Lys Ile Ala Val Leu Gly Phe Ala Phe Lys Lys
325 330 335

Asp Thr Gly Asp Thr Arg Glu Thr Pro Ala Ile Asp Val Cys Lys Gly
340 345 350

Leu Leu Gly Asp Lys Ala Arg Leu Ser Ile Tyr Asp Pro Gln Val Thr
355 360 365

Glu Asp Gln Ile Gln Arg Asp Leu Thr Met Asn Lys Phe Asp Trp Asp
370 375 380

His Pro Ile His Leu Gln Pro Thr Ser Pro Thr Thr Val Lys Gln Val
385 390 395 400

```
Ser Val Val Trp Asp Ala Tyr Glu Ala Thr Lys Asp Ala His Ala Val
                405                 410                 415

Cys Ile Leu Thr Glu Trp Asp Glu Phe Lys Lys Leu Asp Tyr Lys Arg
            420                 425                 430

Ile Phe Asp Asn Met Gln Lys Pro Ala Phe Val Phe Asp Gly Arg Asn
        435                 440                 445

Ile Val Asn Ala Asp Glu Leu Arg Gln Ile Gly Phe Ile Val Tyr Ser
    450                 455                 460

Ile Gly Lys Pro Leu Asp Ser Trp Leu Lys Asp Met Pro Ala Val Ala
465                 470                 475                 480
```

<210> SEQ ID NO 76
<211> LENGTH: 1482
<212> TYPE: DNA
<213> ORGANISM: Glycyrrhiza uralensis

<400> SEQUENCE: 76

```
atggaagtac attgggtttg catgtccgct gccactttgt tggtatgcta catttttgga      60

agcaagtttg tgaggaattt gaatgggtgg tattatgatg taaaactaag aaggaaagaa     120

cacccactac ccccaggtga catgggatgg cctcttatcg gcgatctatt gtccttcatc     180

aaagatttct catcgggtca ccctgattca ttcatcaaca accttgttct caaatatgga     240

cgaagtggta tctacaagac tcacttgttt gggaatccaa gcatcattgt ttgygagcct     300

cagatgtgta ggcgagttct cactgatgat gtgaacttta agcttggtta tccaaaatct     360

atcaaagagt tggcacgatg tagacccatg attgatgtct ctaatgcgga acataggctt     420

tttcgacgcc tcattacttc cccaatcgtg ggtcacaagg cgctagcaat gtacctagag     480

cgtcttgagg aaattgtgat caattcgttg gaagaattgt ccagcatgaa gcaccccgtt     540

gagctcttga aagagatgaa gaaggtttcc tttaaagcca ttgtccacgt yttcatgggc     600

tcttccaatc aggacatcat taaaaaaatt ggaagttcgt ttactgattt gtacaatggc     660

atgttctcta tccccattaa cgtacctggt tttacattcc acaaagcact cgaggcacgt     720

aagaagctag ccaaaatagt tcaacccgtt gtggatgaaa ggcggttgat gatagaaaat     780

ggtccacaag aagggagcca aagaaaagat cttattgata ttcttttgga agtcaaagat     840

gagaatggac gaaaattgga ggacgaggat attagcgatt tattaatagg gcttttgttt     900

gctggccatg aaagtacagc aaccagttta atgtggtcaa ttacatatct tacacagcat     960

ccccatatct tgaaaaaggc taaggaagag caggaagaaa taacgaggac aagatttcc     1020

tcgcagaaac aattaagtct taaggaaatt aagcaaatgg tttatctttc tcaggtaatt    1080

gatgaaactt tacgatgtgc caatattgcc tttgcaactt ttcgagaggc aactgctgat    1140

gtgaacatca atggttatat catacccaaag ggatggagag tgctaatttg ggcaagagcc   1200

attcatatgg attctgaata ttacccaaat ccagaagaat ttaatccatc gagatgggat    1260

gattacaatg ccaaagcagg aaccttcctt ccttttggag caggaagtag actttgtcct    1320

ggagccgact tggcgaaact tgaaatttcc atatttcttc attatttcct ccttaattac    1380

aggttggaga gaataaatcc agaatgtcac gttaccagct taccagtatc taarcccaca    1440

gacaattgtc tcgctaaggt gataaaggtc tcatgtgctt ag                       1482
```

<210> SEQ ID NO 77
<211> LENGTH: 493
<212> TYPE: PRT
<213> ORGANISM: Glycyrrhiza uralensis
<220> FEATURE:

<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (478)..(478)
<223> OTHER INFORMATION: Xaa can be any naturally occurring amino acid

<400> SEQUENCE: 77

```
Met Glu Val His Trp Val Cys Met Ser Ala Ala Thr Leu Leu Val Cys
1               5                   10                  15

Tyr Ile Phe Gly Ser Lys Phe Val Arg Asn Leu Asn Gly Trp Tyr Tyr
            20                  25                  30

Asp Val Lys Leu Arg Arg Lys Glu His Pro Leu Pro Pro Gly Asp Met
        35                  40                  45

Gly Trp Pro Leu Ile Gly Asp Leu Leu Ser Phe Ile Lys Asp Phe Ser
    50                  55                  60

Ser Gly His Pro Asp Ser Phe Ile Asn Asn Leu Val Leu Lys Tyr Gly
65                  70                  75                  80

Arg Ser Gly Ile Tyr Lys Thr His Leu Phe Gly Asn Pro Ser Ile Ile
                85                  90                  95

Val Xaa Glu Pro Gln Met Cys Arg Arg Val Leu Thr Asp Asp Val Asn
            100                 105                 110

Phe Lys Leu Gly Tyr Pro Lys Ser Ile Lys Glu Leu Ala Arg Cys Arg
        115                 120                 125

Pro Met Ile Asp Val Ser Asn Ala Glu His Arg Leu Phe Arg Arg Leu
    130                 135                 140

Ile Thr Ser Pro Ile Val Gly His Lys Ala Leu Ala Met Tyr Leu Glu
145                 150                 155                 160

Arg Leu Glu Glu Ile Val Ile Asn Ser Leu Glu Glu Leu Ser Ser Met
                165                 170                 175

Lys His Pro Val Glu Leu Leu Lys Glu Met Lys Lys Val Ser Phe Lys
            180                 185                 190

Ala Ile Val His Val Phe Met Gly Ser Ser Asn Gln Asp Ile Ile Lys
        195                 200                 205

Lys Ile Gly Ser Ser Phe Thr Asp Leu Tyr Asn Gly Met Phe Ser Ile
    210                 215                 220

Pro Ile Asn Val Pro Gly Phe Thr Phe His Lys Ala Leu Glu Ala Arg
225                 230                 235                 240

Lys Lys Leu Ala Lys Ile Val Gln Pro Val Val Asp Glu Arg Arg Leu
                245                 250                 255

Met Ile Glu Asn Gly Pro Gln Glu Gly Ser Gln Arg Lys Asp Leu Ile
            260                 265                 270

Asp Ile Leu Leu Glu Val Lys Asp Glu Asn Gly Arg Lys Leu Glu Asp
        275                 280                 285

Glu Asp Ile Ser Asp Leu Leu Ile Gly Leu Leu Phe Ala Gly His Glu
    290                 295                 300

Ser Thr Ala Thr Ser Leu Met Trp Ser Ile Thr Tyr Leu Thr Gln His
305                 310                 315                 320

Pro His Ile Leu Lys Lys Ala Lys Glu Glu Gln Glu Glu Ile Thr Arg
                325                 330                 335

Thr Arg Phe Ser Ser Gln Lys Gln Leu Ser Leu Lys Glu Ile Lys Gln
            340                 345                 350

Met Val Tyr Leu Ser Gln Val Ile Asp Glu Thr Leu Arg Cys Ala Asn
        355                 360                 365
```

-continued

```
Ile Ala Phe Ala Thr Phe Arg Glu Ala Thr Ala Asp Val Asn Ile Asn
    370                 375                 380

Gly Tyr Ile Ile Pro Lys Gly Trp Arg Val Leu Ile Trp Ala Arg Ala
385                 390                 395                 400

Ile His Met Asp Ser Glu Tyr Tyr Pro Asn Pro Glu Glu Phe Asn Pro
                405                 410                 415

Ser Arg Trp Asp Asp Tyr Asn Ala Lys Ala Gly Thr Phe Leu Pro Phe
            420                 425                 430

Gly Ala Gly Ser Arg Leu Cys Pro Gly Ala Asp Leu Ala Lys Leu Glu
        435                 440                 445

Ile Ser Ile Phe Leu His Tyr Phe Leu Leu Asn Tyr Arg Leu Glu Arg
    450                 455                 460

Ile Asn Pro Glu Cys His Val Thr Ser Leu Pro Val Ser Xaa Pro Thr
465                 470                 475                 480

Asp Asn Cys Leu Ala Lys Val Ile Lys Val Ser Cys Ala
                485                 490
```

```
<210> SEQ ID NO 78
<211> LENGTH: 1617
<212> TYPE: DNA
<213> ORGANISM: Glycyrrhiza uralensis
<220> FEATURE:
<221> NAME/KEY: misc_feature
<222> LOCATION: (1009)..(1009)
<223> OTHER INFORMATION: n is a, c, g, or t

<400> SEQUENCE: 78

atggatgcat cttccacacc aggggctatc tgggttgttc tgacagtgat actagctgcg     60

attcccatat gggcatgcca tatggtgaac acgctgtggc tgaggccaaa gaggttggaa    120

aggcatctca gagctcaagg tcttcatggt gacccttaca agctctcact tgacaactcc    180

aagcaaacct atatgctcaa gttgcaacaa gaagcacaat caaaatccat tggtctctcc    240

aaagatgatg ctgcaccacg aatcttctcc cttgcccatc aaactgtaca caaatatgga    300

aagaactcct ttgcatggga agggacagca ccaaaggtga tcatcacaga cccagagcaa    360

attaaggaag tctttaacaa gattcaggac ttccccaaac caaaattaaa tcccatcgcc    420

aagtatatta gcatcggtct aatacagtat gagggtgaca aatgggccaa acatcgaaag    480

attatcaatc cggcattcca cttagaaaaa ttgaaaggta tgctgccagc attttctcat    540

agctgccatg aaatgattag caaatggaag gggttattgt catcagatgg aacatgtgag    600

gttgatgttt ggcccttcct tcaaaatctc acttgtgatg taatttctag gacggcattc    660

ggaagcagct atgcagaagg agcaaaaata tttgaacttt tgaaaaggca gggatatgct    720

ttgatgacag cacgatacgc acgcattcca ttatggtggc ttctaccatc aactaccaaa    780

aggaggatga aggaaattga aagaggcata cgtgattcac ttgaaggtat cattagaaaa    840

cgagaaaaag cattgaagag tggcaaaagc accgatgacg acttattagg catacttttg    900

caatcaaatc acattgaaaa taaaggagat gaaaacagta agagtgctgg aatgaccacc    960

caagaagtaa tggaggaatg caaacttttt tacctggcag ggcaagagnt tgaaaataaa   1020

ggagatgaaa acagtaagag tgctggaatg accacccaag aagtaatgga ggaatgcaaa   1080

ctttttttacc tggcagggca agagaccacc gcagctttgc tggcctggac aatggtgtta   1140

ttaggcaagc atcctgaatg gcaagcacgc gcaaggcagg aagttttgca agtaaccatg   1200

attttatatg aggtactcag gctgtaccca cctgggattt acctcacccg agctcttcga   1260

aaggatttga aacttggaaa ccttttgcta cctgctggag tacaggtttc cgtaccaata   1320
```

```
cttttgattc accatgatga aggtatatgg ggcaatgatg caaaggagtt caatcctgaa   1380

aggtttgctg aaggaattgc aaaggcaaca aaaggccaag tttgctattt ccccttttgga   1440

tggggtccta gaatatgtgt tgggcaaaac tttgccttat tagaagccaa gattgtattg   1500

tcattgctgc tgcagaattt ctcatttgag ctatctccga cttatgcaca tgttcctacc   1560

acggtgctta ctttgcagcc aaaacatggg gcacccatca ttctgcataa actgtaa      1617


<210> SEQ ID NO 79
<211> LENGTH: 538
<212> TYPE: PRT
<213> ORGANISM: Glycyrrhiza uralensis
<220> FEATURE:
<221> NAME/KEY: misc_feature
<222> LOCATION: (337)..(337)
<223> OTHER INFORMATION: Xaa can be any naturally occurring amino acid

<400> SEQUENCE: 79

Met Asp Ala Ser Ser Thr Pro Gly Ala Ile Trp Val Val Leu Thr Val
1               5                   10                  15

Ile Leu Ala Ala Ile Pro Ile Trp Ala Cys His Met Val Asn Thr Leu
            20                  25                  30

Trp Leu Arg Pro Lys Arg Leu Glu Arg His Leu Arg Ala Gln Gly Leu
        35                  40                  45

His Gly Asp Pro Tyr Lys Leu Ser Leu Asp Asn Ser Lys Gln Thr Tyr
    50                  55                  60

Met Leu Lys Leu Gln Gln Glu Ala Gln Ser Lys Ser Ile Gly Leu Ser
65                  70                  75                  80

Lys Asp Asp Ala Ala Pro Arg Ile Phe Ser Leu Ala His Gln Thr Val
                85                  90                  95

His Lys Tyr Gly Lys Asn Ser Phe Ala Trp Glu Gly Thr Ala Pro Lys
            100                 105                 110

Val Ile Ile Thr Asp Pro Glu Gln Ile Lys Glu Val Phe Asn Lys Ile
        115                 120                 125

Gln Asp Phe Pro Lys Pro Lys Leu Asn Pro Ile Ala Lys Tyr Ile Ser
    130                 135                 140

Ile Gly Leu Ile Gln Tyr Glu Gly Asp Lys Trp Ala Lys His Arg Lys
145                 150                 155                 160

Ile Ile Asn Pro Ala Phe His Leu Glu Lys Leu Lys Gly Met Leu Pro
                165                 170                 175

Ala Phe Ser His Ser Cys His Glu Met Ile Ser Lys Trp Lys Gly Leu
            180                 185                 190

Leu Ser Ser Asp Gly Thr Cys Glu Val Asp Val Trp Pro Phe Leu Gln
        195                 200                 205

Asn Leu Thr Cys Asp Val Ile Ser Arg Thr Ala Phe Gly Ser Ser Tyr
    210                 215                 220

Ala Glu Gly Ala Lys Ile Phe Glu Leu Leu Lys Arg Gln Gly Tyr Ala
225                 230                 235                 240

Leu Met Thr Ala Arg Tyr Ala Arg Ile Pro Leu Trp Trp Leu Leu Pro
                245                 250                 255

Ser Thr Thr Lys Arg Arg Met Lys Glu Ile Glu Arg Gly Ile Arg Asp
            260                 265                 270

Ser Leu Glu Gly Ile Ile Arg Lys Arg Glu Lys Ala Leu Lys Ser Gly
        275                 280                 285

Lys Ser Thr Asp Asp Asp Leu Leu Gly Ile Leu Leu Gln Ser Asn His
    290                 295                 300
```

-continued

Ile Glu Asn Lys Gly Asp Glu Asn Ser Lys Ser Ala Gly Met Thr Thr
305 310 315 320

Gln Glu Val Met Glu Glu Cys Lys Leu Phe Tyr Leu Ala Gly Gln Glu
325 330 335

Xaa Glu Asn Lys Gly Asp Glu Asn Ser Lys Ser Ala Gly Met Thr Thr
340 345 350

Gln Glu Val Met Glu Glu Cys Lys Leu Phe Tyr Leu Ala Gly Gln Glu
355 360 365

Thr Thr Ala Ala Leu Leu Ala Trp Thr Met Val Leu Leu Gly Lys His
370 375 380

Pro Glu Trp Gln Ala Arg Ala Arg Gln Glu Val Leu Gln Val Thr Met
385 390 395 400

Ile Leu Tyr Glu Val Leu Arg Leu Tyr Pro Pro Gly Ile Tyr Leu Thr
405 410 415

Arg Ala Leu Arg Lys Asp Leu Lys Leu Gly Asn Leu Leu Leu Pro Ala
420 425 430

Gly Val Gln Val Ser Val Pro Ile Leu Leu Ile His His Asp Glu Gly
435 440 445

Ile Trp Gly Asn Asp Ala Lys Glu Phe Asn Pro Glu Arg Phe Ala Glu
450 455 460

Gly Ile Ala Lys Ala Thr Lys Gly Gln Val Cys Tyr Phe Pro Phe Gly
465 470 475 480

Trp Gly Pro Arg Ile Cys Val Gly Gln Asn Phe Ala Leu Leu Glu Ala
485 490 495

Lys Ile Val Leu Ser Leu Leu Leu Gln Asn Phe Ser Phe Glu Leu Ser
500 505 510

Pro Thr Tyr Ala His Val Pro Thr Thr Val Leu Thr Leu Gln Pro Lys
515 520 525

His Gly Ala Pro Ile Ile Leu His Lys Leu
530 535

<210> SEQ ID NO 80
<211> LENGTH: 2088
<212> TYPE: DNA
<213> ORGANISM: Glycyrrhiza uralensis

<400> SEQUENCE: 80
atggcaagct tcacccttca cacagaaacc gttcagtcat ggctactcct cagcagactt 60
cacatactgc tgcacctcgc agttgtactg ctcctcttat actaccgcat cacacgtttc 120
cccttccatg ctccsactct accgtggact ctgatgaccg taggtgaggc tattatggca 180
gtgctgtggt tcttcaacca ggccttccgg tggcggccgg tgagccgctc ggtgatgacg 240
gagaagctgc ccagcgacgc gaagctgccg gggcttgaca tattcgtgtg cacgcttgac 300
cccgagaagg agcccaccgt ggaggtgatg aacactctgg tctctgccct tgccatggac 360 taccccccctg acaagctctc cgtttacctc tccgacgatg gcgccgcccc ggtcactctt 420
tacggcgtga gagaggcttc tgagttcgcg agggtgtggg tccctttctg caaaaagtat 480
gggatcaagt caaggtgtcc caaggttttc ttctctccca gtgctgagga tgaacacctt 540
cttcgcaccg acgagttcag gtcagagcga gacctcatca aggctaaata cgagaaaatg 600
cagaaaaata ttgagaaatt tggttcggat gccaaaaatt gtcgtatggt gactgacaga 660
cctcctcgga tcgagatatt gattgaccaa ccagacatgc cacgtgttgt ttacgtgtct 720
cgggaaagaa ggccatcact ccctcacaag ttcaaaggag gagccctcaa tacattgctc 780

```
agagtctcag gtctaatcag caatgggcct tatgtacttg tagtggactg tgatatgtat    840

tgcaatgacc catcctcagc caaacaagcc atgtgtttct ttcttgatcc tgaaacctct    900

aaatytattg catttgtcca attccctcaa atgtttcaca accttggcaa aaaagacatc    960

tatgacaatc aatctaggac tgcttttaag acaatgtggc aagggatgga tggactaaga   1020

ggtcctggtc tttctggcag cggtaattac ttgaatagaa gtgcattact atttggaagt   1080

ccaaatcaaa aagatgacta tctggatgat gcccaaaact acttrggcaa gtctaccatg   1140

tacatagaat cactaaaggc cattcgtgga caaaaaacta tgaaaaagaa tatttcaaga   1200

gatgaaattt tacgagaagc tcaagtatta gcctcttgtt cctatgagac aaacacagaa   1260

tggggagcag aggtaggatt ctcatatggc atcttactgg agagttcaat cactggctat   1320

cttttycact gcagaggatg gaaatcagca tatctttacc caaagacacc atgtttctta   1380

gggtgtgccc caactgacat caaggaagga atgctccaat tggtgaagtg gttgtctgaa   1440

tactgcttgc trggattctc taaatacagc cctttcactt atggcttttc aagaatgccc   1500

attatgccta ccttagtcta ttgcttcttg acaacwacaa ccctttattc cattgtcttc   1560

atcctttatg gcattgtccc ccaagtttgc ttcttaaaag gaatacccgt gtttccaaag   1620

gtcacagacc cttggtttgc agtgtttgca acactgtata tatccaccca gattcaacat   1680

ttgatagagg tcctttctgg tgatggctct gtggcaatgt ggtgggatga acagkgaatc   1740

tggattctga agtcagtcac tagcgtgttc gcaatcatag aggcagctaa gaaagggtta   1800

ggattgaaca agaagaaatt catgttgtca aacaaagcaa ttgacaagga gaagctcaag   1860

aagtatgagc aaggtaggtt tgatttccaa ggtgcagctc tgttcatgtc cccaatggtt   1920

gtgttgctca tagtgaacgt tgtttccttc attggtggca tatggagact attcaatgca   1980

aaggatattg aagatatgtt tggtcagctt ttcctagtta gttatgtaat ggcccttagt   2040

tatcccattt ttgaagggat aataaccatg aaaagcaaga gtggatag                2088
```

<210> SEQ ID NO 81
<211> LENGTH: 695
<212> TYPE: PRT
<213> ORGANISM: Glycyrrhiza uralensis
<220> FEATURE:
<221> NAME/KEY: misc_feature
<222> LOCATION: (302)..(302)
<223> OTHER INFORMATION: Xaa can be any naturally occurring amino acid
<220> FEATURE:
<221> NAME/KEY: misc_feature
<222> LOCATION: (375)..(375)
<223> OTHER INFORMATION: Xaa can be any naturally occurring amino acid
<220> FEATURE:
<221> NAME/KEY: misc_feature
<222> LOCATION: (442)..(442)
<223> OTHER INFORMATION: Xaa can be any naturally occurring amino acid
<220> FEATURE:
<221> NAME/KEY: misc_feature
<222> LOCATION: (579)..(579)
<223> OTHER INFORMATION: Xaa can be any naturally occurring amino acid

<400> SEQUENCE: 81

```
Met Ala Ser Phe Thr Leu His Thr Glu Thr Val Gln Ser Trp Leu Leu
1               5                   10                  15

Leu Ser Arg Leu His Ile Leu Leu His Leu Ala Val Val Leu Leu Leu
            20                  25                  30

Leu Tyr Tyr Arg Ile Thr Arg Phe Pro Phe His Ala Pro Thr Leu Pro
        35                  40                  45

Trp Thr Leu Met Thr Val Gly Glu Ala Ile Met Ala Val Leu Trp Phe
```

-continued

```
    50                  55                  60

Phe Asn Gln Ala Phe Arg Trp Arg Pro Val Ser Arg Ser Val Met Thr
65                  70                  75                  80

Glu Lys Leu Pro Ser Asp Ala Lys Leu Pro Gly Leu Asp Ile Phe Val
                85                  90                  95

Cys Thr Leu Asp Pro Glu Lys Glu Pro Thr Val Glu Val Met Asn Thr
            100                 105                 110

Leu Val Ser Ala Leu Ala Met Asp Tyr Pro Pro Asp Lys Leu Ser Val
        115                 120                 125

Tyr Leu Ser Asp Asp Gly Ala Ala Pro Val Thr Leu Tyr Gly Val Arg
    130                 135                 140

Glu Ala Ser Glu Phe Ala Arg Val Trp Val Pro Phe Cys Lys Lys Tyr
145                 150                 155                 160

Gly Ile Lys Ser Arg Cys Pro Lys Val Phe Phe Ser Pro Ser Ala Glu
                165                 170                 175

Asp Glu His Leu Leu Arg Thr Asp Glu Phe Arg Ser Glu Arg Asp Leu
            180                 185                 190

Ile Lys Ala Lys Tyr Glu Lys Met Gln Lys Asn Ile Glu Lys Phe Gly
        195                 200                 205

Ser Asp Ala Lys Asn Cys Arg Met Val Thr Asp Arg Pro Pro Arg Ile
    210                 215                 220

Glu Ile Leu Ile Asp Gln Pro Asp Met Pro Arg Val Val Tyr Val Ser
225                 230                 235                 240

Arg Glu Arg Arg Pro Ser Leu Pro His Lys Phe Lys Gly Gly Ala Leu
                245                 250                 255

Asn Thr Leu Leu Arg Val Ser Gly Leu Ile Ser Asn Gly Pro Tyr Val
            260                 265                 270

Leu Val Val Asp Cys Asp Met Tyr Cys Asn Asp Pro Ser Ser Ala Lys
        275                 280                 285

Gln Ala Met Cys Phe Phe Leu Asp Pro Glu Thr Ser Lys Xaa Ile Ala
    290                 295                 300

Phe Val Gln Phe Pro Gln Met Phe His Asn Leu Gly Lys Lys Asp Ile
305                 310                 315                 320

Tyr Asp Asn Gln Ser Arg Thr Ala Phe Lys Thr Met Trp Gln Gly Met
                325                 330                 335

Asp Gly Leu Arg Gly Pro Gly Leu Ser Gly Ser Gly Asn Tyr Leu Asn
            340                 345                 350

Arg Ser Ala Leu Leu Phe Gly Ser Pro Asn Gln Lys Asp Asp Tyr Leu
        355                 360                 365

Asp Asp Ala Gln Asn Tyr Xaa Gly Lys Ser Thr Met Tyr Ile Glu Ser
    370                 375                 380

Leu Lys Ala Ile Arg Gly Gln Lys Thr Met Lys Lys Asn Ile Ser Arg
385                 390                 395                 400

Asp Glu Ile Leu Arg Glu Ala Gln Val Leu Ala Ser Cys Ser Tyr Glu
                405                 410                 415

Thr Asn Thr Glu Trp Gly Ala Glu Val Gly Phe Ser Tyr Gly Ile Leu
            420                 425                 430

Leu Glu Ser Ser Ile Thr Gly Tyr Leu Xaa His Cys Arg Gly Trp Lys
        435                 440                 445

Ser Ala Tyr Leu Tyr Pro Lys Thr Pro Cys Phe Leu Gly Cys Ala Pro
    450                 455                 460

Thr Asp Ile Lys Glu Gly Met Leu Gln Leu Val Lys Trp Leu Ser Glu
465                 470                 475                 480
```

-continued

```
Tyr Cys Leu Leu Gly Phe Ser Lys Tyr Ser Pro Phe Thr Tyr Gly Phe
                485                 490                 495

Ser Arg Met Pro Ile Met Pro Thr Leu Val Tyr Cys Phe Leu Thr Thr
            500                 505                 510

Thr Thr Leu Tyr Ser Ile Val Phe Ile Leu Tyr Gly Ile Val Pro Gln
        515                 520                 525

Val Cys Phe Leu Lys Gly Ile Pro Val Phe Pro Lys Val Thr Asp Pro
    530                 535                 540

Trp Phe Ala Val Phe Ala Thr Leu Tyr Ile Ser Thr Gln Ile Gln His
545                 550                 555                 560

Leu Ile Glu Val Leu Ser Gly Asp Gly Ser Val Ala Met Trp Trp Asp
                565                 570                 575

Glu Gln Xaa Ile Trp Ile Leu Lys Ser Val Thr Ser Val Phe Ala Ile
            580                 585                 590

Ile Glu Ala Ala Lys Lys Gly Leu Gly Leu Asn Lys Lys Lys Phe Met
        595                 600                 605

Leu Ser Asn Lys Ala Ile Asp Lys Glu Lys Leu Lys Lys Tyr Glu Gln
    610                 615                 620

Gly Arg Phe Asp Phe Gln Gly Ala Ala Leu Phe Met Ser Pro Met Val
625                 630                 635                 640

Val Leu Leu Ile Val Asn Val Val Ser Phe Ile Gly Gly Ile Trp Arg
                645                 650                 655

Leu Phe Asn Ala Lys Asp Ile Glu Asp Met Phe Gly Gln Leu Phe Leu
            660                 665                 670

Val Ser Tyr Val Met Ala Leu Ser Tyr Pro Ile Phe Glu Gly Ile Ile
        675                 680                 685

Thr Met Lys Ser Lys Ser Gly
    690                 695
```

<210> SEQ ID NO 82
<211> LENGTH: 1445
<212> TYPE: DNA
<213> ORGANISM: Glycyrrhiza uralensis

<400> SEQUENCE: 82

```
atgaccatgg gtaacgagaa tcgggagctg cacataatct tcttcccctt tctggcgaac      60

ggccacatca tcccctgcgt ggacttggcc agagtcttcg ccgcaagagg aatcagagcc     120

accatagtca ccacccacct caacgttccc tacatttcca gaaccatcgg aaaagccaac     180

atcaacatca gaaccatcaa gttcccttcc accgaagact ctggccttcc cgaaggctgc     240

gagaataccg agtcagcact cgcccctgac aagttcatca agttcatgaa ggccaccctg     300

ctcctgaggg acccacttga acacgtgtta caggaagagc aaccacactc ttggtcgccg     360

acatgttctt cccttgggcc accgactccg ccgcaaaatt cggcatccct aggatcgtgt     420

tccacggcct cggttacttc ccactctgcg ttcttgcatg cacgagacag tacaagcctc     480

aggacaaggt ttcatcttac acggaaccct tcgtggttcc gaatctcccg ggtgaaataa     540

cactgacgaa gatgcagctg ccgcagttgc ctcagcacga caaggtcttc acccagttgt     600

tggaagagtc aaacgaatcg gagttgaaga gcttcggtgt gattgtaaac agcttctacg     660

aacttgaacc ggtttacgcg gatcattaca ggaacgagct tgggagaaga gcttggcatt     720

tgggtccggt ttcattatgc agtagggaca cggaggaaaa atcgcggagg ggaagggaag     780

ctgcaattga tgagaacgag tgcttgaagt ggcttcaatc aaaggaaccc aattcggttg     840
```

```
tttatgtttg tttcggtagc atgatggttt tcagtgacgc tcagctaaaa gagattgcga    900

tgggtcttga ggcttcaggg aagccattca tatgggtggt gaagaaagga ggggctaaaa    960

gtgaaggtga gaaattggag tggcttccag aagggtttga ggagagaatg ggggaaagta   1020

ataagggact aatcataagg ggttgggcac cacaggtgat gattttggac catggagcgg   1080

ttggagggtt tgtgacacat tgtgggtgga attcaacgct ggaaggagtg tgtgcagggg   1140

tgccaatggt gacttggccc atgtatgggg aacaatttta caacgccaag tttctgacgg   1200

acatagtgaa aattggggtg ggtgttgggg ttcaaacgtg gattgggatg ggaggaggag   1260

agcctgtgaa gaaggaagtg atagagcagg cagtgagaag gataatggtg gggcaggaag   1320

cagaggaaat gagaaacaga gccaaggaac tgagccagat ggcaaagcgt gctgtggagg   1380

aaggaggatc gtctcacaac gattttaact ctttaattga ggatttgagg tcgcgtgccc   1440

attaa                                                              1445
```

<210> SEQ ID NO 83
<211> LENGTH: 481
<212> TYPE: PRT
<213> ORGANISM: Glycyrrhiza uralensis

<400> SEQUENCE: 83

```
Met Thr Met Gly Asn Glu Asn Arg Glu Leu His Ile Ile Phe Phe Pro
1               5                   10                  15

Phe Leu Ala Asn Gly His Ile Ile Pro Cys Val Asp Leu Ala Arg Val
            20                  25                  30

Phe Ala Ala Arg Gly Ile Arg Ala Thr Ile Val Thr Thr His Leu Asn
        35                  40                  45

Val Pro Tyr Ile Ser Arg Thr Ile Gly Lys Ala Asn Ile Asn Ile Arg
    50                  55                  60

Thr Ile Lys Phe Pro Ser Thr Glu Asp Ser Gly Leu Pro Glu Gly Cys
65                  70                  75                  80

Glu Asn Thr Glu Ser Ala Leu Ala Pro Asp Lys Phe Ile Lys Phe Met
                85                  90                  95

Lys Ala Thr Leu Leu Leu Arg Asp Pro Leu Glu His Val Leu Gln Glu
            100                 105                 110

Glu Gln Pro His Cys Leu Val Ala Asp Met Phe Phe Pro Trp Ala Thr
        115                 120                 125

Asp Ser Ala Ala Lys Phe Gly Ile Pro Arg Ile Val Phe His Gly Leu
    130                 135                 140

Gly Tyr Phe Pro Leu Cys Val Leu Ala Cys Thr Arg Gln Tyr Lys Pro
145                 150                 155                 160

Gln Asp Lys Val Ser Ser Tyr Thr Glu Pro Phe Val Val Pro Asn Leu
                165                 170                 175

Pro Gly Glu Ile Thr Leu Thr Lys Met Gln Leu Pro Gln Leu Pro Gln
            180                 185                 190

His Asp Lys Val Phe Thr Gln Leu Leu Glu Glu Ser Asn Glu Ser Glu
        195                 200                 205

Leu Lys Ser Phe Gly Val Ile Val Asn Ser Phe Tyr Glu Leu Glu Pro
    210                 215                 220

Val Tyr Ala Asp His Tyr Arg Asn Glu Leu Gly Arg Arg Ala Trp His
225                 230                 235                 240

Leu Gly Pro Val Ser Leu Cys Ser Arg Asp Thr Glu Glu Lys Ser Arg
                245                 250                 255

Arg Gly Arg Glu Ala Ala Ile Asp Glu Asn Glu Cys Leu Lys Trp Leu
```

260 265 270

Gln Ser Lys Glu Pro Asn Ser Val Val Tyr Val Cys Phe Gly Ser Met
275 280 285

Met Val Phe Ser Asp Ala Gln Leu Lys Glu Ile Ala Met Gly Leu Glu
290 295 300

Ala Ser Gly Lys Pro Phe Ile Trp Val Val Lys Lys Gly Gly Ala Lys
305 310 315 320

Ser Glu Gly Glu Lys Leu Glu Trp Leu Pro Glu Gly Phe Glu Glu Arg
325 330 335

Met Gly Glu Ser Asn Lys Gly Leu Ile Ile Arg Gly Trp Ala Pro Gln
340 345 350

Val Met Ile Leu Asp His Gly Ala Val Gly Gly Phe Val Thr His Cys
355 360 365

Gly Trp Asn Ser Thr Leu Glu Gly Val Cys Ala Gly Val Pro Met Val
370 375 380

Thr Trp Pro Met Tyr Gly Glu Gln Phe Tyr Asn Ala Lys Phe Leu Thr
385 390 395 400

Asp Ile Val Lys Ile Gly Val Gly Val Gly Val Gln Thr Trp Ile Gly
405 410 415

Met Gly Gly Gly Glu Pro Val Lys Lys Glu Val Ile Glu Gln Ala Val
420 425 430

Arg Arg Ile Met Val Gly Gln Glu Ala Glu Glu Met Arg Asn Arg Ala
435 440 445

Lys Glu Leu Ser Gln Met Ala Lys Arg Ala Val Glu Glu Gly Gly Ser
450 455 460

Ser His Asn Asp Phe Asn Ser Leu Ile Glu Asp Leu Arg Ser Arg Ala
465 470 475 480

His

<210> SEQ ID NO 84
<211> LENGTH: 1521
<212> TYPE: DNA
<213> ORGANISM: Glycyrrhiza uralensis

<400> SEQUENCE: 84
atggactcct ttggggttga aggtgatcac caagccgaca ccacagtgct gaaggcggtt 60
tttcttccct tcatctcaaa aagtcatctc atccgtgagg tggacaaagc aaggatcttc 120
gccatgcacg gcgtggatgt caccatcatc accacgccgg ccaacgctgc cactttccaa 180
acctccattg accgcgactc cagccgcggc cgctccatca gaacgcacat cgttccgttc 240
ccccaagtcc ccggtctacc acagggactc gagagactcg acgccgacac tcctcaacac 300
ttgctctcca agatctacca tggactatcc attctgcaag agcagttcca acaactgttc 360
cgtgaaatga ggccagattt catagtcact gacatgtact acccttggag cgtcgatgcc 420
gccgccgagt tggggattcc gaggttggtt tgtaacggtg gaagctactt cgctcagtca 480
gctgttaact ccgttgagct attttcacca caagccaagg ttgattcaaa taccgagact 540
tttctgcttc ctgggttacc ccatgaggtt gagatgacac gtttgcaact accggattgg 600
cttagaggag caccgaatga gtacacctat ttgatgaaga tgatcaagga ttcagagagg 660
aagagttatg ggtcattgtt caatagcttt tatgagcttg aagggactta tgaggaacat 720
tacaagaaag ccatgggaac caagagttgg agtgtggggc cagtttcttt gtgggtgaac 780
caagatgctt ctgataaggc ttgtaggggg gatgttaaag aaggaaaagg agatggggtg 840

```
gtgcttactt ggctggattc taaaacagag gactctgttt tgtatgtgag ttttgggagc    900

atgaacaagt tccctaaaac tcagcttgtt gagatagctc atgccctcga agattctggc    960

catgatttca tttgggtcgt tggcaaaatt gaagaaggtg aaggtggtgc tgattttttg   1020

agggaatttg agaagaaagt gaaagaaaaa aacagaggtt atctgatatg gggttgggca   1080

ccacagcttc tgattctgga gcatcctgcg gttggagcag tggtgactca ttgtgggtgg   1140

aacaccgtta tggaaagtgt gaatgcaagt ttgccattgg caacttggcc attgtttgcg   1200

gagcagttct tcaatgagaa gctagtggtt gatgtggtga agattggtgt gccagttggg   1260

gttaaggaat ggagaaattg gaatgagttt ggggatgagg ttgtgaagag ggaggacata   1320

ggaaaggcca ttgctttttt gatgggtggt ggggatgaat ccttggaaat gaggaagagg   1380

gtcaaggtgc tcagtggtgc tacaaagaaa gctattcagg ttggtgggtc ttctcacacc   1440

aagttgaaag aactcataga agagctcaag tcaatcaagc tacaaaaggt caacaacaaa   1500

ttaatggagg cagtggctta a                                             1521


<210> SEQ ID NO 85
<211> LENGTH: 506
<212> TYPE: PRT
<213> ORGANISM: Glycyrrhiza uralensis

<400> SEQUENCE: 85

Met Asp Ser Phe Gly Val Glu Gly Asp His Gln Ala Asp Thr Thr Val
1               5                   10                  15

Leu Lys Ala Val Phe Leu Pro Phe Ile Ser Lys Ser His Leu Ile Arg
            20                  25                  30

Glu Val Asp Lys Ala Arg Ile Phe Ala Met His Gly Val Asp Val Thr
        35                  40                  45

Ile Ile Thr Thr Pro Ala Asn Ala Ala Thr Phe Gln Thr Ser Ile Asp
    50                  55                  60

Arg Asp Ser Ser Arg Gly Arg Ser Ile Arg Thr His Ile Val Pro Phe
65                  70                  75                  80

Pro Gln Val Pro Gly Leu Pro Gln Gly Leu Glu Arg Leu Asp Ala Asp
                85                  90                  95

Thr Pro Gln His Leu Leu Ser Lys Ile Tyr His Gly Leu Ser Ile Leu
            100                 105                 110

Gln Glu Gln Phe Gln Gln Leu Phe Arg Glu Met Arg Pro Asp Phe Ile
        115                 120                 125

Val Thr Asp Met Tyr Tyr Pro Trp Ser Val Asp Ala Ala Ala Glu Leu
    130                 135                 140

Gly Ile Pro Arg Leu Val Cys Asn Gly Gly Ser Tyr Phe Ala Gln Ser
145                 150                 155                 160

Ala Val Asn Ser Val Glu Leu Phe Ser Pro Gln Ala Lys Val Asp Ser
                165                 170                 175

Asn Thr Glu Thr Phe Leu Leu Pro Gly Leu Pro His Glu Val Glu Met
            180                 185                 190

Thr Arg Leu Gln Leu Pro Asp Trp Leu Arg Gly Ala Pro Asn Glu Tyr
        195                 200                 205

Thr Tyr Leu Met Lys Met Ile Lys Asp Ser Glu Arg Lys Ser Tyr Gly
    210                 215                 220

Ser Leu Phe Asn Ser Phe Tyr Glu Leu Glu Gly Thr Tyr Glu Glu His
225                 230                 235                 240

Tyr Lys Lys Ala Met Gly Thr Lys Ser Trp Ser Val Gly Pro Val Ser
                245                 250                 255
```

```
Leu Trp Val Asn Gln Asp Ala Ser Asp Lys Ala Cys Arg Gly Asp Val
            260                 265                 270

Lys Glu Gly Lys Gly Asp Gly Val Val Leu Thr Trp Leu Asp Ser Lys
        275                 280                 285

Thr Glu Asp Ser Val Leu Tyr Val Ser Phe Gly Ser Met Asn Lys Phe
    290                 295                 300

Pro Lys Thr Gln Leu Val Glu Ile Ala His Ala Leu Glu Asp Ser Gly
305                 310                 315                 320

His Asp Phe Ile Trp Val Val Gly Lys Ile Glu Glu Gly Glu Gly Gly
                325                 330                 335

Ala Asp Phe Leu Arg Glu Phe Glu Lys Lys Val Lys Glu Lys Asn Arg
            340                 345                 350

Gly Tyr Leu Ile Trp Gly Trp Ala Pro Gln Leu Leu Ile Leu Glu His
        355                 360                 365

Pro Ala Val Gly Ala Val Val Thr His Cys Gly Trp Asn Thr Val Met
    370                 375                 380

Glu Ser Val Asn Ala Ser Leu Pro Leu Ala Thr Trp Pro Leu Phe Ala
385                 390                 395                 400

Glu Gln Phe Phe Asn Glu Lys Leu Val Val Asp Val Val Lys Ile Gly
                405                 410                 415

Val Pro Val Gly Val Lys Glu Trp Arg Asn Trp Asn Glu Phe Gly Asp
            420                 425                 430

Glu Val Val Lys Arg Glu Asp Ile Gly Lys Ala Ile Ala Phe Leu Met
        435                 440                 445

Gly Gly Gly Asp Glu Ser Leu Glu Met Arg Lys Arg Val Lys Val Leu
    450                 455                 460

Ser Gly Ala Thr Lys Lys Ala Ile Gln Val Gly Gly Ser Ser His Thr
465                 470                 475                 480

Lys Leu Lys Glu Leu Ile Glu Glu Leu Lys Ser Ile Lys Leu Gln Lys
                485                 490                 495

Val Asn Asn Lys Leu Met Glu Ala Val Ala
            500                 505
```

<210> SEQ ID NO 86
<211> LENGTH: 1563
<212> TYPE: DNA
<213> ORGANISM: Arabodopsis thaliana

<400> SEQUENCE: 86

```
atgtctctat ttctgaagcc cttcctcttc ctatacgaca ccactcttag tcttctctta     60

cttctgttca atggatggag tcttgaggat acagcagcag cccaaaagag gcgtgaagca    120

gacaaaaatg ctgcagaaac tgaatggatc caactccaat acttgtggac caaaacaagg    180

agtgttgtac tacttcccgt tttcaagggt ttggtggtta tgtgtttggt tctatccatt    240

atagtgttct tcgagagttt ttacatgaac tttgtgatac tcttcgtcaa gttatttaaa    300

cgtaaacccc ataaagtgta caaatgggag gccatgcaag aagatgttga ggttggaccc    360

gataactacc caatggttct tatccaaata ccaatgtaca atgaaaaaga ggaaggtgtg    420

gacgtagaga ttgcaaaatg gcaaagccaa ggcataaaca taaggtgtga aaggagagat    480

aacaggaacg gctacaaagc cggagctatg aaagaagctc ttacgcagag ctacgtcaag    540

caatgcgact tcgtagcagt cttcgatgct gatttccaac ccgagcccga ttatctcatc    600

cgcgctgtcc ctttccttgt ccacaaccct gacgttgctc tagttcaagc ccgatggata    660
```

```
tttgttaacg cgaacaaatg cttgatgacg aggatgcaag agatgtctct caactatcat    720

ttcaaagtgg aacaagaatc agggtcgact agacatgctt tcttcgggtt taatggaacc    780

gcgggtgtat ggagaatatc ggcaatggaa gcagcaggag gatggaaatc aaggaccaca    840

gtagaggaca tggacttggc tgttcgtgtt ggtcttcatg gctggaaatt tgtctacctt    900

aacgacctca cggtgagaaa cgagcttcca agcaaattta aggcctacag attccagcaa    960

cataggtggt cctgtggacc ggcgaatcta tttagaaaaa tgacgatgga gatcattttc   1020

aataagagag tatcaatttg gaagaagttt tatgtgatct acagcttttt cttcgtaagg   1080

aaagtggcgg tacacttctt gacattcttc ttctactgta taattgtgcc aacaagtgtc   1140

ttcttccctg aaatccacat cccatcttgg tctaccattt acgttccctc tttgatcagt   1200

atcttccaca ccctggcaac tccaagatcc ttctacctcg tgatattttg ggtcttgttc   1260

gagaatgtaa tggctatgca tcgaaccaaa ggtacgtgca ttggcctact tgaaggagga   1320

agagtaaacg aatgggttgt gaccgaaaaa ctaggagatg ctttgaagag taagctactc   1380

tctcgggtag tccaaagaaa atcttgttat caaagagtga attccaagga agtgatggtg   1440

ggggtataca tattaggatg tgcactctat ggcctgatct atgggcacac atggttacat   1500

ttctatcttt ttcttcaggc cacagccttt ttcgtctccg gttttggttt tgtcggaacc   1560

taa                                                                 1563
```

<210> SEQ ID NO 87
<211> LENGTH: 520
<212> TYPE: PRT
<213> ORGANISM: Arabodopsis thaliana

<400> SEQUENCE: 87

```
Met Ser Leu Phe Leu Lys Pro Phe Leu Phe Leu Tyr Asp Thr Thr Leu
1               5                   10                  15

Ser Leu Leu Leu Leu Leu Phe Asn Gly Trp Ser Leu Glu Asp Thr Ala
            20                  25                  30

Ala Ala Gln Lys Arg Arg Glu Ala Asp Lys Asn Ala Ala Glu Thr Glu
        35                  40                  45

Trp Ile Gln Leu Gln Tyr Leu Trp Thr Lys Thr Arg Ser Val Val Leu
    50                  55                  60

Leu Pro Val Phe Lys Gly Leu Val Val Met Cys Leu Val Leu Ser Ile
65                  70                  75                  80

Ile Val Phe Phe Glu Ser Phe Tyr Met Asn Phe Val Ile Leu Phe Val
                85                  90                  95

Lys Leu Phe Lys Arg Lys Pro His Lys Val Tyr Lys Trp Glu Ala Met
            100                 105                 110

Gln Glu Asp Val Glu Val Gly Pro Asp Asn Tyr Pro Met Val Leu Ile
        115                 120                 125

Gln Ile Pro Met Tyr Asn Glu Lys Glu Glu Gly Val Asp Val Glu Ile
    130                 135                 140

Ala Lys Trp Gln Ser Gln Gly Ile Asn Ile Arg Cys Glu Arg Arg Asp
145                 150                 155                 160

Asn Arg Asn Gly Tyr Lys Ala Gly Ala Met Lys Glu Ala Leu Thr Gln
                165                 170                 175

Ser Tyr Val Lys Gln Cys Asp Phe Val Ala Val Phe Asp Ala Asp Phe
            180                 185                 190

Gln Pro Glu Pro Asp Tyr Leu Ile Arg Ala Val Pro Phe Leu Val His
        195                 200                 205
```

```
Asn Pro Asp Val Ala Leu Val Gln Ala Arg Trp Ile Phe Val Asn Ala
    210                 215                 220

Asn Lys Cys Leu Met Thr Arg Met Gln Glu Met Ser Leu Asn Tyr His
225                 230                 235                 240

Phe Lys Val Glu Gln Glu Ser Gly Ser Thr Arg His Ala Phe Phe Gly
                245                 250                 255

Phe Asn Gly Thr Ala Gly Val Trp Arg Ile Ser Ala Met Glu Ala Ala
            260                 265                 270

Gly Gly Trp Lys Ser Arg Thr Thr Val Glu Asp Met Asp Leu Ala Val
        275                 280                 285

Arg Val Gly Leu His Gly Trp Lys Phe Val Tyr Leu Asn Asp Leu Thr
    290                 295                 300

Val Arg Asn Glu Leu Pro Ser Lys Phe Lys Ala Tyr Arg Phe Gln Gln
305                 310                 315                 320

His Arg Trp Ser Cys Gly Pro Ala Asn Leu Phe Arg Lys Met Thr Met
                325                 330                 335

Glu Ile Ile Phe Asn Lys Arg Val Ser Ile Trp Lys Lys Phe Tyr Val
            340                 345                 350

Ile Tyr Ser Phe Phe Phe Val Arg Lys Val Ala Val His Phe Leu Thr
        355                 360                 365

Phe Phe Phe Tyr Cys Ile Ile Val Pro Thr Ser Val Phe Phe Pro Glu
    370                 375                 380

Ile His Ile Pro Ser Trp Ser Thr Ile Tyr Val Pro Ser Leu Ile Ser
385                 390                 395                 400

Ile Phe His Thr Leu Ala Thr Pro Arg Ser Phe Tyr Leu Val Ile Phe
                405                 410                 415

Trp Val Leu Phe Glu Asn Val Met Ala Met His Arg Thr Lys Gly Thr
            420                 425                 430

Cys Ile Gly Leu Leu Glu Gly Gly Arg Val Asn Glu Trp Val Val Thr
        435                 440                 445

Glu Lys Leu Gly Asp Ala Leu Lys Ser Lys Leu Leu Ser Arg Val Val
    450                 455                 460

Gln Arg Lys Ser Cys Tyr Gln Arg Val Asn Ser Lys Glu Val Met Val
465                 470                 475                 480

Gly Val Tyr Ile Leu Gly Cys Ala Leu Tyr Gly Leu Ile Tyr Gly His
                485                 490                 495

Thr Trp Leu His Phe Tyr Leu Phe Leu Gln Ala Thr Ala Phe Phe Val
            500                 505                 510

Ser Gly Phe Gly Phe Val Gly Thr
        515                 520
```

<210> SEQ ID NO 88
<211> LENGTH: 2274
<212> TYPE: DNA
<213> ORGANISM: Arabodopsis thaliana

<400> SEQUENCE: 88

```
atggcggatt caagcttttc tcttcctcct ctttgtgaaa ggatctcata cacgaactat     60

tttctaagag ctgtatatct cacggttcta ggccttttct tttctcttct cttgcaccga    120

atccgacata cgagcgaata cgacaacgtt tggctcgtgg ctttcttttg tgaatcttgt    180

ttcttcttgg tatgtctgct tattacttgc ctaaaatgga gtcctgctga tactaaaccc    240

tttcctgata gacttgatga aagggttcat gaccttcctt cggtggatat gttcgtgccc    300

acagcagatc cggttcgaga gccaccgatt atggttgtgg acaccgtgct ttcgctgtta    360
```

gctgtaaatt atccggcaaa taaactagct tgttatgtgt cggacgatgg atgctcacct 420
ctcacttatt tctctctcaa ggaagcttct aagttcgcca agatttgggt accgttctgc 480
aaaaagtaca acactagagt tagagctcct tctagatatt ttctgaaacc tataagcgtc 540
gcaacagagg attatgaatt caatagagac tgggaaaaga cgaagaggga gtacgagaag 600
ttgaggcgga aagtggaaga tgccaccgga gattctcata tgttggatgt agaagatgat 660
tttgaagcat tctcaaacac aaaaccaaat gatcattcaa ctctagttaa ggtggtatgg 720
gagaacaagg gaggtgtagg agacgagaaa gagatccctc atatcatata catatcaaga 780
gagaaaagac caaattatgt tcataatcaa aaatgtggag ccatgaactt tctggcaaga 840
gtgtcagggt tgatgacaaa cgcaccatac atcttgaacg tggattgcga catgtatgcc 900
aatgatgcag atgtagtccg acaagcaatg tgtatacttc tgcaagaatc attaaatatg 960
aaacattgtg cttttgttca attccgtcaa gaattctatg attcaagcac cgagctaata 1020
gtcgtcctac aatcacattt gggacgagga atcgcgggaa tccaaggacc gatatatata 1080
ggatcaggat gcgtccacac gagaagagtt atgtatggtt tatctccaga cgatttcgaa 1140
gttgatggaa gtctttcttc agttgctaca agggagtttt tggttaagga tagtttagcg 1200
agaagatttg gtaattctaa agagatgatg aaatcagtgg ttgatgcaat acaaagaaat 1260
ccaaatccac aaaatatact tacaaactcc atagaagcgg ctcgagaagt gggacattgt 1320
cagtacgagt accaaaccag ctggggaaac accatcggct ggttatatga ttcagtggcg 1380
gaagatttaa acacgagtat cggaatacat tcgagaggtt ggactagctc atacatttct 1440
ccggatacac ctgcatttct tggatctatg ccggcaggag tacccgaggc gttactccag 1500
cagcgtcgat gggcgacagg atggatcgaa atccttttca acaagcaaag tccgttgcga 1560
ggattgttta gcaagaaaat aagattccga caacgattag cttatctttg cattatcacc 1620
tgtctaaggt caatccctga gcttatttat tgtctccttc ctgcttattg cctactccac 1680
aactctacct tattccccaa gggactttat ttaggcataa ctgtcacact tgttgggata 1740
cattgtctct atactctatg ggaatttatg agccttggtt attccgtaca atcgtggcta 1800
gtctcccaat cagtttggag aatagtagcc actagtagtt ggttatttag catctttgat 1860
atcacactca agcttcttgg catctcggaa acggtgttca taatcactaa aaagactgtg 1920
gctgggacca agtcagcatt agggtctgga ccctctcaag gagaagacgt tggtccaaac 1980
tcagacttgt ttaaatttga atttgatggc tcactttgtt tcttgcctgg cacatttatt 2040
gtgttggtga atatagccgc tctagctgtt ttttctgtgg gtctacaacg gtcgagttac 2100
agccatgaag gaggtggttc gggtctggca gaggcttgcg gatgtgtttt ggtaatgatg 2160
ttgttccttc catttctaat gggtttgttt aagaaaggaa aatatggaac cccattgtct 2220
actctctcta tagctggctt tttagcagtt ttatttgttg ttttctctgt ttga 2274

<210> SEQ ID NO 89
<211> LENGTH: 757
<212> TYPE: PRT
<213> ORGANISM: Arabodopsis thaliana

<400> SEQUENCE: 89

Met Ala Asp Ser Ser Phe Ser Leu Pro Pro Leu Cys Glu Arg Ile Ser
1 5 10 15

Tyr Thr Asn Tyr Phe Leu Arg Ala Val Tyr Leu Thr Val Leu Gly Leu
20 25 30

```
Phe Phe Ser Leu Leu Leu His Arg Ile Arg His Thr Ser Glu Tyr Asp
        35                  40                  45

Asn Val Trp Leu Val Ala Phe Phe Cys Glu Ser Cys Phe Phe Leu Val
    50                  55                  60

Cys Leu Leu Ile Thr Cys Leu Lys Trp Ser Pro Ala Asp Thr Lys Pro
65                  70                  75                  80

Phe Pro Asp Arg Leu Asp Glu Arg Val His Asp Leu Pro Ser Val Asp
                85                  90                  95

Met Phe Val Pro Thr Ala Asp Pro Val Arg Glu Pro Pro Ile Met Val
            100                 105                 110

Val Asp Thr Val Leu Ser Leu Leu Ala Val Asn Tyr Pro Ala Asn Lys
        115                 120                 125

Leu Ala Cys Tyr Val Ser Asp Asp Gly Cys Ser Pro Leu Thr Tyr Phe
    130                 135                 140

Ser Leu Lys Glu Ala Ser Lys Phe Ala Lys Ile Trp Val Pro Phe Cys
145                 150                 155                 160

Lys Lys Tyr Asn Thr Arg Val Arg Ala Pro Ser Arg Tyr Phe Leu Lys
                165                 170                 175

Pro Ile Ser Val Ala Thr Glu Asp Tyr Glu Phe Asn Arg Asp Trp Glu
            180                 185                 190

Lys Thr Lys Arg Glu Tyr Glu Lys Leu Arg Arg Lys Val Glu Asp Ala
        195                 200                 205

Thr Gly Asp Ser His Met Leu Asp Val Glu Asp Asp Phe Glu Ala Phe
    210                 215                 220

Ser Asn Thr Lys Pro Asn Asp His Ser Thr Leu Val Lys Val Val Trp
225                 230                 235                 240

Glu Asn Lys Gly Gly Val Gly Asp Glu Lys Glu Ile Pro His Ile Ile
                245                 250                 255

Tyr Ile Ser Arg Glu Lys Arg Pro Asn Tyr Val His Asn Gln Lys Cys
            260                 265                 270

Gly Ala Met Asn Phe Leu Ala Arg Val Ser Gly Leu Met Thr Asn Ala
        275                 280                 285

Pro Tyr Ile Leu Asn Val Asp Cys Asp Met Tyr Ala Asn Asp Ala Asp
    290                 295                 300

Val Val Arg Gln Ala Met Cys Ile Leu Leu Gln Glu Ser Leu Asn Met
305                 310                 315                 320

Lys His Cys Ala Phe Val Gln Phe Arg Gln Glu Phe Tyr Asp Ser Ser
                325                 330                 335

Thr Glu Leu Ile Val Val Leu Gln Ser His Leu Gly Arg Gly Ile Ala
            340                 345                 350

Gly Ile Gln Gly Pro Ile Tyr Ile Gly Ser Gly Cys Val His Thr Arg
        355                 360                 365

Arg Val Met Tyr Gly Leu Ser Pro Asp Asp Phe Glu Val Asp Gly Ser
    370                 375                 380

Leu Ser Ser Val Ala Thr Arg Glu Phe Leu Val Lys Asp Ser Leu Ala
385                 390                 395                 400

Arg Arg Phe Gly Asn Ser Lys Glu Met Met Lys Ser Val Val Asp Ala
                405                 410                 415

Ile Gln Arg Asn Pro Asn Pro Gln Asn Ile Leu Thr Asn Ser Ile Glu
            420                 425                 430

Ala Ala Arg Glu Val Gly His Cys Gln Tyr Glu Tyr Gln Thr Ser Trp
        435                 440                 445

Gly Asn Thr Ile Gly Trp Leu Tyr Asp Ser Val Ala Glu Asp Leu Asn
```

```
    450                 455                 460

Thr Ser Ile Gly Ile His Ser Arg Gly Trp Thr Ser Ser Tyr Ile Ser
465                 470                 475                 480

Pro Asp Thr Pro Ala Phe Leu Gly Ser Met Pro Ala Gly Val Pro Glu
                485                 490                 495

Ala Leu Leu Gln Gln Arg Arg Trp Ala Thr Gly Trp Ile Glu Ile Leu
            500                 505                 510

Phe Asn Lys Gln Ser Pro Leu Arg Gly Leu Phe Ser Lys Lys Ile Arg
        515                 520                 525

Phe Arg Gln Arg Leu Ala Tyr Leu Cys Ile Ile Thr Cys Leu Arg Ser
    530                 535                 540

Ile Pro Glu Leu Ile Tyr Cys Leu Leu Pro Ala Tyr Cys Leu Leu His
545                 550                 555                 560

Asn Ser Thr Leu Phe Pro Lys Gly Leu Tyr Leu Gly Ile Thr Val Thr
                565                 570                 575

Leu Val Gly Ile His Cys Leu Tyr Thr Leu Trp Glu Phe Met Ser Leu
            580                 585                 590

Gly Tyr Ser Val Gln Ser Trp Leu Val Ser Gln Ser Val Trp Arg Ile
        595                 600                 605

Val Ala Thr Ser Ser Trp Leu Phe Ser Ile Phe Asp Ile Thr Leu Lys
    610                 615                 620

Leu Leu Gly Ile Ser Glu Thr Val Phe Ile Ile Thr Lys Lys Thr Val
625                 630                 635                 640

Ala Gly Thr Lys Ser Ala Leu Gly Ser Gly Pro Ser Gln Gly Glu Asp
                645                 650                 655

Val Gly Pro Asn Ser Asp Leu Phe Lys Phe Glu Phe Asp Gly Ser Leu
            660                 665                 670

Cys Phe Leu Pro Gly Thr Phe Ile Val Leu Val Asn Ile Ala Ala Leu
        675                 680                 685

Ala Val Phe Ser Val Gly Leu Gln Arg Ser Ser Tyr Ser His Glu Gly
    690                 695                 700

Gly Gly Ser Gly Leu Ala Glu Ala Cys Gly Cys Val Leu Val Met Met
705                 710                 715                 720

Leu Phe Leu Pro Phe Leu Met Gly Leu Phe Lys Lys Gly Lys Tyr Gly
                725                 730                 735

Thr Pro Leu Ser Thr Leu Ser Ile Ala Gly Phe Leu Ala Val Leu Phe
            740                 745                 750

Val Val Phe Ser Val
        755
```

<210> SEQ ID NO 90
<211> LENGTH: 2190
<212> TYPE: DNA
<213> ORGANISM: Arabodopsis thaliana

<400> SEQUENCE: 90

```
atggtaaaca aagacgaccg gattagaccg gttcatgaag ccgacggtga accgcttttt     60

gagactagga gaagaaccgg tagagtgatt gcgtaccggt ttttctcagc ctcggttttc    120

gtgtgtatct gtttgatttg gttctacaga attggtgaga ttggtgataa ccgtaccgtt    180

ttagatcgat taatctggtt tgttatgttt attgtggaga tttggttcgg tttatattgg    240

gtagtcacac aatcttcccg gtggaatccg gtttggcgat ttcccttctc cgatagactc    300

tctcggagat acggaagcga ccttccgagg ctcgacgtct tcgtttgcac ggcggatccg    360
```

```
gtgattgagc cgccgttgtt ggtggtaaac acagtcttat ctgtgacggc tcttgactac    420
ccaccggaga aactcgccgt ttatctctca gatgacggtg gttctgagct gacgttctat    480
gctctcacgg aggcagctga gtttgctaaa acttgggttc ccttctgcaa gaagttcaac    540
gttgagccaa catctcccgc tgcttacttg tcttccaagg caaactgtct tgattctgcg    600
gctgaggagg tggctaagct gtatagagaa atggcggcga ggattgaaac ggcggcgaga    660
ctgggacgaa taccggagga ggcgcgggtg aagtacggtg acgggttttc acagtgggat    720
gctgacgcta ctcgaagaaa ccatggaacc attcttcaag ttttggtaga tggaagagaa    780
gggaatacaa tagcaatacc aacgttggtg tatttatcaa gagaaaagag acctcaacat    840
catcataact tcaaggctgg agcaatgaac gcattgctga gggtttcttc gaaaattact    900
tgtgggaaaa tcatactaaa cttggactgt gatatgtacg caaacaactc aaagtcaaca    960
cgcgacgcgc tctgcatcct cctcgatgag aaagagggaa aagagattgc tttcgtgcag   1020
tttccgcagt gttttgacaa tgttacaaga aatgatttgt atggaagcat gatgcgagta   1080
ggaattgatg tggaatttct tggattggat ggaaatggtg gtccgttata cattggaact   1140
ggatgctttc acagaagaga tgtgatctgt ggaagaaagt atggagagga agaagaagaa   1200
gaagaatctg agagaattca cgaaaattta gagcctgaga tgattaaggc tctcgcgagc   1260
tgcacttatg aggaaaacac tcaatgggga aaggagatgg gtgtgaaata tggttgcccg   1320
gtagaggatg taataactgg tttgacgatt cagtgtcgcg gatggaaatc agcctacctg   1380
aacccggaaa agcaagcatt tctcggggta gcgccgacca atttgcatca aatgctagtg   1440
cagcagagga gatggtcaga gggagacttt cagattatgc tttcgaagta tagtccggtt   1500
tggtatggaa aaggaaagat cagtttagga ctgatacttg gttactgttg ctattgtctt   1560
tgggctccat cttcactacc tgtgctcatt tactctgttt tgacttctct ctgtctcttc   1620
aaaggcattc ctctgtttcc aaaggtctcg agctcgtggt ttattccgtt tggatacgtc   1680
actgttgcag ctaccgcata tagcctagcc gagttcttgt ggtgcggagg gacgttccgt   1740
ggatggtgga acgagcaaag gatgtggctt tatagaagaa caagctcgtt tcttttcgga   1800
tttatggaca cgattaagaa gctacttgga gtttctgagt ctgcgtttgt gatcacagca   1860
aaagtagcag aagaagaagc agcagagaga tacaaggaag aggtaatgga gtttggagtg   1920
gagtctccca tgtttctcgt cctcggaaca ctcggtatgc tcaatctctt ctgcttcgcc   1980
gcagcggttg cgagacttgt ttccggagac ggtggagatt tgaaaacaat ggggatgcaa   2040
tttgtgataa caggagtact agttgtcata aactggcctc tgtataaagg tatgttgttg   2100
aggcaagaca aaggaaagat gccaatgagc gttacagtta aatcagttgt tttagcttta   2160
tctgcctgta cctgtttagc gtttttgtaa                                    2190
```

<210> SEQ ID NO 91
<211> LENGTH: 729
<212> TYPE: PRT
<213> ORGANISM: Arabodopsis thaliana

<400> SEQUENCE: 91

```
Met Val Asn Lys Asp Asp Arg Ile Arg Pro Val His Glu Ala Asp Gly
1               5                   10                  15

Glu Pro Leu Phe Glu Thr Arg Arg Arg Thr Gly Arg Val Ile Ala Tyr
            20                  25                  30

Arg Phe Phe Ser Ala Ser Val Phe Val Cys Ile Cys Leu Ile Trp Phe
        35                  40                  45
```

-continued

```
Tyr Arg Ile Gly Glu Ile Gly Asp Asn Arg Thr Val Leu Asp Arg Leu
    50                  55                  60

Ile Trp Phe Val Met Phe Ile Val Glu Ile Trp Phe Gly Leu Tyr Trp
65                  70                  75                  80

Val Val Thr Gln Ser Ser Arg Trp Asn Pro Val Trp Arg Phe Pro Phe
                85                  90                  95

Ser Asp Arg Leu Ser Arg Arg Tyr Gly Ser Asp Leu Pro Arg Leu Asp
            100                 105                 110

Val Phe Val Cys Thr Ala Asp Pro Val Ile Glu Pro Pro Leu Leu Val
        115                 120                 125

Val Asn Thr Val Leu Ser Val Thr Ala Leu Asp Tyr Pro Pro Glu Lys
    130                 135                 140

Leu Ala Val Tyr Leu Ser Asp Asp Gly Gly Ser Glu Leu Thr Phe Tyr
145                 150                 155                 160

Ala Leu Thr Glu Ala Ala Glu Phe Ala Lys Thr Trp Val Pro Phe Cys
                165                 170                 175

Lys Lys Phe Asn Val Glu Pro Thr Ser Pro Ala Ala Tyr Leu Ser Ser
            180                 185                 190

Lys Ala Asn Cys Leu Asp Ser Ala Ala Glu Glu Val Ala Lys Leu Tyr
        195                 200                 205

Arg Glu Met Ala Ala Arg Ile Glu Thr Ala Ala Arg Leu Gly Arg Ile
    210                 215                 220

Pro Glu Glu Ala Arg Val Lys Tyr Gly Asp Gly Phe Ser Gln Trp Asp
225                 230                 235                 240

Ala Asp Ala Thr Arg Arg Asn His Gly Thr Ile Leu Gln Val Leu Val
                245                 250                 255

Asp Gly Arg Glu Gly Asn Thr Ile Ala Ile Pro Thr Leu Val Tyr Leu
            260                 265                 270

Ser Arg Glu Lys Arg Pro Gln His His His Asn Phe Lys Ala Gly Ala
        275                 280                 285

Met Asn Ala Leu Leu Arg Val Ser Ser Lys Ile Thr Cys Gly Lys Ile
    290                 295                 300

Ile Leu Asn Leu Asp Cys Asp Met Tyr Ala Asn Asn Ser Lys Ser Thr
305                 310                 315                 320

Arg Asp Ala Leu Cys Ile Leu Leu Asp Glu Lys Glu Gly Lys Glu Ile
                325                 330                 335

Ala Phe Val Gln Phe Pro Gln Cys Phe Asp Asn Val Thr Arg Asn Asp
            340                 345                 350

Leu Tyr Gly Ser Met Met Arg Val Gly Ile Asp Val Glu Phe Leu Gly
        355                 360                 365

Leu Asp Gly Asn Gly Gly Pro Leu Tyr Ile Gly Thr Gly Cys Phe His
    370                 375                 380

Arg Arg Asp Val Ile Cys Gly Arg Lys Tyr Gly Glu Glu Glu Glu Glu
385                 390                 395                 400

Glu Glu Ser Glu Arg Ile His Glu Asn Leu Glu Pro Glu Met Ile Lys
                405                 410                 415

Ala Leu Ala Ser Cys Thr Tyr Glu Glu Asn Thr Gln Trp Gly Lys Glu
            420                 425                 430

Met Gly Val Lys Tyr Gly Cys Pro Val Glu Asp Val Ile Thr Gly Leu
        435                 440                 445

Thr Ile Gln Cys Arg Gly Trp Lys Ser Ala Tyr Leu Asn Pro Glu Lys
    450                 455                 460

Gln Ala Phe Leu Gly Val Ala Pro Thr Asn Leu His Gln Met Leu Val
```

```
465                 470                 475                 480

Gln Gln Arg Arg Trp Ser Glu Gly Asp Phe Gln Ile Met Leu Ser Lys
                485                 490                 495

Tyr Ser Pro Val Trp Tyr Gly Lys Gly Lys Ile Ser Leu Gly Leu Ile
            500                 505                 510

Leu Gly Tyr Cys Cys Tyr Cys Leu Trp Ala Pro Ser Ser Leu Pro Val
        515                 520                 525

Leu Ile Tyr Ser Val Leu Thr Ser Leu Cys Leu Phe Lys Gly Ile Pro
    530                 535                 540

Leu Phe Pro Lys Val Ser Ser Ser Trp Phe Ile Pro Phe Gly Tyr Val
545                 550                 555                 560

Thr Val Ala Ala Thr Ala Tyr Ser Leu Ala Glu Phe Leu Trp Cys Gly
                565                 570                 575

Gly Thr Phe Arg Gly Trp Trp Asn Glu Gln Arg Met Trp Leu Tyr Arg
            580                 585                 590

Arg Thr Ser Ser Phe Leu Phe Gly Phe Met Asp Thr Ile Lys Lys Leu
        595                 600                 605

Leu Gly Val Ser Glu Ser Ala Phe Val Ile Thr Ala Lys Val Ala Glu
    610                 615                 620

Glu Glu Ala Ala Glu Arg Tyr Lys Glu Glu Val Met Glu Phe Gly Val
625                 630                 635                 640

Glu Ser Pro Met Phe Leu Val Leu Gly Thr Leu Gly Met Leu Asn Leu
                645                 650                 655

Phe Cys Phe Ala Ala Ala Val Ala Arg Leu Val Ser Gly Asp Gly Gly
            660                 665                 670

Asp Leu Lys Thr Met Gly Met Gln Phe Val Ile Thr Gly Val Leu Val
        675                 680                 685

Val Ile Asn Trp Pro Leu Tyr Lys Gly Met Leu Leu Arg Gln Asp Lys
    690                 695                 700

Gly Lys Met Pro Met Ser Val Thr Val Lys Ser Val Val Leu Ala Leu
705                 710                 715                 720

Ser Ala Cys Thr Cys Leu Ala Phe Leu
                725
```

<210> SEQ ID NO 92
<211> LENGTH: 2283
<212> TYPE: DNA
<213> ORGANISM: Arabodopsis thaliana

<400> SEQUENCE: 92

```
atggagactc atagaaagaa ctcggtcgtc ggcaacatcc tccacacgtg tcatccttgc      60

cggcgcacca ttccatatag aatctacgcc atatttcaca cgtgtggcat catagctctc     120

atgtatcacc atgtacactc acttgtcaca gcaaacaaca ctcttataac atgtcttctt     180

ctcctctccg atattgttct cgccttcatg tgggcaacca caacttccct ccgcttaaac     240

ccggttcatc ggaccgagtg cccggagaaa tatgcagcta aaccggagga ctttccaaag     300

ctggacgtgt ttatatgcac ggctgatccg tacaaggagc ctccaatgat ggttgttaac     360

accgctttat cggtgatggc ttacgagtat ccgtcagata agatctcggt gtatgtatcg     420

gacgatggag gatcgtcgtt gactttcttt gctcttattg aagctgctaa gttctctaag     480

cagtggttgc ccttttgcaa gaagaataat gttcaagatc ggtctcctga agtttatttc     540

tcttcagagt cacattctcg aagtgatgaa gctgaaaacc ttaagatgat gtacgaagac     600

atgaagagta gagtagaaca tgtggtggag agtggaaaag ttgaaactgc gtttatcaca     660
```

```
tgcgaccaat ttcgtggggt attcgatttg tggaccgaca aattcagtcg tcatgaccat    720
cccacaatta ttcaggtgtt gcaaaatagc gagacagata tggacaatac cagaaaatat    780
ataatgccaa acctaatcta tgtttcaaga gagaagagta aagtttcacc acatcatttc    840
aaagctggtg ctcttaatac tttgctacga gtatcagggg tgatgacaaa ttcaccgatc    900
attctaacac tagactgtga tatgtattcg aacgacccgg caacactggt tcgtgctttg    960
tgctatttaa cagatcctga aatcaaatcc ggtttaggat atgtgcagtt tcctcagaaa   1020
tttctaggaa taagcaaaaa tgatatatat gcttgtgaaa acaaacgcct cttcattatt   1080
aatatggttg ggtttgatgg tctaatgggt ccaactcatg tgggaactgg ttgtttcttt   1140
aatcgacgag ctttctatgg acctccatat atgttgattt taccggagat aaatgaacta   1200
aagccttatc ggattgcgga taagtctatc aaagcccaag atgttttgtc attagcacac   1260
aatgtagcag gatgtatcta tgagtacaat accaattggg gatccaagat tggattcaga   1320
tatgggtcat tagtagaaga ctactacaca gggtttatgc tccattgtga aggatggaga   1380
tcagtatttt gcaacccaaa aaaagctgca ttttatggag attccccaaa gtgcctagtt   1440
gatcttgtgg gtcaacaaat ccgttgggca gttgggcttt tcgaaatgtc cttttcaaag   1500
tatagcccaa ttacctatgg aatcaagtca ctggaccttt taatgggttt aggttattgc   1560
aactctccgt ttaagccatt ttggtcaatt cctctgaccg tctatggact tttaccacag   1620
cttgcactca tttctggagt tagtgtcttc cccaaggcat ctgatccgtg gttttggctt   1680
tacatcattt tattctttgg ggcttatgcc caagatctat cagacttttt attggaagga   1740
ggaacttatc ggaaatggtg gaacgatcaa agaatgttga tgataaaagg actctcttca   1800
ttcttctttg gttttataga gttcattctc aaaaccctaa acctctccac acctaagttc   1860
aacgtcacca gtaaagccaa tgatgatgac gaacagagga agcggtacga gcaagaaatc   1920
tttgatttcg gaacctcttc gtccatgttc ttgcccttga ccacggttgc catagtgaat   1980
ctgcttgctt ttgtctgggg gctttatggt attctcttct gcggaggaga actctacctt   2040
gagctgatgc tggtgagctt cgcggtggtg aattgcttac cgatctacgg ggctatggtg   2100
ttgaggaaag atgatggaaa attatcaaaa agaacttgtt tcttagctgg gaacctccac   2160
gttggttctt attgtgtcaa gttacttcgt cctcaagtaa cttcacccct taggttaatt   2220
cacaacaata atacgtctgg ctggttcaag cggaagaaac acaatatgaa tgaatctgtg   2280
taa                                                                 2283
```

<210> SEQ ID NO 93
<211> LENGTH: 2088
<212> TYPE: DNA
<213> ORGANISM: Spinacia oleracea

<400> SEQUENCE: 93

```
atggcaactt ctcacattcg caatgtccaa ttaaccagag ccattgttaa ccgtctccac     60
atcttcctcc attccgtagc catcttctcg ctcttctact accgtttcac ttccttcttc    120
aactccgaca tctccatact tgcttactcc ttactcacca ccgccgaact cttcttaacc    180
tttctatggg cttttactca ggctttccgg tggcgtcccg taatgaggga agtctccggg    240
tacgaatcca tcaaacccga acaactaccg ggtttggatg tcttcattgt cactgctgac    300
ccgacaaagg agccagttct ggaggtgatg aactccgtga tatcatccat ggcgttggat    360
tatccggttg atagactggc ggtttacttg tcggatgacg gtggttctcc gttgtcgaag    420
```

```
gaggcgatta agaaggctta tgagtttgct aagctttgga ttccttttg taataagtat    480

aatgttaaga caaggtgtcc tcaggctttc ttctcgcctc ttgctgatgg ggaaaggctt    540

gattggaatt ctgagtttat ggctgatcaa ttggaactcc agaccaaata tgaagctttt    600

agaaactatg tggagaaaga aagtggagat aacaccaaat gtactgcagt tcatgatcga    660

cctccttgcg ttgagattat acatgacaac aaacagaacg gagaaagtga tgtgaagatg    720

ccccttctgg tttatgtagc cagggaaaag agacctggtc gtcctcatcg tttcaaagct    780

ggagccctta atgctcttct tcgagtatcc agtttaatga gcaatgcacc ttacttattg    840

gtgttggatt gtgatatgta ctgccatgat ccaacttctg ctcgtcaatc tatgtgcttc    900

catcttgaca caaacatggc ttcctctctt gcatatgtgc aataccctca aattttctat    960

aatgttagca aaaatgacat ctatgatggc caagccagat cagctcatat gacgaaatgg   1020

aaaggcatgg atggactcag aggcccggtc ttgaatggaa ctgggtatta tttgaagcga   1080

aaagcattat ttggaaagcc taataacgaa gatgaatacc tcaacagtca accagaaaag   1140

gcctttggct cctccacaaa attaattgct gcactaagag agaactccaa gcaaaatctt   1200

gccataaagg aattgacaga agatgagttg taccaagagg ctagaaattt ggctacttgc   1260

acatatgaag caaacacact atggggcagt gaggtaggat attcgtatga gtgcttgttg   1320

gagagtacat tcactggata tatgttacat tgcagaggat ggaaatctgt gtatctttac   1380

ccaaaaagac catgcttctt gggatgcaca acgattgata tgaaggatgc tacggttcaa   1440

ctaataaaat ggacctcctc attacttgga attgccctgt cgaagtctag ccctctaact   1500

ttggccatgt ccagtatgtc aatcctgcaa agcatgtgtt acgcgtacat cacatttaca   1560

ggccttttttg cagctccatt ggttatatat ggtgttgtcc ttccaataag cctattgaag   1620

ggctttccta ttttccctaa ggtatcggat ccatggattt tgccatttgt gttgatattt   1680

gtatcctccc atcttcaaca tctatatgag gtcctggaaa gtgacaaatc agcaacacaa   1740

tggtggaatg aggtgagaat ttggatgatg aaatcagtga cagcctgttt gtttgggttg   1800

acggaagcga taatgaagaa gattggagta caaactgcaa cattcagatt aacaaataag   1860

gtagttgaga aggaaaagat ggataaatac gagaaggaga ggtttgattt ctcaggagca   1920

gctatgctta tggttcctct taatattttg gtggtactaa atatggtgtc attcattggt   1980

ggactcatga gggtcataat caacaacagt tatgatcaaa tgtttgcaca acttttcctc   2040

tcctttttttg tcctacttct tagctaccct gttgttaagg gatggtta               2088
```

<210> SEQ ID NO 94
<211> LENGTH: 704
<212> TYPE: PRT
<213> ORGANISM: Beta vulgaris

<400> SEQUENCE: 94

```
Met Ser Ser Leu His Ile Cys Lys Val Gln Thr Thr Arg Ala Ile Leu
1               5                   10                  15

Ser Arg Phe His Ile Leu Phe His Ser Leu Ala Ile Leu Ala Leu Phe
            20                  25                  30

Tyr Tyr Arg Phe Thr Ser Phe Ser Thr Thr Lys Ser Gly Ile Leu Pro
        35                  40                  45

Trp Thr Leu Leu Thr Thr Ala Glu Val Val Leu Gly Phe Val Trp Ala
    50                  55                  60

Leu Thr Gln Ala Phe Arg Trp Arg Pro Val Leu Arg Asp Val Ala Gly
65                  70                  75                  80
```

```
Trp Asp Ser Ile Lys Glu Glu Gln Leu Pro Gly Val Asp Val Phe Ile
                85                  90                  95

Cys Thr Ala Asp Pro Ile Lys Glu Pro Val Leu Glu Val Met Asn Thr
            100                 105                 110

Val Leu Ser Ala Met Ala Leu Asp Tyr Pro Ala Glu Lys Leu Gly Val
        115                 120                 125

Tyr Leu Ser Asp Asp Gly Gly Ser Pro Leu Thr Arg Glu Ala Ile Lys
    130                 135                 140

Glu Ala Ser Lys Phe Ala Lys Val Trp Leu Pro Phe Cys Ser Lys Tyr
145                 150                 155                 160

Gly Ile Lys Thr Arg Cys Pro Gln Ala Phe Phe Ser Ser Phe Cys Asp
                165                 170                 175

Gly Glu Arg Leu Asp Trp Asn Gln Asp Phe Lys Ala Asp Glu Leu Val
            180                 185                 190

Leu Lys Ser Lys Tyr Glu Ala Phe Lys Asn Tyr Val Glu Lys Ala Ser
        195                 200                 205

Glu Asp Glu Ser Lys Cys Thr Met Ala His Asp Arg Ser Pro Cys Val
    210                 215                 220

Glu Ile Ile His Asp Asn Lys Gln Asn Gly Glu Gly Glu Val Lys Met
225                 230                 235                 240

Pro Leu Leu Val Tyr Val Ser Arg Glu Lys Arg Pro Asn Arg Pro His
                245                 250                 255

Arg Phe Lys Ala Gly Ala Leu Asn Ala Leu Leu Arg Val Ser Gly Val
            260                 265                 270

Leu Ser Asn Gly Pro Tyr Leu Leu Val Leu Asp Cys Asp Met Tyr Cys
        275                 280                 285

Asn Asp Pro Thr Ser Ala Arg Gln Ser Met Cys Phe His Leu Asp Pro
    290                 295                 300

Lys Leu Ala Pro Ser Leu Ala Phe Val Gln Tyr Pro Gln Ile Phe Tyr
305                 310                 315                 320

Asn Thr Ser Lys Asn Asp Ile Tyr Asp Gly Gln Ala Arg Ser Ala Tyr
                325                 330                 335

Lys Thr Lys Trp Gln Gly Met Asp Gly Ile Arg Gly Pro Val Leu Thr
            340                 345                 350

Gly Thr Gly Tyr Tyr Leu Lys Arg Lys Ala Leu Tyr Gly Gln Pro His
        355                 360                 365

Asn Glu Asp Glu Phe Leu Ile Asn Gln Pro Glu Lys Ala Phe Gly Ser
    370                 375                 380

Ser Thr Lys Phe Ile Ala Ser Val Ser Ser Asn Ser Lys Gln Asn Met
385                 390                 395                 400

Ala Leu Lys Glu Met Thr Arg Asp Asp Leu Leu Glu Glu Ala Lys Asn
                405                 410                 415

Leu Ala Thr Cys Ala Tyr Glu Ser Asn Thr Glu Trp Gly Asn Lys Ile
            420                 425                 430

Gly Tyr Ser Tyr Glu Cys Leu Leu Glu Ser Thr Phe Thr Gly Tyr Leu
        435                 440                 445

Leu His Cys Lys Gly Trp Ile Ser Val Tyr Leu Tyr Pro Lys Arg Pro
    450                 455                 460

Cys Phe Leu Gly Cys Thr Thr Ile Asp Met Lys Asp Ala Met Val Gln
465                 470                 475                 480

Leu Met Lys Trp Thr Ser Gly Leu Leu Gly Val Gly Ile Ser Lys Phe
                485                 490                 495

Ser Pro Leu Thr Tyr Ala Phe Ser Arg Met Ser Ile Leu Gln Ser Met
```

```
            500                 505                 510

Cys Tyr Gly Tyr Phe Thr Phe Ser Ala Leu Phe Gly Val Ser Phe Leu
        515                 520                 525

Ile Tyr Gly Ile Val Leu Pro Val Cys Leu Leu Lys Gly Val Pro Val
    530                 535                 540

Phe Pro Lys Val Ser Asp Pro Trp Ile Gly Val Phe Val Val Val Phe
545                 550                 555                 560

Ala Ser Ser Leu Leu Gln His Leu Tyr Glu Val Leu Ser Ser Asp Asp
                565                 570                 575

Ser Ile Lys Thr Trp Trp Asn Glu Ile Arg Ile Trp Ile Ile Lys Ser
            580                 585                 590

Val Thr Ala Ser Leu Phe Gly Thr Met Asp Ala Ile Met Lys Lys Ile
        595                 600                 605

Gly Ile Gln Lys Ala Ser Phe Arg Leu Thr Asn Lys Val Val Asp Lys
    610                 615                 620

Glu Lys Leu Glu Lys Tyr Glu Lys Gly Lys Phe Asp Phe Gln Gly Ala
625                 630                 635                 640

Ala Val Phe Met Val Pro Leu Ile Ile Leu Val Val Leu Asn Met Val
                645                 650                 655

Ser Phe Val Gly Gly Leu Arg Arg Ala Ile Ile Asn Lys Asn Cys Asp
            660                 665                 670

Glu Met Phe Gly Gln Leu Phe Leu Ser Phe Phe Leu Leu Val Leu Ser
        675                 680                 685

Tyr Pro Val Leu Glu Gly Ile Val Thr Lys Val Arg Lys Gly Arg Asp
    690                 695                 700
```

<210> SEQ ID NO 95
<211> LENGTH: 2656
<212> TYPE: DNA
<213> ORGANISM: Beta vulgaris

<400> SEQUENCE: 95

```
catcacagcc acatgggaaa caaaaagtct taacctcggc catctcgtgt gcctcgtgca     60

cattcaacat tgattttaat tgtgtgcttt ctccaaaatg taccatacta tatcatcttg    120

tcagaattcc aaactccaac tataaccacc attgaagtca tctacacaca aacacacaca    180

ctctttctcc ctaaaaatgt cttctctcca catttgcaaa gtccaaacaa caagagcaat    240

acttagccgt ttccacatac tcttccactc cttagccatc cttgctttat tctactaccg    300

ttttacatcg ttctctacca ccaaatcagg catacttcca tggaccttac taaccacagc    360

agaggtggtt ctaggctttg tatgggcgtt aacacaggcc tttcgatggc ggcctgtgtt    420

gcgagatgta gctggatggg attccatcaa ggaggaacaa ctgccagggg tggacgtgtt    480

catatgcaca gctgatccaa taaaggagcc ggtgttagag gtgatgaaca cggtgctttc    540

ggcgatggca ttggattacc cggcagagaa gttgggtgtt tatctttcgg atgatggagg    600

ttctcccttg actagggagg ctattaagga ggcttctaag tttgctaagg tttggcttcc    660

tttttgtagt aagtatggta tcaagactag gtgtcctcag gctttcttct cttctttttg    720

tgatggggaa agacttgatt ggaatcagga ctttaaggct gatgaattgg tgctcaagtc    780

aaaatatgaa gcttttaaga attatgtgga gaaagcaagt gaagatgaaa gcaaatgcac    840

catggcacat gatcgttccc cttgcgttga gattatacat gacaacaagc aaaatggaga    900

aggcgaagtg aaaatgcccc ttttggtcta cgtatccagg gaaaagagac caaatcgtcc    960

tcatcgtttc aaagccggag ctcttaatgc tcttctcaga gtatcaggtg tattgagcaa   1020
```

```
cgggccttac ttattggtgt tggactgtga tatgtactgc aatgatccaa cttctgctcg   1080

tcaatctatg tgctttcatc ttgacccaaa attggctcct tcacttgcat ttgtgcaata   1140

cccacaaatt ttctacaaca ccagtaaaaa tgatatctat gatggccaag ctagatccgc   1200

gtacaagaca aaatggcaag gaatggatgg tattagagga ccagtcttga caggaacagg   1260

gtattacttg aagaggaaag cattgtatgg acaacctcat aacgaagatg aatttctcat   1320

taatcaacca gagaaggcct tcggctcctc cacaaaattc attgcgtcag ttagttcaaa   1380

ctccaagcaa aatatggcct tgaaggaaat gacaagagac gacttgttag aagaggctaa   1440

aaatttggct acttgtgcat atgaatcaaa cactgaatgg ggtaacaaga ttggatattc   1500

gtatgagtgt ttgttggaga gtacatttac cggatatctc ttacattgca aaggatggat   1560

ttccgtgtat ctttacccaa aaagaccctg cttcttagga tgcacgacga ttgacatgaa   1620

agatgccatg gttcaactaa tgaaatggac ctctggatta ctaggagttg gcatatcaaa   1680

gtttagccct ctaacttatg ccttttcgag gatgtctata ttacaaagca tgtgctacgg   1740

ttacttcaca ttttcagccc ttttcggagt ttcgttctta atatatggca tcgtccttcc   1800

agtatgccta ttgaagggtg ttcctgtttt tcctaaggta tcggatccat ggattggagt   1860

tttcgtggta gtatttgcat cctccctcct tcaacattta tacgaggttc tctcaagtga   1920

cgattccatt aaaacatggt ggaacgagat cagaatttgg atcatcaaat cggtaacagc   1980

ttccttattt ggaacaatgg atgcaataat gaaaaagatc ggcatacaaa aggctagttt   2040

ccgattaact aacaaggttg tggacaagga aaagctcgaa aaatatgaga agggcaagtt   2100

tgatttccaa ggagcagctg tgttcatggt tcctcttatc attttagtgg tactaaatat   2160

ggtgtcattt gttggcggat taagaagggc aataatcaac aagaattgtg atgaaatgtt   2220

tgggcaactt ttcctctcat tctttctctt agttcttagc taccccgttt tagaagggat   2280

agtaacaaaa gtaagaaaag gacgtgattg agatgaattt gcattgtttg gtaaaagatc   2340

caaacttaga gaaagagatt gcgtaggaga tcaaaggaaa caatgtgaga gatttacagg   2400

cttcatgagg cttaagacct cattaatttt tgtgacaatt tacaaattct gtctctatat   2460

tttggtcaag acgtatcatt tgaaaatttc catggttagg tagttagatt tcaatgttcc   2520

acgtttgtaa ataagaagat aaaataagga aatttgtgat tttagcttta catttctatg   2580

agatagtcct ttgttgtgat gaaagttgtg ttcttagtga aaataataaa acgtgacatc   2640

aaaattttga gtatat                                                   2656
```

```
<210> SEQ ID NO 96
<211> LENGTH: 706
<212> TYPE: PRT
<213> ORGANISM: Chenopodium quinoa

<400> SEQUENCE: 96

Met Ala Ala Thr His Ile Cys Lys Val Gln Thr Lys Arg Val Ile Ile
1               5                   10                  15

Asn Arg Ile His Ile Leu Phe His Ser Leu Ala Ile Leu Ala Leu Phe
            20                  25                  30

Tyr Tyr Arg Phe Ser Ser Phe Ser Asn Pro His Ile Ser Leu Phe Pro
        35                  40                  45

Trp Val Leu Leu Thr Ile Ala Asp Leu Val Phe Thr Phe Ile Trp Ala
    50                  55                  60

Met Thr Gln Ala Phe Arg Trp Arg Pro Val Leu His Asp Val Ser Gly
65                  70                  75                  80
```

-continued

```
Tyr Glu Ser Ile Asn Pro Arg Asp Leu Pro Lys Ile Asp Ile Phe Ile
                85                  90                  95

Cys Thr Ala Asp Pro Thr Lys Glu Pro Val Leu Glu Val Met Asn Ser
            100                 105                 110

Val Ile Ser Ser Met Ala Leu Asp Tyr Pro Pro Glu Lys Met Ala Val
        115                 120                 125

Tyr Leu Ser Asp Asp Gly Gly Ser Pro Leu Thr Arg Glu Ala Ile Lys
    130                 135                 140

Lys Ala Val Glu Phe Ala Lys Val Trp Ile Pro Phe Cys Asn Met Tyr
145                 150                 155                 160

Gly Ile Lys Thr Arg Cys Pro Asp Ala Phe Phe Ser Ala Leu Gly Asn
                165                 170                 175

Asp Glu Arg Leu His Arg Asp Gln Asp Phe Asn Ala His Glu Ser Leu
            180                 185                 190

Leu Lys Ser Lys Tyr Glu Ala Phe Lys Lys Tyr Val Glu Lys Glu Ser
        195                 200                 205

Gly Asp Ile Asn Lys Cys Thr Val Val His Asp Arg Glu Pro Cys Ile
    210                 215                 220

Glu Ile Ile His Asp Ser Lys Gln Asp Gly Glu Ala Glu Val Lys Met
225                 230                 235                 240

Pro Leu Val Val Tyr Val Ala Arg Glu Lys Arg Pro Gly His Pro His
                245                 250                 255

Arg Phe Lys Ala Gly Ala Leu Asn Ala Leu Leu Arg Val Ser Gly Leu
            260                 265                 270

Leu Ser Asn Ala Pro Tyr Leu Leu Val Leu Asp Cys Asp Met Tyr Cys
        275                 280                 285

His Asp Pro Thr Ser Ala Arg Gln Ser Met Cys Phe His Leu Asp Pro
    290                 295                 300

Asn Met Ser Pro Ser Leu Ala Phe Val Gln Tyr Pro Gln Ile Phe Tyr
305                 310                 315                 320

Asn Thr Ser Lys Asn Asp Ile Tyr Asp Gly Gln Ala Arg Ser Ala His
                325                 330                 335

Thr Thr Lys Trp Gln Gly Met Asp Gly Leu Arg Gly Pro Val Leu Asn
            340                 345                 350

Gly Thr Gly Tyr Tyr Leu Lys Lys Lys Ala Ile Tyr Gly Arg Pro His
        355                 360                 365

Asn Glu Asp Glu Tyr Leu Ile Asn Glu Pro Glu Lys Ala Phe Gly Ser
    370                 375                 380

Ser Thr Lys Phe Ile Ala Ser Leu Lys Glu Asn Ser Asn Gln Asp Leu
385                 390                 395                 400

Val Leu Lys Glu Phe Thr Asn Asp Leu Leu Gln Glu Ala Arg Asn Leu
                405                 410                 415

Ala Thr Cys Thr Tyr Glu Ala Asn Ser Leu Trp Gly Val Glu Val Gly
            420                 425                 430

Phe Ser Tyr Asp Cys Leu Leu Glu Ser Ser Tyr Thr Gly Tyr Leu Leu
        435                 440                 445

His Cys Lys Gly Trp Arg Ser Val Tyr Leu Tyr Pro Lys Arg Pro Cys
    450                 455                 460

Phe Leu Gly Cys Thr Thr Ile Asp Met Lys Asp Ala Ile Val Gln Leu
465                 470                 475                 480

Ile Lys Trp Thr Ser Gly Leu Leu Gly Val Ala Met Ser Lys Phe Ser
                485                 490                 495
```

-continued

```
Pro Leu Thr Tyr Ala Met Ser Arg Met Ser Ile Leu Gln Ser Met Cys
            500                 505                 510

Tyr Ala Tyr Ile Thr Cys Ser Gly Leu Leu Ala Val Pro Leu Phe Ile
        515                 520                 525

Tyr Gly Val Val Leu Pro Phe Cys Leu Leu Lys Gly Val Pro Val Phe
    530                 535                 540

Pro Lys Val Ser Asp Pro Trp Met Leu Gly Phe Val Phe Val Phe Val
545                 550                 555                 560

Ser Ser His Val Gln His Leu Phe Glu Val Leu Ala Ser Asp His Ser
                565                 570                 575

Val Gln Gln Trp Trp Asn Glu Val Arg Ile Trp Ile Met Lys Ala Ile
            580                 585                 590

Thr Ala Cys Leu Phe Gly Ser Thr Glu Ala Ile Met Lys Lys Ile Gly
        595                 600                 605

Ile Gln Lys Thr Thr Phe Arg Leu Thr Asn Lys Val Val Glu Lys Glu
    610                 615                 620

Lys Leu Asp Lys Tyr Glu Lys Gly Lys Phe Asp Phe Ser Gly Ala Ala
625                 630                 635                 640

Met Leu Met Val Pro Leu Ile Ile Leu Thr Ile Leu Asn Leu Val Ser
                645                 650                 655

Phe Val Gly Gly Leu Val Arg Val Ile Asn His Asn Asn Tyr Asp Asp
            660                 665                 670

Met Phe Gly Gln Leu Phe Leu Ser Phe Tyr Leu Leu Leu Leu Ser Tyr
        675                 680                 685

Pro Thr Phe Glu Gly Ile Val Thr Lys Val Thr Asp Lys Leu Arg Lys
    690                 695                 700

Lys Glu
705


<210> SEQ ID NO 97
<211> LENGTH: 2524
<212> TYPE: DNA
<213> ORGANISM: Chenopodium quinoa

<400> SEQUENCE: 97

aaaagtgaaa ctggtgactt agtcttgtgt cacccgggtt cctcgagcac atattcttca      60

agattttggt tttttgtacg gagtatttat atacacaaaa attaggaacc aaataggaag     120

actcatatca tttcaaaatg gcggcaacac acatttgcaa agtccaaacc aaaagagtca     180

ttatcaaccg tattcatatc ctctttcact ctttagccat tcttgctctc ttctactacc     240

gtttctcgtc tttctccaac cctcatatct cccttttttcc atgggtatta ttgactatcg     300

ccgacctcgt tttcaccttc atttgggcca tgactcaggc cttccgttgg cgccccgtct     360

tgcacgatgt gtctggctat gagtccatca atccacgcga tcttccaaag atcgatattt     420

ttatatgcac cgctgatccc accaaggagc ctgtgttgga agtgatgaac tcggtgatat     480

catccatggc gctcgattat ccgcctgaaa aaatggcggt gtatttgtcg gatgatggtg     540

gttctccttt gactagagag gctattaaga aggctgttga atttgctaag gtttggattc     600

ctttttgtaa tatgtatggt attaagacta ggtgtcctga tgctttcttc tccgctttgg     660

gtaatgatga aagacttcat cgtgatcaag actttaacgc tcatgaatca ctcctcaagt     720

cgaaatacga agcttttaag aaatatgtgg agaaagaaag cggtgatatt aataaatgca     780

ccgttgtgca tgatcgtgaa ccttgcattg agattataca tgacagtaaa caggatggag     840

aagctgaagt gaaaatgccc cttgtagttt atgtagccag ggaaaagaga ccaggtcatc     900
```

```
ctcatcgttt caaagctgga gcccttaacg ctcttctccg agtatcagga ctattgagca    960

atgcgcctta cttattggtg ttagactgtg atatgtactg tcatgatcca acctctgctc   1020

gtcaatctat gtgcttccat cttgacccga acatgtctcc ctctcttgcc tttgttcaat   1080

accctcaaat tttctacaac actagtaaaa atgatatcta tgatggtcaa gccagatcag   1140

ctcatacgac gaaatggcaa ggcatggatg gactcagagg accggtcttg aatggaactg   1200

ggtattatct gaagaagaag gcgatatatg gaaggcccca taatgaagat gaatacctca   1260

tcaatgaacc agaaaaggct tttggttctt ccacaaaatt cattgcttca cttaaagaaa   1320

actcgaacca ggatcttgtc ttgaaggaat tcacaaacga tttgttacaa gaggctagaa   1380

atttggctac ttgcacttat gaagcaaact cgctatgggg tgttgaggta gggttttcgt   1440

atgattgcct gttggagagt tcatacactg gatatctctt acattgtaaa ggatggagat   1500

ctgtgtatct ttatcccaaa agaccgtgct tcttgggatg cacgacaatt gacatgaagg   1560

atgctattgt tcaattaata aaatggactt ccggattact tggagttgcc atgtcaaagt   1620

ttagccctct tacttatgcc atgtccagaa tgtctatatt gcaaagcatg tgttacgcgt   1680

acatcacgtg ttcaggtctt ctagcagttc cactctttat atatggtgtt gttctaccat   1740

tctgcctact taagggcgtt cctgtttttc ctaaggtatc ggatccatgg atgttgggtt   1800

tcgtgtttgt atttgtatcc tcccatgttc aacatctatt cgaagtgcta gcaagtgatc   1860

attcagtgca acagtggtgg aatgaggtga gaatctggat catgaaagcg ataacagcct   1920

gcttgtttgg atcaactgaa gcaataatga agaagattgg gatacagaaa acaacattca   1980

gattaacaaa taaggttgtg gagaaagaga agttggataa atacgagaag ggaaagttcg   2040

atttctcagg agcagcaatg ctaatggttc ctctcatcat tttgactata ctaaatttgg   2100

tgtcgttcgt tgggggactt gtaagggtga tcaaccacaa caactatgat gatatgttcg   2160

ggcaactttt cctgtcattt tatctcctac ttcttagcta ccctactttc gaagggattg   2220

ttacaaaagt tacagacaaa cttagaaaga aagaataagg agtgattgag taactgccta   2280

gtacagtttt cacttcactt ctctagatta gtccttgttt ttgtttatgt ttattaagat   2340

cagcaacact tgtagacggt tgcaataatg agttcaatac cgtttgttct gtccctcttg   2400

caagaacaag tatataaata cttttcatta gccggttgca ttgttggatt catatagatg   2460

aatatttcaa atatttcatc tttttgaact tacacactaa tgatttatat ctggaatttt   2520

gaaa                                                                2524
```

<210> SEQ ID NO 98
<211> LENGTH: 715
<212> TYPE: PRT
<213> ORGANISM: Medicago sativa

<400> SEQUENCE: 98

```
Met Ala Thr Phe Thr Phe His Lys Glu Thr Val Gln Pro Leu Leu Pro
1               5                   10                  15

Leu Arg Arg Ala Tyr Ile Ile Phe His Phe Thr Cys Val Leu Phe Leu
            20                  25                  30

Phe Tyr Tyr Arg Ile Ser Asn Leu Phe Ile Ser Tyr Pro Trp Phe Leu
        35                  40                  45

Met Thr Ile Ala Glu Ile Ile Leu Ser Phe Leu Trp Phe Phe Asn Gln
    50                  55                  60

Ala Phe Arg Trp Arg Leu Val Asn Arg Ser Val Met Thr Glu Lys Leu
65                  70                  75                  80
```

-continued

```
Pro Pro Glu Glu Lys Leu Pro Gly Leu Asp Ile Phe Val Cys Thr Ile
                85                  90                  95

Asp Pro Glu Lys Glu Pro Thr Val Asp Val Met Asn Thr Val Ile Ser
            100                 105                 110

Ala Ile Ala Met Asp Tyr Pro Ser Asn Lys Leu Ser Ile Tyr Leu Ser
        115                 120                 125

Asp Asp Gly Gly Ser Pro Ile Thr Leu Phe Gly Ile Lys Glu Ala Phe
    130                 135                 140

Glu Phe Ala Lys Val Trp Val Pro Phe Cys Lys Lys Tyr Asp Val Lys
145                 150                 155                 160

Ser Arg Cys Pro Lys Phe Phe Phe Thr Ala Leu Gly Glu Asn Glu Arg
                165                 170                 175

Leu His Arg Pro Arg Glu Phe Glu Glu Val Arg Asp Gln Ile Lys Lys
            180                 185                 190

Arg Leu Asn Arg Val Asp Pro Asn Ser Ser Gln Val Glu Asn Ser Lys
        195                 200                 205

Glu His Met Pro Thr Lys Ala Lys Tyr Glu Lys Met Gln Lys Asn Ile
    210                 215                 220

Glu Lys Phe Gly Ser Asn Leu Lys Asn Leu Cys Met Val Thr Asp Arg
225                 230                 235                 240

Pro Ser Arg Ile Glu Ile Ile Asn Asp Gln Lys Glu Met Pro Leu Val
                245                 250                 255

Val Tyr Val Ser Arg Glu Lys Arg Pro Ser Val Pro His Arg Phe Lys
            260                 265                 270

Gly Gly Ala Leu Asn Thr Leu Leu Arg Val Ser Gly Leu Ile Ser Asn
        275                 280                 285

Gly Pro Tyr Val Leu Val Val Asp Cys Asp Met Asn Cys Asn Asp Ala
    290                 295                 300

Ser Ser Ala Lys Gln Ser Met Cys Phe Phe Leu Asp Pro Glu Thr Ser
305                 310                 315                 320

Lys Asp Val Ala Phe Val Gln Phe Pro Gln Met Phe His Asn Leu Ser
                325                 330                 335

Lys Lys Asp Ile Tyr Asp Ser Gln Thr Arg Thr Ala Phe Thr Thr Lys
            340                 345                 350

Trp Lys Gly Met Asp Gly Leu Arg Gly Pro Gly Leu Thr Gly Ser Gly
        355                 360                 365

Asn Tyr Ile Ser Arg Ser Ala Leu Leu Phe Gly Ser Pro Asn Gln Lys
    370                 375                 380

Gly Asp Tyr Leu Leu Asp Ala Leu Tyr Asn Phe Gly Lys Ser Asn Met
385                 390                 395                 400

Tyr Val Glu Ser Leu Lys Ala Leu Arg Gly Gln Gln Thr Lys Lys Gln
                405                 410                 415

Asn Ile Ser Arg Asp Val Ile Leu Gln Glu Ala Cys Glu Val Ala Ser
            420                 425                 430

Cys Ser Tyr Glu Arg Asn Thr Asn Trp Gly Asn Glu Val Gly Phe Ser
        435                 440                 445

Tyr Ala Ile Lys Leu Glu Ser Thr Val Thr Gly Tyr Leu Leu His Cys
    450                 455                 460

Arg Gly Trp Arg Ser Thr Tyr Leu Tyr Pro Lys Arg Pro Cys Phe Leu
465                 470                 475                 480

Gly Cys Ala Pro Thr Asp Met Lys Glu Gly Leu Ile Gln Pro Ile Lys
                485                 490                 495
```

-continued

```
Trp Ser Ser Glu Leu Leu Leu Leu Ala Ile Ser Lys Tyr Ser Pro Phe
            500                 505                 510

Thr Tyr Gly Leu Ser Arg Leu Pro Thr Ile His Cys Leu Thr Phe Cys
        515                 520                 525

Tyr Leu Val Ser Thr Thr Gln Phe Ala Thr Ala Tyr Ile Leu Tyr Gly
    530                 535                 540

Phe Val Pro Gln Ile Cys Phe Leu Lys Gly Ile Pro Val Tyr Pro Lys
545                 550                 555                 560

Val Thr Asp Pro Trp Phe Ile Val Phe Thr Val Leu Tyr Leu Ser Ser
                565                 570                 575

Gln Ile His His Tyr Ile Glu Val Ile Ser Thr Gly Gly Ser Ser Met
            580                 585                 590

Ile Trp Trp Asn Glu Gln Arg Ser Gly Ile Val Lys Ser Ile Gly Cys
        595                 600                 605

Val Phe Ala Ile Ile Glu Thr Ala Lys Lys Lys Phe Gly Leu Asn Lys
    610                 615                 620

Ala Lys Phe Thr Leu Ser Asp Lys Ala Ile Asp Lys Asp Lys Leu Lys
625                 630                 635                 640

Lys Tyr Glu Gln Gly Lys Phe Asn Phe Asp Gly Ala Ala Leu Leu Met
                645                 650                 655

Ala Pro Val Ile Val Leu Leu Thr Ile Asn Ile Val Cys Phe Phe Gly
            660                 665                 670

Gly Leu Trp Arg Leu Leu Asn Val Arg Asp Phe Asp Glu Met Phe Gly
        675                 680                 685

Gln Leu Phe Leu Ile Ile Tyr Ile Leu Ala Leu Ser His Pro Ile Val
    690                 695                 700

Glu Gly Ile Ile Ser Met Lys Arg Lys Ser Gly
705                 710                 715


<210> SEQ ID NO 99
<211> LENGTH: 2148
<212> TYPE: DNA
<213> ORGANISM: Medicago sativa

<400> SEQUENCE: 99

atggcaacct tcacatttca caaagaaaca gttcaaccat tgttacctct aagaagagct      60

tacataatct tccacttcac atgtgtcttg tttctctttt actaccgtat cagcaatttg     120

tttatttcat atccatggtt tctaatgaca atagctgaga ttattctatc atttctatgg     180

tttttcaacc aagcattccg ttggaggctg gtgaatcgtt cagttatgac cgagaaatta     240

ccgccggagg agaagttgcc gggactcgac atatttgtgt gtaccattga tcctgaaaaa     300

gaaccaacgg ttgatgttat gaacactgtt atttctgcta ttgcaatgga ttacccttct     360

aataaacttt ctatttatct ttctgatgat ggaggttctc ctattactct ttttgggatc     420

aaagaggctt ttgaatttgc taaagtttgg gttccttttt gtaaaaaata tgatgttaag     480

tcaaggtgtc ctaagttttt cttcactgct ttgggtgaga atgaacgact tcatcgacct     540

cgtgaatttg aagaagtgag ggaccagatt aagaagagat taaatagagt ggatcctaac     600

tcatcacaag ttgaaaactc caaggaacat atgcccacca aagccaaata cgagaaaatg     660

cagaaaaata ttgagaaatt cggaagcaac ctaaagaatc tttgtatggt gaccgataga     720

ccttctcgga tcgagatcat taatgaccaa aaagaaatgc cactagttgt ttatgtatct     780

cgtgaaaaaa gaccatctgt tcctcacaga ttcaaaggag gagctctcaa tacattgctt     840

agggtgtcag ggctaatcag caatggacct tatgtacttg tcgtagattg tgatatgaat     900
```

```
tgtaatgatg catcatcagc caaacaatcc atgtgctttt ttcttgatcc tgaaacctct     960

aaagatgttg cttttgttca attccctcaa atgtttcaca accttagcaa gaaagacata    1020

tatgatagtc agactaggac tgcttttacg acaaagtgga agggaatgga tggattaaga    1080

ggtccaggtc taactggcag tggaaattat ataagtagaa gtgcattact ctttggaagt    1140

ccaaaccaaa aaggggacta tctacttgat gctctataca actttggcaa gtctaacatg    1200

tatgtagaat cactaaaagc gttacgtggt caacaaacta agaagcagaa tatttcaaga    1260

gatgtaattt tacaagaagc atgtgaagtg gcttcttgtt cctatgagag aaacacaaat    1320

tggggtaatg aggtgggatt ctcgtatgct ataaaacttg agagtaccgt tactggctat    1380

ctcctccatt gtagaggatg gagatcaact tatctttacc ctaaaagacc atgtttctta    1440

ggatgtgctc caactgacat gaaagaggga ttgattcaac cgataaagtg gtcatctgaa    1500

cttttgttgc ttgcaatctc taaatatagc ccattcactt atggcctttc aagattgccc    1560

actattcatt gtttaacttt ttgttacttg gtaagcacaa cccaatttgc aacagcctac    1620

atcttatatg gattcgttcc tcagatttgc ttcttgaagg gaatacctgt atatccaaag    1680

gttacagatc cttggtttat agtgtttaca gtattgtatc tatccagtca aattcatcat    1740

tatattgagg taatttcaac tggtggctcc tcgatgattt ggtggaatga acaaagaagt    1800

gggattgtaa aatcaattgg gtgcgttttc gcaattatag aaacagcgaa aaaaaagttt    1860

gggttgaaca aggcaaaatt cactttatcg gacaaagcaa ttgacaaaga taagctaaag    1920

aaatatgagc agggtaagtt taattttgat ggtgcagcat tgctcatggc accagtgatt    1980

gtgttactca caataaatat tgtttgcttc tttggtggtt tatggagact actcaatgtg    2040

agggattttg atgaaatgtt tggtcaactt ttcctcatta tctatatact tgctctaagt    2100

catcctattg tggaggggat tatatctatg aagcggaaga gtgggtag                 2148
```

<210> SEQ ID NO 100
<211> LENGTH: 696
<212> TYPE: PRT
<213> ORGANISM: Glycine max

<400> SEQUENCE: 100

```
Met Ala Thr Phe His Thr Glu Thr Val Gln Ser Gly Leu Ala Leu Ser
1               5                   10                  15

Arg Leu His Ile Leu Phe His Ser Val Ala Leu Leu Phe Leu Tyr Tyr
            20                  25                  30

Tyr Arg Ile Ser His Ile Leu Leu Glu Pro Ser Phe Val Trp Ile Phe
        35                  40                  45

Met Thr Ile Ala Glu Leu Ile Phe Gly Glu Leu Trp Leu Phe Lys Gln
    50                  55                  60

Ala Phe Arg Trp Arg Pro Val Ser Arg Ala Val Met Pro Glu Lys Leu
65                  70                  75                  80

Pro Ser Asp Gly Lys Leu Pro Ala Leu Asp Ile Phe Val Cys Thr Val
                85                  90                  95

Asp Pro Glu Lys Glu Pro Thr Val Gln Val Met Asp Thr Val Ile Ser
            100                 105                 110

Ala Ile Ala Met Asp Tyr Pro Ser Asn Lys Leu Ala Val Tyr Leu Ser
        115                 120                 125

Asp Asp Gly Gly Cys Pro Val Thr Leu Tyr Gly Ile Arg Glu Ala Ser
    130                 135                 140

Arg Phe Ala Lys Glu Trp Val Pro Phe Cys Arg Lys Tyr Gly Ile Asn
```

-continued

```
145                 150                 155                 160

Ser Arg Cys Pro Lys Ala Phe Phe Ser Pro Met Gly Glu Asp Glu Arg
                165                 170                 175

Glu Leu Leu Leu Leu Arg Asn His Glu Phe Leu Ala Glu Gln Glu Gln
            180                 185                 190

Leu Lys Ala Lys Tyr Asn Ile Met Gln Lys Asn Ile Asp Glu Phe Gly
        195                 200                 205

Arg Asp Pro Lys Asn Arg Ser Ile Val Phe Asp Arg Pro Ala Arg Ile
    210                 215                 220

Glu Ile Ile Asn Glu Gln Ser Glu Ile Pro Leu Val Val Tyr Val Ser
225                 230                 235                 240

Arg Glu Arg Arg Pro Asn Val Pro His Thr Tyr Lys Gly Gly Ala Leu
                245                 250                 255

Asn Thr Leu Leu Arg Val Ser Gly Leu Phe Ser Asn Gly Pro Tyr Val
            260                 265                 270

Leu Val Val Asp Cys Asp Met Tyr Cys Asn Asp Pro Ser Ser Ala Lys
        275                 280                 285

Gln Ala Met Cys Phe Phe Leu Asp Pro Glu Thr Ser Lys Asp Ile Ala
    290                 295                 300

Phe Val Gln Phe Pro Gln Met Phe His Asn Leu Ser Met Lys Asp Ile
305                 310                 315                 320

Tyr Asp Ser Gln His Arg His Ala Phe Thr Thr Met Trp Gln Gly Met
                325                 330                 335

Asp Gly Leu Arg Gly Pro Gly Leu Ser Gly Ser Gly Asn Tyr Leu Ser
            340                 345                 350

Arg Ser Ala Leu Ile Phe Pro Ser Pro Tyr Glu Lys Asp Gly Tyr Glu
        355                 360                 365

His Asn Ala Gln Asn Lys Phe Gly Asn Ser Thr Met Tyr Ile Glu Ser
    370                 375                 380

Leu Lys Ala Ile Gln Gly Gln Gln Thr Tyr Lys Thr Ser Ile Ser Arg
385                 390                 395                 400

Asn Val Ile Leu Gln Glu Ala Gln Ala Val Ala Ser Cys Ser Tyr Glu
                405                 410                 415

Ile Asp Thr Asn Trp Gly Asn Glu Val Gly Phe Ser Tyr Val Ile Leu
            420                 425                 430

Leu Glu Ser Thr Val Thr Gly Tyr Leu Leu His Cys Arg Gly Trp Arg
        435                 440                 445

Ser Thr Tyr Leu Tyr Pro Lys Arg Pro Cys Phe Leu Gly Cys Ala Pro
    450                 455                 460

Thr Asp Phe Met Glu Gly Met Leu Gln Leu Val Lys Trp Ser Ser Glu
465                 470                 475                 480

Leu Phe Leu Leu Gly Ile Ser Lys Tyr Ser Pro Phe Thr Tyr Gly Ile
                485                 490                 495

Ser Arg Ile Pro Ile Leu His Asn Phe Thr Phe Cys Tyr Phe Thr Ser
            500                 505                 510

Thr Cys Gln Tyr Ile Val Ala Leu Ile Val Tyr Gly Ile Ile Pro Gln
        515                 520                 525

Val Cys Phe Leu Lys Gly Thr Pro Val Phe Pro Lys Val Thr Glu Pro
    530                 535                 540

Trp Phe Val Val Phe Ala Ile Leu Tyr Val Ser Ser Gln Ser Gln His
545                 550                 555                 560

Leu Ile Glu Val Leu Tyr Gly Gly Gly Ser Leu Gly Thr Trp Trp Asp
                565                 570                 575
```

```
Glu Gln Arg Ile Trp Ile Val Lys Ser Ile Val Gly Gly Ile Phe Gly
            580                 585                 590

Ser Ile Leu Ala Ile Lys Lys Arg Phe Gly Leu Asn Lys Ala Lys Phe
        595                 600                 605

Ile Leu Ser Asn Lys Val Val Ala Lys Glu Lys Phe Glu Lys Tyr Glu
    610                 615                 620

Gln Gly Lys Phe Glu Phe Glu Asp Ala Ala Leu Phe Met Ser Pro Leu
625                 630                 635                 640

Val Gly Leu Leu Ile Val Asn Ile Leu Cys Phe Phe Gly Gly Leu Trp
                645                 650                 655

Arg Leu Phe Asn Val Lys Asp Phe Glu Lys Met Ser Gly Gln Leu Phe
            660                 665                 670

Leu Leu Gly Tyr Leu Ala Ala Leu Ser Tyr Pro Ile Phe Glu Gly Ile
        675                 680                 685

Ile Thr Met Lys Ser Lys Val Gln
    690                 695


<210> SEQ ID NO 101
<211> LENGTH: 2336
<212> TYPE: DNA
<213> ORGANISM: Glycine max

<400> SEQUENCE: 101

tatatgcatg ttgaccggta aacatggcga ccttccacac agaaaccgtg caatcagggt     60

tggccttgag cagactccac atcctattcc actcggtggc actcttgttt ctctattact    120

accgcataag ccacatctta ctggaaccaa gctttgtatg gattttcatg accatagcgg    180

agcttatctt cggcgagctc tggctcttca aacaggcgtt ccggtggcgg cccgtgtcga    240

gggccgtcat gccggagaag ctgccgagcg acggcaagct tccggcgctc gacatcttcg    300

tctgcacggt tgaccccgaa aaggagccga cggtgcaggt gatggacacc gtcatctccg    360

ccattgccat ggactacccc tccaacaagc tcgccgtgta cctttccgac gatggcgggt    420

gtccggtgac tctgtatggg atcagagagg cttctcggtt cgcaaaggag tgggttccgt    480

tctgcagaaa gtatgggatc aattcacggt gccccaaggc cttcttctct cccatggggg    540

aggatgaacg tgaactgctt cttcttcgca accatgaatt cttggcagag caagaacaac    600

tcaaggctaa atacaatata atgcaaaaaa atattgacga atttggaaga gaccctaaaa    660

atcgttccat tgtgtttgat agaccagctc gcattgagat tataaatgag caatccgaaa    720

taccactggt tgtttatgtg tctcgtgaaa gaaggccaaa tgttcctcat acatacaaag    780

ggggagccct caacacattg ctcagagtct cagggctatt cagtaacggg ccctatgtac    840

ttgtagttga ttgtgatatg tattgcaatg atccatcatc agctaaacaa gccatgtgct    900

tttttcttga tcctgaaacc tccaaagata ttgcttttgt ccaattccct caaatgtttc    960

acaaccttag catgaaagac atctacgata gtcaacatag gcatgctttt acaacaatgt   1020

ggcaaggaat ggatggacta agaggtccag gtctttctgg tagtggcaat tacttaagta   1080

gaagtgcatt aatctttcca agcccatatg aaaaagacgg ctatgaacat aatgcccaaa   1140

acaaatttgg caactctacc atgtacattg aatcattaaa ggccattcaa ggacaacaaa   1200

cttataaaac gagcatttca agaaatgtga ttttacagga agcacaagca gtggcctctt   1260

gttcctatga aatagacaca aattggggta atgaggtagg attctcatat gttatattac   1320

tggagagtac agttactggc tatcttcttc actgtagagg atggagatca acttaccttt   1380
```

```
accccaaaag accttgtttc ttgggatgtg cccccactga cttcatggaa ggcatgcttc   1440

agttggtgaa atggagttct gaacttttct tgctaggaat atccaaatac agccctttca   1500

cttatgggat ttcaagaatt cctattctgc acaactttac cttttgctac ttcacatcta   1560

catgtcaata tattgttgcc ttaatagtat atggcatcat tcctcaagta tgcttcttga   1620

aaggaactcc tgtgtttcct aaggttacag aaccatggtt tgtagttttt gcaatattat   1680

atgtatcctc tcaaagtcaa catttgattg aagtccttta tggtggtggc tctttgggaa   1740

catggtggga tgaacaaaga atatggattg taaagtcaat tgttggaggc atatttggat   1800

ctatactagc aatcaagaaa cgttttgggt taaacaaagc aaaattcatt ttatcaaata   1860

aagttgttgc caaagagaag tttgagaaat atgaacaagg taagttcgag ttcgaagatg   1920

cagctttgtt catgtctcca ttggttggat tactcatagt gaatattctt tgcttctttg   1980

gtggtttatg gagactattt aatgtgaaag attttgaaaa gatgtctggc caactttttc   2040

tacttggcta tctggcggcg ctcagttatc ccatttttga ggggataata accatgaaaa   2100

gcaaggtgca atagtagttt gtcaatgatt aggctaattt aggtatttga actttgttca   2160

caaataattt gcttcatatg aaaatctaaa gtgcatgcta aatgtttgta tcttaatatg   2220

taattagcgt gcttttattt catgcatgag aatatggcta tcgattttaa ttaggagcaa   2280

aatgtatgtt cttactccat ttttaatgca atttctttat tttcttgcca attaaa       2336
```

```
<210> SEQ ID NO 102
<211> LENGTH: 695
<212> TYPE: PRT
<213> ORGANISM: Glycyrrhiza uralensis

<400> SEQUENCE: 102

Met Ala Ser Phe Thr Leu His Thr Glu Thr Val Gln Ser Trp Leu Leu
1               5                   10                  15

Leu Ser Arg Leu His Ile Leu Leu His Leu Ala Val Val Leu Leu Leu
            20                  25                  30

Leu Tyr Tyr Arg Ile Thr Arg Phe Pro Phe His Ala Pro Thr Leu Pro
        35                  40                  45

Trp Thr Leu Met Thr Val Gly Glu Ala Ile Met Ala Val Leu Trp Phe
    50                  55                  60

Phe Asn Gln Ala Phe Arg Trp Arg Pro Val Ser Arg Ser Val Met Thr
65                  70                  75                  80

Glu Lys Leu Pro Ser Asp Ala Lys Leu Pro Gly Leu Asp Ile Phe Val
                85                  90                  95

Cys Thr Leu Asp Pro Glu Lys Glu Pro Thr Val Glu Val Met Asn Thr
            100                 105                 110

Leu Val Ser Ala Leu Ala Met Asp Tyr Pro Pro Asp Lys Leu Ser Val
        115                 120                 125

Tyr Leu Ser Asp Asp Gly Ala Ala Pro Val Thr Leu Tyr Gly Val Arg
    130                 135                 140

Glu Ala Ser Glu Phe Ala Arg Val Trp Val Pro Phe Cys Lys Lys Tyr
145                 150                 155                 160

Gly Ile Lys Ser Arg Cys Pro Lys Val Phe Phe Ser Pro Ser Ala Glu
                165                 170                 175

Asp Glu His Leu Leu Arg Thr Asp Glu Phe Arg Ser Glu Arg Asp Leu
            180                 185                 190

Ile Lys Ala Lys Tyr Glu Lys Met Gln Lys Asn Ile Glu Lys Phe Gly
        195                 200                 205
```

-continued

```
Ser Asp Ala Lys Asn Cys Arg Met Val Thr Asp Arg Pro Pro Arg Ile
    210                 215                 220

Glu Ile Leu Ile Asp Gln Pro Asp Met Pro Arg Val Val Tyr Val Ser
225                 230                 235                 240

Arg Glu Arg Arg Pro Ser Leu Pro His Lys Phe Lys Gly Gly Ala Leu
                245                 250                 255

Asn Thr Leu Leu Arg Val Ser Gly Leu Ile Ser Asn Gly Pro Tyr Val
            260                 265                 270

Leu Val Val Asp Cys Asp Met Tyr Cys Asn Asp Pro Ser Ser Ala Lys
        275                 280                 285

Gln Ala Met Cys Phe Phe Leu Asp Pro Glu Thr Ser Lys Ser Ile Ala
    290                 295                 300

Phe Val Gln Phe Pro Gln Met Phe His Asn Leu Gly Lys Lys Asp Ile
305                 310                 315                 320

Tyr Asp Asn Gln Ser Arg Thr Ala Phe Lys Thr Met Trp Gln Gly Met
                325                 330                 335

Asp Gly Leu Arg Gly Pro Gly Leu Ser Gly Ser Gly Asn Tyr Leu Asn
            340                 345                 350

Arg Ser Ala Leu Leu Phe Gly Ser Pro Asn Gln Lys Asp Asp Tyr Leu
        355                 360                 365

Asp Asp Ala Gln Asn Tyr Leu Gly Lys Ser Thr Met Tyr Ile Glu Ser
    370                 375                 380

Leu Lys Ala Ile Arg Gly Gln Lys Thr Met Lys Lys Asn Ile Ser Arg
385                 390                 395                 400

Asp Glu Ile Leu Arg Glu Ala Gln Val Leu Ala Ser Cys Ser Tyr Glu
                405                 410                 415

Thr Asn Thr Glu Trp Gly Ala Glu Val Gly Phe Ser Tyr Gly Ile Leu
            420                 425                 430

Leu Glu Ser Ser Ile Thr Gly Tyr Leu Phe His Cys Arg Gly Trp Lys
        435                 440                 445

Ser Ala Tyr Leu Tyr Pro Lys Thr Pro Cys Phe Leu Gly Cys Ala Pro
    450                 455                 460

Thr Asp Ile Lys Glu Gly Met Leu Gln Leu Val Lys Trp Leu Ser Glu
465                 470                 475                 480

Tyr Cys Leu Leu Gly Phe Ser Lys Tyr Ser Pro Phe Thr Tyr Gly Phe
                485                 490                 495

Ser Arg Met Pro Ile Met Pro Thr Leu Val Tyr Cys Phe Leu Thr Thr
            500                 505                 510

Thr Thr Leu Tyr Ser Ile Val Phe Ile Leu Tyr Gly Ile Val Pro Gln
        515                 520                 525

Val Cys Phe Leu Lys Gly Ile Pro Val Phe Pro Lys Val Thr Asp Pro
    530                 535                 540

Trp Phe Ala Val Phe Ala Thr Leu Tyr Ile Ser Thr Gln Ile Gln His
545                 550                 555                 560

Leu Ile Glu Val Leu Ser Gly Asp Gly Ser Val Ala Met Trp Trp Asp
                565                 570                 575

Glu Gln Gly Ile Trp Ile Leu Lys Ser Val Thr Ser Val Phe Ala Ile
            580                 585                 590

Ile Glu Ala Ala Lys Lys Gly Leu Gly Leu Asn Lys Lys Lys Phe Met
        595                 600                 605

Leu Ser Asn Lys Ala Ile Asp Lys Glu Lys Leu Lys Lys Tyr Glu Gln
    610                 615                 620

Gly Arg Phe Asp Phe Gln Gly Ala Ala Leu Phe Met Ser Pro Met Val
```

625 630 635 640

Val Leu Leu Ile Val Asn Val Val Ser Phe Ile Gly Gly Ile Trp Arg
645 650 655

Leu Phe Asn Ala Lys Asp Ile Glu Asp Met Phe Gly Gln Leu Phe Leu
660 665 670

Val Ser Tyr Val Met Ala Leu Ser Tyr Pro Ile Phe Glu Gly Ile Ile
675 680 685

Thr Met Lys Ser Lys Ser Gly
690 695

<210> SEQ ID NO 103
<211> LENGTH: 2088
<212> TYPE: DNA
<213> ORGANISM: Glycyrrhiza uralensis

<400> SEQUENCE: 103
atggcaagct tcacccttca cacagaaacc gttcagtcat ggctactcct cagcagactt 60
cacatactgc tgcacctcgc agttgtactg ctcctcttat actaccgcat cacacgtttc 120
cccttccatg ctccgactct accgtggact ctgatgaccg taggtgaggc tattatggca 180
gtgctgtggt tcttcaacca ggccttccgg tggcggccgg tgagccgctc ggtgatgacg 240
gagaagctgc ccagcgacgc gaagctgccg gggcttgaca tattcgtgtg cacgcttgac 300
cccgagaagg agcccaccgt ggaggtgatg aacactctgg tctctgccct tgccatggac 360 taccccccctg acaagctctc cgtttacctc tccgacgatg gcgccgcccc ggtcactctt 420
tacggcgtga gagaggcttc tgagttcgcg agggtgtggg tccctttctg caaaaagtat 480
gggatcaagt caaggtgtcc caaggttttc ttctctccca gtgctgagga tgaacacctt 540
cttcgcaccg acgagttcag gtcagagcga gacctcatca aggctaaata cgagaaaatg 600
cagaaaaata ttgagaaatt tggttcggat gccaaaaatt gtcgtatggt gactgacaga 660
cctcctcgga tcgagatatt gattgaccaa ccagacatgc cacgtgttgt ttacgtgtct 720
cgggaaagaa ggccatcact ccctcacaag ttcaaaggag gagccctcaa tacattgctc 780
agagtctcag gtctaatcag caatgggcct tatgtacttg tagtggactg tgatatgtat 840
tgcaatgacc catcctcagc caaacaagcc atgtgtttct ttcttgatcc tgaaacctct 900
aaatctattg catttgtcca attccctcaa atgtttcaca accttggcaa aaaagacatc 960
tatgacaatc aatctaggac tgcttttaag acaatgtggc aagggatgga tggactaaga 1020
ggtcctggtc tttctggcag cggtaattac ttgaatagaa gtgcattact atttggaagt 1080
ccaaatcaaa aagatgacta tctggatgat gcccaaaact acttaggcaa gtctaccatg 1140
tacatagaat cactaaaggc cattcgtgga caaaaaacta tgaaaaagaa tatttcaaga 1200
gatgaaattt tacgagaagc tcaagtatta gcctcttgtt cctatgagac aaacacagaa 1260
tggggagcag aggtaggatt ctcatatggc atcttactgg agagttcaat cactggctat 1320
cttttccact gcagaggatg gaaatcagca tatctttacc caaagacacc atgtttctta 1380
gggtgtgccc caactgacat caaggaagga atgctccaat tggtgaagtg gttgtctgaa 1440
tactgcttgc taggattctc taaatacagc cctttcactt atggcttttc aagaatgccc 1500
attatgccta ccttagtcta ttgcttcttg acaacaacaa ccctttattc cattgtcttc 1560
atcctttatg gcattgtccc ccaagtttgc ttcttaaaag gaatacccgt gtttccaaag 1620
gtcacagacc cttggtttgc agtgtttgca acactgtata tatccaccca gattcaacat 1680
ttgatagagg tcctttctgg tgatggctct gtggcaatgt ggtgggatga acagggaatc 1740
tggattctga agtcagtcac tagcgtgttc gcaatcatag aggcagctaa gaaagggtta 1800
ggattgaaca agaagaaatt catgttgtca aacaaagcaa ttgacaagga gaagctcaag 1860
aagtatgagc aaggtaggtt tgatttccaa ggtgcagctc tgttcatgtc cccaatggtt 1920
gtgttgctca tagtgaacgt tgtttccttc attggtggca tatggagact attcaatgca 1980
aaggatattg aagatatgtt tggtcagctt ttcctagtta gttatgtaat ggcccttagt 2040
tatcccattt ttgaagggat aataaccatg aaaagcaaga gtggatag 2088

<210> SEQ ID NO 104
<211> LENGTH: 694
<212> TYPE: PRT
<213> ORGANISM: Lotus japonicus

<400> SEQUENCE: 104

Met Ala Asn Phe Thr Leu His Thr Glu Thr Val Gln Ala Trp Leu Pro
1 5 10 15

Leu Ser Arg Leu His Ile Leu Ile His Ser Val Phe Val Ile Leu Leu
20 25 30

Leu Tyr Tyr Arg Thr Thr Arg Leu Ile His Ala Pro Thr Ala Pro Trp
35 40 45

Ile Leu Met Thr Val Ala Glu Ala Leu Leu Ala Val Leu Trp Leu Phe
50 55 60

Asn Gln Ala Phe Arg Trp Arg Pro Val Ser Arg Ser Val Lys Thr Glu
65 70 75 80

Lys Leu Pro Arg Asp Glu Asn Leu Pro Gly Leu Asp Ile Phe Val Cys
85 90 95

Thr Ile Asp Pro Glu Lys Glu Pro Thr Ala Gly Val Met Asp Thr Val
100 105 110

Val Ser Ala Val Ala Met Asp Tyr Pro Pro Asp Lys Leu Ser Val Tyr
115 120 125

Leu Ser Asp Asp Gly Gly Cys Ala Val Thr Glu Tyr Gly Ile Arg Glu
130 135 140

Ala Cys Glu Phe Ala Lys Val Trp Val Pro Phe Cys Arg Lys Tyr Gly
145 150 155 160

Ile Lys Ser Arg Cys Pro Lys Val Phe Phe Ser Pro Met Gly Glu Asp
165 170 175

Glu Glu Ile Leu Arg Thr Asp Glu Phe Arg Ala Glu Gln Glu Lys Ile
180 185 190

Lys Ala Gln Tyr Glu Thr Met Gln Lys Asn Ile Glu Lys Phe Gly Ser
195 200 205

Asp Pro Lys Asn Cys Arg Ile Val Thr Asp Arg Pro Ser Lys Ile Glu
210 215 220

Val Ile Asn Glu Gln Ser Glu Ile Pro Arg Val Val Tyr Val Ser Arg
225 230 235 240

Glu Arg Arg Pro Ser Leu Pro His Lys Phe Lys Gly Gly Ala Leu Asn
245 250 255

Thr Leu Val Arg Val Ser Gly Leu Ile Ser Asn Gly Pro Tyr Val Leu
260 265 270

Ala Val Asp Cys Asp Met Tyr Cys Asn Asp Pro Ser Ser Ala Lys Gln
275 280 285

Ala Met Cys Phe Phe Leu Asp Pro Glu Thr Ser Lys Tyr Ile Ala Phe
290 295 300

Val Gln Phe Pro Gln Met Phe His Asn Leu Ser Lys Lys Asp Ile Tyr

-continued

```
305                 310                 315                 320

Asp Asn Gln Ser Arg Thr Ala Phe Lys Ala Met Trp Gln Gly Met Asp
                325                 330                 335

Gly Leu Ser Gly Pro Gly Leu Ser Gly Ser Gly Asn Tyr Leu Ser Arg
            340                 345                 350

Ser Ala Leu Leu Phe Gly Ser Pro Asn Gln Lys Gly Asp Tyr Leu Leu
        355                 360                 365

Asp Ala Gln Asn Tyr Phe Gly Glu Ser Pro Leu Tyr Ile Glu Ser Leu
    370                 375                 380

Lys Ala Ile Arg Gly Gln Gln Thr Thr Lys Lys Asn Ile Ser Arg Asp
385                 390                 395                 400

Glu Ser Leu Leu Glu Ala Lys Val Val Ala Ser Ala Ser Tyr Glu Thr
                405                 410                 415

Asn Thr Glu Trp Gly Ser Glu Val Gly Phe Ser Tyr Gly Ile Leu Leu
            420                 425                 430

Glu Ser Thr Ile Thr Gly Tyr Leu Leu His Cys Arg Gly Trp Lys Ser
        435                 440                 445

Ala Tyr Leu Tyr Pro Lys Thr Pro Cys Phe Leu Gly Cys Ala Pro Thr
    450                 455                 460

Asp Ile Lys Glu Gly Met Leu Gln Leu Val Lys Trp Leu Ser Glu Leu
465                 470                 475                 480

Cys Leu Phe Ala Val Ser Lys Tyr Ser Pro Phe Thr Tyr Gly Phe Ser
                485                 490                 495

Arg Leu Pro Ile Met Pro Thr Phe Thr Tyr Cys Phe Leu Ala Ala Ser
            500                 505                 510

Ser Leu Tyr Ala Ile Val Phe Ile Leu Tyr Gly Ile Val Pro Gln Val
        515                 520                 525

Cys Phe Leu Lys Gly Ile Pro Val Phe Pro Lys Ala Thr Asp Pro Trp
    530                 535                 540

Phe Ala Val Phe Ala Val Leu Tyr Val Ala Thr Gln Ile Gln His Leu
545                 550                 555                 560

Ile Glu Val Leu Ser Gly Asn Gly Ser Val Ser Met Trp Trp Asp Glu
                565                 570                 575

Gln Arg Ile Trp Ile Leu Lys Ser Val Thr Ser Val Phe Ala Met Ile
            580                 585                 590

Glu Gly Ile Lys Lys Trp Leu Gly Leu Asn Lys Lys Lys Phe Asn Leu
        595                 600                 605

Ser Asn Lys Ala Val Asp Lys Glu Lys Val Lys Lys Tyr Glu Gln Gly
    610                 615                 620

Arg Phe Asp Phe Gln Gly Ala Ala Leu Tyr Met Ser Pro Met Val Val
625                 630                 635                 640

Leu Leu Leu Val Asn Ile Val Cys Phe Phe Gly Gly Leu Trp Arg Leu
                645                 650                 655

Phe Lys Glu Lys Asp Phe Ala Asp Met Phe Gly Gln Leu Phe Leu Leu
            660                 665                 670

Ser Tyr Val Met Ala Leu Ser Tyr Pro Ile Leu Glu Gly Ile Val Thr
        675                 680                 685

Met Lys Met Lys Ser Gly
    690
```

<210> SEQ ID NO 105
<211> LENGTH: 2085
<212> TYPE: DNA
<213> ORGANISM: Lotus japonicus

<400> SEQUENCE: 105
atggccaatt tcactctcca cacagaaacc gttcaagcat ggctccctct aagcagactc 60
cacattctta tacactcagt gttcgtcatc cttctcctct actaccgcac aacgcgtctc 120
atccacgcgc cgaccgcgcc gtggatcctg atgaccgttg cggaggctct cctcgccgtg 180
ctttggctct tcaaccaggc cttccggtgg cgaccggtga gccgctccgt gaagacagag 240
aagctgccgc gcgacgagaa tctccccggg ctggacatat ttgtgtgcac gattgatcct 300
gagaaggagc caacggcagg ggtgatggac acggttgttt ccgccgtggc gatggattac 360
ccgccggata agctatccgt gtatctttct gatgatggtg gttgcgccgt gacggagtat 420
gggattagag aggcttgtga gtttgccaag gtgtgggttc ctttttgtag aaagtatggg 480
atcaagtcga ggtgtccaaa agttttcttc tctccgatgg gggaagatga agagattcta 540
aggacagatg agttcagagc agagcaagag aagatcaagg cccaatacga gactatgcag 600
aaaaacatcg agaaatttgg ttcagacccc aaaaattgtc gtattgtgac tgacagaccc 660
tctaagatcg aggttataaa tgagcaatca gaaatcccac gtgttgtgta cgtctctcgt 720
gaaagaaggc catcacttcc tcacaagttc aaaggaggag ctctcaacac attggtcaga 780
gtgtcaggtc taatcagcaa tggaccttat gtgcttgcag tggattgtga tatgtattgc 840
aatgatccat cctctgccaa gcaagcaatg tgcttcttcc ttgatccaga aacatctaaa 900
tacattgcat ttgtccaatt ccctcaaatg tttcacaacc ttagtaagaa agacatctat 960
gataatcaat ctaggactgc ttttaaggca atgtggcaag gcatggatgg actcagtggt 1020
ccaggtcttt ctggcagtgg taactacttg agtagaagtg cattgctatt tggaagtcca 1080
aaccaaaaag gtgactatct gcttgatgct caaaactact ttggcgagtc tcccttgtac 1140
attgaatcat tgaaggccat ccgtggacaa caaactacca aaaagaatat ctcaagagac 1200
gaaagtttac tagaagctaa agtggtggcc tctgcttcct acgagacaaa cacagaatgg 1260
ggctcagagg ttggattctc atatggcatc ttactggaga gtactattac tggttacctt 1320
ttgcactgca gaggatggaa atcagcttat ctttacccaa aaacaccatg tttcttaggg 1380
tgtgccccca ctgacattaa agaaggcatg cttcagttgg tgaagtggtt gtctgagctt 1440
tgcttgtttg ctgtctctaa gtacagccct tttacatatg ggttttcaag attgcccatt 1500
atgcctacct tcacttattg tttcctggca gcttcatccc tatatgctat tgtcttcatc 1560
ctttatggca ttgtacctca agtgtgcttc ttgaaaggaa tccctgtgtt tccaaaggcc 1620
acagaccctt ggtttgcagt gtttgcagta ttgtatgtag ccacccagat tcaacatttg 1680
attgaagtcc tttctggcaa tggctcggtc tcgatgtggt gggatgaaca aagaatttgg 1740
attctgaagt cagttactag cgtatttgca atgatagagg gaatcaagaa atggttagga 1800
ttgaacaaga aaaaattcaa cctgtcaaac aaagcggttg acaaggagaa ggtcaagaaa 1860
tatgagcaag gtaggtttga tttccaagga gcagctctgt acatgtctcc aatggttgtg 1920
ttgctcctag tgaacattgt ttgcttcttt ggcggtttat ggagactgtt taaggagaaa 1980
gattttgcag atatgtttgg tcaacttttc ctactcagct atgtgatggc tctcagttat 2040
cccattcttg aggggatagt aactatgaaa atgaagagtg ggtag 2085

<210> SEQ ID NO 106
<211> LENGTH: 350
<212> TYPE: DNA
<213> ORGANISM: Artificial Sequence
<220> FEATURE:

-continued

<223> OTHER INFORMATION: SOAP5_VIGS_spinach

<400> SEQUENCE: 106
ttccgtagcc atcttctcgc tcttctacta ccgtttcact tccttcttca actccgacat 60
ctccatactt gcttactcct tactcaccac cgccgaactc ttcttaacct ttctatgggc 120
ttttactcag gctttccggt ggcgtcccgt aatgagggaa gtctccgggt acgaatccat 180
caaacccgaa caactaccgg gtttggatgt cttcattgtc actgctgacc cgacaaagga 240
gccagttctg gaggtgatga actccgtgat atcatccatg gcgttggatt atccggttga 300
tagactggcg gtttacttgt cggatgacgg tggttctccg ttgtcgaagg 350

<210> SEQ ID NO 107
<211> LENGTH: 438
<212> TYPE: DNA
<213> ORGANISM: Artificial Sequence
<220> FEATURE:
<223> OTHER INFORMATION: BvCSL_VIGS_red beet

<400> SEQUENCE: 107
ccttcggctc ctccacaaaa ttcattgcgt cagttagttc aaactccaag caaaatatgg 60
ccttgaagga aatgacaaga gacgacttgt tagaagaggc taaaaatttg gctacttgtg 120
catatgaatc aaacactgaa tggggtaaca agattggata ttcgtatgag tgtttgttgg 180
agagtacatt taccggatat ctcttacatt gcaaaggatg gatttccgtg tatctttacc 240
caaaaagacc ctgcttctta ggatgcacga cgattgacat gaaagatgcc atggttcaac 300
taatgaaatg gacctctgga ttactaggag ttggcatatc aaagtttagc cctctaactt 360
atgccttttc gaggatgtct atattacaaa gcatgtgcta cggttacttc acattttcag 420
cccttttcgg agtttcgt 438

<210> SEQ ID NO 108
<211> LENGTH: 2148
<212> TYPE: DNA
<213> ORGANISM: Artificial Sequence
<220> FEATURE:
<223> OTHER INFORMATION: MsCSL_asRNA_Medicago sativa

<400> SEQUENCE: 108
ctacccactc ttccgcttca tagatataat cccctccaca ataggatgac ttagagcaag 60
tatatagata atgaggaaaa gttgaccaaa catttcatca aaatccctca cattgagtag 120
tctccataaa ccaccaaaga agcaaacaat atttattgtg agtaacacaa tcactggtgc 180
catgagcaat gctgcaccat caaaattaaa cttaccctgc tcatatttct ttagcttatc 240
tttgtcaatt gctttgtccg ataaagtgaa ttttgccttg ttcaacccaa actttttttt 300
cgctgtttct ataattgcga aaacgcaccc aattgatttt acaatcccac ttctttgttc 360
attccaccaa atcatcgagg agccaccagt tgaaattacc tcaatataat gatgaatttg 420
actggataga tacaatactg taaacactat aaaccaagga tctgtaacct ttggatatac 480
aggtattccc ttcaagaagc aaatctgagg aacgaatcca tataagatgt aggctgttgc 540
aaattgggtt gtgcttacca agtaacaaaa agttaaacaa tgaatagtgg gcaatcttga 600
aaggccataa gtgaatgggc tatatttaga gattgcaagc aacaaaagtt cagatgacca 660
ctttatcggt tgaatcaatc cctctttcat gtcagttgga gcacatccta agaaacatgg 720
tcttttaggg taaagataag ttgatctcca tcctctacaa tggaggagat agccagtaac 780
ggtactctca agttttatag catacgagaa tcccacctca ttaccccaat ttgtgtttct 840

-continued

```
ctcataggaa caagaagcca cttcacatgc ttcttgtaaa attacatctc ttgaaatatt    900

ctgcttctta gtttgttgac cacgtaacgc ttttagtgat tctacataca tgttagactt    960

gccaaagttg tatagagcat caagtagata gtccccttt tggtttggac ttccaaagag    1020

taatgcactt ctacttatat aatttccact gccagttaga cctggacctc ttaatccatc   1080

cattcccttc cactttgtcg taaaagcagt cctagtctga ctatcatata tgtctttctt   1140

gctaaggttg tgaaacattt gagggaattg aacaaaagca acatctttag aggtttcagg   1200

atcaagaaaa aagcacatgg attgtttggc tgatgatgca tcattacaat tcatatcaca   1260

atctacgaca agtacataag gtccattgct gattagccct gacaccctaa gcaatgtatt   1320

gagagctcct cctttgaatc tgtgaggaac agatggtctt ttttcacgag atacataaac   1380

aactagtggc atttcttttt ggtcattaat gatctcgatc cgagaaggtc tatcggtcac   1440

catacaaaga ttctttaggt tgcttccgaa tttctcaata tttttctgca ttttctcgta   1500

tttggctttg gtgggcatat gttccttgga gttttcaact tgtgatgagt taggatccac   1560

tctatttaat ctcttcttaa tctggtccct cacttcttca aattcacgag gtcgatgaag   1620

tcgttcattc tcacccaaag cagtgaagaa aaacttagga caccttgact taacatcata   1680

ttttttacaa aaaggaaccc aaactttagc aaattcaaaa gcctctttga tcccaaaaag   1740

agtaatagga gaacctccat catcagaaag ataaatagaa agtttattag aagggtaatc   1800

cattgcaata gcagaaataa cagtgttcat aacatcaacc gttggttctt tttcaggatc   1860

aatggtacac acaaatatgt cgagtcccgg caacttctcc tccggcggta atttctcggt   1920

cataactgaa cgattcacca gcctccaacg gaatgcttgg ttgaaaaacc atagaaatga   1980

tagaataatc tcagctattg tcattagaaa ccatggatat gaaataaaca aattgctgat   2040

acggtagtaa aagagaaaca agacacatgt gaagtggaag attatgtaag ctcttcttag   2100

aggtaacaat ggttgaactg tttctttgtg aaatgtgaag gttgccat                2148
```

<210> SEQ ID NO 109
<211> LENGTH: 1431
<212> TYPE: DNA
<213> ORGANISM: Spinacia oleracea

<400> SEQUENCE: 109

```
atggccaaat ctgagcaaga aacaatggcc aaatctgagc aagaaacatc catcaaactt     60

gtttcagaat gctttgtaaa accaaaatat gagattaaat ccgctaagca accttaccac    120

ttaggtccca tggatctagt tatgttaact atcgatccta tacaaaaagg tcttgtcttt    180

acaataaaga attccccact ctttttgtca tccgaatccc atgataatat tgaaattatt    240

cgaaccaaag ttgtgtcacg tttattagaa aagcttaaac actcactttc tatagctcta    300

gtccacttct acccgttagc aggtcgtttc actacacaaa aacaacccga gcataacacg    360

agcttggtct ttattgattg caacaaaggt cccggagcgc ggttcatcca cgctacttcc    420

cttgacttta ctatctccga tatactttca ccggttgatg tttccatcgt tcattctttc    480

tttgatctcg gtgaaaagca tgtaaactac gattgtcata ctaaggcgtt gctatcgatc    540

caggtaacag aacttttaga tggggtgttt attgggttta gcatgagtca tagtgtggtt    600

gatggtacct cttttattca ttttgtcaat accttgtctg aaattttttaa atctgatgat   660

tttaccacta tttcacgtgc cccaatactt aattataggc cttgtgatat tccgatcctt    720

aaatttccgt ttcttgatgt ggaggggttt atatgtcgtg cgtataaccc tgggccgtta    780
```

agggaaagaa tcttccactt ttcactaaat tcgatgctga gactcaaggc catggctaac 840
caagaatgtg gtacccaaaa tgttttatca tctttccaag ctttgactgc ggttgtatgg 900
aggtccatca cccgagttcg gaacttacca aaggatgagc aaaccacgtg ttttatggct 960
atgggttctc gaactaggct caacccgcct ctttcggatg actattttgg gaattttatg 1020
attagtacca aatttgcttg caaggcagag gaattattgg gtaacagttt aggttgggta 1080
gcaatgaatt tacgtaaaat cattatgtcc actgacgaga aatcgatact tgctacgtac 1140
aaagcattgg ctgattcccc aatagtgatt ccgcgtgaaa cgatccccgg tcctcatggg 1200
atgaccagag taataattgg aggatcttca aggttcgata tgtatgggcc tgaatttgga 1260
ttgggtcgag ctttggccgc tcgcatgggt tatgggaata aggatgatgg gaaaataaca 1320
gcaaatcctg ggtgtgaagg aggtggaagt gttgatttgg aaatttgcct taggcctcat 1380
attatggcct ctcttgaagt tgatcaagag tttatgggtt ttgtgtccta g 1431

<210> SEQ ID NO 110
<211> LENGTH: 1191
<212> TYPE: DNA
<213> ORGANISM: Spinacia oleracea

<400> SEQUENCE: 110
atgactccaa atctgcaaat agtaaccaac ggaggcaaac cggaaaatga tgaagcagaa 60
cccgtatcac ctaccggaca atacttcaac agcaaagtgt tgtctgtttg tgtccttgcc 120
attctagaaa ttgatgttcc tatagatgac tcgtgtgtaa ttccacaact ccgtgatgtc 180
ttcctaccca tgaaccccag attttcatct atcatgatat ctgacaataa agatgtaaaa 240
caatggaaaa gagtggaagt gaaccttcaa gatcatgttg tcgtccctag cgtcccagat 300
ggcttatcgg ttgaatcata cgacaagtac tttgatgaat atctgacaaa aataacagtg 360
gatccattac cacaggatag gcctttatgg gaacttcatg ttataaaata cccaacaagc 420
aaagcagcgg gtcatttcat ctggaagctt caccatgcac ttggtgacgg ctacactcta 480
atgggagtac ttctgtccgg cgtgaacaga gcagatgatc cttcccttcc gttaactttc 540
ccttcaacac gatcaagctc actagttaca aacaacaaga tgaatattat cagctgggtg 600
ccaagaactt tttcagcaat ctacaacggt gtttataatt ttggatggag ttttctaaaa 660
agcacttgca aggcagatga taagacacct atcagatccg gaaatgaagg tctgggtttc 720
cacccaatga agatctcgac aatagaacta tccctagacc aaatcaaatt tatcaaaaca 780
aaactcggcg caacggtaaa tgacattctt gcaggcataa ttttcctcgg ggttcgaaaa 840
tacatgcaag caactgatac agaatctgga aactcagaat caacggcatt ggtgctgttt 900
aacactagga acattggagg ttatatgacc gctgagcaaa tgaagaaagc acaaatgaaa 960
atatggggga accaatttgc atttttgcat atagcaatac ctcaattaat caatgacaaa 1020
tgctcgaacc cccttgacta tgtctatgaa gcacgaaaac agatctctag gttcaaaagc 1080
tcaccatcag tctatctaac agctcagtgc ctagagctgc taggaaatgc aaaggacctg 1140
aggcagcagc tgaatttatc cagagtacaa cgaataaagc aagcatatta a 1191

<210> SEQ ID NO 111
<211> LENGTH: 1043
<212> TYPE: DNA
<213> ORGANISM: Spinacia oleracea

<400> SEQUENCE: 111
atgttagagc tagcagaaga cgaggtgaag aacttcttca aggtatgggc aatagttttt 60
gcatctttaa gctattgtta ttacataggc aagctaatta atccaaaagg ttatacaaga 120
ttagtagcaa taatcccaat tattactctc tttttagcac ttcctttaaa tctcacatct 180
tttcatcttg gtggtatgac ttgtttcttt attgcttggc ttgctaattt caaactcttg 240
ctttttgctt ttgataaggg cccactttgc gctaattctt caatctcatt cgccaaattt 300
cttgcacttt cttgcttacc catcaaaatc caacacccac ctcataaaaa gtcattaaaa 360
tcacacccat ctatttataa ttacatcatt aaagggatac ttttatgtct aataattaaa 420
atctatgatt atggtgatta cattcatcca aaaatcatat ggctaatctt tttcttccac 480
tcctatttta ccatagagtt agtctttgca ttcctagcaa catcgactaa tattttgtta 540
gggctcgaac tggagccaca gttcaatgaa ccccttaatat caacctcatt gcaagacttt 600
tggggtaaga gatggaatat catggtgaca aggatactta ggcctacggt gtaccttccc 660
acactagagt actccactaa ggtcgttgga cgcacgtggg ccacacttcc ggcggtgatg 720
tccacgttct ttgtgtcagc cattatgcac gagctcatct tctactactt ggggcgcaac 780
tggcccacat tcgaggtgac gtggttcttt ctcctgcatg gattatgtct ttgtgttgag 840
attgtcgcta agaagttagt tggtgggaaa tggaggatcc cacggtggat ttccggccct 900
gccacggtgt tgtttgtggt gggtactggg ttttggctgt tcttgccgcc gttgttgaag 960
gctgggttgg atactagacc gtttcaagag tttgcggccg ttgccaagtt tgtaaggagt 1020
ttgaaggcag ctctcacatt ttg 1043

<210> SEQ ID NO 112
<211> LENGTH: 1530
<212> TYPE: DNA
<213> ORGANISM: Spinacia oleracea

<400> SEQUENCE: 112
atggctcctc cttcttcttc ttcaactacg ggttctggta atggttctag ttttgcagtc 60
aatataatgg cgtcgttcta catttcccca caacaacctt ccaccacaaa ttcacattct 120
atccctctca ctttctttga cattccttgg cttcaatatc ctccgctcca acctctcttc 180
ttctttcaac ttccatctac accccaatct tcttcttctt cttcttcttc ttcttcttct 240
tctttcgacc acaacttgta cttggagttt agctccacca tcctccctag gctcaaacac 300
tccctcgctt ctgccttgca atattacttt cccttttctg gaaaactcac cactactacc 360
catactatcc cgaataacct agttttctcg acagactcat cagattctgt tgagttgact 420
gtttctctgt gtgatgctga ttttaatggt ctatgcagct ttctacccag gtctactcat 480
ctcttccaac aattggttcc ctccttgcca aatattgaat cctccaacct cactacattc 540
cctgcacctt tattagctat tcagatcaca ttctttccca cctcttctcc tggtttctct 600
attggctttg cttctcatcc tgtgctttct gatcagagga ccttcagtaa cttcctttac 660
tcttgggcct ctttctccaa gtttgataat ctaaacattt cacttgcccc ttccttccct 720
gtctctgaca ggtctgtcat tctcgaccct gatagacttg agccccttct gttggagcag 780
tggttgggat tggagtccaa accaaccatg tcaacaaaga tgaagctacg tcctcctcct 840
gcttatgtcc gtggctcgct ccggtccaca ttcgtcatgg gcccatctga tattgctaat 900
gctacacaat ggttacaaac ccagtgtgag aagctcaaca gatcatatcc tgttctcttg 960
tcaccctacg tcgtcacttg tgcctttata tggacctgtt ttctgagagc ccgagtccag 1020
aacagtgctg ttactaaagc caaagcaaaa ggcaccatgt actttggatt tattgctggt 1080

```
ggtattaccc gtttacccta tcgggtacct gctaagtatc ttggcaactg tgtcgggttt   1140

ggacgggcag cagcgcagag ggaggagcta ctgaaggaag gtgaggggat gttggcagct   1200

gctgatgcaa ttgggctaac cattaaaaag ttggataaag atgttttagg aggagctgag   1260

aaatggatat atgaatggca gacattaatg gaatccgaag atcatattca tgtggttggg   1320

tcgcccaagg tgaaccttta tgagacggat tttggtgggg ggaaaccgaa gaagatagag   1380

gaaatttcaa ctgatgttac cagagccatc tctcttacac agagcaggga catgaaaagg   1440

ggaattgaaa ttggcctcac tttaccaaac tccattatgg atgacttctc ctctatcttc   1500

actcaaggcc tccttgtttt tcaaaattag                                    1530
```

<210> SEQ ID NO 113
<211> LENGTH: 476
<212> TYPE: PRT
<213> ORGANISM: Spinacia oleracea

<400> SEQUENCE: 113

```
Met Ala Lys Ser Glu Gln Glu Thr Met Ala Lys Ser Glu Gln Glu Thr
1               5                   10                  15

Ser Ile Lys Leu Val Ser Glu Cys Phe Val Lys Pro Lys Tyr Glu Ile
            20                  25                  30

Lys Ser Ala Lys Gln Pro Tyr His Leu Gly Pro Met Asp Leu Val Met
        35                  40                  45

Leu Thr Ile Asp Pro Ile Gln Lys Gly Leu Val Phe Thr Ile Lys Asn
    50                  55                  60

Ser Pro Leu Phe Leu Ser Ser Glu Ser His Asp Asn Ile Glu Ile Ile
65                  70                  75                  80

Arg Thr Lys Val Val Ser Arg Leu Leu Glu Lys Leu Lys His Ser Leu
                85                  90                  95

Ser Ile Ala Leu Val His Phe Tyr Pro Leu Ala Gly Arg Phe Thr Thr
            100                 105                 110

Gln Lys Gln Pro Glu His Asn Thr Ser Leu Val Phe Ile Asp Cys Asn
        115                 120                 125

Lys Gly Pro Gly Ala Arg Phe Ile His Ala Thr Ser Leu Asp Phe Thr
    130                 135                 140

Ile Ser Asp Ile Leu Ser Pro Val Asp Val Ser Ile Val His Ser Phe
145                 150                 155                 160

Phe Asp Leu Gly Glu Lys His Val Asn Tyr Asp Cys His Thr Lys Ala
                165                 170                 175

Leu Leu Ser Ile Gln Val Thr Glu Leu Leu Asp Gly Val Phe Ile Gly
            180                 185                 190

Phe Ser Met Ser His Ser Val Val Asp Gly Thr Ser Phe Ile His Phe
        195                 200                 205

Val Asn Thr Leu Ser Glu Ile Phe Lys Ser Asp Asp Phe Thr Thr Ile
    210                 215                 220

Ser Arg Ala Pro Ile Leu Asn Tyr Arg Pro Cys Asp Ile Pro Ile Leu
225                 230                 235                 240

Lys Phe Pro Phe Leu Asp Val Glu Gly Phe Ile Cys Arg Ala Tyr Asn
                245                 250                 255

Pro Gly Pro Leu Arg Glu Arg Ile Phe His Phe Ser Leu Asn Ser Met
            260                 265                 270

Leu Arg Leu Lys Ala Met Ala Asn Gln Glu Cys Gly Thr Gln Asn Val
        275                 280                 285

Leu Ser Ser Phe Gln Ala Leu Thr Ala Val Val Trp Arg Ser Ile Thr
```

```
    290                 295                 300

Arg Val Arg Asn Leu Pro Lys Asp Glu Gln Thr Thr Cys Phe Met Ala
305                 310                 315                 320

Met Gly Ser Arg Thr Arg Leu Asn Pro Pro Leu Ser Asp Asp Tyr Phe
                325                 330                 335

Gly Asn Phe Met Ile Ser Thr Lys Phe Ala Cys Lys Ala Glu Glu Leu
            340                 345                 350

Leu Gly Asn Ser Leu Gly Trp Val Ala Met Asn Leu Arg Lys Ile Ile
        355                 360                 365

Met Ser Thr Asp Glu Lys Ser Ile Leu Ala Thr Tyr Lys Ala Leu Ala
    370                 375                 380

Asp Ser Pro Ile Val Ile Pro Arg Glu Thr Ile Pro Gly Pro His Gly
385                 390                 395                 400

Met Thr Arg Val Ile Ile Gly Gly Ser Ser Arg Phe Asp Met Tyr Gly
                405                 410                 415

Pro Glu Phe Gly Leu Gly Arg Ala Leu Ala Ala Arg Met Gly Tyr Gly
            420                 425                 430

Asn Lys Asp Asp Gly Lys Ile Thr Ala Asn Pro Gly Cys Glu Gly Gly
        435                 440                 445

Gly Ser Val Asp Leu Glu Ile Cys Leu Arg Pro His Ile Met Ala Ser
    450                 455                 460

Leu Glu Val Asp Gln Glu Phe Met Gly Phe Val Ser
465                 470                 475


<210> SEQ ID NO 114
<211> LENGTH: 396
<212> TYPE: PRT
<213> ORGANISM: Spinacia oleracea

<400> SEQUENCE: 114

Met Thr Pro Asn Leu Gln Ile Val Thr Asn Gly Gly Lys Pro Glu Asn
1               5                   10                  15

Asp Glu Ala Glu Pro Val Ser Pro Thr Gly Gln Tyr Phe Asn Ser Lys
            20                  25                  30

Val Leu Ser Val Cys Val Leu Ala Ile Leu Glu Ile Asp Val Pro Ile
        35                  40                  45

Asp Asp Ser Cys Val Ile Pro Gln Leu Arg Asp Val Phe Leu Pro Met
    50                  55                  60

Asn Pro Arg Phe Ser Ser Ile Met Ile Ser Asp Asn Lys Asp Val Lys
65                  70                  75                  80

Gln Trp Lys Arg Val Glu Val Asn Leu Gln Asp His Val Val Val Pro
                85                  90                  95

Ser Val Pro Asp Gly Leu Ser Val Glu Ser Tyr Asp Lys Tyr Phe Asp
            100                 105                 110

Glu Tyr Leu Thr Lys Ile Thr Val Asp Pro Leu Pro Gln Asp Arg Pro
        115                 120                 125

Leu Trp Glu Leu His Val Ile Lys Tyr Pro Thr Ser Lys Ala Ala Gly
    130                 135                 140

His Phe Ile Trp Lys Leu His His Ala Leu Gly Asp Gly Tyr Thr Leu
145                 150                 155                 160

Met Gly Val Leu Leu Ser Gly Val Asn Arg Ala Asp Asp Pro Ser Leu
                165                 170                 175

Pro Leu Thr Phe Pro Ser Thr Arg Ser Ser Ser Leu Val Thr Asn Asn
            180                 185                 190
```

```
Lys Met Asn Ile Ile Ser Trp Val Pro Arg Thr Phe Ser Ala Ile Tyr
        195                 200                 205

Asn Gly Val Tyr Asn Phe Gly Trp Ser Phe Leu Lys Ser Thr Cys Lys
    210                 215                 220

Ala Asp Asp Lys Thr Pro Ile Arg Ser Gly Asn Glu Gly Leu Gly Phe
225                 230                 235                 240

His Pro Met Lys Ile Ser Thr Ile Glu Leu Ser Leu Asp Gln Ile Lys
                245                 250                 255

Phe Ile Lys Thr Lys Leu Gly Ala Thr Val Asn Asp Ile Leu Ala Gly
            260                 265                 270

Ile Ile Phe Leu Gly Val Arg Lys Tyr Met Gln Ala Thr Asp Thr Glu
        275                 280                 285

Ser Gly Asn Ser Glu Ser Thr Ala Leu Val Leu Phe Asn Thr Arg Asn
    290                 295                 300

Ile Gly Gly Tyr Met Thr Ala Glu Gln Met Lys Lys Ala Gln Met Lys
305                 310                 315                 320

Ile Trp Gly Asn Gln Phe Ala Phe Leu His Ile Ala Ile Pro Gln Leu
                325                 330                 335

Ile Asn Asp Lys Cys Ser Asn Pro Leu Asp Tyr Val Tyr Glu Ala Arg
            340                 345                 350

Lys Gln Ile Ser Arg Phe Lys Ser Ser Pro Ser Val Tyr Leu Thr Ala
        355                 360                 365

Gln Cys Leu Glu Leu Leu Gly Asn Ala Lys Asp Leu Arg Gln Gln Leu
    370                 375                 380

Asn Leu Ser Arg Val Gln Arg Ile Lys Gln Ala Tyr
385                 390                 395


<210> SEQ ID NO 115
<211> LENGTH: 347
<212> TYPE: PRT
<213> ORGANISM: Spinacia oleracea

<400> SEQUENCE: 115

Met Leu Glu Leu Ala Glu Asp Glu Val Lys Asn Phe Phe Lys Val Trp
1               5                   10                  15

Ala Ile Val Phe Ala Ser Leu Ser Tyr Cys Tyr Tyr Ile Gly Lys Leu
            20                  25                  30

Ile Asn Pro Lys Gly Tyr Thr Arg Leu Val Ala Ile Ile Pro Ile Ile
        35                  40                  45

Thr Leu Phe Leu Ala Leu Pro Leu Asn Leu Thr Ser Phe His Leu Gly
    50                  55                  60

Gly Met Thr Cys Phe Phe Ile Ala Trp Leu Ala Asn Phe Lys Leu Leu
65                  70                  75                  80

Leu Phe Ala Phe Asp Lys Gly Pro Leu Cys Ala Asn Ser Ser Ile Ser
                85                  90                  95

Phe Ala Lys Phe Leu Ala Leu Ser Cys Leu Pro Ile Lys Ile Gln His
            100                 105                 110

Pro Pro His Lys Lys Ser Leu Lys Ser His Pro Ser Ile Tyr Asn Tyr
        115                 120                 125

Ile Ile Lys Gly Ile Leu Leu Cys Leu Ile Ile Lys Ile Tyr Asp Tyr
    130                 135                 140

Gly Asp Tyr Ile His Pro Lys Ile Ile Trp Leu Ile Phe Phe Phe His
145                 150                 155                 160

Ser Tyr Phe Thr Ile Glu Leu Val Phe Ala Phe Leu Ala Thr Ser Thr
                165                 170                 175
```

```
Asn Ile Leu Leu Gly Leu Glu Leu Glu Pro Gln Phe Asn Glu Pro Leu
            180                 185                 190

Ile Ser Thr Ser Leu Gln Asp Phe Trp Gly Lys Arg Trp Asn Ile Met
        195                 200                 205

Val Thr Arg Ile Leu Arg Pro Thr Val Tyr Leu Pro Thr Leu Glu Tyr
    210                 215                 220

Ser Thr Lys Val Val Gly Arg Thr Trp Ala Thr Leu Pro Ala Val Met
225                 230                 235                 240

Ser Thr Phe Phe Val Ser Ala Ile Met His Glu Leu Ile Phe Tyr Tyr
                245                 250                 255

Leu Gly Arg Asn Trp Pro Thr Phe Glu Val Thr Trp Phe Phe Leu Leu
            260                 265                 270

His Gly Leu Cys Leu Cys Val Glu Ile Val Ala Lys Lys Leu Val Gly
        275                 280                 285

Gly Lys Trp Arg Ile Pro Arg Trp Ile Ser Gly Pro Ala Thr Val Leu
    290                 295                 300

Phe Val Val Gly Thr Gly Phe Trp Leu Phe Leu Pro Pro Leu Leu Lys
305                 310                 315                 320

Ala Gly Leu Asp Thr Arg Pro Phe Gln Glu Phe Ala Ala Val Ala Lys
                325                 330                 335

Phe Val Arg Ser Leu Lys Ala Ala Leu Thr Phe
            340                 345


<210> SEQ ID NO 116
<211> LENGTH: 509
<212> TYPE: PRT
<213> ORGANISM: Spinacia oleracea

<400> SEQUENCE: 116

Met Ala Pro Pro Ser Ser Ser Ser Thr Thr Gly Ser Gly Asn Gly Ser
1               5                   10                  15

Ser Phe Ala Val Asn Ile Met Ala Ser Phe Tyr Ile Ser Pro Gln Gln
            20                  25                  30

Pro Ser Thr Thr Asn Ser His Ser Ile Pro Leu Thr Phe Phe Asp Ile
        35                  40                  45

Pro Trp Leu Gln Tyr Pro Pro Leu Gln Pro Leu Phe Phe Phe Gln Leu
    50                  55                  60

Pro Ser Thr Pro Gln Ser Ser Ser Ser Ser Ser Ser Ser Ser Ser Ser
65                  70                  75                  80

Ser Phe Asp His Asn Leu Tyr Leu Glu Phe Ser Ser Thr Ile Leu Pro
                85                  90                  95

Arg Leu Lys His Ser Leu Ala Ser Ala Leu Gln Tyr Tyr Phe Pro Phe
            100                 105                 110

Ser Gly Lys Leu Thr Thr Thr Thr His Thr Ile Pro Asn Asn Leu Val
        115                 120                 125

Phe Ser Thr Asp Ser Ser Asp Ser Val Glu Leu Thr Val Ser Leu Cys
    130                 135                 140

Asp Ala Asp Phe Asn Gly Leu Cys Ser Phe Leu Pro Arg Ser Thr His
145                 150                 155                 160

Leu Phe Gln Gln Leu Val Pro Ser Leu Pro Asn Ile Glu Ser Ser Asn
                165                 170                 175

Leu Thr Thr Phe Pro Ala Pro Leu Leu Ala Ile Gln Ile Thr Phe Phe
            180                 185                 190

Pro Thr Ser Ser Pro Gly Phe Ser Ile Gly Phe Ala Ser His Pro Val
```

```
        195                 200                 205

Leu Ser Asp Gln Arg Thr Phe Ser Asn Phe Leu Tyr Ser Trp Ala Ser
    210                 215                 220

Phe Ser Lys Phe Asp Asn Leu Asn Ile Ser Leu Ala Pro Ser Phe Pro
225                 230                 235                 240

Val Ser Asp Arg Ser Val Ile Leu Asp Pro Asp Arg Leu Glu Pro Leu
                245                 250                 255

Leu Leu Glu Gln Trp Leu Gly Leu Glu Ser Lys Pro Thr Met Ser Thr
            260                 265                 270

Lys Met Lys Leu Arg Pro Pro Pro Ala Tyr Val Arg Gly Ser Leu Arg
        275                 280                 285

Ser Thr Phe Val Met Gly Pro Ser Asp Ile Ala Asn Ala Thr Gln Trp
    290                 295                 300

Leu Gln Thr Gln Cys Glu Lys Leu Asn Arg Ser Tyr Pro Val Leu Leu
305                 310                 315                 320

Ser Pro Tyr Val Val Thr Cys Ala Phe Ile Trp Thr Cys Phe Leu Arg
                325                 330                 335

Ala Arg Val Gln Asn Ser Ala Val Thr Lys Ala Lys Ala Lys Gly Thr
            340                 345                 350

Met Tyr Phe Gly Phe Ile Ala Gly Gly Ile Thr Arg Leu Pro Tyr Arg
        355                 360                 365

Val Pro Ala Lys Tyr Leu Gly Asn Cys Val Gly Phe Gly Arg Ala Ala
    370                 375                 380

Ala Gln Arg Glu Glu Leu Leu Lys Glu Gly Glu Gly Met Leu Ala Ala
385                 390                 395                 400

Ala Asp Ala Ile Gly Leu Thr Ile Lys Lys Leu Asp Lys Asp Val Leu
                405                 410                 415

Gly Gly Ala Glu Lys Trp Ile Tyr Glu Trp Gln Thr Leu Met Glu Ser
            420                 425                 430

Glu Asp His Ile His Val Val Gly Ser Pro Lys Val Asn Leu Tyr Glu
        435                 440                 445

Thr Asp Phe Trp Trp Gly Lys Pro Lys Lys Ile Glu Glu Ile Ser Thr
    450                 455                 460

Asp Val Thr Arg Ala Ile Ser Leu Thr Gln Ser Arg Asp Met Lys Arg
465                 470                 475                 480

Gly Ile Glu Ile Gly Leu Thr Leu Pro Asn Ser Ile Met Asp Asp Phe
                485                 490                 495

Ser Ser Ile Phe Thr Gln Gly Leu Leu Val Phe Gln Asn
            500                 505
```

<210> SEQ ID NO 117
<211> LENGTH: 1419
<212> TYPE: DNA
<213> ORGANISM: Spinacia oleracea

<400> SEQUENCE: 117

```
atggccgcct caaacaaaga gcaaagcaag ctacatattg ctatgtttcc ttggtttgca     60

tatggtcata taaacccatt catccagctc tctaacaagc tttcctccca tggcatccaa    120

atctctttct tctcaatacc aggaaacatt gatcgtatca aatcctccct taatctctca    180

cctcccaacc agctcatccc cctcactatt cccccaactg aaggactctc tcccaacttt    240

gacagcagct ctgaagtaac acctcaaact gctcagcttc tcacactagc acttgatcaa    300

atgcagcccc aagtcaaagc tctattccct cacccccagc cacaagttat cctctttgat    360
```

```
tttgcatatc actggcttcc ctcagtagct tctgaactag gcatcaaagc tgttcatttc     420

aatacattcc cagctgttat caattcatat ctcactgtcc cttcaagaat gactgatcca     480

aataaaccac cgacatttga ggacttgaag aaccctcctc aaggctatcc caaaacctca     540

accgcctcag tgaaaacctt cgaagctcaa gattacctat tccttttcaa gagtttcgat     600

ggcggaccgt gccatttcga aaagatattg gcattcacaa acagctgtga tgctatactt     660

tacaggacct gcaatgaaat agaaggtcca ttcatagatt acttcaagac ccaaataaat     720

aaaccactgc ttttagctgg cccaagtgtt cctctaccac cctctggtga actggatgaa     780

aaatgggaga tgtggttagg taaatttcct gaaaagtcag tcatatactg cagcttcgga     840

agcgagacat acttgaatga tgctcagatt caggagctta cacttgggtt ggagctcact     900

ggtctgccct ttatcttggt tttgaatttt ggaacaagta acagcaccga tgcccacaat     960

aagctagaag catcattacc agaaggattt agagagagaa tcaaagacag gggcgttctg    1020

catacaggat gggtgcaaca gcaaaacatt ttagcacaca gaagcatagg atgctttctt    1080

actcacgcag ggttcagctc tgtaatagag ggtattgtga atgactgtca attagcattt    1140

ctacctctaa aggctgacca gtttatgatc gctaagctat ttagtgggga tctgaaagca    1200

ggggtggagg taaatcgaag agatgaagat gggtcttttg ccaaagaaga tattttcgaa    1260

gcaataaaga cgatcatggt ggatactgat aaagaaccaa gtagatccat cagggagaat    1320

catagcaatt ggagaaagtt tttgatgaat aaggagattg aagctagtta tattgcaaat    1380

ttagctcatg aactcaaggc attggttcaa aaagcttag                           1419
```

<210> SEQ ID NO 118
<211> LENGTH: 472
<212> TYPE: PRT
<213> ORGANISM: Spinacia oleracea

<400> SEQUENCE: 118

```
Met Ala Ala Ser Asn Lys Glu Gln Ser Lys Leu His Ile Ala Met Phe
1               5                   10                  15

Pro Trp Phe Ala Tyr Gly His Ile Asn Pro Phe Ile Gln Leu Ser Asn
            20                  25                  30

Lys Leu Ser Ser His Gly Ile Gln Ile Ser Phe Phe Ser Ile Pro Gly
        35                  40                  45

Asn Ile Asp Arg Ile Lys Ser Ser Leu Asn Leu Ser Pro Pro Asn Gln
    50                  55                  60

Leu Ile Pro Leu Thr Ile Pro Pro Thr Glu Gly Leu Ser Pro Asn Phe
65                  70                  75                  80

Asp Ser Ser Ser Glu Val Thr Pro Gln Thr Ala Gln Leu Leu Thr Leu
                85                  90                  95

Ala Leu Asp Gln Met Gln Pro Gln Val Lys Ala Leu Phe Pro His Pro
            100                 105                 110

Gln Pro Gln Val Ile Leu Phe Asp Phe Ala Tyr His Trp Leu Pro Ser
        115                 120                 125

Val Ala Ser Glu Leu Gly Ile Lys Ala Val His Phe Asn Thr Phe Pro
    130                 135                 140

Ala Val Ile Asn Ser Tyr Leu Thr Val Pro Ser Arg Met Thr Asp Pro
145                 150                 155                 160

Asn Lys Pro Pro Thr Phe Glu Asp Leu Lys Asn Pro Pro Gln Gly Tyr
                165                 170                 175

Pro Lys Thr Ser Thr Ala Ser Val Lys Thr Phe Glu Ala Gln Asp Tyr
            180                 185                 190
```

```
Leu Phe Leu Phe Lys Ser Phe Asp Gly Gly Pro Cys His Phe Glu Lys
        195                 200                 205

Ile Leu Ala Phe Thr Asn Ser Cys Asp Ala Ile Leu Tyr Arg Thr Cys
    210                 215                 220

Asn Glu Ile Glu Gly Pro Phe Ile Asp Tyr Phe Lys Thr Gln Ile Asn
225                 230                 235                 240

Lys Pro Leu Leu Leu Ala Gly Pro Ser Val Pro Leu Pro Pro Ser Gly
                245                 250                 255

Glu Leu Asp Glu Lys Trp Glu Met Trp Leu Gly Lys Phe Pro Glu Lys
            260                 265                 270

Ser Val Ile Tyr Cys Ser Phe Gly Ser Glu Thr Tyr Leu Asn Asp Ala
        275                 280                 285

Gln Ile Gln Glu Leu Thr Leu Gly Leu Glu Leu Thr Gly Leu Pro Phe
    290                 295                 300

Ile Leu Val Leu Asn Phe Gly Thr Ser Asn Ser Thr Asp Ala His Asn
305                 310                 315                 320

Lys Leu Glu Ala Ser Leu Pro Glu Gly Phe Arg Glu Arg Ile Lys Asp
                325                 330                 335

Arg Gly Val Leu His Thr Gly Trp Val Gln Gln Gln Asn Ile Leu Ala
            340                 345                 350

His Arg Ser Ile Gly Cys Phe Leu Thr His Ala Gly Phe Ser Ser Val
        355                 360                 365

Ile Glu Gly Ile Val Asn Asp Cys Gln Leu Ala Phe Leu Pro Leu Lys
    370                 375                 380

Ala Asp Gln Phe Met Ile Ala Lys Leu Phe Ser Gly Asp Leu Lys Ala
385                 390                 395                 400

Gly Val Glu Val Asn Arg Arg Asp Glu Asp Gly Ser Phe Ala Lys Glu
                405                 410                 415

Asp Ile Phe Glu Ala Ile Lys Thr Ile Met Val Asp Thr Asp Lys Glu
            420                 425                 430

Pro Ser Arg Ser Ile Arg Glu Asn His Ser Asn Trp Arg Lys Phe Leu
        435                 440                 445

Met Asn Lys Glu Ile Glu Ala Ser Tyr Ile Ala Asn Leu Ala His Glu
    450                 455                 460

Leu Lys Ala Leu Val Gln Lys Ala
465                 470
```

<210> SEQ ID NO 119
<211> LENGTH: 1386
<212> TYPE: DNA
<213> ORGANISM: Spinacia oleracea

<400> SEQUENCE: 119

```
atgtgtgacg acaaaaaatc atctgttttg agcatagcat tttatccgtg gtttgctctt      60

ggtcacctta cttcatttct ccgattagcc aacaaacttg cacaaaatgg tcacaatgtg     120

tcctatttta tcccaactaa tacattacct agattacttc ctcacaacca ttaccctggc     180

caccttactt tcatccccgt caccgtccca cccgttgacg gcctccctct cagagccgag     240

accaccaacg atgtcccctc ctcggctata caccttctta tgactgccat ggatttgacc     300

cgtgacacta tcgaggccca tttggttagt atcaaacccg atgttgtttt ctacgacttt     360

gcttattgga ttcccgatct agcccgaaaa cacgggttca agtcagtact ctacattaca     420

tcctatatag caagatgtgc ttattttgcc cccgatttga agtcgggtca tcagtccact     480
```

-continued

```
ggggccgaaa ttattgcgcc accaccgggt tttccgtctc agcatttccg gatgcaagca    540

cacgaggctg agactgtggc agacgtaggt aaagagcaag atggattaca aggtataact    600

atttctgaaa ggatgcgcat tgcttttgga aaatgcgacg caattggagt aaagagttgt    660

aaggagatgg aaaaggtgta tattgactac tgtgagaaga tatttggtaa gtctgtacta    720

ctagcaggtc ctatggtccc taaaacccca tcttccaaac ttgatgaata ttttgatggt    780

tggcttacgg gttttggtgc tgctactgtg atttattgtg catttgggag tgaatgtgtt    840

ctcgaaatta accaatttca acaacttctt cttggactag agctcacagg aaggccattt    900

ttggtggcca tgaagccgcc taagaagtat gaaacaatag agtcggcctt accagaaggg    960

tttgagaaga gaacaaaagg aaggggaatc gtacatgagg gttgggtgca gcaacaactg   1020

atattgcaac atccatcagt aggatgtttc ataactcatt gtggagttgg gtctctttcg   1080

gaagctatgg tcagcaaatg tcaagtagtg ttgatgcctc aagctgtaga ccaattcatc   1140

aatgcgagga tgatgagttt agagttgaag attggggttg aggttgagaa gagagaagat   1200

gatggtttgt tcacaaagga ggctgtgcat aaggcggtct ctttggtgat ggaggaagaa   1260

agtgaagtcg caaaagagat gagggtaagt catgataaat ggagagaatt cttattacag   1320

gaaggtcttg aggattctta tatcagtagc ttcattcaga gtctacgaca gttaacgatt   1380

ggatga                                                              1386


<210> SEQ ID NO 120
<211> LENGTH: 461
<212> TYPE: PRT
<213> ORGANISM: Spinacia oleracea

<400> SEQUENCE: 120

Met Cys Asp Asp Lys Lys Ser Ser Val Leu Ser Ile Ala Phe Tyr Pro
1               5                   10                  15

Trp Phe Ala Leu Gly His Leu Thr Ser Phe Leu Arg Leu Ala Asn Lys
            20                  25                  30

Leu Ala Gln Asn Gly His Asn Val Ser Tyr Phe Ile Pro Thr Asn Thr
        35                  40                  45

Leu Pro Arg Leu Leu Pro His Asn His Tyr Pro Gly His Leu Thr Phe
    50                  55                  60

Ile Pro Val Thr Val Pro Pro Val Asp Gly Leu Pro Leu Arg Ala Glu
65                  70                  75                  80

Thr Thr Asn Asp Val Pro Ser Ser Ala Ile His Leu Leu Met Thr Ala
                85                  90                  95

Met Asp Leu Thr Arg Asp Thr Ile Glu Ala His Leu Val Ser Ile Lys
            100                 105                 110

Pro Asp Val Val Phe Tyr Asp Phe Ala Tyr Trp Ile Pro Asp Leu Ala
        115                 120                 125

Arg Lys His Gly Phe Lys Ser Val Leu Tyr Ile Thr Ser Tyr Ile Ala
    130                 135                 140

Arg Cys Ala Tyr Phe Ala Pro Asp Leu Lys Ser Gly His Gln Ser Thr
145                 150                 155                 160

Gly Ala Glu Ile Ile Ala Pro Pro Pro Gly Phe Pro Ser Gln His Phe
                165                 170                 175

Arg Met Gln Ala His Glu Ala Glu Thr Val Ala Asp Val Gly Lys Glu
            180                 185                 190

Gln Asp Gly Leu Gln Gly Ile Thr Ile Ser Glu Arg Met Arg Ile Ala
        195                 200                 205
```

-continued

Phe Gly Lys Cys Asp Ala Ile Gly Val Lys Ser Cys Lys Glu Met Glu
210 215 220

Lys Val Tyr Ile Asp Tyr Cys Glu Lys Ile Phe Gly Lys Ser Val Leu
225 230 235 240

Leu Ala Gly Pro Met Val Pro Lys Thr Pro Ser Ser Lys Leu Asp Glu
245 250 255

Tyr Phe Asp Gly Trp Leu Thr Gly Phe Gly Ala Ala Thr Val Ile Tyr
260 265 270

Cys Ala Phe Gly Ser Glu Cys Val Leu Glu Ile Asn Gln Phe Gln Gln
275 280 285

Leu Leu Leu Gly Leu Glu Leu Thr Gly Arg Pro Phe Leu Val Ala Met
290 295 300

Lys Pro Pro Lys Lys Tyr Glu Thr Ile Glu Ser Ala Leu Pro Glu Gly
305 310 315 320

Phe Glu Lys Arg Thr Lys Gly Arg Gly Ile Val His Glu Gly Trp Val
325 330 335

Gln Gln Gln Leu Ile Leu Gln His Pro Ser Val Gly Cys Phe Ile Thr
340 345 350

His Cys Gly Val Gly Ser Leu Ser Glu Ala Met Val Ser Lys Cys Gln
355 360 365

Val Val Leu Met Pro Gln Ala Val Asp Gln Phe Ile Asn Ala Arg Met
370 375 380

Met Ser Leu Glu Leu Lys Ile Gly Val Glu Val Glu Lys Arg Glu Asp
385 390 395 400

Asp Gly Leu Phe Thr Lys Glu Ala Val His Lys Ala Val Ser Leu Val
405 410 415

Met Glu Glu Glu Ser Glu Val Ala Lys Glu Met Arg Val Ser His Asp
420 425 430

Lys Trp Arg Glu Phe Leu Leu Gln Glu Gly Leu Glu Asp Ser Tyr Ile
435 440 445

Ser Ser Phe Ile Gln Ser Leu Arg Gln Leu Thr Ile Gly
450 455 460

<210> SEQ ID NO 121
<211> LENGTH: 1338
<212> TYPE: DNA
<213> ORGANISM: Spinacia oleracea

<400> SEQUENCE: 121
atggggtggc cggtggtggg cgagtcattt gaattttttc aaaccgggtg gaaaggttac 60
ccggaaaagt tcatatttga tagactgaac aagtacaccc caagccaagt gttcaagact 120
tccatcgtag gagaaaaggt tgcggtttta tgtggcgcgg cgggtaacaa gttcttgtac 180
tcaaacgaga acaagttagt acaagcttgg tggcctagct ctgttgataa gatctttcct 240
tcttctaccc aaacttcctc caaagaagag gctaagaaga tgcggaaact cctccctaac 300
ttcctcaagc ccgaggcttt acataggtac atacccatca tggatagcat tgccatccgg 360
cacatggagt ccgggtggga gggaaaggac aaggtagaag tcttcccttt ggctaagaat 420
tacaccttct ggctggcttg ccgactcttc ttaagcgtcg aggacccggc tcatgtagcc 480
aagttctccg aaccattcaa cgacatagcc gcagggatca tctcgatgcc aatcgacctc 540
cccggaacac ccttcaaccg agggatcaag tcgtctaacg tcgtaaggaa agagttgagg 600
gccatcataa agcagaggaa acttgactta gcagatggca aggcttcacc tacacaagat 660
attctgtctc atatgttgtt gacttgtact gaagatggca agtttatgag tgaaatggat 720

```
attgctgata agattctggg acttcttatt ggtggacatg atactgctag tgcttcttgt    780

acttttgttg ttaagtttct tgctgagctt cctcacatat atgaaggtgt ctacaaagag    840

caaatggaga tagcaaattc aaaaaaagca ggagaacttc taaattggga ggacatacaa    900

aaaatgaaat actcatggaa tgtagcttgt gaagttatgc gtttggctcc tccacttcaa    960

ggtggtttca gggaagccct ttctgatttc atgtataacg gattccaaat ccccaagggc   1020

tggaagttat attggagtgc aaattcaaca catatgaacc cggaatgctt cccggagccc   1080

aagacgttcg acccatcgag gttcgacggt acgggaccag caccatacac atacgtcccc   1140

ttcggaggag gaccgagaat gtgcccgggc aaggagtatg caaggctaga gatattagtg   1200

ttcatgcaca acgttgtcaa gaggtttaaa tgggaaaaaa tgcttcctga tgagaaggtt   1260

attgtcaatc ccatgcctat cccagaacat ggccttcctg tccgcctttt ccctcatcct   1320

cgaactgtag ctgcttaa                                                  1338

<210> SEQ ID NO 122
<211> LENGTH: 1077
<212> TYPE: DNA
<213> ORGANISM: Spinacia oleracea

<400> SEQUENCE: 122

atggaccgca ctcggcctga ggtggagtct atcctatcaa cccagaagcc cgaccttgtc     60

ttctacgaca tggcccattg gatacccgat attgctagca agctcgggat caagtcagtg    120

tcatacaaca gtgtatgtgc tatttctatg tcccatgtca gacctagcgt ccttccaaaa    180

gcagcagcaa catcacaagt agctttgtca tcatcgtcat atgtcggtag tgtccctcag    240

tggagtcgca atgatcacaa ctcatcagtc tattttgggg atgagattac cttacttgaa    300

cgctctatca tctccctctc atctgcagat gcaatagcca tccgcacatg cagggagatt    360

gaaggagtat attgtgaccg tgttgctgcc acattcaaca agcctgtcct tgtcactagc    420

cacgccttgc ctgatcttga actccaactc tctccgttgg agactcgatg ggctgactgg    480

ctagctaggt ttgggccaag atcagtgatc ttttgctgcc ttggtagtca gcatgtctta    540

gacgcagccc aactgcagga gttagccttg gggttagaaa tgacaggact acccttcttg    600

atggctgtaa agcctcctgt aggctatgcc tcattgaagg agctgctgcc agaaggttat    660

aatgatcggg ttagtgggag aggggtggtt catggtgggt gggtgcagca acagcagata    720

ctggcgcacc catcattagg gtgctttgtg acccattgtg ggtcttcgtc catgtgggag    780

gggttagtga gtgaaactca gctggtacta ctcccacagc tgccagacca aactctgaac    840

gcaaagttga tggcagatga gctcaaggtg ggtgtgaagg tggagcgaca acagaacggg    900

tgggtgtcaa agcaaggtct atgtgaagcc atcaacagag tgatggatga agatagtgat    960

ataagtcatg tagtgagaaa gaatcatgct aaatacacaa gtatgttgat tagccctgac   1020

tttatcactg gctacattga caacttcatc aaggatttac aagcccttat ttcttag      1077

<210> SEQ ID NO 123
<211> LENGTH: 366
<212> TYPE: PRT
<213> ORGANISM: Spinacia oleracea

<400> SEQUENCE: 123

Met Leu Val Tyr Asp Ala Tyr Phe Pro Trp Ala Leu Asp Val Ala Lys
1               5                   10                  15

Asp His Asn Ile Leu Ala Ala Ala Tyr Phe Val Ser Ser Cys Ala Tyr
```

```
            20                  25                  30

Val Ala Ser Phe Tyr Pro Met Phe Leu Glu Glu Phe Gly Ser Asp Asp
        35                  40                  45

Gln His Pro Val Val Ala Ala Glu Ser Val Pro Gly Leu Leu Val Glu
    50                  55                  60

Leu Pro Ser Arg Glu Glu Met Glu Arg Tyr Ala Pro Lys Cys Ala Gln
65                  70                  75                  80

Ser Ser Ser Ser Asp Asp Lys Pro Asp Thr Gly Lys Lys Pro Leu His
                85                  90                  95

Pro Val Tyr Gln Met Val Val Ser Ser Ile Thr Thr Leu His Leu Ala
            100                 105                 110

Asp Phe Val Leu Phe Asn Ser Phe Asp His Leu Glu His Gln Val Val
        115                 120                 125

Lys Trp Met Thr Asn Leu Trp Arg Val Lys Thr Val Gly Pro Leu Leu
    130                 135                 140

Pro Ser Ala Tyr Leu Asp Lys Arg Ile Glu Ser Asp Val Asn Tyr Cys
145                 150                 155                 160

Val Lys Pro Tyr Lys Pro Asn Asn Glu Ala Cys Met Ser Trp Leu Asn
                165                 170                 175

Ala Lys Gln Val Ala Ser Val Val Tyr Val Ser Phe Gly Ser Val Ala
            180                 185                 190

Lys Leu Ser Val Glu Gln Ile Ser Glu Ile Ala Lys Ala Leu Lys Gln
        195                 200                 205

Ile Pro Ser Ser Phe Leu Trp Ile Val Arg Glu Ala Glu Gln Glu Lys
    210                 215                 220

Leu Pro Asn Asp Phe Ile Thr Glu Thr Ser Glu Lys Gly Leu Val Met
225                 230                 235                 240

Ser Trp Cys Pro Gln Leu Asp Val Leu Ala His Glu Ala Val Gly Cys
                245                 250                 255

Phe Ile Thr His Cys Gly Trp Asn Ser Val Ile Glu Ala Thr Ser Phe
            260                 265                 270

Gly Val Pro Met Leu Gly Met Pro Gln Phe Met Asp His Phe Leu Asp
        275                 280                 285

Ala His Phe Leu Glu Lys Val Trp Gly Val Gly Ile Arg Val Lys Ala
    290                 295                 300

Asp Glu Lys Asn Phe Val Thr Cys Asp Glu Ile Lys Arg Gly Leu Glu
305                 310                 315                 320

Lys Ile Ile Tyr Gly Glu Arg Gly Asn Lys Ile Lys Glu Asn Ala Thr
                325                 330                 335

Lys Trp Lys Glu Leu Ala Lys Glu Ala Val Gly Glu Gly Gly Ser Ser
            340                 345                 350

Asp Asn Ser Thr Gly Glu Ile Ile Lys Trp Leu Ala Ser Ser
        355                 360                 365


<210> SEQ ID NO 124
<211> LENGTH: 358
<212> TYPE: PRT
<213> ORGANISM: Spinacia oleracea

<400> SEQUENCE: 124

Met Asp Arg Thr Arg Pro Glu Val Glu Ser Ile Leu Ser Thr Gln Lys
1               5                   10                  15

Pro Asp Leu Val Phe Tyr Asp Met Ala His Trp Ile Pro Asp Ile Ala
            20                  25                  30
```

-continued

```
Ser Lys Leu Gly Ile Lys Ser Val Ser Tyr Asn Ser Val Cys Ala Ile
        35                  40                  45

Ser Met Ser His Val Arg Pro Ser Val Leu Pro Lys Ala Ala Ala Thr
    50                  55                  60

Ser Gln Val Ala Leu Ser Ser Ser Ser Tyr Val Gly Ser Val Pro Gln
65                  70                  75                  80

Trp Ser Arg Asn Asp His Asn Ser Ser Val Tyr Phe Gly Asp Glu Ile
                85                  90                  95

Thr Leu Leu Glu Arg Ser Ile Ile Ser Leu Ser Ser Ala Asp Ala Ile
            100                 105                 110

Ala Ile Arg Thr Cys Arg Glu Ile Glu Gly Val Tyr Cys Asp Arg Val
        115                 120                 125

Ala Ala Thr Phe Asn Lys Pro Val Leu Val Thr Ser His Ala Leu Pro
    130                 135                 140

Asp Leu Glu Leu Gln Leu Ser Pro Leu Glu Thr Arg Trp Ala Asp Trp
145                 150                 155                 160

Leu Ala Arg Phe Gly Pro Arg Ser Val Ile Phe Cys Cys Leu Gly Ser
                165                 170                 175

Gln His Val Leu Asp Ala Ala Gln Leu Gln Glu Leu Ala Leu Gly Leu
            180                 185                 190

Glu Met Thr Gly Leu Pro Phe Leu Met Ala Val Lys Pro Pro Val Gly
        195                 200                 205

Tyr Ala Ser Leu Lys Glu Leu Leu Pro Glu Gly Tyr Asn Asp Arg Val
    210                 215                 220

Ser Gly Arg Gly Val Val His Gly Gly Trp Val Gln Gln Gln Gln Ile
225                 230                 235                 240

Leu Ala His Pro Ser Leu Gly Cys Phe Val Thr His Cys Gly Ser Ser
                245                 250                 255

Ser Met Trp Glu Gly Leu Val Ser Glu Thr Gln Leu Val Leu Leu Pro
            260                 265                 270

Gln Leu Pro Asp Gln Thr Leu Asn Ala Lys Leu Met Ala Asp Glu Leu
        275                 280                 285

Lys Val Gly Val Lys Val Glu Arg Gln Gln Asn Gly Trp Val Ser Lys
    290                 295                 300

Gln Gly Leu Cys Glu Ala Ile Asn Arg Val Met Asp Glu Asp Ser Asp
305                 310                 315                 320

Ile Ser His Val Val Arg Lys Asn His Ala Lys Tyr Thr Ser Met Leu
                325                 330                 335

Ile Ser Pro Asp Phe Ile Thr Gly Tyr Ile Asp Asn Phe Ile Lys Asp
            340                 345                 350

Leu Gln Ala Leu Ile Ser
        355
```